US012760368B2

(12) United States Patent
Mellios et al.

(10) Patent No.: US 12,760,368 B2
(45) Date of Patent: Oct. 13, 2026

(54) CIRCULAR RNAs FOR DIAGNOSIS OF DEPRESSION AND PREDICTION OF RESPONSE TO ANTIDEPRESSANT TREATMENT

(71) Applicants: UNM Rainforest Innovations, Albuquerque, NM (US); The Board of Regents of the University of Texas System, Austin, TX (US)

(72) Inventors: Nikolaos Mellios, Albuquerque, NM (US); Madhukar H. Trivedi, Albuquerque, NM (US)

(73) Assignees: UNM Rainforest Innovations, Albuquerque, NM (US); The Board of Regents of the University of Texas System, Austin, TX (US)

( * ) Notice: Subject to any disclaimer, the term of this patent is extended or adjusted under 35 U.S.C. 154(b) by 443 days.

(21) Appl. No.: 18/547,830

(22) PCT Filed: Feb. 25, 2022

(86) PCT No.: PCT/US2022/017936

§ 371 (c)(1),
(2) Date: Aug. 24, 2023

(87) PCT Pub. No.: WO2022/183011

PCT Pub. Date: Sep. 1, 2022

(65) Prior Publication Data

US 2024/0200139 A1 Jun. 20, 2024

Related U.S. Application Data

(60) Provisional application No. 63/154,168, filed on Feb. 26, 2021.

(51) Int. Cl.
*C12Q 1/6883* (2018.01)

(52) U.S. Cl.
CPC ..... *C12Q 1/6883* (2013.01); *C12Q 2600/106* (2013.01); *C12Q 2600/118* (2013.01); *C12Q 2600/158* (2013.01); *C12Q 2600/178* (2013.01)

(58) Field of Classification Search
CPC ............ C12Q 1/6883; C12Q 2600/106; C12Q 2600/118; C12Q 2600/158; C12Q 2600/178
See application file for complete search history.

(56) References Cited

U.S. PATENT DOCUMENTS

| | | | |
|---|---|---|---|
| 5,773,244 | A | 6/1998 | Ares, Jr. et al. |
| 6,210,931 | B1 | 4/2001 | Feldstein et al. |
| 2025/0340870 | A1 | 11/2025 | Mellios et al. |

FOREIGN PATENT DOCUMENTS

| | | | | |
|---|---|---|---|---|
| CN | 105861716 A | 8/2016 | | |
| WO | 9201813 | 2/1992 | | |
| WO | 2015034925 | 3/2015 | | |
| WO | 2016011222 | 1/2016 | | |
| WO | WO-2019210033 A1 * | 10/2019 | ........... | C12Q 1/6883 |
| WO | WO-2022183011 A1 | 9/2022 | | |
| WO | WO-2022183011 A9 | 9/2022 | | |
| WO | WO-2022192914 A1 | 9/2022 | | |
| WO | WO-2022192914 A9 | 8/2023 | | |

OTHER PUBLICATIONS

Brown C, US Pharm 36.11 (2011): HS3-HS8 (Year: 2011).*
Geddes J, Lancet, 2013, 381(9878): 1672-82 (Year: 2013).*
"European Application Serial No. 22760497.2, Response to Communication pursuant to Rules 161 (2) and 162 EPC filed Apr. 8, 2024", 19pgs (Year: 2024).*
Shi Y et al. Preprints with The Lancet. Ssrn. Dec. 3, 2020: 1-25 (Year: 2020).*
"European Application Serial No. 22760497.2, Partial Supplementary European Search Report mailed Jun. 3, 2025", 15 pgs.
"Australian Application Serial No. 2022226678, First Examination Report mailed Jun. 12, 2025", 4 pgs.
"Japanese Application Serial No. 2023-552167, Response Filed Jul. 4, 2025 to Notification of Reasons for Rejection mailed Jan. 7, 2025", w o English Claims, 8 pgs.
"European Application Serial No. 22760497.2, Extended European Search Report mailed Aug. 25, 2025", 14 pgs.
Cui, Xuelian, "Hsa_circRNA_103636: potential novel diagnostic and therapeutic biomarker in Major depressive disorder", XP093278171, (Sep. 1, 2016), 11 pgs.
Song, Ruize, "Plasma Circular RNA DYM Related to Major Depressive Disorder and Rapid Antidepressant Effect Treated by Visual Cortical Repetitive Transcranial Magnetic Stimulation", Journal of Affective Disorders, Elsevier Biochemical Press, Amsterdam, NL, vol. 274, XP086208271, (May 25, 2020), 8 pgs.
"*Homo sapiens* chromosome 5 clone RP11-342F17, complete sequence", GenBank: AC093270.3, (May 1, 2002), 42 pgs.

(Continued)

*Primary Examiner* — Samuel C Woolwine
*Assistant Examiner* — Kara N Kovach
(74) *Attorney, Agent, or Firm* — Schwegman, Lundberg & Woessner, P.A.

(57) ABSTRACT

A plurality of circular RNAs (circRNAs) the expression of which is correlated with diagnosis for Major Depressive Disorder (MDD) and Bipolar Disorder (BD) and response to treatment with various antidepressants is provided. The circRNAs are useful for compositions, kits, assays, and methods for the identification, diagnosis, screening, treatment, and/or monitoring of brain disorders such as MDD and BD.

19 Claims, 58 Drawing Sheets

Specification includes a Sequence Listing.

(56) References Cited

OTHER PUBLICATIONS

"International Application Serial No. PCT/US2022/017936, International Search Report mailed Jun. 2, 2022", 5 pgs.
"International Application Serial No. PCT/US2022/017936, Written Opinion mailed Jun. 2, 2022", 8 pgs.
"International Application Serial No. PCT/US2022/071110, International Search Report mailed May 24, 2022", 6 pgs.
"International Application Serial No. PCT/US2022/071110, Written Opinion mailed Jun. 24, 2022", 7 pgs.
Dingding, Mo, et al., "A universal approach to investigate circRNA protein coding function", Sci Rep, v.9, n.1, (2019), 11684.
Dube, Umber, et al., "Alzheimer-associated circular RNA circHOMERI regulates synaptic gene expression and cognition", Alzheimer's & Dementia, vol. 16, suppl. 2, e042335,, (2020), 1-2.
Santer, Laura, et al., "Circular RNAs: a novel class of functional RNA molecules with a therapeutic perspective", Molecular Therapy, vol. 27, No. 8, (2019), 1350-1363.
Zhang, Yang, et al., "Optimized RNA-targeting CRISPR/Casl3d technology outperforms shRNA in identifying functional circRNA", Genome Biology, vol. 22, article No. 41, (Jan. 21, 2021), 1-22.
"International Application Serial No. PCT US2022 017936, International Preliminary Report on Patentability mailed Sep. 7, 2023", 10 pgs.
"International Application Serial No. PCT US2022 071110, International Preliminary Report on Patentability mailed Sep. 21, 2023", 9 pgs.
"U.S. Appl. No. 18/549,887, Preliminary Amendment filed Apr. 1, 2024", 8 pgs.
"U.S. Appl. No. 18/549,887, Supplemental Preliminary Amendment filed Apr. 30, 2024", 4 pgs.
"Singaporean Application Serial No. 11202306244P, Voluntary Amendment Filed Mar. 22, 2024", W English Claims, 21 pgs.
"Japanese Application Serial No. 2023-552167, Notification of Reasons for Rejection mailed Jan. 7, 2025", W English Translation, 14 pgs.
Barrett, S P, "Circular RNA biogenesis can proceed through an exon-containing lariat precursor", Elife 4, e07540, (2015), 18 pgs.
Chang, "Modification of DNA ends can decrease end joining relative to homologous recombination in mammalian cells", Proc. Natl. Acad. Sci. USA 84:4959-4963, (1987), 5 pgs.
Das, D, "Identification and Characterization of Circular Intronic RNAs Derived from Insulin Gene", Int J Mol Sci. 2020;21(12):4302, (Jun. 17, 2020), 17 pgs.
Jinek, "A Programmable Dual-RNA-Guided DNA Endonuclease in Adaptive Bacterial Immunity", Science 337:816, (2012), 14 pgs.
Ragan, C, "Insights into the biogenesis and potential functions of exonic circular RNA", Sci Rep. Feb. 14, 2019;9(1):2048, (Feb. 14, 2019), 18 pgs.
Trivedi, Madhukar, "Establishing moderators and biosignatures of antidepressant response in clinical care (EMBARC): Rationale and design", J. Psychiatric Res., 78, (2016), 32 pgs.
"Japanese Application Serial No. 2023-552167, Notification of Reasons for Rejection mailed Sep. 16, 2025", W English Translation, 6 pgs.
"European Application Serial No. 22760497.2, Response filed Mar. 11, 2026 to Extended European Search Report mailed Aug. 25, 2025", 365.
"Canadian Application Serial No. 3,211,847, Voluntary Amendment Filed Feb. 25, 2026", 30 pgs.
"Australian Application Serial No. 2022226678, Response filed Apr. 1, 2026 to Subsequent Examination Report mailed Jan. 5, 2026", 38 pgs.
"Japanese Application Serial No. 2023-552167, Response filed Mar. 15, 2026 to Notification of Reasons for Rejection mailed Sep. 16, 2025", W English Claims, 24 pgs.
"Japanese Application Serial No. 2023-552167, Notification of Reasons for Refusal mailed Apr. 14, 2026", w English translation, 18 pgs.
"U.S. Appl. No. 18/549,887, Non Final Office Action mailed May 6, 2026", 21 pgs.
Zhao, Mingyu, "Circ-HOMER1 enhances the inhibition of miR-1322 on CXCL6 to regulate the growth and aggressiveness of hepatocellular carcinoma cells", Journal of cellular biochemistry, 12111, [Online]. Retrieved from the Internet https doi.org 10.1002 jcb.29672, 2020, 4440-4449.
Zimmerman, Amber J, "A psychiatric disease-related circular RNA controls synaptic gene expression and cognition", Molecular Psychiatry, 25, pp. 2712-2727, [Online]. Retrieved from the Internet https doi.org 10.1038s41380-020-0653-4, 2020, 16 pgs.
"U.S. Appl. No. 18/549,887, Response filed Feb. 11, 2026 to Restriction Requirement mailed Jan. 9, 2026", 7 pgs.
"U.S. Appl. No. 18/549,887, Restriction Requirement mailed Jan. 9, 2026", 7 pgs.
"Australian Application Serial No. 2022226678, Subsequent Examination Report mailed Jan. 5, 2026", 5 pgs.

* cited by examiner

| AREA UNDER THE ROC CURVE | |
|---|---|
| AREA | 0.8333 |
| STD. ERROR | 0.1154 |
| 95% CONFIDENCE INTERVAL | 0.6071 TO 1.000 |
| P VALUE | 0.0455 |

SSRI REMISSION PREDICTION BASED ON circMIR5695 (circRNA ARRAY PROFILING FROM 100 PBMC SAMPLES FROM THE FRANCE COHORT)

SSRI NR vs SSRI R AT BASELINE (circMIR5695)

| AREA UNDER THE ROC CURVE | |
|---|---|
| AREA | 1.000 |
| STD. ERROR | 0.000 |
| 95% CONFIDENCE INTERVAL | 1.000 TO 1.000 |
| P VALUE | 0.0027 |

SNRI REMISSION PREDICITION BASED ON circRERE (circRNA ARRAY PROFILING FROM 100 PBMC SAMPLES FROM THE FRANCE COHORT)

SNRI NR vs SNRI R AT BASELINE AT BASELINE (circRERE)

| AREA UNDER THE ROC CURVE | |
|---|---|
| AREA | 0.9722 |
| STD. ERROR | 0.04268 |
| 95% CONFIDENCE INTERVAL | 0.886 TO 1.000 |
| P VALUE | 0.0065 |

SSRI AND SNRI REMISSION PREDICITION BASED ON circCHIC1 (circRNA ARRAY PROFILING FROM 100 PBMC SAMPLES FROM THE FRANCE COHORT)

SSRI NR vs SSRI R (circCHIC1)

| AREA UNDER THE ROC CURVE | |
|---|---|
| AREA | 1.000 |
| STD. ERROR | 0.000 |
| 95% CONFIDENCE INTERVAL | 1.000 TO 1.000 |
| P VALUE | 0.0027 |

SNRI NR vs SNRI R (circCHIC1)

| AREA UNDER THE ROC CURVE | |
|---|---|
| AREA | 1.000 |
| STD. ERROR | 0.000 |
| 95% CONFIDENCE INTERVAL | 1.000 TO 1.000 |
| P VALUE | 0.0039 |

SSRI NR vs SSRI R (circCOMT)

| AREA UNDER THE ROC CURVE | |
|---|---|
| AREA | 1.000 |
| STD. ERROR | 0.000 |
| 95% CONFIDENCE INTERVAL | 1.000 TO 1.000 |
| P VALUE | 0.0027 |

SNRI NR vs SNRI R (circCOMT)

| AREA UNDER THE ROC CURVE | |
|---|---|
| AREA | 0.8611 |
| STD. ERROR | 0.1314 |
| 95% CONFIDENCE INTERVAL | 0.6037 TO 1.000 |
| P VALUE | 0.0374 |

SSRI REMISSION AND SSRI vs SNRI TREATMENT PREDICTIONS BASED ON circRALGAPB LEVELS (circRNA ARRAY PROFILING FROM 100 PBMC SAMPLES FROM THE FRANCE COHORT)

SSRI NR vs SSRI R (BASELINE)

| AREA UNDER THE ROC CURVE | |
|---|---|
| AREA | 0.9048 |
| STD. ERROR | 0.08585 |
| 95% CONFIDENCE INTERVAL | 0.7365 TO 1.000 |
| P VALUE | 0.0152 |

SSRI 8 WEEK vs SNRI 8 WEEK

| AREA UNDER THE ROC CURVE | |
|---|---|
| AREA | 1.000 |
| STD. ERROR | 0.000 |
| 95% CONFIDENCE INTERVAL | 1.000 TO 1.000 |
| P VALUE | <0.0001 |

circDDX50 SSRI NR vs SSRI R

| AREA UNDER THE ROC CURVE | |
|---|---|
| AREA | 1.000 |
| STD. ERROR | 0.000 |
| 95% CONFIDENCE INTERVAL | 1.000 TO 1.000 |
| P VALUE | 0.0027 |

SNRI NR vs SNRI R

| AREA UNDER THE ROC CURVE | |
|---|---|
| AREA | 0.9722 |
| STD. ERROR | 0.04268 |
| 95% CONFIDENCE INTERVAL | 0.8886 TO 1.000 |
| P VALUE | 0.0065 |

SSRI NR vs SSRI R (BASELINE)

| | |
|---|---|
| AREA UNDER THE ROC CURVE | |
| AREA | 0.9167 |
| STD. ERROR | 0.08138 |
| 95% CONFIDENCE INTERVAL | 0.7572 TO 1.000 |
| P VALUE | 0.0163 |

BASELINE SSRI REMISSION PREDICITION BASED ON 2 circRNAs (circRNA ARRAY PROFILING FROM 100 PBMC SAMPLES FROM THE FRANCE COHORT)

97.3% SPECIFICITY & 100% SENSITIVITY (RATIO = 1)
SSRI NR vs ALL OTHER GROUPS (BASELINE)

| AREA UNDER THE ROC CURVE | |
|---|---|
| AREA | 0.9910 |
| STD. ERROR | 0.01150 |
| 95% CONFIDENCE INTERVAL | 0.9684 TO 1.000 |
| P VALUE | 0.0001 |

BASELINE SNRI REMISSION PREDICITION BASED ON 2 circRNAs (circRNA ARRAY PROFILING FROM 100 PBMC SAMPLES FROM THE FRANCE COHORT)

100% SPECIFICITY & 83.3% SENSITIVITY (RATIO = 1.5)
SNRI R vs ALL BUT SSRI (BASELINE)

| AREA UNDER THE ROC CURVE | |
|---|---|
| AREA | 0.9722 |
| STD. ERROR | 0.03062 |
| 95% CONFIDENCE INTERVAL | 0.9122 TO 1.000 |
| P VALUE | 0.0004 |

| AREA UNDER THE ROC CURVE | |
|---|---|
| AREA | 1.000 |
| STD. ERROR | 0.000 |
| 95% CONFIDENCE INTERVAL | 1.000 TO 1.000 |
| P VALUE | 0.0003 |

SSRI R vs ALL BUT SSRI (BASELINE)

| AREA UNDER THE ROC CURVE | |
|---|---|
| AREA | 1.000 |
| STD. ERROR | 0.000 |
| 95% CONFIDENCE INTERVAL | 1.000 TO 1.000 |
| P VALUE | 0.0003 |

SERTRALINE RESPONSE PREDICTION BASED ON circICAM1 (circRNA ARRAY PROFILING FROM 100 WHOLE BLOOD SAMPLES FROM THE EMBARC COHORT)

SSRI R vs NR (BASELINE)

| AREA UNDER THE ROC CURVE | |
|---|---|
| AREA | 1.000 |
| STD. ERROR | 0.000 |
| 95% CONFIDENCE INTERVAL | 1.000 TO 1.000 |
| P VALUE | <0.0001 |

SSRI R vs NR (BASELINE)

| AREA UNDER THE ROC CURVE | |
|---|---|
| AREA | 0.7667 |
| STD. ERROR | 0.08907 |
| 95% CONFIDENCE INTERVAL | 0.5921 TO 0.9412 |
| P VALUE | 0.0128 |

SSRI R vs NR (1 WEEK)

| AREA UNDER THE ROC CURVE | |
|---|---|
| AREA | 0.8978 |
| STD. ERROR | 0.06066 |
| 95% CONFIDENCE INTERVAL | 0.7789 TO 1.000 |
| P VALUE | 0.0002 |

SSRI R vs NR (1 WEEK)

| AREA UNDER THE ROC CURVE | |
|---|---|
| AREA | 0.7778 |
| STD. ERROR | 0.09071 |
| 95% CONFIDENCE INTERVAL | 0.6000 TO 0.9556 |
| P VALUE | 0.0095 |

SSRI R vs NR (1 WEEK)

| AREA UNDER THE ROC CURVE | |
|---|---|
| AREA | 0.8267 |
| STD. ERROR | 0.07483 |
| 95% CONFIDENCE INTERVAL | 0.6800 TO 0.9733 |
| P VALUE | 0.0023 |

SSRI R vs NR (1 WEEK)

| AREA UNDER THE ROC CURVE | |
|---|---|
| AREA | 0.8800 |
| STD. ERROR | 0.06655 |
| 95% CONFIDENCE INTERVAL | 0.7496 TO 1.000 |
| P VALUE | 0.0004 |

SSRI R vs NR (BASELINE)

| AREA UNDER THE ROC CURVE | |
|---|---|
| AREA | 0.8800 |
| STD. ERROR | 0.07732 |
| 95% CONFIDENCE INTERVAL | 0.7285 TO 1.000 |
| P VALUE | 0.0004 |

SSRI R vs NR (1 WEEK)

| AREA UNDER THE ROC CURVE | |
|---|---|
| AREA | 0.7867 |
| STD. ERROR | 0.08493 |
| 95% CONFIDENCE INTERVAL | 0.6202 TO 0.9531 |
| P VALUE | 0.0075 |

SSRI R vs NR (BASELINE)

| AREA UNDER THE ROC CURVE | |
|---|---|
| AREA | 1.000 |
| STD. ERROR | 0.000 |
| 95% CONFIDENCE INTERVAL | 1.000 TO 1.000 |
| P VALUE | <0.0001 |

SSRI R vs NR (BASELINE)

| AREA UNDER THE ROC CURVE | |
|---|---|
| AREA | 0.8533 |
| STD. ERROR | 0.08533 |
| 95% CONFIDENCE INTERVAL | 0.6861 TO 1.000 |
| P VALUE | 0.0010 |

SERTRALINE RESPONSE PREDICTION BASED ON circVDAC2, circTRIM69, OR circCYP24A1
(circRNA ARRAY PROFILING FROM 100 WHOLE BLOOD SAMPLES FROM THE EMBARC COHORT)
circRNA ARRAY (EMBARC) - BASELINE (WHOLE BLOOD)

SSRI R vs NR (BASELINE)

| AREA UNDER THE ROC CURVE | |
|---|---|
| AREA | 0.9956 |
| STD. ERROR | 0.007354 |
| 95% CONFIDENCE INTERVAL | 0.9811 TO 1.000 |
| P VALUE | <0.0001 |

SSRI R vs NR (BASELINE)

| AREA UNDER THE ROC CURVE | |
|---|---|
| AREA | 1.000 |
| STD. ERROR | 0.000 |
| 95% CONFIDENCE INTERVAL | 1.000 TO 1.000 |
| P VALUE | <0.0001 |

SSRI R vs NR (BASELINE)

| AREA UNDER THE ROC CURVE | |
|---|---|
| AREA | 1.000 |
| STD. ERROR | 0.000 |
| 95% CONFIDENCE INTERVAL | 1.000 TO 1.000 |
| P VALUE | <0.0001 |

SSRI R vs NR (BASELINE)

| AREA UNDER THE ROC CURVE | |
|---|---|
| AREA | 1.000 |
| STD. ERROR | 0.000 |
| 95% CONFIDENCE INTERVAL | 1.000 TO 1.000 |
| P VALUE | <0.0001 |

SSRI R vs NR (BASELINE)

| AREA UNDER THE ROC CURVE | |
|---|---|
| AREA | 1.000 |
| STD. ERROR | 0.000 |
| 95% CONFIDENCE INTERVAL | 1.000 TO 1.000 |
| P VALUE | <0.0001 |

| ARTIFICIAL hsa_circ_0130587 (circMIR5695) JUNCTION SEQUENCE (3' END - 5' END OF circRNA) |
|---|
| TTTGAATTTTCAGAGGAAAAGACAGTGAGAGAGCAAGAGCAGATTGAGAAGCAGAAGAGTGAGTCGCAAAAAGAGAAAATGACAGAAATGGAGCACCCTG (SEQ ID NO. 242)<br>GGAAAAGAAACCAAGTCTCCTTGAATCAGTTTATCCCAATGTCTTCTGGTTTTCTATGTTGGCTACAGTCAAGATAACCTATTACTAAGGTAGGTTGTGT (SEQ ID NO. 243) |

| ARTIFICIAL hsa_circ_0023881 (circPICALM) JUNCTION SEQUENCE (3' END - 5' END OF circRNA) |
|---|
| CTGTAATGACGCAACCAACCTTAATATACAGCCAGCCTGTCATGAGACCTCCAAACCCCTTTGGCCCTGTATCAGGAGCACAG (SEQ ID NO. 244)<br>GCACCCCCTGTAATGGCCTATCCTGCTACTACACCAACAGGCATGATAGGATATGGAATTCCTCCACAAATGGGAAGTGTTC (SEQ ID NO. 245) |

| ARTIFICIAL hsa_circ_0131196 (circTULP4) JUNCTION SEQUENCE (3' END - 5' END OF circRNA) |
|---|
| GCGAGGAGTGGTTGGGGTGACTTTCACCTCTAGTCACTGTCGCAGGGACAGGAGTACTCCACAGAGGATAAATTTCAACCTCCGGGGCCACAATAGCGAG (SEQ ID NO. 246)<br>TCCTGGGTCAAGCTGAGTATCTCCACGTTTAGGTGCACAAATACTATTTTGTGAAGATCTTAAATTTGTGGTATAAGAACTTGAAGGAAATAGAACTGAT (SEQ ID NO. 247) |

| ARTIFICIAL hsa_circ_0091072 (circCHIC1) JUNCTION SEQUENCE (3' END - 5' END OF circRNA) |
|---|
| GGCTCTCCCGGTCAATGTGAAATGGCTGCTGTGTGGTTGTCTCTGCTGCTGTTGCACACTGGGTTGCAGCCTATGGCCTGTTATTTGTCTCAACAAAAGA (SEQ ID NO. 248)<br>GTTTGGCTTGAGCAACAAGTTTGATACTGAATTTCCCTCCGTTCTAACAGGGAAGGTGGCCCCAGAAGAATTTAAAACCAGCATTGGCCGTGTGAATGCA (SEQ ID NO. 249) |

| ARTIFICIAL hsa_circ_0007422 (circSATB2) JUNCTION SEQUENCE (3' END - 5' END OF circRNA) |
|---|
| TCCCCAGCATGAGAGGGATGTCATCTATGAGGAGGAGTCAAGGCATCACCACAGCGAACGCATGCAACACGTGGTCCAGCTTCCCCCTGAGCCGGTGCAG (SEQ ID NO. 250)<br>GTTTGATGATTCCTGTCTTTTGTGTCGTGGAGCAGTTGGACGGCTCTCTTGAATATGACAACAGAGAAGAACACGCCGAGTTTGTCCTGGTGCGGAAAGA (SEQ ID NO. 251) |

FIG. 27

| ARTIFICIAL hsa_circ_0007097 (circDDX50) JUNCTION SEQUENCE (3' END - 5' END OF circRNA) |
|---|
| GAGTAGTAATGCAGTGTCTCAGATTACCAGAATGTGCCTCCTGAAAGGAAATATGGGTGTTTGCTTTGATGTTCCTACAACTGAGT<br>CAGAAAGGTTACAG (SEQ ID NO. 252)<br>GTCTCTGGCTTCCGTTTCTTACGCTGCTGTTGATTTTTTCCGACCATCAGCTCAGAGACTGATAGAAGAGAAAGGTGCAGTGGATG<br>CATTGGCTGCAGCT (SEQ ID NO. 253) |

| ARTIFICIAL hsa_circ_0009581 (circRERE) JUNCTION SEQUENCE (3' END - 5' END OF circRNA) |
|---|
| GAGCATGGCGGCATTTGCAGGAATGTGTGATGGAGGCTCTACAGAGGACGGCTGTGTCGCAGCCTCTCGGGATGACACCACTCTGA<br>ATGCACTGAACACA (SEQ ID NO. 254)<br>AGGGAAGTGTAACATCTCCCATTTTTCTGACATATTTGCTGCTAGAGAGTTTAAAGCCCGAGTGGATTCATTTTTCTACATATTAG<br>GATATAACCCTGAG (SEQ ID NO. 255) |

| ARTIFICIAL hsa_circ_0060342 (circRALGAPB) JUNCTION SEQUENCE (3' END - 5' END OF circRNA) |
|---|
| TCGCACCAATAGTGGTATTAGTTCAGCAAGTGGTGGAAGCACGGAGCCCACGACTCCCGATAGTGAGAGACCTGCTCAAGCTCTCT<br>TAAGAGATTATG (SEQ ID NO. 256)<br>GGGCAATGTTAAATATTGTTCAAGATTCAGCACTTTTGGAAGCCATTGGTTGCCAGATGGAGATGGGTGGTGGAGAAAATAACCTG<br>AAGAGTCATAG (SEQ ID NO. 257) |

| ARTIFICIAL hsa_circ_0001946 (circCDR1as) JUNCTION SEQUENCE (3' END - 5' END OF circRNA) |
|---|
| TACCCAGTCTTCCATCAACTGGCTCAATATCCATGTCTTCCAACGTCTCCAGTGTGCTGATCTTCTGACATTCAGGTCTTCCAGTG<br>TCTGCAATATCCAG (SEQ ID NO. 258)<br>GGTTTCCGATGGCACCTGTGTCAAGGTCTTCCAACAACTCCGGGTCTTCCAGCGACTTCAAGTCTTCCAATAATCTCAAGGTCTTC<br>CAGATAATCCTGAG (SEQ ID NO. 259) |

| ARTIFICIAL hsa_circ_0062277 (circCOMT) JUNCTION SEQUENCE (3' END - 5' END OF circRNA) |
|---|
| CATCCCCCAGCTGAAGAAGAAGTATGATGTGGACACACTGGACATGGTCTTCCTCGACCACTGGAAGGACCGGTACCTGCCGGACA<br>CGCTTCTCTTGGAG (SEQ ID NO. 260)<br>AAATAACATCTGCTTTGCTGCCGAGCTCAGAGGAGACCCCAGACCCCTCCCGCAGCCAGAGGGCTGGAGCCTGCTCAGAGGTGCTT<br>TGAAGAGGATCCCT (SEQ ID NO. 261) |

FIG. 27 (CONT.)

| ARTIFICIAL hsa_circ_0005133 (circDDR1) JUNCTION SEQUENCE (3' END - 5' END OF circRNA) |
|---|
| TGCCGGGGGCCTGGGCAAGGAGTTCTCCCGGAGCTACCGGCTGCGTTACTCCCGGGATGGTCGCCGCTGGATGGGCTGGAAGGACC<br>GCTGGGGTCAGGAG (SEQ ID NO. 262)<br>AGATGCTGCCCCCACCCCCTTAGGCCCGAGGGATCAGGAGCTATGGGACCAGAGGCCCTGTCATCTTTACTGCTGCTGCTCTTGGT<br>GGCAAGTGGAGATG (SEQ ID NO. 263) |

| ARTIFICIAL hsa_circ_0103668 (circTRIM69) JUNCTION SEQUENCE (3' END - 5' END OF circRNA) |
|---|
| TGAGCAAGGATTCTGGCTTTTAAGACTAAGGAACCAAACTGATCTAAAGGCTCTGGATTTGCCTTCTTTCAGTCTGACACTGACTA<br>ACAACCTCGACAAG (SEQ ID NO. 264)<br>GCCTGTCTCCACTAACTCTGGACCCTAAAACAGCTCACCCAAATCTGGTGCTCTCCAAAAGCCAAACCAGCGTCTGGCATGGTGAC<br>ATTAAGAAGATAAT (SEQ ID NO. 265) |

| ARTIFICIAL hsa_circ_0027446 (circHMGA2) JUNCTION SEQUENCE (3' END - 5' END Of circRNA) |
|---|
| TCTAAAGCAGCTCAAAAGAAAGCAGAAGCCACTGGAGAAAAACGGCCAAGAGGCAGACCTAGGAAATGG<br>(SEQ ID NO. 266)<br>GAACCAACCGGTGAGCCCTCTCCTAAGAGACCCAGGGGAAGACCCAAAGGCAGCAAAAACAAGAGTCCC<br>(SEQ ID NO. 267) |

| ARTIFICIAL hsa_circ_0060930 (circCYP24A1) JUNCTION SEQUENCE (3' END - 5' END OF circRNA) |
|---|
| CAGGCCACAGACAATGAGCCTGTTGAGATGCTACACTCAGGCACCCTGGTGCCCAGCCGGGAACTCCCCATCGCGTTTTGCCAGCG<br>ATAATACGCCTCAG (SEQ ID NO. 268)<br>GACAGGAGGAAACGCAGCGCCAGCAGCATCTCATCTACCCTCCTTGACACCTCCCCGTGGCTCCAGCCAGACCCTAGAGGTCAGCC<br>TTGCGGACCAACAG (SEQ ID NO. 269) |

| ARTIFICIAL hsa_circ_0075410 (circDUSP22) JUNCTION SEQUENCE (3' END - 5' END OF circRNA) |
|---|
| GCAAGAACAAGGTGACACATATTCTGTCTGTCCACGATAGTGCCAGGCCTATGTTGGAG (SEQ ID NO. 270)<br>ATCCTGCCCGGCCTGTACATCGGCAACTTCAAAGATGCCAGAGACGCGGAACAATTGA (SEQ ID NO. 271) |

FIG. 27 (CONT.)

| ARTIFICIAL hsa_circ_0049241 (circICAM1) JUNCTION SEQUENCE (3' END - 5' END OF circRNA) |
|---|
| ACACCTGGCAAATTTGATTTTTTTTTTTTTCCAGAGACGGGGTCTCGCAACATTGCCCAGACTTCCTTTGTGTTAGTTAATAAAG CTTTCTCAACTGCC (SEQ ID NO. 272)<br>CCCCCCGGTATGAGATTGTCATCATCACTGTGGTAGCAGCCGCAGTCATAATGGGCACTGCAGGCCTCAGCACGTACCTCTATAAC CGCCAGCGGAAGAT (SEQ ID NO. 273) |

| ARTIFICIAL hsa_circ_0035301 (circMAPK6) JUNCTION SEQUENCE (3' END - 5' END OF circRNA) |
|---|
| TAGAATTTGTTTCATCTATTTTATTTTATTGAATACTGTCTGTATCTTTGGTTATCCTGTTTGAAGAAAAAGGACAAATAAAACAT GGCCAGCAAATACA (SEQ ID NO. 274)<br>CCCCTCTTCCTCGCCCTCTCTCGCGGGTCGGGGTTACATGGCGGCGACTGCGGCAAAGCGAGAGCCTCGGAGACGCCGCTGCCGCC AGCACAGCCGGAGA (SEQ ID NO. 275 |

| ARTIFICIAL hsa_circ_0007335 (circVDAC2) JUNCTION SEQUENCE (3' END - 5' END OF circRNA) |
|---|
| GGAACACTGATAACACTCTGGGAACAGAAATCGCAATTGAAGACCAGATTTGTCAAGGTTTGAAACTGACATTTGATACTACCTTC TCACCAAACACAGG (SEQ ID NO. 276)<br>GAATTTTCAACGTCCGGTTCATCTAATACAGACACTGGTAAAGTTACTGGGACCTTGGAGACCAAATACAAGTGGTGTGAGTATGG TCTGACTTTCACAG (SEQ ID NO. 277) |

| ARTIFICIAL hsa_circ_0005615 (circNFATC3) JUNCTION SEQUENCE (3' END - 5' END OF circRNA) |
|---|
| AGTATCCTTTAAAGAAAGATTCATGTGGTGATCAGTTTCTTTCAGTTCCTTCACCCTTTACCTGGAGCAAACCAAAGCCTGGCCAC ACCCCTATATTTCG (SEQ ID NO. 278)<br>ATCTTGAGCCAGATGATTGTGCATCCATTTACATCTTTAATGTAGATCCACCTCCATCTACTTTAACCACACCACTTTGCTTACCA CATCATGGATTACC (SEQ ID NO. 279) |

| ARTIFICIAL hsa_circ_0002082 (circMALAT1) JUNCTION SEQUENCE (3' END - 5' END OF circRNA) |
|---|
| CCAGCTGAGTGATAAAGGCTGAGTGTTGAGGAAATTTCTGCAGTTTTAAGCAGTCGTATTTGTGATTGAAGCTGAGTACATTTTGC TGGTGTATTTTTAG (SEQ ID NO. 280)<br>AAACTTTGTCTGCGAACACTCTTTAATGGACCAGATCAGGATTTGAGCGGAAGAACGAATGTAACTTTAAGGCAGGAAAGACAAAT TTTATTCTTCATAA(SEQ ID NO. 281) |

FIG. 27 (CONT.)

| ARTIFICIAL hsa_circ_0050124 (circFKBP8) JUNCTION SEQUENCE (3' END - 5' END OF circRNA) |
|---|
| ACGTCATCCAGGCCCTGGATCTCAGTGTCCCACTCATGGACGTGGGGAGACGGCCATGGTCACTGCTGACTCCAAGTACTGCTAC GGCCCCCAAGGCAG (SEQ ID NO. 282) |
| GAATTGTGCGGGCGCGGGAATTATGGGGTGGGGCTGGGAGGGTCTCTCAAAGTGGGGCTCCGAGCCCGGGAGGAGCAGGCAGG TGAGGGTTAGGGAG (SEQ ID NO. 283) |

| ARTIFICIAL hsa_circ_0080968 (circADAM22) JUNCTION SEQUENCE (3' END - 5' END OF circRNA) |
|---|
| CTGGCAATGGTGTTGCTGGCACCAATATCATAATAGGCATAATTGCTGGCACCATTTTAGTGCTGGCCCTCATATTAGGAATAACT GCGTGGGGTTATAA (SEQ ID NO. 284) |
| GTGAATGTAAATGCGAGGACACGTGGTCCGGGTGCATAATGGGAGACACTGGCTATTATCTTCCTAAAAAGTTCACCCAGTGTAAT ATTGAAGAGTATCA (SEQ ID NO. 285) |

| ARTIFICIAL hsa_circ_0000907 (circMYO9B) JUNCTION SEQUENCE (3' END - 5' END OF circRNA) |
|---|
| GAGCACCAACTTCCTCATCCACTGCCTCACCGCCCTCAGCCAGAAGGGCTACGCCAGCGGCGTCGAGAGGACCATCCTGGGTGCTG GCCCTGTGCTGGAG (SEQ ID NO. 286) |
| CTCCAGGACACGCGCGCCCCGAGCCTGGGAGGCATGCTGAAGCCAGGCGGCCGGCAGGATGAGTGTGAAAGAGGCAGGCAGCTCGG GCCGCCGGGAGCAG (SEQ ID NO. 287) |

| ARTIFICIAL hsa_circ_0006649 (circDLG5) JUNCTION SEQUENCE (3' END - 5' END OF circRNA) |
|---|
| GCGGGAGCGAAACCTGCTGCAGCAGTCATGGAGGACATGAAGCGGCTCCACGAGGAGGACCAGAAGGAGATCGGTGACCTCCGTG CCCAGCAGCAGCAG (SEQ ID NO. 288) |
| GCCCTACCACAGGCTGAATCCTGACTATGAGAGGCTGAAGATCCAGTGCGTGCGAGCCATGTCGGACCTGCAGAGCCTGCAGAACC AGCACACCAACGCC (SEQ ID NO. 289) |

FIG. 27 (CONT.)

SEQ ID NO. 1 Homo Sapiens -
hsa_circ_0068464|NM_001967|EIF4A2
SEQ ID NO. 2 Homo Sapiens -
hsa_circ_0054033|NM_003162|STRN
SEQ ID NO. 3 Homo Sapiens -
hsa_circ_0111746|ENST00000367187.3|PIK3C2B
SEQ ID NO. 4 Homo Sapiens -
hsa_circ_0066556|NM_002942|ROBO2
SEQ ID NO. 5 Homo Sapiens -
hsa_circ_0013953|NM_004284|CHD1L
SEQ ID NO. 6 Homo Sapiens -
hsa_circ_0009574|NM_012102|RERE
SEQ ID NO. 7 Homo Sapiens -
hsa_circ_0049241|NM_000201|ICAM1
SEQ ID NO. 8 Homo Sapiens -
hsa_circ_0007352|None|None
SEQ ID NO. 9 Homo Sapiens -
hsa_circ_0018594|NM_002727|SRGN
SEQ ID NO. 10 Homo Sapiens -
hsa_circ_0017449|NM_014023|WDR37
SEQ ID NO. 11 Homo Sapiens -
hsa_circ_0062191|NM_018943|TUBA8
SEQ ID NO. 12 Homo Sapiens -
hsa_circ_0010210|NM_018125|ARHGEF10L
SEQ ID NO. 13 Homo Sapiens -
hsa_circ_0006148|NM_144660|SAMD8
SEQ ID NO. 14 Homo Sapiens -
hsa_circ_0029696|NM_145061|SKA3
SEQ ID NO. 15 Homo Sapiens -
hsa_circ_0123503|NM_015141|GPD1L
SEQ ID NO. 16 Homo Sapiens -
hsa_circ_0052712|NM_015909|NBAS
SEQ ID NO. 17 Homo Sapiens -
hsa_circ_0063526|NM_002883|RANGAP1
SEQ ID NO. 18 Homo Sapiens -
hsa_circ_0103668|ENST00000558173.1|TRIM69
SEQ ID NO. 19 Homo Sapiens -
hsa_circ_0000442|NM_015335|MED13L
SEQ ID NO. 20 Homo Sapiens -
hsa_circ_0008305|NM_001199649|PTK2
SEQ ID NO. 21 Homo Sapiens -
hsa_circ_0025638|NM_001164746|RASSF8
SEQ ID NO. 22 Homo Sapiens -
hsa_circ_0087903|NM_032012|C9orf5
SEQ ID NO. 23 Homo Sapiens -
hsa_circ_0015382|NM_020318|PAPPA2

FIG. 28

SEQ ID NO. 24 Homo Sapiens -
hsa_circ_0006349|NM_018056|TMEM39B
SEQ ID NO. 25 Homo Sapiens -
hsa_circ_0029975|NM_015678|NBEA
SEQ ID NO. 26 Homo Sapiens -
hsa_circ_0000157|NM_000655|SELL
SEQ ID NO. 27 Homo Sapiens -
hsa_circ_0001176|NM_001037335|PRIC285
SEQ ID NO. 28 Homo Sapiens -
hsa_circ_0001101|NM_020830|WDFY1
SEQ ID NO. 29 Homo Sapiens -
hsa_circ_0001520|NM_152624|DCP2
SEQ ID NO. 30 Homo Sapiens -
hsa_circ_0008857|NM_007348|ATF6

SEQ ID NO. 31 Homo Sapiens -
hsa_circ_0058058|NM_004044|ATIC
SEQ ID NO. 32 Homo Sapiens -
hsa_circ_0092330|NM_001670|ARVCF
SEQ ID NO. 33 Homo Sapiens -
hsa_circ_0098630|NM_030674|SLC38A1
SEQ ID NO. 34 Homo Sapiens -
hsa_circ_0009012|NM_004603|STX1A
SEQ ID NO. 35 Homo Sapiens -
hsa_circ_0001240|NM_145912|NFAM1
SEQ ID NO. 36 Homo Sapiens -
hsa_circ_0000959|NM_014931|PPP6R1
SEQ ID NO. 37 Homo Sapiens -
hsa_circ_0057551|NM_001127257|SLC39A10
SEQ ID NO. 38 Homo Sapiens -
hsa_circ_0001655|None|None
SEQ ID NO. 39 Homo Sapiens –
hsa_circ_0029934|NM_033111|N4BP2L2
SEQ ID NO. 40 Homo Sapiens -
hsa_circ_0042488|NM_015626|WSB1
SEQ ID NO. 41 Homo Sapiens -
hsa_circ_0115791|ENST00000286827.3|TIAM1
SEQ ID NO. 42 Homo Sapiens -
hsa_circ_0003915|NM_001172509|SATB2
SEQ ID NO. 43 Homo Sapiens -
hsa_circ_0001009|NM_018062|FANCL
SEQ ID NO. 44 Homo Sapiens -
hsa_circ_0001820|NM_145647|WDR67
SEQ ID NO. 45 Homo Sapiens -
hsa_circ_0058651|NM_025139|ARMC9
SEQ ID NO. 46 Homo Sapiens -
hsa_circ_0080968|NM_021723|ADAM22

FIG. 28 (CONT.)

SEQ ID NO. 47 Homo Sapiens -
hsa_circ_0005387|NM_004667|HERC2
SEQ ID NO. 48 Homo Sapiens -
hsa_circ_0008132|NM_138492|PRELID2
SEQ ID NO. 49 Homo Sapiens -
hsa_circ_0108522|ENST00000300605.6|HDHD2
SEQ ID NO. 50 Homo Sapiens -
hsa_circ_0005303|NM_001172218|SCMH1
SEQ ID NO. 51 Homo Sapiens -
hsa_circ_0011451|NM_022753|S100PBP
SEQ ID NO. 52 Homo Sapiens -
hsa_circ_0025597|NM_001174097|LDHB
SEQ ID NO. 53 Homo Sapiens -
hsa_circ_0071375|NM_007246|KLHL2
SEQ ID NO. 54 Homo Sapiens -
hsa_circ_0120478|NR_036441|VRK2
SEQ ID NO. 55 Homo Sapiens -
hsa_circ_0060930|NM_000782|CYP24A1
SEQ ID NO. 56 Homo Sapiens -
hsa_circ_0015364|NM_022457|RFWD2
SEQ ID NO. 57 Homo Sapiens -
hsa_circ_0072654|NM_005869|CWC27
SEQ ID NO. 58 Homo Sapiens -
hsa_circ_0043912|NM_001040431|CCDC56
SEQ ID NO. 59 Homo Sapiens -
hsa_circ_0008912|NM_144982|ZFC3H1
SEQ ID NO. 60 Homo Sapiens -
hsa_circ_0001819|NM_015902|UBR5
SEQ ID NO. 61 Homo Sapiens -
hsa_circ_0000564|NM_030621|DICER1
SEQ ID NO. 62 Homo Sapiens -
hsa_circ_0027446|NM_003483|HMGA2
SEQ ID NO. 63 Homo Sapiens -
hsa_circ_0018031|NM_001172303|MASTL
SEQ ID NO. 64 Homo Sapiens -
hsa_circ_0002067|NM_139179|DAGLB
SEQ ID NO. 65 Homo Sapiens -
hsa_circ_0084904|NM_015496|KIAA1429
SEQ ID NO. 66 Homo Sapiens -
hsa_circ_0131987|ENST00000370733.4|KIAA1586
SEQ ID NO. 67 Homo Sapiens -
hsa_circ_0058520|NM_001135187|AGFG1
SEQ ID NO. 68 Homo Sapiens -
hsa_circ_0002474|NM_001083|PDE5A
SEQ ID NO. 69 Homo Sapiens -
hsa_circ_0037139|NM_000517|HBA2

FIG. 28 (CONT.)

SEQ ID NO. 70 Homo Sapiens -
hsa_circ_0041694|NM_002532|NUP88
SEQ ID NO. 71 Homo Sapiens -
hsa_circ_0006093|NM_139179|DAGLB
SEQ ID NO. 72 Homo Sapiens -
hsa_circ_0000691|NM_014699|ZNF646
SEQ ID NO. 73 Homo Sapiens -
hsa_circ_0003653|NM_001142966|GREB1L
SEQ ID NO. 74 Homo Sapiens -
hsa_circ_0062277|NM_000754|COMT
SEQ ID NO. 75 Homo Sapiens -
hsa_circ_0130587|None|None
SEQ ID NO. 76 Homo Sapiens -
hsa_circ_0001167|NM_020820|PREX1
SEQ ID NO. 77 Homo Sapiens –
hsa_circ_0073009|NM_003633|ENC1
SEQ ID NO. 78 Homo Sapiens -
hsa_circ_0077578|NM_014454|SESN1
SEQ ID NO. 79 Homo Sapiens -
hsa_circ_0035944|NM_001144823|DENND4A
SEQ ID NO. 80 Homo Sapiens -
hsa_circ_0044301|NM_002265|KPNB1
SEQ ID NO. 81 Homo Sapiens -
hsa_circ_0070805|NM_001083|PDE5A
SEQ ID NO. 82 Homo Sapiens -
hsa_circ_0076560|NM_020750|XPO5
SEQ ID NO. 83 Homo Sapiens -
hsa_circ_0082319|NM_016478|ZC3HC1
SEQ ID NO. 84 Homo Sapiens -
hsa_circ_0018309|NM_001040084|ANXA8
SEQ ID NO. 85 Homo Sapiens -
hsa_circ_0005379|NM_001494|GDI2
SEQ ID NO. 86 Homo Sapiens -
hsa_circ_0002569|NM_014159|SETD2
SEQ ID NO. 87 Homo Sapiens -
hsa_circ_0055161|NM_019885|CYP26B1
SEQ ID NO. 88 Homo Sapiens -
hsa_circ_0001142|NM_080476|PIGU
SEQ ID NO. 89 Homo Sapiens -
hsa_circ_0049965|NM_031941|USHBP1
SEQ ID NO. 90 Homo Sapiens -
hsa_circ_0087631|NM_014282|HABP4
SEQ ID NO. 91 Homo Sapiens -
hsa_circ_0008057|NM_001990|EYA3
SEQ ID NO. 92 Homo Sapiens -
hsa_circ_0035301|NM_002748|MAPK6

FIG. 28 (CONT.)

SEQ ID NO. 93 Homo Sapiens -
hsa_circ_0060342|NM_020336|RALGAPB
SEQ ID NO. 94 Homo Sapiens -
hsa_circ_0000041|NM_001166006|EPB41
SEQ ID NO. 95 Homo Sapiens -
hsa_circ_0063598|NM_001003796|NHP2L1
SEQ ID NO. 96 Homo Sapiens -
hsa_circ_0000740|NM_020162|DHX33
SEQ ID NO. 97 Homo Sapiens -
hsa_circ_0028198|NM_016238|ANAPC7
SEQ ID NO. 98 Homo Sapiens -
hsa_circ_0000636|NM_001145358|SIN3A
SEQ ID NO. 99 Homo Sapiens -
hsa_circ_0072954|NM_138782|FCHO2
SEQ ID NO. 100 Homo Sapiens -
hsa_circ_0089131|NM_007313|ABL1
SEQ ID NO. 101 Homo Sapiens -
hsa_circ_0125866|NM_001166139|LCORL
SEQ ID NO. 102 Homo Sapiens -
hsa_circ_0127236|ENST00000273963.5|KLHL8
SEQ ID NO. 103 Homo Sapiens –
hsa_circ_0061170|NR_037882|RTEL1TNFRSF6B
SEQ ID NO. 104 Homo Sapiens -
hsa_circ_0082440|NM_021807|EXOC4
SEQ ID NO. 105 Homo Sapiens -
hsa_circ_0081481|NM_033506|FBXO24
SEQ ID NO. 106 Homo Sapiens -
hsa_circ_0037376|NM_002952|RPS2
SEQ ID NO. 107 Homo Sapiens -
hsa_circ_0004928|NM_057159|LPAR1
SEQ ID NO. 108 Homo Sapiens -
hsa_circ_0024379|NM_001040455|SIDT2
SEQ ID NO. 109 Homo Sapiens -
hsa_circ_0001160|NM_001098797|TOX2
SEQ ID NO. 110 Homo Sapiens -
hsa_circ_0031570|NM_015473|HEATR5A
SEQ ID NO. 111 Homo Sapiens -
hsa_circ_0007021|NM_006734|HIVEP2
SEQ ID NO. 112 Homo Sapiens -
hsa_circ_0010027|NM_006474|PDPN
SEQ ID NO. 113 Homo Sapiens -
hsa_circ_0052372|NM_005762|TRIM28
SEQ ID NO. 114 Homo Sapiens -
hsa_circ_0091072|NM_001039840|CHIC1
SEQ ID NO. 115 Homo Sapiens -
hsa_circ_0011898|NM_022733|SMAP2

FIG. 28 (CONT.)

SEQ ID NO. 116 Homo Sapiens -
hsa_circ_0075826|NR_015410|LINC00340
SEQ ID NO. 117 Homo Sapiens -
hsa_circ_0000315|NM_020238|INCENP
SEQ ID NO. 118 Homo Sapiens -
hsa_circ_0020275|NM_002775|HTRA1
SEQ ID NO. 119 Homo Sapiens -
hsa_circ_0082218|NM_001458|FLNC
SEQ ID NO. 120 Homo Sapiens -
hsa_circ_0005133|None|None
SEQ ID NO. 121 Homo Sapiens -
hsa_circ_0000937|NM_000709|BCKDHA
SEQ ID NO. 122 Homo Sapiens -
hsa_circ_0006615|NM_022782|MPHOSPH9
SEQ ID NO. 123 Homo Sapiens -
hsa_circ_0000543|NM_014992|DAAM1
SEQ ID NO. 124 Homo Sapiens -
hsa_circ_0000282|NM_001113528|METTL15
SEQ ID NO. 125 Homo Sapiens -
hsa_circ_0025984|NM_018976|SLC38A2
SEQ ID NO. 126 Homo Sapiens -
hsa_circ_0006404|NM_001455|FOXO3
SEQ ID NO. 127 Homo Sapiens -
hsa_circ_0008289|NM_012454|TIAM2
SEQ ID NO. 128 Homo Sapiens -
hsa_circ_0018905|NM_144660|SAMD8
SEQ ID NO. 129 Homo Sapiens -
hsa_circ_0028628|NM_181578|RFC5
SEQ ID NO. 130 Homo Sapiens -
hsa_circ_0087888|NM_032012|C9orf5
SEQ ID NO. 131 Homo Sapiens -
hsa_circ_0008990|NM_012335|MYO1F
SEQ ID NO. 132 Homo Sapiens -
hsa_circ_0005414|NM_138410|CMTM7
SEQ ID NO. 133 Homo Sapiens -
hsa_circ_0092382|ENST00000324109.4|DNMBP
SEQ ID NO. 134 Homo Sapiens -
hsa_circ_0035957|NM_001144823|DENND4A
SEQ ID NO. 135 Homo Sapiens -
hsa_circ_0006688|TCONS_l2_00026000|TCONS_l2_00026000
SEQ ID NO. 136 Homo Sapiens -
hsa_circ_0008348|NM_001193485|LIMS1
SEQ ID NO. 137 Homo Sapiens -
hsa_circ_0016348|NM_172362|KCNH1
SEQ ID NO. 138 Homo Sapiens -
hsa_circ_0050444|NM_018025|GPATCH1

FIG. 28 (CONT.)

SEQ ID NO. 139 Homo Sapiens -
hsa_circ_0084789|NM_024721|ZFHX4
SEQ ID NO. 140 Homo Sapiens -
hsa_circ_0088511|NM_033334|NR6A1
SEQ ID NO. 141 Homo Sapiens -
hsa_circ_0026467|NM_002273|KRT8
SEQ ID NO. 142 Homo Sapiens -
hsa_circ_0022623|NM_024771|NAA40
SEQ ID NO. 143 Homo Sapiens -
hsa_circ_0008584|NM_001105244|PTPRM
SEQ ID NO. 144 Homo Sapiens -
hsa_circ_0087497|NM_013417|IARS
SEQ ID NO. 145 Homo Sapiens -
hsa_circ_0045871|NM_004710|SYNGR2
SEQ ID NO. 146 Homo Sapiens -
hsa_circ_0001730|NM_004444|EPHB4
SEQ ID NO. 147 Homo Sapiens -
hsa_circ_0001029|NM_003494|DYSF
SEQ ID NO. 148 Homo Sapiens -
hsa_circ_0056390|NM_001145928|SAP130
SEQ ID NO. 149 Homo Sapiens -
hsa_circ_0004858|NM_017798|YTHDF1
SEQ ID NO. 150 Homo Sapiens -
hsa_circ_0088059|NM_022486|SUSD1
SEQ ID NO. 151 Homo Sapiens -
hsa_circ_0056264|NM_020909|EPB41L5
SEQ ID NO. 152 Homo Sapiens -
hsa_circ_0006502|NM_138778|WDR85
SEQ ID NO. 153 Homo Sapiens -
hsa_circ_0080217|NM_015198|COBL
SEQ ID NO. 154 Homo Sapiens -
hsa_circ_0003813|NM_078474|TM2D3
SEQ ID NO. 155 Homo Sapiens -
hsa_circ_0045581|NM_001545|ICT1
SEQ ID NO. 156 Homo Sapiens -
hsa_circ_0049637|NM_004343|CALR
SEQ ID NO. 157 Homo Sapiens -
hsa_circ_0038011|NM_015027|PDXDC1
SEQ ID NO. 158 Homo Sapiens -
hsa_circ_0128496|NM_001142556|HMMR
SEQ ID NO. 159 Homo Sapiens -
hsa_circ_0001834|NM_003070|SMARCA2
SEQ ID NO. 160 Homo Sapiens -
hsa_circ_0075410|NM_020185|DUSP22
SEQ ID NO. 161 Homo Sapiens -
hsa_circ_0001151|NM_018840|C20orf24

FIG. 28 (CONT.)

SEQ ID NO. 162 Homo Sapiens -
hsa_circ_0028067|NM_014325|CORO1C
SEQ ID NO. 163 Homo Sapiens -
hsa_circ_0032777|NM_012111|AHSA1
SEQ ID NO. 164 Homo Sapiens -
hsa_circ_0007097|NM_024045|DDX50
SEQ ID NO. 165 Homo Sapiens -
hsa_circ_0006530|NM_024766|CAMKMT
SEQ ID NO. 166 Homo Sapiens -
hsa_circ_0004771|NM_003489|NRIP1
SEQ ID NO. 167 Homo Sapiens -
hsa_circ_0073608|NM_152624|DCP2
SEQ ID NO. 168 Homo Sapiens -
hsa_circ_0005210|NM_031922|REPS1
SEQ ID NO. 169 Homo Sapiens -
hsa_circ_0007765|NM_002647|PIK3C3
SEQ ID NO. 170 Homo Sapiens -
hsa_circ_0101802|NM_002687|PNN
SEQ ID NO. 171 Homo Sapiens -
hsa_circ_0072088|NM_016107|ZFR
SEQ ID NO. 172 Homo Sapiens -
hsa_circ_0047232|NM_198129|LAMA3
SEQ ID NO. 173 Homo Sapiens -
hsa_circ_0074407|NM_020117|LARS
SEQ ID NO. 174 Homo Sapiens -
hsa_circ_0003695|NM_007166|PICALM
SEQ ID NO. 175 Homo Sapiens -
hsa_circ_0087234|NM_001190482|PCSK5
SEQ ID NO. 176 Homo Sapiens -
hsa_circ_0009581|NM_012102|RERE
SEQ ID NO. 177 Homo Sapiens -
hsa_circ_0129585|NM_023039|ANKRA2
SEQ ID NO. 178 Homo Sapiens -
hsa_circ_0001062|NM_198581|ZC3H6
SEQ ID NO. 179 Homo Sapiens -
hsa_circ_0071210|NM_001199282|LRBA
SEQ ID NO. 180 Homo Sapiens -
hsa_circ_0053907|NM_206943|LTBP1
SEQ ID NO. 181 Homo Sapiens -
hsa_circ_0007422|NM_001172509|SATB2
SEQ ID NO. 182 Homo Sapiens -
hsa_circ_0027966|NM_032148|SLC41A2
SEQ ID NO. 183 Homo Sapiens -
hsa_circ_0008030|NM_001114093|LSM14A
SEQ ID NO. 184 Homo Sapiens -
hsa_circ_0001348|NM_207296|MBNL1

FIG. 28 (CONT.)

SEQ ID NO. 185 Homo Sapiens -
hsa_circ_0050547|NM_005499|UBA2
SEQ ID NO. 186 Homo Sapiens -
hsa_circ_0001058|NM_173647|RNF149
SEQ ID NO. 187 Homo Sapiens -
hsa_circ_0041623|NM_015528|RNF167
SEQ ID NO. 188 Homo Sapiens -
hsa_circ_0074930|NM_003062|SLIT3
SEQ ID NO. 189 Homo Sapiens -
hsa_circ_0092332|NM_032447|FBN3
SEQ ID NO. 190 Homo Sapiens -
hsa_circ_0023928|NM_007166|PICALM
SEQ ID NO. 191 Homo Sapiens -
hsa_circ_0007997|NM_022079|HERC4
SEQ ID NO. 192 Homo Sapiens -
hsa_circ_0000185|NM_006085|BPNT1
SEQ ID NO. 193 Homo Sapiens -
hsa_circ_0001216|NM_001079539|XBP1
SEQ ID NO. 194 Homo Sapiens -
hsa_circ_0039908|NM_017803|DUS2L
SEQ ID NO. 195 Homo Sapiens -
hsa_circ_0075533|NM_006567|FARS2
SEQ ID NO. 196 Homo Sapiens -
hsa_circ_0001219|NM_153051|MTMR3
SEQ ID NO. 197 Homo Sapiens -
hsa_circ_0006491|NM_015559|SETBP1
SEQ ID NO. 198 Homo Sapiens -
hsa_circ_0003195|NM_017735|TTC27
SEQ ID NO. 199 Homo Sapiens -
hsa_circ_0057319|NM_002210|ITGAV
SEQ ID NO. 200 Homo Sapiens -
hsa_circ_0026700|NM_031157|HNRNPA1
SEQ ID NO. 201 Homo Sapiens -
hsa_circ_0009155|NM_017749|AMBRA1
SEQ ID NO. 202 Homo Sapiens -
hsa_circ_0005273|NM_001199649|PTK2
SEQ ID NO. 203 Homo Sapiens -
hsa_circ_0078264|NM_001029884|PLEKHG1
SEQ ID NO. 204 Homo Sapiens -
hsa_circ_0071439|NM_017867|C4orf27
SEQ ID NO. 205 Homo Sapiens -
hsa_circ_0037127|NM_001243249|NPRL3
SEQ ID NO. 206 Homo Sapiens -
hsa_circ_0142668|ENST00000455084.1|TTTY10
SEQ ID NO. 207 Homo Sapiens -
hsa_circ_0092337|NM_033251|RPL13

FIG. 28 (CONT.)

SEQ ID NO. 208 Homo Sapiens -
hsa_circ_0038981|NM_000034|ALDOA
SEQ ID NO. 209 Homo Sapiens -
hsa_circ_0002799|NM_007345|ZNF236
SEQ ID NO. 210 Homo Sapiens -
hsa_circ_0069977|NM_001144978|MTHFD2L
SEQ ID NO. 211 Homo Sapiens -
hsa_circ_0017972|NM_005028|PIP4K2A
SEQ ID NO. 212 Homo Sapiens -
hsa_circ_0003201|NM_020773|TBC1D14
SEQ ID NO. 213 Homo Sapiens -
hsa_circ_0065149|NM_014159|SETD2
SEQ ID NO. 214 Homo Sapiens -
hsa_circ_0071681|NM_004237|TRIP13
SEQ ID NO. 215 Homo Sapiens -
hsa_circ_0084642|NM_001080416|MYBL1
SEQ ID NO. 216 Homo Sapiens -
hsa_circ_0053317|NM_199193|BRE
SEQ ID NO. 217 Homo Sapiens -
hsa_circ_0000443|NM_015335|MED13L
SEQ ID NO. 218 Homo Sapiens -
hsa_circ_0040726|NM_014615|KIAA0182
SEQ ID NO. 219 Homo Sapiens -
hsa_circ_0087331|NM_005077|TLE1
SEQ ID NO. 220 Homo Sapiens -
hsa_circ_0073942|NM_002715|PPP2CA
SEQ ID NO. 221 Homo Sapiens -
hsa_circ_0013526|NM_006135|CAPZA1
SEQ ID NO. 222 Homo Sapiens -
hsa_circ_0131196|TCONS_00011401|TCONS_00011401
SEQ ID NO. 223 Homo Sapiens -
hsa_circ_0004738|NM_022897|RANBP17
SEQ ID NO. 224 Homo Sapiens -
hsa_circ_0026568|NM_000889|ITGB7
SEQ ID NO. 225 Homo Sapiens -
hsa_circ_0061276|NM_003489|NRIP1
SEQ ID NO. 226 Homo Sapiens -
hsa_circ_0002919|NM_001284|AP3S1
SEQ ID NO. 227 Homo Sapiens -
hsa_circ_0000907|NM_004145|MYO9B
SEQ ID NO. 228 Homo Sapiens -
hsa_circ_0023115|NM_000852|GSTP1
SEQ ID NO. 229 Homo Sapiens -
hsa_circ_0001816|NM_014754|PTDSS1
SEQ ID NO. 230 Homo Sapiens -
hsa_circ_0004128|NM_001005735|CHEK2

FIG. 28 (CONT.)

SEQ ID NO. 231 Homo Sapiens -
hsa_circ_0077109|NM_001010844|IRAK1BP1
SEQ ID NO. 232 Homo Sapiens -
hsa_circ_0014724|NR_036564|CCT3
SEQ ID NO. 233 Homo Sapiens -
hsa_circ_0039626|NM_016284|CNOT1
SEQ ID NO. 234 Homo Sapiens -
hsa_circ_0075166|NM_022455|NSD1
SEQ ID NO. 235 Homo Sapiens -
hsa_circ_0123780|ENST00000301831.4|ULK4
SEQ ID NO. 236 Homo Sapiens -
hsa_circ_0077032|NM_004370|COL12A1
SEQ ID NO. 237 Homo Sapiens - hsa_circ_0099053|ENST00000359742.4|GRIP1
SEQ ID NO. 238 Homo Sapiens - hsa_circ_0002082|NR_002819|MALAT1
SEQ ID NO. 239 Homo Sapiens - hsa_circ_0007335|NM_001184783|VDAC2
SEQ ID NO. 240 Homo Sapiens - hsa_circ_0050124|NM_012181|FKBP8
SEQ ID NO. 241 Homo Sapiens - hsa_circ_0005615|NM_004555|NFATC3

FIG. 28 (CONT.)

SEQUENCE LISTING

```
<160> NUMBER OF SEQ ID NOS: 433

<210> SEQ ID NO 1
<211> LENGTH: 228
<212> TYPE: DNA
<213> ORGANISM: Homo Sapiens

<400> SEQUENCE: 1

gaatggaagt tggatacact ttgtgacttg tacgagacac tgaccattac acaggctgtt      60

atttttctca atacgaggcg caaggtggac tggctgactg agaagatgca tgccagagac     120

ttcacagttt ctgctctgca tggtgacatg gaccagaagg agagagatgt tatcatgagg     180

gaattccggt cagggtcaag tcgtgttctg atcactactg acttgttg                  228


<210> SEQ ID NO 2
<211> LENGTH: 137
<212> TYPE: DNA
<213> ORGANISM: Homo Sapiens

<400> SEQUENCE: 2

tggaagcatt gacatttcct ccttcttctg gaaagtcatt catcatggga gcagatgaag      60

cccttgaaag tgaactggga cttggagaac tagcaggcct tacggtggcc aatgaagcag     120

actcactaac ttatgat                                                    137


<210> SEQ ID NO 3
<211> LENGTH: 189
<212> TYPE: DNA
<213> ORGANISM: Homo Sapiens

<400> SEQUENCE: 3

tgtgatttgg tgtacacctt cttccaccca ctgccccggg atgagaaggc tatgggcacc      60

agcccagctc ctaagtcctc agatggcaca tgggcccggc ccgtcggaaa ggtgggaggg     120

gaggtgaagc tgtccatctc ctacaaaaac aataaactct tcatcatggt gatgcatatt     180

cggggcttg                                                             189


<210> SEQ ID NO 4
<211> LENGTH: 327
<212> TYPE: DNA
<213> ORGANISM: Homo Sapiens

<400> SEQUENCE: 4

gatcgcgtct tcgccaggag gactttcccc cgcggattgt ggagcatcct tccgatgtca      60
```

```
tcgtctctaa gggcgagccc acgactctga actgcaaggc ggagggccgg ccaacgccca    120

ccattgagtg gtacaaagat ggggagcgag tggagactga caaggacgat ccccggtccc    180

acaggatgct tctgcccagc ggatccttat tcttcttgcg catcgtgcac gggcgcagga    240

gtaaacctga tgaaggaagc tacgtttgtg ttgcgaggaa ctatcttggt gaagcagtga    300

gtcgaaatgc gtctctggaa gtggcat                                        327
```

```
<210> SEQ ID NO 5
<211> LENGTH: 748
<212> TYPE: DNA
<213> ORGANISM: Homo Sapiens

<400> SEQUENCE: 5

gtggagttgg catgaactta acagcagcag atactgtgat tttgttgac agtgacttta      60

atcctcagaa tgacttgcaa gcagctgcca gggctcatcg cattggccaa aacaagtctg    120

ttaaagttat tcggctgatt ggtcgagaca ctgtggaaga aatagtctat aggaaagcag    180

cctccaaact gcagctcacc aacatgatca tagaaggagg ccattttact ctgggagccc    240

agaaacccgc tgccgatgct gacctccagt tgagtgagat actcaaattt ggtttggata    300

aactgctggc ctctgagggg agcaccatgg atgaaataga cctggagtcc atactgggag    360

aaacaaaaga tggccagtgg gtctctgatg ccttgcctgc agcagaagga gggagcagag    420

atcaagagga aggaaaaaat catatgtact tatttgaagg taaagattat tctaaagagc    480

ccagtaagga agacagaaaa tcatttgaac aactggtaaa ccttcagaaa acccttttgg    540

agaaagctag tcaagagggc cgatcactcc gaaataaagg cagtgttctc atcccaggcc    600

ttgtggaggg atctaccaaa aggaagcggg ttctgagtcc agaagagctg gaggacagac    660

agaagaaaag acaagaagca gctgccaaga gaaggagact catagaggag aagaagaggc    720

aaaaggaaga ggctgaacat aagaaaaa                                       748
```

```
<210> SEQ ID NO 6
<211> LENGTH: 373
<212> TYPE: DNA
<213> ORGANISM: Homo Sapiens

<400> SEQUENCE: 6

gaggctgaac agtacccagg gggagattcg tgtcggtcct agtcatcagg ccaaacttcc     60

agatctgcaa ccatttcctt ctccagatgg tgatacagtg acccaacatg aggaactggt    120

ctggatgcct ggagttaacg actgtgacct ccttatgtac ttgagggcag caaggagcat    180

ggcggcattt gcaggaatgt gtgatggagg ctctacagag gacggctgtg tcgcagcctc    240

tcgggatgac accactctga atgcactgaa cacactgcat gaaagcggtt acgatgctgg    300

caaagccctg cagcgcctgg tgaagaagcc tgtgcccaag ctcatcgaga agtgctggac    360

cgaggacgaa gtg                                                       373
```

```
<210> SEQ ID NO 7
<211> LENGTH: 1501
<212> TYPE: DNA
<213> ORGANISM: Homo Sapiens

<400> SEQUENCE: 7

ccccccggta tgagattgtc atcatcactg tggtagcagc cgcagtcata atgggcactg     60

caggcctcag cacgtacctc tataaccgcc agcggaagat caagaaatac agactacaac    120
```

```
aggcccaaaa agggaccccc atgaaaccga acacacaagc cacgcctccc tgaacctatc    180

ccgggacagg gcctcttcct cggccttccc atattggtgg cagtggtgcc acactgaaca    240

gagtggaaga catatgccat gcagctacac ctaccggccc tgggacgccg gaggacaggg    300

cattgtcctc agtcagatac aacagcattt ggggccatgg tacctgcaca cctaaaacac    360

taggccacgc atctgatctg tagtcacatg actaagccaa gaggaaggag caagactcaa    420

gacatgattg atggatgtta aagtctagcc tgatgagagg ggaagtggtg ggggagacat    480

agccccacca tgaggacata caactgggaa atactgaaac ttgctgccta ttgggtatgc    540

tgaggcccca cagacttaca gaagaagtgg ccctccatag acatgtgtag catcaaaaca    600

caaaggccca cacttcctga cggatgccag cttgggcact gctgtctact gaccccaacc    660

cttgatgata tgtatttatt catttgttat tttaccagct atttattgag tgtcttttat    720

gtaggctaaa tgaacatagg tctctggcct cacggagctc ccagtcctaa tcacattcaa    780

ggtcaccagg tacagttgta caggttgtac actgcaggag agtgcctggc aaaaagatca    840

aatggggctg ggacttctca ttggccaacc tgcctttccc cagaaggagt gatttttcta    900

tcggcacaaa agcactatat ggactggtaa tggttacagg ttcagagatt acccagtgag    960

gccttattcc tcccttcccc ccaaaactga cacctttgtt agccacctcc ccacccacat   1020

acatttctgc cagtgttcac aatgacactc agcggtcatg tctggacatg agtgcccagg   1080

gaatatgccc aagctatgcc ttgtcctctt gtcctgtttg catttcactg ggagcttgca   1140

ctatgcagct ccagtttcct gcagtgatca gggtcctgca agcagtgggg aagggggcca   1200

aggtattgga ggactccctc ccagctttgg aagcctcatc cgcgtgtgtg tgtgtgtgta   1260

tgtgtagaca agctctcgct ctgtcaccca ggctggagtg cagtggtgca atcatggttc   1320

actgcagtct tgacctttg ggctcaagtg atcctcccac ctcagcctcc tgagtagctg   1380

ggaccatagg ctcacaacac cacacctggc aaatttgatt tttttttttt ttccagagac   1440

ggggtctcgc aacattgccc agacttcctt tgtgttagtt aataaagctt tctcaactgc   1500

c                                                                   1501
```

```
<210> SEQ ID NO 8
<211> LENGTH: 2089
<212> TYPE: DNA
<213> ORGANISM: Homo Sapiens

<400> SEQUENCE: 8

gcccaaggtc ccggaggcta tggcagcggc taccatcgtg cacgacacgt ctgaggccgt     60

ggagctctgc cctgcttacg gcttgtacct gaagcccatc accaagatga ccatcagcgt    120

ggcactcccg cagctgaagc agccggggaa gtccatctcc aactgggagg tgatggagag    180

gctgaagggc atggtgcaga accaccagtt ctccacgctg cgtatttcca agagcaccat    240

ggacttcatc cgcttcgagg gggaggtgga gaacaagagc ctggtcaagt cttttctggc    300

ctgcctggac ggcaagacca tcaagctcag cggcttctcc gacatcctga aggtgcgcgc    360

ggccgagttc aagatcgact tccccacccg ccacgactgg gactccttct tccgcgacgc    420

caaggacatg aacgagaccc tgccggggga gcggccggac accatccacc tggaggggct    480

gccctgcaag tggttcgccc tgaaggagtc gggctccgag aagcccagcg aggacgtcct    540

ggtcaaggtg tttgagaagt tcggggagat ccggaatgtg gacatcccca tgctggaccc    600

ctaccgggag gagatgacgg gccgcaactt ccacaccttc agtttcgggg ggcacttgaa    660

cttcgaggcc tatgtgcagt accgcgagta catgggcttc atccaggcca tgagcgccct    720
```

gcgcgggatg aaactcatgt acaagggcga ggacggcaag gccgtggcct gcaacatcaa 780
ggtgagtcct gggcaccgag agagccacgc gcttcctccc tctggcgact tccttccagc 840
agggtcagca gaacgctccc agccacaccc ctgaggctgt ggggacctcc cctaagtaaa 900
atggcagcaa cagtcctgtg cctgtccaat ttcagaggca caggcgtgag gtggagtagg 960
ggtcccgtgc tgtggttttg gaaatttggt atcttaagga agatgtgggg gagacacagg 1020
tcatatagta ggtgagggat ggagcctcag gaactctgac agggatttga accgtgtcag 1080
aaccaagaga acccggcctt cccagaatgc accttgaaac cagggctgaa cgttcccttt 1140
agcctcatgt gctttttat tttttttatt ttttttattt ttattttttt ttcgaggcag 1200
agtctcgatc tgtttcctgg actggagtgc agtggcgcaa tctttgctca gtgcatcctc 1260
cgcctcctgg gttcgagcga ttcttctgcc tcagcctccc gagtagctgg gactacaggc 1320
gcgtgccatc acacctggct aatttttgta tttttagtag aaacagggtt ttgccgtatt 1380
ggccaggctg gtctcgaact cctgacctca tgaactgcct gcctcgccct cccaaagtgc 1440
tgggattaca ggcgtgagcc actgcgctca gcctagcctc gtgttttgac cgtgttggct 1500
tcacagtgac aaatgagcca gcctcctgga gggggttttg tggccttaag atgtgccctg 1560
tgggtgtggg caggcggcct gctcagtgac tgtggccaca gggaatggtg gagccgggta 1620
gcggaagggg agctgtgtct cgcagcggtg gcgtgtcact tgtgttcagt aagtggcgag 1680
ggctagttgg tgttcctcgc tgagtcgtaa ctccgtggga tgagctaagt cttgagccac 1740
tgatggtgac ttgaagggat tggtttggct tctgggctcc actgtctggg tctgcaccgg 1800
acatgagtgg tgagcggtga gcggtgagcg ggcgctcagg ctctgaggcc actcggccct 1860
acggcccagg agagggcgcc tggccgtgtg tctgggggt tttgggggaa ggccatctga 1920
cactgttttt gcttttaaag gtttcttttg attcgaccaa acacctgagt gatgcctcaa 1980
ttaagaagcg gcagctggag aggcagaagc ttcaggaact ggagcagcaa agagaagaac 2040
aaaagcgcag agagaaggaa gcggaggaga ggcagcgagc ggaggaaag 2089

<210> SEQ ID NO 9
<211> LENGTH: 1089
<212> TYPE: DNA
<213> ORGANISM: Homo Sapiens

<400> SEQUENCE: 9
gttatcctac gcggagagcc aggtaccaat gggtgcgctg caatccagac agtaattctg 60
caaactgcct tgaagaaaaa ggaccaatgt tcgaactact tccaggtgaa tccaacaaga 120
tcccccgtct gaggactgac ctttttccaa agacgagaat ccaggacttg aatcgtatct 180
tcccactttc tgaggactac tctggatcag gcttcggctc cggctccggc tctggatcag 240
gatctgggag tggcttccta acggaaatgg aacaggatta ccaactagta gacgaaagtg 300
atgctttcca tgacaacctt aggtctcttg acaggaatct gccctcagac agccaggact 360
tgggtcaaca tggattagaa gaggatttta tgttataaaa gaggattttc ccaccttgac 420
accaggcaat gtagttagca tattttatgt accatggtta tatgattaat cttgggacaa 480
agaattttat agaaattttt aaacatctga aaaagaagct taagttttat catccttttt 540
tttctcatga attcttaaag gattatgctt taatgctgtt atctatttta ttgttcttga 600
aaatacctgc attttttggt atcatgttca accaacatca ttatgaaatt aattagattc 660
ccatggccat aaaatggctt taaagaatat atatatattt ttaaagtagc ttgagaagca 720
aattggcagg taatatttca tacctaaatt aagactctga cttggattgt gaattataat 780
gatatgcccc ttttcttata aaaacaaaaa aaaaaataat gaaacacagt gaatttgtag 840
agtgggggta tttgacatat tttacagggt ggagtgtact atatactatt acctttgaat 900
gtgtttgcag agctagtgga tgtgtttgtc tacaagtatg attgctgtta cataacaccc 960
caaattaact cccaaattaa aacacagttg tgctgtcaat acctcatact gctttacctt 1020
tttttcctgg atatctgtgt attttcaaat gttactatat attaaagcag aaatataacc 1080
aaaggttaa 1089

<210> SEQ ID NO 10
<211> LENGTH: 842
<212> TYPE: DNA
<213> ORGANISM: Homo Sapiens

<400> SEQUENCE: 10
tacgtagaga aatcgacact cttaatgaac gtttagctgc tgaaggacaa gcgattgatg 60
gagcagagct gagtaagggc caactcaaaa caaaagccag tcacagcacc agccagctct 120
cccagaaact gaagaccact tacaaggctt ccaccagcaa gattgtctcc agctttaaga 180
ccacgacatc gagagctgcc tgccagctcg tgaaggagta catcggccac cgggacggca 240
tctgggatgt cagcgtggcc aagacacagc cagtggtgct cgggactgca tcagccgatc 300
acacggcttt gctgtggagc atagagacag ggaagtgcct agtcaagtac gcaggccacg 360
tgggctcagt aaattctatc aaatttcatc cctcagagca gttggctctc actgcttctg 420
gagatcagac tgctcatatc tggagatacg cggtgcagct gccgacaccc cagcctgttg 480
ctgacactag tatatctggg gaagatgaag tagagtgctc tgacaaggac gagcccgacc 540
tcgatgggga tgtgtccagc gactgcccca ccatccgcgt cccactgaca tccctcaaga 600
gccaccaggg cgtggtcatc gcctccgact ggctggttgg ggggaagcag gctgtgactg 660
cctcctggga ccggacggca aacctgtacg acgtggagac gtccgagctc gttcactctc 720
tgacagggca cgaccaggag ttgacgcact gctgcacaca ccccacccag cggctcgtgg 780
tgacctcctc ccgtgacacg actttccgcc tctgggattt cagggacccc tccatccact 840
cg 842

<210> SEQ ID NO 11
<211> LENGTH: 681
<212> TYPE: DNA
<213> ORGANISM: Homo Sapiens

<400> SEQUENCE: 11
acagatgctt gctctggcct gcagggcttc ctgattttcc acagttttgg tgggggcact 60
ggctccggct tcacttctct gctgatggaa cgcctctccc tggattatgg caagaaatcc 120
aagctggagt ttgccatcta cccagccccc caggtctcta ctgcagtggt ggagccctac 180
aactccatcc tgaccaccca caccacactg gaacattcag attgtgcttt catggtggac 240
aacgaagcca tctatgacat ctgccgcagg aaccttgaca ttgagcgccc tacctatacc 300
aacctcaacc gcctcatcag tcagattgtg tcctcaatca ctgcttctct ccgctttgac 360
ggggccctca atgtggacct cactgagttc cagaccaacc tggtgcccta cccccgcatc 420
cacttcccgc tggtcaccta cgcgcccatc atctctgccg agaaagccta tcacgaacag 480
ctctctgtgg ccgagataac cagctcctgc tttgagccca acagccagat ggtgaagtgc 540
gacccgagac atggcaagta catggcctgc tgcatgctct accggggcga cgtggtgccc 600
aaggatgtga atgtcgctat tgctgccatc aagaccaaga ggaccatcca gtttgtagac 660
tggtgtccca caggcttcaa g 681

<210> SEQ ID NO 12
<211> LENGTH: 1627
<212> TYPE: DNA
<213> ORGANISM: Homo Sapiens

<400> SEQUENCE: 12
gtgtgtagct gggacggtgc tggtctgagc tggaccttgt ctgatggctt cctccaaccc 60
tcctccacag cctgccatag gagatcagct ggttccagga gtcccaggcc cctcctctga 120
ggcagaggac gacccaggag aggcgtttga gtttgatgac agtgatgatg aagaggacac 180
cagcgcagcc ctgggcgtcc ccagccttgc tcctgagagg gacacagacc ccccactgat 240
ccacttggac tccatccctg tcactgaccc agacccagca gctgctccac ccggcacagg 300
ggtgccagcc tgggtgagca atggggatgc agcggacgca gccttctccg ggggcccggca 360 ctccagctgg aagcggaaga gttcccgtcg cattgaccgg ttcactttcc ccgccctgga 420
agaggatgtg atttatgacg acgtcccctg cgagagccca gatgcgcatc agcccggggc 480
agagaggaac ctgctctacg aggatgcgca ccgggctggg gcccctcggc aggcggagga 540
cctaggctgg agctccagtg agttcgagag ctacagcgag gactcggggg aggaggccaa 600
gccggaggtc gaggtcgagc ccgccaagca ccgagtgtcc ttccagccca agctttctcc 660
agacctgact aggctaaagg agagatacgc caggactaag agagacatct tggctttgag 720
agttgggggg agagacatgc aggagctgaa gcacaagtac gattgtaaga tgacccagct 780
catgaaggcc gccaagagcg ggaccaagga tgggctggag aagacacgga tggccgtgat 840
gcgcaaagtc tccttcctgc acaggaagga cgtcctcggt gactcggagg aggaggacat 900
ggggctcctg gaggtcagcg tttcggacat caagcccccca gccccagagc tgggccccat 960
gccagagggc ctgagccctc agcaggtggt ccggaggcat atcctgggct ccatcgtgca 1020
gagcgaaggc agctacgtgg agtctctgaa gcggatactc caggactacc gcaacccccct 1080 gatggagatg gagcccaagg cgctgagcgc ccgcaagtgc caggtggtgt tcttccgcgt 1140
gaaggagatc ctgcactgcc actccatgtt ccagatcgcc ctgtcctccc gcgtggctga 1200
gtgggattcc accgagaaga tcggggacct cttcgtggcc tcgttttcca agtccatggt 1260
gctagatgtg tacagtgact acgtgaacaa cttcaccagt gccatgtcca tcatcaagaa 1320
ggcctgcctc accaagcctg ccttcctcga gttcctcaag cgacggcagg tgtgcagccc 1380
agaccgtgtc accctctacg ggctgatggt caagcccatc cagaggttcc cacagttcat 1440
actcctgctt caggacatgc tgaagaacac ccccaggggc catccggaca ggctgtcgct 1500
gcagctggcc ctcacagagc tggagacgct ggctgagaag ctgaacgagc agaagcggct 1560
ggctgaccag gtggctgaga tccagcagct gaccaagagc gtcagtgacc gcagcagcct 1620
caacaag 1627

<210> SEQ ID NO 13
<211> LENGTH: 593
<212> TYPE: DNA
<213> ORGANISM: Homo Sapiens

<400> SEQUENCE: 13
gcagcggagg aggaaatggc aggtcctaat caactctgca ttcgccgctg gactaccaag 60

```
catgtagctg tgtggctgaa ggatgaaggc ttttttgaat atgtggacat tttatgcaat    120

aagcaccgac ttgatggaat cacattgcta acattgactg aatatgatct ccggtctcct    180

cctctggaaa tcaaagtctt aggggacatt aaaaggttaa tgctctcagt ccgaaaattg    240

cagaaaatac atattgatgt tttagaagag atgggctaca acagtgacag tcccatgggt    300

tccatgaccc ctttcatcag tgctcttcag agtacagact ggctctgtaa tggggagctt    360

tcccatgact gtgacggacc cataactgac ttgaattctg atcagtacca gtacatgaat    420

ggtaaaaaca aacattctgt tcgaagattg gacccagaat actggaagac tatactgagt    480

tgtatatatg tttttatagt atttggattt acatctttca ttatggttat agtccatgag    540

cgagtgcctg acatgcagac ctatccacca ctcccagata tattcttaga cag           593
```

<210> SEQ ID NO 14
<211> LENGTH: 726
<212> TYPE: DNA
<213> ORGANISM: Homo Sapiens - hsa_circ_0029696⟩_145061A3

<400> SEQUENCE: 14

```
actttgaaga ttatccaatg agaattttat atgaccttca ttcagaagtt cagactctaa     60

aggatgatgt taatattctt cttgataaag caagattgga aaatcaagaa ggcattgatt    120

tcataaaggc aacaaaagta ctaatggaaa aaaattcaat ggatattatg aaaataagag    180

agtatttcca gaagtatgga tatagtccac gtgtcaagaa aaattcagta cacgagcaag    240

aagccattaa ctctgaccca gagttgtcta attgtgaaaa ttttcagaag actgatgtga    300

aagatgatct gtctgatcct cctgttgcaa gcagttgtat ttctgagaag tctccacgta    360

gtccacaact ttcagatttt ggacttgagc ggtacatcgt atcccaagtt ctaccaaacc    420

ctccacaggc agtgaacaac tataaggaag agcccgtaat tgtaacccca cctaccaaac    480

aatcactagt aaaagtacta aaaactccaa aatgtgcact aaaaatggat gattttgagt    540

gtgtaactcc taaattagaa cactttggta tctctgaata tactatgtgt ttaaatgaag    600

attacacaat gggacttaaa aatgcgagga ataataaaag tgaggaggcc atagatacag    660

aatccaggct caatgataat gtttttgcca ctcccagccc catcatccag cagttggaaa    720

aaagtg                                                               726
```

<210> SEQ ID NO 15
<211> LENGTH: 280
<212> TYPE: DNA
<213> ORGANISM: Homo Sapiens

<400> SEQUENCE: 15

```
gttgccatgt caaatcttag cgaggctgtg caggatgcag acctgctggt gtttgtcatt     60

ccccaccagt tcattcacag aatctgtgat gagatcactg ggagagtgcc caagaaagcg    120

ctgggaatca ccctcatcaa gggcatagac gagggccccg aggggctgaa gctcatttct    180

gacatcatcc gtgagaagat gggtattgac atcagtgtgc tgatgggagc caacattgcc    240

aatgaggtgg ctgcagagaa gttctgtgag accaccatcg                          280
```

<210> SEQ ID NO 16
<211> LENGTH: 586
<212> TYPE: DNA
<213> ORGANISM: Homo Sapiens

<400> SEQUENCE: 16

```
tttgtccaca ctagaaattg aaaatagagc ccaagacctt catctctttg agactttgaa     60
```

gactgatcca gaagcctttc accagcacat ggtcaagtat atttacccta ctattggtgg 120
ctttgatcac gaaaggctgc agtattattt cactcttctg gaaaactgtg gctgtgcaga 180
tttggggaac tgtgccatta aaccagaaac ccacattcga ctgctgaaga agtttaaggt 240
tgttgcatca ggtcttaatt acaaaaagct gacagatgaa aacatgagtc ctcttgaagc 300
attggagcca gttctttcaa gtcaaaatat cttgtctatt tccaaacttg ttcccaaaat 360
ccctgaaaag gatggacaga tgctttcccc aagctctctg tacaccatct ggttacagaa 420
gttgttctgg actggagacc ctcatctcat taaacaagtc ccaggctctt caccggagtg 480
gcttcatgcc tatgatgtct gcatgaagta ctttgatcgt ctccacccag gtgacctcat 540
cactgtggta gatgcagtta cattttctcc aaaagctgtg accaag 586

<210> SEQ ID NO 17
<211> LENGTH: 1298
<212> TYPE: DNA
<213> ORGANISM: Homo Sapiens

<400> SEQUENCE: 17
tctgcagatc tccaggggag cccaccagcc tagtcaacat ggcctcggaa gacattgcca 60
agctggcaga gacacttgcc aagactcagg tggccggggg acagctgagt ttcaaaggca 120
agagcctcaa actcaacact gcagaagatg ctaaagatgt gattaaagag attgaagact 180
ttgacagctt ggaggctctg cgtctggaag gcaacacagt gggcgtggaa gcagccaggg 240
tcatcgccaa ggccttagag aagaagtcgg agttgaagcg ctgccactgg agtgacatgt 300
tcacgggaag gctgcggacc gagatcccac cagccctgat ctcactaggg gaaggactca 360
tcacagctgg ggctcagctg gtggagctgg acttaagcga caacgcattc gggcccgacg 420
gtgtgcaagg cttcgaggcc ctgctcaaga gctcagcctg cttcaccctg caggaactca 480
agctcaacaa ctgtggcatg ggcattggcg gcggcaagat cctggctgca gctctgaccg 540
aatgtcaccg gaaatccagt gcccaaggca agcctctggc cctgaaggtc tttgtggctg 600
gcagaaaccg tctggagaat gatggcgcca ctgccttggc agaagctttt agggtcatcg 660
ggaccctgga ggaggtccac atgccacaga atgggatcaa ccaccctggc atcactgccc 720
tggcccaggc tttcgctgtc aaccccctgc tgcgggtcat caacctgaat gacaacacct 780
tcactgagaa gggcgccgtg gccatggccg agaccttgaa gaccttgcgg caggtggagg 840
tgattaattt tggggactgc ctggtgcgct ccaagggtgc agttgccatt gcagatgcca 900
tccgcggcgg cctgcccaag ctaaaggagc tgaacttgtc attctgtgaa atcaagaggg 960
atgctgccct ggctgttgct gaggccatgg cagacaaagc tgagctggag aagctggacc 1020
tgaatggcaa caccctggga gaagaaggct gtgaacagct tcaggaggtg ctggagggct 1080
tcaacatggc caaggtgctg gcgtccctca gtgatgacga ggacgaggag gaggaggagg 1140
aaggagaaga ggaagaagag gaagcagaag aagaggagga ggaagatgag gaagaggagg 1200
aagaagagga ggaggaggag gaagaagagc ctcagcagcg agggcaggga gagaagtcag 1260
ccacgccctc acggaagatt ctggacccta acactggg 1298

<210> SEQ ID NO 18
<211> LENGTH: 365
<212> TYPE: DNA
<213> ORGANISM: Homo Sapiens

<400> SEQUENCE: 18
gcctgtctcc actaactctg gaccctaaaa cagctcaccc aaatctggtg ctctccaaaa 60
gccaaaccag cgtctggcat ggtgacatta agaagataat gcctgatgat cctgagaggt 120
ttgactcaag tgtggctgta ctgggctcaa gaggcttcac ctctggaaag tggtactggg 180
aagtagaagt agcaaagaag acaaaatgga cagttggagt tgtcagagaa tccatcattc 240
ggaagggcag ctgtcctcta actcctgagc aaggattctg gcttttaaga ctaaggaacc 300
aaactgatct aaaggctctg gatttgcctt ctttcagtct gacactgact aacaacctcg 360
acaag 365

<210> SEQ ID NO 19
<211> LENGTH: 7273
<212> TYPE: DNA
<213> ORGANISM: Homo Sapiens

<400> SEQUENCE: 19
gctgaactca cgggaatcaa atggcgtagg tacaattttg gagggcatgg ggactgtgga 60
cccataattt cagccccagc ccaagatgat ccaattctgt taagtttcat ccgctgtctg 120
caagctaacc tgctttgtgt atggcgtcgt gatgtcaaac cagattgcaa agagttatgg 180
atattctggt ggggagatga acccaaccta gtgggtgtaa tacatcatga actgcagggt 240
aaggtttctg tttttttctt aaaaattatt tgcatcatat ttttttgaac attgataaat 300
ttcaaacaga ttattaagac ttgtctaaaa gaacgatctt aagtgtttca tggatgtctc 360
tctcaaaagg aacattctca cccctcttcc tcccatccct gttttttttt cctaactctt 420
gtccttttcc agttatgctg agaatcagaa ccttgtgaac cgctgctgtt aaatgagagt 480
attgtgtctc ctgggtgcgg tggggtggaa accaggctaa gatccactgt ttttaaatga 540
tagtgaattg tgagtaacta acaagacagt gaattgaaca gttactgttt ttttccttgg 600
actgtggttg ttatggttca ctgccagctg aactctttgg tggaaaattg gagagtgata 660
cagaaattta gttttgagcc taattggaca aaattgtgag attacattga atagtatttt 720
gaggaaagat gaatatatgg gatctggtct gaattgggtg tagcaaattt tcttttgctt 780
ttatttctgt ttttcatgta atttggtgat tccaggaaac attggctccg gtgttgcctg 840
atttttagct tcagattgca tctgatatct ggaaactgaa ttaatgtaag agtttcattt 900
ttctgtgctg ctttatatat ttaccacagt tttatgagca ggaactttta tcagttgtct 960
ttgaatttct ggtaaaaatt tttacctttt tatctaagtg tttctattta gtatgcaaag 1020
ggattttctc aagcaagact aattctaatc tttagttagg gtattaactc tttttgactt 1080
agtctcttag aaccatcttt tattatctcc aaactatatt gtgttaatct gtgtctgaaa 1140
aatttcagat cgtgtttgaa atgttttgtt acttgatgtt tttaatgttt ttttttttta 1200
aaggaaggag taaaactaac tgtaatgtat gttcgaggct ctgttctaaa gcttttacat 1260
ttgcctgaag gatttcctgc caacttttgc ttgacacctt gctagttttt cttggcagcc 1320
attttttatc tgtgatatct cctgccacag cagccagagg gcggtaaacc acaatggact 1380
aattgaactg tttactttat ggtccatttg tctgttcagc tcaaaccttt atcctgatat 1440
tttttagggt atttggtcta taaataagag aaccattgtg ggtgacattg cttgcttagc 1500
tgggtaatca gcaaagtccc agaacttaac attcatctca aagcctgttc tatgtagtta 1560
gcagttaact taggtaaaat tagagtttca gaacatctgg attctgttta tcagaatttt 1620
aaaaataaga tgtcacctag aagataatta caacattttt gtttgtccat taaaatatga 1680
aaacatattt ttactttttt tccctatgta gtagagaggt ataaagcttt ttaaaaagtg 1740

```
tctttcttat ctttcatgat tgtttctgac tgtcatcttc tgtttctctg tattaatctc   1800
ttacgtttta gctttttggt ctgctctttg ttagtgtggt acatataatt ttgtaatgat   1860
gaggaaacca aacccaactg ctaatgaggg ttatttagtt gataatatag aataaattta   1920
tttatctatg ccaacggaga aaatcgtcag tgttcttaga aatagcttat taaattattg   1980
tgttattttt catgggcttt gttactgagt taacaaaaag gagtagggca tttaaatttt   2040
gggatagttg ctttagattg catgtgtaaa ttaatatctt aagtattttt tggtaaagag   2100
ttaagcaaag attgaattat ttttagatat ttttaaaatt acagaaacac tacatttaag   2160
ttagaaaatt aggaaaacag tcatcatatg gagagaacaa agaaataaaa atactgaagt   2220
ctgaaagagt tttagatgtt ttatgtgtaa atgaaattgg taccatacag tttttctaat   2280
tttctaatta aatgtagtat tgtgaatatt ttctcttggg aatgattact tttctttgga   2340
gtttgatagt ggtataaact gtttatattt tgtattctat caggaaagta ttacagtaat   2400
ggaataatta taatttcatt gagtgcgtct cctcttttta atatgaattt tgagcaagtt   2460
tttagattca tttatatgaa gtgtccattt ttgtaggtaa aagtagttga aaaaggtaat   2520
gtatggttca acctaataac agaaaatatc tagccttaat tagaaaaata agtcataaag   2580
acaactttgt ttcaaataag gggaaatacg atagcagtca tgaaaaactg aaggatacaa   2640
agagaatatt ttaattggta gccatacaaa gtggagatat tttagaatct atttcattct   2700
ctaatatatt tgagtcattt tattttgggt aaaataaatt ataggcggag catggtggct   2760
cacgctggtt atcccaacac tttgggaggc tgagggggcc caaatgcttg aggccaggaa   2820
tttgagacca gcctgaccaa tatggtgaaa ccctgtgttt acaaaaaata aaaaaaaaaa   2880
attagccagg tgtggtgacg tgcacctgta attccaacta ctcgggtgac tggggctgga   2940
ggatcactta aacccaggag gccaaggttg cagtgagcag agataatgcc actgcactcc   3000
atcctgggca acaaagtgac acctgtctca aaaaataaaa taaataaata gtagcagaat   3060
ccttttagca ggctttaatg ttaagcatga gattaccatt atttgtaaca ttttttaaat   3120
agggacattt tactgtttct tacattgctg cttatttatg ttatttggca tttcctggct   3180
ggtcacggtg gctcacgcct gtaatccctg cactttggga ggcctaggca ggaggatcac   3240
ctgagttcag gagttggaga ccagcctggc caacatagtg aaaccccctc tctagtaaaa   3300
ataaacaaaa attagctggg catggtggtg ggtgcctgta atcccagcta ctggagaggc   3360
tgagacagga cagtcgctgg aaaccgggag gcagaggtta cagtgggctg agatcacgcc   3420
acagcactct gctgggcaac acagcaagac tccatctcaa taaataaata aataaataaa   3480
taaataaata gcagaatcct gttagctggc ttaaattaag catgacatta ccattattta   3540
acattttttt taatagaggc attttattgt ttcttaaatt gctttttagt tatttggcat   3600
ttccctttgt cttcatagcg tactccaaat agcgtcctac caagaaacct cacggtgaga   3660
tgtaatacca aagcaaccat cttgcattta aatgtataaa gtatcccata aaatgagaat   3720
aatcctacag ggtacacaca caagttagtt ttatgatatt atactttttg tttaattgct   3780
tgacatatct ctgaaatagt ctgagagaag gctataacac atttataatc tgtccttgtc   3840
acttggataa acacttgggt tcctgtctgg ggaattgtta atgcgtgtgg tgtagtgatt   3900
cagagcacgg gctctgggtt gcttgggttt gaatgcttgc atagtcacta gctgtgtatt   3960
cttgatctaa ttatttaact taaactgtgc ctcagttttc tcactgtgaa ttaggttatg   4020
aggttaagaa aaattaaaag tacttagagc agcatatata gcagttaatc tataattgta   4080
```

```
actattgcta ctgctactgt gcaaagacct acaggctgcg aatgaattgt ggcaagaaca   4140
ggttacctgg ggcttagggt aggagtgaaa tagtctcccc tctaaaaggc tgagtaggtg   4200
ggtcatagta tggagtacac agaaccaagg ataagacatt tagacttaat ttgatagatt   4260
ttgaggaatt aaacatttct gatcaggaaa gcgatataat taggaagatt aacttagtaa   4320
taatacagga ttaatgtgta cagggaaacc ataatattgt gattttaaaa ttctaaattg   4380
gaatataaac ttaaatattc tgttcaggat acagatgtat ttaaattaaa aatactaatg   4440
attatatact ataattcata ttaatagtct ttaacacttt tattatacct ttgctgtttt   4500
ggcttgacta aattctacat tttaatttaa gttttagaga ttaatacagt gtgctgagtg   4560
gacttctcct aatctaccaa acaaatactt cttacttttt tttttttttt tttttccttt   4620
agacagagtc ttgctctgtt gcccaggctg gagtgcagtg atgcaatctt ggctcactgc   4680
aacctctgcc tcccgggttc aaatgattct cctgcctcag ccttctgagt agctgggatt   4740
gcaggtgtat gccaccacac ctggccaatt tttgtatttt tagtagagat ggggtttcac   4800
catgttggcc aggttgatct caaactccca acctcaatcg atccgcccgc ctcggcctcc   4860
caaagtgctg ggattacagg cgtgagccac tgggcctggc aacaaatgct ttttaaataa   4920
acacaatatt ctcgccaatt cactgcctgt tagttagtgg tgggaaagac atgcaatctg   4980
gaaaacccaa aatagtacag agagcaagca cagaactgcc aattgcttgc cccaaagcat   5040
tacaaatctc tggtccagaa ggagaagtat cagattcagc ctagtatgtg cttaagaatg   5100
tttgtcgaat cagttaatga aacgtatttt atgaggttct aatgtagcgc agtattgcac   5160
tcccggcaga ttgacttata ataaatttgt gaaaattttt aatgatttga taatgcgagg   5220
atattgaagc ctagttaaaa taaagcatat tatttctggt tttaattccc aaggggatag   5280
aaatagccaa tttttggggt atattttcta ccacaaatat ttagcactaa atatgcactg   5340
tctacaattt taaaatttat gttgtctctt tttttgatta ttagacatat aaattaagga   5400
tacatctgta caactctaaa aatgattgtc cctataacag tatcagaagt cttctgaatt   5460
ggttttattg tcagtgcagg ggtagattgg cagttattac cctttgttgt gaatttagag   5520
acataaatat tgctttttct atttttaaga gtgctgccac ctgtgccagg aggtgtgggc   5580
gattgtaaaa acattagaca taagagagcc tggaaaaatg gatctgtttt ctgacagtga   5640
ccacggtgta agataattta agatactagt actattgttt attgaactca ttgcaagtgg   5700
gcattttgta ggagtgtggg aaggctggat ttttttagtt ttgtaatctg tatctataga   5760
ttacagtcta caattccaaa tggtgggatt gataaaacct ttgtttagat aactccaagc   5820
aagaacctag cttctccact cctcctagct ttttattttt aaatatattt acacacttat   5880
atgcatatgc ctctttttcc acctaaacta tttgaggcaa ttttcagact tcacggacct   5940
ttgcccctaa atacttcagc atttaagtcc tgtgaatgag aatgtgaagc actcttttac   6000
gtaaccagag cacttttggc atgctcaaga aatttaatat cgatataatt aaattatcta   6060
atatttagtc catattcaaa tttcccaatt gtcttagcaa taccttttat agttttctct   6120
ctctctgatc cagaatgcaa tcaggatcac acatttttag atggcttgtg tcctctcatt   6180
tagaatattc ctgaagttgt cttggggatc aatgatattg atgttatttg aagggagcag   6240
tttagttgtc ctgtaaaata tcccacattt tgaatttgtc taattgtttt cttacagtta   6300
gagtcaggat aaacatattt ggcaagaata ctgagtaggt gatgttgtgt cctttccacg   6360
gcatcacatc agaaacaggt catgtcagtt tgtctcaata ttgatggtac tgagcttgat   6420
cccttgatta aggtagtgtc tgccagattt ctccagtgta aagatatcct ttcctttgt   6480
```

aattgttaag taaatttggg atgaaacttt gagattgtgt gaatatctct ttcctcaaaa 6540
gagcctaatt ttgagcctgt ttaaaccaac cgaaaaattc cggaatcacc tgcttttaga 6600
aaatcagttg agatcacatg aagactgcat ttttaagtca cagcagagtt caagaggaga 6660
agagaataaa atattgaaga tctaccaaag gcaaattata atggcaatgt cacactatga 6720
aaatgaatag cccctattgc ttagcatacc taaaaagaga agtgttgaca ttgaattttc 6780
caaaatcata gacaataatg tatgtaggaa tatattactg tgtatcttag agtctgtgaa 6840
ctttcaattg atttttgatg gtttctggtt atccttaact aaatggtaaa aataatttca 6900
tcggtattat acatgaattt attatcagtt gaaattaaaa aattgctttc tggaaaagta 6960
atgactattt tatatataaa ttgacaggaa taagattatc tcttgtcatt ttgaaaattt 7020
ctttcaagga gaaaatctga tctttgactc attttcactc tgtttttcta tctttttttt 7080
tagtggtatt aaatttgtga gtcattgaaa ttaatccctg actgaattgg aaaggaattg 7140
tatttgcagt atttggattt atttattttt caggtatgga attctggtga ttttgaaaac 7200
atgaatgata ccattttgca gcagcattgt agatttgtag tattttagat tggtatcaca 7260
gtgcacctga aaa 7273

<210> SEQ ID NO 20
<211> LENGTH: 584
<212> TYPE: DNA
<213> ORGANISM: Homo Sapiens

<400> SEQUENCE: 20
aaaagatgtt ggtttaaagc gatttttttcc taagagttta ctggattctg tcaaggccaa 60
aacactaaga aaactgatcc aacaaacatt tagacaattt gccaacctta atagagaaga 120
aagtattctg aaattctttg agatcctgtc tccagtctac agatttgata aggaatgctt 180
caagtgtgct cttggttcaa gctggattat ttcagtggaa ctggcaatcg gcccagaaga 240
aggaatcagt tacctaacgg acaagggctg caatcccaca catcttgctg acttcactca 300
agtgcaaacc attcagtatt caaacagtga agacaaggac agaaaaggaa tgctacaact 360
aaaaatagca ggtgcacccg agcctctgac agtgacggca ccatccctaa ccattgcgga 420
gaatatggct gacctaatag atgggtactg ccggctggtg aatggaacct cgcagtcatt 480
tatcatcaga cctcagaaag aaggtgaacg ggctttgcca tcaataccaa agttggccaa 540
cagcgaaaag caaggcatgc ggacacacgc cgtctctgtg tcag 584

<210> SEQ ID NO 21
<211> LENGTH: 1246
<212> TYPE: DNA
<213> ORGANISM: Homo Sapiens

<400> SEQUENCE: 21
ctgactacac agacttagtc ttctccactc cgtgttcctg cagctagaga catgacctaa 60
caccctgatg accactctca gggaccttga gtgactggcc ggtgcaccat ggaacttaaa 120
gtatgggtgg atggagttca gaggattgtt tgtggagtca ctgaagtcac aacttgccag 180
gaggttgtca tagccttagc tcaagcaata ggtcgaactg gaaggtacac ccttatagag 240
aaatggagag atactgaaag acacttagca cctcatgaaa atcctatcat atccttaaac 300
aaatgggggc agtatgctag tgatgtgcag ctcattctac gacgaactgg gccgtctctc 360
agtgagcgac ccacttcaga cagtgtggct cgaattcctg aaagaacttt atacaggcag 420
agtctgcccc ccttagctaa actgaggcct cagattgaca aatcaatcaa aaggagggaa 480
ccgaaaagga aatcactgac atttacagga ggtgccaaag gattaatgga catttttgga 540
aaaggtaaag aaactgagtt taagcaaaag gtgctgaata actgcaaaac aacagcagat 600
gagttgaaga agctaatccg tctgcagaca gagaagcttc aatccattga gaaacagctg 660
gaatctaatg aaatagaaat aagattttgg gagcaaaagt ataattccaa ccttgaagag 720
gaaattgtcc gtctagagca aaagatcaaa agaaacgatg tagaaattga ggaggaagaa 780
ttctgggaaa atgaattaca gattgaacag gaaaatgaaa aacagctgaa ggatcaactt 840
caagaaataa gacagaaaat aacagaatgt gaaaacaaat taaaggacta tttggcacag 900
atccggacta tggaaagtgg tcttgaagca gaaaaaattgc aacgggaagt tcaagaggca 960
caggtcaatg aggaagaggt taaaggaaag atcggtaagg tcaaagggga gattgacatt 1020
caaggccagc agagtctgag gttggaaaat ggcatcaaag ctgtggaaag atctcttgga 1080
caagccacca aacgcttaca ggacaaagaa caggaactgg agcagttgac taaggagttg 1140
cggcaagtca atctccagca gttcatccag cagacaggga caaaagttac cgttttgcca 1200
gcggagccca ttgaaataga ggcctcacat gcagacattg aaaggg 1246

<210> SEQ ID NO 22
<211> LENGTH: 1308
<212> TYPE: DNA
<213> ORGANISM: Homo Sapiens

<400> SEQUENCE: 22
aagcagtgga caggggagaa tccgctccaa cgttgtccac ctccccttca ccctcctccc 60
cttcacccac ttccccttca cctactctgg gcagacgaag gcctgaaata ggaacgtttc 120
ttagaaagaa gaaaactagt gacatctact ttgtgtctct agtttgggcc attgtcgtca 180
tgcagatctg gttgaacctg tggattgtgc agttgctgcc agtgccgatt gcagtctgga 240
tactcaaaaa gcttgtcatt cactttggag ttgtggattt cctagagaaa cgctaccatg 300
tgtggtgggg cattatagaa agcttcctga aggagcggca gggagctctc gcgccttggc 360
ccattgtcgg gcttggaaaa ttcttgttaa aagttgatag caagctctgg cactggctaa 420
ataagaagat gatcatctgg ttggagaaga tgttagataa aataattagc attttcatca 480
tatttttgtt agtgatagga actcttcttt tagccctact cctgactgca aaggtacatc 540
aagagagtgt acacatgatt gaagtcacaa gtaatttgat taatgaaact ctagcaaatc 600
accctgagtg ggcaaattgg cttcctgagg ctcaggtagt ccaaagagcc ctgaattctg 660
cggctaacaa cgtgtatcag tatggacgag aatggataac tcacaagctc cataaaattc 720
taggagataa ggtgaacaat actgctgtaa ttgaaaagca agtactagaa ctttgggaca 780
gactgtatca ctcttggttt gtaaagaatg taacacactc tggaaggcac aaaggacaga 840
agttgcatgt cagtcgtcag aatagctggc tgggagacat tctggactgg caggatattg 900
tttcctttgt tcacgagaac attgagacat ttctttcgat cttggagtct ctgtggatcg 960
ttatgagccg gaatgtgagc ctgctgttca ccactgtcac tacactcttg accatcctct 1020
tctacagcgg gacagccctt ctcaattttg tactctctct gataattttc ctgaccacac 1080
tattttatct attaagttcc agtgatgagt actacaagcc agtgaagtgg gtgataagcc 1140
tgactccact atctcagcca ggtccttctt ctaatattat tggccagtct gtggaagaag 1200
ctatcagagg ggtgtttgat gcttccctca aaatggctgg cttctatgga ttgtatacct 1260
ggctgactca tactatgttt ggcatcaata ttgtcttcat accatcag 1308

<210> SEQ ID NO 23
<211> LENGTH: 1072
<212> TYPE: DNA
<213> ORGANISM: Homo Sapiens

<400> SEQUENCE: 23
gtgtgtttga taactgctcc cacactgtca gtgacaaagg ctgggccctg gggatccgct 60
cagggaagga caagggaaag cgggatgctc gcttcttctt ctccctctgc accgaccgcg 120
tgaagaaagc caccatcttg attagccaca gtcgctacca accaggcaca tggacccatg 180
tggcagccac ttacgatgga cggcacatgg ccctgtatgt ggatggcact caggtggcta 240
gcagtctaga ccagtctggt cccctgaaca gccccttcat ggcatcttgc cgctctttgc 300
tcctgggggg agacagctct gaggatgggc actatttccg tggacacctg ggcacactgg 360
ttttctggtc gaccgccctg ccacaaagcc attttcagca cagttctcag cattcaagtg 420
gggaggagga agcgactgac ttggtcctga cagcgagctt tgagcctgtg aacacagagt 480
gggttccctt tagagatgag aagtacccac gacttgaggt tctccagggc tttgagccag 540
agcctgagat tctgtcgcct ttgcagcccc cactctgtgg gcaaacagtc tgtgacaatg 600
tggaattgat ctcccagtac aatggatact ggcccccttcg gggagagaag gtgatacgct 660
accaggtggt gaacatctgt gatgatgagg gcctaaaccc cattgtgagt gaggagcaga 720
ttcgtctgca gcacgaggca ctgaatgagg ccttcagccg ctacaacatc agctggcagc 780
tgagcgtcca ccaggtccac aattccaccc tgcgacaccg ggttgtgctt gtgaactgtg 840
agcccagcaa gattggcaat gaccattgtg accccgagtg tgagcaccca ctcacaggct 900
atgatggggg tgactgccgc ctgcagggcc gctgctactc ctggaaccgc agggatgggc 960
tctgtcacgt ggagtgtaac aacatgctga acgactttga cgacggagac tgctgcgacc 1020
cccaggtggc tgatgtgcgc aagacctgct ttgaccctga ctcacccaag ag 1072

<210> SEQ ID NO 24
<211> LENGTH: 646
<212> TYPE: DNA
<213> ORGANISM: Homo Sapiens

<400> SEQUENCE: 24
gtttgggatg tacattccgt tcctgcagct gaattgcgac ctccgcaaga caagcctctt 60
caaccacatg gcctccatgg ggccccggga ggcggtcagt ggcctggcaa agagccggga 120
ctacctcctg acactgcggg agacgtggaa gcagcacaca agacagctgt atggcccgga 180
cgccatgccc acccatgcct gctgcctgtc acccagcctc atccgcagtg aggtggagtt 240
cctcaagatg gacttcaact ggcgcatgaa ggaagtgctc gtcagctcca tgctgagcgc 300
ctactatgtg gcctttgtgc ctgtctggtt cgtgaagaac acacattact atgacaagcg 360
ctggtcctgt gaactcttcc tgctggtgtc catcagcacc tccgtgatcc tcatgcagca 420
cctgctgcct gccagctact gtgacctgct gcacaaggcc gccgcccatc tgggctgttg 480
gcagaaggtg gacccagcgc tgtgctccaa cgtgctgcag cacccgtgga ctgaagaatg 540
catgtggccg cagggcgtgc tggtgaagca cagcaagaac gtctacaaag ccgtaggcca 600
ctacaacgtg gctatcccct ctgacgtctc ccacttccgc ttccat 646

<210> SEQ ID NO 25
<211> LENGTH: 945
<212> TYPE: DNA

<213> ORGANISM: Homo Sapiens

<400> SEQUENCE: 25
ctggttggtg gagaatttga cttggagatg aactttatta tccaggatgc tgagagtata 60
acatgtatga cagagctttt ggagcactgt gatgtaacat gtcaagcaga aatatggagc 120
atgtttacag ccattctacg aaaaagtgtt cggaatttac agactagcac agaagttggg 180
ctaattgaac aagtattgct gaaaatgagt gctgtagatg acatgatagc agatcttcta 240
gttgatatgt tgggggttct tgccagctac agcatcactg tcaaggagtt gaagcttttg 300
ttcagcatgc ttcgaggaga aagtggaatc tggccaagac atgcagtaaa attattatca 360
gttcttaatc agatgccaca gagacacggt cctgatactt ttttcaattt ccctggttgt 420
agcgctgcgg caattgcctt gcctcctatt gcaaagtggc cttatcagaa tggcttcacc 480
ttaaacactt ggtttcgtat ggatccatta aataatatta atgttgataa ggataaacct 540
tatctttatt gttttcgtac tagcaaagga gttggttact ctgctcattt tgttggcaac 600
tgtttaatag tcacatcatt gaagtccaaa ggaaaaggtt ttcagcattg tgtgaaatat 660
gattttcaac cacgcaagtg gtacatgatc agcattgtcc acatttacaa tcgatggagg 720
aacagtgaaa ttcggtgtta tgttaatgga caactggtat cttatggtga tatggcttgg 780
catgttaaca caaatgatag ctatgacaag tgctttcttg gatcatcaga aactgctgat 840
gcaaataggg tattctgtgg tcaacttggt gccgtgtatg tgttcagtga agcactcaac 900
ccagcacaga tatttgcaat tcatcagtta ggacctggat ataag 945

<210> SEQ ID NO 26
<211> LENGTH: 342
<212> TYPE: DNA
<213> ORGANISM: Homo Sapiens

<400> SEQUENCE: 26
agagtatggg agccagagga acatcattat ctaataagtc acctaaggga aagagaaatg 60
aaaagatgtt gccaggcagg gagaaggaag aggagaaaga gtgtggggta atgaatgcca 120
aggaaacaaa gaaaggggaa cggtttcaaa cattgccaag agaaccagta agtatcccct 180
ggatgcaaca agggtgtcag tggggagact atttgcagtg cagacatcaa gacagaggtc 240
agacggccaa gcattgagca ttactgagga tgagaaagta gagacagaac aagcagtcat 300
ctcttttaaa atgtttggct gtgaaggaga agtggggcag gg 342

<210> SEQ ID NO 27
<211> LENGTH: 190
<212> TYPE: DNA
<213> ORGANISM: Homo Sapiens

<400> SEQUENCE: 27
gcgggaccta ggccaggtgt ctgtcggcag ttttgagatc ctgccagggc ggcagttccg 60
ggtcgtggtg ctcagcactg tgcacacctg ccagagcctg ctcagccctg gggcactggc 120
ccctgagttc ttcaccgacg cccgcgtgct caacaccgtc ctgacccgcg cccagtccca 180
gctggtggta 190

<210> SEQ ID NO 28
<211> LENGTH: 466
<212> TYPE: DNA
<213> ORGANISM: Homo Sapiens

<400> SEQUENCE: 28
gtagtgtcgc ctgcctctgg tgggacccta ttcagcggtt actcttctca ggagcatctg 60
acaacagcat catcatgtgg gacatcggag gaaggaaagg ccggacgctg ttacttcagg 120
gccatcatga caaggtgcag tcgctgtgct accttcagct caccaggcag ctcgtctcct 180
gttcctcgga cggcggaatt gcagtgtgga acatggatgt tagcagagaa gaggctcctc 240
agtggttgga aagtgattct tgtcagaaat gtgagcagcc atttttctgg aacataaagc 300
agatgtggga caccaagacg ctggggctaa gacaacatca ctgcaggaaa tgcgggcagg 360
ctgtctgcgg gaagtgcagc agcaagcgct caagttaccc agtcatgggc ttcgagttcc 420
aagtccgggt ttgtgattct tgttacgact ccatcaaaga tgaaga 466

<210> SEQ ID NO 29
<211> LENGTH: 889
<212> TYPE: DNA
<213> ORGANISM: Homo Sapiens

<400> SEQUENCE: 29
ccgatttatt ttgcatattc ccagcgagga aagagacaat gcaatccgag tgtgttttca 60
gattgaactt gcccattggt tttacttgga tttctacatg cagaacacac caggattacc 120
tcagtgtggg ataagagact ttgctaaagc tgtcttcagt cattgtccgt ttttgctgcc 180
tcaaggtgaa gatgtggaaa aagttttgga tgaatggaag gaatataaaa tgggagtacc 240
aacatatggt gcaattattc ttgatgagac acttgaaaat gtactactag ttcaggggta 300
cctagcaaaa tcaggctggg gatttccaaa aggaaaagta aataaagaag aagctcctca 360
tgattgtgct gctagagagg tctttgaaga aactggtttt gatatcaaag actatatttg 420
taaggatgat tacattgaac ttcgaatcaa tgaccagctt gctcgtttgt acatcattcc 480
aggaattcca aaagacacaa aatttaaccc aaaaactaga agagaaattc ggaacattga 540
gtggttctct attgagaaat tgccttgtca tagaaatgat atgaccccca aatccaaact 600
tggtttggca cctaacaaat tttttatggc cattcccttt atcagaccat taagggactg 660
gctttctcga agatttggcg attcctcaga cagtgacaat ggattttcct caactggtag 720
cacgccggct aaacccactg tggaaaaatt gagtcgaacc aaattccgcc acagtcagca 780
gttatttcct gacggttctc ctggtgacca gtgggtaaag cacaggcaac cactgcagca 840
aaagccatat aataatcatt ctgaaatgtc tgacctttta aaaggaaag 889

<210> SEQ ID NO 30
<211> LENGTH: 532
<212> TYPE: DNA
<213> ORGANISM: Homo Sapiens

<400> SEQUENCE: 30
catgttggaa caggattcca ggagaatgaa ccctagtgtg agccctgcaa atcaaaggag 60
gcaccttcta ggattttctg ctaaagaggc acaggacaca tcagatggta ttatccagaa 120
aaacagctac agatatgatc attctgtttc aaatgacaaa gccctgatgg tgctaactga 180
agaaccattg ctttacattc ctccacctcc ttgtcagccc ctaattaaca caacagagtc 240
tctcaggtta aatcatgaac ttcgaggatg ggttcataga catgaagtag aaaggaccaa 300
gtcaagaaga atgacaaata atcaacagaa aacccgtatt cttcagggtg ctctggaaca 360
gggctcaaat tctcagctga tggctgttca atacacagaa accactagta gtatcagcag 420
gaactcaggg agtgagctac aagtgtatta tgcttcaccc agaagttatc aagacttttt 480
tgaagccatc cgcagaaggg gagacacatt ttatgttgtg tcatttcgaa gg 532

<210> SEQ ID NO 31
<211> LENGTH: 512
<212> TYPE: DNA
<213> ORGANISM: Homo Sapiens

<400> SEQUENCE: 31
ccttatttag tgtctctgac aaaaccggcc ttgtggaatt tgcaagaaac ctgaccgctc 60
ttggtttgaa tctggtcgct tccggaggga ctgcaaaagc tctcagggat gctggtctgg 120
cagtcagaga tgtctctgag ttgacgggat ttcctgaaat gttgggggga cgtgtgaaaa 180
ctttgcatcc tgcagtccat gctggaatcc tagctcgtaa tattccagaa gataatgctg 240
acatggccag acttgatttc aatcttataa gagttgttgc ctgcaatctc tatccctttg 300
taaagacagt ggcttctcca ggtgtaactg ttgaggaggc tgtggagcaa attgacattg 360
gtggagtaac cttactgaga gctgcagcca aaaaccacgc tcgagtgaca gtggtgtgtg 420
aaccagagga ctatgtggtg gtgtccacgg agatgcagag ctccgagagt aaggacacct 480
ccttggagac tagacgccag ttagccttga ag 512

<210> SEQ ID NO 32
<211> LENGTH: 340
<212> TYPE: DNA
<213> ORGANISM: Homo Sapiens

<400> SEQUENCE: 32
cggtcacagc ctcataccaa gggctggaga gacgatcatg caggtcccag gaggctggaa 60
ctgtgggagc agcacagggg aatgggcttg tgggtctggg gtggcgttct gggtgtggcc 120
cgcctcgcag tgaccacact gaagtgggca ccgtcctgca ggcagaaggt gtgccgtgag 180
ggcagaggct tcctcccatg gacccttcct ggcggttacc gcccttttgc tcccctccac 240
tgaggactcc ctgttccttt gctcccggtg ccctcatgca caccagctgt ggccagtctt 300
tcctgagggc cagccctgtg cctagggtgc cctgccccac 340

<210> SEQ ID NO 33
<211> LENGTH: 192
<212> TYPE: DNA
<213> ORGANISM: Homo Sapiens

<400> SEQUENCE: 33
caagtttatt tctgatcgtg aaagtagaag aagtctcaca aacagccatt tggaaaaaaa 60
gaagtgtgat gagtatattc caggtacaac ctccttaggc atgtctgttt ttaacctaag 120
caacgccatt atgggcagtg ggattttggg actcgccttt gccctggcaa acactggaat 180
cctacttttt ct 192

<210> SEQ ID NO 34
<211> LENGTH: 309
<212> TYPE: DNA
<213> ORGANISM: Homo Sapiens

<400> SEQUENCE: 34
cctcagggtg ctttcctgaa gtcctgcccc gagccccaac ccaaccctga ggagggggcc 60
ctctggagct cgggtgcccc cggccccgca gggagagatg attgacagga tcgagtacaa 120
tgtggaacac gcggtagact atgtggagag ggccgtgtct gacaccaaga aggccgtcaa 180
gtaccagagc aaggcgcgcc ggaagaaaat catgatcatc atctgctgtg tgatcctggg 240
catcgtcatc gcctccactg ttgggggcat cttcgcctag aagccaccca aactgccact 300
ccactccag 309

<210> SEQ ID NO 35
<211> LENGTH: 330
<212> TYPE: DNA
<213> ORGANISM: Homo Sapiens

<400> SEQUENCE: 35
gaggacagtc agtgacccac accggcctgc ccatcatggc ctccctggcc aacacagcta 60
tctccttcag ctgcaggatc acctatccat acactcccca attcaaggtt ttcacagtca 120
gctactttca tgaagatctc cagggacaga ggagccctaa gaagccaaca aactgccacc 180
ctggactggg cacagagaac cagagccaca ccctggactg ccaggtcacc cttgtgctgc 240
cgggagcatc ggccactggc acctactact gctctgtcca ctggccacac tccacggtga 300
gaggcagcgg caccttcatc ctggtcagag 330

<210> SEQ ID NO 36
<211> LENGTH: 266
<212> TYPE: DNA
<213> ORGANISM: Homo Sapiens

<400> SEQUENCE: 36
gcgccatctt ctccatcaga ctcccctgag ccctgggcct cttcctcgtc ctcctcttcc 60
tcatcatcat caaactgctg gatgcggtcc ttgtagcata tctcaagtag gttggcgttg 120
ggctgcaggg cacaggggtg ggaggatggg ccacactgcc cacagcccca cacccctcca 180
cccgccacaa ccaggggaca gggcagtact cacgttctca tcgtcagcat tgagggagaa 240
ggtgatgttg gctgtcttgt caaaag 266

<210> SEQ ID NO 37
<211> LENGTH: 1227
<212> TYPE: DNA
<213> ORGANISM: Homo Sapiens

<400> SEQUENCE: 37
gaaaaataga aatgaaggta catatgcaca caaaattttg cctcatttgt ttgctgacat 60
ttatttttca tcattgcaac cattgccatg aagaacatga ccatggccct gaagcgcttc 120
acagacagca tcgtggaatg acagaattgg agccaagcaa attttcaaag caagctgctg 180
aaaatgaaaa aaaatactat attgaaaaac tttttgagcg ttatggtgaa aatggaagat 240
tatccttttt tggtttggag aaacttttaa caaacttggg ccttggagag agaaaagtag 300
ttgagattaa tcatgaggat cttggccacg atcatgtttc tcatttagat attttggcag 360
ttcaagaggg aaagcatttt cactcacata accaccagca ttcccataat catttaaatt 420
cagaaaatca aactgtgacc agtgtatcca caaaaagaaa ccataaatgt gatccagaga 480
aagagacagt tgaagtgtct gtaaaatctg atgataaaca tatgcatgac cataatcacc 540
gcctacgtca tcaccatcgt ttgcatcatc atcttgatca taacaacact caccattttc 600
ataatgattc cattactccc agtgagcgtg gggagcctag caatgaacct tcaacagaga 660
ccaataaaac ccaggaacaa tctgatgtta aactaccgaa aggaaagagg aagaaaaaag 720
ggaggaaaag taatgaaaat tctgaggtta ttacaccagg ttttcccccct aaccatgatc 780 agggtgaaca gtatgagcat aatcgggtcc acaaacctga tcgtgtacat aacccaggtc 840

```
attctcatgt acatcttcca gaacgtaatg gtcatgatcc tggtcgtgga caccaagatc    900

ttgatcctga taatgaaggt gaacttcgac atactagaaa gagagaagca ccacatgtta    960

aaaataatgc aataatttct ttgagaaaag atctaaatga agatgaccat catcatgaat   1020

gtttgaacgt cactcagtta ttaaaatact atggtcatgg tgccaactct cccatctcaa   1080

ctgatttatt tacatacctt tgccctgcat tgttatatca aatcgacagc agactttgta   1140

ttgagcattt tgacaaactt ttagttgaag atataaataa ggataaaaac ctggttcctg   1200

aagatgaggc aaatataggg gcatcag                                       1227
```

<210> SEQ ID NO 38
<211> LENGTH: 20725
<212> TYPE: DNA
<213> ORGANISM: Homo Sapiens

<400> SEQUENCE: 38

```
ataaagaaac tgaggctcaa tgaacttgta acgctttagt gtcagagctc tagaatgggt     60

gaaggccaga ttcagaccca ggcatcgtga ctcccaagtc tgcttgtgga tccttgaaag    120

caagggtgag ccataagcat tgcacctttg agagaactgg taagttagaa ccgcagggac    180

ttctgagagc ttccttcatc attttctgca tgcctcccag tgtgcatagt ctctgctcct    240

tctcccgtta gcatgagccg tgtgtgtgat acagtgtgag cactggtgtg gagggttcag    300

atccatgtgg gtggccccca cactctagcc aagtgagcat gtaaagatgt ttttatgtag    360

cttcatcgat aattaacttc cactctctgc ctcattccat gcctccccac ttgccttcct    420

ccctccctcc agcctgggtg cttgggggcc taggctgggg acctcactgt gactagctta    480

gcaattctct agctccagga ggctgccagg acccaggcgg gagtgcagga agttttcaag    540

gtctgtgctc cagggtgtgt gatgacttga ctgctccctg aagagctcgc tgcttataat    600

cgcatagttt ttggcatgtg ctctctgaca aaagaacaga tgtttcctac aagaacaaaa    660

gaacagggca taactgttgg cctaacgctt tgccactaat aacattgaaa gtggaagcaa    720

caagtcctaa cgagaaggtc cctacaggat catgaagcca gtgccaggga attggagtca    780

aaatgaaaga actcacggct gcttttacgt tttaataggc agtgtgctgg atgtttttta    840

acctctttgg ataaatagca acaggctatt ctttctagct gtgttcatga attttgtagc    900

tgtacagtaa tgatggcttc acaagttccc ttacaagatc ccaagcccgt gtccatttca    960

gagacacact gagagggtta tgacaggctc ggccaaccct gcagcatcag cctacagtcc   1020

atatatgggg gaagccttag ctaaatcgca gctctcagcc aaactaaaaa caccagagca   1080

agtttttctc tttgttgctg gctggaactt caaagcacgg agagcccaca cacaaaaatg   1140

aaaaacaaag aaccctaaaa aagggcccag cctcagagcc cacccccaaa agtttagtat   1200

gcctcttgtg ttaaaaacct ttcaccccat atgtcacatg tcacccaggg tttcagtcgc   1260

gttcctagag tcattcctct gatttttcat ctctgaagaa tatcttcttt gaggttgtcc   1320

ttggctttcg cccaaaggaa agacatttat tttttctcat tctttccccc aaccacctac   1380

cctgactatt tcttcaaact aacagacaca gtgaaaatat tatttaaatg tttttaactt   1440

cttttaccat gaactgttgt caccaaaaag gttcaatgtt cgggtttagt aagtcatggt   1500

tagcaaagaa cattcacagc atctgatgtc aacaggatct ttacaaatct ctcctcctat   1560

ttcccttgga ctttattgag agggatggat actatatccc aatgtggcaa ctggacatcc   1620

tcatttatat ttgtggtccc agcttatacc tttttcctga tgttctgttt gctgatttgc   1680

atgattcatt atatgatcac ctcttcttta agaaggggtt ttgaaaatat ttcttatgat   1740
```

```
tctagcaatt tatatcaaat tttatggtgc tatcattata atgcgaatgt gggaaatgca   1800
gaaccaaaac cttgaagcga cttgaaattt tcataaggca aatccattca tcacatatac   1860
atttgagtcc atgttatttt tctgaaaatg tggttgagct aatgcaatta tgaaaatgtt   1920
gtttcttgga aatgaaaagg ttttgtgttc agcagggtac ataaagtagg tgtaagcact   1980
ctcatatttg ggctccaaat atgggttaca tgttgagact gagtgccagt tgaggagcac   2040
attaaaaaaa cacccaatca tatgattgtg ttattcatag ttatacattc tgtgtcccag   2100
agactaaata tcaacagcag attccttcaa agattggatg ggtatgagtg acaaagtgac   2160
ggatcttaac atcttgaaat ggtggcagaa ttgagttagc tgtttttata aaaaaaaata   2220
ggccaggacg gaagttagac acattagtgc tgctgaattt gttttgaatc aactctgtgg   2280
ctctaggcaa ccagatttct ctccatgtgt cggtttcctg atctgcaaaa tgggcataaa   2340
tgtgttttct ctaggacctc tctcaaaatt ctcacgaaga taaaacaggc ctttatttgg   2400
gatagtgctt tgaaagtaac gcatattaca catgtttctc aagctgtact taaaacagca   2460
ggctgtgatt ttgaggcagc cacatcagaa ggtgtctgga gctctcggcc tctgtggggc   2520
atgctcagag tgaattgaaa tttttggtca gtgaatcctg gtggctaaat gactattttc   2580
catatttaat tcatctattt ttagcttatt ttcatgactt gattcagaac ttaatagaaa   2640
caaatgtgca tctattacaa ttcaaaattg aacttcctgg gtggtgttgg gtgggagaaa   2700
cagagattga aatgagagag agagagagga aaacttaaca tttctatggt aataaaaaag   2760
tagtttttac aaaactgaaa acactaaaaa ttgaacccac aaaaatggta tgatgaaacc   2820
aactgaattt ctgcatttgg aagcaaacca gaactcggtg actgtactca ggtctctctc   2880
ttcttttcaa actgttggat gcctttgctt catcgctgtg ttgttgatgt ttgcatttta   2940
attataacaa tgacacttac ctgtccctat ttaagccatc atgaaaactc tgtgttgaaa   3000
atctgcttga ctggatgaaa agtctaaaaa acgcaggagg atagcactgc tgtccccaag   3060
ccatatgggc aagtgatttg aggtcatttt ccagcaggag tgacaaattt aactcaagtg   3120
gtctcccctt ctacctccca tttcttgtgg gtaaggtctg ggtcaatgat tatagtcagt   3180
gactacgaat gagtggattt ctagggagag gcacatgtat cctgttaggc tgtcagtatg   3240
ccgtggtttg cctgagagag tgcaggttta cccctgtggc ccagcccgat gattaattgt   3300
acctcttttc attcctaagg tgtttggatt tgggtgagaa gttgtgtgat catactattc   3360
atgctgggtg ctgagcacac aacctgggca ttagggtctc tgtgtcctca tcaagtggga   3420
ggtctggccc agataacata aaccagttgt cattgcatgg gatcagggta gacctaggtg   3480
ctttgatgac aatctgttgg tctgtgctct tccctttaat atatattccc aaactaattg   3540
tctcactaaa ttcactaagt gcagtttctg gctgcaacat ttctacttgg gaaagacgcc   3600
agaattgtca gccagtaaag acttcagacc tttcttggcc aatttgccaa aaaaacatca   3660
gagggagtta ttgatctttt cccttgtact cattcagcta attttttttt ctgtttcctt   3720
tcttttcttc ttcttaagct gacatccaat aaaagctatt tctttgaggt gccagcaaca   3780
tgtcagcacc aataccattg acaatatgaa ttgtagtccc cccacctcca tttctctaca   3840
aatgtccttt tcttggttct gttgacaaca caggtatttg tcaagctttg ctttcctctt   3900
gcatttattc atgggtgact ttgaacctgg actggttcat gggactaaat tccatttgga   3960
tactgtgttt gaatactact gcaagttgca tgcttaaaaa tttattaaac agtatacacc   4020
acttatcaga gcaatcttat tttatactta atttatagaa gaaagcccag tagattagtc   4080
```

```
agggacatct caatagctag tttctcagca ggagcaaatt ttggatttgg ccttcagaaa   4140
tatgaactat tctttcagaa atttctggca ctgaatagtg ctacacttcc ccccgtgaga   4200
gctgttcact taccaccttt tcttagctgg aggcccaggc tcatactagc ctatgaggta   4260
caattaaaga ggaggcctag agaattgcag gcataattac cacagagatg ggcaaggtag   4320
ttatggtgac aataaatatg taagatatct gggaagcttt tttttttttt tttttttgag   4380
acagagtctc actctgttgc ccaggttgga gtgcagtggt gtgatcttgg ctcactgcaa   4440
cctccacctc ccaagttcaa gtgattctcc tgcttcagcc tcccaagtag ctgagattac   4500
aggcatgcac cactacaagc agctaatttg ttttgtattt ttagtagaga cggggtttca   4560
ccatgttgtt caggctggtc ctgaactcct gacctcaaat tatccacctg cctcagcctc   4620
ccaaagtgct gggattacag gcatgagcca ccgtgcctgg cctctgaaaa gttttttttt   4680
tttttttttt tctgagatgg agttttgctc ttcttgccta ggctggagtg caatggtgcg   4740
atcttggcac actgcaacct ccgccacctc tggatagtga caactatgaa cagattaata   4800
tgcaaactga tggttgggac agtcatttga caaatttgca actgatttgc ctgaattatc   4860
ctgaaaatat ctcacccttt cacttgaatg atgctgtgca gaacactctg ctgatgcttg   4920
aaggtatttc ctgtgtagag tcccccagtg agtacaaaaa tatgggccaa gtgtagccca   4980
gacatctgag taactctcac tcaattgtgg atccacatga gaagaagtaa aaccaatgtc   5040
ccatttccta cattgacgca gaggatgctg cttatctcag cacctggctt gtcaagcagc   5100
cacgctcaaa cctctgatcc tctttgatcc tgcctgatac tgcttcatag aatttcaatt   5160
ccagaagaac tcaaatcagc aatcttttct ttatattcca tttcttccct gcttctgccc   5220
actcaccttt tctcgtggtc ctaggatcag ggcgtttgag gttatataac ttaatatgag   5280
taggaatcac ttggagttag gaagagagaa gtgttgatat agtggaatat aagtaattta   5340
caaattgata tatgcattct aaatatatgc ctgtgaaatt tctgtaattc taaaatggga   5400
atagaaccaa aatgtttagt cagacatgat aattatagct aacatttatt gaaggcttat   5460
aacgggccag ctactgttct aattgcttta catttattag ctaatgttct cacaatagcc   5520
caatgagaca attcttatca ccattttaca aagcaagaaa taggcgcaga gaggttgtga   5580
cttgttcaaa gtcaccactg ggtgatggag tcaatattgg gacccgtgtc ttgtgactcc   5640
cccagtcaca gtgccatgct gccggtacag ttccaaaatg atattaacac ttgcccctta   5700
actttgaaag agttttgcaa agcctggtct tataatatgt aaataacagt gcttgaattt   5760
cttggctgat aagtattaat aaccagaaag taatatttta gaatgcggta tccctggata   5820
ttaattagct tgcttatata tgttagtcct ctagggctgc tgcgataaag gaccacagac   5880
tgggtagctt aacacagcag caatttcttc tctctcagtt ttggaggctg gaagtctaaa   5940
gtggaggtgc tggcagggac gtgctctctc agaaggttct aggggaggat ccctcctgtc   6000
tcttccagcc tctgctggct ctccttggcc ttccttgcct tgtgaacgca gctcccttgt   6060
gaacgcagct ccctgccttc atcacatgga attctccctg ggtgtgtgtc tgtgtctaca   6120
tttttctctt ctcaaaagga caccagtggc ctggtgcagt ggctcacgcc tataatccga   6180
ccactttggg aggccgaggc aggtggatca cctgaggtca ggagttccag accagcctga   6240
ccaatatggt gaaaccctat ctctactaaa aacacaaaaa ttagccacac gtggtggcat   6300
gcgcctgtaa tccaagctac ttgggaggct gaggcgggag aatcacttga acctgggagg   6360
tgtaggttgc agtgagacaa gatcacacca ttgcactcca gcctggggaa caagagcaaa   6420
accctatctc aaaaaaataat aataaaaaaa ttaaattaaa gatttaaatt taaatttaaa   6480
```

```
aaaaggacac cagtcattcc cctcatcctg gtataacttc atcttaactt gatgacgtct   6540
gcagaaaccc tatttccaaa taaggtcacc caaggtcttg gagtttagga cttaaacatg   6600
actttttggg gcacacaatc aacaacaata tacatatctg cttaggctat attatcacct   6660
atgttttaat tttgagaata aaacaagaat aatgtttccc ccatgcaatt tctttctttt   6720
tcctccaaca cacgtgcata attcttttat ttcttcctta aaacagcatc tgatctacca   6780
gcagatgttt cccccataat aacaggcaca taatacccca cttcagaggt ctgggatcgg   6840
gtggagtggt tctcatgata gctttttatt ttatagcaga cctcttttta ttttgtcttc   6900
taaattgctt ttccattact tgtttataat attaatagtt aaaaccatag tatgggagtg   6960
atcatatagt tgacatttac aattaacatt gtacggccag gatttctcca tgttattgca   7020
aaaacttagc tgatttgtta acattcctta taatatttca gcaaattaaa aatatacaat   7080
taaatctttc tcatagttgg cacttaggtt gtttccattt ttttcttttg tgttagtact   7140
gcagtgaata tttatgctta tatctttttt cttcctttgt tctttttttcc aagaggaatt   7200
tctaaaagaa tataatattt tggtgtctct tgatagccta tcgtttgata ttgattgctg   7260
tcagaaattg cactggaatc accccaatat tgtttcacaa gctgatcata taaaattttg   7320
ttttaaatag ccttttattg cttacatttt aacttcattg ttattatggt tgaacacttt   7380
tcaaatgtat ttcttctaaa cattaaaatc atctgggaac tgaaaaaaaa aaaagacagc   7440
ttatctttct ttcgcagttg ttaaaaacat gtgagaagga agttagattg aattagttgc   7500
ataacccaat atttaaggtt tcctgagttg atacggccac atattttttt tgttcctaat   7560
gctcaaattt ccaaatttca tacttaaaag agccaacatt aacacacaga cacacacaca   7620
cacacacaca cacacacaca cgtacatttg ctttattaag ataaatttgt tagaacaaaa   7680
gacctagtat atataacttg ttttgcttaa ataacattat ttaaatgtat actgtgttca   7740
gtggtgcatt ccccctagtt tagtatggtg aacacatgtc ctaaatattc agtataaact   7800
tgtagaatgg aagatgattc accccttaat gaatttataa gtatctgctt aaattatctt   7860
tagtaaataa aattagcagc ttatcagtca cttttctaaa atggctcctt gctaaattaa   7920
tttgcaagtt tatcaaatta catttatgac tttaaaatat atagtaatat gcattcatta   7980
ggaatttatc tcagatttct gaaatgtatg catttaagat tctatggatg attagaggag   8040
acatatttta aaaagtgtat atcttcaatg atatgtcttt gaagtcatat ctactttata   8100
tcaattattc gtaattgaat acaagagggt gcaattgagg gctggcaaaa ggggatttta   8160
gttaaccaat atgattatcc tttatttaaa gttaattata tttttcact tctcctgttt   8220
tacagcaagt gtggagttgg ctccaaactc agagtctgtc tgggtactca gtcctacatc   8280
tgtttaatgt cggtgtcctt cttggcctct tcccatagac attgggttgc tttagactta   8340
tgagtcttgg ccttggcgga tgggacagtg agctcagtct tcattcactg acttgaggat   8400
ttagtagatc ttgattctgg ctctcttctg atccaagaac cacactacag agctaagtaa   8460
tcaggcttcc tgctttatga gctaaacatg tatatgtata taatatgcat atattataca   8520
tgtatgtgta tatatatata tataactgta tatatatata tatataactg tatatatata   8580
tatatatata tatataactg tatatatata tatatatata tatatataac tgtatatata   8640
tatagctgaa caacgtgagt ttgagctatg caggcccatg tatgtgtgga ttttcttcca   8700
cttttgctac ctatgagatg gcagaccaaa tcctcctctt cttcctcctt tcagcctgct   8760
caacatgaag atgatgagga tgaaggcctt tatgatgatc cacttccact taatgaagag   8820
```

```
taaatatatt ttctcttcct tataattttt aacaacatct tttatctagc ttactttatt   8880
gtaagaatac agaatataat acacataaca tataaaatat gtgctcatca actgtttatg   8940
ttattactaa ggcttccagt caattagtag ttaagttttt ggaaagtcaa aaatcttaca   9000
taaatttact gctatgtagg gggtcagccc cactaacccc catgttgttc aagggtcagc   9060
tagacacaca tgcacacata tatgcacaca catatctatc tataaatttt catcttatgt   9120
cttttgtatt ctgggcttgg tttgcaattc taatgtgaat ggagggccaa ctatttgtca   9180
cagaaaagga gaaagatgct actaaaatca acttcaactg ctttagcccc aaagagagta   9240
gcattactta ttcttagact gaaatctttt tatttaaata aaatatgttg atagagaact   9300
gttggtgcag tgtttgagtg ctcaagagac tggactggag agaaacaaag aacctaagag   9360
atagctgatg tcctctgcag gaggaatgaa gaggggtaag gaggagaaaa agtgagaatg   9420
agcctggttt tctgaaagtc taatgagacg tgctagccaa ttaggatttc ctgttagtgg   9480
tggtgactga aagaaatgaa aaaaagaagg aatgtctaac atttaatttt aaattgttta   9540
ttcatgttgt tactatttaa tttccttcat ctctctagtc ctttcaaagg aaagaggcca   9600
tgttccctgt ctgggtagac aaggggtcag tgaaaagaga acaggtagga aagtcattct   9660
acttcttgga agtaatatcc ttggtttgat tgtccaaaac accatccttg aattctcttt   9720
gctagaaaga gctcctgtat cagctgagaa ggcctccatt tgagccaaca ctattcccaa   9780
tcagccttgt ctgatcccag aatggctttc tgagaacagg aaggttttca attcttccta   9840
ccacaccaac cagtctcgga taggctgtag gacctggaac atcatagcaa gtgatatttg   9900
gggttcacat tgattatagt ctgccacaaa gggctacaga atcttccaaa ggctgtggtg   9960
caaacatctg cctgcttatt ccttattctt ggggctgatc ctggccacct ggagtctgct  10020
ggtcaccaag atccccagct tggacagact aattcctgga ctctgctctc cctttcctga  10080
tatttcttct ttatactttg gctgctttca actcgaggtt tttgacctac ctccatcttt  10140
gtctctagaa taataggtgc ccattcactt tcccatgata agtcttttgc ctttgttcac  10200
agggagggca ttccctacat ttccagtctt agcttttccc agaaggacta gcagagtctc  10260
aatcctaatc actatttaaa gtagtaccca aaccagacta gcacaaccca ccaagcccca  10320
gccctccctc ctgagctact acaggttcaa ctggttgact ggtcccctag caccttgcaa  10380
agaacatgca ctcagtgtat atttcttaat aagtggatga atgttttatt ctattgggga  10440
gacagaagaa gagtaacaag agagacattc tagtagaaaa gtaatattaa tgaggctaaa  10500
tgtattcatt tgtcttttta cctaatagac aataaaagat tgccctattg gaagagaagc  10560
tcaaggctag atgaaatgcc aaagggtctt ttgtaagaag tttccaggta tccttaagct  10620
tgtggtagtc accccctggag tatctttttt aaagttcaaa gatatccatt atagacgcag  10680
ggggaaaagc acaaaaagaa aaacaaaaac atttagagtt acattaggca ggatttaggt  10740
acatacagaa gttcgttagc gaggtgccta acttttgtgc aggtttgtgt ttctgtaaat  10800
aaatcacact cggaattatc tacttggcag agaggggaga gacctgagat ttagaaacaa  10860
acaatcaaat ggagaaccga ggtttgagtt tggtgcattc tctataaatt atataaatta  10920
tcttaagcaa tcaccagccc cttgaagttt tatttgcctc atctgcatat tgaaaataat  10980
aattgttgcc ctgcttgctt ctagactttt tttttttta ggatagagat gaggaaaata  11040
gtaactaatt ttatacatat atatatatat atatatatat atattttaac agagctgttt  11100
ttagctaaaa atcaagtgtg gtctctcccc aaacccaggg agtagctgag attctctgtg  11160
gagggagaac ctaccggagg agaatgttag ggcctgtgca gaaaatagga ttgaaagaaa  11220
```

catggtcaat ctcatgttta ggaaaaattc ttgtaaagat ttttgtttct acttgactag 11280
gtcaataaag ataaggcact aaagataggc aatctaaatg ccattttaca catatggtgg 11340
atggataact ctgtgtccta atatttctga accttagtta ccttatatgt aaagtaaaaa 11400
aaagtaccaa tccatacatc catttccttt ttgccatctc ttgtcgacta ggcacttttc 11460
aggattttcc aaggagatca ttgaaacttt gttttgcttt tctgcaaaga tgtgtatatg 11520
aagttgtgtt tgctgtctgg ccttatgaga gactcagtgc ttttctgaca ctaacattct 11580
ggggctcttt gtccagtcct tcctccttgg tcttccatgg ttctctgaga tgcaggtaat 11640
tgaatgcttg agctgggaaa aagcttttgt tctatgatga ttctaagtct tactctctca 11700
ttgcaaacac taaagtgtag ttctaagcgc aagtacagtt ttcctcattt ttatttatct 11760
ttcccaagat tttatagcaa agtttttgtt ttctgcacca cctctaccct gctacccctc 11820
cttaagcccc tacgcagctg aaagctggaa gctgaaacgt tttcaacttg agcagacagg 11880
ttgaagatgc tgccaaacca tgtggaaata cattggtata gactggaact ttgtgtaaga 11940
aaaattcaca tttttagaat ctttactata tttggcttac ctgggttaag caattgcatg 12000
ttttcatggg gagaggccca aggcctagta gcttaatgtg caaatcacaa ggctggggct 12060
ctggaggaaa tcctagcctt tgaggagtgg cagctgtgta aaaactcaac agaggaagga 12120
caaactgtgt tctctccttc tcaccattgc cctctgtctt cctcttcttc actctcagcc 12180
tatgtgaaaa aatcagatcc aggctgggca cagtggctca tgcctgtaat cccagcactt 12240
tgggagccca aggcgggcgg atcacgaggt caggagttcg agaccagcct ggccaatatg 12300
gtgaaatgct gtctctagta aaaatacaaa aaaaaaaaaa aaaaaaaatt agccaggtgt 12360
ggtggtgctc acctgtagtc ccagctactc gagaggatga ggcagaagaa ttgcttgaac 12420
ccaggaggcg gaggttgcag tgagccaaga tcatgccact gcacttcagc ctgggcgaca 12480
gagtgagagg ccatttcaaa aaaaatcgga tccattttcc taaagcaact atcttatccc 12540
taagttaatt tcaaacctac atatcatctt ccagaccata tttttaatat tgacaatttt 12600
atactgactt ggtaaaattg gtgacaaaga ttatttcata tttttggttc aaatataata 12660
tagtcaatgt ccagtcagtg tcaagacagt tttcacccaa attatgaagg ctaagagaaa 12720
cattcacctc aagcgggaat gtcccttctg cttggtggtc atttctagtt atcttagaga 12780
ccttcagagt tcacacctga aggacaagtg agggcaactt gggcttcttt atttcaattt 12840
tactgaattt tgatcattaa tcagattaga tctctacatt tatggcatac actacacata 12900
catgcactca tatttaccta tatgaataat tgcaataaat atatttcttc tcaaagtaac 12960
aaaattttaa ctaaaaaaca aatctaacaa gcacttaaat tgggactgat cattcatata 13020
caaaatgctc cttttgtttt tgttttttgg ctttagagaa gaaccaaatc aaggatctgt 13080
caaactccta ccatatatta gaagtatgtc acatgtaata caatgatcta atattagata 13140
gcaatggatc ttatataaga actgaaaaaa agttagaatt gaaacaatgt catgtgaaca 13200
tgaggggggtt ggaaatattt ttaaacgaat gtttctcatt gttgcatggg tagtgagagt 13260
aactgccaaa atgtgggcaa aactggagaa ttatgcaatg ggaggaaaga aatcaaaaca 13320
tgcaatataa tttcgactct attgttatca gaattttttt tgaattaata ataaaattca 13380
gcaggtggaa tgagtcagtt gatgactcag gaaggcccat aggaaactta aaactgttaa 13440
gcagaacact tcttccttca ccacgaattt cagttttctt caaatggcct ttcaacagaa 13500
aattgcatct gtaggctctc catcccccac ccccacaacc cacatttgac tttgagcctt 13560

```
tatgaaaatg atagattgcc actacagatt gttcgcatat tttttttca gttttaggaa  13620
aacaaatgaa acaagtgttt tgaagatgtc tccagaggtg cccagtacaa gggggtggga  13680
atggagacgt aagtgaggaa atggtctgtt ttgtgacttg gaataagcag agtactccta  13740
gttctggcct tgactcccac ctgtatcctt gaaatggttt tctaacttgt ctccctggta  13800
gaatctctcc agtgtttcca tgacactgct ggaggagtga tctttctgaa tcacagtggt  13860
gatcatgatg attttctgat gcgaattagg cagtatctcc ccctgcggcc accctacgtc  13920
cttccactgt gagcttcttt catctacttt ttggctctgt gaaacccctg cacccgagtg  13980
cacatttgtc tctctcttaa ggatgtcgac tccatgtgga tgctgacttt gtttttcact  14040
tatctctgcc ttttctttct ttttgttttt tttttttga gacggagtct cgctctgtcg  14100
cgcaggctgg agtgcagtgg tgcgatctgg gctcactgca aactccgtct cccgggttca  14160
caccattctc ctgcctcagc ctcccactgg gactacaggc gcccgccacc acgcccagct  14220
aatttttgt atttctagta gagataaggt ttcaccgtgt tagccaggat ggtctcgatc  14280
tcctgacctc gtgatacacc cgcctcggcc tcccaaagtg ctgggcactt atctctgctt  14340
tcaaatgttg cctcctcctg gaggcctccc ccatctcatg ccttgcgtgt tgtccattgt  14400
atcttctcct ctgttctcag aggatttggt ctctgcctca cttagcactt catagtgctc  14460
tgtcatgatt cacatgtttt ctccactgtg tgttcccatc atagttgact gaacccttca  14520
tatttggtga ccttaatagt cccttacaac atcatattcc ttactaggtt tcagaggaca  14580
gcgtgcgcta acagcatgaa catagatttt tctggttgac ctttgtattc ctgactgagt  14640
cttgtcctga tatttcttgg acctgtggca atgccttctt tttgaggaag tcccctcatc  14700
accagtcttc ctgccgatac tctcatggag acagtgccat tgcttagggt gctatatcct  14760
ggggcttcca atcttcaagg tcctcacatg tttgcactat cctgagttac atgtgccaga  14820
agcttcctgt gttctgtgta gctataagga caatgccttt ttcttctcag gattcaccat  14880
tggtccccag ggagggacag gccgagaagc aggtaggcaa gagactgagg cagatcacca  14940
tcaactggtt tttcaaattc agtcacggtg tgtatccagt ctcaatctca gctgcaatac  15000
cctggtacct ttctctttcc tttcatcact taggcagtca ctaacgttta gtaggtgctg  15060
tctgaaactt cagaacgctc tgggactctc tgacgaaggc ctttgtgttc ctgcaaacct  15120
ccctcttgtc cctgaccagt ttggtcactg ttgtttggta cccaaccctg ccctattttt  15180
ctctaggctg gtcaggctct gacgccttgt agctgaattc ccaggctgag ccacacttct  15240
ggtacactta actgaaagcc tggagagaac ctacaaaaaa tattacaaag cagggaacaa  15300
aaatcttaaa actggacact gaaaatggac gccttataag agcatctcag aatttcaaat  15360
tcaactgcct ctgaggcccc cagagaatac aatattctac tctaaataaa aaccacatac  15420
gtcatggtgc ctttttttct tttcttttct tttcttttg agatggggtc ttgctttgtt  15480
gcccaggctg gagtgcagtg gcacaatctc agctcattgc aacctccgcc tcctgggctc  15540
aagtgattct cctgcctcag cctcccgagt agctgggatt acagatgcca accaccatgc  15600
ctggctaatt tttttatttt tagcagagat ggggttttac tatgttggcc aggctggtct  15660
tgaactcctg acctcaggtg atccacccgc ctcggcctcc caaagtgctg gaattacagg  15720
cgtgaaccac cgcacccggc ccattgtgcc ttttattaac attattaaaa tatagctctt  15780
tattgacacc tcagctctct gtaccaggaa agaatgtcta ctttattttg gtaaaattga  15840
agggaatctc taaaatattc ccatctggaa cacaaggata ttgtgttttc aaatctcaat  15900
ctcctttaa gaagatatac ttttagttgt cgaatttttc ttactactgg gggatttata  15960
```

ctcaaattac tggtggcaca ctcaatagcc tgattgcaat gattttcagt gcgtgatgga 16020
caccatattt gagaggtgtt gatctgaaag gaagttagag acgtcatacc tattaccacg 16080
atgcataatt tgaaagtgga gtggaaagat ctagatagta gaacaataga taaccttagt 16140
aataatctta tccttagata ccgctagact tctatgaaaa tttgtcaata ccattccact 16200
ctcgcttttc tgaaaaactt ggtgtttcgg acttcagcat ttttctgatt ttataattta 16260
tgtcaccttt ctagtacagc gtggcagcac tccctagtag accacttaat tgtgatattt 16320
cacaattgcc aatcagggat cgtggccaat ggcaggaaag caaaagtatc cacagcaggt 16380
tttgaaaaac agtcatgaga gacagctggc atgcaccttt gctctcttcc tctccatcac 16440
tgcctctgac ttgctgcctt gaagatggat ttagccatct tggattctga aggtgaggca 16500
tgaggaaggt gagctggaaa gaccctgggt gctaaataag cccagacagc tcacctctgg 16560
gcctcattca catgacagag aaaaaaactt tctatcttgt ttaagccact gttttcaatc 16620
tatttttttt cctctgtcac acatagccaa accaaaccct aaatgattca ggtattatgg 16680
agaatgaaga tcctagattc ggtaagattt tttttttttt tttttttttt ttttgagaca 16740
gagtcttgct ctgtcgccca ggctggagtg cagtggtgcg atctcagctc actgcaagct 16800
ccgcctcccg ggttcacgcc attctcctgc ctcagcctcc ccagtagcta ggactacggg 16860
cacccgccac catgcctggc taattgtttt tgtatttttt ttagtagaga tggggtttca 16920
ctgtgttagc caggatggtc tcgatctcct gaccttgtga tccgcccgcc tcggcctccc 16980
agagtgctgg gattacaggc atgagccacc gcgcccggcc tcggtaagat ttttaattac 17040
tgcactgacc tagtcagtcg atgtctcaat ttgtgtatga gaaagccaca tataaatgta 17100
ttatatttta gtgtgcactg tgcagctgat tagattttct gcatgaaaat atgaaagtac 17160
tacaacagaa ttcaaaataa agtagaattt atgagcttgg ggtagatcct cttaactttc 17220
ctcctttatg tttggaataa ttttttttta agtttacaca aaattatctc atcatgggag 17280
aggaaacttc ttcctcatcc caatagtaag tttaacaagt accgtagttt gttttgcctc 17340
aatattcctg attcacatag cacagtgttt aatattgacc aaaagatgcc ttcagctcac 17400
atcaggcaaa ggaagtggtt acctgatgct gtggtctgta agtctgtttc tcccctggat 17460
tcatatattg aaacctaatc ttcaatatga tgatattagg aggtgaggcc ttttggaggt 17520
ggttaggtca tgagggtcga gctctcatag aaggaattgg tgtccttata aatgaagctc 17580
cagagagctc cctcacccct tccaccatgt gagaatacag ccagaaggca tcatctatga 17640
agcagaaagg gggacctcac cagacaccaa atctgccagc accttgatct tagacttctc 17700
ggcctccaaa actgtgagaa ataaatttct gttgcttata agccacccag tctatggtat 17760
tttgtgatag cagctgcaat aaacgaagat gcctgactac attgactaaa gagaagataa 17820
aacctaatct tagaaaagtt tcttctcatt tatttagggc ttgattcttc ctgtaccttg 17880
gctgtattcc aatggcaaat caggactttt ctgtgtatct aaacactggc tgcctataga 17940
gcaggaattg gtccctcaga acaactgttt ccacactgac ttgtgggaat ctttttgagt 18000
gttttgagag ttcaagggtt ggcagagcct gggatggcag gactctaaag agctctgagt 18060
caggatatgc ctgtgctggt attggtcatt catttgaatg ggttttctga ctatattatt 18120
agcaaaatat tttctctcca gcaaaggctc aaattacatt gcaatcttat ttttttttta 18180
aacggtgtct cactctgtcg cccaggctgg agtgcaatgg tgtgatctca gctcattgca 18240
acctccgcca cctcctgggt tcaagtgatt ctcctgcctc ggcctccgta gtagctggga 18300

```
ttacaggtgg ccaccaccac acccagctaa tttttttttt ttttttcatt tttcttagta  18360
gagacggggt ttcaccatgt tggccaggct ggtctcaaac tcctgacctt gtgatctgcc  18420
cgcctcagcc tcccaaagtg ctgggattac aggcatgagc caccgcaccc cacctgcagc  18480
cttattttat aattaacata tatgctcttt ttacaggttt ccttgactag ggattaagat  18540
ggttaatttg tggctctcat gagatacaag cagtgtataa taattattat tttttccatg  18600
ggactactcc cctaagtttg ctcatctcca gtgcagatat ttgcctgttt tcactgtggc  18660
ctggacaaat gagtatgaag gcatttgtgc agaggttttc aaactatgtt cttagatctt  18720
gtaggatccc acagaggtgt ctcaagcttt ggagaagaga gtaagatggt tcttgatcct  18780
cttaccggct tgctttactc acaggtggag actggtgaga tgggaggagg aggcaaaatt  18840
taaggaaatt caatcagact atcattttcc tatacaacca ttaggtgcct acacatctgt  18900
tattttattt tattttattt ttgagacgga gtcttgccct gtcacccaga ctggagtgca  18960
atggcatgat ctcggctcac tgcaacctcc gcctcctggg tttaagcaat tctcctgcct  19020
cggtctcctg agtagctggg attacaggtg tgcaccacca ggcctggcta attttttgta  19080
cctttagtag agatgggggt gggggggtttc accatgttgg ccaggctggt ctcgaactcc  19140
tgacctcgtg atccaccctc ctcagcctcc caaagtggtg gcattacagg catgcgccac  19200
cgcacctggc cagtttattc ttttaacctc aaaaatgcat gagcaaaggt gaaggaaata  19260
gcactaatga cattgacagg tgagaaaact gagggtaagt ggattttaga acgtcacctc  19320
atcagttaat ggtgtctctt gggtctgagt cttaagattt ttccaccaag ttgaatgagg  19380
acagagctac ttcatgattg tctatgtaga cattgccacc acaataacac cttgtgagag  19440
agctaatcaa ggcaacttgc ttttggccct gttcaattct aggctgtgtt atcctttact  19500
ataaagcaca ttgacccacc atgaatggag gccttaagat tgacctccct tcattccacc  19560
ctccggtatt gatggagctc ctgagttaac acagtccaat ggggaaaaca gacgaacaat  19620
taagatggaa tgtcaagagt gccacaaggg agatgtgagt cgtatgcaag aaagcgagtg  19680
gggggaacac gtaacagctc tggttcagga atctgataag gtttcgtaga gaagacagca  19740
tttcagtggg cttggtggag atgggcagga gtttgtcggg cacagaaaag agcaaatggc  19800
atccaggcag gctcattaca tacaaaagca tcttcatggg aaggcacgtg gcacgtttgg  19860
aatcagtagg aatccatcac aggtagagcc aaagtaagtt gagagaagag gcagatgaga  19920
cttaagcaag tcacttgaga gaagtggcac atcttcagtt tcatatattt aagattgtaa  19980
catctgggag aagaatcaaa gtgaaaatgt cacctatggg tatgaaatta ggtccattta  20040
tttatttatt tagacaagag tctcgctcta ttgcccaggc tggagtgcag tagtgagatc  20100
tcactgcaac ctctgcctcc tggcttcaag tcactctcat gcttcagtct cccgtgtagc  20160
tgggattgca ggtatgcacc accatgcctg gctaattttt gtaatttttt tttttttatta  20220
gagatggggt tttgctatgt tggccaggct ggtctcgaac tcctgacctc aggtgatcca  20280
catgcctcgg cctcccaaac tgctgggcgt gagccaccat gcctggcctt gagtcctttt  20340
agtgtctctt cctgtctctt gggtttttga gtgaacctgc agcacctctt cattcccggg  20400
cccttccttt tctcccacaa cctcccctcc ctctcttttg caccctgcag gtgcatgcat  20460
acattgcctc ctcttttcct tctccctgct tttctgacga aagttctggt ccttctgttg  20520
agagctggct ccttggatat agcacagata cctacttatt tgtgtttcag ttcccttgcc  20580
tgccaaaatc tcagatggag ctttaggact catggaagac cttcctcaag ggggacttga  20640
agtgctctgg gaaaaatatg cgagtgtgac cctttccagg gggcagcacg aggatggcca  20700
```

aacccgctac tctccctggg gctgg 20725

<210> SEQ ID NO 39
<211> LENGTH: 1825
<212> TYPE: DNA
<213> ORGANISM: Homo Sapiens

<400> SEQUENCE: 39
agaaagagtt ttgaagaaaa ctgggcatag gctcagcaaa accaaacaga agaggaacag 60
aaaaagaaac aaaaagcaga acagtcagaa tagaatcatg gaggaaaact cattagaatt 120
cttaagtgat cttacaccgg gagatcagga cccatctcag agtgaagagg aagacattga 180
aaagaccaga agagaatcag aatatccctt cattgatggt ctacaaaatg aagtcggaga 240
ttttgtgact ggatataaag aaaaaagatg gaaaaataaa gatcctaaag acagtttcca 300
aaacgttatg tctatagttg aattagacaa cacaccaaag aattacctct ctaaggaagg 360
tgataacttg tttgtaagtt tgttactgag gccaaatgaa atctccgtta cttgtccaat 420
actgactcaa aacctttcct gtgtaacaac tgatgactgc tctggcatga aggtagaaaa 480
gcatattaga aataggcata ccatagcatt agacacccag gacctttctg cggaaacttc 540
atgcttattt atgaagaaga gagaaatagt agataaaaat ctctcacatg aacccattct 600
gtgccatcaa catggaatca gaatgtcaga taaagtttta agagaggaac aagtgtatac 660
aactaaaatc aatcactggg ctttttttcac aaccaattta tctgatgaag atttacagct 720
gggctctgac agacagccct attttggtag ctggcctgca ggacctcata agtttatatg 780
tgaacagaga ccaaagaaag atagagcatg taagttggct ggtcctgaca gcagggggca 840
atggattcaa atgatcttca cttcggtggc agcatcagaa ccaggaaaca atccagaaat 900
attgacagac aaactactga taggaaatga agatttttca cctccacctg aaactatgga 960
ttcattcata gaaacaaacc tcttcagaag ctgcttacct caaccggata taccaaagaa 1020
tgccttagaa tcaacaaaaa ataagaaaag gaggaagaaa aggattttca atttggtacc 1080
aaattttgac ttattaggac agagtcgtat cggtgtaaaa gaaagggaga aatgtgacct 1140
gttaacaaaa aaccatggac taaaaattac tttgggagaa gaaaaagata gaatttcaga 1200
aaggaacagt gaagaggaga ataaacaaaa acttatgacc tttgatcatc atccattgtg 1260
gttttacctt gatattatca aagctacccc tttaaatatt gatggacagc gttattctca 1320
ttgcctgtca tttaacagac taaggtgctc tgcatcttta tacaaaaatt atattccttc 1380
ttttgtgcta cataatttat ctagtatttg gaagccatct tttacaaaca agaaactgtt 1440
tttgactttc gaatctcaga caagagtagg taataaacta aatgatgcag ggtttatttc 1500
tccagaaatt ttacatagtc atcctgatac ttcgtgctct ttgggagtca cttctgattt 1560
tcacttttta aatgaaaggt ttgatagaaa gctgaaaaga tgggaagaac ctaaggaatt 1620
accagctgag gacagccaag acttaacaag cactgactac cgttcccttg agctaccatt 1680
atcacaaggg tttgcctttc aattagtaaa gctttttgga tctccaggcg ttccaatgga 1740
atccttgttg cctgatgact atgtggttcc ccttgactgg aagacactaa agatgatcta 1800
cttgcaatgg aagatgtcag tggag 1825

<210> SEQ ID NO 40
<211> LENGTH: 570
<212> TYPE: DNA
<213> ORGANISM: Homo Sapiens

<400> SEQUENCE: 40
tgagattacg tactataggt gaacttttag ctcctgcagc tccttttgac aagaaatgtg 60
gtcgtgaaaa ttggactgtt gcttttgctc cagatggttc atactttgct tggtcacaag 120
gacatcgcac agtaaagctt gttccgtggt cccagtgcct tcagaacttt ctcttgcatg 180
gcaccaagaa tgttaccaat tcaagcagtt taagattgcc aagacaaaat agtgatggtg 240
gtcagaaaaa taagcctcgt gaacatatta tagactgtgg agatatagtc tggagtcttg 300
cttttgggtc atcagttcca gaaaaacaga gtcgctgtgt aaatatagaa tggcatcgct 360
tcagatttgg acaagatcag ctacttcttg ctacagggtt gaacaatggg cgtatcaaaa 420
tatgggatgt atatacagga aaactcctcc ttaacttggt agatcatact gaagtggtca 480
gagatttaac ttttgctcca gatggaagct tgatcctggt gtcagcttca agagacaaaa 540
ctctcagagt atgggacctg aaagatgatg 570

<210> SEQ ID NO 41
<211> LENGTH: 1151
<212> TYPE: DNA
<213> ORGANISM: Homo Sapiens

<400> SEQUENCE: 41
gtttttggcg cattctcaca gacttagatg aaactgtgat ggccaccgca gggggcaggt 60
gctgacatcg tccccagccc tgtggctgtt catccggaca tcatttccaa cctcaatatc 120
taaatgccac agtgctcttg gagcaagttg ggctggggac cactgttgcc ttttaagacc 180
ataaaaccat gggaaacgca gaaagtcaac atgtagagca cgagttttat ggagaaaagc 240
atgccagcct ggggcgcaag cacacttccc gctccctgcg cctctcgcac aagacgcgga 300
ggaccaggca cgcttcctcg ggaaggtga tccacaggaa ctccgaagtg agcacccgat 360
ccagcagcac ccccagcatc ccccagtccc tggctgaaaa tggcctggag cccttctccc 420
aagatggtac cctagaagac ttcgggagcc ccatctgggt ggaccgagtg gacatgggct 480
tgagacctgt gtcttacact gactcttctg tcactcccag cgtagacagc agcatcgtcc 540
tcacagcagc ctctgtgcag agcatgccag acactgagga gagcaggctt tacggggatg 600
acgctacata tttggctgag ggaggcagga ggcagcattc ctatacatcc aatgggccca 660
ctttcatgga gacggcgagc tttaagaaga aacgctccaa atctgcagac atctggcggg 720
aggacagcct ggaattctca ctctctgatc tgagccaaga acatttaaca agcaacgaag 780
aaatcttggg ttccgccgaa gagaaggact gcgaggaggc tcgggggatg gaaacgcggg 840
cgagtccgcg gcagctcagc acctgtcaga gagccaattc cttgggtgac ttgtatgctc 900
agaaaaactc tggagtgaca gcaaacgggg ggccggggag caaatttgca ggctactgtc 960
ggaatttggt gtctgatatt cccaatcttg caaaccataa gatgccacca gctgctgctg 1020
aagagactcc tccgtacagt aattataaca cacttccctg taggaaatct cactgtctct 1080
ctgaaggtgc caccaaccca caaattagcc atagcaacag catgcaaggc agaagagcta 1140
aaacaactca g 1151

<210> SEQ ID NO 42
<211> LENGTH: 531
<212> TYPE: DNA
<213> ORGANISM: Homo Sapiens

<400> SEQUENCE: 42
gtttgatgat tcctgtcttt tgtgtcgtgg agcagttgga cggctctctt gaatatgaca 60

```
acagagaaga acacgccgag tttgtcctgg tgcggaaaga tgtgcttttt agccagctgg    120

tggagactgc gctcctggcc ctggggtatt ctcacagctc tgcggcccag gcccaaggaa    180

taatcaagct gggaaggtgg aaccctctcc ccctcagtta tgtgacagat gcacccgacg    240

cgacagtggc cgacatgcta caagatgtct atcatgttgt gacgttgaaa atccaattac    300

aaagttgttc aaagttggaa gacttgcctg cggagcagtg gaaccatgcc acagtccgca    360

atgccttaaa ggaactgctc aaagagatga accagagcac attagccaaa gaatgccctc    420

tctcccagag tatgatttca tccattgtaa atagcacata ttatgccaat gtgtcagcaa    480

ccaagtgcca ggagtttggg agatggtata aaaagtacaa gaagattaaa g             531
```

```
<210> SEQ ID NO 43
<211> LENGTH: 278
<212> TYPE: DNA
<213> ORGANISM: Homo Sapiens

<400> SEQUENCE: 43

ggaagagact tccaccttag gatagtgttg cctgaagatt tacaactgaa gaatgcaaga     60

ttattatgta gttggcagct gagaacaata cttagtggat accatcgaat agtacaacag    120

agaatgcagc actctcctga tctaatgagc tttatgatgg agttgaagat gcttttggaa    180

gttgccttaa agaatagaca agagctgtat gcactacctc ctcctcccca gttctactca    240

agccttattg aagagatagg aactcttggt tgggataa                            278
```

```
<210> SEQ ID NO 44
<211> LENGTH: 361
<212> TYPE: DNA
<213> ORGANISM: Homo Sapiens

<400> SEQUENCE: 44

aatgaattac cagatggatt aaacaaaaag cgtttacaaa tcttattaaa aggctatggt     60

gaatatccaa caaaatacag aatgttcatt tggcgctctc tgctacaact gcctgaaaat    120

catactgcgt ttagtaccct catagataag ggactcatg tggcatttct caaccttcag     180

aagaaatacc ccatcaaaag taggaagcta ctcagagtat tacagagaac cttatctgca    240

ttagctcact ggtctgtcat ttttagtgac acaccatatc ttccactctt ggcatttcca    300

tttgtaaaat tattccagaa caaccaactc atctgttttg aagttattgc tactctcata    360

a                                                                    361
```

```
<210> SEQ ID NO 45
<211> LENGTH: 158
<212> TYPE: DNA
<213> ORGANISM: Homo Sapiens

<400> SEQUENCE: 45

aaatcttgca gcagctccac cagcagctgg ttgaagctga acgtaggtca gtgacatacc     60

tcaaacggta caataagatc caggccgact accacaatct cattggagtc acagcagagc    120

tggtggattc tctagaggcc acagtcagcg gcaagatg                            158
```

```
<210> SEQ ID NO 46
<211> LENGTH: 1114
<212> TYPE: DNA
<213> ORGANISM: Homo Sapiens

<400> SEQUENCE: 46
```

gtgaatgtaa atgcgaggac acgtggtccg ggtgcataat gggagacact ggctattatc 60
ttcctaaaaa gttcacccag tgtaatattg aagagtatca tgacttcctg aatagtggag 120
gtggtgcctg ccttttcaac aaaccttcta agcttcttga tcctcctgag tgtggcaatg 180
gcttcattga aactggagag gagtgtgatt gtggaacccc ggccgaatgt gtccttgaag 240
gagcagagtg ttgtaagaaa tgcaccttga ctcaagactc tcaatgcagt gacggtcttt 300
gctgtaaaaa gtgcaagttt cagcctatgg gcactgtgtg ccgagaagca gtaaatgatt 360
gtgatattcg tgaaacgtgc tcaggaaatt caagccagtg tgcccctaat attcataaaa 420
tggatggata ttcatgtgat ggtgttcagg gaatttgctt tggaggaaga tgcaaaacca 480
gagatagaca atgcaaatac atttgggggc aaaaggtgac agcatcagac aaatattgct 540
atgagaaact gaatattgaa gggacggaga agggtaactg tgggaaagac aaagacacat 600
ggatacagtg caacaaacgg gatgtgcttt gtggttacct tttgtgtacc aatattggca 660
atatcccaag gcttggagaa ctcgatggtg aaatcacatc tactttagtt gtgcagcaag 720
gaagaacatt aaactgcagt ggtgggcatg ttaagcttga agaagatgta gatcttggct 780
atgtggaaga tgggacacct tgtggtcccc aaatgatgtg cttagaacac aggtgtcttc 840
ctgtggcttc tttcaacttt agtacttgct tgagcagtaa agaaggcact atttgctcag 900
gaaatggagt ttgcagtaat gagctgaagt gtgtgtgtaa cagacactgg ataggttctg 960
attgcaacac ttacttccct cacaatgatg atgcaaagac tggtatcact ctgtctggca 1020
atggtgttgc tggcaccaat atcataatag gcataattgc tggcaccatt ttagtgctgg 1080
ccctcatatt aggaataact gcgtggggtt ataa 1114

<210> SEQ ID NO 47
<211> LENGTH: 446
<212> TYPE: DNA
<213> ORGANISM: Homo Sapiens

<400> SEQUENCE: 47
ggcaagtgtg gtcttgggga gatggtgact atgggaaatt gggcagaggt ggtagtgatg 60
gctgcaaaac cccaaagctg attgaaaagc ttcaagactt ggatgtggtc aaagtccgct 120
gtggaagtca gttttccatt gctttgacga aagatggcca agtttattca tggggaaaag 180
gtgacaacca gagacttgga catggaacag aggaacatgt tcgttatcca aaactcttag 240
aaggcttgca agggaagaag gtgattgatg tggctgcagg ctccacccac tgcctggctc 300
tgactgagga cagcgaggtc cacagctggg ggagcaacga ccagtgccag cactttgaca 360
ccttgcgcgt gaccaagcca gaacctgcag cattgccagg actggacacc aaacacatag 420
tgggaattgc ctgtgggcct gcccag 446

<210> SEQ ID NO 48
<211> LENGTH: 672
<212> TYPE: DNA
<213> ORGANISM: Homo Sapiens

<400> SEQUENCE: 48
gtttccacgc tttgagaagg actgaatgag atcatgcgca tggcagcttc tctaggatag 60
caccctgcgt gaacacagta gctgctcagt taagtctttg atgggtgtga tcctgattca 120
gcttgatcaa ttctgcagtc atactggatt gtgtttgaaa aggtgtccag aaaaacctgg 180
ccatctgcct cctgtcttcc cagtacccca accccatgga taaaaatgtc atctcagtaa 240
aaatcatgga ggaaaaaaga gatgaatcaa caggggtcat ctacagaaag aggattgcaa 300
tctgtcagaa cgtggttcca gaaattttaa ggaaggtgag cattttgaaa gtacctaata 360
tccaattaga agaggagtca tggctcaatc ctcgggaaag aaacatggcc atacggagtc 420
actgccttac gtggacacag tatgcatcca tgaaggaaga gtctgtcttc cgggaaagta 480
tggaaaaccc aaattggaca gagttcattc aaagaggcag gatttcaatc acaggggttg 540
gatttctcaa ctgtgtttta gaaacttttg ccagcacatt cttacgacag ggagcccaga 600
agggaattag aatcatggag atgctgctaa aggaacagtg tggtgccccc ttagctgaat 660
aaagaatcat ca 672

<210> SEQ ID NO 49
<211> LENGTH: 294
<212> TYPE: DNA
<213> ORGANISM: Homo Sapiens

<400> SEQUENCE: 49
gttacgtggt gcttctgtaa tcattaggtt tgtgaccaat acaaccaaag agagcaagca 60
agacctgtta gaaaggttga gaaaattgga atttgatatc tctgaagatg aaatattcac 120
atctctgact gcagccagaa gtttactaga gcggaaacaa gtcagaccca tgctgctagt 180
tgatgatcgg gcactacctg atttcaaagg aatacaaaca agtgatccta atgctgtggt 240
catgggattg gcaccagaac attttcatta tcaaattctg aatcaagcat tccg 294

<210> SEQ ID NO 50
<211> LENGTH: 8279
<212> TYPE: DNA
<213> ORGANISM: Homo Sapiens

<400> SEQUENCE: 50
atttctacat cgtactaagg aagaatgatt tcctatttga tatagctgaa ccatgcaaaa 60
atcagatcct tgaaaaggtc agaacctgta tttatacata gtagaaatag agagttatcc 120
tctattaggc tgtgtatgaa tatatgtgtc acaaaaaaca gagcaaatga aaaaacttcc 180
cctttcttga cattttattc tgcagttttt acaaattatg tgtgccttta taatgtgcaa 240
actacactac ttaaaagtat gtgtagagta ctgttattaa tcctgtttta tagaaacaat 300
aatgggctaa gagacttatt caaaatcctg taactaatag ctgtaagata aagcccagat 360
cttttgcctc taagtcttaa cctttccact acattgtaag ttcgtaatta gtatcagaat 420
ttagtagaca tgtagtatgc aagctgtatg aacattggaa ataatgtata taaaagtcta 480
tgaaaaagtg ttaaaacccc tttatggatg ttaagtatca taaataattc agatcttgac 540
cttcaatagc taacatataa tcttgggatg ataccagagt cctcaatata taatatacca 600
ttggcttagt atagcaagca aaattcttta caaggtgcct catttctact tttctagcct 660
cagctcattc agtttctgtc atctgtccct gtagcttact ttgtcccttt tcatctgtaa 720
taaatggcta gcattgtcca aacacattgt ccctttccat ttctatgttc aattccacat 780
aattaggaag aatgcctgaa atgcctattt gtctttcttc ggataatcct agctcaactt 840
catctcctcc atgaagcttt cctcaacccc cccccaaccc ctggcaaagt taatcattcc 900
cttctgtttt cccagagcac tttttatagc aaatctctgt atagcaaaaa tcacacgatg 960
attgtatatt tgaattgcta tctttcctac taatctgtga gttctttgtg agcatgaaca 1020
gggacttaca cttatttgtc tttgtgtctt taacatgtta ctactaggct tagattttgt 1080
tactcagctc agatgtattt tgtttaatga ataaaataag agctacagtt ctttccttat 1140

-continued

```
aaggatctgt atgtacagta ttctaagtgg gagactgacc acacaaaaat acctaaaaac   1200
acatagatat atgtaaaacg atatagtgta tgcttgaggt aaaataatgg aatgatcaga   1260
gccaggttga gttatttagg gaaggattcc tctaggttag tagttggcaa tctatggccc   1320
acaggccaaa tctatctgcc accagttttt tgtaaataaa gttttactgg aacatagcca   1380
tgttcatttg ttagtgtatt atatgtctgc cttaatgcta tgataacaga gttgagcagt   1440
tgcaacagag accatatgtc ctgtaaaact gaaaatattt gccatctggc cctttacaga   1500
aaaagtttgc caacccctgc tctaggagtg ggctttggat atgaaaagaa gaggaatgtg   1560
aattggtgaa gcataagtgt gcatcataat gcaatgaaaa caagccatag tagtaggtat   1620
gctaggtaag aaagctccac tccaattcag tttgtcagag agacctatgc tgaagagatt   1680
aaatgtcaag aatgtttgga ttgagaaaga gggaacacaa atctaatgga aagaaatttt   1740
gaagtaaaca ctccgggcct gcagcaaaat agtttcctaa atagtagcaa aggatgatga   1800
tgaaggaaaa ggaagcagca acataaatta acattgactg agtgtttact atgtgccagg   1860
tactgttcta agtggtgtgt gtgtgtgtgt gtgtgtgtgt gtgtctccta tttaatcctc   1920
tcaacaacta aatgagataa ttgctattat tgtctttatt ttgctgcgga ggaaactcag   1980
gcacaggagg ctaagttaac ttggtcaagt taatacaact ggtaagtgat agaaccaagt   2040
ctgaacccag gctgtcagtc tgcagagtct tcataataga gaaggggaaa tctggagata   2100
tttggtaaaa atacttttaa gcttggagta aggtacttag tccaagtaat tgggaaatgt   2160
actatcccaa catggtaaag agaaaatgaa cagacaataa aagagtaatg atggaaggca   2220
gggtttccaa ttagaagagt atactatgga ttaggcagaa tgggcagggc aaggaagcag   2280
atacttaaga catgttatat agtcatacag taagatacat tatatagtca gtcattgcgt   2340
ttaaccttga tgagaccaga aagcaattaa cttttccttg cacacatgaa agctgtccta   2400
aaatacttga agagctggta tatccaattg agatatagat tagcagtgac tttcaaggag   2460
gtaaggggca ttcaaccttc ccacaaaaat atacacacct tagtatccca agtgtattat   2520
aattggtgga ggtgtcaagt catagcacac accattctct ctcattctgt ctccctaaga   2580
ggactggttc ctgtccaacc ctgtatgatt gctatggtaa atatttaccc ctttggacaa   2640
ttttttttaaa aaaatacata tatattgtat gcatgttaaa gtaatacata tgcactatga   2700
aaattttgcc aatagaagta taccaaatgc aaacattggc tagagatggt aggattggag   2760
atggaaggag gaggagacat taaactaaat gactttcaac atttcttcca aatctgtagt   2820
tctatgttta taccagcaga gtggtaagca caaaggaaaa gaccacaatg tgactttgac   2880
atggttggct tgaatagagg ataaaatggt ataggagaaa atccaatata tgaaatctaa   2940
atttatagag cagattactt tgcagtgaac cttggactta tttttataaa gattactttt   3000
aactagccat tttgatatgt tcaaatatac ttaattttaa taaaaaattt catttacact   3060
taacttgtca gtagtatatt tactgtgtaa aataaagcag acacacattg ttcattattt   3120
caaagaagga agagatttca gccaagttat gttgtagtag ctacagtgga aataattgag   3180
ctgggccttg cccataaacc tgcaatatga tagaacttaa aaggggacca ggcatggtaa   3240
ctcacacctg taatcccaga actttgggag gccaagacag gaggattgct tgaggccagg   3300
agttcaagac cagcctggat aacatagtga gacctcgcct ctacaaaaaa taaaaaagtt   3360
agccaggcgc attgatgcac accagtaatc ctagccactc agaaggctga ggtgggagga   3420
ttgcgtgagt ccaggagttt gaggctgcag tgaactatga tcatgccact gtactccagc   3480
ctgagcaaca gggtgagacc ctgtctctta aaaactaact aacttaaaag ataccttagg   3540
```

```
tatgtaaggt atgtaaagtg cctaccacag tgccagtaaa tggtagatgg agacgcagaa   3600
gagaaaaaag atgatggtgg tgatgatgct gttgttatgt cttctgtccc catatcacac   3660
ttctgtaagg cttcagaaag aaagttggta ttgtatatat ttgtatacac acatacatac   3720
atgcacacac acactgtcca tgctacaaaa cctaaacttg cacagtgttg tttataaaaa   3780
ccaggactca gatttgaagt ctcagatttg gaaggaactt taaaggttac ccagtccagc   3840
ctccctcttc ctcctaatga tttagtatct tcaccaatag gttattttac ctctgctttc   3900
acatccttag tgatggcaaa ttcatgcctc tccttcccag agagcttatc ccacttttgg   3960
atacagagct ctgactggca gaaagttctt cctaataata tgctgaagtc tatctaccta   4020
tagcttccac ccactggttc taattctctc ccttggggta atattgaaga agtagagcaa   4080
atctcatctc tctcctacat gaaatccctc cagatatttg caaacagctc tcatgtttcc   4140
cctgagtctt tccttctagt taaccttccc tagtttctta aattctcact cttcttgttg   4200
ctttacttta aatgagattg tgcatttgta tctcattcaa aatataggac ctagaatgaa   4260
acataaaatc ctacttctga tatgtttgga ctggcaagaa tggagcatcc aggactgtca   4320
tcgtctttat tccaaatatt gactggaata atgatgatgc tgatgcattg cttatttaat   4380
gacatcagat ccatatatgt ctgctaggaa ctatgaagtg gcactatagg aaccactgaa   4440
cttcttctct gttcaagaag catgagccag aagcattcca aaaagcatta gcttctctta   4500
cgctctgcct cacacctctg caagtttctg gaaagggtaa acattataca tagttaaaga   4560
atactaggac tgcctgtagg acaaaggaag tcatggcatt ttcattagcc acttattgct   4620
agctgcatta cttgttaaag gaaatactgg tgttctcatg ggttcttttc tgtgcataca   4680
caaagatgta tagttgctac aaagcaagtg gagcaggggg acaccaaaga gatatgctcc   4740
atcttctttg ttcacctctg ctacatggag gagataggat ttattgcttt ctttgagaaa   4800
gagattggcc agtttccttc ctcccccttc ttctggtgga tcattccaga agaatattgc   4860
atctcatcat agttatctcc taataaagta aaagtaaatg aaggagagct ggagacagag   4920
aatcagctga gatgtgctgg aaatactcgg ctgggcgcag tggctcgtgc cttgtaatcc   4980
catcactttg ggaggccgag gcgggtggat cacctgaggt caggagttca agaccaacct   5040
ggccaacatg atgaaaccct gtctctacta aaaatacaaa aaattagcca ggcttggtga   5100
caggcacctc tcatcccagc tactcaggag gctgaggcag gagaatcgct ggaacccgcg   5160
aggcagaggt tgcagtgagc caacatcatg ccactgcact ccagcctgag caaccagagt   5220
gaaactccgt ctcaaaacaa agtaacaaca acaacaaaaa aaacttgtta atgagagagt   5280
ggctgatcag tggcacatca cagatgaatc ctctgtctcc tgcctccctg tagcttgtcc   5340
ttccatcacc acagtgagta gatgttctgc tcacagcttt tccattttga tttctctgca   5400
tattggcata gtattatgat ttatctaaaa ctgagagttc tgtcttttct tattgaattt   5460
tcagaagtat gtttgatgca tcttttttct gttttccagt ttccatttct aggggaagta   5520
ttcttctctt cctgttcttt gaaatactta acacaatatc tggcatgtag taaacactta   5580
aaatgataat tatatattaa taatttgact tattactata caggtgataa tttgtaacta   5640
agtttttaat tgtatcttaa tatatgaaga attctacttt tccttgcttc aaggggtggc   5700
ctgttgtgat tgttttatta cattttgaaa ggatactacc atagccttac agattcttct   5760
actacctatt atacttcttt caacgacttc cagaaatacg gagtcattac attctccaga   5820
tctgcactat gcaatgagta gccacaacca tgtatgtcta attaaatgta aatttaataa   5880
```

aaattaaata caattaaaaa tgcactcagt ttgcactagc tacatttcaa gtcctaaata 5940
gccacatgtg gctagtggct acccattgga caacaggaat attgaacatt tccatcattg 6000
cattaaattt tgagaggctg aggctggcag attcttgagg tcaggagttc gagaccagcc 6060
tggccaacat ggtgaaaccc catctctact aaaaatacaa aaattagcca agcatggcgg 6120
cacatgccta taatcccagc tactctggag gcactgcttt ggatattcgt agtctatgct 6180
cttgtgctct tttcttagaa attgaagagg atatattttc tagggtgttc ctaagactaa 6240
tctcttaatg tttcagggct ctgaacatgc attttgagga ttcacgttac tgttcttatt 6300
ccagcccctt agtgccatta ctatcttttg gaataaatac aagaactttc acatcctcca 6360
agaagattat actaccataa attttatttt gtttattttt atttatttat ttattttgag 6420
acagtgtttc tgttgcccag gctggagtgc agtggtatga ccatagctca ctgcagcctt 6480
gacctcctga gctcaggtga tcctcctgcc ttaacctccc aagtagctgg aactataggt 6540
gcacacacca ccacacctgg ctaattttta tatttttttt tttttgtag agatggggtt 6600
tcaccatgtt tctgagtctc aaactcctag agatgggggt ctcactgtgt tgtccaggct 6660
ggtctcgaac tcttgagttc aggcgattcc cccctacttc agcctcctaa aatactggga 6720
ttacaggtgg tcctcctgcc ttaacctctt tacaggtgtg agccaccaca cccagccatt 6780
aagcactttc aaagccattt tttcatttgt tatttacagc agcccagtga agcaagtagc 6840
attgggatta ttattcccat tttactaata agaaaactga gattcagtta agttacagcc 6900
tgaagtcttt ttgtttttg gggtttttt tttttttttt gaccaagtct cactctgtcg 6960
cctaggttgg agtgcagtgg catgatctca gctcactgca acctccgcct cctgggttca 7020
agtgattctg atgcctcagc ctctcgagta gccgggatta caagcatgtg ccaccatgct 7080
tggctaattt ttgtattttt agtagagatg gggtttcgcc atgttggcca ggctggtctc 7140
gaactcctga cctcaagcat ccgtcagcct cagcctttca aagtgctggg actacagacg 7200
tgagccaccg tgtctggcca tgttacctgc ctaacgtctt aaagggaaaa taaacattaa 7260
ggcaaaatag aggagattca gatcagggta aaattttaac gtcaaattca gcatttttg 7320
ttttgttttt actttgtttt tgttctactt tactcccact ccgactgtaa taaaagagtg 7380
aaagttcttt aggggaactg aggtactccc aaagaattgc tacagtccca tttgtcctgt 7440
gatcatgtgc ttggggtgcc ataacagaat accacagact gagtggctta aacaatagaa 7500
atttatatcc tcaaagttct gggggctgga agttcagtgt caggatgcta gcggcagagg 7560
ctagagatga ggtctttctc cttagcttat agatgacacc ttctctctga gtcctcatgt 7620
agcatttttc tctatgtgag agaaagagat atctctcatg tctcatcctt ttgttttaaa 7680
gaaaccaatt atatcagatt agggtctcac ctgtatgact ttatttaacc ttaattacct 7740
ccttaaatgc cctgtctcca aatgtagtca cattgggggt tagggcttta acgtatgaat 7800
ttgggggaga cacagttcag cccataacac catgttaatg ggtttttagt gtcttttgat 7860
attctggctt aacctggtta gctggaaact aaatttagta tttgaatggg accaaatgta 7920
gcaaatatct gtattcttta tttctgtgaa tatagaggct taattaaatt caacctgtgg 7980
tacttgctgt aaggtacttt gcaactccaa gatattctaa tagcaaaaaa tctgtatcta 8040
aatttcctac ttttcttata atgtagccta attgttaata attagagatc tcagtacttt 8100
acaggtaata aatgttcttc tccttcctcc ccacctacct tttttacaga tggagaaatt 8160
agcatacaaa gaaactgact tgtcagaagt cagagcaagg tattggtgga tccagggata 8220
aatcccaaac ttcttaaccc ctagaccggt ttttagtcca ttgactatgc agcctaatg 8279

<210> SEQ ID NO 51
<211> LENGTH: 1231
<212> TYPE: DNA
<213> ORGANISM: Homo Sapiens

<400> SEQUENCE: 51
gaaggtggga gtcaatcatt ttgacaagtc tcctgaaagg aacagctagc aggaactgaa 60
accttttcc atttggtctc gtggcaaagg cagagattgc tccagcagct ccacacaaaa 120
tgatgtgctc acgggtgccc tctgaacagt cttctggtac ctctctcttg cctaaagacg 180
gtgccccatt ttcttgggat tccttggatg aggatggatt ggatgactcc ttgctggagc 240
tgtcagaggg agaagaagat gatggtgatg taaattacac agaggaagag attgatgcac 300
tgttgaagga agatgaccca tcatatgagc agtcttctgg ggaagatgat ggtgggcatg 360
ttgagaaggg agaaagaggg agtcaaattc tacttgatac tccccgagag aaaaattcat 420
cgtacagcct gggaccagta gctgagactc ctgacctctt caaactacct cagctaagta 480
catcaagtgg tcatggacca gctcatacta aaccattaaa cagacgctct gtactagaaa 540
agaatcttat aaaagtaact gttgcaccat ttaatccaac agtttgtgat gctctgcttg 600
ataaggacga gactgattcg tccaaagata ctgaaaaact ctcttccctt ggagaagaga 660
tgagagaaga tggtcttagc ccaaatgaaa gcaaactttg tactgaatct gaagggatca 720
gccccaataa ctctgcctgg aatgggcccc agctctcttc ttcaaacaat aactttcaac 780
agactgtctc tgataaaaat atgcctgaca gtgagaaccc tacgtctgta ttctctcgga 840
tctcagacca ttcagagact cctaatatgg agttatcctg cagaaatggt ggttcacaca 900
agtcaagttg tgaaatgaga tctctggttg tttccacctc atcaaacaaa caggatgttc 960
ttaacaagga ttctgggaag atgaaaggcc atgagagaag actaggcaaa gtcattcctg 1020
ttctacaaac taagaccagg actaatgttc cgacgttttc acagtcaaat ctagaacagc 1080
agaagcagct ttatctcagg agtgtcattg ctcatataga agacccagag gacactaacc 1140
aaggtatctc gggggagctt tgtgccttga tggatcaagt tcatcatatg cagcactcaa 1200
aatggcagca tccttcggac ctcaccacgc g 1231

<210> SEQ ID NO 52
<211> LENGTH: 1539
<212> TYPE: DNA
<213> ORGANISM: Homo Sapiens

<400> SEQUENCE: 52
tccgcacgac tgttacagag gtctccagag ccttctctct cctggtaggt ttcggctcag 60
gaccctgaat cctggcccac aggcaagcct gatgggacgt gcggggtagt acttgtatgg 120
ggagacgcgg gaaggaggaa gaagcacatc tgtcctccgc ggcctttagc tctgagcatc 180
cggccgcggg ccctgacttt gccgctcagt ttggggcgca ggggggccg tgccctggcg 240
gaggagcaga aggcagaggg tagcagctgc ggctcagcgg agagacttgt tgcatttgca 300
gctaaaacca ggccctactt gtccttgtgc aaaatggcaa ctcttaagga aaaactcatt 360
gcaccagttg cggaagaaga ggcaacagtt ccaaacaata agatcactgt agtgggtgtt 420
ggacaagttg gtatggcgtg tgctatcagc attctgggaa agtctctggc tgatgaactt 480
gctcttgtgg atgttttgga agataagctt aaaggagaaa tgatggatct gcagcatggg 540
agcttatttc ttcagacacc taaaattgtg gcagataaag attattctgt gactgccaat 600

```
tctaagattg tagtggtaac tgcaggagtc cgtcagcaag aaggggagag tcggctcaat    660

ctggtgcaga gaaatgttaa tgtcttcaaa ttcattattc ctcagatcgt caagtacagt    720

cctgattgca tcataattgt ggtttccaac ccagtggaca ttcttacgta tgttacctgg    780

aaactaagtg gattacccaa acaccgcgtg attggaagtg gatgtaatct ggattctgct    840

agatttcgct accttatggc tgaaaaactt ggcattcatc ccagcagctg ccatggatgg    900

attttggggg aacatggcga ctcaagtgtg gctgtgtgga gtggtgtgaa tgtggcaggt    960

gtttctctcc aggaattgaa tccagaaatg ggaactgaca atgatagtga aaattggaag   1020

gaagtgcata agatggtggt tgaaagtgcc tatgaagtca tcaagctaaa aggatatacc   1080

aactgggcta ttggattaag tgtggctgat cttattgaat ccatgttgaa aaatctatcc   1140

aggattcatc ccgtgtcaac aatggtaaag ggatgtatg gcattgagaa tgaagtcttc   1200

ctgagccttc catgtatcct caatgcccgg ggattaacca gcgttatcaa ccagaagcta   1260

aaggatgatg aggttgctca gctcaagaaa agtgcagata ccctgtggga catccagaag   1320

gacctaaaag acctgtgact agtgagctct aggctgtaga aatttaaaaa ctacaatgtg   1380

attaactcga gcctttagtt ttcatccatg tacatggatc acagtttgct ttgatcttct   1440

tcaatatgtg aatttgggct cacagaatca aagcctatgc ttggtttaat gcttgcaatc   1500

tgagctcttg aacaaataaa attaactatt gtagtgtgc                           1539
```

<210> SEQ ID NO 53
<211> LENGTH: 518
<212> TYPE: DNA
<213> ORGANISM: Homo Sapiens

<400> SEQUENCE: 53

```
atgcacaaag cagggtcatc agaagcctct cgattcaaaa gatgataata ccgaaaaaca     60

ctgcccagtg acagtgaatc cttggcatat gaagaaagct ttcaaagtca tgaacgaatt    120

aagaagtcaa aatttgctgt gcgatgtcac aattgtggca gaagacatgg aaatttctgc    180

tcatagagtg gtgctggccg cctgtagtcc ttattttcat gccatgttta caggtgagat    240

gagtgagagc cgagcaaaga gagttagaat aaaagaggta gatggctgga ccctgaggat    300

gctaattgat tatgtttaca ctgcagaaat tcaggttaca gaagaaaatg tacaggtact    360

tctcccagca gctggtctct tacagttaca ggatgtgaag aagacttgtt gtgaattttt    420

ggaatcccag cttcaccctg tcaactgctt aggaatccgg gcttttgctg atatgcatgc    480

atgtaccgac cttctgaaca aggccaacac ctatgcag                             518
```

<210> SEQ ID NO 54
<211> LENGTH: 685
<212> TYPE: DNA
<213> ORGANISM: Homo Sapiens

<400> SEQUENCE: 54

```
aagtgatgcc accaaaaaga aatgaaaaat acaaacttcc tattccattt ccagaaggca     60

aggttctgga tgatatggaa ggcaatcagt gggtactggg caagaagatt ggctctggag    120

gatttggatt gatatattta gagacactgg ccatttttct ctctccaatg cttagtgtgg    180

agtaaaggca gcttcccgca aatttatttc aagcaagagc aatcggaagc ttcgacatgt    240

gtgaaagagg cgcatagaga acatagcttc catttcagct ttccccacaa ataaaccaga    300

gaaagatgca agacatgtag taaaagtgga atatcaagaa aatggcccgt tattttcaga    360

acttaaattt tatcagagag ttgcaaaaaa agactgtatc aaaaagtgga tagaacgcaa    420
```

acaacttgat tatttaggaa ttcctctgtt ttatggatct ggtctgactg aattcaaggg 480
aagaagttac agatttatgg taatggaaag actaggaata gatttacaga agatctcagg 540
ccagaatggt acctttaaaa agtcaactgt cctgcaatta ggtatccgaa tgttggatgt 600
actggaatat atacatgaaa atgaatatgt tcatggtgat ataaaagcag caaatctact 660
tttgggttac aaaaatccag accag 685

<210> SEQ ID NO 55
<211> LENGTH: 1953
<212> TYPE: DNA
<213> ORGANISM: Homo Sapiens

<400> SEQUENCE: 55
gacaggagga aacgcagcgc cagcagcatc tcatctaccc tccttgacac ctccccgtgg 60
ctccagccag accctagagg tcagccttgc ggaccaacag gaggactccc agctttccct 120
tttcaagagg tccccagaca ccggccaccc tcttccagcc cctgcggcca gtgcaaggag 180
gcaccaatgc tctgaggctg tcgcgtggtg cagcgtcgag catcctcgcc gaggtccttt 240
ctgctgcctg tcccgcctca ccccgctcca tcacaccagc tggccctctt tgcttccttt 300
tcccagaatc gttaagcccc gactcccact agcacctcgt accaacctcg ccccacccca 360
tcctcctgcc ttcccgcgct ccggtgtccc ccgctgccat gagctccccc atcagcaaga 420
gccgctcgct tgccgccttc ctgcagcagc tgcgcagtcc gaggcagccc ccgagactgg 480
tgacatctac ggcgtacacg tcccctcagc cgcgagaggt gccagtctgc ccgctgacag 540
ctggtggcga gactcagaac gcggccgccc tgccgggccc caccagctgg ccactgctgg 600
gcagcctgct gcagattctc tggaaagggg gtctcaagaa acagcacgac accctggtgg 660
agtaccacaa gaagtatggc aagattttcc gcatgaagtt gggttccttt gagtcggtgc 720
acctgggctc gccatgcctg ctggaagcgc tgtaccgcac cgagagcgcg tacccgcagc 780
ggctggagat caaaccgtgg aaggcctatc gcgactaccg caaagaaggc tacgggctgc 840
tgatcctgga aggggaagac tggcagcggg tccggagtgc ctttcaaaag aaactaatga 900
aaccagggga agtgatgaag ctggacaaca aaatcaatga ggtcttggcc gattttatgg 960
gcagaataga tgagctctgt gatgaaagag gccacgttga agacttgtac agcgaactga 1020
acaaatggtc gtttgaaagt atctgcctcg tgttgtatga gaagagattt gggcttctcc 1080
agaagaatgc aggggatgaa gctgtgaact tcatcatggc catcaaaaca atgatgagca 1140
cgtttgggag gatgatggtc actccagtcg agctgcacaa gagcctcaac accaaggtct 1200
ggcaggacca cactctggcc tgggacacca ttttcaaatc agtcaaagct tgtatcgaca 1260
accggttaga gaagtattct cagcagccta gtgcagattt cctttgtgac atttatcacc 1320
agaatcggct ttcaaagaaa gaattgtatg ctgctgtcac agagctccag ctggctgcgg 1380
tggaaacgac agcaaacagt ctaatgtgga ttctctacaa tttatcccgt aatccccaag 1440
tgcaacaaaa gcttcttaag gaaattcaaa gtgtattacc tgagaatcag gtgccacggg 1500
cagaagattt gaggaatatg ccgtatttaa aagcctgtct gaaagaatct atgaggctta 1560
cgccgagtgt accatttaca actcggactc ttgacaaggc aacagttctg ggtgaatatg 1620
ctttacccaa aggaacagtg ctcatgctaa atacccaggt gttgggatcc agtgaagaca 1680
attttgaaga ttcaagtcag tttagacctg aacgttggct tcaggagaag gaaaaaatta 1740
atccttttgc gcatcttcca tttggcgttg gaaaaagaat gtgcattggt cgccgattag 1800

```
cagagcttca actgcatttg gctctttgtt ggattgtccg caaatacgac atccaggcca   1860

cagacaatga gcctgttgag atgctacact caggcaccct ggtgcccagc cgggaactcc   1920

ccatcgcgtt ttgccagcga taatacgcct cag                                1953


<210> SEQ ID NO 56
<211> LENGTH: 251
<212> TYPE: DNA
<213> ORGANISM: Homo Sapiens

<400> SEQUENCE: 56

acaaagaaac agccttggta taatagcacg ttagcatcaa gacgaaaacg acttactgct     60

cattttgaag acttggagca gtgttacttt tctacaagga tgtctcgtat ctcagatgac    120

agtcgaactg caagccagtt ggatgaattt caggaatgct tgtccaagtt tactcgatat    180

aattcagtac gacctttagc cacattgtca tatgctagtg atctctataa tggttccagt    240

atagtctcta g                                                         251


<210> SEQ ID NO 57
<211> LENGTH: 339
<212> TYPE: DNA
<213> ORGANISM: Homo Sapiens

<400> SEQUENCE: 57

aaattttagt ttactttcat ttggagagga agctgaggaa gaagaggagg aagtaaatcg     60

agttagtcag agcatgaagg gcaaaagcaa aagtagtcat gacttgctta aggatgatcc    120

acatctcagt tctgttccag ttgtagaaag tgaaaaaggt gatgcaccag atttagttga    180

tgatggagaa gatgaaagtg cagagcatga tgaatatatt gatggtgatg aaaagaacct    240

gatgagagaa agaattgcca aaaaattaaa aaaggacaca agtgcgaatg ttaaatcagc    300

tggagaagga gaagtggaga agaaatcagt cagccgcag                           339


<210> SEQ ID NO 58
<211> LENGTH: 753
<212> TYPE: DNA
<213> ORGANISM: Homo Sapiens

<400> SEQUENCE: 58

gcaacatggc gtcttcggga gctggtgacc ctctggattc taagcgtgga gaggccccgt     60

tcgctcagcg tatcgacccg actcgggaga agctgacacc cgagcaactg cattccatgc    120

ggcaggcgga gcttgcccag tggcagaagg tcctaccacg gcggcgaacc cggaacatcg    180

tgaccggcct aggcatcggg gccctggtgt tggctattta tggttacacc ttctactcga    240

tttcccagga gcgtttccta gatgagctag aagacgaggc caaagctgcc cgagcccgag    300

ctctggcaag ggcgtcaggg tcctaatctg gatgggtatt gatcatgtcc aacctgctgg    360

agccccttca catggtggat gatgccccat gaccctgtag aaattgaatc ctgctcacaa    420

cattgttggc cttcttacta accttggacc gtgattgagc ccaagaaacc agggacttac    480

gcatttggcc aatgtcaaaa gaacagaact ttgcccactg cacacttgct gtgtacaatg    540

actgagccct ttcttgtagt ttgtttcctt gtttgagagg tgtgcatgcg accgtggctt    600

ttcccaaagt ttctgacttt gtggtttacc cccttcacct tccagggacg cagttgttac    660

gaggttagac gtggcagctc tgtgcagtgt ttgagcctac agtgggatac atagggtcaa    720

attgagaata ataaactgag tcattctcct gga                                 753
```

<210> SEQ ID NO 59
<211> LENGTH: 491
<212> TYPE: DNA
<213> ORGANISM: Homo Sapiens

<400> SEQUENCE: 59
ctcctccatt tacaacctac aaagataaaa gaaagtggaa gccaaagttt tggagaaaac 60
ctatttcaga taatagcttc agtagtgatg aggaacagtc tacaggacca attaagtatg 120
ctttccagcc agagaaccaa ataaatgttc cagctctgga tacagttgtc actccagatg 180
atgtcagata ctttacaaat gagactgatg acatcgctaa tttagaagca agtgtgcttg 240
aaaatccttc tcatgtacaa ctttggctca agcttgcgta caagtacttg aatcaaaatg 300
agggggagtg ctcagaatcc ttggattctg ctttaaatgt tctggcgcga gcattggaaa 360
ataacaaaga caatccagaa atttggtgcc attacctcag attgttctca aaaagaggaa 420
ccaaggacga ggtgcaggaa atgtgtgaaa cagctgttga atatgctcca gattatcaaa 480
gcttttggac t 491

<210> SEQ ID NO 60
<211> LENGTH: 324
<212> TYPE: DNA
<213> ORGANISM: Homo Sapiens

<400> SEQUENCE: 60
gttacgagaa gtttctgaga agctgaacaa atataattta aacagccacc ccccttttgaa 60 tgtattggaa caggctacta ttaaacagtg tgtggtggga ccaaatcatg ctgcctttct 120
tcttgaggat ggtagagttt gcaggattgg tttttcagta cagccagaca gattggaatt 180
gggtaaacct gataataatg atgggtcaaa gttgaacagc aactcggggg cagggaggac 240
gtcaaggcct ggtaggacaa gcgactctcc atggtttctc tcaggttctg agactctagg 300
caggctggca ggcaacacct tagg 324

<210> SEQ ID NO 61
<211> LENGTH: 167
<212> TYPE: DNA
<213> ORGANISM: Homo Sapiens

<400> SEQUENCE: 61
gttacctagg gtatgaatta atacagactt ggaaactctg aaagaactta gaatcagcat 60
tttgagagca gaagcttggg catgctgtga ttttccaata aactgctatc acaatgtcaa 120
aatgcagttc agacaagagc aacacagaga tctcaaacat taaaacg 167

<210> SEQ ID NO 62
<211> LENGTH: 138
<212> TYPE: DNA
<213> ORGANISM: Homo Sapiens

<400> SEQUENCE: 62
gaaccaaccg gtgagccctc tcctaagaga cccaggggaa gacccaaagg cagcaaaaac 60
aagagtccct ctaaagcagc tcaaaagaaa gcagaagcca ctggagaaaa acggccaaga 120
ggcagaccta ggaaatgg 138

<210> SEQ ID NO 63
<211> LENGTH: 138
<212> TYPE: DNA
<213> ORGANISM: Homo Sapiens

<400> SEQUENCE: 63
gttgttaaaa aagcagacat gatcaacaaa aatatgactc atcaggtcca agctgagaga 60
gatgcactgg cactaagcaa aagcccattc attgtccatt tgtattattc actgcagtct 120
gcaaacaatg tctacttg 138

<210> SEQ ID NO 64
<211> LENGTH: 209
<212> TYPE: DNA
<213> ORGANISM: Homo Sapiens

<400> SEQUENCE: 64
ggtatttctc aagctgccag atacgtttac caacgactca tcaacgacgg gattttgagc 60
caagccttca gcattgctcc tgagtaccgg ctggtcatag tgggccacag cctcgggggc 120
ggggcggccg ccctgctggc caccatgctc agagccgcct acccgcaggt caggtgctac 180
gccttctccc caccccgggg gctgtggag 209

<210> SEQ ID NO 65
<211> LENGTH: 1346
<212> TYPE: DNA
<213> ORGANISM: Homo Sapiens

<400> SEQUENCE: 65
aatatcgata acttgatgac cccagaagga gttggcctta ccactgcctt acgtgttctc 60
tgtaatgttg catgcccacc acctcctgtt gaaggtcaac agaaagatct gaaatggaat 120
cttgccgtta ttcagctttt ttctgctgaa ggaatggaca cgtttattcg agttctgcaa 180
aaattgaaca gtattctgac tcagccttgg aggctccatg tcaacatggg gactaccctt 240
cacagagtta ctactatttc aatggctcgc tgcacactca ctcttcttaa aactatgtta 300
acggaactcc tgagaggtgg atcctttgag tttaaggaca tgcgtgttcc ttcagcgctt 360
gttactttac atatgctcct gtgctctatc cccctctcag gtcgtttgga tagtgatgaa 420
cagaaaattc agaatgatat cattgatatt ttactgactt ttacacaagg agttaatgaa 480
aaactcacaa tctcagaaga gactctggcc aataatactt ggtctttaat gttaaaagaa 540
gttctttctt caatcttgaa ggttcctgaa ggattttttt ctggactcat actcctttca 600
gagctgctgc ctcttccatt gcccatgcaa acaactcagg ttattgagcc acatgatata 660
tcagtggcac tcaacacccg aaaattgtgg agcatgcacc ttcatgttca agcaaagttg 720
ctccaagaaa tagttcgctc tttctctggc acaacctgcc agcccattca acatatgtta 780
cggcgtattt gtgttcaatt gtgtgacctt gcctcaccaa ctgcacttct gattatgaga 840
actgtgttgg atttgattgt agaagacttg caaagcactt cagaagataa agaaaaacag 900
tatactagcc aaaccaccag gttgcttgct cttcttgatg ctctggcttc acacaaagct 960
tgtaaattag ctattttgca tctaattaat ggaactatta aaggtgatga aagatatgca 1020
gagatattcc aggatctttt agctttggtg cggtctcctg gagacagtgt tattcgccaa 1080
cagtgtgttg aatatgtcac atccattttg cagtctctct gtgatcagga cattgcactt 1140
atcttaccaa gctcttctga aggttctatt tctgaactgg agcagctctc caattctcta 1200
ccaaataaag aattgatgac ctcaatctgt gactgtctgt tggctacgct agctaactct 1260
gagagcagtt acaactgttt actgacatgt gtcagaacaa tgatgtttct tgcagagcat 1320
gattatggat tatttcattt aaaaag 1346

<210> SEQ ID NO 66
<211> LENGTH: 3193
<212> TYPE: DNA
<213> ORGANISM: Homo Sapiens

<400> SEQUENCE: 66
gaaggaccat cgagacctgt tcttgaatac atcgatctgg tctgtggtga tgatgaaaac 60
cctagcgcct attatagtga tattctgttt cctaaaatgc caaaacgaca gggtgatttt 120
ttgcattttt taaatgtgaa gaaggtgaaa acagacacag aaaataatga agtgagcaaa 180
aatcactgca gattgtctaa ggcaaaggaa ccacatttcg agtatattga acaaccaatc 240
attgaagaaa agccatcact ttcatcaaag aaagaaatag ataatcttgt gcttccagat 300
tgttggaatg aaaaacaagc atttatgttt acagaacaat acaaatggct tgaaataaaa 360
gaaggtaaat taggatgtaa ggattgttca gcagttcggc atttgggatc gaaagcagaa 420
aagcatgtcc atgtgtccaa ggaatggatt gcatatttag taacccctaa tggcagtaat 480
aaaactacta ggcaagcttc tctacgaaaa aaaattaggg aacatgatgt ttctaaagcc 540
catggtaaaa ttcaggattt gttaaaggaa tcaactaatg attcaatttg taatttagtg 600
cataaacaaa ataataaaaa tattgatgct actgtaaaag ttttcaatac tgtttacagt 660
ttagtaaaac ataacagacc tttatctgat attgaggggg caagagaatt acaggaaaaa 720
aatggagagg taaattgttt aaatacacgt tacagtgcaa caagaatagc agaacatatt 780
gcaaaagaaa tgaagatgaa gatatttaag aatattatag aagagaatgc caaaatctgt 840
atcataattg atgaggcatc tacagtttca aagaaaacca ccctagtgat ttatctccag 900
tgcacaattc agtcagctcc tgcacctgtt atgttatttg tggctttaaa agaattggtg 960
tcaactatag cagagtgtat tgtcaataca ttattgacta ctttaaatga ttgtggtttt 1020
acaaatgaat atttgaaagc aaatttaatt gcattttgtt ctgatggtgc taatacaatc 1080
ctgggaagaa agtctggagt agctacaaaa ttgttagaaa attttcctga aatcatcatt 1140
tggaactgtt taaatcatcg attacaattg tcacttgatg attctatatc cgaaataaaa 1200
caaattaatc atttaaaaat atttattgat aaaatttatt ctatttatca tcaacctaat 1260
aaaaatcaaa ccaagcttct aggaactgta gctaaagaac ttgaaactga aattattaaa 1320
attggtcgag taatgggacc aagatgggcg gcatgtagtt tacaagctgc tactgctgta 1380
tggcatgcat atcctatatt atatatgcat ttttctcatt cttactctgg tttggcgaag 1440
agattagcta acattaattt cttacaagac cttgctttaa tgattgacat tcttgaagaa 1500
ttttcagtac tttcaactgc attacagtca agatcaacta atattaagaa agcacaaaaa 1560
ttgatcaaac gtaccataag agctttggaa aatttaaaaa ttggtactgg aaagtatgaa 1620
tctcaaattg aagatttgat caagtcagat aagtttaaag atattccatt taataaaaac 1680
aataaattta atgctcttcc taggagtata ttactagaca atataattca gcacatgaac 1740
ctacgccttt tatctgacag aaaccatgaa gatattttta attactttga tttgctggaa 1800
ccttccacat ggccttatga agaaataact tcaccatgga tagctggtga aaaaacatta 1860
tttcatttgt gtaaaatttt aaaatatgaa gttgatttga atgattttcg ggaatttgta 1920
aataataata taaaatcaaa caatgtttca attcctacaa ctatatacaa agctaaaaag 1980
atagttagca ccattgcaat caatagtgct gaagctgaaa ggggtttcaa tttaatgaac 2040
ataatttgta caagggtgag aaatagttta acaatagatc atgtatcaga tttaatgaca 2100
ataaatttac tggggaaaga attagcagat tgggatgcaa caccgtttgt aaaatcttgg 2160
tcaaattgca accacaggtt ggctacagat acaagagttc ggcaaaagtc aacaaaagtc 2220
ttccatgaga atcaattggc tatatggaac ttaaaataga atattgtata cgtttttttgt 2280 catctgtaaa ttatgtacta cacatccttt atatacataa aggtcttttt tttttttgga 2340
aagccagtta aacttttatc agcatgttgc tgtttaaaag gcgttcttta agaagataat 2400
cttgaagatt ggttttagaa gctatagttt tttagagatt ggcccatgtt tgctagagtg 2460
ggtcataata catattccat gaagttctgt acagaacaaa caccgtttat aattttgtac 2520
tgttttactt taagtaagga tgcaaaaaat agcaggactc agctaagttc taagccctgg 2580
aggttatatt aaataaaaga gaaatggaat aaaaactgta agccttttgg ctcttgtctt 2640
tctcatttcc atatctgtgc tatctagtat ggtagccact agctacatgt ggctgatcag 2700
cttagggcta aaagtaaaat ttttatttat ttacttttac ttaaatatga aaactgaaac 2760
aatgtgaaat atttttctgc ttagctttac tgtttttcag taatacattt tactctgtta 2820
ccttgcataa gatatggttg ttgtagtgtg cctgtcaaac ttgtgtgtca tttccaatat 2880
tgaatataaa catattgctg atagatatga tactgctgtc agcagatgga ttcaatgcaa 2940
gttatttttt ctacaaattg atgtaacatc atgtttatct gaatatttta tgcagacaac 3000
aggaattaca gtgattcctg tgtaaattat aactggtaat tgaaatactt attttaatca 3060
tgattaaatt atttttctag tttacacatg aatatgagca aatttttaaa tttaaaatga 3120
aggcatactg aaaaagaatc aagtggcgat gcagaaccta gtacaactgg aacagtaaac 3180
agactcaaag aag 3193

<210> SEQ ID NO 67
<211> LENGTH: 433
<212> TYPE: DNA
<213> ORGANISM: Homo Sapiens

<400> SEQUENCE: 67
gtctgtaaac agatttggct aggattattt gatgatagat cttcagcaat tccagacttc 60
agggatccac aaaaagtgaa agagtttcta caagaaaagt atgaaaagaa aagatggtat 120
gtcccgccag aacaagccaa agtcgtggca tcagttcatg catctatttc agggtcctct 180
gccagtagca caagcagcac acctgaggtc aaaccactga aatctctttt aggggattct 240
gcaccaacac tgcacttaaa taagggcaca cctagtcagt ccccagttgt aggtcgttct 300
caagggcagc agcaggagaa gaagcaattt gaccttttaa gtgatctcgg ctcagacatc 360
tttgctgctc cagctcctca gtcaacagct acagccaatt ttgctaactt tgcacatttc 420
aacagtcatg cag 433

<210> SEQ ID NO 68
<211> LENGTH: 679
<212> TYPE: DNA
<213> ORGANISM: Homo Sapiens

<400> SEQUENCE: 68
agaaatggtc aatgcatggt ttgctgagag agttcacacc atccctgtgt gcaaggaagg 60
tatcagaggc cacaccgaat cttgctcttg tcccttgcag cagagtcctc gtgcagataa 120
cagtgcccct ggaacaccaa ccaggaaaat ctctgcctct gaatttgacc ggcctcttag 180
acccattgtt gtcaaggatt ctgagggaac tgtgagcttc ctctctgact cagaaaagaa 240
ggaacagatg cctctaaccc ctccaaggtt tgatcatgat gaaggggacc agtgctcaag 300
actcttggaa ttagtgaagg atatttctag tcatttggat gtcacagcct tatgtcacaa 360
aattttcttg catatccatg gactgatatc tgctgaccgc tattccctgt tccttgtctg 420
tgaagacagc tccaatgaca agtttcttat cagccgcctc tttgatgttg ctgaaggttc 480
aacactggaa gaagtttcaa ataactgtat ccgcttagaa tggaacaaag gcattgtggg 540
acatgtggca gcgcttggtg agcccttgaa catcaaagat gcatatgagg atcctcggtt 600
caatgcagaa gttgaccaaa ttacaggcta caagacacaa agcattcttt gtatgccaat 660
taagaatcat agggaagag 679

<210> SEQ ID NO 69
<211> LENGTH: 239
<212> TYPE: DNA
<213> ORGANISM: Homo Sapiens

<400> SEQUENCE: 69
ctcctaagcc actgcctgct ggtgaccctg gccgcccacc tccccgccga gttcacccct 60
gcggtgcacg cctccctgga caagttcctg gcttctgtga gcaccgtgct gacctccaaa 120
taccgttaag ctggagcctc ggtagccgtt cctcctgccc gctgggcctc ccaacgggcc 180
ctcctcccct ccttgcaccg gcccttcctg gtctttgaat aaagtctgag tgggcagca 239

<210> SEQ ID NO 70
<211> LENGTH: 451
<212> TYPE: DNA
<213> ORGANISM: Homo Sapiens

<400> SEQUENCE: 70
atcccaagtg tccttcaaga tatcactgta ctcatgaagc tggtgtacat agtgttgggc 60
taacttggat tcataaactt cacaaatttc ttggatcaga tgaagaagat aaggatagtt 120
tacaggaact ctctacagaa cagaaatgct ttgttgaaca catcctttgt acgaagccat 180
tgccctgcag gcagccagct ccaattcgag gattttggat tgtacctgac attctgggac 240
ccacgatgat ctgcatcacc agtacctatg aatgcctcat atggccgtta ttaagtacag 300
tccatccagc gtctcctccc ctgctttgta ctcgagaaga tgttgaagtg gcagagtctc 360
ccctccgtgt tctggctgaa accccagatt cctttgaaaa gcatattaga agcattttgc 420
aacgtagtgt tgccaatcca gcatttttga a 451

<210> SEQ ID NO 71
<211> LENGTH: 351
<212> TYPE: DNA
<213> ORGANISM: Homo Sapiens

<400> SEQUENCE: 71
ggtatttctc aagctgccag atacgtttac caacgactca tcaacgacgg gattttgagc 60
caagccttca gcattgctcc tgagtaccgg ctggtcatag tgggccacag cctcgggggc 120
ggggcggccg ccctgctggc caccatgctc agagccgcct acccgcaggt caggtgctac 180
gccttctccc caccccgggg gctgtggagc aaagctctgc aggaatattc tcagagcttc 240
atcgtgtcac tcgtcctggg gaaggatgtg attcccaggc tcagtgtgac caacttggaa 300
gatctgaaga gaagaatctt gcgagtggtc gcgcactgca ataaacccaa g 351

<210> SEQ ID NO 72
<211> LENGTH: 85
<212> TYPE: DNA
<213> ORGANISM: Homo Sapiens

<400> SEQUENCE: 72
acacagcagc caggggggtac ccagtgacct tcccctgaac agaaagacca ttccattctg 60
gctacagtgt aatggaggag cccag 85

<210> SEQ ID NO 73
<211> LENGTH: 951
<212> TYPE: DNA
<213> ORGANISM: Homo Sapiens

<400> SEQUENCE: 73
gtgcacaaaa agctttaaac aagttaaaat ctaggcaaca gactccctga agtgttgact 60
gcccaactta atcatgactg tgattcaaaa atgttaataa ataaaccaag gtgtagatca 120
tggggaattc atatgctggg caactgaaat ctgctcgatt tgaggaagct ctccacaact 180
ccatagaagc ctccctcaga tgtagtagtg tggtaccacg gccaattttt tcccagctat 240
acctggaccc tgaccagcat cctttctcat ctgcagatgt caaacccaag gtggaggatc 300
tggacaaaga tttggtaaac cgctacactc aaaatggaag tctggatttt tctaacaatc 360
taacagttaa tgaaatggaa gatgatgaag acgatgaaga aatgtctgat tcaaacagcc 420
caccaattcc ctattcacaa aaacctgccc cagaaggatc ttgcactaca gatggttttt 480
gtcaagcagg aaaggatttg cgtttggtat cactgtgtat ggaacaaatt gacatcccag 540
caggattcct cctggtgggg gccaagtctc ccaatctgcc tgaacacatc ctagtttgtg 600
ctgtggacaa gcgatttcta ccagatgatc atggaaaaaa tgcactttta gggttttctg 660
gaaattgtat cggctgtgga gaaagaggat ttcgatattt cacggaattt tccaaccaca 720
ttaacttgaa gctcaccact cagccaaaga agcagaagca cttaaagtac tacctagtca 780
gaagctccca gggtgtactg tctaaaggac ctcttatctg ctggaaagaa tgtagaagcc 840
gacaatcctc tgcttcttgc cactctatta agccaagctc ttcagtgtcg tcaactgtga 900
ccccagaaaa tgggacaact aatggataca aatcaggatt cactcagaca g 951

<210> SEQ ID NO 74
<211> LENGTH: 706
<212> TYPE: DNA
<213> ORGANISM: Homo Sapiens

<400> SEQUENCE: 74
aaataacatc tgctttgctg ccgagctcag aggagacccc agacccctcc cgcagccaga 60
gggctggagc ctgctcagag gtgctttgaa gatgccggag gccccgcctc tgctgttggc 120
agctgtgttg ctgggcctgg tgctgctggt ggtgctgctg ctgcttctga ggcactgggg 180
ctggggcctg tgccttatcg gctggaacga gttcatcctg cagcccatcc acaacctgct 240
catgggtgac accaaggagc agcgcatcct gaaccacgtg ctgcagcatg cggagcccgg 300
gaacgcacag agcgtgctgg aggccattga cacctactgc gagcagaagg agtgggccat 360
gaacgtgggc gacaagaaag gcaagatcgt ggacgccgtg attcaggagc accagccctc 420
cgtgctgctg gagctggggg cctactgtgg ctactcagct gtgcgcatgg cccgcctgct 480
gtcaccaggg gcgaggctca tcaccatcga gatcaacccc gactgtgccg ccatcaccca 540
gcggatggtg gatttcgctg gcgtgaagga caaggtcacc cttgtggttg gagcgtccca 600
ggacatcatc cccagctga agaagaagta tgatgtggac acactggaca tggtcttcct 660
cgaccactgg aaggaccggt acctgccgga cacgcttctc ttggag 706

<210> SEQ ID NO 75
<211> LENGTH: 62046
<212> TYPE: DNA
<213> ORGANISM: Homo Sapiens

<400> SEQUENCE: 75
ggaaaagaaa ccaagtctcc ttgaatcagt ttatcccaat gtcttctggt tttctatgtt 60
ggctacagtc aagataacct attactaagg taggttgtgt gtttctagac caccaaatct 120
gttcaataga cctttttgca tctgagtgga caggtcctag atgacactgg agacatagag 180
gtgaactccc tccctggcct tcaggtactc acattgcatt tgggaaccta ggcattaagc 240
aaacaaccat gatacaatgt gctaagtgct atcactaaag tataaacaaa gtggtttgag 300
gggcgttatg ttcccccata ttgacctgaa gctgtagtat tttgactgct tctagagtac 360
ctgtatgtct ctgcatgtcc aggcagtctg atttattaac agggccctct tttaatcttg 420
gagtctctat gtggatgata aactgtatgg tctttctatt tataaatcaa aaaccaatat 480
aggaggctag tttaatttgt gagcaaatat gtttctattt attaagaatt cttgagttgc 540
ctgcctctac attagtggtt gaggcagtgg agtgagttcc tgatctgact cacctttctc 600
accaacagtg atacttgtac tttagcatat acatgagaga ctgagttgat tctatagcct 660
aactggaatt tattcattcc ttcatccatc tactcaatga atcaattcta catttactga 720
gcactgattg tgtgtcagcc aatctactag gcacgtggga tacagtgatg atctatatag 780
atatatctct gcccccacag aacttacaga gtggagcctc aaaaagtgat ttcaatttta 840
tccatctgct ttgtgtcttc tctttaaatc cttgctaccc aaagtaggct ctcaatatta 900
gcagcatcag tgtcacccag aagcttgtta gaaatggaga acttaggccc acctcacacc 960
tattgaatct gaatctgcag tttcaaaaga tcctcaataa tctgagcaga ttctgattca 1020
gttggtctag ggtcttcact tctgacaaac tcgcaggcaa tgtcaatgct gttggtccat 1080
ggatcgcact ttaagggact tccccagttc tttacaaaat gtgggttgca acccaatagt 1140
gggtcatgaa atcaatatag tgagttgtaa ctagcacatt caaaaatatt ttaaaatagg 1200
atagagtaca caaacaattc agagtgcatt tcatgtcatg atgaaggcat tgttgcatga 1260
aacttgaatc agctttttgt acatctgcac acagacacaa acacagatgt atgtagactg 1320
agttctgatg aaaacgtatt tcttaatacg ggtcgcagct gataacagtt tgaaagttat 1380
tgttctagac aagcttatct aggccagaaa gaagtcctca gaagtgattc cagtctagaa 1440
cagagagctc agatcaaagg ggttctgtta atattagaac tatccagaat cccagtgagg 1500
acatccagga aaaagtagaa cagtggggct agaaagatcc tctactaggg gtgacagctg 1560
tgtgctgatt ggatgatgag atgcccatga ttagtggctt gtaccagttg gcattaggtt 1620
tttgcatgac ccaagatttt ggactgtgag ctccttgaag gtgggacctg tatgttactc 1680
ctagaggcta aaacagtgcc tttcccgcag gggagtttc cgcagtgtac tgtgactttt 1740
tatatctttc atactactca atataccaca tgtaacaaat gaggtctttt ctgtctttcc 1800
actgggaatc atgtattatt catctttgct tttttctagg gcctactcca atatctagag 1860
atggcagata ttcagtaagt ttattcactt aacaaatatt ttatttgtta ttcagcaaag 1920
aagattttct ctcagctata ttacatcagt tttagaaggc acacagatga acaggcttga 1980
taaagagcaa atctgtgaaa aacaaacact tgtggactaa atggtatcac atttacagag 2040
ctgtaagaga ggtataagtc accctgggca ccgagtttta tgctgtattg attaactttc 2100
catttccctt ggttcaattt tagtttctct cttagaatta tgtttctacc ctttgcattc 2160

-continued

```
tcaccgccaa tcatttattg ctgcacgtgt ctttcccccct ccatatactg tgctccttaa   2220
ttcactaagg gactgtacta acatagccta aatacccacc ttccagccac ccttcaggag   2280
ggtattagct gtatttgtgc acagcgagag tgccttcaag gcagagggct tcctccccta   2340
tacttcacct ccaaatctct ttcctttcca caaatgctag tgctaggcag ctgtgctcac   2400
tattattcgt cttctctgta gttcttgact ttgcctgtac gttataaaca cttggtattt   2460
taatatttcc catgtccagg ttgcagttca aaccaatgaa gtcagaatct ctggaggtgg   2520
gacaaaggta tttgtagttt ttaggcttct cagatgattc caatgtgcag tgaagattga   2580
atgctattgc ttagaggaaa attcagtcac ctgatatttg aagtttaggt aatttcctta   2640
gccctcaaaa tatgttcatt tcttttctag tccttagtat ccctgcccaa gtctgaaaat   2700
atttatattg ctatttaatc agaagtaaag caattaaaat gtacatgtta ctcaagaaga   2760
agaaacatta gaacattgct caacttatca cctgtgtggt tattaagcta ttgtctctat   2820
ttcaaaagca cctttctgta ttctactttg tgactctggg tttttttcac catctagctc   2880
ttaggtggca ctagaagagg accacaagcc tgccagaggg aggagagtat tgcttcttcc   2940
tgttcccatt agtgtcacct cagcagtgac ttttcaccct ggagtggcag gcaagtttct   3000
agattatttg agtactcccc aaatcagtct tgctgcaccc cctgagagat accagcagca   3060
atgaagtgtg agtcccagct ctgggctccc ccctccaaga ttctgggttt tcgtaatccc   3120
ttgtgcttat taatgctgtt accttagggt cctttttttt ttttttttta attttcaatg   3180
cttgtccagc aagtttccta tactaaattg ctatatggaa acatctattc ttctctcctt   3240
tgactgtacc taactcaaaa tgccttctca tttaacaacc agtgctctgc aacaaggtga   3300
gctttctagg aaggcaaata acaagaaggc tcaggttggc ttgtctccat tttggggcaa   3360
tgggagtgtg ctggaagtct tccaaggaac aagagtgaga agaagatgct agaatgaaga   3420
ggtggacaga catagggggag gaaagcgcac tggatacaaa ctttattacc ttcattattt   3480
tgctaggtct gtcttagctg agagactctg agagtattaa tcagagataa atgggaagta   3540
agtaatagtc tatagtaatc catagtggca tttattaata atacaaatct tctggcctcc   3600
atctcttctt cttcccataa gcccacagtt tgtccacaca taagcatatg tggttttgtc   3660
cttaataata gggtagtgca aatagttaat tcactactcc tagtgccacg agtggcacgt   3720
tggagaccat cctgtctgtt cttatgtaac ctgtcataaa tccacgtgga tatgtatctc   3780
attaagacag ccatttagga tttgcttttt cagaattgtc tactttggtc agtagtattt   3840
taactgtaaa ataaggatgg tttcacttgg tccaagtgtc cctactgtac ctaatacatt   3900
taactttaca aacagtttta tacaagcaat acattaacca atgagctgta atgagtagaa   3960
tttggatgtt catgagggag atttaaattc acacaccatt ttcctagact ccttcactgt   4020
cttgacactt tcctattatt agctctcttt ttggagatat tttgtgttaa aattccaaaa   4080
agttctcagt caccatctga gaatttttgc gtatacaaca atgtaaagaa aaactaggcc   4140
ttgctaagat gaagtaccca ggatcaactg gtagcctagg agtttgacta tggtccacga   4200
ttcaaattgg tgggccaaac aataacaaag gtggactttt gggggttact tttgtacatt   4260
tgctttttgt atcctcgcta aagaggtgaa gtaactagta gccagtgtgt tgaggggaaa   4320
ttcactactg cctggaggct ctactgtgta ttctacacct cctggtctcc aatgagatct   4380
ttatttcttg ttttgaatac ttatattaac tccagaaaaa atttagttct agaatctgga   4440
tactgagcaa cactgcagct ctctttctta gttcaaatag tctcatctgc ttttctttga   4500
tgaatctttt tctttgtagg atctgtttct ctgtgggatc aacattttct ctctgtgtgt   4560
```

```
cagaaagaat gtcttttacc gtccttgaca gggagagtca ctttctgttg catgtgagca   4620
atcagagcaa tcatccttct ctcacgttga atgagtaggt caaacagtat tagtaatatt   4680
gcctagttta ctctaatgtt gattatatta gttttttttgc atttttgtg atctagagct   4740
tcagttgaac ctttcattct gaccatgatt atttagtaag accacagatc catccactaa   4800
cttaaaggag aatgaatgac caactgtaac cccgccatct gattaggaaa acaaggaaac   4860
aaacaaaggc aataaagccc ttcaaaaatg tttttaacca gaaaacactg aatagtagaa   4920
atatcactgt aaatggagtc aggcgatgtg gattctagtc aaagctctac cacttattaa   4980
ctgcgtgacc atagaatgtc gcttaacctc tctgaacctt agtttcctat tccataatgc   5040
aaaacgtaag ttataatatg cgttttgtcc accttacaga caaggatctt ttacagaggc   5100
tggaaattcc tccaactcgt ctgttcaggt tgactttctg gaaaagtgtt ttattctcag   5160
aggatttgat tattgagtta tctttctatt ctgctgctgt cagtagattt gccataaatg   5220
tttcctgaga gtctctctct tgaagagatt caggccccag ttaagttcat cccaattaaa   5280
aatagaaccc tgagatgcag cagctgtagc acctcttaaa cctcttcaaa taacattgaa   5340
cgattaagtg gctgctactg tggagatagt gcccacaaaa ccagcagcag gccctctcgg   5400
aaaatgataa cactctaagt ggctgtcagt ccttagtcat ttctagtcat tcaggggatg   5460
ttgccttatc ttctacaagt tctaaaagtt cctgggaaga gaagaatcac ataaattctt   5520
tatttaaaaa aatccccctt cccacagcaa aattctctaa aacaatacta aacaagcagg   5580
catgcgcaat tctaatgaag tctatcattt gagtggaaga gaattgctat ggttaccaat   5640
gtttctgtct ggcagttttg ggataaaagt ctgatgaagt gatattgtct ggaaaatgag   5700
cattgattcc tagggagatg gaagaattta cttttttttct tcctatttct tgaatacatg   5760
gctagctttc aaatatatga ctcaacaatt acattcggct tgaatggatt tttttctgac   5820
attgtttctt attttcttct gatttatcaa ggagagttta aaaataaact ttccttatcc   5880
catccataat agaaatttca gctattaaga acttaccaag tgaaaaatta tagaaatcac   5940
taaagttcag agggagatct ctttattata tttcaacagc tatttgcttt ggagacattt   6000
cttttccccc tttgtaaagc taaattgcat atatcactat ttattaataa gcagaatgac   6060
aattatttag gctgccaaat ctcttttata aacatttcgt tagctaggta ggatttttat   6120
atactttccc aaagggccaa gttgacagac atgggctttc actttatttc catagagatc   6180
tggatccaaa tccctgggtc caaatatatg ccattcactt cccatattta gtcctgttat   6240
ctctctgaag actggcccaa gagaggcctt tctgatgaga catttagcac agcgattaat   6300
cactagataa acatgtgaat gggtccattt gcaaagtgaa agctccctaa acagaggctt   6360
gtcctttaca aaaagagcag gtccaatttt ccttaaaagt tcatggttgc ctatgtggtg   6420
tgatttgaga aatcctgaac cttctgttcc cattactttc cctgttgagc tctacatttc   6480
atagtgtatc actcctgtgg atgaaacctg gcctctccag ggcagtttct ctaataaatg   6540
gccatagtcc tgggaaaggt cctgatgcct tagtgtgcag tgtgcttgac accataagat   6600
cctttcttct ttgataaaaa aaaaaaaaaa aaagactaag acaagaaaac tggtggctgt   6660
tggggaaagg tgtggaaaga atgaaagaag aaaaccgatg catggaaaga tggtaaagta   6720
ccaatggacc ggtgtgagtc aggttctgaa tttaggagtg aggactcaaa tatgcctgtt   6780
tactgggtta gcttttggaa cgatcctatg gaacatatat cctatgaaca ttatagaagt   6840
cactaaagct gactgcaaat tgagtgtaag ttgagagtat ctttctggaa aaacaaattg   6900
```

gaaatattta tcaaagggat aaagaactta catatattta gaaccaaaaa tttcaattgc 6960
aggactctat cctaagaaaa acaattagca atgaacacgt ttcaacccaa agatgttcac 7020
tgggacatta tttaaaatag caaaaatatt agaacaagtt acatgtttat taatagagaa 7080
atgaatacta tggaaataaa tttatgctgt aaaagtgacc aaataaagct tggctcaggg 7140
gctcatgcct gtaatcccag cactttggga ggctgaggtg ggccgatcat ctgaggtcag 7200
gagttcgaaa ccagcctgac caacatggtg aaatttcatc actactaaaa ataaaaaaaa 7260
ttagccaggt gtggtggcgc atgcctgtaa tcccagctac tctggtgagt gaggcaggag 7320
aatcacgtga acctgggaag aggaggttgt agtgagctga gatcacgcca ctgcactcac 7380
cctgggtgac agagcaagat tccatctcaa aatatagtat ataaaatatg ctaataatat 7440
gatctcaaac atataaaata ggtaaaagaa aggaatttta atagtggttg tccatggatg 7500
attgctattt ttatttattc cttttcatat cttctaaatt tttcagaatg gtcatttatt 7560
acttttaggt acaaaaaagt tatttaaaaa ttcatccaaa agcaaatgtt tgtgtcaacg 7620
ttacaaacct aaaatatgga tgtcctctaa ggaggttgac ttcagctgta tagctatttc 7680
ccagtggata attaaagacc tgtcagactt tctctcatat atgagtcctt tatgtttaag 7740
ggctgtaatt ctatataaaa tgtctgcata gaataacatt tggcacctga tgtttgattc 7800
tggatagtat tgtagttctc tattgccaaa tgtgagacta aaaagttaga tggaggttag 7860
catcaagaaa tgttttctaa gcttttcccc tggaactgga caatggtaga aatgtgccag 7920
aagcaaagga agcctgtgga ataagtctct ttcagcccaa agttatatta aatagtttca 7980
tctattcact ggacatagat ttgagtcatc aaacttcttc cctaagtttg gtttgcttcc 8040
catgtttcag atatatctga agagcaggtc tggcctcact gccttggtac catttggtg 8100 atcttccctt cacctggaat gcatcttaaa cctctcctat ctcaggtttc ttaggcccac 8160
gttaggtaat agctctttga aacttctact attgccccca attggtgtga tctccccatc 8220
ctttgaactt ccatggcaca cttatatggt gttttcatat taactctatt agattatcaa 8280
tttcttaagc acaaggtctg ctgtgcctta ctcaactttg tattccccat gtcttgccca 8340
tcttagcaga actgaatttg tttatttaat gaatcaggta ctagtttggc tggcccaaag 8400
tctgactgtc tcacttcatg ccatttagat atgatgccca tttattagct ctaaaaaatc 8460
acaagtaaga ataacaatga atttttcaaa acttcttgat gaaatatctt tctagaataa 8520
actattaaga aaacaaaaac atagagcaca gagctacaaa cttaagttac cagggtgctc 8580
taccatggtt tattgatctt tagtagtgtg gaagaacaac ctgtgctttc gtgttagaaa 8640
gaactgggtt tgaagctaat cttgacaatt attggcagtg aaattttggg ttaatgttct 8700
atcttcttca agtttagttt ccttactttc aaaatgtgga attagttaat taatggctgt 8760
ctcctagtgc tgttgtgagg gttatataaa atgatgtatg aaagcactta gcaaagtatc 8820
tggcacacag atttaagtct ctatgctcat gaggacagag aatccatcat gtccaggaca 8880
atttatgttc tcttggaaag tcagggttat atcccctaga ctttgcaggg tagttaattt 8940
ctgggtctat tattctgaaa tcaccaatct actctcataa ccacccccca ctccgccaca 9000
cagacacaca aacagctcat ctgaaaattt tgtaggaata ctgatgttgg gctctgatat 9060
ggtttggcag tgtccccacc caaatctcat tttgaattgt agctcccata attcccatgt 9120
gtcataggag ggacctgatg ggagataatt gaatcatgga gggaggtttt cccatgctgt 9180
tcttgtgata gtgaataagt ctcatgagat ctgatcgttt tataaagggg cgttcccctg 9240
cacatgctgt cttgcctgcc atgtaagact ttgctcccca ttcatcttct gccatgattg 9300

```
tgaggcctcc ctagccatgt ggaactggga gcccattaaa cctctttcct ttataaatta   9360
cccagtctcg ggtatgtctt tattagcagc atgagaacag actaatacag gctcagaaaa   9420
taatacctcc aaatgagagc ctccacagca gccttagaag aaaaagtttt tctctgacct   9480
tctcttgccc tcctatctct cagtcccatt tttcctcaag gctaggcata gaaaccagaa   9540
tccttcccca aggaaggtca tagaaagcag aacctctttt cccaaaagcc agccataaat   9600
cctgaaaata ttatatgtaa gaactgacca taaagaaatt atctgaccca cattgtttga   9660
ttctaggaca taagactgcc atttcagaga gggctgtgcc ccacaccaga aggaaggaat   9720
gcatgttcag agaagccaag aagaatctag actggctggc cctgctgggc ttccccactc   9780
attctcttag ctttagatct taccctttt gtccaggcat atttctacat gactgctcat   9840
actttgttga atctaagcat aaaaatggac aatttcccct atatctttgg gttttaatta   9900
tgaaggctct catgtataca cattagataa atttatatgc catttctttt gttaatcagt   9960
ctgcttcata tcagtgattt tcagcaaacc tctaggggcc agagccctgg ttctcacatt  10020
gagctggaat attgaaggaa tttctgcagt gaaatcgtat ttggctgtac atatataatc  10080
tgtgaacctc ttaaataatt aaagcataac ttactaataa agcaggaaag tttagtgggc  10140
tccagaaccg aaaccagttg gatttaaaat cctgctgcta tacttaacct ctctgtttct  10200
gagttttctt atctgtaatg tgcgatgata atatctgcct tgtagccttg ctttaaggat  10260
aaaatgagct aatgtctaac aagcacttaa aacagtgcct agtatatagt aagccctcaa  10320
caaaagctag caattcccaa ttaattgatt taaaagctgg agctcttaaa ggactatgtt  10380
gagccaaagt attccaataa ctaaatgaag ctcctgtagt agagttggag ccatcttttg  10440
ggggcaggaa gggagtgtat ggcgatttgt gccttatagt ggtttggatt tgttaacagc  10500
actagtcaag gaacacagtg cgctgaaaaa gttgccagac gccagatgag ataaggagcg  10560
tcctgtgagt aaggacagac ttgaacactc ccagcacata gacaaaggaa gtgatggctc  10620
tgcctaagaa atcttgtcct tcaaccttga cttcactgga tttttttttc agacactgct  10680
aatcatgtaa ataaacataa gaacttcctg atagtggact atctctgttt tcagatgtaa  10740
ttcctacctc tatttgcaac atgggtattt aataaaagag gaataaagag gcatgcttga  10800
atggataatc aagtaaacag attttctgat attaaaaaaa taaaggaagt atataatttg  10860
ctctggttat ctggtctata ttttatggct aagtcatttt aacatttcag ggactttctt  10920
cttgtataat acctagacct ttactttcat atattgaaac ttctctactg attgattagg  10980
tttgttgttg ttgttctgtc tcacttattt ccatttattg tctgttgtac tttttgagtt  11040
tttttaaaaa cttaagcttt tgattgaata tctgggtttt taaaataata tttttaattt  11100
ataatttaag agatgattta cttagtttaa aaattttttt tctgcttcct gcactgtttt  11160
ctctgagtct ctttctaggt tttttggttt tgtcttttga ttgtggctca tgcatttttt  11220
gttaggggat ttcctcaaat gtctggagaa cctagactgt ccattcataa ttataaatga  11280
tgtactaaaa aggtattggt aataggctta atagcatatt aacaaagagt atgcaaactt  11340
tcttatggga ggagatcccc aaaatgtctg tcttagttct tttctcttgg gtccgttagt  11400
ttctctggag aggaatttta ttctatctgg ctggtcttag gttggatggc agtattctca  11460
gagctgaatg tgggcatgga atgagtggtc tcactcttca gcattcagac tttcacttaa  11520
ttgccctctt ttttagtgca ggtgtcatag attgcaataa cagcaccaat tctgcatgcg  11580
tccttgtatt cacatccttt gctgtgagac tgctgtttct ctccctgaat aggtggggtc  11640
```

-continued tttttatggg gtcccgagtc tattctactt tgggcaataa aatatgacag gattgacact 11700
gtatcacttc caaggttagg cttcaaaaag tgtgcatttt tgtctgttct ctcaggcctg 11760
tcactggcat aagaacattt tgaacatggc tgccagatga tgagaggctt gtagatcaga 11820
gtggagtcca catagtcacc ctagccaaag ccagcctaga tcaaccaacc aatgttccag 11880
catgtgagca tgcgcagaca ggatccacct cctagccaat cttcagctaa caccatattc 11940
ctaagcaata ctgttttatg gttgtatacc gctggagtta tgtgattgtt tgctataaag 12000
cattattggc ataacagata attacagggt ttcaccacca tcctcagatg caaatctctt 12060
tagaaattaa cctcctgtct tttgcccaga ctggggagaa gtcaccaagc tataggggta 12120
gggagggatc aggacatcaa actgcacctt atattaatct ttaattaatc tgggctccat 12180
actcgatctc tgatgtgaca attcctgagc ttttccaggg ccctgtggct caagtggggt 12240
catttctttt tgaatctctc tctgcaggcg ccaggttttg acctggtcta tgctcagaca 12300
ctttccattt ttagaggttt tatttttcac tcttctttgc gttgataccc tccttggttc 12360
actttgcccg tggggtttgg gctctttagt ttttttcctc ttatatgaag aaattttagg 12420
aggaagtggg ggtaaacatg tgcttttaca ttccatgttt agccagaaat gtctccaggt 12480
tttaattttt caccttgact ttaaaacttt tttttcact tgtaaatgtt catctggtag 12540
gtgtgattta cttcagggtg ttaaatggca tgattataaa catctctctg aataatttaa 12600
tataataata attggctcct atccaatgct ttttctcttc ttcattgaat ctcatatata 12660
aatttatttc atggatattt atcaaggttc tattatgggc cacgtatagt gccaacatta 12720
gtgaaacagt gggaaacaca acagacatgg tccctgtcct taaggaactt atgatatagt 12780
ggtttatcac tagtcttctt gaagtacttc tttctgcctt gtcttagtaa atatcctaag 12840
atcacccatc acctacctcc gttgttcact ggagtttata gtgtggtgag ccagcgtaag 12900
agtggaatca cagagttgtc aatttaaata ttgggcagta acttacccct ttttaagcct 12960
tgggatcttc agtgtaggat gaaatgttaa aaaaaattag actatattgt caacatttaa 13020
aaattaagag ctctctcttc tttctccgaa acacacatgc atgcacattc tgatttctcg 13080
cttctttcaa aaaatcaaga tactgcaata ttgggccact ttcctacatg atattaagca 13140
gaactcagta tgggctggcc tccttagatg ggcatggtct gtgtaatttg cctaggacac 13200
caccacttcc cattatagta agaaagtttt atacatttgt gttatttgtc tggcctttat 13260
gggcattgaa gttttccacc tgctttagat attaggaaat ggcagtgcta tttaaaaaaa 13320
ttcctaaagg aatactaatc tgttaacctg tagctttcaa agacatgaga cattatattt 13380
ttcccagata ttatagatca gaagttctta aatattaatg tatttactca tatacacatt 13440
tagtcataga ttttaaatat atttcaacgt ttagttgttg aaaactaaat gaagtaacaa 13500
cagtacttga taatgactgg gttgcagatt ctcaactagc tttgaccttc ttagatgttt 13560
cattttgtga aatccataat ttatttgatt tctggccctt tgtgttaact cactggactc 13620
atttgctctc ttggtctaca gcctcctctg aattgcttct gccctgtttt cactttgatc 13680
cagtttccac acagttctga acccatggct ccatttatca aacctcacgc tgtgccttca 13740
gaagcagtct tcatgttttc tctccctggc atttgggcta tgggcatccc ttaaagatcc 13800
cagcctggtt cattcttcta gtcccataag cctctgatta actttagtgg ttcaacagaa 13860
ctgcatctct gcaggctctt gcctggtcca gccttgctta aaccacccct cctaagatca 13920
aaaaagaggg ttcaaatatc ttgttaaccc tagggtcctg tgatggttat ccaagttgag 13980
cagaatactg ttgagatatt aagattgatt tgaacactga agtgaacttc ccacccatga 14040
aaatacatga ataaggattt tcctctcttc cttaggaaaa aaataaatct ttgttcctct 14100
gataatccta ttgcccttgt attttgccta atttcttcaa gagatataca ctcaacaaaa 14160
aatcaaatat aattcaaggg tgttgtagtc gagaacaata ttagaagaag gaggttgatg 14220
accggtctcc ttctctgcag tgttcagtgc acttctgaga attgtgcttt gccatgcata 14280
ccaccaaagg agggagggag atgcagataa actagaggtt gtcctcagga gagcctttag 14340
gatggattgt gggaacccaa agggcaccca tgtgaggagt agttgagaag atagggaaga 14400
gtatgcttgg agaagaggag actttggggt cgggagtggt agtttgagag agggcaggaa 14460
catagctgtc atcagaacta tcaaattgtc acatggaaga aagggtaaat gactccaaag 14520
gattgaagtt gactcaatgg gtagaaacct cagaaagata tatttgggtt ctggttttct 14580
ttttctttct ctttttttatt taaagaagag ccatccaaat cttttttttt taattatact 14640
ttaagttttt tattatactt taagttttag ggtacatgtg cacaacgtgc aggtttgtta 14700
catatgtaca catgtaccat gttggtgtgc tgcacccatt aactcttcat ttaacattag 14760
gtatatctcc taatgctatc cctccccccct cccccccaccc cacgacaggc cccggtgtgt 14820
gatgttcccc ttcctgtgtc catgtgttct cattgttcaa ttcccaccta tgagtgagaa 14880
cacgtggtgt ttgctgaacg cgcccgatct cgtccaaatc ttaagttttc tgtgagggag 14940
aatagtctgg acctctatgc aactaagcat aaagtggatg accacttggt ggggatattg 15000
tagaagggat tgactcattg acagggtgat tggaccagat gatctttaag atttccctct 15060
atcctgggat tctacagtgt ttaaaaattg tcatgacagg agattcctgc acattttaaa 15120
aattaaaatc acaatattgt acgtgcttta gaaagcctag cggaatggat ttaattctgc 15180
ctattgtagt gataataatg caatattaat atgtggatat gatctgttta tggattactc 15240
atatagacaa attagacata tttattggtc aacaagtgcc actacacatt gttggaatac 15300
atgtggctgc tttttttcata aattaatcat tggagtgaat taagatgaga acataacaaa 15360
tgtcagctca taacaaatgt catctaattc tagaccccaa tttatagatg aaaataatat 15420
atattcattt tcttccttct ctctttccaa attggtagag aaaagatata aatattcctc 15480
ttatatcatc acttagagat aagaatatgc taaatctgga aaattctgtt aggaggacct 15540
ataatggaat aattctgcct catttctttc acatgagata aacttcactt ttattagtat 15600
ttctccccag agtcttctct aatcttctca atttgggttc ttcccatttt ctcccatgtc 15660
cttggaccac ttactgtgtt ttaactagag catggttata tgtaaatatg tgtgttttcc 15720
ccagtggatg gcaaaaagga atcttccttg cacatttttg taatccccac aatacctact 15780
gcctttcctg cgtggggtga ttctcaatag acgtttgtgg tttgaaatca tttcaaatca 15840
caaataagca ccttcactta tgcactacat atttggtcca gcagttaata tgacagtact 15900
cattaaatat cccatgtgat attgtgatga acttgctttg gaagttattg atcatgacca 15960
ttatatgaga agaagaaaaa cctgattact ctgaacacgt aggagcacag cagaaaagaa 16020
aatgcaccta aaaggatttt tgttttctga tttttttttt tttttttgca cagctttcaa 16080
gtgcagacaa ctttttcttg ttgtctagag ccattgcttc cagagcttat gaggagctat 16140
aaaagaggtc aggacacctg ggtctagtct cagctctacc acgaactagc aatgtggcca 16200
agcaccaagc ctttctggtc ttagctttct catttataaa atgaagaagc caaagttaac 16260
tggatttcta gcccctgcca actctcatat ctctaacagt aagttgagag atttttctct 16320
ctctgacatt gtcccctttc tttccacctc tcacaatgtg cgcaacttga gataagttac 16380
ttcacctctg tgtggctcag ctttcccatg tatacaatgg gagataccta ctttttagtg 16440
ttgtgattag gattaaatga gttaatgcat gtgaagtgtt ggaacagtgt ctgatgtgga 16500
atactcacta atgttaactt tttattttac tactttgctg aaaatgttag tgtatttcca 16560
gttgttaaaa ttacaaacca acccctcaca tggtgcctga ctcaggaact ttaccgacta 16620
tgggttttca atctatttta tatcattcct ctttattttt taatttttag tttttgatgc 16680
agtgtctccc actcttgccc aggctagagt gcagtgatgc aatcatagct cactgcagcc 16740
ttgatatccc agcctcaggt gatcctcctg cttcagcctc ctaagtagct gggatgacag 16800
gcatgtgcta ccgtgactgg atttaaaaaa aatttttttt atgtagaacg aggtattact 16860
atgttgccca ggctacattc ctctttaaag tagcattata taaaattgta tttccgtctg 16920
ttctcagaat atctctgatc attcacacac tgtagtctat aattttctat ctgtatcccc 16980
taccctgtgt tgctcagtgt gtttgttttt acacaactaa tctttggctt ctggctcact 17040
gtcctgtgtt gagggaccat gtagagactt cggtgtttgc catttccatg ctcatagaac 17100
tcattagtac aatagatgga gacacctggt gcatagagat ggaggactca gcatgagaat 17160
gtcccatttt ccatagccct catttttgct tggagcatga tgaatgttac actggcatag 17220
ttaagaggtc catcagttca gttcagtata ttataagtaa aattaaatat attgagcatt 17280
tcatctgtga taagctctgt tctagttttg tatatatgag aaaatatatc caactggagg 17340
tagaagagag aaagatatga agagaacaac agcggggtct ttgttctcaa ggagtctgca 17400
ctgttgctcg atgtggtgct ctagatatca gggagaagta tgccttggaa gataataatt 17460
gacacctaca tagaaattca atggatacaa aatcctttta tatatgtaat atcgtttaat 17520
ccttcatcac tattatttga tttaatccaa agtttaacta agttttgcag aggttaaata 17580
acgtgccagc aggctgccca gccagaacgg gaagtcagaa tgttcttctg cctgtagggt 17640
gtgtgctcca atgtgcctgg agaagaagaa tgtgataatg gataaaacgc agaggttcct 17700
tgtatgtttt actgtttttt tttgttagtc tgtagtacac ttctgattct ccaaagtggt 17760
acacaatttt ccaactttga atttttgaca gagtcatgat ttaaagcttc aagcatatga 17820
ttatgagatg gtggttctca acatttacca caacctccca gcaaaccaca cagcagtcaa 17880
ctctcaagat ttcttccagg agggtaaagg gatttttctc ttcacatgcc atccaactcc 17940
atgggaaaac attagcagtg acaaatgact ctggatgaat gcttgaatcc gaggtaaata 18000
tgagcctttg ctcctccaca taagaaaggt gccatcagag tattctctat gaatacattt 18060
gaaagacaac atctgaacaa ttttggttat tatctattag ccttcaggag aatttctata 18120
attacgaagc acgcagtggg aagtgttatt gcttggagcc aagtctattt atgttgatat 18180
ttgtagatat ttacatttat tttctttggc agacatagac aaacacattt ctgaaaacta 18240
ctttgtctgt ggaaaaacga agcagaatat actttaaaaa aatctaccac agaaaggata 18300
ataatagctt tcatgtctga agacaacaga caggcatgaa atataagaat tattttatcc 18360
tggacaagag aattggtgtt agagcaaatt ttgaccatgt cacagtctgg ataactctta 18420
ggtttaaaac ttgcaccccc atagacctca gtccacagag gagataactg atctggggct 18480
tagcagtatt ggcagggtgg tgcattatgg gatttagcta tagagtgttt gctccccaaa 18540
gagagaactg caggaatttt aagaacttgc atcaattccc ctgtgtagaa cagtatgtct 18600
aagtatattt caagtaaatc ctcaactcaa cacataaagc tgcagttaca ccacgccttt 18660
aaaaggaaat tagagcacag aaacgaggcc agactgcccc tcctggagac aaatcccctg 18720
ttcatctctt caactgctgt cagtccttaa gtatgtttac ctcctgtccc acccacccca 18780
ctaccacatc agtttcaggc tcttgatttt ttcttccagg cctcaaaaag catgtagcaa 18840
tttatataat ttttttagac attgtttttc tagcaaatta attcagatca caatgctttt 18900
tgtgatgaat tttaaaacat tgattatctt ttttttttaa gaaagtcctc aaaaatggtc 18960
tttgaagggg agatttgctc tgatgagtat gatataaaac ctcagccttt gaataaatac 19020
aatatgcctt gctggcatag taactaggtt gcttggatga ggatgcatac taattagggc 19080
aacttaatgg cataatgact agggtcattt attcatggtt ggttgttctt caaatgtaat 19140
ttgggagaga gtgccaatgc atacccattc taccttcaat agagagagtg gaattccaca 19200
ggtttatggg gacaaatagg acaacacagg taatttcaca gatttgcagt tagcagtttt 19260
ctatttgata cccacagttt ttaacagttt tagctccaaa catgttagaa ttaaacctca 19320
ttgcctgtag agtttaaaag acagcattat catctgtatg tgtatgaggt ggcaacaact 19380
ttgaagacaa acataaggca taggtggcac aggttcaagg acctgtcact ctgtggactc 19440
acttctgaat tgttcagttg cttttgctct tagtcacctg catctagtag atgcattttg 19500
gaatatccca agaaagtgaa aatgacctaa cattattcaa gctgtgcttt ggtgtttctc 19560
ctgttgacct ttgcctgtta cttgactttg gttgagtaaa gagctatgac atggatatcc 19620
tatcatttca tattctggcc tagtcctata tctatctcaa tgtataattt tcctgcagtc 19680
atactgtcta atgagtgctg gtgagaatta tgtatcatag gtttgaaata agatctattt 19740
taatttttga agagtgatga ccaatatgcc attccgtcta tttgactgaa actgattgca 19800
gtagtagatt atattctctc caagacagta atgacaccac gactgttttt aatgacttcc 19860
aacataggaa gaaaaactta gaactcagaa ctcagggtgg gtgtggtaga agaattatcg 19920
tataaaatcc atatgtttta gagttggttg tactgtagta gaagagctca ggtatgtttt 19980
gggttagtat agtccctcaa acaatttctt tcaaatgttt tctttcaacc aaatctgaaa 20040
cacattttgc caaaactttt tttcccttaa tttttaaagg catgtgtatt taaagggaca 20100
tttaatccat atgttttggc tcatttacac ttaactcatc aggatattgt ttttaagagt 20160
tatttgagct ccacaaaacc cattttataa gtcttttctt ccgcagtaca aggaagttgt 20220
gttttgctgg aaacagaaat ggaacccaca aaataattaa gttcggatga aaattgagaa 20280
tgtacaaggt ttccgaaagc cactaaactt aacttagaaa aacatgttat tctcttgcag 20340
ttttttagtt acttctagat atcaatatgc tttagccaag gtgctaaatt agaacatctt 20400
ttaaatcttt atttcgcagt taagtgtcta aatgcttatt tcccaaaata ccatctttag 20460
tgtaatggat aaaagcaagg ttaaaaaaat aaggagcata tacaaaaaag tgagctctaa 20520
atttcttttg aggttgatgc agagctatga tcttgaacct tcattgtgcc ttttctctcc 20580
ttgccagtct tttcatggaa ttatgcctgc tatgcccata aaagttcctt ctgctgtgtt 20640
tcatgaatgt aggtagctac tgctacacag gatctcactg tgtctgcatc ctcagcacct 20700
tcagagccct cagatatttc ctgctgggta gaaggatgga tctagggaat ttattagaca 20760
atatagtggg atttcccttc tgtcttgtat ttctcaggaa gattggtatc tgaggatatt 20820
cctggagaga actcaagaaa atcaacatat gctttagata gggtatatac agacaatgtc 20880
cctgaagagt tgggtgagag ataaagccct tcagatcagc attgacctga aattatattc 20940
tcatcatttt agagagaagt tgagcacctc tgaaataaat tttgtctatt gaacctcaat 21000
atctaatgaa aagaactacc ctttctcaat aaaaaaaaaa ttactacaac attttccata 21060
ggccccagaa ttccttgagc aaaccttctg taatgagttg agttgttgat actccccttt 21120

```
tcttctcata tttgggtaga tatctgagta aaaatcaatt tcaattagag aaggtaagag  21180
caaaaaatta ataagatttt tatatttcat agtaaaatat aaaaatgtgt attagacaac  21240
aattagtaaa caagtaacaa aatggcagta gtaaggccta atgtataaat aataacatta  21300
aatgtaaatg aactaaatta gtcacttaaa agacagtatg gctgaatgga ttaaacaata  21360
agacccaatt atatgttgcc tacaagaaag tcacttcacc tgaaaagaca tacatagact  21420
gaaagtgaag ggatgggaaa agatatttca tgcaaatata aaccaaaaag aacaggagtg  21480
tctatactta aatcagataa aatagagttt aagtcaaaaa ctgaaaagag agacaaagaa  21540
gaggattcta taatgataaa acgtcaattt agcaagagga cataccatag taaatacata  21600
tgcaaccaac actgaagcac tcatatatat aagaaaatat taatagatct aaagagaaag  21660
acagattaca atacaataga agtaggatac ttcaacaccc cgcttttggc aaggacagat  21720
cagccagaaa atcaacaaac aaacattgct gtttgactgt attgtagatt aaatggactt  21780
aacatacctt tagagaacat ttcatccagt tggatgtgaa cacacatttt tttgattacc  21840
acatgaaaca ttcttcagga cagaccatat gttagaccac aaaacaagtc tcaacaaatt  21900
ataaaaaggt ctaaatcata tcaagtatat tttctgaaca caatgaaata aaacaagaaa  21960
tcaatagcta gaggaacttc agaaaccata caaatacatg gaaattaggc aacgtgctct  22020
tgaacaacca gtggatcaat gaagaaatta agaaggacaa taaaaaattt cgagaatcaa  22080
ataaagacag aacacaacac acctgaacct atgagataca gaaaaagcag cactgaggga  22140
attttatacc agtaaatgcc tacatccaaa taataaaaaa aatttaaata attaacctaa  22200
caattcactt ccaggttact agaaaagcaa gaacaaatca aaccccaaaa tagtagaagg  22260
aaagaaataa caaagatctg ggcagaaata aatgaaattg agactaaaag aaaaatacaa  22320
aatattaaca aaattaaact ggttttgaaa aaataaacaa atggacaaac ctttagctag  22380
atcaactaag aaaaaaagag ataagaccca aataaataaa atcagaaatg agaaaggaac  22440
attatgatgg ttagcacaga aatacaaagg atcattagag accattatga acaactatat  22500
gccaaaaaat tagaaaactt agaagaaatg gatatattct gaacacatac aactcaccaa  22560
gattgaacca tgaaaaaata gaaaacctaa acaaaccaat catgaataat gagattaaag  22620
cagtagtcta aatttggtca tcaaagaaaa accaaggacc tgaaggattc actgctgaat  22680
tctaccaaaa catttgaaga agtactaata ccaattatac taaaatcatt taaaaattaa  22740
agaggaagga atacttccaa attcattgta tacagccagc attaagctaa taccaaaacc  22800
agacaaagac acacacacaa agtaaaacta caagccagta tccctgatga acacagaagc  22860
aaaaatgccc ccaaaaatac tagcaaacag aattcaacaa cccgttaaaa aaatcattct  22920
caatgatcaa gtgggattca cctcatagat gcaaagacag ttcaacatac acaaatcaat  22980
aaacacaata cattatgtca acagaatcaa ggacaaaatc catgtgataa tttttataaa  23040
tgctgaaaaa gcacttgata aaattcaaca tccctttatg ataaaaacct tcaacaaatt  23100
gggtatagaa ggaacatatc tcaacacaat caaggccata tattacaagc tcacagttaa  23160
aatcatacag aaagagtaaa cattgaaagc ctttctacaa agatctgtaa taagataagg  23220
aagcccactt tcaccatatg tattcaacag agtactggga atcctagcca aagcaattag  23280
gcaagagaaa gaaataaagg acatccaaat tggaaagcag gaagtcaaat tattattatt  23340
ttttttgca gaagacttga tcttatattt agaaaaacct gaagactctg ccaaaaaact  23400
tttagaactg aaaatttgta aaattttaag atacaaataa catcttagta aaattacaag  23460
atacaaataa catataaaca tcactagtgt ttctatatgc caacagagat ctatctgaaa  23520
```

aagtaatcaa gaaaacaatt tcatttacaa tagctacaaa aatatcaaaa tacaaattta 23580
accaaagatg tgaaaaatct ctgtgaggca actaaaacac tgatgaaaga agttgaagag 23640
gatatgaaaa atggaaaata tcccatgcca tggatgataa aaattaatat tgttaaaatg 23700
tctatactac cctaagtgaa ctacaatcaa aacaccagtg acattcttca cagaaataga 23760
aaaacaatcc tagaattcac atggaattac aaaagatctg gcacagctaa ggcaatcctg 23820
agcaaaaaga acaaagctgg aaacatcata ccacctgatt tcaaattaca tgacaaaact 23880
ataataaaca taacagcata gtactggcat aaaaacagag acatagacca atggaagagg 23940
atagagaccc cagaagtaag tgcatgtatt tacagtcaac tcatatttga caaaggcacc 24000
aagaatatac gctgggggaa aaggacagtc tctttaataa atgatgctgg gaaaacagga 24060
tatccatatg tagaaaaatg aaaaaaaaaa gacccctacc tttcaccatg tacaaaaatt 24120
aactcaaatt ggattaaaga cttaaatgta aaatctgaaa ctataaaact agtagaaaac 24180
attggggaca tacaggacat tggacttagc aaagattttt ttggataaga cttcaaaagc 24240
acaggcaaca aaaataaaaa cagacacatg gtattacata aagctaaaaa gcttctgaac 24300
agcaaaggaa ataattaaca aagtgaagag acaacctaca gaacaggaga aaatattttc 24360
aaactatcca tctgaaaagg aattaataac cagagtatgt aaagaactca aacaacttat 24420
taacaaaaaa gcaagctagc aagcaagaaa aaaaatctga tttaaaaatg agcaaaagag 24480
cttaatagac atttctcaaa agtagacata caaatggcca caaatgctca atatcactaa 24540
tcatcaggga aatgcaaatc aaaaccacaa tcagatatta tctgattggc tttatcaaaa 24600
aagaaaaaat aacgaatgct ggcaaggacg cagagaaagg agaacactgg taaactgttg 24660
gtgagaatgt caaatcatta tggaaaacag taggaggttc ctcagaaaaa caaagatagt 24720
actactatat gattaatcat tccattgctg ggtatatgtc caaaagagag gaaataagta 24780
tgtcaaaggg atatctgcag tttcacgttt attgcagtag tatttgcaat agccaagata 24840
tggaatcaac ctaagtgtcc atctacagat gaatagataa agcaaatata gtgtatatac 24900
acaacggaat atcattcagc cataaaaaag ttaatgaaat cctgtcattt gcagcaacat 24960
ggataggact ggaggtcatt ataagtgaaa taagccagtc acagaaggac aaataatgga 25020
tgttttgaat cataggtagg ggcaaataaa agtagatctc atggatatag aatagaatag 25080
tagttaccag aggctgtcaa gagaaggtgg aagaggataa agttggttaa tgagtacaaa 25140
aatatagtta atagaaggaa tgtgttctat tatttgaaag tacagtagga aaattatagt 25200
taacaataat ttattgtata tttcaaaata gctagaaaag aagaattata atgttcccat 25260
cacaaagaaa agataaatat ttgagttgat gaatagttca attactctga cttgatcact 25320
atatgttgta tatgtatatt aaaataccat gttcacaaaa atgtgtacaa ctgtgatata 25380
gcaataaaaa tacaataaaa gtgtgttatg aatagctgaa tatctggtaa tataaataaa 25440
aatctttaaa atcttaacag tctgaatact agagagtaaa ttttatttct taaaagactt 25500
ttactacagt caattttgtc atgcaatatt aatggagtgt aatgagtttg atagggcagt 25560
tctatgtatg tgctgtcttc cctttgagaa tgaatatgaa ttcttttctg tcaacattgc 25620
atatagataa tattaatcat ttgaagcaca cactgtggct atacctgagg taaggtgttc 25680
tggtgttgat aaatgaatga atcatcctca gagatttaga tgaaattctt gaaaagtttg 25740
ctattatttt taaggcaaat atttaatttg ggaacagagg tccatctttc tgaatatttg 25800
aggcttctaa aatgtacaaa aaggaatctg tttgacattt ctgagaaata gaggaatcca 25860
atgatataag ggtcttttct gaaagcatta aaaaatttag ttataatctt gaatgataac 25920
tttcagtgtt ttatcacaat gaaagtattt cattgaccca aattaatgga ctgtttattt 25980
ttttatactg taatgctagt gaagttgtag ggaaaattat atacctagat atgtatttgt 26040
ataaatatat aaaccttctc aatatctggc ttcagtagtc ttacatttta tttattgaaa 26100
tttaaaaact ttagtaagtc agttctcata aatattaacc taggaaaaca ataatgcata 26160
cttagcagca aggttaattt atggacctgc atttgatgtg ccctttttatt ttcctggttc 26220 aattcctgga ttaagtaata attctaattt taagaaataa tatgaagtta tccaaataaa 26280
tatagaagta gctgaaacta tttttgcat attttaaatt ttattaaatt taaatagtaa 26340
aactaataca tatatccaga ctataaaata aaaatattat aggtatggct acaatctcct 26400
ttgatcatta ccatgaatct tgatcctttt ttgagaagta gcaacagcat ttaatttgat 26460
gtatatcttt tcagaagatt ttattttat ttatgtaaca aatatatata aatatttttt 26520
caagactgag tcttgctcta ttgcccaggt gggagtgcag tggtgtgatc ttggctcact 26580
gcaatctctg cctcctgggt tcaagcaatt ctcctgcctc agcctcccaa gtagctggga 26640
ttacaggcgc ctgctaccac acctggctaa tttttgtatt tttagtagag atggggtttc 26700
accatgttgg ccaatctggt cttgaactct tgacctcaaa tgatccaccc acctcactct 26760
cccaaagtgc tgggattaca ggtgtgagcc atcatgccca gcctatgtaa caaatattta 26820
tggccacata ctatctatat agtttttttt gatgtgtgtg ttttaaaatg taaatagtat 26880
tttaatgtat gtggttattt tgtaacttct atttggctac cttgctaaac tttctaatgt 26940
gaactctaac aattcacaag ttaatttctt agaggttttt ttggtaatta ttatatcatt 27000
tgcaaataat gataattttg tctgttttta ttctgattct tatatctgat ttgttattgt 27060
cttggataga caaggatggt gcagaagtgc tggatagata atgatagtat tttgcattat 27120
tccttacttt aagaaattac ttctaatatt ttatccatta agtatggtac ttattacata 27180
tttccactag tgacatttat taaaagggtt ttcttctatt tctaatttca gaagattaaa 27240
aatgaggtat taaattttag tcaatacctt tacattactt attttttgtc ttttgtcttt 27300
taatatggag aattggtagg ttctctagta ttgaaccatc cttgtattcc tgggataagc 27360
cctatttggt cctgatgtgt aattaaaaaa aaatccctgt atctgatttg ctaatatgta 27420
attcaaggtg tatatatctt catttataaa agttatttgt ccatgatttc ctttcttgtg 27480
ctttctcttg ttttggtatt agtgctatat ttgcttggta aaatggatca gataatttct 27540
tatctttgtc tttactttga aaagtttata taacacaaga attatgtgtt ttttaaggat 27600
gtgataaaat tcacaagcaa aatcttgagt tgggtgccat ttcaagtata gtcttttctg 27660
ttagcttaat gtattcagtg gttactgatg tgcgtgtttt aaaaattctt tgagctgatt 27720
ttgatgattt ttctagaaat ttgaccattt tagctaagtg ttcatatagg tatgctaaaa 27780
tttccacctt aaaatggaag attcattatt gctttctcac ttgccagggg cagagaaatt 27840
gttctacttg acaagttaat tttagctttc caccaacaaa acaacctaca gagtatttgt 27900
actatatgct gctttagttt ttgtggtctc tcagtgaagt tagttatttt gcaatcaaat 27960
aattatggga aattttgctt ttaaaaaaat caagtgacaa tgtattttca taatgacacc 28020
ttcgattcca gaattcagga atcatagaat taaaaaatgc ttcgaatttt cttaaactcc 28080
atgtttcctc accagtgaaa tagaaaataa caaatagcta tctcatgagg gtagttatat 28140
taaagtacat aatgactcta ctggtcttca tacaacattt gtgtgtgtta agttataggg 28200
ataagtttgt attaatatat gccctttgct ttagagaaaa cgtacttagc aaactgtgaa 28260
tttgaataag agagttttcc tctatgtgta agtaattata attgaatctg gggcttggac 28320
tatttctaat catcttaatt aattagcagg ataaagcata aatggactat tttgtctaat 28380
tttggttatc aaacaagtag acctgtcagc ttaactaaaa ataaaatgaa caaataatta 28440
agtgattgca tgtagctagt tacagcttta atcaatgtaa tcagtcaaat aagttaaata 28500
gtcaaaagta tttgtgtttt cacacacatg ttaaatcagt gagaatgatt ttgttgtctt 28560
actgtaattg taggaaagta gcaaatttga atatatcatt caagcatgaa tatataggtt 28620
gtactgctgt tgcaaaaatt aaaattgaca gaaagataaa tttatctact ccaagtccac 28680
caagcctggc aggccagtga aggtgatgtg agaagaatgg tcaggagatg aggtcaagaa 28740
cctgaactat atattctgtt aagtttggga cacagttaac caacttaaat ccgttatttt 28800
ggaaaaggag attatatatg gtgtatattc agtatcagct gaacaacttc tctttagcaa 28860
catttgctca gttctggcct ttatctttga ccttctttgc aagatattaa taaatgcttt 28920
ttattctaag cgtaagtgaa gtcaagtcta gttaattaaa taatattttc tttctcatag 28980
ttttgcatta agacttcact atttcaagac tttgtctcaa ctgtccttgc cattttcttg 29040
tcaattttaa agtatttcct tctctaccag ggaaagtgct tccaatttct cctcataaga 29100
acatttgtct tactgtctta aaatttcaaa tcgaagacac agattaagtg gctagaggtt 29160
tgtgtccttt ttatacttcc ttgcattatt ctcctcaata aagttaaact gtgtcacaca 29220
gcaataaatg tacattttta ctgatggagt ttccagactt tttgtgatta ggagattttc 29280
tgtcttttac ctaactcttc atccctggag aagaagatgt gtgatacata gtgagaataa 29340
ataatatact ggagagagga ggggaggagt gattaagaaa gtcatatttg cattgcttta 29400
tagagcaagg agcagacctt tcagcccaac aattccacat ccttgagaga tgcttctacc 29460
agaggggggc acaaatatca gatatattgt gatcactttc atggcatttg agtttgattt 29520
gtatttgtat tataatttct gaacatcact atcacatatt ttatttttaa ataaatgagt 29580
ggagttgtct aaatgactta attgtaactt ttgatttgta ggtagaaatt gcgttaagaa 29640
ataacagaaa gaacatgaat ttatagtcag aaaacccagg ttagaatttg agctgtgcta 29700
tattttagct gtattaattt gatgaaggca ctcacaattt ctgaatttta gtagacacat 29760
caacatgaat gataaatatta atctcatcag gctgttgtga agataaaata aaatgttttt 29820
gtaaagcact agtaagctgt ctgacaccta aaagaacttt aatgtctatt aattcctctt 29880
ttgctcaata gctatattaa cagtgctgag agcagggaga ctcctgttat gtccccagct 29940
ccatttctca gaaaatatct gaccttggta gttcccataa atgttctgag tctcaatttt 30000
ctaaactgta gaatgagaag aagtatctgt tcaaataaaa ggtccgtctt agagaaattt 30060
tgtgactatt aaatgagaaa ataatatgca ataaactttg aaaattatag agtgctaaag 30120
atatataagc catttccttt aaaagaaaat attagttcag gcactaatgt tgtatacact 30180
gtattttatc tcaaaatcag aataaataga cattcaggaa aaaaaagttc ttaatatttt 30240
aacacatatt tccttgtcat gtttcaccac atgtatcctt ggtcattttt ctaagtccct 30300
gtgcaaatag gactccaaaa aataattttt ttctgagtat taacatttgt tcttttacaa 30360
atataattgt gggtcactga aaggccctta gcttcctatg aaacaactaa gagtagcttg 30420
aatcttctcc tagaagccat atatacataa gggtatggag aatattggga gttttatttt 30480
gaatgaagat aaatggaaaa ttttaggttg aaagaaaaat gagattactt attaagatca 30540
aataaaatta atattgttag aagttgtttt ttgaaagcta atacttatct aaaagaaagg 30600
tcccttgaca gagtaaattt gcttgagctg cagattttct ttttctttta tttttggata 30660
atttcatcag atttggaaaa gaattaagaa ttgtctctgt tattgtcatt tagacttttt 30720
ctgaacaata gaactaattt accaacacgg aagaaacatg ccaaatcact gaccatagcc 30780
cttgaaagga agggtttggt ttttaaaaaa attaaattag atctataagt ttgagaaatt 30840
tcagcatgtt ttttataatt ctttattatt gtgaaattgg aaaaactcat gacattgctt 30900
tatgtaacca agtgttgctt ggctgcatac ataagctttg tgctgataag tggggcatct 30960
gttataatgc ttagaaatac ttggagttag tgtctgggct ctaggatggg gccgcttgac 31020
tcactgtgat ctgaattgga acacactgct ttattccaca gccatctaga cagaaagtga 31080
ggacaacaat ttaccagtta aagcaacaaa gcaattgagg tagacagaaa gtaattagtt 31140
tttaatgatc ttttggaagt cacatgaata gattgatttc tgttttgatc ttgtttgaat 31200
taatagctgc ttttgagtct tcaatcccac ttgagtatgc attgtttctc catttcacgg 31260
tctggtgctc ctgaagttta ggttttgctt ggccaattgt tccgttttgt aaagctcaga 31320
ccagtgtttt tgtgttcctt agctttaaac attgttgtgg tgttttcctt ttatttctat 31380
agctgtttcc tcttgggaat ttgatggggc tattatcact tccacagggc taacatccaa 31440
attggaggtt cttatttgga agctaaaatt ggaaaaaatt ggcgtgaatt catttctcac 31500
taaaaccgta acccaggctc cgtgttcctt gggaagagca ttttctgctc ttgtcctggt 31560
tgctgcccag actttttctt ctctcctttt tggattatgt gagttactta gaaccagcta 31620
atgagggtgc aggaagcagt ttgtatggcc ggtgccactg ttatgactaa aaagcttttc 31680
cccaaaataa atagtagttt gcctctcccc aaagctttgc agacaatgaa tcacaatatc 31740
cctcactttt gcccaaacat tgtccctttt tttcttatca gacagatgtc tacatccctt 31800
cactctgctt ccctgttgcc catttgattc tcagacactc ttccttgtca ggaaggtact 31860
aaaggcttaa tatcttttta attctctctt gtttatttgt ttttgatgaa tcaagctatg 31920
catgtatgtt tttataaaat tattttttga gaagatgtgg aagatgaaaa aagccaaatt 31980
cctacagaga gattttcaag atttttaaac agacctcctg atttttctat acaattaagt 32040
tctttaatat atgacttttt aatactgttg tgctttaaaa taatttttca cttaaaatga 32100
tcacctttcc atgccaataa atatagatct ccatcctact ttttaaagac tgccagtgaa 32160
agttttatat ctctatggtc ctagacatta gggtaactat aggaagaaaa taggtgtgat 32220
ttgaaaatag agaagatcaa agaaatatca tttactaagt ctttctagaa agcagaaatg 32280
agaagaaatg gtttgataag gtcaaaagaa attgcaacct ggtgtgaatc aacagatttt 32340
agaacactaa ccaaacacta cacttacatt aagtgtgaat gagcattttg gaactttaat 32400
agattggtgc tgggatgctg aatctcttca ccatccctca ctccctagga cagaggaggg 32460
aagtagaaaa agaaagagag cacagagaaa tggtagaaaa taagatgcag gagccaaatt 32520
ggaaaagaac gacagagaac gctggactag caggttggga gtagtcttaa gagagagaaa 32580
aggagagggg gctatgggat atttacagcc aactttccat ttagcgccag gcacccagtg 32640
gagaaaagac aatttatcct tgtcatagcc ctggctgcac tgctgctcct cctgccaggc 32700
attttgttcc cagaaggcac tccccagtaa tgtaaggaga aggtgggaga gggggagaga 32760
aggtcagtaa cgacttccat ggtcagcacc ctagtcgttt tcagcagccg tttcagggtt 32820
cttcaacagc cttgtcactt tatctactgt gtctgtttac ttctctctgg atttccattt 32880
tatgttttgt ataattgggt atctctagct ctctatttct cccattcagc tgagctaaaa 32940
ttaaatttta aatttttgtt taagctcctt ttttatgttt tatattatca ttttgccctc 33000
aaccttttac tttctacagg ttaaaaatct gatattttaa aaataaatct ccaggtggac 33060
caaaggttca tattaatcca tcatctttgt gcttttagta tttcattggc aaatatccca 33120
caggattatt ttatctcaaa cattttattt catgaagaga tatgaatttg gtccttttgc 33180
agaatcctgg gagaacttaa ccttcaggaa aaagacaaaa tgattgcctt cttccaagcc 33240
agtgactcag tttgaatata catgatggga agtgtgcatc tgccagtgac ctttgggata 33300
atttggactt ttggcctttt tccaaaataa ggaagcagta gaacagttgc gtcttgtttt 33360
atgaattcag tctcattcat aatccagtat ttggaaattt cccacctttt ccagcagaag 33420
ttgcctagct ctaatatgga cactgagtat cctcatcatg agacatgttt tgtgtgacac 33480
tctggcctat ttgctccaga ggaaaaagta gcagcaggat taggcgatgg attcaaattc 33540
caactctctt cctctatcga actgatattc taactgtagt ttggttcctt gatatgttta 33600
atgaggtttt aatagcatct acctcatagg attgttgtga tgactaaatg aaattttttt 33660
tttttttttg agacagagtt tcactcttct tgcccaggtt gcagtgcaat agcgtgatct 33720
cggctcactg caacctccac ctcccaggtt caagcaattg tcctgcctca gctcccgagt 33780
agctgggatt acaggtgtct gccacagtgc cccgctaatt tcttgtattt ttagtagagg 33840
cggggtttca ccatgctggc caggctggtc ttgaactctt aacctcaggt gatccacctg 33900
cctcagcctc ccaaagtgtt gggattacag gcatgagcca ctgcgcccag cctaaatgac 33960
attttatttg tgcttaagtt ctccataagt agtaactact gatattacta aattatttat 34020
attgtttcta ctaaaagtga ttattagaca taatgtcaag atgctcatat tctgcttagg 34080
ggttaaaata cttaggcatt aattacctag aggatactga agtgctaaac tctatggtga 34140
tggtcatatt ttcaattgta ggctctcagg ttaaggaaag atttaagcag ttcagcaagt 34200
ggggataaga tgaccttcct gaagaggtga ggattgaatt gggcctggaa gagtaggtag 34260
aatttaaaag acacaaaagg gaatttaagg ttcaaaagag gaggtcaggg gagaaaaagt 34320
atgagtaagc atataacaaa agactataga gttttagagc tatttttgtg gatttttttcg 34380
ttctctttcc cccctttttat tggtatcctt ttatggaatc tcatttcatt ttttagctgt 34440
tacctgtgcc aaaataataa acatgctcat gatgtcatgt cactttaaat ctctaagaat 34500
cttggtttac tattcagctg ttgctttgaa agtgcacaat tctggaatta attctgggga 34560
gctgtgtttg cagaagtgct tatatttagg agaattgaga gtttatattc ctagagacaa 34620
catcaaattg ctaaggaaaa gctgcattcc acgaaccagg aaacacaatc tagtgttcat 34680
gatggctgtt cgtccatgta ttaaggaatt tgtactgagt ggtcaactgc agtaagtgct 34740
actggaatgc ttcgtccctg cggtacctta cctcatgtcc tcactctccc tcatagtcac 34800
agactgtgaa ggaagctgtg gaggtgggga tttaaaaaga agaggaaatc actggagagc 34860
cagagggctg tttaaaattc tacaagtgaa gcaggttaaa aacataaccc agcatttctc 34920
tctttgcaac tagatgcaag attaggaagg catttaaaaa aaaaagtggg agttgaacaa 34980
tgagaacaca tggacacagg gagggaaaca tcacacactg gggcctgtcg tgggggtagg 35040
gggctaggga agggatagca tcaggagaaa tacctaatgt agatgacggg ttgacgggtg 35100
cagcaaacca ccatggcaca tgtatactta tgtaacaaac ctgcatgttc tgcacatgta 35160
ccccagaact taaagtataa taattaaaaa aaaattcctg agattgtatg atgctctata 35220
taaaatttag aaagaggtta aattaaataa tatttagcta tttgttcatt taaatctttc 35280
taccactcct ggtattgccc tgtttacctc tcagttagtc tggtccatgg ctggagcctg 35340
gctagccagg ccacaggtct ctgaccagaa gaccgtctta cctggcaaag gacacatggc 35400
ttccttcaag gccgagcata tcaacccaat gcagaaatga cagtgaatat cacaaatgca 35460
ttttaggctt taaaagttta attaaatgta ggggcagttt atgtgattta tttaattaca 35520
tgcgttcttt ctcaaagcac cttattttcc atgaaagccc ctataatgaa ggttcccctg 35580
gtcactgtat ctgggcatca cttagaagga ttttaagcaa ggcaatacag tgcagcatgt 35640
ttgaaattaa acagatgtgg gttgaagttc tgtctccacc acatattagc tgaatgatct 35700
ggggtaagtt atttaacctc tctaagctta ttttcccccc tttaaagtaa aactaataat 35760
agtattactg caaagttttt attactaata agactaataa tagtattatt ccaaagtttt 35820
ttaagaagta aaaactaaaa gagagtcatt tagtcgagtg attaatataa ccactagatt 35880
agattgataa tagtgaatat tttttaaaaa tgtagtggtt atcaatatct taacattatt 35940
aatgtatgac atagtaaatg taacaattaa cattaaaaca gtcaatgtta gctattatta 36000
taattgtcat aagacttgat tcagttaact tttgtaagaa tgtttcctca cctgcaacat 36060
gaggataata ttaatattac ctacagacag atgctataaa ctacatccag gtgtgctgtg 36120
agaattaaat gagctgctgg gtgtggctgt gatttacaaa ccatagtgta attattgtgt 36180
caaagttgaa agcaagtaga tagtatctgg taggactttt gacctcaatg taatgaccag 36240
aatctgcaag acagcatttt ggtgagtgct aatcttttga tttagggcca gtgtttctgg 36300
aaagccagaa ggatggtttg taatgaagca gaatgttttg cccagaacgg ctggctaagc 36360
agttgcaaat tctgttttct ttgcctgtta aagccatttt agcttaagtg ttgttgtagc 36420
tactatggag tcctagctag tgtcttactg tacagaatta ttcatcattt tctaagagaa 36480
tcattttgat aaggaacatt ctctttattt tgtatctcta ttggggtcat cttatggggc 36540
atccaccttg ggatacacaa tttgtgagac attttcagtg atattattta atattgtcct 36600
tacaatcacc ctctgaagta tgcattatca tctatattta cagacaagaa aagtgaaact 36660
cagtaacttg cctaacatta aatgagagag ctgagattaa ccctcttacc aaactcaagt 36720
taggtatatg ctcttaccac tgcattggtt cactggtttt catattactt tagtgtaagc 36780
acagaaaaag ggaaggcaat aggagttctc aacccagagc agtgctaccc cactaaggag 36840
tgtttgaaga gggtattgat tgcctaactg agttaagggg ctgctggatt tgttgggcag 36900
ggatcagcag tgccaaatat tctgcagtgc tcaggactat acaactgaag aattttccca 36960
cctgagcagc cagcagtgat tcatgaatgt ctctcttgac cttttctgaa aagataaaag 37020
tggactgtgt ctgtattagt atgactatat tttgtagttt tcacttggat gctttttgtg 37080
atataggaaa acccaaccct tacttcccaa gtgatatgac ttgaattctt tttccctcta 37140
aaacttgtgt tgaaatttaa tccctaatgt tgcggtattg agaggtgagg cctttaagaa 37200
gtgagtgggt cagagctctc ataaatagat tagtccattc atggattaat ggactaatgg 37260
actaatagat taatgaatta tcatgggtga agaactggtg gctttatagg aagaggaaga 37320
gagacctgag ctagcacatc agtacactta gccccctcac tatgtgatac cctgtgcagc 37380
tttgggatcc tttagagagt cctcactagc aagaaagatt ttaccagatg tgtctcctca 37440
accttggatg gtccagcctc cagaactaga agaaacaaat gtcagtttct tggaattacc 37500
cagtttcagg gattctgtta taaacaatag aaaatgaacc aagacacaaa gcaagatgaa 37560
attgtttcat ctttaggtgt ttgtataaac cttatcacag tacctcaatc gctgtatcca 37620
taagcatgag caccatttta ttcattactg gctttgtggt gcctagcatt gagtctagct 37680
agtagcaggt gctcaagtaa tacttgtgaa tacgagggca tagtggtttc tctatcatct 37740
atgaagctca ggagacaggc ctgaaggcat ggattgtctg tgcttactgc tcttcctccc 37800
tgccctccaa ataaacagaa ccagttatcc aacttggttt aaaaacatta gtgtttcagc 37860
ggccattaaa aatacattgc atattgctct tcctgaattc ttgctccttt tctgactaac 37920
atgtgatctg atagcttagg gtctcatttg gtcaccagca cccttctagg aaggaatgtt 37980
ctattccttg aatctggctg agtgatggtt gccttacaaa gattattttt cacgtcagct 38040
tccttaagtt gtagatccat ttttttccc cttgtgtact ttgagtgata gagctattac 38100
tagagctggg gtgtgttttc taaatggttg gctagagcaa aagcatcata ttacatttct 38160
taagaaagga ctttaattta ttagaattat tagttctcat tttctacctg ttaacctttg 38220
aaatattatt tacttttcct tctggcattt gcatatacct tggggttatt tttctctttt 38280
tatatcgatc aaatatactt tcatatattg taaatgtatg taaagcactt caggttggca 38340
ctagtccttt tcaattacta gttaaaacgc tatgatgccc tttgagaaag aactatataa 38400
atttcatatt ttaatttatg agctctcagt tatgttactt gcttaagttc ccttagcaat 38460
taagtagagg aattaaaata agaactaaac atgcctgatt cctagttatt tggcttcaat 38520
attttttaag agtttccctt cctcttccct ccatttgtga tttcttcctt cctctctttc 38580
tcccaaggaa ctccattact gactttcttc tacatcttac ataaaattgt taatttcctt 38640
actatactta taaccttaca cttagagctc agggtagacc caaggaacga ttgttaactt 38700
aggtcagacc tgagcaccgt gggacctgcc caacctctct ctcaccttgc caaatgcctc 38760
ccactttcat agtatcccca tcaccaattt cttgacaaaa gtagactatc cccactgtct 38820
cccacccttt tattcacccc ttctctttcc ctccttccct ccctcccttc catccttcct 38880
tccctttcct tccttccttc ccttcctttc accctttttcc ttccttcctt cctctctgtc 38940
ttttctttct ttctttcttt ctttctttct ttctttcttt ctttctttct ttctttcttt 39000
ccttctttct ccttccttcc ttgtcttttt ctttctttc tctttctttc tttctttctt 39060
tctttctttc tttctttctt ttctttcttt cttttctttc tttcctctct ctctcccctc 39120
cctccctccc ttcctccctt ccttccttcc tttttctctc tttctctgtt tctctctctc 39180
tcttttcttt cttttttttc tgttacaggc agcatgtatt ctgatgttgt tttatttagt 39240
tctctctcct tttttgggga ttgggtaagt atggtagtgg gtatgtgtcc tcacacagaa 39300
aagtttaaac tgcaatttga atgaaatttt gtaacttcct gaaatgcaga ttaggttgtg 39360
gcatgctagt tcactttgga ttcatgtgat gtcaccaaat ggctaaaaaa aaaaaaaaaa 39420
atcaaacatg atcagcacag ttattacttt ttaaagcctt ttgagaaaaa catgtgtgtt 39480
gaagaacagg atagtggaca caaaaataac ttcagtctct aagtgggtag agaattgttt 39540
taacttgata atgtgtttga aaagaagata agacagtggt ttgggaagtc actgccctct 39600
gccctgtgtg gaatccaagg attattagca ttacaagaag aaattgcaga tgatcattac 39660
taaatgaaga gattactggg agacacatgc ctcaggtcaa agaagacaat ggggattaag 39720
agattacaac taatacagag atgatattaa ctgttttccc aaggttgaat acaaaggaaa 39780
taagaacaac tatttctcag gctggagtag ggagtggtgc tggagctgag gttgctttta 39840
aatattcttt ctaaatttgg ccccaaattc tttaggttag ttgtattact caggaagaaa 39900
gattgaagcc atgttgattt ggatactgtg tcaaaactca gtcttgattc actgtgcttg 39960
ctgtccttcc tcagtcactg ctgttgcaat tcaagtcctg aagacagggt aggaatccaa 40020
cctgaggcag ttatgggaga gactgtaaat tcccacactg gttttcagag acccggagtc 40080

```
taaacccatt tttgaccaga agaatgtgat ggaatttctt acacgctcag atacttcatc  40140
tgcaaaattg agggaataat gctagattat tttcacaatt ccagataatt gctaaacatg  40200
taggtacctc tcaaagatcc acagcattag aagcactgaa aatctatgcg gttgttcaat  40260
aatattatat cttggaaata tcattccagg atgaaagttc atgaatgttt tcccttcaag  40320
aaggctataa catttatgac ataatttata cagacattat ttatacagtt ttggaataat  40380
ttatttcatt ttaaaagggc taataacttt ttatttaagg ataataaaat gaatttacat  40440
acaaaacact taaacatttc cctaaagtgt gttttggtct aaacaatggt gaaaaccatt  40500
aggcaaaatt tgacattgaa gtaaactgaa aacaagttgt ctgacttagt tttaacctga  40560
gacatttaat ttagtttcaa gatttttata aaaataaagc caagtttcaa tgtgtacgtt  40620
cacttgacat aagactatca catattgtaa agtaaattat agtgtaaaat atgagtatat  40680
gactaagaag atactgtcac tttaagccat tctttaaaaa attctgccaa acagaaattt  40740
agaggttgcg ctttccttat ttagctgggt taatctctta gttgccaagg gcagattgat  40800
ttgtttataa acttgttaaa ccaaatctgc acataaccac atcacagata ataaagtagg  40860
aaaagaccac tcagattgtc attctgtatc cactcaccac atcagtcttg ttaatgtcta  40920
atttaactgt ttaagcaatg tatgctgcat tgcatgtttt gcacattgta tttttaagtg  40980
atgtgttgat gattgttaac catgtgtgtg ggtgtgcctg aaaagatcca atgtgcagcc  41040
agaattcctt tttcattgac atacccaggc tgggctactg tcagtgagtc attctcactg  41100
cattgacact gaggccccca tgtgcggtct tacgtgtttg agaccagatg ccaggcatat  41160
ttattccacg ttggtaccac tagcataggg aagactgtat gccactcatt ggttactggc  41220
agttaaaact tttttcttga catctgccac tttttaaaag ccccctaatt ttgtaataaa  41280
taagttcttt ccactaccac ttagcaaata agctttcagt ctttatagtg tattgctacc  41340
taatacatgg aattataaac cttgtgagat ttaaattttc tttgaacgtg acatttagtt  41400
ttcttagcaa tttttatgat ggtgttgtcc tgttagtgtt aggtatcagt aataaagata  41460
tgtgtgtgtg tgtatgtgtg tgtgtgtgtg tgtgtgtgtc tgtagcagaa gtttaaagaa  41520
gatgaagtga ctttctgacg ggtgatagca tgaacccttg tatggaaaag ttttactgta  41580
gcacgtagaa atttacacat cacaacttaa gaagagagaa atgtggtttt cttttctaga  41640
atctaactta tactcttgag gttctgttat gcttagagga gataatgtca tttcttctag  41700
cccagtagca atttgatcca gttgattttt cttagccaaa attgaatatt ttagttattg  41760
ttcatttcaa agcccggcca cttctcagta aagggcatct ggaagaattt ctttccattt  41820
tcctcagtgg catctgggaa cactgggaaa agtcatttcc aatcaggcag tgaggcaggg  41880
acatgacttt gatttttttg ttgtcctcct ggttcctgca ggtcttggcc cagtggtgcc  41940
tgggcttgcc tggtccaagc atggactgat cttttgagca tcctactaat ttctataact  42000
gatgctcgtg caccccttgat tttgagattc ctgatcaatg ttgatggact gttttagacc  42060
taggttctga gcacctttgc atcacccatg acagtccatg gggccttcca ttttccatac  42120
ctcactggtg tgtgtgaacc ttgtggggtt ggtctctaaa ctcattgtat taggctgttt  42180
gagttgttat aaagaaatac ctgagactag gtaatttaaa aagaaaagat atttaattgg  42240
cttactattc tgcagcctat acaagcatgg ctccagcatc ttcttatggg gcccgaggaa  42300
tcttacaatc ataggagaag ttgaaggggg agcaggcatt ttatatggca agagcgggag  42360
taagactggc agggaggtgc cacacacttt caaagaactc gatctcgtga gaactcactc  42420
actatcacaa ggacagcacc aagccattca tgaaggatca gcccccatgg ccaaaacact  42480
```

ttccaccagg ccccacctcc aacattcagt attacatttt aacatgagat ctggagggga 42540
caaacatcca aactatatca ttctgcctct ggcccctcaa atctcatatc cttcttacac 42600
tgcaaaataa aatcatcccc tgccaatagt ccccgcaaat cttaactcat tacagcatca 42660
agtccaaagt cctaagtctc atctgagact catcttccac ctatgagcct gtaaaatcaa 42720
aacaagttat ttgctcccaa gatacaatgg taatacagtc atggagtaca cattcttatc 42780
tcaaaaggga caaactggcc aaaagaaagg gacagtaggc tccatgcaag cctgaaaccc 42840
agcaggcaag ttattaaatc tctttttctt tttgagacgg agtctcgctc tgtcacccag 42900
gctggagtgc agtggcgcag tctcagctca ctgcaagctc tgcctcccag gttcacgcca 42960
ttctcctgcc tcagccttcc aagtagctgg gactacacgt gcccgccacc atgcccgggt 43020
aatttttttt tttaatattt ttagtagaga tggggtttca acgtgttagc caggatggtc 43080
tcaatctcct tacctcatga tccgccggcc tcagcctccc aaagtgctgg gattacaggt 43140
gtgagccacc gtgcccagcc ttttggaagt tattaaatct taaagctcca aaataatccc 43200
ctttgattcc atgtccctca tctaggtcac actggtgcaa gggtgggctc ccaagtcctt 43260
gggcagctct gcccttgtgg ctttgtaggg tgtagtttct gttgctgctc tcacaggttg 43320
gagttgagtg tgtgtggatt ttgcacactg aggttgcaag ctgctggtga ctctactatt 43380
ctccggtctg agggggtgga ggaccccctc ccacagctcc actaggcagt gtcattgtgg 43440
ggactctgtg tgggggctcc accccacatt tcccctggca ctgccctcgt agagtttctc 43500
tgtgggggca acacccatat agcaggcttc tgcctcagct cccaggcttt cctatccatc 43560
ctctggaata taggtgggag ctgtcaagcc tccttcactc ctgcagtctg tgcacctgca 43620
ggcttatcac aagaacagac taacattcgt cagtactagt tttatgtatt agtacattct 43680
tgtgttgcta taaagaaata ccagagactg ggtcatttat aaagaaaaga agtttaaatg 43740
gctcatgatt ctgcaggctg tacaagcatg gctccagcat ctgcttctgg tgagggccgt 43800
catggtggaa ggtgaagggg aagcaagcat ctcacatgac catagtggga gcaagagaga 43860
gagggaggag gtgccacaaa cttttaaaca accgaatcta gcaagaattt gcttactatc 43920
acgaggctag caccaagcca ttcatgagag atctgccccc aggatccaat ctcctcccaa 43980
caggccccat ctccaacatt ggagattaaa ttttaacatg agatttggat ggacaaacat 44040
ccaaactata tcactcatac acaggcatct tcctcagcgg tggaatctgc ctcttcagct 44100
gggtccactc ctgctgccat tgtgaggttg taccattcca aatgcagagt ttctctgaaa 44160
ggtttttgat agggccagtc tctgcccagg aaagcagagg atcaacaatg gtccctcaga 44220
tgcccccaaa cctacatcac tgcttctcct gtccatagac tgctctctgt ccctgaggtt 44280
tgacctctgg gtagggaggc aggaagtggg ctgcccacct ctgatacctc gtccacactt 44340
cctcttcttc tttctgccag catagaaatg gcttttcatt tcagttctta tcttctagaa 44400
ttgacaatag attattgtct ttcttttcta ctctgggaag catgtaatta ttgatctgag 44460
tccttcaagt ttggctttta tatacaaata cttagctttg gagaatttca atagaaccct 44520
tttcctcctc aagaaagcct ggctcctgct aaaccaaaag cctttgcatt cagggaatag 44580
ccttgctatg gatgtaaaat ttcatattat aaagctgtaa actgattgat gactgctgct 44640
cttggctgtg tgttgctctt ttcctgagtc aatgaacccc gctggattaa gagggtgcag 44700
ggaagataag gagaactata ggaaagttac aatttgaagt ttacctgtga tgaaatgaca 44760
ttggcttaat atcacaaaaa gattaatcat ccagtacatc agcatcatct gtaagccacc 44820
aattgactgt tgggattttt tagatgggtc tgatgaaaag gaattaaatt tacatttgga 44880
tttctattaa tgactgtata gtttgttcaa aagagagtta ctctagtttt ctttaccttg 44940
ctgttattca gctatttttt ctctctttta taatttagtc tttacatttt taaattgtaa 45000
aataaaatgc agatacagaa tgctctccca tgaatttgtg tacatgttaa tgaattgctt 45060
agtaaatttt aaggcaaaag cctttgtaac caacactaga tcaaatagaa ctttgtcagc 45120
cactcataag cccctctata tcctctattc caatcataat cccctccctt ctgccatatg 45180
taataattat gctatataac agaataatag taataagctt attactatta tttttgataa 45240
tcacttcctt gtatgtgtgt gtatgtttag tttgaacatt tatataagtc cactcctaca 45300
cattgtaatt tagtcttttc cattatttaa aatttgatca gtcttttgaa accttcagtc 45360
tatggttctt ctctctacct caatcttttc cctgtgcttt ttctgtcgaa cacctggact 45420
gtttgacctg taaagtttcc catggtctgg actttgctga atgcatgctc atggtatagt 45480
ttggtatgtt cctttgtcct tttgtatttt ctgcaaatta gcagctggat ccagacactg 45540
gatcagattc aagttcaata tctttggcaa tactagaagg agtgtttggg aagactatag 45600
gaggaagctc atgtctattt ctttttatga ggccaacaat tgttgatgtt tagtgtctaa 45660
atctattata taataggttc tttagtgcta ctttcatgct ctggatcctt atggtatatg 45720
aaagattcaa aaaatgtcag gcaaatagga gacaagcttc cccaaattgt actgtattta 45780
ttttttacat tctaaatgcc ttttacttat tgcatttggt ataaaccagg ttgcaaaggc 45840
cacttcaagc ttggggcaat gtcgagccaa attttaggga aaaaagcaat ttctgtggct 45900
ctatctccca cctgcttttg tggaacttct ccctcctaca aaggcctctc tctctcacca 45960
gttactgtgg gaagttctag atggtgtctt ttggatgctc ttgaaatggt attctcagct 46020
accacgtggc atctttctgt cacttccctc gttgcccatc cagctctgac ttcctttggt 46080
gatgtcttct ttaaagcctc tgggctctgt gaaacattac ttaggtggcc ccttgcagtt 46140
gctactgcta ctgtgcagat gtgggtgaca tttcccactg atgccaaagg gcagagtgtg 46200
ctaattttc ttctaaatgt ctgttttctc ctcctcttgg gacacctgta atacacttct 46260
caacctctct tgcaatgtga tgtgaccgtg taactaattt ctagacaatg ctagatattt 46320
gcaagtgata tgtgccactt tgtggatagc tggtttgtcc cctccaaact ttctttcccc 46380
tttgtgctgg ctagatccaa atggtgatgg cactctgggc ggaggtctgc aaataccttta 46440
ggctttagtg tcatatggtc tctgtcatga ctatggtact cagttcagct gttattgtgc 46500
aaaactagcc atagacaatg cgtaaacaaa tatgtatggt tttgttccca taaaacttta 46560
tttacaaaaa gaatctctga gctatatttt gctggtacct tccctagagg atagcagagc 46620
cacaagacag aaagaacttg gccactgatc actacataga ggaaagctgc ttgtcaacca 46680
ggaacagcca tcttccacta ttataatacg gacaaataag tttctattgt atttcattca 46740
tgttttagtt tcctatgtct gccataacac agtattatta caaagtaaga ggcttaaaac 46800
agtggaattt tattgtcttg cagttctaga ggccagaaat ccaaaatcaa ggactgtggt 46860
ccctctgaaa cctctagagg agaatccttc cctgcctctt cctagctttg ggtggcatcg 46920
gtcagtcctg gtcactacaa tctgcctctg tcctcacata gcattctccc tgtgtgtttg 46980
tctctgtgtc tcttctcctc tctctcttgt ttttcaaata ataacattgt acatagtttt 47040
attttcatga agtcaacagg aattggaagg aaactacaaa atataagtga taaaaaaagt 47100
gtgaaataat acaattttac agcaggacta tcctgtctga tctcttacct cgggtgtttt 47160
aacatactct tccctcactt ctggacatat tcatggctct tctcttataa agacaccagt 47220
catgttggat caagaaacca gcttgctcca gtatgacctc atagtcatgt atatcttaat 47280
tacatctgca aagaccctat ttccttataa ggttacactc agatatatta aagattagaa 47340
ctttaaacat gtctttttgg aggtcacaat tcacctcaca aagtgattat atgctcttag 47400
ggagacttat tactgaagcc cactggacta tgaccatgct gtacttcact gatactggaa 47460
aaatttattt ttcacacttt tttcctcacc caaagtgtct cagagttgtt gctattgctt 47520
cttttttttt tctttttcaa aaaatatatt tacgtgaaag aagagtcacc atctttctag 47580
acctcatgct caagtccatg gagactagaa ggaaggcaga gatgattctg gagaggtaag 47640
aaggacagcg atctcaacaa taggaagact tcatgctgaa gcattgttct actcgctcct 47700
cctggtgact gtgtagctgt gtttctaact ctccttccct cagcataagc tcttgccagg 47760
ggtctcttta gtcagatata ctcttgacca gcattacttc cttttctctt gaccctcctg 47820
cttaccaccc tcacagacat gacgagacct gtttaatccc aaactgaaaa cagcagacac 47880
tctgacctca tatgctttta ctgagagcta taaaacgtgt taaagactaa tgataattag 47940
aacttcatct ccatctccaa acaataatct tcttttaggt gaagctaaca aatgattggt 48000
tgacaggagc ctgtcagaaa actcctattt agacaatttt cttcaagcaa gaagaaagaa 48060
ataaaagtac agaaagttta gaaataaaag tacagaaagt ttagaaatcg aagtacaaat 48120
cggggtgagt caaaaggtca aaacttaatc tgtggcacac attggcagcc accacctggt 48180
acatctggta ttatggttct ttttattatt attattttta aatattttat tatactttaa 48240
gttctgggat acatgtgcag aatgtgcagg tttgttacat aggtatacat gtgccatggt 48300
ggtttgctgc acccatcaac ctgtcatcta catcaggtat ttctcctaat gctaaccctc 48360
cccttgtccc ccaacccccc tacaggccct ggcatatgat gttcccctcc ctgtgcccat 48420
atgttctcat tgttcaactc ccacttataa gtgagaacat gtggtgtttg gttttctgtt 48480
cctatgatag ttttctgaga aagacagttt ccagcttcat ccacgtccct gcaaaggaca 48540
tgaactcatt ctttattata gctgcataat attccatggt atatatgtgc cacattttct 48600
ttatccagtc tattattgat gggcatttgg gttggtttca agtctttgct attgtgaata 48660
gtgctgcaat aaacatatgt gtgcatgtgt ctttatatta gaatgattta taatcctttg 48720
ggtatatacc cagtaatggg atggctgggt caaatggtat ttctagttct agatccttga 48780
ggaattgcca ctctgtcttc cacaatggtt gaactattat ttacactccc accaacagtg 48840
taaaagcatt cctatttctc cacattctct ccagcatctg ttgtttcttg actttttaat 48900
gatcgccatt ctaactgggg tgagatagta tctcatttgt ggttttgatt tgcatttctc 48960
taatgaacag tgatgatgag cttttttttc atatgtttgt tggctgcata aatgtcttct 49020
tttgagaagt gcctgttaat atccttcacc cactttttga tggatatcaa aagtggatat 49080
ccatctggat attagccctt tctcagatgg atagattgca aaaattttct cccattctgt 49140
gggttgccta ttcactttga tgatagtttc ttttgctgtg cagaagctct ttagtttaat 49200
tagatcctat ttatcaattt tggcttttgt tgccgttgct tttggtgttt tagtcatgaa 49260
gtctttgccc atgcctatgt cctgaatggt attgcctagg ttttcttcta ggttttttat 49320
ggttttaggt cttaagttta agcctttaat ccatcttgag ttaatttttg tataaggtgt 49380
aagtaaaggg tccagtttca gtttctgca tatggcaaag ccagatttcc caacaccatt 49440
tattaaacag ggaattcttt ccccatttct tgtttttgtc aagtttgtca aagatcagat 49500
ggttgtagat gtgtggtgtt attttcgagg cctctgttct gttccattgg tctatatatc 49560
tgttttgtta ccagtaccat tctgttttgg ttactgtagc cttgtagtat agtttgaagt 49620
cagctagtgt gatgcctcaa gctttgttct ttttgcttag gattgtcttg gctatgcagc 49680
ctcttttttg gttccatata aaatttaaag aagtttttg taattcggtg aagaaagtca 49740
atggtagctt gatgggacta gcattgaatc tataaattac ttcaggcagc atggccattt 49800
ttatgatatt gattcttcct atccatgagc atggaatgtt tttccattta tttgtgtcct 49860
ctcttatttc cttgagcagt ggtttgtagt attccttgaa gaggtccttc acatcccttg 49920
taagttggat tcctaggtat ttcattctct ttgtagcaat tgtgaatagg agttcactca 49980
tgatttggct ctctgtatat tatttgtgta taggaatgct tgtggttttt gcacattgat 50040
tttgtatcct gagactttgc tgaaattgct tatcagctta aggagatttt gggctgagat 50100
gatggggttt tctgaatata caatcatgtt atctgcaaac agagacaatt ttacttcctc 50160
tcttcctatt tgaataccct ttattttgtt ctcttgcctg tttgccctga ccagaacttc 50220
caatactagg ttgagtagga gtggtgagag agggcatcct tgccttgtgc tggttttcaa 50280
aaggaatgct tccagttttt gcccattcag tatgacattg gctgtgggtt tttcataaat 50340
agctcttatt attttgagat actttccatc aataccttgt ttattgagag tttttagcgt 50400
gaaggggtgt tgaattttat cgaaggcctt ttctgcatct attgagataa tcatgtggtt 50460
tttgtcatta gttctgttta tgtgatggat tactgatttg catatgttga accagccttg 50520
catcccaggg atgaagccga cttgatcatg gtggataagc tttttaatgt gctgctggat 50580
ttggtttgac agtattttac tgaggatttt tgtatcaatg ttcctcaggg atatcggcct 50640
gaaattttct ctttttgttg tgtctctgcc aggttttggt atcaggatga tgctggcctc 50700
ataaaatgat ttagggagga gtccctcttt tctattgttt ggaatagttt cgtaaggaat 50760
ggtaccagct cctctttgta cctctggtag aattcggctg tgaatcggtc tggtcctggg 50820
ctttttttgg ttggtaggtt attaattact ccctcaattt cagaaattgt tattggtcta 50880
ttcacttcta tgcatagagg tgtttatagt attctctgat ggtagtttgt atttctgtgg 50940
gatcagtggt gatattccct ttatcatttt ttattctgtc tatttgattc ttctctcttt 51000
tctgttttat tagtctggct agcagtctac ctattttgtt aatcttttca aaaagcctgc 51060
tcctggattc attgattttt cgaagggttt ttcatgttgc tgtctccttc agttctgctc 51120
tgatattagt tatttcttgt cttctgctag cttttgaatt tgtttgctct tgcttctcta 51180
gttattttaa ttgtgatgtt agggtgttgc ttttagatct ttctcacttt ctcctgtggg 51240
catttagtgc tataaatttc cctctaaaca ctgctttagc tgcatcccag agattctggc 51300
atgttgtgtc tttgttctca ttggtttcaa ataacttatt tatttctgcc ttcgttttgt 51360
tatttatgca gtagtcattc aggagcaggt tgttcagttt ccatgtagtt gcacctgtgt 51420
tgagtgagtt tcttaatcct gagttctaat ttgattgcac tgtggtctga gtaactgttt 51480
gttatgattt ctgttctttt gcagttgcta aggagtgttt tacttccaat tatgtggtca 51540
gttttagaat aagtgctatg tggtgctgag aagaatgtat attctgctga tttgaggtgg 51600
agagttttgt agatgtgtat taggtccact tgatccagag ctgagctcaa gtcctgaata 51660
tcctttttaa ttttctgtct cattgatctg tctaatattg acagtggagt gttaaattct 51720
cccactatta ttgtatgcga gttgaagtct tttgtaggtc tctaagaact tgctttatga 51780
atctgggtgc ttctgtattg ggtgcatata tatttaggat agttagttct tcttgttgca 51840
ttgatccctt tatcattctg taatgttctt ctttgtattt ttcttttaat ctttgttggt 51900
ttaaagtctg ttttatcaga gactaggatt gcaacccctg cttttttttg cgttccattt 51960
ccttggtaag tcttcctcca tccctttatt ttgagcctat gtgtgtcttt gcacatgaga 52020
tgtgtctcct gaatacagca cactgatggg tcttgactct ttatccaatg tgctagtctg 52080
tgtcttttaa ctggggcact tagtccattt acatgtaaat ttaatatcgt tggctgggtg 52140
cagtggctca cgcctgtaat cccagcactt tgggaggctt aggtgggcga atcacaaggt 52200
caggagttca agaccagtct ggccaacatg gtgaaacccc gtctctacta aaaataaaga 52260
aaattagctg ggcgtagtgg tgggtgccta taatcccagc tactcaggag gctgaggcag 52320
gagaatcact tgaacctggg agacggaggt tgcactgagc cgagatgggt gccactgtac 52380
tccagcccag tgatagagtg agaccgtgcc tcaaaaaaaa aaaaaaaatt gctatgtgtg 52440
aatttgatcc tgtcattatg atgctagctg gttattttgc ccattagttg atgcagtatt 52500
ttcatagtgt tgatggtctt tacatttcag tatgtttttg cagtggctga taatggtttt 52560
tcctttccat atttagtgct tccttcagga gttcttgtaa ggcaggccgg cttgtgacaa 52620
aaatccctca gcatttgctt gtctttaaag gattttattt ctcctttgct tatgaagctt 52680
agtttgggtg gatatgaaat tctgggttga aaattctttt ctttaagaat gttgaatatt 52740
ggtccccact ctcttctggc ttctagggtt tctgcagaga gatctgctgt tagtctgatg 52800
ggcttccctt tgtgggtaac ccaacctttc tctctggctg cccttaacat ttgctccttc 52860
atttcaacct tggtgaatct gatgattatg tgtcttgggg ttgctcttct cagggagtat 52920
ctttgtggta ttctctgtat ttcctgaatt tgtatattgg cctgtcttgc taggttggag 52980
aagttctcct ggataatatc ctgaagtgtg ttttccaagt tggttccttt ctccctgtca 53040
ttttgaggta catcaatcaa atgtaggttt ggtcttttca catagtccca tatttcttgg 53100
aggctttgtt cattcctttt aattcttttt tctctaatct tgtcttcatg ctttatttca 53160
ttaagttcac cttcagtctt tgatatcctt tcttccgctt gatcgatttg gctattcata 53220
cttgtgtaag cttcatgaag ttcttgtgct gtgtttttca gctccatcag gtcatttatt 53280
ttcttctcta aactggttat tctaattagc agttcctgta accttttatc aaggttctta 53340
gcttccttcc attgggtttt tggaattttc agccttttttg ctctattttt aattcatctt 53400
catggcttta tctacctttg gtctttggtg ttggaggtct ttggatgggg tttttgcatg 53460
ggcatccttt ttgctgatgt tgatgctatt cctttctgtt ttttttcctt ctaatagtca 53520
gggccctctt ctacaggtct gctggagttt gctggagttc cactccagac cctgtttgtc 53580
tgggtatcac cagcggaggc tgcagaacaa caaagattgc tgcctgttcc ttcctctgga 53640
agcttcgtcc cagaggggca cccaccagat gccagccgga gctctcctgt ataaggtgtc 53700
tcccagacag gatgcacggg ggtcaaggac ccacttgagg aggcagtctg tcccttagca 53760
gagctcgagc gctatgctgg gagatccact gctctcttca gagccagcag gcaggagcat 53820
ttaattctgc tgaagctgca cccagagctg ccccttcccc caggtgctct gtcccaggga 53880
gatgggagtt ttatctataa gcccctgact ggggctgctg cctttctttc agagatggcc 53940
tgcccagaga ggaggaatct agagaggcag tgtagctaca gtggcttcat ggtgctgcgg 54000
tgggttctgc acccagttcg aacttcctgg aggctttgtt tacagtgtga ggagaaaact 54060
gcctactcaa gcctcaataa tgaccagtgt cccacccccc accaagctca agtgtcccag 54120
gttgacttca gagtgctgtg ctggcagcaa gaatttcaag ccagtgcatc ttagcctgtc 54180
aggcttcatt gggggtggga tccactgagc aagacctctt ggctccctga cttcagcccc 54240
ctttccaggg gagtgaatgg ttctgtctcg ctggcattcc atacaccact ggggtatgaa 54300

```
aaaaactcct gcagctagct cggtgtctgc ccaaatggct gcccagtttt gtgcttgaaa  54360
cccagggccc tggtggtgta ggcacccgag ggaatctcct ggtctgtggg ttgcgaaaac  54420
catgggaaaa gcatagtgtc tgggccagat agcactgttc ctcatggcac agtccctaac  54480
agcttccctt ggctagggga ggaagttctc tgaccccttg cacttcccag gtgaggtgat  54540
gcctcaccct gcttctgctc accctccatg ggctgcaccc actgtctaac cagtcccaat  54600
gagacgaagt gggtacctca attggaaatg cagaaatcac ctgccttctt ctttgatctc  54660
actgggagct gcagaccaga gctcttccta gccatcttgc cagccatctg ttatggttct  54720
taaaacatta atttgctatt gtgtgttcag cttatctaaa aaataaagta tgggaatcag  54780
tgaattttga ggagaaggca atgctcttat gtgtgtgtat atggtgtgtg tctgtatttg  54840
tgcctatgga taatcattag tttctcaaat gtatgcaagt gatacagcac atatgtgtat  54900
ttcccagtct tcatacgctc aacagaccag ccttcttttt ccacctcgga catatgtttc  54960
tgggtaggtt tcctgatttg taatcagtca gcctctgata ttcactgtga ctttggtttc  55020
cagccctgtc tggaagaact ccagcctggg agaatgtaaa cattttattc agaagcctgt  55080
gatgttggaa agaggaggtt ttggatgatt tttgtttttg tttggacttg ggtcagtgtc  55140
tcccatttat agctggaatg tgaactgcat ggcttcagat gtgttttgga agattgatgt  55200
gggcctcatg aaactcagct acagtggagc ctcaggagac taggagctgg ttatcatatt  55260
aagaaacaca tttcttttta tcagtgaata ttaatgctga acagtgaagc tgtggaactc  55320
cttctcttac accggcaacc tcagccctcc tagaaaagct gtgtagtcag aaccagtgtt  55380
agggggagtt ctttatggtt tctccaacag tcgttgatac tgagtaaaaa gggactaccc  55440
aggggatttc aagtcaaaat ctaagaacta aacttatttc tgttaatgat atgaatgaca  55500
tgtcattggt gaatggaaag aaaatgctct caatatatgg agctatagga ataaatgcta  55560
gaagtgaggc taagtttttg ccagctgtat cctactgatc atattggcca ttatgttaga  55620
attgccactt tccctctcct tggatgaaaa gaggtcttat tttatttttc caagaaggag  55680
tcttgctctg tcacccaggc tggagtgcag tggcgcgatc ttggctcacc gcaacctctg  55740
cctcctgggt tcaagcgatt ctcctgcctc agcctcccaa gtagctggga ttacaggagt  55800
gtgccacctc gcccagctaa tttttatatt tttagtagag aaggagtttc accctgttgg  55860
ccaggctggt ctcaaattcc tgaccttgtg atctgccagc ctcggcctcc caaagtgctg  55920
ggattacagg tgcgagccac catgccctgc catgaaaaga aatgttataa aagtacaaac  55980
cacttgtgct ttattttatg ggtgagtcta cttgtggtgg atccacttgt ctcataccat  56040
tatgtctact tctttccttt ttgattgcta agaaaatttt ccatcttttc caacgaaaat  56100
gcaggatcta aaacagaatt gcaaagttat tccaaaatca aaccaaacaa acgaacaaac  56160
taatcattaa catttaaaaa tcaggagatc gcacctaaga atctgcattt cttcagtctc  56220
ctggaatgca ggtgcatgtg gtagcactga gtctgcattt ctgcatactg gaactgggta  56280
gatggagcta ccttttaatg tgacacgtgc tcccagtctt attaaggcag gccagcttta  56340
cccatttgtg tgagctgccc tgtccttgta ggcatttgaa tttttaacgt ttggtctata  56400
ggaaagaaaa cttctgcaat attttttttt cttccttgag actctaagtg atgttttgga  56460
attggaaatg agctatggtt agtgaatgga aatggtcagt ggaaatatgt aattaaaggg  56520
acttccctag agccacgatc taaatgtatt tgggcaacaa tggtgcttag tgttacccat  56580
gtcgaaaaga ctcatcagtc tgaacttagt tttcacagat acatgctcag gggaaacgtt  56640
tcctcctgaa gatgattcct cttggttttg actgcctgga tcagttcata aagctggagt  56700
```

```
tatggcttct tcaaaaaagc ctgtctctca tgctgtggta aaatatgtgg tcacctggct  56760
ggtgaagagt ttctgggtcc cataatattt tacataggac acaaaaaatg gaatgctttt  56820
ggacttaaac ctgttttctt ttcaactcct tctgcctaga ggagatggta gcctcagaag  56880
agttcttact tccccttcct agaactgtgc aaatctttca ggtcccagct ggtaatggag  56940
aaattacttt ttgttattta aaaaatataa acaggaaaaa taaaaaccat gatatttcat  57000
gaaatacaac ttcttttctg ttttctacta aataagacaa attttttttt atatgtgttc  57060
aggttcctga ctgtctttag tactttacct tctcatggtc tctactctct tgcaatttat  57120
tttatatagt ctttttccag gaatcctccc gtctcattag atttttcttt ttgttccttt  57180
ccatgctgct gtattttcct tttattttag aacctgtgtc taattttcca gctctctact  57240
tttattctta ttttcctttt gtcagcctgg tgtcttttat tttctattgt ttcatttttt  57300
ccctctctgt gcccttttc atgtgctatt atacagggtt tgcttatttt tcacttctgt  57360
tcagtttgtt ttattctctt accatgcatt catacctcct gcttcaaaac caaaaaaccc  57420
gaaactgatt cttacttttt taattgtaac cctctcccta gtttatttac actaacttta  57480
cactatgagt tttttatact tgaaattgcc aaaatttcct tatcacttag ttttctccca  57540
gtttcccata gaaaattcag tggatgttct ttccatatgt cagctgctgt ggtaacccaa  57600
gacagaggtc attatgttca gttctgatca cattttgttc tttcgctggc tgtattacct  57660
gaaggaagcc acagtctctg tctgggtctc attttttttt atctagtaaa gttaacaggg  57720
agaacaaggt gtggttctca gatgaggcac acctgtgagc tcgccagaac tgtgctacct  57780
caggtctcac tccacacttc ctgacgtggt atctgcattt ttacaagatc tcccgctgat  57840
ctgtgccctc atggaagttt gagaagcaca atctcgatgc tctttggggg tttttccagg  57900
tttaactttg ctgaaaataa gggaaaacct attttactaa gtgaaaataa gtgaaatatt  57960
ttaataagtg aaaataaggg aaaaacataa agtgaaaact gctttggtta caaggcacag  58020
tagaataacc tgggaagcat caataaaatg tcaatgcctt agaggtccct cctcagggca  58080
gctgattcag aaactctggg gatggtattt tttactgtac caggtgattt taatgagcag  58140
gttgatcccc acttaaatat gctatttaac tttgacctcc tttactgatg ccctcagtgc  58200
tgccctcttt tggttgtgag gtaagtaatt actatggaaa gaggaacttc gaagtatttg  58260
gtttcatcta cttaaaccca ccagaattta ttctggggag gccataactg gggagataga  58320
taactatcga aggaggctat atgtattttt atagcgttat gaaagcaaaa gcaggattcg  58380
cttacttttt tttttttctc aagactgatt aaggcttttg ctggcaatgg gagtgtttgt  58440
ggtaacagaa ggaagtaacc ctggcaagtg atagatagac attgtatcct aagagtcttg  58500
ggggtggtgg gtgccgggga tatgtcagtg ggatggtttt atttcatcag aacttggtgc  58560
tggtgttgac tggatactca caattagcca catgctatga ttgggttact gaacattagg  58620
ttctaattta tttttaatta tttcaggttg ttgaactgta gctgatttaa gaaaacttga  58680
aaccaagatt tttttttta actgctctta tagtattctt agtgtgagaa ctggggaggg  58740
aatagtcata aaacaatttg tcacaagagt ggagggtgtg acaatactat taggtggtga  58800
tactttaatg ttgtagtttt aaaatcggat cttgagaaac tgtgtcttta aagatttttt  58860
cttttttaa gagagagagt ttcgctcttg tcgcccaggc tggagtgcaa tggtgtgatc  58920
tcggctcact gcaacttctg cctcccggct tcaaacgatt ctcctgcctc agcctcccga  58980
gtacctagga ttacgggcag cctgctacca tgcccagcta atttttgtat ttttagtaga  59040
```

```
gaaaggtttc atcatattgg ctaggctggt ctcaaactcc tgatctcagg tgatccaccc  59100
gcctcagcct cccaaacggc tgggattaca ggcaagagcc accacacctg gcctttaaag  59160
ggctttttaa aaaaaggtta aatgtttttc accagtgctc aatgagaaac acaaacatga  59220
ttacattgtt tggagtggct gaattacttg atcaaaattt aaaaaaaaag gtattttccc  59280
taagtggttt ttgcttagta cagcaccttt ttttcccctc agttttcatg tcctgaatta  59340
tttctgcatc attaagttta gctgaggagc caaaattctg tcattgtggg gggattgctg  59400
aggtgtcaca tcgacaaagg gaggtactta gaataagatg tcattttggt ctgttcttga  59460
gtgttactcc aagaagttat gtgagcagag aaacactaat cctgtgggcc atctgtcttt  59520
cccatcatgt ggcagaaccc ccatgcagaa tctctagtca aggttggacc atggctgcat  59580
ttcattacat ctgaaaagag tccccggtag ttatgtgatt tttacctcac agattgctca  59640
gaatcacata aagcctcaac aaatatttcc tcacagattt attctagccc tggtcaaaag  59700
tgtgaagtag gacattttct tcaagtgtat tttttttct gtcttattga aacactttca  59760
atactgttag cgtgactttg tgtcccatcc gtccaatatt tgctgtactc acagctgtta  59820
cctctgcagg aaatctttgc aaactagagt cttcattctt tcatggttct aggcagtaag  59880
cttagaaggg acagtggagc tgtaacactc actgtttcat aagtttttaa acttatgctg  59940
taaaagtctc tgatacatgc aagatcagag aaaatgtaga acaaaggagg catatagatg  60000
aggtgaggat actgggaaga taataaattt gcacagaagg gaagggagtt tataaaatgt  60060
gggaagagtc aggaaaggct ggcaggaggt gaaccggggt gtaagaagga tgtgtacaat  60120
atgtaggtag agaagatatg tcatgaggcc tcgcaatgcc ctcattacca ttatggttag  60180
gtagttgcca acacatgttt tcggagcacc tactgtgtgc caaacattat tctggtgctc  60240
agggtatggc agtaaatgag cctagcagaa tttctgtctt caaggagcta acattctatt  60300
ctagtaaaaa agttctcttg cccttgctaa gtttgaaatg cctgtttatg gcaaaggagt  60360
agaaatggta gatgctttat ataaaaatat atgatttgtc ttggcaaagc atccttgagg  60420
agagattagt acagtgcaaa aaagtattga gtaacattct ccccgtttcc acctttctgt  60480
caggtcatag atataaatta caattctggc cctcattcac cctcacatag ctttctggca  60540
tcctttccca ttctctgaac atgagaggaa tgagaaggtt atttggaagg tcgctgatct  60600
taggagttgt cctgctacag ttaccggaga atcttgaatt tcatctgaaa agactgcaag  60660
gcagtcgggg caagcatgct atgagaagtc aactggtaag cagaccccag agatgagaag  60720
catatgggaa gccaacccca tgatttgctt ccttaaaaag tatgggctgt ggatggattt  60780
taaatcctac tctaaataca agactggtgt tagcggttgt ttgcaggaaa accaaaggaa  60840
cttagcatcc ttcagtgtgt tacagagact gtgtggcctc aagcagtgaa gtgaagaatt  60900
ctttttgtct ttttcctcat atgcccaacc tggaaaccag cagaattttt gatggtgcat  60960
ctggttcctg gtgtgctgca gaagtgatta gtgtgtcatg tcactgtggc ctctttctct  61020
gccccaggag aatgtctggg gaacagaaga gcagagtcct gcctgggatc atgtgggtgg  61080
gggagctatt ccttctcaac agatagtgtg agaagcactg atccaaggtc ctggctgctc  61140
aaagtgtgtt cctaggagct tgctggacat gcagaatctc aagttccatc ccagaacctg  61200
atgtttttat ttggagcact ggccttggca acacatgttc cttcctcacc tttctgcagc  61260
ctctcactcc ccactgtcgc ccactcctca taggctatcc tcaggaatgg cattggtgga  61320
gtgttggtga aggtgtagct gcaagcattc tgatctttat tttacaaact ctaaacccag  61380
aagactccaa acccagaaaa gtctaagtca cagaaagcaa aggaacagtc ttatttcaga  61440
```

cacatctaca gtctttgctg gttaaatgtc aggaagccca caaaaagctg ccagacattt 61500
cagggtatga atttcgtatc tgtacttctt gacatctgct gggctaccat gcccttcaat 61560
ttaccaaaat atggaaattt ccttatggca ttctacccaa ataatgagga aaatgttgat 61620
gcttctctca gcctcaggac cttaaagcca cactgttcct aaccacgctt gcctatatgg 61680
cacttagcac tttacacaaa aaacaaacag aggtgtttat tccctggcag ttaatataaa 61740
tgctttctgt tttgtaaaat aggaacagta tttgattcca ttatcacaga tctcttgtgg 61800
acaagtcaaa attcttcaat taaggttata tctagttaaa ggaatttttc tctttggtct 61860
acatccccac cctgaatgtc cttgcctgtt agttccttgc aggtgaaagg taaaaaacct 61920
ttgcaacttc atgctataat tgtgcctttg aattttcaga ggaaaagaca gtgagagagc 61980
aagagcagat tgagaagcag aagagtgagt cgcaaaaaga gaaaatgaca gaaatggagc 62040
accctg 62046

<210> SEQ ID NO 76
<211> LENGTH: 103
<212> TYPE: DNA
<213> ORGANISM: Homo Sapiens

<400> SEQUENCE: 76
gtagatggag gcaggtgcat gtgtgatggg aagtgtggtg acgggttgtg tgggcacacg 60
ggatgaggcg cagatggctg gggtttggg aggtgaatgg atg 103

<210> SEQ ID NO 77
<211> LENGTH: 2584
<212> TYPE: DNA
<213> ORGANISM: Homo Sapiens

<400> SEQUENCE: 77
ctcactccat cactcgatga gataatatga gatttctact tcggagaggc caagtctaat 60
gaagagaaaa aaaggaaaag aagttgcaag actcgaataa aatctgctgc accttgtaaa 120
tgctctaact ggacatgaag gaaaggggcg agggaggggg gtgggatttt tggtgcaagt 180
agcacatggt ttaaatatga atgaacaaac ctgtgatcta gtccttgtct tgtaattgtg 240
gattaatgtc aatgttaatc agcccctcaa agggagagaa aagctggacc ttttcccttg 300
ctgtaccata ttcagcattt gatttccatg ggccccacca tttatgtgta gaatttgaaa 360
tggttgtcac ctctctctga ggacagagct tgaagcctcc acaccagctg ctgctggaga 420
ttcaaagccc aactgtgggt ccgagaggga agctggctgg gctggctgaa gaatgaagac 480
cactggactc tccgttaatc tctaaggggt ctgctcccca ggaacgtttc tgaacaatgg 540
ggactttgtt ggtagccatt tggtagatgt tcttttctat ttataagtga ctttaaactt 600
tcccttggct gttaagaagt ttgttataga tttagctatt tattgttcga tgcctgcatg 660
ctgaaacaat gcctacagct gtcttcacat gtatggacgt gtgtgaatgg ttgtacgttt 720
tgcacatttt gtggctgttg agatgtgctt tgctgcacaa acatgaaaat ttttgagtta 780
caatttggag cataactgga gggtgggttg gggaggggtg gatttttaaa atgtcaagac 840
agggaaggat gacaaaatgg aaatttaaat gacatcctag aggtagagaa accgtggaga 900
tcgcttttct cagactcacc aacttttaat gggatttcat ggggtttggt tgtgctgata 960
gggtaagggg aggctgcttt ctgcccttct ccccactccc atctgattta cttaattcag 1020
tctcagctgc tgaaatttgg aaaggaccaa attgctttac agttttttc tttgtgtagt 1080

```
atcttgaaat cctggaaaat tctatggaat agttctgtat atagggcaca agtaaaggca   1140

ttgtccaaag tttatttatt tatttattac cctaagaatg ctttgccata accacattta   1200

atgggaaaaa cggcagtatc acagatgtaa attaactcac cagatttact gggcctgaac   1260

tcattctctt cttgctatat gatttagcaa gttctagaag gtctccaaga caataattac   1320

attggcacaa tgtatacttc agtgctcacc cgtaggcaaa tctcttttta aaaaactctt   1380

tggtgcacaa gtaacacatt tggccacaaa acaccaaaga attgtaggca gtggccccta   1440

ttgagaagtt ttccggtaga gttggaaatc agttgtgaat acattctttg ctagttggag   1500

tgcttgttta ctaagcatgt gccgtcgtag gtattagtgc tagtctcaga taggtgcttc   1560

ccctgaggtg caggggaaga ccaaagtttg caactcgaac tgctttcgtc catgtttctc   1620

acattgctgt attttagaaa ataggggtta agactgataa caacctttta cattgtgact   1680

gtgtttgcat tgtctaatga cagataaatc cttaacattt ctctccacct tagtacttta   1740

gactaattgt gtttgtccgt ccatgccatg aatgagtggg ctgtagttgg gcctaaataa   1800

atgagctgtt ggaagaaaag aatcacagta ctttccagca gtcagtccct ggttcctaga   1860

tgtgttctaa gcaatgcaaa tgtctaattg tcccccagtg ggcatagtca gtgtcgttta   1920

tattgtagca gttacagctc tgtagtttat gatgcaaatc tgccaagaga gatgtatgtg   1980

tcactgcatg gcttctgaaa gcaggatgaa ttttctgcag ctgtttcaaa gttggggtct   2040

gttcttgaat cctctattaa ttactgtgtg tgagccagag ggagctgtgg taagggttgg   2100

gcccccagcc tgtagggaac tttctggact cccactcttt gaatcgatat aggcatttgg   2160

tctcactact tgaccattct caccctgtga aacgtcccac actttgaagc aaatacaatt   2220

cacagcacag tacacacaaa aaccttggca taagacagag aaggttcttc ttattttgtg   2280

ggctggttgc tgtagaaaca cataacaaag ggcagccctc cacttctggt ataattgtgt   2340

agccccttttt ctttgggctt gacacctgtc ttgaataaga gtgattagag ctgcataatg   2400

tccctctctt ggctattgac catgtggttc acgtacaaaa ctctgtataa gttgaaggaa   2460

aatgttcatg ttcatatgta cttgtttgct atgactacat tttgaggttt tgtaaaactg   2520

ttattttttt ttttttcaca atgtgaaact gaaggtcaat aaattattag agattttctc   2580

ttca                                                                2584
```

<210> SEQ ID NO 78
<211> LENGTH: 693
<212> TYPE: DNA
<213> ORGANISM: Homo Sapiens

<400> SEQUENCE: 78

```
gaacttggca ttagaattcc tcgaccacta ggacagggac caagcagatt catcccagaa     60

aaggagatcc tccaagtggg gagtgaagac gcacagatgc atgctttatt tgcagattct    120

tttgctgctt tgggccgttt ggataacatt acgttagtga tggttttcca cccacaatat    180

ttagaaagtt tcttaaaaac tcagcactat ctactgcaaa tggatgggcc gttaccccta    240

cattatcgtc actacattgg aataatggct gcggcaagac atcagtgctc ctacttagtg    300

aacctgcatg taaatgattt ccttcatgtt ggtggggacc ccaagtggct caatggttta    360

gagaatgctc ctcaaaaact acagaattta ggagaactta acaaagtgtt agcccataga    420

ccttggctta ttaccaaaga acacattgag ggacttttaa aagctgaaga gcacagctgg    480

tcccttgcgg aattggtaca tgcagtagtt ttactcacac actatcattc tcttgcctca    540

ttcacattcg gctgtggaat cagtccagaa attcattgtg atggtggcca cacattcaga    600
```

cctccttctg ttagcaacta ctgcatctgt gacattacaa atggcaatca cagtgtggat 660
gagatgccgg tcaactcagc agaaaatgtt tct 693

<210> SEQ ID NO 79
<211> LENGTH: 856
<212> TYPE: DNA
<213> ORGANISM: Homo Sapiens

<400> SEQUENCE: 79
gcctaatttg tagatatcct caagaagatt atgagtcatt ctcactaccg gaatctgttc 60
ctctattttg tttaccaatg ggtgcaacca ttgaatgttg gccatcaaat agcaaatacc 120
ctctgcctgt attttctact tttgttttaa ctggagcctc agctgaaaag gtttatggtg 180
ctgctattca gttttatgaa ccatactctg aggagaatct cacagaaaag cagagacttc 240
ttttgggttt aacatcagca gatgggaagt ctgatagttc caaaacaatt catactaaca 300
aatgcatctg tcttctttct cactggcctt tttttgatgc attcaggaag tttctgactt 360
ttctgtatcg ttattccatc tctgggcctc atgtccttcc aattgagaag catatttctc 420
attttatgca taaagttcct tttccatctc ctcagagacc acggatttta gttcagttat 480
caccacatga taatctgatt ctcagtcagc ctgtgtcttc acctcttcca ctaagtggtg 540
gcaagttttc aacactactg cagaatttag gccctgaaaa tgctgtgaca ctactggtgt 600
ttgcagtaac agaacataaa attcttatcc attccctacg gccatccgtg cttactagtg 660
tgacagaagc attagtgtct atgattttcc ctttccactg gccatgcccg tatgttcctc 720
tctgcccact ggctttagca gatgtcttga gtgcaccatg tccattcata gtagggattg 780
attcaagata ctttgatctc tatgatcctc caccagatgt cagttgtgtt gatgtagata 840
ccaacactat ttctca 856

<210> SEQ ID NO 80
<211> LENGTH: 213
<212> TYPE: DNA
<213> ORGANISM: Homo Sapiens

<400> SEQUENCE: 80
atcacaatcg aagcaatgaa aagtgacatt gatgaggtgg ctttacaagg gatagaattc 60
tggtccaatg tctgtgatga ggaaatggat ttggccattg aagcttcaga ggcagcagaa 120
caaggacggc cccctgagca caccagcaag ttttatgcga agggagcact acagtatctg 180
gttccaatcc tcacacagac actaactaaa cag 213

<210> SEQ ID NO 81
<211> LENGTH: 1480
<212> TYPE: DNA
<213> ORGANISM: Homo Sapiens

<400> SEQUENCE: 81
agaaatggtc aatgcatggt ttgctgagag agttcacacc atccctgtgt gcaaggaagg 60
tatcagaggc cacaccgaat cttgctcttg tcccttgcag cagagtcctc gtgcagataa 120
cagtgcccct ggaacaccaa ccaggaaaat ctctgcctct gaatttgacc ggcctcttag 180
acccattgtt gtcaaggatt ctgagggaac tgtgagcttc ctctctgact cagaaaagaa 240
ggaacagatg cctctaaccc ctccaaggtt tgatcatgat gaaggggacc agtgctcaag 300
actcttggaa ttagtgaagg atatttctag tcatttggat gtcacagcct tatgtcacaa 360
aattttcttg catatccatg gactgatatc tgctgaccgc tattccctgt tccttgtctg 420
tgaagacagc tccaatgaca agtttcttat cagccgcctc tttgatgttg ctgaaggttc 480
aacactggaa gaagtttcaa ataactgtat ccgcttagaa tggaacaaag gcattgtggg 540
acatgtggca gcgcttggtg agcccttgaa catcaaagat gcatatgagg atcctcggtt 600
caatgcagaa gttgaccaaa ttacaggcta caagacacaa agcattcttt gtatgccaat 660
taagaatcat agggaagagg ttgttggtgt agcccaggcc atcaacaaga aatcaggaaa 720
cggtgggaca tttactgaaa aagatgaaaa ggactttgct gcttatttgg cattttgtgg 780
tattgttctt cataatgctc agctctatga gacttcactg ctggagaaca agagaaatca 840
ggtgctgctt gaccttgcta gtttaatttt tgaagaacaa caatcattag aagtaatttt 900
gaagaaaata gctgccacta ttatctcttt catgcaagtg cagaaatgca ccattttcat 960
agtggatgaa gattgctccg attctttttc tagtgtgttt cacatggagt gtgaggaatt 1020
agaaaaatca tctgatacat taacaaggga acatgatgca aacaaaatca attacatgta 1080
tgctcagtat gtcaaaaata ctatggaacc acttaatatc ccagatgtca gtaaggataa 1140
aagatttccc tggacaactg aaaatacagg aaatgtaaac cagcagtgca ttagaagttt 1200
gctttgtaca cctataaaaa atggaaagaa gaataaagtt ataggggttt gccaacttgt 1260
taataagatg gaggagaata ctggcaaggt taagcctttc aaccgaaatg acgaacagtt 1320
tctggaagct tttgtcatct tttgtggctt ggggatccag aacacgcaga tgtatgaagc 1380
agtggagaga gccatggcca agcaaatggt cacattggag gttctgtcgt atcatgcttc 1440
agcagcagag gaagaaacaa gagagctaca gtcgttagcg 1480

<210> SEQ ID NO 82
<211> LENGTH: 482
<212> TYPE: DNA
<213> ORGANISM: Homo Sapiens

<400> SEQUENCE: 82
cccaattttg acatgcttta taaccatgtg aagcaactcc tctccaatga gctactcctg 60
acacaaatgg agaagtgtgc cctcatggaa gccctggttc tcattagcaa ccaatttaag 120
aactacgagc gtcagaaggt gttcctagag gagctgatgg caccagtggc cagcatctgg 180
ctttctcaag acatgcacag agtgctgtca gatgttgatg ctttcattgc gtatgtgggt 240
acagatcaga agagctgtga cccaggcctg gaggatccgt gtggcttaaa ccgtgcacga 300
atgagctttt gtgtatacag cattctgggt gtggtgaaac gaacttgctg gcccactgac 360
ctagaagagg ccaaagctgg gggatttgtg gtgggttata catccagtgg aaatccaatc 420
ttccgtaacc cctgcacaga gcagattctg aaacttcttg acaatttgct tgcgcttata 480
ag 482

<210> SEQ ID NO 83
<211> LENGTH: 1031
<212> TYPE: DNA
<213> ORGANISM: Homo Sapiens

<400> SEQUENCE: 83
ataagcaacg atgtgctgag ctgaagaaag ccttgtgtac tgcccatgag aagttctgtt 60
tctggccaga cagcccatcc ccagaccgat ttgggatgtt gcccctggat gagcctgcta 120
ttcttgttag tgaattccta gatcgttttc aaagcctttg tcacttggac ctccagcttc 180
cttccctaag gccggaggac ttgaaaacta tgtgcttgac agaagacaag atcagtcttc 240
tcctacactt gcttgaagat gaacttgatc accgaactga tgagagaaaa actacaatca 300
aattaggctc agacatccaa gtccacgtca ctgcctgtat tctctctgtg tgtggctggg 360
cgtgtagttc ctctttggaa tccatgcagc tctccctgat aacatgttcg caatgtatga 420
ggaaggtggg gctctggggc ttccagcaga ttgaatcgtc catgactgac ctggatgcat 480
cctttggcct gaccagctcc ccaatcccag gccttgaggg gcgaccagag cgcttacctc 540
tggtgcctga atctcctcgg aggatgatga cccggagcca ggatgccact ttctccccag 600
gctcagagca ggctgaaaag agccctggtc ccattgtctc tcgaactcgg agctgggact 660
cttccagtcc tgttgaccgt cctgagccag aggctgctag ccccaccacc agaactcgcc 720
cagtgacccg aagcatggga acaggagaca cccctggcct ggaggtacca tctagccctc 780
tgcggaaagc caagcgagct cgcctctgct cctccagcag ttcggacaca tcttcccgaa 840
gcttctttga tcccacctct cagcatagag actggtgccc ttgggtgaat atcacacttg 900
gcaaagaaag cagggagaat ggtggaactg aaccagatgc cagcgcccca gcagagccag 960
gctggaaagc agtgctgacc atcctcttgg cgcacaaaca gtctagccag ccagctgaaa 1020
cggactccat g 1031

<210> SEQ ID NO 84
<211> LENGTH: 186
<212> TYPE: DNA
<213> ORGANISM: Homo Sapiens

<400> SEQUENCE: 84
attgaacagg agggtgtcac agtgaagagc agctcccact tcaacccaga ccctgatgca 60
gagaccctct acaaagccat gaaggggatc gggaccaacg agcaggctat catcgatgtg 120
ctcaccaaga gaagcaacac gcagcggcag cagatcgcca agtccttcaa ggctcagttc 180
ggcaag 186

<210> SEQ ID NO 85
<211> LENGTH: 674
<212> TYPE: DNA
<213> ORGANISM: Homo Sapiens

<400> SEQUENCE: 85
gaatgtatcc tgtcaggtat aatgtcagtg aatggcaaga aagttcttca tatggatcga 60
aacccttact acggaggaga gagtgcatct ataacaccat tggaagattt atacaaaaga 120
tttaaaatac caggatcacc acccgagtca atggggagag gaagagactg gaatgttgac 180
ttgattccca agttccttat ggctaatggt cagctggtta agatgctgct ttatacagag 240
gtaactcgct atctggattt taaagtgact gaagggagct ttgtctataa gggtggaaaa 300
atctacaagg ttccttccac tgaagcagaa gccctggcat ctagcctaat gggattgttt 360
gaaaaacgtc gcttcaggaa attcctagtg tatgttgcca acttcgatga aaaagatcca 420
agaacttttg aaggcattga tcctaagaag accacaatgc gagatgtgta taagaaattt 480
gatttgggtc aagacgttat agattttact ggtcatgctc ttgcacttta cagaactgat 540
gattacttag atcaaccgtg ttatgaaacc attaatagaa ttaaacttta cagtgaatct 600
ttggcaagat atggcaaaag cccatacctt tatccactct atggccttgg agaactgccc 660
caaggatttg caag 674

<210> SEQ ID NO 86

<211> LENGTH: 903
<212> TYPE: DNA
<213> ORGANISM: Homo Sapiens

<400> SEQUENCE: 86
gaggtatatc gaattccaaa gaaaagtcaa actgaaaagg aaaacacaac aactgaacga 60
ggaagggatg ctgttggctt cagagatcaa acacctgccc cgaagactcc taataggtca 120
agagagagag acccagacaa gcaaactcaa aataaagaga aaaggaaacg aagaagctcc 180
ctctcaccac cctcttctgc ctatgagcgg ggaacaaaaa ggccagatga cagatatgat 240
acaccaactt ctaaaaagaa agtacgaatt aaagaccgca ataaactttc tacagaggaa 300
cgccggaagt tgtttgagca agaggtggct caacgggagg ctcagaaaca acagcaacag 360
atgcagaacc tgggaatgac atcaccactg ccctatgact ctcttggtta taatgccccg 420
catcatccct ttgctggtta cccaccaggt tatcccatgc aggcctatgt ggatcccagc 480
aaccctaatg ctggaaaggt gctcctgccc acacccagca tggacccagt gtgttctcct 540
gctccttatg atcatgctca gcccttggtg ggacattcta cagaacccct ttctgcccct 600
ccaccagtac cagtggtgcc acatgtggca gctcctgtgg aagtttccag ttcccagtat 660
gtggcccaga gtgatggtgt agtacaccaa gactccagcg ttgctgtctt gccagtgccg 720
gcccccggcc cagttcaggg acagaattat agtgtttggg attcaaacca acagtctgtc 780
agtgtacagc agcagtactc tcctgcacag tctcaagcaa ccatatatta tcaaggacag 840
acatgtccaa cagtctatgg tgtgacatca ccttattcac agacaactcc accaattgta 900
cag 903

<210> SEQ ID NO 87
<211> LENGTH: 432
<212> TYPE: DNA
<213> ORGANISM: Homo Sapiens

<400> SEQUENCE: 87
gtcttctcca agatcttcag ccacgaggcc ctggagagtt acctgcccaa gatccagctg 60
gtgatccagg acacactgcg cgcctggagc agccaccccg aggccatcaa cgtgtaccag 120
gaggcgcaga agctgacctt ccgcatggcc atccgggtgc tgctgggctt cagcatccct 180
gaggaggacc ttgggcacct ctttgaggtc taccagcagt ttgtggacaa tgtcttctcc 240
ctgcctgtcg acctgccctt cagtggctac cggcggggca ttcaggctcg gcagatcctg 300
cagaaggggc tggagaaggc catccgggag aagctgcagt gcacacaggg caaggactac 360
ttggacgccc tggacctcct cattgagagc agcaaggagc acgggaagga gatgaccatg 420
caggagctga ag 432

<210> SEQ ID NO 88
<211> LENGTH: 1736
<212> TYPE: DNA
<213> ORGANISM: Homo Sapiens

<400> SEQUENCE: 88
gcataaatga gacatttttg agagttggta agagttacaa ggaactaaaa ggaagcagat 60
agtttaacat aaaactgtct tataatgagt gctgcccaca atgaaaaagg atgctgtcca 120
tgaaagagag tttcccgtca tcagaaatgt tcaagactta aagccacttg ctggggatga 180
ggtaaagggg gttagataaa cgctaaggcc ctttttggtt gtgggggtat ctaacaattt 240
ggtctgtagc tgcctgctta gtctgagtga acttgtatat ctaatttttc agtggttgaa 300

```
ggcctttcac tgttggactt gggagtatct ccgtattctg gagcagtatt tcatgaaact    360
ccattaataa tatacctctt tcatttccta attgactatg ctgaattggt gtttatgata    420
actgatgcac tcactgctat tgccctgtat tttgcaatcc aggacttcaa taaagttgtg    480
tttaaaaagc agaaactcct cctagaactg gaccagtatg ccccagatgt ggccgaactc    540
atccggaccc ctatggaaat gcgttacatc cctttgaaag tggccctgtt ctatctctta    600
aatccttaca cgattttgtc ttgtgttgcc aagtctacct gtgccatcaa caacaccctc    660
attgctttct tcattttgac tacgataaaa ggcagtgctt tcctcagtgc tatttttctt    720
gccttagcga cataccagtc tctgtaccca ctcaccttgt ttgtcccagg actcctctat    780
ctcctccagc ggcagtacat acctgtgaaa atgaagagca aagccttctg gatcttttct    840
tgggagtatg ccatgatgta tgtgggaagc ctagtggtaa tcatttgcct ctccttcttc    900
cttctcagct cttgggattt catccccgca gtctatggct ttatactttc tgttccagat    960
ctcactccaa acattggtct tttctggtac ttctttgcag agatgtttga gcacttcagc   1020
ctcttctttg tatgtgtgtt tcagatcaac gtcttcttct acaccatccc cttagccata   1080
aagctaaagg agcaccccat cttcttcatg tttatccaga tcgctgtcat cgccatcttt   1140
aagtcctacc cgacagtggg ggacgtggcg ctctacatgg ccttcttccc cgtgtggaac   1200
catctctaca gattcctgag aaacatcttt gtcctcacct gcatcatcat cgtctgttcc   1260
ctgctcttcc ctgtcctgtg gcacctctgg atttatgcag gaagtgccaa ctctaatttc   1320
ttttatgcca tcacactgac cttcaacgtt gggcagatcc tgctcatctc tgattacttc   1380
tatgccttcc tgcggcggga gtactacctc acacatggcc tctacttgac cgccaaggat   1440
ggcacagagg ccatgctcgt gctcaagtag gcctggctgg cacagggctg catggacctc   1500
agggggctgt ggggccagaa gctgggccaa gccctccagc cagagttgcc agcaggcgag   1560
tgcttgggca gaagaggttc gagtccaggg tcacaagtct ctggtaccaa aagggaccca   1620
tggctgactg acagcaaggc ctatggggaa gaactgggag ctccccaact tggaccccca   1680
ccttgtggct ctgcacacca aggagccccc tcccagacag gaaggagaag aggcag       1736
```

<210> SEQ ID NO 89
<211> LENGTH: 404
<212> TYPE: DNA
<213> ORGANISM: Homo Sapiens

<400> SEQUENCE: 89

```
gttcaagagc tgcaggattc cctcttgagg ctggagccct gcccacatct ttcccacaac     60
caagcaggtg gctcaggcag tggttctagc agctctgagg cagacaggga accctgggag    120
actcaggact ccttctccct ggctcacccc ctgcttcggc gcctccgcag ccattccagc    180
acccagatcc ttgggtctct tcccaaccag cccctcagtc ctgagatgca catcatggaa    240
gcccagatgg agcaactccg ggggagcatt gagaagctca aatgctttaa tcgtctgcta    300
tcagctgtgc tacagggata caagggccgc tgtgaaggcc tcagcatgca gctaggccag    360
cgggaggctg aggccacagc attgcatctg gccttgcagt acag                     404
```

<210> SEQ ID NO 90
<211> LENGTH: 478
<212> TYPE: DNA
<213> ORGANISM: Homo Sapiens

<400> SEQUENCE: 90
gccagaagcg gactcctaga agaggggagc agcaaggatg gaatgacagc cgtgggccgg 60
aggggatgct cgaaagagct gagcggagat cctacaggga ataccgaccc tatgagacag 120
agaggcaggc agacttcaca gctgagaagt ttccagatga aaaaccaggt gataggtttg 180
atcgagacag accgttgaga ggacgtggag gcccgagagg gggtatgcgc ggcagaggca 240
gaggtggccc tgggaacaga gtttttgacg cttttgacca gagaggaaag cgagaatttg 300
aaagatatgg tgggaatgac aaaatagcag tcagaactga agacaacatg ggtggatgtg 360
gagttcgaac ctggggatcg ggtaaagata ccagtgatgt ggagccaact gcaccgatgg 420
aggaacccac agtggtggag gagtcccagg gcaccccgga agaggagtct ccagccaa 478

<210> SEQ ID NO 91
<211> LENGTH: 328
<212> TYPE: DNA
<213> ORGANISM: Homo Sapiens

<400> SEQUENCE: 91
gtgaaaaaag ccaagatgca ggaatcagga gagcaaacta taagtcaagt aagcaatcca 60
gatgtcagtg atcagaagcc tgaaacatca agccttgctt caaaccttcc catgtcagag 120
gaaattatga catgcaccga ttacatccct cgctcatcca atgattatac ctcacaaatg 180
tattctgcaa aaccttatgc acatattctc tcagttcctg tttcggaaac tgcttaccct 240
ggacagactc aataccagac actacagcag actcaaccct atgctgtcta ccctcaggca 300
acccaaacgt atggactacc tccttttg 328

<210> SEQ ID NO 92
<211> LENGTH: 4225
<212> TYPE: DNA
<213> ORGANISM: Homo Sapiens

<400> SEQUENCE: 92
cccctcttcc tcgccctctc tcgcgggtcg gggttacatg gcggcgactg cggcaaagcg 60
agagcctcgg agacgccgct gccgccagca cagccggaga cctgagccga cactgggggc 120
agtccgcgag ccccgcactc tctcgatgag tcggagaagt cccgttgtat cagagtaaga 180
tggacggtag ctttgattgt gattgtggtg agctggagcc acctgatcac taacaaaaga 240
catcttctgt taaccaacag ccgccagggc ttcctgttga aataaatata tagcaacaaa 300
ggaaaaaaag aagcaaaacg gaaatagtgc ttaccagcac cttagaatga tgctgctcag 360
gaccagtcca acactgaatg tatctgcact gtgaggagaa tgttcataga agcctgttgt 420
gtgcatattt attcacattt ttgttaaatg ttaaatcgtt tagcacggta atctgagtgc 480
acagtatgtc atttcattcc gtttgagttt cttgttttcg ttaaatgtct gcagagttgc 540
tgcccctttc ttgaactatg agtactgcaa tctttttaat tctcaatatg aatagagctt 600
tttgagcttt aaatctaagg ggaactcgac aggcctgttt ggcatatgca atgaacatca 660
agaaaccatc ttgctgtgga agcataatta tttttcttct cccttttttga aagatctttc 720 cttttgatgc cagttttctt ccttgtttac acaagttcaa tttgaaagga aaaggcaata 780
gtaagggttt caaaatggca gagaaatttg aaagtctcat gaacattcat ggttttgatc 840
tgggttctag gtatatggac ttaaaaccat tgggttgtgg aggcaatggc ttggtttttt 900
ctgctgtaga caatgactgt gacaaaagag tagccatcaa gaaaattgtc cttactgatc 960
cccagagtgt caaacatgct ctacgtgaaa tcaaaattat tagaagactt gaccatgata 1020
acattgtgaa agtgtttgag attcttggtc ccagtggaag ccaattaaca gacgatgtgg 1080

```
gctctcttac ggaactgaac agtgtttaca ttgttcagga gtacatggag acagacttgg   1140
ctaatgtgct ggagcagggc cctttactgg aagagcatgc caggcttttc atgtatcagc   1200
tgctacgggg gctcaagtat attcactctg caaatgtact gcacagagat ctcaaaccag   1260
ctaatctttt cattaatacg gaagacttgg tgctgaagat aggtgacttt ggtcttgcac   1320
ggatcatgga tcctcattat tcccataagg gtcatctttc tgaaggattg gttactaaat   1380
ggtacagatc tccacgtctt ttactttctc ctaataatta tactaaagcc attgacatgt   1440
gggctgcagg ctgcatcttt gctgaaatgc tgactggtaa aacccttttt gcaggtgcac   1500
atgaacttga acagatgcag ctgattttag aatctattcc tgttgtacat gaggaagatc   1560
gtcaggagct tctcagcgta attccagttt acattagaaa tgacatgact gagccacaca   1620
aacctttaac tcagctgctt ccaggaatta gtcgagaagc actggatttc ctggaacaaa   1680
ttttgacatt tagccccatg gatcggttaa cagcagaaga agcactctcc catccttaca   1740
tgagcatata ttcttttcca atggatgagc caatttcaag ccatcctttt catattgaag   1800
atgaagttga tgatattttg cttatggatg aaactcacag tcacatttat aactgggaaa   1860
ggtatcatga ttgtcagttt tcagagcatg attggcctgt acataacaac tttgatattg   1920
atgaagttca gcttgatcca agagctctgt ccgatgtcac tgatgaagaa gaagtacaag   1980
ttgatccccg aaaatatttg gatggagatc gggaaaagta tctggaggat cctgcttttg   2040
ataccaatta ctctactgag ccttgttggc aatactcaga tcatcatgaa aacaaatatt   2100
gtgatctgga gtgtagccat acttgtaact acaaaacgag gtcatcatca tatttagata   2160
acttagtttg gagagagagt gaagttaacc attactatga acccaagctt attatagatc   2220
tttccaattg gaaagaacaa agcaaagaaa aatctgataa gaaaggcaaa tcaaaatgtg   2280
aaaggaatgg attggttaaa gcccagatag cgctagagga agcatcacag caactggctg   2340
gaaaagaaag ggaaaagaat cagggatttg attttgattc ctttattgca ggaactattc   2400
agcttagttc ccagcatgag cctactgatg ttgttgataa attaaatgac ttgaatagct   2460
cagtgtccca actagaattg aaaagtttga tatcaaagtc agtaagccaa gaaaaacagg   2520
aaaaaggaat ggcaaatctg gctcaattag aagccttgta ccagtcttct tgggacagcc   2580
agtttgtgag tggtggggag gactgttttt tcataaatca gttttgtgag gtaaggaagg   2640
atgaacaagt tgagaaggaa aacacttaca ctagttactt ggacaagttc tttagcagga   2700
aagaagatac tgaaatgcta gaaactgagc cagtagagga tgggaagctt ggggagagag   2760
gacatgagga aggatttctg aacaacagtg gggagttcct ctttaacaag cagctcgagt   2820
ccataggcat cccacagttt cacagtccag ttgggtcacc acttaagtca atacaggcca   2880
cattaacacc ttctgctatg aaatcttccc ctcaaattcc tcatcaaaca tacagcagca   2940
ttctgaaaca tctgaactaa aacactcagc agacatttat ctttgtattc ttcatgaaat   3000
gtgttttgtc ttttttttatt actagtgttt aagtcatttt ttacttgaat cagatggtgt   3060
catttagtaa ggattttatg agttcttgtt ttttaaaatc cagactttct ttttctacat   3120
gtgagatagt tttcatttta actggcatgt catttgcaca caaaaataaa gactagagca   3180
aaataatgca acgcaggagg agaaaagaaa tgcactaaga caagaacatt ctctcataga   3240
acattgatct gttttacagg aaacaaacct tgccttgaaa tttacacagt gagactgtac   3300
ataattgcat gaaaatagct attttttttcc taagacattt ttcattcatg aatattttca   3360
agtttttcat actgtacaca tttcttaaaa cacatgatac cagcagcaac tgaaaatgaa   3420
```

```
tgccgaattt ggtacacatg tgttatctac ctcaaggtaa caagagtatg tggcaaaaca   3480

tataccaccc atagtgcttc acaaaatgca cttctattta gccagcgttt attgtagtaa   3540

actattctta ataaaactca ctcactgttt ataaatgttc tggtatgcat tctttatagt   3600

gaagtgttaa tacatcacat cttatttatt ttagcaaatc agtatatttt ctgtatttaa   3660

ttataaaaaa ttaacttagt ttttaaaatt tatttgcaaa tatactttac tttttccatt   3720

tggcactatg gtttgttgcc tacctagctg catctataat gtcagcttat cctaaggctg   3780

tccacgtact taatttactt aagtgttcat tttaagtaac gtgctcactg tgtataggaa   3840

tttgtatttt ggaggtgctt gatctatcta caaagaaaaa ttaattagga attactttat   3900

tataaaatgc tcctagaagt cttaattgtg tttatttttt aaaaaaacaa atgttagact   3960

tgtgtgcatg gaagtaatta aggtacatca ttattgtagt ttgaaagttg tacatgataa   4020

gacattttgt ttttactgta tgtttttact gaatgatcta ttccccatcc caaggcaagc   4080

atgaataaaa ttaggttaaa cgtagcatgt ggcatcgcag tctcttagaa tttgtttcat   4140

ctattttatt ttattgaata ctgtctgtat ctttggttat cctgtttgaa gaaaaaggac   4200

aaataaaaca tggccagcaa ataca                                         4225
```

<210> SEQ ID NO 93
<211> LENGTH: 195
<212> TYPE: DNA
<213> ORGANISM: Homo Sapiens

<400> SEQUENCE: 93

```
gggcaatgtt aaatattgtt caagattcag cacttttgga agccattggt tgccagatgg     60

agatgggtgg tggagaaaat aacctgaaga gtcatagtcg caccaatagt ggtattagtt    120

cagcaagtgg tggaagcacg gagcccacga ctcccgatag tgagagacct gctcaagctc    180

tcttaagaga ttatg                                                     195
```

<210> SEQ ID NO 94
<211> LENGTH: 656
<212> TYPE: DNA
<213> ORGANISM: Homo Sapiens

<400> SEQUENCE: 94

```
cctgctcagg aagaactcag agaagatcca gattttgaaa ttaaggaagg agaaggactt     60

gaagagtgct ccaaaataga agtaaaagaa gaaagccctc aatcaaaagc agaaacagaa    120

ttaaaagctt cccaaaaacc aatcagaaaa cacaggaaca tgcactgcaa ggtttctttg    180

ttggatgaca cagtttatga atgtgttgtg gagaaacatg ctaagggaca agatttgctt    240

aaacgagtat gtgagcatct caatcttttg gaagaagact attttggtct agccatttgg    300

gataacgcaa cctctaagac atggctggat tccgccaaag aaataaaaaa gcaggttcgt    360

ggtgtccctt ggaattttac atttaatgta aagttttatc cacctgaccc agcacagtta    420

acagaagaca taacaagata ttatttatgt cttcagcttc ggcaggacat agttgcagga    480

cgtctgccct gttcctttgc aaccttagca ttattaggtt cttacaccat ccagtctgaa    540

ctgggagact acgacccaga actccatggc gtggattatg ttagtgattt taaactggcc    600

ccgaatcaga ccaaggaact tgaagagaag gtcatggaac tgcataagtc atacag         656
```

<210> SEQ ID NO 95
<211> LENGTH: 1500
<212> TYPE: DNA
<213> ORGANISM: Homo Sapiens

<400> SEQUENCE: 95
gccgcgcggg gccatttccg ctgctgcttc tgtgagtttt tccggtgcac gcgagtgctt 60
ctgaaacgtc agctgcgctc ccctaggagt gctgagcccg cggaaccgca gccatgactg 120
aggctgatgt gaatccaaag gcctatcccc ttgccgatgc ccacctcacc aagaagctac 180
tggacctcgt tcagcagtca tgtaactata agcagcttcg gaaaggagcc aatgaggcca 240
ccaaaaccct caacaggggc atctctgagt tcatcgtgat ggctgcagac gccgagccac 300
tggagatcat tctgcacctg ccgctgctgt gtgaagacaa gaatgtgccc tacgtgtttg 360
tgcgctccaa gcaggccctg gggagagcct gtggggtctc caggcctgtc atcgcctgtt 420
ctgtcaccat caaagaaggc tcgcagctga aacagcagat ccaatccatt cagcagtcca 480
ttgaaaggct cttagtctaa acctgtggcc tctgccacgt gctccctgcc agcttccccc 540
ctgaggttgt gtatcatatt atctgtgtta gcatgtagta ttttcagcta ctctctattg 600
ttataaaatg tagtactaaa tctggtttct ggatttttgt gttgttttttg ttctgtttta 660
cagggttgct atccccccttc ctttcctccc tccctctgcc atccttcatc cttttatcct 720
cccttttttgg aacaagtgtt cagagcagac agaagcaggg tggtggcacc gttgaaaggc 780
agaaagagcc aggagaaagc tgatggagcc aggacagaga tctggttcca gctttcagcc 840
actagcttcc tgttgtgtgc ggggtgtggt ggaattaaac agcattcatt gtgtgtccct 900
gtgcctggca cacagaatca ttcatacgtg ttcaagtgat caaggggttt catttgctct 960
tgggggatta ggtatcattt ggggaggaag catgtgttct gtgaggttgt tcggctatgt 1020
ccaagtgtcg tttactaatg tacccctgct gtttgctttt ggtaatgtga tgttgatgtt 1080
ctccccctac ccacaaccat gcccttgagg gtagcagggc agcagcatac caaagagatg 1140
tgctgcagga ctccggaggc agcctgggtg ggtgagccat ggggcagttg acctgggtct 1200
tgaaagagtc gggagtgaca agctcagaga gcatgaactg atgctggcat gaaggattcc 1260
aggaagatca tggagacctg gctggtagct gtaacagaga tggtggagtc caaggaaaca 1320
gcctgtctct ggtgaatggg actttctttg gtggacactt ggcaccagct ctgagagccc 1380
ttcccctgtg tcctgccacc atgtgggtca gatgtactct ctgtcacatg aggagagtgc 1440
tagttcatgt gttctccatt cttgtgagca tcctaataaa tctgttccat tttgatgaca 1500

<210> SEQ ID NO 96
<211> LENGTH: 399
<212> TYPE: DNA
<213> ORGANISM: Homo Sapiens

<400> SEQUENCE: 96
gttggctata cagtgcgctt tgatgatgtc acctcagaag acaccaggat caagtttctg 60
acagatggca tgcttctgcg tgaagcaatt tcagactctt tgcttcggaa atacagctgt 120
gtcattttgg atgaagctca cgaacggact atccacacag atgtgctctt tggagtggtg 180
aaagctgcac agaagaggag aaaggaactc gggaaacttc ctctgaaagt gattgtgatg 240
tcagctacga tggatgtgga cctgttctct cagtatttca atggcgcccc cgtcctctac 300
ctagagggtc ggcagcatcc gatccaggtg ttttacacca aacagcctca gaatgattac 360
ctgcacgccg cgcttgtctc cgtcttccag atccaccag 399

<210> SEQ ID NO 97
<211> LENGTH: 307
<212> TYPE: DNA

<213> ORGANISM: Homo Sapiens

<400> SEQUENCE: 97
tgagttattc tccccacctc agaagtacca gcttttggtg tatcatgcag attctctctt 60
tcatgataag gaatatcgga atgctgtgag taagtatacc atggctttac agcagaagaa 120
agcgctaagt aaaacttcaa aagtgagacc ttcaactgga aattctgcat ctactccaca 180
aagtcagtgt cttccatctg aaattgaagt gaaatacaaa atggctgaat gttatacaat 240
gctaaaacaa gataaagatg ccattgctat acttgatggg atcccttcaa gacaaagaac 300
tcccaaa 307

<210> SEQ ID NO 98
<211> LENGTH: 642
<212> TYPE: DNA
<213> ORGANISM: Homo Sapiens

<400> SEQUENCE: 98
gtggaggatg cgctatctta tcttgaccag gtgaagctgc agtttggtag tcagcctcag 60
gtctacaatg atttccttga catcatgaag gaatttaaat ctcagagcat cgacaccccca 120 ggagtgatta gtcgtgtgtc ccagctattc aaaggccacc ccgatctgat aatgggattc 180
aacaccttct tgccccctgg ctacaaaatt gaggtgcaaa ccaatgacat ggtgaatgtg 240
acaactcctg gccaggttca tcagattccc acccatggca tccagccaca gcctcaacca 300
ccaccccaac atccttccca gccttcagcc cagtcagccc cagctcctgc ccagccagct 360
cctcagcccc cacctgccaa agtcagcaag ccctcccaac tgcaagcaca tactccggcc 420
agtcagcaga ctcccccact tccaccgtat gcatccccac gttctccgcc ggtccagcct 480
cacacaccag tgacaatctc gttgggaacg gccccatcct tgcagaacaa tcaacctgtg 540
gagtttaatc atgccatcaa ctatgttaat aagatcaaga acagatttca gggccaacca 600
gacatctaca aagcattcct ggagattttg cacacatatc ag 642

<210> SEQ ID NO 99
<211> LENGTH: 370
<212> TYPE: DNA
<213> ORGANISM: Homo Sapiens

<400> SEQUENCE: 99
agctaccata gaggaggcat actccaggtc aatgacaaaa ctagcaaaat ctgcaagcaa 60
ttattcacaa cttggaacat ttgcaccagt atgggatgta ttcaaaacat ctacagagaa 120
attagcaaat tgtcacttgg atcttgttag aaaattacaa gaattaataa aggaagttca 180
gaagtatgga gaagaacaag taaagtctca taaaaagact aaagaagaag ttgcaggaac 240
tctggaagct gtccaaacca ttcagagcat aactcaggcc ctccagaaat ccaaggaaaa 300
ttacaatgcc aagtgtgtag aacaggagcg tttgaaaaag gaaggagcta cacaaagaga 360
aatagaaaag 370

<210> SEQ ID NO 100
<211> LENGTH: 273
<212> TYPE: DNA
<213> ORGANISM: Homo Sapiens

<400> SEQUENCE: 100
ctctacgtct cctccgagag ccgcttcaac accctggccg agttggttca tcatcattca 60
acggtggccg acgggctcat caccacgctc cattatccag ccccaaagcg caacaagccc 120
actgtctatg gtgtgtcccc caactacgac aagtgggaga tggaacgcac ggacatcacc 180
atgaagcaca agctgggcgg gggccagtac ggggaggtgt acgagggcgt gtggaagaaa 240
tacagcctga cggtggccgt gaagaccttg aag 273

<210> SEQ ID NO 101
<211> LENGTH: 528
<212> TYPE: DNA
<213> ORGANISM: Homo Sapiens

<400> SEQUENCE: 101
gttttgagag tattttagaa gggctttatg gaccacggct acgaagagac ctcagtttat 60
ttgaagactg tgaaccagaa gagctgactg actggtctat ggatgaaaaa tgttcatttt 120
gtaacctaca gagagaagca gtcagtgatt gtataccatc tcttgattct tcacagtcaa 180
caccaacaga ggagctatca tctcagggcc agtccaacac tgataagatt gaatgccaag 240
cagaaaatta cctaaatgca ctctttcgaa agaaagatct tcctcagaac tgtgatccta 300
acattcccct agttgctcag gaattaatga aaaagatgat acgtcaattt gcgattgagt 360
acatttcaaa aagtggtaaa actcaagaga atagaaatgg ttcaattgga ccaagtatag 420
tatgtaaaag tatccaaatg aatcaagcag aaaactccct tcaggaagag caggaaggcc 480
ccttagacct cactgtgaat cgaatgcaag aacaaaatac tcagcaag 528

<210> SEQ ID NO 102
<211> LENGTH: 1975
<212> TYPE: DNA
<213> ORGANISM: Homo Sapiens

<400> SEQUENCE: 102
tcacagcaaa ctgtacaatg gcagttgagt gggttttgaa aaacgtctga attgtagtgt 60
ctacatctac cttctgcctt ctctctaccc tttgaaaaaa aataaatggc atgtttgaga 120
agagagctct attaaaagag gaatattgca aatggcttca gattctatga gtagtaaaca 180
agctaggaat cacattacaa aggggaaaag gcaacaacag caccagcaaa taaagaacag 240
atcctcaatt agtgatggtg atggagaaga ttcctttatt tttgaagcaa atgaagcttg 300
gaaagatttt catggttctc ttcttcgatt ttatgaaaat ggagaactct gtgatgtcac 360
actcaaggtt ggctcaaagc taatctcttg tcacaagctg gtattggctt gtgttattcc 420
ctactttaga gccatgtttc tttctgaaat ggctgaagcc aagcaaacgc tgattgagat 480
tagagatttt gatggtgatg caatagaaga cttggtaaag tttgtctatt cttcacggct 540
cactttgact gttgacaatg tccagcctct cttatatgca gcctgtattc tgcaggttga 600
actggtggct agagcttgtt gtgaatacat gaagttacat tttcatccct ccaattgcct 660
ggcagtaaga gcctttgcag aaagtcacaa tcgaatagac ttaatggaca tggcggatca 720
gtatgcctgt gaccatttta ctgaagtagt ggagtgtgaa gactttgtaa gtgtatcacc 780
gcagcacctc cataagcttt tgtcctccag tgatctaaat attgaaaatg aaaagcaggt 840
ctataatgct gccatcaagt ggcttcttgc caatcctcag catcattcca aatggttgga 900
tgaaacactt gcacaggttc gcctgccatt gttgccggtt gattttctta tgggtgttgt 960
ggcaaaagaa cagattgtca agcaaaatct aaaatgtaga gatttactgg atgaagcaag 1020
aaattaccac cttcacttga gtagcagagc agtacctgac tttgaatact ccattcggac 1080
taccccaagg aagcatactg ctggtgtgct gttttgtgta ggtggtcgag gtggatctgg 1140
tgaccccttt cgcagtattg aatgctattc tatcaacaaa aacagttggt tctttggacc 1200
agaaatgaat agtcgaaggc gacatgtggg tgtaatctct gtggaaggta aagtgtatgc 1260
agtaggtgga catgatggaa atgaacattt agggagtatg gagatgtttg atcctctcac 1320
taataaatgg atgatgaagg catcaatgaa cacaaagagg cgaggaattg ccttggcttc 1380
cttaggaggc ccaatttatg caattggagg gttagatgac aatacttgct tcaatgatgt 1440
ggagagatat gacatagaat ctgatcagtg gagtacagtg gcaccaatga atactccccg 1500
tggaggagtt ggctctgttg ctctagtaaa ccatgtttat gcagtaggtg gcaatgatgg 1560
aatggcttct ttatctagcg tggagagata tgatccacat ctggataagt ggatagaagt 1620
taaagaaatg ggtcagcgaa gagcaggcaa tggagttagc aagcttcatg gttgcttata 1680
cgtagttggt ggttttgatg ataattctcc tctgagttca gttgagcggt atgacccccg 1740
aagcaacaag tgggattatg tggcagcact tactactccc agaggtggag tgggaatcgc 1800
aacagtgatg ggcaaaatct ttgcagttgg tggtcataat ggcaatgcat acttaaatac 1860
agtagaagcg tttgatccag tgctgaatag gtgggagctt gttggatctg tgtctcactg 1920
cagagctgga gcaggagtag ctgtgtgttc ctgtttaact agccaaattc gagat 1975

<210> SEQ ID NO 103
<211> LENGTH: 220
<212> TYPE: DNA
<213> ORGANISM: Homo Sapiens

<400> SEQUENCE: 103
agccgcagag cacacaacat tgacctgaag gggacagtcg tgatctttga cgaagctcac 60
aacgtggaga agatgtgtga agaatcggca tcctttgacc tgactcccca tgacctggct 120
tcaggactgg acgtcataga ccaggtgctg gaggagcaga ccaaggcagc gcagcagggt 180
gagccccacc cggagttcag cgcggactcc cccagcccag 220

<210> SEQ ID NO 104
<211> LENGTH: 292
<212> TYPE: DNA
<213> ORGANISM: Homo Sapiens

<400> SEQUENCE: 104
gtgtcagcag ttgagtcttt ggagggcccc ctgctccagg tggaaggact gagtgacctt 60
cgactagagc ttcacagcaa gaagatgaac cttcacttgg ttctcataga tgaactacac 120
cggcacctgt acatcaaatc gactagccga gttgtgcagc gtaacaagga aaaagggaaa 180
atcagctccc tcgtgaaaga tgcttctgtt cctctgattg atgttacaaa cctccctact 240
cctcgaaaat tccttgatac ctctcactat tctactgctg gaagctcaag tg 292

<210> SEQ ID NO 105
<211> LENGTH: 236
<212> TYPE: DNA
<213> ORGANISM: Homo Sapiens

<400> SEQUENCE: 105
acacgaaggg cctgtatttc caggcatttg gaggccgccg ccgatgtctc agcaagagcg 60
tggccccctt gctagcccac ggctaccgcc gcttcttgcc caccaaggat cacgtcttca 120
ttcttgacta cgtggggacc ctcttcttcc tcaaaaatgc cctggtctcc accctcggcc 180
agatgcagtg gaagcgggcc tgtcgctatg ttgtgttgtg tcgtggagcc aaggat 236

<210> SEQ ID NO 106
<211> LENGTH: 942
<212> TYPE: DNA
<213> ORGANISM: Homo Sapiens

<400> SEQUENCE: 106
cttcttttcc gacaaaacac caaatggcgg atgacgccgg tgcagcgggg gggcccgggg 60
gccctggtgg ccctgggatg gggaaccgcg gtggcttccg cggaggtttc ggcagtggca 120
tccggggccg gggtcgcggc cgtggacggg gccggggccg aggccgcgga gctcgcggag 180
gcaaggccga ggataaggag tggatgcccg tcaccaagtt gggccgcttg gtcaaggaca 240
tgaagatcaa gtccctggag gagatctatc tcttctccct gcctattaag gaatcagaga 300
tcattgattt cttcctgggg gcctctctca aggatgaggt tttgaagatt atgccagtgc 360
agaagcagac ccgtgccggc cagcgcacca ggttcaaggc atttgttgct atcggggact 420
acaatggcca cgtcggtctg ggtgttaagt gctccaagga ggtggccacc gccatccgtg 480
gggccatcat cctggccaag ctctccatcg tccccgtgcg cagaggctac tgggggaaca 540
agatcggcaa gccccacact gtcccttgca aggtgacagg ccgctgcggc tctgtgctgg 600
tacgcctcat ccctgcaccc aggggcactg gcatcgtctc cgcacctgtg cctaagaagc 660
tgctcatgat ggctggtatc gatgactgct acacctcagc ccggggctgc actgccaccc 720
tgggcaactt cgccaaggcc acctttgatg ccatttctaa gacctacagc tacctgaccc 780
ccgacctctg gaaggagact gtattcacca agtctcccta tcaggagttc actgaccacc 840
tcgtcaagac ccacaccaga gtctccgtgc agcggactca ggctccagct gtggctacaa 900
catagggttt ttatacaaga aaaataaagt gaattaagcg tg 942

<210> SEQ ID NO 107
<211> LENGTH: 39106
<212> TYPE: DNA
<213> ORGANISM: Homo Sapiens

<400> SEQUENCE: 107
gtgtcatcct tgaaggatag aataaatcag ctgtcgtgtt ctcagtgaaa agtggaaaga 60
agttttaaag gatctgcaaa atagaattat gagacagagg aaagaaagaa acagacaatc 120
tgatctctat cttcatcggc caggtaagat ttgaagtgtt taaagaacgg gattcagttt 180
ggttacaaaa gagtagctgg gtcccaggga tgggtttttc agttaggata atctgaacta 240
catttgagag agaatttcta gcaaactgcc tgtccaagga tctcatggct ggccttggaa 300
ggtagtgagc ttcccgttat tggaagtgtt ccagcagaca tagagaatag attctgcagt 360
gactaaagga ttggataaga tgtagaacta gacctcagaa gttttcttcc aatgatgaga 420
tgctataaat tttatgaaca acatacttaa aatagcttta agacactcta cacgaattcg 480
aggctgaaat aagactagtt aaactataat cagtcaattg attattaaaa ccaagcacag 540
acttacaccc actacataca cttatgctca caaatgataa atgccaggat agtttggatt 600
gcctttgaag tttattattt gcaggtgtag aagctcttaa gttttagttt gtagtgtttc 660
taaaagtgag gcattctctt gaactgtctt tgatgatttg atgttcatac attatgtctg 720
ctgtgaattt ggaaagcact gcagaatcac tttttcaaag atcagaggaa tgtgggatag 780
aataaattaa gtttctggct aatatttggt attcttcttt agggatatgc tttcagagat 840
ctgtttctgg aaggagaagg gaagtcatga cattttatgt gaactcaact gggcaatgtg 900
aggttttcct atcattagct aataatatac atttaaagtc acatggaagt gtgttgcctg 960

```
tgatctgaat ttttattcct aaataaatta gagattaaaa tctgtggttt ccagttcaag   1020
ggtagggtac caaaaaaaat tgtctgatgt gggtttttat gtcattaaga aaggcggcaa   1080
cagctaagta ttattggctt ttccctttc ttggttgcac tggtcctttt cccttatctt   1140
gaaaggcggt agtaaatgtt gactttttgc ctctaattca cctcaatgat tgtacatttt   1200
aacatgtttt aagataggtg gttttagccc ctaccttatt ttcctggtct cttgcttcca   1260
ctgctctggt tcccaagaat caaaattgag gccagatgta tgttaacatc aagaaactct   1320
gactggcgct cttgttctct ccctccccag atattaatgc aagaagggaa ctaggacacc   1380
aggaacagcc actgttaaca ttctcctata atttctgcct gttattcctc tgcaagacct   1440
ttatgagagc tgaatgtatt tttgttctgt gttttaaaat tttaacattt aaaggcagtg   1500
ctttcctgtc acattgtaag tctctgaaaa cattgtatat aaatatatag atatattgca   1560
tatttgtttt caattttaaa gtgggatttt cttgcacaaa ggtttgtata caattctatg   1620
gccaactgac ctatctatgt atccatatat atatatatat atatatatat atatatatat   1680
atatatatat atttcctaa ttatgaaatg agaaatgaaa atatgtaaag tgtaaactat   1740
ataaacaaca aaaacaaatg agaatttgta aaatataaaa atcatagtaa cttagcatcc   1800
ataataaaat ctctattagt gtttgtaagt accaagtctt ttcccctcca tatttagaca   1860
tataatttat tcaattattg attagaaatt ataggtaaaa atcatccaaa tcatgcaaat   1920
tctgaaaaac tagaaatagc agctgttaac agtattggta tatgtccctt catatactca   1980
aatacatata tatatgccca gtattatttt ctattaattt ttaaataact ttttttacta   2040
taaaagtgat tcatatataa ttcagaaccc ctggaaaata taaaaatgta aacaaaaaat   2100
ggactgaaat atttccactc aaacataaac caatcatttt taccaattct tccaaatatg   2160
tacacttatg tctgtaaacc ccacactttt caaaaaataa aaatgacaca agtatatatt   2220
gctttgtggc tttttaaaaa atatttagga atgtatcaaa cattttttgtg ttaataaatg   2280
ctcaataaaa tttgttttgg tatgaatttt tttttttaaa tctcattcct gactctaaac   2340
ctcactttga gatttcccat ctgtgcctct gtgtaattcg tttgtagtga tggtccactt   2400
tactaattat ctcttcagtt gcacttaatc agctgtatta ctcacctact gaatatctaa   2460
tttgaaatac tgtgttttta tatttctagg aaccctgttt ctattttat tttaggaacc   2520
ctgtttacat cttcttaaaa gttgtaagtc atttttaata tattatcctt taatatgtcc   2580
tcttttactt ttaaacttat taaacatttt tattttatag tctgtattgg ataatcccag   2640
tatctgtaga ctttgtaagt ctgcttcgac tgtttgttct tttgatgac tcttgtaaat   2700
gttgacttgt ttctgtatgt gctttgcgat cccaccccac tccccattct cccaatgtaa   2760
gctcatgttt ctaggaactt tttctctggg aattctttga gagcttaagg tgaatcagtt   2820
cagaaagaat ttgtgttttc ttctgtttga tgcattaaag gcactctcaa cccatgtcca   2880
catcaggttg aattattagc ttgaggtttt tgggtggcta caccagcagt aggaattcag   2940
gtcatcccca gtttattaag ggcaagtgtc cggatataaa ttctcagggg cgactctttc   3000
ctacctagat ccatgtagat ccatgtgtga gacagtcaca ttttctgacc ctctccctgt   3060
gtgacttggg tcagtatttt ttctattagt tcagctgtta agggtaggat gtcccagctt   3120
tttgcagagg tctttgatct gacttccatt tttcacttga tttctgcttt taaaagccaa   3180
aactcaaggt cacctgggat tattgggata taatcggctg acagactccc tagtttatta   3240
ttgttatttt tttcttttcc gagttgattt cttgattact tttgcttctt gggagattca   3300
tgacttttgc caacttgggt aaacatttac agaggtggag gtgtgtgctt atgtatgcat   3360
```

acacacacag cagttttaca tgtttttgtg ctagaagagt tttcactgta ttttgctctt 3420
agtattctgg gaaaagacgt ctatagtgtg acttttaaaa tagcaggaca tattttgtcc 3480
ttcaaatata ttgttattaa taagattttt ttttttgag atggagtctt gttctattgc 3540
ccaggttgga gtgcagtggc acaatcttgg ctcactgcaa cctccacctc ccaggttcaa 3600
gtgattctcc tgtcttagcc taccgagtag ctgggattac aggtgcccac gaccacaccg 3660
agctaatttt tgtattttta gtagagatgg ggtttcacca tgttggccat gctggtcttg 3720
aactcctgac ctcaggtgat ctgcctgcct tggcctccca aaatgctggg attacaggtg 3780
tgagccaccg cgctcggcat cttaaattaa taccacttct cgaaacctta gggttgcttt 3840
caatttcccg gatatagttt tgtaatgatt gtcttcaata ggtatgttag cacagattgc 3900
tgtttctttt ccaatgataa acatcttgaa gtaggattgc taggtcaaag ggtgtgtttg 3960
tctggctttt gatacatatt gccaaaatca tccttcaggg acaggatgag atttttccat 4020
actgaaaccc ctgatcacag tgctcgaaag tgcagcaact tcattaaact gaatattata 4080
aatttagaaa gattatcaat gtgttggggg caatggcatt ttatttttaa aattagatta 4140
tttaatcact ttaagttagg cacaattttt tcttatgctc atcgatcatt tgtatttcat 4200
aaatttcttg tggatgttta tcaaccattt ttctattggg atgctcatct aaaaatttac 4260
ttgtttaagc tatatattta atacatataa ttttcgtttt taaactttaa gaatgttaac 4320
agtttatgat gtgatataaa gcatttttc aaatatgcat ttgtttaata taatgaagct 4380
ttgaatgttt aggtagtgca ttaggccatt tttatactgc tgtaaagaaa tacctaagac 4440
tgggtaattt ataaagaaaa gaaatttaat tggctcacaa ttctgcgggc tctacaggaa 4500
gcatggtgct ggcatctgct cggcttctgg ggaggcctca caaaatttac agtcatggca 4560
gtaggtgaag gggaggaggg cacctcatgt ggtgaaaaca ggagcaaaca agcaccactg 4620
aaagagagag agaaagggag agaaggagtg agttagttgg ggtgaggtga cacatacttt 4680
taaatgacaa tatcttgaga gaactcagat cacttaccac caagagaatg ttccagaacc 4740
attcatgagg gatctgtccc catgatccaa acacctccca tcaggcccca ggtataacac 4800
tggggattac atttcaatgt gagatttggt tggagacaaa tatccaaact attttaggta 4860
gttaccttta tcagtctttt ctttggcctt atgctaaaat agcctcctct caatctgtga 4920
ctatataaac attctactgt attttcttct agatctctta aggctttatt tttcatactc 4980
aattctaatg cataaacatt tgtttatgtg ctataaagat ttataccttta tacccctgtg 5040 aatttatttg agttggcttg cctgtgtacc tatttggagg tgtgatttgg atcaacccaa 5100
attatttggg attttttttg tgtgttgagt ctgtaacttt tgaatatgta attaccatgg 5160
catggaattg gtaatataga tgtttgcaca ggcaatggtg aactccaaat tcatgatgga 5220
acaagcaggt gcgtgtgtta aggaagaagg aataagttaa aggatgtgcc aagacagaaa 5280
gttaattata atgcttaacc tttagggatc atttccccaa cattttgtat gtttcttttt 5340
cttcctaatg gccattggga atggaatgtg tgggattgac taggaaggct cttgcatcat 5400
caggattttc agtgacttga gaaagctggg aagattatat taccagcact ttgtgtcttg 5460
tgtacagcct tttgcatgca tgcatgaatg aagaaaatca tttgacagga aatagttgtg 5520
ttagaatact tgtgcttttg ggcaaaccaa ttcttcagtt catttttcat ttctagtggc 5580
tatatgcctt cattaattcc tccttttatt gttcaattac cctttattga gcactgtcta 5640
tattgccagg cacactgagc attaggataa aaaaataatt atagtgctgg ctttatcctc 5700
aggaagctca aagtccagca gttgtctcat aactgaatag ggtttagtgt gatgaatgtt 5760
atgacttatg tgcaaggtac agaggtgatg gcatatagca gggcacacca acacactgct 5820
gatgatgtgt gtgtggcagt gattaaggag actcctgaga catcagctgg acattggaag 5880
attgaaagat aaagggagtt caccttgtgg ataggcagtg gaagaaggca ttttaattgt 5940
gaaaacagaa tatggaaggc atgaagtaac atgatgtttt ctaggaactc caggtagttt 6000
tgttggtaaa taatgttaag acttgctagt ggatgaggca gaggctggat caggggaggt 6060
cttggggaat gtacaaagga atctgaagtt tgcttcctcc ttcccaattc ttcttttttt 6120
tttttttttt tttttttttt ttttgagaca gggtctcact cgttgctcag gctggagtac 6180
agtggtgcca tcacagtata ctgcaacctc cacctcctgg gctcaggtaa ttctctcacc 6240
tcagcctccc gagtagctgg gactacacag tcacacacca ccacacccag ctaatttttt 6300
tcaccatgtt gcccaggctg gtctcctgag ctcaagtgat ccacctacct gggcctccta 6360
cagtgctggg attacaggca tgagccgtca cgcctggccc acctccctcc caattcttaa 6420
caattgaaag gatttccaca attttgttag atcattgcag gaggttaaat tggagagaga 6480
cagagagaaa tgaaatgaga ttagagctag agaacttttt tttttttttt tttttttttg 6540
agactttgtc acccaggcta gagtacagtg ttgtaatcat ggctaactgc agcttcgacc 6600
tcttgggctc aaccaatgct tgcgctttag ccttttgagt acctggaacc acaggcacac 6660
gccatcacac ccagctatgt ttgtttgttt tttgtagaga tggggtctca ctttgttgcc 6720
caggcttgtc tcaaattcat gggctcaagt gatcctccca ctttagcctc ccaaaatgct 6780
gagattacag gcatgagcca ccgtgctcaa ccaagaatgg atttgaatct attaagttgg 6840
aatgttggac tacattctgg aatgggatgc ataattaagt atcaccagac tataagtgtc 6900
tgtggaattg attggtatgg ataagatggc ctaaggagag taagcagaag tagaatagga 6960
aagggccaag tacagagctt gggggtaagc caacatttcc tagtcatcag aggaagagga 7020
tcctgcaaag aagcttgaga aaaggctatc acaaagttgg ataagaatca agggagcatg 7080
gtgttgtgag tagggcaaaa ttaaaacgag tgattaatga tgcaaaatgc caacagaggg 7140
tcaagtaaga tgaggacaga gaaagaacct ttttagaggt cagtgatctt aaggttttga 7200
gttggggtgg aggaagccat ggttcatcat ataaaaatgt aaaagcaata agcacagttt 7260
cttcagtatc ctgggccttg aaaagggagg atggggtagg ggaacgagag agaaggaaga 7320
agttggggtc aagggagtac tttttctttc ttgaatagga aacctagcat gtttatattc 7380
tgaggactgg gaaatgagga gagaacaaaa ctgaagccac agaagagaga ataattgaat 7440
gaagtaaact gcagtgcaaa acaagatgtg gccaattgaa gactaggatg aatgggagag 7500
atatcttgca aagtcattgt tagccaaaat tggtgacggt gactatcact ggaggatcaa 7560
gacatgcatt tcacaaatgt ttatgagcac aaagaactat ggcagctgtg tactgggtga 7620
aggatggagc cttgattatg ccctcatgga atgattagtt tttcttaagt ctgagttgtt 7680
gggatgaact tcattgaaat agttaatgtg actttgacac tactaagagt atgaatatta 7740
catgttagtt ggaatagtgg tccaagacat atgcaaataa attcagttat ttctgagtta 7800
tgaattctga gcccaattat ttttaccatt atatttttgt ttctgtgagc catataaatc 7860
tgagatacag ctggaggttt gggggaataa ttcctaggat atgtggctgc accatctccc 7920
cttaactccc acaaagaatg gtttggtttt catggtccgg ctccttggga tggtggagga 7980
ggaagcttct gacctggcca cactgcattg gctcatgggt gactgccctt tctgtgattg 8040
cagccaccac tttttagtcc ctgatcccca aataatagtt cactgtactt atcttaccct 8100
ccccaaagag aaggagattt tccttccaaa taagaaaact ctttagggca tcctcaggga 8160
tgcctatgtg tttgtaacac ttttagcacc caacatagcc ctttctcttt tgatttgtgg 8220
ttcactctat taagcaaatt acattcattg tccctagaga atgggttcta agtagatttg 8280
tgtgccaccc tgctggtctc actcttgcgg gcttttactt gagatgcgag ggtgcatgtg 8340
ttgactctgt cttaccgtgg agtgttctgg cttgcctact aaactccagg gatagggaca 8400
gccataatcc tgccttctct gtttgtgact gaatctctgt ggtttaaata ctttatataa 8460
aacttacaca tttcagctga ttaataacag ctatgcagga acattcaatt ctgaggcaat 8520
tttaatgtag tcgttgataa aatacaaact atcataataa aactgtttaa tttacagttg 8580
attccacagg atcaggggat ttccatttca aatgggctcc tgatgatctg cctggattcc 8640
cagaatttct catctgggta tacaaattag gtttcttgta accaacactt catattttat 8700
ttatttattt tttttgtaga gatggggtct caccatgtgg accaggctgg tctcaaactc 8760
ctggcctcaa gcaattctcc tgcctcaggc ccacagactg ccgggattac aagtgtgagc 8820
caccatgcct ggctcccttc atattttaaa gagaagttac acctacagcg ctttcgactt 8880
ttgatggaca catctttcta gagcatagtt cttgcattcc tcttttactg aaagttgtta 8940
attgctttgt tccattagcc ttagcaggaa aaatcctatc tctggagttt taggtccctt 9000
ggtttatctt aatttcgatt aggaataaga gaatacctac ctattcagct ctcaaacagc 9060
aatgaatatt gcactgtgtt catcctcatt acctcccatt attagtttac attctgggac 9120
actttttcta tctttaatga taagttcatt cagaaatatg ttcccacatt gagccatact 9180
tctggttttg tgtgattaac tttggcaccc catgagtagt gtctgttaaa attaaatgct 9240
tgttttgcct caagagagct agaatacata cacatattac cgtgatttac tgttaagtgt 9300
gcagattgag gtggtttaga agtttaaaat tggtttccga agggaaattt acaagaaaag 9360
tataacagat gaatatgtga ttagaactgc attccttttt taagtaaatt aaacagtttt 9420
attatgatag cttgtatttt atcaatgact acattaaaat tgcctctgga attgaatgtt 9480
cctgcgtagt tgttattaat cagctgaaac atgtaagtgt tatataaagt aaaaagagct 9540
ataaaccaag gagaaagtct gaagatagaa ctttaaaaaa ccactgttat ttccaggtaa 9600
aatatttaat ttccaaagaa ggttagcata tgttaaaagc taaatcttgt tctgcatttg 9660
ttggctacat ttatatgaat ttttatatgg aagttcctat ccagggtatt tattagtcat 9720
tttggaagtt tttatccagg gtattgatta gttggcatct tatatgttct ttcagaagct 9780
gtatgtatta tttttaaaaa tagaattcta attgagcttt taatctgtct gctgaatcag 9840
gaacattaca tgactttctt tggaggggaa ggaagccagt ggttagtttt aggtataaaa 9900
gagatcttca agcacggtct ttttaacttc ttgtttctgt attatttcag gaaatagagg 9960
cagctttccc tacattagat tgttagcaca gaataacagt agaagggttc agaaatgaag 10020
ctaaaaggaa ataagagacc agcatgatgc tggagttccc ctaggccagt caaattatgt 10080
tcaggccttt agtccatctg gatgttagtt ctatgtatga tatgaagttg gggtgtctga 10140
ttaggtatat ttttcctttt gccttagaac cattttttttt tccagtccct ttatgtcccc 10200
actgtaatgt catgtgtatc atttatgtaa gactgttttg aaactttgtg tacctctgaa 10260
tgtctagcct ggaacaattg tcacattacc ttcattacat ggcttttaat atgtcttact 10320
cattggtagg tcaagtcctc tacttctatt ctcttaattt gtcttggcta ttttggtcct 10380
tagcatttca ctggaaattt aggagcaggt ttatctatag acttccttgg actttgaatt 10440
taaataatca ttttgattgc aaataagggc agttttgact ctttcactcc ttacatgtta 10500
tttattgttg tcttgtttca ttgaattaac taggctgtct agaactgtgt tgaatagtag 10560
gagtaatagt gagattcttg ttattcctga tattgaagaa aatgcttcta aagagaaccc 10620
tattcctttt tgaggagtat tatttaaaac agctcagcat ttccatgtgt ttgattttag 10680
catattaaaa cataggaaac atgcagtgaa caaaaggggt tattatgagc ttagtgtacc 10740
agctgtctta aggttttcat tgttttagag gcatttagtt agatttaatt ctgactccaa 10800
aatgaccgac ctctctggag actgtatttt gtaggagaga ataagagtat ttccatttta 10860
atggaaaagt ggcaaagctt ccttccactt cgtaattttt gtggacagta ttccagcatt 10920
gtccaacaga tttttgtgat aatggaaaat gtatttctgc actgtgcacg taggagagca 10980
actatcatat tggacagtgt gggcctagac tttggagttc taaccatgcc ccatttacta 11040
gctgcacagg ttcctgcctg gtttcagaag gcttattctt ttgggctagc acagctcaca 11100
ctgaggcacg tggctggggg agtagagcag tccttgctgg attgcagcca tggctctcct 11160
tttagcctga tgcctttgtg caagtgagca gctggcacca ttgacaaggg tgatcctggt 11220
gactacctct ggaggctctg gaccctgact gctgaaacag gagaaaaccc tggccccatg 11280
cccctaagaa gtcacccgat caaagtggag cctgttgttt ccctagtcac aagtcaatac 11340
taagagattt ggctagtgac aaggaaattt ttcatgttag aattcttgta cccagctctt 11400
tttagaactg gactactgtt ctcccatatt caggaggcca tgaaccaacc agtagattgt 11460
ttattgtgct tgctgattta tgaaaaaact tctttgtaca gagcttctga aaggggtaag 11520
agaaagggag aatagcagtg ttatggactg aagaatgtgt ctccctgaaa ttcatatgtt 11580
gaaatctcag tccccaaggc gatggtatta ggaggtgatt aggtcataag ggctccgccc 11640
tcatgaatga gattaggggc cttataaaag agaccctaca gtcggtgtgt tgactcacac 11700
ctgtaatccc agcactctgg gaggctgagg cagaagattt gcttgagctc aggagtttga 11760
gaccaacctg ggcaacacag caagaccctg tgtctactat taataaatat tttaaaaaat 11820
tagcctggtg tggtggcgtg tgcgtgtagt ttcagcttct tgggaggctt aggtggcaga 11880
atcacttgag cctaggagtt taagtctata gtgaggtaga tcgcgccact ccagcctggg 11940
tgacagcaag accctgtcct aacatgctct taggagtttc ataaatgtga ccccagaaga 12000
gctctctagc cctgtttcca cttatgaggc taaattgaga agatcgcaga ccacaacccc 12060
gaagaggcct catcagagcc caactttgtt gtcaccctgg tcttcgactt ccagccttca 12120
gatctgtaag aaagaaatgt ttgttgttta agccacccag tctgtggtag ctttcatagc 12180
agcctgaact gactaagaca agtggatagc tgtctggttg ttttagaaag cagggctgca 12240
tggtgtgggg atgctgctgc tactcattcc tgctcattcc agtgttctgg aaaatgaggt 12300
agggtggggg aggtctgaac cttctaattt atttctagct gttctttttt agcaattaaa 12360
gcattcgttg gacaccagtt gcttttaatt cagttccatc tgcactgtac ttaatagata 12420
ttactcccag gttcttataa atggctggtt gttattcttg gtttcagagc tattttgagt 12480
ttttgtcttc atttgtattt tgactggaaa ttgggtgtgg acatattggg gagttggggc 12540
tgacatcatc tttattcaga agtcacttta tgaccatgtg cgggatatat taatttcact 12600
acagcttttg atcttaataa aatgtctctg ggttgagctg actgatcacg aagattttaa 12660
actttaatgt ttcctaagag gattgataca gccatccaga gaataacata gtatatagga 12720
gttatctttt gacagatcaa gttccatttc caaatgatat aaaacccacc tgtgtccaca 12780
tccttatgcc ttcttttgaa tctatgattt gataacttaa gaaatctatc tatgcattag 12840

```
atattgcctt tccggtagag ctatggtgtg atcttatgct catgaacaga aaatgaattt  12900
aagaatcctc agacctattg tccagttctt ttctttaaga agaacttgct attgactttg  12960
tcaaaactaa atctgttgcc ttgggcgaca ccctccaaaa ttcagattca gatggattac  13020
actaatagct ttatgctaca gatcaagtca tataatgtga aggtacaatt gcagctccct  13080
tattgttgta gacgcttgcc gggatgaagt tctcaaactt aacatgctct taggagtttc  13140
attaaacatg tgtgtgtatt tttaatgtcc aggatttata aatggtaaca cctgccctca  13200
gttctttttt gcactggtcc acggtgtttc agttacagtc tttattgaat aattcaaaag  13260
ttctctcctg aaacaatatt tctggcagtc cttataattg accaggtgga atgaccttca  13320
gtttggatga aagtccaatt tatttattta tttaataaaa ttccaaattt gccttttctg  13380
ccaggtatta aaagcactta aaactttttc taatcaacaa tactgaacac ttcagacact  13440
tatcagagac tttagtcttg aattatgtat tattttaaat tattatttcc agttctatta  13500
aaggccatgt gaggccactg atttttttaaa tggacagttt agtgagtggt tcttaaagtg  13560
tggccccatg agcagcacca gcatcacttg gagatttgtt aataaatgca aattcttgga  13620
tccaccccag acctactgaa tcagacatgc agtggggtgg ggctcataca tctgtgtttg  13680
aacaagccct ccagtgaatt ctgtgtgcca catattacaa tttgagaacc actggtgtaa  13740
tgcagtagtt aacacaccta gctttcaacc tagacccact ttgggtgctt gttaaaatac  13800
agattcttgg ttctctctcg cacagcatct tatgcaccag ctttggagaa gacacaggac  13860
tcagtgttac tatattctgc agtaaagctt gctctgctca ccttatatca tattagatca  13920
cttactagca ataaatgtag aatataatac gtttgttcta gtccaagtat ctgtgaagaa  13980
ctctgattta agataatggc atgtaatcag acatacgctt cagaattaag gagacttaaa  14040
aaatacagat gtctagtttc tactaaataa aaaactctgt taaaagtctg gttttgtttt  14100
gtgtttaagt ttcatgggtg ctataccatc caagaaccat ttatttttat cttcagcttt  14160
cattgagagt tgataggaga agaaatagcc atattaatat ttttgtatat tttataccat  14220
ttgataactc ttactaggaa ttagtagaag aaaataacat ctctctctct caatagttaa  14280
tacgcaactc ttcattttcc cttttgcttt ggttaccaga gagctcagag taaaattttg  14340
cactcagttt tgaaatacct atttcccttg cttactttaa tccatgactc ttgttcttta  14400
taatcttctg taacctatct gaaacttatt tggaagtaga tggggcccca aaactaagta  14460
aatgatggaa tatctgccct ttgctttgaa atgggcttct tgattgactc tttcccagct  14520
tggggtcagt gtcttcttta tatcatcctt cctttcatag acacaataca attgttggta  14580
gcctcactgt gaaagagtta atgtttccca ataccaggca ctgacatagg cagtaggaaa  14640
aatctggttc attttgtttc aaaatacacc ataccacgaa taagtacaaa cagctgcaat  14700
ttgggcttgg ggccaaaaga aatcagtgtg gtgctatgaa ttccagctga gaggaggagt  14760
tcatgtaact tagatcagag atcagtctct gtaacgagac catcagaccc cagaagggga  14820
agggtccttg tatgtcactt cagttacctc catcgctacc accaaaagaa actggggtag  14880
ttctttggag aggtggcctt ttagaaatct aaaattatac ccttggagcc gcttctctgc  14940
aattggctga acacatcaca ttttatccct tgcccccagc actgtattac tgtaaaatgg  15000
ggaaatctgg gaatacaaaa gatttagaga cttgccacct gctcatttta tcgctatgac  15060
ttggcttaaa acaacagtcg ctgtaacctc agccctttgg cacacgcttc cttctcaagc  15120
cccaggaaat tcttggtcag gtcgcaccca cagccactga gtctggttgt ttcttcttct  15180
```

```
cccagatttt ttagggaata tcagtttagt aaaacttatt tttttgtaag cggactcctt  15240
ttgtatcaga attcctttcc tttaaaaaat atttttatat ttattattat tttttaagta  15300
gagatggcat cttgctatgt tggccaggct ggtctcgaac ccctggtctc aagtgattgt  15360
cctgccttgg cctcggagag tgttggagtt acaggcttga gccaccacac ccagcccaga  15420
attccctttc taatgtcata atgccttatc tcttttttgg agtggtcatc aaatcccttt  15480
tcacactagt tagaagtttt ctgtgtgata ttctccattc tctacatatt tggactatcc  15540
cactgtgttt ttctggacat gtaggacagc atctttcagg cccattagca gatagaagtc  15600
tttcaagtgg ggcctcacag ctgtttttag gtctccggtt ggtttttagg tcatgtctca  15660
gacatagggg ctttgtggct actttgtggt tttactatct cctcatagtt tattaaaaaa  15720
gaggctcctt ttcccttcca ttttctactg ctttcctgat aaaagacttc agccattatt  15780
tttaaaagtg tccgctatta tattttaaac cctttcataa caggaaaaca ggagttaacc  15840
actcacataa gttagagagg ggaccccccct tttttggtga ttttcatagt tactaaatca  15900
ttgtgaacag agaaaagtca cttaattccc tttgcttcac ttcctgattt cttcaacaga  15960
gtggtaacat ttgagatgct attcatagaa ttgtatatca aagaatgagg ccagctcttt  16020
cttggtgctc cctcaagttg gtaaaatcac gtatgtgact tctcaggaag ccagagtatt  16080
tacatatcct cgacccagct gggaataatt catcctctag tacaatacta gttttcttta  16140
gattcccctc tatatttact gttttagaga ggtattgcca agagggtttt caatgaggaa  16200
gaatggtaat atgctgggag caggaaagga aatgaaatta agcgtctcat tatttttccc  16260
atgctgaagt agatattagg attgtattcc acaggtctta ttttcttccc cctccccacc  16320
tcaaaacttc aggcaggatg tataagtcta gacttaggtt atatactgat ttttttttaag  16380
cttttatctc cagtttaatt agaggctggt gaaggaaact gggtttctta tttggctctc  16440
aaactttgaa aataaacaaa actttcatat atttgaatag cacattgtgg gccaaacaac  16500
atctggaaga gattagtctc actggtaggc agaagaaatt tcataatgta ccatcttcaa  16560
agaacatggt acctcgtcac atttctcatg tgacatgtat cctggaaaca gaagtactta  16620
gggccacatt gctggagcat ctgcctttgt ctttgttttg tgtttaacat aaatgtgtct  16680
ttctaatact atgatatttc tttagctttt ttgaaaacac agctaaactt ggtggtacga  16740
tgctgcctgc gctgttgact gtggtctaga cttctccttt ttcagaagac ctatttgact  16800
tttggcaacg tgcctcttag agtttgtgat ttgtttgaga catcttttcc tgtcttctct  16860
aaaatcaggc acatatgtgt ctggggtagt catgtacttt gtaacagtca cttttagcca  16920
gatcttgggg atgtctattc ttatggttag tagtgacaca tgaaccctct cttccactta  16980
aaattatttt atgtaagatg actgcttctc cttctatccc tgctccttcc tctcctcctc  17040
ctctactctg cctccctcaa acttatagaa aagttgcaag tacagtaaaa aagtgtgaag  17100
aagcttttat ctccctaagt caattaagag tgaattgttt acactgatgc gctaacatct  17160
tcaaatactc tgtttttctc acaaacaagc acattcttca acatagtcac aaagcaacca  17220
ctgaaatcag taaattcacc ctattatctt actatcatct aattatcaga tcccattgaa  17280
attttcccat attgtcacaa caatatcctt gatagtgaag gatccagctc atcatcttgc  17340
actgtattta taattaggtc ttttctaagt ctactttatt atggaatagt ttctaacttt  17400
tttcttggct tttataccct tgatctcttg attataggct gttcattgtg tagaatgttc  17460
ctcagtgggt ttgttacatg tttcctgttg attaaattca gatttcaaac ttttggcagg  17520
aacatgacag aagtgatatt ctcattgcat tttgtcaggt ggcacacact gttgatttgc  17580
```

tccattattg gtgatgttat tttgatcact tgattaaagt gatgtcttcc agacttattt 17640
actgtacagt tattattttg cactttatgg taagtatttt ctagggaagt gtttgagtct 17700
ttgtaaatat caatttttg gtcaaacttt tatttgtatt aaaatgaact tacggattcc 17760
tttttcattt tcaaacttag aaataattag accagtgagt acctttcaaa ctagtttcct 17820
tgtccttttt acatgtctgc ataattcttt taagtgctgt cttaactgtc tgctcaaggt 17880
aaccaaggca tcatgtattt ccctaatctg aggaacaggc atatctccaa ggagcctggc 17940
acctttctgt agagaatggt attaagagac gaagatgtaa gtgttaggtg tgctcattgt 18000
tattgggata tcactattcc caggcttctc actgtgcaac acacacattg ataactgttt 18060
ttatttctat ttctattgaa aacctctctc cttctctcct ggattacctc tttctttctc 18120
tcctggttga cccctcacct ttcaggcttt gacacaaact ctgggctacc ttcccatggg 18180
gacatcctct tcacctcact tagactctga cactctgcgt tgggctgccc ttggagccac 18240
tgaggaacat tctacacaat aaacagccta taatcaagag atcaagggta taaaagccag 18300
gaaaaaactt aaaaactatt ccataataat ttttaaaaat tagtttgtgg tatgagaaca 18360
catggacaca ggcaggggaa catcacacac caggggcctg ttggtgggtg aggggctggg 18420
gaagggatag cattaggaga aatacctaat gtaaatgaca agttgatggg tgcagcaaac 18480
caacatagca catgtatacc tatgtaacaa acctgcacgt ggtgcacatg taccctagaa 18540
cttaaagtat attaaaaaaa aattagtttg tggttagtgg tcatattttc ttgtatgcca 18600
gagttttcca tttaaggaga atgttcttta aatattacat tttaaaaagt tgtaaaatag 18660
cgtttttctt taagacttat gctttctttt aattttttca ttgataacat agactacata 18720
tatttaaagt atacaatttg atttgttttg acgtatgcat atactctcga aattatcact 18780
gcaatgaaga tggtgaacat atccaacact cctcagcttt tctcctgttg tttgaaatcc 18840
ttccctcatg tcattctgct cttatactcc caggcaacca cttaattgct tttggtcact 18900
ataaattagt ttgcattttc tacagtttta tataatggaa tcatacagta agtgttgtgt 18960
tttgtctggt ttattttact cggcttattt tgagagtgat agatagtatt atacatacca 19020
gtagttcatt tgtttttatt gctgggtagt cttctgtttt atggatacat aacaatttgt 19080
ccattcattt atgaatggac atttgagctg tttccagttt ttggctattt acagataaaa 19140
ctactagaag catttgtgct caagtctttg tatagacaac tactttattt tctcttgggt 19200
aaatacctag gagttaaatg gcagaactgg ataattaact tttaaagaaa ctgtcagatt 19260
attttccaga ctgattctat cttacattcc cacatcagtg tgtgagagtt gcagcttctt 19320
taaatcctca ctgacacttg gtatggttgg ttttttcaat tttatccatt ctaatagtca 19380
tgtagtggtg tttcattgtg gttttaattt gcatttttcc taattgctct tctatgctta 19440
tctgccatcc gtatattatc tttggtaaac tgtcccaatc ttttgcccct ttttgaattt 19500
tgaaatttct tatatgcttt ggatacaagt tccttatgga catatacttt gaaagtattt 19560
tctctcagtt tgtggcttgc catttaattt atttaacaat gtcttttaaa aagtaaattt 19620
aaatgaagtt cagtttttct gtttgttctt tatagatcct gcttttgata ttttgactaa 19680
agaaaaaaaa aaacaagctt ttaaagaatt taagttagtt ttatccagaa gtcttactga 19740
gagctataga ctgactgagg actacagcct gggaggagtc tttcagaaag gttctgttgg 19800
ccaggagtgg tggctcacgc ctgtaatccc agcactttgg gaggccgagg tgggcggatc 19860
acctgaggtc aggagtttga gaccagcctg accaacatgg agaaacccca tctctactaa 19920
aaatacaaat ggcacatacc tgtaatccca gctacttggg aggctgaggc aggagaattg 19980
ctcgaacctg ggaggcggag gttgcagtga gccaagatcg tgccattgca ctccagcctg 20040
ggcaacaaga gtgaaactgt cccaaaaaac aacaacaaca acaacaacaa caacaacaac 20100
aacaacaaca aaacaaacca gaaagattct atcagactgc tccaaaatag tgtttcagct 20160
cacagtttat atacaggttc agtgcatata aaatcacatc aaagtttggg tgcaagagtc 20220
tatctagtta tagattacag aagtgtaatc actaaccctg tcaggtgttc tcttatgtgt 20280
aggaaaaggc aaggactagg gccatttatc ttttaaggaa tacagtgact caggcaagag 20340
ctggagggtg ggaggccctg ttctctattc tgttttgtct tcaatgcacg tttctggaga 20400
gctacacgtt gtcacagagt caggggcttt gggaaagtat gttgacaagc agaaatgagc 20460
aaatatgtct tcttacattt gttactttgg ctcacaggta tcttatctaa ggaaactttg 20520
cttacgcaaa gtacacaatg attttctctt atgttttcct ctagaagttt tatggttcta 20580
agttttatat ttaggtttat gaccctttc agttaatttt tgtatatggt atgaggtatg 20640
aatcagttgg ttttttcagt ttatattttt gcttatggat atctaatagt tccaccatga 20700
ttttaaaatt gtgacttcat atttaaaagt ggagaaaatg ctatactaca ctgtcttaat 20760
catttattat acttttaatg tctctgacag ggacaatagt aatgacccct ctttcaattt 20820
tattattagt catttatatc ttctcacctt ttttctcgac taatctggtt agagcgttag 20880
caattgtatt gatgttctta aagaaacatc ttttggattt gttttatagt ttctatataa 20940
ttatctacta ttttattttt tcctgcttac tttgatttta attaaattat ccttttctag 21000
tttttgatgg taaaagatga ggtcatttat ttgagacttt tcttcttttc tattataggt 21060
gtttaatgct atggttttcc tctttggcac tggtttagtg acatcccaca aattttgata 21120
tgttttgttt tcctcttcat ttagttcaaa atattcaatt caaaagattt tttaattacc 21180
tcctttgact tctttgattt ataaggtata tacagataca ttacttagtt tccagcattt 21240
gatgattttc cagagatcat tctgttattg ataatttaag tgtggtcaga gaacagactt 21300
tttatgactc aaattctttt acatttattg agacttgttt tatggcccag aatatggtct 21360
atattggtac agatttcttt tgttcttgag aggaatgtgt agtctggtgt tgggttgagt 21420
cttttcaaaa tgtcaaatta gatcaagttg actacttgta ttgttcatgt ctcttatatc 21480
cttactgatt ttttctgttc tgtcaattaa tgactgaggc atatttatct ctggctatat 21540
ttgtggattt gtttatttat ccagttactc gtttttactt cgtatgtttc aaaaatctgt 21600
aattagatgc atacactttt aggattgtta tgtcatcttg ataaagagac tctatcatta 21660
tgaaataacc ttttttttta aaatccctgc taatatgttt tgctctaaaa tctactaatc 21720
tactctgtta gattttaata ttgatacttc agctttgttt tgtttagtgt tagctgggta 21780
tttcgttttt ttatcctttt acttttaatc tatttgtgtc ttcatgttta aagtatggtt 21840
catgtaggga gcatatagtt gtgtcttgct tttttatcca gtctcataat ctatgccttt 21900
taattgagtt gtttagacca cttacattta atgagtgtat atatatgtgt tttcatatgg 21960
ttatgtttaa atctatcatc ttgcttttgt ctattgtcac atttgttcta ttttttggat 22020
ttggtatact ttatgatttc attttatctt cttgttggat tgttagccat aattctttat 22080
tttattttta gtggttgatt cagtgtgtgc agtaggcttt aatttattgt aggcaacttt 22140
taagtgacat cgtacccctt tatgtatagt acaagaacct cacaacaata cagtatactt 22200
actttactcc cctgcttttt aaaacttttg taataaactc tattgttatt ttcattatct 22260
ttttagaaca actttattga ggtataattt aataccataa aagccagcca tttaaaattc 22320
aatagttttt gatatattaa gagttctgca gcagtggcat gtgcctgtat tcccagctat 22380
tcaggaggca gagacaggat cacttgagca caggagttta aggccagcct gggcaacaga 22440
gccagtcctt gtctccagat agatagatag ataatgtgca atcatcactc caatcaagct 22500
cagaaaatgt ttatcattcc aagagaaacc tcatatttgt tttcaatcac tccctattta 22560
tcctcttcca aactcctgaa aaacacgaat ctactttctt tctcatagat ttacctatct 22620
tggacatttc atgtaaacag gcttatagat ttgtggcctt ttttgattgg cttttcactt 22680
agaaaaaaat gcacaatact gcatgttgta gtatgtatct ttctttcttt ttttgttgct 22740
gctcaataat attccattgt ttaaaaatac catatttaac tttatccttt caacagttga 22800
tagacatttg gattatttct actttttgat gattctgtaa tgcttctatg aatattcttg 22860
gagaagtttt tgtgtggata tatattttca gttcttttgg gcatatactt aggagtggaa 22920
ttgctggatc atatgaaaat gctatttaat attttgagga actaccagat tttcacagtg 22980
gctgcacctt ttatattccc accagcaatg tataagggtt ccaatttctc cacattctta 23040
accaacactt gttattatgt cttttaaatt atagccatcc tagtagttat gaagtgtgaa 23100
tttggctttt gtttccctaa tggctaaagg atatccagtg tcttttcata ttcttgttag 23160
ccatttgtct gttttcttag aaaaatatct attcagatat ttaatcattt taaaattagc 23220
ttgtctcttc attattgaat tgcaggagtt ctttattctg gatacaagtc ccttatgatt 23280
tgcaaatatt tttctttcta tgagttgttt tcaattatat ttttcagata cttatataat 23340
aaaatggttt ttatatttat ccatgttatt actattaata tttttggtat ccttcatttc 23400
tttatgagga tccatatttt catgtggtat aattttcttt ctgtctgatg aacttctttt 23460
taacatttct tatggtccaa cgtctgctta tgatgaattc tttcaccttt tgtatgtttg 23520
aaaatgtttt tattttactt tcacctctga acatttttta atgtgtataa agttctagat 23580
tgatagttcc cccacttccc attattttaa agatgttgat cacctgtctt tttgcttgga 23640
ttgtttctga tgagaaatct gctgtcattc ttatccttgt tcctctctag gtgtcttttt 23700
ttttctttaa tccagtaact ttaaagattt tattgttatg gttttgtaaa tttgattgtg 23760
catttttctt tgtttcctgt gctcatgctt cattgagctt gttgagtctg tgggtttata 23820
gtgtttattt ttagccttgt tttttcactc tccctttttg ctttggggac tccagttacg 23880
tgtacagttg acccacgaac aatgcagatc catttatatg catatttttt tccaaccaaa 23940
tgcagatcag aaatatagta ttcatggtat gcgaacccca caggtatgga gggccaactt 24000
tatatatata tatatatata catgtaggtt ccacagggct gtctgtggtg taactgccca 24060
atgggttctc cttacctact ccccaggtgg aactgattta tcaagacagg agacttgcaa 24120
tagcgaaaga gtttaattca tgtagagcca gctgaatggg tgactggagt tttattactc 24180
aaatcagtct ccccccaaat ttggagactg aagtttttaa agaataattt cgtgagtagg 24240
gggccaggga gtagggagtg ttattggtgg cactggagat gaaattattg ggagttgaaa 24300
tattatataa acatatatat tatataaaca tatgtattat acaattgaat ataataccta 24360
ttatatatgc aatatattat atagaataaa cataataatt gaatagatat ataatagttg 24420
aattgcatgt aaatgtagtt ttaataacaa ggttgccaag tactgtatta ctggatgctt 24480
acattgttcc taaaattatc ctatcataca tgatattgca ttaagcatcc ttgtagcaaa 24540
ttctttgtcc tttatatttt tcccatagta taaattccta gtggtggagt tacatgcctt 24600
ctgattcagc acacttttta ggatcttgat ggaaaccatg catatacaca catttcccta 24660

```
atattagcat tccagaaagg ttacaacagt ttcacctata ccagaaatac atttgagcgc  24720
ctattttcct actttgtata caaacacatc agaaaaccat ctttcaagga taactttctt  24780
atgttgaggc agttttaaat cacaatcatt caagcactca gtattgattt tgattcattc  24840
tcccaaaggt gcttgaattt taagctactt gaaaccttaa ataatggaag atgtctctgt  24900
taagagaact ctctgctgtt gaacactgtt attcagggct gaatcacttt acttaccaca  24960
gccacagact tctatattct gactagctat ttcgacactt tgtttccacc cccattggtc  25020
tcttttcttc cctaattttc ttcccttcac ttcatatatt cacattcctt ctattttagg  25080
ccatttggga attacttttt ttttttagaa tagttaactt tttaaatttt tgttttattt  25140
ttaatttttg tggagacaga gtttcactat attgccctgg ctggtctcaa actcctgggc  25200
tcaagcaatc ctccggcctt ggcctctcaa agtgctggaa ttacaggcat gagccaccat  25260
acttggctga aaattacttc tcatgttaga aacatgcact tactcttaga atgaaatatt  25320
tttcaagact catctgtggt tggaagagtc tagcctgccc gaagcttggt tatagaggtt  25380
gtaattgtcc ttgttctgaa aactacggac tgaaaacacc ccagcttggc acagtggcgc  25440
cctcagtaga aatgtatcca ccctataggg tgcttctcct gtaagtggaa atcctaattc  25500
aaatttatat ctgcattgct ctaggtccct atgcaaatgg ctgagggtca tggcatgcac  25560
acacaaagaa gatcaagagt ttagatgact ctggaaagaa acagggcaga atgaagtctg  25620
tctcttaccc agagtagagt tctacttttc aagaggattt ttttcagtct tctttgtgga  25680
atcctcctca tttcccctta aaatgtagat ctcattcctt ctcttcttgc tctctgtctt  25740
catgagtgat cacactccct tgagctcaat tttctccaac tcagaaatct gtagttccag  25800
gcctttcctg atttactact tctaagtaga gatttttctcc cattttctaa gcattgtaac  25860
acaaactagc ttgaccttga ggctaaacag tttggccaat atatcctttg ccttcatagt  25920
gacacttatt ctaagatagt aatctccata atttgaattt tacaattctt ggttattttg  25980
gtaagtgtca ggatagcatt cctctccatc aggaccactt ctaaagtgaa aactatacag  26040
ctgggaatac agtctttgaa attaagacag tgtttactta tataagtttt ggccagtttc  26100
tccagcttct agaatacctg acctggccca tcatgacctg ataaaataca tgtaaaaagg  26160
cgcaattgtg ttaattgtgt ttctctctct gcagtcagtg tgcgcaggat gggctagttg  26220
tatttcttcc ttggaatgcg ttagctctgt gccctgtaga aaaaatgata gacttttaga  26280
ccaatttgaa aataaaagat ctaattgaaa agctggagaa gcaaatgaaa agactgatct  26340
tatttgtgga aaaggattta tgaacatgaa atatattgta tcctgtgagt acactgaagc  26400
aagatcttag ggctgacact ttgaggaaga gaggaaagta gccacagaga gaggaaagca  26460
gcctgtagcc acaggtggcg atggtatttt aaaacaaaac ataaggtagt catttggttt  26520
ctcaaatgca tttctgattt ctttgttctg aatctgcatg tgaagcaaat gaacccatag  26580
cctccttcat cccagctgaa ccatttgctt cactgtcagt gaagggggta gagtcagtgg  26640
tagggataag taacccagat aaaaagttta gcatggccat gtctctgtca tcctgttttc  26700
ccctttcctt tttctttttg attctttaaa acggaaattc tgattttatc aactttagaa  26760
atgaaacagt attgattggc tcctttctca aaaggtgaag aatgttctcc tttttcttgt  26820
gattttctgg agttttcatc ttagcttatt agttacacgt atttcaactg tatagctttt  26880
ttttttttcct attagttaaa actgcattct tttttttttg tcaccgttac tatcacaggt  26940
attctgtgct tatctggatt gacaagctgc tcttgccaaa ggtttcctga gcacattatt  27000
ttgatttgtc atatgagtag ttgtattatg tgtttgaaca aatttttcag ggagaaatat  27060
```

```
atcttaatta taccatatga tccagcaatc tcactgctaa gtatataccc aaaagaaaga  27120
aaatcagcat attgaagagg tatcttcact ctcatgttta ttgcagcact gttcacaata  27180
gccaagattt ggaagcagcc taagtgtcca ttaacagaaa aatggataaa gaaaatgtgg  27240
tacttataca caatggagta ttattcagcc agaaaaggaa taagatcttg tcatttgcaa  27300
caacatggat ggaactggag gtcactgtgt taagtgaagt aagctagtca cagataaact  27360
ttgcatgttc ttatttgtag gaactaaaaa aattaattga acatatggag acagagaata  27420
gaaggatagt tacgaggggc taggaaggtg ggttggttaa tgggtacaga aatatagtta  27480
aatagaatga ataagatcta gtatttggta gcataacagg gtaaatttat tgtacatttt  27540
ataatagtta aaagagtata gttggattat tggattgttt gtaacacaaa gaaaggataa  27600
gtgcttgagg tgatgcgtac ccatttacca tgatgtgact attacatatt gcatgcctgc  27660
atcagaatat cccatatacc ccacaaatat atacacctac tatgtaccca caaaaattaa  27720
aaataaaaat attaaaagtg gcttgttttt gttattgcag gtaaacaaag gcttgattgg  27780
ctgtagaatt tttgagtcgt tccatatttc tgacaaaatc ttgaaattta ttccttcatc  27840
ttatttgttg gggtgaggtt aatggctgtg tccagcccat ttttttccca ttatgatttg  27900
atttattttc cccatttgat ttttttaatg ggatttcttt taatttttaa agcttattaa  27960
cttaaacctg ttttgcactt atcatttact tcatagtttt cctggaattt gtcacacttt  28020
tttaaattat ggtaaaatac acataacata aaatttaccc tcttaaccat ttaaatgtac  28080
agttcagtag tgttaagtat attcagactg ttgtgcaacc aatctccaga actcttttcg  28140
tcttgtaaaa ctgaaacccc gtacccatta cacagcaatt tctcattcat ccctctcccc  28200
cagtccctgg caagtactac tgtactttgt ctctattaat ttgactatta gctaccttat  28260
atatgtggag tatttgtcct tttttgactg gcttatttca cttagcataa tgtcttcagg  28320
gttcatccat gtcatagcat atgccagaat atccttttga aggctggatg ataagccatt  28380
gtatgtatat accaatttag tttatgtctg ttcatctgtt gttgaaaact tgggttgctt  28440
ctacctcttg gctcttgtag atagtgctgc tacaaacatg ggtatacaaa tatctctttg  28500
aaagatcatt aacagttatt ttggatatat acccagaggt gggattgcta aatcatatgg  28560
taatcctatt ttaatttttt tgaggaacct ctatactgtt ttccatagtg attgtaccat  28620
ttttggtccc accagcagtg ctgggttcca gtttgttcac atccttgcta atacttcttt  28680
tctttttttg ataatggcta tcttaatggg tgtcagatgt tatcttacta ttttgatttg  28740
catttgcatt ttactgatga ttagtgatgt tgagcatctc ttcatgtttg gccgtgtgtg  28800
tgtgtgtgtg tgtgtgtgtg tgtgtgtgta tgtgtatata catttttgta gaagtgtcta  28860
ctcaagtctt ttgcccaatt tttaagttgt ttgttggttt gttgtttttg attttgagtt  28920
gtaggagtta ggaaagttta cttttattgc taagtaactt ctgttccact tatttttgtc  28980
aagtatgccg attatgttga atctttatgt cctgcgattt atatccataa tttcttttta  29040
aatttttta ttttatttt ttattattat actttaagtt ctggggtaca tgtgcacaac  29100
atgcaggttt gttacataag tatacatgtg ccatgttggt ttgctgcatc catcaactcg  29160
tcatttacat taggtatttc tcctaatgct atccctcccc tagtccatca ccccctgaca  29220
ggccccagtg tgtgatgttc ccctccctgt gtccatgtgt tcttattgtt caactcccac  29280
ttatgagtga gaatatgtgg tgtttggttt tctcttcttg tgttactttg ctgagaatga  29340
tggtttccag tttcatccat gtccctgaaa aggacataaa ctcatccatt tttatggctg  29400
```

catagtattc catggtgtat atgtaccaca ttttctttat tcagtctatc atttgatgtg 29460
catttgggtt ggttccaagt ctttgctatt gtgaacaatg ctgcagtaaa catatgtgtg 29520
tatgtgtctt tatagtagaa tgatttataa tcttttaggt gtatacccag taatgggatg 29580
gctgagtcaa atggtatttc tagttctaga tccttgagga gttgccacac tgtgttccac 29640
aatggttgaa ctaatttaca ctcctaccaa cactgtaaaa gcattcctat tttccccaca 29700
tcctctccag catctgttga ttcctgactt tttaatgctc gccattctaa atgatgtgag 29760
atggtatctc attgtggttt tgatttgcat ttctgtaacg agcagtgatg atgaacattt 29820
tttcataagt ttgttggctg cataaatgtc ttcttttgag aagtgtctgt tcatatcctt 29880
tgcctacttt ttgatgaggt tgttttcttc ttgtaaattt gtttatttgt agattctgta 29940
tgtccataat ttctaattaa tctagtaaat tccattattg taagcacatg tactttttcc 30000
caagccagac ttccatggca ccaacttggt tttctgcagt ggcacttctg tcttttgtag 30060
ttttaaattt ttagtttctg cagtgatttt tttttatttc cttaaaaaat tttaaaatca 30120
aacttgtaaa tgtttataat ttaaaaatgt ataggtagat actttatttg gcaaacaatg 30180
ttagctatca cttttaccat gttcactata ttgttcacag tatgataagt attactccag 30240
gtgtcttagg tacattaatc aattcaattc ttatagtcat atgtggcagc cttactatta 30300
ttatacccat tttacagagg agaaatctga ggcaaggaga catgacataa cctgcccaag 30360
gtcatactgg caggacaagg atttgaacct aggcagttgg attccctagc gtactgtact 30420
tgtaactact atgcagcact gcctctcttc ctccttttct taaaaaaaga aatgtatgtg 30480
ctttatttga attctgactc aaccaaccaa actgttaaaa gttataagaa aatcagggga 30540
ttgtgaactt accgaatatt tgatgatatc aagtacctct gattaatttt ttaactgtga 30600
tgatggtaag gtagtttcct tataaaagag ttcttttaag gacaaaacag ctaaatatgt 30660
aaacataaag ttacttacag catatgtatt atgctgagtt atttacagaa gaaattaaat 30720
gatgcttggg atttgttcct ctatattatc tttaaatata ttcattttaa ttgatataca 30780
tttgtacata tttatgggat acagtgtgat attttgatac atgtatatac aatgtgtaat 30840
gatcaaatta aggcaattaa catatccatc acctcaaacc ttcatcattt ctttatacgg 30900
gtaacagtca aagtcctctc ttctagctat ttgaaaaaat acaataaatt gttgtttgct 30960
ataagtcact cttcagatct atagaacact agaacttatt tttgctatct aggtataact 31020
ttgtacatcc attaaccaaa ctctccctat ccctccctgt cccctaggct tcctggtatc 31080
tagtaagcac tatcctactc tctacttctg tgggatcaac ttttttagct cccacatagg 31140
agcgagaaca ttgcagtatt tatctttctg tgcctgactt acttcgctta acatgcagtc 31200
ctccaggctc acccgtgttg ctgcaaatga caggatgtat gtaatttaaa gtgtcaaata 31260
gctctgaggc ttgccaggaa agaggagtcc ttgcttgctt cctacaattt taccttcccc 31320
agagctacca ctttcagttg ttttggcagc ctcatttgat atttgcattt aatctgtaag 31380
atttttttta acttcttttt gaaaattttt aaaattgtga atgatatgtt ttgaaatatg 31440
tgctatgtgg aattctaagg tttttatttc tttttatctt actagtttgg aatatttata 31500
gatgtaccat gtgcaaagtg taccattcac atactcccat cctgaacctc cttttcttag 31560
tatagttagg tcatgatttt gactaggcca ttattcagtg ttaataggat gatgaccttg 31620
ttaatgctgt tcatacctga gccatgtaga attctatgaa tccttttcct cttctgcaaa 31680
ttttttgttc tatttaaact aattgttctt ttgatgtttg cttagttttc tatgtgcttt 31740
ttactcattc agtcctaaat gctcttggtt atccaaatct cctcttgata tactacttct 31800
tgagtctttt tgcttatcac ccaaggattt cccttcacaa ttatgccagg aattcctttt 31860
tttctccctc ttgtattgga ctcctgtttc ctgtatcaca tgcctgtctt tttcttagtt 31920
tcctccctgt tttgcagaag aacatctgcc aatagaattc taggttgtca actgccttcc 31980
tcattgcttc attgtcttct agctttcagg gttgctgttg aaaagtccag agactttctg 32040
attcctaatc ttttgcttat gagcttccct acctgctttt tgatatttta taggaccttt 32100
ttaatatcct tacagttaaa aaaacacaac tcatgatgac agatgctgtg tttaatgtgg 32160
gcatattgaa atcaaatgaa atgggcaggt aggcactcag tgggccctta cagtctacac 32220
agttatgacc ttacgtttta ggaaatattt tgagttagtc atttgacttc actccacccc 32280
atttccttta ctcttttatt ctggaattct atttggctat tagacctgct ggactcattt 32340
tgtagccttc tcatttttac tgttctagtc ttctttactt tttttttttt aactctacat 32400
tttgggcaca ttccttaaag ttatattcca atctgtctac tgaatttttt ttgaattctt 32460
aaaaattgac atataaaatt ataagtattt atcatgcaca atatgatgtt ttgagtatat 32520
atatattgtg gaatggttaa gtctagctaa ttaacaaatg cattacctca catagccacc 32580
atttgtttgc ggtaagaaca gttaacatcc actcccttgg cattttccaa gaataccatg 32640
tatcatcatt atctatagtc actgtcctac acgatggatc tgaccttatt cctcctaact 32700
gcaatagatc tcctgtctaa ctgtaaatat gtatcctttg atcaacatct tcccaactcc 32760
ctctccccac aaccacccca gcctttggta accaccactt tgctctctac ttctgtggga 32820
aaaacttttt tagattttga attaccactt tttaagcatc ctgtttttgt ttgaataagt 32880
gcaatatatt cttctcgatg ttactattgt taaacctatt catctgctca gattccagag 32940
agaaaaatct ttccgtctca ggccttagat gatgtaagac tggcttcaga tgctatttag 33000
ctctgatagg cggaagagat aataagaaag aagacaagct tcagctctga actgcctgta 33060
tctcatcttg ttcctccagg tttgggcttc aggaatttct tctattttgt ttatatcaga 33120
ctatagggct ctctgaagaa tgatacatag tttgaaaaat ttccccattt tatctaaatt 33180
gttgtatatc tgtaatagtt ttctaaagtt tttagaataa atttgtcctt tccaggtttc 33240
agcattgatg gtttcttctt tcctccttta ttgcttttca ttcatctatt ctgttttgga 33300
gacgaaggct ttaaaatctt tacccacgta gcttccccca gctacctctg agaagtctgt 33360
tttatctttt gcatcactaa ttttattttt tgctttttaa aaatattcta ctttctgctt 33420
cattggttgc ttttattcaa gttcataatt cagattttct tttctggtta gcgcagactc 33480
ttttctggtc tcatatttct ttctatggct acctgctcta tgtgcaaaga ttctactatg 33540
tcccctggaa ttttaagaac atgagctaga aattttctgt taatagagtt ttctctttta 33600
tatagtatat ctatttctta agtaaatatt tgctctgatt ctagaatctt cccctttttct 33660
gaaccacaat gtgttctatt tgcctggtgg atttagattt ttctcctttg cttatcctta 33720
gggaagtcaa tgcatattca gtattgggta ttgccttgtt ttctttcctt ctttccttct 33780
ttccttcctt ccttccttcc ttccttcctt ccttccttcc ttccttcctt ccttccttcc 33840
ttccctcctt ccttccctcc ctccctcccg ccctccctcc ctccttcctt ccttccttcc 33900
ttctttcctt ctgttttaaa attttacttt aagttccggg atacatgtgc agaacatgca 33960
gtttcttaca taggtataca tgtgccatgg tggtttgatg cacctatcaa ctcgtcatct 34020
aggttttaag ccccgcgtgc attagtaacc ctgtgttctt tcaagaaact tgtatgagtc 34080
actatttgac tcaagtccag acaaaggaaa aaggttacat ttgtagtaga ttaatttacc 34140

```
aattatgaat tcatattcct gtgaggcctg ggaaaagagc cagcatcagc tccagaagta  34200
atcaaaggga agtttgcctc aaaccaaaga ctttgtttta ggtatttggt gtggcactca  34260
gtaattagca aggtcattgt cacttggcat ggctgccctt gccaggagcc agctgggagt  34320
gtctttttcc catgtgtttt ctgtggtagt catcatggcc acctgtcaac cagaagtaaa  34380
tgcagccaga ggttacttgc ttggctggcc tctgaagcca ggagcccttt taaaggagtt  34440
agtgtgtttt aaatgtaccc caagtcttcc tgggcttagt tccctcagcc cccatcgctc  34500
taaactaggg gtatcattat gggtttagtg gattctcatt tgcttatttt ctggttgtgc  34560
agttgcagtt tcacatgaag aggatatcgt gttttagtcc ttttgtcaac ctcccatgtt  34620
gattctttca agtatatatt tctgaacgtt taagatctat ttatagtttc cagggctgat  34680
tcaggatatt cctctgttat aatcaactgg tcatttcttt ggtaatctgg cacaaagaaa  34740
taagcttata gctttcttat ttggaaattg tattttatat atgtgatttg aatcataggg  34800
gggatattga ggtaatttag acccagtgat tgtaaaggaa tggatgaatg atccaataaa  34860
taaatagatg acaaagctca tcttttgcag gtgagaggca ttagaagtaa ttttacggtt  34920
ttgagaagag aaatatagat gagaagagat gcctaggaga atagaaaatg gagacaacta  34980
ggaaagaaga gaagaggcag cagtaatgct ccaagggcag ttggagagcc tgatgtcagc  35040
tgggcaaacc cacattgctt catggttttc tgtggctaga acacagtttt gaagctcaag  35100
caaaggaaat ggagagttag gttggtggca ggttggaaga gttgcagaac aggtatccaa  35160
gtacttggaa gagttcagag gggtgtattt cttagtctca ctctgttgcc caggctggag  35220
tgcagtggtg caatctcggc tcactgcaac ttctgcctcc caggttcaag cagctctctg  35280
cctcagcctc ctgagtagct gggattacag gcgcctgccg ccacgcctgg ctaaattttt  35340
tttttttttt ttttgtattt ttagtagaca cggggtttca ccatcttggc caggctggtc  35400
ttgaactcct gacctcatga tccacccaca tcggcgtctc aaaatgctag gattacagac  35460
gtgaaccacc acacccagcc agggatgtat ttctttaaaa attattgtgc aactctctag  35520
ttgacagtct ggggctctgg taaggcgggg gttcatctgt caaagtgagc cagcttactc  35580
agctagatac tgtatggcat gattacttag ggtaatgtct tttttgtctt gtttagttcc  35640
cccatgattt gtgcagtttt gtaaataagt tgagaagtaa atagatttca tgatataatt  35700
ttaagacttc actcccaagg gaaaactgat ttataccttt gaagttatgt catttagccc  35760
ttgtatttgg caaagtaagc atacactatt ttataaagcg ttcttgtaat gtgtgaatag  35820
gttcaacaaa attagacgtg tcgcatgttt taggagaagg cagttaattt tctgtcttat  35880
tttcttcttg aaaatgtgaa actaacaatc tgtcatgttt attaggcatc tcaaggaaat  35940
gaaacatcca aatgagggtt aaatggttaa aattttatat agatgagaag agcacaaggt  36000
tctctgtctc agggttactc tgcaggtcat ctgactttca tcctactttc tccatttttt  36060
atctgacatt tttgcttaaa gattccatgt gctttccatc tctttttaat ctttgatcac  36120
atggaatatt ggcctatgga aagagtatga atcttagcat aggccctggt tcagacctca  36180
gctctttcat ttcctgactg tgtgactgtg ggtatgttgc ataacctcac aatacctttc  36240
aaagcctcag atgtctcctc tgtaaaataa ctgaatagta tctgcctcaa actgttgggg  36300
aaatgactgc tccaaagctc agcatccagt ggcctttcat gaaatcccag tctcgcatct  36360
ttccctctgc tgttgttagt aataacgtca tatgacatat ttgtttggtg gatctcatcc  36420
atttctattt cgctttcctt actctaagct aggtgcctct atttaccttt taggcaactc  36480
tctatattct gaatattgaa aatattttaa ggttatattg cttaatgaca tagcttggtg  36540
```

aaatgatatt ggacctgagc atatagtatg cgtccttaag aatggaatct tatgtgcttg 36600
attttttgct ttttagttgt attattgata tattcattta tgtcacatag agcaagataa 36660
tgtgaattat aaatacataa gagggagaaa ggaaaaatga aagtaggagt gggcaaaaaa 36720
taatgccagg aataataaat acatgagaag gagaaaggaa aaatgaaagt aggagtgagc 36780
aaaaaatagt gccaggaata agttcagtgt aaaacagtgc accttggggt tcctgtaatt 36840
ttcttgggta ggtttggcac tctagcagtc atcttgaaaa aagaaaggtc ctgtatacat 36900
atgcttttct cctgggttgt ttatttactt tcacagtgtg ataaacaagt ctcatttgtt 36960
cctaaaactg ggactaagga gaatatcagt actgtcacag ggcagctgtg gaattcggtg 37020
ttgaatgtca tgacaagata acttgagaac tttactactt atttgtgaat gaaaataatt 37080
gctgtaatgg gagaagaaaa taggaaggct ctacagttct aagcagccag aacctaaagt 37140
gattgaaact gtagtatcaa ggatgctgca caaaaatgta gcaattaaaa atttaagctt 37200
atagaagttg ctgtcaaacc tagattattt cttagaaaag cagcacttct gagctcctca 37260
tttgcccagt atccctgagc taatataggg tagcaccaag ggatgtgggg gacaaaggac 37320
ttggattaaa tgtccaactc cacagttcct gctgtgcaag acttggatct tgtgacatct 37380
ggttcattac ttttactatt atgaaaagta tcatttccca atagtttaaa aagtgttcag 37440
gtatcatctt gcatgttggt gaaactagga agtatattta cagacaaaag ctccttaaag 37500
gcaaggttgg cttagcctta cttttttttt ttgagacgga gtcttgctct gttgcccagg 37560
ctggagtgca gtggcacgat ctcggctcac tgcaacctcc gcctcctggg ttctagtgat 37620
tctcctgcct cagcctcctg agtaggtgtg tgccaccacg cccagctaat ttttatattt 37680
taagtagaga tggggtttca ccatgttggt caggctggtc tcaaattcct gacctctaat 37740
gatctgcccc cactggcctc ccaaagtttt gagattacag gcctgagctg ctgtgcccag 37800
ccaataacgt cttttgaata aaagaaaaga tattgttagg gagtatgaac atcaccagaa 37860
aatgaaaatg tttcttaaaa ataaacgaat ttttaaaaat tattttctta aaatgaaaaa 37920
ttttttttctt ctggactaaa ttgcaatgtg gaaagagtca catcagcctt tggacagaac 37980
tagggctgtg atttactaca gggaagttag catctttctg agttttctta atgaacacgt 38040
gaataagaga tttggttata ctttgtgctt atttagcatc ctctctttga ggatgtcaaa 38100
aggattttag aaatgttctc tttctcacac aggtggacgt ctgatttatg aagctcccca 38160
tccacctatc tgagtacctg acttctcagg actgacacct acagcatcag gtacacagct 38220
tctcctagca tgacttcgat ctgatcagca aacaagaaaa tttgtctccc gtagttctgg 38280
ggcgtgttca ccacctacaa ccacagagct gtcatggctg ccatctctac ttccatccct 38340
gtaatttcac agccccagtt cacagccatg aatgaaccac agtgcttcta caacgagtcc 38400
attgccttct tttataaccg aagtggaaag catcttgcca cagaatggaa cacagtcagc 38460
aagctggtga tgggacttgg aatcactgtt tgtatcttca tcatgttggc caacctattg 38520
gtcatggtgg caatctatgt caaccgccgc ttccattttc ctatttatta cctaatggct 38580
aatctggctg ctgcagactt ctttgctggg ttggcctact tctatctcat gttcaacaca 38640
ggacccaata ctcggagact gactgttagc acatggctcc ttcgtcaggg cctcattgac 38700
accagcctga cggcatctgt ggccaactta ctggctattg caatcgagag gcacattacg 38760
gttttccgca tgcagctcca cacacggatg agcaaccggc gggtagtggt ggtcattgtg 38820
gtcatctgga ctatggccat cgttatgggt gctataccca gtgtgggctg gaactgtatc 38880
tgtgatattg aaaattgttc caacatggca cccctctaca gtgactctta cttagtcttc 38940
tgggccattt tcaacttggt gacctttgtg gtaatggtgg ttctctatgc tcacatcttt 39000
ggctatgttc gccagaggac tatgagaatg tctcggcata gttctggacc ccggcggaat 39060
cgggatacca tgatgagtct tctgaagact gtggtcattg tgcttg 39106

<210> SEQ ID NO 108
<211> LENGTH: 166
<212> TYPE: DNA
<213> ORGANISM: Homo Sapiens

<400> SEQUENCE: 108
cgcaaagact tccccagcaa cagcttttat gtggtggtgg tggtgaagac cgaagaccaa 60
gcctgcgggg gctccctgcc tttctacccc ttcgcagaag atgaaccggt cgatcaaggg 120
caccgccaga aaaccctgtc agtgctggtg tctcaagcag tcacgt 166

<210> SEQ ID NO 109
<211> LENGTH: 87
<212> TYPE: DNA
<213> ORGANISM: Homo Sapiens

<400> SEQUENCE: 109
gtccttgata taccttggag tggggacttg atcctggggg caagggcctt ggagttaggg 60
acagggtctg ggtattgact ctgggag 87

<210> SEQ ID NO 110
<211> LENGTH: 363
<212> TYPE: DNA
<213> ORGANISM: Homo Sapiens

<400> SEQUENCE: 110
gtctccttga cagtatcttg tcagttattc ttcatcctag catttctgtt cgactagcag 60
cagcttggtg tttacactgc attgccgtgg cattaccctc ctacctaaca ccactcttgg 120
atcgttgcct tgaacggctt actggacata agtcttcacc tgaagcagtg actggcttca 180
gttttgctgt agcagctttg ttgggagcag taaaacattg tcctttagga attcctcatg 240
gaaaaggcaa gattattatg acattagcag aggatttgct gtgttctgct gctcaaaaca 300
gtcgcctttc agctcagcgc acacaagctg gatggttgct gatttctgct ctgatgacat 360
tag 363

<210> SEQ ID NO 111
<211> LENGTH: 8827
<212> TYPE: DNA
<213> ORGANISM: Homo Sapiens

<400> SEQUENCE: 111
gtatgataaa gaagagtcgt atcagctgag cagtcgtgat tgtgattacg tccctggttg 60
actcatgaat aggctttgta atggtagatt gttcttttgg acacacagcc aaaatgctaa 120
agttcactgg gaggtctgct aaggtttctt acatcaaaga gttgacagag aaaggactta 180
ctaaatgaaa atattattta gtagtttcta gtaaacctca aaaatcattc caaattggaa 240
catacactat gtttacatgt ttaagttaaa ctgagtcatg aagctaaccg ctgacttatg 300
tatgctttca gtagtgttgc ctaaatgttc tcatttaaaa gaagtcccca taggattatg 360
agatgtgcat atagtacgat gtcatttttc ttgggaaact ttcagcttac ttatgcaata 420
aggaaattta aggttatttg agtacatctg gaataatagc tttagatttt tgaaatttgt 480

```
ctttttgggg tagcttttcc ctttttcctt gacaaaatat aacacaacga tcctatttcc    540
tatctgagct tagttcaagt tgttatggtg gcaaagttat gggttatgaa atgcacaaaa    600
atgttggtac agatatactt agtggcccac ttaagaaaat aaaattggag attaagaata    660
gagggaaggt tgtggctcct tggtattatg ttaggagagc agaatccatt atagtacact    720
cttacagtta aacaatttgg ggacaaacaa ggttatgtga gtgacaaagt ttcataaaac    780
tagaaagcac tatgttaatg caagattact ttctaaaaat attgattctc attccctttt    840
ttccttcaca ataaaattgt atggaacgtt tgtgtggtag aacaaggaga acttctaaag    900
tgcatgttag tttcatcctt tgaggccaca tattgggtct cctgcattct atctgtttac    960
tctctataag atttaaaaca gagagagtaa atagacagaa ggcagaggac ccaactatgt   1020
ggcctcaaaa gatgtggccg caaaggtact atgaaagtat ttagtagtag tattataggg   1080
accagttact ccagatttgt atgaacaata atccccagtt ttgatgcagc atcatgttgg   1140
aggtgctaag taggatcctt agacttatta gttgaatctc ataatcacca ggagattaac   1200
atactatttt atgaaaaatg gagtgtgaaa agtccttatg gactgcatag attctgaatt   1260
tttataacat taatccaaac ccagtacctt gtctgtaatt atagtctaag catatgtgat   1320
ttgattaaca catgaattac aaatatatct actttgggc atatattcca ccttttgtac    1380
tgcagaaaaa ttttgtgcct ttgcagtgac caaaactata gttctgttta gggtcagtag   1440
gagaagatgt ttttcctctt aactgagaag tttatgtttc ttggaggaaa atcctagaat   1500
aaatgcaatc ttccattgta tcttggaatt acaatttgaa atatcttaaa cagtattttt   1560
tgaaagaatt ggttgtctac tgtatgcctt ttccaatgaa ctacataaat aaaggcagag   1620
tttgtctttt cctctctgaa tgcctaatgc ctagaacggt gcctgacccg gagtagttgc   1680
tcagagcacg ggtgctgaat gaggaaataa agatgatact gctatctctc atatttcaga   1740
tgctattttg tagtcttcgg tcataatttt agaattctct tttggtaag aggtttaaaa    1800
aagtgagata ttatttgatt tttaatgaaa tgtaaacata tagcagatgc acaataaaca   1860
tttattaaat taaaaaacca ctgaaagaaa catgatactg caatcctggt gctttattta   1920
ctattctaat catctgcagt cctccttttg catctaatga gagtcatttt ttaaaaagct   1980
cattgaccta ttgatttata aaagaagaca tttagcaaag ctgaagagag gcccacttga   2040
atttgaatca ttttaactag cacttaaccc tcggccttta cctagcggtt tgagatccaa   2100
agattctttg agttcttaaa cctatttcat atttgattat ttattgccta acaggatctt   2160
tgatgctaca tttgagcctt tctggacatc gggattatgg attaaaagcc gttgctgtac   2220
ctcctgcctg gtactgtgcc tgacatagaa tctaggggct ccacagggct ggctttgtgg   2280
gcatgtgacc tgtgcatttg tacagggctc caagctcaga agggccctga gtttggttaa   2340
atgatctgct gtcactgtct tgaaattaat ttttgagcaa ggggtcttca tttctctgcc   2400
ttgctaaggt acaactgaat aaaaaacaga tggtgtgttt gggatccatc caatatatca   2460
gctgaattgg aatattattt ggaatcaaat atgaatggtt ttgaaaaaga aaatcttctc   2520
caaagtgttc aatatatcct cttggttgga acataggaga ctgtagctaa catcatggga   2580
aatgtaatag gtagcattaa ctatcttatt tttaaatgtc atctgttata ttttggttca   2640
tgcttatctt attgttcact attaaatatt taactatgat ttttttttt ttgagacgga    2700
gtcttgctct gttgcccagg ctggagtaca gtggcacgat ctcagctcac tgcaacctcc   2760
gcctcccgga ttcaagcaat tccctacctc agcctcccga gtagctggga ttacaggctc   2820
```

-continued

```
ccacaccatg cctggctaat ttttgtattt ttagtagaga cagagtttca ccatcttggc   2880
caggctggtc ttgaactcct gacctcgtga tccacccgcc ttggcctccc aaagtgctgg   2940
gattaccagg catgagccac cgcgcctggc ctaaatattt aactatgaaa tatttatctc   3000
ttattagtgg tataattatt tactaattac tgatttattg ataatagttt gttagatgtt   3060
gggcaggatt tatattaaaa catgtttgtt ttctggagag tactatgtgt ttacatgaat   3120
acatgttcat ataaatacta tgtatttaca tgctcatacc tgcaaaataa taggagggga   3180
caagacagtc ttttaaaaaa atctgttttt gaggctctct agggatgtac atgtcataat   3240
tcttattgag agccagttct gttgcttaat cagacttacg actggaaaag aggcagtcag   3300
tatagagtgg gaccagaact gtgggtttca gagctggcct gcctgggttt gagtactgtc   3360
tcagttactt tctagttgta tgacttttgg caagttacgt ttatcccctt agcctccagt   3420
ttgctcacct gtaaaaccag gatacctctt aaaacagacc ttatgaggct taagtgtact   3480
aatatatgta aagaacctgg cctgtagtaa gcactcaata aatgaagttc aggccactct   3540
ggatcttact attttaaaat tttagaagta tacttatgtg gttatttata tttattaaat   3600
gcgaattgag agcttgtgtt gctatcccca aagacatcat agtcaagtga aggaactgac   3660
ttgcaattca agaattagga tattggaata agggcaaaag taggggggaag cagagggtga   3720
aaagaagggc ctggagggag ccctaaaccc tccttgcaga agaggtgaaa tggaacattc   3780
cctcagctgc ctttggaagg atcaatagac actgagagca gcttggtgag agtttgagaa   3840
tgcatagcga gtttggggaa ttttaaagag cttagtatgg ctgaagttta aaggacaagt   3900
gggagattgt gaaaaatggg atagagatgt aagatgaggc cagatcctga ggatgtggac   3960
tagacagaga ggagggaaat gaagaaaggg tcacgtctta gacgccaacg aagttgagtt   4020
tccccaaaga gactttaagc atcaatacca tatgctatgg agagttaaag taagataaga   4080
actgaaaagt gattaataat taggaaattg ccagcatgta gtttgatctg tcatttgcta   4140
tttagggtga ttgactattt aagctttgat tttttggaag tgtggagaag gcatttaaat   4200
tagatcccaa agtttctgac taaaggagga ttaagtccta gatttccaaa agaagtttga   4260
caatcctttt tctccctagt tatttcagat taggattaac tactggtttg agattaatac   4320
atggcctgac ttagattgta atcctcagta gggatagggc aatagagcct tattttatca   4380
ctgtaacttc agaatctgat gggattttta gttcataatg ataattaaaa aaaactgaac   4440
atcagacact tttctaggcc ttttacatgt gttatcctct tttcttttga ggaagagtct   4500
cattgtatga ccaaggctgg agtgcagtgg cacaatctcg gctcactgca acctctgcct   4560
cctgggttca agcgattctc gtgcctcagc ctccccagta gctgggatta cgggcgtgtg   4620
ccaccacgcc tggctaattt ttgtatattt aatagagaca ggtttcgcca tgttggccag   4680
gctggtctcg aactcctggc ctcaagcaat ctgcctgcct cccaaagtgc tgggattgca   4740
ggcatgagcc accttgcgca gcctatcctc atattttaaa ctttttattt ttttgaggca   4800
gggctgtttg tcttcttatt ttatagatga aaacattgga agggcagaga agttaaatat   4860
cttgtcacac tgctagtatg ttttggagct tgcatttaag ctccggcagt cctaattcaa   4920
atcccagact ttcctttttc atgacctgct tccttactgt agctctgtat acttttgctg   4980
aatgaatggg tgaatgaatg aataaattgg ggaaaagaga tggatttata tatgtatatt   5040
gagacaggat ctccctctgt cactcactgt ggattgcagt ggcatgataa tagctcacta   5100
cagcctctac ctcctgggct cacaggatcc tcctacctca gtctcccaag tagctgggac   5160
tacaggcatg tgctccgatt cccagctaat tttttaaatt ttttgtagaa atgggttctc   5220
```

```
cctatgttgc ttaggctgat ctggaactcc tgggctcaag tgatcctcct gcctcagctt   5280
cccaaagtgc taggattaca ggcgtgagct accatgccca gctggattaa taaattttta   5340
atccagacta gtcaatctga gtataaaatt ttttatctcc ttgttggtgg taggtacctc   5400
atccctttta ttttcttcag agaagtttat tcttctgtta cctatgtgat aacccagttt   5460
ctaaattctt gaagcacagg atgtattcag gaattgattt cctggaaatt agggaatttc   5520
caaatgagtt ctccctcctg ctatccaata agaatcatgg ggtcttggtt gtcagagagg   5580
aggtctttaa tacatacctg tgatctggat agtacaagag tggacaccat gggtagggct   5640
caaagtgaag ccgtgagcca ctcacatgtg acggaggact agaccaaggt cagctctgca   5700
tgccgaacct ttggaagcca ggacttcgga gatacaaaga taattgagtg acaaataagt   5760
agcagaatat gatagaaggg atattatcct tacatttgtg actttctttt tagctataac   5820
tctgtgacct catgtagcag ttacacaaaa tgggactgta attcttacct ttggagataa   5880
aatgagtggt agaggaaatg tttgttaggc ttatagaaag atccaactat tgtgtcttta   5940
cagtgaacag aataattaaa tttgatagaa ccaactttcc tactgtagaa atacttttaa   6000
agagtttatg tctaatgaca taaaaatata cttaggaagc tctgttttta tacagaacaa   6060
agtgtttttc aacttctgtt gttacatcct ttgaataggt taacatttct gcctcctttg   6120
aggactaatt ctttgctctt tcacatcagt gaccaatgta gagtttgctt acatttattt   6180
acaacttatt aacattacta gagaatagca cactaaatgt gaaaggaaca gagtaagatc   6240
catgtcaggg tatcaatttt taactcaata aacttatcag tattttaaaa tgccatttta   6300
ttatttttgc atagataatg tatattacat cttatttccc aaagcttaat aggtttgaac   6360
atggacttta tttgtagaag gcaagtaaga gaataattat aaaagtgggt ctttgagtag   6420
aataatgata aacttaccca tattataaac tgcattgtga catgtgtttc cttaaaagaa   6480
atgtgattct gaaaaaaatg gcttgcattt gagcctgtta ctgtggatct agatttgcat   6540
agaagacatt tatagacggt tcctgatgtg agctgcagct ggtaaaatac attccttacc   6600
tatccaataa gaatataata ggatttgctt tttaattttt aaagcacaat tatgagtcaa   6660
tattaaacta taaagctctg aaactggcga agaaaacaac tatcaggaag agagcagaga   6720
atattttgta tatttcacat aaagggcatt taacagtatt gttttctaat tttactttca   6780
tttcaatctg tttcattaaa aaagaaagtt gaggtgactt gcctcaaagg tctgtataat   6840
ttttgaggct tctttctgct tgtgtttttg taactgtaaa ataagaacac actgaaaata   6900
tactggaatt aagaaagcca gtgtgagtaa atgaaaatgt cattaaattt ggtagagaaa   6960
tggacagatg ggtaacttga agttaataaa gacataaaaa tcaaagcaga ggaatgtatt   7020
ttaagaataa aacaatctaa attgcatgac ttaaaagtaa aataataggt agggaattat   7080
gtattataaa gaaacatgaa tgtgttaact acaggtgtta atatttaaaa aattatagtg   7140
ggaatgattt gagacttcag acttggttac atggctttta tgacatcact ttttctaaat   7200
tactggaacc tgtgtttgtt tttacattgt tttgtcatga gaaaatacat ttatataact   7260
taaggctctt ttcttcattt atttcacctt gtcttcaaaa aattacatga acatgttaat   7320
tccctaaaag tgaaagaaca ttatgttttt tattggtgaa taagaagttg ttatggagtg   7380
ctctattttt acagctgtgc ttcagggtat cacgttctga agaggtcagc ttggcatgat   7440
ctcatgggca tgaatcttgg ggagacaatt ctgaaacagc cacaggcctg cagcgtcgca   7500
aagccagggc agaacatcca gatgctgtcg ttaggaggca cgcggtctgt taaagcttta   7560
```

gggtggaaga cccaggagga tgcagctaga agaatgccgc atccacattc gtggcaactc 7620
tctgggtgct gttgtaattt taactcttga gttcgtttaa tagaaaaaaa taaatagggc 7680
tgtgagcgat ggctcaggcc tttaatctca gcactttggg aggccgaggc aggcggatca 7740
cctgaggtca ggactttgag accagcctgg ccaaaatggc gaaacccggt ctctattgat 7800
aaataaataa aagtaaataa aataaatagg gaaaaataaa tagggaggca aagaggaaag 7860
ggtttaagga aaaaggtatt gagactgaag tagagagact gttgtagttt catttcatgg 7920
ctcacattgt tcttgttaaa attacagacg ctccgggcat gatggctcac gtctataatc 7980
ccagcacttt gggaggccaa ggtgggtgga ttgcttgagg tcagaagttt gaaaccagcc 8040
tggccaacat ggcaaaacct gtctactaaa aatgcaaaaa tcagccaggc gtggtggtgc 8100
atgcctgtaa tcccagctac tcgagaggct gaagcaggag aactgcttga acccaggagg 8160
cggagcttgc agtgagccaa ggttgctcca ctgcgctgta gcctgggcaa cagagcaaga 8220
ctctatctca aaaaaaaaaa attacagaag catattatga ttttgagaag gtgtgtgaag 8280
ctactttctt tatctgataa gagcagaatt tctgtgtcta atactcagat atgattattt 8340
gggatatgga ttagctttgc tgtctttact ttggactcct ctgtatcaag gttggtggta 8400
gttgagtaca tgtgtgattg gaagttgttt ataagattct tatttaatga aataagttag 8460
gaaatactaa tgttttccca tcatttagaa atatgtgtta tattttttat catcactgtt 8520
aatgagaata aaatttgtta tttggaatcc acatgcactc agaattgttg ccacttgcag 8580
cgcatgtagt gtcacgtgga tgtcattcat acctgttgct tctgctgcgg tggctgtcac 8640
tgtccctatg cagagctgta ccaagatctg cactcagaaa attttgagga aaattgttta 8700
atagggttgg agtgatataa cctttgtttt cattattcat gtattctgtt tttcatatca 8760
agtaggttga tgatcctgga gaagagagaa ttagtgataa aaccaacagt acatcacata 8820
cgaaact 8827

<210> SEQ ID NO 112
<211> LENGTH: 264
<212> TYPE: DNA
<213> ORGANISM: Homo Sapiens

<400> SEQUENCE: 112
ccagcacagg ccagccagaa gatgacactg agactacagg tttggaaggc ggcgttgcca 60
tgccaggtgc cgaagatgat gtggtgactc caggaaccag cgaagaccgc tataagtctg 120
gcttgacaac tctggtggca acaagtgtca acagtgtaac aggcattcgc atcgaggatc 180
tgccaacttc agaaagcaca gtccacgcgc aagaacaaag tccaagcgcc acagcctcaa 240
acgtggccac cagtcactcc acgg 264

<210> SEQ ID NO 113
<211> LENGTH: 136
<212> TYPE: DNA
<213> ORGANISM: Homo Sapiens

<400> SEQUENCE: 113
ggccagccaa gtctcgggat ggtgaacgta ctgtctattg caacgtacac aagcatgaac 60
cccttgtgct gttttgtgag agctgtgata ctctcacctg ccgagactgc cagctcaatg 120
cccacaagga ccacca 136

<210> SEQ ID NO 114
<211> LENGTH: 211

<212> TYPE: DNA
<213> ORGANISM: Homo Sapiens

<400> SEQUENCE: 114
gtttggcttg agcaacaagt ttgatactga atttccctcc gttctaacag ggaaggtggc 60
cccagaagaa tttaaaacca gcattggccg tgtgaatgca tgtttgaaaa aggctctccc 120
ggtcaatgtg aaatggctgc tgtgtggttg tctctgctgc tgttgcacac tgggttgcag 180
cctatggcct gttatttgtc tcaacaaaag a 211

<210> SEQ ID NO 115
<211> LENGTH: 1061
<212> TYPE: DNA
<213> ORGANISM: Homo Sapiens

<400> SEQUENCE: 115
ggccgcgatg ggcctcttgg aacattggtg tgttcatctg cattcgatgt gctggaatcc 60
acaggaatct gggggtgcac atatccaggg taaagtcagt taacctcgac cagtggactc 120
aagaacagat tcagtgcatg caagagatgg gaaatggaaa ggcaaaccga ctttatgaag 180
cctatcttcc tgagaccttt cggcgacctc agatagaccc agctgttgaa ggatttattc 240
gagacaaata tgagaagaag aaatacatgg accgaagtct ggacatcaat gcctttagga 300
aagaaaaaga tgacaagtgg aaaagaggga gcgaaccagt tccagaaaaa aaattggaac 360
ctgttgtttt tgagaaggtg aaaatgccac agaaaaaaga agacccacag ctacctcgga 420
aaagctcccc gaaatccaca gcgcctgtca tggatttgtt gggccttgat gctcctgtgg 480
cctgctccat tgcaaatagt aagaccagca ataccctaga gaaggattta gatctgttgg 540
cctctgttcc atccccttct tcttccggtt ccagaaaggt tgtaggttcc atgccaactg 600
cagggagtgc cggctctgtt cctgaaaatc tgaacctgtt tccggagcca gggagcaaat 660
cagaagaaat aggcaagaaa cagctctcta aagactccat tctttcactg tatggatccc 720
agacgcctca aatgcctact caagcaatgt tcatggctcc cgctcagatg gcatatccca 780
cagcctaccc cagcttcccc ggggttacac ctcctaacag cataatgggg agcatgatgc 840
ctccaccagt aggcatggtt gctcagccag gagcttctgg gatggttgcc cccatggcca 900
tgcctgcagg ctatatgggt ggcatgcagg catcaatgat gggtgtgccg aatggaatga 960
tgaccaccca gcaggctggc tacatggcag gcatggcagc tatgccccag actgtgtatg 1020
gggtccagcc agctcagcag ctgcaatgga accttactca g 1061

<210> SEQ ID NO 116
<211> LENGTH: 322
<212> TYPE: DNA
<213> ORGANISM: Homo Sapiens

<400> SEQUENCE: 116
gtaaaatcta ctggtggagt cactccatta ttcttatctg tggagatcta gatcttgatt 60
tgaaagtttc tgagaaaatc ttcagctcag acttgagggt caactttacc agctgaagga 120
tctgcattta ctgctcaacc acatctaatt tgatgtcctc tgcagattta aaatgtgtgc 180
cttcttttcc gtcaccaagt catccctggg ttactactga acatccttct caattccccc 240
cgacccatgg atggctgttc tccattgtct gtttcaccag atgtcctcaa aacaaacaga 300
cagaagaagg aagtggctaa tg 322

<210> SEQ ID NO 117

<211> LENGTH: 252
<212> TYPE: DNA
<213> ORGANISM: Homo Sapiens

<400> SEQUENCE: 117
gccgagcagc tgcgcaggca gaaggtggag gaggacaagc ggcggcggct ggaggaggtg 60
aagctgaagc gtgaggaacg cctccgcaag gtgctgcagg cccgcgagcg ggtggagcag 120
atgaaggagg agaagaagaa gcagattgag cagaagtttg ctcagatcga cgagaagact 180
gagaaggcca aggaggagcg gctggcagag gagaaggcca agaaaaaggc ggcggccaag 240
aagatggagg ag 252

<210> SEQ ID NO 118
<211> LENGTH: 718
<212> TYPE: DNA
<213> ORGANISM: Homo Sapiens

<400> SEQUENCE: 118
tggtggtctc aaggaaaacg acgtcataat cagcatcaat ggacagtccg tggtctccgc 60
caatgatgtc agcgacgtca ttaaaaggga aagcaccctg aacatggtgg tccgcagggg 120
taatgaagat atcatgatca cagtgattcc cgaagaaatt gacccatagg cagaggcatg 180
agctggactt catgtttccc tcaaagactc tcccgtggat gacggatgag gactctgggc 240
tgctggaata ggacactcaa gacttttgac tgccattttg tttgttcagt ggagactccc 300
tggccaacag aatccttctt gatagtttgc aggcaaaaca aatgtaatgt tgcagatccg 360
caggcagaag ctctgccctt ctgtatccta tgtatgcagt gtgctttttc ttgccagctt 420
gggccattct tgcttagaca gtcagcattt gtctcctcct ttaactgagt catcatctta 480
gtccaactaa tgcagtcgat acaatgcgta gatagaagaa gccccacggg agccaggatg 540
ggactggtcg tgtttgtgct tttctccaag tcagcaccca aaggtcaatg cacagagacc 600
ccgggtgggt gagcgctggc ttctcaaacg gccgaagttg cctcttttag gaatctcttt 660
ggaattggga gcacgatgac tctgagtttg agctattaaa gtacttctta cacattgc 718

<210> SEQ ID NO 119
<211> LENGTH: 190
<212> TYPE: DNA
<213> ORGANISM: Homo Sapiens

<400> SEQUENCE: 119
gaccccgagg gtaagcccaa gaaggccaac atccgggaca atggggatgg cacgtacact 60
gtgtcctacc tgccggacat gagtggccgg tacaccatca ccatcaagta tggcggtgat 120
gagatcccct actcgccctt ccgcatccat gctctgccca ctggggatgc cagcaagtgc 180
ctcgtcacag 190

<210> SEQ ID NO 120
<211> LENGTH: 743
<212> TYPE: DNA
<213> ORGANISM: Homo Sapiens

<400> SEQUENCE: 120
agatgctgcc cccaccccct taggcccgag ggatcaggag ctatgggacc agaggccctg 60
tcatctttac tgctgctgct cttggtggca agtggagatg ctgacatgaa gggacatttt 120
gatcctggtg aggagactga atcatgggtc cctgagggcc agggcttggg aggtagagag 180
ttgggggcct tgacctgtta catgcctgct ttttactcag ccaagtgccg ctatgccctg 240
ggcatgcagg accggaccat cccagacagt gacatctctg cttccagctc ctggtcagat 300
tccactgccg cccgccacag caggtacttg gcacacctgg cacacttgta gctgccccga 360
gaggagctcc tgggacctct acttcccctc caacccctct gcccatgcca gtgaaacccc 420
tgcaggctga gggggcaaat gaagtggggt ttaaatactg gagatggagg cagacctggg 480
gccagatgtt ctctgtgccc ctcttcaccc tcaggttgga gagcagtgac ggggatgggg 540
cctggtgccc cgcagggtcg gtgtttccca aggaggagga gtacttgcag gtggatctac 600
aacgactgca cctggtggct ctggtgggca cccagggacg gcatgccggg ggcctgggca 660
aggagttctc ccggagctac cggctgcgtt actcccggga tggtcgccgc tggatgggct 720
ggaaggaccg ctggggtcag gag 743

<210> SEQ ID NO 121
<211> LENGTH: 1059
<212> TYPE: DNA
<213> ORGANISM: Homo Sapiens

<400> SEQUENCE: 121
caccccccca ggcagcagca gcagttttca tctctggatg acaagcccca gttcccaggg 60
gcctcggcgg agtttataga taagttggaa ttcatccagc ccaacgtcat ctctggaatc 120
cccatctacc gcgtcatgga ccggcaaggc cagatcatca accccagcga ggacccccac 180
ctgccgaagg agaaggtgct gaagctctac aagagcatga cactgcttaa caccatggac 240
cgcatcctct atgagtctca gcggcagggc cggatctcct tctacatgac caactatggt 300
gaggagggca cgcacgtggg gagtgccgcc gccctggaca acacggacct ggtgtttggc 360
cagtaccggg aggcaggtgt gctgatgtat cgggactacc ccctggaact attcatggcc 420
cagtgctatg gcaacatcag tgacttgggc aaggggcgcc agatgcctgt ccactacggc 480
tgcaaggaac gccacttcgt cactatctcc tctccactgg ccacgcagat ccctcaggcg 540
gtgggggcgg cgtacgcagc caagcgggcc aatgccaaca gggtcgtcat ctgttacttc 600
ggcgaggggg cagccagtga gggggacgcc catgccggct tcaacttcgc tgccacactt 660
gagtgcccca tcatcttctt ctgccggaac aatggctacg ccatctccac gcccacctct 720
gagcagtatc gcggcgatgg cattgcagca cgaggccccg ggtatggcat catgtcaatc 780
cgcgtggatg gtaatgatgt gtttgccgta tacaacgcca caaaggaggc ccgacggcgg 840
gctgtggcag agaaccagcc cttcctcatc gaggccatga cctacaggat cgggcaccac 900
agcaccagtg acgacagttc agcgtaccgc tcggtggatg aggtcaatta ctgggataaa 960
caggaccacc ccatctcccg gctgcggcac tatctgctga gccaaggctg gtgggatgag 1020
gagcaggaga aggcctggag gaagcagtcc cgcaggaag 1059

<210> SEQ ID NO 122
<211> LENGTH: 304
<212> TYPE: DNA
<213> ORGANISM: Homo Sapiens

<400> SEQUENCE: 122
atgtggccaa ttagatagtg ctttgcatga agctactagt cgcgtgagaa cacttgaaaa 60
taagaataac ttactggaaa ttgaagtgaa tgatttgaga gaacgcttca gtgcagccag 120
cagtgcttcc aaaattttgc aggaacgaat tgaagaaatg agaacaagca gtaaagaaaa 180
agacaatacc atcattcgac taaaatctag actgcaagat ttagaagaag catttgagaa 240
tgcttacaaa ctctcagatg ataaagaagc tcaactaaaa caagagaaca aaatgtttca 300
agat 304

<210> SEQ ID NO 123
<211> LENGTH: 287
<212> TYPE: DNA
<213> ORGANISM: Homo Sapiens

<400> SEQUENCE: 123
aacagaattc agccatggcc ccaagaaaga gaggtggacg aggtatttca ttcatctttt 60
gctgtttccg aaataatgat cacccagaaa tcacgtatcg gctgcgaaat gatagcaact 120
ttgcgcttca gaccatggaa ccagcattgc ccatgccccc tgtggaggag ctggatgtca 180
tgttcagtga actggtggat gaactggacc tcacagacaa acacagagaa gccatgtttg 240
cacttccagc tgagaaaaaa tggcaaatat actgtagcaa gaaaaag 287

<210> SEQ ID NO 124
<211> LENGTH: 4715
<212> TYPE: DNA
<213> ORGANISM: Homo Sapiens

<400> SEQUENCE: 124
ctggttcctc cctctttgaa ctcatctgga tctggcttat ttcaaatgtc catccccaca 60
ggtgagaaag tagtttagat tttagaatca aacagtcttg atttagagtc ttagttctgc 120
ctctttctag ctatgagatt tttaggtcaa tgacttaatc tttctatgtc tgtattttta 180
tacctttaaa atgaggtact gttaatacct acctcatggg atgttatgaa tattaaataa 240
gtttatgcaa tttgtttatc ataacattgt ttaataaatg ttagttataa ttgcttttag 300
aattatcatg taagataata catagttata ttaattatta ttgtcattat gctaagattt 360
tggaaacttt cattggcata caccaagatg atgattggca gttatttcct gtctttacct 420
gcttggttcc ttaatatgca cagatagaac tgtttaagat ttgaggcctg ggacactgca 480
ttcaacttcc ctcaccttgc aaagtgctct ggcatctgcc ttttgttata gactttctcc 540
ccttgtcagt gtaaatactg aaggctatac ctgtgcaatg ctctgaatat tggtgtctcc 600
cctaaattcc tgtgttgaaa cctaatagta ttaagaaatg agacctttgg ggaagtgatt 660
aagttatgag tgttctaccc tcacaaatgg aattaatgct cttataaaag attgcaggga 720
gttgctttgt ccttctgcca tgtgaggaca cagcaagagg ctccctttta agcagagaac 780
atgccttcac cagacactga atctgctggc attttgatct tggacttccc agcctctaga 840
actatgagaa ataaatttcc gtttcaataa attacccagt ctaagatgtt ttgttgtagc 900
accctaaatg gactgagaca gcgtgtcaca attacagaca ctgctgcact gagctgtatt 960
agtgtcttct tttaacccca gacttacttt ttattgattg tgatttttcc atcacttctt 1020
ggctttagat aaaaataact aatatcatac aaatgtcatc aacaaatcag aagttctttc 1080
ttatctgtct tctattcttt gaccctctcc ttctatattc atatgctgct ggctttctgg 1140
aagctacttt tttctcagta aagaaggtac aaggtttaat ttttagccat ttcttgttct 1200
gaagcctgaa aattctgcaa ggctaaaatc ttgagtcacc ttcattacct ttacatttac 1260
attcattgtt gattatttat ttagctcatt actgacatga ggagacagaa tctgtgttta 1320
ttttaaataa actctttttt tctcttttga caaatacaaa tataagtata gacctatata 1380
ttataattaa cacctctgca tccattccta agtactatta tatatttatt cttagaatat 1440
ttggcttaaa agtttcaaaa ctgattcatg aaagtcaacg tgtatatttg aaatgcaaat 1500

```
gatatttata ttatgataac tgagaaaatg aattacctct tcacaaactt gagataatcc   1560
atttttattg cctacgtcat ttgaacatat ccatatggta caggataaga atagcagctt   1620
gttcagtaca agaatgacta tacctagaaa gacttcattt tatcttgggt aaataataca   1680
tatttagaga catattttat tacatatgag aaaattttag tagaaccctt catgtttggg   1740
cttctgagtt attaaaagag tgaaaacaat agttgtattt tctctaaatc gtcaactaat   1800
taagtcaaat gagtttgcta taattacatg tataatcctc ctgttctcga caccccccat   1860
ttttgcctga tatttaaagt aaaactgaga caaacagctg ctggattgga ttatctactt   1920
tagtatttta ttcctttttt cctgagagaa tgcaatctaa atttaatgca caattcaatg   1980
tacattttag tgcctgctgt gtatggggaa atagacttgg catggggaat gctcagaagc   2040
tcaagataag gcctctgtac cacaagataa agctcattgt ctaatagata gacaagtaaa   2100
cctctatgag atcaggtaag taaatctcct ggcagggaaa ataccaaaca tattctaaat   2160
tcaaacttaa attatttgag gaatatacat tcttattttc tctgttagca ttgttactca   2220
tttaattcaa ttccagacac tgttttgggg cagatattaa atcatattct ggtattacag   2280
ctggataaaa aggtcaacat aatgccttct tactttatca ggaaagacag ataattaaga   2340
agtatttatt taagataagt gtcaggaccc aaaaacatta aataccaagg cagtatgctt   2400
taaatagcat ggaataacta tgttatttaa ataaaatacc attacaacaa ataattacaa   2460
gaaggaagag tactcattac ataggacaca ttatggacct ttcataggac aaataaaata   2520
ataagatatc gctgattaag atatcattga tcaagttaag ttagctattt aaggaatact   2580
tctataaaac aggctttttt tcttatggta aaattcttac agttttcaat ggtacaccat   2640
tactttcata ataaagttaa acttttctgc ttaccacagg aggccattga ggatatggcc   2700
tttcttttct ctagattcat ctcttacaat tttacaacag ttttttcata ccctccttga   2760
aatctaaact actttcacat tagctcacaa tgttgtgtca tacctctctt catgtctatg   2820
tgctgtttat ttacgtagcg ttattcatcc cacttatgtt tcaagactta gcactatttt   2880
ctctgcaaaa tcatccagat acttccaatt tgatttaaat ttttctcttc tgttcctcag   2940
cacaccttgt gctaccttta tccaagcttt tcatcattct cttggtttac ttccatatat   3000
tatatgctcc ttgaagtatt gctgtatctt aacagacttt atacttttca aaccctggca   3060
tatagtacat actcaatatc atatggatgg atggctagat gaataaatga atggatgatg   3120
atttttttcat tttctatatc aaatgtataa aatagaaatt agatataatg ggctgagttc   3180
atcttaattt gcattttaca atgtaaatag aacctttaaa aatatccaga ctactcttta   3240
aaatatgtta taagtctaga tctaagttct agagagaatt gtggagtaaa ctgcagattc   3300
acttcctcag taaatattta tgtaaaaatg ttaagtgata aaccctgatt agatatacca   3360
tatcctatct tccagtgggc tcaaaatcct tattactagc ttttactatg gagaaaatag   3420
ttttcactac tatttccact tgcagtcctg tgccaaggga atctatatgg gaattatata   3480
tattatcact agaaaaagat gcttagatac tctatattat aaataaactt tatttttgaa   3540
taatgctagt ctgtgttcac tgaatctaaa aaattcatgt ttggcatgcg aactcctatg   3600
cataaaaatt ttttctttga aagaaaaagt atactatata atagtaagtt attaaataat   3660
aattaaagat attataattc atgcaataat ttaaaaagta ctttttatat gaacacgttt   3720
atttattttg tgtcttctag catttttcat atcagcaagt atattaaaag gaacatattg   3780
tgtgcaatgt gtaggcccag cataggattc tctatactaa aattttgcaa tgatactggt   3840
```

taattgctag atttcaggca cctttctaac ctccgtttta gtgggcgtga aagggtttat 3900
ttgtaagaga tattgctgct gacagaattt tatctttttc tcctggaatc tcaacagcta 3960
ctcccatgtt ataggcatcc ccagaaagct cgtcaaagga tttccaccca cactctgaat 4020
atctaacagg gcttgaccca tttttttttct cttattaata tagcagcata cacatcatga 4080
agaaagatag aataaggact agtctaagct tggaatttca aaaagttatc tacctgtatg 4140
caaggaattg aagcggacaa caaaattagc ctttattttt tttaaattat gcccttaaca 4200
atcttatcac attaaggaat cacatctaat ttcatgaata tagttttatt ttgagtggct 4260
taaaatgtac atttgtattc ttaaatgcag tgactataaa tgccaaaaat agagtgcact 4320
ataaatcaag aattctcctt tgtactcaat tgttaggaca taatatactg cttaataaca 4380
tagataataa ttaaaagaag actaaagctt tgtgtagtaa tcctagtaga atcctttgga 4440
agtaatcagg atagttataa gacagaatat gaaaatacat gtttaaagta attttcttgt 4500
ataaatgatt acattttttt gtttatgtaa accattagct ttttttgttt tccttatgta 4560
acatctaaat actcatatat agactgtggc taattttttt tttaacttaa aggataaaag 4620
tccctctgga atacaacact gcattcagtt ttccctctta actctctatt gttgggcaag 4680
ttactccaag cctcagtcac ctcatcttcc ttatg 4715

<210> SEQ ID NO 125
<211> LENGTH: 3022
<212> TYPE: DNA
<213> ORGANISM: Homo Sapiens

<400> SEQUENCE: 125
gctttgttct tcctgttaag tggtgtactg gtgatgaccg gaagcatggc cttgattgtt 60
ttggattggg tacacaatgc acctggaggt ggccattaat tggcaccact caaactcaaa 120
ctcagtccat ctgatgccag tgttgagtaa actcaactac tatgaaattt cacctaatgt 180
tttcagtttc acttcctttt gaagtgcaga ttcctcgctg gttcttctga gtgcagaata 240
agtgaacttt tttgttttgt tttgtttttt taagaaactt atctgtatgt tagaaatgga 300
tatgaacaac aaaaccacga gtctcgggtt aagggaagtg acaattttat tccattccag 360
agaatggaca aactcttaac ttttatcaag ccacatgctt ggctgtgtca ttgtttaact 420
tggatatttt atgattttac ttgaatgtgc ctaatggaac catttgatgt gagaaacaat 480
tctttttaat ttacagcaaa atattgaata accattgaca aaaacactat tattttttgt 540
accaaaaata cttaaagacc tcagaagcac tcttttactt ttaagaaatt gctttttttga 600 actttattca gaagcagtta tcaataaatt ccataaaata atgtcattgg tatttaaaaa 660
tgaatattaa tataatgaaa tggtttgcct ttttgtaggc ataataagcc aaatactttt 720
ttacccaaaa taatttttag agaaaatgat gtaatgaaaa attgtaccat gaattaggag 780
catagttttt tccatttaaa cgtcaccatt acttaaaaga tgattgatta ttgctatacc 840
aaatcagatg aactctgttc atcacttttc ttctctgtcc ccaaacaatt tggttcattc 900
agactgaaat gtttgtgtct tcaacttatt agaatggaag ataatgcaga tatttctgtg 960
ggaaataaaa taactaattt tgaggtacca aatagtgcaa ttgggtaaaa cagggtttat 1020
tcagttgcat ctgtctccag tgttgtattg acagctctgg gtcttttttt gggccagccc 1080
ttttttgaca ttgcttccag cagtggaaaa tgggcatttg atggcaatag gccaaaatta 1140
ttgtgtccag agagtacact ttttcaaaat gctcacctac tggaagtgtg aattacttga 1200
caatgtatgg cttagttgtg ttcatgtttt gtctacagta gaggtctaat ccacaggtta 1260

```
cacctatgtt tgatatgata taagttctct ttgcgtaggc cactgggttt ctcatgcagt   1320
aagctttata aaaactcatt tgcactggac tgtcatctca ttcttgtaca acgtagaatt   1380
acttgtttac atccaacaaa tggttagcta gggaaaacag tgcaaactga gtgttagtag   1440
tcattttggt ccaactgcat gtcaaccctt ccatttcaat cccagttaga aatgaaaata   1500
attactttga aacttggctt taagagcaca tttatcgtac gtcacagtgt atggtgaata   1560
tattattaaa taatgtggta cttcgctcat caggcataat gtctaaaatc taatatacat   1620
aattccatta agtggttgaa ggaagcaaat aatggaattg tcaattggtc atctggctgt   1680
aaggtttgcc cttgaactaa aaatgttgtt tggggcaagg gccagaaatg tggagacatg   1740
gtttttgtta cgcattcttg tattatatgt gactaaattt acaaacaaga tacatgtgta   1800
attaaagacc cttatggaac tggaagacgt cttgtagtgc tacattgggt gaaaccgttg   1860
gtccattttt gtctgtttct atgaagataa aataattggg ggccatctag aaatagaaag   1920
gcagtgggaa gacagattct acggcactgc tttcatttaa ttgggcttta ggcactccat   1980
tcgaatgcag aacctcacct ctagttgaga ccaagaattg gcaaatttgc atgagctcct   2040
ggaaagagtt gctgactttg tatctaagac ctgccaggga ataccaagag ttgtttctac   2100
agactttttt tttttttttt gtatgggaga agatactgtg gcaaccagga aggaatggaa   2160
aaaaaattct tttctctaca gcaaattaat gtgaggaagc tcctccaatc ctctggctat   2220
ttaaggttca aaatcaagtg cctagggaaa attccaatgg atgattttct gggagctatc   2280
ttgtctacct tgaggttcct gaacaatgaa ttcccattaa tgagcagtct tcagtattaa   2340
aaccactgtc ttgtcacctc attttgcatt actgtcttcc gtggatgttt cagttacaac   2400
tgtaatgtta tttatagaac aacattaatc cattaaagct aacctatttt tcaatattta   2460
tgataatcta tgtacatata ttgtctgtcc atatgtattt gtaaataggt tgtatataat   2520
gtcaggtttg ggtcttgggt tcaagtgtat atattcctgt aagtttctta actgcatttt   2580
gatgaattca cattatgtaa ctataagaat tgtcccaaaa gtacctgtac agaaaattga   2640
atattgaaaa attgacaaat tgtgtacaaa cactaaaaaa aacttgttta aattgtattt   2700
gcaataaaca acatcaaatt ttttcatgaa atcttggtac aaattcagat ctcttattta   2760
aaatttaaat aaggaataca ttttcaaaat gcagtaatca aaatgtgatc tagtgtaatg   2820
aaataaaatg tgatctagtg taatggaaga cctttgagaa cctgggtgta ttaactttgt   2880
gtatatagtg taaatatccc cactgtactg ttagaggcca acaattctag tatggcttgt   2940
tggcaaagag tgctacaccg tttcaatgaa acaatgtatg tttgttttaa ctgaactaaa   3000
ataaatacat gcttaatcct ga                                             3022
```

```
<210> SEQ ID NO 126
<211> LENGTH: 1435
<212> TYPE: DNA
<213> ORGANISM: Homo Sapiens

<400> SEQUENCE: 126

aactccatcc ggcacaacct gtcactgcat agtcgattca tgcgggtcca gaatgaggga     60
actggcaaga gctcttggtg gatcatcaac cctgatgggg ggaagagcgg aaaagccccc    120
cggcggcggg ctgtctccat ggacaatagc aacaagtata ccaagagccg tggccgcgca    180
gccaagaaga aggcagccct gcagacagcc cccgaatcag ctgacgacag tccctcccag    240
ctctccaagt ggcctggcag ccccacgtca cgcagcagtg atgagctgga tgcgtggacg    300
```

gacttccgtt cacgcaccaa ttctaacgcc agcacagtca gtggccgcct gtcgcccatc 360
atggcaagca cagagttgga tgaagtccag gacgatgatg cgcctctctc gcccatgctc 420
tacagcagct cagccagcct gtcaccttca gtaagcaagc cgtgcacggt ggaactgcca 480
cggctgactg atatggcagg caccatgaat ctgaatgatg ggctgactga aaacctcatg 540
gacgacctgc tggataacat cacgctcccg ccatcccagc catcgcccac tgggggactc 600
atgcagcgga gctctagctt cccgtatacc accaagggct cgggcctggg ctccccaacc 660
agctccttta acagcacggt gttcggacct tcatctctga actccctacg ccagtctccc 720
atgcagacca tccaagagaa caagccagct accttctctt ccatgtcaca ctatggtaac 780
cagacactcc aggacctgct cacttcggac tcacttagcc acagcgatgt catgatgaca 840
cagtcggacc ccttgatgtc tcaggccagc accgctgtgt ctgcccagaa ttcccgccgg 900
aacgtgatgc ttcgcaatga tccgatgatg tcctttgctg cccagcctaa ccagggaagt 960
ttggtcaatc agaacttgct ccaccaccag caccaaaccc agggcgctct tggtggcagc 1020
cgtgccttgt cgaattctgt cagcaacatg ggcttgagtg agtccagcag ccttgggtca 1080
gccaaacacc agcagcagtc tcctgtcagc cagtctatgc aaaccctctc ggactctctc 1140
tcaggctcct ccttgtactc aactagtgca aacctgcccg tcatgggcca tgagaagttc 1200
cccagcgact tggacctgga catgttcaat gggagcttgg aatgtgacat ggagtccatt 1260
atccgtagtg aactcatgga tgctgatggg ttggatttta actttgattc cctcatctcc 1320
acacagaatg ttgttggttt gaacgtgggg aacttcactg gtgctaagca ggcctcatct 1380
cagagctggg tgccaggctg aaggatcact gaggaagggg aagtgggcaa agcag 1435

<210> SEQ ID NO 127
<211> LENGTH: 1311
<212> TYPE: DNA
<213> ORGANISM: Homo Sapiens

<400> SEQUENCE: 127
gctcacttca tggactcact ttgcgtgctt gttaaatgtg ctgtgttgct cccaagacca 60
tgtaaagcct actgaccact aacctccctc acagcagaaa ctagacgtca ggttaaaatg 120
ggcaactccg acagtcagta caccccttcaa ggatctaaaa atcatagcaa tactattact 180
ggtgctaagc aaattccttg ctccctgaaa atacgtggca ttcatgcaaa agaggaaaag 240
tcattgcatg gatggggtca cggaagcaac ggagcaggtt acaagtccag gtccctggcc 300
cgaagctgcc tttctcactt taagagtaac cagccttacg catcgagact cggtggcccc 360
acatgcaagg tctccagagg tgttgcctac tccacgcaca ggacaaatgc cccagggaag 420
gatttccagg gcatcagtgc tgctttctca actgagaatg gcttccactc tgttggccac 480
gagctggcag ataaccacat cacctccaga gactgcaacg gacaccttct caactgctac 540
gggaggaatg agagcattgc ctccacccca ccgggcgaag accgcaagag cccccgagtg 600
ctcatcaaaa cgctggggaa gctggatggg tgtttaaggg tcgagttcca caatggtggc 660
aaccccagca aagtgcctgc agaggactgc agtgagccgg tgcagctgct gaggtactca 720
cctaccttag catcggaaac ctcccctgtg cctgaagcca ggagggggtc cagcgccgat 780
tccctgccca gccatcgccc ctctcccacg gactctcgcc tgcggtccag caaaggcagc 840
tccctgagtt ctgagtcatc ctggtacgac tccccttggg gcaatgctgg agagctgagc 900
gaggctgagg gctccttcct ggcccccggc atgcctgacc ccagtctcca tgccagcttc 960
ccacctggcg atgccaaaaa gcctttcaac caaagctctt ccctctcctc cctccgggaa 1020
ctgtacaaag atgccaacct ggggagcctc tccccctcag gtatccgcct ttctgatgaa 1080
tacatgggca cgcatgccag cctgagcaac cgtgtctctt ttgcttccga cattgatgtg 1140
ccctccagag tggcacacgg ggaccccatc cagtacagtt ccttcactct cccctgtcgg 1200
aagcccaaag cctttgttga ggatactgcg aagaaggact ccctcaaagc caggatgcga 1260
cggatcagtg actggacggg aagcctctca aggaagaaaa ggaaactcca g 1311

<210> SEQ ID NO 128
<211> LENGTH: 807
<212> TYPE: DNA
<213> ORGANISM: Homo Sapiens

<400> SEQUENCE: 128
gcagcggagg aggaaatggc aggtcctaat caactctgca ttcgccgctg gactaccaag 60
catgtagctg tgtggctgaa ggatgaaggc ttttttgaat atgtggacat tttatgcaat 120
aagcaccgac ttgatggaat cacattgcta acattgactg aatatgatct ccggtctcct 180
cctctggaaa tcaaagtctt aggggacatt aaaaggttaa tgctctcagt ccgaaaattg 240
cagaaaatac atattgatgt tttagaagag atgggctaca acagtgacag tcccatgggt 300
tccatgaccc ctttcatcag tgctcttcag agtacagact ggctctgtaa tggggagctt 360
tcccatgact gtgacggacc cataactgac ttgaattctg atcagtacca gtacatgaat 420
ggtaaaaaca aacattctgt tcgaagattg gacccagaat actggaagac tatactgagt 480
tgtatatatg tttttatagt atttggattt acatctttca ttatggttat agtccatgag 540
cgagtgcctg acatgcagac ctatccacca ctcccagata tattcttaga cagcgttcct 600
agaatcccat gggcctttgc catgacggaa gtatgtggca tgattctgtg ctatatttgg 660
ctcctggttc ttcttcttca caagcacagg tcaatacttc tgcgaaggct ctgtagtctg 720
atgggaactg tattcttgct tcgctgcttt accatgtttg tgacctccct ctccgtgcca 780
ggacaacacc tgcagtgtac tggaaag 807

<210> SEQ ID NO 129
<211> LENGTH: 356
<212> TYPE: DNA
<213> ORGANISM: Homo Sapiens

<400> SEQUENCE: 129
ggttgaaaaa taccggccac agaccctgaa tgatctcatt tctcatcagg acattctgag 60
taccattcag aagtttatca atgaagaccg actgccacac ttgcttctct acggtccccc 120
agggacaggc aagacatcta ccatcctagc ctgtgcgaaa cagctatata aagacaaaga 180
atttggctcc atggtcttgg agctgaatgc ttcagatgac cgaggaatag acatcattcg 240
aggaccgatc ctgagctttg ctagcacaag gacaatattt aagaaaggct ttaagctagt 300
gatcttggat gaagcagacg ccatgactca ggacgcccag aatgccttga gaagag 356

<210> SEQ ID NO 130
<211> LENGTH: 471
<212> TYPE: DNA
<213> ORGANISM: Homo Sapiens

<400> SEQUENCE: 130
aggggtgttt gatgcttccc tcaaaatggc tggcttctat ggattgtata cctggctgac 60
tcatactatg tttggcatca atattgtctt cataccatca gcattagcag caatccttgg 120

```
agcagtgcca ttcctgggga catactgggc agcagtacct gcagttcttg acctgtggct    180

gacacaaggg ttaggatgca aggccatttt actgttgatt tttcatctct tgccaacata    240

ctttgtagat actgcaatct actctgacat atcaggaggt ggccatcctt acctgacagg    300

cttggcagtg gccggtggag catactacct aggcctggaa ggagcaatca tcggtcctat    360

tcttctctgc atacttgtgg ttgcttccaa tatctatagt gccatgctag tgagtcccac    420

gaattcagtt cccacgccaa accagacccc atggcctgct cagcctcagc g             471
```

<210> SEQ ID NO 131
<211> LENGTH: 329
<212> TYPE: DNA
<213> ORGANISM: Homo Sapiens

<400> SEQUENCE: 131

```
gagttgatgg agacctccaa gaagctggtt caagctccct aaacccagag ctggaggaag     60

accctgctga acagatgacg tcacagtcag aggcagaagc cccaggattg gtagacagac    120

agacgttgga atgagagaaa cagagtccgg accccaggta gggtggaact cagccctctg    180

caggcccagc tccccgttgt acaccccagg cccaccttga tcttggagcc ggcggtgctg    240

gggcgcccct tcttgtctcc atccagcttc tcggggaaga gcatccggag gaaggccctg    300

ggtaggaaag gggagaggag gagttggag                                      329
```

<210> SEQ ID NO 132
<211> LENGTH: 4059
<212> TYPE: DNA
<213> ORGANISM: Homo Sapiens

<400> SEQUENCE: 132

```
ttcaatataa aagaacaaac cgttacgaga ggagctagaa ggcaccttaa gaggcaagtg     60

aaccctttgg acagcatcac tttgaagtta ctctacacag aaacatctgt cttccaggag    120

cctcccagct gcttcactcc gtcctgaagt cagaacccct acctccagtc ctctctgaat    180

tcaggcgtgt ttgtgcattt gcttttctaa ctgggaacac gaagacacct gagagggttg    240

gagctggcgg gaggagggca gggataaaca ccccagcgcc ttttccccac tattgtcttg    300

ttctttcttc cacttcacct ttgctttctt ttttaacttg tatattaagt tcaggggtac    360

ttgtgtaggt ttcttatatg gtaaacttgt gtcatgggag ggggttgttg tacagattat    420

tttgtcaccc aggaattaag cttctaaata attcaggggg ccccagcatt tgcagaagtt    480

acctactggc tttagaagaa tttctgaaaa gtttgatgtc agtcaaatct ttttttttt    540

tttaacttaa tatgctggct aagatgctgg ctatttaaag ttggaatgaa tgaatccctg    600

ggcaaaaagg aagcttttag gagcacgcat aagcacacac catactctgg ctaaattaga    660

ttttctaaaa ttgggctttc ctaaagaaag tcatatggta gatggccata ggcccagtga    720

accgaattca gaaagtgtta tttcatgagc aagtttccca gaaaggttcg agatgtttct    780

gatagagcag gaatgtactt cctactacac agtactcagc cctggaggct cagagcagga    840

agacctgacc tgcacaggcc ccttttgttg gctgggaaac ttccacatcc ctgtgtcacc    900

atgaaaaaga gctaactttg tcttcaacga cgagttggaa aattatttta atctctgcat    960

taaactagat gcaaaattgc ctctctacct aggaatcacg ctgcataatc ccacattatc   1020

tgcattttca gtcatgcctt gaataatgat acttgagttc ttgaggaggt cattgtgggg   1080

ctgggaagac ccctagactt ccccatgtag atgtggcctg gaagtaagac taacgtagca   1140

gcaaagccct ggcgatcatg cacactcctg agtaaggcag aggtgtgaat cattatatca   1200
```

```
ccatggctgg ctagcttcag aggaaccgaa aaaatgaaaa cacttgcgtt gctcattagc   1260
aaagggaaat acacaaatgt tgagggactc tttgtgtcac agccacactc ttctgtttcg   1320
atctggtaag cagagcactc tccatacctg cttcaagctt ccagctgaga gttctctttt   1380
agctgttgta cctattgctg aggatcttga tagtgggcta gcaacaaggg gctttagaaa   1440
ataagagcat ttcagcatca actgttttaa ctggagtaag atccattttg tgatttgatt   1500
tgatttttat tttttagag acagactttc actctgtctt gcaggctgga gtgcagtgac    1560
gtgataatag ctcactgcaa cctcaacctc ctaggctcaa ttgatcctcc cacctcagcc   1620
tcccaagttg ctgagaccac aggtgcatgc caccacgccc agctagtttt tgtatttttt   1680
gtagagacag ggtcttgctt gttgcccagg ctggtctcaa actcctggct tcaggtgatc   1740
cacccgcctt ggcctcccaa agtgctggga ttgcaggcgt gagcctggga tgccaggcat   1800
gcaccaggcc ccattttgtg atttaattct cattgtagac tgacattttc tatagcagaa   1860
tttttcaaca gtagtactgt agttgagggg ccacatttgg ggctggagat gggtaactct   1920
ttactatggg agctctccta tttattgcag ggtgcttagc agcaccctgg gcctctaccc   1980
actaaatgcc agtagcaacc cccatccccg caaattgtgt aaaccaaaaa tatatacaca   2040
cattgccaaa tgtcccatag gacacaaaat catataccca tacgctaaca cacccataca   2100
ctaacaccac acgcatacac acacacacac acacacacac acacacacac actttaagac   2160
tcgctgctct ggccaggcgt ggtggctcac acctgtaatc acagcacttt ggggagctgg   2220
ggcaggcaga ttacttgagt tcaggagttt aagaccagtc tggccaacat ggtggaaccc   2280
cctctctact aaaaatgcaa aaattagctg ggcatggtgg tgcatacctg tagtcccagc   2340
tactctggag gctgaggcaa gagaatcgct tgaatctcgt aggcagagtt gcagtgagcc   2400
aagatcatgc tactgcactc cagcctgggc aacagagtga gactccatct caaaaaaaaa   2460
agaatcactc ctccatagga gagaggcagt gtataaaata atcttttttc taaattggtt   2520
gtgcatttta aatagattcc tggctggaaa caatggctta cgtccataat cccagcactt   2580
tgggaggcca aggcaggggg attgcttgag ctcaggagtt tgaaaccagc ctgggccaca   2640
tggcaaaacc ccgtctctac tacaaatatg aaaattagcc aggcatgatg gcacacgcct   2700
gtaatcctag ctacttgaga agctaaggtg ggaggatgac ttgagcccag gaagcagagg   2760
ttgcagtgag ctgagattgg ttcactgcac tcctgcctgg ggaacagagc cagactctat   2820
ctcagaaaaa caaaaactaa ataactaaat aaataagtag attctaagat tttacacaca   2880
ttgaatcccg tgtgttactg gtttgttccc tacatggagt agacaggttt tctctttggc   2940
cttcacggaa gctcagactg ttactcattc tactttcttg tactcatgca ttgctaatag   3000
ttttcatctg gttattaatt cagtagcagg ccgttaagca tgttcactcg tgctgagata   3060
tttcttagtg agctctcacc acatgccctg atggtgagca gcctcacctc ttaaacagga   3120
ttcctgcatg gttgagaacc cgtccacctt tctcggcttg ttatgatcag agcttacact   3180
tttgggaggt agaactgcat ctgacatgga ggaacatggt ccttagagtc agacagacct   3240
ggattcaaat cccacttctg cttacaagcc agatagcctt ggactgatga ttgaacctgc   3300
atgcctccgt ttccccttat gaacatgggg atgattttgt ctacctggca gggttctgca   3360
tggccttagc gagatcacgt atgtcagaca tcagtaaatg gtaacttgtt atctgtcagt   3420
tgatagctgt aaggtatgaa ttaccatctt tgtaggtcaa aaaccatcaa atattggcaa   3480
cttcgtacaa ttgggcctaa tatgtaaacc ccaggtcacc atcacgctgt cctctttgct   3540
```

```
ctatggatat ccagcagatg aaagggatgg ttctgctttg ttattttctt gttttcctgc   3600

ttcttctgag gggcttccc gctggcacaa tctaacaaac ttcagagagg acgaagtcag   3660

tctctgctgt catcagtgtt cacagacagt agtttcaaag tgtgtaccac atgaagttgc   3720

agtcttccaa ccttccagcc agtgtgtatg gaaataacct gaattgtatt aatagcagtt   3780

cttcaatgtg ggcctgctgg gggatgcttg gttgttttcc gttgtttgtt ccctgggtgc   3840

ccgtcttggg caagcatttc tctgatgtct ctatttatgt ggcaggtcac cctgctgatt   3900

gccttcatct gtgtgcggag ctccctgtgg accaactaca gcgcctacag ctactttgaa   3960

gtggtcacca tttgcgactt gataatgatc ctcgcctttt acctggtcca cctcttccgc   4020

ttctaccgcg tgctcacctg tatcagctgg cccctgtcg                          4059
```

<210> SEQ ID NO 133
<211> LENGTH: 236
<212> TYPE: DNA
<213> ORGANISM: Homo Sapiens

<400> SEQUENCE: 133

```
tcctcaagta ccgtaagggt gatgaagata gccttatgga gaaaatttcc aaactgaaca     60

tccactccat catcaagaaa tccaaccgag ttagcagtca cctgaagcat ctcactggct    120

ttgctcctca gataaaagat gaagtatttg aagaaacaga aaaaaacttc cgaatgcaag    180

aaagattgat taagtctttt atccgagacc tgtctctcta cctccagcac atccgg        236
```

<210> SEQ ID NO 134
<211> LENGTH: 662
<212> TYPE: DNA
<213> ORGANISM: Homo Sapiens

<400> SEQUENCE: 134

```
ttatttctca aactctgagg ctgcggagtt cacacattga aatctgtcat ctttttcaga     60

gagaaacttt cggtaatgta tgtaaccttc tgtaatggaa gatgattgaa gacaaggggc    120

ctcgtgttgc tgactacttt gttgtagcag gattaactga tgtttcaaag cctctagaag    180

aagaaattca cttcaatgat gcttgtcata aagtagctaa accaaaagaa cctattacag    240

atgtttcagt tattatcaaa tctcttgggg aggaagtccc acaggattat atctgtattg    300

atgttacccc aactggattg tcagctgatc ttaataatgg aagtcttgtg gggccacaga    360

tttacctttg ctatagaaga ggaagagata agcctccact tacagatctg gggggttttat   420

atgactggaa agaaagattg aaacagggtt gtgaaattat tcagagtact ccctatgggc    480

gccccgcaaa tattagtggg agtacctcat cacaaagaat ttatatcact taccgaagag    540

cctctgaaaa catgactcag aatacgttgg ctgtcactga catatgtatt attataccca    600

gtaaaggaga aagcccacca cacacgttct gcaaagtcga caagaatctc aataacagta    660

tg                                                                   662
```

<210> SEQ ID NO 135
<211> LENGTH: 268
<212> TYPE: DNA
<213> ORGANISM: Homo Sapiens

<400> SEQUENCE: 135

```
gtcaggttgc caagaaggaa gatctcatca gtgcgtttgg aacagatgac caaactgaaa     60

tctgtaagca gattttgact aaaggagaag ttcaagtatc agataaagac acacacaact    120

ggagcagatg tttagggaca ttgcaattat tgtggcagac aaatgtgtga ctcctgaaac    180
```

aaagagacca tacaccgtga tccttattga gagagccatg aaggacatcc actatttggt 240
gaaaaccaac aggagtacaa aacagcag 268

<210> SEQ ID NO 136
<211> LENGTH: 271
<212> TYPE: DNA
<213> ORGANISM: Homo Sapiens

<400> SEQUENCE: 136
gtgaattcat cattggccga gttatcaaag ccatgaataa cagctggcat ccggagtgct 60
tccgctgtga cctctgccag gaagttctgg cagatatcgg gtttgtcaag aatgctggga 120
gacacctgtg tcgcccctgt cataatcgtg agaaagccag aggccttggg aaatacatct 180
gccagaaatg ccatgctatc atcgatgagc agcctctgat attcaagaac gacccctacc 240
atccagacca tttcaactgc gccaactgcg g 271

<210> SEQ ID NO 137
<211> LENGTH: 474
<212> TYPE: DNA
<213> ORGANISM: Homo Sapiens

<400> SEQUENCE: 137
gtcctacagc tgggctcaga catccttccc cagtacaagc aagaggcacc aaagactccc 60
cctcacatca tcttacatta ttgtgttttt aagaccacgt gggattggat catcttgatc 120
ttgaccttct atacagccat cttggtccct tataatgtct ccttcaaaac caggcagaat 180
aatgtggcct ggctggttgt tgatagcatc gtggatgtta tctttttggt ggacattgtg 240
ctcaattttc ataccacctt tgttggacca gcaggggagg tgatttctga ccccaaactt 300
atccgcatga actacctgaa gacgtggttt gtgattgacc ttctgtcctg tttgccatat 360
gatgtcatca acgcttttga gaacgtggat gaggttagtg cctttatggg tgatccaggg 420
aagattggtt ttgctgatca gattccacca ccactggagg ggagagagag tcag 474

<210> SEQ ID NO 138
<211> LENGTH: 325
<212> TYPE: DNA
<213> ORGANISM: Homo Sapiens

<400> SEQUENCE: 138
accgtcaaca aagatgtgga cgcacaggct gaaggagaag ggagccgccc atccatggac 60
ttattcaggg ccatctttgc cagttcctca gatgaaaagt cctcatcctc cgaggatgag 120
caaggtgaca gtgaagatga tcaggcaggc tctggggagg ccaacttcca aagctcccaa 180
gacactgact tgggggaaac atcatctgtg gctcacgctc ttgtgccagc accccaggag 240
ccgccacctt ccttcccgat acaaaagatg cagatagatg aaagagaaga gttcggcccg 300
cggctgcctc ccgtcttctg cccca 325

<210> SEQ ID NO 139
<211> LENGTH: 3139
<212> TYPE: DNA
<213> ORGANISM: Homo Sapiens

<400> SEQUENCE: 139
gtccctgaca ggctggatga aatgagatcc ccatgtagca attgccatgg aaacctgtga 60
ctcccctcct atctcaaggc aggaaaatgg gcagagcaca tcaaagctat gtggaacgac 120

```
acaacttgat aatgaggtgc cagagaaagt tgcagggatg gagcctgaca gggaaaacag    180
ctccacagat gacaacctga aaacggatga gcgcaaaagt gaagccttgc tgggtttcag    240
cgttgagaat gcagctgcca ctcaggttac ctcagcaaag gagataccct gcaacgaatg    300
tgccacttct tttcccagtt tacagaaata catggaacac cactgcccta atgcccgcct    360
tcctgtcctg aaggatgaca acgagagcga gatcagcgag ttagaggaca gtgacgtgga    420
aaatctaaca ggggagatcg tttaccagcc tgatgggtca gcatatataa ttgaggactc    480
caaagaaagt gggcagaatg cacagactgg ggcaaatagc aaactctttt ctacagcgat    540
gttcctggac tccctggcat ctgctggaga gaagagtgat cagtctgctt ctgcacctat    600
gtcgttctac ccacagatca tcaacacttt tcatatcgct tcatccctcg ggaaaccatt    660
tacagccgat caggctttcc caaatacctc agcattagca ggagttggtc ctgtgttgca    720
cagtttccgt gtctatgatc tccgacacaa gagagagaaa gactatctaa ccagtgatgg    780
ctcagccaaa aactcctgtg tgtccaaaga tgtccctaac aatgtggact tgtccaaatt    840
cgatggttgt gttagcgatg ggaaaaggaa acctgtttta atgtgtttct tgtgcaagtt    900
gtcttttggt tatatcaggt catttgtaac ccatgctgtg catgatcatc ggatgaccct    960
caatgacgag gagcagaagc tcctcagtaa taaatgcgtc tccgccataa tacaggggat   1020
tggcaaagac aaagaacctc ttataagctt tctggaacca aaaaaatcca cttctgttta   1080
tccccatttt tctactacaa acctcatagg acccgatcca accttccgcg gtttatggag   1140
cgcttttcat gttgaaaatg gtgactcttt gccggctggc tttgccttct taaaaggaag   1200
cgcgagcacc tcgagctcag cagagcagcc gctggggatt acccaaatgc caaaggctga   1260
agtgaatctg gggggctgt ctagtttagt agtgaacacc ccaattacct ctgtctccct   1320
cagccactca tcgtctgagt ctagcaagat gtcagagagc aaagaccaag agaacaactg   1380
tgaaaggcca aaagaaagca acgttttaca cccaaacggg gagtgccctg tcaaaagtga   1440
acccactgaa ccgggagatg aggatgaaga agatgcgtac tccaatgaac ttgatgacga   1500
ggaagtatta ggtgaactca ccgatagtat tggtaacaaa gatttccctc tcttaaacca   1560
aagcatttct cctttatcat ccagtgtgct aaaatttatt gaaaagggta cctcgtcctc   1620
ctcggcgact gtttctgatg acacagaaaa gaaaaaacag actgctgctg ttagggccag   1680
tggcagtgtt gctagtaact atggcatcag tggcaaggac tttgcagacg caagtgccag   1740
taaagacagt gccacagctg ctcatccaag tgaaatagcc cggggagacg aagacagttc   1800
agccactcct caccagcatg gctttacccc gagtactcct ggcacaccag ggcctggagg   1860
agacggctca ccgggcagtg gcatcgagtg tccaaagtgc gacactgtgt tggggtcttc   1920
gaggtctctt ggtggtcata tgactatgat gcactcgagg aactcatgca aaaccctcaa   1980
atgtcctaaa tgtaactggc actacaaata tcagcagacc ctggaggccc atatgaagga   2040
gaaacaccct gagccgggtg gctcttgtgt ttattgtaag actggacagc ctcaccccag   2100
gcttgcccgg ggtgagagtt acacgtgtgg ctataaaccc ttccgttgtg aggtttgtaa   2160
ctactctacc actaccaaag gcaacctcag tattcatatg cagtcggaca agcacctgaa   2220
caatgttcag aatctccaaa atggcaatgg tgagcaggtg tttggccact ctgccccagc   2280
ccccaacacc agcctcagtg gctgcggaac accctctccg tccaaaccca aacagaaacc   2340
cacctggcgg tgtgaagttt gtgattatga aaccaatgtc gccaggaacc tccgaattca   2400
tatgaccagc gaaaagcaca tgcataatat gatgcttttg cagcagaaca tgaagcagat   2460
ccagcataat ctgcacttgg gcctcgcccc ggcggaagca gagctttatc agtactacct   2520
```

agcccagaac ataggcctga ccggaatgaa gctggaaaac cctgccgacc ctcagctgat 2580
gatcaatcca ttccagctgg atccagcgac agcagcggct ttggcaccag ggctcgtaaa 2640
taatgagctg ccgcctgaaa tccggcttgc cagtggtcag ctaatgggtg atgacctgtc 2700
cctccttact gcaggagagc tgtcacctta tatcagtgac ccagcgctga agctattcca 2760
gtgtgctgtt tgcaacaaat tcacctctga cagcctggag gccctaagtg tgcatgtgag 2820
cagtgagcgc tctctccctg aagaggaatg gagggcagta attggagata tctaccagtg 2880
caagctctgc aactacaaca ctcagctcaa agccaacttc cagctacact gcaagactga 2940
taaacatatg cagaaatatc aactggtggc tcacattaaa gaagggggca aaagcaatga 3000
gtggaggttg aagtgtattg ccattggcaa ccctgttcac ctaaaatgta acgcctgtga 3060
ctattacacc aacagtgtgg ataaattacg cttgcatacc accaatcaca ggcacgaggc 3120
ggccctgaag ctctacaag 3139

<210> SEQ ID NO 140
<211> LENGTH: 383
<212> TYPE: DNA
<213> ORGANISM: Homo Sapiens

<400> SEQUENCE: 140
atatcggaag aagaaatcga aaggatcatg tctgggcagg agtttgagga agaggccaat 60
cactggagca accatggtga tagtgaccac agttcccctg ggaacagggc ttcggagagc 120
aaccagccct caccaggctc cacactgtct tccagtaggt ctgtggaact gaatggattc 180
atggccttca gggaacagta catgggaatg tctgtgcctc cacattacca atatataccg 240 cacctttttta gctattctgg ccactcacca cttctgcccc aacaagctcg cagcctggat 300
ccccagtcat acagtctgat tcaccagctg ttatcagccg aggacctgga accattgggc 360
acgcccatgt tgattgaaga tgg 383

<210> SEQ ID NO 141
<211> LENGTH: 491
<212> TYPE: DNA
<213> ORGANISM: Homo Sapiens

<400> SEQUENCE: 141
gctggagtct gggatgcaga acatgagtat tcatacgaag accaccagcg gctatgcagg 60
tggtctgagc tcggcctatg gggcctcac aagccccggc ctcagctaca gcctgggctc 120
cagctttggc tctggcgcgg gctccagctc cttcagccgc accagctcct ccagggccgt 180
ggttgtgaag aagatcgaga cacgtgatgg gaagctggtg tctgagtcct ctgacgtcct 240
gcccaagtga acagctgcgg cagcccctcc cagcctaccc ctcctgcgct gccccagagc 300
ctgggaagga ggccgctatg cagggtagca ctgggaacag gagacccacc tgaggctcag 360
ccctagccct cagcccacct ggggagttta ctacctgggg acccccttg cccatgcctc 420 cagctacaaa acaattcaat tgcttttttt ttttggtcca aaataaaacc tcagctagct 480
ctgccaatgt c 491

<210> SEQ ID NO 142
<211> LENGTH: 339
<212> TYPE: DNA
<213> ORGANISM: Homo Sapiens

<400> SEQUENCE: 142

```
gttgaatgtc tccattgaat gtaagcgagt gtctggactg gagccagcca ccgtggattg     60

ggccttcgac ctgaccaaaa cgaatatgca aaccatgtat gagcagagcg agtggggctg    120

gaaggaccga gagaaacggg aggaaatgac agatgaccga gcctggtacc tcatcgcgtg    180

ggaaaacagc tccgtccctg ttgccttttc tcacttccgg tttgacgtgg agtgtgggga    240

tgaagtcctg tactgctatg aagtgcagtt ggaaagcaag gtgcggcgga aaggcctggg    300

gaagttcctc atacagatcc tgcagctcat ggccaacag                           339
```

<210> SEQ ID NO 143
<211> LENGTH: 1548
<212> TYPE: DNA
<213> ORGANISM: Homo Sapiens

<400> SEQUENCE: 143

```
gtacttgaat ctaaaacaaa tatggacaca cagagcaaga aaatagctga acagtgagta     60

tgtgaagagt aaaccaacag acaccaggat tattcaccat aggccagcct tctagctccc    120

aagatgttcc ctccctgcca gtcttcattg tctctcagta ttgagatgtc agcctccttt    180

ccatattacc tggaataatt gccaagcagt catgccactt gaaaatgagg taacaagtcc    240

tttgattgaa ctggcagtcc cactccctgt catagcatcc ttgtatcagt gttgtttatt    300

catttcatgg tctgttctct caagaaataa gcatcaggag tggacagtga tgtttggggg    360

gatcccaagg cacatgggag gcagatctta cctctttctg aggaggccac agagagctgg    420

atagtccctc tgtctgctcc ctggtagctg gaatgtggat ctgtgactcc atgcagccaa    480

ctggaagctt aatgcaggga atgtgaactt tgaactagtt agagattatt cactgtgagg    540

cttttgcaaa gggcacaggc tggatgagtg gccgtgagcg tccgtgttcc tgagcagact    600

gtgctgtggc ccaatcctgt gcgtgtctcc tcttcaggct cctgccggag catgcttctc    660

taatcttacc atttatcact gacccttcgg tgaaactctc ttctgtttaa atttaccagg    720

gtacactttg taatacttgg gaccaagaat ttgaagatag taatcagaca aatcaaacaa    780

ctagtagtag tggagagaca cgtagcccta caggaagggg tagaattatc attaaaaaca    840

cagacaaacc agagactgcc tgaaaaaaaa aaaaagatga actggaaaga ttcaaagtag    900

gctctattgg aggtgagtat ggaaaacaag cttagctttt tattttgaag tttccttcca    960

ggagttggat actgtgatct cttcaatcag catgtttata tagtgaggag gaagaccaga   1020

aatgagaaga ggaataagaa aatggcagca cagccttttg ggtatggat aagggtggtc    1080

ttcctgctac agcagaggag aggggcatgt gtggcccatg tggaagagca actgagttgg   1140

tggctgactg aatttgggtc cgaagcaaaa ataggatatg aggataggta taagaatttt   1200

attttgtgct atgtgtgtca tttggctttt aaactgtcta gaaataaaat gagatgaaaa   1260

caatctgccc tcatttcttg gttgcttttc ttaaatatca ttggcccaaa gcatagccaa   1320

gccttttatt tagaaaatcc taccttcaaa aagtgatagg ttacactaat tatatttgtg   1380

ctgttctaca gattttctat tttgcactgg tcctttacct gctgctcgct gtgcgggcag   1440

ctaaggtgag agtttgaaga ctatggactt ttaagctgag aggctgctgt ggtcatacag   1500

ttttcaacac aaaacttgtt ctccctctag tgttccactt gcacaggg                1548
```

<210> SEQ ID NO 144
<211> LENGTH: 269
<212> TYPE: DNA
<213> ORGANISM: Homo Sapiens

<400> SEQUENCE: 144
gtggtatgca ttgggtcagt ggcggaactt gaagaactgt caggagcaaa gatctcagat 60
ctccacagag agagtgttga ccacctgacc attccttcac gctgtgggaa gggatccttg 120
caccgcatct ctgaagtgtt tgactgttgg tttgagagtg gcagcatgcc ctatgctcag 180
gttcattacc cgtttgaaaa caagagggag tttgaggatg cttttcctgc agatttcatt 240
gccgagggca tcgaccaaac cagaggatg 269

<210> SEQ ID NO 145
<211> LENGTH: 238
<212> TYPE: DNA
<213> ORGANISM: Homo Sapiens

<400> SEQUENCE: 145
gtcttcgcct tgatcgtgtt ctcctgcatc tatggtgagg gctacagcaa tgcccacgag 60
tctaagcaga tgtactgcgt gttcaaccgc aacgaggatg cctgccgcta tggcagtgcc 120
atcggggtgc tggccttcct ggcctcggcc ttcttcttgg tggtcgacgc gtatttcccc 180
cagatcagca acgccactga ccgcaagtac ctggtcattg gtgacctgct cttctcag 238

<210> SEQ ID NO 146
<211> LENGTH: 362
<212> TYPE: DNA
<213> ORGANISM: Homo Sapiens

<400> SEQUENCE: 146
gtactaaggt ctacatcgac cccttcactt atgaagaccc taatgaggct gtgagggaat 60
ttgcaaaaga gatcgatgtc tcctacgtca agattgaaga ggtgattggt gcaggtgagt 120
ttggcgaggt gtgccggggg cggctcaagg ccccagggaa gaaggagagc tgtgtggcaa 180
tcaagaccct gaagggtggc tacacggagc ggcagcggcg tgagtttctg agcgaggcct 240
ccatcatggg ccagttcgag caccccaata tcatccgcct ggagggcgtg gtcaccaaca 300
gcatgcccgt catgattctc acagagttca tggagaacgg cgccctggac tccttcctgc 360
gg 362

<210> SEQ ID NO 147
<211> LENGTH: 148
<212> TYPE: DNA
<213> ORGANISM: Homo Sapiens

<400> SEQUENCE: 147
gtcgggaggg ccgaggcgcc gcttgtgggt cccctcgctg gagagggctg gctgggcgag 60
gccggctcga atctctggct cctggcttag agcagttgct cttaaagggg aacgggccac 120
ccccggctgc tccagtgggc taggctgg 148

<210> SEQ ID NO 148
<211> LENGTH: 264
<212> TYPE: DNA
<213> ORGANISM: Homo Sapiens

<400> SEQUENCE: 148
ccaaggtggt gccccagcag atcacgcaca cttctcctcg gatccagcca gactaccctg 60
ccgagaggag tagcctgatt cccatctccg gacatcgggc ctctcccaat cctgtggcca 120
tggaaacccg aagtgacaac agaccgtctg ttcccgttca gttccaatat tttttgccaa 180
cttacccccc ttctgcatac ccactggcgg cacataccta caccccaatc accagttccg 240
tgtccactat ccgacagtat ccag 264

<210> SEQ ID NO 149
<211> LENGTH: 1521
<212> TYPE: DNA
<213> ORGANISM: Homo Sapiens

<400> SEQUENCE: 149
agtaacagtt acccctcaat gagcgacccc tacctgtcca gctattaccc gccgtccatt 60
ggatttcctt actccctcaa tgaggctccg tggtctactg caggggaccc tccgattcca 120
tacctcacca cctacggaca gctcagtaac ggagaccatc attttatgca cgatgctgtt 180
tttgggcagc ctgggggcct ggggaacaac atctatcagc acaggttcaa ttttttccct 240
gaaaaccctg cgttctcagc atgggggaca agtgggtctc aaggtcagca gacccagagc 300
tccgcgtatg ggagcagcta cacctacccc ccgagctccc tgggtggcac ggtggttgat 360
gggcagccag gctttcacag cgacaccctc agcaaggccc ccgggatgaa cagcctggag 420
cagggcatgg ttggcctgaa gattggggac gtcagctcct ccgccgtcaa gacggtgggc 480
tctgtcgtca gcagcgtggc actgactggt gtcctttctg gcaacggtgg gacaaatgtg 540
aacatgccag tttcaaagcc gacctcgtgg gctgccattg ccagcaagcc tgcaaaacca 600
cagcctaaaa tgaaaacaaa gagcgggcct gtcatggggg gtgggctgcc ccctccaccc 660
ataaagcata acatggacat tggcacctgg gataacaagg ggcctgtgcc gaaggcccca 720
gtcccccagc aggcaccctc tccacaggct gccccacagc cccagcaggt ggctcagcct 780
ctcccagcac agcccccagc tttggctcaa ccgcagtatc agagccctca gcagccaccc 840
cagacccgct gggttgcccc acgcaacaga aacgcggcgt ttgggcagag cggaggggct 900
ggcagcgata gcaactctcc tggaaacgtc cagcctaatt ctgcccccag cgtcgaatcc 960
caccccgtcc ttgaaaaact gaaggctgct cacagctaca acccgaaaga gtttgagtgg 1020
aatctgaaaa gcgggcgtgt gttcatcatc aagagctact ctgaggacga catccaccgc 1080
tccattaagt actccatctg gtgtagcaca gagcacggca acaagcgcct ggacagcgcc 1140
ttccgctgca tgagcagcaa ggggcccgtc tacctgctct tcagcgtcaa tgggagtggg 1200
catttttgtg gggtggccga gatgaagtcc cccgtggact acggcaccag tgccggggtc 1260
tggtctcagg acaagtggaa ggggaagttt gatgtccagt ggatttttgt taaggatgta 1320
cccaataacc agctccggca catcaggctg gagaataacg acaacaaacc ggtcacaaac 1380
tcccgggaca cccaggaggt gcccttagaa aaagccaagc aagtgctgaa aattatcagt 1440
tcctacaagc acacaacctc catcttcgac gactttgctc actacgagaa gcgccaggag 1500
gaggaggagg tggtgcgcaa g 1521

<210> SEQ ID NO 150
<211> LENGTH: 153
<212> TYPE: DNA
<213> ORGANISM: Homo Sapiens

<400> SEQUENCE: 150
acatagatga gtgtgaagtt tctggcctgt gcaggcatgg agggcgatgc gtgaacactc 60
atgggagctt tgaatgctac tgtatggatg gatacttgcc aaggaatgga cctgaacctt 120
tccacccgac caccgatgcc acatcatgca cag 153

<210> SEQ ID NO 151
<211> LENGTH: 293

<212> TYPE: DNA
<213> ORGANISM: Homo Sapiens

<400> SEQUENCE: 151
tgacaaaaat gctgagtttc ttccgtagaa cactagggcg tcggtctatg cgtaaacatg 60
cagagaagga acgactccga gaagcacaac gcgccgccac acatattcct gcagctggag 120
attctaagtc catcatcacg tgtcgggtgt cccttctgga tggtactgat gttagtgtgg 180
acttgccaaa aaaagccaaa ggacaagagt tgtttgatca gattatgtac cacctggacc 240
tgattgaaag cgactatttt ggtctgagat ttatggattc agcacaagta gca 293

<210> SEQ ID NO 152
<211> LENGTH: 309
<212> TYPE: DNA
<213> ORGANISM: Homo Sapiens

<400> SEQUENCE: 152
ggggcgacga tggccttctg aggggctggg acaccagggt acccggcaaa tttctcttca 60
ccagcaaaag acacaccatg ggtgtgtgca gcatccagag cagccctcat cgggagcaca 120
tcctggccac gggaagctat gatgaacaca tcctactgtg ggacacacga aacatgaagc 180
agccgttggc agatacgcct gtgcagggtg gggtatggag aatcaagtgg caccctttcc 240
accaccacct gctcctggcc gcctgcatgc acagtggctt taagatcctc aactgccaaa 300
aggcaatgg 309

<210> SEQ ID NO 153
<211> LENGTH: 440
<212> TYPE: DNA
<213> ORGANISM: Homo Sapiens

<400> SEQUENCE: 153
ccatgcgatg atggacctac tggttgaact ttgccttcag aaccacctga atccatccca 60
ccatgccctt gaaattcggt cttcagaaac ccaacaacct ttgagtttta agccaaatac 120
tttgattggg accctgaatg tgcatactgt gtttctgaaa gaaaaagttc ctgaagagaa 180
ggttaagcct ggtcccccta aggtgcctga gaaatctgtg cgtttggtcg tgaattacct 240
gcggacacaa aaagctgttg tgcgtgtgag ccctgaggtt cctctccaga atattctccc 300
agtcatttgt gcaaagtgtg aggtcagccc agagcacgtg gttctcctca gggacaacat 360
tgccggagag gagctggagc tgtccaagtc cctgaacgag ctcgggataa aggagctcta 420
cgcgtgggac aacagaagag 440

<210> SEQ ID NO 154
<211> LENGTH: 251
<212> TYPE: DNA
<213> ORGANISM: Homo Sapiens

<400> SEQUENCE: 154
gatcaagact tcaaatccca aaagaacttc atcattaaca tgacttgcag attttgctgg 60
cagcttcctg aaacagatta cgagtgtacc aactccacca gctgcatgac ggtgtcctgt 120
cctcggcagc gctaccctgc caactgcacg gtgcgggacc acgtccactg cttgggtaac 180
cgtacttttc ccaaaatgct atattgcaat tggactggag gctataagtg gtctacggct 240
ctggctctaa g 251

<210> SEQ ID NO 155

<211> LENGTH: 654
<212> TYPE: DNA
<213> ORGANISM: Homo Sapiens

<400> SEQUENCE: 155
atcgcttgac aatatcttat tgtcggagta gtggtcctgg ggggcagaat gtgaacaaag 60
tgaattccaa ggcagaagtc aggttccatt tggcaactgc cgagtggatc gcggagcccg 120
tgcggcagaa gatagccatc acgcataaaa acaagatcaa caggttagga gagttgatcc 180
tcacctctga gagcagccgc tatcagttcc ggaatctggc agattgcctg cagaaaattc 240
gagacatgat cactgaggcc agccagacac cgaaggagcc aacaaaagaa gatgttaaac 300
ttcatagaat caggatagaa aacatgaatc gggaaaggct gagacaaaag agaattcatt 360
ctgctgtaaa gacaagcagg agggtcgaca tggactgaaa tcaccctctg cagctgggag 420
ggctcttctg ggcgtccggg cagctgcagc tgagaggact ttcacaccat aaggagattt 480
ctgtttttct ttttggctgt taatgcttgt ctataacatt ggagccatca caagaatgtt 540
catttggaat gaaggctgca ggcactggtt gcagacgtct ttataggcag tcaccatgtt 600
gtcaaacctt aataatgcac ctcatgtatt agtcacaata aaaatcagaa ctca 654

<210> SEQ ID NO 156
<211> LENGTH: 1911
<212> TYPE: DNA
<213> ORGANISM: Homo Sapiens

<400> SEQUENCE: 156
gcggcgtccg tccgtactgc agagccgctg ccggagggtc gttttaaagg gcccgcgcgt 60
tgccgccccc tcggcccgcc atgctgctat ccgtgccgct gctgctcggc ctcctcggcc 120
tggccgtcgc cgagcctgcc gtctacttca aggagcagtt tctggacgga gacgggtgga 180
cttcccgctg gatcgaatcc aaacacaagt cagattttgg caaattcgtt ctcagttccg 240
gcaagttcta cggtgacgag gagaaagata aaggtttgca gacaagccag gatgcacgct 300
tttatgctct gtcggccagt ttcgagcctt tcagcaacaa aggccagacg ctggtggtgc 360
agttcacggt gaaacatgag cagaacatcg actgtggggg cggctatgtg aagctgtttc 420
ctaatagttt ggaccagaca gacatgcacg gagactcaga atacaacatc atgtttggtc 480
ccgacatctg tggccctggc accaagaagg ttcatgtcat cttcaactac aagggcaaga 540
acgtgctgat caacaaggac atccgttgca aggatgatga gtttacacac ctgtacacac 600
tgattgtgcg gccagacaac acctatgagg tgaagattga caacagccag gtggagtccg 660
gctccttgga agacgattgg gacttcctgc cacccaagaa gataaaggat cctgatgctt 720
caaaaccgga agactgggat gagcgggcca agatcgatga tcccacagac tccaagcctg 780
aggactggga caagcccgag catatccctg accctgatgc taagaagccc gaggactggg 840
atgaagagat ggacggagag tgggaacccc cagtgattca gaaccctgag tacaagggtg 900
agtggaagcc ccggcagatc gacaacccag attacaaggg cacttggatc cacccagaaa 960
ttgacaaccc cgagtattct cccgatccca gtatctatgc ctatgataac tttggcgtgc 1020
tgggcctgga cctctggcag gtcaagtctg gcaccatctt tgacaacttc ctcatcacca 1080
acgatgaggc atacgctgag gagtttggca acgagacgtg gggcgtaaca aaggcagcag 1140
agaaacaaat gaaggacaaa caggacgagg agcagaggct taaggaggag gaagaagaca 1200
agaaacgcaa agaggaggag gaggcagagg acaaggagga tgatgaggac aaagatgagg 1260
atgaggagga tgaggaggac aaggaggaag atgaggagga agatgtcccc ggccaggcca 1320
aggacgagct gtagagaggc ctgcctccag ggctggactg aggcctgagc gctcctgccg 1380
cagagctggc cgcgccaaat aatgtctctg tgagactcga gaactttcat ttttttccag 1440
gctggttcgg atttggggtg gattttggtt ttgttcccct cctccactct cccccacccc 1500
ctccccgccc tttttttttt tttttttaa actggtattt tatctttgat tctccttcag 1560
ccctcacccc tggttctcat ctttcttgat caacatcttt tcttgcctct gtccccttct 1620
ctcatctctt agctcccctc caacctgggg ggcagtggtg tggagaagcc acaggcctga 1680
gatttcatct gctctccttc ctggagccca gaggagggca gcagaagggg gtggtgtctc 1740 caaccccccca gcactgagga agaacggggc tcttctcatt tcacccctcc ctttctcccc 1800
tgcccccagg actgggccac ttctgggtgg ggcagtgggt cccagattgg ctcacactga 1860
gaatgtaaga actacaaaca aaatttctat taaattaaat tttgtgtctc c 1911

<210> SEQ ID NO 157
<211> LENGTH: 259
<212> TYPE: DNA
<213> ORGANISM: Homo Sapiens

<400> SEQUENCE: 157
gtggaagatg agctcagctc cccagtggtg gtgttcagat ttttccagga attaccaggc 60
tcagatccgg tgtttaaagc cgtcccagtg cccaacatga caccttcagg agtcggccgg 120
gagaggcact cgtgtgacgc gctgaatcgc tggctgggag aacagctgaa gcagctggtg 180
cctgcaagcg gcctcacagt catggatctg gaagctgagg gcacgtgttt gcggttcagc 240
cctttgatga ccgcagcag 259

<210> SEQ ID NO 158
<211> LENGTH: 179
<212> TYPE: DNA
<213> ORGANISM: Homo Sapiens

<400> SEQUENCE: 158
gttgtgcacc atctccaggt gcttatgatg ttaaaacttt agaagtattg aaaggaccag 60
tatcctttca gaaatcacaa agatttaaac agcaaaaaga atctaaacaa aatcttaatg 120
ttgacaaaga tactaccttg cctgcttcag ctagaaaagt taagtcttcg gaatcaaag 179

<210> SEQ ID NO 159
<211> LENGTH: 169
<212> TYPE: DNA
<213> ORGANISM: Homo Sapiens

<400> SEQUENCE: 159
ctcccgcggc tccagcctcc gcgccctccc ggccggcgcg agtgtgtctg cgcgtgagtg 60
tgagtgtgag tgtgtgttgt gcgcgcagga gccagtgcgt cgggagcagc ggctcgggca 120
gctgctcctg cccgcaccct cccctggagc ccggggagga caaggcgag 169

<210> SEQ ID NO 160
<211> LENGTH: 117
<212> TYPE: DNA
<213> ORGANISM: Homo Sapiens

<400> SEQUENCE: 160
atcctgcccg gcctgtacat cggcaacttc aaagatgcca gagacgcgga acaattgagc 60
aagaacaagg tgacacatat tctgtctgtc cacgatagtg ccaggcctat gttggag 117

<210> SEQ ID NO 161
<211> LENGTH: 104
<212> TYPE: DNA
<213> ORGANISM: Homo Sapiens

<400> SEQUENCE: 161
gatgaatttt tagatgtgat ctactggttc cgacagatca ttgctgtggt cctgggtgtc 60
atttggggag ttttgccatt acgagggttc ttgggaatag cagg 104

<210> SEQ ID NO 162
<211> LENGTH: 2681
<212> TYPE: DNA
<213> ORGANISM: Homo Sapiens

<400> SEQUENCE: 162
aggaccctgg ccacgaatca tttgccatct cctctaccaa agactcaaaa tgtatggccc 60
tggtagtcag ctgggaaagt ctggcaataa cagctgggct aaggaacgtg gatgctcaat 120
tgcctgccaa gggtctctta cttcagcccg gctacatgcc cccagcattg gagagaggcc 180
actttcacac atgcgttgga agggtaagag actctggcaa aaataaattc gtctctctgc 240
atttagcagt gggctcaggg ccatgaggaa gggaattaga ggaaaggaat tagcaacagc 300
ccaccatgtg tctcgtctgg catgagtgga caggtgttag ctctcctctg tatatgagga 360
tctgattttc agctgagttg tcgatgttga accatgttcc atttccactt agatttttat 420
ccaggctcct tctatctaac caacatgaac agaatgtcct gcagtagcac ataggaaaat 480
tacattgggt gcagtctagg aaatcttaat cagggagggc ctggtgatct gaaagcacaa 540
agctttcagt gtctatcaga tgatttagtc gaatttggag tctgaaatga cacataagac 600
agcctaggaa cctagctctg tgtcacctcc cctccccttc agagtccctg gtttactagg 660
gaagtggctg tggtggatga tcagctcagt gaaaacccag cctggttttg tttccccccg 720
acaatagccc ctgcattttt cctttcctag gtcccaactg ttactgctgt atcactccag 780
gccttcctca agtctggttt actgtcaaat agcttcctag cccagtacct ggctttgagc 840
ttgttcctgt gtaagctgtc cagtgtgctc ctgccacatt tactgtcatc ctaaacatca 900
ctttgatcac attgctttcc atttaaatac ttttgctctg cttttcccag acctggctct 960
tacccgttag gctgctttag gctgactttt cctgtttctc actgtgtacc acttagcact 1020
aggcggtttg gtagtgagtt gctctgatta ttacgtctgt gttagaagga gattagaagg 1080
cttttgaagt caagggtgat ggctgtgtct tttgaattcc tcccatagct attcttgttg 1140
aaacactctg ggaatagac acaattctca gacagcagag tgttgatgtc tagggaaaat 1200
gtttacaatc tgaaaaatta ccttggcagg ctgaggacaa agccacaaaa tcgtaacttg 1260
tttttcggct ttcttcagcc tcacctctac cagagaattt cactttggag ttttcttatc 1320
tgtaaaaggg gaagggttga agtacattat ctgtcagctc ccacccaacc ctgaaaggct 1380
aattttcttt aattctttcc cttaatcttt ccattgaaat taaaactgat gagctgtttc 1440
tggatcttga attaggaatt tttcatttct ttgtaattct ttccctgacg cattttgcag 1500
ttgtctccgg gtatgtgctg ctaaaagaaa tttggattgc aatttggcta ctttttagga 1560
gagcagacaa aatgccatac cattctgttt ttcctacttg gagcatttca tttgtaaaag 1620
taaagctttc agtttggtgc ataattctaa cataattctc actcttcctt tgcagacacg 1680
atgaggcgag tggtacgaca gagcaagttt cggcatgtat ttgggcaagc ggtgaaaaat 1740
gaccagtgct atgatgacat ccgggtttct cgtgtgacct gggatagttc cttttgtgct 1800

```
gtcaatccca gatttgttgc cataatcata gaggcaagtg ggggaggagc gttccttgtc   1860

ctccctctgc acaagactgg tcgaattgac aaatcttacc ctacagtatg tggccacaca   1920

ggaccagtgc tggacataga ctggtgccca cataacgatc aggtcattgc cagcggttca   1980

gaggactgca cggtcatggt atggcagatc ccagaaaatg gactcaccct ttccctgact   2040

gaacctgtgg tgattttgga aggccactca aagagagtcg gcatcgtggc ttggcatcca   2100

acggcccgca atgtgcttct tagtgcaggc tgtgataatg ccattatcat ctggaatgtg   2160

ggaacagggg aagcccttat aaacttggac gatatgcatt cagacatgat ttacaatgtg   2220

agctggaacc ggaatggcag tctgatctgc acagcttcca aagacaagaa agtgagagtc   2280

attgatccca ggaaacaaga gattgttgct gagaaggaga aagcacatga aggagcaaga   2340

cccatgagag ccatcttcct ggccgatggc aatgtcttca ccactgggtt cagccgcatg   2400

agcgagcggc agctggctct ctggaatccg aaaaatatgc aggaaccaat tgctcttcat   2460

gagatggaca ctagcaatgg ggtgttgctg cctttctatg accctgacac cagcatcatt   2520

tacttatgtg gaaagggtga cagcagtatt cgctattttg agatcacgga tgaatccccg   2580

tacgtccact acctcaacac attcagcagc aaggagcctc agagagggat gggttacatg   2640

cccaagaggg gacttgatgt taacaaatgt gagattgcca g                        2681
```

<210> SEQ ID NO 163
<211> LENGTH: 372
<212> TYPE: DNA
<213> ORGANISM: Homo Sapiens

<400> SEQUENCE: 163

```
agttcaccca gggcatgatc ttacctacaa tgaatggaga gtcagtagac ccagtggggc     60

agccagcact gaaaactgag gagcgcaagg ctaagcctgc tccttcaaaa acccaggcca    120

gacctgttgg agtcaaaatc cccacttgta agatcactct taaggaaacc ttcctgacgt    180

caccagagga gctctataga gtgtttacca cccaagagct ggtgcaggcc tttacccatg    240

ctcctgcaac attagaagca gacagaggtg gaaagttcca catggtagat ggcaacgtct    300

ctggggaatt tactgatctg gtccctgaga aacatattgt gatgaagtgg aggtttaaat    360

cttggccaga gg                                                        372
```

<210> SEQ ID NO 164
<211> LENGTH: 340
<212> TYPE: DNA
<213> ORGANISM: Homo Sapiens

<400> SEQUENCE: 164

```
gtctctggct tccgtttctt acgctgctgt tgatttttc cgaccatcag ctcagagact      60

gatagaagag aaaggtgcag tggatgcatt ggctgcagct ttagcccaca tttctggtgc    120

atcaagcttt gaaccacgat ctttgatcac ctctgataag ggtttgtga ccatgactct    180

ggaaagccta gaggaaatac aggatgtcag ctgtgcttgg aaagaactta acagaaagct    240

gagtagtaat gcagtgtctc agattaccag aatgtgcctc ctgaaaggaa atatgggtgt    300

ttgctttgat gttcctacaa ctgagtcaga aaggttacag                          340
```

<210> SEQ ID NO 165
<211> LENGTH: 247
<212> TYPE: DNA
<213> ORGANISM: Homo Sapiens

<400> SEQUENCE: 165
gcatctggcc atctgaagag gttttggctt actactgcct caagcacaat aatatattca 60
gggcccttgc tgtgtgtgag ctagggggtg gcatgacatg cttggctggg ctcatggttg 120
ctatttctgc agatgtcaaa gaagttctgt taactgatgg gaatgaaaag gccatcagaa 180
atgtgcaaga catcatcaca aggaatcaga aggctggtgt gtttaagacc cagaaaatat 240
caagctg 247

<210> SEQ ID NO 166
<211> LENGTH: 203
<212> TYPE: DNA
<213> ORGANISM: Homo Sapiens

<400> SEQUENCE: 166
gaagtgtttg gattgtgagc tatttcagaa ctgttctcag gactcattat tttaacattt 60
gggagaaaca cagccagaag atgcacactt gactgaagga ggacagggaa tctgaagact 120
ccggatgaca tcagagctac ttttcaacag ccttctcaat tttctttctc agaaagcaga 180
ggctcagagc ttggagacag acg 203

<210> SEQ ID NO 167
<211> LENGTH: 753
<212> TYPE: DNA
<213> ORGANISM: Homo Sapiens

<400> SEQUENCE: 167
ccgatttatt ttgcatattc ccagcgagga aagagacaat gcaatccgag tgtgttttca 60
gattgaactt gcccattggt tttacttgga tttctacatg cagaacacac caggattacc 120
tcagtgtggg ataagagact ttgctaaagc tgtcttcagt cattgtccgt ttttgctgcc 180
tcaaggtgaa gatgtggaaa aagttttgga tgaatggaag gaatataaaa tgggagtacc 240
aacatatggt gcaattattc ttgatgagac acttgaaaat gtactactag ttcaggggta 300
cctagcaaaa tcaggctggg gatttccaaa aggaaaagta aataaagaag aagctcctca 360
tgattgtgct gctagagagg tctttgaaga aactggtttt gatatcaaag actatatttg 420
taaggatgat tacattgaac ttcgaatcaa tgaccagctt gctcgtttgt acatcattcc 480
aggaattcca aaagacacaa aatttaaccc aaaaactaga agagaaattc ggaacattga 540
gtggttctct attgagaaat tgccttgtca tagaaatgat atgaccccca aatccaaact 600
tggtttggca cctaacaaat tttttatggc cattcccttt atcagaccat taagggactg 660
gctttctcga agatttggcg attcctcaga cagtgacaat ggattttcct caactggtag 720
cacgccggct aaacccactg tggaaaaatt gag 753

<210> SEQ ID NO 168
<211> LENGTH: 982
<212> TYPE: DNA
<213> ORGANISM: Homo Sapiens

<400> SEQUENCE: 168
atcatggagc tttgtggtgc aacaagactt ggttattttg gaagaagtca gttctacatt 60
gctttgaaac ttgtagctgt tgcccagtct ggtttccctt taagagtgga aagtataaat 120
acagtaaagg accttcctct gccaagattt gttgcttcaa agaatgaaca ggaatctcgc 180
catgcagcct catattcttc agattctgaa aatcaagggt cgtattctgg tgtaattccc 240
ccaccacctg gcagggggca agtgaaaaag ggatccgtaa gccatgatac ggttcagcct 300
cgtacatctg cagatgcaca ggaacctgca tccccagtag tttcaccaca gcaatcccca 360
ccaacttctc cacacacatg gaggaagcac agccgtcatc ccagcggtgg gaatagtgag 420
aggcctctcg cgggacctgg gccattttgg tctccctttg gtgaagcaca atcaggttct 480
tctgctggtg atgcagtgtg gtcagggcat tccccacctc cacctcaaga aaactgggtc 540
agttttgcag atactccacc aaccagtact cttttaacca tgcatcctgc ttctgtccag 600
gaccagacaa cagtacgaac tgtagcatca gctacaactg ccattgaaat tcgtaggcaa 660
tccagtagtt atgatgatcc ctggaaaata acagatgaac aaagacagta ttatgtaaat 720
cagtttaaaa ccattcagcc tgatctaaac ggatttattc caggatctgc agctaaagag 780
ttttttacaa aatcaaaact tcctattctt gaactttctc atatttggga actctcagac 840
tttgataaag atggtgcatt gacactggat gagttttgtg ctgcttttca tctggtggtt 900
gctaggaaga atggctatga tttaccagaa aaacttcctg aaagcttaat gcccaaactg 960
attgatttgg aagattcagc ag 982

<210> SEQ ID NO 169
<211> LENGTH: 779
<212> TYPE: DNA
<213> ORGANISM: Homo Sapiens

<400> SEQUENCE: 169
gtatgtgata gtggaatgtg aagatcaaga tactcagcag agagatccaa agacccatga 60
gatgtacttg aacgtaatga gaagattcag ccaagcattg ttgaagggtg ataagtctgt 120
cagagttatg cgttctttgc tggctgcaca acagacattt gtagatcggt tggtgcatct 180
aatgaaggca gtacaacgcg aaagtggaaa tcgtaagaaa aagaatgaga gactacaggc 240
attgcttgga gataatgaaa agatgaattt gtcagatgtg gaacttatcc cgttgccttt 300
agaaccccaa gtgaaaatta gaggaataat tccggaaaca gctacactgt ttaaaagtgc 360
ccttatgcct gcacagttgt tttttaagac ggaagatgga ggcaaatatc cagttatatt 420
taagcatgga gatgatttac gtcaagatca acttattctt caaatcattt cactcatgga 480
caagctgtta cggaaagaaa atctggactt gaaattgaca ccttataagg tgttagccac 540
cagtacaaaa catggcttca tgcagtttat ccagtcagtt cctgtggctg aagttcttga 600
tacagaggga agcattcaga actttttag aaaatatgca ccaagtgaga atgggccaaa 660
tgggattagt gctgaggtca tggacactta cgttaaaagc tgtgctggat attgcgtgat 720
cacctatata cttggagttg gagacaggca cctggataac cttttgctaa caaaaacag 779

<210> SEQ ID NO 170
<211> LENGTH: 295
<212> TYPE: DNA
<213> ORGANISM: Homo Sapiens

<400> SEQUENCE: 170
caaaagcggc gccaggaaat tgaacaaaaa cttgaagttc aggcagaaga agagagaaag 60
caggttgaaa atgaaaggag agaactgttt gaagagaggc gtgctaaaca gacagaactg 120
cggcttttgg aacagaaagt tgagcttgcg cagctgcaag aagaatggaa tgaacataat 180
gccaaaataa ttaaatatat aagaactaag acaaagcccc atttgtttta tattcctgga 240
agaatgtgtc cagctaccca aaaactaata gaagagtcac agagaaaaat gaacg 295

<210> SEQ ID NO 171

<211> LENGTH: 693
<212> TYPE: DNA
<213> ORGANISM: Homo Sapiens

<400> SEQUENCE: 171
cccttacgtc gtcctgactc atctgatgac cgttatgtaa tgacaaaaca tgccaccatt 60
tatccaactg aagaggagtt acaggcagtt cagaaaattg tttctattac tgaacgtgct 120
ttaaaactcg tttcagacag tttgtctgaa catgagaaga acaagaacaa agagggagat 180
gataagaaag agggaggtaa agacagagct ttgaaaggag ttttgcgagt gggagtattg 240
gcaaaaggat tacttctccg aggagataga aatgtcaacc ttgttttgct gtgctcagag 300
aaaccttcaa agacattatt aagccgtatt gcagaaaacc tacccaaaca gcttgctgtt 360
ataagccctg agaagtatga cataaaatgt gctgtatctg aagcggcaat aattttgaat 420
tcatgtgtgg aacccaaaat gcaagtcact atcacactga catctccaat tattcgagaa 480
gagaacatga gggaaggaga tgtaacctcg ggtatggtga aagacccacc ggacgtcttg 540
gacaggcaaa aatgccttga cgctctggct gctctacgcc acgctaagtg gttccaggct 600
agagctaatg gtctgcagtc ctgtgtgatt atcatacgca ttcttcgaga cctctgtcag 660
cgagttccaa cttggtctga ttttccaagc tgg 693

<210> SEQ ID NO 172
<211> LENGTH: 298
<212> TYPE: DNA
<213> ORGANISM: Homo Sapiens

<400> SEQUENCE: 172
aactgtcagc acaacaccgc gggagagcac tgtgaacgct gccaggaggg ctactatggc 60
aacgccgtcc acggatcctg cagggcctgc ccatgtcctc acactaacag ctttgccact 120
ggctgtgtgg tgaatggggg agacgtgcgg tgctcctgca aagctgggta cacaggaaca 180
cagtgtgaaa ggtgtgcacc gggatatttc gggaatcccc agaaattcgg aggtagctgc 240
caaccatgca gttgtaacag caatggccag ctgggcagct gtcatcccct gactggag 298

<210> SEQ ID NO 173
<211> LENGTH: 1583
<212> TYPE: DNA
<213> ORGANISM: Homo Sapiens

<400> SEQUENCE: 173
gcatgtgctg ataagttgaa aagagaaata gagctgtatg gttgcccccc tgattttcca 60
gatgaagaag aggaagagga agaaaccagt gttaaaacag aagatataat aattaaggat 120
aaagctaaag gaaaaaagag taaagctgct gctaaagctg gatcttctaa ataccagtgg 180
ggcattatga aatcccttgg cctgtctgat gaagagatag taaaattttc tgaagcagaa 240
cattggcttg attatttccc gccactggct attcaggatt taaaaagaat gggtttgaag 300
gtagactggc gtcgttcctt catcaccact gatgttaatc cttactatga ttcatttgtc 360
agatggcaat tttaacatt aagagaaaga aacaaaatta aatttgggaa gcggtataca 420
atttactctc cgaaagatgg acagccttgc atggatcatg atagacaaac tggagagggt 480
gttggacctc aggaatatac tttactcaaa ttgaaggtgc ttgagccata cccatctaaa 540
ttaagtggcc tgaaaggtaa aaatattttc ttggtggctg ctactctcag acctgagacc 600
atgtttgggc agacaaattg ttgggttcgt cctgatatga agtacattgg atttgagacg 660
gtgaatggtg atatattcat ctgtacccaa aaagcagcca ggaatatgtc ataccagggc 720

```
tttaccaaag acaatggcgt ggtgcctgtt gttaaggaat taatgggggga ggaaattctt    780

ggtgcatcac tttctgcacc tttaacatca tacaaggtga tctatgttct cccaatgcta    840

actattaagg aggataaagg cactggtgtg gttacaagtg ttccttccga ctcccctgat    900

gatattgctg ccctcagaga cttgaagaaa aagcaagcct tacgagcaaa atatggaatt    960

agagatgaca tggtcttgcc atttgagccg gtgccagtca ttgaaatccc aggttttgga   1020

aatctttctg ctgtaaccat ttgtgatgag ttgaaaattc agagccagaa tgaccgggaa   1080

aaacttgcag aagcaaagga gaagatatat ctaaaaggat tttatgaggg tatcatgttg   1140

gtggatggat ttaaaggaca gaaggttcaa gatgtaaaga agactattca gaaaaagatg   1200

attgacgctg gagatgcact tatttacatg gaaccagaga aacaagtgat gtccaggtcg   1260

tcagatgaat gtgttgtggc tctgtgtgac cagtggtact tggattatgg agaagagaat   1320

tggaagaaac agacatctca gtgcttgaag aacctggaaa cattctgtga ggagaccagg   1380

aggaattttg aagccacctt aggttggcta caagaacatg cttgctcaag aacttatggt   1440

ctaggcactc acctgccttg ggatgagcag tggctgattg aatcactttc tgactccact   1500

atttacatgg cattttacac agttgcacac ctattgcagg ggggtaactt gcatggacag   1560

gcagagtctc cgctgggcat tag                                             1583
```

<210> SEQ ID NO 174
<211> LENGTH: 371
<212> TYPE: DNA
<213> ORGANISM: Homo Sapiens

<400> SEQUENCE: 174

```
gattcactcc ttctccagtt gcacagccac acccttcagc tggccttaat gttgactttg     60

aatctgtgtt tggaaataaa tctacaaatg ttattgtaga ttctgggggc tttgatgaac    120

taggtggact tctcaaacca acagtggcct ctcagaacca gaaccttcct gttgccaaac    180

tcccacctag caagttagta tctgatgact tggattcatc tttagccaac cttgtgggca    240

atcttggcat cggaaatgga accactaaga atgatgtaaa ttggagtcaa ccaggtgaaa    300

agaagttaac tgggggatct aactggcaac caaaggttgc accaacaacc gcttggaatg    360

ctgcaacaat g                                                          371
```

<210> SEQ ID NO 175
<211> LENGTH: 576
<212> TYPE: DNA
<213> ORGANISM: Homo Sapiens

<400> SEQUENCE: 175

```
gcatgggact cgctgtgctg gagaagtggc agccgctgca aacaattcgc actgcacagt     60

cggaattgct ttcaacgcca agatcggagg agtgcgaatg ctggacggag atgtcacgga    120

catggttgaa gcaaaatcag ttagcttcaa cccccagcac gtgcacattt acagcgccag    180

ctggggcccg gatgatgatg gcaagactgt ggacggacca gccccccctca cccggcaagc    240

ctttgaaaac ggcgttagaa tggggcggag aggcctcggc tctgtgtttg tttgggcatc    300

tggaaatggt ggaaggagca aagaccactg ctcctgtgat ggctacacca acagcatcta    360

caccatctcc atcagcagca ctgcagaaag cggaaagaaa ccttggtacc tggaagagtg    420

ttcatccacg ctggccacaa cctacagcag cggggagtcc tacgataaga aaatcatcac    480

tacagatctg aggcagcgtt gcacggacaa ccacactggg acgtcagcct cagcccccat    540
```

ggctgcaggc atcattgcgc tggccctgga agccaa 576

<210> SEQ ID NO 176
<211> LENGTH: 379
<212> TYPE: DNA
<213> ORGANISM: Homo Sapiens

<400> SEQUENCE: 176
agggaagtgt aacatctccc atttttctga catatttgct gctagagagt ttaaagcccg 60
agtggattca tttttctaca tattaggata taaccctgag acaaggaggc tgaacagtac 120
ccagggggag attcgtgtcg gtcctagtca tcaggccaaa cttccagatc tgcaaccatt 180
tccttctcca gatggtgata cagtgaccca acatgaggaa ctggtctgga tgcctggagt 240
taacgactgt gacctcctta tgtacttgag ggcagcaagg agcatggcgg catttgcagg 300
aatgtgtgat ggaggctcta cagaggacgg ctgtgtcgca gcctctcggg atgacaccac 360
tctgaatgca ctgaacaca 379

<210> SEQ ID NO 177
<211> LENGTH: 516
<212> TYPE: DNA
<213> ORGANISM: Homo Sapiens

<400> SEQUENCE: 177
ctgaatgcaa tatccataca tctccttctc cgggaattca agtaaggcat gtctacaccc 60
cctctacaac aaagcatttc tcacccataa aacagtcaac cactttaacc aacaaacaca 120
gaggaaatga ggtctctacc acacctctgt tagcaaattc tttgtctgtt caccagttgg 180
ctgctcaggg agagatgctc tatctggcta ctcgtatcga acaagaaaat gttatcaatc 240
acacggatga agaaggattt actcctctga tgtgggctgc agcacacggg caaatagctg 300
tggtagagtt cctacttcag aatggtgctg atccccaact tttaggaaaa ggtcgagaaa 360
gtgcactgtc gttggcctgt agtaaaggct acacagatat tgtcaaaatg ctgcttgatt 420
gtggagttga tgtaaatgaa tatgattgga atggaggaac acctctgctt tatgctgtac 480
atggaaatca tgtgaaatgt gtaaagatgc tcttag 516

<210> SEQ ID NO 178
<211> LENGTH: 181
<212> TYPE: DNA
<213> ORGANISM: Homo Sapiens

<400> SEQUENCE: 178
agaagatggc gaattagaag atggtgaaat agacgatgca ggatttgaag aaatacaaga 60
aaaagaagca aaagagaatg aaaagcagaa aagtgagaaa gcctacagaa aatcaagaaa 120
aaaacataag aaagagagag agaagaaaaa atccaaaagg agaaaacgtg agaaacataa 180
g 181

<210> SEQ ID NO 179
<211> LENGTH: 602
<212> TYPE: DNA
<213> ORGANISM: Homo Sapiens

<400> SEQUENCE: 179
gaggatagca aacaagctca atttttagcc ttggcagtag tatactttat ctctgttctt 60
atggtctcca agtacagaga cattttggaa ccccaaaatg aaaggcatag ccagtcatgt 120
acagaaactg gcagtgaaaa tgagaatgta tcactctctg aaatcacacc agcagcattc 180
agcactttaa ctacggcatc agtggaagaa tctgaaagca catcatctgc tcgaaggagg 240
gactcaggca ttggggaaga aacagccact ggtttaggaa gccatgtgga agtaactcct 300
cacacagcac ctcctggtgt cagtgcaggc ccagatgcaa tcagcgaggt gctatctact 360
ctttctttag aagtcaataa gtctccggaa accaaaaatg atagaggaaa tgacttggac 420
actaaggcta caccgtcagt ttcagtttca aaaaacgtca atgtgaaaga cattctccga 480
agcttggtta acataccagc agatggagtc acagtggatc ctgcccttct gccaccagcc 540
tgccttggag cccttggtga tctatctgtg gaacaacccg tgcagttcag atcttttgac 600
ag 602

<210> SEQ ID NO 180
<211> LENGTH: 175
<212> TYPE: DNA
<213> ORGANISM: Homo Sapiens

<400> SEQUENCE: 180
tgtggcaaag cgctccctgg cctttcaaag caagaggact gctgtggaac tgtgggtacc 60
tcctggggct ttaacaaatg ccagaaatgc cccaagaaac catcttatca tggatacaac 120
caaatgatgg aatgcctacc gggttataag cgggttaaca acaccttttg ccaag 175

<210> SEQ ID NO 181
<211> LENGTH: 1571
<212> TYPE: DNA
<213> ORGANISM: Homo Sapiens

<400> SEQUENCE: 181
gtttgatgat tcctgtcttt tgtgtcgtgg agcagttgga cggctctctt gaatatgaca 60
acagagaaga acacgccgag tttgtcctgg tgcggaaaga tgtgcttttt agccagctgg 120
tggagactgc gctcctggcc ctggggtatt ctcacagctc tgcggcccag gcccaaggaa 180
taatcaagct gggaaggtgg aaccctctcc ccctcagtta tgtgacagat gcacccgacg 240
cgacagtggc cgacatgcta caagatgtct atcatgttgt gacgttgaaa atccaattac 300
aaagttgttc aaagttggaa gacttgcctg cggagcagtg gaaccatgcc acagtccgca 360
atgccttaaa ggaactgctc aaagagatga accagagcac attagccaaa gaatgccctc 420
tctcccagag tatgatttca tccattgtaa atagcacata ttatgccaat gtgtcagcaa 480
ccaagtgcca ggagtttggg agatggtata aaaagtacaa gaagattaaa gtggaaagag 540
tggaacgaga aaacctttca gactattgtg ttctgggcca gcgtccaatg catttaccaa 600
atatgaacca gctggcatcc ctggggaaaa ccaacgaaca gtctcctcac agccaaattc 660
accacagtac tccaatccga aaccaagtgc ccgcattaca gcccatcatg agccctggtc 720
ttctttctcc ccagcttagt ccacaacttg taaggcaaca aatagccatg gcccatctga 780
taaaccaaca gattgccgtt agccggctcc tggctcacca gcatcctcaa gccatcaacc 840
agcagttcct gaaccatcca cccatcccca gagcagttaa gccagagcca accaactctt 900
ccgtggaagt ctctccagat atctaccagc aagtcagaga tgagctgaag agggccagtg 960
tgtcccaagc tgtctttgca agagtggcat tcaaccgcac acagggattg ttgtctgaga 1020
ttctgcgtaa ggaagaagac cctcggacag cctctcagtc tcttctagta aacctgaggg 1080
ccatgcagaa tttcctcaat ctgccagaag tggagcgaga tcgcatctac caggatgaga 1140
gggagcggag catgaatccc aatgtgagca tggtctcctc ggcctccagc agtcccagct 1200

```
cctcccgaac ccctcaggcc aaaacctcga caccgacaac agacctccct attaaggtgg   1260

acggcgccaa catcaacatc acagctgcca tttatgacga gatccaacag gagatgaaaa   1320

gggccaaggt gtctcaagcc ctgtttgcca aagtggctgc aaataaaagt cagggctggc   1380

tgtgtgaact gctccgctgg aaggagaacc caagcccaga aaccgcaccc ctctgggaaa   1440

acctctgtac catccgtcgc ttcctgaacc ttccccagca tgagagggat gtcatctatg   1500

aggaggagtc aaggcatcac cacagcgaac gcatgcaaca cgtggtccag cttccccctg   1560

agccggtgca g                                                        1571
```

<210> SEQ ID NO 182
<211> LENGTH: 1703
<212> TYPE: DNA
<213> ORGANISM: Homo Sapiens

<400> SEQUENCE: 182

```
atccagtcct tctgtggaac ttctgaacat cttttattag tggaaatatt ttctacacaa     60

tgaagtcaac aacttaattt aaaccagtgt ttgtgcggtt ctgattcatc tgctgtggtt    120

cccgaagctt gagatctaag gagtacaggg tcttttgtga tgacaatatg actaatagta    180

aaggaagatc tattaccgat aaaacaagtg gtggtccaag tagtggagga ggttttgtag    240

attggacttt acgtttaaac acaattcaat ccgacaagtt tttaaattta ctcttgagta    300

tggttccagt gatttaccag aaaaaccaag aagacaggca caaaaaagca aacggcattt    360

ggcaagatgg attatcaact gcagtacaga cttttagtaa tagatctgag caacacatgg    420

agtatcacag tttctcagag cagtcttttc atgccaataa tgggcacgca tcatcaagct    480

gcagccaaaa gtatgatgac tatgccaatt ataattactg tgatggaagg gagacttcag    540

aaaccactgc catgttacaa gatgaagata tatctagtga tggtgatgaa gatgctattg    600

tagaagtgac cccaaaatta ccaaaggaat ccagtggcat catggcattg caaatacttg    660

tgcccttttt gctagctggt tttggaacag tttcagctgg catggtactg gatatagtac    720

agcactggga ggtgttcaga aaagttacag aagttttcat tttagtccct gcacttcttg    780

gtctcaaagg gaacttggaa atgacattgg catccagatt atccactgca gtaaatattg    840

ggaagatgga ttcacccatt gaaaagtgga acctaataat tggcaacttg gctttaaagc    900

aggttcaggc aacagtagtg ggttttctag cagctgtggc agcaattata ttgggctgga    960

ttccagaagg aaaatattac cttgatcatt ccatacttct gtgctctagc agtgtggcaa   1020

ctgccttcat tgcatctctt ctgcagggaa taataatggt tggggttatc gttggttcaa   1080

agaagactgg tataaatcct gataatgttg ctacacccat tgctgctagt tttggcgacc   1140

ttataactct tgccatattg gcttggataa gtcagggctt atactcctgt cttgagacct   1200

attactacat ttctccatta gttggtgtat ttttcttggc tctaacccct atttggatta   1260

taatagctgc caaacatcca gccacaagaa cagttctcca ctcaggctgg gagcctgtca   1320

taacagctat ggttataagt agcattgggg gccttattct ggacacaact gtatcagacc   1380

caaacttggt tgggattgtt gtttacacgc cagttattaa tggtattggt ggtaatttgg   1440

tggccattca ggctagcagg atttctacct acctccattt acatagcatt ccaggagaat   1500

tgcctgatga acccaaaggt tgttactacc catttagaac tttctttggt ccaggagtaa   1560

ataataagtc tgctcaagtt ctactgcttt tagtgattcc tggacattta attttcctct   1620

acactattca tttgatgaaa agtggtcata cttctttaac tataatcttc atagtagtgt   1680

atttatttgg cgctgtgtta cag                                           1703
```

<210> SEQ ID NO 183
<211> LENGTH: 660
<212> TYPE: DNA
<213> ORGANISM: Homo Sapiens

<400> SEQUENCE: 183
ttcgatcctt tggtacagaa gacagaccga cagatcgtcc aataccacct cgagatgaag 60
tctttgaata cattatattc cgtgggagtg acattaaaga ccttactgtt tgtgagccac 120
caaaaccaca gtgttctttg cctcaagacc cagctattgt tcagtcctca ctaggctcat 180
cgacttcttc attccagtcc atgggttctt atggaccttt cggcaggatg cccacataca 240
gtcagttcag tccgagttcc ttagttgggc agcagtttgg tgctgttggt gttgctggaa 300
gctctttgac atcctttgga acagaaacat caaacagtgg taccttaccc caaagtagtg 360
cggttggttc tgcctttaca caggatacaa gatctctaaa aacacagtta tctcaaggtc 420
gctcaagccc tcagttagac cctttgagaa aaagcccaac catggaacaa gcagtgcaga 480
ccgcctcagc ccacttacct gctccagcag ctgttgggag aaggagtcct gtatcaacca 540
ggcctttgcc atctgccagc caaaaggcag gagagaatca ggagcacagg cgagctgaag 600
tacacaaagt ttcaaggcca gaaaatgagc aactcagaaa tgataacaag agacaagtag 660

<210> SEQ ID NO 184
<211> LENGTH: 963
<212> TYPE: DNA
<213> ORGANISM: Homo Sapiens

<400> SEQUENCE: 184
gttggtacta agaagtgcct ttcctgacgt ctctgctgct tggaaccgct tctagagcag 60
tctctgcttt tgccttgctt gctgccagct agactgtgac gacagcacat ccaccctcca 120
cctctagccc agacaccccc atttctactt ataatcaaga gaaaagctct aagtatctgg 180
cattgcccta ggctgcttta gtgttaaaag aaaagtttgc tgaaaaagta agatatcttc 240
tgccaggaaa tcaaggagga aaaaaaaaat cattttctcg attttgctct aaactgctgc 300
atctgtctat gccaaactaa tcaataccga ttgcaccacc aaactccatt gcaaattcag 360
ctgtgaggag attccctttc agacaacttt gctgaaagca gcttggaaat tcggtgtcga 420
agggtctgcc acgttttcat gcttgcattt tgggctccaa attggcactg ggaaggggtt 480
actgagagca caaggctgat accaggccct acttttaaac gttcatctac ttacaatcct 540
agtatttctc taaaaaccaa aacctctttg aattaacagt ttcatgctgt gaatttctag 600
tgggagatct tttccttgat attgacgaca caattttcca tgtactttta aagcagggag 660
tggggaaaag tattttgagg ggacattttc atcatcagtt cagctttttt tttttggttg 720
ttgctctttt ttggggggt tgggtttgtt ggtttcactg aaacatttaa ctacctgtaa 780
aatctaaaca tggctgttag tgtcacacca attcgggaca caaaatggct aacactggaa 840
gtatgtagag agttccagag ggggacttgc tcacggccag acacggaatg taaatttgca 900
catccttcga aaagctgcca agttgaaaat ggacgagtaa tcgcctgctt tgattcattg 960
aaa 963

<210> SEQ ID NO 185
<211> LENGTH: 970
<212> TYPE: DNA
<213> ORGANISM: Homo Sapiens

<400> SEQUENCE: 185 cttttttaaag atgacatcag gtatctgttg acaatggaca aactatggcg gaaaaggaaa 60
cctccagttc cgttggactg ggctgaagta caaagtcaag gagaagaaac gaatgcatca 120
gatcaacaga atgaacccca gttaggcctg aaagaccagc aggttctaga tgtaaagagc 180
tatgcacgtc ttttttcaaa gagcatcgag actttgagag ttcatttagc agaaaagggg 240
gatggagctg agctcatatg ggataaggat gacccatctg caatggattt tgtcacctct 300
gctgcaaacc tcaggatgca tattttcagt atgaatatga agagtagatt tgatatcaaa 360
tcaatggcag ggaacattat tcctgctatt gctactacta atgcagtaat tgctgggttg 420
atagtattgg aaggattgaa gattttatca ggaaaaaatag accagtgcag aacaattttt 480
ttgaataaac aaccaaaccc aagaaagaag cttcttgtgc cttgtgcact ggatcctccc 540
aaccccaatt gttatgtatg tgccagcaag ccagaggtga ctgtgcggct gaatgtccat 600
aaagtgactg ttctcacctt acaagacaag atagtgaaag aaaaatttgc tatggtagca 660
ccagatgtcc aaattgaaga tggaaaagga acaatcctaa tatcttccga agagggagag 720
acggaagcta ataatcacaa gaagttgtca gaatttggaa ttagaaatgg cagccggctt 780
caagcagatg acttcctcca ggactatact ttattgatca acatccttca tagtgaagac 840
ctaggaaagg acgttgaatt tgaagttgtt ggtgatgccc cggaaaaagt ggggcccaaa 900
caagctgaag atgctgccaa aagcataacc aatggcagtg atgatggagc tcagccctcc 960
acctccacag 970

<210> SEQ ID NO 186
<211> LENGTH: 320
<212> TYPE: DNA
<213> ORGANISM: Homo Sapiens

<400> SEQUENCE: 186
gaacaggaaa tatagtggtc attatgatta gctatccaaa aggaagagaa attttggagc 60
tggtgcaaaa aggaattcca gtaacgatga ccataggggt tggcacccgg catgtacagg 120
agttcatcag cggtcagtct gtggtgtttg tggccattgc cttcatcacc atgatgatta 180
tctcgttagc ctggctaata ttttactata tacagcgttt cctatatact ggctctcaga 240
ttggaagtca gagccataga aaagaaacta agaaagttat tggccagctt ctacttcata 300
ctgtaaagca tggagaaaag 320

<210> SEQ ID NO 187
<211> LENGTH: 1094
<212> TYPE: DNA
<213> ORGANISM: Homo Sapiens

<400> SEQUENCE: 187
gggttccttg tggaggctca cccagacaat gcctgcagcc ccattgcccc accaccccca 60
gccccggtca atgggtcagt ctttattgcg ctgcttcgaa gattcgactg caactttgac 120
ctcaaggtcc taaatgccca gaaggctgga tatggtgccg ctgtagtaca caatgtgaat 180
tccaatgaac ttctgaacat ggtgtggaat agtgaggaaa tccagcagca gatctggatc 240
ccgtctgtat ttattgggga gagaagctcc gagtacctgc gtgccctctt tgtctacgag 300
aagggggctc gggtgcttct ggttccagac aataccttcc ccttgggcta ttacctcatc 360
cctttcacag ggattgtggg actgctggtt ttggccatgg gagcagtaat gatagctcgt 420
tgtatccagc accggaaacg gctccagcgg aatcgactta ccaaagagca actgaaacag 480
attcctacac atgactatca gaagggagac cagtatgatg tctgtgccat ttgcctggat 540
gaatatgagg atggggacaa gctgcgggta ctcccctgtg ctcatgccta ccacagccgc 600
tgcgtggacc cctggctcac tcagacccgg aagacctgcc ccatttgcaa gcagcctgtt 660
catcggggtc ctggggacga agaccaagag gaagaaactc aagggcaaga ggagggtgat 720
gaaggggagc caagggacca ccctgcctca gaaaggaccc cacttttggg ttctagcccc 780
actcttccca cctcctttgg ttccttagcc ccagctcccc ttgtttttcc tgggccttca 840
acagatcccc cactgtcccc tccctcttcc cctgttatcc tggtctaata accccccaca 900
catacacctc tggtgaccta tttgcacaga ccgtcgtctt ccctccagtc ttctgaggga 960
taggggacat tccatcccaa gcttctccct tacccacacc tatccttttg aggggctttg 1020
gggtggagct ggggcaagca gagggactgg gtcttcactt cttgggctaa taaaattgtt 1080
tctttgtgga ctaa 1094

<210> SEQ ID NO 188
<211> LENGTH: 378
<212> TYPE: DNA
<213> ORGANISM: Homo Sapiens

<400> SEQUENCE: 188
taccctcaac aacaacaaca tcagtcgcat cctggtcacc agcttcaacc acatgccgaa 60
gatccgaact ctgcgcctcc actccaacca cctgtactgc gactgccacc tggcctggct 120
ctcggattgg ctgcgacagc gacggacagt tggccagttc acactctgca tggctcctgt 180
gcatttgagg ggcttcaacg tggcggatgt gcagaagaag gagtacgtgt gcccagcccc 240
ccactcggag cccccatcct gcaatgccaa ctccatctcc tgcccttcgc cctgcacgtg 300
cagcaataac atcgtggact gtcgaggaaa gggcttgatg gagattcctg ccaacttgcc 360
ggagggcatc gtcgaaat 378

<210> SEQ ID NO 189
<211> LENGTH: 900
<212> TYPE: DNA
<213> ORGANISM: Homo Sapiens

<400> SEQUENCE: 189
tgctctgggc accacagtct gccccttcag gctcctggac actctctcct gtggcctttg 60
tgatgtggct atccctgctc tcccactgcc tcacaggcac tgccttctct gccccctcct 120
tttgtctgtc atggtgggtc tttagctaag ttcttcttgg gcttcccaca ccacacgacc 180
ccacccccca ggcaagctgc ttgtcccctg gggatcttgg ggatcccaca gaccattggc 240
ctttgctggc aactcttcct caacttgttt cctccccccg tactgactca ttcattcttt 300
ccccaactgt ttgccaagga cctgcctttc actaggccct gagctcagat gcagaagtga 360
gctgaaaaac catttctgcc ttgagttttt cagtccagca aaggaaacag agattaatta 420
gacccctaac taggttctca acagaggacc attttacccc catagtacat tttgaagtgt 480
ctgcgagaca tttttgatca tcacaattgg gatccgccat ggtagttcac tcttgtggga 540
tattgaggta gggggatcat ttgaggccag gagttcaaga ccagcctagg caacatagca 600
agacccccca tctctacaaa aagttaaaag attagccagg catgttggtg cacacctgta 660
gtcccagcta ctcaggaggc tgaggcagga ggatcccttg agcccaggac gtcaaggctg 720
cagtgcacta tggttgcacc actgcactcc agcctgggca acagagtgag actcccaact 780

```
ccaaacagac aattggaggc ggataggttt tcctggtgtc aagcgggtgg aagccaggga    840

tgctgttcaa tgtcccacag tgcaaggagg cctcctccct agagaatgat ctggccccaa    900


<210> SEQ ID NO 190
<211> LENGTH: 1024
<212> TYPE: DNA
<213> ORGANISM: Homo Sapiens

<400> SEQUENCE: 190

acttaattca gtgcacaaat gagatgaatg tgaacatccc acagttggca gacagtttat     60

ttgaaagaac tactaatagt agttgggtgg tggtcttcaa atctctcatt acaactcatc    120

atttgatggt gtatggaaat gagcgtttta ttcagtattt ggcttcaaga aacacgttgt    180

ttaacttaag caatttttg gataaaagtg gattgcaagg atatgacatg tctacattta    240

ttaggcggta tagtagatat ttaaatgaga aagcagtttc atacagacaa gttgcatttg    300

atttcacaaa agtgaagaga ggggctgatg gagttatgag aacaatgaac acagaaaaac    360

tcctaaaaac tgtaccaatt attcagaatc agatggatgc acttcttgat tttaatgtta    420

atagcaatga acttacaaat ggggtaataa atgctgcctt catgctcctg ttcaaagatg    480

ccattagact gtttgcagca tacaatgaag gaattattaa tttgttggaa aaatattttg    540

atatgaaaaa gaaccaatgc aaagaaggtc ttgacatcta taagaagttc ctaactagga    600

tgacaagaat ctcagagttc ctcaaagttg cagagcaagt tggaattgac agaggtgata    660

taccagacct ttcacaggcc cctagcagtc ttcttgatgc tttggaacaa catttagctt    720

ccttggaagg aaagaaaatc aaagattcta cagctgcaag cagggcaact acactttcca    780

atgcagtgtc ttccctggca agcactggtc tatctctgac caaagtggat gaaagggaaa    840

agcaggcagc attagaggaa gaacaggcac gtttgaaagc tttaaaggaa cagcgcctaa    900

aagaacttgc aaagaaacct catacctctt taacaactgc agcctctcct gtatccacct    960

cagcaggagg gataatgact gcaccagcca ttgacatatt ttctacccct agttcttcta   1020

acag                                                                1024


<210> SEQ ID NO 191
<211> LENGTH: 234
<212> TYPE: DNA
<213> ORGANISM: Homo Sapiens

<400> SEQUENCE: 191

acatttgaag acagtgattt gttccatttg attggtgtta tctgtggctt agcaatttat     60

aattgtacca ttgtggacct ccattttcct ttggctttat ataagaaact actgaaaaag    120

aagccatcct tggatgattt gaaagaacta atgcctgatg ttgggagaag catgcaacag    180

ttactggatt atccagaaga tgacatagag gaaacatttt gtcttaattt tacg          234


<210> SEQ ID NO 192
<211> LENGTH: 235
<212> TYPE: DNA
<213> ORGANISM: Homo Sapiens

<400> SEQUENCE: 192

acttattgac agtgccaaag ctcggtactg gacacaacga gggacctggg tctacgataa     60

cgcgcttttg ctcctcctga agtgtctttg gtccaacgtt gttccagagt gtaccatggc    120

ttccagtaac actgtgttga tgcggttggt agcctccgca tattctattg ctcaaaaggc    180

aggaatgata gtcagacgtg ttattgctga aggagacctg ggtattgtgg agaag         235
```

<210> SEQ ID NO 193
<211> LENGTH: 199
<212> TYPE: DNA
<213> ORGANISM: Homo Sapiens

<400> SEQUENCE: 193
aacatctccc catggattct ggcggtattg actcttcaga ttcagagtct gatatcctgt 60
tgggcattct ggacaacttg gacccagtca tgttcttcaa atgcccttcc ccagagcctg 120
ccagcctgga ggagctccca gaggtctacc cagaaggacc cagttcctta ccagcctccc 180
tttctctgtc agtggggac 199

<210> SEQ ID NO 194
<211> LENGTH: 224
<212> TYPE: DNA
<213> ORGANISM: Homo Sapiens

<400> SEQUENCE: 194
atatcaaaca aagaattact ctgtacaaag ccagaacaca tatatcaaag taatcctgaa 60
gtatcagaac aaaataatag gctgtaacag aggaggaaat gattttgaat agcctctctc 120
tgtgttacca taataagcta atcctggccc caatggttcg ggtagggact cttccaatga 180
ggctgctggc cctggattat ggagcggaca ttgtttactg tgag 224

<210> SEQ ID NO 195
<211> LENGTH: 292
<212> TYPE: DNA
<213> ORGANISM: Homo Sapiens

<400> SEQUENCE: 195
ttatttgctg gtataaagga tggagaaagc ctgcagctct ttgaacaaag ttctcgctct 60
gcgcataaac aagagacaca caccatggag gccgtgaagc ttgtagagtt tgatcttaag 120
caaacgctta ccaggctcat ggcacatctt tttggagatg agctggagat aagatgggta 180
gactgctact tccctttac acatccttcc tttgagatgg agatcaactt tcatggagaa 240
tggctggaag ttcttggctg cggggtgatg gaacaacaac tggtcaattc ag 292

<210> SEQ ID NO 196
<211> LENGTH: 264
<212> TYPE: DNA
<213> ORGANISM: Homo Sapiens

<400> SEQUENCE: 196
gtgtcagttt tcaacctttg agcagtgtca agagtggctg aagagactga acaacgcaat 60
ccgaccacct gctaaaatag aagatctctt ctcatttgca taccatgctt ggtgcatgga 120
ggtctatgcc agtgaaaaag agcaacatgg agacctgtgc agaccagggg agcatgtaac 180
ttcaaggttt aaaaacgagg tggagaggat gggttttgat atgaacaacg cctggaggat 240
ttccaacatc aatgagaagt acaa 264

<210> SEQ ID NO 197
<211> LENGTH: 658
<212> TYPE: DNA
<213> ORGANISM: Homo Sapiens

<400> SEQUENCE: 197
ttgcagatct gatctcttct gaacacctca tcgtgtctcc atccctggga atctgaccct 60
agcaactgga ccactttgtt cttggaattt tgggtgtcct cttttctcac ctttcccttt 120
tcccttttcc ccttccccct cctgagaact ccggaagact gtagagattg tcatggagtc 180
cagggaaacc ttaagcagct cccggcaaag agggggcgag tcagacttcc tgccggtctc 240
ctcagccaag cccccagctg ctcctggctg tgcaggagaa cctttgctct ccactccagg 300
acctgggaag gggatcccgg tgggcggaga gcgcatggag ccagaggagg aggatgaact 360
aggctcaggg cgggatgtgg attccaactc caacgcggac agtgagaaat gggtggcagg 420
agatggtttg gaagagcagg aattttctat caaggaggca aacttcacag agggaagtct 480
gaagctaaag attcagacca caaagcgggc taagaaaccc ccaaagaatt tggagaacta 540
tatatgtcca cctgagatca agatcaccat caagcagtct ggggaccaga aggtgtcccg 600
tgctggaaaa aatagcaaag ccacgaagga ggaagaaaga agccactcca aaaagaag 658

<210> SEQ ID NO 198
<211> LENGTH: 271
<212> TYPE: DNA
<213> ORGANISM: Homo Sapiens

<400> SEQUENCE: 198
acaacagttg atatttctac ttggtgtgag cagtttgcaa ctttttgttc agagcaactg 60
gacggggccc cctgttgact tacaccctca ggactttttg tcatctgttt tgttccagca 120
attcagtgag gttaaaggac tggatgcatt tgttctgagc ctgctcactc tagatggtga 180
atcaatctac agcctgacct cgaagcctat actactgtta ttagcacgca ttatcctagt 240
gaatgtaaga cataaactga cagctattca g 271

<210> SEQ ID NO 199
<211> LENGTH: 574
<212> TYPE: DNA
<213> ORGANISM: Homo Sapiens

<400> SEQUENCE: 199
gctgacagag tacttcttgg tggtcctggt agcttttatt ggcaaggtca gcttatttcg 60
gatcaagtgg cagaaatcgt atctaaatac gaccccaatg tttacagcat caagtataat 120
aaccaattag caactcggac tgcacaagct atttttgatg acagctattt gggttattct 180
gtggctgtcg gagatttcaa tggtgatggc atagatgact ttgtttcagg agttccaaga 240
gcagcaagga ctttgggaat ggtttatatt tatgatggga agaacatgtc ctccttatac 300
aattttactg gcgagcagat ggctgcatat ttcggatttt ctgtagctgc cactgacatt 360
aatggagatg attatgcaga tgtgtttatt ggagcacctc tcttcatgga tcgtggctct 420
gatggcaaac tccaagaggt ggggcaggtc tcagtgtctc tacagagagc ttcaggagac 480
ttccagacga caaagctgaa tggatttgag gtctttgcac ggtttggcag tgccatagct 540
cctttgggag atctggacca ggatggtttc aatg 574

<210> SEQ ID NO 200
<211> LENGTH: 3648
<212> TYPE: DNA
<213> ORGANISM: Homo Sapiens

<400> SEQUENCE: 200
tctcctaaag agcccgaaca gctgaggaag ctcttcattg gagggttgag ctttgaaaca 60
actgatgaga gcctgaggag ccattttgag caatggggaa cgctcacgga ctgtgtggta 120
atgagagatc caaacaccaa gcgctccagg ggctttgggt ttgtcacata tgccactgtg 180

-continued gaggaggtgg atgcagctat gaatgcaagg ccacacaagg tggatggaag agttgtggaa 240
ccaaagagag ctgtctccag agaagattct caaagaccag gtgcccactt aactgtgaaa 300
aagatatttg ttggtggcat taaagaagac actgaagaac atcacctaag agattatttt 360
gaacagtatg gaaaaattga agtgattgaa atcatgactg accgaggcag tggcaagaaa 420
aggggctttg cctttgtaac ctttgacgac catgactccg tggataagat tgtcattcag 480
aaataccata ctgtgaatgg ccacaactgt gaagttagaa aagccctgtc aaagcaagag 540
atggctagtg cttcatccag ccaaagaggt cgaagtggtt ctggaaactt tggtggtggt 600
cgtggaggtg gtttcggtgg gaatgacaac ttcggtcgtg gaggaaactt cagtggtcgt 660
ggtggctttg gtggcagccg tggtggtggt ggatatggtg gcagtgggga tggctataat 720
ggatttggta atgatggtgg ttatggagga ggcggccctg gttactctgg aggaagcaga 780
ggctatggaa gtggtggaca gggttatgga aaccagggca gtggctatgg cgggagtggc 840
agctatgaca gctataacaa cggaggcgga ggcggctttg gcggtggtag tggaagcaat 900
tttggaggtg gtggaagcta caatgatttt gggaattaca acaatcagtc ttcaaatttt 960
ggacccatga agggaggaaa ttttggaggc agaagctctg gcccctatgg cggtggaggc 1020
caatactttg caaaaccacg aaaccaaggt ggctatggcg gttccagcag cagcagtagc 1080
tatggcagtg gcagaagatt ttaattagga aacaaagctt agcaggagag gagagccaga 1140
gaagtgacag ggaagctaca ggttacaaca gatttgtgaa ctcagccaag cacagtggtg 1200
gcagggccta gctgctacaa agaagacatg ttttagacaa atactcatgt gtatgggcaa 1260
aaaactcgag gactgtattt gtgactaatt gtataacagg ttattttagt ttctgttctg 1320
tggaaagtgt aaagcattcc aacaaagggt tttaatgtag attttttttt ttgcacccca 1380
tgctgttgat tgctaaatgt aacagtctga tcgtgacgct gaataaatgt cttttttta 1440 atgtgctgtg taaagttagt ctactcttaa gccatcttgg taaatttccc caacagtgtg 1500
aagttagaat tccttcaggg tgatgccagg ttctatttgg aatttatata caacctgctt 1560
gggtggagaa gccattgtct tcggaaacct tggtgtagtt gaactgatag ttactgttgt 1620
gacctgaagt tcaccattaa aagggattac ccaagcaaaa tcatggaatg gttataaaag 1680
tgattgttgg cacatcctat gcaatatatc taaattgaat aatggtacca gataaaatta 1740
tagatgggaa tgaagcttgt gtatccatta tcatgtgtaa tcaataaacg atttaattct 1800
cttgaatgaa atgacaactg tatggatttg ggactggcag agatttggac tttccctacc 1860
cactccccct gataataatg ttgaatgctt ctatcacaat tcaagttcaa agctctgcca 1920
gggaatagaa actagctgct ggctaatgcc gctccataaa tccgcagatt tgaagtgtct 1980
gggaggcctt ttaaaaataa ctaatatcag aaagcatttt aatgaacgta aagataggct 2040
tacattaaag gaaaactgca gtttgactgg gttctggttg ggtgggcctt cagaggttct 2100
atcagttaac tatactaatt aatttggaga ttcaaaccat accaatagaa actaaatttt 2160
tctacataat ttcatgttaa ctgcagtttc cctttatggc acaaggggtc acacaaccta 2220
cctaaaatgt taattgtata gaaaatgatt tctaaacctt taacagttaa tatccaataa 2280
tgtgttattt gtacatagat tcttttgagc cttacctttg gtgctctctc aatttcagtg 2340
ctattgtacc tagtagcata gagatttgtc tatcaatagg actgtatatt ccatcccatg 2400
ggtgtgttgg aagtttgggg aggaggaggg tggtgggagg tgggtgggag gtggtggtgg 2460
gtgggaaagc atgggtgata gttccatgat actggctgag tttgcaatag caggtggaac 2520
cctaactatt gagggagttt gcagatacct caggattcgt gacaatgcct ttaaagatcc 2580
aggagagatg ttcagctact aggaactgct agcaagtata gcgcgaatgg ctccgagctc 2640
agacactcta cagctgagag tagacacttg tggtatgtgg agtacagata agccaggggc 2700
aggccacggc acgctccatg aaagctagga gggagtgaaa tatcagtgat catcgcaagg 2760
aaggaggcag acaagagtaa ggcacacctg actcttagga ctagcagtca gaaccaggag 2820
gaaaggtttt attgctatgc gggtaggtaa gaacagattt tacttacatc catatagtta 2880
cttaaagtcc agttttctgt taaacatttt tcttaatata ttgagccaaa actagtccag 2940
ttaagctgaa cttggttttt ctggagatga attgttttaa attgacaccc tattgatggc 3000
tcccagttga aggaagtgag cacattattt gtactgtgaa tataaatttt tgcccttttta 3060 tttatcttcc tttgacccat ttccttaaaa taatggctca aagtaataga cttccccaaa 3120
tggtgggggg atgggtgggt tattaatggg aggtatgggg ggtttagctt gagatgggac 3180
ttggtcttag agctagttct aaaggttgtt tacttttcta gggaggagtc tgctactagt 3240
cttatcagct cttaaaaaca gaaactcatc tgtccaagtt cgtggcagaa aggtaagttt 3300
ttacaaatta gtgctcagca aaagaatgcc ctgcgttccc aaagtaaaag aatgacaagc 3360
tgtaccttaa accaaaacac ttcgtaatct catccaattg caaaaagagt tattagccaa 3420
ccaggtattc ccagtagtga cagtggatat aactgtgtag tcattcacct ctgcttatat 3480
gaatacttta caacctcttt tgccttttgc aggaacgtcc ttgtgaagac ctttatctga 3540
gccactgtac ttcgttatca ctgccatgca gtttacatga gctgttctgc agctcaaatt 3600
ccattttgtg aatgggtttt ttttttaat aaactgtatt taacttag 3648

<210> SEQ ID NO 201
<211> LENGTH: 182
<212> TYPE: DNA
<213> ORGANISM: Homo Sapiens

<400> SEQUENCE: 201
ggacaatggt gacagatcca ggcaccgagc tccacgcaat gcccggatgt ctgcaccttc 60
gcttggacgc tttgtcccaa ggcgtttctt gctgcctgag tacttgcctt atgctgggat 120
ttttcatgaa cgtggacagc ctggcttggc tactcactct tctgttaaca gggtcctggc 180
ag 182

<210> SEQ ID NO 202
<211> LENGTH: 357
<212> TYPE: DNA
<213> ORGANISM: Homo Sapiens

<400> SEQUENCE: 202
cccagcagac cgggttatcc cagtccgagg tccagcgaag gattttatcc cagcccacag 60
cacatggtac aaaccaatca ttaccaggtt tctggctacc ctggttcaca tggaatcaca 120
gccatggctg gcagcatcta tccaggtcag gcatctcttt tggaccaaac agattcatgg 180
aatcatagac ctcaggagat agcaatgtgg cagcccaatg tggaggactc tacagtattg 240
gacctgcgag ggattgggca agtgttgcca acccatctga tggaagagcg tctaatccga 300
cagcaacagg aaatggaaga agatcagcgc tggctggaaa aagaggaaag atttctg 357

<210> SEQ ID NO 203
<211> LENGTH: 198
<212> TYPE: DNA
<213> ORGANISM: Homo Sapiens

<400> SEQUENCE: 203
agtgaagagt tccacattta tacccagtat tgcactaact atccaaggtc cgtggctgtg 60
ctaacagagt gtatgaggaa caagatactg gccaaattct tcagggagcg tcaggaaact 120
ctgaaacact cgctgcctct ggggtcctat ctcttgaaac cagttcagcg gattctcaag 180
tatcatctcc ttctgcat 198

<210> SEQ ID NO 204
<211> LENGTH: 503
<212> TYPE: DNA
<213> ORGANISM: Homo Sapiens

<400> SEQUENCE: 204
gttgtgacaa agacctttca tggtgcaggc ttggttgttc cagtagataa aaatgatgtt 60
gggtaccgag agctccctga aacagatgct gacctcaaga gaatttgcaa gacaatagtt 120
gaggctgcaa gtgatgagga gagactaaaa gcttttgctc ccattcagga aatgatgact 180
tttgtgcagt ttgctaatga tgaatgtgat tatggcatgg ggcttgaatt gggaatggat 240
ctcttttgct atggctcaca ttattttcat aaagttgctg gccagctttt acctcttgca 300
tataatctgt tgaagaggaa tctgtttgca gaaattattg aggagcatct ggcaaacaga 360
agtcaagaga acatagacca acttgctgca tgagtaaggt ggctttgatt ggtgtacagt 420
atttcaaagg actagtatta aacttgtgat ttttgttttg tttttaagga atacaaaaaa 480
taaacattta ctaaaaacgt tta 503

<210> SEQ ID NO 205
<211> LENGTH: 237
<212> TYPE: DNA
<213> ORGANISM: Homo Sapiens

<400> SEQUENCE: 205
gttttccagc ttgcagctca tctggtgtac tggggcaagg ccatcatcat ctacccgctg 60
tgtgagaaca acgtctacat gctgtctccc aatgccagcg tatgtctgta ctccccgctg 120
gccgagcagt tctcccacca gttcccatct catgacctgc cgtccgttct tgccaagttc 180
tccttgccgg tctccttgtc agaatttagg aatcccctgg cccccgctgt gcaggag 237

<210> SEQ ID NO 206
<211> LENGTH: 3135
<212> TYPE: DNA
<213> ORGANISM: Homo Sapiens

<400> SEQUENCE: 206
agttctcaac taatgaaaaa tcattgcatt atcttgagag caatagcaat gatcatgcca 60
acagtaattc agactgtgtc ataagttggg tcacacagtc cctattttca aactttgtgg 120
atgtctgtca actggcagtg aattgtattc aggagaaaag aagtctaaag taagtagtcc 180
aagtgtatga tgtcaagaat ctgcccatac ttggtagtcc cttgctactg tacaataata 240
gtggtgcaca tttgaaggac tgagatgcca ctaactctct gctccaccat tttggggtca 300
cagtgcatat cagtggaggg aagcaagtgt ttagagggat cctggctttg gaagacattt 360
gtgatgatgc tggttgaaag caaaagcata cagcactcag tattaccagg tggtctccaa 420
tctgaatcct ggttgataag atacaacttt gctcaaaatt tgctttttat ggggatgtat 480
gtggtggctt atgtctttaa tcctggcact ttgggaggct gaggcgggcg gatcacgagg 540

```
tcaggagatc gagaccagcc agtctggcca acatggtgaa aacctgtctg tactgaaaat    600
ataaaaatta gccaggtgtg gtgacatgtg cctgtaatcc tagctactgg ggaggctgag    660
ccaggagaat cacttgaact caggagaaag aagttgcagc gagccgagat tgtgcaactg    720
cactccagcc tgggcaacct agtgagactc cgtctaaaaa aatttttttt tttgcttctt    780
aatcctattt tacgtaatac aggggaaaag ttgagtagaa aattccagaa gtgcctttct    840
tcccattgca gaagacagag gacccctgca cctgacttgc agttgtcttc cactgtgagt    900
ctctcaggaa cccagaagcc tgaccttaga gattacacaa tacttcgtag ctcagtgtgt    960
gtgccaggaa gtgtcagggt ttgagcttcc aattcttaaa ttccgcttca tctcaggtac   1020
actcctgctt tgtctctgac tgtttttcct gctaggccaa tatattagga gatgtcaaag   1080
ggctgagagt gtaccagccc aacttagctg acctttctta gagccactgc ttatcaacca   1140
actcaagacc tgacacagga cattccctgg ctgatcaaaa aataatgata agagctttaa   1200
gggaggggca caataaaagg gtaaatctca aagcaggtgg ctgtactttg ggcttgctca   1260
ggacataatg taactgtcct gggtctggaa ataactcaga tggactcaca gagcagaccc   1320
agatacaaag cagacatctg taggggcttt tactacccca ttcatgttca tatatgccat   1380
agtaatgaat gtattatagg atgtgttctt gtttgttttt ctttctattt ttctctgtct   1440
ttgtcaagga atcccatatt tgcaaagtcc cttgccctta ctgcattaga aatgggcatt   1500
agaaatggga ctgaatgttg ggtccatcta gcatcctggg gccttgatta taaatacagt   1560
ttgtaaaatg gattacagaa gcaaatgaaa gattgtttac cggcatctta tttggtgggg   1620
aggaaatgta attcagtaca gtagtagccc aggttttgtg gagacagagg tacattgggg   1680
aaagctgggg ctaggagttt cttattggga cctttagtat atgggtgaat tttgtcaggg   1740
tctggtatgc ggaaagattc atagaagtag ttgtcagcag acaaaagaga tttgtcagca   1800
aactaaaaat ctcataccct gagacagtga tggaggaaag aaacttgtca ggaaggtttt   1860
ctagaagatg ctgcattctg cagtggacat tttcacagct gaaaaataag tggcaacatc   1920
ctaagtactc ataatatcaa ggtggtaaaa tcctgctctg cttttgagca agatgatata   1980
agtgaatcaa tacattcatg ctattaaggt tataggtttt tacagctttc acttgcatga   2040
aaaaacatgt tgtctatgct tctgcagttc tcagggcagt gaacctaagc caggagctgc   2100
ttaggcatta aggcttctat acccagaatc gtgtgctaag ctttctctcc aagtcagcac   2160
aacaaagcaa accagagcat cgtaccaaca acctgaaagg tcacctgact ccttccttct   2220
cactcccatt ctgtacttct gcatacgtgg gcaggcaagt gaatggtaag taagcctgca   2280
aacagccttt ctttgtatag ggaatgacag gcatttcatc agcaactcca ggatggcagg   2340
ccgttatcct gaaacctatc agaacagctc ctgcttggct tccaaaatat cacaattttg   2400
gaaatgtaca aaggttagtt ttcacagtcc ttgaagcctc tttccaccct ggccatagcc   2460
catgtcagca gtaacctatg tctttgtttt acatatcatg ttgttttact cacctggtgc   2520
ctccagtgcc ctatagggtc cctgagctgt cctgatactc tttcttagat cctgtcaaaa   2580
cactcacttc aacaaattct gcccttggac tctgatggga ggttctgata aagaaaatta   2640
ttgaaaaccg cattatttaa atgtggttat atttcagctg gacctggaaa taaagacgaa   2700
atactgcttc gtgactgtgc tttaaggaat ttttgcttct aggagatgat tgtgagccag   2760
gcagaggtga aggagcagga gcaaatagcc aaggcacagt tcacagtgct ggattttctt   2820
gtggatatag ctgcattgtt gttccttctg ccttgtccaa ctgcttcctg gtatccctac   2880
cctcaccttt tcgttatctt ttcatctctc taatcattga gaaaaagagt acaaaaagcc   2940
```

agattttgca gttccctatt ttgtattcca ggttgaagag tgctctggct gtagagggtc 3000
cccacgatct gtcatctagt aactcaccag atacataaga tattttgcct gctatgaagc 3060
cattggagaa tcaggtccag ctgtgtccta cagatttata ccctcacttt ggatgcactg 3120
tgaatcttga aacaa 3135

<210> SEQ ID NO 207
<211> LENGTH: 360
<212> TYPE: DNA
<213> ORGANISM: Homo Sapiens

<400> SEQUENCE: 207
ccgtcctggt gcgcggggac agtgaggctt ggctccttta tcagtgacac cggtccctgg 60
gtcttgctgg ggtgagaaga accaaaacat tgtgggtgat gagctaagcg ggactgctaa 120
ggttcacctg tgcgtttccg cagagataac cttaatggac atggcaaggc tgtgtgactt 180
ggaggcagct tttccattg acgttgctct ccctaaaatg cttcgtattc caaaatattt 240
ctagaaagac cttgtaggat aaggttgata aagagtccat tgtatacgtt tccgggtagt 300
taaattaggg aacagttttc tctgccccgc ccgtggttca caggtagata actgtctcgt 360

<210> SEQ ID NO 208
<211> LENGTH: 1324
<212> TYPE: DNA
<213> ORGANISM: Homo Sapiens

<400> SEQUENCE: 208
gaacttgcta ctaccagcac catgccctac caatatccag cactgacccc ggagcagaag 60
aaggagctgt ctgacatcgc tcaccgcatc gtggcacctg gcaagggcat cctggctgca 120
gatgagtcca ctgggagcat tgccaagcgg ctgcagtcca ttggcaccga gaacaccgag 180
gagaaccggc gcttctaccg ccagctgctg ctgacagctg acgaccgcgt gaacccctgc 240
attgggggtg tcatcctctt ccatgagaca ctctaccaga aggcggatga tgggcgtccc 300
ttcccccaag ttatcaaatc caagggcggt gttgtgggca tcaaggtaga caagggcgtg 360 gtcccctgg cagggacaaa tggcgagact accacccaag ggttggatgg gctgtctgag 420
cgctgtgccc agtacaagaa ggacggagct gacttcgcca agtggcgttg tgtgctgaag 480
attggggaac acacccctc agccctcgcc atcatggaaa atgccaatgt tctggcccgt 540
tatgccagta tctgccagca gaatggcatt gtgcccatcg tggagcctga gatcctccct 600
gatggggacc atgacttgaa gcgctgccag tatgtgaccg agaaggtgct ggctgctgtc 660
tacaaggctc tgagtgacca ccacatctac ctggaaggca ccttgctgaa gcccaacatg 720
gtcaccccag gccatgcttg cactcagaag ttttctcatg aggagattgc catggcgacc 780
gtcacagcgc tgcgccgcac agtgcccccc gctgtcactg ggatcacctt cctgtctgga 840
ggccagagtg aggaggaggc gtccatcaac ctcaatgcca ttaacaagtg cccccctgctg 900 aagccctggg ccctgacctt ctcctacggc cgagccctgc aggcctctgc cctgaaggcc 960
tggggcggga agaaggagaa cctgaaggct gcgcaggagg agtatgtcaa gcgagccctg 1020
gccaacagcc ttgcctgtca aggaaagtac actccgagcg gtcaggctgg ggctgctgcc 1080
agcgagtccc tcttcgtctc taaccacgcc tattaagcgg aggtgttccc aggctgcccc 1140
caacactcca ggccctgccc cctcccactc ttgaagagga ggccgcctcc tcggggctcc 1200
aggctggctt gcccgcgctc tttcttccct cgtgacagtg gtgtgtggtg tcgtctgtga 1260
atgctaagtc catcaccctt tccggcacac tgccaaataa acagctattt aagggggagt 1320
cggc 1324

<210> SEQ ID NO 209
<211> LENGTH: 487
<212> TYPE: DNA
<213> ORGANISM: Homo Sapiens

<400> SEQUENCE: 209
atggagtttt aacattgaat gcggagaaca ctaattatgc ctatcaagtt ccaaacttcc 60
ataaatgtga aatctgtcta ctatcttttc caaaagaatc ccagtttcaa cgccacatga 120
gggatcacga gcgaaatgac aagccacatc gatgtgacca gtgcccccaa acatttaatg 180
ttgaattcaa cctgacactt cataaatgca cccacagcgg ggaagatcct acctgccctg 240
tgtgtaacaa gaaattctcc agagtggcta gtctcaaagc gcatattatg ctacatgaaa 300
aggaagagaa tctcatctgt tctgagtgtg gggatgagtt tactctgcag agtcagctgg 360
ccgtgcacat ggaggagcac cgccaggagc tggctggaac ccggcagcat gcctgcaagg 420
cctgcaagaa agagttcgag acctcctcgg agctgaagga acacatgaag actcattaca 480
aaattag 487

<210> SEQ ID NO 210
<211> LENGTH: 308
<212> TYPE: DNA
<213> ORGANISM: Homo Sapiens

<400> SEQUENCE: 210
acatgaagcc attattatat caggaaccga aatggccaag catatccaga aagaaataca 60
gcgaggtgtg gaatcatggg tttcccttgg aaacagaaga cctcacctca gtataatttt 120
agtgggagat aacccagcaa gccatacata tgtcaggaat aagataagag ctgcctctgc 180
tgtaggtatt tgtagtgagc tcattctaaa acctaaggat gtttctcagg aagaactttt 240
ggacgtaact gatcaattga atatggaccc aagagtcagc ggtatattag ttcagttacc 300
actaccag 308

<210> SEQ ID NO 211
<211> LENGTH: 153
<212> TYPE: DNA
<213> ORGANISM: Homo Sapiens

<400> SEQUENCE: 211
aattccctga ccaggagcgc acccctcccc aacgactccc aggcccgcag tggagctcgt 60
tttcacactt cctacgacaa aagatacatc atcaagacta ttaccagtga agacgtggcc 120
gaaatgcaca acatcctgaa gaaataccac cag 153

<210> SEQ ID NO 212
<211> LENGTH: 389
<212> TYPE: DNA
<213> ORGANISM: Homo Sapiens

<400> SEQUENCE: 212
aaatctccca gcaaaaccag ctgaagaagc tcagaagcac agacagcagt atgaagaaat 60
ggtggttcag gccaaaaagc gagagctgaa agaagcccag cgaaggaaga agcagctgga 120
agaaagatgc agagtcgagg aaagcattgg aaacgctgtg ctcacctgga ataatgagat 180
cttacctaac tgggaaacaa tgtggtgctc tagaaaagtt cgagatttat ggtggcaggg 240
aatccctcca agtgtgagag gcaaagtctg gagcttagcc attggcaacg agttaaatat 300
cacccacgag ctctttgaca tctgtcttgc ccgagccaag gagaggtggc ggtcccttag 360
cacaggaggc tctgaagtgg agaacgaag 389

<210> SEQ ID NO 213
<211> LENGTH: 854
<212> TYPE: DNA
<213> ORGANISM: Homo Sapiens

<400> SEQUENCE: 213
caactgaacg aggaagggat gctgttggct tcagagatca aacacctgcc ccgaagactc 60
ctaataggtc aagagagaga gacccagaca agcaaactca aaataaagag aaaaggaaac 120
gaagaagctc cctctcacca ccctcttctg cctatgagcg gggaacaaaa aggccagatg 180
acagatatga tacaccaact tctaaaaaga aagtacgaat taaagaccgc aataaacttt 240
ctacagagga acgccggaag ttgtttgagc aagaggtggc tcaacgggag gctcagaaac 300
aacagcaaca gatgcagaac ctgggaatga catcaccact gccctatgac tctcttggtt 360
ataatgcccc gcatcatccc tttgctggtt acccaccagg ttatcccatg caggcctatg 420
tggatcccag caaccctaat gctggaaagg tgctcctgcc cacacccagc atggacccag 480
tgtgttctcc tgctccttat gatcatgctc agcccttggt gggacattct acagaacccc 540
tttctgcccc tccaccagta ccagtggtgc cacatgtggc agctcctgtg gaagtttcca 600
gttcccagta tgtggcccag agtgatggtg tagtacacca agactccagc gttgctgtct 660
tgccagtgcc ggcccccggc ccagttcagg gacagaatta tagtgtttgg gattcaaacc 720
aacagtctgt cagtgtacag cagcagtact ctcctgcaca gtctcaagca accatatatt 780
atcaaggaca gacatgtcca acagtctatg gtgtgacatc accttattca cagacaactc 840
caccaattgt acag 854

<210> SEQ ID NO 214
<211> LENGTH: 277
<212> TYPE: DNA
<213> ORGANISM: Homo Sapiens

<400> SEQUENCE: 214
cccatcgatt tgagtgcatg cactgttgca cttcacattt tccagctgaa tgaagatggc 60
cccagcagtg aaaatctgga ggaagagaca gaaaacataa ttgcagcaaa tcactgggtt 120
ctacctgcag ctgaattcca tgggctttgg gacagcttgg tatacgatgt ggaagtcaaa 180
tcccatctcc tcgattatgt gatgacaact ttactgtttt cagacaagaa cgtcaacagc 240
aacctcatca cctggaaccg ggtggtgctg ctccacg 277

<210> SEQ ID NO 215
<211> LENGTH: 1041
<212> TYPE: DNA
<213> ORGANISM: Homo Sapiens

<400> SEQUENCE: 215
atccctgggt atcagtatgt gtcacctgaa ggcaattgta tagaacatgt tcagcctact 60
tctgccttta ttcagcaacc cttcattgat gaagatcctg ataaggaaaa gaaaataaag 120
gaacttgaga tgcttcttat gtcagctgag aatgaagtta gaagaaagcg aattccatca 180
cagcctggaa gtttttctag ctggtctggt agtttcctca tggatgataa catgtctaat 240
actctaaata gccttgacga gcacactagt gagttttaca gtatggatga aaatcagcct 300
gtgtctgctc agcagaattc acccacaaag ttcctggccg tggaggcaaa cgctgtgtta 360
tcctctttgc agaccatccc agaatttgca gagactctag aacttattga atctgatcct 420
gtagcatgga gtgacgttac cagttttgat atttctgatg ctgctgcttc tcctatcaaa 480
tccaccccag ttaaattaat gagaattcag cacaatgaag gagccatgga atgccaattt 540
aacgtcagtc ttgtacttga agggaaaaaa aacacttgta atggtggcaa cagtgaagct 600
gttcctttaa catccccaaa tatagccaag tttagcactc caccagccat cctcagaaag 660
aagagaaaaa tgcgagtggg tcattcccca ggcagcgaac ttagggatgg ctcattgaac 720
gatggtggta atatggcgct aaaacataca ccactgaaaa cactaccatt ttctccttca 780
cagtttttca acacatgtcc tggtaatgaa caacttaata tagaaaatcc ttcatttaca 840
tcaaccccta tttgtgggca gaaagctctc attacaactc ctcttcataa ggaaacaact 900
cccaaagatc aaaaggaaaa tgtagggttt agaacaccta ctattagaag atctatactg 960
ggtaccacac caagaactcc tactcctttt aagaatgcgc ttgctgctca ggagaaaaaa 1020
tatggacctc ttaaaattgt g 1041

<210> SEQ ID NO 216
<211> LENGTH: 171
<212> TYPE: DNA
<213> ORGANISM: Homo Sapiens

<400> SEQUENCE: 216
tgcacttgga ggctcctcag ctcttcatat cccagctttt ccaggaggag gatgtctcat 60
tgattacgtt cctcaagtat gccacctgct caccaacaag gtgcagtacg tgattcaagg 120
gtatcacaaa agaagagagt atattgctgc ttttctcagt cactttggca c 171

<210> SEQ ID NO 217
<211> LENGTH: 7173
<212> TYPE: DNA
<213> ORGANISM: Homo Sapiens

<400> SEQUENCE: 217
gctgaactca cgggaatcaa atggcgtagg tacaattttg gagggcatgg ggactgtgga 60
cccataattt cagccccagc ccaagatgat ccaattctgt taagtttcat ccgctgtctg 120
caagctaacc tgctttgtgt atggcgtcgt gatgtcaaac cagattgcaa agagttatgg 180
atattctggt ggggagatga acccaaccta gtgggtgtaa tacatcatga actgcagggt 240
aaggtttctg tttttttctt aaaaattatt tgcatcatat ttttttgaac attgataaat 300
ttcaaacaga ttattaagac ttgtctaaaa gaacgatctt aagtgtttca tggatgtctc 360
tctcaaaagg aacattctca cccctcttcc tcccatccct gttttttttt cctaactctt 420
gtccttttcc agttatgctg agaatcagaa ccttgtgaac cgctgctgtt aaatgagagt 480
attgtgtctc ctgggtgcgg tggggtggaa accaggctaa gatccactgt ttttaaatga 540
tagtgaattg tgagtaacta acaagacagt gaattgaaca gttactgttt ttttccttgg 600
actgtggttg ttatggttca ctgccagctg aactctttgg tggaaaattg gagagtgata 660
cagaaattta gttttgagcc taattggaca aaattgtgag attacattga atagtatttt 720
gaggaaagat gaatatatgg gatctggtct gaattgggtg tagcaaattt tcttttgctt 780
ttatttctgt ttttcatgta atttggtgat tccaggaaac attggctccg gtgttgcctg 840
atttttagct tcagattgca tctgatatct ggaaactgaa ttaatgtaag agtttcattt 900
ttctgtgctg ctttatatat ttaccacagt tttatgagca ggaactttta tcagttgtct 960
ttgaatttct ggtaaaaatt tttacctttt tatctaagtg tttctattta gtatgcaaag 1020
ggattttctc aagcaagact aattctaatc tttagttagg gtattaactc tttttgactt 1080
agtctcttag aaccatcttt tattatctcc aaactatatt gtgttaatct gtgtctgaaa 1140
aatttcagat cgtgtttgaa atgttttgtt acttgatgtt tttaatgttt ttttttttta 1200
aaggaaggag taaaactaac tgtaatgtat gttcgaggct ctgttctaaa gcttttacat 1260
ttgcctgaag gatttcctgc caacttttgc ttgacacctt gctagttttt cttggcagcc 1320
attttttatc tgtgatatct cctgccacag cagccagagg gcggtaaacc acaatggact 1380
aattgaactg tttactttat ggtccatttg tctgttcagc tcaaaccttt atcctgatat 1440
tttttagggt atttggtcta taaataagag aaccattgtg ggtgacattg cttgcttagc 1500
tgggtaatca gcaaagtccc agaacttaac attcatctca aagcctgttc tatgtagtta 1560
gcagttaact taggtaaaat tagagtttca gaacatctgg attctgttta tcagaatttt 1620
aaaaataaga tgtcacctag aagataatta caacattttt gtttgtccat taaaatatga 1680
aaacatattt ttactttttt tccctatgta gtagagaggt ataaagcttt ttaaaaagtg 1740
tctttcttat ctttcatgat tgtttctgac tgtcatcttc tgtttctctg tattaatctc 1800
ttacgtttta gctttttggt ctgctctttg ttagtgtggt acatataatt ttgtaatgat 1860
gaggaaacca aacccaactg ctaatgaggg ttatttagtt gataatatag aataaattta 1920
tttatctatg ccaacggaga aaatcgtcag tgttcttaga aatagcttat taaattattg 1980
tgttattttt catgggcttt gttactgagt taacaaaaag gagtagggca tttaaatttt 2040
gggatagttg ctttagattg catgtgtaaa ttaatatctt aagtattttt tggtaaagag 2100
ttaagcaaag attgaattat ttttagatat ttttaaaatt acagaaacac tacatttaag 2160
ttagaaaatt aggaaaacag tcatcatatg gagagaacaa agaaataaaa atactgaagt 2220
ctgaaagagt tttagatgtt ttatgtgtaa atgaaattgg taccatacag tttttctaat 2280
tttctaatta aatgtagtat tgtgaatatt ttctcttggg aatgattact tttctttgga 2340
gtttgatagt ggtataaact gtttatattt tgtattctat caggaaagta ttacagtaat 2400
ggaataatta taatttcatt gagtgcgtct cctcttttta atatgaattt tgagcaagtt 2460
tttagattca tttatatgaa gtgtccattt ttgtaggtaa aagtagttga aaaaggtaat 2520
gtatggttca acctaataac agaaaatatc tagccttaat tagaaaaata agtcataaag 2580
acaactttgt ttcaaataag gggaaatacg atagcagtca tgaaaaactg aaggatacaa 2640
agagaatatt ttaattggta gccatacaaa gtggagatat tttagaatct atttcattct 2700
ctaatatatt tgagtcattt tattttgggt aaaataaatt ataggcggag catggtggct 2760
cacgctggtt atcccaacac tttgggaggc tgagggggcc caaatgcttg aggccaggaa 2820
tttgagacca gcctgaccaa tatggtgaaa ccctgtgttt acaaaaaata aaaaaaaaaa 2880
attagccagg tgtggtgacg tgcacctgta attccaacta ctcgggtgac tggggctgga 2940
ggatcactta aacccaggag gccaaggttg cagtgagcag agataatgcc actgcactcc 3000
atcctgggca acaaagtgac acctgtctca aaaaataaaa taaataaata gtagcagaat 3060
ccttttagca ggctttaatg ttaagcatga gattaccatt atttgtaaca ttttttaaat 3120
agggacattt tactgtttct tacattgctg cttatttatg ttatttggca tttcctggct 3180
ggtcacggtg gctcacgcct gtaatccctg cactttggga ggcctaggca ggaggatcac 3240

```
ctgagttcag gagttggaga ccagcctggc caacatagtg aaaccccctc tctagtaaaa   3300
ataaacaaaa attagctggg catggtggtg ggtgcctgta atcccagcta ctggagaggc   3360
tgagacagga cagtcgctgg aaaccgggag gcagaggtta cagtgggctg agatcacgcc   3420
acagcactct gctgggcaac acagcaagac tccatctcaa taaataaata aataaataaa   3480
taaataaata gcagaatcct gttagctggc ttaaattaag catgacatta ccattattta   3540
acattttttt taatagaggc attttattgt ttcttaaatt gctttttagt tatttggcat   3600
ttccctttgt cttcatagcg tactccaaat agcgtcctac caagaaacct cacggtgaga   3660
tgtaatacca aagcaaccat cttgcattta aatgtataaa gtatcccata aaatgagaat   3720
aatcctacag ggtacacaca caagttagtt ttatgatatt atactttttg tttaattgct   3780
tgacatatct ctgaaatagt ctgagagaag gctataacac atttataatc tgtccttgtc   3840
acttggataa acacttgggt tcctgtctgg ggaattgtta atgcgtgtgg tgtagtgatt   3900
cagagcacgg gctctgggtt gcttgggttt gaatgcttgc atagtcacta gctgtgtatt   3960
cttgatctaa ttatttaact taaactgtgc ctcagttttc tcactgtgaa ttaggttatg   4020
aggttaagaa aaattaaaag tacttagagc agcatatata gcagttaatc tataattgta   4080
actattgcta ctgctactgt gcaaagacct acaggctgcg aatgaattgt ggcaagaaca   4140
ggttacctgg ggcttagggt aggagtgaaa tagtctcccc tctaaaaggc tgagtaggtg   4200
ggtcatagta tggagtacac agaaccaagg ataagacatt tagacttaat ttgatagatt   4260
ttgaggaatt aaacatttct gatcaggaaa gcgatataat taggaagatt aacttagtaa   4320
taatacagga ttaatgtgta cagggaaacc ataatattgt gattttaaaa ttctaaattg   4380
gaatataaac ttaaatattc tgttcaggat acagatgtat ttaaattaaa aatactaatg   4440
attatatact ataattcata ttaatagtct ttaacacttt tattatacct ttgctgtttt   4500
ggcttgacta aattctacat tttaatttaa gttttagaga ttaatacagt gtgctgagtg   4560
gacttctcct aatctaccaa acaaatactt cttacttttt tttttttttt tttttccttt   4620
agacagagtc ttgctctgtt gcccaggctg gagtgcagtg atgcaatctt ggctcactgc   4680
aacctctgcc tcccgggttc aaatgattct cctgcctcag ccttctgagt agctgggatt   4740
gcaggtgtat gccaccacac ctggccaatt tttgtatttt tagtagagat ggggtttcac   4800
catgttggcc aggttgatct caaactccca acctcaatcg atccgcccgc ctcggcctcc   4860
caaagtgctg ggattacagg cgtgagccac tgggcctggc aacaaatgct ttttaaataa   4920
acacaatatt ctcgccaatt cactgcctgt tagttagtgg tgggaaagac atgcaatctg   4980
gaaaacccaa aatagtacag agagcaagca cagaactgcc aattgcttgc cccaaagcat   5040
tacaaatctc tggtccagaa ggagaagtat cagattcagc ctagtatgtg cttaagaatg   5100
tttgtcgaat cagttaatga aacgtatttt atgaggttct aatgtagcgc agtattgcac   5160
tcccggcaga ttgacttata ataaatttgt gaaaattttt aatgatttga taatgcgagg   5220
atattgaagc ctagttaaaa taaagcatat tatttctggt tttaattccc aaggggatag   5280
aaatagccaa tttttggggt atattttcta ccacaaatat ttagcactaa atatgcactg   5340
tctacaattt taaaatttat gttgtctctt tttttgatta ttagacatat aaattaagga   5400
tacatctgta caactctaaa aatgattgtc cctataacag tatcagaagt cttctgaatt   5460
ggttttattg tcagtgcagg ggtagattgg cagttattac cctttgttgt gaatttagag   5520
acataaatat tgctttttct atttttaaga gtgctgccac ctgtgccagg aggtgtgggc   5580
gattgtaaaa acattagaca taagagagcc tggaaaaatg gatctgtttt ctgacagtga   5640
```

```
ccacggtgta agataattta agatactagt actattgttt attgaactca ttgcaagtgg   5700
gcattttgta ggagtgtggg aaggctggat ttttttagtt ttgtaatctg tatctataga   5760
ttacagtcta caattccaaa tggtgggatt gataaaacct ttgtttagat aactccaagc   5820
aagaacctag cttctccact cctcctagct ttttattttt aaatatattt acacacttat   5880
atgcatatgc ctctttttcc acctaaacta tttgaggcaa ttttcagact tcacggacct   5940
ttgcccctaa atacttcagc atttaagtcc tgtgaatgag aatgtgaagc actcttttac   6000
gtaaccagag cacttttggc atgctcaaga aatttaatat cgatataatt aaattatcta   6060
atatttagtc catattcaaa tttcccaatt gtcttagcaa taccttttat agtttctct    6120
ctctctgatc cagaatgcaa tcaggatcac acatttttag atggcttgtg tcctctcatt   6180
tagaatattc ctgaagttgt cttggggatc aatgatattg atgttatttg aagggagcag   6240
tttagttgtc ctgtaaaata tcccacattt tgaatttgtc taattgtttt cttacagtta   6300
gagtcaggat aaacatattt ggcaagaata ctgagtaggt gatgttgtgt cctttccacg   6360
gcatcacatc agaaacaggt catgtcagtt tgtctcaata ttgatggtac tgagcttgat   6420
cccttgatta aggtagtgtc tgccagattt ctccagtgta aagatatcct ttcctttttgt  6480
aattgttaag taaatttggg atgaaacttt gagattgtgt gaatatctct ttcctcaaaa   6540
gagcctaatt ttgagcctgt ttaaaccaac cgaaaaattc cggaatcacc tgcttttaga   6600
aaatcagttg agatcacatg aagactgcat ttttaagtca cagcagagtt caagaggaga   6660
agagaataaa atattgaaga tctaccaaag gcaaattata atggcaatgt cacactatga   6720
aaatgaatag cccctattgc ttagcatacc taaaaagaga agtgttgaca ttgaattttc   6780
caaaatcata gacaataatg tatgtaggaa tatattactg tgtatcttag agtctgtgaa   6840
ctttcaattg atttttgatg gtttctggtt atccttaact aaatggtaaa aataatttca   6900
tcggtattat acatgaattt attatcagtt gaaattaaaa aattgctttc tggaaaagta   6960
atgactattt tatatataaa ttgacaggaa taagattatc tcttgtcatt ttgaaaattt   7020
ctttcaagga gaaaatctga tctttgactc attttcactc tgtttttcta tctttttttt   7080
tagtggtatt aaatttgtga gtcattgaaa ttaatccctg actgaattgg aaaggaattg   7140
tatttgcagt atttggattt atttattttt cag                                7173
```

<210> SEQ ID NO 218
<211> LENGTH: 419
<212> TYPE: DNA
<213> ORGANISM: Homo Sapiens

<400> SEQUENCE: 218

```
gcatgagcca tgagcccaag tcccccttcgc tagggatgct ttccaccgcg accaggacca   60
ccgccaccgt caaccccctc accccctcgc cgctcaatgg cgccctggtg cccagcggca  120
gccccgccac cagcagcgcg ctgtcggccc aggccgcgcc atcctccagc tttgccgccg  180
cgctgcgcaa gctcgccaaa caggcggagg agcccagagg gtcctcactg agcagcgagt  240
cgtcccccgt gtcctctccg gccaccaacc acagctcccc cgccagcaca cccaagcgcg  300
tgcccatggg ccctatcatc gtcccccctg ggggccacag cgtgcccagc accccccccg  360
tggtgaccat cgctccaacc aaaaccgtga atggtgtctg gaggagtgag agccggcag   419
```

<210> SEQ ID NO 219
<211> LENGTH: 277
<212> TYPE: DNA

<213> ORGANISM: Homo Sapiens

<400> SEQUENCE: 219
ccttaaattg gaatgtgaga aactggcaag tgaaaagaca gaaatgcaga ggcactatgt 60
gatgtattat gaaatgtcat atggattaaa cattgaaatg cacaaacaga ctgaaatcgc 120
caagagattg aatacgattt gtgcacaagt catcccattt ctgtctcagg aacatcaaca 180
acaggtggcc caggctgttg aacgtgccaa acaggtgacc atggcagaat tgaatgccat 240
catcggggta cgtggcctac caggtctacc tcctaca 277

<210> SEQ ID NO 220
<211> LENGTH: 371
<212> TYPE: DNA
<213> ORGANISM: Homo Sapiens

<400> SEQUENCE: 220
atcttctgtc tacatggtgg tctctcgcca tctatagata cactggatca tatcagagca 60
cttgatcgcc tacaagaagt tccccatgag ggtccaatgt gtgacttgct gtggtcagat 120
ccagatgacc gtggtggttg ggtatatct cctcgaggag ctggttacac ctttgggcaa 180
gatatttctg agacatttaa tcatgccaat ggcctcacgt tggtgtctag agctcaccag 240
ctagtgatgg agggatataa ctggtgccat gaccggaatg tagtaacgat tttcagtgct 300
ccaaactatt gttatcgttg tggtaaccaa gctgcaatca tggaacttga cgatactcta 360
aaatactctt t 371

<210> SEQ ID NO 221
<211> LENGTH: 977
<212> TYPE: DNA
<213> ORGANISM: Homo Sapiens

<400> SEQUENCE: 221
agcagctctt aaagctttgg attcggctgt cgtggagata acgggcacca gaaaaacttg 60
taggagtagc aacagctatt tggtcggatg gaggccagaa gccaagaata atcgaaacac 120
gctgccagcg cccattagat ggatgggaaa tgagtgtaac tcattgggaa agatattaga 180
cttcaaatca cctaaggcaa accctacttc ctggggcgcg ggcgcgggcg ctggcgttag 240
gagacgtcac tcccgcgcat aactgacatg gggccctctt ggtcggcgtt tccgggcggg 300
tccttccgac ggccgccgcg gtgattccat cactcggctt tcttcccggc ctgcctcgcg 360
cccgtagccg ggctgggcca gaacagccca agatggccga cttcgatgat cgtgtgtcgg 420
atgaggagaa ggtacgcata gctgctaaat tcatcactca tgcacccccca ggggaattta 480 atgaagtatt caatgacgtt cggctactac ttaataatga caatctcctc agggaagggg 540
cagcacatgc atttgcccag tataacatgg atcagttcac gcctgtgaag atagaaggat 600
atgaagatca ggtcttaatt acagagcacg gtgacctggg taatagcaga tttttagatc 660
caagaaacaa aatttccttt aaatttgacc acttacggaa agaagcaagt gacccccagc 720
cagaagaagc agatggaggt ctgaagtctt ggagagaatc ctgtgacagt gctttaagag 780
cctatgtgaa agaccattat tccaacggct tctgtactgt ttatgctaaa actatcgatg 840
ggcaacagac tattattgca tgtattgaaa gccaccagtt tcagcctaaa aacttctgga 900
atggtcgttg gagatcagag tggaagttca ccatcacacc acctacagcc caggtggttg 960
gcgtgcttaa gattcag 977

<210> SEQ ID NO 222
<211> LENGTH: 2334
<212> TYPE: DNA
<213> ORGANISM: Homo Sapiens

<400> SEQUENCE: 222

```
tcctgggtca agctgagtat ctccacgttt aggtgcacaa atactatttt gtgaagatct     60
taaatttgtg gtataagaac ttgaaggaaa tagaactgat ttgttacttc taaaagattt    120
gtaagactcc agggcctccc agccgtgaat aatctgatgg ttcctgaaat gactggggaa    180
gcagacgctt cgtatggcag ttgaagagtg tgtgtctatg tgcatttaaa accttctttc    240
tgtacttaca cattcacacg ggaagacagg ctcattcttg tgcacacttg agagttttac    300
aactgatgaa aattaattta agaatcagat ggagcaactt gacaccagtg ggctcaggag    360
cccggggaga aaaatacatc actaatggcc agttttccat atggtctgca cgggtaaaga    420
aagtctgcaa aaagaagaaa aaaaaatttg cgcagattaa accacaaaaa tattctccag    480
tttaaagaag gaactaagtg agaaggtgac tgagaaagaa gtgtgatttc aaacattgca    540
gcggctcaca cagtgtttgt tgcactttat ttttcagtgg gtttggtgat ttggacggat    600
taaaattcta gactgaaaag taactcctac tgtggttatg gctagaggaa agcaagttca    660
agtatgatgg gacaagtttg aataatgaac tgattccttt gcctatctta attaactgta    720
tttgagaaat tttaatttat tattcccccc ctttttttcct gcatctatag gataatattg    780
taaaatagca attgaaacca ataattatta aataaatatc aaggaaaatc caagcaaagc    840
tttctttttg ttggactagt ggtgtggtgt ttggagacag tctctgaatg tgaacaggaa    900
agcacccatc agcaaaacac tatcactctc tagggagaca gctgggggaa tctgactctg    960
gcttctgctt ttgttttaag ggattaactt ccctgtcaag tccaagaaga cttgcgtatg   1020
agaagattac ctgatggact taattctaag attagctttt ttcatcaaga tggaaaaaga   1080
tctttaggag cagaaaaggg gagtgctaac tgggggagcg agaagggaga cgagcaaaag   1140
aaacaaaatc ttgccacgtg gctctgtttt gtcagcaaga ggatttaaga ctcacccagg   1200
gcaaacactg ggaccactgt aagagcgctg gaacattctg cctcttgagt gaaggggcct   1260
tctttctagc ctctatggca ctgaggggtg cgccggctgg tggaggagca gtccgatgga   1320
gccctgcgtt ccccggggac acagggccaa gctttgaggt ggaaagtttc tggttctgaa   1380
acaacaagga gagagtctgt ttttcttcct aaaatttgga ctcttgtctg cacaaactct   1440
ggtctgtttt gcacggtttg tgtgcctttt tttcccttta tgcaatcttt ttcagcttta   1500
gcagcagaaa tttgtctagt tcaggaaaca tgctagaggg tggcttcaga aggaagatga   1560
tcctgtgtat tctgtctctg catccgaact tttgaagaga aaaattcgag ctagagggat   1620
tcttaaagcc ttaagttact tgaaatctat gtatttgcaa ccctttgtct ctggaatcat   1680
attacactaa actggaatct caggctgaat gagaataacc aagtggagta aaaagaagaa   1740
aaccgtttct tgatcaccac ttaattaacg atgctctttc tccaaaggat cagcacgttc   1800
ttcctctgag aacttgaaaa tacaaatgga ccccatgttt ttttaagcat taccttttct   1860
tagaagactg ccatcatctt ttatagagga attttttcac tatgcattcg gtggatcttt   1920
ataaaatact gaccttctaa ttagattcag gtcagtctta attaaagggg gaaaaaagca   1980
acgcaagcca accacaaaaa cacatatacc aatgaaagaa attggtttaa atttcacagc   2040
attaacatta ctttttaagt aaaacagttc attgaagaaa gtatgtatgc agcagtggaa   2100
catgggcctg tgctttgcag cgattccaac atcctgtgcc tgtcctggaa ggggcgtgtc   2160
```

cccaagagtg agaaggagaa gcctgtgtgc aggagacgct actatgagga aggctggctg 2220
gccacgggca acgggcgagg agtggttggg gtgactttca cctctagtca ctgtcgcagg 2280
gacaggagta ctccacagag gataaatttc aacctccggg gccacaatag cgag 2334

<210> SEQ ID NO 223
<211> LENGTH: 354
<212> TYPE: DNA
<213> ORGANISM: Homo Sapiens

<400> SEQUENCE: 223
gtaatcagat cctgtccctt gggagcctct caaaagatca gatttatcca atgaaactca 60
agggcatctc catctgctat tcagctctca agtctgcctt gtgtggaaat tatgtcagct 120
ttggcgtctt caagttgtat ggggacaacc attttgacaa tgtactccag gcttttgtca 180
aaatgctgct gtcagtgtcc cacagtgact tgctacaata ccggaaactg agccagtctt 240
attatccact cctggaatgt ctcactcagg accatatgag cttcatcatc aacttagagc 300
ctcctgtact catgtatgtt ctcacatcta tctcagaggg actcactact cttg 354

<210> SEQ ID NO 224
<211> LENGTH: 2056
<212> TYPE: DNA
<213> ORGANISM: Homo Sapiens

<400> SEQUENCE: 224
gttttggttc ctttgtggac aaaacggtgc tgccctttgt gagcacagta ccctccaaac 60
tgcgccaccc ctgccccacc cggctggagc gctgccagtc accattcagc tttcaccatg 120
tgctgtccct gacgggggac gcacaagcct tcgagcggga ggtggggcgc cagagtgtgt 180
ccggcaatct ggactcgcct gaaggtggct tcgatgccat tctgcaggct gcactctgcc 240
aggagcagat tggctggaga aatgtgtccc ggctgctggt gttcacttca gacgacacat 300
tccatacagc tggggacggg aagttgggcg gcattttcat gcccagtgat gggcactgcc 360
acttggacag caatggcctc tacagtcgca gcacagagtt tgactaccct tctgtgggtc 420
aggtagccca ggccctctct gcagcaaata tccagcccat ctttgctgtc accagtgccg 480
cactgcctgt ctaccaggag ctgagtaaac tgattcctaa gtctgcagtt ggggagctga 540
gtgaggactc cagcaacgtg gtacagctca tcatggatgc ttataatagc ctgtcttcca 600
ccgtgaccct tgaacactct tcactccctc ctggggtcca catttcttac gaatcccagt 660
gtgagggtcc tgagaagagg gagggtaagg ctgaggatcg aggacagtgc aaccacgtcc 720
gaatcaacca gacggtgact ttctgggttt ctctccaagc cacccactgc ctcccagagc 780
cccatctcct gaggctccgg gcccttggct tctcagagga gctgattgtg gagttgcaca 840
cgctgtgtga ctgtaattgc agtgacaccc agccccaggc tccccactgc agtgatggcc 900
agggacacct acaatgtggt gtatgcagct gtgcccctgg ccgcctaggt cggctctgtg 960
agtgctctgt ggcagagctg tcctccccag acctggaatc tgggtgccgg gctcccaatg 1020
gcacagggcc cctgtgcagt ggaaagggtc actgtcaatg tggacgctgc agctgcagtg 1080
gacagagctc tgggcatctg tgcgagtgtg acgatgccag ctgtgagcga catgagggca 1140
tcctctgcgg aggctttggt cgctgccaat gtggagtatg tcactgtcat gccaaccgca 1200
cgggcagagc atgcgaatgc agtggggaca tggacagttg catcagtccc gagggagggc 1260
tctgcagtgg gcatggacgc tgcaaatgca accgctgcca gtgcttggac ggctactatg 1320
gtgctctatg cgaccaatgc ccaggctgca agacaccatg cgagagacac cgggactgtg 1380
cagagtgtgg ggccttcagg actggcccac tggccaccaa ctgcagtaca gcttgtgccc 1440
ataccaatgt gaccctggcc ttggccccta tcttggatga tggctggtgc aaagagcgga 1500
ccctggacaa ccagctgttc ttcttcttgg tggaggatga cgccagaggc acggtcgtgc 1560
tcagagtgag accccaagaa aagggagcag accacacgca ggccattgtg ctgggctgcg 1620
tagggggcat cgtggcagtg gggctggggc tggtcctggc ttaccggctc tcggtggaaa 1680
tctatgaccg ccgggaatac agtcgctttg agaaggagca gcaacaactc aactggaagc 1740
aggacagtaa tcctctctac aaaagtgcca tcacgaccac catcaatcct cgctttcaag 1800
aggcagacag tcccactctc tgaaggaggg agggacactt acccaaggct cttctccttg 1860
gaggacagtg ggaactggag ggtgagagga agggtgggtc tgtaagacct tggtagggga 1920
ctaattcact ggcgaggtgc ggccaccacc ctacttcatt ttcagagtga cacccaagag 1980
ggctgcttcc catgcctgca accttgcatc catctgggct accccaccca agtatacaat 2040
aaagtcttac ctcaga 2056

<210> SEQ ID NO 225
<211> LENGTH: 80
<212> TYPE: DNA
<213> ORGANISM: Homo Sapiens

<400> SEQUENCE: 225
gaagtgtttg gattgtgagc tatttcagaa ctgttctcag gactcattat tttaacattt 60
gggagaaaca cagccagaag 80

<210> SEQ ID NO 226
<211> LENGTH: 204
<212> TYPE: DNA
<213> ORGANISM: Homo Sapiens

<400> SEQUENCE: 226
agtgaagata cacaacagca aatcatcagg gagactttcc atttggtatc taagagagat 60
gaaaatgttt gtaatttcct agaaggagga ttattaattg gaggatctga caacaaactg 120
atttatagac attatgcaac gttatatttt gtcttctgtg tggattcttc agaaagtgaa 180
cttggcattt tagatctaat tcaa 204

<210> SEQ ID NO 227
<211> LENGTH: 898
<212> TYPE: DNA
<213> ORGANISM: Homo Sapiens

<400> SEQUENCE: 227
ctccaggaca cgcgcgcccc gagcctggga ggcatgctga agccaggcgg ccggcaggat 60
gagtgtgaaa gaggcaggca gctcgggccg ccgggagcag gcggcctacc acctgcacat 120
ctacccccag ctgtccacca ccgagagcca ggcctcgtgc cgcgtgactg ccaccaagga 180
cagcaccacc tcggacgtca tcaaggacgc cattgccagc ctgcggctgg acggcaccaa 240
atgttatgtg ctggtggagg tcaaagagtc gggaggcgag gaatgggtgc tggacgccaa 300
cgactcgcct gtgcaccggg tgctgctatg gccccggcgg gcacaggacg agcaccctca 360
ggaggatggc tactacttcc tgctgcagga gcgcaacgca gatggaacca tcaagtacgt 420
gcatatgcag ctggtggcgc aggccacagc cacccggcgc ctagtggagc gtggcctcct 480
gccacggcag caggcggact ttgatgacct gtgtaacctc cccgagctaa ccgagggcaa 540
cctcctgaag aacctcaagc accgcttcct gcaacaaaag atctacacgt acgcggggag 600
catcctggtg gccatcaacc cctttaagtt cctgcccatc tacaacccca agtacgtgaa 660
gatgtatgag aaccagcagc tgggcaagct ggagccacac gtcttcgcgc tggccgacgt 720
ggcctactac accatgctca ggaagcgcgt gaaccagtgc atcgtgatct cgggtgagag 780
cggctccggc aagacccaga gcaccaactt cctcatccac tgcctcaccg ccctcagcca 840
gaagggctac gccagcggcg tcgagaggac catcctgggt gctggccctg tgctggag 898

<210> SEQ ID NO 228
<211> LENGTH: 299
<212> TYPE: DNA
<213> ORGANISM: Homo Sapiens

<400> SEQUENCE: 228
gccgctgcgc ggccctgcgc atgctgctgg cagatcaggg ccagagctgg aaggaggagg 60
tggtgaccgt ggagacgtgg caggagggct cactcaaagc ctcctgccta tacgggcagc 120
tccccaagtt ccaggacgga gacctcaccc tgtaccagtc caataccatc ctgcgtcacc 180
tgggccgcac ccttgggctc tatgggaagg accagcagga ggcagccctg gtggacatgg 240
tgaatgacgg cgtggaggac ctccgctgca aatacatctc cctcatctac accaactat 299

<210> SEQ ID NO 229
<211> LENGTH: 249
<212> TYPE: DNA
<213> ORGANISM: Homo Sapiens

<400> SEQUENCE: 229
gttctcatca gctcccccag ccatgcagca atttttgtgg gtcaggccct gctttgcaga 60
agcagcttgt ggttgtctaa tgggctaggg gaagacaggc ttgcttaatt cagcccaggt 120
ctaaagcaat ctgctccact gagctttcac aggaagaaat cagctgagat tttgaactct 180
tgtttctgtt tccaaactca actagaaatg gaggtattta ttgattgacc tcctaaaaca 240
tcaacacag 249

<210> SEQ ID NO 230
<211> LENGTH: 981
<212> TYPE: DNA
<213> ORGANISM: Homo Sapiens

<400> SEQUENCE: 230
gtcgtgatgt ctcgggagtc ggatgttgag gctcagcagt ctcatggcag cagtgcctgt 60
tcacagcccc atggcagcgt tacccagtcc caaggctcct cctcacagtc ccagggcata 120
tccagctcct ctaccagcac gatgccaaac tccagccagt cctctcactc cagctctggg 180
acactgagct ccttagagac agtgtccact caggaactct attctattcc tgaggaccaa 240
gaacctgagg accaagaacc tgaggagcct accccctgccc cctgggctcg attatgggcc 300
cttcaggatg gatttgccaa tcttgagaca gagtctggcc atgttaccca atctgatctt 360
gaactcctgc tgtcatctga tcctcctgcc tcagcctccc aaagtgctgg gataagaggt 420
gtgaggcacc atccccggcc agtttgcagt ctaaaatgtg tgaatgacaa ctactggttt 480
gggagggaca aaagctgtga atattgcttt gatgaaccac tgctgaaaag aacagataaa 540
taccgaacat acagcaagaa acactttcgg attttcaggg aagtgggtcc taaaaactct 600
tacattgcat acatagaaga tcacagtggc aatggaacct ttgtaaatac agagcttgta 660
gggaaaggaa aacgccgtcc tttgaataac aattctgaaa ttgcactgtc actaagcaga 720
aataaagttt ttgtcttttt tgatctgact gtagatgatc agtcagttta tcctaaggca 780
ttaagagatg aatacatcat gtcaaaaact cttggaagtg gtgcctgtgg agaggtaaag 840
ctggctttcg agaggaaaac atgtaagaaa gtagccataa agatcatcag caaaaggaag 900
tttgctattg gttcagcaag agaggcagac ccagctctca atgttgaaac agaaatagaa 960
attttgaaaa agctaaatca t 981

<210> SEQ ID NO 231
<211> LENGTH: 5178
<212> TYPE: DNA
<213> ORGANISM: Homo Sapiens

<400> SEQUENCE: 231
gtctgcatta catttactga atttggaaaa atgcaaaata tttgtaactt tcttgttgaa 60
aagctagata gctctgttgt catcagccca ccccagttct atcatactcc aggttctgtt 120
gagaatcttc gacggcaagc ctgtcttgtt gctgttgaga atgcgtggcg caaagctcaa 180
gaagtctgta accttgttgg ccaaacctta ggaaaacctt tactaatcaa agaagaagaa 240
acaaaagaat gggaaggcca aatagatgat caccagtcat ccagactctc aagttcatta 300
actgtacaac aaaaaatcaa aagtgcaaca atacatgctg cttcaaaagt atttataact 360
tttgaggtaa agggaaaaga gaagagaaaa aagcaccttt gaaattccaa acaaattata 420
ttgtacttgt atctttttac ctatttttat actttttata atgtttacgt ttgtcctgaa 480
tatatatata tatatatata tatatatata tatggtatag gagataagct atttctttcc 540
aaaatctata aatctttgaa tatagtccca cagaatactt atgttcactt tctattttta 600
aaagactact ctgaaaaaca ctcttggata ataaatgtat tatgtgcata cttatatact 660
gacagttcat acaagcacat gtgtaatatt tctattataa ggacagatat tgacccttgc 720
atttcataat ttttaaagat atttaagcta aaattttctc agccacattt ttatataaaa 780
ccaaatttta tgtaaaaact aggcttcaat aagttagcta aattttttaa attgtaagac 840
aaaattttta tggaaaagaa ttcctatatc ccatcaaacc taataatttt ccacaactaa 900
aaatgagtat aaatacataa ttttaagtgc atcctgtcag gtctgatatt taattttact 960
ttagttagaa gctaagtagt taccctgtta cttcttcatg gatgctaaca gaagacttga 1020
gattcccaga cagaaacaaa ggactattac tcatggcaca acaaggagca tgagcatcag 1080
cacattctca ttgcttcccc ttgtcccagg tcccatgggg gcaaaatgat atggccatat 1140
gcaatatggc tacatataca gcaggctttt gttgtaggta aagaatactg agcttggagg 1200
gttcactgct ttttatccat gaacagaagc aaacctgctc tttgcctcat cccttataga 1260
tgctcactca aaactcaata ctgagaaatg gcccaggtaa agaacagcca aggtctttca 1320
tgcttgccac acccagcaat atgtttagga aggtgaagtc tactgagggc tatctcacat 1380
ctaacagttt ctttactagg accagagacc attttggtaa gatgcagata acaaccccaa 1440
ccttaacaac ttcacaacat gaatagaaat agtgataaat aattcatagc tttttacaaa 1500
agaataatga ggtataatag gaaaatgttt tgatgccaaa aataaaagag ttaatgtttg 1560
gatcggactc caacagggct ccttagagtg atacaaatac aaagcaaacg atatgtgtaa 1620
tttaaaattt cctagtgcac atgttttttt atttttcttt ttcgagatgg agtctttctc 1680
tgtcgcccaa gctggagtgc agtggtacga tctcagctca ctgcaacctc tgcctcctga 1740
atttaagcga ttctcctgcc tcagcctccc aagtagctgg gattacaggc gtgagccact 1800
gcatctggcc ctgtacgcac atttttaaaa ataaaacttt aaaaaagaaa cagttgaaac 1860
taattttaat aacattttat ttaaccaaat atatcaaaaa tattatttca gcatgtaatc 1920
agtatttttt aaattgagat atttgtttta tcttcaaaat tcagtgtata tttttacata 1980
atagcacatc tcaattcaca tgctaaattt tcatcagaaa tattttatct gtatttaaat 2040
ttcctaaaat gtacagttga aaaaaagaga ttcacatacc caggttgttc tagcatgcct 2100
aaaaaatctt gtaactggat caagtatcag tttttaaatt agttaaaatt aaataaaatt 2160
taaaatttag ttcctcagtc acactagcca tatttcaagt acttgaaggc cacaaatggc 2220
ttgagactac cttgctgaac agaccaaggt caaacactga gataataatg attcttaagg 2280
ccatttgaaa gttaacagca agtatgtatt actgctatct acagtaagaa ttacatttta 2340
tctacaggca atcataagcc atgtctgtta tgcagcatag gctttccatt ctctatacat 2400
ctaggtcata gagtttttcc attgataaat ctggatgttt atataccaac agtactttct 2460
tacaacatat tccagtatat agtgtccagc ttcacccact ttttaaagtg gccctgaaac 2520
aattttattc atcttattgg agtgttgctg taggggaaga gtagaagcta agaagagttt 2580
gagttcaaca ccattatatc caaatcctga ccttactact ggaatgtaag ctccttgaaa 2640
gtggagatct tgtctgtctt gttcacagtt gtgttcccag ccccagaggt agtctcaggg 2700
ccaatatcaa gtatgctctc aaatatttgc tgggaaaatt tactagctgg ataaaaggca 2760
agttacttta atctctttaa tcttcctttg tccttacaaa tgaaagagac taatagtact 2820
taaccttgca gtgttattat aaggattaaa gttgataaat atatgatcat gagaacaatt 2880
gctagcacat aacggtcact ctgaaaatag tagctgatat atcagctgca ttgtttgatt 2940
attgttggct caattaaaag ttggcttttc caaatcctcc attaggaaga atttttaaat 3000
agccatattg aaaataaagt tgtcagaaaa ccaatgtaac atatgttgaa tttttattac 3060
caaaaagaag ttactatcca gttgtacaga aaagtagaat gaggttgtgc atcaagaaaa 3120
aaattgttcg ttctcaacaa aaatttaatc acatgggtag tttttttttt tttagctatg 3180
ggttcatgct gtatttggtt gcatcatatt tgataaagaa gcttccaact tagcatgaaa 3240
tacctaaaga caattttttt tttaagttag taggcacttt ttagaatttc caggaacttt 3300
taaagatgtt gtctccaaaa aaaacaaaaa aatcctgtaa agtatacaat cctacatttt 3360
tctatagaag agcttaggga agaaatcatt caaagattgg aaagacttat gtgtagtatt 3420
ctgtatacta aagggtatca aatttagttg tcagttgata gcaatttaat ttcttgatac 3480
atggcataca ctggaatctt atgatgaatt atttagggga cctgtgccac aaagtctact 3540
agaataaacc tatcctaaac ttaatcctgt tagaatttcc ttcttttgaa ctctgtttaa 3600
aaaaaaaaaa atctttccag aaagtaggaa gttataattt ctattttctg aaagacaaac 3660
aaaaattcta aataggatat ttgaaacaga cccactgtat cctaaatgga agtgctatta 3720
aaaggaaatg ctattaaaat aagatttcat atattactga taattcataa tgaattttag 3780
gattccattc aattacatac taaaaattac atttttata gtggcaatgt acttttatca 3840
gtattcttat ttgacggtca atttgagttc agtgtaaaca aataggactt agaaaaataa 3900
tttgtaactc aagatgctgt acctcatcct ataattgttg ttttgtaata ttccttctca 3960
ggaatatggg ctaaggatat ctcaactctg tcagatttgt tgataagaat ttaatagtaa 4020
ggagttctta tagcctataa aaagcatgaa ttatgagatc aaatgtggga gttactatat 4080
gattatctgc attacaaaat gaaagcaaat gctttattta ttccaacaaa aaaagaccta 4140
tataaattag tttaagctaa catttagaca tttactatta catatatggt atttgcaacc 4200
aaatcactga gtttgttgtt gtcgttgttt gaggctgttg ctctgtcacc caggatggag 4260
tgcaagtagc tcaatcatag cttactgcag cctaaaaact cctgggctga agaaatcctc 4320
tcacctcagc cttttaagta gctgaaacat taggtgcaca ccaccaggcc tggctaattt 4380
tttattagtg ataaggtctt gctatgttgc ccaggctggt ctcaaactcc tggcttcaag 4440
cagtcctgcc tcagcttccc agagtgctgg actacaggct tgagccactg cacccagccc 4500
caaatagctt ctactcataa cctagtgtgg cctaaattta tttaaaatgc ccgggtaggc 4560
caggcacgtt ggctcacgcc tgtaatccca gcacttggga ggccgaggta ggcagatcac 4620
ttgaggtcag gagttcgaga ccaacctggc caatatattg aaaccctgtc tcttctaaaa 4680
atacagaagt tactcaggcg tggtggcgtg tgactgtaat ctcagctacc ggggaggctg 4740
aagcagaaga aacgctcgaa cctgggaggc agagcttaca gtgagccgag atcgcaccac 4800
tgcacttcag cctgggtgac aaagtgagac tccatctaca tacatacata catacataca 4860
tacatacata catacataca tacatacata aaatgcccag tatcttacaa gactgtagtt 4920
cacagtgggt aattcaaatc agacactgct cttcaagaga ggtaatatta atagaaatct 4980
ttcaagaagg attgttttct actattaaaa caataaaact cttataaacc tgtttatcag 5040
aaggatattt ctgtttcagc aactcctgga atccttcttc aacatcccaa ccaacaatta 5100
ctcccagata gccatgtcac ctgtgaatta tcatgaatcc cacatcaaat gaacaaatac 5160
tgcctctgga ctctgaat 5178

<210> SEQ ID NO 232
<211> LENGTH: 273
<212> TYPE: DNA
<213> ORGANISM: Homo Sapiens

<400> SEQUENCE: 232
gccagaacac aaagcgtgaa tccggaagaa aagttcaatc tggaaacatc aatgctgcca 60
agactattgc agatatcatc cgaacatgtt tgggacccaa gtccatgatg aagatgcttt 120
tggacccaat gggaggcatt gtgatgacca atgatggcaa tgccattctt cgagagattc 180
aagtccagca tccagcggcc aagtccatga tcgaaattag ccggacccag gatgaagagg 240
ttggagatgg gaccacatca gtaattattc ttg 273

<210> SEQ ID NO 233
<211> LENGTH: 4474
<212> TYPE: DNA
<213> ORGANISM: Homo Sapiens

<400> SEQUENCE: 233
gagtgtttct caggagctat cagaaactat cctcaccatg gtagccaatt gcagtaatgt 60
tatgaataag gccagacaac caccacctgg agttatgcca aaaggacgtc ctcctagtgc 120
tagcagctta gatgccattt ctcctgttca gattgaccct cttgctggaa tgacatctct 180
tagtataggt ggttcagctg cccctcacac ccagagtatg cagggttttc ctccaaattt 240
gggttctgca ttcagtaccc ctcagtcacc agcaaaagca tttccacccc tttcaacccc 300
caatcagacc actgcattca gtggtattgg aggactttca tcacagcttc cagtaggtgg 360
tcttggcaca ggcagcctga ctggtatagg aactggtgct cttggactcc ctgcagtgaa 420
taacgaccct tttgtacaga ggaaactggg cacctctgga ctgaatcagc ctacattcca 480
gcagagtaag atgaaacctt cggacttgtc tcaggtgtgg ccagaggcaa accagcactt 540

```
tagtaaagag atagatgatg aagcaaacag ctatttccag cgaatatata atcatccacc    600
acatccaacc atgtctgttg atgaggtatt agaaatgctg cagagattta aagactctac    660
tataaagagg gaacgagaag tatttaactg tatgctaagg aacttgtttg aagaatatcg    720
tttttttccc cagtatcctg ataaagagtt acatataaca gcctgcctat ttggtggtat    780
aattgagaaa ggactggtca cttacatggc actaggtctg gctctacgat atgttcttga    840
agccttacgc aagccttttg gatccaaaat gtattatttc gggattgctg cactagatag    900
atttaaaaac agattgaagg actatcccca gtattgtcag catttggctt ctatcagtca    960
ctttatgcaa tttccacatc atttacagga gtatattgag tatggacagc agtctagaga   1020
tcctcctgtg aaaatgcaag gctctatcac aacccctgga agtattgcac tggctcaggc   1080
ccaggctcag gcccaggttc cagcaaaagc tcctcttgct ggtcaagtta gcactatggt   1140
aaccacctca acaactacca ctgttgctaa aacggttacg gtcaccaggc caactggagt   1200
cagctttaag aaagatgtgc caccttctat taatactaca aatatagata cgttgcttgt   1260
ggccacagat caaactgaga gaattgtgga gcccccagaa aatatccagg agaaaattgc   1320
ttttatttc aataatctct cacagtcaaa tatgacacaa aaggttgaag agctaaagga    1380
aacggtgaaa gaagaattta tgccttgggt ttcacagtat ctggttatga agagagtcag   1440
tattgagcca aactttcata gcctgtattc aaacttcctt gacacgctga agaatcctga   1500
atttaacaag atggttctga atgagaccta cagaaacatt aaagtgctcc tgacctctga   1560
taaagctgca gccaatttct cagatcgttc tttgctgaag aacttgggac attggctagg   1620
aatgatcaca ttagctaaaa acaaacccat cttacacact gacttggatg tgaaatcatt   1680
gctgctagag gcttatgtta aaggacaaca agaattgctc tatgtagtgc cctttgttgc   1740
caaagtctta gaatctagca ttcgtagtgt ggtttttagg ccaccaaacc cttggacaat   1800
ggcaattatg aatgtattag ctgagctaca tcaggagcat gacttaaagt taaacttgaa   1860
gtttgaaatc gaggttctct gcaagaacct tgcattagac atcaatgagc taaaacctgg   1920
aaacctccta aaggataaag atcgcctgaa gaatttagat gagcaactct ctgctccaaa   1980
gaaagatgtc aagcagccag aagaactccc tcccatcaca accacaacaa cttctactac   2040
accagctacc aacaccactt gtacagccac ggttccacca cagccacagt acagctacca   2100
cgacatcaat gtctattccc ttgcgggctt ggcaccacac attactctga atccaacaat   2160
tcccttgttt caggcccatc cacagttgaa gcagtgtgtg cgtcaggcaa ttgaacgggc   2220
tgtccaggag ctggtccatc ctgtggtgga tcgatcaatt aagattgcca tgactacttg   2280
tgagcaaata gtcaggaagg attttgccct ggattcggag gaatctcgaa tgcgaatagc   2340
agctcatcac atgatgcgta acttgacagc tggaatggct atgattacat gcagggaacc   2400
tttgctcatg agcatatcta ccaacttaaa aaacagtttt gcctcagccc ttcgtactgc   2460
ttccccacaa caaagagaaa tgatggatca ggcagctgct caattagctc aggacaattg   2520
tgagttggct tgctgtttta ttcagaagac tgcagtagaa aaagcaggcc ctgagatgga   2580
caagagatta gcaactgaat ttgagctgag aaaacatgct aggcaagaag gacgcagata   2640
ctgtgatcct gttgttttaa catatcaagc tgaacggatg ccagagcaaa tcaggctgaa   2700
agttggtggt gtggacccaa agcagttggc tgtttacgaa gagtttgcac gcaatgttcc   2760
tggcttctta cctacaaatg acttaagtca gcccacggga tttttagccc agcccatgaa   2820
gcaagcttgg gcaacagatg atgtagctca gatttatgat aagtgtatta cagaactgga   2880
gcaacatcta catgccatcc caccaacttt ggccatgaac cctcaagctc aggctcttcg   2940
```

aagtctcttg gaggttgtag ttttatctcg aaactctcgg gatgccatag ctgctcttgg 3000
attgctccaa aaggctgtag agggcttact agatgccaca agtggtgctg atgctgacct 3060
tctgctgcgc tacagggaat gccacctctt ggtcctaaaa gctctgcagg atggccgggc 3120
atatgggtct ccatggtgca acaaacagat cacaaggtgc ctaattgaat gtcgagatga 3180
atataaatat aatgtggagg ctgtggagct gctaattcgc aatcatttgg ttaatatgca 3240
gcagtatgat cttcacctag cgcagtcaat ggagaatggc ttaaactaca tggctgtggc 3300
atttgctatg cagttagtaa aaatcctgct ggtggatgaa aggagtgttg ctcatgttac 3360
tgaggcagat ctgttccaca ccattgaaac cctcatgagg attaatgctc attccagagg 3420
caatgctcca gaaggattgc cccagctgat ggaagtagtg cgatccaact atgaagcaat 3480
gattgatcgt gctcatggag gcccaaactt tatgatgcat tctgggatct ctcaagcctc 3540
agagtatgat gaccctccag gcctgaggga gaaggcagag tatcttctga gggaatgggt 3600
gaatctctac cattcagcag cagctggccg cgacagtacc aaagctttct ctgcatttgt 3660
tggacagatg caccagcaag gaatactgaa gaccgatgat ctcataacaa ggttctttcg 3720
tctgtgtact gaaatgtgtg ttgaaatcag ttaccgtgct caggctgagc agcagcacaa 3780
tcctgctgcc aatcccacca tgatccgagc caagtgctat cacaacctgg atgcctttgt 3840
tcgactcatt gcactgctcg tgaaacactc aggggaggcc accaacactg tcacaaagat 3900
taatctgctg aacaaggtcc ttggtatagt agtgggagtt ctccttcagg atcatgatgt 3960
tcgtcagagt gaatttcagc aacttcccta ccatcgaatt tttatcatgc ttctcttgga 4020
actcaatgca cctgagcatg tgttggaaac cattaatttc cagacactta cagctttctg 4080
caatacattc cacatcttga ggcctaccaa agctcctggc tttgtatatg cctggcttga 4140
actgatttcc catcggatat ttattgcaag aatgctggca catacgccac agcagaaggg 4200
gtggcctatg tatgcacagc tactgattga tttattcaaa tatttagcgc ctttccttag 4260
aaatgtggaa ctcaccaaac ctatgcaaat cctctacaag ggcactttaa gagtgctgct 4320
ggttcttttg catgatttcc cagagttcct ttgtgattac cattatgggt tctgtgatgt 4380
gatcccacct aattgtatcc agttaagaaa tttgatcctg agtgcctttc caagaaacat 4440
gaggctcccc gacccattca ctcctaatct aaag 4474

<210> SEQ ID NO 234
<211> LENGTH: 180
<212> TYPE: DNA
<213> ORGANISM: Homo Sapiens

<400> SEQUENCE: 234
gtcggttgat gcgctgtgtc cgctgtcctg tggcatacca cgccaatgac ttttgcctgg 60
ctgctgggtc aaagatcctt gcatctaata gtatcatctg ccctaatcac tttaccccta 120
ggcggggctg ccgaaatcat gagcatgtta atgttagctg gtgctttgtg tgctcagaag 180

<210> SEQ ID NO 235
<211> LENGTH: 878
<212> TYPE: DNA
<213> ORGANISM: Homo Sapiens

<400> SEQUENCE: 235
ggttttgtct ccacaattat ccgtttactt gacagcccct caacatgcat tagagcaaaa 60
gccttcctgg ttcttctata tattttgatt tataaccgtg agatgttgct gctcagttgc 120

```
caagcaagac tggtgatgta catcgagaga gacagcagaa agaccactcc aggcaaggag    180

cagcaaagtg gcaatgaata cctgtccaaa tgcctggatc ttctcatctg tcacattgtg    240

caggagctgc cacgaatcct gggtgacatt cttaactcct tggctaatgt ttctggacgt    300

aaacacccat caacagttca agtgaaacag ctgaagttgt gtctcccccct gatgcctgta    360

gtgcttcacc tcgtaacttc acaggtattt cgacctcaag ttgtgacaga agagtttctt    420

ttcagctatg gaactattct tagtcatatt aaatctgtag actcaggaga aacgaacata    480

gatggagcca taggactgac agcatcagaa gaatttatca agatcacatt gtcagctttt    540

gaagcaataa tacagtatcc tattttattg aaagactatc gctccacggt tgttgactat    600

atactgccac ccttggtgtc cttggttcaa agccaaaatg tggagtggag actctttagc    660

ttgcggttgc tctcagaaac cacatctcta ctcgtgaacc aggagtttgg ggatggcaag    720

gagaaggcca gtgttgattc tgacagcaat cttctggctc tcattcgaga tgtcttactt    780

ccccagtatg agcacattct tttagaacct gacccagtac cagcatatgc tctgaaactg    840

ctagtcgcga tgactgaaca caacccaact ttcacaag                            878
```

<210> SEQ ID NO 236
<211> LENGTH: 5130
<212> TYPE: DNA
<213> ORGANISM: Homo Sapiens

<400> SEQUENCE: 236

```
aacgtggttc tcctcaagat ttagttacta aagacatcac tgacacatca attggggctt     60

attggacatc tgctccagga atggttcgcg gttacagggt ctcatggaaa tcactttatg    120

atgatgttga cactggagag aaaaatctgc ctgaagatgc aattcatacg atgatagaaa    180

atctgcagcc agagaccaaa tacagaattt cagtatttgc cacttacagc agtggagaag    240

gagaaccttt gactggagat gccacaactg aattatctca agattccaaa accctgaaag    300

tagatgaaga aacagaaaac acaatgagag ttacatggaa accagcacca gggaaagtcg    360

tcaactaccg tgttgtctat cgccctcatg ggagagggaa gcaaatggtt gctaaggtgc    420

cccccacagt cacttcgaca gtgttaaagc gacttcagcc acagaccaca tatgacatca    480

cagttcttcc tatttacaag atgggagaag gaaagcttag gcaaggatca ggaacaacag    540

cttctcggtt taagtctcct agaaacctca aaacatctga cccaaccatg tcaagcttcc    600

gagtgacttg ggagcctgcc cctggggaag tgaagggtta taaagtcaca ttccacccta    660

cgggggatga cagaagactg gggggagttag tggttggacc ctatgacaac acagttgttt    720

tggaggaact tagggctggt accacctata aagtaaatgt ttttggaatg tttgatggag    780

gagaaagctc accacttgtt ggacaagaaa tgacaaccct ttccgacaca actgttatgc    840

caattttatc ttctgggatg gagtgtctca ccagagctga ggcagacatt gtgttgctgg    900

tggatggatc atggagcatc ggccgggcaa attttagaac cgtgaggagt ttcatttctc    960

gtattgtgga agtctttgac attggcccca aaagagtaca aattgctctt gctcagtata   1020

gtggggatcc cagaacagag tggcagttaa atgcacacag agacaagaag agcttgttgc   1080

aagctgtggc aaacttgccg tacaaaggag gcaatactct cacaggcatg gctttgaatt   1140

tcattcgcca acagaacttc aggacccaag ctggcatgag acctcgagct cgaaaaattg   1200

gtgtgctcat tactgatgga aaatcacaag acgatgttga agcaccttca aagaaactca   1260

aggatgaggg agtggagctg tttgctattg gtattaaaaa tgctgatgaa gtcgaattaa   1320

agatgattgc aactgatcct gatgataccc atgcatacaa tgtggcagat tttgagtcac   1380
```

```
tctccaggat agtggatgat ctcaccatta atttgtgtaa cagtgtcaaa ggtccaggtg   1440
atttggaagc accttctaac ttagttattt ctgagcgaac ccatcgttct tttagagtga   1500
gctggacacc accttctgac agtgtggatc gatataaggt ggaatactat ccagtttctg   1560
gagggaaacg tcaagaattt tatgtgagtc gaatggaaac tagcacagtg ctgaaagatc   1620
tgaaacctga aactgaatat gttgtcaatg tgtattctgt ggtagaagat gaatatagtg   1680
agcctctgaa ggggacagaa aaaaccttgc cagtgcctgt agtcagcctg aatatttatg   1740
atgttggccc taccaccatg catgtgcagt ggcagcctgt gggaggagct actggctaca   1800
tcttgtcata caaacctgtt aaggacacag agccaacaag acccaaagag gtgcgtttgg   1860
ggccaacagt gaatgacatg cagctgactg accttgttcc caacacggag tatgcagtca   1920
cagtccaggc tgtcctgcac gacctcacta gtgaacctgt cactgttcgg gaagtcacct   1980
tgcctttacc cagacctcag gatctgaaac tcagagatgt gactcacagc actatgaatg   2040
tcttttggga acctgtgcct ggaaaagtgc gtaaatatat tgttcgatac aaaacaccag   2100
aagaggatgt caaagaggta gaggtggaca gatcagagac cagcacttcc ctcaaagacc   2160
tcttctcaca gaccttgtac acagtcagcg tttctgcagt acatgacgag gggagtctc    2220
ctccagtgac tgctcaagaa actacccgac ccgtgccagc cccaacaaac ttaaagatta   2280
ctgaagtaac atcagagggt ttcagaggga cttgggatca tggagcttca gatgtgtctc   2340
tctacagaat aacttgggca ccttttggaa gctcagataa gatggagacc atcttaaatg   2400
gagatgaaaa cactttggtg ttcgaaaacc tgaaccccaa caccatctat gaagtttcca   2460
ttactgccat ctatcctgat gagtcagaaa gtgatgacct gattggcagt gagcgcacac   2520
tgcctatctt aacaacacaa gctcccaaaa gtggcccacg aaaccttcaa gtgtacaatg   2580
caacatctaa cagcctgact gttaagtggg atcctgctag tggtcgtgtg cagaaatata   2640
ggatcactta tcagccttcc acaggggaag gcaatgagca aacgaccaca ataggaggac   2700
ggcagaacag tgtggtcctg cagaaactga agccagacac tccttacact atcaccgtat   2760
cctctctgta tcctgatggt gaaggaggtc ggatgacggg aagaggcaag accaaacctc   2820
taaacactgt aaggaacctg agagtgtatg acccttctac cagcaccttg aatgtccgct   2880
gggaccatgc agagggaaat cctcgtcagt acaagctctt ctatgcacca gcagcaggtg   2940
gtccagagga actggtacca atccccggga ataccaatta tgccattctt aggaatctgc   3000
agccagatac ctcatacact gtgactgtag ttcccgttta tactgaaggt gatgggggac   3060
gcacatcaga tactggaagg acattgatga gaggactggc aagaaatgtc caagtataca   3120
atcctacacc taacagcctc gatgttcgct gggaccctgc tccaggacct gtgctgcaat   3180
atcgcgttgt gtattctcct gtggatggca caagaccctc agaatctata gtagtgccag   3240
gaaacacgcg catggtgcat ctggagcggc tgattccgga cacactctat tccgtgaacc   3300
ttgtggctct gtactcggat ggagagggaa atcccagccc tgcccagggc cgaacgctac   3360
cacgcagtgg accaaggaac ctgagagtct ttggtgaaac aaccaatagc ctctcggtag   3420
cctgggatca tgctgatggg ccagttcagc agtacaggat catctattct cccactgttg   3480
gtgatccaat tgatgaatat accacagtcc caggcagaag aaacaatgta atactgcagc   3540
ccctgcaacc tgacactcca tataaaatta ctgttattgc tgtttatgaa gatggagatg   3600
gtggccatct aacaggaaat ggaagaactg tgggactcct tcctcctcag aacatacaca   3660
tctctgacga atggtataca agattcaggg tgtcctggga tccttcacct tctccagttc   3720
```

```
ttggatataa aatagtatat aagccagtgg gttccaatga gcccatggaa gcctttgttg   3780

gagaaatgac atcatatacc ttacacaatc tcaatcccag caccacctac gatgtgaatg   3840

tttatgctca atatgattct ggactcagtg tccccttgac agatcaaggc actacattat   3900

atttaaatgt aacagatctg aaaacttacc agattgggtg ggatacattc tgtgtcaaat   3960

ggtcacctca ccgggcagcc acctcctaca ggctaaaact aagccctgca gatggaacaa   4020

ggggacaaga aattacagtg cgtggatcag aaaccagtca ctgcttcact ggcctttcac   4080

cagacactga ttatggtgtc actgtttttg tgcagacacc aaatctcgag ggaccaggag   4140

tctctgttaa agaacatacc actgtgaaac caacagaagc ccctacagag ccacccacac   4200

ctcctccccc tcccaccatt ccaccagccc gggatgtatg caaaggggcc aaggcagata   4260

ttgtgttctt gactgatgcc tcctggagca ttggggacga taattttaac aaagttgtaa   4320

aattcatctt caatactgtg ggaggctttg atgaaatcag tcctgctggg attcaggttt   4380

catttgtgca atacagcgat gaggtcaagt ctgagttcaa gctgaacacg tacaatgaca   4440

aggccctagc ccttggggcc ctccagaata ttaggtacag aggaggaaac acaagaacag   4500

gcaaggccct cacgtttatc aaggagaaag tcttgacttg ggagagcggc atgaggaaga   4560

atgtccctaa ggtgttggtt gtggtcacgg acggtcggtc ccaggatgag gtcaagaagg   4620

cggctttggt catccagcag tcagggttca gtgtctttgt agttggtgtg gctgatgtcg   4680

actacaatga gcttgccaac attgccagca aaccaagtga acggcacgtg ttcattgtgg   4740

acgactttga atcttttgag aagatcgaag acaatcttat tacatttgtt tgtgaaactg   4800

ccacttcaag ttgtcctctc atttatttgg atggctacac ctcaccaggt tttaaaatgc   4860

ttgaagcata caacctgaca gaaaagaatt ttgcttctgt acaaggagta tctttggagt   4920

cagggtcttt ccccagctac tcagcataca ggattcagaa gaatgcgttt gtgaatcagc   4980

ctacagcaga cctacaccca aatggactcc ctccttcata cacgattata ttattattca   5040

gacttctccc agaaactccc agtgaccctt ttgcaatttg gcaaatcaca gacagagact   5100

acaaaccaca agttggagtg attgcagatc                                    5130
```

<210> SEQ ID NO 237
<211> LENGTH: 447
<212> TYPE: DNA
<213> ORGANISM: Homo Sapiens

<400> SEQUENCE: 237

```
atgagagtcc ctacactaaa tccgccagcc agacaaagcc gcctgatgga gcgttggctg     60

tgaggagaca gagcatccca gaggaattca agggctccac agtcgtcgag ctgatgaaga    120

aggaaggcac taccctgggt ctgacggtat cgggaggaat tgataaggat ggcaagccaa    180

gagtatctaa tctgcggcaa ggaggaattg ctgctagaag tgaccagctg gatgtgggtg    240

actacatcaa agcagtgaat ggaatcaacc tggccaaatt ccgccatgac gagatcatca    300

gcttgctgaa gaatgtggga gaaagagtgg ttcttgaagt agagtacgag cttccaccgg    360

tctctgtgca aggatcaagt gttattttcc gaacagtgga ggtcacatta cataaagaag    420

gcaatacctt tggttttgta attcgag                                         447
```

<210> SEQ ID NO 238
<211> LENGTH: 867
<212> TYPE: DNA
<213> ORGANISM: Homo Sapiens

<400> SEQUENCE: 238

```
aaactttgtc tgcgaacact ctttaatgga ccagatcagg atttgagcgg aagaacgaat     60

gtaactttaa ggcaggaaag acaaatttta ttcttcataa agtgatgagc atataataat    120

tccaggcaca tggcaataga ggccctctaa ataaggaata aataacctct tagacaggtg    180

ggagattatg atcagagtaa aaggtaatta cacattttat ttccagaaag tcaggggtct    240

ataaattgac agtgattaga gtaatacttt ttcacatttc caaagtttgc atgttaactt    300

taaatgctta caatcttaga gtggtaggca atgttttaca ctattgacct tatataggga    360

agggaggggg tgcctgtggg gttttaaaga attttccttt gcagaggcat ttcatccttc    420

atgaagccat tcaggatttt gaattgcata tgagtgcttg gctcttcctt ctgttctagt    480

gagtgtatga gaccttgcag tgagtttatc agcatactca aaattttttt cctggaattt    540

ggagggatgg gaggaggggg tggggcttac ttgttgtagc tttttttttt tttacagact    600

tcacagagaa tgcagttgtc ttgacttcag gtctgtctgt tctgttggca agtaaatgca    660

gtactgttct gatcccgctg ctattagaat gcattgtgaa acgactggag tatgattaaa    720

agttgtgttc cccaatgctt ggagtagtga ttgttgaagg aaaaaatcca gctgagtgat    780

aaaggctgag tgttgaggaa atttctgcag ttttaagcag tcgtatttgt gattgaagct    840

gagtacattt tgctggtgta tttttag                                        867
```

<210> SEQ ID NO 239
<211> LENGTH: 206
<212> TYPE: DNA
<213> ORGANISM: Homo Sapiens

<400> SEQUENCE: 239

```
gaattttcaa cgtccggttc atctaataca gacactggta aagttactgg gaccttggag     60

accaaataca agtggtgtga gtatggtctg actttcacag aaaagtggaa cactgataac    120

actctgggaa cagaaatcgc aattgaagac cagatttgtc aaggtttgaa actgacattt    180

gatactacct tctcaccaaa cacagg                                         206
```

<210> SEQ ID NO 240
<211> LENGTH: 1553
<212> TYPE: DNA
<213> ORGANISM: Homo Sapiens

<400> SEQUENCE: 240

```
gaattgtgcg ggcgcgggga attatggggg tgggggctgg gagggtctct caaagtgggg     60

ctccgagccc gggaggagca ggcaggtgag ggttagggag gggatgcggc gggctggttt    120

gatggctgtg ccacactctt ctgagcttgg ggcctggggg acggaggggt tggttattgg    180

ttcaggaggt ctggggcaag gaagaggctg tagaatgtgg tgggacctcg accactcctg    240

gaaaggaggc tgctttgagg gggtgggacc gaggcctgat gagaggagga tggtctcctg    300

gggaaggatt tgggccaggg tccctgatgt tggggttgtg ggggatagtg ttagattcag    360

agtgtggaag gaaaaaacgc ttggggtttc tgggtgatta cagttggtgc ttttggggag    420

ggtctcccct ttggagaaga ggctggaggt gggaggccct ggtaaaagat tcaatttccc    480

ccagtggcct tagaggctct aaaaatggct tccctaaggc ctcggaggct gtcctctcca    540

caaaaatccc agcacccttc gctcagctta taatcaggca aagccacagg gcctgaagcc    600

ccaggttcaa atcctccttt ggcctttggc tttctctgtg accttgggca aatgcctttg    660

cccctctggc ctgtttcctg ttctgcaaaa tgttgagggg aatcttccct acttcctgga    720
```

```
gtatttgtaa acattaaata ataattagct ctaataatgg ctaacactat ttgagcctga    780

tgccaagggc ttgatgcatg ggttaatttc tcccaacaag ctggggttgt tgttacaccc    840

actgtataga tgaggaaact gaggcctgga gcccttgagt tacacagaaa gtgatcggca    900

gtgtggggaa tcagtacagt ggagactttg aggggctgtg taggattctg acccacatct    960

ctgcccccca cttccagggc caattcctgt ccccccagca gcatggcatc gtgtgctgaa   1020

ccctctgagc cctctgcccc actgcccgcc ggggtcccac cgctcgagga cttcgaggta   1080

ctggatgggg ttgaggatgc agagggtgag gaggaagagg aggaggaaga ggaggaagag   1140

gatgacctga gtgagctgcc accgctggag gacatgggac aacccccggc ggaggaggct   1200

gagcagcctg ggccctggc ccgagagttc cttgctgcca tggagcccga gcccgcccca   1260

gccccggccc cagaagagtg gctggacatt ctggggaacg ggctgttgag gaagaagacg   1320

ctggtcccag ggccgccagg ttcgagccgc ccggtcaagg gccaggtggt caccgtacat   1380

ctgcagacgt cgctggagaa tggcacacgg gtgcaggagg agccggagct ggtgttcact   1440

ctgggtgact gtgacgtcat ccaggccctg gatctcagtg tcccactcat ggacgtgggg   1500

gagacggcca tggtcactgc tgactccaag tactgctacg gcccccaagg cag           1553
```

```
<210> SEQ ID NO 241
<211> LENGTH: 1135
<212> TYPE: DNA
<213> ORGANISM: Homo Sapiens

<400> SEQUENCE: 241

atcttgagcc agatgattgt gcatccattt acatctttaa tgtagatcca cctccatcta     60

ctttaaccac accactttgc ttaccacatc atggattacc gtctcactct tctgttttgt    120

caccatcgtt tcagctccaa agtcacaaaa actatgaagg aacttgtgag attcctgaat    180

ctaaatatag cccattaggt ggtcccaaac cctttgagtg cccaagtatt caaattacat    240

ctatctctcc taactgtcat caagaattag atgcacatga agatgaccta cagataaatg    300

acccagaacg ggaatttttg gaaaggcctt ctagagatca tctctatctt cctcttgagc    360

catcctaccg ggagtcttct cttagtccta gtcctgccag cagcatctct tctaggagtt    420

ggttctctga tgcatcttct tgtgaatcgc tttcacatat ttatgatgat gtggactcag    480

agttgaatga agctgcagcc cgatttaccc ttggatcccc tctgacttct cctggtggct    540

ctccaggggg ctgccctgga gaagaaactt ggcatcaaca gtatggactt ggacactcat    600

tatcacccag gcaatctcct tgccactctc ctagatccag tgtcactgat gagaattggc    660

tgagccccag gccagcctca ggaccctcat caaggcccac atccccctgt gggaaacgga    720

ggcactccag tgctgaagtt tgttatgctg ggtccctttc accccatcac tcacctgttc    780

cttcacctgg tcactccccc aggggaagtg tgacagaaga tacgtggctc aatgcttctg    840

tccatggtgg gtcaggcctt ggccctgcag tttttccatt tcagtactgt gtagagactg    900

acatccctct caaaacaagg aaaacttctg aagatcaagc tgccatacta ccaggaaaat    960

tagagctgtg ttcagatgac caagggagtt tatcaccagc ccgggagact tcaatagatg   1020

atggccttgg atctcagtat cctttaaaga aagattcatg tggtgatcag tttctttcag   1080

ttccttcacc ctttacctgg agcaaaccaa agcctggcca cacccctata tttcg        1135

<210> SEQ ID NO 242
<211> LENGTH: 100
<212> TYPE: DNA
<213> ORGANISM: Artificial
```

<220> FEATURE:
<223> OTHER INFORMATION: hsa_circ_0130587 (circMIR5695) junction
      sequence 3' End

<400> SEQUENCE: 242
tttgaatttt cagaggaaaa gacagtgaga gagcaagagc agattgagaa gcagaagagt     60
gagtcgcaaa aagagaaaat gacagaaatg gagcaccctg                          100

<210> SEQ ID NO 243
<211> LENGTH: 100
<212> TYPE: DNA
<213> ORGANISM: Artificial
<220> FEATURE:
<223> OTHER INFORMATION: hsa_circ_0130587 (circMIR5695) junction
      sequence 5' End

<400> SEQUENCE: 243
ggaaaagaaa ccaagtctcc ttgaatcagt ttatcccaat gtcttctggt tttctatgtt     60
ggctacagtc aagataacct attactaagg taggttgtgt                          100

<210> SEQ ID NO 244
<211> LENGTH: 83
<212> TYPE: DNA
<213> ORGANISM: Artificial
<220> FEATURE:
<223> OTHER INFORMATION: hsa_circ_0023881 (circPICALM) junction sequence
      3' End

<400> SEQUENCE: 244
ctgtaatgac gcaaccaacc ttaatataca gccagcctgt catgagacct ccaaacccct     60
ttggccctgt atcaggagca cag                                             83

<210> SEQ ID NO 245
<211> LENGTH: 82
<212> TYPE: DNA
<213> ORGANISM: Artificial
<220> FEATURE:
<223> OTHER INFORMATION: hsa_circ_0023881 (circPICALM) junction sequence
      5' End

<400> SEQUENCE: 245
gcaccccctg taatggccta tcctgctact acaccaacag gcatgatagg atatggaatt     60
cctccacaaa tgggaagtgt tc                                              82

<210> SEQ ID NO 246
<211> LENGTH: 100
<212> TYPE: DNA
<213> ORGANISM: Artificial
<220> FEATURE:
<223> OTHER INFORMATION: hsa_circ_0131196 (circTULP4) junction sequence
      3' End

<400> SEQUENCE: 246
gcgaggagtg gttggggtga ctttcacctc tagtcactgt cgcagggaca ggagtactcc     60
acagaggata aatttcaacc tccggggcca caatagcgag                          100

<210> SEQ ID NO 247
<211> LENGTH: 100
<212> TYPE: DNA
<213> ORGANISM: Artificial
<220> FEATURE:
<223> OTHER INFORMATION: hsa_circ_0131196 (circTULP4) junction sequence
      5' End

<400> SEQUENCE: 247
tcctgggtca agctgagtat ctccacgttt aggtgcacaa atactatttt gtgaagatct 60
taaatttgtg gtataagaac ttgaaggaaa tagaactgat 100

<210> SEQ ID NO 248
<211> LENGTH: 100
<212> TYPE: DNA
<213> ORGANISM: Artificial
<220> FEATURE:
<223> OTHER INFORMATION: hsa_circ_0091072 (circCHIC1) junction sequence 3' End

<400> SEQUENCE: 248
ggctctcccg gtcaatgtga aatggctgct gtgtggttgt ctctgctgct gttgcacact 60
gggttgcagc ctatggcctg ttatttgtct caacaaaaga 100

<210> SEQ ID NO 249
<211> LENGTH: 100
<212> TYPE: DNA
<213> ORGANISM: Artificial
<220> FEATURE:
<223> OTHER INFORMATION: hsa_circ_0091072 (circCHIC1) junction sequence 5' End

<400> SEQUENCE: 249
gtttggcttg agcaacaagt ttgatactga atttccctcc gttctaacag ggaaggtggc 60
cccagaagaa tttaaaacca gcattggccg tgtgaatgca 100

<210> SEQ ID NO 250
<211> LENGTH: 100
<212> TYPE: DNA
<213> ORGANISM: Artificial
<220> FEATURE:
<223> OTHER INFORMATION: hsa_circ_0007422 (circSATB2) junction sequence 3' End

<400> SEQUENCE: 250
tccccagcat gagagggatg tcatctatga ggaggagtca aggcatcacc acagcgaacg 60
catgcaacac gtggtccagc ttccccctga gccggtgcag 100

<210> SEQ ID NO 251
<211> LENGTH: 100
<212> TYPE: DNA
<213> ORGANISM: Artificial
<220> FEATURE:
<223> OTHER INFORMATION: hsa_circ_0007422 (circSATB2) junction sequence 5' End

<400> SEQUENCE: 251
gtttgatgat tcctgtcttt tgtgtcgtgg agcagttgga cggctctctt gaatatgaca 60
acagagaaga acacgccgag tttgtcctgg tgcggaaaga 100

<210> SEQ ID NO 252
<211> LENGTH: 100
<212> TYPE: DNA
<213> ORGANISM: Artificial
<220> FEATURE:
<223> OTHER INFORMATION: hsa_circ_0007097 (circDDX50) junction sequence 3' End

<400> SEQUENCE: 252
gagtagtaat gcagtgtctc agattaccag aatgtgcctc ctgaaaggaa atatgggtgt 60
ttgctttgat gttcctacaa ctgagtcaga aaggttacag 100

<210> SEQ ID NO 253
<211> LENGTH: 100
<212> TYPE: DNA
<213> ORGANISM: Artificial
<220> FEATURE:
<223> OTHER INFORMATION: hsa_circ_0007097 (circDDX50) junction sequence 5' End

<400> SEQUENCE: 253
gtctctggct tccgtttctt acgctgctgt tgattttttc cgaccatcag ctcagagact 60
gatagaagag aaaggtgcag tggatgcatt ggctgcagct 100

<210> SEQ ID NO 254
<211> LENGTH: 100
<212> TYPE: DNA
<213> ORGANISM: Artificial
<220> FEATURE:
<223> OTHER INFORMATION: hsa_circ_0009581 (circRERE) junction sequence 3' End

<400> SEQUENCE: 254
gagcatggcg gcatttgcag gaatgtgtga tggaggctct acagaggacg gctgtgtcgc 60
agcctctcgg gatgacacca ctctgaatgc actgaacaca 100

<210> SEQ ID NO 255
<211> LENGTH: 100
<212> TYPE: DNA
<213> ORGANISM: Artificial
<220> FEATURE:
<223> OTHER INFORMATION: hsa_circ_0009581 (circRERE) junction sequence 5' End

<400> SEQUENCE: 255
agggaagtgt aacatctccc atttttctga catatttgct gctagagagt ttaaagcccg 60
agtggattca tttttctaca tattaggata taaccctgag 100

<210> SEQ ID NO 256
<211> LENGTH: 98
<212> TYPE: DNA
<213> ORGANISM: Artificial
<220> FEATURE:
<223> OTHER INFORMATION: hsa_circ_0060342 (circRALGAPB) junction sequence 3' End

<400> SEQUENCE: 256
tcgcaccaat agtggtatta gttcagcaag tggtggaagc acggagccca cgactcccga 60
tagtgagaga cctgctcaag ctctcttaag agattatg 98

<210> SEQ ID NO 257
<211> LENGTH: 97
<212> TYPE: DNA
<213> ORGANISM: Artificial
<220> FEATURE:
<223> OTHER INFORMATION: hsa_circ_0060342 (circRALGAPB) junction sequence 5' End

<400> SEQUENCE: 257
gggcaatgtt aaatattgtt caagattcag cacttttgga agccattggt tgccagatgg 60
agatgggtgg tggagaaaat aacctgaaga gtcatag 97

<210> SEQ ID NO 258

<211> LENGTH: 100
<212> TYPE: DNA
<213> ORGANISM: Artificial
<220> FEATURE:
<223> OTHER INFORMATION: hsa_circ_0001946 (circCDR1as) junction sequence
3' End

<400> SEQUENCE: 258
tacccagtct tccatcaact ggctcaatat ccatgtcttc caacgtctcc agtgtgctga 60
tcttctgaca ttcaggtctt ccagtgtctg caatatccag 100

<210> SEQ ID NO 259
<211> LENGTH: 100
<212> TYPE: DNA
<213> ORGANISM: Artificial
<220> FEATURE:
<223> OTHER INFORMATION: hsa_circ_0001946 (circCDR1as) junction sequence
5' End

<400> SEQUENCE: 259
ggtttccgat ggcacctgtg tcaaggtctt ccaacaactc cgggtcttcc agcgacttca 60
agtcttccaa taatctcaag gtcttccaga taatcctgag 100

<210> SEQ ID NO 260
<211> LENGTH: 100
<212> TYPE: DNA
<213> ORGANISM: Artificial
<220> FEATURE:
<223> OTHER INFORMATION: hsa_circ_0062277 (circCOMT) junction sequence
3' End

<400> SEQUENCE: 260
catcccccag ctgaagaaga agtatgatgt ggacacactg gacatggtct tcctcgacca 60
ctggaaggac cggtacctgc cggacacgct tctcttggag 100

<210> SEQ ID NO 261
<211> LENGTH: 100
<212> TYPE: DNA
<213> ORGANISM: Artificial
<220> FEATURE:
<223> OTHER INFORMATION: hsa_circ_0062277 (circCOMT) junction sequence
5' End

<400> SEQUENCE: 261
aaataacatc tgctttgctg ccgagctcag aggagacccc agacccctcc cgcagccaga 60
gggctggagc ctgctcagag gtgctttgaa gaggatccct 100

<210> SEQ ID NO 262
<211> LENGTH: 100
<212> TYPE: DNA
<213> ORGANISM: Artificial
<220> FEATURE:
<223> OTHER INFORMATION: hsa_circ_0005133 (circDDR1) junction sequence
3' End

<400> SEQUENCE: 262
tgccgggggc ctgggcaagg agttctcccg gagctaccgg ctgcgttact cccgggatgg 60
tcgccgctgg atgggctgga aggaccgctg gggtcaggag 100

<210> SEQ ID NO 263
<211> LENGTH: 100
<212> TYPE: DNA
<213> ORGANISM: Artificial
<220> FEATURE:

<223> OTHER INFORMATION: hsa_circ_0005133 (circDDR1) junction sequence 5' End

<400> SEQUENCE: 263
agatgctgcc cccaccccct taggcccgag ggatcaggag ctatgggacc agaggccctg 60
tcatctttac tgctgctgct cttggtggca agtggagatg 100

<210> SEQ ID NO 264
<211> LENGTH: 100
<212> TYPE: DNA
<213> ORGANISM: Artificial
<220> FEATURE:
<223> OTHER INFORMATION: hsa_circ_0103668 (circTRIM69) junction sequence 3' End

<400> SEQUENCE: 264
tgagcaagga ttctggcttt taagactaag gaaccaaact gatctaaagg ctctggattt 60
gccttctttc agtctgacac tgactaacaa cctcgacaag 100

<210> SEQ ID NO 265
<211> LENGTH: 100
<212> TYPE: DNA
<213> ORGANISM: Artificial
<220> FEATURE:
<223> OTHER INFORMATION: hsa_circ_0103668 (circTRIM69) junction sequence 5' End

<400> SEQUENCE: 265
gcctgtctcc actaactctg gaccctaaaa cagctcaccc aaatctggtg ctctccaaaa 60
gccaaaccag cgtctggcat ggtgacatta agaagataat 100

<210> SEQ ID NO 266
<211> LENGTH: 69
<212> TYPE: DNA
<213> ORGANISM: Artificial
<220> FEATURE:
<223> OTHER INFORMATION: hsa_circ_0027446 (circHMGA2) junction sequence 3' End

<400> SEQUENCE: 266
tctaaagcag ctcaaaagaa agcagaagcc actggagaaa aacggccaag aggcagacct 60
aggaaatgg 69

<210> SEQ ID NO 267
<211> LENGTH: 69
<212> TYPE: DNA
<213> ORGANISM: Artificial
<220> FEATURE:
<223> OTHER INFORMATION: hsa_circ_0027446 (circHMGA2) junction sequence 5' End

<400> SEQUENCE: 267
gaaccaaccg gtgagccctc tcctaagaga cccaggggaa gacccaaagg cagcaaaaac 60
aagagtccc 69

<210> SEQ ID NO 268
<211> LENGTH: 100
<212> TYPE: DNA
<213> ORGANISM: Artificial
<220> FEATURE:
<223> OTHER INFORMATION: hsa_circ_0060930 (circCYP24A1) junction sequence 3' End

<400> SEQUENCE: 268
caggccacag acaatgagcc tgttgagatg ctacactcag gcaccctggt gcccagccgg 60
gaactcccca tcgcgttttg ccagcgataa tacgcctcag 100

<210> SEQ ID NO 269
<211> LENGTH: 100
<212> TYPE: DNA
<213> ORGANISM: Artificial
<220> FEATURE:
<223> OTHER INFORMATION: hsa_circ_0060930 (circCYP24A1) junction sequence 5' End

<400> SEQUENCE: 269
gacaggagga aacgcagcgc cagcagcatc tcatctaccc tccttgacac ctccccgtgg 60
ctccagccag accctagagg tcagccttgc ggaccaacag 100

<210> SEQ ID NO 270
<211> LENGTH: 59
<212> TYPE: DNA
<213> ORGANISM: Artificial
<220> FEATURE:
<223> OTHER INFORMATION: hsa_circ_0075410 (circDUSP22) junction sequence 3' End

<400> SEQUENCE: 270
gcaagaacaa ggtgacacat attctgtctg tccacgatag tgccaggcct atgttggag 59

<210> SEQ ID NO 271
<211> LENGTH: 58
<212> TYPE: DNA
<213> ORGANISM: Artificial
<220> FEATURE:
<223> OTHER INFORMATION: hsa_circ_0075410 (circDUSP22) junction sequence 5' End

<400> SEQUENCE: 271
atcctgcccg gcctgtacat cggcaacttc aaagatgcca gagacgcgga acaattga 58

<210> SEQ ID NO 272
<211> LENGTH: 100
<212> TYPE: DNA
<213> ORGANISM: Artificial
<220> FEATURE:
<223> OTHER INFORMATION: hsa_circ_0049241 (circICAM1) junction sequence 3' End

<400> SEQUENCE: 272
acacctggca aatttgattt tttttttttt tccagagacg gggtctcgca acattgccca 60
gacttccttt gtgttagtta ataaagcttt ctcaactgcc 100

<210> SEQ ID NO 273
<211> LENGTH: 100
<212> TYPE: DNA
<213> ORGANISM: Artificial
<220> FEATURE:
<223> OTHER INFORMATION: hsa_circ_0049241 (circICAM1) junction sequence 5' End

<400> SEQUENCE: 273
ccccccggta tgagattgtc atcatcactg tggtagcagc cgcagtcata atgggcactg 60
caggcctcag cacgtacctc tataaccgcc agcggaagat 100

<210> SEQ ID NO 274
<211> LENGTH: 100

<212> TYPE: DNA
<213> ORGANISM: Artificial
<220> FEATURE:
<223> OTHER INFORMATION: hsa_circ_0035301 (circMAPK6) junction sequence
3' End

<400> SEQUENCE: 274
tagaatttgt ttcatctatt ttattttatt gaatactgtc tgtatctttg gttatcctgt 60
ttgaagaaaa aggacaaata aaacatggcc agcaaataca 100

<210> SEQ ID NO 275
<211> LENGTH: 100
<212> TYPE: DNA
<213> ORGANISM: Artificial
<220> FEATURE:
<223> OTHER INFORMATION: hsa_circ_0035301 (circMAPK6) junction sequence
5' End

<400> SEQUENCE: 275
cccctcttcc tcgccctctc tcgcgggtcg gggttacatg gcggcgactg cggcaaagcg 60
agagcctcgg agacgccgct gccgccagca cagccggaga 100

<210> SEQ ID NO 276
<211> LENGTH: 100
<212> TYPE: DNA
<213> ORGANISM: Artificial
<220> FEATURE:
<223> OTHER INFORMATION: hsa_circ_0007335 (circVDAC2) junction sequence
3' End

<400> SEQUENCE: 276
ggaacactga taacactctg ggaacagaaa tcgcaattga agaccagatt tgtcaaggtt 60
tgaaactgac atttgatact accttctcac caaacacagg 100

<210> SEQ ID NO 277
<211> LENGTH: 100
<212> TYPE: DNA
<213> ORGANISM: Artificial
<220> FEATURE:
<223> OTHER INFORMATION: hsa_circ_0007335 (circVDAC2) junction sequence
5' End

<400> SEQUENCE: 277
gaattttcaa cgtccggttc atctaataca gacactggta aagttactgg gaccttggag 60
accaaataca agtggtgtga gtatggtctg actttcacag 100

<210> SEQ ID NO 278
<211> LENGTH: 100
<212> TYPE: DNA
<213> ORGANISM: Artificial
<220> FEATURE:
<223> OTHER INFORMATION: hsa_circ_0005615 (circNFATC3) junction sequence
3' End

<400> SEQUENCE: 278
agtatccttt aaagaaagat tcatgtggtg atcagtttct ttcagttcct tcacccttta 60
cctggagcaa accaaagcct ggccacaccc ctatatttcg 100

<210> SEQ ID NO 279
<211> LENGTH: 100
<212> TYPE: DNA
<213> ORGANISM: Artificial
<220> FEATURE:
<223> OTHER INFORMATION: hsa_circ_0005615 (circNFATC3) junction sequence 5' End

<400> SEQUENCE: 279
atcttgagcc agatgattgt gcatccattt acatctttaa tgtagatcca cctccatcta 60
ctttaaccac accactttgc ttaccacatc atggattacc 100

<210> SEQ ID NO 280
<211> LENGTH: 100
<212> TYPE: DNA
<213> ORGANISM: Artificial
<220> FEATURE:
<223> OTHER INFORMATION: hsa_circ_0002082 (circMALAT1) junction sequence
3' End

<400> SEQUENCE: 280
ccagctgagt gataaaggct gagtgttgag gaaatttctg cagttttaag cagtcgtatt 60
tgtgattgaa gctgagtaca ttttgctggt gtatttttag 100

<210> SEQ ID NO 281
<211> LENGTH: 100
<212> TYPE: DNA
<213> ORGANISM: Artificial
<220> FEATURE:
<223> OTHER INFORMATION: hsa_circ_0002082 (circMALAT1) junction sequence
5' End

<400> SEQUENCE: 281
aaactttgtc tgcgaacact ctttaatgga ccagatcagg atttgagcgg aagaacgaat 60
gtaactttaa ggcaggaaag acaaatttta ttcttcataa 100

<210> SEQ ID NO 282
<211> LENGTH: 100
<212> TYPE: DNA
<213> ORGANISM: Artificial
<220> FEATURE:
<223> OTHER INFORMATION: hsa_circ_0050124 (circFKBP8) junction sequence
3' End

<400> SEQUENCE: 282
acgtcatcca ggccctggat ctcagtgtcc cactcatgga cgtgggggag acggccatgg 60
tcactgctga ctccaagtac tgctacggcc cccaaggcag 100

<210> SEQ ID NO 283
<211> LENGTH: 100
<212> TYPE: DNA
<213> ORGANISM: Artificial
<220> FEATURE:
<223> OTHER INFORMATION: hsa_circ_0050124 (circFKBP8) junction sequence
5' End

<400> SEQUENCE: 283
gaattgtgcg ggcgcgggga attatggggg tgggggctgg gagggtctct caaagtgggg 60
ctccgagccc gggaggagca ggcaggtgag ggttagggag 100

<210> SEQ ID NO 284
<211> LENGTH: 100
<212> TYPE: DNA
<213> ORGANISM: Artificial
<220> FEATURE:
<223> OTHER INFORMATION: hsa_circ_0080968 (circADAM22) junction sequence
3' End

<400> SEQUENCE: 284
ctggcaatgg tgttgctggc accaatatca taataggcat aattgctggc accattttag 60
tgctggccct catattagga ataactgcgt ggggttataa 100

<210> SEQ ID NO 285
<211> LENGTH: 100
<212> TYPE: DNA
<213> ORGANISM: Artificial
<220> FEATURE:
<223> OTHER INFORMATION: hsa_circ_0080968 (circADAM22) junction sequence
5' End

<400> SEQUENCE: 285
gtgaatgtaa atgcgaggac acgtggtccg ggtgcataat gggagacact ggctattatc 60
ttcctaaaaa gttcacccag tgtaatattg aagagtatca 100

<210> SEQ ID NO 286
<211> LENGTH: 100
<212> TYPE: DNA
<213> ORGANISM: Artificial
<220> FEATURE:
<223> OTHER INFORMATION: hsa_circ_0000907 (circMYO9B) junction sequence
3' End

<400> SEQUENCE: 286
gagcaccaac ttcctcatcc actgcctcac cgccctcagc cagaagggct acgccagcgg 60
cgtcgagagg accatcctgg gtgctggccc tgtgctggag 100

<210> SEQ ID NO 287
<211> LENGTH: 100
<212> TYPE: DNA
<213> ORGANISM: Artificial
<220> FEATURE:
<223> OTHER INFORMATION: hsa_circ_0000907 (circMYO9B) junction sequence
5' End

<400> SEQUENCE: 287
ctccaggaca cgcgcgcccc gagcctggga ggcatgctga agccaggcgg ccggcaggat 60
gagtgtgaaa gaggcaggca gctcgggccg ccgggagcag 100

<210> SEQ ID NO 288
<211> LENGTH: 20
<212> TYPE: DNA
<213> ORGANISM: Artificial
<220> FEATURE:
<223> OTHER INFORMATION: circCHIC1-F1

<400> SEQUENCE: 288
gttgtctctg ctgctgttgc 20

<210> SEQ ID NO 289
<211> LENGTH: 20
<212> TYPE: DNA
<213> ORGANISM: Artificial
<220> FEATURE:
<223> OTHER INFORMATION: circCHIC1-R1

<400> SEQUENCE: 289
ccaccttccc tgttagaacg 20

<210> SEQ ID NO 290
<211> LENGTH: 20
<212> TYPE: DNA
<213> ORGANISM: Artificial
<220> FEATURE:

<223> OTHER INFORMATION: circCHIC1-F2

<400> SEQUENCE: 290
aatgtgaaat ggctgctgtg 20

<210> SEQ ID NO 291
<211> LENGTH: 20
<212> TYPE: DNA
<213> ORGANISM: Artificial
<220> FEATURE:
<223> OTHER INFORMATION: circCHIC1-R2

<400> SEQUENCE: 291
ccaccttccc tgttagaacg 20

<210> SEQ ID NO 292
<211> LENGTH: 20
<212> TYPE: DNA
<213> ORGANISM: Artificial
<220> FEATURE:
<223> OTHER INFORMATION: circCHIC1-F3

<400> SEQUENCE: 292
tctcccggtc aatgtgaaat 20

<210> SEQ ID NO 293
<211> LENGTH: 20
<212> TYPE: DNA
<213> ORGANISM: Artificial
<220> FEATURE:
<223> OTHER INFORMATION: circCHIC1-R3

<400> SEQUENCE: 293
ccaccttccc tgttagaacg 20

<210> SEQ ID NO 294
<211> LENGTH: 20
<212> TYPE: DNA
<213> ORGANISM: circCHIC1-F4

<400> SEQUENCE: 294
ggttgtctct gctgctgttg 20

<210> SEQ ID NO 295
<211> LENGTH: 20
<212> TYPE: DNA
<213> ORGANISM: Artificial
<220> FEATURE:
<223> OTHER INFORMATION: circCHIC1-R4

<400> SEQUENCE: 295
ccaccttccc tgttagaacg 20

<210> SEQ ID NO 296
<211> LENGTH: 21
<212> TYPE: DNA
<213> ORGANISM: circCHIC1-F5

<400> SEQUENCE: 296
ccggtcaatg tgaaatggct g 21

<210> SEQ ID NO 297
<211> LENGTH: 20
<212> TYPE: DNA
<213> ORGANISM: Artificial

<220> FEATURE:
<223> OTHER INFORMATION: circCHIC1-R5

<400> SEQUENCE: 297
tgttgctcaa gccaaactct 20

<210> SEQ ID NO 298
<211> LENGTH: 20
<212> TYPE: DNA
<213> ORGANISM: Artificial
<220> FEATURE:
<223> OTHER INFORMATION: circCHIC1-F6

<400> SEQUENCE: 298
ccggtcaatg tgaaatggct 20

<210> SEQ ID NO 299
<211> LENGTH: 22
<212> TYPE: DNA
<213> ORGANISM: circCHIC1-R6

<400> SEQUENCE: 299
acttgttgct caagccaaac tc 22

<210> SEQ ID NO 300
<211> LENGTH: 19
<212> TYPE: DNA
<213> ORGANISM: Artificial
<220> FEATURE:
<223> OTHER INFORMATION: circCHIC1-F7

<400> SEQUENCE: 300
tctgctgctg ttgcacact 19

<210> SEQ ID NO 301
<211> LENGTH: 22
<212> TYPE: DNA
<213> ORGANISM: Artificial
<220> FEATURE:
<223> OTHER INFORMATION: circCHIC1-R7

<400> SEQUENCE: 301
ttaaattctt ctggggccac ct 22

<210> SEQ ID NO 302
<211> LENGTH: 21
<212> TYPE: DNA
<213> ORGANISM: Artificial
<220> FEATURE:
<223> OTHER INFORMATION: circCHIC1-F8

<400> SEQUENCE: 302
atgtgaaatg gctgctgtgt g 21

<210> SEQ ID NO 303
<211> LENGTH: 22
<212> TYPE: DNA
<213> ORGANISM: Artificial
<220> FEATURE:
<223> OTHER INFORMATION: circCHIC1-R8

<400> SEQUENCE: 303
cttgttgctc aagccaaact ct 22

<210> SEQ ID NO 304

<211> LENGTH: 21
<212> TYPE: DNA
<213> ORGANISM: Artificial
<220> FEATURE:
<223> OTHER INFORMATION: circCHIC1-F9

<400> SEQUENCE: 304
ggtcaatgtg aaatggctgc t 21

<210> SEQ ID NO 305
<211> LENGTH: 21
<212> TYPE: DNA
<213> ORGANISM: Artificial
<220> FEATURE:
<223> OTHER INFORMATION: circCHIC1-R9

<400> SEQUENCE: 305
ttgttgctca agccaaactc t 21

<210> SEQ ID NO 306
<211> LENGTH: 20
<212> TYPE: DNA
<213> ORGANISM: Artificial
<220> FEATURE:
<223> OTHER INFORMATION: circMIR5695-F1

<400> SEQUENCE: 306
gcagaagagt gagtcgcaaa 20

<210> SEQ ID NO 307
<211> LENGTH: 22
<212> TYPE: DNA
<213> ORGANISM: Artificial
<220> FEATURE:
<223> OTHER INFORMATION: circMIR5695-R1

<400> SEQUENCE: 307
gccaacatag aaaaccagaa ga 22

<210> SEQ ID NO 308
<211> LENGTH: 20
<212> TYPE: DNA
<213> ORGANISM: Artificial
<220> FEATURE:
<223> OTHER INFORMATION: circMIR5695-F2

<400> SEQUENCE: 308
gcagaagagt gagtcgcaaa 20

<210> SEQ ID NO 309
<211> LENGTH: 23
<212> TYPE: DNA
<213> ORGANISM: Artificial
<220> FEATURE:
<223> OTHER INFORMATION: circMIR5695-R2

<400> SEQUENCE: 309
gaaaaccaga agacattggg ata 23

<210> SEQ ID NO 310
<211> LENGTH: 20
<212> TYPE: DNA
<213> ORGANISM: Artificial
<220> FEATURE:
<223> OTHER INFORMATION: circMIR5695-F3

<400> SEQUENCE: 310
gcagaagagt gagtcgcaaa 20

<210> SEQ ID NO 311
<211> LENGTH: 23
<212> TYPE: DNA
<213> ORGANISM: Artificial
<220> FEATURE:
<223> OTHER INFORMATION: circMIR5695-R3

<400> SEQUENCE: 311
agccaacata gaaaaccaga aga 23

<210> SEQ ID NO 312
<211> LENGTH: 21
<212> TYPE: DNA
<213> ORGANISM: Artificial
<220> FEATURE:
<223> OTHER INFORMATION: circMIR5695-F4

<400> SEQUENCE: 312
agcagaagag tgagtcgcaa a 21

<210> SEQ ID NO 313
<211> LENGTH: 23
<212> TYPE: DNA
<213> ORGANISM: Artificial
<220> FEATURE:
<223> OTHER INFORMATION: circMIR5695-R4

<400> SEQUENCE: 313
ccagaagaca ttgggataaa ctg 23

<210> SEQ ID NO 314
<211> LENGTH: 20
<212> TYPE: DNA
<213> ORGANISM: Artificial
<220> FEATURE:
<223> OTHER INFORMATION: circMIR5695-F5

<400> SEQUENCE: 314
gcagaagagt gagtcgcaaa 20

<210> SEQ ID NO 315
<211> LENGTH: 23
<212> TYPE: DNA
<213> ORGANISM: Artificial
<220> FEATURE:
<223> OTHER INFORMATION: circMIR5695-R5

<400> SEQUENCE: 315
gccaacatag aaaaccagaa gac 23

<210> SEQ ID NO 316
<211> LENGTH: 20
<212> TYPE: DNA
<213> ORGANISM: Artificial
<220> FEATURE:
<223> OTHER INFORMATION: circMIR5695-F6

<400> SEQUENCE: 316
aaatggagca ccctgggaaa 20

<210> SEQ ID NO 317
<211> LENGTH: 25
<212> TYPE: DNA

<213> ORGANISM: Artificial
<220> FEATURE:
<223> OTHER INFORMATION: circMIR5695-R6

<400> SEQUENCE: 317
gtaataggtt atcttgactg tagcc 25

<210> SEQ ID NO 318
<211> LENGTH: 20
<212> TYPE: DNA
<213> ORGANISM: Artificial
<220> FEATURE:
<223> OTHER INFORMATION: circMIR5695-F7

<400> SEQUENCE: 318
gacagaaatg gagcaccctg 20

<210> SEQ ID NO 319
<211> LENGTH: 23
<212> TYPE: DNA
<213> ORGANISM: Artificial
<220> FEATURE:
<223> OTHER INFORMATION: circMIR5695-R7

<400> SEQUENCE: 319
aataggttat cttgactgta gcc 23

<210> SEQ ID NO 320
<211> LENGTH: 20
<212> TYPE: DNA
<213> ORGANISM: Artificial
<220> FEATURE:
<223> OTHER INFORMATION: circMIR5695-F8

<400> SEQUENCE: 320
acatccccac cctgaatgtc 20

<210> SEQ ID NO 321
<211> LENGTH: 21
<212> TYPE: DNA
<213> ORGANISM: Artificial
<220> FEATURE:
<223> OTHER INFORMATION: circMIR5695-R8

<400> SEQUENCE: 321
ttttcccagg gtgctccatt t 21

<210> SEQ ID NO 322
<211> LENGTH: 21
<212> TYPE: DNA
<213> ORGANISM: Artificial
<220> FEATURE:
<223> OTHER INFORMATION: circMIR5695-F9

<400> SEQUENCE: 322
ggagcaccct gggaaaagaa a 21

<210> SEQ ID NO 323
<211> LENGTH: 22
<212> TYPE: DNA
<213> ORGANISM: Artificial
<220> FEATURE:
<223> OTHER INFORMATION: circMIR5695-R9

<400> SEQUENCE: 323
acctgtccac tcagatgcaa aa 22

<210> SEQ ID NO 324
<211> LENGTH: 21
<212> TYPE: DNA
<213> ORGANISM: Artificial
<220> FEATURE:
<223> OTHER INFORMATION: circMIR5695-F10

<400> SEQUENCE: 324
tacatcccca ccctgaatgt c 21

<210> SEQ ID NO 325
<211> LENGTH: 22
<212> TYPE: DNA
<213> ORGANISM: Artificial
<220> FEATURE:
<223> OTHER INFORMATION: circMIR5695-R10

<400> SEQUENCE: 325
acttggtttc ttttcccagg gt 22

<210> SEQ ID NO 326
<211> LENGTH: 21
<212> TYPE: DNA
<213> ORGANISM: Artificial
<220> FEATURE:
<223> OTHER INFORMATION: circMIR5695-F11

<400> SEQUENCE: 326
atccccaccc tgaatgtcct t 21

<210> SEQ ID NO 327
<211> LENGTH: 21
<212> TYPE: DNA
<213> ORGANISM: Artificial
<220> FEATURE:
<223> OTHER INFORMATION: circMIR5695-R11

<400> SEQUENCE: 327
tggtttcttt tcccagggtg c 21

<210> SEQ ID NO 328
<211> LENGTH: 21
<212> TYPE: DNA
<213> ORGANISM: Artificial
<220> FEATURE:
<223> OTHER INFORMATION: circMIR5695-F12

<400> SEQUENCE: 328
gaaatggagc accctgggaa a 21

<210> SEQ ID NO 329
<211> LENGTH: 22
<212> TYPE: DNA
<213> ORGANISM: Artificial
<220> FEATURE:
<223> OTHER INFORMATION: circMIR5695-R12

<400> SEQUENCE: 329
gtgtcatcta ggacctgtcc ac 22

<210> SEQ ID NO 330
<211> LENGTH: 20
<212> TYPE: DNA
<213> ORGANISM: Artificial
<220> FEATURE:

<223> OTHER INFORMATION: circCOMT-F1

<400> SEQUENCE: 330
acatggtctt cctcgaccac 20

<210> SEQ ID NO 331
<211> LENGTH: 20
<212> TYPE: DNA
<213> ORGANISM: Artificial
<220> FEATURE:
<223> OTHER INFORMATION: circCOMT-R1

<400> SEQUENCE: 331
cttcaaagca cctctgagca 20

<210> SEQ ID NO 332
<211> LENGTH: 20
<212> TYPE: DNA
<213> ORGANISM: Artificial
<220> FEATURE:
<223> OTHER INFORMATION: circCOMT-F2

<400> SEQUENCE: 332
atggtcttcc tcgaccactg 20

<210> SEQ ID NO 333
<211> LENGTH: 20
<212> TYPE: DNA
<213> ORGANISM: Artificial
<220> FEATURE:
<223> OTHER INFORMATION: circCOMT-R2

<400> SEQUENCE: 333
cttcaaagca cctctgagca 20

<210> SEQ ID NO 334
<211> LENGTH: 20
<212> TYPE: DNA
<213> ORGANISM: Artificial
<220> FEATURE:
<223> OTHER INFORMATION: circCOMT-F3

<400> SEQUENCE: 334
tcttcctcga ccactggaag 20

<210> SEQ ID NO 335
<211> LENGTH: 20
<212> TYPE: DNA
<213> ORGANISM: Artificial
<220> FEATURE:
<223> OTHER INFORMATION: circCOMT-R3

<400> SEQUENCE: 335
cttcaaagca cctctgagca 20

<210> SEQ ID NO 336
<211> LENGTH: 20
<212> TYPE: DNA
<213> ORGANISM: Artificial
<220> FEATURE:
<223> OTHER INFORMATION: circCOMT-F4

<400> SEQUENCE: 336
gtggacacac tggacatggt 20

<210> SEQ ID NO 337
<211> LENGTH: 21
<212> TYPE: DNA
<213> ORGANISM: Artificial
<220> FEATURE:
<223> OTHER INFORMATION: circCOMT-R4

<400> SEQUENCE: 337
gggatcctct tcaaagcacc t 21

<210> SEQ ID NO 338
<211> LENGTH: 20
<212> TYPE: DNA
<213> ORGANISM: Artificial
<220> FEATURE:
<223> OTHER INFORMATION: circCOMT-F5

<400> SEQUENCE: 338
ttcctcgacc actggaagga 20

<210> SEQ ID NO 339
<211> LENGTH: 21
<212> TYPE: DNA
<213> ORGANISM: Artificial
<220> FEATURE:
<223> OTHER INFORMATION: circCOMT-R5

<400> SEQUENCE: 339
tcttcaaagc acctctgagc a 21

<210> SEQ ID NO 340
<211> LENGTH: 20
<212> TYPE: DNA
<213> ORGANISM: Artificial
<220> FEATURE:
<223> OTHER INFORMATION: circCOMT-F6

<400> SEQUENCE: 340
atggtcttcc tcgaccactg 20

<210> SEQ ID NO 341
<211> LENGTH: 20
<212> TYPE: DNA
<213> ORGANISM: Artificial
<220> FEATURE:
<223> OTHER INFORMATION: circCOMT-R6

<400> SEQUENCE: 341
gggatcctct tcaaagcacc 20

<210> SEQ ID NO 342
<211> LENGTH: 19
<212> TYPE: DNA
<213> ORGANISM: Artificial
<220> FEATURE:
<223> OTHER INFORMATION: circCOMT-F7

<400> SEQUENCE: 342
ccggacacgc ttctcttgg 19

<210> SEQ ID NO 343
<211> LENGTH: 21
<212> TYPE: DNA
<213> ORGANISM: Artificial
<220> FEATURE:
<223> OTHER INFORMATION: circCOMT-R7

<400> SEQUENCE: 343
tcaaagcacc tctgagcagg c 21

<210> SEQ ID NO 344
<211> LENGTH: 24
<212> TYPE: DNA
<213> ORGANISM: Artificial
<220> FEATURE:
<223> OTHER INFORMATION: circCOMT-F8

<400> SEQUENCE: 344
cacgcttctc ttggagaaat aaca 24

<210> SEQ ID NO 345
<211> LENGTH: 21
<212> TYPE: DNA
<213> ORGANISM: Artificial
<220> FEATURE:
<223> OTHER INFORMATION: circCOMT-R8

<400> SEQUENCE: 345
agggatcctc ttcaaagcac c 21

<210> SEQ ID NO 346
<211> LENGTH: 20
<212> TYPE: DNA
<213> ORGANISM: Artificial
<220> FEATURE:
<223> OTHER INFORMATION: circPICALM-F1

<400> SEQUENCE: 346
agcctgtcat gagacctcca 20

<210> SEQ ID NO 347
<211> LENGTH: 20
<212> TYPE: DNA
<213> ORGANISM: Artificial
<220> FEATURE:
<223> OTHER INFORMATION: circPICALM-R1

<400> SEQUENCE: 347
tcctatcatg cctgttggtg 20

<210> SEQ ID NO 348
<211> LENGTH: 20
<212> TYPE: DNA
<213> ORGANISM: Artificial
<220> FEATURE:
<223> OTHER INFORMATION: circPICALM-F2

<400> SEQUENCE: 348
tgtaatgacg caaccaacct 20

<210> SEQ ID NO 349
<211> LENGTH: 20
<212> TYPE: DNA
<213> ORGANISM: Artificial
<220> FEATURE:
<223> OTHER INFORMATION: circPICALM-R2

<400> SEQUENCE: 349
gcaggatagg ccattacagg 20

<210> SEQ ID NO 350
<211> LENGTH: 20

<212> TYPE: DNA
<213> ORGANISM: Artificial
<220> FEATURE:
<223> OTHER INFORMATION: circPICALM-F3

<400> SEQUENCE: 350
tgtaatgacg caaccaacct 20

<210> SEQ ID NO 351
<211> LENGTH: 20
<212> TYPE: DNA
<213> ORGANISM: Artificial
<220> FEATURE:
<223> OTHER INFORMATION: circPICALM-R3

<400> SEQUENCE: 351
tcctatcatg cctgttggtg 20

<210> SEQ ID NO 352
<211> LENGTH: 20
<212> TYPE: DNA
<213> ORGANISM: Artificial
<220> FEATURE:
<223> OTHER INFORMATION: circPICALM-F4

<400> SEQUENCE: 352
tgagacctcc aaaccccttt 20

<210> SEQ ID NO 353
<211> LENGTH: 20
<212> TYPE: DNA
<213> ORGANISM: Artificial
<220> FEATURE:
<223> OTHER INFORMATION: circPICALM-R4

<400> SEQUENCE: 353
acttcccatt tgtggaggaa 20

<210> SEQ ID NO 354
<211> LENGTH: 20
<212> TYPE: DNA
<213> ORGANISM: Artificial
<220> FEATURE:
<223> OTHER INFORMATION: circPICALM-F5

<400> SEQUENCE: 354
aacccctttg gccctgtatc 20

<210> SEQ ID NO 355
<211> LENGTH: 22
<212> TYPE: DNA
<213> ORGANISM: Artificial
<220> FEATURE:
<223> OTHER INFORMATION: circPICALM-R5

<400> SEQUENCE: 355
acacttccca tttgtggagg aa 22

<210> SEQ ID NO 356
<211> LENGTH: 21
<212> TYPE: DNA
<213> ORGANISM: Artificial
<220> FEATURE:
<223> OTHER INFORMATION: circPICALM-F6

<400> SEQUENCE: 356
ctgtaatgac gcaaccaacc t 21

<210> SEQ ID NO 357
<211> LENGTH: 21
<212> TYPE: DNA
<213> ORGANISM: Artificial
<220> FEATURE:
<223> OTHER INFORMATION: circPICALM-R6

<400> SEQUENCE: 357
tgcctgttgg tgtagtagca g 21

<210> SEQ ID NO 358
<211> LENGTH: 20
<212> TYPE: DNA
<213> ORGANISM: Artificial
<220> FEATURE:
<223> OTHER INFORMATION: circPICALM-F7

<400> SEQUENCE: 358
tgtaatgacg caaccaacct 20

<210> SEQ ID NO 359
<211> LENGTH: 20
<212> TYPE: DNA
<213> ORGANISM: Artificial
<220> FEATURE:
<223> OTHER INFORMATION: circPICALM-R7

<400> SEQUENCE: 359
gcctgttggt gtagtagcag 20

<210> SEQ ID NO 360
<211> LENGTH: 20
<212> TYPE: DNA
<213> ORGANISM: Artificial
<220> FEATURE:
<223> OTHER INFORMATION: circTULP4-F1

<400> SEQUENCE: 360
aggagtcaag gcatcaccac 20

<210> SEQ ID NO 361
<211> LENGTH: 20
<212> TYPE: DNA
<213> ORGANISM: Artificial
<220> FEATURE:
<223> OTHER INFORMATION: circTULP4-R1

<400> SEQUENCE: 361
ttcaagagag ccgtccaact 20

<210> SEQ ID NO 362
<211> LENGTH: 20
<212> TYPE: DNA
<213> ORGANISM: Artificial
<220> FEATURE:
<223> OTHER INFORMATION: circTULP4-F2

<400> SEQUENCE: 362
aggagtcaag gcatcaccac 20

<210> SEQ ID NO 363
<211> LENGTH: 20
<212> TYPE: DNA
<213> ORGANISM: Artificial

<220> FEATURE:
<223> OTHER INFORMATION: circTULP4-R2

<400> SEQUENCE: 363
ctgctccacg acacaaaaga 20

<210> SEQ ID NO 364
<211> LENGTH: 20
<212> TYPE: DNA
<213> ORGANISM: Artificial
<220> FEATURE:
<223> OTHER INFORMATION: circTULP4-F3

<400> SEQUENCE: 364
tgaggaggag tcaaggcatc 20

<210> SEQ ID NO 365
<211> LENGTH: 20
<212> TYPE: DNA
<213> ORGANISM: Artificial
<220> FEATURE:
<223> OTHER INFORMATION: circTULP4-R3

<400> SEQUENCE: 365
ttcaagagag ccgtccaact 20

<210> SEQ ID NO 366
<211> LENGTH: 21
<212> TYPE: DNA
<213> ORGANISM: Artificial
<220> FEATURE:
<223> OTHER INFORMATION: circTULP4-F4

<400> SEQUENCE: 366
gaggaggagt caaggcatca c 21

<210> SEQ ID NO 367
<211> LENGTH: 20
<212> TYPE: DNA
<213> ORGANISM: Artificial
<220> FEATURE:
<223> OTHER INFORMATION: circTULP4-R4

<400> SEQUENCE: 367
acaaactcgg cgtgttcttc 20

<210> SEQ ID NO 368
<211> LENGTH: 20
<212> TYPE: DNA
<213> ORGANISM: Artificial
<220> FEATURE:
<223> OTHER INFORMATION: circTULP4-F5

<400> SEQUENCE: 368
caaggcatca ccacagcgaa 20

<210> SEQ ID NO 369
<211> LENGTH: 20
<212> TYPE: DNA
<213> ORGANISM: Artificial
<220> FEATURE:
<223> OTHER INFORMATION: circTULP4-R5

<400> SEQUENCE: 369
ttcaagagag ccgtccaact 20

<210> SEQ ID NO 370
<211> LENGTH: 19
<212> TYPE: DNA
<213> ORGANISM: Artificial
<220> FEATURE:
<223> OTHER INFORMATION: circTULP4-F6

<400> SEQUENCE: 370
atcaccacag cgaacgcat 19

<210> SEQ ID NO 371
<211> LENGTH: 21
<212> TYPE: DNA
<213> ORGANISM: Artificial
<220> FEATURE:
<223> OTHER INFORMATION: circTULP4-R6

<400> SEQUENCE: 371
caaactcggc gtgttcttct c 21

<210> SEQ ID NO 372
<211> LENGTH: 21
<212> TYPE: DNA
<213> ORGANISM: Artificial
<220> FEATURE:
<223> OTHER INFORMATION: circTULP4-F7

<400> SEQUENCE: 372
tgaggaggag tcaaggcatc a 21

<210> SEQ ID NO 373
<211> LENGTH: 20
<212> TYPE: DNA
<213> ORGANISM: Artificial
<220> FEATURE:
<223> OTHER INFORMATION: circTULP4-R7

<400> SEQUENCE: 373
gtccaactgc tccacgacac 20

<210> SEQ ID NO 374
<211> LENGTH: 20
<212> TYPE: DNA
<213> ORGANISM: Artificial
<220> FEATURE:
<223> OTHER INFORMATION: circTULP4-F8

<400> SEQUENCE: 374
catcaccaca gcgaacgcat 20

<210> SEQ ID NO 375
<211> LENGTH: 21
<212> TYPE: DNA
<213> ORGANISM: Artificial
<220> FEATURE:
<223> OTHER INFORMATION: circTULP4-R8

<400> SEQUENCE: 375
ttcaagagag ccgtccaact g 21

<210> SEQ ID NO 376
<211> LENGTH: 20
<212> TYPE: DNA
<213> ORGANISM: Artificial
<220> FEATURE:
<223> OTHER INFORMATION: circTULP4-F9

<400> SEQUENCE: 376
ggagtggttg gggtgacttt 20

<210> SEQ ID NO 377
<211> LENGTH: 20
<212> TYPE: DNA
<213> ORGANISM: Artificial
<220> FEATURE:
<223> OTHER INFORMATION: circTULP4-R9

<400> SEQUENCE: 377
tcaactgcca tacgaagcgt 20

<210> SEQ ID NO 378
<211> LENGTH: 20
<212> TYPE: DNA
<213> ORGANISM: Artificial
<220> FEATURE:
<223> OTHER INFORMATION: circRERE-F1

<400> SEQUENCE: 378
tttgcaggaa tgtgtgatgg 20

<210> SEQ ID NO 379
<211> LENGTH: 20
<212> TYPE: DNA
<213> ORGANISM: Artificial
<220> FEATURE:
<223> OTHER INFORMATION: circRERE-R1

<400> SEQUENCE: 379
atgaatccac tcgggcttta 20

<210> SEQ ID NO 380
<211> LENGTH: 20
<212> TYPE: DNA
<213> ORGANISM: Artificial
<220> FEATURE:
<223> OTHER INFORMATION: circRERE-F2

<400> SEQUENCE: 380
gcatttgcag gaatgtgtga 20

<210> SEQ ID NO 381
<211> LENGTH: 20
<212> TYPE: DNA
<213> ORGANISM: Artificial
<220> FEATURE:
<223> OTHER INFORMATION: circRERE-R2

<400> SEQUENCE: 381
atgaatccac tcgggcttta 20

<210> SEQ ID NO 382
<211> LENGTH: 20
<212> TYPE: DNA
<213> ORGANISM: Artificial
<220> FEATURE:
<223> OTHER INFORMATION: circRERE-F3

<400> SEQUENCE: 382
ctctcgggat gacaccactc 20

<210> SEQ ID NO 383

<211> LENGTH: 20
<212> TYPE: DNA
<213> ORGANISM: Artificial
<220> FEATURE:
<223> OTHER INFORMATION: circRERE-R3

<400> SEQUENCE: 383
atgaatccac tcgggcttta 20

<210> SEQ ID NO 384
<211> LENGTH: 20
<212> TYPE: DNA
<213> ORGANISM: Artificial
<220> FEATURE:
<223> OTHER INFORMATION: circRERE-F4

<400> SEQUENCE: 384
tgcaggaatg tgtgatggag 20

<210> SEQ ID NO 385
<211> LENGTH: 20
<212> TYPE: DNA
<213> ORGANISM: Artificial
<220> FEATURE:
<223> OTHER INFORMATION: circRERE-R4

<400> SEQUENCE: 385
atgaatccac tcgggcttta 20

<210> SEQ ID NO 386
<211> LENGTH: 20
<212> TYPE: DNA
<213> ORGANISM: Artificial
<220> FEATURE:
<223> OTHER INFORMATION: circRERE-F5

<400> SEQUENCE: 386
gcggcatttg caggaatgtg 20

<210> SEQ ID NO 387
<211> LENGTH: 22
<212> TYPE: DNA
<213> ORGANISM: Artificial
<220> FEATURE:
<223> OTHER INFORMATION: circRERE-R5

<400> SEQUENCE: 387
acacttccct tgtgttcagt gc 22

<210> SEQ ID NO 388
<211> LENGTH: 21
<212> TYPE: DNA
<213> ORGANISM: Artificial
<220> FEATURE:
<223> OTHER INFORMATION: circRERE-F6

<400> SEQUENCE: 388
ggcatttgca ggaatgtgtg a 21

<210> SEQ ID NO 389
<211> LENGTH: 22
<212> TYPE: DNA
<213> ORGANISM: Artificial
<220> FEATURE:
<223> OTHER INFORMATION: circRERE-R6

<400> SEQUENCE: 389
acacttccct tgtgttcagt gc 22

<210> SEQ ID NO 390
<211> LENGTH: 20
<212> TYPE: DNA
<213> ORGANISM: Artificial
<220> FEATURE:
<223> OTHER INFORMATION: circRALGAPB-F1

<400> SEQUENCE: 390
gttcagcaag tggtggaagc 20

<210> SEQ ID NO 391
<211> LENGTH: 20
<212> TYPE: DNA
<213> ORGANISM: Artificial
<220> FEATURE:
<223> OTHER INFORMATION: circRALGAPB-R1

<400> SEQUENCE: 391
ttttctccac cacccatctc 20

<210> SEQ ID NO 392
<211> LENGTH: 19
<212> TYPE: DNA
<213> ORGANISM: Artificial
<220> FEATURE:
<223> OTHER INFORMATION: circRALGAPB-F2

<400> SEQUENCE: 392
ttcagcaagt ggtggaagc 19

<210> SEQ ID NO 393
<211> LENGTH: 20
<212> TYPE: DNA
<213> ORGANISM: Artificial
<220> FEATURE:
<223> OTHER INFORMATION: circRALGAPB-R2

<400> SEQUENCE: 393
ttttctccac cacccatctc 20

<210> SEQ ID NO 394
<211> LENGTH: 20
<212> TYPE: DNA
<213> ORGANISM: Artificial
<220> FEATURE:
<223> OTHER INFORMATION: circRALGAPB-F3

<400> SEQUENCE: 394
gttcagcaag tggtggaagc 20

<210> SEQ ID NO 395
<211> LENGTH: 20
<212> TYPE: DNA
<213> ORGANISM: Artificial
<220> FEATURE:
<223> OTHER INFORMATION: circRALGAPB-R3

<400> SEQUENCE: 395
atctccatct ggcaaccaat 20

<210> SEQ ID NO 396
<211> LENGTH: 19
<212> TYPE: DNA

<213> ORGANISM: Artificial
<220> FEATURE:
<223> OTHER INFORMATION: circRALGAPB-F4

<400> SEQUENCE: 396
cagcaagtgg tggaagcac 19

<210> SEQ ID NO 397
<211> LENGTH: 20
<212> TYPE: DNA
<213> ORGANISM: Artificial
<220> FEATURE:
<223> OTHER INFORMATION: circRALGAPB-R4

<400> SEQUENCE: 397
ttttctccac cacccatctc 20

<210> SEQ ID NO 398
<211> LENGTH: 23
<212> TYPE: DNA
<213> ORGANISM: Artificial
<220> FEATURE:
<223> OTHER INFORMATION: circRALGAPB-F5

<400> SEQUENCE: 398
gtggtattag ttcagcaagt ggt 23

<210> SEQ ID NO 399
<211> LENGTH: 25
<212> TYPE: DNA
<213> ORGANISM: Artificial
<220> FEATURE:
<223> OTHER INFORMATION: circRALGAPB-R5

<400> SEQUENCE: 399
atttaacatt gccccataat ctctt 25

<210> SEQ ID NO 400
<211> LENGTH: 23
<212> TYPE: DNA
<213> ORGANISM: Artificial
<220> FEATURE:
<223> OTHER INFORMATION: circRALGAPB-F6

<400> SEQUENCE: 400
agtggtatta gttcagcaag tgg 23

<210> SEQ ID NO 401
<211> LENGTH: 25
<212> TYPE: DNA
<213> ORGANISM: Artificial
<220> FEATURE:
<223> OTHER INFORMATION: circRALGAPB-R6

<400> SEQUENCE: 401
atttaacatt gccccataat ctctt 25

<210> SEQ ID NO 402
<211> LENGTH: 24
<212> TYPE: DNA
<213> ORGANISM: Artificial
<220> FEATURE:
<223> OTHER INFORMATION: circRALGAPB-F7

<400> SEQUENCE: 402
agtggtatta gttcagcaag tggt 24

<210> SEQ ID NO 403
<211> LENGTH: 25
<212> TYPE: DNA
<213> ORGANISM: Artificial
<220> FEATURE:
<223> OTHER INFORMATION: circRALGAPB-R7

<400> SEQUENCE: 403
atttaacatt gccccataat ctctt 25

<210> SEQ ID NO 404
<211> LENGTH: 25
<212> TYPE: DNA
<213> ORGANISM: Artificial
<220> FEATURE:
<223> OTHER INFORMATION: circRALGAPB-F8

<400> SEQUENCE: 404
gcaccaatag tggtattagt tcagc 25

<210> SEQ ID NO 405
<211> LENGTH: 25
<212> TYPE: DNA
<213> ORGANISM: Artificial
<220> FEATURE:
<223> OTHER INFORMATION: circRALGAPB-R8

<400> SEQUENCE: 405
atttaacatt gccccataat ctctt 25

<210> SEQ ID NO 406
<211> LENGTH: 20
<212> TYPE: DNA
<213> ORGANISM: Artificial
<220> FEATURE:
<223> OTHER INFORMATION: circDDX50-F1

<400> SEQUENCE: 406
atgtgcctcc tgaaaggaaa 20

<210> SEQ ID NO 407
<211> LENGTH: 20
<212> TYPE: DNA
<213> ORGANISM: Artificial
<220> FEATURE:
<223> OTHER INFORMATION: circDDX50-R1

<400> SEQUENCE: 407
caacagcagc gtaagaaacg 20

<210> SEQ ID NO 408
<211> LENGTH: 20
<212> TYPE: DNA
<213> ORGANISM: Artificial
<220> FEATURE:
<223> OTHER INFORMATION: circDDX50-F2

<400> SEQUENCE: 408
tgtgcctcct gaaaggaaat 20

<210> SEQ ID NO 409
<211> LENGTH: 20
<212> TYPE: DNA
<213> ORGANISM: Artificial
<220> FEATURE:

<223> OTHER INFORMATION: circDDX50-R2

<400> SEQUENCE: 409
aatgcatcca ctgcaccttt 20

<210> SEQ ID NO 410
<211> LENGTH: 20
<212> TYPE: DNA
<213> ORGANISM: Artificial
<220> FEATURE:
<223> OTHER INFORMATION: circDDX50-F3

<400> SEQUENCE: 410
tgtgcctcct gaaaggaaat 20

<210> SEQ ID NO 411
<211> LENGTH: 20
<212> TYPE: DNA
<213> ORGANISM: Artificial
<220> FEATURE:
<223> OTHER INFORMATION: circDDX50-R3

<400> SEQUENCE: 411
caacagcagc gtaagaaacg 20

<210> SEQ ID NO 412
<211> LENGTH: 22
<212> TYPE: DNA
<213> ORGANISM: Artificial
<220> FEATURE:
<223> OTHER INFORMATION: circDDX50-F4

<400> SEQUENCE: 412
agaaaggtta caggtctctg gc 22

<210> SEQ ID NO 413
<211> LENGTH: 20
<212> TYPE: DNA
<213> ORGANISM: Artificial
<220> FEATURE:
<223> OTHER INFORMATION: circDDX50-R4

<400> SEQUENCE: 413
caatgcatcc actgcacctt 20

<210> SEQ ID NO 414
<211> LENGTH: 22
<212> TYPE: DNA
<213> ORGANISM: Artificial
<220> FEATURE:
<223> OTHER INFORMATION: circDDX50-F5

<400> SEQUENCE: 414
aaaggttaca ggtctctggc tt 22

<210> SEQ ID NO 415
<211> LENGTH: 20
<212> TYPE: DNA
<213> ORGANISM: Artificial
<220> FEATURE:
<223> OTHER INFORMATION: circDDX50-R5

<400> SEQUENCE: 415
caatgcatcc actgcacctt 20

<210> SEQ ID NO 416
<211> LENGTH: 22
<212> TYPE: DNA
<213> ORGANISM: Artificial
<220> FEATURE:
<223> OTHER INFORMATION: circDDX50-F6

<400> SEQUENCE: 416
aaaggttaca ggtctctggc tt 22

<210> SEQ ID NO 417
<211> LENGTH: 21
<212> TYPE: DNA
<213> ORGANISM: Artificial
<220> FEATURE:
<223> OTHER INFORMATION: circDDX50-R6

<400> SEQUENCE: 417
atgcatccac tgcacctttc t 21

<210> SEQ ID NO 418
<211> LENGTH: 20
<212> TYPE: DNA
<213> ORGANISM: Artificial
<220> FEATURE:
<223> OTHER INFORMATION: circSATB2-F1

<400> SEQUENCE: 418
aggagtcaag gcatcaccac 20

<210> SEQ ID NO 419
<211> LENGTH: 20
<212> TYPE: DNA
<213> ORGANISM: Artificial
<220> FEATURE:
<223> OTHER INFORMATION: circSATB2-R1

<400> SEQUENCE: 419
ttcaagagag ccgtccaact 20

<210> SEQ ID NO 420
<211> LENGTH: 20
<212> TYPE: DNA
<213> ORGANISM: Artificial
<220> FEATURE:
<223> OTHER INFORMATION: circSATB2-F2

<400> SEQUENCE: 420
aggagtcaag gcatcaccac 20

<210> SEQ ID NO 421
<211> LENGTH: 20
<212> TYPE: DNA
<213> ORGANISM: Artificial
<220> FEATURE:
<223> OTHER INFORMATION: circSATB2-R2

<400> SEQUENCE: 421
ctgctccacg acacaaaaga 20

<210> SEQ ID NO 422
<211> LENGTH: 20
<212> TYPE: DNA
<213> ORGANISM: Artificial
<220> FEATURE:
<223> OTHER INFORMATION: circSATB2-F3

<400> SEQUENCE: 422
tgaggaggag tcaaggcatc 20

<210> SEQ ID NO 423
<211> LENGTH: 20
<212> TYPE: DNA
<213> ORGANISM: Artificial
<220> FEATURE:
<223> OTHER INFORMATION: circSATB2-R3

<400> SEQUENCE: 423
ttcaagagag ccgtccaact 20

<210> SEQ ID NO 424
<211> LENGTH: 21
<212> TYPE: DNA
<213> ORGANISM: Artificial
<220> FEATURE:
<223> OTHER INFORMATION: circSATB2-F4

<400> SEQUENCE: 424
gaggaggagt caaggcatca c 21

<210> SEQ ID NO 425
<211> LENGTH: 20
<212> TYPE: DNA
<213> ORGANISM: Artificial
<220> FEATURE:
<223> OTHER INFORMATION: circSATB2-R4

<400> SEQUENCE: 425
acaaactcgg cgtgttcttc 20

<210> SEQ ID NO 426
<211> LENGTH: 20
<212> TYPE: DNA
<213> ORGANISM: Artificial
<220> FEATURE:
<223> OTHER INFORMATION: circSATB2-F5

<400> SEQUENCE: 426
caaggcatca ccacagcgaa 20

<210> SEQ ID NO 427
<211> LENGTH: 20
<212> TYPE: DNA
<213> ORGANISM: Artificial
<220> FEATURE:
<223> OTHER INFORMATION: circSATB2-R5

<400> SEQUENCE: 427
ttcaagagag ccgtccaact 20

<210> SEQ ID NO 428
<211> LENGTH: 19
<212> TYPE: DNA
<213> ORGANISM: Artificial
<220> FEATURE:
<223> OTHER INFORMATION: circSATB2-F6

<400> SEQUENCE: 428
atcaccacag cgaacgcat 19

<210> SEQ ID NO 429
<211> LENGTH: 21

-continued

```
<212> TYPE: DNA
<213> ORGANISM: Artificial
<220> FEATURE:
<223> OTHER INFORMATION: circSATB2-R6

<400> SEQUENCE: 429

caaactcggc gtgttcttct c                                              21


<210> SEQ ID NO 430
<211> LENGTH: 21
<212> TYPE: DNA
<213> ORGANISM: Artificial
<220> FEATURE:
<223> OTHER INFORMATION: circSATB2-F7

<400> SEQUENCE: 430

tgaggaggag tcaaggcatc a                                              21


<210> SEQ ID NO 431
<211> LENGTH: 20
<212> TYPE: DNA
<213> ORGANISM: Artificial
<220> FEATURE:
<223> OTHER INFORMATION: circSATB2-R7

<400> SEQUENCE: 431

gtccaactgc tccacgacac                                                20


<210> SEQ ID NO 432
<211> LENGTH: 20
<212> TYPE: DNA
<213> ORGANISM: Artificial
<220> FEATURE:
<223> OTHER INFORMATION: circSATB2-F8

<400> SEQUENCE: 432

catcaccaca gcgaacgcat                                                20


<210> SEQ ID NO 433
<211> LENGTH: 21
<212> TYPE: DNA
<213> ORGANISM: Artificial
<220> FEATURE:
<223> OTHER INFORMATION: circSATB2-R8

<400> SEQUENCE: 433

ttcaagagag ccgtccaact g                                              21
```

CIRCULAR RNAs FOR DIAGNOSIS OF DEPRESSION AND PREDICTION OF RESPONSE TO ANTIDEPRESSANT TREATMENT

CROSS-REFERENCE TO RELATED APPLICATIONS

This application is a U.S. National Stage Filing under 35 U.S.C. 371 from International Application No. PCT/US2022/017936, filed on Feb. 25, 2022, and published as WO 2022/183011 A1 on Sep. 1, 2022, which application claims the benefit of the filing date of U.S. Provisional Application No. 63/154,168, filed on Feb. 26, 2021, the disclosures of which are incorporated by reference herein.

SEQUENCE LISTING

This application contains a Sequence Listing which has been submitted electronically in ASCII format and is hereby incorporated by reference in its entirety. Said ASCII copy, created on Feb. 23, 2022, is named "CG-Sequence-1" and is 490 Kbytes in size.

TECHNICAL FIELD

The technology relates to the field of medical and therapeutic diagnostics, and in particular systems, methods, and compositions for the detection and treatment of psychiatric disorders using circular RNA biomarkers.

BACKGROUND

Major Depressive Disorder (MDD; also known as "unipolar depression", "monopolar depression", or just "depression") is a psychiatric disorder that affects close to 10% of the world's population and is the second leading cause of disability and overall global disease burden worldwide. Although treatment with various antidepressants such as Selective Serotonin Reuptake Inhibitors (SSRIs), serotonin and norepinephrine reuptake inhibitors (SNRIs), Monoamine oxidase inhibitors (MAOIs), tricyclic antidepressants, and phycological therapy, such as cognitive behavioral therapy, has demonstrated clinical efficacy, the inherent complexity and heterogeneity of the disease and the "trial by error" approach in choosing the particular antidepressant treatment for each patient only allows for a subset of patients to respond to the first choice of treatment. As a result, the average percentage of patients with MDD that achieve response (more than 50% improvement of total score based on symptoms) or remission (elimination of depressive symptoms and a return to premorbid levels of functioning) to the first prescribed antidepressant treatment is around 30-50%. Furthermore, close to 30% of patients with MDD appear to be treatment-resistant in multiple antidepressant drug treatments. Lastly, a small subset of patients with depressive symptoms, initially diagnosed with MDD, end up being diagnosed with Bipolar Disorder (BD), thus making the differentiation between MDD and BD an important priority. It is therefore imperative to predict and monitor therapeutic efficacy and uncover better therapeutic alternatives for MDD. Moreover, the identification of early biomarkers for MDD severity can serve as a valuable tool in evaluating a patient's risk for complications and can help with excluding other differential diagnosis.

Existing RNA biomarker approaches are based on detecting linear RNA expression in adult peripheral samples such as blood. However, linear mRNAs are prone to degradation and most have very low half-lives (a few hours), thus making their expression unstable and transient, especially in blood/serum samples, which contain high levels of enzymes that break down linear RNA.

SUMMARY

To address the problems outlined above, the disclosure provides for the use of circular RNAs (circRNA) as biomarkers of psychiatric disorders, such as MDD, BD and the like. As described below, circRNA are produced from the backsplicing and covalent joining of exons and/or introns and are by far the most resistant to degradation RNA molecules with half-lives of several days to one week making them more suitable to use as diagnostic biomarkers.

In one embodiment, circRNAs can serve as robust biomarkers in blood and other peripheral samples, or cellular samples such as samples comprising neurons, based on a subset of specific circRNAs, e.g., either before treatment (baseline) or some weeks after treatment, that is significantly altered in the blood of patients with Major Depressive Disorder (MDD) or Bipolar Disorder (BD) and may be associated with response to specific antidepressant treatment. Moreover, a subset of circRNAs can predict MDD severity and can discriminate between MDD and BD. As a result, the disclosure provides for the use of circRNAs as a biomarker for diagnosis of MDD, response or remission to antidepressant treatment, as well as for predicting disease severity and the possibility for relapse. According to one embodiment, the present disclosure provides compositions, kits, assays, systems, and methods for the identification, diagnosis, screening, treatment and/or monitoring of brain disorders including, but not necessarily limited to, psychiatric disorders such as MDD and BD. According to a specific embodiment, the present disclosure provides a plurality of circRNAs biomarkers, the expression of which is indicative of such disorders or with response to various treatments, such as administration of one or more anti-depressants With half-lives of several days, circRNAs can serve as robust biomarkers in blood and other peripheral samples. As disclosed herein, the expression of one or more circRNAs may be altered in the blood, or other fluid or tissue sample of a patient with a psychiatric disorder such as MDD or BD. The up or down-regulation of the expression of one or more of the circRNAs can be associated with response to an antidepressant treatment. Thus, circRNAs may be employed as a biomarker to identify a psychiatric disorder such as MDD or BD, and for response to antidepressant treatment as well as for predicting disease severity and the possibility for relapse. In particular, a relationship has been identified between circRNAs and diagnosis of MDD or BD and optionally response to antidepressant medication. The relationship found between circRNAs, MDD, BD, and response to treatment may allow for the use of those circRNAs as biomarkers to identify psychiatric disorders such as MDD or BD in patients during early stages of the disease, or before the onset of the disease, to follow therapeutic efficacy of antidepressants and/or design drug targets. Thus, the properties of the circRNAs not only allow for their use as robust peripheral biomarkers of MDD or BD, and/or disease severity, but also as strong predictors of response to treatment.

For example, detecting the presence or amount of one or more specific circRNAs allows for fast and accurate prediction of response to antidepressant mediations for MD, for a more accurate prediction of an individual's risk for developing serious MDD-related complications and/or chances for disease relapse, and/or for early diagnosis of MDD. Thus, according to an embodiment or aspect, the present disclosure provides compositions, kits, assays, systems, and methods for the identification, diagnosis, screening, treatment and/or monitoring of brain disorders including, but not necessarily limited to, MDD or BD. According to a specific embodiment, the present disclosure provides a plurality of circRNAs, the expression of which can be detected and correlated with, for example, responsiveness of a MDD patient to anti-depressant therapy, progression of MDD, and/or relapse of MDD.

In one example, the disclosure provides a composition comprising one or more isolated nucleic acids comprising a sequence having at least 80%, 85%, 90%, 95%, 96%, 97%, 98% or 99% nucleic acid sequence identity to one or more of SEQ ID Nos. 1-241, or the complement thereof, a composition comprising two or more isolated nucleic acids comprising a sequence having at least 80%, 85%, 90%, 95%, 96%, 97%, 98% or 99% nucleic acid sequence identity to a combination of two or more of SEQ ID Nos. 1-241, or the complement thereof, or a probe or primer that detects at least one of circCDR1as, circTULP4, circCHIC1, circMIR5695, circRALGAPB, circCOMT, circPICALM, circDDX50, circRERE, or circSATB2, circICAM1, circDDR1, circADAM22, circMALAT1, circHMGA2, circCYP24A1, circDLG5, circMYO9B, circNFATC3, circDUSP22, circFKBP8, circVDAC2, circTRIM69, or detects at least one of SEQ ID NO's. 1-241, or a plurality of probes that detect any combination of two or more of circCDR1as, circTULP4, circCHIC1, circMIR5695, circRALGAPB, circCOMT, circPICALM, circDDX50, circRERE, or circSATB2, circICAM1, circDDR1, circADAM22, circMALAT1, circHMGA2, circCYP24A1, circDLG5, circMYO9B, circNFATC3, circDUSP22, circFKBP8, circVDAC2, circTRIM69, or any combination thereof, e.g., two or more probes that detect two or more of SEQ ID Nos. 1-241. In one embodiment, the probe has a sequence having at least 80%, 85%, 90%, 95%, 96%, 97%, 98% or 99% nucleic acid sequence identity to the complement of one of SEQ ID Nos. 1-241.

Further provided is a panel of probes comprising probes specific for two or more of circCDR1as, circTULP4, circCHIC1, circMIR5695, circRALGAPB, circCOMT, circPICALM, circDDX50, circRERE, or circSATB2, circICAM1, circDDR1, circADAM22, circMALAT1, circHMGA2, circCYP24A1, circDLG5, circMYO9B, circNFATC3, circDUSP22, circFKBP8, circVDAC2, circTRIM69, or SEQ ID NOs. 1-241, or a plurality of primers specific for two or more of SEQ ID Nos. 1-241, wherein the probes or primers have a sequence having at least 80%. 85%, 90%, 95%, 96%, 97%, 98% or 99% nucleic acid sequence identity to, or to the complement of, one of SEQ ID Nos. 1-241.

Also provided is an assay for detecting a mammal having or at risk of having MDD or BD comprising: one or more probes configured to identify the presence of at least one circRNA selected from circCDR1as, circTULP4, circCHIC1, circMIR5695, circRALGAPB, circCOMT, circPICALM, circDDX50, circRERE, or circSATB2, circICAM1, circDDR1, circADAM22, circMALAT1, circHMGA2, circCYP24A1, circDLG5, circMYO9B, circNFATC3, circDUSP22, circFKBP8, circVDAC2, circTRIM69, or SEQ ID NOs. 1-241 or a sequence having at least 80%, 85%, 90%, 95%, 96%, 97%, 98% or 99% nucleic acid sequence identity to one or more of SEQ ID Nos. 1-241, or the complement thereof. In one embodiment, the probes comprise a sequence specific for two or more of circCDR1as, circTULP4, circCHIC1, circMIR5695, circRALGAPB, circCOMT, circPICALM, circDDX50, circRERE, or circSATB2, circlCAM1, circDDR1, circADAM22, circMALAT1, circHMGA2, circCYP24A1, circDLG5, circMYO9B, circNFATC3, circDUSP22, circFKBP8, circVDAC2, circTRIM69, or SEQ ID NOs. 1-241. In one embodiment, the probe comprises a sequence that spans the splice junction of the circRNA in an asymmetric manner. In one embodiment, the assay includes one or more primers configured to amplify a sequence specific for at least one of circCDR1as, circTULP4, circCHIC1, circMIR5695, circRALGAPB, circCOMT, circPICALM, circDDX50, circRERE, or circSATB2, circICAM1, circDDR1, circADAM22, circMALAT1, circHMGA2, circCYP24A1, circDLG5, circMYO9B, circNFATC3, circDUSP22, circFKBP8, circVDAC2, circTRIM69, or SEQ ID NOs. 1-241 or a sequence having at least 80%, 85%, 90%, 95%, 96%, 97%, 98% or 99% nucleic acid sequence identity to one or more of SEQ ID Nos. 1-241, or the complement thereof. In one embodiment, the primer includes a sequence that spans the splice junction of the circRNA in an asymmetric manner.

Further provided is a method for diagnosing MDD or BD in a mammal, such as a human, sometimes referred to as a subject or patient. The method includes providing or obtaining a test physiological sample from the mammal; assaying the test sample using probes and/or primers configured to identify the presence of and/or amplify one or more of circCDR1as, circTULP4, circCHIC1, circMIR5695, circRALGAPB, circCOMT, circPICALM, circDDX50, circRERE, or circSATB2, circICAM1, circDDR1, circADAM22, circMALAT1, circHMGA2, circCYP24A1, circDLG5, circMYO9B, circNFATC3, circDUSP22, circFKBP8, circVDAC2, circTRIM69, or SEQ ID NOs. 1-241; and comparing the presence or amount of one or more of SEQ ID Nos. 1-241 or a sequence having at least 80%, 85%, 90%, 95%, 96%, 97%, 98% or 99% nucleic acid sequence identity to one or more of SEQ ID Nos. 1-241, or the complement thereof, in the test sample to a control sample. In one embodiment, the sample is a physiological fluid sample. In one embodiment, the sample is a blood sample. In one embodiment, the mammal is a human suffering from, or at risk for developing a psychiatric condition, such as MDD or BD.

In one embodiment, a method to predict response or remission to an anti-depressant in a subject is provided. The method including providing or obtaining a test physiological sample from the subject; assaying the test sample using probes and/or primers configured to identify the presence of and/or amplify one or more of circCDR1as, circTULP4, circCHIC1, circMIR5695, circRALGAPB, circCOMT, circPICALM, circDDX50, circRERE, or circSATB2, circICAM1, circDDR1, circADAM22, circMALAT1, circHMGA2, circCYP24A1, circDLG5, circMYO9B, circNFATC3, circDUSP22, circFKBP8, circVDAC2, circTRIM69, or SEQ ID NOs. 1-241; and comparing the presence or amount of one or more of circCDR1as, circTULP4, circCHIC1, circMIR5695, circRALGAPB, circCOMT, circPICALM, circDDX50, circRERE, or circSATB2, circICAM1, circDDR1, circADAM22, circMALAT1, circHMGA2, circCYP24A1, circDLG5, circMYO9B, circNFATC3, circDUSP22, circFKBP8, circVDAC2, circTRIM69, or SEQ ID NOs. 1-241 or a sequence having at least 80%, 85%, 90%, 95%, 96%, 97%, 98% or 99% nucleic acid sequence identity to one or more of SEQ ID Nos. 1-241, or the complement thereof, in the test sample to a control sample. In one embodiment, the anti-depressant is useful to treat monopolar depression. In one embodiment, the sample is a physiological fluid sample. In one embodiment, the sample is a blood sample. In one embodiment, the subject is a human.

In one embodiment, a method to monitor progression of, or relapse of, MDD or BD in a subject is provided. The method includes providing or obtaining a test physiological sample from the subject; assaying the test sample using probes and/or primers configured to identify the presence of and/or amplify one or more of circCDR1as, circTULP4, circCHIC1, circMIR5695, circRALGAPB, circCOMT, circPICALM, circDDX50, circRERE, or circSATB2, e.g., identify or amplify SEQ ID Nos. 1-241 or a sequence having at least 80%, 85%, 90%, 95%, 96%, 97%, 98% or 99% nucleic acid sequence identity to one or more of SEQ ID Nos. 1-241, or the complement thereof; and comparing the presence or amount in the test sample to a sample from the mammal obtained at an earlier point in time. In one embodiment, the sample is a physiological fluid sample. In one embodiment, the sample is a blood sample. In one embodiment, the subject is a human.

Figure 1A:
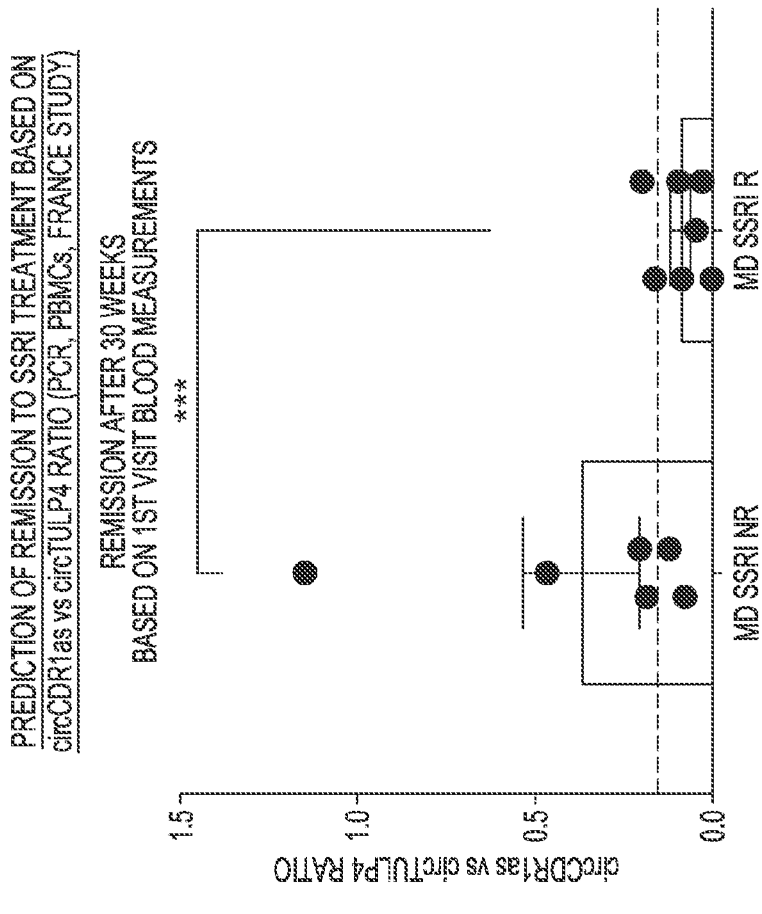
FIGS. 1A-1B. Baseline blood PBMC circCDR1as vs circTULP4 ratio predicts remission after SSRI treatment (University of Marseille, France samples). (A) MDD patients that did not achieve remission after 30 weeks of treatment (MDD SSRI NR) display a higher baseline PBMC circCDR1as vs circTULP4 ratio ($p<0.001$, two-tailed one sample t-test, N=7 per group) than patients that achieved remission (MDD SSRI R). Data were acquired with circRNA-specific qRT-PCR in total RNA extracted from blood PBMCs (peripheral blood mononuclear cells) derived from the University of Marseille in France. (B) Differences in the PBMC circCDR1as vs circTULP4 ratio have an excellent predictive value for predicting remission after long-term SSRI treatment based on receiver operating characteristic curve (ROC curve; a graphical plot that illustrates the diagnostic ability of a binary classifier system). Area under the curve=0.833 (more than 0.80 is considered excellent) and $p=0.0455$ ($p<0.05$ is considered significant).

*p<0.05, based on ANOVA with Tukey's post-hoc corrections for multiple comparisons, N=15 for SERT R and SERT NR and N=8 for Control. (D) Differences in circMIR5695 levels 1 week after treatment have an excellent predictive value for predicting response after 8 weeks of Sertraline treatment based on receiver operating characteristic curve (ROC curve; a graphical plot that illustrates the diagnostic ability of a binary classifier system). Area under the curve=0.8978 and p=0.0002.

FIGS. 19A-19D. Sertraline response prediction based on circRALGAPB. (A) Patients with MDD that achieved response after 8 weeks of Sertraline treatment (Sert R) exhibit increased circRALGAPB levels at baseline (before treatment) compared to MDD patients that did not achieve response to Sertraline (SERT NR) and unaffected Controls (Control). Data were acquired with circRNA array profiling in total RNA extracted from whool blood derived from the University of Texas Southwestern (EMBARC study). **p<0.01, *p<0.05, based on ANOVA with Tukey's post-hoc corrections for multiple comparisons, N=15 for SERT R and SERT NR and N=8 for Control. (B) Differences in baseline circRALGAPB levels have a very good predictive value for predicting response after 8 weeks of Sertraline treatment based on receiver operating characteristic curve (ROC curve; a graphical plot that illustrates the diagnostic ability of a binary classifier system). Area under the curve=0.7689 and p=0.0121. (C) Patients with MDD that achieved response after 8 weeks of Sertraline treatment (Sert R) exhibit increased circRALGAPB levels one week after treatment compared to MDD patients that did not achieve response to Sertraline (SERT NR) and unaffected Controls (Control). Data were acquired with circRNA array profiling in total RNA extracted from whool blood derived from the University of Texas Southwestern (EMBARC study). p<0.01. *p<0.001, based on ANOVA with Tukey's post-hoc corrections for multiple comparisons, N=15 for SERT R and SERT NR and N=8 for Control. (D) Differences in circRALGAPB levels 1 week after treatment have an excellent predictive value for predicting response after 8 weeks of Sertraline treatment based on receiver operating characteristic curve (ROC curve; a graphical plot that illustrates the diagnostic ability of a binary classifier system). Area under the curve=0.8889 and p=0.0003.

FIGS. 20A-20D. Sertraline response prediction based on circDUSP22 or circFKBP8. (A) Patients with MDD that achieved response after 8 weeks of Sertraline treatment (Sert R) exhibit increased circDUSP22 levels at baseline (before treatment) compared to MDD patients that did not achieve response to Sertraline (SERT NR). Data were acquired with circRNA array profiling in total RNA extracted from whool blood derived from the University of Texas Southwestern (EMBARC study). *p<0.05, based on ANOVA with Tukey's post-hoc corrections for multiple comparisons, N=15 for SERT R and SERT NR and N=8 for Control. (B) Differences in baseline circDUSP22 levels have an excellent predictive value for predicting response after 8 weeks of Sertraline treatment based on receiver operating characteristic curve (ROC curve; a graphical plot that illustrates the diagnostic ability of a binary classifier system). Area under the curve=0.8578 and p=0.0008. (C) Patients with MDD that achieved response after 8 weeks of Sertraline treatment (Sert R) exhibit increased circFKBP8 levels at baseline (before treatment) compared to MDD patients that did not achieve response to Sertraline (SERT NR) and unaffected Controls (Control). Data were acquired with circRNA array profiling in total RNA extracted from whool blood derived from the University of Texas Southwestern (EMBARC study). *p<0.001, p<0.01, based on ANOVA with Tukey's post-hoc corrections for multiple comparisons, N=15 for SERT R and SERT NR and N=8 for Control. (D) Differences in baseline circFKBP8 levels have an excellent predictive value for predicting response after 8 weeks of Sertraline treatment based on receiver operating characteristic curve (ROC curve; a graphical plot that illustrates the diagnostic ability of a binary classifier system). Area under the curve=0.8400 and p=0.0015.

FIGS. 21A-21F. Sertraline response prediction based on circDLG5, circMYO9B, or circADAM22. (A) Patients with MDD that achieved response after 8 weeks of Sertraline treatment (Sert R) exhibit increased circDLG5 levels 1 week after treatment compared to MDD patients that did not achieve response to Sertraline (SERT NR), unaffected Controls (Control), or patients with MDD that were given Placebo and did not respond to treatment (Placb). Data were acquired with circRNA array profiling in total RNA extracted from whool blood derived from the University of Texas Southwestern (EMBARC study). ***p<0.001, *p<0.05, based on ANOVA with Tukey's post-hoc corrections for multiple comparisons, N=15 for SERT R and SERT NR and N=8 for Control and Placb. (B) Differences in circDLG5 levels 1 week after treatment have a very good predictive value for predicting response after 8 weeks of Sertraline treatment based on receiver operating characteristic curve (ROC curve; a graphical plot that illustrates the diagnostic ability of a binary classifier system). Area under the curve=0.8267 and p=0.0095. (C) Patients with MDD that achieved response after 8 weeks of Sertraline treatment (Sert R) exhibit increased circMYO9B levels 1 week after treatment compared to MDD patients that did not achieve response to Sertraline (SERT NR), unaffected Controls (Control), or patients with MDD that were given Placebo and did not respond to treatment (Placb). Data were acquired with circRNA array profiling in total RNA extracted from whool blood derived from the University of Texas Southwestern (EMBARC study). **p<0.0001, *p<0.001, **p<0.01, *p<0.05, based on ANOVA with Tukey's post-hoc corrections for multiple comparisons, N=15 for SERT R and SERT NR and N=8 for Control and Placb. (D) Differences in circMYO9B levels 1 week after treatment have an excellent predictive value for predicting response after 8 weeks of Sertraline treatment based on receiver operating characteristic curve (ROC curve; a graphical plot that illustrates the diagnostic ability of a binary classifier system). Area under the curve=0.8267 and p=0.0023. (E) Patients with MDD that achieved response after 8 weeks of Sertraline treatment (Sert R) exhibit increased circADAM22 levels 1 week after treatment compared to MDD patients that did not achieve response to Sertraline (SERT NR), unaffected Controls (Control), or patients with MDD that were given Placebo and did not respond to treatment (Placb). Data were acquired with circRNA array profiling in total RNA extracted from whool blood derived from the University of Texas Southwestern (EMBARC study). **p<0.0001, *p<0.001, based on ANOVA with Tukey's post-hoc corrections for multiple comparisons, N=15 for SERT R and SERT NR and N=8 for Control and Placb. (F) Differences in circADAM22 levels 1 week after treatment have an excellent predictive value for predicting response after 8 weeks of Sertraline treatment based on receiver operating characteristic curve (ROC curve; a graphical plot that illustrates the diagnostic ability of a binary classifier system). Area under the curve=0.8800 and p=0.0004.

FIGS. 22A-22D. Sertraline response prediction based on circNFATC3. (A) Patients with MDD that achieved response after 8 weeks of Sertraline treatment (Sert R) exhibit increased circNFATC3 levels at baseline (before treatment) compared to MDD patients that did not achieve response to Sertraline (SERT NR) and unaffected Controls (Control). Data were acquired with circRNA array profiling in total RNA extracted from whool blood derived from the University of Texas Southwestern (EMBARC study). *p<0.0001, *p<0.01, based on ANOVA with Tukey's post-hoc corrections for multiple comparisons, N=15 for SERT R and SERT NR and N=8 for Control. (B) Differences in baseline circNFATC3, levels have an excellent predictive value for predicting response after 8 weeks of Sertraline treatment based on receiver operating characteristic curve (ROC curve; a graphical plot that illustrates the diagnostic ability of a binary classifier system). Area under the curve=0.8800 and p=0.0004. (C) Patients with MDD that achieved response after 8 weeks of Sertraline treatment (Sert R) exhibit increased circNFATC3 levels one week after treatment compared to MDD patients that did not achieve response to Sertraline (SERT NR), unaffected Controls (Control), and patients with MDD that were given Placebo and did not respond to treatment (Placb). Data were acquired with circRNA array profiling in total RNA extracted from whool blood derived from the University of Texas Southwestern (EMBARC study). ***p<0.001, *p<0.05, based on ANOVA with Tukey's post-hoc corrections for multiple comparisons, N=15 for SERT R and SERT NR and N=8 for Control and Placb. (D) Differences in circNFATC3 levels 1 week after treatment have a very good predictive value for predicting response after 8 weeks of Sertraline treatment based on receiver operating characteristic curve (ROC curve; a graphical plot that illustrates the diagnostic ability of a binary classifier system). Area under the curve=0.7687 and p=0.0075.

FIGS. 23A-23D. Sertraline response prediction based on circHMGA2 or circMALAT1. (A) Patients with MDD that achieved response after 8 weeks of Sertraline treatment (Sert R) exhibit decreased circHMGA2 levels at baseline (before treatment) compared to MDD patients that did not achieve response to Sertraline (SERT NR) and unaffected Controls (Control). Data were acquired with circRNA array profiling in total RNA extracted from whool blood derived from the University of Texas Southwestern (EMBARC study). *p<0.0001, based on ANOVA with Tukey's post-hoc corrections for multiple comparisons, N=15 for SERT R and SERT NR and N=8 for Control. (B) Differences in baseline circHMGA2 levels have an outstanding predictive value for predicting response after 8 weeks of Sertraline treatment based on receiver operating characteristic curve (ROC curve; a graphical plot that illustrates the diagnostic ability of a binary classifier system). Area under the curve=1.000 and p<0.0001. (C) Patients with MDD that achieved response after 8 weeks of Sertraline treatment (Sert R) exhibit increased circMALAT1 levels at baseline (before treatment) compared to MDD patients that did not achieve response to Sertraline (SERT NR) and unaffected Controls (Control). Data were acquired with circRNA array profiling in total RNA extracted from whool blood derived from the University of Texas Southwestern (EMBARC study). *p<0.001, p<0.01, based on ANOVA with Tukey's post-hoc corrections for multiple comparisons. N=15 for SERT R and SERT NR and N=8 for Control. (D) Differences in baseline circMALAT1 levels have an excellent predictive value for predicting response after 8 weeks of Sertraline treatment based on receiver operating characteristic curve (ROC curve; a graphical plot that illustrates the diagnostic ability of a binary classifier system). Area under the curve=0.8533 and p=0.0010.

FIGS. 24A-24F. Sertraline response prediction based on circVDAC2, circTRIM69, or circCYP24A1. (A) Patients with MDD that achieved response after 8 weeks of Sertraline treatment (Sert R) exhibit decreased circVDAC2 levels at baseline (before treatment) compared to MDD patients that did not achieve response to Sertraline (SERT NR) and unaffected Controls (Control). Data were acquired with circRNA array profiling in total RNA extracted from whool blood derived from the University of Texas Southwestern (EMBARC study). **p<0.0001, based on ANOVA with Tukey's post-hoc corrections for multiple comparisons, N=15 for SERT R and SERT NR and N=8 for Control. (B) Differences in baseline circVDAC2 levels have an outstanding predictive value for predicting response after 8 weeks of Sertraline treatment based on receiver operating characteristic curve (ROC curve; a graphical plot that illustrates the diagnostic ability of a binary classifier system). Area under the curve=0.9956 and p<0.0001. (C) Patients with MDD that achieved response after 8 weeks of Sertraline treatment (Sert R) exhibit decreased circTRIM69 levels at baseline (before treatment) compared to MDD patients that did not achieve response to Sertraline (SERT NR) and unaffected Controls (Control). Data were acquired with circRNA array profiling in total RNA extracted from whool blood derived from the University of Texas Southwestern (EMBARC study). p<0.0001. p<0.01, based on ANOVA with Tukey's post-hoc corrections for multiple comparisons, N=15 for SERT R and SERT NR and N=8 for Control. (D) Differences in baseline circTRIM69 levels have an outstanding predictive value for predicting response after 8 weeks of Sertraline treatment based on receiver operating characteristic curve (ROC curve; a graphical plot that illustrates the diagnostic ability of a binary classifier system). Area under the curve=1.000 and p<0.0001. (E) Patients with MDD that achieved response after 8 weeks of Sertraline treatment (Sert R) exhibit decreased circCYP24A1 levels at baseline (before treatment) compared to MDD patients that did not achieve response to Sertraline (SERT NR) and unaffected Controls (Control). Data were acquired with circRNA array profiling in total RNA extracted from whool blood derived from the University of Texas Southwestern (EMBARC study). **p<0.0001, p<0.01, based on ANOVA with Tukey's post-hoc corrections for multiple comparisons, N=15 for SERT R and SERT NR and N=8 for Control. (F) Differences in baseline circCYP24A1 levels have an outstanding predictive value for predicting response after 8 weeks of Sertraline treatment based on receiver operating characteristic curve (ROC curve: a graphical plot that illustrates the diagnostic ability of a binary classifier system). Area under the curve=1.000 and p<0.0001.

Figure 25B:
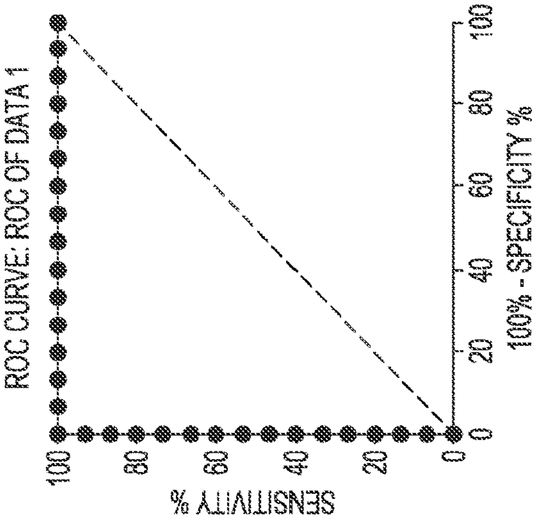
Figure 25A:
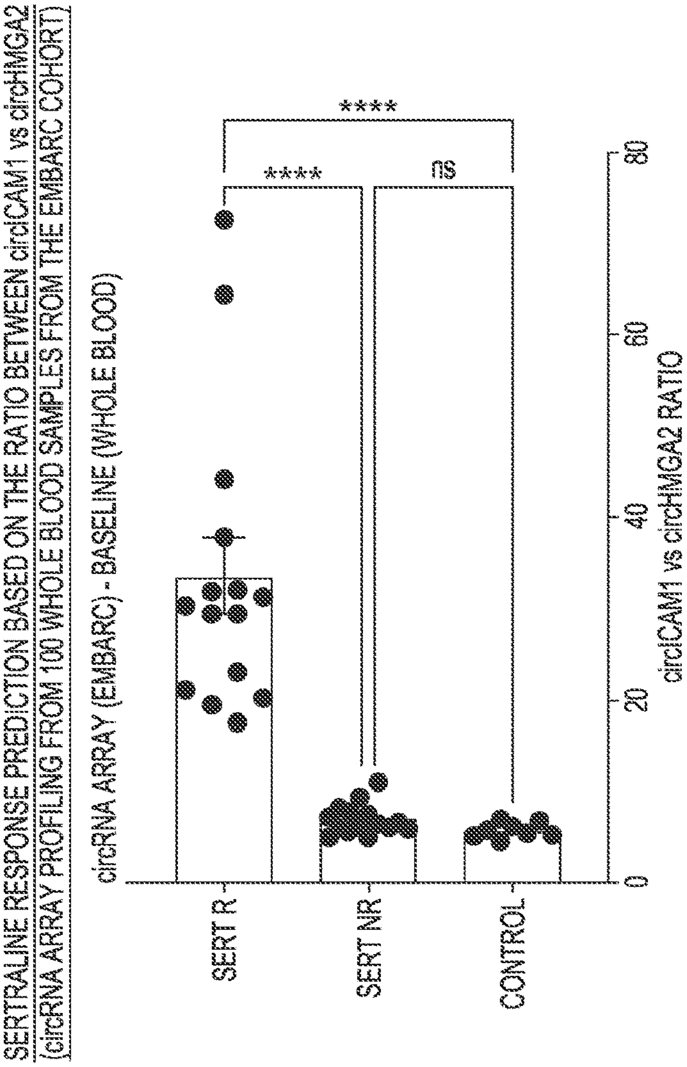

FIGS. 25A-25B. Sertraline response prediction based on the ratio of circICAM1 vs circHMGA2. (A) Patients with MDD that achieved response after 8 weeks of Sertraline treatment (Sert R) exhibit an increased circICAM1 vs circHMGA2 ratio at baseline (before treatment) compared to MDD patients that did not achieve response to Sertraline (SERT NR) and unaffected Controls (Control). Data were acquired with circRNA array profiling in total RNA extracted from whool blood derived from the University of Texas Southwestern (EMBARC study). *p<0.0001, based on ANOVA with Turkey's post-hoc corrections for multiple comparisons, N=15 for SERT R and SERT NR and N=8 for Control. (B) Differences in baseline circICAM1 vs circHMGA2 ratio have an outstanding predictive value for predicting response after 8 weeks of Sertraline treatment based on receiver operating characteristic curve (ROC curve; a graphical plot that illustrates the diagnostic ability of a binary classifier system). Area under the curve=1.000 and p<0.0001.

Figure 26A:
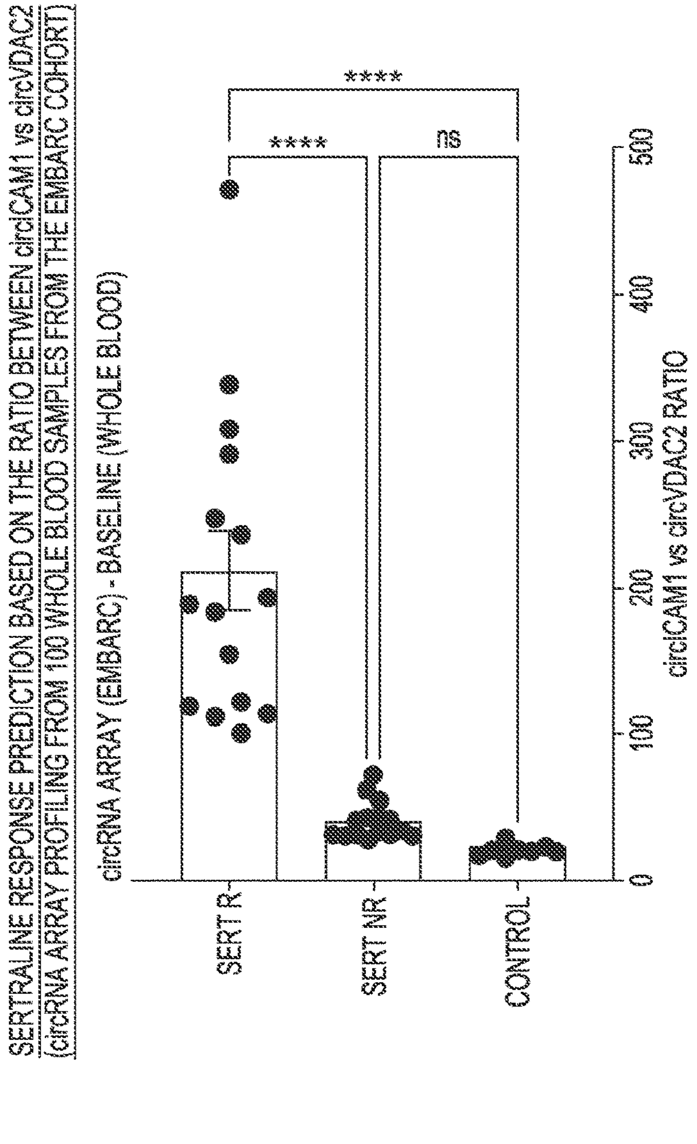
Figure 26B:
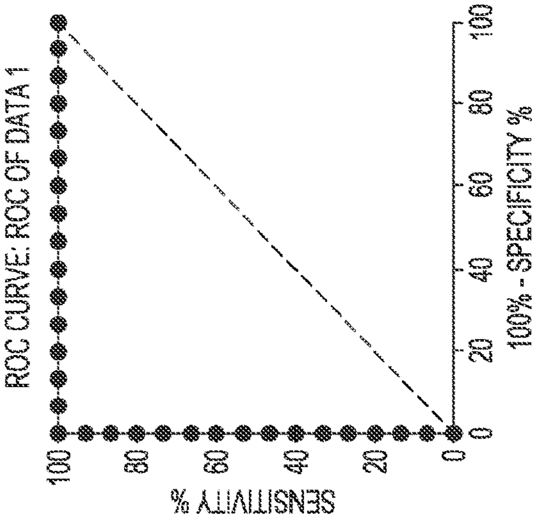

FIGS. 26A-26B. Sertraline response prediction based on the ratio of circICAM1 vs circHMGA2. (A) Patients with MDD that achieved response after 8 weeks of Sertraline treatment (Sert R) exhibit an increased circICAM1 vs circVDAC2 ratio at baseline (before treatment) compared to MDD patients that did not achieve response to Sertraline (SERT NR) and unaffected Controls (Control). Data were acquired with circRNA array profiling in total RNA extracted from whool blood derived from the University of Texas Southwestern (EMBARC study). ****p<0.0001, based on ANOVA with Tukey's post-hoc corrections for multiple comparisons, N=15 for SERT R and SERT NR and N=8 for Control. (B) Differences in baseline circICAM1 vs circVDAC2 ratio have an outstanding predictive value for predicting response after 8 weeks of Sertraline treatment based on receiver operating characteristic curve (ROC curve; a graphical plot that illustrates the diagnostic ability of a binary classifier system). Area under the curve=1.000 and p<0.0001.

FIG. 27. Backspliced junction sequences for selected circRNAs. Graph showing the sequences of the unique circRNA backspliced junction for an exemplary number of species of selected circRNAs (SEQ ID NO's 242-287) PCR primers are designed to span these backspliced circRNA junction sequences.

FIG. 28. Exemplary number of species of selected circRNA-specific PCR primers for top circRNA candidates. Graph showing primer pair for PCR-based detection of selected circRNAs (SEQ ID NO's 288-433).

DETAILED DESCRIPTION

According to an embodiment the present disclosure provides compositions, kits, assays, systems, and methods for the identification, diagnosis, screening, treatment and/or monitoring of brain disorders including, but not necessarily limited to, psychiatric disorders, such as Major Depressive Disorder (MDD) and Bipolar Disorder (BD). For the purposes of the present disclosure the term "Major Depressive Disorder (s)" or "MDD" is a term that describes a psychiatric disease also known as "unipolar depression", "monopolar depression", or just "depression" and includes all subtypes and classifications of such illness. The term "Bipolar Disorder" or "BD" is a term for the spectrum of psychiatric disorders formerly called manic-depressive illness or manic depression and includes all subtypes and classifications of such illness, including Bipolar Disorder type I, Bipolar disorder type II, and Cyclothymic Disorder (also called Cyclothymia). The term antidepressant treatment is a broad term that encompasses all drugs used for treatment of MDD, including but not limited to Selective Serotonin Reuptake Inhibitors (SSRIs), serotonin and norepinephrine reuptake inhibitors (SNRIs), Monoamine oxidase inhibitors (MAOIs), tricyclic antidepressants, and other atypical antidepressants.

According to a specific embodiment, the present disclosure provides a plurality of circular RNAs (circRNAs) the expression of which is correlated with MDD diagnosis or severity, or response or remission to specific antidepressant treatment. CircRNAs are a category of long non-coding RNAs (ncRNAs) that are derived from the circularization and covalent joining of backspliced exons and/or introns. CircRNAs are particularly enriched in the mammalian brain (at least 100,000 different circRNAs have been identified in the human brain), yet, with few exceptions, lack the capacity of being translated into protein. Some circRNAs are known to sequester microRNAs (miRNAs) by containing partial complementary sequences and others to associate with RNA-binding proteins (RBPs) and transcription factors. Recent work has suggested that circRNAs could be altered in neurological and psychiatric disorders and that they could be responsible for regulating brain development, maturation, plasticity, and aging. Due to their closed loop structure, circRNAs are particularly resistant to degradation thus exhibit very high stability, with half-lives ranging from a few days to a week. This unparallel stability allows circRNAs to accumulate in various tissues and bodily fluids, whereas their tissue- and disease state-specificity allows them to serve as ideal biomarkers.

Tables 1-9 provide the specific circRNAs which showed significantly altered expression based on circRNA array profiling in the blood of individuals diagnosed with MDD that were found to exhibit remission to different antidepressant treatments vs patients with MDD that did not achieve remission after antidepressant treatment or circRNAs that show altered expression 8 weeks after treatment vs baseline (before treatment). For the purposes of the present disclosure, the circRNAs provided in Tables 1-9 are collectively referred to herein as "MDD-treatment predictive circRNAs".

Specifically, Table 1 provides circRNAs which showed significantly altered expression at baseline (before onset of treatment) in peripheral blood mononuclear cells (PBMCs) derived from the blood of patients with MDD that achieved remission after 30 weeks of SSRI treatment (SSRI-R baseline) vs patients with MDD that did not achieve remission after 30 weeks of SSRI treatment (SSRI-NR baseline).

Table 2 provides circRNAs which showed significantly altered expression 8 weeks after treatment in peripheral blood mononuclear cells (PBMCs) derived from the blood of patients with MDD that achieved remission after 30 weeks of SSRI treatment (SSRI-R 8 week) vs patients with MDD that did not achieve remission after 30 weeks of SSRI treatment (SSRI-NR 8 week).

Table 3 provides circRNAs which showed significantly altered expression at baseline (before onset of treatment) in peripheral blood mononuclear cells (PBMCs) derived from the blood of patients with MDD that achieved remission after 30 weeks of SNRI treatment (SNRI-R baseline) vs patients with MD D that did not achieve remission after 30 weeks of SSRI treatment (SNRI-NR baseline).

Table 4 provides circRNAs which showed significantly altered expression 8 weeks after treatment in peripheral blood mononuclear cells (PBMCs) derived from the blood of patients with MDD that achieved remission after 30 weeks of SNRI treatment (SNRI-R 8 week) vs patients with MDD that did not achieve remission after 30 weeks of SSRI treatment (SNRI-NR 8 week).

Table 5 provides circRNAs which showed significantly altered expression 8 weeks after treatment vs baseline (before treatment) in peripheral blood mononuclear cells (PBMCs) derived from the blood of patients with MDD that achieved remission after 30 weeks of SSRI treatment (SSRI-R 8 week vs SSRI-R baseline).

Table 6 provides circRNAs which showed significantly altered expression 8 weeks after treatment vs baseline (before treatment) in peripheral blood mononuclear cells (PBMCs) derived from the blood of patients with MDD that did not achieve remission after 30 weeks of SSRI treatment (SSRI-NR 8 week vs SSRI-NR baseline).

Table 7 provides circRNAs which showed significantly altered expression 8 weeks after treatment vs baseline (before treatment) in peripheral blood mononuclear cells (PBMCs) derived from the blood of patients with MDD that achieved remission after 30 weeks of SNRI treatment (SNRI-R 8 week vs SNRI-R baseline).

Table 8 provides circRNAs which showed significantly altered expression 8 weeks after treatment vs baseline (before treatment) in peripheral blood mononuclear cells (PBMCs) derived from the blood of patients with MDD that did not achieve remission after 30 weeks of SNRI treatment (SNRI-NR 8 week vs SNRI-NR baseline).

Table 9 provides circRNAs which showed significantly altered expression 8 weeks after treatment vs baseline (before treatment) in peripheral blood mononuclear cells (PBMCs) derived from the blood of patients with MDD who achieved remission after 30 weeks of MAOI treatment (MAOI-R 8 week vs MAOI-R baseline). For the purposes of the present disclosure, the term "significantly altered expression" means that the expression of a circRNA in patient samples is significantly lower or higher between two groups of compared samples via two-tailed Student's t-test with $p<0.05$ as a cutoff p-value for statistical significance and a fold change of more 1.5-fold (either reduction or increase).

Tables 10-14 provide the specific circRNAs which showed significantly altered expression based on circRNA array profiling in the blood of individuals diagnosed with either MDD or BD vs unaffected controls or circRNAs that show altered expression 8 weeks after treatment vs baseline (before treatment) in either patients with MDD or BD, or controls. For the purposes of the present disclosure, the circRNAs provided in Tables 10-14 are collectively referred to herein as "MDD and BD diagnosis-related circRNAs".

Specifically, Table 10 provides circRNAs which showed significantly altered expression at baseline (before onset of treatment) in peripheral blood mononuclear cells (PBMCs) derived from the blood of patients with MDD (MDD baseline) vs controls (Control Baseline).

Table 11 provides circRNAs which showed significantly altered expression 8 weeks after treatment in peripheral blood mononuclear cells (PBMCs) derived from the blood of patients with MDD (MDD 8 week) vs controls (Control 8 week).

Table 12 provides circRNAs which showed significantly altered expression at baseline (before onset of treatment) in peripheral blood mononuclear cells (PBMCs) derived from the blood of patients with BD (BD baseline) vs controls (Control Baseline).

Table 13 provides circRNAs which showed significantly altered expression 8 weeks after treatment in peripheral blood mononuclear cells (PBMCs) derived from the blood of patients with BD (BD 8 week) vs controls (Control 8 week).

Table 14 provides circRNAs which showed significantly altered expression 8 weeks after treatment vs baseline (before treatment) in peripheral blood mononuclear cells (PBMCs) derived from the blood of patients with BD (BD 8 week vs BD baseline). For the purposes of the present disclosure, the term "significantly altered expression" means that the expression of a circRNA in patient samples is significantly lower or higher between two groups of compared samples via two-tailed Student's t-test with $p<0.05$ as a cutoff p-value for statistical significance and a fold change of more 1.5-fold (either reduction or increase).

Tables 15-18 provide the specific circRNAs which showed significantly altered expression based on circRNA array profiling in whole blood of individuals diagnosed MDD that were treated with Sertraline for 8 weeks and either responded (Sert R) or did not respond to treatment (Sert NR). For the purposes of the present disclosure, the circRNAs provided in Tables 15-18 are collectively referred to herein as "Sertraline treatment-related circRNAs".

Specifically, Table 15 provides circRNAs which showed significantly altered expression at baseline (before onset of treatment) in whole blood of individuals diagnosed MDD that were treated with Sertraline for 8 weeks and either responded (Sert R) or did not respond to treatment (Sert NR).

Table 16 provides circRNAs which showed significantly altered expression 1 week after treatment in whole blood of individuals diagnosed MDD that were treated with Sertraline for 8 weeks and either responded (Sert R) or did not respond to treatment (Sert NR).

Table 17 provides circRNAs which showed significantly altered expression 1 week after treatment in whole blood of individuals diagnosed MDD that were treated with Sertraline for 8 weeks and responded (Sert R)vs baseline expression in the same patients (Sert R 1 week vs Sert R baseline).

Table 18 provides circRNAs which showed significantly altered expression 1 week after treatment in whole blood of individuals diagnosed MDD that were treated with Sertraline for 8 weeks and did not respond (Sert NR) vs baseline expression in the same patients (Sert NR 1 week vs Sert NR baseline).

Each of the 18 Tables includes the unique transcript start and end chromosomal coordinates (tx Start and tx End), the chromosome (Chr) number and strand, the circRNA type, the circRNA alias based on circBase (http://circbase.mdc-berlin.de) or other circRNA databases the relative to Control fold change and uncorrected p-value, and the host gene symbol for significantly altered circRNAs ($p<.05$, two-tailed Students t-test)." All circRNA array experiments used for Tables 1-16 were performed by employing a commercially available circRNA microarray platform that uses 13,617 circRNA splice junction probes designed based on previous RNA sequencing and circRNA annotation data (Service sold by Arraystar Inc.). Additional methods for identifying these brain disorder-associated circRNA biomarkers are discussed in the Experimental section below.

Figure 16A:
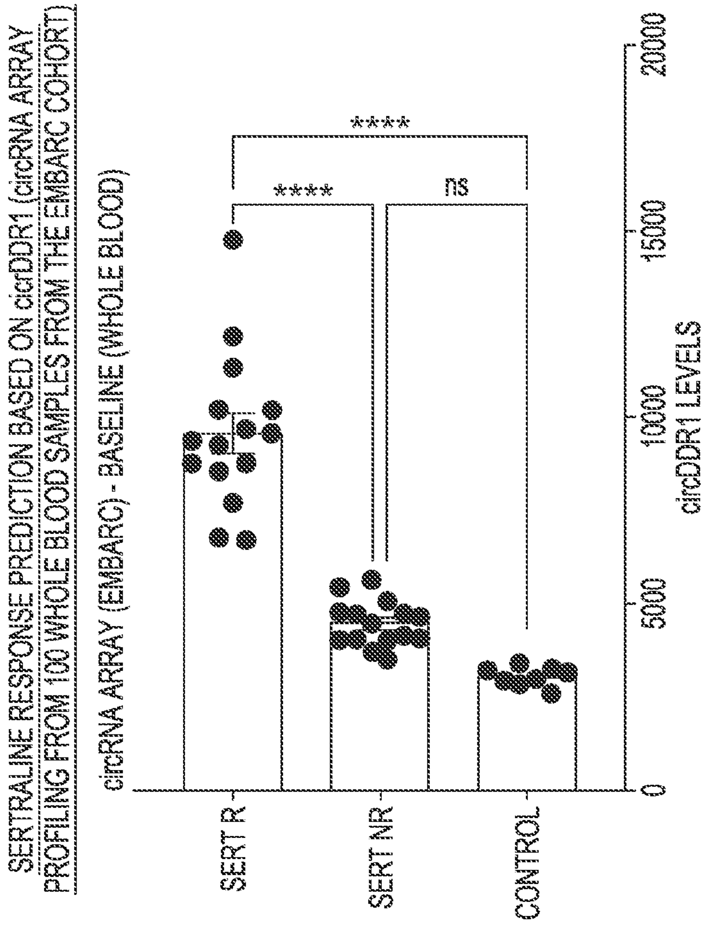
FIGS. 16A-16C. Sertraline response prediction based on circDDR1. (A) Patients with MDD that achieved response after 8 weeks of Sertraline treatment (Sert R) exhibit increased circDDR1 levels at baseline (before treatment) compared to MDD patients that did not achieve response to Sertraline (SERT NR) and unaffected Controls (Control). Data were acquired with circRNA array profiling in total RNA extracted from whool blood derived from the University of Texas Southwestern (EMBARC study). *p<0.0001, based on ANOVA with Tukey's post-hoc corrections for multiple comparisons, N=15 for SERT R and SERT NR and N=8 for Control. (B) Differences in baseline circDDR1 levels have an outstanding predictive value for predicting response after 8 weeks of Sertraline treatment based on receiver operating characteristic curve (ROC curve; a graphical plot that illustrates the diagnostic ability of a binary classifier system). Area under the curve=0.9022 and p=0.0002. (C) Comparison of whole blood circDDR1 expression after 1 week of treatment vs baseline in MDD patients that either achieved reponse (Sert R) or not (SERT NR) to Sertraline and unaffected Controls (Control). Data were acquired with circRNA array profiling in total RNA extracted from whool blood derived from the University of Texas Southwestern (EMBARC study). p<0.01, based on ANOVA with Tukey's post-hoc corrections for multiple comparisons. N=15 for all SERT groups and N=8 for Control.
Figure 16B:
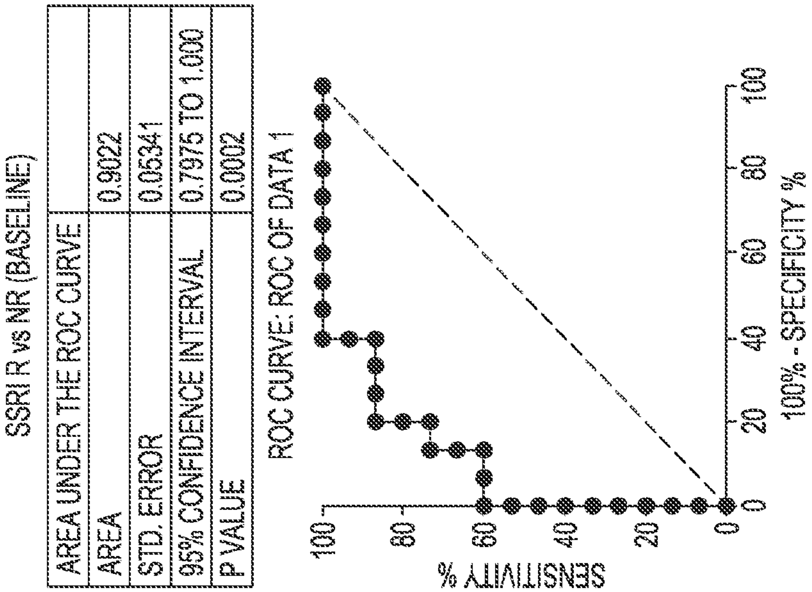
Figure 16C:
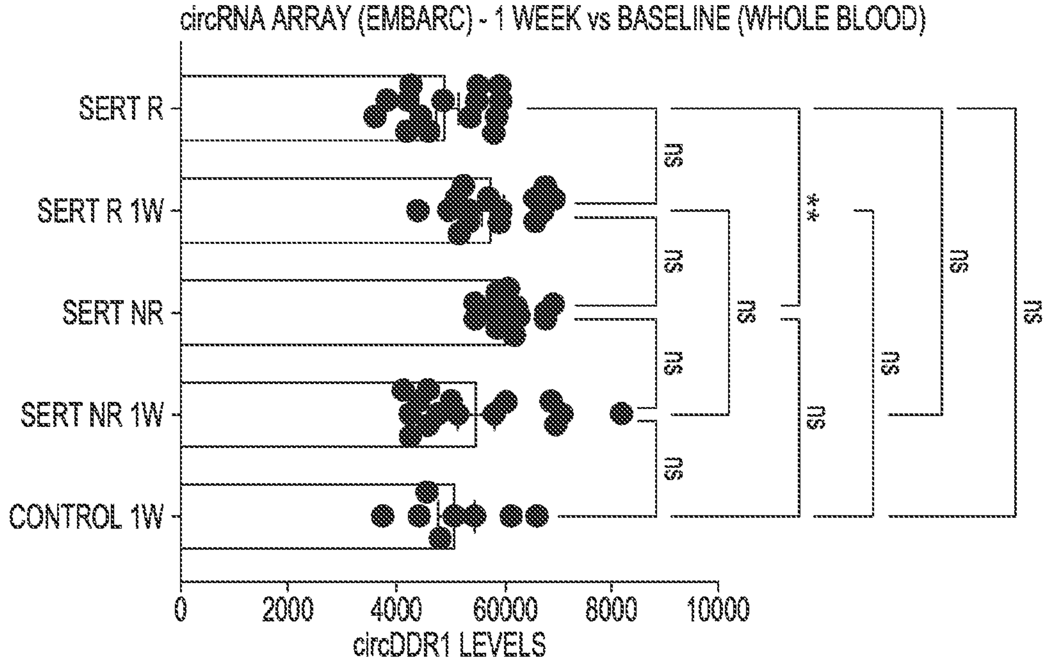
Figure 17A:
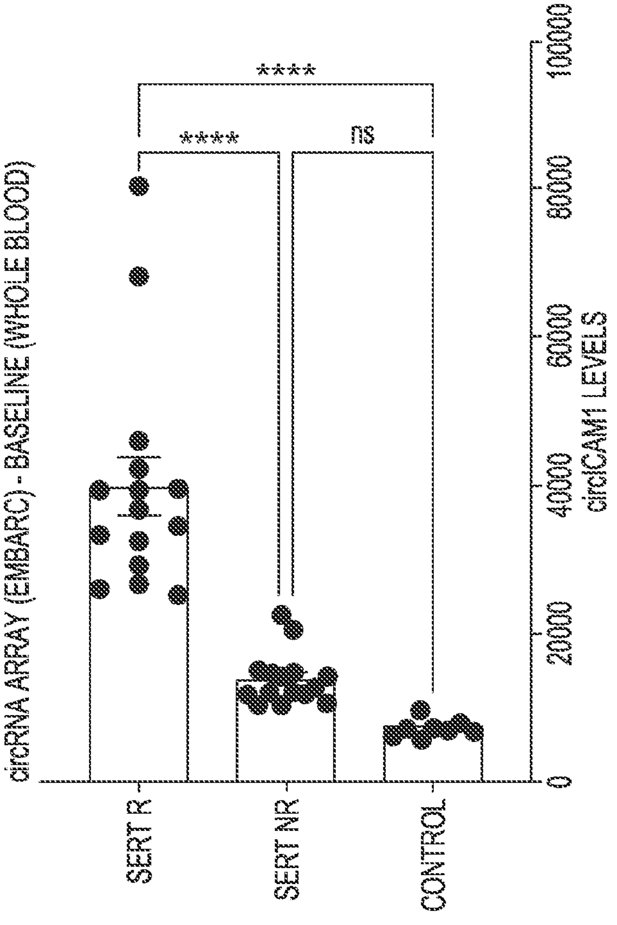
FIGS. 17A-17C. Sertraline response prediction based on circICAM1. (A) Patients with MDD that achieved response after 8 weeks of Sertraline treatment (Sert R) exhibit increased circICAM1 levels at baseline (before treatment) compared to MDD patients that did not achieve response to Sertraline (SERT NR) and unaffected Controls (Control). Data were acquired with circRNA array profiling in total RNA extracted from whool blood derived from the University of Texas Southwestern (EMBARC study). ****p<0.0001, based on ANOVA with Tukey's post-hoc corrections for multiple comparisons, N=15 for SERT R and SERT NR and N=8 for Control. (B) Differences in baseline circlCAM1 levels have an outstanding predictive value for predicting response after 8 weeks of Sertraline treatment based on receiver operating characteristic curve (ROC curve; a graphical plot that illustrates the diagnostic ability of a binary classifier system). Area under the curve=1.000 and p<0.0001. (C) Comparison of whole blood circICAM1 expression after 1 week of treatment vs baseline in MDD patients that either achieved reponse (Sert R) or not (SERT NR) to Sertraline and unaffected Controls (Control). Data were acquired with circRNA array profiling in total RNA extracted from whool blood derived from the University of Texas Southwestern (EMBARC study). *p<0.0001, *p<0.001*p<0.01, based on ANOVA with Tukey's post-hoc corrections for multiple comparisons, N=15 for all SERT groups and N=8 for Control.
Figure 17B:
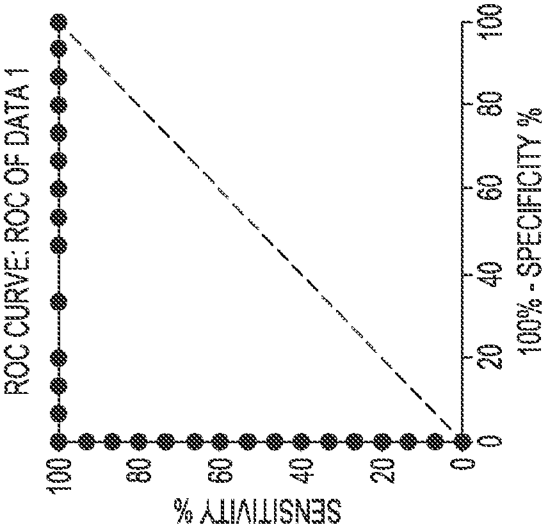
Figure 17C:
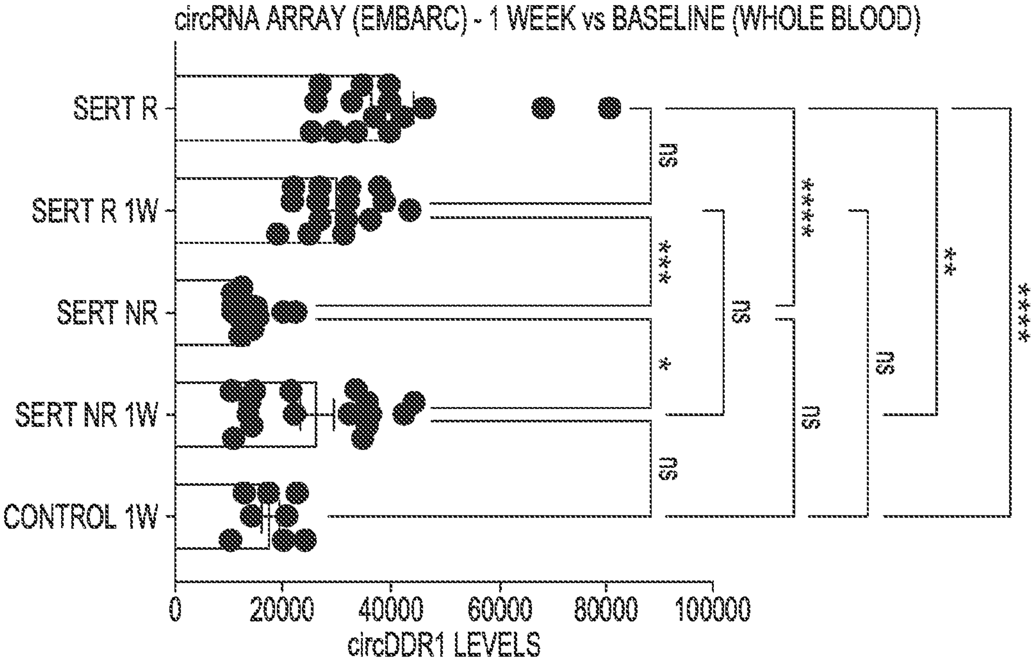
Figure 18A:
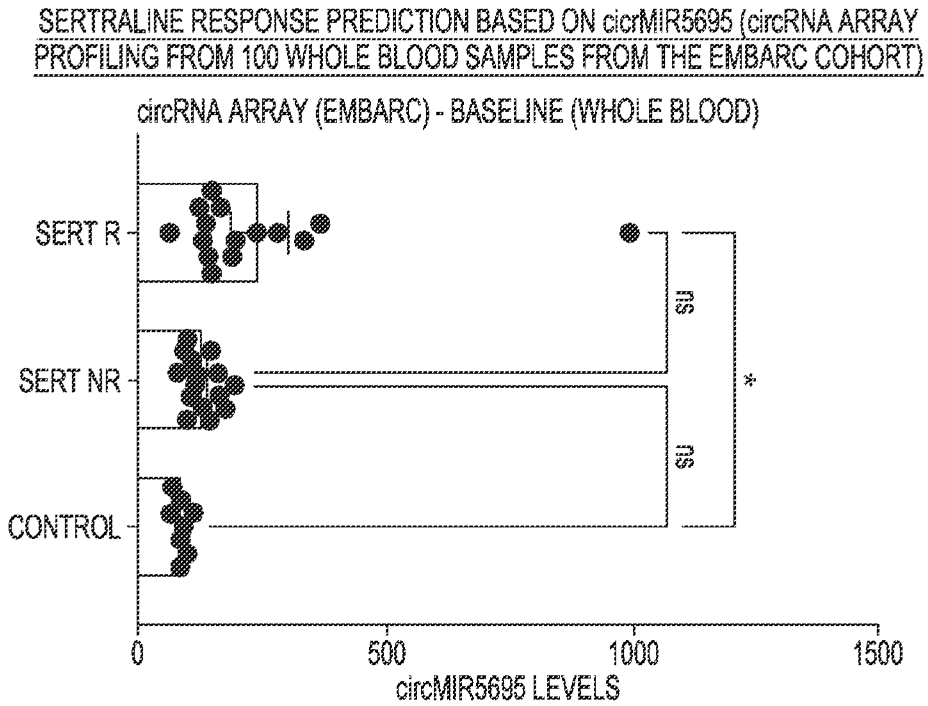
FIGS. 18A-18D. Sertraline response prediction based on circMIR5695. (A) Patients with MDD that achieved response after 8 weeks of Sertraline treatment (Sert R) exhibit increased circMIR5695 levels at baseline (before treatment) compared to MDD patients that did not achieve response to Sertraline (SERT NR) and unaffected Controls (Control). Data were acquired with circRNA array profiling in total RNA extracted from whool blood derived from the University of Texas Southwestern (EMBARC study). *p<0.05, based on ANOVA with Tukey's post-hoc corrections for multiple comparisons, N=15 for SERT R and SERT NR and N=8 for Control. (B) Differences in baseline circMIR5695 levels have an very good predictive value for predicting response after 8 weeks of Sertraline treatment based on receiver operating characteristic curve (ROC curve; a graphical plot that illustrates the diagnostic ability of a binary classifier system). Area under the curve=0.7667 and p=0.0128. (C) Patients with MDD that achieved response after 8 weeks of Sertraline treatment (Sert R) exhibit increased circMIR5695 levels one week after treatment compared to MDD patients that did not achieve response to Sertraline (SERT NR) and unaffected Controls (Control). Data were acquired with circRNA array profiling in total RNA extracted from whool blood derived from the University of Texas Southwestern (EMBARC study).
Figure 18B:
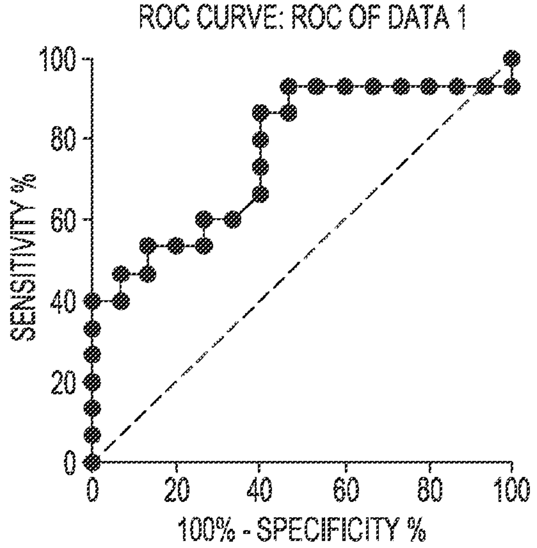
Figure 18D:
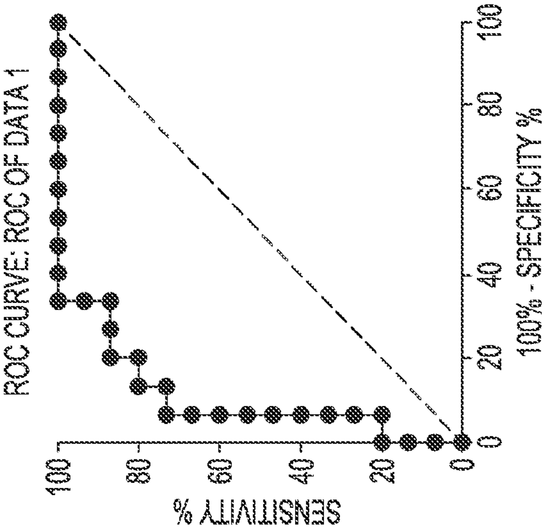
Figure 18C:
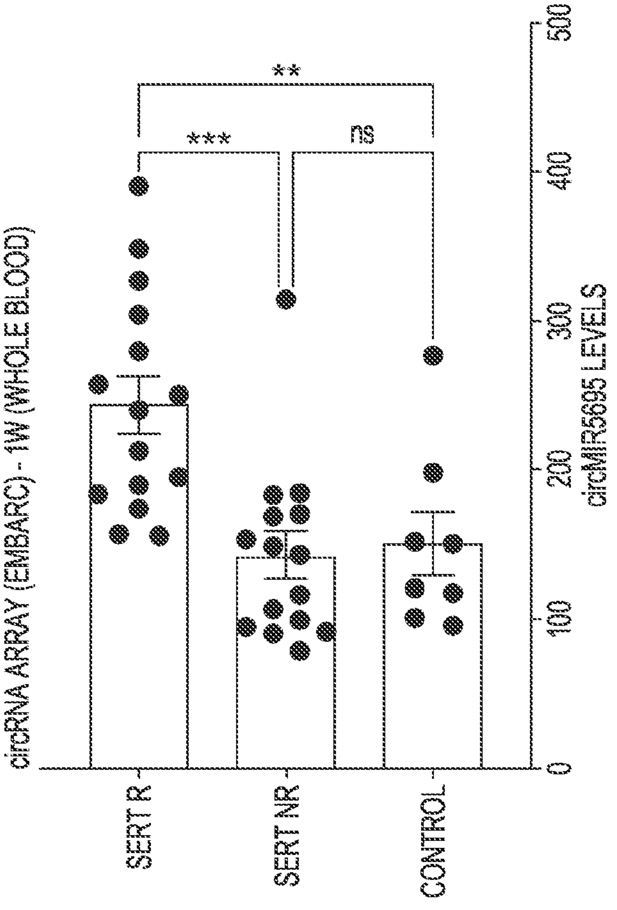
Figure 19B:
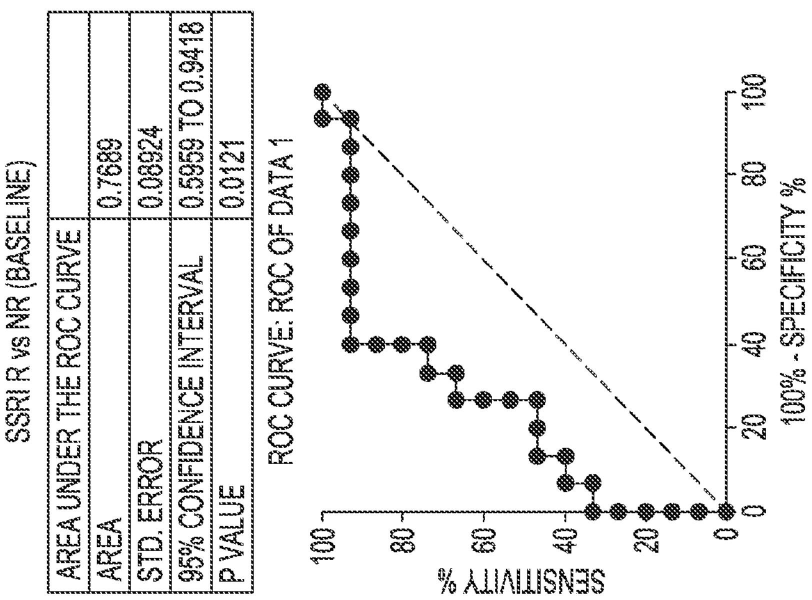
Figure 19A:
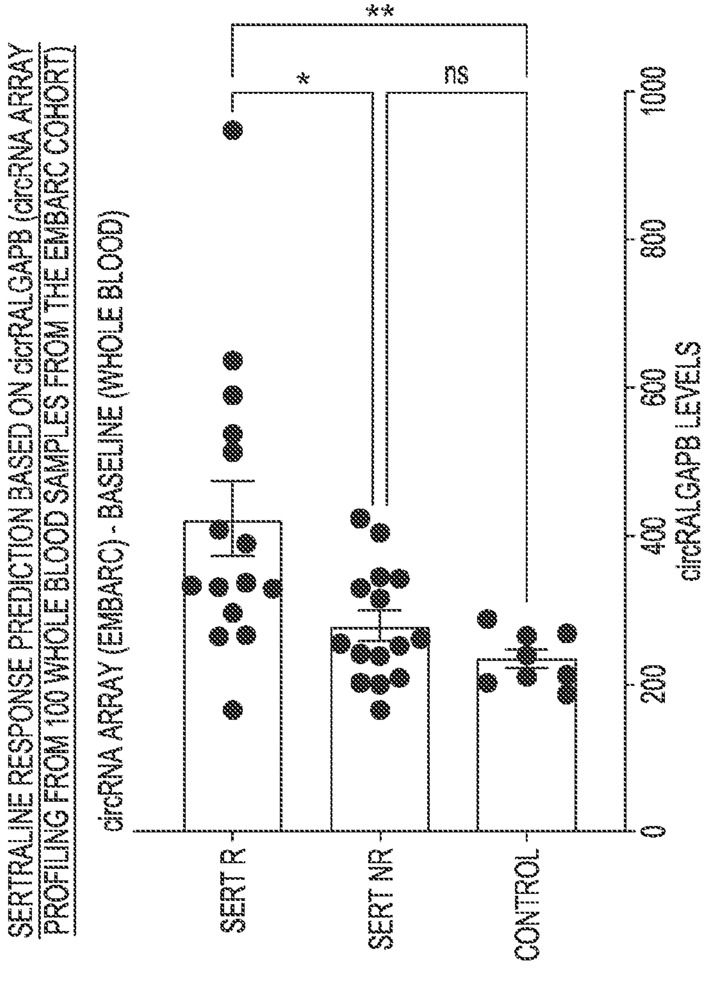
Figure 19D:
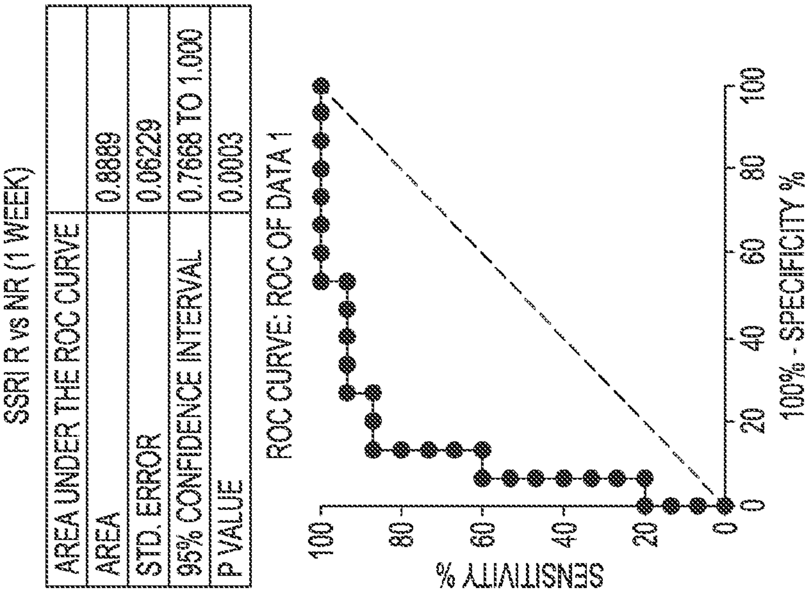
Figure 19C:
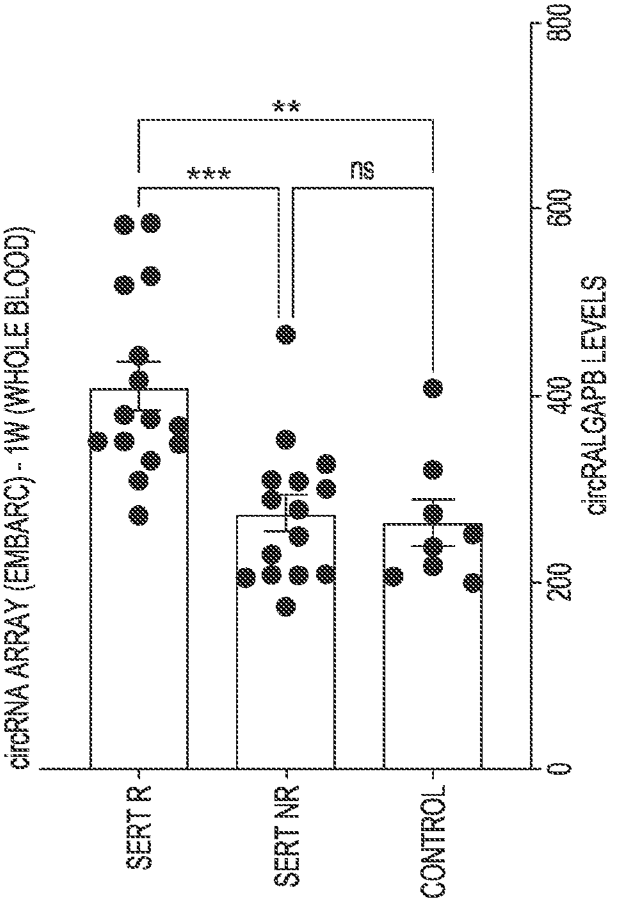
Figure 20B:
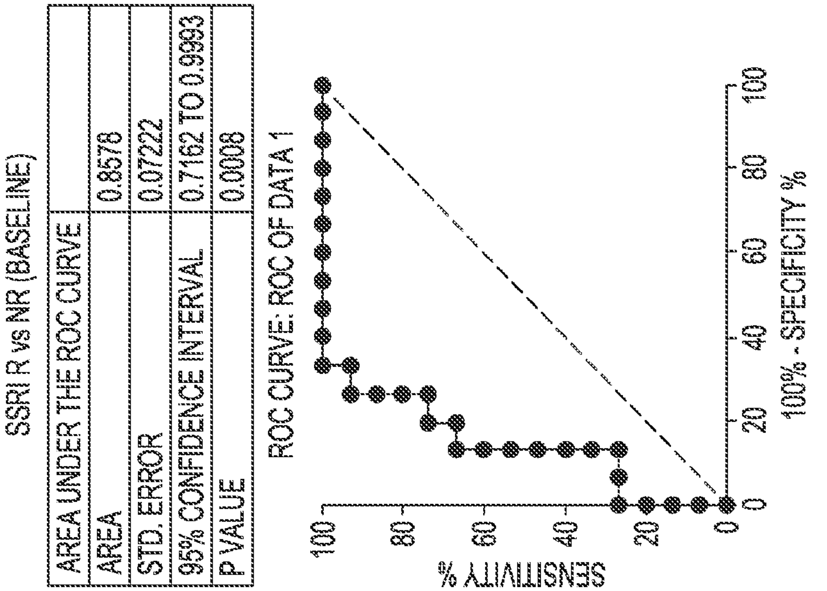
Figure 20A:
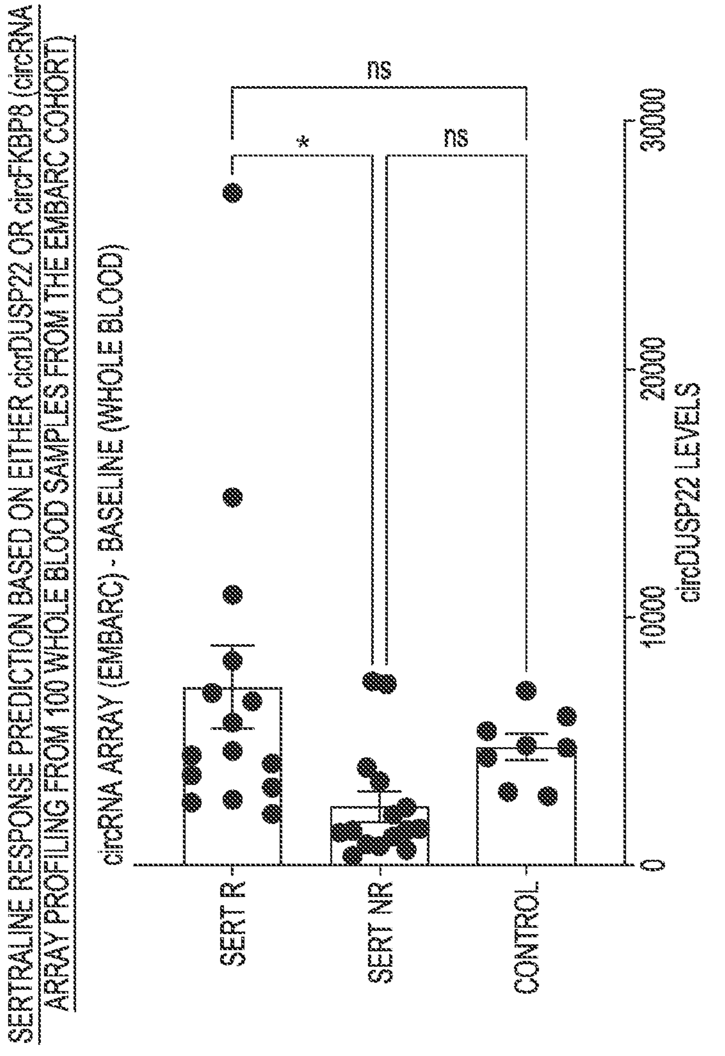
Figure 20C:
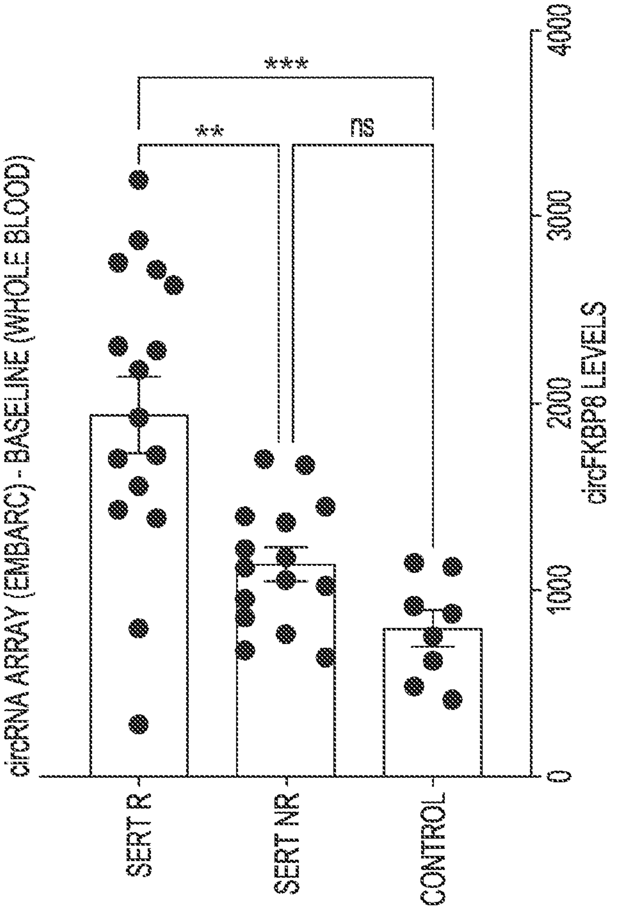
Figure 20D:
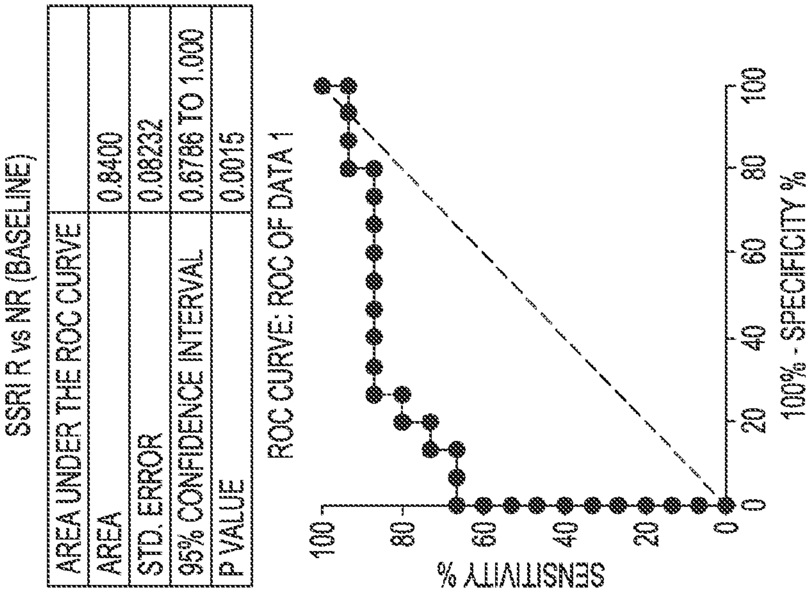
Figure 21A:
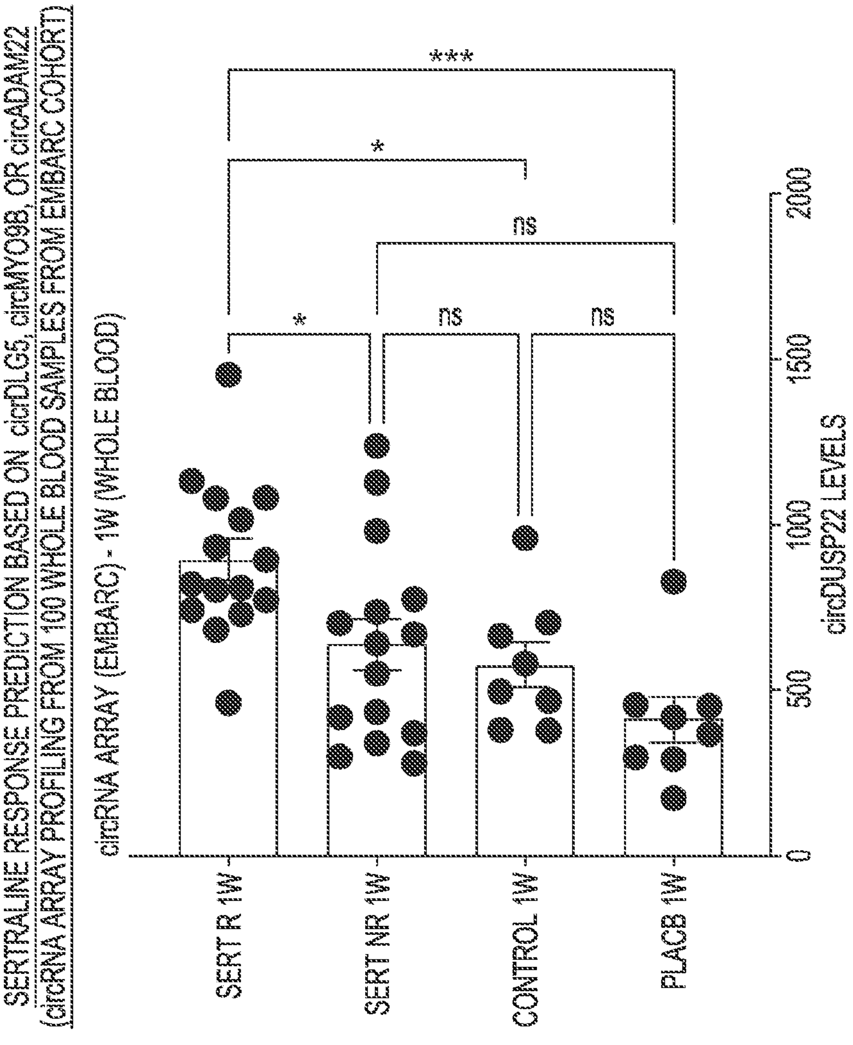
Figure 21B:
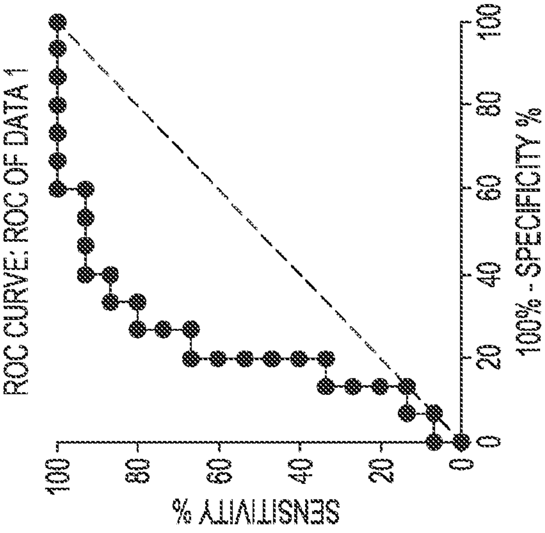
Figure 21C:
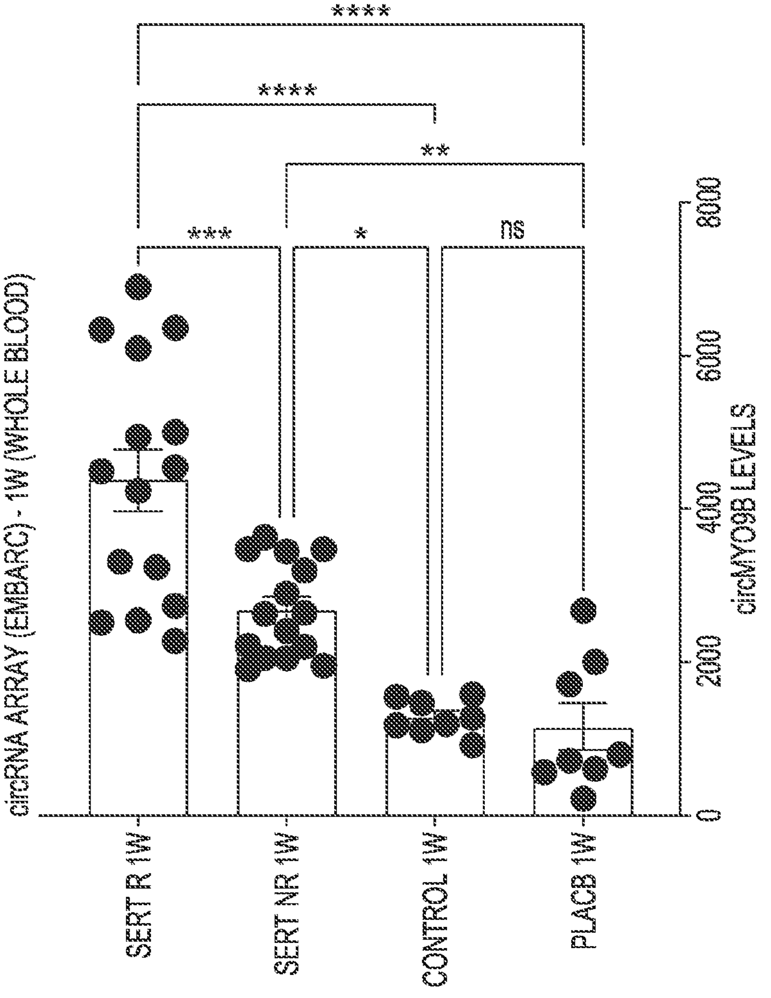
Figure 21D:
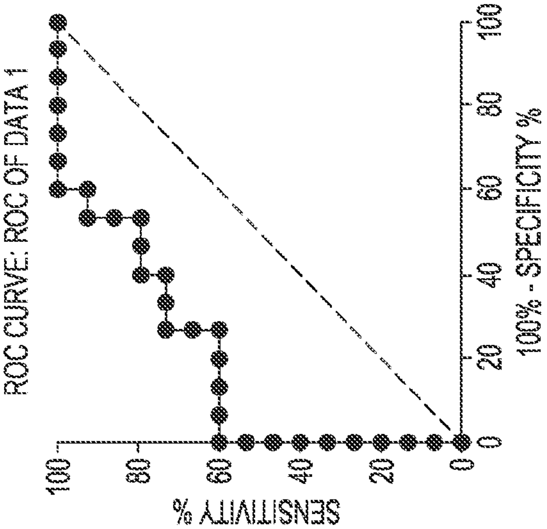
Figure 21E:
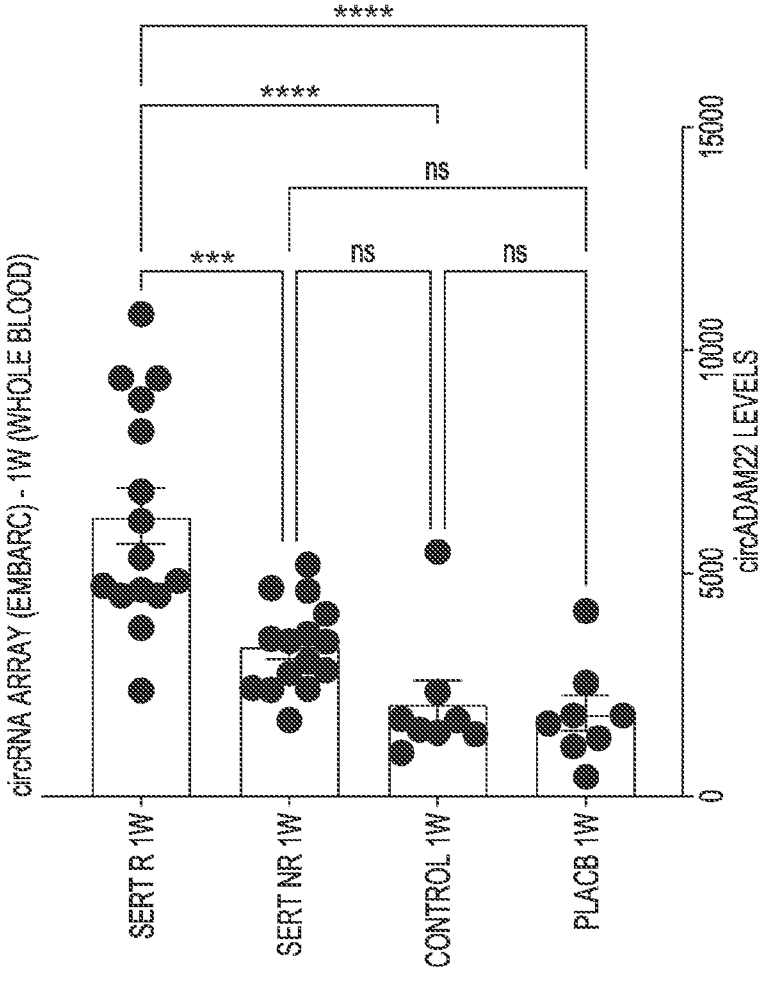
Figure 21F:
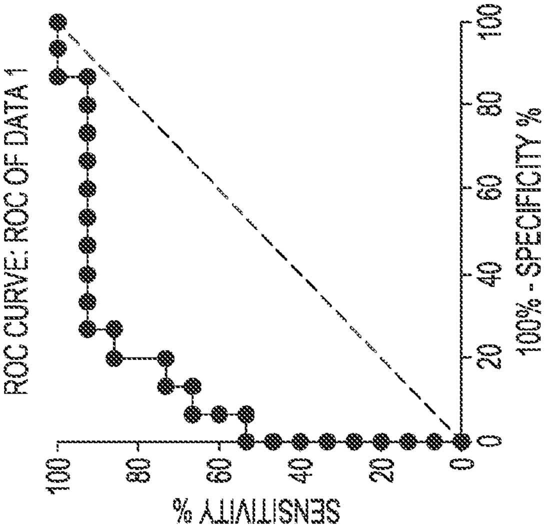
Figure 22B:
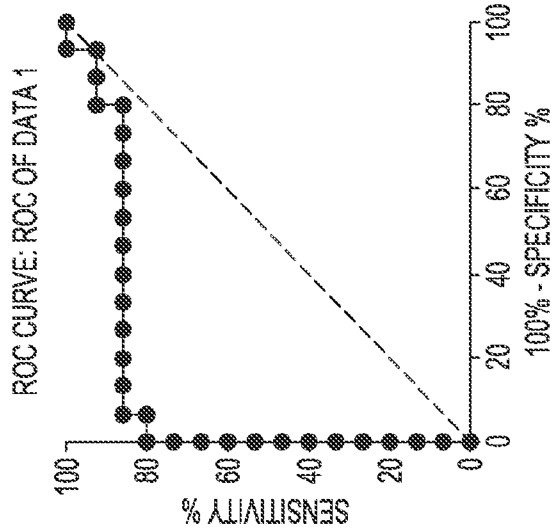
Figure 22A:
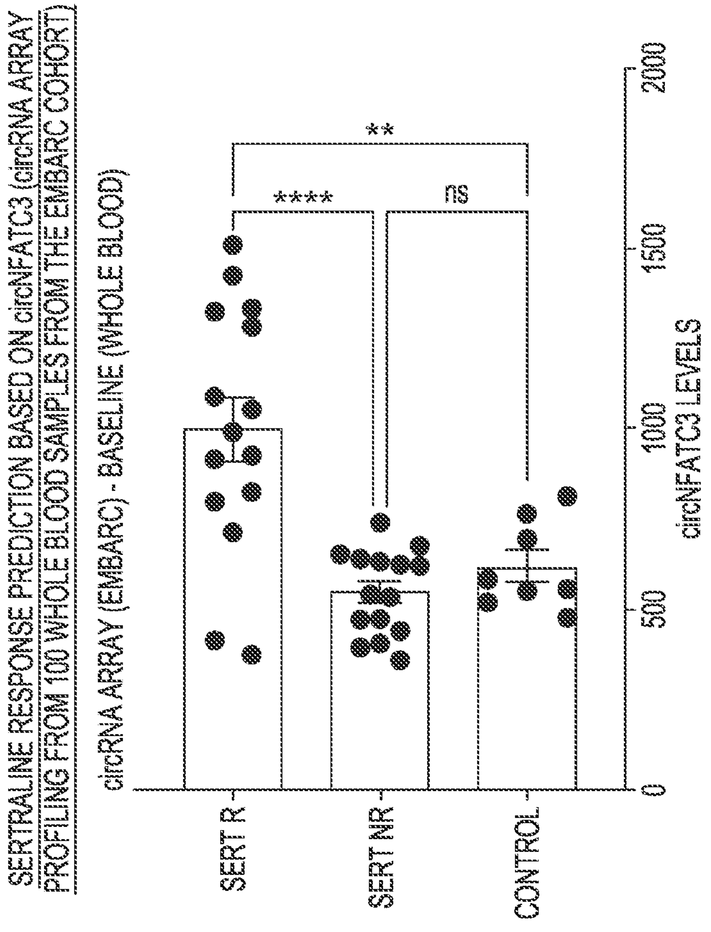
Figure 22D:
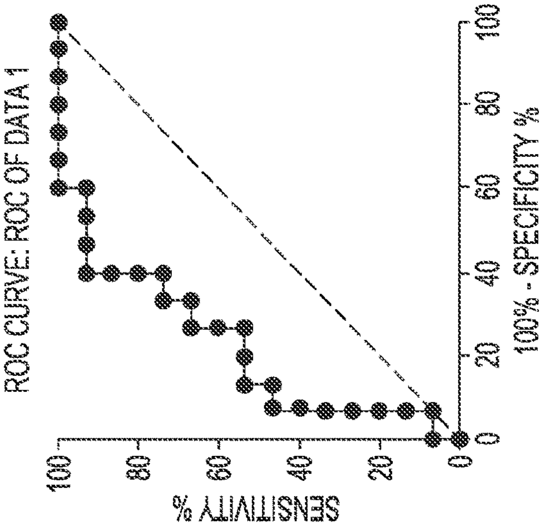
Figure 22C:
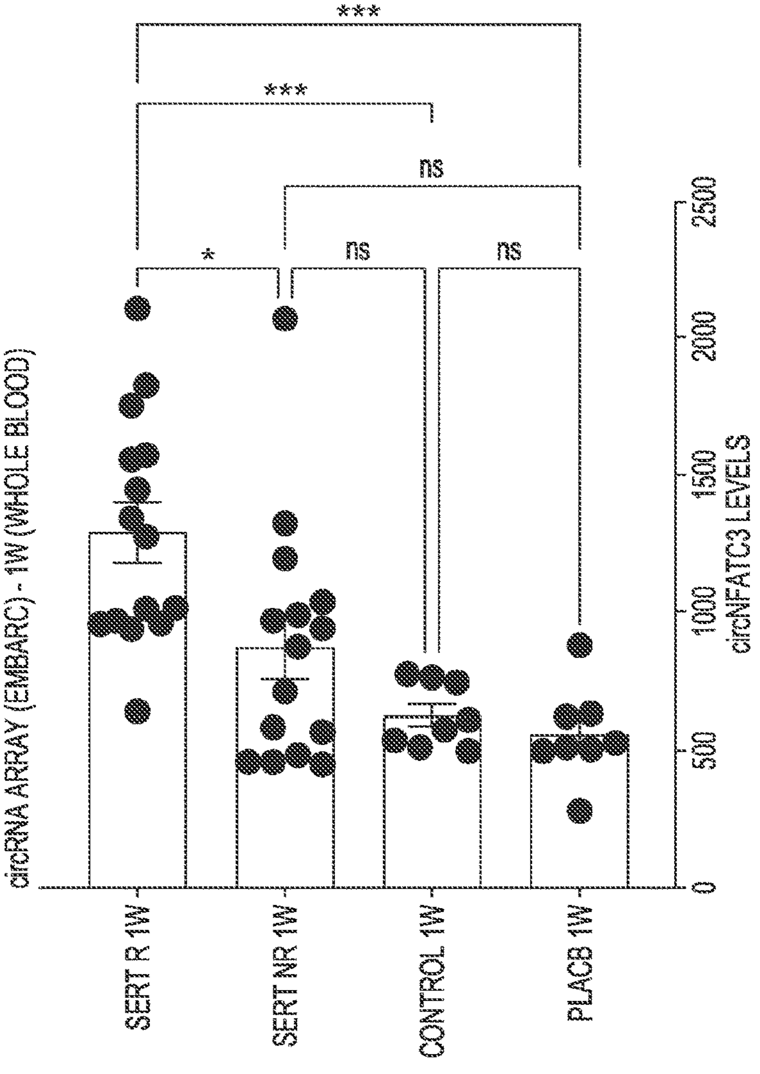
Figure 23A:
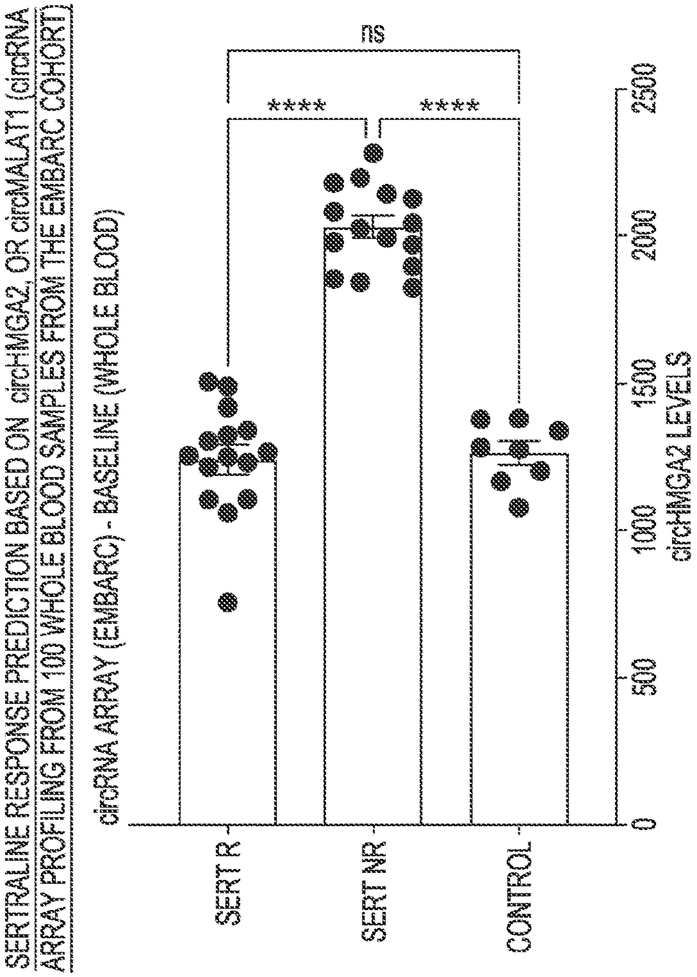
Figure 23B:
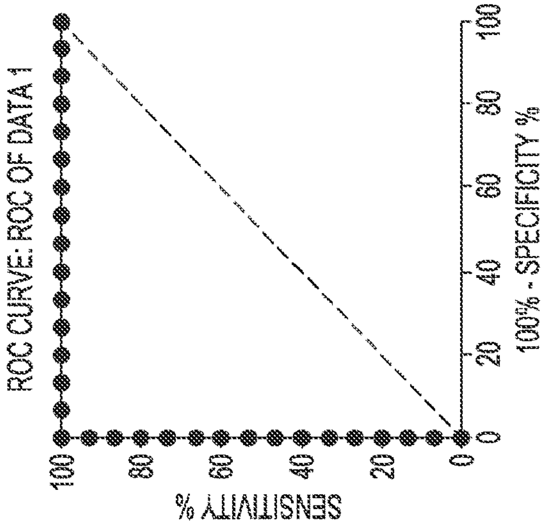
Figure 23C:
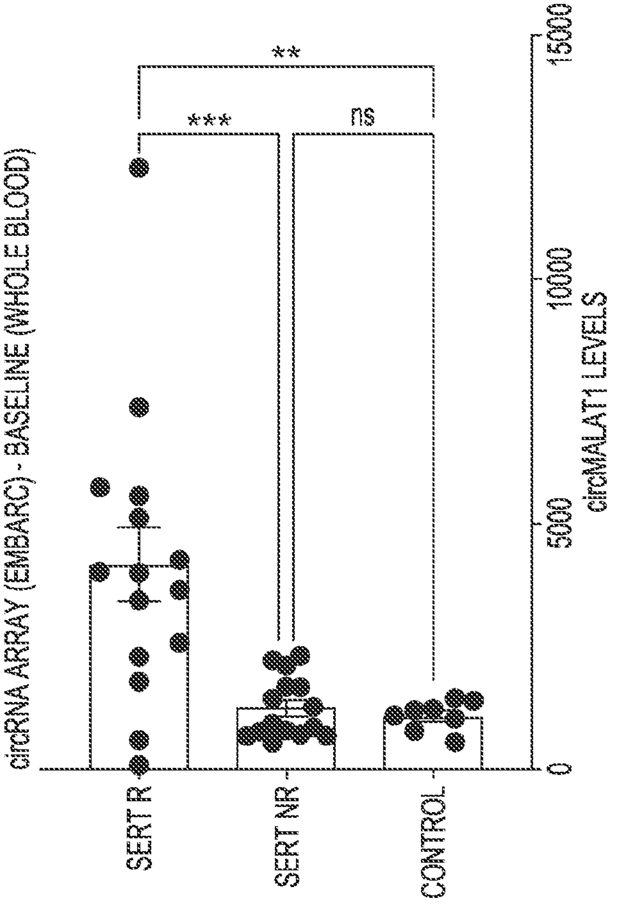
Figure 23D:
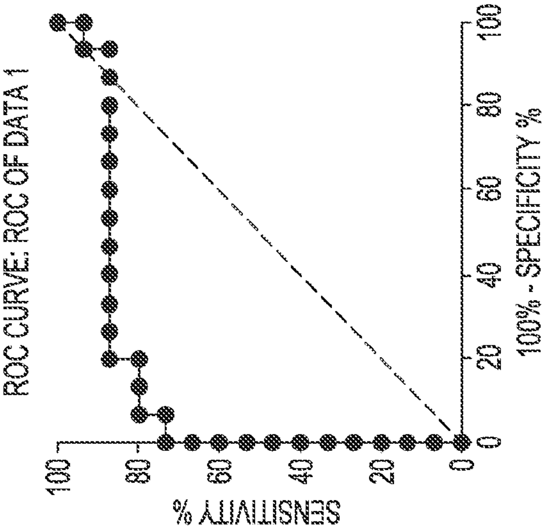
Figure 24A:
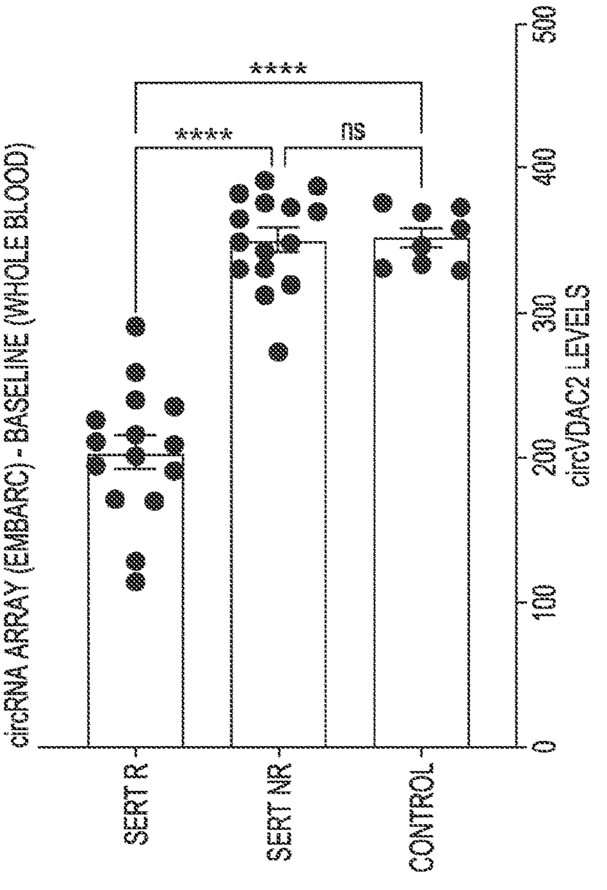
Figure 24B:
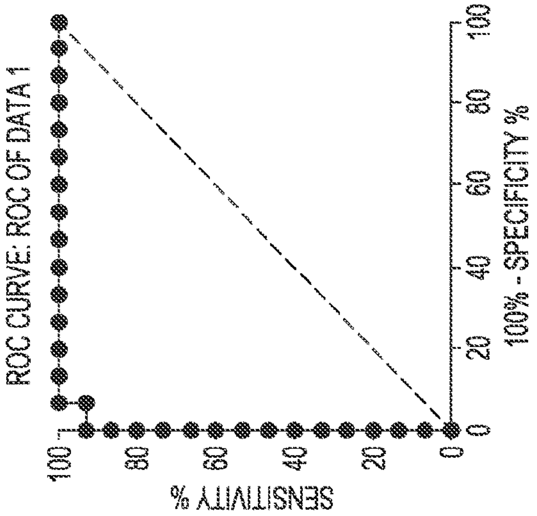
Figure 24D:
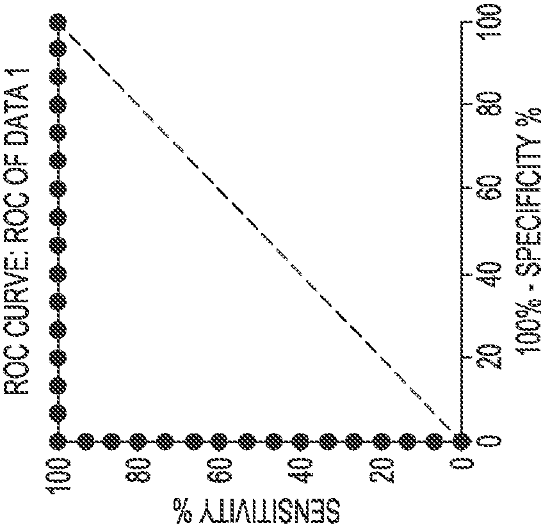
Figure 24C:
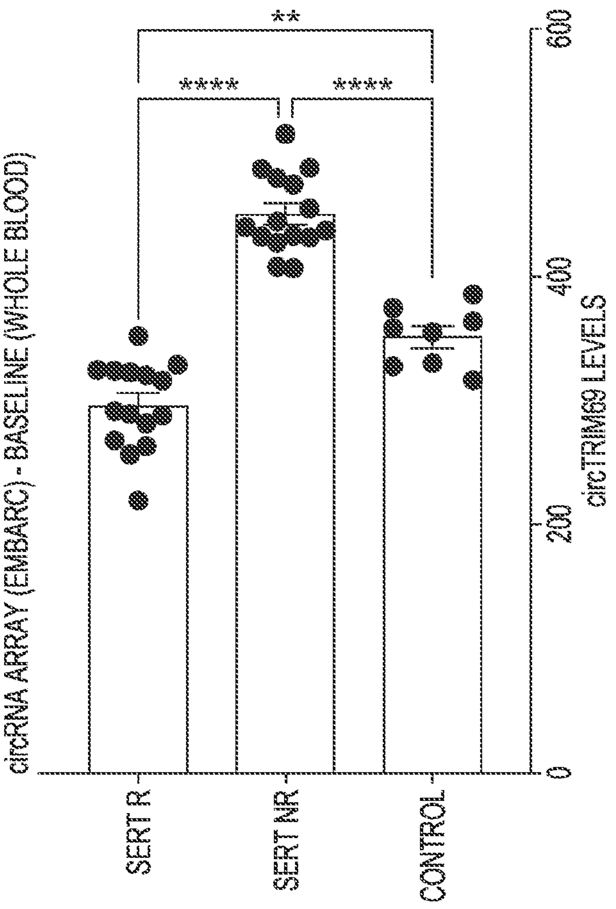
Figure 24F:
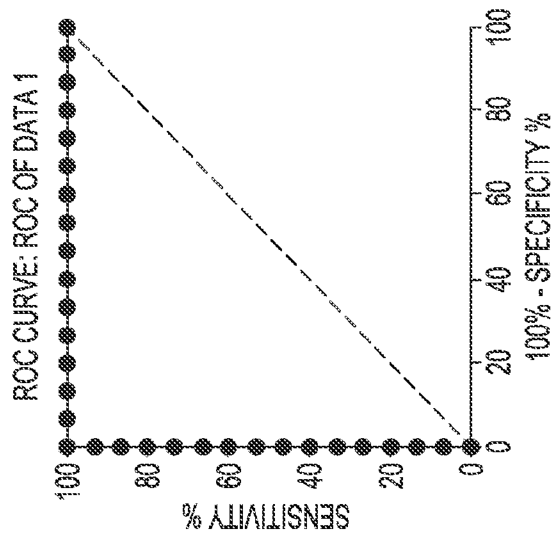
Figure 24E:
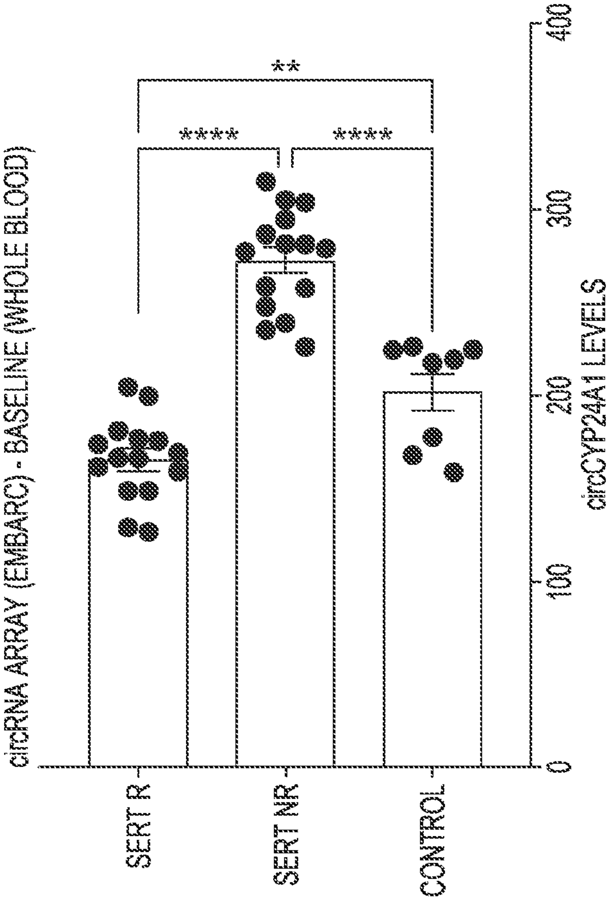

Given that harsh RNaseR treatment can partially digest some circRNAs together with all linear RNAs, thus making circRNA screening semi-quantitative and given the high cost of such screening methods, the present disclosure also provides novel validated and sequence-verified circRNA-specific qRT-PCR primers aimed at the unique circRNA-specific splice junction, which enable the measurement of a subset of dysregulated circRNAs in non RNaseR-treated samples. The sequences of the backspliced junctions of a few selected circRNAs are shown in FIG. 16. PCR primers are designed so as to span the unique circRNA backspliced junctions, so that they specifically detect the circRNA of interest and not other linear or circular isoforms derived from the same gene.

Figure 1B:
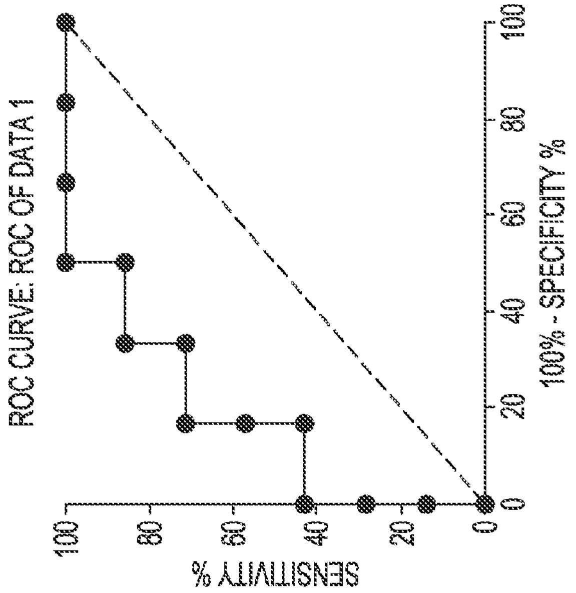
Figure 2A:
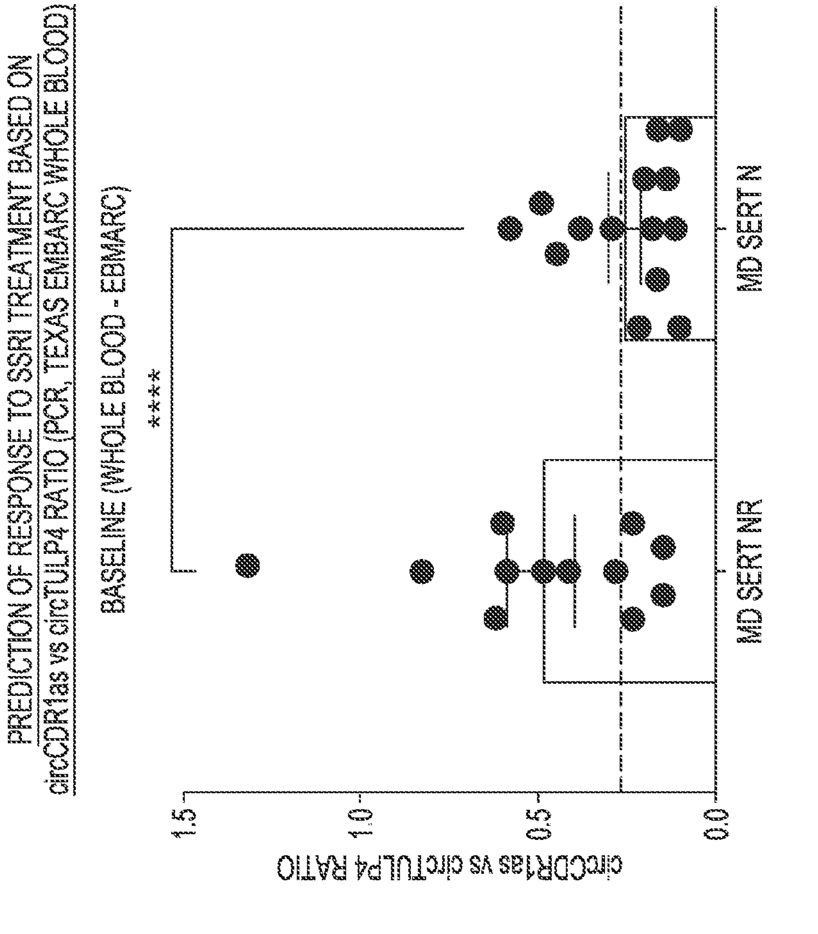
FIGS. 2A-2B. Blood circCDR1as vs circTULP4 ratio before treatment predicts response after 8 weeks of Sertraline treatment (EMBARC study, University of Texas Southwestern, whole blood). (A) Major Depressive Disorder (MDD) patients that did not respond to 8 weeks of Sertraline treatment (MDD Sert NR) display a higher blood circCDR1as vs circTULP4 ratio ($p<0.001$, two-tailed one sample t-test, N=12 per group) than patients that responded to treatment (MDD Sert R) at baseline. Data were acquired with circRNA-specific qRT-PCR in total RNA extracted from whole blood derived from the EMBARC study. (B) Differences in the circCDR1as vs circTULP4 ratio before treatment have a very good predictive value for predicting response after 8 weeks of Sertraline treatment based on receiver operating characteristic curve (ROC curve; a graphical plot that illustrates the diagnostic ability of a binary classifier system). Area under the curve=0.7679 and $p=0.0206$ ($p<0.05$ is considered significant).
Figure 2B:
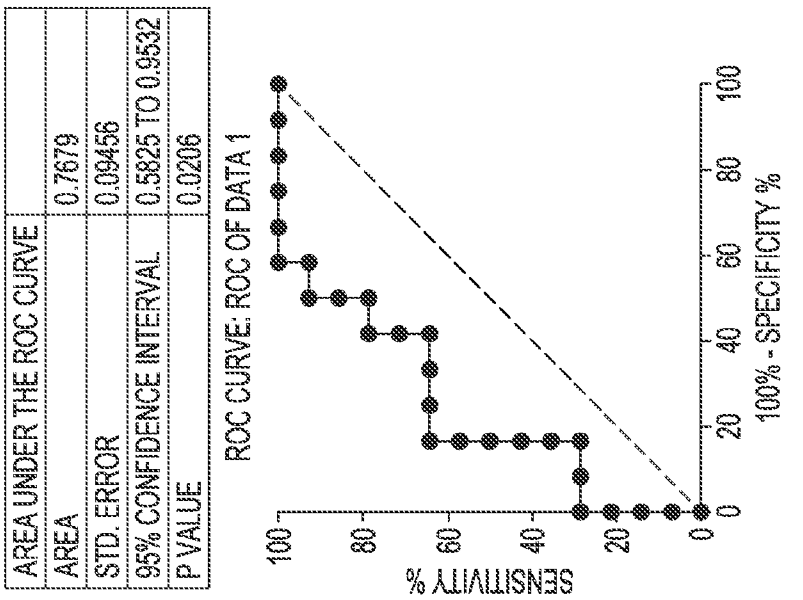
Figure 3A:
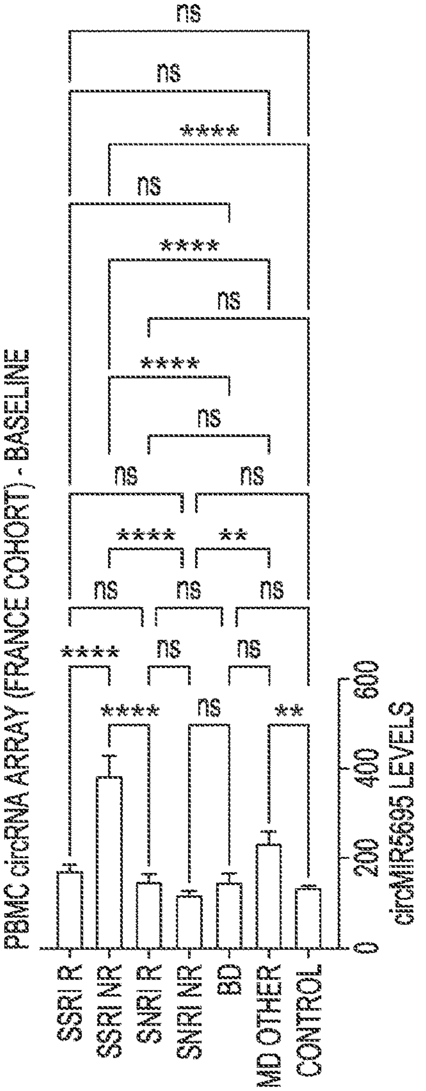
FIG. 3A-3C. CircRNA profiling reveals that circMIR5695 is a novel biomarker with excellent diagnostic abilities to predict remission to SSRI antidepressant treatment (PBMCs, France samples). (A-B) MDD patients that did not achieve remission after 30 weeks of treatment (SSRI NR) display higher baseline levels of circMIR5695 (A) than patients that achieved remission (SSRI R). These differences between those two groups are erased following 8 weeks as SSRI R circMIR5695 levels increase significantly relative to baseline, thus following the initial improvements in disease severity (B). Data were acquired with circRNA array profiling in total RNA extracted from blood PBMCs derived from the University of Marseille in France. **$p<0.0001$. *$p<0.001$. **$p<0.01$. *$p<0.05$, based on ANOVA with Tukey's post-hoc corrections for multiple comparisons, N=5-7 per group. (C) Differences in baseline circMIR5695 levels have an outstanding predictive value for predicting remission after long-term SSRI treatment based on receiver operating characteristic curve (ROC curve: a graphical plot that illustrates the diagnostic ability of a binary classifier system). Area under the curve=1.000 (100% specificity and sensitivity) and $p=0.0027$ ($p<0.05$ is considered significant).
Figure 3B:
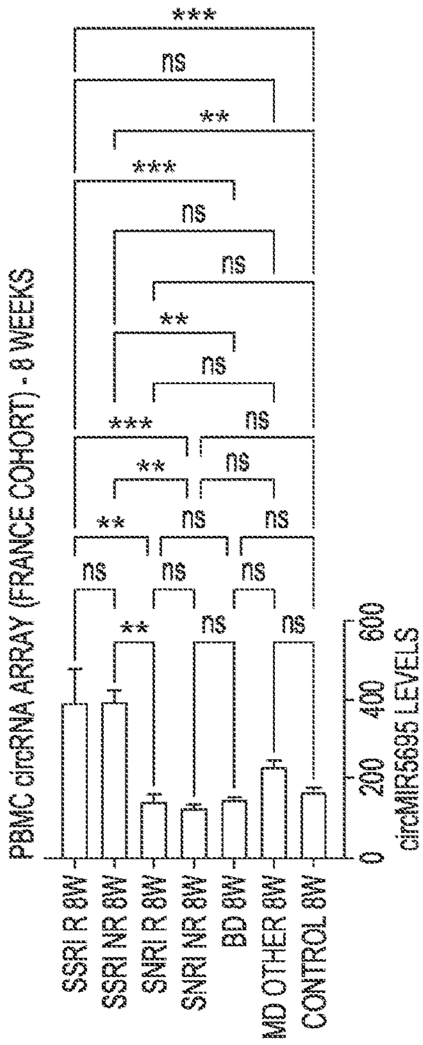
Figure 3C:
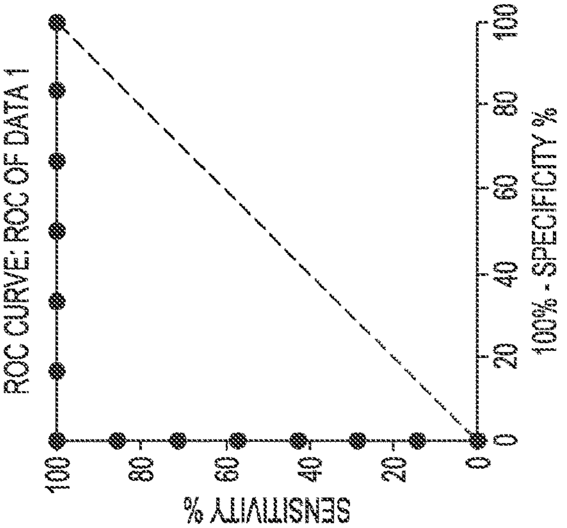
Figure 4A:
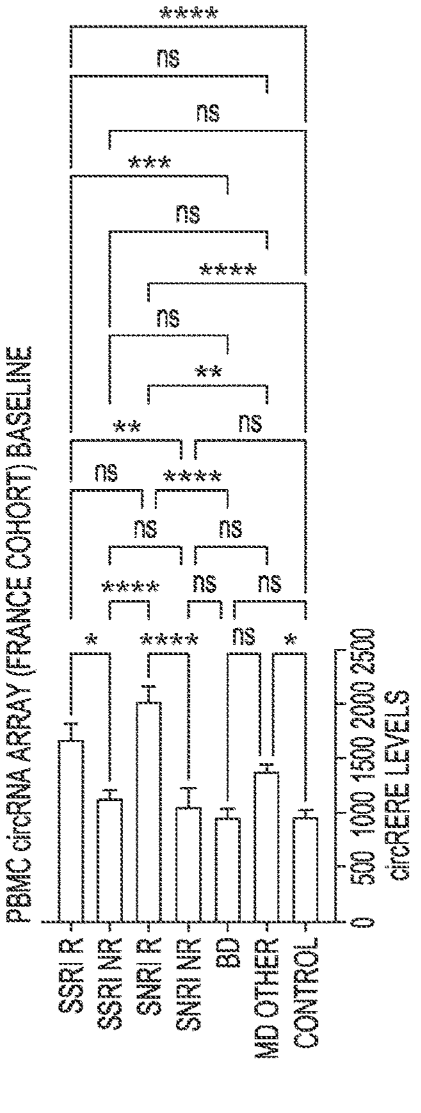
FIGS. 4A-4C. CircRNA profiling reveals that circRERE is a novel biomarker with excellent diagnostic abilities to predict remission to SNRI treatment (France samples). (A-B) MDD patients that achieved remission after 30 weeks of treatment with SNRIs (SNRI R) displayed higher baseline levels of circRERE (A) than patients that did not achieve remission (SNRI NR). These differences between those two groups are erased following 8 weeks as SNRI treatment as circRERE levels increase significantly relative to baseline in SNRI NR (B). Data were acquired with circRNA array profiling in total RNA extracted from blood PBMCs derived from the University of Marseille in France. **$p<0.0001$, *$p<0.001$, **$p<0.01$, *$p<0.05$, based on ANOVA with Tukey's post-hoc corrections for multiple comparisons, N=5-7 per group. (C) Differences in baseline circRERE levels have an outstanding predictive value for predicting remission after long-term SNRI treatment based on receiver operating characteristic curve (ROC curve; a graphical plot that illustrates the diagnostic ability of a binary classifier system). Area under the curve=0.9722 and $p=0.0065$.
Figure 4B:
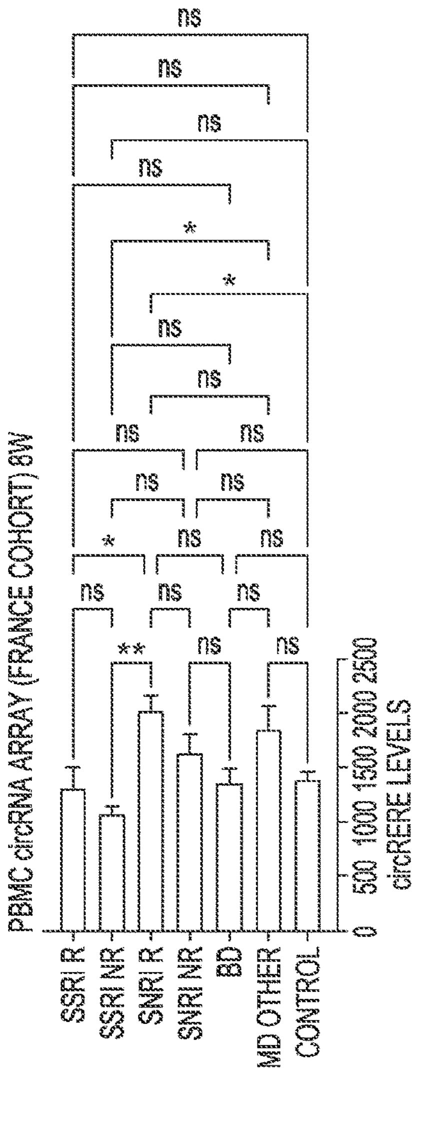
Figure 4C:
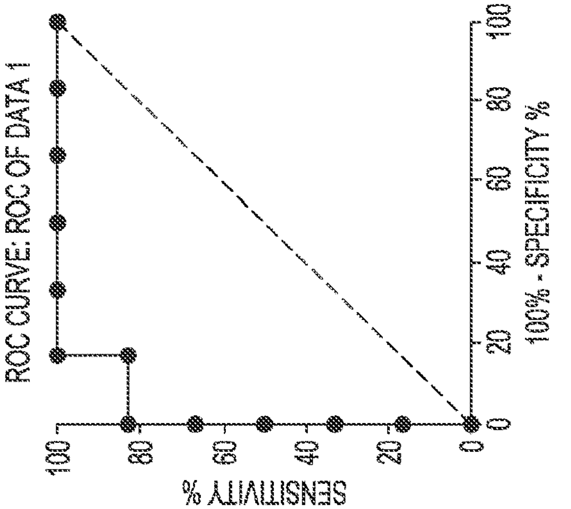
Figure 5A:
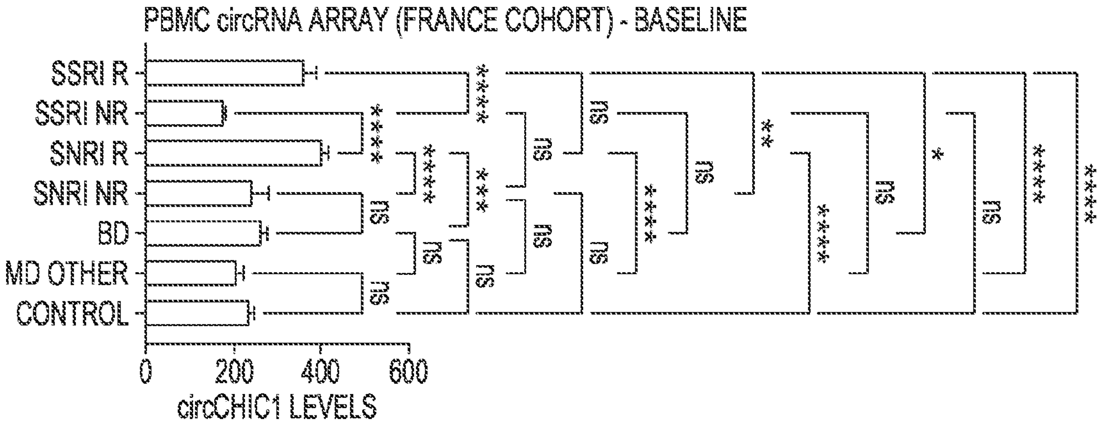
FIGS. 5A-5D. CircRNA profiling reveals that circCHIC1 is a novel biomarker with excellent diagnostic abilities to predict remission to both SSRI and SNRI treatment (France samples). (A-B) MDD patients that achieved remission after 30 weeks of treatment with SNRIs (SNRI R) or SSRIs (SSRI R) displayed higher baseline levels of circCHIC1 in PBMCs (A) than patients that did not achieve remission to either category of antidepressant (SNRI NR and SSRI NR). These differences between those two groups are erased following 8 weeks of treatment as circCHIC1 are similar between R and NR groups for both SSRIs and SNRIs (B). Data were acquired with circRNA array profiling in total RNA extracted from blood PBMCs derived from the University of Marseille in France. **$p<0.0001$. *$p<0.001$. **$p<0.01$, *$p<0.05$, based on ANOVA with Tukey's post-hoc corrections for multiple comparisons, N=5-7 per group. (C) Differences in baseline circCHIC1 levels have an outstanding predictive value for predicting remission both after long-term SNRI and SSRI treatment based on receiver operating characteristic curve (ROC curve; a graphical plot that illustrates the diagnostic ability of a binary classifier system). Area under the curve=1.0000 for both groups and $p=0.0027$ (SSRI) or $p=0.0039$ (SNRI).
Figure 5B:
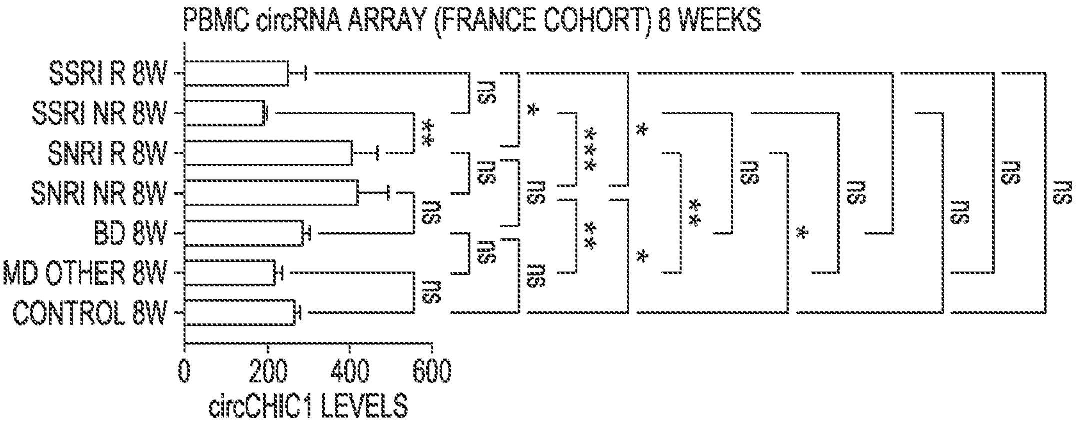
Figure 5C:
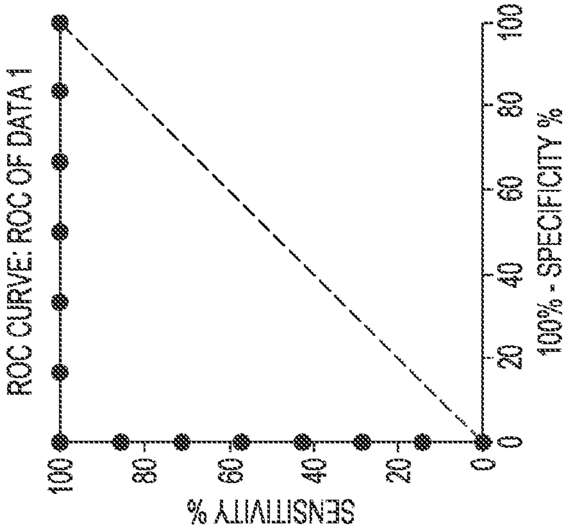
Figure 5D:
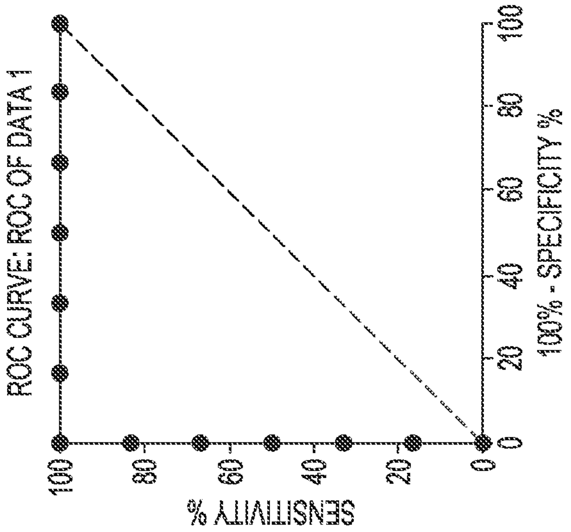
Figure 6A:
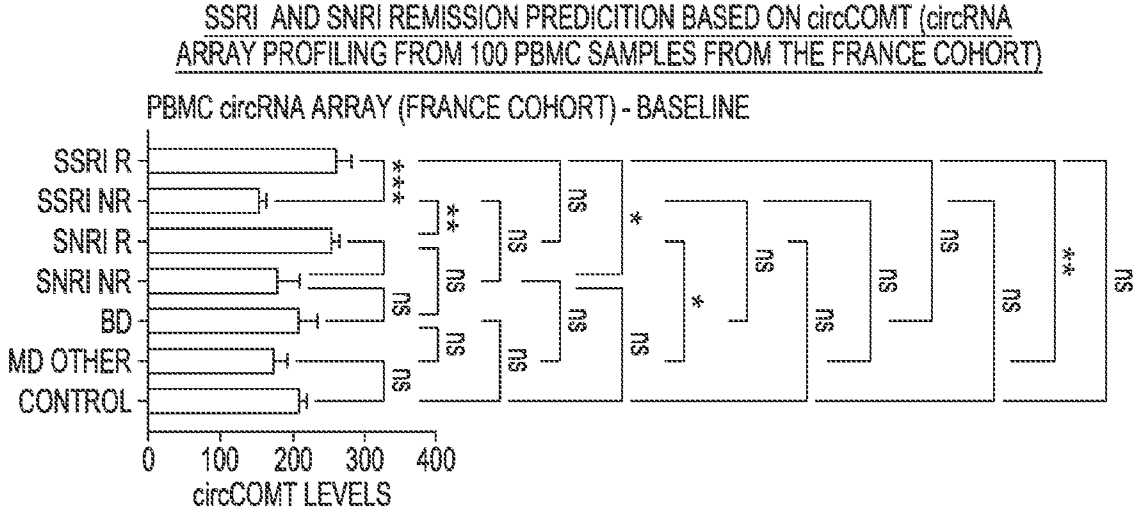
FIGS. 6A-6D. CircRNA profiling reveals that circCOMT is a novel biomarker with excellent diagnostic abilities to predict remission to both SSRI and SNRI treatment (France samples). (A-B) MDD patients that achieved remission after 30 weeks of treatment with SNRIs (SNRI R) or SSRIs (SSRI R) displayed higher baseline levels of circCOMT in PBMCs (A) than patients that did not achieve remission to either category of antidepressant (SNRI NR and SSRI NR). These differences between those two groups are erased following 8 weeks of treatment as circCOMT are similar between R and NR groups for both SSRIs and SNRIs (B). Data were acquired with circRNA array profiling in total RNA extracted from blood PBMCs derived from the University of Marseille in France. *p<0.001, p<0.01, *p<0.05, based on ANOVA with Tukey's post-hoc corrections for multiple comparisons, N=5-7 per group. (C) Differences in baseline circCOMT levels have an outstanding predictive value for predicting remission both after long-term SNRI and SSRI treatment based on receiver operating characteristic curve (ROC curve; a graphical plot that illustrates the diagnostic ability of a binary classifier system). Area under the curve=1.0000 with p=0.0027 (SSRI) and 0.8611 with p=0.0374 (SNRI).
Figure 6B:
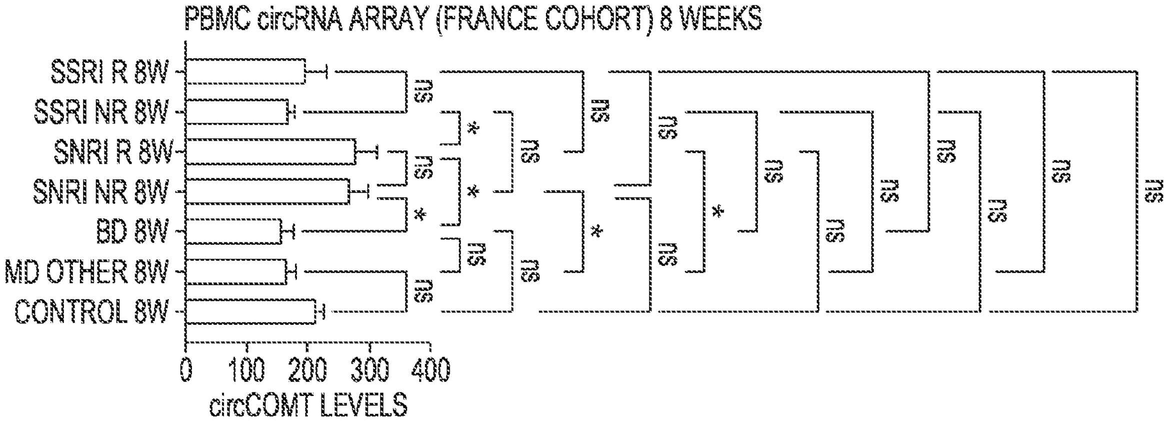
Figure 6C:
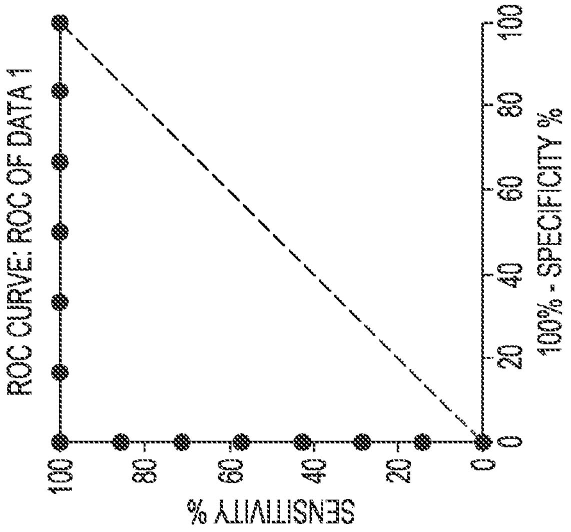
Figure 6D:
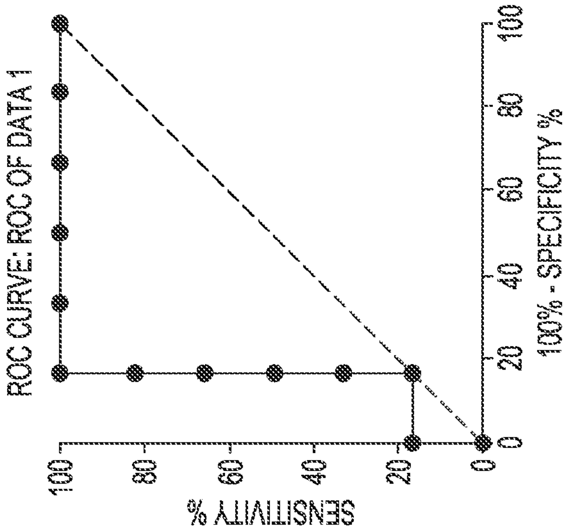
Figure 7A:
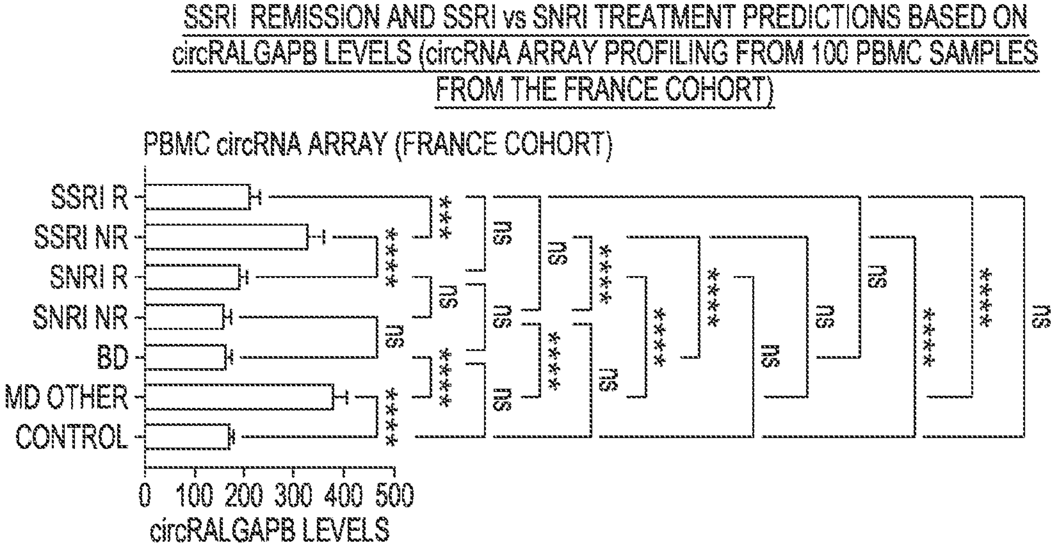
FIGS. 7A-7D. Levels of circRALGAPB in blood PBMCs predict remission to SSRIs before treatment and distinguish those treated with SSRIs vs SNRIs 8 weeks after treatment. (A-B) MDD patients that achieved remission after 30 weeks of treatment with SSRIs (SSRI R) displayed higher baseline levels of circRALGAPB in PBMCs (A) than patients that did not achieve remission after treatment (SSRI NR). These differences between those two groups are erased following 8 weeks of treatment as circRALGAPB are similar between SSRI R and NR groups (B). Moreover, after 8 weeks of treatment SSRI-treated patient samples exhibit higher circRALGAPB levels than SNRI-treated samples regardless of remission (B). Data were acquired with circRNA array profiling in total RNA extracted from blood PBMCs derived from the University of Marseille in France. **p<0.0001, *p<0.001, **p<0.01, *p<0.05, based on ANOVA with Tukey's post-hoc corrections for multiple comparisons, N=5-7 per group. (C) Differences in baseline circRALGAPB levels have an outstanding predictive value for predicting remission after long-term SSRI treatment and for predicting whether patients were treated with SNRIs or SSRIs 8 weeks after treatment based on receiver operating characteristic curve (ROC curve; a graphical plot that illustrates the diagnostic ability of a binary classifier system). Area under the curve=0.9048 with p=0.0152 (SSRI R vs NR) and 1.000 with p<0.0001 (SSRI 8 week vs SNRI 8 week).
Figure 7B:
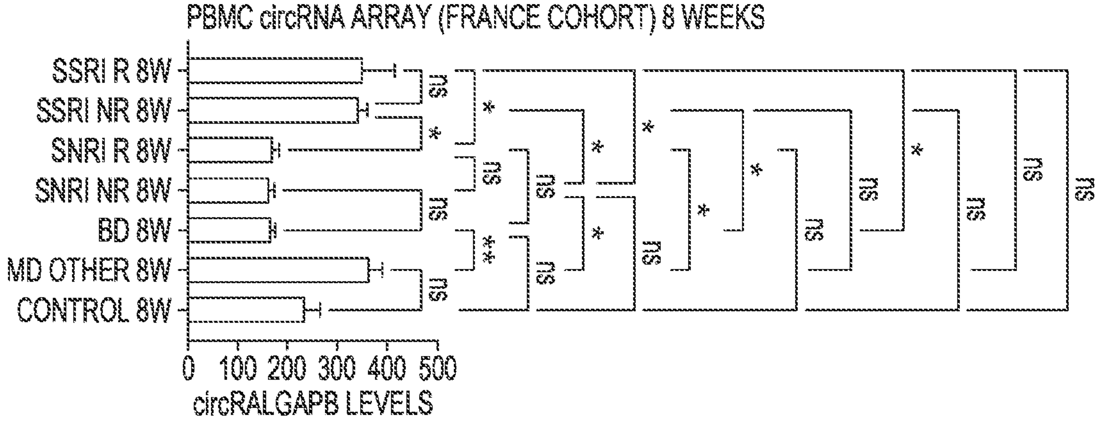
Figure 7C:
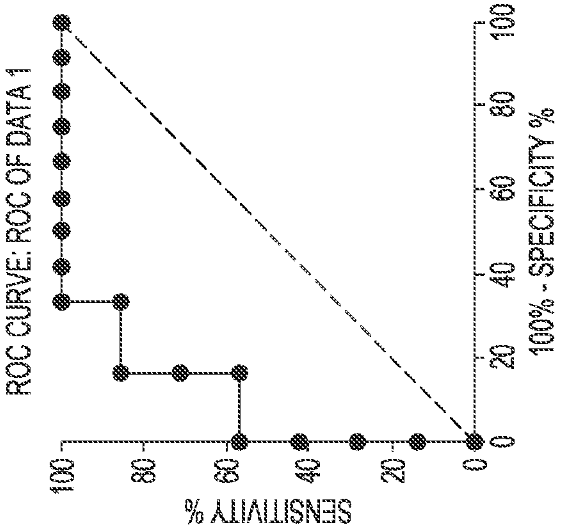
Figure 7D:
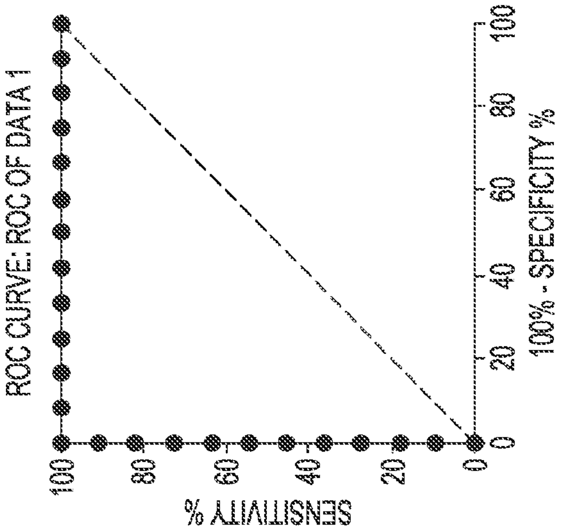
Figure 8A:
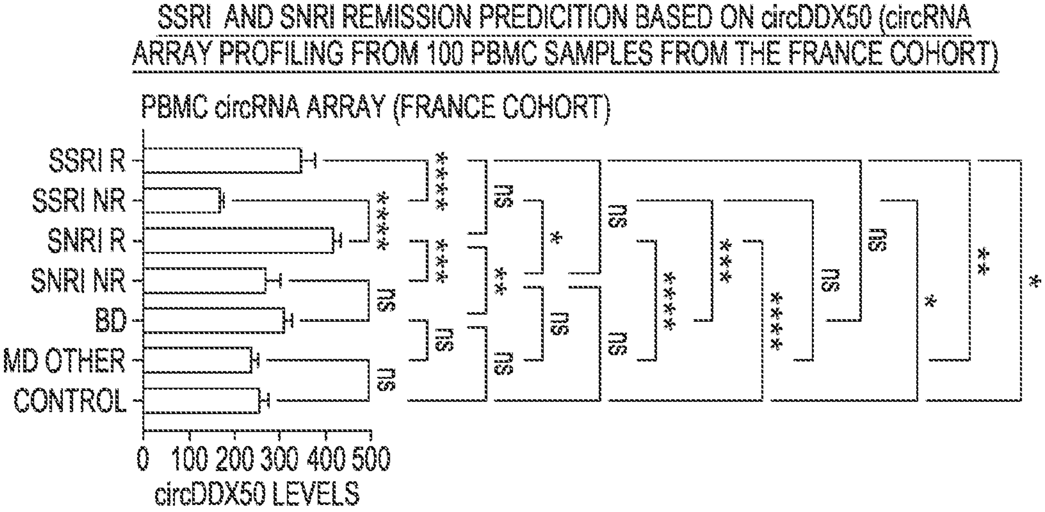
FIG. 8A-8D. CircRNA profiling reveals that circDDX50 is a novel biomarker with excellent diagnostic abilities to predict remission to both SSRI and SNRI treatment (France samples). (A-B) MDD patients that achieved remission after 30 weeks of treatment with SNRIs (SNRI R) or SSRIs (SSRI R) displayed higher baseline levels of circDDX50 in PBMCs (A) than patients that did not achieve remission to either category of antidepressant (SNRI NR and SSRI NR). These differences between those two groups are erased following 8 weeks of treatment as circDDX50 are similar between R and NR groups for both SSRIs and SNRIs (B). Data were acquired with circRNA array profiling in total RNA extracted from blood PBMCs derived from the University of Marseille in France. *p<0.001, p<0.01, *p<0.05, based on ANOVA with Tukey's post-hoc corrections for multiple comparisons, N=5-7 per group. (C) Differences in baseline circDDX50 levels have an outstanding predictive value for predicting remission after long-term SSRI and SNRI treatment based on receiver operating characteristic curve (ROC curve; a graphical plot that illustrates the diagnostic ability of a binary classifier system). Area under the curve=1.000 (100% specificity and sensitivity) and p=0.0027 for SSRI R vs SSRI NR and 0.9722 and p=0.0065 for SNRI R vs SNRI NR.
Figure 8B:
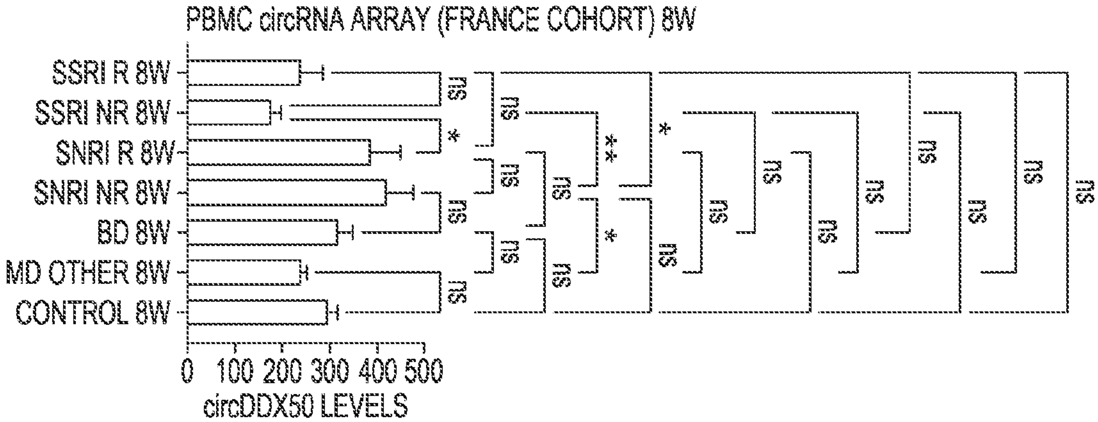
Figure 8C:
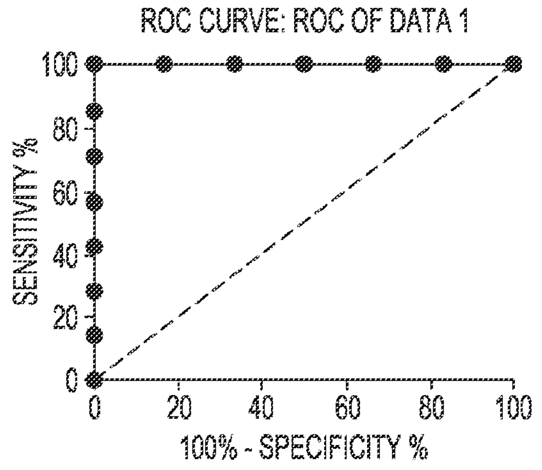
Figure 8D:
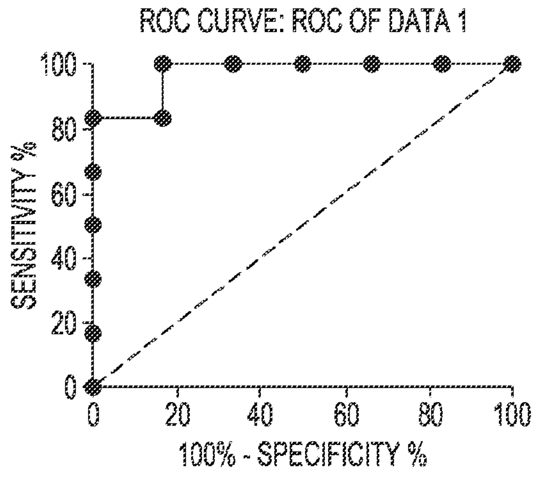
Figure 9A:
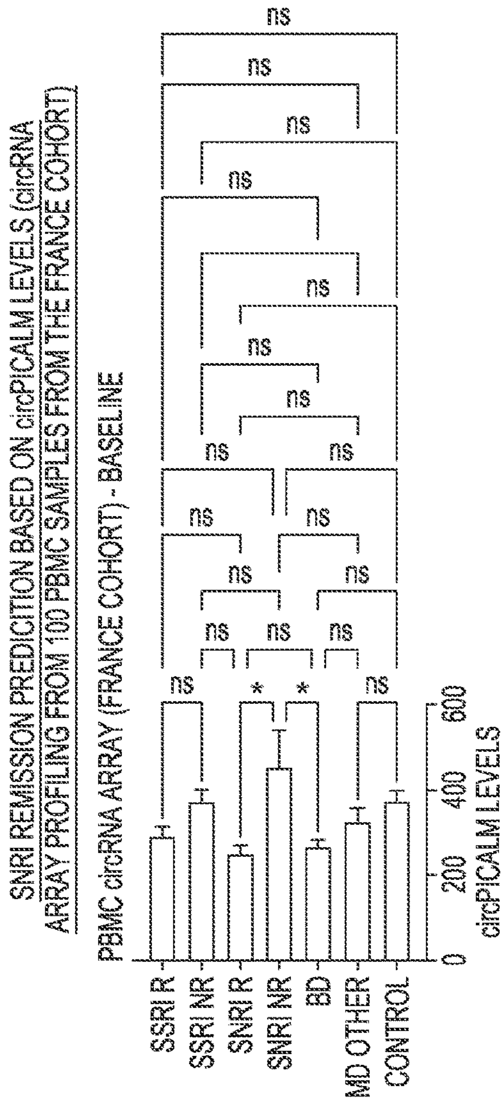
FIGS. 9A-9B. CircRNA profiling reveals that circPICALM is a novel biomarker with excellent diagnostic abilities to predict remission to SNRI treatment (France samples). (A-B) MDD patients that achieved remission after 30 weeks of treatment with SNRIs (SNRI R) displayed lower baseline levels of circPICALM levels (A) than patients that did not achieve remission (SNRI NR). Data were acquired with circRNA array profiling in total RNA extracted from blood PBMCs derived from the University of Marseille in France. *p<0.05, based on ANOVA with Tukey's post-hoc corrections for multiple comparisons, N=5-7 per group. (B) Differences in baseline circPICALM levels have an outstanding predictive value for predicting remission atter long-term SNRI treatment based on receiver operating characteristic curve (ROC curve; a graphical plot that illustrates the diagnostic ability of a binary classifier system). Area under the curve=0.9167 and p=0.0163.
Figure 9B:
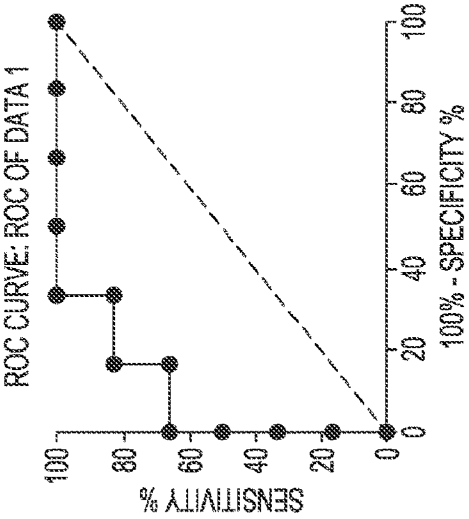
Figure 10A:
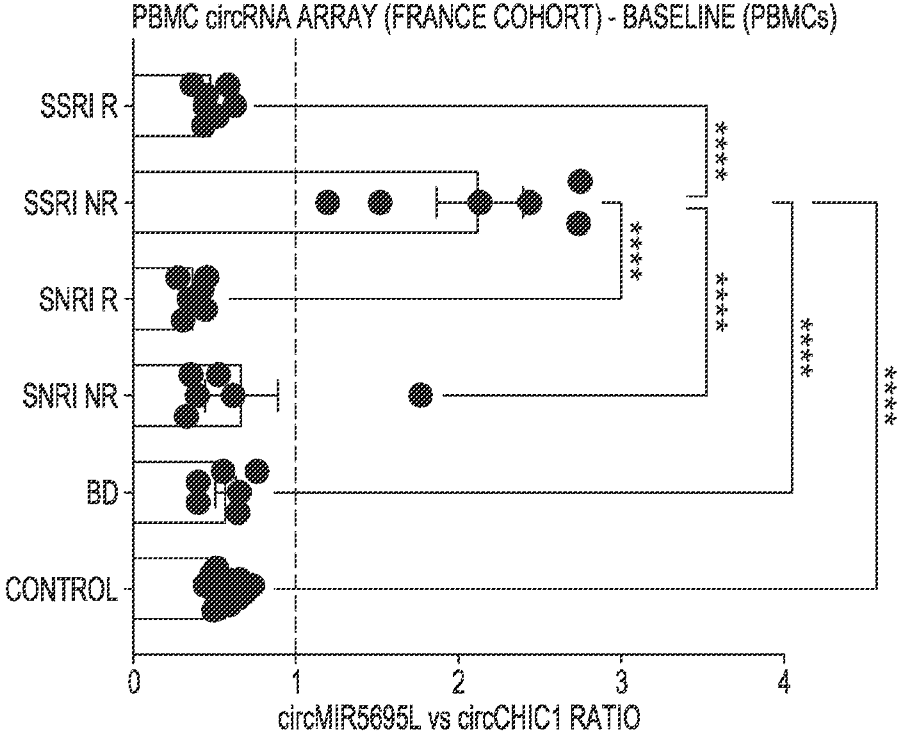
FIGS. 10A-10B. Baseline SSRI remission prediction based on the ratio between circMIR5695 and circCHIC1. (A) Patients with MDD that do not achieve remission 30 weeks after SSRI treatment (SSRI NR) exhibit increased circMIR5695 vs circCHIC1 ratio at baseline (before treatment). Data were acquired with circRNA array profiling in total RNA extracted from blood PBMCs derived from the University of Marseille in France. ****p<0.0001, based on ANOVA with Tukey's post-hoc corrections for multiple comparisons, N=5-7 per group. (B) Differences in baseline circMIR5695 vs circCHIC1 ratio have an outstanding predictive value for predicting remission after long-term SSRI treatment based on receiver operating characteristic curve (ROC curve; a graphical plot that illustrates the diagnostic ability of a binary classifier system). Area under the curve=0.9910 and p=0.0001.
Figure 10B:
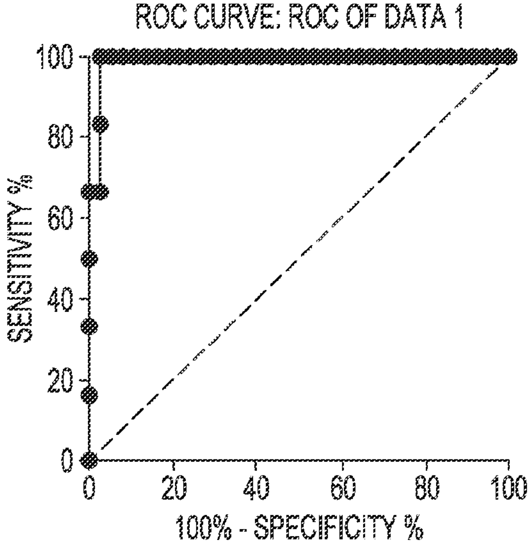
Figure 11:
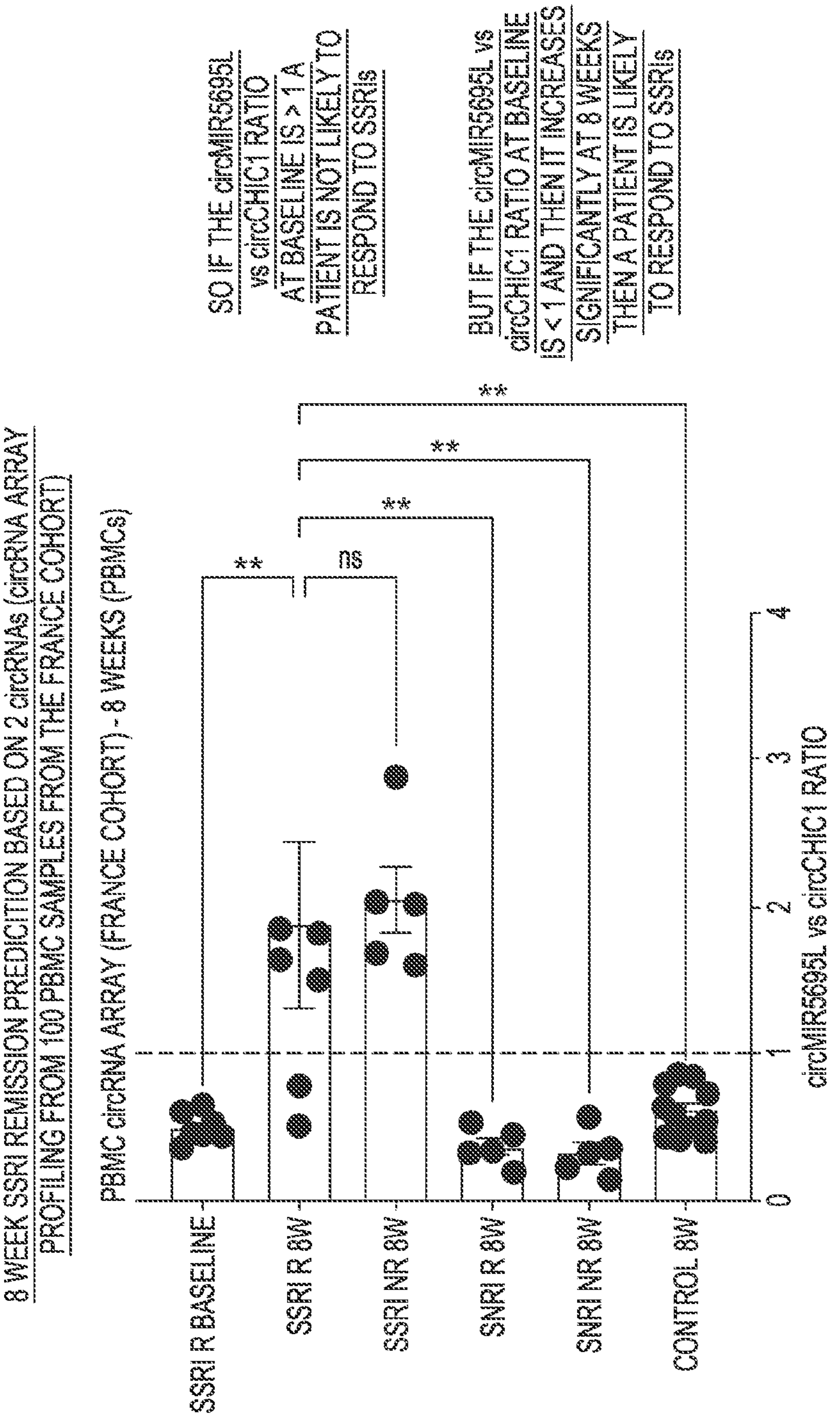
FIG. 11. SSRI remission prediction 8 weeks after treatment based on the ratio between circMIR5695 and circCHIC1. (A) Patients with MDD that do not achieve remission 30 weeks after SSRI treatment (SSRI NR) still exhibit increased circMIR5695 vs circCHIC1 ratio 8 weeks after treatment. Moreover, patients with MDD that achieve remission after 30 weeks of treatment (SSRI R) increase the baseline circMIR5695 vs circCHIC1 ratio after 8 weeks of treatment. Data were acquired with circRNA array profiling in total RNA extracted from blood PBMCs derived from the University of Marseille in France. p<0.01, based on ANOVA with Tukey's post-hoc corrections for multiple comparisons, N=5-7 per group. An explanation of the algorithm based on FIGS. 10 and 11** is shown on the right of the figure.
Figure 12B:
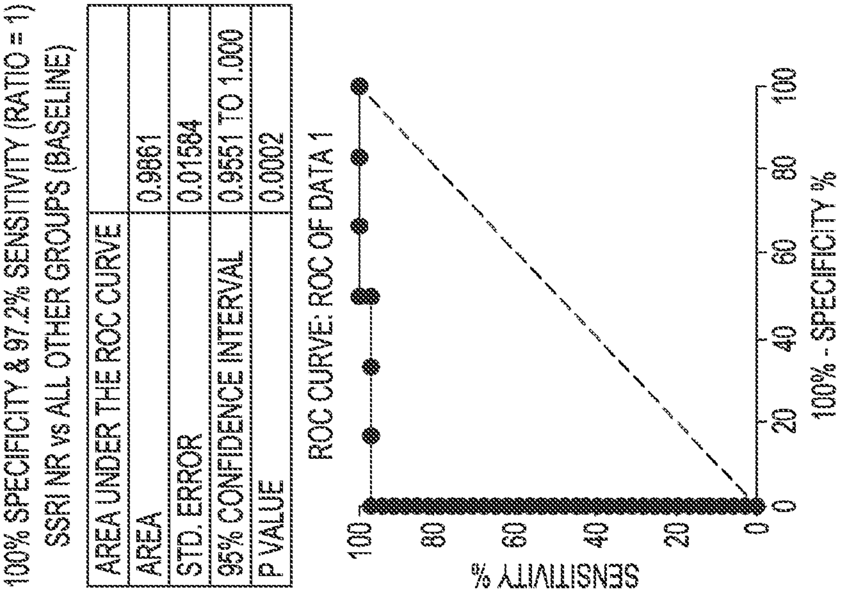
FIGS. 12A-12B. Baseline SSRI remission prediction based on the ratio between circRALGAPB and circCHIC1. (A) Patients with MDD that do not achieve remission 30 weeks after SSRI treatment (SSRI NR) exhibit increased circRALGAPB vs circCHIC1 ratio at baseline (before treatment). Data were acquired with circRNA array profiling in total RNA extracted from blood PBMCs derived from the University of Marseille in France. ****p<0.0001, based on ANOVA with Tukey's post-hoc corrections for multiple comparisons, N=5-7 per group. (B) Differences in baseline circRALGAPB vs circCHIC1 ratio have an outstanding predictive value for predicting remission after long-term SSRI treatment based on receiver operating characteristic curve (ROC curve; a graphical plot that illustrates the diagnostic ability of a binary classifier system). Area under the curve=0.9861 and p=0.0002.
Figure 12A:
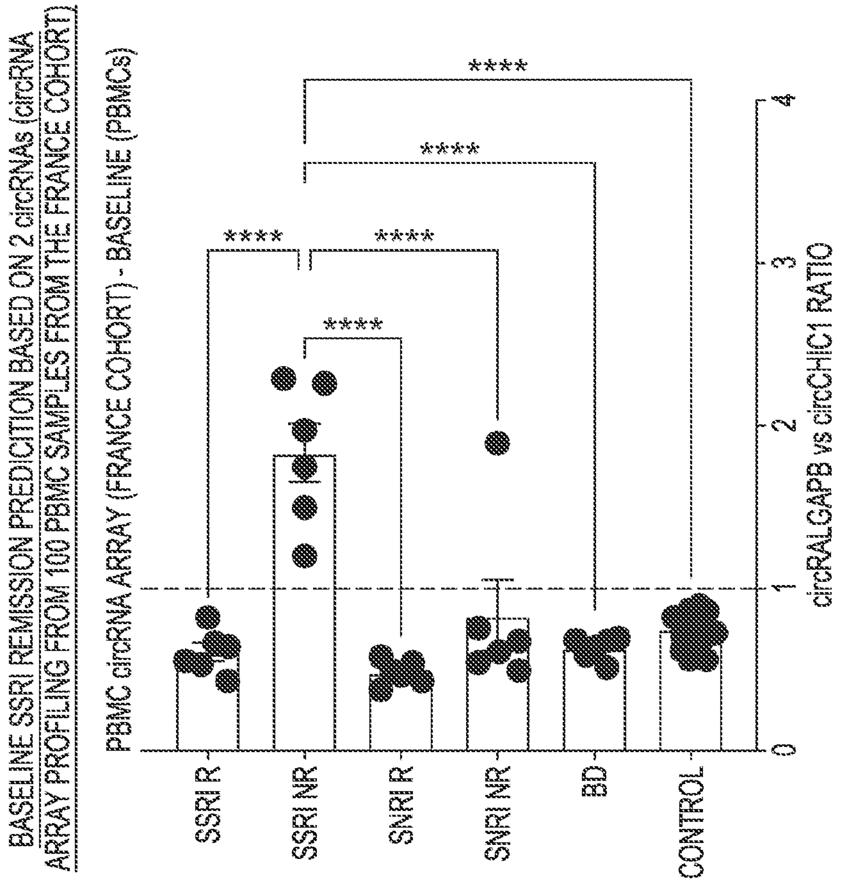
Figure 13A:
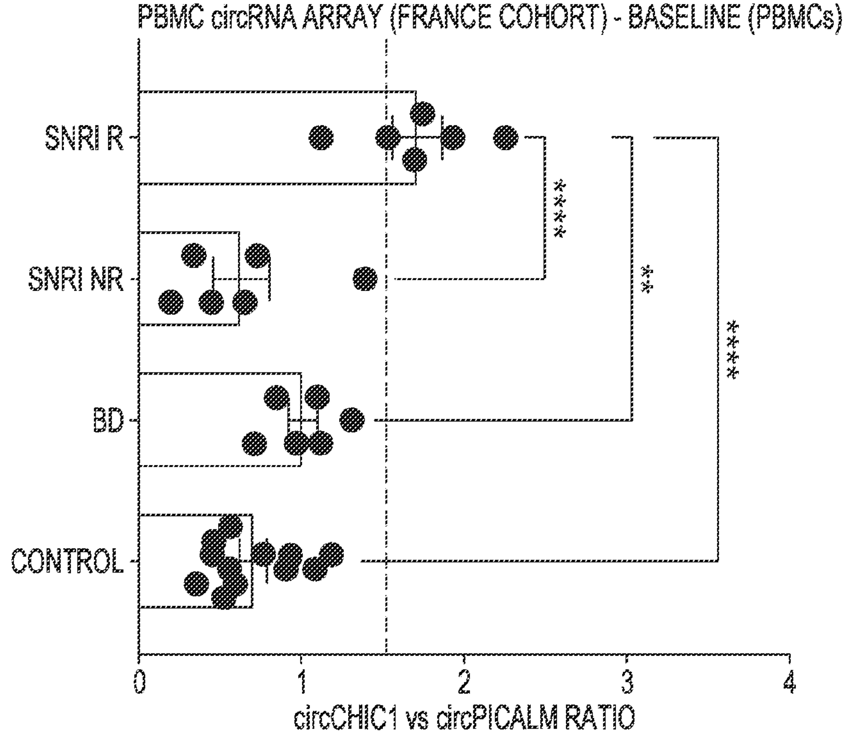
FIGS. 13A-13B. Baseline SNRI remission prediction based on the ratio between circCHIC1 and circPICALM. (A) Patients with MDD that achieve remission 30 weeks after SNRI treatment (SNRI R) exhibit increased circCHIC1 vs circPICALM ratio at baseline (before treatment). Data were acquired with circRNA array profiling in total RNA extracted from blood PBMCs derived from the University of Marseille in France. **p<0.0001, *p<0.001, **<p<0.01, based on ANOVA with Tukey's post-hoc corrections for multiple comparisons, N=5-7 per group. (B) Differences in baseline circCHIC1 vs circPICALM ratio have an outstanding predictive value for predicting remission after long-term SNRI treatment based on receiver operating characteristic curve (ROC curve; a graphical plot that illustrates the diagnostic ability of a binary classifier system). Area under the curve=0.9722 and p=0.0004.
Figure 13B:
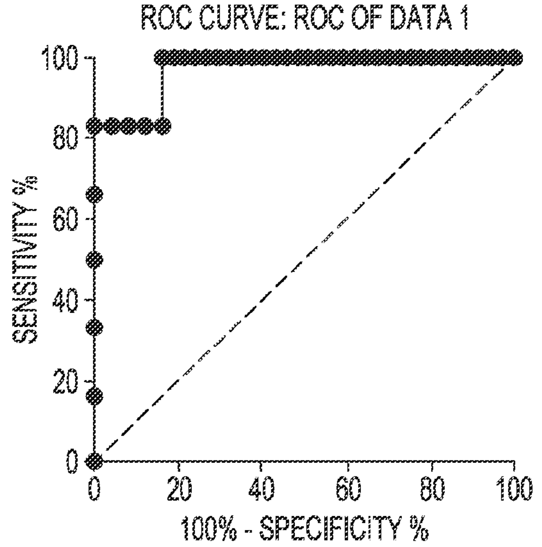
Figure 14:
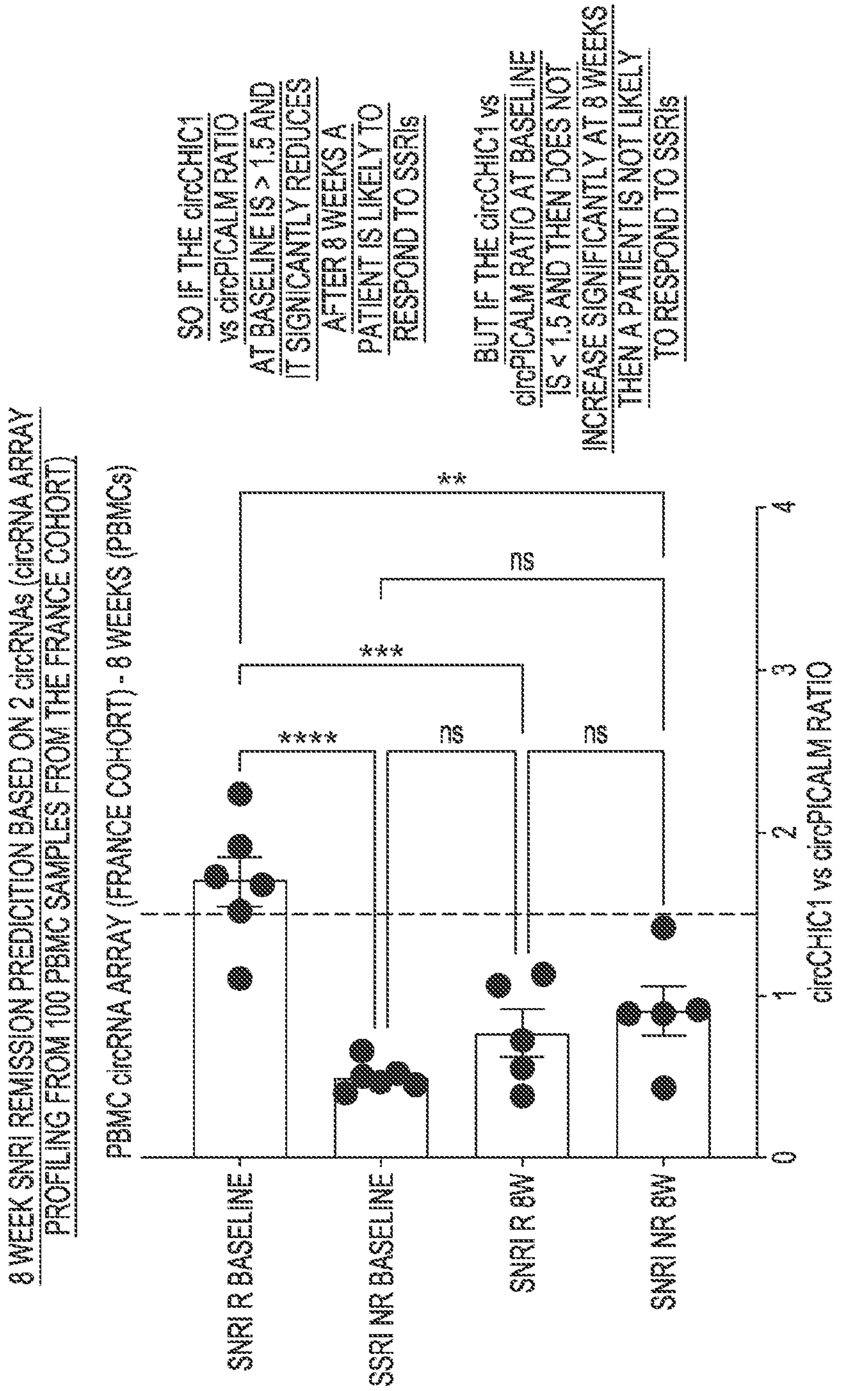
FIG. 14. SNRI remission prediction 8 weeks after treatment based on the ratio between circCHIC1 and circPICALM. (A) Patients with MDD that do not achieve remission 30 weeks after SNRI treatment (SNRI NR) still exhibit reduced circCHIC1 vs circPICALM ratio 8 weeks after treatment. Moreover, patients with MDD that achieve remission after 30 weeks of treatment (SNRI R) decrease the baseline circCHIC1 vs circPICALM ratio after 8 weeks of treatment. Data were acquired with circRNA array profiling in total RNA extracted from blood PBMCs derived from the University of Marseille in France. **p<0.0001, *p<0.001, p<0.01, based on ANOVA with Tukey's post-hoc corrections for multiple comparisons, N=5-7 per group. An explanation of the algorithm based on FIGS. 13 and 12** is shown on the right of the figure.
Figure 15A:
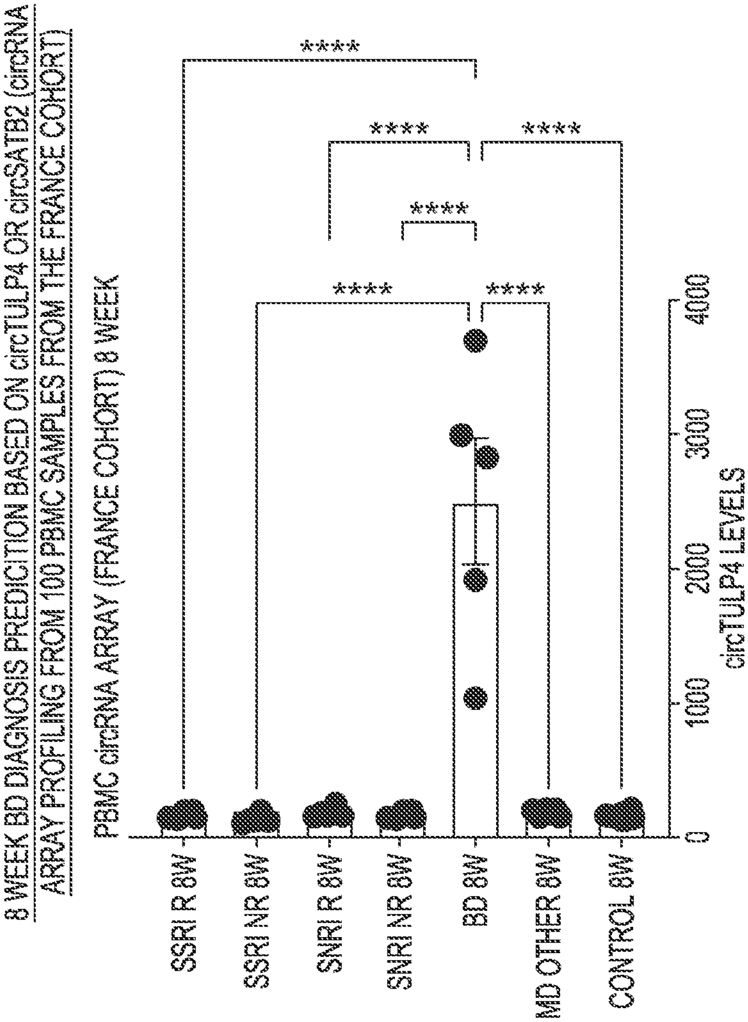
FIGS. 15A-15D. Levels of circTULP4 and circSATB2 are significantly elevated in BDD patients 8 weeks after treatment. (A) Patients with depressive symptoms that were originally misdiagnosed with MDD but were later shown to suffer from BD show significantly elevated circTULP4B levels 8 weeks after treatment (regardless of type of treatment). Data were acquired with circRNA array profiling in total RNA extracted from blood PBMCs derived from the University of Marseille in France. *p<0.0001, based on ANOVA with Turkey's post-hoc corrections for multiple comparisons, N=5-7 per group. (B) Differences in baseline circTULP4 levels have an outstanding predictive value for predicting BDD diagnosis based on receiver operating characteristic curve (ROC curve; a graphical plot that illustrates the diagnostic ability of a binary classifier system). Area under the curve=1.000 and p=0.0003. (C) Patients with depressive symptoms that were originally misdiagnosed with MDD but were later shown to suffer from BD show significantly elevated circSATB2 levels 8 weeks after treatment (regardless of type of treatment). Data were acquired with circRNA array profiling in total RNA extracted from blood PBMCs derived from the University of Marseille in France. ****p<0.0001, based on ANOVA with Tukey's post-hoc corrections for multiple comparisons, N=5-7 per group. (B) Differences in baseline circSATB2 levels have an outstanding predictive value for predicting BDD diagnosis based on receiver operating characteristic curve (ROC curve; a graphical plot that illustrates the diagnostic ability of a binary classifier system). Area under the curve=1.000 and p=0.0003.
Figure 15B:
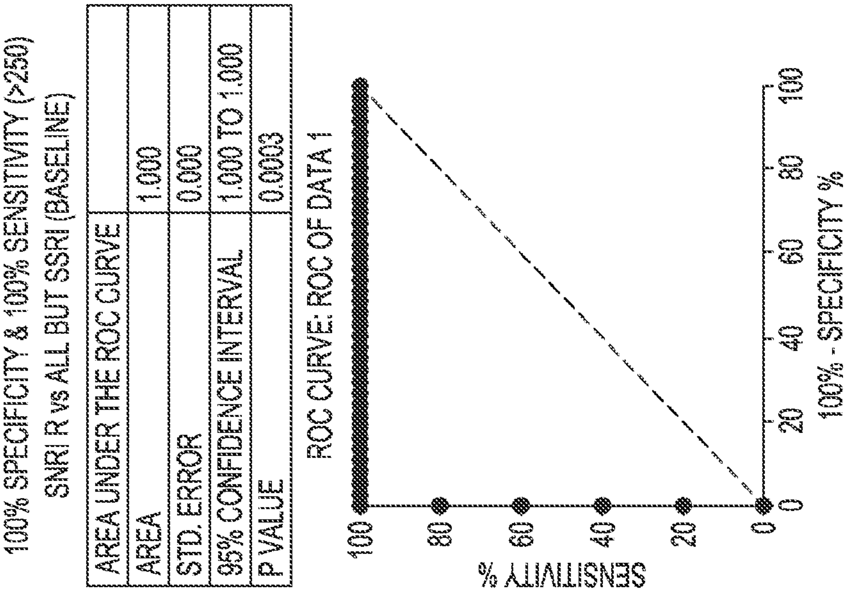
Figure 15C:
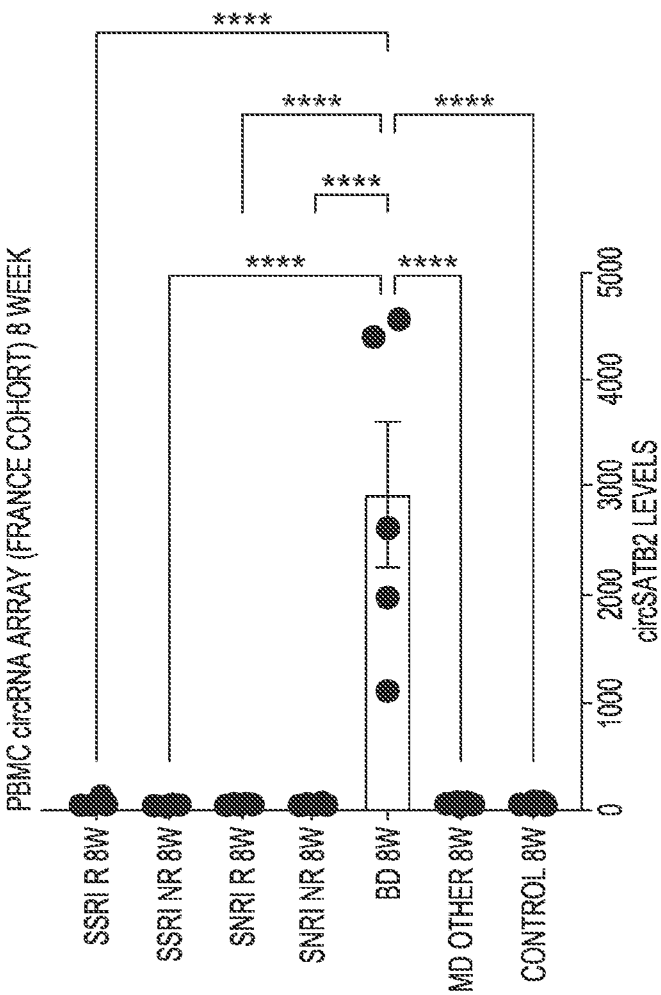
Figure 15D:
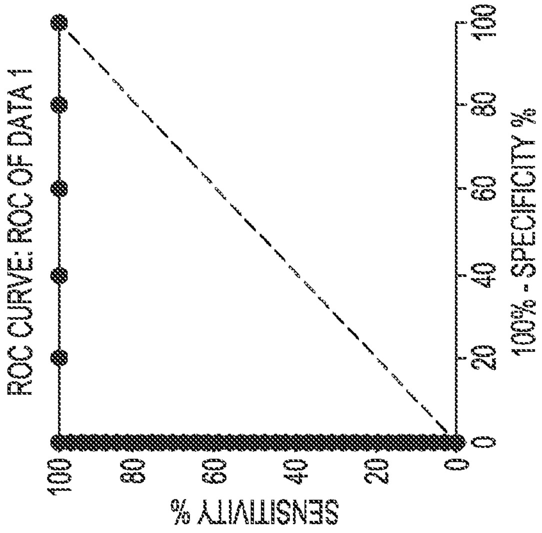

According to a specific embodiment, the present disclosure provides circCDR1as (also known as CDR1as; circRNA alias via circbase and circinteractome databases: hsa_circ_0001946; see also FIG. 16) and circTULP4 (also known as circTCONS_00011401; circRNA alias via circbase and circinteractome databases: hsa_circ_0131196; see also FIG. 16) as biomarkers predicting response or remission to SSRI treatment in either whole blood (FIG. 1)

or PBMCs or other blood-derived samples from patients with MDD (FIG. 2), as well as other biological fluids including saliva and urine, either before treatment (baseline), or after the start of antidepressant treatment. The backspliced junction sequence used for the detection of human circCDR1as and circ TULP4 are shown in FIG. 27, whereas the primers designed for their detection via PCR are shown in FIG. 28. These two circRNAs could be used alone or in conjunction with each other to predict response or remission of MDD patients to SSRI treatment.

According to a specific embodiment, the present disclosure provides that circTIAM1 (hsa_circ_0115791), circCHIC1 (hsa_circ_0091072), circSYNGR2 (hsa_circ_0045871), circSLC41A2 (hsa_circ_0027966), circCOL12A1(hsa_circ_0077032), circCOBL (hsa_circ_0080217), circHERC2 (hsa_circ_0005387), circICT1 (hsa_circ_0045581), circDDX50 (hsa_circ_0007097), circARHGEF10L (hsa_circ_0010210), circCOMT (hsa_circ_0062277), circWSB1 (hsa_circ_0042488), circKIAA1429 (hsa_circ_0084904), circNBAS (hsa_circ_0052712), circPDXDC1 (hsa_circ_0038011), circBPNT1 (hsa_circ_0000185), circMIR5695 (hsa_circ_0130587), circGRIP1 (hsa_circ_0099053), circNUP88 (hsa_circ_0041694), circEPHB4 (hsa_circ_0001730), circSETBP1 (hsa_circ_0006491), circHDHD2 (hsa_circ_0108522), circSIN3A (hsa_circ_0000636), circPPP6R1 (hsa_circ_0000959), circPDE5A (hsa_circ_0002474), circPDE5A (hsa_circ_0070805), circAHSA1 (hsa_circ_0032777), circLTBP1 (hsa_circ_0053907), circDAAM1 (hsa_circ_0000543), circPICALM (hsa_circ_0003695), circLRBA (hsa_circ_0071210), circCHD1L (hsa_circ_0013953), circTTC27 (hsa_circ_0003195), circLIMS1 (hsa_circ_0008348), circPIK3C2B (hsa_circ_0111746), circNRIP1 (hsa_circ_0004771), circLSM14A (hsa_circ_0008030), circPIP4K2A (hsa_circ_0017972), and circMBNL1 (hsa_circ_0001348) (see also FIG. 27-28), or any of the significantly altered circRNAs between SSRI R (those that achieved response or remission to SSRIs) and SSRI NR (those that did not achieve response or remission to SSRIs) shown in Table 1 (baseline) and Table 2 (8 weeks after treatment) and included in sequences 1-241, or circRNAs altered after SSRI treatment vs baseline in SSRI R patients (Table 5; SSRI R 8 week vs SSRI R baseline), or SSRI NR patients (Table 6; SSRI NR 8 week vs SSRI NR baseline) and included in sequences 1-241 (selected Table 5-6 circRNAs are: circMIR5695 (hsa_circ_0130587), circDNMBP (hsa_circ_0092382), circSTX1A (hsa_circ_0009012), circUSHBP1 (hsa_circ_0049965), circTMEM245 (hsa_circ_0087903), circGREB1L (hsa_circ_0003653), circROBO2 (hsa_circ_0066556), circHIVEP2 (hsa_circ_0007021), circIARS (hsa_circ_0087497), circFOXO3 (hsa_circ_0006404), circANXA8 (hsa_circ_0018309), circATIC (hsa_circ_0058058), circENC1 (hsa_circ_0073009), circPTK2 (hsa_circ_0005273), circWSB1 (hsa_circ_0042488), circITGAV hsa_circ_0057319), circATF6 (hsa_circ_0008857), circABL1 (hsa_circ_0089131), circAMBRA1 (hsa_circ_0009155), circRANGAP1 (hsa_circ_0063526), circSELL (hsa_circ_0000157) and circZC3H6 (hsa_circ_0001062), as biomarkers predicting response or remission to SSRI treatment in either whole blood or PBMCs or other blood-derived samples from patients with MDD, as well as other biological fluids including saliva and urine, either before treatment (baseline), or at various intervals after the start of antidepressant treatment. The backspliced junction sequences for some of these circRNAs are shown in FIG. 27, whereas the primers designed for their detection via PCR are shown in FIG. 28. Any of these circRNAs mentioned above in this paragraph and outlined in detail in Tables 1, 2, 5, and 6 could be used alone or in conjunction with each other to predict response or remission of MDD patients to SSRI treatment.

According to a specific embodiment, the present disclosure provides that circRERE (hsa_circ_0009574), circTOX2 (hsa_circ_0001160), circZFHX4 (hsa_circ_0084789), circHEATR5A (hsa_circ_0031570), circITGAV (hsa_circ_0057319), circGRIP1 (hsa_circ_0099053), circPPP2CA (hsa_circ_0073942), circDDX50 (hsa_circ_0007097), circYTHDF1 (hsa_circ_0004858), circRERE (hsa_circ_0009581), hsa_circ_0001655 (no name; only circRNA alias available), circNBEA (hsa_circ_0029975), circFLNC (hsa_circ_0082218), circRNF167 (hsa_circ_0041623), circICT1 (hsa_circ_0045581), circPTPRM (hsa_circ_0008584), circXBP1 (hsa_circ_0001216), circGSTP1 (hsa_circ_0023115), circANAPC7 (hsa_circ_0028198), circl.DHB (hsa_circ_0025597), circZFC3H1 (hsa_circ_0008912), circVRK2 (hsa_circ_0120478), circDENND4A (hsa_circ_0035957), and circPIK3C3 (hsa_circ_0007765), or any of the significantly altered circRNAs between SNRI R (those that achieved response or remission to SNRIs) and SNRI NR (those that did not achieve response or remission to SNRIs) shown in Table 3 (baseline) and Table 4 (8 weeks after treatment) and included in sequences 1-241, or circRNAs altered after SNRI treatment vs baseline in SNRI R patients (Table 7; SNRI R 8 week vs SNRI R baseline), or SSRI NR patients (Table 8; SNRI NR 8 week vs SNRI NR baseline) and included in sequences 1-241 (selected Table 5-6 circRNAs are: circSAP130 (hsa_circ_0056390), circNFAM1 (hsa_circ_0001240), circTMEM245 (hsa_circ_0087903), circHBA2 (hsa_circ_0037139), circGREB1L (hsa_circ_0003653), circGPD1L (hsa_circ_0123503), circDHX33 (hsa_circ_0000740), circITGAV (hsa_circ_0057319), circRERE (hsa_circ_0009574), circRNF167 (hsa_circ_0041623), circIRAK1BP1 (hsa_circ_0077109), circC4orf27 (hsa_circ_0071439), circDDX50 (hsa_circ_0007097), circSTX1A (hsa_circ_0009012), circRFC5 (hsa_circ_0028628), circC20orf24 (hsa_circ_0001151), circANXA8 (hsa_circ_0018309), circBPNT1 (hsa_circ_0000185), circTMEM245 (hsa_circ_0087888), circARHGEF10L (hsa_circ_0010210), circWSB1 (hsa_circ_0042488), and circNR6A1 (hsa_circ_0088511)), as biomarkers predicting response or remission to SSRI treatment in either whole blood or PBMCs or other blood-derived samples from patients with MDD, as well as other biological fluids including saliva and urine, either before treatment (baseline), or at various intervals after the start of antidepressant treatment. The backspliced junction sequences for some of these circRNAs are shown in FIG. 27, whereas the primers designed for their detection via PCR are shown in FIG. 28. Any of these circRNAs mentioned above in this paragraph and outlined in detail in Tables 3, 4, 7, and 8 could be used alone or in conjunction with each other to predict response or remission of MDD patients to SNRI treatment.

According to a specific embodiment, the present disclosure provides that any of the significantly altered circRNAs before and after treatment with MAOIs in MAOI R (those that achieved response or remission to MAOIs) shown in Table 9 (MAOI R 8 week vs MAOI R baseline), such as circFCHO2 (hsa_circ_0072954), circDENND4A (hsa_circ_0035944), circSLC38A1 (hsa_circ_0098630), circEPB41 (hsa_circ_0000041), circPTK2 (hsa_circ_0008305), circNAA40 (hsa_circ_0022623), circREPS1 (hsa_circ_0005210), circCAMKMT (hsa_circ_0006530), circKIAA1586 (hsa_circ_0131987), circMYBL1 (hsa_circ_0084642), circMPHOSPH9 (hsa_circ_0006615), circTBC1D31 (hsa_circ_0001820), circSLC39A10 (hsa_circ_0057551), circRERE (hsa_circ_0009581), circSLC38A2 (hsa_circ_0025984), circSBDSP1 (hsa_circ_0006688), circPTDSS1 (hsa_circ_0001816), circFANCL (hsa_circ_0001009), circCCT3 (hsa_circ_0014724), and circBRE (hsa_circ_0053317), as biomarkers predicting response or remission to MAOI treatment in either whole blood or PBMCs or other blood-derived samples from patients with MDD, as well as other biological fluids including saliva and urine, either before treatment (baseline), or at various intervals after the start of antidepressant treatment. Any of these circRNAs mentioned above in this paragraph and outlined in detail in Table 9 and shown in sequences 1-241 could be used alone or in conjunction with each other to predict response or remission of MDD patients to MAOI treatment.

According to a specific embodiment, the present disclosure provides that any of the significantly altered circRNAs between patients with MDD and Controls shown in Table 10 (baseline MDD vs baseline Controls) and Table 11 (8 weeks after treatment MDD vs Control 8 weeks after first visit), such as circRALGAPB (hsa_circ_0060342), circTBC1D14 (hsa_circ_0003201), circMASTL (hsa_circ_0018031), circEXOC4 (hsa_circ_0082440), circHNRNPA1 (hsa_circ_0026700), circSTRN (hsa_circ_0054033), circWDFY1 (hsa_circ_0001101), circNHP2L1 (hsa_circ_0063598), circITGB7 (hsa_circ_0026568), circSELL (hsa_circ_0000157), circSUSD1 (hsa_circ_0088059), circFBN3 (hsa_circ_0092332), circLARS (hsa_circ_0074407), circTRIP13 (hsa_circ_0071681), circDAGLB (hsa_circ_0006093), circDPH7 (hsa_circ_0006502), circPRELID2 (hsa_circ_0008132), circDAGLB (hsa_circ_0002067), circMIR5695 (hsa_circ_0130587), circUBA2 (hsa_circ_0050547), circS100PBP (hsa_circ_0011451), circITGAV (hsa_circ_0057319), circSAMD8 (hsa_circ_0018905), circNRIP1 (hsa_circ_0061276), circAKAP17A (hsa_circ_0007352), circTBC1D14 (hsa_circ_0003201), circHNRNPA1 (hsa_circ_0026700), circSYNGR2 (hsa_circ_0045871), circRALGAPB (hsa_circ_0060342), circSAMD8 (hsa_circ_0006148), circDNMBP (hsa_circ_0092382), circCWC27 (hsa_circ_0072654), circCORO1C (hsa_circ_0028067), circMTHFD2L (hsa_circ_0069977), circPLEKHG1 (hsa_circ_0078264), circARMC9 (hsa_circ_0058651), circN4BP2L2 (hsa_circ_0029934), and circPNN (hsa_circ_0101802), as biomarkers facilitating the diagnosis of BDD in either whole blood or PBMCs or other blood-derived samples, as well as other biological fluids including saliva and urine, either before treatment (baseline), or at various intervals after the start of antidepressant or other form of psychiatric treatment. The backspliced junction sequences for some of these circRNAs are shown in FIG. 27, whereas the primers designed for their detection via PCR are shown in FIG. 28. Any of these circRNAs mentioned above in this paragraph and outlined in detail in Tables 10 and 11 and shown in sequences 1-241 could be used alone or in conjunction with each other to diagnose MDD in patients with or without depressive symptoms.

According to a specific embodiment, the present disclosure provides that circSRGN (hsa_circ_0018594), circTM2D3 (hsa_circ_0003813), circAGFG1 (hsa_circ_0058514), circDCP2 (hsa_circ_0001520), circAGFG1 (hsa_circ_0058520), circRFWD2 (hsa_circ_0015364), circMED13L (hsa_circ_0000443), circDCP2 (hsa_circ_0073608), circRNF149 (hsa_circ_0001058), circSCMH1 (hsa_circ_0005303), circDICER1 (hsa_circ_0000564), circEYA3 (hsa_circ_0008057), circPAPPA2 (hsa_circ_0015382), circKPNB1 (hsa_circ_0044301), circTLE1 (hsa_circ_0087331), circMTMR3 (hsa_circ_0001219), circMED13L (hsa_circ_0000442), circHLHL2 (hsa_circ_0071375), circKCNH1 (hsa_circ_0016348), circPICALM (hsa_circ_0023928), circSATB2 (hsa_circ_0003915), circHTRA1 (hsa_circ_0020275), circSATB2 (hsa_circ_0007422), circCAPZA1 (hsa_circ_0013526), circKLHL8 (hsa_circ_0127236), circCASC15 (hsa_circ_0075826), circSIDT2 (hsa_circ_0024379), circFBXO24 (hsa_circ_0081481), circTULP4 (hsa_circ_0131196), circHELZ2 (hsa_circ_0001176), circNPRL3 (hsa_circ_0037127), circTUBA8 (hsa_circ_0062191), circKRT8 (hsa_circ_0026467), circMETTL15 (hsa_circ_0000282), circGSE1 (hsa_circ_0040726), circFARS2 (hsa_circ_0075533), circPIGU (hsa_circ_0001142), circCHEK2 (hsa_circ_0004128), circEPB41L5 (hsa_circ_0056264), circALDOA (hsa_circ_0038981), circFBXO24 (hsa_circ_0081481), circSATB2 (hsa_circ_0007422), circHTRA1 (hsa_circ_0020275), circCAPZA1 (hsa_circ_0013526), circSATB2 (hsa_circ_0003915), circMETTL15 (hsa_circ_0000282), circTULP4 (hsa_circ_0131196), circFARS2 (hsa_circ_0075533), circCASC15 (hsa_circ_0075826), circNSD1 (hsa_circ_0075166), circSIDT2 (hsa_circ_0024379), circEPB41L5 (hsa_circ_0056264), circNPRL3 (hsa_circ_0037127), circHELZ2 (hsa_circ_0001176), circGSE1 (hsa_circ_0040726), circTUBA8 (hsa_circ_0062191), circCHEK2 (hsa_circ_0004128), circMYO1F (hsa_circ_0008990), circPIGU (hsa_circ_0001142), and circLPAR1 (hsa_circ_0004928), or any of the significantly altered circRNAs between patients with BDD and Controls or patients with MDD shown in Table 12 (baseline BD vs baseline Contris) and Table 13 (8 weeks after treatment BD vs Control 8 weeks after first visit) some of which are shown in sequences 1-241, or circRNAs altered after various types of treatment vs baseline in BDD patients regardless or not if these patients responded to such treatments (Table 14; BD 8 week vs BD R baseline), such as some of which are shown in sequences 1-241, as biomarkers facilitating the diagnosis of BDD in either whole blood or PBMCs or other blood-derived samples, as well as other biological fluids including saliva and urine, either before treatment (baseline), or at various intervals after the start of antidepressant or other form of psychiatric treatment. The backspliced junction sequences for some of these circRNAs are shown in FIG. 27, whereas the primers designed for their detection via PCR are shown in FIG. 28. Any of these circRNAs mentioned above in this paragraph and outlined in detail in Tables 12, 13, and 14 and shown in sequences 1-241 could be used alone or in conjunction with each other to diagnose BD in patients with or without depressive symptoms.

According to a specific embodiment, the present disclosure provides that circDDR1 (hsa_circ_0005133), circHERC4 (hsa_circ_0007997), circLAMA3 (hsa_circ_0047232), circCYP24A1 (hsa_circ_0060930), circSESN1 (hsa_circ_0077578), circTRIM69 (hsa_circ_0103668), circSLIT3 (hsa_circ_0074930), circHMGA2 (hsa_circ_0027446), circRPS2 (hsa_circ_0037376), circRASSF8 (hsa_circ_0025638), circHMMR (hsa_circ_0128496), circDUSP22 (hsa_circ_0075410), circICAM1 (hsa_circ_0049241), circRPL13 (hsa_circ_0092337), circCYP26B1 (hsa_circ_0055161), circMAPK6 (hsa_circ_0035301), circCCDC56 (hsa_circ_0043912), circPPP6R1 (hsa_circ_0000959), circXPO5 (hsa_circ_0076560), circULK4 (hsa_circ_0123780), circVDAC2 (hsa_circ_0007335), circNFATC3 (hsa_circ_0005615), circMALAT1 (hsa_circ_0002082), and circFKBP8 (hsa_circ_0050124), circSMARCA2 (hsa_circ_0001834), circARVCF (hsa_circ_0092330), circSKA3 (hsa_circ_0029696), circZNF236 (hsa_circ_0002799), circRTEL1-TNFRSF6B (hsa_circ_0061170), circGPATCH1 (hsa_circ_0050444), circCNOT1 (hsa_circ_0039626), circWDR37 (hsa_circ_0017449), circCMTM7 (hsa_circ_0005414), circDYSF (hsa_circ_0001029), circMIR5695 (hsa_circ_0130587), circDUS2L (hsa_circ_0039908), circRALGAPB (hsa_circ_0060342), circADAM22 (hsa_circ_0080968), circMYO9B (hsa_circ_0000907), circSETD2 (hsa_circ_0065149), circPCSK5 (hsa_circ_0087234), circZFR (hsa_circ_0072088), circUBR5 (hsa_circ_0001819) circSETD2 (hsa_circ_0002569), and circDLG5 (hsa_circ_0006649) (see also FIG. 27-28), or any of the significantly altered circRNAs between Sertraline responders (Sert R) and Sertraline non-responders (Sert NR) shown in Table 15 (baseline) and Table 16 (1 week after treatment) and included in sequences 1-241, as biomarkers predicting response or remission to Sertraline treatment in either whole blood or PBMCs or other blood-derived samples from patients with MDD, as well as other biological fluids including saliva and urine, either before treatment (baseline), or at various intervals after the start of antidepressant treatment. The backspliced junction sequences for some of these circRNAs are shown in FIG. 27, whereas the primers designed for their detection via PCR are shown in FIG. 28. Any of these circRNAs mentioned above in this paragraph and outlined in detail in Tables 15, or 16 and sequences 1-241 could be used alone or in conjunction with each other to predict response or remission of MDD patients to Sertraline treatment.

According to a specific embodiment, the present disclosure provides that circDYSF (hsa_circ_0001029), circDDR1 (hsa_circ_0005133), circSTRN (hsa_circ_0054033), circTIAM2 (hsa_circ_0008289), circRANBP17 (hsa_circ_0004738), circHERC4 (hsa_circ_0007997), circTRIM28 (hsa_circ_0052372), circRPL13 (hsa_circ_0092337), circINCENP (hsa_circ_0000315), circGDI2 (hsa_circ_0005379), circSMAP2 (hsa_circ_0011898), circlCAM1 (hsa_circ_0049241), circHABP4 (hsa_circ_0087631), circCALR (hsa_circ_0049637), circZNF646 (hsa_circ_0000691), circPREX1 (hsa_circ_0001167), circAP3S1 (hsa_circ_0002919), circZC3HC1 (hsa_circ_0082319), circBCKDHA (hsa_circ_0000937), circPDPN (hsa_circ_0010027), circDYSF (hsa_circ_0001029), circDDR1 (hsa_circ_0005133), circAMBRA1 (hsa_circ_0009155), circTTTY10 (hsa_circ_0142668), circHERC4 (hsa_circ_0007997), circANKRA2 (hsa_circ_0129585), circLCORL (hsa_circ_0125866), circTRIM28 (hsa_circ_0052372), circRPL13 (hsa_circ_0092337), circEIF4A2 (hsa_circ_0068464), circGDI2 (hsa_circ_0005379), circSMAP2 (hsa_circ_0011898), circlCAM1 (hsa_circ_0049241), circTMEM39B (hsa_circ_0006349), circHABP4 (hsa_circ_0087631), circCALR (hsa_circ_0049637), circZNF646 (hsa_circ_0000691), circAP3S1 (hsa_circ_0002919), circZC2HC1 (hsa_circ_0082319), and circBCKDHA (hsa_circ_0000937) (see also FIG. 27-28), or any of the significantly altered circRNAs after 1 week of Sertraline treatment vs baseline (before treatment) in either responders (Sert R) or non-responders (Sert NR) to Sertraline shown in Table 17 (Sert R) and Table 18 (Sert NR) and included in sequences 1-241, as biomarkers predicting response or remission to Sertraline treatment in either whole blood or PBMCs or other blood-derived samples from patients with MDD, as well as other biological fluids including saliva and urine, either before treatment (baseline), or at various intervals after the start of antidepressant treatment. The backspliced junction sequences for some of these circRNAs are shown in FIG. 27, whereas the primers designed for their detection via PCR are shown in FIG. 28. Any of these circRNAs mentioned above in this paragraph and outlined in detail in Tables 17, or 18 and sequences 1-241 could be used alone or in conjunction with each other to predict response or remission of MDD patients to Sertraline treatment.

According to an embodiment, the present disclosure provides a composition, kit or assay, comprising a panel of at least 1 circRNA, wherein the circRNA is a biomarker for either predicting response or remission to antidepressant treatment, or diagnosis of MDD and BD, or evaluation of disease severity in a subject in need thereof. According to a further embodiment, the present disclosure provides a composition comprising a panel of at least 2 circRNAs, where the 2 circRNAs are circRNA biomarkers related to response or remission to antidepressant treatment, or diagnosis of MDD and BD, or evaluation of disease severity in a subject in need thereof. According to a still further embodiment, the present disclosure provides a composition comprising a panel of a plurality of circRNAs, where the plurality circRNAs are circRNA biomarkers related to response or remission to antidepressant treatment, or diagnosis of MDD and BD, or evaluation of disease severity in a subject in need thereof. In one embodiment, this plurality of circRNA biomarkers may include 3 or more, or 2 to 10, 2 to 25, 2 to 50, 2 to 100, 2 to 200, 2 to 500, 2 to 1000, 2 to 2000, or 2 to 4000, or more than 4000 circRNAs, where the circRNAs are brain disorder-associated circRNA biomarkers. According to an embodiment, at least one of the circRNAs in the composition may include one or a plurality of circRNAs shown in Tables 1-18 and/or sequences 1-241. According to an embodiment, at least one of the circRNAs in the composition may be circCDR1as, circTULP4, circCHIC1, circMIR5695, circRALGAPB, circCOMT, circPICALM, circDDX50, circRERE, or circSATB2, circICAM1, circDDR1, circADAM22, circMALAT1, circHMGA2, circCYP24A1, circDLG5, circMYO9B, circNFATC3, circDUSP22, circFKBP8, circVDAC2, and circTRIM69, or a circRNAs shown in Tables 1-18 and/or sequences 1-241.

According to an embodiment, the present disclosure provides an assay for the identification, diagnosis, screening, treatment and/or monitoring of a patient who has been or is being diagnosed, treated for, or who is suspected of having MDD or BD. For the purposes of the present disclosure, the terms "patient" or "subject" refer to any animal (e.g., mammal), including, but not limited to, humans, non-human primates, equines, canines, felines, rodents, and the like.

In an embodiment, the assay may include obtaining or providing a sample from a patient or an individual with or with an increased risk for MDD or BD (family history of brain disease and/or genetic predisposition, or a person with developmental delay or other clinical symptoms that could be associated with increased risk for developing a brain disorder) and measuring the expression of one or more of the circRNA biomarkers disclosed herein to produce an expression profile. According to an embodiment, at least one of the circRNAs in the expression profile may be circTULP4. According to another specific embodiment, at least one of the circRNAs in the expression profile may be circCDR1as. According to another specific embodiment, at least one of the circRNAs in the expression profile may be circCHIC1. According to another specific embodiment, at least one of the circRNAs in the expression profile may be circPICALM. According to another specific embodiment, at least one of the circRNAs in the expression profile may be circSATB2. According to another specific embodiment, at least one of the circRNAs in the expression profile may be circCOMT. According to another specific embodiment, at least one of the circRNAs in the expression profile may be circRERE. According to another specific embodiment, at least one of the circRNAs in the expression profile may be circMIR5695. According to another specific embodiment, at least one of the circRNAs in the expression profile may be DDX50. According to another specific embodiment, at least one of the circRNAs in the expression profile may be circRALGAPB. According to another specific embodiment, at least one of the circRNAs in the expression profile may be circICAM1. According to another specific embodiment, at least one of the circRNAs in the expression profile may be circDDR1. According to another specific embodiment, at least one of the circRNAs in the expression profile may be circADAM22. According to another specific embodiment, at least one of the circRNAs in the expression profile may be circMALAT1. According to another specific embodiment, at least one of the circRNAs in the expression profile may be circHMGA2. According to another specific embodiment, at least one of the circRNAs in the expression profile may be circCYP24A1. According to another specific embodiment, at least one of the circRNAs in the expression profile may be circDLG5. According to another specific embodiment, at least one of the circRNAs in the expression profile may be circMYO9B. According to another specific embodiment, at least one of the circRNAs in the expression profile may be circNFATC3. According to another specific embodiment, at least one of the circRNAs in the expression profile may be circDUSP22. According to another specific embodiment, at least one of the circRNAs in the expression profile may be circFKBP8. According to another specific embodiment, at least one of the circRNAs in the expression profile may be circVDAC2. According to another specific embodiment, at least one of the circRNAs in the expression profile may be circTRIM69. According to another specific embodiment, at least one of the circRNAs in the expression profile may be selected from SEQ ID NOs. 1-241, or Tables 1-18. The assay may further include probes, or primers to detect one or more of the circRNAs described above.

The assay may further include the step of comparing the patient's expression profile to a baseline. For identification, diagnostic, screening, or risk assessment purposes, the baseline may be an expression profile derived from one or more unaffected individuals (i.e. "a control profile") or from one or more affected individuals (i.e. a "disease-state profile"). For treatment or monitoring purposes the baseline may be a control profile, disease state profile, or a previously obtained expression profile from the same individual. Because brain disorders such as MDD and BD tend to be highly inherited, there may circumstances wherein it is useful or informative for the baseline to be an expression profile derived from one or more individuals who are blood relatives of the patient.

According to some embodiments the assay may include or provide access to a database of expression profiles including, for example, control profiles, disease-state profiles, and the like. The database may include expression profiles from individuals or consolidated expression profiles from groups of individuals. The database may be curated such that all identifying information from any specific individual is scrubbed. The database may enable review of individual or consolidated expression profiles over time in order to, for example, monitor and/or evaluate disease progression, drug-response, therapy response, etc.

According to an embodiment, the sample may be, or may be produced from, a bodily fluid such as blood (including blood products such as serum, whole blood, plasma, and blood components and cells) cerebral fluid, saliva, urine, or blood from umbilical cords. According to another embodiment, the sample may be, or may be produced from, bodily tissue, such as a skin biopsy, umbilical cord tissue, or deciduous teeth.

According to a specific example, the sample may be neurons taken from the patient (such as those in the gut's enteric system) or derived from the patient from any cells from the aforementioned bodily fluids and tissues. For example, the neurons could be derived from induced pluripotent stem cells (iPSCs), embryonic stem cells, mesenchymal stem cells, or engineered somatic cells, which can in turn be derived from cells of bodily fluids and tissues as described by Kastenberg Z. J., et al, (2008) Alternative sources of pluripotency: science, ethics, and stem cells. Transplant Rev (Orlando) 22,215-222, which is hereby incorporated by reference for all purposes.

According to a specific embodiment, the neurons are derived from IPSCs, iPSCs are similar to embryonic stem cells (ESC) in that iPSCs can be expanded indefinitely at the pluripotent stage and are able to differentiate into all three primary germ layers and, therefore, potentially into all the cell types of the body, iPSCs are derived from somatic cells and the process does not involve the use of embryonic cells, removing ethnical concerns. Moreover, iPSC cells can be derived from patient samples that are easily and even non-invasively obtained such as skin, saliva, blood, or urine samples.

According to various embodiments, the assay may include any number of sample preparation techniques and compositions including, for example, sample isolation and/or culturing and suitable reagents therefore, the use of suitable buffering solutions, etc.

According to another embodiment, the assay may include amplification of one or more brain disorder-associated circRNA biomarkers in a patient sample. Suitable amplification techniques include, for example, polymerase chain reaction (PCR), including Quantitative Real-Time PCR (qRT-PCR), reverse transcription PCR (RT-PCR), quantitative reverse transcription RT-PCR (QRT-PCR), Multiplex PCR, Nested PCR, Quantitative PCR, Hot-start PCR, Touchdown PCR, Assembly PCR, and droplet PCR.

In general, PCRs and qRT-PCRs employ the use of primers which are specifically designed to hybridize to and amplify a sequence of interest using multiple cycles of denaturation, annealing of primer pairs to opposite strands, and primer extension to exponentially produce copies of target nucleic acid sequence. Such PCRs can also be done following reverse transcription of RNA, including RNase-R-treated RNA. Accordingly, the present disclosure includes PCR and qRT-PCR primers that amplify at least a portion of one or more brain disorder-associated circRNA biomarkers to facilitate detection and/or quantification thereof.

According to an embodiment, at least one of the circRNAs being amplified may be selected from the group consisting of: circCDR1as, circTULP4, circCHIC1, circMIR5695, circRALGAPB, circCOMT, circPICALM, circDDX50, circRERE, or circSATB2, circlCAM1, circDDR1, circADAM22, circMALAT1, circHMGA2, circCYP24A1, circDLG5, circMYO9B, circNFATC3, circDUSP22, circFKBP8, circVDAC2, and circTRIM69.

According to an embodiment, at least one of the circRNAs being amplified may be selected from: a circRNA encoded by the nucleotide sequences according to SEQ ID NO. 1-124.

According to an embodiment, at least one of the circRNAs being amplified may be selected from: a circRNA encoded by the nucleotide sequences according to Tables 1-18.

According to an embodiment, at least one of the circRNAs being amplified may be MDD-a MDD treatment predictive circRNAs selected from: a circRNA encoded by the nucleotide sequences according to Tables 1-9.

According to an embodiment, at least one of the circRNAs being amplified may be a MDD and BD diagnosis-related circRNAs selected from: a circRNA encoded by the nucleotide sequences according to Tables 10-14.

According to an embodiment, at least one of the circRNAs being amplified may be a Sertraline treatment-related circRNAs selected from: a circRNA encoded by the nucleotide sequences according to Tables 15-18.

According to an embodiment, the assay may be or include a hybridization assay wherein a sample from a patient is obtained and interrogated using one or more probes designed to hybridize to one or more of the brain disorder-associated circRNA biomarkers or an amplicon thereof. Those of skill in the art will be familiar with a variety of different hybridization assays for detecting RNA including, but not limited to, microarrays, Northern blotting, PCR arrays, and other related technologies. Accordingly, the present disclosure provides probes that hybridize to one or more of the brain disorder-associated circRNA biomarkers disclosed herein or an amplicon thereof. Those of skill in the art will be familiar with the process for designing appropriate probes. Depending on the particular assay begin designed, it will be understood that the probes may be appropriately labeled. Examples of commonly used labels for hybridization assay probes include, for example, radiolabels, chemiluminescent labels, intercalating dyes, fluorochromes, etc.

According to an embodiment, the assay may be or include DNA or RNA sequencing techniques. Those of skill in the art will be familiar with a variety of sequencing techniques including, but not necessarily limited to, chain terminator (Sanger) sequencing, dye terminator sequencing, pyrosequencing and single-molecule sequencing, or Nanopore or other related long-read. In some cases, RNA sequences may be reverse transcribed into DNA sequencing prior to sequencing.

According to various embodiments, the present disclosure provides a kit comprising various reagents to enable the performance of one or more assays, including optionally instructions for use of the assay, wherein the assay comprises obtaining or providing a sample from a patient and measuring the expression of one or more circRNA biomarkers disclosed herein to produce an expression profile. The kit may include, for example, buffers, primers, and/or probes as needed in order to perform the assay. The kit may include only some or all of the reagents to complete the assay. The kit may further include a database or access to a database to which the expression profile obtained from the assay may be compared.

According to various embodiments, the present disclosure provides methods for the identification, diagnosis, screening, treatment, risk assessment, and/or monitoring of brain disorders such as MDD and BD. In general, the method comprises obtaining, providing, or receiving a patient sample; assaying the sample to determine the expression levels of one or more of the brain disorder-associated circRNA biomarkers disclosed herein; and comparing the expression level to a baseline profile. The baseline profile may be, for example, a control profile, a disease-state profile, or a previously obtained expression profile from the same individual or one or more blood relatives of the patient. Comparison of the expression level of one or more of the brain disorder-associated circRNA biomarkers in the patient sample to the baseline can then be used to identify, diagnose, screen, treat, assess risk, or monitor one or more brain disorders in the patient. For example, a specific expression profile compared to a baseline profile may indicate that a patient is more or less likely to respond to a particular medication, or a specific dose of a given medication, such as antidepressants, or that a particular medication is or is not providing a benefit or has adverse effects. Such information can be used by the patient, a caretaker, or a medical provider to make both medical and non-medical decisions including, for example, starting, stopping, or changing medication(s), changing dosage(s), etc.

As used herein, a biological marker ("biomarker" or "marker") is a characteristic that is objectively measured and evaluated as an indicator of normal biologic processes, pathogenic processes, or pharmacological responses to therapeutic interventions, consistent with NIH Biomarker Definitions Working Group (1998). Markers can also include patterns or ensembles of characteristics indicative of particular biological processes. The biomarker measurement can increase or decrease to indicate a particular biological event or process. In addition, if the biomarker measurement typically changes in the absence of a particular biological process, a constant measurement can indicate occurrence of that process. The circRNA biomarkers may be used for diagnostic and prognostic purposes, as well as for therapeutic, drug screening and patient stratification purposes (e.g., to group patients into a number of "subsets" for evaluation), as well as other purposes described herein.

As used herein, "circular RNA" is understood as a circular polynucleotide that can encode at least one protein as define herein. The production of circRNAs can be performed using various methods provided in the art. For example, U.S. Pat. No. 6,210,931 teaches a method of synthesizing circRNAs by inserting DNA fragments into a plasmid containing sequences having the capability of spontaneous cleavage and self-circularization. U.S. Pat. No. 5,773,244 teaches producing circRNAs by making a DNA construct encoding an RNA cyclase ribozyme, expressing the DNA construct as an RNA, and then allowing the RNA to self-splice, which produces a circRNA free from intron in vitro. WO1992001813 teaches a process of making single strand circular nucleic acids by synthesizing a linear polynucleotide, combining the linear nucleotide with a complementary linking oligonucleotide under hybridization conditions, and ligating the linear polynucleotide. The person skilled in the art may also use methods provided in WO2015034925 or WO2016011222 to produce circular RNA. Accordingly, methods for producing circular RNA as provided in U.S. Pat.

Nos. 6,210,931, 5,773,244, WO1992001813, WO2015034925 and WO2016011222 are incorporated herewith by reference.

The term “sequence identity” or “identity,” as used herein in the context of two nucleic acid or polypeptide sequences, refers to the residues in the two sequences that are the same when aligned for maximum correspondence over a specified comparison window.

As used herein, the term “sequence identity” may refer to the value determined by comparing two optimally aligned sequences (e.g., nucleic acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity. A sequence that is identical at every position in comparison to a reference sequence is said to be 100% identical to the reference sequence, and vice-versa.

An “expression vector” is a nucleic acid capable of replicating in a selected host cell or organism or in vitro. An expression vector can replicate as an autonomous structure, or alternatively can integrate, in whole or in part, into the host cell chromosomes or the nucleic acids of an organelle, or it may be used as a shuttle for delivering foreign DNA to cells, and thus replicate along with the host cell genome. Thus, expression vectors are polynucleotides capable of replicating in a selected in vitro system, host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an “expression cassette”. In contrast, as described in the examples herein, a “cassette” is a polynucleotide containing a section of an expression vector. The use of the cassette assists in the assembly of the expression vectors. An expression vector is a replicon, such as plasmid, phage, virus, chimeric virus, or cosmid, and which contains the desired polynucleotide sequence operably linked to the expression control sequence(s).

A polynucleotide sequence is “operably linked to an expression control sequence(s)” (e.g., a promoter and, optionally, an enhancer) when the expression control sequence controls and regulates the transcription and/or translation of that polynucleotide sequence. As used herein, the phrase “gene product” refers to an RNA molecule, such as a circRNA or a protein. Moreover, the term “gene” may sometime refer to the genetic sequence, the transcribed and possibly modified mRNA of that gene, or the translated protein of that mRNA.

Notably, all DNA sequences provided may encompass all RNA and amino acid sequences, as well as primers and probes for detection of the same and vice versa as would be ascertainable by those of ordinary skill in the art, for example through Uracil substitutions as well as redundant codons. Additionally, all sequences include codon-optimized embodiments as would be ascertainable by those of ordinary skill in the art. As such, the term “encoding” or “coding sequence” or “coding” means both encoding a nucleotide and/or amino acid sequence and vice versa.

The terms “approximately” and “about” refer to a quantity, level, value or amount that varies by as much as 30%, or in another embodiment by as much as 20%, and in a third embodiment by as much as 10% to a reference quantity, level, value or amount. As used herein, the singular form “a.” “an,” and “the” include plural references unless the context clearly dictates otherwise.

The terms and expressions that have been employed are used as terms of description and not of limitation, and there is no intent in the use of such terms and expressions to exclude any equivalent of the features shown and described or portions thereof, but it is recognized that various modifications are possible.

TABLE 1

(SSRI R baseline vs SSRI NR baseline)

| TxStart | TxEnd | Chrom | Strand | circRNA type | Alias | Fold change | P-value | Gene Symbol |
|---|---|---|---|---|---|---|---|---|
| 32638325 | 32649224 | chr21 | − | exonic | hsa_circ_0115791 | 1.5018 | 0.000003 | TIAM1 |
| 72797242 | 72804408 | chrX | + | exonic | hsa_circ_0091072 | 1.9375 | 0.000017 | CHIC1 |
| 76166897 | 76167135 | chr17 | + | exonic | hsa_circ_0045871 | 1.9043 | 0.000019 | SYNGR2 |
| 105238249 | 105322472 | chr12 | − | exonic | hsa_circ_0027966 | 1.6933 | 0.000021 | SLC41A2 |
| 75823317 | 75875495 | chr6 | − | exonic | hsa_circ_0077032 | 1.7154 | 0.000037 | COL12A1 |
| 51258546 | 51261286 | chr7 | − | exonic | hsa_circ_0080217 | 1.6267 | 0.000080 | COBL |
| 28505922 | 28508315 | chr15 | − | exonic | hsa_circ_0005387 | 1.5518 | 0.000091 | HERC2 |
| 73015794 | 73017356 | chr17 | + | exonic | hsa_circ_0045581 | 1.5767 | 0.000115 | ICT1 |
| 70696691 | 70703013 | chr10 | + | exonic | hsa_circ_0007097 | 2.0708 | 0.000121 | DDX50 |
| 17907047 | 17953998 | chr1 | + | exonic | hsa_circ_0010210 | 2.2325 | 0.000165 | ARHGEF10L |
| 19948721 | 19951822 | chr22 | + | exonic | hsa_circ_0062277 | 1.6795 | 0.000186 | COMT |
| 25628813 | 25631937 | chr17 | + | exonic | hsa_circ_0042488 | 2.0049 | 0.000221 | WSB1 |
| 95518727 | 95524317 | chr8 | − | exonic | hsa_circ_0084904 | 2.0901 | 0.000230 | KIAA1429 |
| 15415607 | 15417225 | chr2 | − | exonic | hsa_circ_0052712 | 1.5149 | 0.000247 | NBAS |
| 129180070 | 129188260 | chr3 | + | exonic | N/A | 1.5406 | 0.000263 | IFT122 |
| 15120499 | 15123913 | chr16 | + | exonic | hsa_circ_0038011 | 1.5351 | 0.000294 | PDXDC1 |
| 220253068 | 220263134 | chr1 | − | sense overlapping | hsa_circ_0000185 | 2.7460 | 0.000333 | BPNT1 |
| 126434011 | 126496057 | chr6 | + | antisense | hsa_circ_0130587 | −2.2679 | 0.000391 | MIR5695 |
| 206889066 | 206889235 | chr2 | − | intronic | N/A | 1.6489 | 0.000403 | INO80D |
| 66923610 | 66990707 | chr12 | − | exonic | hsa_circ_0099053 | 2.1011 | 0.000424 | GRIP1 |
| 25151491 | 25162936 | chr16 | + | exonic | N/A | 1.7777 | 0.000427 | LOMT1 |
| 80160631 | 80173542 | chr5 | + | sense overlapping | N/A | 2.0464 | 0.000482 | MSH3 |

TABLE 1-continued (SSRI R baseline vs SSRI NR baseline)

| TxStart | TxEnd | Chrom | Strand | circRNA type | Alias | Fold change | P-value | Gene Symbol |
|---|---|---|---|---|---|---|---|---|
| 5292121 | 5302970 | chr17 | − | exonic | hsa_circ_0041694 | 1.5569 | 0.000490 | NUP88 |
| 187498055 | 187506315 | chr2 | + | exonic | hsa_circ_0057319 | 2.7310 | 0.000520 | ITGAV |
| 30142548 | 30149539 | chr20 | + | exonic | hsa_circ_0059702 | 1.8693 | 0.000558 | HM13 |
| 17370097 | 17370831 | chr19 | − | exonic | hsa_circ_0049965 | 2.0677 | 0.000561 | USHBP1 |
| 6481519 | 6481649 | chr16 | + | intronic | hsa_circ_0000668 | 1.6645 | 0.000571 | RBFOX1 |
| 48259473 | 48260829 | chr10 | + | exonic | hsa_circ_0018309 | 1.8689 | 0.000602 | ANXA8 |
| 111800296 | 111853435 | chr9 | − | exonic | hsa_circ_0087903 | 2.0569 | 0.000639 | TMEM245 |
| 133534776 | 133536765 | chr5 | − | exonic | hsa_circ_0073942 | 1.5869 | 0.000640 | PPP2CA |
| 891302 | 892653 | chr1 | − | exonic | hsa_circ_0009205 | 1.5074 | 0.000655 | NOC2L |
| 25478063 | 25487229 | chr13 | − | exonic | hsa_circ_0029775 | 2.0288 | 0.000663 | CENPJ |
| 62283373 | 62304039 | chr11 | − | exonic | hsa_circ_0022429 | 1.5024 | 0.000687 | AHNAK |
| 118456876 | 118465835 | chr12 | + | exonic | hsa_circ_0028630 | 1.5177 | 0.000689 | RFC5 |
| 42641806 | 42641893 | chr20 | + | intronic | hsa_circ_0001160 | 1.9879 | 0.000822 | TOX2 |
| 151130894 | 151131115 | chrX | − | exonic | hsa_circ_0091710 | 1.5155 | 0.000852 | GABRE |
| 88655653 | 88667506 | chr9 | − | exonic | hsa_circ_0087400 | 1.5495 | 0.000856 | GOLM1 |
| 41884185 | 41884424 | chr19 | + | exonic | hsa_circ_0051220 | 1.5561 | 0.000864 | TMEM91 |
| 143238332 | 143247159 | chr6 | − | intronic | hsa_circ_0007021 | −1.5032 | 0.000869 | HIVEP2 |
| 127300370 | 127302466 | chr9 | − | exonic | hsa_circ_0088511 | 1.7699 | 0.000946 | NR6A1 |
| 109952549 | 109964548 | chr1 | − | exonic | N/A | 1.8552 | 0.000956 | PSMA5 |
| 29927157 | 29931571 | chr8 | − | exonic | hsa_circ_0083834 | 1.8197 | 0.000962 | SARAF |
| 27024168 | 27024508 | chr10 | + | exonic | hsa_circ_0018004 | 1.7368 | 0.000970 | PDSS1 |
| 74091854 | 74134875 | chr5 | − | exonic | N/A | 1.5740 | 0.000981 | FAM169A |
| 3659367 | 3659754 | chr1 | − | exonic | N/A | 1.6898 | 0.000988 | TP73-AS1 |
| 95027210 | 95027835 | chr9 | − | exonic | hsa_circ_0087497 | 1.9855 | 0.001081 | IARS |
| 140646904 | 140812121 | chr4 | − | exonic | hsa_circ_0071000 | 2.1707 | 0.001127 | MAML3 |
| 51459757 | 51459882 | chr3 | − | exonic | hsa_circ_0065902 | 1.6289 | 0.001152 | VPRBP |
| 118456876 | 118460164 | chr12 | + | exonic | hsa_circ_0028628 | 1.6679 | 0.001160 | RFC5 |
| 31849672 | 31852977 | chr14 | − | exonic | hsa_circ_0031570 | 1.5811 | 0.001183 | HEATR5A |
| 7414685 | 7414883 | chr5 | + | exonic | N/A | 1.6612 | 0.001217 | ADCY2 |
| 77616277 | 77620283 | chr8 | + | exonic | hsa_circ_0084789 | 1.8931 | 0.001283 | ZFHX4 |
| 18945987 | 18983955 | chr18 | + | exonic | hsa_ciro_0003653 | 2.1341 | 0.001296 | GREB1L |
| 12632755 | 12639440 | chr1 | − | exonic | hsa_circ_0010020 | 1.5176 | 0.001351 | DHRS3 |
| 31789187 | 31803431 | chr13 | + | exonic | hsa_circ_0002635 | 2.0464 | 0.001354 | B3GALTL |
| 80361812 | 80364358 | chr17 | − | exonic | hsa_circ_0000815 | 1.6063 | 0.001382 | OGFOD3 |
| 5664833 | 5667376 | chr4 | − | exonic | hsa_circ_0004228 | 1.5499 | 0.001601 | EVC2 |
| 79607545 | 79612827 | chr6 | + | exonic | hsa_circ_0077109 | 2.2303 | 0.001604 | IRAK1BP1 |
| 170650618 | 170658898 | chr4 | − | exonic | hsa_circ_0071439 | 2.1418 | 0.001676 | C4orf27 |
| 41133645 | 41134997 | chr13 | − | exonic | hsa_circ_0030042 | 1.6225 | 0.001720 | FOXO1 |
| 4845635 | 4848517 | chr17 | + | exonic | hsa_circ_0041623 | 1.9075 | 0.001728 | RNF167 |
| 46804823 | 46810323 | chr11 | − | exonic | N/A | 1.5385 | 0.001833 | CKAP5 |
| 101654702 | 101656154 | chr10 | − | exonic | N/A | 2.5440 | 0.001893 | DNMBP |
| 128750760 | 128754065 | chr2 | − | exonic | hsa_circ_0056390 | 1.9386 | 0.002033 | SAP130 |
| 74533340 | 74562028 | chr9 | + | exonic | N/A | 1.5589 | 0.002082 | C9orf85 |
| 42335263 | 42407667 | chr13 | − | exonic | hsa_circ_0030101 | 1.6283 | 0.002097 | VWA8 |
| 158994451 | 159050851 | chr6 | + | exonic | hsa_circ_0078488 | 1.6916 | 0.002154 | TMEM181 |
| 67154014 | 67159945 | chr16 | + | exonic | hsa_circ_0039787 | 1.7811 | 0.002317 | C16orf70 |
| 51706885 | 51716483 | chr14 | + | exonic | hsa_circ_0031896 | 1.6088 | 0.002577 | TMX1 |
| 37061800 | 37067498 | chr3 | + | exonic | N/A | 1.6328 | 0.002609 | MLH1 |
| 20889643 | 20953727 | chr18 | − | exonic | hsa_circ_0006015 | 1.6062 | 0.002725 | TMEM241 |
| 152913372 | 152916781 | chrX | + | exonic | hsa_circ_0091751 | 1.5195 | 0.002806 | DUSP9 |
| 95914772 | 95918564 | chr12 | − | exonic | hsa_circ_0027779 | 1.5689 | 0.002836 | USP44 |
| 94653105 | 94669388 | chr10 | + | exonic | hsa_circ_0019171 | 1.6410 | 0.002875 | EXOC6 |
| 5364258 | 5365866 | chr17 | − | exonic | hsa_circ_0000740 | 1.6562 | 0.002881 | DHX33 |
| 74385612 | 74397235 | chr17 | − | exonic | hsa_circ_0045801 | 1.5466 | 0.003049 | UBE2O |
| 161816238 | 161833102 | chr1 | + | exonic | hsa_circ_0008857 | 2.2692 | 0.003052 | ATF6 |
| 48466115 | 48472118 | chr20 | + | exonic | hsa_circ_0006359 | 1.5135 | 0.003172 | SLC9A8 |
| 216177220 | 216190861 | chr2 | + | exonic | hsa_circ_0058058 | 1.7336 | 0.003183 | ATIC |
| 35236117 | 35236221 | chr20 | + | exonic | hsa_circ_0001151 | 1.8026 | 0.003229 | C20orf24 |
| 100035289 | 100052403 | chr2 | − | exonic | hsa_circ_0001052 | 1.7393 | 0.003323 | REV1 |
| 50388196 | 50399175 | chr12 | − | exonic | hsa_circ_0026195 | 1.9220 | 0.003405 | RACGAP1 |
| 32050486 | 32053287 | chr1 | + | exonic | hsa_circ_0011297 | 1.5304 | 0.003500 | TINAGL1 |
| 55621921 | 55634000 | chr15 | + | exonic | hsa_circ_0035381 | 1.7669 | 0.003501 | PIGB |
| 21335426 | 21338430 | chr20 | + | exonic | N/A | 2.0130 | 0.003509 | XRN2 |
| 153555574 | 153562137 | chr7 | + | intergenic | N/A | 1.5657 | 0.003534 | |
| 28090104 | 28096621 | chr15 | − | exonic | hsa_circ_0034189 | 1.5624 | 0.003844 | OCA2 |
| 126434011 | 126498481 | chr6 | + | sense overlapping | N/A | 1.5453 | 0.003990 | RP11-527F13.1 |
| 45921422 | 45972988 | chr22 | + | exonic | hsa_circ_0063745 | 1.5073 | 0.004043 | FBLN1 |
| 66252643 | 66255478 | chr11 | + | exonic | N/A | 1.7355 | 0.004094 | DPP3 |
| 29190547 | 29196560 | chr22 | − | exonic | hsa_circ_0062722 | 1.7773 | 0.004258 | XBP1 |
| 14685190 | 14685289 | chr12 | + | intronic | hsa_circ_0000379 | 1.6110 | 0.004274 | RP11-502N13.2 |
| 8525984 | 8568734 | chr1 | − | exonic | hsa_circ_0009574 | 1.6844 | 0.004462 | RERE |
| 219114086 | 219114644 | chr2 | + | exonic | hsa_circ_0058218 | 1.6016 | 0.004896 | ARPC2 |
| 123471177 | 123512691 | chr3 | − | exonic | hsa_circ_0002768 | 1.8179 | 0.004897 | MYLK |

TABLE 1-continued (SSRI R baseline vs SSRI NR baseline)

| TxStart | TxEnd | Chrom | Strand | circRNA type | Alias | Fold change | P-value | Gene Symbol |
|---|---|---|---|---|---|---|---|---|
| 70502751 | 70505255 | chr16 | + | exonic | N/A | 1.5531 | 0.005102 | FUK |
| 90261231 | 90398157 | chr5 | + | exonic | N/A | 1.5483 | 0.005546 | GPR98 |
| 46795476 | 46795608 | chr2 | − | sense overlapping | hsa_circ_0000999 | 1.6931 | 0.005635 | LOC100506142 |
| 61833638 | 61835159 | chr20 | − | exonic | hsa_circ_0004858 | 1.5431 | 0.005655 | YTHDF1 |
| 141810557 | 141900868 | chr8 | − | exonic | hsa_circ_0007521 | 1.6181 | 0.005859 | PTK2 |
| 65228581 | 65237897 | chr2 | + | exonic | hsa_circ_0054971 | 1.6081 | 0.006009 | SLC1A4 |
| 109336203 | 109339348 | chr1 | + | exonic | hsa_circ_0000100 | 1.5165 | 0.006307 | STXBP3 |
| 42152047 | 42152455 | chr17 | + | exonic | hsa_circ_0044013 | 1.6089 | 0.006506 | G6PC3 |
| 27382878 | 27394372 | chr8 | + | exonic | hsa_circ_0083766 | 1.5243 | 0.006629 | EPHX2 |
| 128488846 | 128489036 | chr7 | + | exonic | hsa_circ_0082218 | 1.6553 | 0.006758 | FLNC |
| 30941049 | 30941149 | chr22 | − | intronic | hsa_circ_0001221 | 1.5610 | 0.007080 | SEC14L6 |
| 101379218 | 101387397 | chr1 | + | exonic | hsa_circ_0013353 | 1.5843 | 0.007298 | SLC30A7 |
| 61537238 | 61545758 | chr20 | − | exonic | hsa_circ_0061137 | 1.8752 | 0.007330 | DIDO1 |
| 41456925 | 41457407 | chr1 | + | intronic | N/A | 2.0106 | 0.007829 | CTPS1 |
| 40174416 | 40174658 | chr17 | + | exonic | hsa_circ_0003530 | 1.8867 | 0.007903 | NKIRAS2 |
| 233353644 | 233363117 | chr1 | − | exonic | hsa_circ_0003314 | 1.6768 | 0.008006 | PONXL2 |
| 45302384 | 45323900 | chr21 | + | sense overlapping | N/A | 1.8768 | 0.008551 | AGPAT3 |
| 105192034 | 105233194 | chr6 | − | exonic | hsa_circ_0004397 | 1.6288 | 0.008596 | HACE1 |
| 67270083 | 67280213 | chr17 | − | exonic | N/A | 1.5128 | 0.008974 | ABCA5 |
| 57237616 | 57250507 | chr4 | − | exonic | N/A | 1.9203 | 0.009057 | AASDH |
| 176339971 | 176340710 | chr5 | − | intronic | N/A | 1.6466 | 0.009064 | UIMC1 |
| 43668295 | 43669265 | chr15 | + | exonic | hsa_circ_0034953 | 1.5320 | 0.009474 | TUBGCP4 |
| 15510546 | 15510663 | chr19 | + | antisense | hsa_circ_0000902 | 1.6727 | 0.010132 | AKAP8L |
| 27820936 | 27830906 | chr2 | + | exonic | hsa_circ_0053294 | 1.5134 | 0.010208 | ZNF512 |
| 35657761 | 35658017 | chr9 | + | antisense | N/A | −1.5758 | 0.010239 | RMRP |
| 40596333 | 40597123 | chr21 | − | exonic | hsa_circ_0001193 | 1.5485 | 0.010516 | BRWD1 |
| 72285678 | 72291210 | chr10 | + | exonic | hsa_circ_0018659 | 1.6621 | 0.011160 | PALD1 |
| 42069936 | 42084913 | chr22 | − | exonic | hsa_circ_0063598 | 1.6462 | 0.011210 | NHP2L1 |
| 37159809 | 37161502 | chr20 | + | exonic | hsa_circ_0060342 | −1.5477 | 0.011360 | RALGAPB |
| 26208168 | 26220646 | chr12 | + | exonic | hsa_circ_0025638 | 1.5734 | 0.011861 | RASSF8 |
| 207705830 | 207746615 | chr2 | + | sense overlapping | hsa_circ_0006005 | 1.6523 | 0.011883 | AC008269.2 |
| 93141396 | 93148280 | chr11 | + | exonic | N/A | 1.6621 | 0.012493 | CCDC67 |
| 133738149 | 133738422 | chr9 | + | exonic | hsa_circ_—0089131 | 1.5895 | 0.012501 | ABL1 |
| 34059659 | 34101636 | chr6 | − | exonic | hsa_circ_0076040 | 1.5210 | 0.013404 | GRM4 |
| 141710989 | 141716304 | chr8 | − | exonic | hsa_circ_0005273 | 2.1229 | 0.013677 | PTK2 |
| 4317362 | 4317697 | chr4 | + | exonic | hsa_circ_0006333 | 1.5933 | 0.015026 | ZBTB49 |
| 3474817 | 3477249 | chr17 | − | exonic | N/A | 1.6794 | 0.015062 | TRPV |
| 20573977 | 20577388 | chr6 | + | intronic | N/A | 1.5175 | 0.021592 | CDKAL1 |
| 80869751 | 80879232 | chr9 | + | exonic | N/A | 1.5449 | 0.025413 | CEP78 |
| 62293536 | 62293836 | chr20 | + | intronic | hsa_circ_0092333 | 1.6388 | 0.025983 | RTEL1 |
| 107031202 | 107050797 | chr6 | − | exonic | hsa_circ_0008514 | 1.5337 | 0.026017 | RTN4IP1 |
| 89123719 | 89131833 | chr14 | − | exonic | N/A | 1.5607 | 0.026590 | EML5 |
| 33866724 | 33872064 | chr20 | − | sense overlapping | hsa_circ_0060055 | 1.5174 | 0.029576 | EIF6 |
| 145439832 | 145440140 | chr1 | + | intronic | hsa_circ_0000122 | −1.5642 | 0.030419 | NBPF10 |
| 13532533 | 13581264 | chr20 | − | intronic | N/A | 1.6154 | 0.030812 | TASP1 |
| 33866724 | 33872295 | chr20 | − | sense overlapping | hsa_circ_0060056 | 1.5147 | 0.033525 | EIF6 |
| 111795586 | 111800397 | chr9 | − | exonic | hsa_circ_0087888 | 1.6422 | 0.036036 | TMEM245 |
| 27447477 | 27447615 | chr10 | + | exonic | hsa_circ_0018031 | 1.5624 | 0.039389 | MASTL |
| 8366 | 14149 | chrM | - | exonic | hsa_circ_0089763 | −1.8150 | 0.040921 | JA760600 |
| 33058531 | 33060824 | chr1 | + | exonic | hsa_circ_0002306 | 1.5647 | 0.042295 | ZBTB8A |
| 127393233 | 127393443 | chr3 | + | exonic | hsa_circ_0067175 | −1.6564 | 0.043061 | ABTB1 |
| 113057425 | 113057606 | chr2 | + | exonic | hsa_circ_0001062 | −1.9426 | 0.043283 | ZC3H6 |
| 7586 | 7982 | chrM | − | exonic | hsa_circ_0089762 | −1.6383 | 0.048019 | JA760602 |
| 33149215 | 33194241 | chr15 | − | exonic | hsa_circ_0005054 | 1.6008 | 0.048353 | FMN1 |

TABLE 2

(SSRI R 8 week vs SSRI NR 8 week)

| TxStart | TxEnd | Chrom | Strand | circRNA type | Alias | Fold change | P-value | GeneSymbol |
|---|---|---|---|---|---|---|---|---|
| 100410368 | 100410830 | chr7 | − | exonic | hsa_circ_0001730 | 1.5019 | 0.000095 | EPHB4 |
| 42281139 | 42281797 | chr18 | + | exonic | hsa_circ_0006491 | −1.7369 | 0.000384 | SETBP1 |
| 44656614 | 44661075 | chr18 | − | exonic | hsa_circ_0108522 | −1.7801 | 0.000401 | HDHD2 |
| 75703832 | 75706652 | chr15 | − | exonic | hsa_circ_0000636 | −1.5598 | 0.000623 | SIN3A |
| 55748067 | 55748333 | chr19 | + | antisense | hsa_circ_0000959 | 1.5630 | 0.001437 | PPP6R1 |

TABLE 2-continued (SSRI R 8 week vs SSRI NR 8 week)

| TxStart | TxEnd | Chrom | Strand | circRNA type | Alias | Fold change | P-value | GeneSymbol |
|---|---|---|---|---|---|---|---|---|
| 120517677 | 120528452 | chr4 | − | exonic | hsa_circ_0002474 | −1.9528 | 0.001518 | PDE5A |
| 120460114 | 120528452 | chr4 | − | exonic | hsa_circ_0070805 | −1.6493 | 0.001766 | PDE5A |
| 77930940 | 77934851 | chr14 | + | exonic | hsa_circ_0032777 | −1.5443 | 0.001839 | AHSA1 |
| 33442618 | 33447218 | chr2 | + | exonic | hsa_circ_0053907 | −1.7083 | 0.001843 | LTBP1 |
| 59730181 | 59758024 | chr14 | + | sense overlapping | hsa_circ_0000543 | −1.6033 | 0.001845 | DAAM1 |
| 85692171 | 85695016 | chr11 | − | exonic | hsa_circ_0003695 | −2.9046 | 0.002190 | PICALM |
| 151749331 | 151753128 | chr4 | − | exonic | hsa_circ_0071210 | −1.8627 | 0.002431 | LABA |
| 146747016 | 146757164 | chr1 | + | exonic | hsa_circ_0013953 | −2.2977 | 0.002539 | CHD1L |
| 32858942 | 32865477 | chr2 | + | exonic | hsa_circ_0003195 | −1.9266 | 0.002794 | TTC27 |
| 109288780 | 109289485 | chr2 | + | exonic | hsa_circ_0008348 | −1.5953 | 0.002904 | LIMS1 |
| 204396775 | 204397348 | chr1 | − | exonic | hsa_circ_0111746 | −1.8689 | 0.002978 | PIK3C2B |
| 16386664 | 16415895 | chr21 | − | exonic | hsa_circ_0004771 | −2.8924 | 0.003198 | NRIP1 |
| 34685382 | 34706566 | chr19 | + | exonic | hsa_circ_0008030 | −2.9817 | 0.003319 | LSM14A |
| 22880557 | 22880710 | chr10 | − | exonic | hsa_circ_0017972 | −2.3943 | 0.003327 | PIP4K2A |
| 152017193 | 152018156 | chr3 | + | exonic | hsa_circ_0001348 | −1.9138 | 0.003377 | MBNL1 |
| 141840570 | 141874498 | chr8 | − | exonic | hsa_circ_0002908 | −2.4499 | 0.003399 | PTK2 |
| 141856358 | 141900868 | chr8 | − | exonic | hsa_circ_0003221 | −2.1285 | 0.003534 | PTK2 |
| 85692171 | 85742653 | chr11 | − | exonic | hsa_circ_0023903 | −3.2167 | 0.003546 | PICALM |
| 34706028 | 34706566 | chr19 | + | exonic | hsa_circ_0050463 | −1.6032 | 0.003660 | LSM14A |
| 86494712 | 86508177 | chr14 | + | intronic | N/A | −1.6016 | 0.003817 | LOC101928767 |
| 16386664 | 16386787 | chr21 | − | exonic | hsa_circ_0061274 | −2.0259 | 0.003887 | NRIP1 |
| 151656409 | 151729550 | chr4 | − | exonic | hsa_circ_0071174 | −2.2857 | 0.003959 | LABA |
| 68126447 | 68129252 | chr14 | − | exonic | N/A | −1.5629 | 0.004014 | VTI1B |
| 152132729 | 152150709 | chr3 | + | exonic | hsa_circ_0001349 | −2.3777 | 0.004189 | MBNL1 |
| 34699833 | 34706566 | chr19 | + | exonic | hsa_circ_0050461 | −2.4186 | 0.004197 | LSM14A |
| 123658355 | 123683844 | chr10 | − | exonic | hsa_circ_0008742 | −1.5210 | 0.004413 | ATE1 |
| 3550981 | 3551192 | chr19 | − | exonic | hsa_circ_0048492 | 1.5268 | 0.004421 | MFSD12 |
| 17928129 | 17932239 | chr20 | − | exonic | hsa_circ_0059501 | −1.5854 | 0.004596 | SNX5 |
| 150496687 | 150512748 | chr5 | − | exonic | hsa_circ_0074598 | −2.5091 | 0.004774 | ANXA6 |
| 14938844 | 14939516 | chr10 | + | exonic | hsa_circ_0006780 | −1.6865 | 0.004945 | SUV39H2 |
| 179043126 | 179043219 | chr5 | − | exonic | hsa_circ_0075281 | −2.6571 | 0.005102 | HNRNPH1 |
| 16415815 | 16415895 | chr21 | − | exonic | hsa_circ_0061276 | −2.2382 | 0.005252 | NRIP1 |
| 24788253 | 24788679 | chr16 | + | exonic | hsa_circ_0038673 | −1.6957 | 0.005331 | TNRC6A |
| 67562936 | 67614669 | chr18 | − | exonic | N/A | −1.9375 | 0.005340 | CD226 |
| 67484716 | 67485741 | chr8 | − | exonic | N/A | −1.9275 | 0.005735 | MYBL1 |
| 93557925 | 93558139 | chr15 | + | exonic | hsa_circ_0037007 | −2.4697 | 0.005838 | CHD2 |
| 64295353 | 64295792 | chrX | + | sense overlapping | hsa_circ_0002532 | −1.8253 | 0.005896 | XLOC_008000 |
| 125597327 | 125603476 | chr8 | − | exonic | N/A | −1.6397 | 0.006301 | MTSS1 |
| 155408117 | 155429689 | chr1 | − | exonic | hsa_circ_0003247 | −1.7020 | 0.006324 | ASH1L |
| 41515056 | 41518061 | chr13 | − | exonic | hsa_circ_0030051 | −2.0521 | 0.006435 | ELF1 |
| 21461899 | 21470081 | chr18 | + | exonic | hsa_circ_0047232 | 1.5636 | 0.006684 | LAMA3 |
| 27834913 | 27838010 | chr17 | + | exonic | hsa_circ_0004800 | −1.8923 | 0.006697 | TAOK1 |
| 146209155 | 146216108 | chr6 | − | sense overlapping | N/A | −2.8635 | 0.006844 | SHPRH |
| 22896855 | 22898646 | chr10 | − | exonic | hsa_circ_0003826 | −2.0194 | 0.006865 | PIP4K2A |
| 151727422 | 151729550 | chr4 | − | exonic | hsa_circ_0071196 | −3.3149 | 0.007151 | LABA |
| 246078831 | 246093239 | chr1 | − | exonic | hsa_circ_0005090 | −1.5370 | 0.007183 | SMYD3 |
| 33160465 | 33161645 | chr1 | − | exonic | hsa_circ_0004895 | 1.7513 | 0.007186 | SYNC |
| 86627164 | 86649052 | chr5 | + | exonic | hsa_circ_0004317 | −1.9832 | 0.007284 | RASA1 |
| 20781375 | 20846409 | chr6 | + | exonic | hsa_circ_0008086 | −1.9626 | 0.007318 | CDKAL1 |
| 19615443 | 19653155 | chr12 | + | exonic | hsa_circ_0006128 | −1.7644 | 0.007336 | AEBP2 |
| 68881420 | 68882183 | chr5 | + | exonic | hsa_circ_0006929 | −1.5243 | 0.007402 | GTF2H2C_2 |
| 75331178 | 75336119 | chr10 | − | exonic | hsa_circ_0007221 | 1.5567 | 0.007626 | USP54 |
| 68717321 | 68795482 | chr2 | + | sense overlapping | hsa_circ_0001024 | −2.4078 | 0.007634 | APLF |
| 120916382 | 120924441 | chr11 | + | exonic | hsa_circ_0000365 | −1.5549 | 0.007654 | TBCEL |
| 17661883 | 17665616 | chr6 | − | exonic | hsa_circ_0075728 | −1.5390 | 0.007905 | NUP153 |
| 134002512 | 134007576 | chr5 | + | exonic | hsa_circ_0003180 | 1.7505 | 0.007913 | SEC24A |
| 107236366 | 107254190 | chr12 | + | exonic | hsa_circ_0028021 | −1.7898 | 0.007996 | RIC8B |
| 211092981 | 211093411 | chr1 | − | exonic | hsa_circ_0006123 | 1.5036 | 0.008016 | KCNH1 |
| 146209155 | 146216113 | chr6 | − | exonic | hsa_circ_0001649 | −2.8604 | 0.008174 | SHPRH |
| 136599002 | 136603825 | chr6 | − | exonic | N/A | −1.7506 | 0.008193 | BCLAF1 |
| 37347101 | 37349807 | chr2 | − | exonic | N/A | −1.5337 | 0.008236 | EIF2AK2 |
| 151719232 | 151729550 | chr4 | − | exonic | hsa_circ_0004636 | −2.8884 | 0.008339 | LRBA |
| 3969740 | 3976050 | chr17 | − | exonic | hsa_circ_0004767 | −1.6996 | 0.008353 | ZZEF1 |
| 79613111 | 79614128 | chr10 | − | exonic | hsa_circ_0006649 | −1.9346 | 0.008466 | DLG5 |
| 103271286 | 103279053 | chr9 | + | exonic | N/A | −1.6497 | 0.008686 | TMEFF1 |
| 155640110 | 155644887 | chr1 | − | exonic | N/A | −1.8231 | 0.008743 | YY1AP1 |
| 95814629 | 95819004 | chr2 | − | sense overlapping | N/A | −1.6332 | 0.008914 | ZNF514 |
| 20507738 | 20527139 | chr2 | − | exonic | hsa_circ_0052867 | −2.1779 | 0.008916 | PUM2 |
| 6630963 | 6632512 | chr12 | + | exonic | hsa_circ_0025162 | 1.5045 | 0.008953 | NCAPD2 |
| 29183972 | 29192818 | chr17 | + | exonic | N/A | 1.8928 | 0.009008 | ATAD5 |

TABLE 2-continued (SSRI R 8 week vs SSRI NR 8 week)

| TxStart | TxEnd | Chrom | Strand | circRNA type | Alias | Fold change | P-value | GeneSymbol |
|---|---|---|---|---|---|---|---|---|
| 149833290 | 149838586 | chr6 | − | exonic | hsa_circ_0009074 | 1.8987 | 0.009065 | PPIL4 |
| 24021149 | 24022915 | chr1 | + | exonic | hsa_circ_0010884 | −1.6693 | 0.009070 | RPL11 |
| 190670377 | 190682906 | chr2 | + | exonic | N/A | −1.8941 | 0.009191 | PMS1 |
| 118422500 | 118430579 | chr11 | − | exonic | hsa_circ_0007372 | 1.5386 | 0.009212 | IFT46 |
| 11905658 | 11907984 | chr2 | + | exonic | hsa_circ_0002229 | −1.5509 | 0.009337 | LPIN1 |
| 117944807 | 117984947 | chr1 | + | exonic | hsa_circ_0000119 | −2.2717 | 0.009361 | MAN1A2 |
| 66337415 | 66352945 | chr17 | + | sense overlapping | N/A | 1.7195 | 0.009461 | ARSG |
| 54265896 | 54294350 | chr4 | + | exonic | hsa_circ_0005912 | −1.8821 | 0.009470 | FIP1L1 |
| 65405871 | 65409531 | chr14 | − | sense overlapping | hsa_circ_0032233 | 1.8031 | 0.009490 | GPX2 |
| 151719232 | 151738409 | chr4 | − | exonic | hsa_circ_0008618 | −2.9526 | 0.009497 | LRBA |
| 37246951 | 37247979 | chr2 | − | exonic | N/A | 1.5723 | 0.009554 | HEATR5B |
| 230723487 | 230744844 | chr2 | − | exonic | hsa_circ_0003273 | −2.1034 | 0.009614 | TRIP12 |
| 150496687 | 150502572 | chr5 | − | exonic | hsa_circ_0074595 | −2.2467 | 0.009688 | ANXA6 |
| 242283166 | 242287606 | chr2 | + | exonic | N/A | −1.6468 | 0.009728 | SEPT2 |
| 153583192 | 153585991 | chrX | − | exonic | hsa_circ_0091934 | −2.3520 | 0.009810 | FLNA |
| 5964676 | 5993389 | chr1 | − | exonic | hsa_circ_0009449 | 1.7679 | 0.009864 | NPHP4 |
| 68155889 | 68225678 | chr16 | + | exonic | hsa_circ_0039929 | −2.9325 | 0.009893 | NFATC3 |
| 34685382 | 34687668 | chr19 | + | exonic | hsa_circ_0006446 | −1.7643 | 0.009960 | LSM14A |
| 47762155 | 47787483 | chr3 | − | exonic | hsa_circ_0065301 | −1.6955 | 0.010013 | SMARCC1 |
| 151682934 | 151729550 | chr4 | − | exonic | hsa_circ_0071185 | −2.0060 | 0.010021 | LRBA |
| 148867767 | 148887990 | chr4 | + | exonic | hsa_circ_0006473 | −1.6269 | 0.010027 | ARHGAP10 |
| 31815277 | 31867987 | chr7 | − | exonic | N/A | 1.5977 | 0.010047 | PDE1C |
| 28290542 | 28310335 | chr22 | − | exonic | hsa_circ_0062688 | −2.0111 | 0.010060 | PITPNB |
| 28306951 | 28310335 | chr22 | − | exonic | hsa_circ_0003056 | −2.2706 | 0.010116 | PITPNB |
| 29845053 | 29845387 | chr16 | + | exonic | hsa_circ_0000688 | 1.5085 | 0.010313 | MVP |
| 44060686 | 44061844 | chr15 | + | exonic | N/A | −3.6916 | 0.010333 | PDIA3 |
| 1902352 | 1941505 | chr4 | + | exonic | hsa_circ_0005881 | 1.5907 | 0.010336 | WHSC1 |
| 69502654 | 69553668 | chr15 | + | exonic | N/A | −1.5085 | 0.010432 | GLCE |
| 171867882 | 171884915 | chr2 | − | exonic | hsa_circ_0057028 | −1.6460 | 0.010471 | TLK1 |
| 68337215 | 68343511 | chr11 | + | exonic | hsa_circ_0023233 | 2.2175 | 0.010486 | PPP6R3 |
| 51381438 | 51387763 | chr10 | + | exonic | hsa_circ_0006820 | −1.9660 | 0.010597 | TIMM23B |
| 148778703 | 148803083 | chr4 | + | exonic | hsa_circ_0071106 | −1.9113 | 0.010671 | ARHGAP10 |
| 39607406 | 39629569 | chr18 | + | exonic | hsa_circ_0007765 | −1.9589 | 0.010819 | PIK3C3 |
| 135710404 | 135715781 | chr7 | + | sense overlapping | N/A | −1.6608 | 0.010894 | AC024084.1 |
| 42415314 | 42416100 | chr22 | + | exonic | hsa_circ_0001239 | 1.6715 | 0.010908 | WBP2NL |
| 27209637 | 27210251 | chr17 | + | antisense | hsa_circ_0000747 | 1.6007 | 0.010922 | FLOT2 |
| 227771508 | 227779067 | chr2 | + | exonic | hsa_circ_0058497 | −1.6975 | 0.011053 | RHBDD1 |
| 28654060 | 28671129 | chr8 | − | exonic | N/A | 1.5208 | 0.011082 | INTS9 |
| 134049441 | 134053797 | chr9 | + | exonic | hsa_circ_0089172 | 1.5469 | 0.011105 | NUP214 |
| 28013458 | 28019595 | chr8 | + | exonic | hsa_circ_0001785 | −1.8771 | 0.011112 | ELP3 |
| 120345268 | 120348235 | chr11 | + | exonic | hsa_circ_0002100 | −1.6270 | 0.011176 | ARHGEF12 |
| 120347369 | 120348235 | chr11 | + | exonic | hsa_circ_0002089 | −2.1830 | 0.011178 | ARHGEF12 |
| 152497615 | 152498816 | chr7 | + | exonic | hsa_circ_0083061 | −1.8146 | 0.011206 | ACTR3B |
| 18324587 | 18379747 | chr22 | − | exonic | N/A | 1.8392 | 0.011206 | MICAL3 |
| 191765289 | 191775047 | chr2 | + | exonic | hsa_circ_0057521 | −2.4383 | 0.011250 | GLS |
| 96233422 | 96261168 | chr9 | + | exonic | hsa_circ_0001875 | −2.7799 | 0.011289 | FAM1204 |
| 5641604 | 5641957 | chr19 | + | exonic | hsa_circ_0005104 | −1.5501 | 0.011424 | SAFB |
| 65055186 | 65063461 | chr11 | + | exonic | hsa_circ_0022812 | 1.5597 | 0.011427 | POLA2 |
| 146767107 | 146824367 | chr4 | − | exonic | N/A | −1.6742 | 0.011449 | ZNF827 |
| 217329319 | 217340174 | chr2 | + | exonic | hsa_circ_0058189 | 1.7374 | 0.011471 | SMARCAL1 |
| 21961646 | 21995303 | chr13 | − | exonic | N/A | −1.5279 | 0.011510 | ZDHHC20 |
| 2967410 | 2969120 | chr20 | + | exonic | hsa_circ_0001127 | −1.8006 | 0.011541 | PTPRA |
| 68334481 | 68343511 | chr11 | + | exonic | hsa_circ_0002038 | −1.8956 | 0.011545 | PPP6R3 |
| 141889569 | 141900868 | chr8 | − | exonic | hsa_circ_0006646 | −1.6797 | 0.011637 | PTK2 |
| 85782606 | 85783383 | chr2 | − | exonic | hsa_circ_0055426 | 1.5806 | 0.011733 | GGCX |
| 231226328 | 231307814 | chr2 | + | sense overlapping | hsa_circ_0001108 | −1.5825 | 0.011972 | SP100 |
| 68160350 | 68160513 | chr16 | + | exonic | hsa_circ_0039930 | −2.0622 | 0.011974 | NFATC3 |
| 173433468 | 173457776 | chr2 | + | exonic | hsa_circ_0057104 | −1.7333 | 0.012060 | PDK1 |
| 110084263 | 110087285 | chr9 | + | exonic | hsa_circ_0001880 | −2.1483 | 0.012100 | RAD23B |
| 72301330 | 72302378 | chr7 | + | sense overlapping | hsa_circ_0006688 | −1.7673 | 0.012126 | SBDSP1 |
| 217329319 | 217332769 | chr2 | + | exonic | hsa_circ_0058188 | 1.6332 | 0.012128 | SMARCAL1 |
| 170906490 | 170912424 | chr3 | − | exonic | hsa_circ_0002387 | −1.8498 | 0.012192 | TNIK |
| 35804797 | 35822225 | chr17 | + | exonic | hsa_circ_0043285 | −1.9346 | 0.012251 | TADA2A |
| 56989531 | 57025950 | chr6 | + | exonic | N/A | −1.9072 | 0.012281 | ZNF451 |
| 8383694 | 8427688 | chr2 | − | exonic | N/A | −2.6179 | 0.012289 | LINC00299 |
| 66044716 | 66053776 | chr15 | − | exonic | hsa_circ_0035957 | −2.3225 | 0.012320 | DENND4A |
| 47752369 | 47782822 | chr20 | − | exonic | hsa_circ_0004648 | −1.5174 | 0.012349 | STAU1 |
| 77759436 | 77764156 | chr15 | + | exonic | hsa_circ_0036429 | −1.6080 | 0.012440 | HMG20A |

TABLE 2-continued (SSRI R 8 week vs SSRI NR 8 week)

| TxStart | TxEnd | Chrom | Strand | circRNA type | Alias | Fold change | P-value | GeneSymbol |
|---|---|---|---|---|---|---|---|---|
| 19615443 | 19626289 | chr12 | + | exonic | hsa_circ_0006420 | −2.6323 | 0.012486 | AEBP2 |
| 28956385 | 28956758 | chr8 | − | sense overlapping | N/A | 1.5923 | 0.012490 | KIF13B |
| 35586872 | 35614627 | chr6 | − | intronic | hsa_circ_0001600 | −2.0845 | 0.012558 | FKBP5 |
| 141874410 | 141900868 | chr8 | − | exonic | hsa_circ_0002483 | −2.1963 | 0.012617 | PTK2 |
| 45059428 | 45059793 | chr15 | + | sense overlapping | N/A | 1.5339 | 0.012697 | TRIM69 |
| 173426947 | 173429801 | chr2 | + | exonic | N/A | −1.7795 | 0.012755 | PDK1 |
| 167915606 | 167924353 | chr5 | + | exonic | hsa_circ_0001551 | −1.7748 | 0.012772 | RARS |
| 65830317 | 65831879 | chr1 | + | exonic | hsa_circ_0002454 | −1.9300 | 0.012776 | DNAJC6 |
| 38948670 | 38964294 | chr22 | − | exonic | hsa_circ_0004795 | 1.5732 | 0.012798 | DMC1 |
| 77193578 | 77227582 | chr18 | + | exonic | hsa_circ_0048025 | 1.5650 | 0.012803 | NATO1 |
| 47079155 | 47108608 | chr3 | − | exonic | hsa_circ_0004692 | −1.7064 | 0.013105 | SETD2 |
| 86627164 | 86633908 | chr5 | + | exonic | hsa_circ_0007507 | −1.7674 | 0.013142 | RASA1 |
| 132273520 | 132273720 | chr2 | + | intronic | hsa_circ_0092325 | 1.6067 | 0.013153 | RNU6-81P |
| 116590610 | 116608496 | chr10 | + | exonic | hsa_circ_0020080 | 1.8078 | 0.013164 | FAM160B1 |
| 176707565 | 176715926 | chr5 | + | exonic | hsa_circ_0075172 | −1.6490 | 0.013194 | NSD1 |
| 123658355 | 123662135 | chr10 | − | exonic | hsa_circ_0020250 | −1.5187 | 0.013212 | ATE1 |
| 27223791 | 27224216 | chr1 | − | exonic | hsa_circ_0011032 | 1.5598 | 0.013238 | GPATCH3 |
| 12539258 | 12539962 | chr11 | + | intronic | N/A | 1.5823 | 0.013299 | PARVA |
| 8674619 | 8684439 | chr1 | − | exonic | hsa_circ_0009594 | −1.5493 | 0.013328 | RERE |
| 96238537 | 96259881 | chr9 | + | exonic | hsa_circ_0087540 | −2.5336 | 0.013370 | FAM120A |
| 23356961 | 23385660 | chr1 | + | exonic | hsa_circ_0007822 | −1.6968 | 0.013375 | KDM1A |
| 145838898 | 145842016 | chr3 | − | exonic | N/A | −1.7581 | 0.013454 | PLOD2 |
| 65743336 | 65744440 | chr15 | − | exonic | hsa_circ_0035892 | −1.5551 | 0.013523 | DPP8 |
| 27373960 | 27374248 | chr16 | + | intronic | hsa_circ_0000684 | 1.6228 | 0.013648 | IL4R |
| 173433468 | 173460751 | chr2 | + | exonic | hsa_circ_0057105 | −1.9300 | 0.013719 | PDK1 |
| 68155889 | 68160513 | chr16 | + | exonic | hsa_circ_0000711 | −3.5357 | 0.013729 | NFATC3 |
| 39738530 | 39743147 | chr17 | − | exonic | hsa_circ_0043614 | 1.5950 | 0.013783 | KRT14 |
| 114886536 | 114919893 | chr9 | − | exonic | hsa_circ_0004286 | 2.4861 | 0.013869 | SUSD1 |
| 73590599 | 73606865 | chr6 | + | intronic | hsa_circ_0002930 | −1.5336 | 0.013910 | KONQ5 |
| 171879381 | 171902872 | chr2 | − | exonic | N/A | −2.4456 | 0.013912 | TLK1 |
| 86992149 | 86993147 | chr2 | + | exonic | N/A | −1.7890 | 0.013933 | RMND5A |
| 85667519 | 85695371 | chr16 | + | exonic | hsa_circ_0040730 | −2.1466 | 0.013976 | GSE1 |
| 72945231 | 72960247 | chr2 | − | exonic | hsa_circ_0009043 | −1.6075 | 0.014100 | EXOC6B |
| 109048081 | 109095099 | chr12 | − | exonic | hsa_circ_0028072 | −2.7821 | 0.014105 | CORO1C |
| 53699213 | 53701307 | chr1 | − | exonic | N/A | −2.5862 | 0.014134 | MAGOH |
| 118774654 | 118787003 | chrX | − | exonic | hsa_circ_0008350 | −1.5741 | 0.014212 | SEPT6 |
| 119222378 | 119236162 | chr3 | + | exonic | hsa_circ_0001330 | −1.8254 | 0.014213 | TIMMDC1 |
| 56144799 | 56149582 | chr2 | − | exonic | hsa_circ_0054663 | 1.8487 | 0.014249 | EFEMP1 |
| 154173659 | 154197163 | chr5 | + | sense overlapping | hsa_circ_0074712 | −1.5952 | 0.014275 | LARP1 |
| 148653869 | 148657467 | chr2 | + | exonic | hsa_circ_0001073 | −1.7845 | 0.014289 | ACVR2A |
| 198273227 | 198274543 | chr2 | + | antisense | hsa_circ_0001089 | 1.7296 | 0.014474 | SF3B1 |
| 131071878 | 131073731 | chr7 | + | exonic | hsa_circ_0002117 | −1.7226 | 0.014493 | MKLN1 |
| 41173043 | 41195087 | chr22 | − | exonic | hsa_circ_0063459 | 1.6180 | 0.014501 | SLC25A17 |
| 62546241 | 62566219 | chr8 | − | exonic | hsa_circ_0009158 | −1.6726 | 0.014595 | ASPH |
| 44053621 | 44055404 | chr15 | + | exonic | hsa_circ_0003598 | −2.0100 | 0.014627 | PDIA3 |
| 21327227 | 21328447 | chr16 | + | sense overlapping | N/A | −1.5909 | 0.014681 | CRYM-AS1 |
| 132551514 | 132551875 | chr12 | + | intronic | N/A | 1.6609 | 0.014740 | EP400 |
| 47531309 | 47549512 | chr16 | + | exonic | hsa_circ_0000698 | −1.8795 | 0.014769 | PHKB |
| 23356961 | 23377013 | chr1 | + | exonic | hsa_circ_0009061 | −2.4057 | 0.014800 | KDM1A |
| 96233422 | 96259881 | chr9 | + | exonic | hsa_circ_0005218 | −3.0499 | 0.014800 | FAM1204 |
| 18917290 | 18923977 | chrX | − | exonic | hsa_circ_0089986 | 1.6443 | 0.014888 | PHKA2 |
| 47474879 | 47481653 | chr7 | − | exonic | hsa_circ_0008729 | 1.5692 | 0.014908 | TNS3 |
| 70510478 | 70521018 | chrX | + | exonic | hsa_circ_0090999 | −1.5930 | 0.015002 | NONO |
| 90192545 | 90193035 | chr15 | + | antisense | hsa_circ_0000649 | 1.5889 | 0.015009 | KIF7 |
| 64271341 | 64295792 | chrX | + | sense overlapping | hsa_circ_0001924 | −2.5253 | 0.015020 | XLOC_007999 |
| 121659715 | 121659969 | chr12 | + | exonic | hsa_circ_0028944 | 1.5168 | 0.015090 | P2RX4 |
| 24982756 | 25002883 | chr12 | − | exonic | hsa_circ_0007579 | 1.5660 | 0.015127 | BCAT1 |
| 45010607 | 45011361 | chr7 | + | antisense | hsa_circ_0001702 | 1.7773 | 0.015128 | MYO1G |
| 37543379 | 37544322 | chr2 | − | exonic | hsa_circ_0000992 | −2.2131 | 0.015144 | PRKD3 |
| 8555122 | 8684439 | chr1 | − | exonic | hsa_circ_0009582 | −1.5451 | 0.015210 | RERE |
| 111923074 | 111924628 | chr12 | − | exonic | hsa_circ_0002273 | −1.7672 | 0.015224 | ATXN2 |
| 140622800 | 140638542 | chr9 | + | exonic | hsa_circ_0004101 | −1.5306 | 0.015326 | EHMT1 |
| 52183609 | 52199707 | chr20 | − | exonic | hsa_circ_0060915 | 1.5817 | 0.015363 | ZNF217 |
| 243858892 | 244006584 | chr1 | − | exonic | hsa_circ_0004649 | −3.0393 | 0.015397 | AKT3 |
| 27143382 | 27152609 | chr12 | − | exonic | hsa_circ_0007478 | 1.5586 | 0.015526 | TM7SF3 |
| 2807472 | 2810500 | chr16 | + | exonic | hsa_circ_0037563 | −1.9677 | 0.015562 | SRRM2 |
| 68155889 | 68157024 | chr16 | + | exonic | hsa_circ_0005615 | −2.4920 | 0.015590 | NFATC3 |
| 92301363 | 92330608 | chr8 | + | exonic | N/A | 1.6696 | 0.015700 | SLC26A7 |
| 61389976 | 61391675 | chr2 | + | sense overlapping | hsa_circ_0005338 | −1.7672 | 0.015773 | C2orf74 |

TABLE 2-continued (SSRI R 8 week vs SSRI NR 8 week)

| TxStart | TxEnd | Chrom | Strand | circRNA type | Alias | Fold change | P-value | GeneSymbol |
|---|---|---|---|---|---|---|---|---|
| 35406809 | 35425759 | chr8 | + | exonic | hsa_circ_0083913 | 1.6167 | 0.015785 | UNC5D |
| 113734352 | 113773970 | chr9 | − | exonic | hsa_circ_0087961 | 1.5581 | 0.015859 | LPAR1 |
| 138784244 | 138842320 | chr5 | − | exonic | hsa_circ_0074216 | 1.8674 | 0.015888 | ECSCR |
| 73215386 | 73228707 | chr2 | − | exonic | hsa_circ_0004699 | 1.5767 | 0.015889 | SFXN5 |
| 99990262 | 100016690 | chr6 | − | exonic | hsa_circ_0077434 | 1.7862 | 0.015914 | CCNC |
| 71867510 | 71884913 | chr14 | + | exonic | hsa_circ_0002722 | 1.5120 | 0.015932 | SIPA1L1 |
| 43197691 | 43198739 | chr17 | − | exonic | hsa_circ_0044158 | 1.5781 | 0.015934 | PLCD3 |
| 41036244 | 41037457 | chr15 | − | exonic | hsa_circ_0004942 | −2.5751 | 0.015959 | RMDN3 |
| 60206913 | 60217693 | chr18 | + | exonic | hsa_circ_0000854 | −1.6160 | 0.016059 | ZCCHC2 |
| 96233422 | 96278551 | chr9 | + | exonic | hsa_circ_0087531 | −2.3310 | 0.016073 | FAM120A |
| 141828375 | 141900868 | chr8 | − | exonic | hsa_circ_0005982 | −2.0899 | 0.016074 | PTK2 |
| 100953713 | 100962162 | chr13 | + | exonic | hsa_circ_0002664 | −1.6026 | 0.016156 | PCCA |
| 52192351 | 52194233 | chr15 | + | exonic | hsa_circ_0004773 | −1.5826 | 0.016223 | TMOD3 |
| 94767247 | 94828743 | chr8 | + | sense overlapping | N/A | 1.6906 | 0.016225 | TMEM67 |
| 47297355 | 47308133 | chr13 | + | exonic | hsa_circ_0002215 | −1.8431 | 0.016230 | LRCH1 |
| 15374347 | 15468949 | chr6 | + | exonic | N/A | −1.7831 | 0.016275 | JARID2 |
| 26518046 | 26519239 | chr17 | + | exonic | N/A | 1.5605 | 0.016402 | NLK |
| 104702610 | 104722244 | chr7 | + | exonic | N/A | −1.9766 | 0.016410 | KMT2E |
| 117944807 | 118009049 | chr1 | + | exonic | hsa_circ_0000120 | −2.9604 | 0.016502 | MAN1A2 |
| 61871449 | 61871624 | chr11 | − | intergenic | N/A | 1.6128 | 0.016524 | |
| 85810160 | 85814886 | chr16 | − | sense overlapping | N/A | 1.6086 | 0.016536 | EMC8 |
| 110321942 | 110350696 | chr2 | − | exonic | hsa_circ_0002076 | 1.5007 | 0.016606 | SEPT10 |
| 24698162 | 24709434 | chr22 | + | exonic | hsa_circ_0007312 | −1.7150 | 0.016625 | SPECC1L |
| 36230203 | 36231267 | chr4 | − | exonic | hsa_circ_0069399 | −3.0122 | 0.016627 | ARAP2 |
| 32050751 | 32053287 | chr1 | + | exonic | hsa_circ_0011299 | 1.5630 | 0.016646 | TINAGL1 |
| 61013821 | 61041513 | chr13 | + | exonic | hsa_circ_0003441 | −2.3062 | 0.016713 | TORD3 |
| 79941429 | 79943483 | chr17 | + | exonic | hsa_circ_0046292 | 1.6277 | 0.016735 | ASPSCR1 |
| 74493579 | 74497377 | chr16 | − | exonic | hsa_circ_0003315 | −2.8588 | 0.016748 | GLG1 |
| 32745359 | 32750312 | chr3 | + | exonic | hsa_circ_0064690 | −1.6801 | 0.016805 | CNOT10 |
| 56277780 | 56284152 | chr4 | + | exonic | hsa_circ_0001414 | −2.9546 | 0.016859 | TMEM165 |
| 43122140 | 43162033 | chr5 | + | exonic | hsa_circ_0001479 | −1.6326 | 0.016898 | ZNF131 |
| 76799640 | 76799724 | chr18 | + | intergenic | hsa_circ_0000858 | 1.6884 | 0.016900 | |
| 45891031 | 45923523 | chr20 | − | exonic | hsa_circ_0001164 | −1.6751 | 0.016977 | ZMYND8 |
| 138824814 | 138847261 | chr9 | − | exonic | hsa_circ_0089506 | 1.5005 | 0.016978 | UBAC1 |
| 65924470 | 65928135 | chr17 | + | exonic | hsa_circ_0045462 | −1.9865 | 0.016988 | BPTE |
| 76642965 | 76662315 | chr14 | + | exonic | hsa_circ_0032746 | −1.8914 | 0.017017 | GPATCH2L |
| 3197902 | 3215945 | chr3 | − | exonic | hsa_circ_0003400 | −1.7297 | 0.017025 | CRBN |
| 155340294 | 155340774 | chr1 | − | exonic | hsa_circ_0007608 | −1.5229 | 0.017070 | ASH1L |
| 7187666 | 7189555 | chr6 | + | exonic | hsa_circ_0075561 | −1.5516 | 0.017151 | RREB1 |
| 64096074 | 64100213 | chr5 | + | exonic | N/A | −1.8185 | 0.017151 | CWC27 |
| 23791389 | 23792692 | chr14 | + | exonic | hsa_circ_0031286 | −2.1584 | 0.017159 | PABPN1 |
| 29210921 | 29238052 | chr18 | − | exonic | hsa_circ_0047347 | −2.1525 | 0.017204 | B4GALT6 |
| 64410315 | 64411053 | chr15 | + | exonic | hsa_circ_0000614 | −2.0305 | 0.017210 | SNX1 |
| 117654716 | 117658311 | chr1 | − | sense overlapping | N/A | 1.6537 | 0.017271 | TRIM45 |
| 235272657 | 235283214 | chr1 | − | exonic | hsa_circ_0017037 | −1.5030 | 0.017297 | TOMM20 |
| 84662298 | 84663507 | chr1 | + | exonic | N/A | −1.8863 | 0.017343 | PRKACB |
| 231307651 | 231314970 | chr2 | + | exonic | hsa_circ_0003922 | −2.0681 | 0.017371 | SP100 |
| 155611306 | 155629068 | chr3 | + | exonic | N/A | −1.6888 | 0.017436 | GMPS |
| 14705328 | 14706127 | chr19 | + | exonic | hsa_circ_0049784 | 1.6248 | 0.017574 | CLEC17A |
| 87920168 | 87928449 | chr6 | + | intronic | hsa_circ_0004383 | −1.6185 | 0.017575 | ZNF292 |
| 26974589 | 26975761 | chr13 | + | exonic | hsa_circ_0003489 | −1.7511 | 0.017589 | CDK8 |
| 16198836 | 16199930 | chr19 | + | exonic | hsa_circ_0005855 | −2.0124 | 0.017604 | TPM4 |
| 35586872 | 35604935 | chr6 | − | exonic | hsa_circ_0076155 | −2.2275 | 0.017657 | FKBPS |
| 15341020 | 15343599 | chr17 | − | sense overlapping | N/A | 1.6022 | 0.017731 | TVP23C-CDRT4 |
| 44046021 | 44048964 | chr15 | + | exonic | hsa_circ_0002151 | −2.1568 | 0.017827 | PDIA3 |
| 9204473 | 9221997 | chr18 | + | exonic | hsa_circ_0003865 | −2.3497 | 0.017827 | ANKRD12 |
| 13435076 | 13443385 | chr11 | − | exonic | hsa_circ_0008967 | −1.8049 | 0.017847 | BTBD10 |
| 179146668 | 179146782 | chr5 | + | exonic | hsa_circ_0075303 | −1.5082 | 0.017957 | CANX |
| 30332294 | 30336893 | chr8 | + | exonic | hsa_circ_0007409 | 1.7014 | 0.018002 | RBPMS |
| 75167801 | 75173934 | chr11 | − | exonic | hsa_circ_0023624 | 1.7157 | 0.018081 | GDPD5 |
| 144966169 | 144969146 | chr2 | − | exonic | hsa_circ_0001072 | −2.6617 | 0.018131 | GTDC1 |
| 78915434 | 78919312 | chr5 | + | exonic | hsa_circ_0001504 | −1.6563 | 0.018147 | PAPD4 |
| 13632601 | 13659064 | chr6 | − | exonic | hsa_circ_0075650 | −2.6297 | 0.018343 | RANBP9 |
| 54292038 | 54294350 | chr4 | + | exonic | hsa_circ_0069748 | −2.1296 | 0.018343 | FIP1L1 |
| 21288066 | 21288532 | chr22 | + | exonic | hsa_circ_0001206 | −1.7298 | 0.018364 | CRKL |
| 42748962 | 42781337 | chr12 | + | exonic | N/A | −1.7713 | 0.018431 | PPHLN1 |
| 213290658 | 213303232 | chr1 | + | exonic | hsa_circ_0005522 | −1.5908 | 0.018455 | RPS6KC1 |
| 4186092 | 4200109 | chr17 | − | exonic | hsa_circ_0003239 | −1.9799 | 0.018456 | UBE2G1 |
| 79083481 | 79090455 | chr15 | − | exonic | N/A | 1.5440 | 0.018478 | ADAMTS7 |
| 70493472 | 70500177 | chr5 | − | exonic | hsa_circ_0072876 | −2.0329 | 0.018530 | GUSBP9 |
| 242265407 | 242275513 | chr2 | + | exonic | hsa_circ_0005154 | −1.5271 | 0.018580 | SEPT2 |

TABLE 2-continued (SSRI R 8 week vs SSRI NR 8 week)

| TxStart | TxEnd | Chrom | Strand | circRNA type | Alias | Fold change | P-value | GeneSymbol |
|---|---|---|---|---|---|---|---|---|
| 16192722 | 16192856 | chr19 | + | exonic | hsa_circ_0002259 | −2.2417 | 0.018618 | TPM4 |
| 80721840 | 80758872 | chr17 | + | exonic | hsa_circ_0046464 | −1.6046 | 0.018640 | TBCD |
| 64410315 | 64415745 | chr15 | + | exonic | hsa_circ_0035818 | −1.9892 | 0.018714 | SNX1 |
| 28758369 | 28763949 | chr7 | + | exonic | hsa_circ_0079675 | 1.8062 | 0.018791 | CREB5 |
| 149613259 | 149639014 | chr3 | + | exonic | hsa_circ_0006801 | −2.8526 | 0.018807 | RNF13 |
| 156848913 | 156849949 | chr1 | + | exonic | hsa_circ_0014798 | 1.5613 | 0.018822 | NTRK1 |
| 79937059 | 79943483 | chr17 | + | exonic | hsa_circ_0046290 | 1.6111 | 0.018849 | ASPSCR1 |
| 8553307 | 8565297 | chrX | − | exonic | N/A | 1.5627 | 0.018866 | KAL1 |
| 196876613 | 196888609 | chr3 | − | exonic | hsa_circ_0068702 | −1.7805 | 0.018895 | DLG1 |
| 230705537 | 230725247 | chr2 | − | exonic | hsa_circ_0004079 | −2.0372 | 0.018930 | TRIP12 |
| 14705443 | 14706127 | chr19 | + | exonic | hsa_circ_0049785 | 1.5780 | 0.018963 | CLEC17A |
| 149563797 | 149619949 | chr3 | + | exonic | hsa_circ_0004565 | −1.6630 | 0.018966 | RNF13 |
| 43292575 | 43297268 | chr5 | − | exonic | hsa_circ_0008621 | −1.6093 | 0.018993 | HMGCS1 |
| 118750908 | 118754014 | chrX | − | exonic | hsa_circ_0091412 | 1.7156 | 0.018999 | SEPT6 |
| 58898635 | 58906171 | chr19 | + | exonic | hsa_circ_0052341 | 1.7055 | 0.019008 | RPS5 |
| 56915571 | 56920595 | chr6 | + | sense overlapping | N/A | −1.6140 | 0.019008 | KIAA1586 |
| 194947437 | 194947585 | chr3 | − | exonic | hsa_circ_0068563 | 1.6914 | 0.019062 | XXYLT1 |
| 44048846 | 44055404 | chr15 | + | exonic | hsa_circ_0002891 | −2.0950 | 0.019089 | PDIA3 |
| 83667030 | 83754378 | chr6 | − | exonic | hsa_circ_0008236 | 1.6479 | 0.019149 | UBE3D |
| 38801306 | 38803739 | chr8 | + | exonic | hsa_circ_0084021 | 2.9589 | 0.019169 | PLEKHA2 |
| 45911303 | 45914319 | chr13 | − | exonic | hsa_circ_0030162 | −2.3649 | 0.019198 | TPT1 |
| 54398613 | 54426184 | chr18 | + | exonic | hsa_circ_0047744 | −1.9733 | 0.019202 | WDR7 |
| 41664100 | 41677086 | chr22 | − | exonic | hsa_circ_0063534 | 1.5414 | 0.019238 | RANGAP1 |
| 47777523 | 47787483 | chr3 | − | exonic | hsa_circ_0065307 | −1.5609 | 0.019254 | SMARCC1 |
| 15374347 | 15410596 | chr6 | + | exonic | hsa_circ_0075671 | −2.0447 | 0.019330 | JARID2 |
| 59179173 | 59179739 | chr15 | − | exonic | hsa_circ_0000604 | −2.2731 | 0.019387 | SLTM |
| 54249939 | 54256040 | chr4 | + | exonic | hsa_circ_0001411 | 2.1023 | 0.019474 | FIPIL1 |
| 191765289 | 191789319 | chr2 | + | exonic | hsa_circ_0001085 | −2.6404 | 0.019491 | GLS |
| 68215377 | 68217269 | chr16 | + | exonic | hsa_circ_0039934 | −1.8921 | 0.019523 | NFATC3 |
| 87925620 | 87928449 | chr6 | + | exonic | hsa_circ_0004058 | −2.0346 | 0.019534 | ZNF292 |
| 10931920 | 10933328 | chr2 | − | exonic | hsa_circ_0007250 | −1.6338 | 0.019549 | PDIA6 |
| 68881420 | 68888157 | chr5 | + | sense overlapping | hsa_circ_0005880 | −1.5666 | 0.019612 | GTF2H2C_2 |
| 109046047 | 109096774 | chr12 | − | exonic | hsa_circ_0028067 | −2.5460 | 0.019634 | CORO1C |
| 107429298 | 107435696 | chr3 | + | exonic | hsa_circ_0001324 | 2.3028 | 0.019652 | BBX |
| 117273764 | 117274087 | chr12 | + | exonic | hsa_circ_0028602 | 1.6425 | 0.019669 | RNFT2 |
| 1003727 | 1006847 | chr12 | + | exonic | hsa_circ_0003251 | −1.6163 | 0.019755 | WNK1 |
| 1004361 | 1004666 | chr16 | − | intronic | N/A | 1.6627 | 0.019798 | LMF1 |
| 56262089 | 56278006 | chr4 | + | sense overlapping | hsa_circ_0069774 | −1.5915 | 0.019798 | TMEM165 |
| 94008811 | 94009042 | chr14 | + | exonic | hsa_circ_0033049 | 1.6240 | 0.019846 | UNC79 |
| 67484716 | 67505429 | chr8 | − | exonic | hsa_circ_0084642 | −2.0976 | 0.020034 | MYBL1 |
| 108697604 | 108724650 | chr1 | − | exonic | N/A | 1.5365 | 0.020038 | SLC25A24 |
| 84225134 | 84235472 | chr9 | − | exonic | hsa_circ_0087319 | 1.5464 | 0.020076 | TLE1 |
| 80721840 | 80861354 | chr17 | + | exonic | hsa_circ_0046468 | −1.6306 | 0.020093 | TBCD |
| 33260901 | 33265112 | chr22 | − | exonic | hsa_circ_0062996 | 1.8503 | 0.020129 | SYN3 |
| 70096955 | 70101437 | chr10 | + | exonic | hsa_circ_0018499 | −1.5359 | 0.020187 | HNRNPH3 |
| 237374147 | 237374353 | chr2 | − | exonic | N/A | 1.6015 | 0.020236 | IQCA1 |
| 35604790 | 35614627 | chr6 | − | intronic | N/A | −2.4942 | 0.020285 | FKBPS |
| 39623696 | 39629569 | chr18 | + | exonic | hsa_circ_0006527 | −1.8777 | 0.020346 | PIK3C3 |
| 35707043 | 35712888 | chr7 | − | exonic | hsa_circ_0001696 | −1.9640 | 0.020360 | HERPUD2 |
| 179007947 | 179020646 | chr5 | + | exonic | N/A | −2.3169 | 0.020381 | RUFY1 |
| 133907680 | 133914026 | chr3 | − | exonic | hsa_circ_0005768 | −1.8981 | 0.020431 | RYK |
| 24002051 | 24026054 | chr22 | − | exonic | hsa_circ_0062545 | −2.0110 | 0.020461 | GUSBP11 |
| 74738317 | 74742410 | chr15 | − | exonic | hsa_circ_0036272 | 1.5185 | 0.020505 | UBL7 |
| 123661905 | 123683844 | chr10 | − | exonic | hsa_circ_0002850 | −1.5986 | 0.020556 | ATE1 |
| 5711031 | 5717503 | chr11 | − | intronic | hsa_circ_0000276 | 1.7139 | 0.020583 | TRIM5 |
| 186504915 | 186505671 | chr3 | + | exonic | hsa_circ_0068465 | −2.0876 | 0.020584 | EIF4A2 |
| 113734352 | 113798481 | chr9 | − | intronic | hsa_circ_0004135 | 1.7647 | 0.020591 | LPAR1 |
| 109046047 | 109048186 | chr12 | − | exonic | hsa_circ_0000437 | −3.3890 | 0.020628 | CORO1C |
| 61838273 | 61842207 | chr17 | − | exonic | hsa_circ_0045219 | −1.9761 | 0.020683 | CCDC47 |
| 46116798 | 46117958 | chr19 | − | exonic | hsa_circ_0008263 | 1.6978 | 0.020721 | EML2 |
| 219366471 | 219414650 | chr1 | + | sense overlapping | hsa_circ_0006963 | −1.5615 | 0.020740 | LYPLAL1 |
| 91855033 | 91855996 | chr7 | − | exonic | N/A | −1.5691 | 0.020794 | KRIT1 |
| 70299035 | 70299440 | chr16 | − | intronic | N/A | 1.6886 | 0.020804 | AARS |
| 9020437 | 9021799 | chr12 | + | exonic | hsa_circ_0025388 | 1.5934 | 0.020815 | A2ML1 |
| 139316347 | 139416814 | chr7 | − | exonic | hsa_circ_0082680 | −1.5891 | 0.020903 | HIPK2 |
| 33714053 | 33719586 | chr20 | − | exonic | N/A | 1.5224 | 0.020934 | EDEM2 |
| 19473732 | 19474599 | chr11 | + | intronic | N/A | 1.5578 | 0.020957 | NAV2 |
| 39595439 | 39609405 | chr18 | + | exonic | hsa_circ_0002560 | −2.3673 | 0.020986 | PIK3C3 |
| 80772106 | 80783018 | chr2 | + | exonic | hsa_circ_0055377 | 1.5650 | 0.020996 | CTNNA2 |
| 77611362 | 77632364 | chr9 | − | exonic | hsa_circ_0087220 | −2.6959 | 0.021027 | C9orf41 |
| 130871231 | 130962340 | chr3 | + | exonic | hsa_circ_0067345 | 1.5496 | 0.021114 | NEK11 |

TABLE 2-continued (SSRI R 8 week vs SSRI NR 8 week)

| TxStart | TxEnd | Chrom | Strand | circRNA type | Alias | Fold change | P-value | GeneSymbol |
|---|---|---|---|---|---|---|---|---|
| 103261046 | 103323802 | chr9 | + | exonic | N/A | −1.5898 | 0.021130 | TMEFF1 |
| 169018296 | 169038600 | chr2 | − | exonic | hsa_circ_0001079 | −2.1784 | 0.021157 | STK39 |
| 47098310 | 47103836 | chr3 | − | exonic | hsa_circ_0065149 | −2.0391 | 0.021185 | SETD2 |
| 53288349 | 53308214 | chr16 | + | exonic | hsa_circ_0000702 | −1.6392 | 0.021200 | CHD9 |
| 201721404 | 201722812 | chr2 | − | exonic | hsa_circ_0057725 | −1.7193 | 0.021365 | CLK1 |
| 45011271 | 45016256 | chr7 | − | exonic | hsa_circ_0080099 | −2.1125 | 0.021453 | MYO1G |
| 35586872 | 35610620 | chr6 | − | exonic | hsa_circ_0001599 | −2.5320 | 0.021492 | FKBP5 |
| 45766370 | 45769539 | chr19 | + | exonic | hsa_circ_0051449 | −1.7197 | 0.021617 | MARK4 |
| 18393289 | 18396093 | chr20 | − | exonic | N/A | 1.6402 | 0.021664 | DZANK1 |
| 132990021 | 133002144 | chr7 | + | sense overlapping | hsa_circ_0001749 | 1.8397 | 0.021680 | EXOC4 |
| 220179447 | 220180680 | chr1 | − | exonic | hsa_circ_0007739 | −1.5811 | 0.021685 | EPRS |
| 73897062 | 73898235 | chr17 | − | exonic | hsa_circ_0045737 | 1.5741 | 0.021700 | MRPL38 |
| 230424926 | 230425086 | chr1 | + | intergenic | hsa_circ_0000193 | 1.5880 | 0.021707 | |
| 149563797 | 149589941 | chr3 | + | exonic | hsa_circ_0067716 | −1.6173 | 0.021737 | RNF13 |
| 13632601 | 13644961 | chr6 | − | exonic | hsa_circ_0001577 | −2.8016 | 0.021772 | RANBP9 |
| 190656515 | 190682906 | chr2 | + | exonic | hsa_circ_0001083 | −1.5113 | 0.021896 | PMS1 |
| 2402279 | 2402762 | chr7 | + | exonic | hsa_circ_0079163 | −1.6198 | 0.021906 | EIF3B |
| 66426136 | 66430767 | chr17 | − | exonic | hsa_circ_0045502 | 1.5510 | 0.021920 | WIPI1 |
| 111819470 | 111826847 | chr9 | − | exonic | hsa_circ_0004109 | −1.8692 | 0.021948 | TMEM245 |
| 47098310 | 47108608 | chr3 | − | exonic | hsa_circ_0002569 | −2.0734 | 0.022019 | SETD2 |
| 45079431 | 45115960 | chr21 | + | exonic | hsa_circ_0061880 | 1.9202 | 0.022065 | RRP1B |
| 197592293 | 197598333 | chr3 | + | exonic | hsa_circ_0008106 | −1.8032 | 0.022086 | LRCH3 |
| 95620775 | 95621425 | chr11 | − | exonic | hsa_circ_0024081 | 1.6566 | 0.022132 | MTMR2 |
| 73100965 | 73101425 | chr7 | + | exonic | hsa_circ_0005588 | −1.9590 | 0.022136 | WBSCR22 |
| 149563797 | 149613347 | chr3 | + | exonic | hsa_circ_0067717 | −1.7931 | 0.022146 | RNF13 |
| 19626181 | 19653155 | chr12 | + | exonic | hsa_circ_0005257 | −1.7572 | 0.022165 | AEBP2 |
| 18768781 | 18769265 | chr17 | + | exonic | hsa_circ_0002278 | −1.8685 | 0.022169 | PRPSAP2 |
| 63269389 | 63286880 | chr1 | + | exonic | hsa_circ_0012823 | −1.6541 | 0.022204 | ATG4C |
| 13579682 | 13584457 | chr6 | + | exonic | hsa_circ_0007218 | −1.8234 | 0.022207 | SIRT5 |
| 47538590 | 47538885 | chr21 | + | intronic | N/A | 1.7103 | 0.022431 | COL6A2 |
| 43010539 | 43011368 | chr6 | − | exonic | N/A | 1.5086 | 0.022443 | CUL7 |
| 75830427 | 75832610 | chr10 | + | exonic | hsa_circ_0007797 | −1.5958 | 0.022469 | VCL |
| 4200011 | 4210418 | chr17 | − | exonic | N/A | −1.7344 | 0.022476 | UBE2G1 |
| 7049707 | 70497677 | chr16 | + | exonic | hsa_circ_0002599 | 1.5360 | 0.022477 | FUK |
| 89999875 | 90002505 | chr16 | + | exonic | hsa_circ_0041125 | 1.5798 | 0.022483 | TUBB3 |
| 179135239 | 179136060 | chr5 | + | exonic | hsa_circ_0005778 | −2.0669 | 0.022502 | CANX |
| 43690238 | 43694048 | chr15 | + | exonic | N/A | −1.5099 | 0.022544 | TUBGCP4 |
| 69120278 | 69121169 | chr12 | + | exonic | hsa_circ_0027485 | −1.7650 | 0.022559 | NUP107 |
| 15860731 | 15863309 | chr1 | + | exonic | hsa_circ_0000018 | −1.8121 | 0.022575 | DNAJC16 |
| 49528047 | 49531564 | chr15 | + | exonic | hsa_circ_0008488 | −1.7500 | 0.022599 | GALK2 |
| 46751970 | 46754992 | chr12 | − | exonic | hsa_circ_0025984 | 1.5738 | 0.022670 | SLC38A2 |
| 92224169 | 92224307 | chr1 | − | exonic | hsa_circ_0013141 | 1.5845 | 0.022855 | TGFBR3 |
| 61509864 | 61512143 | chr14 | + | exonic | N/A | 1.5610 | 0.022905 | SLC38A6 |
| 31266516 | 31269158 | chr15 | − | exonic | N/A | −1.5986 | 0.022949 | MTMR10 |
| 89979183 | 89979271 | chr16 | + | intronic | hsa_circ_0000728 | 1.5557 | 0.023005 | MC1R |
| 135025037 | 135042232 | chrX | − | sense overlapping | N/A | 1.8066 | 0.023016 | RP11-97N5.2 |
| 35890583 | 35893796 | chr21 | − | intronic | N/A | 1.6380 | 0.023079 | RCAN1 |
| 77006164 | 77033932 | chr7 | − | exonic | hsa_circ_0080831 | −1.7490 | 0.023108 | GSAP |
| 31488182 | 31489281 | chr16 | + | exonic | hsa_circ_0039172 | 1.8084 | 0.023176 | TGFB111 |
| 36865777 | 36868169 | chr17 | + | sense overlapping | hsa_circ_0000760 | −1.7599 | 0.023213 | MLLT6 |
| 113832487 | 113833403 | chr13 | − | exonic | N/A | 1.5427 | 0.023230 | PCID2 |
| 75892977 | 75893559 | chr15 | − | sense overlapping | N/A | 1.6221 | 0.023249 | SNUPN |
| 80758739 | 80861354 | chr17 | + | exonic | hsa_circ_0046507 | 1.5740 | 0.023286 | TBCD |
| 53289511 | 53302038 | chr16 | + | exonic | hsa_circ_0039365 | −2.1939 | 0.023291 | CHD9 |
| 152004981 | 152006276 | chr1 | − | exonic | hsa_circ_0014205 | 1.5844 | 0.023307 | S100A11 |
| 205585605 | 205593019 | chr1 | − | exonic | hsa_circ_0000175 | −2.9369 | 0.023342 | ELK4 |
| 2659529 | 2661781 | chr4 | + | exonic | hsa_circ_0068925 | −1.6363 | 0.023351 | FAM193A |
| 34450934 | 34459751 | chr20 | + | exonic | hsa_circ_0060158 | −1.9987 | 0.023437 | PHF20 |
| 20212215 | 20212724 | chr3 | − | exonic | N/A | 1.6458 | 0.023513 | SGOL1 |
| 47441689 | 47446190 | chrX | + | exonic | hsa_circ_0090446 | 1.8191 | 0.023586 | TIMP1 |
| 75933300 | 75933614 | chr7 | + | exonic | hsa_circ_0080788 | 1.5202 | 0.023593 | HSPB1 |
| 42579888 | 42589854 | chr15 | + | exonic | hsa_circ_0034804 | 1.5287 | 0.023647 | GANC |
| 155742856 | 155753880 | chr1 | − | exonic | hsa_circ_0014628 | −1.6456 | 0.023729 | GON4L |
| 107260799 | 107263621 | chr11 | − | exonic | N/A | −2.2833 | 0.023736 | CWF19L2 |
| 28458581 | 28544344 | chr12 | + | exonic | hsa_circ_0008250 | −2.1409 | 0.023750 | CCDC91 |
| 20315704 | 20333558 | chr13 | − | exonic | N/A | −1.5723 | 0.023826 | PSPC1 |
| 106739425 | 106774574 | chr2 | − | exonic | hsa_circ_0055943 | −2.2463 | 0.023879 | UXS |
| 105121498 | 105135700 | chr7 | − | exonic | hsa_circ_0081854 | −1.5696 | 0.023899 | PUS7 |
| 149563797 | 149639014 | chr3 | + | exonic | hsa_circ_0001346 | −1.6757 | 0.023938 | RNF13 |
| 960930 | 1004666 | chr16 | − | exonic | hsa_circ_0000664 | 1.5532 | 0.024045 | LMF1 |
| 72302181 | 72302378 | chr7 | + | exonic | hsa_circ_0008708 | −1.8333 | 0.024095 | SBDSP1 |

TABLE 2-continued (SSRI R 8 week vs SSRI NR 8 week)

| TxStart | TxEnd | Chrom | Strand | circRNA type | Alias | Fold change | P-value | GeneSymbol |
|---|---|---|---|---|---|---|---|---|
| 41994031 | 42017061 | chr22 | − | exonic | hsa_circ_0063583 | 1.6411 | 0.024141 | DESI1 |
| 46224309 | 46235694 | chr10 | + | exonic | hsa_circ_0006465 | −1.8303 | 0.024191 | FAM21C |
| 20910208 | 20914622 | chr17 | − | exonic | hsa_circ_0042458 | 1.6034 | 0.024218 | USP22 |
| 2985909 | 3000467 | chr11 | − | exonic | N/A | −1.6246 | 0.024220 | NAP1L4 |
| 1735857 | 1770677 | chr1 | − | exonic | hsa_circ_0005907 | −2.0217 | 0.024262 | GNB1 |
| 33073307 | 33078670 | chr21 | − | exonic | hsa_circ_0007207 | 1.6706 | 0.024288 | SCAF4 |
| 43528083 | 43544806 | chr13 | − | exonic | hsa_circ_0000479 | −2.2154 | 0.024303 | EPSTH |
| 16327848 | 16345099 | chr3 | + | exonic | hsa_circ_0001273 | −1.8969 | 0.024338 | OXNAD1 |
| 117957334 | 117963271 | chr1 | + | exonic | hsa_circ_0013737 | −3.8776 | 0.024350 | MAN1A2 |
| 31841015 | 31844174 | chr14 | − | exonic | hsa_circ_0031569 | 1.6170 | 0.024364 | HEATR5A |
| 242396161 | 242415402 | chr2 | + | exonic | N/A | 1.5727 | 0.024371 | FARP2 |
| 10286215 | 10288043 | chr19 | − | exonic | hsa_circ_0049224 | −2.2327 | 0.024384 | DNMT1 |
| 246754813 | 246755243 | chr1 | + | exonic | hsa_circ_0017310 | −1.8094 | 0.024403 | CNST |
| 115249247 | 115337531 | chr9 | + | exonic | hsa_circ_0088102 | 1.6098 | 0.024411 | KIAA1958 |
| 36415395 | 36424928 | chr11 | + | intronic | hsa_circ_0005044 | −2.7269 | 0.024446 | PRR5L |
| 151960100 | 152012423 | chr7 | − | exonic | hsa_circ_0006784 | −2.0893 | 0.024499 | KMT20 |
| 24680620 | 24681035 | chr14 | − | exonic | hsa_circ_0031359 | −2.1906 | 0.024543 | CHMP4A |
| 69039612 | 69104760 | chr8 | + | exonic | N/A | 1.7587 | 0.024647 | PREX2 |
| 168920009 | 168986268 | chr2 | − | exonic | hsa_circ_0005882 | −1.9069 | 0.024668 | STK39 |
| 77065301 | 77065626 | chr4 | − | exonic | hsa_circ_0070040 | −2.5347 | 0.024668 | NUP54 |
| 53672262 | 53681075 | chrX | − | exonic | hsa_circ_0001922 | −1.6132 | 0.024675 | HUWE1 |
| 36121010 | 36128402 | chr14 | − | exonic | hsa_circ_0004823 | −1.8069 | 0.024691 | RALGAPA1 |
| 71369656 | 71370884 | chr11 | + | intergenic | N/A | 1.5643 | 0.024757 | |
| 151181822 | 151188100 | chr7 | − | exonic | hsa_circ_0082951 | −1.9583 | 0.024759 | RHEB |
| 95494501 | 95507595 | chr4 | + | exonic | hsa_circ_0070467 | −2.1615 | 0.024777 | PDLIMS |
| 30412464 | 30435989 | chr8 | − | sense overlapping | N/A | 1.5260 | 0.024803 | GTF2E2 |
| 189455528 | 189456563 | chr3 | + | exonic | hsa_circ_0068514 | 1.6186 | 0.024868 | TP63 |
| 14821320 | 14821476 | chrY | + | exonic | hsa_circ_0092232 | 1.6892 | 0.024871 | USP9Y |
| 8352261 | 8352391 | chr20 | − | antisense | hsa_circ_0001132 | 1.5716 | 0.024925 | PLCB1 |
| 40988349 | 40990765 | chrX | − | antisense | hsa_circ_0001915 | 1.7825 | 0.024988 | USP9X |
| 123230137 | 123253755 | chr9 | − | exonic | hsa_circ_0088284 | −1.6206 | 0.025013 | CDK5RAP2 |
| 102521074 | 102527646 | chr13 | − | exonic | hsa_circ_0030793 | 1.6545 | 0.025061 | FGF14 |
| 103550652 | 103550795 | chr10 | − | intronic | hsa_circ_0000256 | −1.6628 | 0.025079 | MGEA5 |
| 6086622 | 6089676 | chr7 | − | exonic | hsa_circ_0079329 | −1.5969 | 0.025113 | EIF2AK1 |
| 165859440 | 165872516 | chr1 | + | exonic | hsa_circ_0015081 | 1.6154 | 0.025135 | UCK2 |
| 58118534 | 58149057 | chr3 | + | exonic | hsa_circ_0066361 | −1.6337 | 0.025196 | FLNB |
| 32502510 | 32504220 | chr1 | + | exonic | hsa_circ_0007231 | −1.6665 | 0.025204 | KHDRBS1 |
| 44436348 | 44445676 | chr2 | + | exonic | hsa_circ_0009062 | −1.7116 | 0.025228 | PPM1B |
| 131060182 | 131130662 | chr7 | + | exonic | hsa_circ_0003047 | −2.0466 | 0.025229 | MKLN1 |
| 133894452 | 133901915 | chr3 | − | exonic | hsa_circ_0067434 | −1.8479 | 0.025241 | RYK |
| 130505247 | 130505768 | chr6 | − | exonic | hsa_circ_0008833 | −1.6151 | 0.025262 | SAMD3 |
| 120346048 | 120348235 | chr11 | + | exonic | hsa_circ_0002955 | −1.9383 | 0.025364 | ARHGEF12 |
| 98985661 | 98987635 | chr7 | + | exonic | hsa_circ_0004299 | −1.6060 | 0.025370 | ARPC1B |
| 134062675 | 134064518 | chr9 | + | exonic | hsa_circ_0089175 | 1.5950 | 0.025409 | NUP214 |
| 97686267 | 97718297 | chr9 | + | exonic | N/A | 1.6458 | 0.025414 | C9orf3 |
| 8076452 | 8088849 | chr18 | + | exonic | hsa_circ_0006114 | 1.5779 | 0.025420 | PTPRM |
| 34093272 | 34093534 | chr11 | + | exonic | hsa_circ_0008227 | −2.1256 | 0.025421 | CAPRIN1 |
| 101450683 | 101451498 | chr3 | + | exonic | hsa_circ_0066701 | 1.6279 | 0.025429 | CEP97 |
| 71229099 | 71256271 | chr15 | + | exonic | hsa_circ_0036113 | 1.6485 | 0.025489 | LRRC49 |
| 77791974 | 77818086 | chr13 | − | exonic | hsa_circ_0004217 | −1.5951 | 0.025517 | MYCBP2 |
| 26490568 | 26499644 | chr17 | + | exonic | hsa_circ_0003638 | −1.5232 | 0.025552 | NLK |
| 10283765 | 10288043 | chr19 | − | exonic | hsa_circ_0000889 | −2.1779 | 0.025668 | DNMT1 |
| 80721840 | 80730383 | chr17 | + | exonic | hsa_circ_0005281 | −1.6350 | 0.025787 | TBCD |
| 34952950 | 35006275 | chr11 | + | exonic | hsa_circ_0021708 | −1.7319 | 0.025818 | PDHX |
| 50131343 | 50141145 | chr14 | − | exonic | hsa_circ_0031787 | −1.8661 | 0.025861 | POLE2 |
| 39001258 | 39019284 | chr22 | − | exonic | N/A | 1.6023 | 0.025866 | FAM227A |
| 62546241 | 62596747 | chr8 | − | exonic | hsa_circ_0008337 | −1.7586 | 0.025894 | ASPH |
| 39328182 | 39329376 | chr4 | − | exonic | hsa_circ_0001403 | −1.6639 | 0.025903 | RFC1 |
| 72182896 | 72184130 | chr5 | + | exonic | hsa_circ_0072932 | −1.6152 | 0.025932 | TNPO1 |
| 77299605 | 77299759 | chr5 | − | intronic | hsa_circ_0001500 | 1.8713 | 0.026041 | AP3B1 |
| 234296902 | 234299129 | chr2 | + | exonic | hsa_circ_0001112 | −2.2256 | 0.026056 | DGKD |
| 94532555 | 94533477 | chr11 | + | exonic | hsa_circ_0004214 | 1.7120 | 0.026079 | AMOTL1 |
| 145594038 | 145595220 | chr1 | − | exonic | hsa_circ_0003693 | −1.6818 | 0.026171 | POLR3C |
| 34302106 | 34313077 | chr20 | − | exonic | hsa_circ_0004870 | −2.1216 | 0.026176 | RBM39 |
| 19068923 | 19069099 | chrX | + | antisense | N/A | 1.5578 | 0.026211 | GPR64 |
| 54119944 | 54120936 | chr2 | − | exonic | hsa_circ_0054547 | −1.6134 | 0.026211 | PSME4 |
| 153581139 | 153581292 | chrX | − | exonic | hsa_circ_0091894 | −1.8918 | 0.026277 | FLNA |
| 116627861 | 116631668 | chr11 | − | exonic | N/A | 1.6017 | 0.026315 | BUD13 |
| 128973475 | 128975403 | chr10 | − | exonic | N/A | 1.6086 | 0.026420 | FAM196A |
| 101189031 | 101190071 | chr7 | + | intronic | hsa_circ_0092287 | 1.6050 | 0.026427 | COL26A1 |
| 39191239 | 39200116 | chr19 | + | exonic | hsa_circ_0050900 | −2.2542 | 0.026446 | ACTN4 |
| 37331786 | 37333735 | chr5 | − | exonic | hsa_circ_0072263 | 1.8231 | 0.026455 | NUP155 |
| 124090477 | 124090706 | chr12 | + | exonic | hsa_circ_0029235 | 1.7561 | 0.026457 | DDX55 |
| 54292038 | 54310270 | chr4 | + | exonic | hsa_circ_0001413 | −2.0783 | 0.026524 | FIP1L1 |

TABLE 2-continued (SSRI R 8 week vs SSRI NR 8 week)

| TxStart | TxEnd | Chrom | Strand | circRNA type | Alias | Fold change | P-value | GeneSymbol |
|---|---|---|---|---|---|---|---|---|
| 171974248 | 171974367 | chr2 | − | exonic | hsa_circ_0057037 | −1.7213 | 0.026593 | TLK1 |
| 144464665 | 144465125 | chr4 | + | sense overlapping | N/A | −2.7497 | 0.026625 | SMARCA5 |
| 80390757 | 80415142 | chr15 | + | exonic | hsa_circ_0000642 | −2.1236 | 0.026663 | ZFAND6 |
| 29784412 | 29819177 | chr22 | − | sense overlapping | hsa_circ_0001218 | −1.6660 | 0.026759 | AP1B1 |
| 21987790 | 21999817 | chr13 | − | exonic | hsa_circ_0006732 | −2.3143 | 0.026760 | ZDHHC20 |
| 129684543 | 129690951 | chr3 | − | sense overlapping | N/A | 1.8094 | 0.026787 | RP11-93K22.6 |
| 29218606 | 29246335 | chr18 | − | exonic | N/A | −2.0657 | 0.026789 | B4GALT6 |
| 52725371 | 52726564 | chr15 | − | sense overlapping | hsa_circ_0000602 | 1.5833 | 0.026883 | MYOSA |
| 49528047 | 49584734 | chr15 | + | exonic | hsa_circ_0035189 | −1.5021 | 0.026887 | GALK2 |
| 29313942 | 29323831 | chr1 | + | exonic | hsa_circ_0011168 | −1.7586 | 0.026943 | EPB41 |
| 66133406 | 66137003 | chr11 | − | exonic | hsa_circ_0022983 | 1.5661 | 0.026945 | SLC29A2 |
| 16192722 | 16197350 | chr19 | + | exonic | hsa_circ_0008432 | −2.1024 | 0.026992 | TPM4 |
| 157839891 | 157841780 | chr3 | + | exonic | hsa_circ_0001355 | −2.0725 | 0.026994 | RSRC1 |
| 135263546 | 135265104 | chr6 | − | exonic | N/A | 1.5398 | 0.027026 | ALDH8A1 |
| 45203311 | 45204674 | chr11 | + | exonic | N/A | 1.5328 | 0.027060 | PRDM11 |
| 61118817 | 61128218 | chr2 | + | exonic | hsa_circ_0001011 | −2.0734 | 0.027069 | REL |
| 153594675 | 153599729 | chrX | − | exonic | hsa_circ_0092022 | −1.8951 | 0.027072 | FLNA |
| 17137883 | 17143936 | chr8 | + | exonic | hsa_circ_0083423 | −1.8896 | 0.027089 | VPS37A |
| 152480271 | 152498816 | chr7 | + | exonic | hsa_circ_0006890 | −1.6938 | 0.027096 | ACTR3B |
| 243736227 | 244006584 | chr1 | − | exonic | hsa_circ_0017248 | −2.5105 | 0.027142 | AKT3 |
| 15939756 | 15946230 | chr19 | + | exonic | hsa_circ_0049851 | 1.7882 | 0.027175 | XLOC_012981 |
| 24021007 | 24046439 | chr2 | − | exonic | hsa_circ_0052941 | −1.7802 | 0.027185 | ATAD2B |
| 86293355 | 86301070 | chr9 | − | exonic | hsa_circ_0087357 | −2.9342 | 0.027186 | UBQLN1 |
| 33060883 | 33063720 | chr7 | − | exonic | hsa_circ_0079800 | −1.7690 | 0.027209 | NT5C3A |
| 75302560 | 75302889 | chr10 | − | exonic | hsa_circ_0018824 | 1.8801 | 0.027235 | USP54 |
| 1747194 | 1770677 | chr1 | − | exonic | hsa_circ_0008702 | −1.8961 | 0.027256 | GNB1 |
| 52311410 | 52358462 | chr15 | + | exonic | hsa_circ_0035301 | 1.5164 | 0.027258 | MAPK6 |
| 99860426 | 99864304 | chr6 | − | exonic | hsa_circ_0001630 | −1.7406 | 0.027277 | PNISR |
| 20632714 | 20641530 | chr13 | + | exonic | hsa_circ_0029636 | −1.7632 | 0.027313 | ZMYM2 |
| 40293372 | 40301685 | chr13 | + | exonic | hsa_circ_0006900 | 1.6920 | 0.027394 | COG6 |
| 95091099 | 95099324 | chr5 | + | exonic | hsa_circ_0007444 | −2.3130 | 0.027495 | RHOBTB3 |
| 41515056 | 41515506 | chr13 | − | exonic | hsa_circ_0030050 | −2.0300 | 0.027523 | ELF1 |
| 186988982 | 187003844 | chr3 | − | intronic | hsa_circ_0009169 | 1.6226 | 0.027597 | MASP1 |
| 121220457 | 121221555 | chr12 | − | exonic | hsa_circ_0028935 | 1.6793 | 0.027603 | SPPL3 |
| 38089338 | 38089486 | chr22 | + | sense overlapping | hsa_circ_0001229 | 1.8923 | 0.027667 | NOL12 |
| 227729319 | 227729842 | chr2 | + | exonic | hsa_circ_0001104 | −2.7117 | 0.027688 | RHBDD1 |
| 243776972 | 244006584 | chr1 | − | exonic | hsa_circ_0017252 | −2.5425 | 0.027699 | AKT3 |
| 13639794 | 13644961 | chr6 | − | exonic | hsa_circ_0001578 | −3.1932 | 0.027743 | RANBP9 |
| 51797729 | 51800460 | chr18 | + | exonic | hsa_circ_0007180 | −1.5779 | 0.027759 | POLI |
| 61013821 | 61068709 | chr13 | + | exonic | N/A | −1.5920 | 0.027761 | TDRD3 |
| 216227368 | 216238260 | chr2 | + | antisense | N/A | 1.6042 | 0.027762 | FN1 |
| 44442444 | 44443967 | chr1 | + | exonic | hsa_circ_0012125 | 1.5822 | 0.027798 | ATP6VOB |
| 34300940 | 34313077 | chr20 | − | exonic | hsa_circ_0008143 | −1.6855 | 0.027831 | RBM39 |
| 46622935 | 46624417 | chr12 | − | sense overlapping | hsa_circ_0000395 | 2.0991 | 0.027907 | SLC38A1 |
| 52840434 | 52845910 | chr12 | − | exonic | hsa_circ_0026399 | 1.6687 | 0.027967 | KRT68 |
| 69206201 | 69216694 | chr5 | + | exonic | hsa_circ_0004837 | −2.0201 | 0.027987 | SMA4 |
| 89961445 | 89977071 | chr16 | + | exonic | hsa_circ_0041100 | 1.7827 | 0.027992 | TCF25 |
| 27269150 | 27269556 | chr1 | + | exonic | hsa_circ_0005087 | −2.1276 | 0.027998 | NUDC |
| 159001971 | 159010814 | chr6 | + | exonic | hsa_circ_0001661 | −1.7863 | 0.028014 | TMEM181 |
| 102038066 | 102045130 | chr7 | + | exonic | hsa_circ_0001735 | −1.6782 | 0.028015 | PRKRIPT |
| 68794472 | 68805135 | chr2 | + | exonic | N/A | −1.6309 | 0.028016 | APLF |
| 158994451 | 159010814 | chr6 | + | exonic | hsa_circ_0004587 | −1.9445 | 0.028149 | TMEM181 |
| 29313942 | 29314417 | chr1 | + | exonic | hsa_circ_0011167 | −1.7850 | 0.028162 | EPB41 |
| 88883054 | 88904247 | chr14 | + | exonic | N/A | −1.8062 | 0.028202 | SPATA7 |
| 1724683 | 1749314 | chr1 | − | exonic | hsa_circ_0009349 | −1.7124 | 0.028239 | GNB1 |
| 21076215 | 21100103 | chr1 | − | exonic | hsa_circ_0000023 | −1.7343 | 0.028243 | HP1BP3 |
| 239090705 | 239093928 | chr2 | − | exonic | hsa_circ_0001116 | −2.1052 | 0.028301 | ILKAP |
| 87017739 | 87018273 | chr3 | − | exonic | hsa_circ_0003806 | 1.5998 | 0.028308 | VGLL3 |
| 73122918 | 73123452 | chr7 | − | exonic | hsa_circ_0008121 | 1.6375 | 0.028438 | STX1A |
| 34922765 | 34936026 | chr19 | + | exonic | hsa_circ_0050516 | −1.5934 | 0.028448 | UBA2 |
| 119219541 | 119232566 | chr3 | + | exonic | hsa_circ_0006884 | −2.1831 | 0.028487 | TIMMDC1 |
| 28800065 | 28802803 | chr1 | + | exonic | hsa_circ_0000038 | −1.8252 | 0.028500 | PHACTR4 |
| 44986659 | 45000952 | chr3 | − | exonic | hsa_circ_0065052 | 1.5848 | 0.028567 | ZDHHC3 |
| 97178494 | 97222866 | chr12 | + | exonic | N/A | 1.7844 | 0.028595 | C12orf55 |
| 102027080 | 102038934 | chr2 | − | exonic | hsa_circ_0004121 | 1.7519 | 0.028668 | RFX8 |
| 66021409 | 66048810 | chr15 | − | exonic | hsa_circ_0035946 | −1.9521 | 0.028790 | DENND4A |
| 24679553 | 24681035 | chr14 | − | exonic | hsa_circ_0031357 | −2.2453 | 0.028794 | CHMP4A |
| 130475969 | 130497153 | chr6 | − | exonic | N/A | −1.7336 | 0.028794 | SAMD3 |
| 32602655 | 32620661 | chr2 | + | exonic | hsa_circ_0053441 | −1.7140 | 0.028859 | BIRC6 |

TABLE 2-continued (SSRI R 8 week vs SSRI NR 8 week)

| TxStart | TxEnd | Chrom | Strand | circRNA type | Alias | Fold change | P-value | GeneSymbol |
|---|---|---|---|---|---|---|---|---|
| 101372434 | 101373305 | chr14 | + | exonic | hsa_circ_0033198 | 1.7579 | 0.028879 | MEG8 |
| 62531536 | 62566219 | chr8 | − | exonic | hsa_circ_0084606 | −2.0066 | 0.028946 | ASPH |
| 72958135 | 72960247 | chr2 | − | exonic | hsa_circ_0001030 | −2.1241 | 0.028953 | EXOC6B |
| 47410171 | 47424963 | chr21 | + | exonic | hsa_circ_0062035 | 1.6641 | 0.029025 | COL6A1 |
| 112116954 | 112121111 | chr12 | − | exonic | hsa_circ_0006396 | −1.6010 | 0.029074 | BRAP |
| 85692787 | 85693046 | chr11 | − | exonic | hsa_circ_0023904 | −2.7278 | 0.029146 | PICALM |
| 138203933 | 138255748 | chr7 | + | exonic | hsa_circ_0082582 | 1.9316 | 0.029206 | TRIM24 |
| 71640490 | 71704162 | chr15 | + | sense overlapping | N/A | 1.5420 | 0.029212 | THSD4 |
| 155823066 | 155823597 | chr1 | − | exonic | hsa_circ_0000139 | −2.1594 | 0.029283 | GON4L |
| 126384726 | 126395456 | chr10 | − | exonic | hsa_circ_0008456 | −1.5278 | 0.029287 | FAM53B |
| 41736871 | 41737203 | chr19 | + | exonic | hsa_circ_0002945 | 1.6207 | 0.029318 | AXL |
| 3778830 | 3781615 | chrX | − | exonic | hsa_circ_0089837 | −1.7945 | 0.029410 | AK000470 |
| 30734587 | 30746317 | chr20 | + | exonic | hsa_circ_0059760 | 1.5123 | 0.029525 | TM9SF4 |
| 117910084 | 117957453 | chr1 | + | exonic | hsa_circ_0013729 | −3.9496 | 0.029562 | MAN1A2 |
| 197986055 | 197987516 | chr2 | − | exonic | N/A | −1.5851 | 0.029565 | ANKRD44 |
| 170162524 | 170168267 | chr6 | + | exonic | hsa_circ_0004237 | 1.8020 | 0.029576 | ERMARD |
| 29319841 | 29344954 | chr1 | + | exonic | hsa_circ_0000041 | −1.6209 | 0.029633 | EPB41 |
| 68882182 | 69736583 | chr5 | + | sense overlapping | hsa_circ_0005896 | 1.5870 | 0.029697 | SMN1 |
| 144464661 | 144465125 | chr4 | + | exonic | hsa_circ_0001445 | −2.8667 | 0.029700 | SMARCA5 |
| 17059499 | 17059748 | chr3 | − | antisense | hsa_circ_0001275 | 1.7322 | 0.029788 | PLCL2 |
| 983990 | 1004666 | chr16 | − | exonic | N/A | 1.5539 | 0.029822 | LMF1 |
| 158204420 | 158223486 | chr5 | − | exonic | hsa_circ_0074817 | 1.5452 | 0.029880 | EBF1 |
| 46290104 | 46295253 | chr1 | + | exonic | hsa_circ_0012277 | 1.6524 | 0.029886 | MAST2 |
| 21415630 | 21415706 | chr1 | − | exonic | hsa_circ_0010497 | −1.5829 | 0.029942 | EIF4G3 |
| 4891946 | 4892613 | chr6 | + | exonic | hsa_circ_0008285 | −3.4513 | 0.029979 | CDYL |
| 104847269 | 104847527 | chr14 | − | intergenic | hsa_circ_0000573 | 1.8921 | 0.030033 | |
| 138340248 | 138341258 | chr3 | + | exonic | hsa_circ_0007080 | 1.5550 | 0.030036 | FAIM |
| 106508143 | 106508231 | chr7 | − | antisense | hsa_circ_0001737 | 1.5415 | 0.030041 | PIK3CG |
| 15444028 | 15477863 | chrX | − | exonic | hsa_circ_0089921 | 1.6243 | 0.030042 | PIR |
| 219366423 | 219414650 | chr1 | + | sense overlapping | hsa_circ_0004417 | −1.7854 | 0.030073 | LYPLAL1 |
| 138824814 | 138853226 | chr9 | − | exonic | hsa_circ_0089507 | 1.6738 | 0.030088 | UBAC1 |
| 67513932 | 67514758 | chr8 | − | exonic | hsa_circ_0004863 | 2.3654 | 0.030150 | MYBL1 |
| 136085784 | 136141886 | chr3 | − | exonic | N/A | −1.6605 | 0.030154 | STAG1 |
| 31205314 | 31214563 | chr1 | − | exonic | hsa_circ_0011205 | 1.5787 | 0.030179 | LAPTM5 |
| 102121473 | 102122174 | chr4 | − | intronic | N/A | 1.6214 | 0.030185 | PPP3CA |
| 14832521 | 14834120 | chrY | + | exonic | hsa_circ_0092235 | 1.5995 | 0.030273 | USP9Y |
| 38792600 | 38794168 | chr21 | + | exonic | hsa_circ_0001190 | −1.6949 | 0.030273 | DYRK1A |
| 197592293 | 197602646 | chr3 | + | exonic | hsa_circ_0008351 | −2.6339 | 0.030374 | LRCH3 |
| 216177220 | 216200847 | chr2 | − | exonic | hsa_circ_0058060 | 1.5125 | 0.030377 | ATIC |
| 42730785 | 42744343 | chr1 | − | exonic | hsa_circ_0006848 | −1.7486 | 0.030656 | FOXJ3 |
| 24679553 | 24679974 | chr14 | − | exonic | hsa_circ_0007326 | −2.0799 | 0.030687 | CHMP4A |
| 2951660 | 2952972 | chr4 | − | exonic | hsa_circ_0006737 | −1.9048 | 0.030689 | NOP14 |
| 1735857 | 1749314 | chr1 | − | exonic | hsa_circ_0009353 | −2.0580 | 0.030721 | GNB1 |
| 46190711 | 46195443 | chr19 | − | exonic | hsa_circ_0051546 | 1.6348 | 0.030749 | SNRPD2 |
| 16794537 | 16824083 | chr10 | − | exonic | hsa_circ_0006577 | −1.5398 | 0.030794 | RSU1 |
| 42509874 | 42510962 | chr19 | − | exonic | hsa_circ_0051260 | 1.5868 | 0.030859 | GRIK5 |
| 592468 | 619543 | chr6 | − | exonic | hsa_circ_0075437 | −1.5541 | 0.030867 | EXOC2 |
| 46934593 | 46950619 | chr16 | + | exonic | hsa_circ_0039219 | 1.6690 | 0.030924 | GPT2 |
| 1117078 | 1118233 | chr10 | + | sense overlapping | hsa_circ_0000204 | 1.6259 | 0.030931 | WDR37 |
| 140648622 | 140652463 | chr9 | + | exonic | hsa_circ_0089727 | −1.7699 | 0.030933 | EHMT1 |
| 12800185 | 12800444 | chr19 | − | exonic | hsa_circ_0049547 | 1.6403 | 0.030939 | FBXW9 |
| 53685473 | 53687313 | chr12 | + | sense overlapping | N/A | 1.5362 | 0.030965 | ESPL1 |
| 128350085 | 128360471 | chr11 | − | exonic | hsa_circ_0002083 | −2.6553 | 0.030983 | ETS1 |
| 33478807 | 33480195 | chr1 | − | exonic | hsa_circ_0011462 | 1.5476 | 0.030998 | AK2 |
| 36668400 | 36669878 | chr2 | + | exonic | hsa_circ_0007386 | −1.7833 | 0.031017 | CRIM1 |
| 80537076 | 80546772 | chr9 | − | sense overlapping | N/A | −2.4223 | 0.031024 | GNAQ |
| 40502897 | 40503739 | chr3 | + | sense overlapping | hsa_circ_0002102 | −1.7671 | 0.031036 | RPL14 |
| 95498782 | 95535315 | chr12 | − | exonic | N/A | 1.7181 | 0.031044 | FGD6 |
| 128922303 | 128928858 | chr2 | + | exonic | hsa_circ_0008298 | −1.7614 | 0.031052 | UGGT1 |
| 112898406 | 112900819 | chr9 | + | exonic | hsa_circ_0008706 | 1.5218 | 0.031075 | PALM2-AKAP2 |
| 155063089 | 155099179 | chr6 | + | exonic | hsa_circ_0078357 | 1.6130 | 0.031138 | SCAF8 |
| 71 193260 | 71229161 | chr15 | + | exonic | N/A | 1.6293 | 0.031152 | LRRC49 |
| 34953607 | 34958487 | chr21 | − | exonic | hsa_circ_0004339 | 1.5081 | 0.031160 | DONSON |
| 124911167 | 124934413 | chr12 | − | exonic | hsa_circ_0000461 | −1.7070 | 0.031171 | NCOR2 |
| 65466985 | 65482828 | chr2 | + | exonic | N/A | −4.6916 | 0.031235 | ACTR2 |
| 33996220 | 33998862 | chr9 | − | exonic | hsa_circ_0086736 | −2.0264 | 0.031243 | UBAP2 |
| 34376033 | 34409158 | chr18 | − | sense overlapping | hsa_circ_0047467 | 1.7789 | 0.031262 | TPGS2 |

TABLE 2-continued (SSRI R 8 week vs SSRI NR 8 week)

| TxStart | TxEnd | Chrom | Strand | circRNA type | Alias | Fold change | P-value | GeneSymbol |
|---|---|---|---|---|---|---|---|---|
| 4192524 | 4200109 | chr17 | − | exonic | hsa_circ_0041555 | −1.5295 | 0.031271 | UBE2G1 |
| 110068659 | 110081160 | chr9 | + | exonic | hsa_circ_0087862 | −2.3854 | 0.031290 | RAD23B |
| 3076997 | 3078169 | chr6 | + | exonic | hsa_circ_0001571 | −2.1668 | 0.031318 | RIPK1 |
| 183361267 | 183390272 | chr3 | + | exonic | hsa_circ_0001368 | −1.7301 | 0.031327 | KLHL24 |
| 117944807 | 117948267 | chr1 | + | exonic | hsa_circ_0000116 | −2.9192 | 0.031380 | MANIA2 |
| 212216334 | 212220759 | chr1 | + | exonic | hsa_circ_0006862 | 1.8309 | 0.031431 | DTL |
| 124121556 | 124132428 | chr8 | + | exonic | hsa_circ_0001820 | −1.7246 | 0.031435 | TBC1D31 |
| 52959282 | 52975384 | chr1 | − | exonic | hsa_circ_0003632 | −1.7735 | 0.031459 | ZCCHC11 |
| 100721965 | 100754399 | chr2 | − | sense overlapping | hsa_circ_0001056 | 1.5000 | 0.031506 | AFF3 |
| 5808203 | 5815904 | chr10 | − | exonic | N/A | −1.7649 | 0.031629 | GDI2 |
| 3424822 | 3426193 | chr11 | + | exonic | hsa_circ_0020845 | 1.9665 | 0.031640 | TSSC2 |
| 100976372 | 101023156 | chr3 | − | exonic | N/A | 1.5595 | 0.031652 | IMPG2 |
| 34951655 | 34957074 | chr21 | − | exonic | hsa_circ_0061548 | 1.6449 | 0.031653 | DONSON |
| 34978930 | 35006275 | chr11 | + | exonic | hsa_circ_0003768 | −1.7293 | 0.031659 | PDHX |
| 24357988 | 24362320 | chr2 | + | exonic | hsa_circ_0007270 | −2.5693 | 0.031720 | FAM228B |
| 76584771 | 76588078 | chr15 | − | exonic | hsa_circ_0003620 | −1.6909 | 0.031739 | ETFA |
| 155095122 | 155131342 | chr6 | + | exonic | hsa_circ_0078367 | −1.5809 | 0.031791 | SCAF8 |
| 61013821 | 61034674 | chr13 | + | exonic | hsa_circ_0004245 | −1.5859 | 0.031834 | TORD3 |
| 42730785 | 42776781 | chr1 | − | exonic | hsa_circ_0004416 | −1.5763 | 0.031895 | FOXJ3 |
| 31315699 | 31315949 | chr20 | − | exonic | hsa_circ_0059797 | 1.6031 | 0.031907 | COMMD7 |
| 128628009 | 128642880 | chr11 | + | exonic | hsa_circ_0000369 | −1.6963 | 0.031917 | FLI1 |
| 78098799 | 78107340 | chr1 | − | sense overlapping | hsa_circ_0006395 | −1.7093 | 0.032010 | ZZZ3 |
| 60613530 | 60642498 | chr17 | + | exonic | hsa_circ_0045128 | −1.5463 | 0.032022 | TLK2 |
| 155547476 | 155551830 | chr3 | − | exonic | hsa_circ_0001350 | −1.8465 | 0.032040 | SLC33A1 |
| 29481207 | 29481422 | chr1 | − | exonic | hsa_circ_0006602 | −2.1371 | 0.032101 | SRSF4 |
| 76082583 | 76083174 | chr17 | + | exonic | hsa_circ_0045862 | 1.7040 | 0.032115 | TNRC6C |
| 5129748 | 5131057 | chr16 | + | exonic | hsa_circ_0037777 | 1.9851 | 0.032162 | ALG1 |
| 86293355 | 86297981 | chr9 | − | exonic | hsa_circ_0001866 | −2.3596 | 0.032168 | UBQLN1 |
| 65272490 | 65272586 | chr11 | + | intronic | hsa_circ_0000326 | −3.2295 | 0.032227 | XLOC_12_002352 |
| 24762046 | 24788679 | chr16 | + | exonic | hsa_circ_0006008 | −1.6618 | 0.032260 | TNRC6A |
| 33467081 | 33467233 | chr3 | − | exonic | hsa_circ_0064742 | −1.9719 | 0.032280 | UBP1 |
| 105563560 | 105564743 | chr6 | − | exonic | hsa_circ_0077526 | 1.6386 | 0.032415 | BVES |
| 42231923 | 42232779 | chr17 | + | exonic | hsa_circ_0007378 | 1.6663 | 0.032545 | C17orf53 |
| 53848509 | 53865591 | chr12 | + | exonic | hsa_circ_0026640 | 1.5875 | 0.032630 | PCBP2 |
| 1735857 | 1737977 | chr1 | − | exonic | hsa_circ_0000007 | −2.2080 | 0.032649 | GNB1 |
| 139042473 | 139043291 | chr5 | − | antisense | hsa_circ_0001539 | 1.6777 | 0.032664 | CXXC5 |
| 31899500 | 31907527 | chr1 | + | exonic | hsa_circ_0011286 | 1.9938 | 0.032684 | SERINC2 |
| 8076452 | 8114825 | chr18 | + | exonic | hsa_circ_0003063 | 1.5778 | 0.032761 | PTPRM |
| 65651210 | 65652469 | chr11 | − | exonic | hsa_circ_0022920 | 1.5536 | 0.032818 | FIBP |
| 34574331 | 34614575 | chr6 | − | exonic | hsa_circ_0009095 | −1.7418 | 0.032865 | C6orf106 |
| 106761645 | 106782539 | chr2 | − | exonic | hsa_circ_0004029 | −1.7569 | 0.032923 | UXS1 |
| 43467278 | 43467478 | chr6 | + | intronic | hsa_circ_0092310 | 1.6371 | 0.032972 | TJAP1 |
| 195415403 | 195416309 | chr3 | + | exonic | hsa_circ_0008267 | −1.9652 | 0.032984 | LINC00969 |
| 77227158 | 77230123 | chr7 | + | exonic | hsa_circ_0080845 | −2.3822 | 0.032988 | PTPN12 |
| 155628480 | 155643155 | chr3 | + | exonic | hsa_circ_0008184 | −1.6439 | 0.032993 | GMPS |
| 77779390 | 77818086 | chr13 | − | exonic | hsa_circ_0030509 | −1.7106 | 0.032995 | MYCBP2 |
| 31 175028 | 31204064 | chr14 | + | exonic | N/A | −1.5955 | 0.033033 | SCFD1 |
| 99001020 | 99002576 | chr7 | − | exonic | N/A | −2.0462 | 0.033038 | PDAP1 |
| 94066434 | 94068129 | chr6 | − | exonic | hsa_circ_0077398 | 1.6380 | 0.033101 | EPHA7 |
| 33606862 | 33613800 | chr18 | − | exonic | hsa_circ_0000842 | −1.8219 | 0.033121 | RPRD1A |
| 102076623 | 102094483 | chr11 | + | exonic | hsa_circ_0005990 | 1.5737 | 0.033167 | YAP1 |
| 43133561 | 43135467 | chr20 | − | intronic | N/A | 1.5761 | 0.033170 | SERINC3 |
| 61083896 | 61141784 | chr13 | + | exonic | N/A | −1.6720 | 0.033189 | TORD3 |
| 110064315 | 110068928 | chr9 | + | exonic | hsa_circ_0006174 | −2.3397 | 0.033202 | RAD23B |
| 33222418 | 33233138 | chr20 | − | exonic | hsa_circ_0059988 | 1.6703 | 0.033205 | PIGU |
| 30330343 | 30389603 | chr20 | + | exonic | hsa_circ_0059711 | 1.6998 | 0.033232 | TPX2 |
| 75040222 | 75091111 | chr4 | + | exonic | hsa_circ_0069982 | −1.5486 | 0.033237 | MTHFD2L |
| 197597030 | 197602646 | chr3 | + | exonic | hsa_circ_0005873 | −2.5311 | 0.033254 | LRCH3 |
| 53701835 | 53714476 | chr12 | − | exonic | hsa_circ_0026616 | 1.8226 | 0.033311 | AAAS |
| 106746129 | 106782539 | chr2 | − | exonic | hsa_circ_0055947 | −1.6099 | 0.033345 | UXS1 |
| 74493579 | 74503971 | chr16 | − | exonic | hsa_circ_0040466 | −2.2733 | 0.033370 | GLG1 |
| 6301901 | 6312055 | chr18 | − | exonic | N/A | −1.5700 | 0.033386 | L3MBTL4 |
| 133135707 | 133138703 | chr6 | + | exonic | hsa_circ_0077877 | 1.7892 | 0.033387 | RPS12 |
| 96305503 | 96312973 | chr9 | + | exonic | hsa_circ_0087557 | −1.5178 | 0.033405 | FAM120A |
| 1747194 | 1749314 | chr1 | − | exonic | hsa_circ_0009360 | −2.1297 | 0.033469 | GNB1 |
| 51860052 | 51913807 | chr1 | − | exonic | hsa_circ_0012425 | −1.5828 | 0.033536 | EPS15 |
| 99890680 | 99896878 | chr13 | + | exonic | hsa_circ_0030720 | −2.0517 | 0.033569 | UBAC2 |
| 131829427 | 131840230 | chr2 | − | exonic | hsa_circ_0003524 | 1.5612 | 0.033570 | FAM168B |
| 142264862 | 142311690 | chr5 | + | exonic | hsa_circ_0074362 | −1.8974 | 0.033603 | ARHGAP26 |
| 4015902 | 4027345 | chr17 | − | exonic | hsa_circ_0041517 | 1.5931 | 0.033618 | ZZEF1 |
| 1737913 | 1749314 | chr1 | − | exonic | hsa_circ_0009357 | 2.6555 | 0.033632 | GNB1 |
| 6947713 | 6948261 | chr1 | + | exonic | hsa_circ_0009544 | 1.5574 | 0.033640 | CAMTA1 |
| 86294689 | 86297981 | chr9 | − | exonic | hsa_circ_0001867 | −2.3437 | 0.033661 | UBQLN1 |

TABLE 2-continued (SSRI R 8 week vs SSRI NR 8 week)

| TxStart | TxEnd | Chrom | Strand | circRNA type | Alias | Fold change | P-value | GeneSymbol |
|---|---|---|---|---|---|---|---|---|
| 180663927 | 180670906 | chr5 | − | exonic | hsa_circ_0075379 | 1.7730 | 0.033670 | GNB2L1 |
| 53024621 | 53027487 | chr17 | + | exonic | hsa_circ_0044695 | 1.5506 | 0.033730 | TOM1L1 |
| 12627938 | 12632881 | chr1 | − | exonic | hsa_circ_0010015 | 1.8961 | 0.033733 | DHRS3 |
| 128354717 | 128360471 | chr11 | − | exonic | hsa_circ_0004296 | −2.0880 | 0.033744 | ETS1 |
| 34929549 | 34936026 | chr19 | + | exonic | hsa_circ_0050532 | −1.5984 | 0.033829 | UBA2 |
| 35812582 | 35812776 | chr20 | + | exonic | hsa_circ_0005759 | 1.5006 | 0.033885 | RPN2 |
| 153924191 | 153928334 | chrX | − | exonic | hsa_circ_0092135 | −1.5605 | 0.033887 | GAB3 |
| 38991050 | 39021238 | chr5 | − | exonic | hsa_circ_0006308 | −1.8962 | 0.033977 | RICTOR |
| 205138290 | 205156934 | chr1 | − | exonic | hsa_circ_0016199 | 1.6794 | 0.033989 | DSTYK |
| 128419929 | 128434922 | chr9 | − | exonic | hsa_circ_0001890 | −1.7683 | 0.034034 | MAPKAP1 |
| 18022177 | 18022367 | chr20 | − | exonic | N/A | 1.6742 | 0.034036 | OVOL2 |
| 49298318 | 49303095 | chr19 | − | exonic | hsa_circ_0051778 | 1.5422 | 0.034038 | BCAT2 |
| 46488643 | 46488876 | chr1 | + | intronic | N/A | 1.7408 | 0.034169 | MAST2 |
| 44383247 | 44386611 | chrX | − | sense overlapping | hsa_circ_0007290 | −1.9927 | 0.034186 | FUNDC1 |
| 98673299 | 98703416 | chr8 | + | exonic | hsa_circ_0002114 | −1.5260 | 0.034198 | MTDH |
| 38205014 | 38205733 | chr8 | − | exonic | hsa_circ_0083996 | −1.8629 | 0.034199 | WHSC1L1 |
| 109489906 | 109492898 | chr2 | + | intronic | N/A | 1.6070 | 0.034241 | CCDC138 |
| 96965240 | 96966735 | chr2 | − | intronic | N/A | 1.6087 | 0.034245 | SNRNP200 |
| 42231920 | 42232779 | chr17 | + | exonic | hsa_circ_0004239 | 1.5565 | 0.034249 | C17orf53 |
| 30565588 | 30569605 | chr8 | − | exonic | hsa_circ_0083866 | −1.6801 | 0.034286 | GSR |
| 35805450 | 35805551 | chr10 | + | exonic | hsa_circ_0018203 | −2.4473 | 0.034370 | CONY |
| 30495147 | 30495584 | chr16 | + | exonic | hsa_circ_0000690 | −2.5353 | 0.034400 | ITGAL |
| 178626309 | 178639698 | chr3 | − | intergenic | N/A | 1.7901 | 0.034409 | |
| 20902997 | 20903293 | chr16 | − | intronic | N/A | 1.5721 | 0.034412 | DCUN1D3 |
| 126370175 | 126384781 | chr10 | − | exonic | hsa_circ_0003570 | −1.6392 | 0.034471 | FAM53B |
| 86292641 | 86297981 | chr9 | − | exonic | hsa_circ_0006466 | −2.4980 | 0.034572 | UBQLN1 |
| 137015277 | 137018525 | chr6 | − | exonic | hsa_circ_0006554 | −2.1769 | 0.034576 | MAP3K5 |
| 83819966 | 83832827 | chr15 | − | exonic | hsa_circ_0000646 | −1.5587 | 0.034629 | HDGFRP3 |
| 45241705 | 45244412 | chr1 | + | exonic | hsa_circ_0012173 | 1.7061 | 0.034632 | RPS8 |
| 40879652 | 40882936 | chr17 | − | exonic | hsa_circ_0043898 | 1.5466 | 0.034668 | EZH1 |
| 85459039 | 85460676 | chr12 | + | exonic | N/A | 1.7047 | 0.034676 | LRRIQ1 |
| 78180292 | 78204241 | chr11 | − | exonic | hsa_circ_0023812 | 1.5943 | 0.034686 | NARS2 |
| 96076482 | 96077487 | chr12 | − | exonic | hsa_circ_0006419 | 1.5752 | 0.034710 | NTN4 |
| 111434013 | 111435155 | chr1 | + | exonic | hsa_circ_0000105 | −1.8094 | 0.034728 | CD53 |
| 25477659 | 25477979 | chr20 | − | intronic | hsa_circ_0092338 | 1.9190 | 0.034736 | NINL |
| 128320084 | 128323309 | chr7 | + | exonic | N/A | 1.5491 | 0.034763 | FAM71F2 |
| 239082174 | 239093928 | chr2 | − | exonic | hsa_circ_0006014 | −2.0679 | 0.034766 | ILKAP |
| 47725960 | 47728788 | chr1 | − | exonic | N/A | 1.5086 | 0.034812 | STIL |
| 33467081 | 33481417 | chr3 | − | exonic | hsa_circ_0064743 | −1.9692 | 0.034846 | UBP1 |
| 43142254 | 43142429 | chr1 | + | exonic | hsa_circ_0011977 | 1.7786 | 0.034879 | PPIH |
| 9002122 | 9025596 | chr11 | − | exonic | hsa_circ_0021120 | 1.7715 | 0.034885 | NRIP3 |
| 75587212 | 75590926 | chr14 | − | exonic | hsa_circ_0032682 | −1.5965 | 0.034934 | NEK9 |
| 57014000 | 57016139 | chr20 | + | exonic | hsa_circ_0001173 | −2.6516 | 0.034939 | VAPB |
| 205156545 | 205156934 | chr1 | − | exonic | hsa_circ_0016201 | 1.5305 | 0.034947 | DSTYK |
| 34921480 | 34925873 | chr19 | + | exonic | hsa_circ_0005325 | −1.7063 | 0.034953 | UBA2 |
| 8759016 | 8759820 | chr11 | − | intronic | N/A | 1.5987 | 0.034979 | ST5 |
| 111883774 | 111890244 | chr10 | + | exonic | hsa_circ_0003357 | −2.3119 | 0.034997 | ADD3 |
| 104678572 | 104681470 | chr7 | + | exonic | hsa_circ_0007395 | −1.6271 | 0.035026 | KMT2E |
| 45073658 | 45290704 | chr6 | − | exonic | N/A | 1.6980 | 0.035036 | SUPT3H |
| 144547886 | 144557755 | chr8 | − | exonic | hsa_circ_0008835 | 1.5176 | 0.035057 | ZC3H3 |
| 32198899 | 32199141 | chr20 | + | exonic | hsa_circ_0059859 | 1.7439 | 0.035071 | CBFA2T2 |
| 125328677 | 125329118 | chr6 | + | intronic | N/A | 1.5617 | 0.035083 | RNF217 |
| 157155854 | 157160177 | chr7 | + | exonic | hsa_circ_0008726 | −1.6256 | 0.035257 | DNAJB6 |
| 30370051 | 30385318 | chr20 | + | exonic | hsa_circ_0003209 | 1.5065 | 0.035274 | TPX2 |
| 3424822 | 3427945 | chr11 | + | exonic | hsa_circ_0020846 | 1.9211 | 0.035344 | TSSC2 |
| 35578644 | 35601650 | chr17 | − | exonic | hsa_circ_0043247 | 1.5156 | 0.035362 | ACACA |
| 61468694 | 61484485 | chr2 | − | exonic | N/A | −1.5620 | 0.035391 | USP34 |
| 108286344 | 108286691 | chr9 | + | intronic | N/A | −1.6769 | 0.035440 | FSD1L |
| 49609654 | 49613024 | chr10 | + | exonic | hsa_circ_0018315 | −2.2318 | 0.035483 | MAPK8 |
| 16353301 | 16372347 | chr8 | − | sense overlapping | N/A | 1.6771 | 0.035524 | MSR1 |
| 197592293 | 197593090 | chr3 | + | exonic | hsa_circ_0008439 | −2.1773 | 0.035544 | LRCH3 |
| 89236034 | 89237562 | chr1 | + | exonic | hsa_circ_0002008 | −2.0787 | 0.035564 | PKN2 |
| 52293467 | 52299842 | chr1 | − | exonic | hsa_circ_0009076 | −1.7093 | 0.035577 | NRD1 |
| 39766030 | 39766488 | chr17 | − | exonic | hsa_circ_0043626 | 1.7563 | 0.035608 | KRT16 |
| 24357988 | 24369956 | chr2 | + | exonic | hsa_circ_0000982 | −2.7893 | 0.035653 | FAM228B |
| 122369651 | 122372262 | chr12 | + | exonic | N/A | 1.5781 | 0.035674 | WDR66 |
| 110062421 | 110068928 | chr9 | + | exonic | hsa_circ_0087855 | −1.9135 | 0.035686 | RAD23B |
| 88044886 | 88047860 | chr5 | − | exonic | hsa_circ_0073271 | 1.5194 | 0.035698 | MEF2C |
| 11958205 | 12016681 | chr17 | + | sense overlapping | N/A | −2.1004 | 0.035715 | MAP2K4 |

TABLE 2-continued (SSRI R 8 week vs SSRI NR 8 week)

| TxStart | TxEnd | Chrom | Strand | circRNA type | Alias | Fold change | P-value | GeneSymbol |
|---|---|---|---|---|---|---|---|---|
| 32659871 | 32665051 | chr20 | + | exonic | hsa_circ_0001139 | −1.8322 | 0.035720 | RALY |
| 66293626 | 66313803 | chr3 | + | exonic | hsa_circ_0004113 | −1.7836 | 0.035736 | SLC25A26 |
| 221186821 | 221189955 | chr2 | + | sense overlapping | N/A | 1.6613 | 0.035772 | AC114765.1 |
| 68434283 | 68439038 | chr15 | + | exonic | hsa_circ_0008378 | −1.5239 | 0.035772 | PIAS1 |
| 153576899 | 153583440 | chrX | − | exonic | hsa_circ_0091840 | 1.5022 | 0.035779 | FLNA |
| 100384118 | 100387214 | chr14 | + | exonic | hsa_circ_0033163 | 1.5347 | 0.035828 | EML1 |
| 52446826 | 52448603 | chr3 | + | exonic | hsa_circ_0004912 | −1.7945 | 0.035860 | PHF7 |
| 77700452 | 77703365 | chr13 | − | exonic | hsa_circ_0000495 | −1.7771 | 0.035912 | MYCBP2 |
| 119624601 | 119635021 | chr3 | − | exonic | hsa_circ_0004225 | −1.7525 | 0.035940 | GSK3B |
| 26789747 | 26802589 | chr10 | + | exonic | N/A | −2.1180 | 0.035961 | APBB1IP |
| 136990420 | 137019820 | chr6 | − | exonic | hsa_circ_0009034 | −1.6863 | 0.035984 | MAP3K5 |
| 34100754 | 34101636 | chr6 | − | exonic | hsa_circ_0076041 | 1.6045 | 0.035995 | GRM4 |
| 91947919 | 91952074 | chr14 | − | exonic | hsa_circ_0003045 | −1.7035 | 0.036019 | SMEK1 |
| 114911523 | 114919893 | chr9 | − | exonic | hsa_circ_0088062 | −1.7219 | 0.036028 | SUSD1 |
| 93480747 | 93482948 | chr15 | + | exonic | hsa_circ_0000654 | −1.7968 | 0.036081 | CHD2 |
| 159004985 | 159010814 | chr6 | + | exonic | hsa_circ_0001663 | −1.7608 | 0.036082 | TMEM181 |
| 38991050 | 38996984 | chr5 | − | exonic | hsa_circ_0072338 | −1.7303 | 0.036107 | RICTOR |
| 179132679 | 179137066 | chr5 | + | exonic | hsa_circ_0001564 | −1.6131 | 0.036128 | CANX |
| 119222378 | 119222868 | chr3 | + | exonic | hsa_circ_0008394 | −2.1416 | 0.036155 | TIMMDC1 |
| 34204740 | 34209207 | chr1 | − | exonic | N/A | 1.6932 | 0.036165 | CSMD2 |
| 243708811 | 243859018 | chr1 | − | exonic | N/A | −1.6088 | 0.036173 | AKT3 |
| 88211723 | 88221044 | chr10 | − | exonic | hsa_circ_0019005 | −1.6649 | 0.036178 | WAPAL |
| 155691307 | 155695810 | chr1 | + | exonic | hsa_circ_0014613 | −2.2550 | 0.036251 | DAP3 |
| 97207245 | 97213809 | chr9 | + | exonic | hsa_circ_0087581 | 1.5678 | 0.036268 | HIATL1 |
| 50438785 | 50442435 | chrX | − | sense overlapping | N/A | 1.5477 | 0.036295 | SHROOM4 |
| 98698895 | 98703416 | chr8 | + | exonic | hsa_circ_0002961 | −1.6777 | 0.036337 | MTDH |
| 126735527 | 126735757 | chr3 | + | intronic | N/A | 1.8570 | 0.036359 | PLXNA1 |
| 76970891 | 76982160 | chr10 | + | exonic | hsa_circ_0018909 | 1.8135 | 0.036394 | VDAC2 |
| 183454505 | 183480067 | chr3 | + | exonic | hsa_circ_0009131 | 1.6077 | 0.036419 | YEATS2 |
| 13604092 | 13610799 | chr20 | − | exonic | hsa_circ_0059476 | 1.5356 | 0.036425 | TASP1 |
| 126355758 | 126370948 | chr10 | − | exonic | hsa_circ_0020321 | −1.5274 | 0.036464 | FAM53B |
| 43702432 | 43704859 | chr18 | + | exonic | hsa_circ_0002481 | −1.5260 | 0.036492 | HAUS1 |
| 201786215 | 201796102 | chr1 | + | exonic | hsa_circ_0015911 | 1.6331 | 0.036492 | NAV1 |
| 57250018 | 57255327 | chr16 | + | exonic | hsa_circ_0039557 | 1.7718 | 0.036497 | RSPRY1 |
| 67431907 | 67490392 | chr14 | + | exonic | hsa_circ_0032253 | 1.5236 | 0.036500 | GPHN |
| 72462067 | 72468534 | chr10 | + | exonic | hsa_circ_0004606 | 1.5412 | 0.036507 | ADAMTS14 |
| 33388679 | 33427756 | chr7 | + | exonic | hsa_circ_0079812 | −1.6586 | 0.036557 | BBS9 |
| 110922882 | 110925748 | chr12 | + | exonic | hsa_circ_0004516 | −1.8110 | 0.036562 | FAM216A |
| 48308935 | 48320523 | chr8 | + | exonic | hsa_circ_0001798 | −2.3926 | 0.036572 | SPIDR |
| 86297865 | 86301070 | chr9 | − | exonic | hsa_circ_0005142 | −2.3086 | 0.036606 | UBQLN1 |
| 27656861 | 27657427 | chr2 | + | sense overlapping | hsa_circ_0000984 | −1.6486 | 0.036612 | NRBP1 |
| 55844499 | 55844644 | chr20 | − | antisense | hsa_circ_0001171 | 1.6291 | 0.036668 | BC037891 |
| 8043537 | 8099878 | chr7 | + | exonic | hsa_circ_0001678 | −1.6693 | 0.036695 | GLCCH |
| 119219541 | 119236162 | chr3 | + | exonic | hsa_circ_0066874 | −1.9705 | 0.036744 | TIMMDC1 |
| 45767941 | 45769539 | chr19 | + | exonic | hsa_circ_0051454 | −1.5268 | 0.036796 | MARK4 |
| 46022924 | 46026674 | chr17 | + | exonic | hsa_circ_0044334 | 1.9457 | 0.036848 | PNPO |
| 110062421 | 110084399 | chr9 | + | exonic | hsa_circ_0087856 | −2.8205 | 0.036922 | RAD23B |
| 86292641 | 86292876 | chr9 | − | exonic | hsa_circ_0087354 | −2.0520 | 0.036949 | UBQLN1 |
| 47603639 | 47604020 | chr11 | + | exonic | hsa_circ_0022015 | 1.5485 | 0.037011 | NDUFS3 |
| 74561481 | 74563895 | chr18 | + | exonic | hsa_circ_0004979 | −1.7678 | 0.037037 | ZNF236 |
| 155695172 | 155695810 | chr1 | + | exonic | hsa_circ_0014614 | −2.2175 | 0.037085 | DAP3 |
| 12039670 | 12056183 | chr10 | − | exonic | hsa_circ_0000213 | −1.7515 | 0.037109 | UPF2 |
| 47341422 | 47342835 | chr19 | − | exonic | hsa_circ_0051641 | 1.5010 | 0.037117 | AP2S1 |
| 1756835 | 1770677 | chr1 | − | exonic | hsa_circ_0009362 | −2.3829 | 0.037120 | GNB1 |
| 56526672 | 56527148 | chr5 | + | exonic | hsa_circ_0001486 | −1.6179 | 0.037126 | GPBP1 |
| 185153374 | 185200840 | chr1 | + | exonic | hsa_circ_0015677 | −2.3340 | 0.037146 | SWT1 |
| 42363987 | 42375484 | chr19 | + | exonic | hsa_circ_0051241 | 1.8720 | 0.037152 | RPS19 |
| 179136873 | 179147561 | chr5 | + | exonic | hsa_circ_0002051 | −1.6872 | 0.037159 | CANX |
| 138244331 | 138256189 | chr3 | − | exonic | N/A | −1.7827 | 0.037177 | CEP70 |
| 40152499 | 40155575 | chr17 | − | exonic | N/A | 1.7778 | 0.037201 | DNAJC7 |
| 58690339 | 58690574 | chr14 | + | exonic | hsa_circ_0032064 | −1.5136 | 0.037241 | ACTR10 |
| 15644268 | 15679480 | chr2 | − | exonic | hsa_circ_0004665 | −1.6259 | 0.037258 | NBAS |
| 32874967 | 32875262 | chr22 | + | exonic | hsa_circ_0008832 | −1.7096 | 0.037353 | FBXO7 |
| 76198579 | 76198832 | chr17 | + | exonic | hsa_circ_0045881 | 1.8934 | 0.037362 | AFMID |
| 75936161 | 75936743 | chr13 | − | exonic | hsa_circ_0030431 | 1.5686 | 0.037379 | TBC1D4 |
| 41536266 | 41541123 | chr1 | − | exonic | hsa_circ_0000061 | 1.5218 | 0.037412 | SCMH1 |
| 242541310 | 242542494 | chr2 | − | exonic | hsa_circ_0004946 | 1.5468 | 0.037430 | THAP4 |
| 144817634 | 144819722 | chr5 | − | sense overlapping | N/A | 1.5679 | 0.037488 | XLOC_005041 |
| 50133322 | 50140649 | chr20 | − | exonic | hsa_circ_0060849 | −1.5205 | 0.037510 | NFATC2 |
| 34111725 | 34113603 | chr11 | + | exonic | hsa_circ_0004851 | −2.0442 | 0.037541 | CAPRIN1 |
| 10554828 | 10555880 | chr17 | − | exonic | N/A | 1.5975 | 0.037566 | MYH3 |

TABLE 2-continued (SSRI R 8 week vs SSRI NR 8 week)

| TxStart | TxEnd | Chrom | Strand | circRNA type | Alias | Fold change | P-value | GeneSymbol |
|---|---|---|---|---|---|---|---|---|
| 129811943 | 129813356 | chr3 | + | exonic | hsa_circ_0067327 | 1.8900 | 0.037627 | ALG1L2 |
| 32703702 | 32704685 | chr2 | + | exonic | hsa_circ_0002408 | −1.8151 | 0.037635 | BIRC6 |
| 53430497 | 53430825 | chrX | − | exonic | hsa_circ_0001921 | −1.9417 | 0.037643 | SMC1A |
| 34147027 | 34149837 | chr17 | + | exonic | hsa_circ_0043138 | −2.7351 | 0.037650 | TAF15 |
| 77631183 | 77632364 | chr9 | − | exonic | hsa_circ_0004189 | −1.9176 | 0.037734 | C9orf41 |
| 90069143 | 90074398 | chr10 | − | exonic | N/A | 1.5189 | 0.037811 | RNLS |
| 27432375 | 27436268 | chr1 | − | exonic | hsa_circ_0007283 | 1.5166 | 0.037825 | SLC9A1 |
| 103558598 | 103567658 | chr10 | − | exonic | hsa_circ_0019612 | −1.9518 | 0.037840 | MGEA5 |
| 103432671 | 103433430 | chr10 | − | exonic | hsa_circ_0019591 | −2.1415 | 0.037846 | FBXW4 |
| 22999874 | 23030758 | chr7 | − | exonic | hsa_circ_0008951 | −2.3526 | 0.037850 | FAM126A |
| 47779518 | 47787483 | chr3 | − | exonic | hsa_circ_0065308 | −1.8437 | 0.037902 | SMARCC1 |
| 6172119 | 6219748 | chr12 | − | exonic | hsa_circ_0025114 | 1.6198 | 0.037928 | VWF |
| 95686858 | 95735544 | chr13 | − | exonic | hsa_circ_0030569 | 1.6380 | 0.037944 | ABCC4 |
| 245018859 | 245019265 | chr1 | − | sense overlapping | hsa_circ_0000200 | −1.6846 | 0.037947 | HNRNPU |
| 149563797 | 149570383 | chr3 | + | exonic | hsa_circ_0006697 | −2.9627 | 0.037958 | RNF13 |
| 140961878 | 140963182 | chr5 | − | exonic | hsa_circ_0008982 | −1.6935 | 0.037964 | DIAPH1 |
| 163876310 | 163899928 | chr6 | + | exonic | hsa_circ_0005328 | −1.7800 | 0.037975 | QKI |
| 34860052 | 34860272 | chr17 | − | intronic | hsa_circ_0092344 | 1.7127 | 0.038049 | MYO19 |
| 91924202 | 91981956 | chr7 | + | exonic | hsa_circ_0002744 | −1.9828 | 0.038108 | ANKIB1 |
| 128525762 | 128528578 | chr2 | − | exonic | hsa_circ_0056362 | −1.6790 | 0.038138 | WDR33 |
| 953289 | 1003975 | chr17 | − | exonic | hsa_circ_0007919 | −1.8089 | 0.038196 | ABR |
| 1747194 | 1756938 | chr1 | − | exonic | hsa_circ_0000008 | −2.4314 | 0.038201 | GNB1 |
| 21377358 | 21437876 | chr1 | − | exonic | hsa_circ_0000026 | −1.5595 | 0.038224 | EIF4G3 |
| 36623756 | 36744685 | chr2 | + | exonic | hsa_circ_0053958 | −1.5476 | 0.038319 | CRIM1 |
| 11984672 | 12016677 | chr17 | + | exonic | hsa_circ_0007456 | −2.0275 | 0.038332 | MAP2K4 |
| 22404921 | 22413359 | chr1 | + | exonic | hsa_circ_0005576 | −1.9845 | 0.038398 | CDC42 |
| 149563797 | 149629870 | chr3 | + | exonic | hsa_circ_0003502 | −2.5366 | 0.038398 | RNF13 |
| 128525214 | 128526514 | chr3 | + | exonic | hsa_circ_0008923 | −1.5736 | 0.038493 | RAB7A |
| 21971315 | 21972024 | chr14 | − | exonic | hsa_circ_0000523 | −1.8506 | 0.038518 | METTL3 |
| 34312491 | 34313077 | chr20 | − | exonic | hsa_circ_0007632 | −2.2193 | 0.038521 | RBM39 |
| 52729602 | 52729875 | chr4 | + | exonic | hsa_circ_0069715 | −2.1222 | 0.038527 | DCUN1D4 |
| 33996220 | 34017187 | chr9 | − | exonic | hsa_circ_0003410 | −1.9770 | 0.038570 | UBAP2 |
| 131909665 | 131911225 | chr9 | + | exonic | hsa_circ_0089039 | 1.5149 | 0.038573 | PPP2R4 |
| 118920468 | 118923974 | chrX | − | exonic | hsa_circ_0091419 | 1.5865 | 0.038580 | RPL39 |
| 52729602 | 52744020 | chr4 | + | exonic | hsa_circ_0001410 | −1.9206 | 0.038581 | DCUN1D4 |
| 67356836 | 67371058 | chr1 | − | exonic | hsa_circ_0006677 | −1.6918 | 0.038593 | WDR78 |
| 53459000 | 53459207 | chr10 | + | intronic | hsa_circ_0000238 | 1.5451 | 0.038598 | PRKG1 |
| 28748408 | 28771483 | chr13 | + | exonic | hsa_circ_0008760 | −2.0041 | 0.038603 | PAN3 |
| 32381495 | 32385259 | chr1 | − | exonic | hsa_circ_0007364 | 2.0968 | 0.038611 | PTP4A2 |
| 1268152 | 1273035 | chr17 | − | exonic | hsa_circ_0041195 | −1.8248 | 0.038626 | YWHAE |
| 45391429 | 45423180 | chr18 | − | exonic | hsa_circ_0000847 | −2.1253 | 0.038701 | SMAD2 |
| 176938577 | 176940848 | chr5 | − | exonic | hsa_circ_0075215 | 1.8653 | 0.038760 | DDX41 |
| 53017589 | 53018231 | chr18 | − | exonic | hsa_circ_0047733 | 1.9297 | 0.038774 | TCF4 |
| 159004985 | 159006457 | chr6 | + | exonic | hsa_circ_0003345 | −1.8382 | 0.038778 | TMEM181 |
| 141595217 | 141595410 | chr8 | − | exonic | hsa_circ_0008113 | −1.5569 | 0.038822 | AGO2 |
| 1735857 | 1756938 | chr1 | − | exonic | hsa_circ_0006869 | −2.5873 | 0.038871 | GNB1 |
| 11958205 | 12016677 | chr17 | + | exonic | hsa_circ_0005603 | −2.2360 | 0.038922 | MAP2K4 |
| 87693930 | 87696805 | chr4 | + | exonic | hsa_circ_0007324 | 1.7571 | 0.038999 | PTPN13 |
| 86292641 | 86293514 | chr9 | − | exonic | hsa_circ_0001865 | −2.1615 | 0.039006 | UBQLN1 |
| 23550956 | 23559842 | chr14 | − | exonic | N/A | −1.9059 | 0.039027 | ACIN1 |
| 119720892 | 119721086 | chr3 | − | exonic | hsa_circ_0006497 | −1.5652 | 0.039043 | GSK3B |
| 15969938 | 16026822 | chrX | + | intergenic | N/A | 1.6676 | 0.039046 | |
| 179195850 | 179198244 | chr5 | + | exonic | N/A | 1.8052 | 0.039080 | MAML1 |
| 31535331 | 31542179 | chr14 | + | exonic | hsa_circ_0031449 | 1.5636 | 0.039311 | AP4S1 |
| 37727937 | 37735069 | chr8 | − | exonic | hsa_circ_0005630 | −1.6116 | 0.039326 | RAB11FIP1 |
| 108186549 | 108206688 | chr11 | + | exonic | hsa_circ_0024231 | −2.2357 | 0.039331 | ATM |
| 74056531 | 74087278 | chr2 | + | exonic | hsa_circ_0055251 | 1.9372 | 0.039359 | STAMBP |
| 34101174 | 34111003 | chr11 | + | exonic | hsa_circ_0000286 | −1.5636 | 0.039374 | CAPRIN1 |
| 41598736 | 41599594 | chr17 | + | exonic | hsa_circ_0003899 | 1.8620 | 0.039404 | DHX8 |
| 6477621 | 6482099 | chr9 | + | exonic | hsa_circ_0007816 | −1.5449 | 0.039438 | UHRF2 |
| 151167656 | 151195266 | chr7 | − | exonic | N/A | −1.6866 | 0.039496 | RHEB |
| 149563797 | 149613357 | chr3 | + | exonic | hsa_circ_0003956 | −2.7978 | 0.039508 | RNF13 |
| 231314886 | 231328865 | chr2 | + | exonic | hsa_circ_0058619 | −2.3148 | 0.039571 | SP100 |
| 14316016 | 14317401 | chr11 | − | exonic | hsa_circ_0004429 | −1.5162 | 0.039649 | RRAS2 |
| 89807211 | 89815175 | chr16 | − | exonic | hsa_circ_0040994 | 1.6182 | 0.039839 | FANCA |
| 151174418 | 151188100 | chr7 | − | exonic | hsa_circ_0082950 | −2.2001 | 0.039845 | RHEB |
| 7491497 | 7491864 | chr17 | − | exonic | hsa_circ_0041939 | 1.7626 | 0.039974 | SOX15 |
| 31947382 | 31971378 | chr22 | + | sense overlapping | hsa_circ_0008323 | 1.6983 | 0.039989 | SFI1 |
| 34304661 | 34313077 | chr20 | − | exonic | hsa_circ_0001147 | −2.2590 | 0.039993 | RBM39 |
| 57535669 | 57535748 | chr15 | + | exonic | hsa_circ_0035426 | 1.5489 | 0.040023 | TCF12 |
| 125032151 | 125042288 | chr3 | − | exonic | hsa_circ_0007557 | −2.3166 | 0.040080 | ZNF148 |

TABLE 2-continued (SSRI R 8 week vs SSRI NR 8 week)

| TxStart | TxEnd | Chrom | Strand | circRNA type | Alias | Fold change | P-value | GeneSymbol |
|---|---|---|---|---|---|---|---|---|
| 20126716 | 20131279 | chr22 | + | exonic | hsa_circ_0004100 | 1.5019 | 0.040088 | ZDHHC8 |
| 65473318 | 65492309 | chr2 | + | sense overlapping | hsa_circ_0001022 | −4.5983 | 0.040094 | ACTR2 |
| 80412669 | 80415142 | chr15 | + | exonic | hsa_circ_0000643 | −2.2696 | 0.040099 | ZFAND6 |
| 50592985 | 50593565 | chr15 | − | exonic | hsa_circ_0002551 | −1.8156 | 0.040219 | GABPB1 |
| 155547476 | 155560408 | chr3 | − | exonic | hsa_circ_0067772 | −1.7048 | 0.040220 | SLC33A1 |
| 140476711 | 140508795 | chr7 | − | exonic | hsa_circ_0007178 | −2.5369 | 0.040227 | BRAF |
| 45860527 | 45860957 | chr19 | − | exonic | hsa_circ_0051470 | 1.6824 | 0.040245 | ERCC2 |
| 44713610 | 44717214 | chr1 | − | intronic | hsa_circ_0000065 | 1.6918 | 0.040320 | ERI3 |
| 47531309 | 47537001 | chr16 | + | exonic | hsa_circ_0039261 | −2.0351 | 0.040448 | PHKB |
| 39411599 | 39414050 | chr22 | + | exonic | hsa_circ_0063369 | −1.5609 | 0.040469 | APOBEC3C |
| 86328535 | 86329135 | chr6 | − | exonic | hsa_circ_0006131 | −1.7184 | 0.040521 | SYNCRIP |
| 101132116 | 101132358 | chr13 | + | intronic | N/A | 1.5164 | 0.040536 | PCCA |
| 50821544 | 50824353 | chr12 | + | exonic | hsa_circ_0003664 | −1.8211 | 0.040579 | LARP4 |
| 40278772 | 40282608 | chr17 | − | exonic | N/A | −2.0512 | 0.040655 | RAB5C |
| 74926381 | 74937998 | chr16 | − | exonic | hsa_circ_0040507 | 1.6723 | 0.040693 | WDR59 |
| 72370568 | 72373320 | chr5 | + | exonic | hsa_circ_0002490 | −1.7797 | 0.040728 | FCHO2 |
| 127295459 | 127298715 | chr3 | − | exonic | hsa_circ_0067161 | 1.6008 | 0.040747 | TPRA1 |
| 71799391 | 71803602 | chr16 | − | exonic | hsa_circ_0007770 | 1.6975 | 0.040787 | AP1G1 |
| 6995910 | 7002978 | chr4 | + | exonic | hsa_circ_0006681 | −2.1694 | 0.040833 | TBC1D14 |
| 46751425 | 46754867 | chr10 | − | exonic | hsa_circ_0007010 | −2.2418 | 0.040880 | BMS1P5 |
| 128995614 | 128996148 | chr4 | + | exonic | hsa_circ_0070933 | −1.7200 | 0.040901 | LARP1B |
| 119219541 | 119222868 | chr3 | + | exonic | hsa_circ_0001329 | −2.1065 | 0.040961 | TIMMDC1 |
| 48216600 | 48246391 | chr19 | + | exonic | hsa_circ_0051695 | 1.6341 | 0.041021 | EHD2 |
| 43906156 | 43909145 | chr7 | − | exonic | hsa_circ_0079973 | 1.7342 | 0.041100 | MRPS24 |
| 153590346 | 153590516 | chrX | − | exonic | hsa_circ_0091994 | −1.5300 | 0.041283 | FLNA |
| 137853422 | 137854380 | chr5 | − | intronic | N/A | 2.0936 | 0.041305 | ETF1 |
| 32715986 | 32717410 | chrX | − | exonic | hsa_circ_0090181 | 1.5039 | 0.041312 | DMD |
| 131006155 | 131014868 | chr5 | − | exonic | hsa_circ_0073859 | −1.9373 | 0.041332 | FNIP1 |
| 113734352 | 113800365 | chr9 | − | exonic | hsa_circ_0087962 | 1.6255 | 0.041349 | LPAR1 |
| 47702783 | 47719801 | chr3 | − | exonic | hsa_circ_0003602 | −1.5540 | 0.041359 | SMARCC1 |
| 42513408 | 42515462 | chr2 | + | exonic | hsa_circ_0054241 | −1.8456 | 0.041364 | EML4 |
| 50810448 | 50832564 | chr22 | + | exonic | hsa_circ_0001258 | −1.6729 | 0.041379 | PPP6R2 |
| 31139461 | 31144271 | chr14 | + | exonic | hsa_circ_0009140 | −1.8515 | 0.041506 | SCFD1 |
| 27445667 | 27449008 | chr16 | + | exonic | hsa_circ_0038728 | 1.5354 | 0.041544 | IL21R |
| 145044816 | 145083858 | chr5 | − | intronic | N/A | 1.5149 | 0.041553 | PRELID2 |
| 155408117 | 155408859 | chr1 | − | exonic | hsa_circ_0000137 | −1.7977 | 0.041566 | ASH1L |
| 34922765 | 34924317 | chr19 | + | exonic | hsa_circ_0050514 | −1.5181 | 0.041604 | UBA2 |
| 26204839 | 26205043 | chr6 | + | sense overlapping | hsa_circ_0001588 | −3.1348 | 0.041613 | HIST1H4E |
| 159437506 | 159492550 | chr5 | + | exonic | hsa_circ_0074834 | 1.5117 | 0.041618 | TTC1 |
| 233334684 | 233344435 | chr1 | − | exonic | hsa_circ_0005223 | −1.6270 | 0.041623 | PCNXL2 |
| 156444899 | 156446994 | chr1 | − | exonic | hsa_circ_0014737 | 1.5294 | 0.041712 | MEF2D |
| 3252272 | 3256234 | chr18 | + | exonic | hsa_circ_0046753 | 1.6464 | 0.041731 | MYL12A |
| 103173821 | 103229087 | chr11 | + | exonic | hsa_circ_0024144 | 1.7050 | 0.041752 | DYNC2H1 |
| 56792449 | 56839544 | chr16 | + | exonic | N/A | 1.5392 | 0.041761 | NUP93 |
| 12999419 | 13042333 | chr18 | + | exonic | hsa_circ_0046999 | −1.6319 | 0.041786 | CEP192 |
| 47497792 | 47581459 | chr16 | + | exonic | hsa_circ_0039254 | −1.6224 | 0.041799 | PHKB |
| 52028142 | 52029002 | chr3 | − | intronic | hsa_circ_0092277 | 1.6808 | 0.041876 | RPL29 |
| 49091920 | 49094856 | chr12 | − | exonic | hsa_circ_0026046 | −1.6945 | 0.041899 | CONT1 |
| 65941524 | 65972074 | chr17 | + | exonic | hsa_circ_0000799 | −1.8771 | 0.041929 | BPTE |
| 145066859 | 145067583 | chr8 | + | exonic | hsa_circ_0085939 | 1.8399 | 0.041952 | GRINA |
| 20939730 | 20939965 | chr2 | − | exonic | hsa_circ_0052877 | 1.9583 | 0.041991 | C2orf43 |
| 12123470 | 12133683 | chr10 | + | exonic | hsa_circ_0003074 | −1.7023 | 0.042019 | DHTKD1 |
| 95110953 | 95111328 | chr10 | − | exonic | N/A | 1.6513 | 0.042025 | MYOF |
| 66625443 | 66625662 | chr11 | − | intronic | hsa_circ_0000331 | 1.7981 | 0.042047 | PC |
| 73429657 | 73429763 | chr11 | − | exonic | hsa_circ_0023509 | −2.3708 | 0.042109 | RAB6A |
| 53421565 | 53421972 | chr12 | + | exonic | hsa_circ_0007889 | −1.7644 | 0.042113 | EIF4B |
| 2972488 | 3000467 | chr11 | − | exonic | hsa_circ_0020816 | −1.9587 | 0.042116 | NAP1L4 |
| 67718636 | 67721428 | chr3 | + | sense overlapping | N/A | 1.6983 | 0.042164 | SUCLG2-AS1 |
| 208841374 | 208842310 | chr2 | − | exonic | hsa_circ_0001095 | −1.8302 | 0.042173 | PLEKHM3 |
| 145151936 | 145152037 | chr8 | + | exonic | hsa_circ_0085959 | 1.6135 | 0.042238 | CYC1 |
| 101553648 | 101572901 | chr10 | + | exonic | hsa_circ_0019442 | 1.6366 | 0.042311 | ABCC2 |
| 80540616 | 80545148 | chr17 | + | exonic | hsa_circ_0046435 | 1.5219 | 0.042329 | FOXK2 |
| 47585118 | 47585318 | chr19 | − | intronic | hsa_circ_0092316 | 1.7182 | 0.042329 | ZC3H4 |
| 196544755 | 196548630 | chr2 | + | exonic | hsa_circ_0057551 | −2.2933 | 0.042371 | SLC39A10 |
| 32659871 | 32666359 | chr20 | + | exonic | hsa_circ_0001140 | −2.0263 | 0.042445 | RALY |
| 231081134 | 231097049 | chr1 | − | exonic | hsa_circ_0000194 | −1.8438 | 0.042457 | TTC13 |
| 34107610 | 34113603 | chr11 | + | exonic | hsa_circ_0000287 | −1.9187 | 0.042468 | CAPRIN1 |
| 34922765 | 34955036 | chr19 | + | exonic | hsa_circ_0050518 | −1.5345 | 0.042588 | UBA2 |
| 64485055 | 64509673 | chr12 | + | exonic | N/A | 1.5918 | 0.042591 | SRGAP1 |
| 68015271 | 68018210 | chr8 | + | exonic | hsa_circ_0084666 | −1.5807 | 0.042597 | CSPP1 |
| 60629662 | 60631116 | chr17 | + | exonic | hsa_circ_0008438 | −2.3637 | 0.042657 | TLK2 |
| 10058810 | 10084547 | chrX | + | exonic | N/A | 1.5813 | 0.042666 | WWC3 |

TABLE 2-continued (SSRI R 8 week vs SSRI NR 8 week)

| TxStart | TxEnd | Chrom | Strand | circRNA type | Alias | Fold change | P-value | GeneSymbol |
|---|---|---|---|---|---|---|---|---|
| 10459084 | 10480201 | chr1 | + | exonic | hsa_circ_0009723 | 1.6153 | 0.042682 | PGD |
| 50045984 | 50074484 | chr5 | + | exonic | hsa_circ_0072430 | −1.8379 | 0.042732 | PARP8 |
| 169854206 | 169863309 | chr3 | − | exonic | hsa_circ_0001965 | −2.5869 | 0.042733 | PHC3 |
| 70146376 | 70148852 | chrX | − | exonic | hsa_circ_0090969 | 1.5732 | 0.042743 | SLC7A3 |
| 30890069 | 30898940 | chr7 | + | exonic | hsa_circ_0079743 | 1.5879 | 0.042754 | FAM188B |
| 18303496 | 18308257 | chr11 | − | exonic | N/A | 1.6815 | 0.042765 | HPS5 |
| 77038816 | 77065626 | chr4 | − | exonic | hsa_circ_0070032 | −1.5167 | 0.042772 | NUP54 |
| 44620882 | 44673174 | chr15 | + | exonic | hsa_circ_0035052 | −1.5269 | 0.042806 | CASC4 |
| 169831147 | 169840532 | chr3 | − | exonic | hsa_circ_0006893 | −1.9704 | 0.042836 | PHC3 |
| 99718694 | 99719539 | chr8 | − | exonic | hsa_circ_0004592 | −1.6378 | 0.042925 | STK3 |
| 109263579 | 109263891 | chrX | + | intronic | N/A | 2.0365 | 0.042938 | TMEM164 |
| 53413693 | 53416411 | chr12 | + | exonic | hsa_circ_0026512 | −2.1165 | 0.043195 | EIF4B |
| 96826060 | 96834012 | chr15 | − | exonic | hsa_circ_0004200 | 1.5813 | 0.043229 | NR2F2-AS1 |
| 97818240 | 97820478 | chr2 | + | exonic | hsa_circ_0055734 | 1.5510 | 0.043260 | ANKRD36 |
| 23023562 | 23030758 | chr7 | − | exonic | hsa_circ_0001682 | −2.3430 | 0.043277 | FAM126A |
| 42992722 | 42993879 | chr6 | + | exonic | N/A | −1.5343 | 0.043310 | RRP36 |
| 41361767 | 41362745 | chr15 | − | exonic | hsa_circ_0007489 | −1.6081 | 0.043333 | INO80 |
| 3182193 | 3186394 | chr3 | + | exonic | N/A | −1.9231 | 0.043371 | TANT |
| 35832287 | 35838568 | chr20 | + | exonic | hsa_circ_0060262 | 1.5231 | 0.043410 | RPN2 |
| 45391429 | 45396935 | chr18 | − | exonic | hsa_circ_0003694 | −2.4684 | 0.043591 | SMAD2 |
| 65323338 | 65339206 | chr1 | − | exonic | hsa_circ_0012872 | −1.6471 | 0.043651 | JAK1 |
| 201790558 | 201796171 | chr2 | − | exonic | N/A | 1.7855 | 0.043722 | ORC2 |
| 76953182 | 76974038 | chr18 | + | exonic | hsa_circ_0003275 | −1.5592 | 0.043778 | ATP9B |
| 102683731 | 102685776 | chr10 | + | exonic | hsa_circ_0006654 | −1.6627 | 0.043801 | FAM178A |
| 39623414 | 39627606 | chr14 | − | exonic | hsa_circ_0005836 | −1.5252 | 0.043804 | TRAPPC6B |
| 52785363 | 52786666 | chr19 | + | exonic | hsa_circ_0052095 | −1.5739 | 0.043835 | ZNF766 |
| 77330650 | 77340944 | chr11 | − | exonic | hsa_circ_0008342 | −1.6271 | 0.043858 | CLNS1A |
| 118832460 | 118887479 | chr6 | − | exonic | hsa_circ_0077736 | −2.1781 | 0.043903 | CEP85L |
| 44346195 | 44346638 | chr13 | − | intronic | N/A | 1.6699 | 0.043909 | ENOX1 |
| 109466421 | 109468140 | chr6 | + | exonic | hsa_circ_0004131 | −1.8661 | 0.043954 | CEP57L1 |
| 108098321 | 108106561 | chr11 | + | exonic | hsa_circ_0003641 | −2.1823 | 0.044003 | ATM |
| 100598717 | 100599535 | chr12 | + | exonic | N/A | −1.5151 | 0.044015 | ACTR6 |
| 149563797 | 149677923 | chr3 | + | exonic | hsa_circ_0067718 | 1.6896 | 0.044020 | ANF13 |
| 111208707 | 111211559 | chr6 | + | exonic | hsa_circ_0005954 | −1.5419 | 0.044027 | AMD1 |
| 20113099 | 20113439 | chr22 | + | intronic | hsa_circ_0092314 | 1.6315 | 0.044125 | RANBP1 |
| 23691404 | 23701688 | chr16 | + | exonic | hsa_circ_0038632 | 1.5718 | 0.044148 | PLK1 |
| 131071878 | 131084192 | chr7 | + | exonic | hsa_circ_0001747 | −1.7192 | 0.044294 | MKLN1 |
| 97026985 | 97029230 | chr14 | + | exonic | hsa_circ_0033126 | −1.8180 | 0.044301 | PAPOLA |
| 155411422 | 155448734 | chr6 | + | exonic | hsa_circ_0078383 | 1.5104 | 0.044302 | TIAM2 |
| 106739425 | 106782539 | chr2 | − | exonic | hsa_circ_0055945 | −1.6484 | 0.044335 | UXS1 |
| 114709055 | 114713283 | chr2 | + | exonic | hsa_circ_0002397 | −1.7202 | 0.044376 | ACTR3 |
| 34144719 | 34149837 | chr17 | + | exonic | N/A | −2.7064 | 0.044384 | TAF15 |
| 65284462 | 65290692 | chr5 | + | exonic | hsa_circ_0001492 | −2.5141 | 0.044470 | ERBB2IP |
| 131060182 | 131084192 | chr7 | + | exonic | hsa_circ_0001746 | −2.2957 | 0.044475 | MKLN1 |
| 159026298 | 159029782 | chr6 | + | exonic | hsa_circ_0078510 | −1.8955 | 0.044501 | TMEM181 |
| 103427642 | 103433430 | chr10 | − | exonic | hsa_circ_0019589 | −2.2273 | 0.044617 | FBXW4 |
| 183650117 | 183652292 | chr4 | + | exonic | hsa_circ_0071488 | 1.5714 | 0.044649 | TENM3 |
| 37971709 | 37976881 | chr8 | + | exonic | hsa_circ_0001790 | −2.1206 | 0.044654 | ASH2L |
| 31452908 | 31468067 | chr1 | − | exonic | hsa_circ_0002452 | −1.6214 | 0.044756 | PUM1 |
| 62462039 | 62470021 | chr11 | − | exonic | hsa_circ_0022505 | 1.6210 | 0.044776 | BSCL2 |
| 40176084 | 40176486 | chr17 | − | antisense | hsa_circ_0000764 | 1.6330 | 0.044826 | NKIRAS2 |
| 13435076 | 13466728 | chr11 | − | exonic | hsa_circ_0003234 | −1.8874 | 0.044850 | BTBD10 |
| 11521928 | 11527733 | chr19 | − | exonic | N/A | 1.5137 | 0.044878 | RGL3 |
| 388708 | 391408 | chr20 | + | exonic | hsa_circ_0059148 | 1.5633 | 0.044991 | RBCK1 |
| 53410256 | 53421972 | chr12 | + | exonic | hsa_circ_0026498 | −1.5654 | 0.045022 | EIF4B |
| 32483331 | 32493965 | chr3 | + | exonic | hsa_circ_0064679 | 1.5029 | 0.045048 | CMTM7 |
| 41774127 | 41787180 | chr19 | + | exonic | hsa_circ_0003079 | −2.1627 | 0.045056 | HNRNPUL1 |
| 88066714 | 88071617 | chr16 | + | exonic | hsa_circ_0040827 | −2.0108 | 0.045069 | BANP |
| 27106071 | 27106460 | chr6 | − | exonic | hsa_circ_0075900 | 1.6204 | 0.045071 | HIST1H2BK |
| 110068659 | 110074018 | chr9 | + | exonic | hsa_circ_0087861 | −1.9349 | 0.045106 | RAD23B |
| 23224688 | 23224917 | chr7 | + | exonic | hsa_circ_0005096 | −1.8399 | 0.045114 | NUPL2 |
| 36492117 | 36507984 | chr6 | − | exonic | hsa_circ_0003131 | −2.2429 | 0.045153 | STK38 |
| 23375403 | 23378804 | chr14 | − | exonic | hsa_circ_0004137 | −2.2794 | 0.045198 | RBM23 |
| 141595217 | 141616013 | chr8 | − | intronic | hsa_circ_0007313 | −1.5158 | 0.045278 | AGO2 |
| 33760537 | 33766320 | chr1 | + | exonic | hsa_circ_0011474 | 1.5403 | 0.045318 | ZNF362 |
| 125032151 | 125050082 | chr3 | − | exonic | hsa_circ_0001333 | −2.4674 | 0.045380 | ZNF148 |
| 36492117 | 36507981 | chr6 | − | exonic | N/A | −2.2956 | 0.045401 | STK38 |
| 99896085 | 99896878 | chr13 | + | exonic | hsa_circ_0030722 | −1.9184 | 0.045414 | UBAC2 |
| 36623756 | 36669878 | chr2 | + | exonic | hsa_circ_0002346 | −1.5245 | 0.045438 | CRIM1 |
| 103338299 | 103341453 | chr7 | − | exonic | hsa_circ_0081778 | 1.5293 | 0.045505 | RELN |
| 48371865 | 48396670 | chr4 | + | sense overlapping | N/A | −1.9103 | 0.045526 | SLAIN2 |
| 83940591 | 83945972 | chr16 | + | exonic | N/A | −1.7148 | 0.045641 | MLYCD |
| 63988322 | 64008672 | chr15 | − | exonic | hsa_circ_0035796 | −3.2916 | 0.045661 | HERC1 |
| 149962163 | 149984551 | chrX | − | exonic | hsa_circ_0001948 | −1.5084 | 0.045711 | CD99L2 |

TABLE 2-continued (SSRI R 8 week vs SSRI NR 8 week)

| TxStart | TxEnd | Chrom | Strand | circRNA type | Alias | Fold change | P-value | GeneSymbol |
|---|---|---|---|---|---|---|---|---|
| 9195548 | 9221997 | chr18 | + | exonic | hsa_circ_0046843 | −2.8282 | 0.045725 | ANKRD12 |
| 167915606 | 167919852 | chr5 | + | exonic | hsa_circ_0009145 | −2.2735 | 0.045736 | RARS |
| 122363276 | 122363756 | chr2 | − | exonic | hsa_circ_0007052 | −2.0318 | 0.045739 | CLASP1 |
| 65139030 | 65141244 | chr1 | + | exonic | hsa_circ_0012850 | 1.5004 | 0.045830 | CACHD1 |
| 77693968 | 77695598 | chr18 | − | intronic | hsa_circ_0006002 | 1.5076 | 0.045948 | PQLC1 |
| 49703556 | 49705398 | chr19 | + | exonic | hsa_circ_0051859 | 1.5173 | 0.045963 | TRPM4 |
| 155054511 | 155116273 | chr6 | + | exonic | hsa_circ_0078353 | −1.7722 | 0.046027 | SCAF8 |
| 179136873 | 179143295 | chr5 | + | exonic | hsa_circ_0001565 | −1.5844 | 0.046058 | CANX |
| 12039670 | 12046726 | chr10 | − | exonic | hsa_circ_0007448 | −1.5379 | 0.046071 | UPF2 |
| 65860865 | 65864782 | chr7 | − | exonic | N/A | 1.5360 | 0.046133 | LINC00174 |
| 86267693 | 86284096 | chr6 | − | exonic | hsa_circ_0001617 | −1.5183 | 0.046258 | SNX14 |
| 114674460 | 114699936 | chr2 | + | exonic | N/A | −1.7215 | 0.046367 | ACTR3 |
| 141811902 | 141820683 | chr3 | − | exonic | hsa_circ_0008304 | −1.8382 | 0.046378 | TFDP2 |
| 48371865 | 48385801 | chr4 | + | exonic | N/A | −2.6373 | 0.046509 | SLAIN2 |
| 107260799 | 107289013 | chr11 | − | exonic | hsa_circ_0006868 | −1.9292 | 0.046511 | CWF19L2 |
| 97141441 | 97170534 | chr10 | − | exonic | N/A | 1.5277 | 0.046545 | SORBS1 |
| 32377296 | 32385259 | chr1 | − | exonic | hsa_circ_0004893 | −1.7376 | 0.046583 | PTP4A2 |
| 122159084 | 122363756 | chr2 | − | exonic | hsa_circ_0056297 | −1.7929 | 0.046599 | CLASP1 |
| 80409378 | 80430686 | chr9 | − | exonic | hsa_circ_0087264 | −2.4072 | 0.046605 | GNAQ |
| 190656515 | 190670480 | chr2 | + | exonic | hsa_circ_0004776 | −1.5615 | 0.046615 | PMS1 |
| 28362054 | 28374937 | chr1 | − | exonic | hsa_circ_0008057 | −1.8104 | 0.046643 | EYA3 |
| 107459490 | 107460490 | chr2 | − | exonic | hsa_circ_0055957 | 1.8067 | 0.046694 | ST6GAL2 |
| 34574331 | 34574681 | chr6 | − | exonic | hsa_circ_0006757 | −1.7001 | 0.046725 | C6orf106 |
| 67864287 | 67868100 | chr1 | − | intergenic | N/A | 1.5204 | 0.046726 | |
| 48196616 | 48206619 | chr8 | + | exonic | hsa_circ_0002157 | −1.8452 | 0.046732 | SPIDR |
| 11348416 | 11350535 | chr3 | + | exonic | hsa_circ_0064288 | 1.6995 | 0.046734 | ATG7 |
| 25193245 | 25198922 | chr4 | − | antisense | N/A | 1.9436 | 0.046771 | SEPSECS-AS1 |
| 138837130 | 138837392 | chr5 | − | exonic | hsa_circ_0074217 | 1.5320 | 0.046805 | ECSCR |
| 85711279 | 85712272 | chr16 | − | exonic | hsa_circ_0040740 | 1.5195 | 0.046815 | GINS2 |
| 65941524 | 65944422 | chr17 | + | exonic | hsa_circ_0000798 | −1.8751 | 0.046839 | BPTP |
| 20083852 | 20089944 | chr11 | + | exonic | hsa_circ_0021493 | 1.5935 | 0.046840 | NAV2 |
| 70650274 | 70674110 | chr8 | − | exonic | hsa_circ_0084727 | 1.6762 | 0.046859 | SLCO5A1 |
| 64377407 | 64378670 | chr7 | + | exonic | N/A | 1.6343 | 0.046938 | ZNF273 |
| 233651859 | 233660931 | chr2 | + | exonic | hsa_circ_0058733 | −1.7097 | 0.046938 | GIGYF2 |
| 95099211 | 95119667 | chr5 | + | exonic | hsa_circ_0006725 | −1.9609 | 0.047076 | RHOBTB3 |
| 157129746 | 157160177 | chr7 | + | exonic | hsa_circ_0083171 | −1.8148 | 0.047079 | DNAJB6 |
| 48573339 | 48573890 | chr2 | + | exonic | hsa_circ_0001002 | −1.6941 | 0.047115 | FOXN2 |
| 50073902 | 50093067 | chr5 | + | exonic | hsa_circ_0072437 | −2.2580 | 0.047205 | PARP8 |
| 22024201 | 22029404 | chr22 | + | exonic | hsa_circ_0062426 | −1.8026 | 0.047409 | PPIL2 |
| 18256591 | 18258636 | chr6 | − | exonic | hsa_circ_0008846 | −2.0104 | 0.047507 | DEK |
| 120343758 | 120348235 | chr11 | + | exonic | hsa_circ_0009021 | −1.5432 | 0.047570 | ARHGEF12 |
| 55516082 | 55527154 | chr15 | − | sense overlapping | N/A | −2.2209 | 0.047597 | RAB27A |
| 137015277 | 137019820 | chr6 | − | exonic | hsa_circ_0006856 | −2.0130 | 0.047697 | MAP3K5 |
| 102195835 | 102196253 | chr11 | − | antisense | hsa_circ_0000352 | 1.7335 | 0.047705 | BIRC3 |
| 120916382 | 120930794 | chr11 | + | exonic | hsa_circ_0003302 | −2.3718 | 0.047713 | TBCEL |
| 37170553 | 37190529 | chr3 | − | exonic | hsa_circ_0003264 | −1.9574 | 0.047730 | LRRFIP2 |
| 153579366 | 153585514 | chr1 | − | exonic | hsa_circ_0014239 | 1.5154 | 0.047753 | S100A16 |
| 1158623 | 1159348 | chr1 | − | exonic | hsa_circ_0000002 | −1.9644 | 0.047770 | SDF4 |
| 63824845 | 63855207 | chr15 | + | exonic | hsa_circ_0002138 | −1.6135 | 0.047773 | USP3 |
| 32602655 | 32641231 | chr2 | + | exonic | hsa_circ_0053442 | −1.5845 | 0.047774 | BIRC6 |
| 24046127 | 24046439 | chr2 | − | exonic | hsa_circ_0003828 | −1.6246 | 0.047829 | ATAD2B |
| 53068519 | 53069224 | chr12 | − | exonic | hsa_circ_0026462 | 1.8157 | 0.047945 | KRT1 |
| 17847367 | 17851128 | chr8 | + | exonic | hsa_circ_0002887 | −1.5094 | 0.047984 | PCM1 |
| 37580879 | 37584043 | chr17 | − | exonic | hsa_circ_0007539 | −1.5822 | 0.047985 | MED1 |
| 23698789 | 23701688 | chr16 | + | exonic | hsa_circ_0038635 | 1.6967 | 0.048080 | PLK1 |
| 76580186 | 76588078 | chr15 | − | exonic | hsa_circ_0036408 | −1.5660 | 0.048085 | ETFA |
| 30618770 | 30619243 | chr6 | + | exonic | hsa_circ_0006109 | 1.5596 | 0.048124 | C6orf136 |
| 77632385 | 77633517 | chr11 | − | exonic | hsa_circ_0023736 | 1.7458 | 0.048150 | INTS4 |
| 2066700 | 2087531 | chr1 | + | exonic | hsa_circ_0009366 | 1.6087 | 0.048195 | PRKOZ |
| 76152218 | 76175765 | chr15 | + | exonic | hsa_circ_0036374 | −1.5280 | 0.048197 | UBE2Q2 |
| 58616696 | 58617086 | chr16 | − | exonic | hsa_circ_0039697 | −1.6532 | 0.048218 | CNOT1 |
| 41377566 | 41379880 | chr15 | − | exonic | hsa_circ_0004279 | −1.5379 | 0.048276 | INO80 |
| 7839009 | 7844817 | chr10 | + | exonic | hsa_circ_0007292 | −3.3660 | 0.048276 | ATP5C1 |
| 19345732 | 19383975 | chr18 | + | exonic | hsa_circ_0007504 | −1.6502 | 0.048324 | MIB1 |
| 35565024 | 35614627 | chr6 | − | sense overlapping | N/A | −1.7705 | 0.048390 | FKBP5 |
| 86292641 | 86301070 | chr9 | − | exonic | hsa_circ_0003715 | −1.8322 | 0.048401 | UBQLN1 |
| 109773499 | 109774408 | chr1 | + | exonic | hsa_circ_0007868 | −1.5277 | 0.048447 | SARS |
| 171851260 | 171969331 | chr3 | + | exonic | hsa_circ_0007148 | −2.6583 | 0.048508 | FNDC3B |
| 114377531 | 114397671 | chr1 | − | exonic | N/A | −1.8161 | 0.048542 | PTPN22 |
| 197541778 | 197547301 | chr3 | + | exonic | hsa_circ_0002266 | −1.5511 | 0.048553 | LRCH3 |
| 92264128 | 92268765 | chr14 | − | exonic | hsa_circ_0032969 | −2.2551 | 0.048606 | TC2A |
| 73418464 | 73431944 | chr11 | − | exonic | hsa_circ_0003908 | −1.9334 | 0.048626 | RAB6A |
| 9208654 | 9239554 | chr18 | + | intronic | hsa_circ_0005715 | −1.7581 | 0.048764 | RP11-21J18.1 |

TABLE 2-continued (SSRI R 8 week vs SSRI NR 8 week)

| TxStart | TxEnd | Chrom | Strand | circRNA type | Alias | Fold change | P-value | GeneSymbol |
|---|---|---|---|---|---|---|---|---|
| 78197050 | 78201759 | chr17 | + | exonic | N/A | 1.5480 | 0.048785 | SLC26A11 |
| 7806826 | 7807115 | chr17 | + | intronic | N/A | 1.6387 | 0.049059 | CHD3 |
| 40477365 | 40477843 | chr15 | + | exonic | hsa_circ_0008946 | 1.5282 | 0.049080 | BUB1B |
| 82984689 | 82989872 | chr11 | − | exonic | N/A | −1.6631 | 0.049104 | CCDC90B |
| 11778020 | 11830089 | chr16 | − | exonic | hsa_circ_0037866 | 1.6774 | 0.049113 | TXNDC11 |
| 187604954 | 187618776 | chr2 | + | exonic | hsa_circ_0057328 | 1.5921 | 0.049150 | FAM171B |
| 62171487 | 62175109 | chr1 | − | sense overlapping | hsa_circ_0000077 | 1.6430 | 0.049202 | TM2D1 |
| 77336007 | 77336863 | chr11 | − | exonic | hsa_circ_0000343 | −2.0494 | 0.049285 | CLNS1A |
| 89123719 | 89131833 | chr14 | − | exonic | N/A | 1.6016 | 0.049325 | EML5 |
| 102542007 | 102559661 | chr12 | + | exonic | hsa_circ_0000432 | 1.5082 | 0.049413 | PARPBP |
| 94645539 | 94649052 | chr9 | − | exonic | N/A | 1.6324 | 0.049423 | ROR2 |
| 118619175 | 118619412 | chr12 | − | exonic | hsa_circ_0000446 | −1.6764 | 0.049493 | TAOK3 |
| 32381491 | 32385259 | chr1 | − | intronic | hsa_circ_0005067 | −1.9216 | 0.049522 | RP11-84A19.4 |
| 7181356 | 7189555 | chr6 | + | exonic | hsa_circ_0007429 | −2.3511 | 0.049537 | RREB1 |
| 7844232 | 7844817 | chr10 | + | exonic | hsa_circ_0017675 | −2.7279 | 0.049551 | ATP5C1 |
| 108175911 | 108179689 | chr13 | − | intronic | hsa_circ_0003145 | 1.6377 | 0.049574 | FAM155A |
| 9991948 | 9995685 | chr1 | − | exonic | hsa_circ_0007803 | −1.7543 | 0.049601 | LZIC |
| 83793096 | 83796975 | chr4 | − | exonic | hsa_circ_0003549 | −1.5754 | 0.049611 | SEC31A |
| 59999085 | 60002460 | chr17 | − | exonic | hsa_circ_0007759 | −1.5722 | 0.049755 | INTS2 |
| 33953282 | 33963789 | chr9 | − | exonic | hsa_circ_0001847 | −1.6689 | 0.049773 | UBAP2 |
| 141622461 | 141640905 | chr3 | + | exonic | N/A | 1.5285 | 0.049776 | ATP1B3 |
| 63970043 | 64005864 | chr15 | − | exonic | hsa_circ_0035775 | −1.6925 | 0.049777 | HERC1 |
| 23015828 | 23030758 | chr7 | − | exonic | hsa_circ_0005251 | −1.7279 | 0.049821 | FAM126A |
| 77296190 | 77296528 | chr5 | + | antisense | hsa_circ_0001499 | 1.5316 | 0.049887 | AP3B1 |
| 80042674 | 80042829 | chr17 | − | exonic | N/A | 1.6185 | 0.049901 | FASN |
| 164514761 | 164515093 | chr4 | + | antisense | hsa_circ_0001455 | 1.8745 | 0.049905 | MARCH1 |

TABLE 3

(SNRI R baseline vs SNRI NR baseline)

| TxStart | TxEnd | Chrom | Strand | circRNA type | Alias | Fold change | P-value | GeneSymbol |
|---|---|---|---|---|---|---|---|---|
| 8525984 | 8568734 | chr1 | − | exonic | hsa__circ__0009574 | 1.5314 | 0.000185 | RERE |
| 42641806 | 42641893 | chr20 | + | intronic | hsa__circ__0001160 | 1.5821 | 0.000414 | TOX2 |
| 77616277 | 77620283 | chr8 | + | exonic | hsa__circ__0084789 | 2.1368 | 0.002435 | ZFHX4 |
| 31849672 | 31852977 | chr14 | − | exonic | hsa__circ__0031570 | 1.8765 | 0.002458 | HEATR5A |
| 187498055 | 187506315 | chr2 | + | exonic | hsa__circ__0057319 | 1.8323 | 0.002492 | ITGAV |
| 66923610 | 66990707 | chr12 | − | exonic | hsa__circ__0099053 | 2.2638 | 0.002535 | GRIP1 |
| 129180070 | 129188260 | chr3 | + | exonic | N/A | 1.7123 | 0.002576 | IFT122 |
| 133534776 | 133536765 | chr5 | − | exonic | hsa__circ__0073942 | 1.5742 | 0.003330 | PPP2CA |
| 70696691 | 70703013 | chr10 | + | exonic | hsa__circ__0007097 | 1.6326 | 0.003519 | DDX50 |
| 61833638 | 61835159 | chr20 | − | exonic | hsa__circ__0004858 | 1.8825 | 0.003672 | YTHDF1 |
| 8555122 | 8601377 | chr1 | − | exonic | hsa__circ__0009581 | 2.0163 | 0.003687 | RERE |
| 156468903 | 56489628 | chr6 | − | intergenic | hsa__circ__0001655 | 1.6003 | 0.004080 | |
| 35615069 | 35633000 | chr13 | + | exonic | hsa__circ__0029975 | 1.9065 | 0.005023 | NBEA |
| 149246283 | 149250107 | chr7 | − | exonic | N/A | 1.9263 | 0.005404 | ZNF767P |
| 128488846 | 128489036 | chr7 | + | exonic | hsa__circ__0082218 | 1.8877 | 0.005522 | FLNC |
| 4845635 | 4848517 | chr17 | + | exonic | hsa__circ__0041623 | 1.7525 | 0.005843 | RNF167 |
| 153940503 | 153944604 | chrX | − | exonic | N/A | 1.5497 | 0.005910 | GAB3 |
| 73015794 | 73017356 | chr17 | + | exonic | hsa__circ__0045581 | 1.5384 | 0.006169 | ICT1 |
| 7754370 | 7755918 | chr18 | + | intronic | hsa__circ__0008584 | 1.7102 | 0.006179 | PTPRM |
| 29191568 | 29192081 | chr22 | − | sense overlapping | hsa__circ__0001216 | 2.0594 | 0.006345 | XBP1 |
| 31631798 | 31638674 | chr14 | − | sense overlapping | N/A | 1.5782 | 0.006617 | HECTD1 |
| 67351934 | 67352712 | chr11 | + | exonic | hsa__circ__0023115 | 1.8745 | 0.006976 | GSTP1 |
| 74533340 | 74562028 | chr9 | + | exonic | N/A | 1.9416 | 0.006976 | C9orf85 |
| 110832905 | 110834257 | chr12 | − | exonic | hsa__circ__0028198 | 2.4445 | 0.007172 | ANAPC7 |
| 21788274 | 21810728 | chr12 | − | exonic | hsa__circ__0025597 | 1.8613 | 0.007603 | LDHB |
| 69853296 | 69856305 | chr12 | + | sense overlapping | N/A | 1.5833 | 0.007736 | RP11-956E11.1 |
| 28090104 | 28096621 | chr15 | − | exonic | hsa__circ__0034189 | 1.7468 | 0.007904 | OCA2 |
| 151771875 | 151789457 | chr4 | − | exonic | hsa__circ__0071224 | 2.0052 | 0.008006 | LRBA |
| 74433139 | 74434317 | chr7 | + | exonic | hsa__circ__0080638 | 1.8834 | 0.008141 | GATSL1 |
| 23395341 | 23396869 | chr14 | − | exonic | hsa__circ__0002928 | 1.5771 | 0.008423 | PRMT5 |
| 21335426 | 21338430 | chr20 | + | exonic | N/A | 1.5627 | 0.008796 | XRN2 |
| 103352525 | 103363738 | chr14 | + | exonic | hsa__circ__0000570 | 1.7182 | 0.008839 | TRAF3 |
| 22108546 | 22117269 | chrX | + | exonic | hsa__circ__0090069 | 2.2282 | 0.008936 | PHEX |
| 20573977 | 20577388 | chr6 | + | intronic | N/A | 2.4541 | 0.009301 | CDKAL1 |
| 242028602 | 242033847 | chr2 | − | exonic | N/A | 1.7173 | 0.009384 | MTERFD2 |

TABLE 3-continued (SNRI R baseline vs SNRI NR baseline)

| TxStart | TxEnd | Chrom | Strand | circRNA type | Alias | Fold change | P-value | GeneSymbol |
|---|---|---|---|---|---|---|---|---|
| 154548756 | 154553990 | chr4 | + | exonic | hsa_circ_0071312 | 1.6730 | 0.009507 | KIAA0922 |
| 36245469 | 36247930 | chr19 | − | exonic | hsa_circ_0050649 | 1.9776 | 0.009699 | HSPB6 |
| 75823317 | 75875495 | chr6 | − | exonic | hsa_circ_0077032 | 1.6710 | 0.009780 | COL12A1 |
| 96485180 | 96489456 | chr13 | − | exonic | hsa_circ_0008274 | 2.0711 | 0.009826 | UGGT2 |
| 158870027 | 158873300 | chr6 | + | exonic | hsa_circ_0002073 | 1.5939 | 0.009869 | TULP4 |
| 1599765 | 1608285 | chr1 | − | exonic | hsa_circ_0009306 | 1.5131 | 0.010222 | SLC35E2B |
| 3185580 | 3209234 | chr10 | − | exonic | hsa_circ_0017502 | 1.6121 | 0.010247 | PITRM1 |
| 37061800 | 37067498 | chr3 | + | exonic | N/A | 2.0940 | 0.010414 | MLH1 |
| 220253068 | 220263134 | chr1 | − | sense overlapping | hsa_circ_0000185 | 2.0243 | 0.010426 | BPNT1 |
| 12359258 | 12364785 | chr1 | + | exonic | hsa_circ_0007677 | 1.5749 | 0.010833 | VPS13D |
| 19746674 | 19775434 | chr16 | + | exonic | hsa_circ_0000680 | 1.7571 | 0.010943 | IQCK |
| 27326903 | 27328069 | chr21 | − | exonic | hsa_circ_0003323 | 1.6652 | 0.011005 | APP |
| 17907047 | 17953998 | chr1 | + | exonic | hsa_circ_0010210 | 1.8775 | 0.011183 | ARHGEF10L |
| 95518727 | 95524317 | chr8 | − | exonic | hsa_circ_0084904 | 1.8499 | 0.011192 | KIAA1429 |
| 79607545 | 79612827 | chr6 | + | exonic | hsa_circ_0077109 | 2.0813 | 0.011296 | IRAK1BP1 |
| 35615069 | 35644989 | chr13 | + | exonic | hsa_circ_0029976 | 1.8871 | 0.011323 | NBEA |
| 45921422 | 45972988 | chr22 | + | exonic | hsa_circ_0063745 | 1.7949 | 0.011450 | FBLN1 |
| 48466115 | 48472118 | chr20 | + | exonic | hsa_circ_0006359 | 1.6020 | 0.011682 | SLC9A8 |
| 3474817 | 3477249 | chr17 | − | exonic | N/A | 1.5577 | 0.011682 | TRPV1 |
| 228401141 | 228402799 | chr1 | + | exonic | hsa_circ_0016771 | 1.9198 | 0.011838 | OBSCN |
| 189851784 | 189858808 | chr2 | + | exonic | hsa_circ_0057362 | 2.1329 | 0.011926 | COL3A1 |
| 3777940 | 3778768 | chr11 | − | intronic | N/A | 1.8378 | 0.011989 | NUP98 |
| 62283373 | 62304039 | chr11 | − | exonic | hsa_circ_0022429 | 1.5531 | 0.012131 | AHNAK |
| 151130894 | 151131115 | chrX | − | exonic | hsa_circ_0091710 | 2.0672 | 0.012280 | GABRE |
| 116734383 | 116744352 | chr11 | − | exonic | hsa_circ_0000357 | 1.7365 | 0.012386 | SIK3 |
| 110819556 | 110834257 | chr12 | − | exonic | hsa_circ_0005785 | 1.9825 | 0.012534 | ANAPC7 |
| 12632755 | 12639440 | chr1 | − | exonic | hsa_circ_0010020 | 1.5988 | 0.012632 | DHRS3 |
| 25628813 | 25631937 | chr17 | + | exonic | hsa_circ_0042488 | 1.7015 | 0.012753 | WSB1 |
| 55282872 | 55287883 | chr18 | − | exonic | hsa_circ_0047771 | 1.7678 | 0.012783 | NARS |
| 37623043 | 37632999 | chr8 | + | exonic | hsa_circ_0083932 | 1.9672 | 0.012829 | PROSC |
| 94653105 | 94669388 | chr10 | + | exonic | hsa_circ_0019171 | 2.4829 | 0.012858 | EXOC6 |
| 76173360 | 76187046 | chr14 | + | exonic | hsa_circ_0032704 | 1.5694 | 0.012973 | TTLL5 |
| 98643320 | 98645505 | chr7 | − | exonic | N/A | 2.4345 | 0.013059 | SMURF1 |
| 186375214 | 186388209 | chr1 | + | sense overlapping | hsa_circ_0000166 | 1.6053 | 0.013324 | C1orf27 |
| 103236273 | 103237246 | chr8 | − | exonic | hsa_circ_0003794 | 1.6891 | 0.013353 | RRM2B |
| 25478063 | 25487229 | chr13 | − | exonic | hsa_circ_0029775 | 1.7763 | 0.013529 | CENPJ |
| 55621921 | 55634000 | chr15 | + | exonic | hsa_circ_0035381 | 1.5991 | 0.013706 | PIGB |
| 110826316 | 110834257 | chr12 | − | exonic | hsa_circ_0028196 | 1.8218 | 0.014350 | ANAPC7 |
| 57237616 | 57250507 | chr4 | − | exonic | N/A | 2.0531 | 0.014492 | AASDH |
| 153555574 | 153562137 | chr7 | + | intergenic | N/A | 1.5521 | 0.014562 | |
| 42604156 | 42604482 | chr12 | − | exonic | hsa_circ_0000392 | 1.9209 | 0.014686 | YAF2 |
| 204154487 | 204157049 | chr2 | + | exonic | hsa_circ_0005307 | 1.6525 | 0.014758 | CYP20A1 |
| 75104453 | 76279715 | chr7 | − | sense overlapping | hsa_circ_0006766 | 1.6305 | 0.014949 | CCL24 |
| 126434011 | 126452004 | chr6 | + | antisense | hsa_circ_0130586 | 1.8855 | 0.015075 | MIR5695 |
| 170650618 | 170658898 | chr4 | − | exonic | hsa_circ_0071439 | 1.6607 | 0.015248 | C4orf27 |
| 64863339 | 64868113 | chr5 | + | exonic | hsa_circ_0072697 | 2.0356 | 0.015286 | PPWD1 |
| 48817428 | 48842572 | chr8 | − | exonic | hsa_circ_0084429 | 1.8985 | 0.015512 | PRKDC |
| 111800296 | 111853435 | chr9 | − | exonic | hsa_circ_0087903 | 1.5360 | 0.015534 | TMEM245 |
| 39543618 | 39545297 | chr14 | − | exonic | hsa_circ_0031724 | 1.6685 | 0.015591 | SEC23A |
| 100443764 | 100494030 | chr8 | + | exonic | hsa_circ_0005984 | 1.5901 | 0.015591 | VPS13B |
| 136035782 | 136048826 | chr3 | + | exonic | N/A | 1.5702 | 0.015697 | PCCB |
| 46783379 | 46798673 | chr18 | − | exonic | hsa_circ_0047641 | 1.5034 | 0.016221 | DYM |
| 36245469 | 36246795 | chr19 | − | exonic | hsa_circ_0050648 | 1.8499 | 0.016536 | HSPB6 |
| 116335174 | 116444414 | chr10 | − | exonic | hsa_circ_0020076 | 1.7048 | 0.016584 | ABLIM1 |
| 35236117 | 35236221 | chr20 | + | exonic | hsa_circ_0001151 | 1.5493 | 0.017307 | C20orf24 |
| 95511601 | 95550574 | chr8 | − | exonic | hsa_circ_0084903 | 2.0644 | 0.017344 | KIAA1429 |
| 3201105 | 3202522 | chr10 | − | exonic | hsa_circ_0017510 | 1.5267 | 0.017962 | PITRM1 |
| 95504879 | 95550574 | chr8 | − | exonic | hsa_circ_0084900 | 2.0336 | 0.018345 | KIAA1429 |
| 113321942 | 113322076 | chr2 | + | exonic | hsa_circ_0056146 | 1.7166 | 0.018453 | POLR1B |
| 26918715 | 26926848 | chr17 | − | intronic | N/A | 1.5737 | 0.018719 | RP11-192H23.4 |
| 95549330 | 95550574 | chr8 | − | exonic | hsa_circ_0006896 | 2.0413 | 0.019136 | KIAA1429 |
| 18624903 | 18633652 | chr7 | + | exonic | hsa_circ_0001680 | 1.5140 | 0.019375 | HDAC9 |
| 6263945 | 6312055 | chr18 | − | exonic | hsa_circ_0000824 | 1.9046 | 0.019661 | L3MBTL4 |
| 90670648 | 90670832 | chr6 | + | antisense | hsa_circ_0001623 | 1.5725 | 0.020241 | BACH2 |
| 74385612 | 74397235 | chr17 | − | exonic | hsa_circ_0045801 | 1.6042 | 0.020467 | UBE2O |
| 212977661 | 212977993 | chr1 | + | exonic | hsa_circ_0016404 | 1.9769 | 0.020961 | TATDN3 |
| 31947298 | 31949280 | chr15 | − | exonic | hsa_circ_0034325 | 1.7913 | 0.021334 | OTUD7A |
| 85685750 | 85687725 | chr11 | − | exonic | hsa_circ_0023881 | −1.7042 | 0.021393 | PICALM |
| 75214169 | 75239275 | chr10 | − | exonic | hsa_circ_0018814 | 1.6793 | 0.021407 | PPP3CB |
| 26343183 | 26349097 | chr13 | + | exonic | N/A | 1.6138 | 0.022653 | ATP8A2 |
| 175211289 | 175211585 | chr4 | + | intronic | N/A | 1.5249 | 0.022969 | CEP44 |

TABLE 3-continued (SNRI R baseline vs SNRI NR baseline)

| TxStart | TxEnd | Chrom | Strand | circRNA type | Alias | Fold change | P-value | GeneSymbol |
|---|---|---|---|---|---|---|---|---|
| 46515157 | 46534363 | chr11 | − | exonic | hsa_circ_0007061 | 1.7079 | 0.023377 | AMBRA1 |
| 42980912 | 42981094 | chr6 | − | sense overlapping | hsa_circ_0001606 | 1.7203 | 0.023850 | MEA1 |
| 52946553 | 52950230 | chr3 | − | exonic | hsa_circ_0001310 | 1.9662 | 0.023964 | SFMBT1 |
| 145379620 | 145383716 | chr5 | + | exonic | N/A | 1.7502 | 0.024021 | SH3RF2 |
| 17629628 | 17633596 | chr4 | + | sense overlapping | N/A | 1.6784 | 0.024134 | MED28 |
| 39923846 | 39924209 | chr19 | − | exonic | hsa_circ_0050998 | 1.5806 | 0.024144 | RPS16 |
| 46529740 | 46534363 | chr11 | − | exonic | hsa_circ_0003110 | 1.5719 | 0.024580 | AMBRA1 |
| 49394608 | 49395791 | chr3 | − | exonic | hsa_circ_0065638 | 1.5023 | 0.024621 | GPX1 |
| 29063135 | 29096287 | chr1 | + | exonic | hsa_circ_0011164 | 2.5323 | 0.024752 | YTHDF2 |
| 110820647 | 10834257 | chr12 | − | exonic | hsa_circ_0028190 | 1.9137 | 0.025125 | ANAPC7 |
| 35148956 | 35149174 | chr9 | − | sense overlapping | N/A | 2.5985 | 0.025289 | RP11-182N22.7 |
| 29190547 | 29196560 | chr22 | − | exonic | hsa_circ_0062722 | 1.5762 | 0.025567 | XBP1 |
| 20240809 | 20240905 | chr2 | − | intronic | hsa_circ_0000981 | 1.7401 | 0.025600 | LAPTM4A |
| 41133645 | 41134997 | chr13 | − | exonic | hsa_circ_0030042 | 2.0631 | 0.025761 | FOXO1 |
| 66589113 | 66590145 | chr11 | + | exonic | hsa_circ_0023033 | 1.5498 | 0.025994 | C11orf80 |
| 49094294 | 49095323 | chr3 | − | exonic | hsa_circ_0002561 | 1.6964 | 0.026158 | QRICH1 |
| 100035289 | 100052403 | chr2 | − | exonic | hsa_circ_0001052 | 1.8484 | 0.026198 | REV1 |
| 114541671 | 114541925 | chr9 | + | antisense | N/A | 1.5307 | 0.026393 | C9orf84 |
| 37583953 | 37584043 | chr17 | − | exonic | hsa_circ_0043438 | 1.5818 | 0.026429 | MED1 |
| 115837905 | 115840678 | chr5 | − | exonic | hsa_circ_0073647 | 1.5977 | 0.026534 | SEMA6A |
| 72205086 | 72222904 | chr4 | + | exonic | hsa_circ_0008676 | 1.8693 | 0.026813 | SLC4A4 |
| 85685750 | 85695016 | chr11 | − | exonic | hsa_circ_0006629 | −1.5051 | 0.026869 | PICALM |
| 62782684 | 62793527 | chr17 | − | exonic | hsa_circ_0002056 | 1.5234 | 0.027556 | PLEKHM1P |
| 49054148 | 49063055 | chr12 | − | exonic | hsa_circ_0026036 | 1.7517 | 0.027752 | KANSL2 |
| 122031337 | 122031452 | chr12 | + | sense overlapping | N/A | 1.5583 | 0.027814 | RP13-941N14.1 |
| 37115061 | 37122590 | chr5 | − | exonic | N/A | 1.5184 | 0.027957 | C5orf42 |
| 126434011 | 126498481 | chr6 | + | sense overlapping | N/A | 1.6732 | 0.028093 | RP11-527F13.1 |
| 36375930 | 36390613 | chr9 | − | exonic | hsa_circ_0001856 | 1.6307 | 0.028141 | RNF38 |
| 334399 | 336173 | chr19 | − | exonic | N/A | 1.6513 | 0.028347 | MIER2 |
| 108603170 | 108615162 | chr4 | − | exonic | hsa_circ_0005965 | 1.9128 | 0.028381 | PAPSS1 |
| 9482139 | 9506356 | chr3 | + | exonic | hsa_circ_0064136 | 1.5789 | 0.028685 | SETD5 |
| 158204420 | 158223483 | chr5 | − | exonic | hsa_circ_0074816 | 1.6913 | 0.029101 | EBF1 |
| 138979956 | 139003046 | chr5 | + | exonic | hsa_circ_0004503 | 2.0622 | 0.029174 | UBE2D2 |
| 25151491 | 25162936 | chr16 | + | exonic | N/A | 1.7188 | 0.029291 | LCMT1 |
| 131271154 | 131271376 | chr9 | + | exonic | hsa_circ_0088807 | 1.7405 | 0.029368 | GLE1 |
| 183831943 | 183848110 | chr2 | − | exonic | N/A | 1.7430 | 0.029497 | NCKAP1 |
| 129928347 | 129937061 | chr9 | + | exonic | N/A | 1.6161 | 0.029959 | RALGPS1 |
| 72020039 | 72022817 | chr12 | − | exonic | hsa_circ_0008912 | 1.7477 | 0.029971 | ZFC3H1 |
| 48839753 | 48842572 | chr8 | − | exonic | hsa_circ_0084443 | 1.7066 | 0.030016 | PRKDC |
| 73414865 | 73428368 | chr15 | + | exonic | N/A | 1.7248 | 0.030460 | NEO1 |
| 45545508 | 45545708 | chr21 | + | intronic | hsa_circ_0092315 | 2.0012 | 0.030584 | PWP2 |
| 59955247 | 59958532 | chr17 | − | exonic | hsa_circ_0045038 | 1.6032 | 0.030693 | INTS2 |
| 36668400 | 36749456 | chr2 | + | exonic | hsa_circ_0053967 | 1.6736 | 0.030940 | CRIM1 |
| 80160631 | 80173542 | chr5 | + | sense overlapping | N/A | 1.9774 | 0.031045 | MSH3 |
| 44441761 | 44443967 | chr1 | + | exonic | hsa_circ_0012123 | 1.6493 | 0.031078 | ATP6V0B |
| 112171726 | 112171872 | chr12 | + | exonic | hsa_circ_0028299 | 1.9826 | 0.031174 | ACAD10 |
| 3252272 | 3256234 | chr18 | + | exonic | hsa_circ_0046753 | 1.7946 | 0.031255 | MYL12A |
| 31764759 | 31766195 | chr1 | 1 | exonic | hsa_circ_0011267 | 1.7769 | 0.031424 | SNRNP40 |
| 3802927 | 3808661 | chr17 | 1 | exonic | hsa_circ_0000735 | 1.5943 | 0.031627 | P2RX1 |
| 137716445 | 137717750 | chr9 | + | exonic | hsa_circ_0003596 | 1.5664 | 0.031822 | COL541 |
| 30142548 | 30149539 | chr20 | + | exonic | hsa_circ_0059702 | 1.6462 | 0.032055 | HM13 |
| 36749234 | 36749456 | chr2 | + | exonic | hsa_circ_0054021 | 1.6854 | 0.032274 | CRIM1 |
| 32677771 | 32678011 | chr20 | − | intronic | hsa_circ_0092291 | 1.5634 | 0.032295 | EIF2S2 |
| 14685190 | 14685289 | chr12 | + | intronic | hsa_circ_0000379 | 1.8548 | 0.032353 | RP11-502N13.2 |
| 134032815 | 134044578 | chr5 | + | exonic | hsa_circ_0003528 | 1.5357 | 0.032783 | SEC24A |
| 44530905 | 44531243 | chr20 | − | exonic | hsa_circ_0060558 | 1.7934 | 0.033468 | PLTP |
| 128317617 | 128323309 | chr7 | + | exonic | hsa_circ_0082182 | 1.5906 | 0.033557 | FAM71F2 |
| 27820936 | 27830906 | chr2 | + | exonic | hsa_circ_0053294 | 1.6581 | 0.033827 | ZNF512 |
| 19638320 | 19638629 | chr1 | − | sense overlapping | N/A | 1.6681 | 0.034556 | AKR7A2 |
| 4029116 | 4033441 | chr16 | − | exonic | hsa_circ_0007586 | 1.5635 | 0.034738 | ADCY9 |
| 136770511 | 136771563 | chr5 | − | intronic | N/A | 1.7884 | 0.034912 | SPOCK |
| 118897646 | 118898434 | chr11 | − | exonic | hsa_circ_0024516 | 1.5564 | 0.035319 | SLC37A4 |
| 50388196 | 50399175 | chr12 | − | exonic | hsa_circ_0026195 | 2.6272 | 0.036108 | RACGAP1 |
| 50850356 | 50850568 | chr12 | + | intronic | N/A | 1.5686 | 0.036172 | LARP4 |
| 99589361 | 99607298 | chr9 | − | exonic | N/A | 1.7981 | 0.036247 | ZNF782 |
| 27473614 | 27474913 | chr16 | − | exonic | hsa_circ_0038737 | 1.7644 | 0.037044 | GTF3C1 |
| 10798306 | 10799354 | chr19 | + | sense overlapping | hsa_circ_0000890 | 1.5262 | 0.037457 | ILF3 |

TABLE 3-continued (SNRI R baseline vs SNRI NR baseline)

| TxStart | TxEnd | Chrom | Strand | circRNA type | Alias | Fold change | P-value | GeneSymbol |
|---|---|---|---|---|---|---|---|---|
| 13532533 | 13581264 | chr20 | – | intronic | N/A | 1.6246 | 0.037814 | TASP1 |
| 111150126 | 111152952 | chr12 | – | intergenic | N/A | 1.7076 | 0.037820 | |
| 173662 | 173882 | chr5 | + | intronic | hsa_circ_0092371 | 1.8132 | 0.038094 | PLEKHG4B |
| 97535283 | 97563284 | chr9 | + | exonic | hsa_circ_0002191 | 1.6034 | 0.038528 | C9orf3 |
| 206889066 | 206889235 | chr2 | – | intronic | N/A | 1.6723 | 0.039391 | INO80D |
| 193181194 | 193205486 | chr1 | + | exonic | hsa_circ_0000167 | 1.7749 | 0.039507 | CDC73 |
| 32198899 | 32199141 | chr20 | + | exonic | hsa_circ_0059859 | 1.6925 | 0.039524 | CBFA2T2 |
| 38656908 | 38666209 | chr15 | + | intergenic | N/A | 1.5933 | 0.039614 | |
| 109952549 | 109964548 | chr1 | – | exonic | N/A | 1.8090 | 0.040483 | PSMA5 |
| 71433787 | 72057538 | chr15 | + | exonic | hsa_circ_0036127 | 1.5906 | 0.040640 | THSD4 |
| 72797242 | 72804408 | chrX | + | exonic | hsa_circ_0091072 | 1.9060 | 0.040678 | CHIC1 |
| 31789187 | 31803431 | chr13 | + | exonic | hsa_circ_0002635 | 2.0545 | 0.040997 | B3GALTL |
| 158204420 | 158223486 | chr5 | – | exonic | hsa_circ_0074817 | 1.7059 | 0.041058 | EBF1 |
| 27440281 | 27440777 | chr1 | – | intronic | N/A | 1.5158 | 0.041332 | SLC9A1 |
| 114860749 | 114875148 | chr9 | – | exonic | hsa_circ_0088046 | 1.5252 | 0.041413 | SUSD1 |
| 100899717 | 100904280 | chr8 | – | exonic | N/A | 1.6879 | 0.041836 | COX6C |
| 74948073 | 74948409 | chr15 | – | exonic | hsa_circ_0004401 | 1.5143 | 0.042836 | EDC3 |
| 41826780 | 41837620 | chr13 | – | exonic | hsa_circ_0030062 | 1.5739 | 0.043026 | MTRF1 |
| 109336203 | 109339348 | chr1 | + | exonic | hsa_circ_0000100 | 1.7133 | 0.043133 | STXBP3 |
| 49713126 | 49720934 | chr3 | + | exonic | hsa_circ_0065673 | 1.5791 | 0.043865 | APEH |
| 75116657 | 75116733 | chr11 | + | intronic | hsa_circ_0023617 | 1.5118 | 0.044063 | RPS3 |
| 27151596 | 27151827 | chr8 | – | exonic | hsa_circ_0083756 | 2.0602 | 0.044743 | TRIM35 |
| 118464661 | 118466796 | chr10 | – | exonic | hsa_circ_0020117 | 1.8173 | 0.045203 | HSPA12A |
| 44788577 | 44789336 | chr15 | + | exonic | hsa_circ_0007705 | 1.6295 | 0.045462 | CTDSPL2 |
| 93141396 | 93148280 | chr11 | + | exonic | N/A | 1.5306 | 0.045499 | CCDC67 |
| 7143737 | 7144998 | chr17 | – | exonic | hsa_circ_0041782 | 1.5484 | 0.046458 | GABARAP |
| 71369656 | 71370884 | chr11 | + | intergenic | N/A | 1.6307 | 0.046581 | |
| 19070216 | 19076702 | chr9 | – | exonic | hsa_circ_0086444 | 1.5799 | 0.046860 | HAUS6 |
| 57048187 | 57069951 | chr18 | – | sense overlapping | N/A | 1.6312 | 0.046930 | XLOC_012858 |
| 42509874 | 42510962 | chr19 | – | exonic | hsa_circ_0051260 | 1.5434 | 0.046978 | GRIK5 |
| 57430575 | 57430887 | chr17 | + | exonic | hsa_circ_0005600 | 1.6191 | 0.047605 | YPEL2 |
| 11940357 | 11940700 | chr16 | – | exonic | hsa_circ_0000673 | 1.7406 | 0.047949 | RSL1D1 |
| 29917108 | 29917448 | chr16 | + | exonic | N/A | 1.5199 | 0.048181 | ASPHD1 |
| 2521314 | 2521523 | chr1 | – | antisense | hsa_circ_0000010 | 1.7186 | 0.048586 | FAM213B |
| 114840817 | 114842445 | chr9 | – | exonic | hsa_circ_0088036 | 1.5323 | 0.048757 | SUSD1 |
| 107419754 | 107420500 | chr6 | – | exonic | N/A | 1.9173 | 0.049657 | BEND3 |
| 113856936 | 113891590 | chr2 | + | exonic | hsa_circ_0056159 | 1.6672 | 0.049768 | IL1RN |

TABLE 4

(SNRI R 8 week vs SNRI NR 8 week)

| TxStart | TxEnd | Chrom | Strand | circRNA type | Alias | Fold change | P-value | GeneSymbol |
|---|---|---|---|---|---|---|---|---|
| 136770511 | 136771563 | chr5 | – | intronic | N/A | 1.5022 | 0.030441 | SPOCK1 |
| 78022381 | 78032779 | chr17 | + | exonic | N/A | 1.5760 | 0.012158 | CCDC40 |
| 72020039 | 72022817 | chr12 | – | exonic | hsa_circ_0008912 | 1.5016 | 0.037839 | ZFC3H1 |
| 58275961 | 58316858 | chr2 | + | exonic | hsa_circ_0120478 | −1.5220 | 0.035991 | VRK2 |
| 66044716 | 66053776 | chr15 | – | exonic | hsa_circ_0035957 | −1.5114 | 0.014728 | DENND4A |
| 39607406 | 39629569 | chr18 | + | exonic | hsa_circ_0007765 | −1.5176 | 0.046923 | PIK3C3 |

TABLE 5

(SSRI R 8 week vs SSRI R baseline)

| TxStart | TxEnd | Chrom | Strand | circRNA type | Alias | Fold change | P-value | GeneSymbol |
|---|---|---|---|---|---|---|---|---|
| 126434011 | 126496057 | chr6 | + | antisense | hsa_circ_0130587 | 2.0698 | 0.001644 | MIR5695 |
| 101654702 | 101656154 | chr10 | – | exonic | hsa_circ_0092382 | −2.4354 | 0.003171 | DNMBP |
| 73114707 | 73115261 | chr7 | – | sense overlapping | hsa_circ_0009012 | −1.7034 | 0.003668 | STX1A |
| 17370097 | 17370831 | chr19 | – | exonic | hsa_circ_0049965 | −1.7113 | 0.003762 | USHBP1 |
| 111800296 | 111853435 | chr9 | – | exonic | hsa_circ_0087903 | −1.7012 | 0.005777 | TMEM245 |
| 18945987 | 18983955 | chr18 | + | exonic | hsa_circ_0003653 | −1.7079 | 0.006069 | GREB1L |
| 77147164 | 77147491 | chr3 | + | exonic | hsa_circ_0066556 | 1.6139 | 0.006441 | ROBO2 |
| 143238332 | 143247159 | chr6 | – | intronic | hsa_circ_0007021 | 1.6169 | 0.006487 | HIVEP2 |
| 95027210 | 95027835 | chr9 | – | exonic | hsa_circ_0087497 | −1.7464 | 0.007557 | IARS |
| 108984657 | 108986092 | chr6 | + | exonic | hsa_circ_0006404 | −1.5114 | 0.007815 | FOXO3 |
| 48259473 | 48260829 | chr10 | + | exonic | hsa_circ_0018309 | −1.5550 | 0.009507 | ANXA8 |
| 216177220 | 216190861 | chr2 | + | exonic | hsa_circ_0058058 | −1.5332 | 0.010567 | ATIC |

TABLE 5-continued (SSRI R 8 week vs SSRI R baseline)

| TxStart | TxEnd | Chrom | Strand | circRNA type | Alias | Fold change | P-value | GeneSymbol |
|---|---|---|---|---|---|---|---|---|
| 73923233 | 73925817 | chr5 | − | exonic | hsa_circ_0073009 | 1.5106 | 0.010595 | ENC1 |
| 141710989 | 141716304 | chr8 | − | exonic | hsa_circ_0005273 | −1.9119 | 0.010713 | PTK2 |
| 25628813 | 25631937 | chr17 | + | exonic | hsa_circ_0042488 | −1.6471 | 0.010842 | WSB1 |
| 187498055 | 187506315 | chr2 | + | exonic | hsa_circ_0057319 | −2.0271 | 0.011654 | ITGAV |
| 161816238 | 161833102 | chr1 | + | exonic | hsa_circ_0008857 | −2.2328 | 0.011729 | ATF6 |
| 133738149 | 133738422 | chr9 | + | exonic | hsa_circ_0089131 | −1.6934 | 0.011899 | ABL1 |
| 46515157 | 46515754 | chr11 | − | exonic | hsa_circ_0009155 | 1.5077 | 0.013820 | AMBRA1 |
| 7402357 | 7402812 | chr17 | + | sense overlapping | N/A | −2.1894 | 0.015177 | POLR2A |
| 41650311 | 41677086 | chr22 | − | exonic | hsa_circ_0063526 | 1.5272 | 0.015651 | RANGAP1 |
| 32878137 | 32881962 | chr20 | − | exonic | hsa_circ_0059914 | −1.8400 | 0.015747 | AHCY |
| 37159809 | 37161502 | chr20 | + | exonic | hsa_circ_0060342 | 1.5862 | 0.015776 | RALGAPB |
| 79607545 | 79612827 | chr6 | + | exonic | hsa_circ_0077109 | −1.8261 | 0.016897 | IRAK1BP1 |
| 7402357 | 7402810 | chr17 | + | exonic | hsa_circ_0000741 | −2.4657 | 0.017273 | POLR2A |
| 23015828 | 23023664 | chr7 | − | exonic | hsa_circ_0001971 | −1.7537 | 0.017619 | FAM126A |
| 72797242 | 72804408 | chrX | + | exonic | hsa_circ_0091072 | −1.5166 | 0.018608 | CHIC1 |
| 30397715 | 30399760 | chr10 | + | antisense | N/A | 1.5584 | 0.018737 | KIAA1462 |
| 107031202 | 107050797 | chr6 | − | exonic | hsa_circ_0008514 | −1.7536 | 0.021261 | RTN4IP1 |
| 31789187 | 31803431 | chr13 | + | exonic | hsa_circ_0002635 | −1.8232 | 0.022004 | B3GALTL |
| 15510546 | 15510663 | chr19 | + | antisense | hsa_circ_0000902 | −1.5746 | 0.023199 | AKAP8L |
| 155408117 | 155408859 | chr1 | − | exonic | hsa_circ_0000137 | −1.8078 | 0.024724 | ASH1L |
| 33866724 | 33872064 | chr20 | − | sense overlapping | hsa_circ_0060055 | −1.6060 | 0.025175 | EIF6 |
| 141810557 | 141900868 | chr8 | − | exonic | hsa_circ_0007521 | −1.6288 | 0.026295 | PTK2 |
| 23015828 | 23030758 | chr7 | − | exonic | hsa_circ_0005251 | −1.6500 | 0.026343 | FAM126A |
| 95518727 | 95524317 | chr8 | − | exonic | hsa_circ_0084904 | −1.6394 | 0.026904 | KIAA1429 |
| 220253068 | 220263134 | chr1 | − | sense overlapping | hsa_circ_0000185 | −1.9964 | 0.027643 | BPNT1 |
| 14643337 | 14643566 | chr10 | − | intronic | hsa_circ_0000217 | −1.5446 | 0.028796 | FAM107B |
| 29927157 | 29931571 | chr8 | − | exonic | hsa_circ_0083834 | −1.5892 | 0.029061 | SARAF |
| 122525703 | 122545912 | chr3 | + | exonic | N/A | −1.5383 | 0.029757 | DIRC2 |
| 35236117 | 35236221 | chr20 | + | exonic | hsa_circ_0001151 | −1.5287 | 0.030291 | C20orf24 |
| 170650618 | 170658898 | chr4 | − | exonic | hsa_circ_0071439 | −1.5939 | 0.032358 | C4orf27 |
| 17910716 | 17974508 | chr4 | − | exonic | hsa_circ_0125866 | 1.5122 | 0.032521 | LCORL |
| 70696691 | 70703013 | chr10 | + | exonic | hsa_circ_0007097 | −1.5731 | 0.034176 | DDX50 |
| 65228581 | 65237897 | chr2 | + | exonic | hsa_circ_0054971 | −1.6453 | 0.034532 | SLC1A4 |
| 886917 | 887077 | chr5 | − | intronic | hsa_circ_0001463 | 1.6030 | 0.038869 | BRD9 |
| 42231920 | 42232779 | chr17 | + | exonic | hsa_circ_0004239 | 1.5663 | 0.039543 | C17orf53 |
| 123718838 | 123721032 | chr10 | − | exonic | hsa_circ_0020256 | −1.7346 | 0.040144 | NSMCE4A |
| 10186276 | 10188722 | chr2 | + | exonic | N/A | 1.5020 | 0.040831 | KLF11 |
| 61537238 | 61545758 | chr20 | − | exonic | hsa_circ_0061137 | −1.6501 | 0.041718 | DIDO1 |
| 123471177 | 123512691 | chr3 | − | exonic | hsa_circ_0002768 | −1.5493 | 0.046050 | MYLK |
| 140646904 | 140812121 | chr4 | − | exonic | hsa_circ_0071000 | −1.8095 | 0.048950 | MAML3 |

TABLE 6

(SSRI NR 8 week vs SSRI NR baseline)

| TxStart | TxEnd | Chrom | Strand | circRNA type | Alias | Fold change | P-value | GeneSymbol |
|---|---|---|---|---|---|---|---|---|
| 169663839 | 169664181 | chr1 | − | intronic | hsa_circ_0000157 | −1.6056 | 0.022536 | SELL |
| 113057425 | 113057606 | chr2 | + | exonic | hsa_circ_0001062 | 1.6457 | 0.043037 | ZC3H6 |

TABLE 7

(SNRI R 8 week vs SNRI R baseline)

| TxStart | TxEnd | Chrom | Strand | circRNA type | Alias | Fold change | P-value | GeneSymbol |
|---|---|---|---|---|---|---|---|---|
| 128750760 | 128754065 | chr2 | − | exonic | hsa_circ_0056390 | −1.5102 | 0.024087 | SAP130 |
| 42807412 | 42807742 | chr22 | − | exonic | hsa_circ_0001240 | 1.5777 | 0.028423 | NFAM1 |

TABLE 8

(SNRI NR 8 week vs SNRI NR baseline)

| TxStart | TxEnd | Chrom | Strand | circRNA type | Alias | Fold change | P-value | GeneSymbol |
|---|---|---|---|---|---|---|---|---|
| 111800296 | 111853435 | chr9 | − | exonic | hsa_circ_0087903 | 1.8899 | 0.011877 | TMEM245 |
| 223470 | 223709 | chr16 | + | exonic | hsa_circ_0037139 | 1.9512 | 0.017074 | HBA2 |

TABLE 8-continued

| (SNRI NR 8 week vs SNRI NR baseline) | | | | | | | | |
|---|---|---|---|---|---|---|---|---|
| TxStart | TxEnd | Chrom | Strand | circRNA type | Alias | Fold change | P-value | GeneSymbol |
| 18945987 | 18983955 | chr18 | + | exonic | hsa_circ_0003653 | 1.9494 | 0.018293 | GREB1L |
| 32180078 | 32181858 | chr3 | + | exonic | hsa_circ_0123503 | 1.5352 | 0.019108 | GPD1L |
| 5364258 | 5365866 | chr17 | − | exonic | hsa_circ_0000740 | 1.6681 | 0.019482 | DHX33 |
| 187498055 | 187506315 | chr2 | + | exonic | hsa_circ_0057319 | 1.7323 | 0.019912 | ITGAV |
| 8525984 | 8568734 | chr1 | − | exonic | hsa_circ_0009574 | 1.5383 | 0.020435 | RERE |
| 74091854 | 74134875 | chr5 | − | exonic | N/A | 1.6290 | 0.023687 | FAM169A |
| 66252643 | 66255478 | chr11 | + | exonic | N/A | 1.5628 | 0.024076 | DPP3 |
| 4845635 | 4848517 | chr17 | + | exonic | hsa_circ_0041623 | 1.7210 | 0.028566 | RNF167 |
| 156012056 | 156012564 | chr1 | − | intronic | N/A | 1.6342 | 0.029507 | UBQLN4 |
| 79607545 | 79612827 | chr6 | + | exonic | hsa_circ_0077109 | 1.7799 | 0.031208 | IRAK1BP1 |
| 170650618 | 170658898 | chr4 | − | exonic | hsa_circ_0071439 | 1.6126 | 0.031283 | C4orf27 |
| 70696691 | 70703013 | chr10 | + | exonic | hsa_circ_0007097 | 1.5803 | 0.031364 | DDX50 |
| 66923610 | 66990707 | chr12 | − | exonic | N/A | 1.6700 | 0.031606 | GRIP1 |
| 73114707 | 73115261 | chr7 | − | sense overlapping | hsa_circ_0009012 | 1.9041 | 0.031930 | STX1A |
| 118456876 | 118460164 | chr12 | + | exonic | hsa_circ_0028628 | 1.5254 | 0.032096 | RFC5 |
| 35236117 | 35236221 | chr20 | + | exonic | hsa_circ_0001151 | 1.7025 | 0.034569 | C20orf24 |
| 48259473 | 48260829 | chr10 | + | exonic | hsa_circ_0018309 | 1.7394 | 0.034896 | ANXA8 |
| 220253068 | 220263134 | chr1 | − | sense overlapping | hsa_circ_0000185 | 2.0231 | 0.035044 | BPNT1 |
| 111795586 | 111800397 | chr9 | − | exonic | hsa_circ_0087888 | 1.6524 | 0.035384 | TMEM245 |
| 17907047 | 17953998 | chr1 | + | exonic | hsa_circ_0010210 | 1.8408 | 0.037018 | ARHGEF10L |
| 25628813 | 25631937 | chr17 | + | exonic | hsa_circ_0042488 | 1.6438 | 0.042449 | WSB1 |
| 127300370 | 127302466 | chr9 | − | exonic | hsa_circ_0088511 | 1.5687 | 0.042681 | NR6A1 |
| 73015794 | 73017356 | chr17 | + | exonic | hsa_circ_0045581 | 1.5305 | 0.042724 | ICT1 |
| 17370097 | 17370831 | chr19 | − | exonic | hsa_circ_0049965 | 1.9508 | 0.044091 | USHBP1 |
| 36530224 | 36531038 | chr19 | − | exonic | N/A | 1.6117 | 0.047183 | THAP8 |

TABLE 9

| (MAOI R 8 week vs MAOI R baseline) | | | | | | | | |
|---|---|---|---|---|---|---|---|---|
| TxStart | TxEnd | Chrom | Strand | circRNA type | Alias | Fold change | P-value | GeneSymbol |
| 72285253 | 72286691 | chr5 | + | exonic | hsa_circ_0072954 | 1.8349 | 0.000170 | FCHO2 |
| 66021409 | 66031213 | chr15 | − | exonic | hsa_circ_0035944 | 1.7516 | 0.000858 | DENND4A |
| 46622935 | 46623422 | chr12 | − | exonic | hsa_circ_0098630 | 1.6345 | 0.000893 | SLC38A1 |
| 29319841 | 29344954 | chr1 | + | exonic | hsa_circ_0000041 | 1.6910 | 0.001005 | EPB41 |
| 141799572 | 141840625 | chr8 | − | exonic | hsa_circ_0008305 | 1.5412 | 0.001095 | PTK2 |
| 63719709 | 63720311 | chr11 | + | exonic | hsa_circ_0022623 | −2.0221 | 0.001172 | NAA40 |
| 139262471 | 139269050 | chr6 | − | exonic | hsa_circ_0005210 | 1.5118 | 0.001210 | REPS1 |
| 44931421 | 44942492 | chr2 | + | exonic | hsa_circ_0006530 | 1.6360 | 0.001351 | CAMKMT |
| 24549443 | 24553954 | chr14 | − | sense overlapping | N/A | −2.9480 | 0.001538 | NRL |
| 56915571 | 56920595 | chr6 | + | sense overlapping | hsa_circ_0131987 | 1.7010 | 0.001635 | KIAA1586 |
| 67484716 | 67505429 | chr8 | − | exonic | hsa_circ_0084642 | 1.8149 | 0.001841 | MYBL1 |
| 123678932 | 123682881 | chr12 | − | exonic | hsa_circ_0006615 | 1.9081 | 0.001877 | MPHOSPH9 |
| 124121556 | 124132428 | chr8 | + | exonic | hsa_circ_0001820 | 1.5577 | 0.001976 | TBC1D31 |
| 32987845 | 32995095 | chr11 | + | exonic | N/A | −2.6040 | 0.002488 | QSER1 |
| 196544755 | 196548630 | chr2 | + | exonic | hsa_circ_0057551 | 2.4728 | 0.002494 | SLC39A10 |
| 8555122 | 8601377 | chr1 | − | exonic | hsa_circ_0009581 | −1.8472 | 0.002802 | RERE |
| 46751970 | 46754992 | chr12 | − | exonic | hsa_circ_0025984 | −1.8197 | 0.002917 | SLC38A2 |
| 72301330 | 72302378 | chr7 | + | sense overlapping | hsa_circ_0006688 | 2.0968 | 0.003139 | SBDSP1 |
| 97304862 | 97305111 | chr8 | − | antisense | hsa_circ_0001816 | −2.1733 | 0.003351 | PTDSS1 |
| 100899717 | 100904280 | chr8 | − | exonic | N/A | −2.1635 | 0.003405 | COX6C |
| 58449076 | 58459247 | chr2 | − | exonic | hsa_circ_0001009 | 1.5667 | 0.003409 | FANCL |
| 156303337 | 156305679 | chr1 | − | exonic | hsa_circ_0014724 | 1.5058 | 0.003476 | CCT3 |
| 28460068 | 28464260 | chr2 | + | exonic | hsa_circ_0053317 | −1.6037 | 0.003942 | BRE |
| 49094294 | 49095323 | chr3 | − | exonic | hsa_circ_0002561 | −1.9022 | 0.004031 | QRICH1 |
| 22108546 | 22117269 | chrX | + | exonic | hsa_circ_0090069 | −2.6250 | 0.004048 | PHEX |
| 120276826 | 120351139 | chr11 | + | exonic | hsa_circ_0024615 | −1.8373 | 0.004300 | ARHGEF12 |
| 10524467 | 10525312 | chr16 | + | exonic | hsa_circ_0037807 | 1.8276 | 0.004409 | ATF7IP2 |
| 149246283 | 149250107 | chr7 | − | exonic | N/A | −1.6823 | 0.004501 | ZNF767P |
| 45954567 | 45959775 | chr10 | − | exonic | hsa_circ_0018273 | 1.6150 | 0.004555 | MARCH8 |
| 129684543 | 129690951 | chr3 | − | sense overlapping | N/A | −2.3824 | 0.004623 | RP11-93K22.6 |
| 46366930 | 46367223 | chr12 | − | intronic | N/A | −1.6981 | 0.004656 | SCAF11 |
| 66303083 | 66397591 | chr17 | + | exonic | N/A | −1.5012 | 0.004762 | ARSG |
| 56049902 | 56062681 | chr7 | + | exonic | hsa_circ_0080251 | −1.8131 | 0.004820 | GBAS |
| 42641806 | 42641893 | chr20 | + | intronic | hsa_circ_0001160 | −1.5897 | 0.004960 | TOX2 |
| 34921480 | 34924317 | chr19 | + | exonic | hsa_circ_0050509 | 1.5887 | 0.005097 | UBA2 |

TABLE 9-continued (MAOI R 8 week vs MAOI R baseline)

| TxStart | TxEnd | Chrom | Strand | circRNA type | Alias | Fold change | P-value | GeneSymbol |
|---|---|---|---|---|---|---|---|---|
| 56883813 | 56890780 | chr4 | + | exonic | N/A | −2.5691 | 0.005230 | CEP135 |
| 15956819 | 15978390 | chr1 | + | exonic | hsa_circ_0010052 | 1.5011 | 0.005308 | DDI2 |
| 210880696 | 210885788 | chr2 | + | sense overlapping | hsa_circ_0007225 | 1.5463 | 0.005318 | RPE |
| 118997417 | 118997916 | chr9 | + | exonic | hsa_circ_0088227 | −1.5939 | 0.005364 | PAPPA |
| 109952549 | 109964548 | chr1 | − | exonic | N/A | −2.6087 | 0.005495 | PSMA5 |
| 204396775 | 204397348 | chr1 | − | exonic | N/A | 1.7779 | 0.005500 | PIK3C2B |
| 129180070 | 129188260 | chr3 | + | exonic | N/A | −1.7308 | 0.005567 | IFT122 |
| 12326937 | 12395884 | chr1 | + | exonic | hsa_circ_0009962 | −2.2646 | 0.005627 | VPS13D |
| 21573713 | 21585332 | chr1 | − | exonic | hsa_circ_0007877 | −1.5050 | 0.005650 | ECE1 |
| 95914772 | 95918564 | chr12 | − | exonic | hsa_circ_0027779 | −1.5237 | 0.005723 | USP44 |
| 59981820 | 59996874 | chr17 | − | exonic | N/A | −2.0125 | 0.005760 | INTS2 |
| 30147413 | 30149539 | chr20 | + | exonic | hsa_circ_0059703 | −1.5822 | 0.005794 | HM13 |
| 233651859 | 233660931 | chr2 | + | exonic | hsa_circ_0058733 | 2.1439 | 0.005838 | GIGYF2 |
| 126434011 | 126498481 | chr6 | + | sense overlapping | N/A | −2.0511 | 0.006019 | RP11-527F13.1 |
| 77759436 | 77764156 | chr15 | + | exonic | hsa_circ_0036429 | 1.6712 | 0.006106 | HMG20A |
| 48561918 | 48565892 | chr20 | + | exonic | hsa_circ_0008212 | −1.9295 | 0.006197 | RNF114 |
| 103649168 | 103699695 | chr10 | − | exonic | hsa_circ_0019627 | −1.5998 | 0.006265 | C10orf76 |
| 75210552 | 75211467 | chr7 | − | exonic | hsa_circ_0080731 | −1.7904 | 0.006408 | HIP1 |
| 217783662 | 217787544 | chr1 | − | exonic | hsa_circ_0002843 | −1.7220 | 0.006454 | GPATCH2 |
| 172325397 | 172325966 | chr2 | + | sense overlapping | hsa_circ_0007529 | −1.6148 | 0.006468 | DCAF17 |
| 68160350 | 68160513 | chr16 | + | exonic | hsa_circ_0039930 | 1.9306 | 0.006598 | NFATC3 |
| 47143393 | 47165936 | chr16 | − | exonic | hsa_circ_0003520 | −1.6588 | 0.006671 | NETO2 |
| 24663284 | 24681487 | chr7 | + | exonic | hsa_circ_0079619 | 1.9079 | 0.006677 | MPP6 |
| 128350085 | 128350346 | chr11 | − | exonic | hsa_circ_0024829 | 2.1692 | 0.006698 | ETS1 |
| 49053687 | 49054402 | chr12 | − | intronic | hsa_circ_0000399 | −1.8103 | 0.006808 | KANSL2 |
| 93185037 | 93221941 | chr10 | + | exonic | hsa_circ_0007168 | 1.5989 | 0.006847 | HECTD2 |
| 152163070 | 152165562 | chr3 | + | exonic | hsa_circ_0007630 | −1.6528 | 0.006942 | MBNL1 |
| 1859238 | 1859834 | chr16 | − | exonic | N/A | 1.9390 | 0.006994 | HAGH |
| 29362337 | 29365938 | chr1 | + | exonic | hsa_circ_0000042 | 2.3063 | 0.007004 | EPB41 |
| 49075877 | 49077050 | chr13 | − | exonic | hsa_circ_0030235 | −1.5939 | 0.007010 | RCBTB2 |
| 48209335 | 48219478 | chr3 | − | exonic | hsa_circ_0005467 | −2.1597 | 0.007014 | CDC25A |
| 17137883 | 17143936 | chr8 | + | exonic | hsa_circ_0083423 | 1.8193 | 0.007079 | VPS37A |
| 46267751 | 46276110 | chr20 | + | exonic | hsa_circ_0060633 | −1.5933 | 0.007148 | NCOA3 |
| 30941049 | 30941149 | chr22 | − | intronic | hsa_circ_0001221 | −2.0133 | 0.007175 | SEC14L6 |
| 47644252 | 47647293 | chr11 | − | exonic | hsa_circ_0022019 | −1.8387 | 0.007183 | MTCH2 |
| 100598717 | 100601564 | chr12 | + | exonic | N/A | 1.5587 | 0.007214 | ACTR6 |
| 77611362 | 77632364 | chr9 | − | exonic | hsa_circ_0087220 | 2.7704 | 0.007237 | C9orf41 |
| 98740342 | 98766983 | chr9 | + | exonic | hsa_circ_0008720 | 1.8843 | 0.007259 | ERCC6L2 |
| 34934748 | 34936026 | chr19 | + | exonic | hsa_circ_0050539 | −1.7983 | 0.007344 | UBA2 |
| 233334684 | 233344435 | chr1 | − | exonic | hsa_circ_0005223 | 1.9882 | 0.007650 | PCNXL2 |
| 77981056 | 77983024 | chr6 | − | intergenic | N/A | 1.6813 | 0.007652 | |
| 29191568 | 29192081 | chr22 | − | sense overlapping | hsa_circ_0001216 | −2.0409 | 0.007935 | XBP1 |
| 198273227 | 198274543 | chr2 | + | antisense | hsa_circ_0001089 | −2.0462 | 0.007937 | SF3B1 |
| 117825700 | 117828459 | chr7 | + | exonic | hsa_circ_0001740 | 1.6879 | 0.007995 | NAA38 |
| 70247563 | 70256383 | chr16 | − | sense overlapping | N/A | 1.7798 | 0.008029 | SMG1P7 |
| 54921379 | 54925426 | chr17 | + | exonic | hsa_circ_0044709 | 1.5162 | 0.008036 | DGKE |
| 120343758 | 120348235 | chr11 | + | exonic | hsa_circ_0009021 | 1.7985 | 0.008045 | ARHGEF12 |
| 69983264 | 69987393 | chr12 | + | exonic | hsa_circ_0002940 | 1.6237 | 0.008137 | CCT2 |
| 99122975 | 99123175 | chr10 | − | intronic | hsa_circ_0092335 | −2.0320 | 0.008247 | RRP12 |
| 80869751 | 80879232 | chr9 | + | exonic | N/A | −2.3285 | 0.008260 | CEP78 |
| 141595217 | 141595410 | chr8 | − | exonic | hsa_circ_0008113 | 2.1803 | 0.008433 | AGO2 |
| 33960823 | 33973235 | chr9 | − | exonic | hsa_circ_0001850 | 1.9596 | 0.008538 | UBAP2 |
| 5314022 | 5320002 | chr17 | − | exonic | hsa_circ_0000739 | 1.5121 | 0.008587 | NUP88 |
| 72863871 | 72865324 | chr7 | − | exonic | N/A | 1.5409 | 0.008633 | BAZ1B |
| 71640490 | 71704162 | chr15 | + | sense overlapping | N/A | −2.0350 | 0.008835 | THSD4 |
| 37623043 | 37632999 | chr8 | + | exonic | hsa_circ_0083932 | −1.8028 | 0.008836 | PROSC |
| 34059659 | 34101636 | chr6 | − | exonic | hsa_circ_0076040 | −2.1951 | 0.008908 | GRM4 |
| 21788274 | 21810728 | chr12 | − | exonic | hsa_circ_0025597 | −1.9156 | 0.008936 | LDHB |
| 50290691 | 50292747 | chr20 | − | exonic | hsa_circ_0004207 | −1.6989 | 0.008968 | ATP9A |
| 59730181 | 59758024 | chr14 | + | sense overlapping | hsa_circ_0000543 | 1.5052 | 0.008994 | DAAM1 |
| 84662298 | 84663507 | chr1 | + | exonic | N/A | 1.6286 | 0.009094 | PRKACB |
| 128354717 | 128360471 | chr11 | − | exonic | hsa_circ_0004296 | 2.0483 | 0.009172 | ETS1 |
| 96826060 | 96834012 | chr15 | − | exonic | hsa_circ_0004200 | −1.7937 | 0.009186 | NR2F2-AS1 |
| 43906156 | 43908975 | chr7 | − | exonic | hsa_circ_0079972 | −1.8953 | 0.009209 | MRPS24 |
| 77394754 | 77404656 | chr11 | − | exonic | hsa_circ_0000344 | 1.5260 | 0.009313 | RSF1 |
| 29313942 | 29323831 | chr1 | + | exonic | hsa_circ_0011168 | 2.2326 | 0.009482 | EPB41 |
| 95504879 | 95550574 | chr8 | − | exonic | hsa_circ_0084900 | −1.5765 | 0.009558 | KIAA1429 |
| 128350085 | 128360471 | chr11 | − | exonic | hsa_circ_0002083 | 2.5938 | 0.009667 | ETS1 |
| 89123719 | 89131833 | chr14 | − | exonic | N/A | −2.0667 | 0.009694 | EML5 |

TABLE 9-continued (MAOI R 8 week vs MAOI R baseline)

| TxStart | TxEnd | Chrom | Strand | circRNA type | Alias | Fold change | P-value | GeneSymbol |
|---|---|---|---|---|---|---|---|---|
| 67513932 | 67514758 | chr8 | − | exonic | hsa__circ__0004863 | 2.2691 | 0.009709 | MYBL1 |
| 117273764 | 117274087 | chr12 | + | exonic | hsa__circ__0028602 | −1.6671 | 0.009772 | RNFT2 |
| 31592304 | 31592917 | chr6 | + | intronic | N/A | −1.9248 | 0.009798 | PRRC2A |
| 152221370 | 152224234 | chr1 | + | exonic | N/A | −1.8915 | 0.009823 | FLG-AS1 |
| 71433787 | 72057538 | chr15 | + | exonic | hsa__circ__0036127 | −2.1346 | 0.009941 | THSD4 |
| 15605050 | 15606052 | chr3 | − | sense overlapping | N/A | −1.6495 | 0.009977 | HACL1 |
| 28090104 | 28096621 | chr15 | − | exonic | hsa__circ__0034189 | −2.2426 | 0.010015 | OCA2 |
| 59739905 | 59763183 | chr18 | − | exonic | hsa__circ__0007528 | −1.7448 | 0.010042 | PIGN |
| 126370175 | 126395456 | chr10 | − | exonic | hsa__circ__0002282 | −1.5016 | 0.010061 | FAM53B |
| 152480271 | 152513673 | chr7 | + | exonic | hsa__circ__0083059 | −1.5143 | 0.010102 | ACTR3B |
| 50358643 | 50367353 | chr7 | + | exonic | hsa__circ__0001708 | 2.2201 | 0.010117 | IKZF1 |
| 53288349 | 53308214 | chr16 | + | exonic | hsa__circ__0000702 | 1.7629 | 0.010268 | CHD9 |
| 80160631 | 80173542 | chr5 | + | sense overlapping | N/A | −1.7492 | 0.010368 | MSH3 |
| 2326785 | 2343345 | chrX | − | exonic | hsa__circ__0002818 | −1.6491 | 0.010421 | DHRSX |
| 19236821 | 19239304 | chr18 | − | exonic | hsa__circ__0047086 | −1.5298 | 0.010469 | ABHD3 |
| 141889569 | 141900868 | chr8 | − | exonic | hsa__circ__0006646 | 1.6288 | 0.010497 | PTK2 |
| 159004985 | 159006457 | chr6 | + | exonic | hsa__circ__0003345 | 2.2874 | 0.010519 | TMEM181 |
| 155093275 | 155094127 | chr7 | + | exonic | N/A | −1.5835 | 0.010544 | INSIG1 |
| 33388679 | 33427756 | chr7 | + | exonic | hsa__circ__0079812 | 1.8452 | 0.010619 | BBS9 |
| 120345268 | 120348235 | chr11 | + | exonic | hsa__circ__0002100 | 1.8652 | 0.010645 | ARHGEF12 |
| 48248829 | 48248993 | chr19 | + | sense overlapping | hsa__circ__0000945 | 1.5123 | 0.010679 | GLTSCR2 |
| 24788253 | 24788679 | chr16 | + | exonic | hsa__circ__0038673 | 1.8570 | 0.010728 | TNRC6A |
| 26343183 | 26349097 | chr13 | + | exonic | N/A | −1.8529 | 0.010729 | ATP8A2 |
| 27447477 | 27447615 | chr10 | + | exonic | hsa__circ__0018031 | −2.3860 | 0.010785 | MASTL |
| 8604615 | 8604944 | chr19 | + | antisense | hsa__circ__0008990 | −1.5469 | 0.010862 | MYO1F |
| 71808337 | 71808960 | chr11 | − | exonic | hsa__circ__0023420 | −2.3234 | 0.010939 | LAMTOR1 |
| 110832905 | 110834257 | chr12 | − | exonic | hsa__circ__0028198 | −2.1798 | 0.010991 | ANAPC7 |
| 66044716 | 66053776 | chr15 | − | exonic | hsa__circ__0035957 | 2.3357 | 0.010997 | DENND4A |
| 27269150 | 27269556 | chr1 | + | exonic | hsa__circ__0005087 | 2.1926 | 0.011034 | NUDC |
| 3201105 | 3202522 | chr10 | − | exonic | hsa__circ__0017510 | −1.7504 | 0.011060 | PITRM1 |
| 7143737 | 7144998 | chr17 | − | exonic | hsa__circ__0041782 | −1.6603 | 0.011075 | GABARAP |
| 77402203 | 77404656 | chr11 | − | exonic | hsa__circ__0004831 | 1.5219 | 0.011125 | RSF1 |
| 151130894 | 151131115 | chrX | − | exonic | hsa__circ__0091710 | −1.8953 | 0.011149 | GABRE |
| 109550361 | 109550978 | chr4 | + | intronic | N/A | −1.6452 | 0.011162 | RPL34 |
| 71090478 | 71102924 | chr3 | − | exonic | hsa__circ__0008234 | 1.6829 | 0.011168 | FOXP1 |
| 4749457 | 4749657 | chr16 | − | intronic | hsa__circ__0092312 | −1.5303 | 0.011168 | ANKS3 |
| 15506703 | 15536599 | chr2 | − | exonic | N/A | 1.6934 | 0.011271 | NBAS |
| 100982814 | 100992513 | chr13 | + | exonic | hsa__circ__0008420 | 1.6021 | 0.011377 | PCCA |
| 116734383 | 116744352 | chr11 | − | exonic | hsa__circ__0000357 | −1.6045 | 0.011403 | SIK3 |
| 33960823 | 33963789 | chr9 | − | exonic | hsa__circ__0001849 | 1.8439 | 0.011476 | UBAP2 |
| 24679553 | 24679974 | chr14 | − | exonic | hsa__circ__0007326 | 2.5026 | 0.011649 | CHMP4A |
| 9482139 | 9506356 | chr3 | + | exonic | hsa__circ__0064136 | −1.8938 | 0.011694 | SETD5 |
| 119176864 | 119182471 | chr3 | − | sense overlapping | hsa__circ__0066869 | −1.5131 | 0.011715 | TMEM39A |
| 120927214 | 120936665 | chr10 | − | exonic | hsa__circ__0020169 | −1.5129 | 0.011758 | PRDX3 |
| 24840803 | 24841057 | chr1 | + | exonic | hsa__circ__0003553 | 1.8500 | 0.011768 | RCAN3 |
| 10798306 | 10799354 | chr19 | + | sense overlapping | hsa__circ__0000890 | −1.6576 | 0.011804 | ILF3 |
| 133534776 | 133536765 | chr5 | − | exonic | hsa__circ__0073942 | −1.6318 | 0.011817 | PPP2CA |
| 156619298 | 156626486 | chr7 | − | exonic | hsa__circ__0083127 | −1.5193 | 0.011870 | LMBR1 |
| 138994170 | 139003046 | chr5 | + | exonic | hsa__circ__0074229 | 2.0394 | 0.011882 | UBE2D2 |
| 56518672 | 56536368 | chr16 | − | sense overlapping | N/A | −2.0384 | 0.011891 | BBS2 |
| 131085277 | 131096351 | chr9 | + | exonic | hsa__circ__0088780 | −1.9666 | 0.012002 | COQ4 |
| 110332157 | 110350696 | chr2 | − | exonic | hsa__circ__0007654 | −1.6768 | 0.012034 | SEPT10 |
| 55844499 | 55844644 | chr20 | − | antisense | hsa__circ__0001171 | −2.0823 | 0.012045 | BC037891 |
| 14832521 | 14834120 | chrY | + | exonic | hsa__circ__0092235 | −1.7025 | 0.012152 | USP9Y |
| 68215377 | 68217269 | chr16 | + | exonic | hsa__circ__0039934 | 1.9886 | 0.012153 | NFATC3 |
| 140622800 | 140638542 | chr9 | + | exonic | hsa__circ__0004101 | 1.6720 | 0.012154 | EHMT1 |
| 101132116 | 101132358 | chr13 | + | intronic | N/A | −1.5708 | 0.012229 | PCCA |
| 18769114 | 18785996 | chr17 | + | exonic | N/A | 1.7089 | 0.012234 | PRPSAP2 |
| 41228572 | 41244373 | chr22 | − | exonic | hsa__circ__0005671 | 1.7365 | 0.012299 | ST13 |
| 141595217 | 141616013 | chr8 | − | intronic | hsa__circ__0007313 | 2.1011 | 0.012380 | AGO2 |
| 25260812 | 25262116 | chr4 | + | intronic | N/A | −1.7092 | 0.012425 | PI4K2B |
| 80992910 | 81006661 | chr17 | − | exonic | N/A | −1.7857 | 0.012583 | B3GNTL1 |
| 12826218 | 12826553 | chr19 | − | exonic | hsa__circ__0049587 | −1.6130 | 0.012634 | TNPO2 |
| 120916382 | 120924441 | chr11 | + | exonic | hsa__circ__0000365 | 2.0421 | 0.012710 | TBCEL |
| 24181170 | 24199945 | chr2 | + | exonic | hsa__circ__0005970 | 1.5222 | 0.012744 | UBXN2A |
| 20974569 | 20990158 | chr2 | − | exonic | hsa__circ__0002271 | −1.7133 | 0.012747 | C2orf43 |
| 73646250 | 73659419 | chr2 | + | exonic | hsa__circ__0055229 | −1.6751 | 0.012759 | ALMS1 |
| 131113791 | 131113904 | chr7 | + | exonic | hsa__circ__0082413 | 1.5084 | 0.012791 | MKLN1 |
| 41705097 | 41795980 | chr3 | − | exonic | N/A | −1.7770 | 0.012797 | ULK4 |
| 57031958 | 57036364 | chr12 | − | exonic | hsa__circ__0027070 | −1.5770 | 0.012808 | ATP5B |

TABLE 9-continued (MAOI R 8 week vs MAOI R baseline)

| TxStart | TxEnd | Chrom | Strand | circRNA type | Alias | Fold change | P-value | GeneSymbol |
|---|---|---|---|---|---|---|---|---|
| 40293372 | 40301685 | chr13 | + | exonic | hsa__circ__0006900 | −1.9188 | 0.012865 | COG6 |
| 114293154 | 114296633 | chr9 | + | exonic | N/A | −1.7889 | 0.012869 | ZNF483 |
| 30740286 | 30740893 | chr16 | + | exonic | hsa__circ__0006127 | −1.6214 | 0.012940 | SRCAP |
| 52773707 | 52790516 | chr20 | − | exonic | hsa__circ__0060930 | −1.8534 | 0.013017 | CYP24A1 |
| 89961445 | 89967202 | chr16 | + | exonic | hsa__circ__0002631 | −1.9644 | 0.013154 | TCF25 |
| 24613084 | 24708279 | chr7 | + | exonic | hsa__circ__0079614 | 2.4232 | 0.013209 | MPP6 |
| 126434011 | 126452004 | chr6 | | antisense | N/A | −1.8482 | 0.013252 | MIR5695 |
| 41456925 | 41457407 | chr1 | + | intronic | N/A | −1.8992 | 0.013252 | CTPS1 |
| 46096161 | 46136418 | chr22 | + | exonic | hsa__circ__0001246 | 1.7983 | 0.013273 | ATXN10 |
| 104432491 | 104433310 | chr8 | + | exonic | N/A | −1.5501 | 0.013280 | DCAF13 |
| 105121498 | 105135700 | chr7 | − | exonic | hsa__circ__0081854 | 1.5258 | 0.013353 | PUS7 |
| 63042932 | 63052295 | chr1 | − | exonic | hsa__circ__0002032 | −1.9483 | 0.013401 | DOCK7 |
| 2972488 | 3000467 | chr11 | − | exonic | hsa__circ__0020816 | 2.4962 | 0.013417 | NAP1L4 |
| 39328182 | 39329376 | chr4 | − | exonic | hsa__circ__0001403 | 1.7462 | 0.013437 | RFC1 |
| 76342171 | 76344812 | chr5 | + | exonic | N/A | 1.7212 | 0.013445 | AGGF1 |
| 113856936 | 113891590 | chr2 | + | exonic | hsa__circ__0056159 | −1.7142 | 0.013511 | IL1RN |
| 11905658 | 11907984 | chr2 | + | exonic | hsa__circ__0002229 | 1.8805 | 0.013545 | LPIN1 |
| 39739039 | 39757359 | chr4 | + | exonic | hsa__circ__0009154 | 1.9825 | 0.013560 | UBE2K |
| 42711141 | 42717906 | chr12 | − | exonic | N/A | 1.5424 | 0.013655 | ZCRB1 |
| 167927595 | 167929110 | chr5 | + | exonic | hsa__circ__0007958 | 1.8524 | 0.013695 | RARS |
| 21306826 | 21329301 | chr1 | − | exonic | hsa__circ__0010486 | −1.5805 | 0.013703 | EIF4G3 |
| 84765030 | 84772711 | chr6 | + | exonic | N/A | −1.8440 | 0.013707 | MRAP2 |
| 21335426 | 21338430 | chr20 | + | exonic | N/A | −1.8149 | 0.013785 | XRN2 |
| 73713630 | 73751785 | chr6 | + | exonic | hsa__circ__0004136 | −1.8696 | 0.013839 | KCNQ5 |
| 73414865 | 73428368 | chr15 | + | exonic | N/A | −1.9192 | 0.013913 | NEO1 |
| 64295353 | 64295792 | chrX | + | sense overlapping | hsa__circ__0002532 | 1.7189 | 0.013968 | XLOC__008000 |
| 100598717 | 100599535 | chr12 | + | exonic | N/A | 1.7027 | 0.014042 | ACTR6 |
| 158204420 | 158223483 | chr5 | − | exonic | hsa__circ__0074816 | −1.8988 | 0.014078 | EBF1 |
| 45891031 | 45923523 | chr20 | − | exonic | hsa__circ__0001164 | 1.8828 | 0.014080 | ZMYND8 |
| 98827555 | 98831466 | chr8 | + | exonic | hsa__circ__0085013 | −1.8293 | 0.014088 | LAPTM4B |
| 12335881 | 12338095 | chr1 | + | exonic | hsa__circ__0009964 | 1.6750 | 0.014171 | VPS13D |
| 226054811 | 226065294 | chr1 | − | exonic | hsa__circ__0016681 | 1.6469 | 0.014204 | TMEM63A |
| 17624791 | 17649531 | chr6 | − | exonic | hsa__circ__0075705 | −1.5925 | 0.014554 | NUP153 |
| 6477621 | 6482099 | chr9 | + | exonic | hsa__circ__0007816 | 1.7042 | 0.014585 | UHRF2 |
| 27440281 | 27440777 | chr1 | − | intronic | N/A | −1.7369 | 0.014644 | SLC9A1 |
| 22024201 | 22029404 | chr22 | + | exonic | hsa__circ__0062426 | 2.0400 | 0.014677 | PPIL2 |
| 15095126 | 15095229 | chr12 | − | sense overlapping | hsa__circ__0000380 | −1.8740 | 0.014770 | ARHGDIB |
| 91808723 | 91810001 | chr14 | − | exonic | hsa__circ__0032959 | 1.5494 | 0.014821 | CCDC88C |
| 24828014 | 24861794 | chrX | + | exonic | hsa__circ__0090162 | 1.6568 | 0.014832 | POLA1 |
| 66655964 | 66670484 | chr16 | − | exonic | hsa__circ__0009167 | −1.5511 | 0.014851 | CMTM4 |
| 42069936 | 42084913 | chr22 | − | exonic | hsa__circ__0063598 | −1.8890 | 0.014923 | NHP2L1 |
| 103213257 | 103239214 | chr10 | + | exonic | N/A | 1.5213 | 0.014936 | BTRC |
| 72945231 | 72960247 | chr2 | − | exonic | hsa__circ__0009043 | 1.6908 | 0.014949 | EXOC6B |
| 159001971 | 159010814 | chr6 | + | exonic | hsa__circ__0001661 | 1.5871 | 0.015038 | TMEM181 |
| 33058531 | 33060824 | chr1 | + | exonic | hsa__circ__0002306 | −2.0008 | 0.015039 | ZBTB8A |
| 142221459 | 142231148 | chr6 | − | exonic | N/A | −2.4912 | 0.015061 | AK097143 |
| 131829427 | 131840230 | chr2 | − | exonic | hsa__circ__0003524 | −1.6668 | 0.015123 | FAM168B |
| 72517312 | 72522216 | chr17 | − | exonic | hsa__circ__0045556 | −1.8537 | 0.015135 | CD300LB |
| 47287161 | 47308084 | chr22 | + | exonic | hsa__circ__0063853 | −1.5145 | 0.015176 | TBC1D22A |
| 128099296 | 128099870 | chr9 | + | exonic | hsa__circ__0003270 | −1.7378 | 0.015201 | GAPVD1 |
| 107216250 | 107230146 | chr4 | − | exonic | hsa__circ__0003673 | −1.6307 | 0.015344 | TBCK |
| 28337816 | 28338222 | chr1 | − | intronic | N/A | −1.9332 | 0.015432 | EYA3 |
| 66021409 | 66048810 | chr15 | − | exonic | hsa__circ__0035946 | 2.5523 | 0.015495 | DENND4A |
| 86088303 | 86090608 | chr2 | − | exonic | hsa__circ__0055451 | 1.5257 | 0.015568 | ST3GAL5 |
| 108186549 | 108206688 | chr11 | + | exonic | hsa__circ__0024231 | 2.8063 | 0.015589 | ATM |
| 185375790 | 185376090 | chr3 | − | intronic | hsa__circ__0092369 | −2.0260 | 0.015642 | IGF2BP2 |
| 72205086 | 72222904 | chr4 | + | exonic | hsa__circ__0008676 | −2.1579 | 0.015665 | SLC4A4 |
| 24663284 | 24708279 | chr7 | + | exonic | hsa__circ__0001686 | 2.4333 | 0.015732 | MPP6 |
| 39090564 | 39090793 | chr19 | − | exonic | hsa__circ__0050867 | −1.7665 | 0.015732 | MAP4K1 |
| 70723046 | 70731808 | chr10 | + | exonic | hsa__circ__0018572 | −1.7088 | 0.015760 | DDX21 |
| 156303337 | 156304709 | chr1 | − | exonic | hsa__circ__0004680 | 2.2938 | 0.015816 | CCT3 |
| 43122140 | 43162033 | chr5 | + | exonic | hsa__circ__0001479 | 1.7654 | 0.015937 | ZNF131 |
| 189851784 | 189858808 | chr2 | + | exonic | hsa__circ__0057362 | −2.2306 | 0.016003 | COL3A1 |
| 53430497 | 53430825 | chrX | − | exonic | hsa__circ__0001921 | 2.1421 | 0.016088 | SMC1A |
| 47585118 | 47585318 | chr19 | − | intronic | hsa__circ__0092316 | −2.1094 | 0.016150 | ZC3H4 |
| 75590748 | 75590926 | chr14 | − | exonic | hsa__circ__0032683 | 1.8203 | 0.016203 | NEK9 |
| 86494712 | 86508177 | chr14 | + | intronic | N/A | 1.6480 | 0.016204 | LOC101928767 |
| 44346195 | 44346638 | chr13 | − | intronic | N/A | −1.9981 | 0.016222 | ENOX1 |
| 138244331 | 138256189 | chr3 | − | exonic | N/A | 2.1616 | 0.016226 | CEP70 |
| 7217398 | 7217478 | chr17 | − | exonic | hsa__circ__0041811 | −2.0343 | 0.016267 | GPS2 |
| 110764194 | 110780253 | chr12 | + | exonic | hsa__circ__0028173 | −1.5481 | 0.016320 | ATP2A2 |
| 148730307 | 148733544 | chr2 | − | exonic | hsa__circ__0001074 | 1.5430 | 0.016328 | ORC4 |
| 19423859 | 19424839 | chr9 | + | exonic | hsa__circ__0086482 | −1.7700 | 0.016348 | ACER2 |
| 151153488 | 151161628 | chr4 | + | exonic | hsa__circ__0071129 | −1.7672 | 0.016459 | DCLK2 |

TABLE 9-continued (MAOI R 8 week vs MAOI R baseline)

| TxStart | TxEnd | Chrom | Strand | circRNA type | Alias | Fold change | P-value | GeneSymbol |
|---|---|---|---|---|---|---|---|---|
| 141622461 | 141640905 | chr3 | + | exonic | N/A | −1.8168 | 0.016486 | ATP1B3 |
| 123183918 | 123185582 | chr4 | + | exonic | N/A | −1.7609 | 0.016563 | KIAA1109 |
| 117365827 | 117402659 | chr12 | + | exonic | hsa_circ_0003677 | 1.5865 | 0.016587 | FBXW8 |
| 97207245 | 97213809 | chr9 | + | exonic | hsa_circ_0087581 | −1.6733 | 0.016640 | HIATL1 |
| 51317536 | 51393924 | chr3 | + | exonic | hsa_circ_0065887 | −1.5355 | 0.016688 | DOCK3 |
| 110978278 | 110980107 | chrX | + | exonic | N/A | −1.8957 | 0.016692 | ALG13 |
| 108057208 | 108061227 | chr11 | − | exonic | N/A | 2.1916 | 0.016722 | NPAT |
| 74533340 | 74562028 | chr9 | + | exonic | N/A | −1.6497 | 0.016726 | C9orf85 |
| 47497809 | 47581459 | chr16 | + | exonic | hsa_circ_0005385 | 1.9053 | 0.016738 | PHKB |
| 48466115 | 48472118 | chr20 | + | exonic | hsa_circ_0006359 | −1.6358 | 0.016747 | SLC9A8 |
| 90261231 | 90398157 | chr5 | + | exonic | N/A | −1.6932 | 0.016749 | GPR98 |
| 100169609 | 100170072 | chrX | − | sense overlapping | N/A | −1.6533 | 0.016755 | XKRX |
| 56419830 | 56448256 | chr16 | − | exonic | hsa_circ_0004120 | −1.6313 | 0.016880 | AMFR |
| 56078736 | 56086030 | chr14 | + | exonic | hsa_circ_0032029 | 1.8256 | 0.016936 | KTN1 |
| 81271271 | 81274523 | chr15 | − | exonic | hsa_circ_0000645 | −1.6010 | 0.016946 | MESDC2 |
| 33310020 | 33313150 | chr17 | + | exonic | hsa_circ_0043082 | −1.5058 | 0.017037 | LIG3 |
| 99589361 | 99607298 | chr9 | − | exonic | N/A | −1.8364 | 0.017083 | ZNF782 |
| 24680620 | 24681035 | chr14 | − | exonic | hsa_circ_0031359 | 2.3469 | 0.017119 | CHMP4A |
| 75936161 | 75936743 | chr13 | − | exonic | hsa_circ_0030431 | −1.8523 | 0.017168 | TBC1D4 |
| 118774654 | 118787003 | chrX | − | exonic | hsa_circ_0008350 | 1.9104 | 0.017172 | SEPT6 |
| 70347082 | 70347209 | chr15 | + | antisense | hsa_circ_0000622 | −1.6393 | 0.017197 | TLE3 |
| 34918468 | 34923339 | chr5 | + | exonic | hsa_circ_0006970 | −1.5592 | 0.017198 | BRIX1 |
| 179316734 | 179319566 | chr1 | + | exonic | hsa_circ_0015454 | −1.7691 | 0.017208 | SOAT1 |
| 33114035 | 33118729 | chr3 | − | exonic | N/A | −1.9651 | 0.017224 | GLB1 |
| 33760537 | 33766320 | chr1 | + | exonic | hsa_circ_0011474 | −1.8835 | 0.017268 | ZNF362 |
| 207025605 | 207025856 | chr2 | + | intronic | N/A | −1.5059 | 0.017304 | EEF1B2 |
| 39739039 | 39776553 | chr4 | + | exonic | hsa_circ_0002590 | 2.1657 | 0.017317 | UBE2K |
| 215259710 | 215298093 | chr1 | + | exonic | hsa_circ_0016459 | −1.6209 | 0.017408 | KCNK2 |
| 54119944 | 54120936 | chr2 | − | exonic | hsa_circ_0054547 | 1.6060 | 0.017486 | PSME4 |
| 141828375 | 141900868 | chr8 | − | exonic | hsa_circ_0005982 | 2.2861 | 0.017550 | PTK2 |
| 125930467 | 125936121 | chr9 | − | sense overlapping | hsa_circ_0001887 | 1.6379 | 0.017558 | STRBP |
| 12800185 | 12800444 | chr19 | − | exonic | hsa_circ_0049547 | −1.7851 | 0.017604 | FBXW9 |
| 213302869 | 213349835 | chr1 | + | exonic | hsa_circ_0007772 | −1.6859 | 0.017677 | RPS6KC1 |
| 93467550 | 93472321 | chr15 | + | exonic | hsa_circ_0007262 | 1.6359 | 0.017748 | CHD2 |
| 37105033 | 37105170 | chr2 | − | exonic | hsa_circ_0054033 | −1.6545 | 0.017832 | STRN |
| 128166326 | 128256170 | chrX | − | sense overlapping | N/A | −1.6391 | 0.017884 | RP11-41L14.1 |
| 48597719 | 48597913 | chr4 | − | intronic | N/A | −1.5402 | 0.017889 | FRYL |
| 13387339 | 13438383 | chr18 | + | exonic | hsa_circ_0047040 | −1.7159 | 0.017908 | LDLRAD4 |
| 21723054 | 21723377 | chr18 | + | exonic | hsa_circ_0008705 | −1.5531 | 0.017915 | CABYR |
| 16875716 | 16881223 | chrX | − | exonic | hsa_circ_0005840 | −1.5906 | 0.017938 | RBBP7 |
| 37246951 | 37247979 | chr2 | − | exonic | N/A | −1.6824 | 0.017946 | HEATR5B |
| 11399891 | 11421526 | chr3 | + | exonic | hsa_circ_0008927 | −1.5419 | 0.017949 | ATG7 |
| 33134028 | 33134537 | chr19 | − | exonic | hsa_circ_0000924 | 1.6382 | 0.017998 | ANKRD27 |
| 139865339 | 139866824 | chrX | + | antisense | hsa_circ_0001946 | −1.8783 | 0.018135 | CDR1 |
| 101402108 | 101415933 | chr14 | + | sense overlapping | N/A | −1.5804 | 0.018150 | SNORD113-4 |
| 33971648 | 33973235 | chr9 | − | exonic | hsa_circ_0001851 | 1.9396 | 0.018201 | UBAP2 |
| 41945763 | 41951402 | chr4 | + | exonic | hsa_circ_0069586 | −1.8550 | 0.018238 | TMEM33 |
| 155628480 | 155643155 | chr3 | + | exonic | hsa_circ_0008184 | 1.7557 | 0.018260 | GMPS |
| 153555574 | 153562137 | chr7 | + | intergenic | N/A | −1.6611 | 0.018275 | |
| 23393072 | 23399247 | chr10 | + | exonic | N/A | −1.8689 | 0.018306 | MSRB2 |
| 65830317 | 65831879 | chr1 | + | exonic | hsa_circ_0002454 | 2.5415 | 0.018445 | DNAJC6 |
| 120517677 | 120528452 | chr4 | − | exonic | hsa_circ_0002474 | 1.6812 | 0.018452 | PDE5A |
| 80721840 | 80730383 | chr17 | + | exonic | hsa_circ_0005281 | 1.6420 | 0.018457 | TBCD |
| 32502510 | 32504220 | chr1 | + | exonic | hsa_circ_0007231 | 1.6224 | 0.018498 | KHDRBS1 |
| 135025037 | 135042232 | chrX | − | sense overlapping | N/A | −2.2584 | 0.018503 | RP11-97N5.2 |
| 29959413 | 29962002 | chr8 | + | exonic | hsa_circ_0007353 | 2.0865 | 0.018544 | LEPROTL1 |
| 67356836 | 67371058 | chr1 | − | exonic | hsa_circ_0006677 | 1.8557 | 0.018621 | WDR78 |
| 68527036 | 68529155 | chr11 | − | exonic | hsa_circ_0023249 | −1.8629 | 0.018631 | CPT1A |
| 27432375 | 27436268 | chr1 | − | exonic | hsa_circ_0007283 | −1.6058 | 0.018637 | SLC9A1 |
| 396147 | 397106 | chr16 | − | exonic | hsa_circ_0005838 | 1.9850 | 0.018653 | AXIN1 |
| 66426136 | 66430767 | chr17 | − | exonic | hsa_circ_0045502 | −1.7107 | 0.018661 | WIPI1 |
| 74385612 | 74397235 | chr17 | − | exonic | hsa_circ_0045801 | −1.9272 | 0.018756 | UBE2O |
| 87808910 | 87812746 | chr4 | − | exonic | hsa_circ_0004262 | −1.8784 | 0.018770 | C4orf36 |
| 48497460 | 48500603 | chr20 | + | exonic | N/A | −1.5530 | 0.018852 | SLC9A8 |
| 63269389 | 63286880 | chr1 | + | exonic | hsa_circ_0012823 | 1.7714 | 0.018873 | ATG4C |
| 148863249 | 148864022 | chr7 | + | exonic | N/A | −1.5242 | 0.018915 | ZNF398 |
| 77333544 | 77340944 | chr11 | − | exonic | hsa_circ_0023696 | 1.9776 | 0.018916 | CLNS1A |
| 22896855 | 22898646 | chr10 | − | exonic | hsa_circ_0003826 | 2.1955 | 0.018930 | PIP4K2A |
| 102195835 | 102196253 | chr11 | − | antisense | hsa_circ_0000352 | −1.8890 | 0.019064 | BIRC3 |
| 65729590 | 65731263 | chr3 | − | intronic | N/A | −1.6004 | 0.019131 | MAGI1 |
| 47702783 | 47719801 | chr3 | − | exonic | hsa_circ_0003602 | 1.7055 | 0.019273 | SMARCC1 |

TABLE 9-continued

| (MAOI R 8 week vs MAOI R baseline) | | | | | | | | |
|---|---|---|---|---|---|---|---|---|
| TxStart | TxEnd | Chrom | Strand | circRNA type | Alias | Fold change | P-value | GeneSymbol |
| 34686976 | 34757703 | chr5 | + | exonic | hsa_circ_0072132 | −1.5833 | 0.019397 | RAI14 |
| 145379620 | 145383716 | chr5 | + | exonic | N/A | −1.8352 | 0.019415 | SH3RF2 |
| 31008859 | 31009242 | chr22 | + | sense overlapping | N/A | −1.6545 | 0.019432 | TCN2 |
| 196876613 | 196888609 | chr3 | − | exonic | hsa_circ_0068702 | 1.8545 | 0.019505 | DLG1 |
| 11354777 | 11356967 | chr3 | + | exonic | hsa_circ_0003862 | −1.5406 | 0.019553 | ATG7 |
| 74140611 | 74143892 | chr2 | + | exonic | hsa_circ_0055264 | −2.0017 | 0.019594 | ACTG2 |
| 9379934 | 9437964 | chr5 | − | exonic | hsa_circ_0006397 | −1.7695 | 0.019782 | SEMA5A |
| 70740402 | 70766591 | chr1 | − | exonic | hsa_circ_0000084 | 1.5192 | 0.019804 | ANKRD13C |
| 128768965 | 128908618 | chr10 | + | exonic | hsa_circ_0020396 | −1.7057 | 0.019808 | DOCK1 |
| 242343242 | 242357524 | chr2 | + | exonic | hsa_circ_0004924 | −1.7817 | 0.019855 | FARP2 |
| 99537069 | 99538527 | chr9 | − | exonic | hsa_circ_0007789 | −1.7825 | 0.019914 | ZNF510 |
| 52157280 | 52161651 | chr5 | + | exonic | hsa_circ_0004840 | −1.5013 | 0.019947 | ITGA1 |
| 44021595 | 44028848 | chr2 | + | exonic | hsa_circ_0054326 | −1.6211 | 0.020107 | DYNC2LI1 |
| 122825299 | 122826244 | chr12 | − | exonic | hsa_circ_0029069 | 1.7407 | 0.020219 | CLIP1 |
| 92264128 | 92268765 | chr14 | − | exonic | hsa_circ_0032969 | 3.1619 | 0.020228 | TC2N |
| 29577406 | 29580649 | chr16 | − | exonic | hsa_circ_0038917 | 1.6481 | 0.020321 | LOC440354 |
| 10286215 | 10288043 | chr19 | − | exonic | hsa_circ_0049224 | 2.6963 | 0.020451 | DNMT1 |
| 46515157 | 46534363 | chr11 | − | exonic | hsa_circ_0007061 | −1.7178 | 0.020461 | AMBRA1 |
| 76205664 | 76216231 | chr1 | + | exonic | hsa_circ_0008129 | 1.5559 | 0.020502 | ACADM |
| 35890583 | 35893796 | chr21 | − | intronic | N/A | −1.7677 | 0.020565 | RCAN1 |
| 101372434 | 101373305 | chr14 | + | exonic | hsa_circ_0033198 | −1.9486 | 0.020612 | MEG8 |
| 12999419 | 13042333 | chr18 | + | exonic | hsa_circ_0046999 | 1.8241 | 0.020668 | CEP192 |
| 17669205 | 17669777 | chr6 | − | exonic | hsa_circ_0002049 | 1.8702 | 0.020673 | NUP153 |
| 78098799 | 78107340 | chr1 | − | sense overlapping | hsa_circ_0006395 | 1.9525 | 0.020680 | ZZZ3 |
| 67988716 | 68007967 | chr8 | + | exonic | N/A | 1.5354 | 0.020699 | CSPP1 |
| 66589113 | 66590145 | chr11 | + | exonic | hsa_circ_0023033 | −1.6796 | 0.020715 | C11orf80 |
| 151771875 | 151789457 | chr4 | − | exonic | hsa_circ_0071224 | −1.5202 | 0.020747 | LRBA |
| 14270933 | 14280545 | chr5 | + | exonic | hsa_circ_0003037 | −1.6523 | 0.020782 | TRIO |
| 6880240 | 6885270 | chr1 | + | exonic | hsa_circ_0009541 | 1.5905 | 0.020786 | CAMTA1 |
| 20972052 | 20972473 | chr1 | + | sense overlapping | N/A | −1.6375 | 0.020803 | PINK1 |
| 59955247 | 59958532 | chr17 | − | exonic | hsa_circ_0045038 | −1.7155 | 0.020807 | INTS2 |
| 110826316 | 110834257 | chr12 | − | exonic | hsa_circ_0028196 | −1.5250 | 0.020851 | ANAPC7 |
| 37326002 | 37328522 | chr5 | − | exonic | hsa_circ_0072255 | −1.8815 | 0.020867 | NUP155 |
| 167677562 | 167677724 | chr1 | − | intergenic | hsa_circ_0000152 | −1.5882 | 0.020887 | |
| 93543741 | 93558139 | chr15 | + | exonic | hsa_circ_0037002 | 1.6686 | 0.020893 | CHD2 |
| 40477365 | 40477843 | chr15 | + | exonic | hsa_circ_0008946 | −1.7444 | 0.020909 | BUB1B |
| 80040477 | 80049438 | chr9 | − | exonic | N/A | −1.6242 | 0.020930 | GNA14 |
| 34789429 | 34789732 | chr6 | + | exonic | hsa_circ_0076054 | −1.7299 | 0.020944 | UHRF1BP1 |
| 94066434 | 94068129 | chr6 | − | exonic | hsa_circ_0077398 | −1.6910 | 0.020972 | EPHA7 |
| 111923074 | 111924628 | chr12 | − | exonic | hsa_circ_0002273 | 2.0655 | 0.021019 | ATXN2 |
| 46319924 | 46322642 | chr12 | − | exonic | hsa_circ_0025967 | 1.7084 | 0.021054 | SCAF11 |
| 70510478 | 70521018 | chrX | + | exonic | hsa_circ_0090999 | 1.6410 | 0.021059 | NONO |
| 68308593 | 68309152 | chr16 | + | exonic | hsa_circ_0007669 | 1.5514 | 0.021061 | SLC7A6 |
| 47531309 | 47581459 | chr16 | + | exonic | hsa_circ_0004791 | 2.0167 | 0.021077 | PHKB |
| 26587169 | 26606215 | chr2 | + | exonic | hsa_circ_0006111 | −1.5691 | 0.021089 | EPT1 |
| 62291306 | 62292503 | chr11 | − | intronic | hsa_circ_0000319 | 3.1119 | 0.021105 | AHNAK |
| 135010665 | 135012215 | chr2 | + | exonic | hsa_circ_0001068 | 1.9264 | 0.021117 | MGAT5 |
| 35812582 | 35812776 | chr20 | + | exonic | hsa_circ_0005759 | −1.5747 | 0.021128 | RPN2 |
| 20682177 | 20688770 | chr15 | − | exonic | hsa_circ_0007563 | 1.5661 | 0.021209 | HERC2P3 |
| 7262372 | 7327916 | chr10 | − | exonic | hsa_circ_0017628 | 1.8192 | 0.021263 | SFMBT2 |
| 44436348 | 44436466 | chr2 | + | exonic | hsa_circ_0054406 | 1.6561 | 0.021291 | PPM1B |
| 33714053 | 33719586 | chr20 | − | exonic | N/A | −1.6981 | 0.021416 | EDEM2 |
| 112096539 | 112098479 | chr12 | − | exonic | hsa_circ_0007776 | 1.5215 | 0.021465 | BRAP |
| 134381500 | 134382901 | chr9 | + | exonic | hsa_circ_0089237 | 1.8112 | 0.021470 | POMT1 |
| 20251685 | 20280587 | chr12 | + | sense overlapping | N/A | −1.5598 | 0.021473 | LOC100506393 |
| 78183551 | 78191447 | chr1 | − | exonic | hsa_circ_0000087 | 1.6251 | 0.021491 | USP33 |
| 100467991 | 100471076 | chr7 | + | exonic | hsa_circ_0081545 | −1.7747 | 0.021497 | TRIP6 |
| 55621921 | 55634000 | chr15 | + | exonic | hsa_circ_0035381 | −1.7867 | 0.021547 | PIGB |
| 158436980 | 158439255 | chr7 | − | exonic | hsa_circ_0083182 | −1.5063 | 0.021553 | NCAPG2 |
| 203382173 | 203383775 | chr2 | + | sense overlapping | N/A | −1.6229 | 0.021555 | BMPR2 |
| 34953607 | 34958487 | chr21 | − | exonic | hsa_circ_0004339 | −1.7990 | 0.021587 | DONSON |
| 159444736 | 159445499 | chr2 | + | intronic | N/A | −1.6958 | 0.021589 | PKP4 |
| 70502751 | 70505255 | chr16 | + | exonic | N/A | −1.5929 | 0.021595 | FUK |
| 85331067 | 85331842 | chr1 | − | exonic | hsa_circ_0013058 | −1.8111 | 0.021658 | LPAR3 |
| 18650180 | 18650530 | chr19 | − | exonic | hsa_circ_0000915 | 1.6671 | 0.021688 | FKBP8 |
| 116335174 | 116444414 | chr10 | − | exonic | hsa_circ_0020076 | −2.0166 | 0.021733 | ABLIM1 |
| 169947225 | 170001116 | chr1 | − | sense overlapping | N/A | 1.7650 | 0.021775 | KIFAP3 |
| 30734587 | 30746317 | chr20 | + | exonic | hsa_circ_0059760 | −1.8378 | 0.021814 | TM9SF4 |
| 77791974 | 77818086 | chr13 | − | exonic | hsa_circ_0004217 | 1.9163 | 0.021916 | MYCBP2 |
| 70588843 | 70594578 | chr8 | − | exonic | hsa_circ_0084725 | −1.8305 | 0.021921 | SLCO5A1 |

TABLE 9-continued (MAOI R 8 week vs MAOI R baseline)

| TxStart | TxEnd | Chrom | Strand | circRNA type | Alias | Fold change | P-value | GeneSymbol |
|---|---|---|---|---|---|---|---|---|
| 22635490 | 22659753 | chr12 | − | exonic | N/A | 1.7007 | 0.021941 | C2CD5 |
| 15970016 | 15976318 | chr1 | + | exonic | hsa_circ_0010058 | 1.7843 | 0.021971 | DDI2 |
| 6086622 | 6089676 | chr7 | − | exonic | hsa_circ_0079329 | 1.7493 | 0.021999 | EIF2AK1 |
| 42363987 | 42375484 | chr19 | + | exonic | hsa_circ_0051241 | 2.1583 | 0.022035 | RPS19 |
| 95257644 | 95279591 | chr13 | + | sense overlapping | N/A | −1.7061 | 0.022064 | GPR180 |
| 90432490 | 90459827 | chr14 | + | exonic | hsa_circ_0032895 | −1.5206 | 0.022074 | TDP1 |
| 141874410 | 141900868 | chr8 | − | exonic | hsa_circ_0002483 | 2.4623 | 0.022099 | PTK2 |
| 47603639 | 47604020 | chr11 | + | exonic | hsa_circ_0022015 | −1.7333 | 0.022103 | NDUFS3 |
| 47512341 | 47522502 | chr6 | + | exonic | N/A | 1.6007 | 0.022111 | CD2AP |
| 18624903 | 18633652 | chr7 | + | exonic | hsa_circ_0001680 | −1.5370 | 0.022151 | HDAC9 |
| 217536827 | 217541605 | chr2 | − | exonic | hsa_circ_0058196 | −1.7204 | 0.022170 | IGFBP5 |
| 22880557 | 22880710 | chr10 | − | exonic | hsa_circ_0017972 | 2.6878 | 0.022178 | PIP4K2A |
| 74371372 | 74372792 | chr16 | − | exonic | hsa_circ_0005647 | 1.6335 | 0.022194 | LOC283922 |
| 67562936 | 67614669 | chr18 | − | exonic | N/A | 1.6806 | 0.022204 | CD226 |
| 78865519 | 78867665 | chr17 | + | exonic | hsa_circ_0000813 | −1.5431 | 0.022219 | RPTOR |
| 91855033 | 91855996 | chr7 | − | exonic | N/A | 1.9828 | 0.022260 | KRIT1 |
| 97041039 | 97055351 | chr9 | + | exonic | hsa_circ_0087564 | −1.8705 | 0.022330 | ZNF169 |
| 222997225 | 223008557 | chr1 | + | exonic | hsa_circ_0000187 | 1.8007 | 0.022335 | RP11-452F19.3 |
| 227771508 | 227779067 | chr2 | + | exonic | hsa_circ_0058497 | 1.8444 | 0.022352 | RHBDD1 |
| 11348632 | 11362551 | chr11 | − | exonic | N/A | −1.7257 | 0.022355 | GALNT18 |
| 118982215 | 119033695 | chr9 | + | exonic | hsa_circ_0088222 | −1.7062 | 0.022408 | PAPPA |
| 34922765 | 34924317 | chr19 | + | exonic | hsa_circ_0050514 | 1.7905 | 0.022470 | UBA2 |
| 29190547 | 29196560 | chr22 | − | exonic | hsa_circ_0062722 | −1.9340 | 0.022518 | XBP1 |
| 151060665 | 151079698 | chr1 | + | exonic | N/A | 1.5913 | 0.022529 | GABPB2 |
| 5214371 | 5220364 | chr19 | − | exonic | N/A | −1.5130 | 0.022530 | PTPRS |
| 40578033 | 40584633 | chr21 | − | exonic | N/A | 2.2882 | 0.022593 | BRWD1 |
| 111372281 | 111585853 | chr7 | − | exonic | hsa_circ_0081968 | −1.8222 | 0.022688 | DOCK4 |
| 65924470 | 65925603 | chr17 | + | exonic | hsa_circ_0004392 | 1.5035 | 0.022711 | BPTF |
| 95966670 | 95970601 | chr5 | + | intronic | N/A | −1.6277 | 0.022723 | CAST |
| 53189837 | 53191453 | chr16 | + | exonic | hsa_circ_0039353 | 1.9711 | 0.022779 | CHD9 |
| 50824277 | 50829407 | chr12 | + | exonic | hsa_circ_0026232 | 1.6637 | 0.022791 | LARP4 |
| 20932159 | 20953727 | chr18 | − | exonic | hsa_circ_0047145 | −1.5853 | 0.022794 | TMEM241 |
| 56419830 | 56423287 | chr16 | − | exonic | hsa_circ_0000704 | −1.5518 | 0.022833 | AMFR |
| 73748522 | 73850873 | chr11 | − | exonic | hsa_circ_0023535 | −1.6953 | 0.022840 | C2CD3 |
| 33442618 | 33447218 | chr2 | + | exonic | hsa_circ_0053907 | 1.6685 | 0.022843 | LTBP1 |
| 39721111 | 39729993 | chr20 | + | exonic | N/A | 1.9700 | 0.022880 | TOP1 |
| 15860731 | 15863309 | chr1 | + | exonic | hsa_circ_0000018 | 2.3419 | 0.022996 | DNAJC16 |
| 101874252 | 101886778 | chr2 | + | exonic | hsa_circ_0055894 | −1.5835 | 0.023011 | CNOT11 |
| 46135263 | 46159290 | chr10 | − | exonic | N/A | 1.9068 | 0.023062 | ZFAND4 |
| 74982416 | 74999720 | chr16 | − | exonic | hsa_circ_0040534 | 1.6681 | 0.023066 | WDR59 |
| 158994451 | 159010814 | chr6 | + | exonic | hsa_circ_0004587 | 1.7580 | 0.023078 | TMEM181 |
| 96044222 | 96064458 | chr8 | + | exonic | hsa_circ_0007549 | −1.5299 | 0.023132 | NDUFAF6 |
| 134249418 | 134249772 | chr8 | − | exonic | hsa_circ_0085646 | −1.7267 | 0.023145 | AX746885 |
| 15758592 | 15761296 | chr16 | + | exonic | hsa_circ_0038054 | −1.7712 | 0.023171 | NDE1 |
| 101891136 | 101904985 | chr9 | + | exonic | hsa_circ_0087731 | −1.6128 | 0.023171 | TGFBR1 |
| 54249939 | 54256040 | chr4 | + | exonic | hsa_circ_0001411 | 2.5706 | 0.023245 | FIP1L1 |
| 60733932 | 60735153 | chr14 | + | exonic | N/A | −1.8768 | 0.023254 | PPM1A |
| 80721840 | 80758872 | chr17 | + | exonic | hsa_circ_0046464 | 1.7978 | 0.023269 | TBCD |
| 113703700 | 113773970 | chr9 | − | exonic | hsa_circ_0004928 | −1.5211 | 0.023270 | LPAR1 |
| 113137647 | 113139646 | chr9 | − | exonic | N/A | −1.6907 | 0.023294 | SVEP1 |
| 72302181 | 72302378 | chr7 | + | exonic | hsa_circ_0008708 | 2.5659 | 0.023357 | SBDSP1 |
| 36211051 | 36212593 | chr1 | − | exonic | hsa_circ_0011588 | −1.6041 | 0.023417 | CLSPN |
| 42914234 | 42938323 | chr8 | + | exonic | hsa_circ_0084172 | 1.5141 | 0.023462 | FNTA |
| 20635192 | 20657172 | chr13 | + | exonic | N/A | −1.6310 | 0.023469 | ZMYM2 |
| 123489400 | 123489932 | chr11 | + | exonic | hsa_circ_0024731 | −1.6432 | 0.023499 | GRAMD1B |
| 72890195 | 72891553 | chr3 | − | exonic | hsa_circ_0005299 | 1.5204 | 0.023539 | SHQ1 |
| 32915309 | 32915477 | chr3 | + | exonic | N/A | −1.5003 | 0.023543 | TRIM71 |
| 69304539 | 69318051 | chr2 | + | exonic | hsa_circ_0055033 | −1.8315 | 0.023574 | ANTXR1 |
| 14938844 | 14939516 | chr10 | + | exonic | hsa_circ_0006780 | 1.7923 | 0.023576 | SUV39H2 |
| 65924470 | 65928135 | chr17 | + | exonic | hsa_circ_0045462 | 2.0241 | 0.023587 | BPTF |
| 34100754 | 34101636 | chr6 | − | exonic | hsa_circ_0076041 | −1.7335 | 0.023661 | GRM4 |
| 112096539 | 112097149 | chr12 | − | exonic | hsa_circ_0007885 | 2.0166 | 0.023753 | BRAP |
| 127294245 | 127294652 | chr3 | − | exonic | hsa_circ_0067159 | −1.5040 | 0.023771 | TPRA1 |
| 52977368 | 53003274 | chr3 | − | exonic | hsa_circ_0066151 | −1.5871 | 0.023826 | SFMBT1 |
| 62650379 | 62653080 | chr11 | + | exonic | hsa_circ_0022587 | −1.6097 | 0.023873 | SLC3A2 |
| 43655238 | 43657441 | chr2 | − | exonic | hsa_circ_0054309 | −1.6222 | 0.023891 | THADA |
| 35487897 | 35488280 | chr14 | + | exonic | hsa_circ_0031647 | 1.5379 | 0.023906 | SRP54 |
| 95686858 | 95735544 | chr13 | − | exonic | hsa_circ_0030569 | −1.6039 | 0.023980 | ABCC4 |
| 25151491 | 25162936 | chr16 | + | exonic | N/A | −2.2283 | 0.024046 | LCMT1 |
| 3197902 | 3215945 | chr3 | − | exonic | hsa_circ_0003400 | 2.0379 | 0.024101 | CRBN |
| 61083896 | 61141784 | chr13 | + | exonic | N/A | 1.6440 | 0.024104 | TDRD3 |
| 5664833 | 5699374 | chr4 | − | exonic | hsa_circ_0069059 | −1.6392 | 0.024237 | EVC2 |
| 15374347 | 15468949 | chr6 | + | exonic | N/A | 2.1128 | 0.024239 | JARID2 |
| 134002512 | 134007576 | chr5 | + | exonic | hsa_circ_0003180 | −1.8963 | 0.024244 | SEC24A |
| 53558502 | 53570574 | chr14 | − | exonic | hsa_circ_0031977 | 1.5450 | 0.024245 | DDHD1 |

TABLE 9-continued

| (MAOI R 8 week vs MAOI R baseline) | | | | | | | | |
|---|---|---|---|---|---|---|---|---|
| TxStart | TxEnd | Chrom | Strand | circRNA type | Alias | Fold change | P-value | GeneSymbol |
| 183361267 | 183390272 | chr3 | + | exonic | hsa_circ_0001368 | 2.2627 | 0.024253 | KLHL24 |
| 96517441 | 96525822 | chr2 | − | exonic | N/A | 1.9482 | 0.024275 | ANKRD36C |
| 72020039 | 72022817 | chr12 | − | exonic | hsa_circ_0008912 | −1.8550 | 0.024344 | ZFC3H1 |
| 29994794 | 30008684 | chr7 | − | exonic | N/A | −1.7225 | 0.024418 | SCRN1 |
| 15644268 | 15679480 | chr2 | − | exonic | hsa_circ_0004665 | 2.5051 | 0.024516 | NBAS |
| 44530905 | 44531243 | chr20 | − | exonic | hsa_circ_0060558 | −1.9777 | 0.024528 | PLTP |
| 231222519 | 231226412 | chr2 | + | exonic | hsa_circ_0008382 | 2.2967 | 0.024544 | SP140L |
| 48311248 | 48337216 | chr16 | + | exonic | hsa_circ_0008558 | 1.8712 | 0.024557 | LONP2 |
| 77631183 | 77632364 | chr9 | − | exonic | hsa_circ_0004189 | 2.4547 | 0.024624 | C9orf41 |
| 1004356 | 1004666 | chr16 | − | exonic | hsa_circ_0007701 | −1.5280 | 0.024743 | LMF1 |
| 74522734 | 74523039 | chr9 | − | intronic | N/A | −1.7979 | 0.024765 | ABHD17B |
| 15629017 | 15651474 | chr2 | − | exonic | hsa_circ_0000978 | 1.8066 | 0.024825 | NBAS |
| 105822015 | 105824354 | chr10 | − | exonic | hsa_circ_0019960 | −1.7361 | 0.024844 | COL17A1 |
| 43668295 | 43669265 | chr15 | + | exonic | hsa_circ_0034953 | −1.7788 | 0.024913 | TUBGCP4 |
| 73985878 | 73991029 | chr4 | − | exonic | hsa_circ_0002831 | 1.6311 | 0.024934 | ANKRD17 |
| 62579578 | 62582288 | chr17 | − | exonic | hsa_circ_0045322 | 1.8921 | 0.024961 | SMURF2 |
| 30209418 | 30210756 | chr22 | − | exonic | hsa_circ_0062794 | −1.7082 | 0.024981 | ASCC2 |
| 70766446 | 70781249 | chr1 | − | exonic | hsa_circ_0003566 | 1.9444 | 0.024999 | ANKRD13C |
| 12678107 | 12678441 | chr18 | − | exonic | hsa_circ_0046974 | −1.5297 | 0.025048 | CEP76 |
| 192880233 | 192880611 | chr1 | − | intergenic | N/A | −1.5667 | 0.025077 | |
| 34789429 | 34791125 | chr6 | + | exonic | hsa_circ_0076055 | −1.6989 | 0.025091 | UHRF1BP1 |
| 23180387 | 23191828 | chr7 | + | exonic | N/A | −1.5959 | 0.025113 | KLHL7 |
| 44395274 | 44401035 | chr18 | − | exonic | hsa_circ_0047585 | −1.8348 | 0.025157 | PIAS2 |
| 80721840 | 80861354 | chr17 | + | exonic | hsa_circ_0046468 | 1.7372 | 0.025171 | TBCD |
| 44436353 | 44436466 | chr2 | + | intronic | N/A | 1.5437 | 0.025248 | PPM1B |
| 52899281 | 52900725 | chr5 | + | exonic | hsa_circ_0005593 | −1.5559 | 0.025254 | NDUFS4 |
| 220179447 | 220180680 | chr1 | − | exonic | hsa_circ_0007739 | 1.5604 | 0.025275 | EPRS |
| 48818462 | 48819092 | chr17 | + | exonic | hsa_circ_0044623 | 1.6179 | 0.025315 | LUC7L3 |
| 9758948 | 9786125 | chr12 | + | sense overlapping | N/A | −1.6755 | 0.025341 | LOC374443 |
| 12214763 | 12215812 | chr10 | − | exonic | N/A | −1.6525 | 0.025351 | NUDT5 |
| 131271154 | 131271376 | chr9 | + | exonic | hsa_circ_0088807 | −1.6833 | 0.025377 | GLE1 |
| 76576097 | 76588078 | chr15 | − | exonic | hsa_circ_0002226 | 1.5520 | 0.025462 | ETFA |
| 34974539 | 34985912 | chr21 | − | exonic | N/A | −1.5792 | 0.025495 | CRYZL1 |
| 34101174 | 34111003 | chr11 | + | exonic | hsa_circ_0000286 | 1.6883 | 0.025530 | CAPRIN1 |
| 9208654 | 9239554 | chr18 | + | intronic | hsa_circ_0005715 | 1.5224 | 0.025559 | RP11-21J18.1 |
| 46189392 | 46196548 | chr17 | + | exonic | hsa_circ_0044353 | −1.5012 | 0.025603 | SNX11 |
| 49713126 | 49720934 | chr3 | + | exonic | hsa_circ_0065673 | −1.5946 | 0.025610 | APEH |
| 24663284 | 24690331 | chr7 | + | exonic | hsa_circ_0001685 | 2.0186 | 0.025641 | MPP6 |
| 52028142 | 52029002 | chr3 | − | intronic | hsa_circ_0092277 | −1.8618 | 0.025653 | RPL29 |
| 131060182 | 131130662 | chr7 | + | exonic | hsa_circ_0003047 | 2.5271 | 0.025668 | MKLN1 |
| 139978870 | 140060651 | chr4 | − | exonic | hsa_circ_0070982 | −1.5593 | 0.025694 | ELF2 |
| 32677771 | 32678011 | chr20 | − | intronic | hsa_circ_0092291 | −1.6537 | 0.025734 | EIF2S2 |
| 75355797 | 75356052 | chr14 | + | exonic | hsa_circ_0032627 | 1.7133 | 0.025740 | DLST |
| 82923943 | 82924546 | chr6 | − | exonic | N/A | 1.5211 | 0.025765 | IBTK |
| 87451065 | 87452507 | chr16 | − | exonic | hsa_circ_0007361 | −1.6267 | 0.025775 | ZCCHC14 |
| 37115061 | 37122590 | chr5 | − | exonic | N/A | −1.5407 | 0.025778 | C5orf42 |
| 77711343 | 77717784 | chr5 | + | exonic | hsa_circ_0002186 | −1.5205 | 0.025847 | SCAMP1 |
| 7318853 | 7327916 | chr10 | − | exonic | hsa_circ_0000211 | 1.6336 | 0.025872 | SFMBT2 |
| 56334222 | 56334387 | chr12 | + | intronic | N/A | −2.0645 | 0.025878 | DGKA |
| 102810157 | 102810726 | chr14 | − | sense overlapping | N/A | −1.6728 | 0.025907 | CINP |
| 54734330 | 54737100 | chr12 | + | exonic | N/A | −1.6678 | 0.025937 | COPZ1 |
| 61468694 | 61484485 | chr2 | − | exonic | N/A | 1.8271 | 0.025945 | USP34 |
| 44106301 | 44119121 | chr21 | + | exonic | hsa_circ_0061828 | −1.8388 | 0.025964 | PDE9A |
| 45041062 | 45042405 | chr17 | + | intronic | hsa_circ_0006682 | −1.7228 | 0.025981 | GOSR2 |
| 3712576 | 3716836 | chr11 | − | exonic | hsa_circ_0006430 | −1.7868 | 0.025988 | NUP98 |
| 18722796 | 18724915 | chr20 | + | sense overlapping | N/A | −1.5311 | 0.025988 | DTD1 |
| 195800800 | 195802231 | chr3 | − | exonic | hsa_circ_0068629 | 1.6400 | 0.026025 | TFRC |
| 45516745 | 45553909 | chr1 | − | exonic | N/A | −1.7993 | 0.026101 | ZSWIM5 |
| 57466030 | 57467869 | chr11 | + | sense overlapping | hsa_circ_0004997 | −1.5481 | 0.026128 | ZDHHC5 |
| 120460114 | 120528452 | chr4 | − | exonic | hsa_circ_0070805 | 1.5899 | 0.026128 | PDE5A |
| 4032518 | 4032815 | chr6 | + | sense overlapping | hsa_circ_0001572 | −1.7462 | 0.026199 | PRPF4B |
| 183831943 | 183848110 | chr2 | − | exonic | N/A | −1.6249 | 0.026255 | NCKAP1 |
| 241402763 | 241407495 | chr2 | + | exonic | hsa_circ_0058934 | −1.8869 | 0.026274 | GPC1 |
| 40161688 | 40179999 | chr20 | − | exonic | hsa_circ_0001159 | 2.4417 | 0.026279 | CHD6 |
| 53685473 | 53687313 | chr12 | + | sense overlapping | N/A | −1.8829 | 0.026304 | ESPL1 |
| 50956259 | 51001129 | chr1 | − | exonic | hsa_circ_0008981 | 1.8961 | 0.026343 | FAF1 |
| 16386664 | 16386787 | chr21 | − | exonic | hsa_circ_0061274 | 1.6360 | 0.026430 | NRIP1 |
| 76069566 | 76069928 | chr7 | + | exonic | hsa_circ_0080802 | −1.7674 | 0.026445 | ZP3 |
| 204354306 | 204356042 | chr2 | − | exonic | hsa_circ_0004564 | −1.6473 | 0.026446 | RAPH1 |
| 138773478 | 138774924 | chr9 | − | exonic | hsa_circ_0001900 | 1.7119 | 0.026455 | CAMSAP1 |

TABLE 9-continued (MAOI R 8 week vs MAOI R baseline)

| TxStart | TxEnd | Chrom | Strand | circRNA type | Alias | Fold change | P-value | GeneSymbol |
|---|---|---|---|---|---|---|---|---|
| 44371545 | 44376369 | chr6 | + | exonic | hsa_circ_0004346 | −1.7435 | 0.026467 | CDC5L |
| 65349233 | 65350779 | chr5 | + | exonic | hsa_circ_0072732 | 2.5468 | 0.026523 | ERBB2IP |
| 158994451 | 159046786 | chr6 | + | exonic | N/A | 2.1383 | 0.026525 | TMEM181 |
| 160015134 | 160016236 | chr6 | − | sense overlapping | N/A | −1.7459 | 0.026543 | XLOC_005900 |
| 34450934 | 34459751 | chr20 | + | exonic | hsa_circ_0060158 | 1.9414 | 0.026575 | PHF20 |
| 23395341 | 23396869 | chr14 | − | exonic | hsa_circ_0002928 | −1.6359 | 0.026598 | PRMT5 |
| 155063089 | 155099179 | chr6 | + | exonic | hsa_circ_0078357 | −1.8908 | 0.026611 | SCAF8 |
| 153734045 | 153737539 | chr1 | + | exonic | hsa_circ_0014306 | −1.7164 | 0.026631 | INTS3 |
| 10460449 | 10480201 | chr1 | + | exonic | hsa_circ_0009725 | −1.8176 | 0.026635 | PGD |
| 159004985 | 159010814 | chr6 | + | exonic | hsa_circ_0001663 | 1.6182 | 0.026645 | TMEM181 |
| 161293403 | 161326630 | chr1 | + | exonic | hsa_circ_0015004 | −1.6185 | 0.026671 | SDHC |
| 7160603 | 7170346 | chr2 | + | exonic | hsa_circ_0000970 | −1.5185 | 0.026686 | RNF144A |
| 120776652 | 120799686 | chr2 | + | exonic | hsa_circ_0056264 | −1.5016 | 0.026687 | EPB41L5 |
| 143382083 | 143486320 | chr6 | + | exonic | N/A | −1.6652 | 0.026721 | AIG1 |
| 40590077 | 40590586 | chr21 | − | exonic | hsa_circ_0061721 | 1.8694 | 0.026735 | BRWD1 |
| 90670648 | 90670832 | chr6 | + | antisense | hsa_circ_0001623 | −1.5169 | 0.026806 | BACH2 |
| 40434005 | 40434149 | chr1 | + | exonic | hsa_circ_0011871 | −1.7201 | 0.026909 | MFSD2A |
| 172782046 | 172809519 | chr2 | + | exonic | hsa_circ_0008032 | 1.5979 | 0.026939 | HAT1 |
| 34832618 | 34832848 | chr20 | + | exonic | hsa_circ_0060176 | −1.7834 | 0.026942 | AAR2 |
| 48191166 | 48192435 | chr12 | − | exonic | N/A | −1.5686 | 0.026958 | HDAC7 |
| 145594038 | 145595220 | chr1 | − | exonic | hsa_circ_0003693 | 2.0544 | 0.027100 | POLR3C |
| 47127684 | 47139571 | chr3 | − | exonic | N/A | 2.1306 | 0.027106 | SETD2 |
| 77830227 | 77835260 | chr11 | − | exonic | hsa_circ_0023787 | −1.7030 | 0.027110 | ALG8 |
| 74239461 | 74251505 | chr7 | − | exonic | hsa_circ_0080628 | 1.9957 | 0.027146 | GTF2IRD2 |
| 71867510 | 71884913 | chr14 | + | exonic | hsa_circ_0002722 | −1.6239 | 0.027188 | SIPA1L1 |
| 41826780 | 41837620 | chr13 | − | exonic | hsa_circ_0030062 | −1.6136 | 0.027234 | MTRF1 |
| 32973011 | 32973508 | chr7 | − | exonic | N/A | −1.5625 | 0.027249 | RP9P |
| 85180577 | 85184493 | chr15 | + | sense overlapping | hsa_circ_0006899 | −1.5856 | 0.027249 | SCAND2P |
| 24679553 | 24681035 | chr14 | − | exonic | hsa_circ_0031357 | 2.3124 | 0.027252 | CHMP4A |
| 6021853 | 6029319 | chr1 | − | exonic | hsa_circ_0009135 | −1.5592 | 0.027254 | NPHP4 |
| 243776972 | 244006584 | chr1 | − | exonic | hsa_circ_0017252 | 2.8223 | 0.027311 | AKT3 |
| 35814866 | 35815138 | chr1 | + | intronic | N/A | −1.6490 | 0.027336 | ZMYM4 |
| 111860382 | 111860606 | chr10 | + | exonic | hsa_circ_0020005 | 1.6735 | 0.027336 | ADD3 |
| 99672757 | 99673253 | chr7 | − | exonic | hsa_circ_0081386 | −1.6982 | 0.027361 | ZNF3 |
| 50592985 | 50596330 | chr15 | − | exonic | hsa_circ_0007983 | −1.8425 | 0.027423 | GABPB1 |
| 65288537 | 65310553 | chr5 | + | exonic | hsa_circ_0005649 | 1.8782 | 0.027478 | ERBB2IP |
| 31175028 | 31204064 | chr14 | + | exonic | N/A | 1.7482 | 0.027500 | SCFD1 |
| 126370175 | 126384781 | chr10 | − | exonic | hsa_circ_0003570 | 1.7721 | 0.027509 | FAM53B |
| 202400743 | 202446940 | chr2 | − | exonic | N/A | −1.7351 | 0.027534 | ALS2CR11 |
| 50210774 | 50212096 | chr19 | + | exonic | hsa_circ_0051959 | −1.5509 | 0.027638 | CPT1C |
| 84112887 | 84132553 | chr14 | + | intergenic | N/A | −1.8216 | 0.027678 | |
| 32678875 | 32824967 | chr2 | + | exonic | hsa_circ_0053651 | 1.5528 | 0.027683 | BIRC6 |
| 48817428 | 48842572 | chr8 | − | exonic | hsa_circ_0084429 | −1.6279 | 0.027691 | PRKDC |
| 100296305 | 100297301 | chrX | − | exonic | hsa_circ_0001937 | 1.7201 | 0.027692 | TRMT2B |
| 48552608 | 48553595 | chr4 | − | exonic | hsa_circ_0069681 | −1.6237 | 0.027738 | FRYL |
| 35436177 | 35438558 | chr6 | + | exonic | hsa_circ_0076138 | −1.6964 | 0.027840 | RPL104 |
| 117150623 | 117150975 | chr11 | + | exonic | hsa_circ_0002743 | 1.5876 | 0.027855 | RNF214 |
| 80721840 | 80739597 | chr17 | + | exonic | hsa_circ_0000818 | 1.5981 | 0.027887 | TBCD |
| 99887644 | 99913012 | chr6 | − | exonic | hsa_circ_0077425 | −1.6777 | 0.027908 | USP45 |
| 40502897 | 40503739 | chr3 | + | sense overlapping | hsa_circ_0002102 | 1.7665 | 0.027949 | RPL14 |
| 77154960 | 77160881 | chrX | + | exonic | hsa_circ_0091114 | −1.5220 | 0.027956 | COX7B |
| 94645539 | 94649052 | chr9 | − | exonic | N/A | −2.0987 | 0.027980 | ROR2 |
| 35622699 | 35644989 | chr13 | + | exonic | hsa_circ_0029984 | −1.6827 | 0.028024 | NBEA |
| 430683 | 440932 | chr19 | − | exonic | N/A | −1.8542 | 0.028088 | SHC2 |
| 122701034 | 122709295 | chr12 | − | exonic | hsa_circ_0029053 | −1.6150 | 0.028100 | DIABLO |
| 73100965 | 73101425 | chr7 | + | exonic | hsa_circ_0005588 | 2.0037 | 0.028101 | WBSCR22 |
| 96692646 | 96694138 | chr12 | − | exonic | hsa_circ_0007881 | 2.0039 | 0.028131 | CDK17 |
| 59739905 | 59751839 | chr18 | − | exonic | hsa_circ_0047841 | −1.5586 | 0.028173 | PIGN |
| 176524542 | 176526377 | chr1 | + | exonic | N/A | −1.6869 | 0.028174 | PAPPA2 |
| 99990262 | 100016690 | chr6 | − | exonic | hsa_circ_0077434 | −1.9508 | 0.028183 | CCNC |
| 145215872 | 145218751 | chr8 | + | exonic | hsa_circ_0085976 | −1.5323 | 0.028184 | MROH1 |
| 33735522 | 33735618 | chr21 | − | sense overlapping | hsa_circ_0001182 | −1.6470 | 0.028187 | URB1 |
| 74948073 | 74948409 | chr15 | − | exonic | hsa_circ_0004401 | −1.5400 | 0.028217 | EDC3 |
| 41994031 | 42017061 | chr22 | − | exonic | hsa_circ_0063583 | −1.6745 | 0.028231 | DESI1 |
| 28956385 | 28956758 | chr8 | − | sense overlapping | N/A | −1.7676 | 0.028239 | KIF13B |
| 236706402 | 236708166 | chr2 | + | exonic | hsa_circ_0058805 | −1.6290 | 0.028269 | AGAP1 |
| 183368083 | 183369064 | chr3 | + | exonic | hsa_circ_0001369 | 2.3313 | 0.028313 | KLHL24 |
| 891302 | 892653 | chr1 | − | exonic | hsa_circ_0009205 | 1.7764 | 0.028313 | NOC21 |
| 138741982 | 138774924 | chr9 | − | exonic | hsa_circ_0004338 | 1.6981 | 0.028357 | CAMSAP1 |
| 39757276 | 39776553 | chr4 | + | exonic | hsa_circ_0003381 | 1.7922 | 0.028417 | UBE2K |
| 31448653 | 31451747 | chr5 | − | exonic | hsa_circ_0004599 | −1.5630 | 0.028427 | DROSHA |

TABLE 9-continued (MAOI R 8 week vs MAOI R baseline)

| TxStart | TxEnd | Chrom | Strand | circRNA type | Alias | Fold change | P-value | GeneSymbol |
|---|---|---|---|---|---|---|---|---|
| 31535331 | 31542179 | chr14 | + | exonic | hsa_circ_0031449 | −1.7182 | 0.028437 | AP4S1 |
| 50054354 | 50057699 | chr13 | + | exonic | hsa_circ_0000483 | 1.5346 | 0.028464 | SETDB2 |
| 6150755 | 6155154 | chr7 | + | exonic | hsa_circ_0007823 | −1.5396 | 0.028538 | USP42 |
| 32198899 | 32199141 | chr20 | + | exonic | hsa_circ_0059859 | −2.0582 | 0.028551 | CBFA2T2 |
| 89807211 | 89815175 | chr16 | − | exonic | hsa_circ_0040994 | −1.6595 | 0.028570 | FANCA |
| 216177220 | 216200847 | chr2 | + | exonic | hsa_circ_0058060 | −1.8336 | 0.028574 | ATIC |
| 50850356 | 50850568 | chr12 | + | intronic | N/A | −1.5227 | 0.028640 | LARP4 |
| 36584932 | 36590519 | chr19 | + | exonic | hsa_circ_0050715 | −1.6729 | 0.028661 | WDR62 |
| 128065409 | 128066156 | chr2 | − | intronic | N/A | −1.5987 | 0.028662 | MAP3K2 |
| 21076215 | 21076375 | chr1 | − | exonic | hsa_circ_0010440 | 2.0129 | 0.028668 | HP1BP3 |
| 36415395 | 36424928 | chr11 | + | intronic | hsa_circ_0005044 | 2.4417 | 0.028668 | PRR5L |
| 231940224 | 231951895 | chr2 | + | exonic | hsa_circ_0001110 | 1.7105 | 0.028695 | PSMD1 |
| 64377407 | 64378670 | chr7 | + | exonic | N/A | −2.0717 | 0.028711 | ZNF273 |
| 78915434 | 78919312 | chr5 | + | exonic | hsa_circ_0001504 | 2.1828 | 0.028735 | PAPD4 |
| 156290629 | 156304709 | chr1 | − | exonic | hsa_circ_0014717 | 2.7643 | 0.028800 | CCT3 |
| 73897062 | 73898235 | chr17 | − | exonic | hsa_circ_0045737 | −1.7814 | 0.028912 | MRPL38 |
| 50190591 | 50192487 | chr14 | + | exonic | hsa_circ_0007809 | 1.5368 | 0.028918 | KLHDC1 |
| 47762155 | 47787483 | chr3 | − | exonic | hsa_circ_0065301 | 1.6989 | 0.028928 | SMARCC1 |
| 79752559 | 79770535 | chr6 | − | exonic | hsa_circ_0001615 | 1.6692 | 0.028949 | PHIP |
| 133894452 | 133901915 | chr3 | − | exonic | hsa_circ_0067434 | 1.8486 | 0.028950 | RYK |
| 38493707 | 38527396 | chr5 | − | exonic | hsa_circ_0072303 | −1.6651 | 0.028981 | LIFR |
| 39679868 | 39681251 | chr17 | − | exonic | hsa_circ_0043598 | −1.7993 | 0.029042 | KRT19 |
| 85961337 | 85968638 | chr11 | + | exonic | hsa_circ_0023948 | −1.7121 | 0.029048 | EED |
| 155874101 | 155874595 | chr1 | − | exonic | hsa_circ_0006575 | 1.6425 | 0.029075 | RIT1 |
| 155615715 | 155640091 | chr3 | + | exonic | hsa_circ_0001352 | 1.5075 | 0.029148 | GMPS |
| 45725077 | 45751207 | chr12 | + | exonic | hsa_circ_0003433 | −1.7912 | 0.029149 | ANO6 |
| 195776154 | 195803993 | chr3 | − | exonic | hsa_circ_0068601 | 1.6887 | 0.029169 | TFRC |
| 41461588 | 41463198 | chr1 | + | exonic | N/A | −1.5129 | 0.029172 | CTPS1 |
| 113143415 | 113153625 | chr1 | − | exonic | hsa_circ_0000108 | 1.7085 | 0.029184 | ST7L |
| 77394754 | 77396204 | chr11 | − | exonic | hsa_circ_0023704 | 1.9964 | 0.029194 | RSF1 |
| 33400458 | 33406211 | chr3 | + | exonic | N/A | −1.6001 | 0.029222 | FBXL2 |
| 2985909 | 3000467 | chr11 | − | exonic | N/A | 1.6881 | 0.029250 | NAP1L4 |
| 61013821 | 61041513 | chr13 | + | exonic | hsa_circ_0003441 | 2.5134 | 0.029286 | TDRD3 |
| 64863339 | 64868113 | chr5 | + | exonic | hsa_circ_0072697 | −1.5329 | 0.029293 | PPWD1 |
| 131013395 | 131044965 | chr5 | − | exonic | hsa_circ_0001524 | 1.5391 | 0.029306 | FNIP1 |
| 51860052 | 51866625 | chr1 | − | exonic | hsa_circ_0012421 | 1.9675 | 0.029324 | EPS15 |
| 74738317 | 74742016 | chr15 | − | exonic | hsa_circ_0036271 | −1.5191 | 0.029341 | UBL7 |
| 65043362 | 65049992 | chr11 | + | exonic | N/A | −1.5640 | 0.029346 | POLA2 |
| 42235891 | 42237586 | chr6 | − | exonic | hsa_circ_0006232 | −1.7568 | 0.029348 | TRERF1 |
| 20902997 | 20903293 | chr16 | − | intronic | N/A | −1.8885 | 0.029399 | DOUN1D3 |
| 138837130 | 138837392 | chr5 | − | exonic | hsa_circ_0074217 | −1.7014 | 0.029424 | ECSCR |
| 19746674 | 19775434 | chr16 | + | exonic | hsa_circ_0000680 | −1.6128 | 0.029462 | IQCK |
| 53837174 | 53858636 | chr12 | + | exonic | hsa_circ_0026634 | −1.5823 | 0.029479 | PCBP2 |
| 34922765 | 34936026 | chr19 | + | exonic | hsa_circ_0050516 | 1.6216 | 0.029493 | UBA2 |
| 53459000 | 53459207 | chr10 | + | intronic | hsa_circ_0000238 | −1.5758 | 0.029540 | PRKG1 |
| 4015902 | 4027345 | chr17 | − | exonic | hsa_circ_0041517 | −1.6688 | 0.029581 | ZZEF1 |
| 151775682 | 151779258 | chr6 | + | intronic | N/A | −1.6705 | 0.029584 | C6orf211 |
| 153227786 | 153228670 | chrX | − | intronic | N/A | −1.5603 | 0.029589 | HCFC1 |
| 78177431 | 78178966 | chr1 | − | exonic | hsa_circ_0012989 | 1.5366 | 0.029611 | USP33 |
| 91211135 | 91252672 | chr14 | − | exonic | N/A | −1.5628 | 0.029628 | TTC7B |
| 88211723 | 88221044 | chr10 | − | exonic | hsa_circ_0019005 | 1.6852 | 0.029667 | WAPAL |
| 128938512 | 128950008 | chr4 | + | exonic | N/A | 1.5680 | 0.029671 | C4orf29 |
| 65307876 | 65310553 | chr5 | + | exonic | hsa_circ_0001494 | 2.1701 | 0.029694 | ERBB2IP |
| 98084309 | 98084588 | chr13 | − | sense overlapping | N/A | −1.5676 | 0.029715 | AY726569 |
| 74239461 | 74248066 | chr7 | − | exonic | hsa_circ_0005811 | 2.1565 | 0.029719 | GTF2IRD2 |
| 108137897 | 108138069 | chr11 | + | exonic | hsa_circ_0007694 | 2.1609 | 0.029722 | ATM |
| 54013510 | 54014377 | chrX | − | exonic | hsa_circ_0009069 | 2.1864 | 0.029756 | PHF8 |
| 243858892 | 244006584 | chr1 | − | exonic | hsa_circ_0004649 | 2.7411 | 0.029778 | AKT3 |
| 34921480 | 34929671 | chr19 | + | exonic | hsa_circ_0006987 | 1.5395 | 0.029811 | UBA2 |
| 155095122 | 155131342 | chr6 | + | exonic | hsa_circ_0078367 | 2.0200 | 0.029844 | SCAF8 |
| 149833290 | 149838586 | chr6 | − | exonic | hsa_circ_0009074 | 2.4037 | 0.029845 | PPIL4 |
| 129752887 | 129773423 | chr4 | + | exonic | hsa_circ_0006563 | 1.5552 | 0.029901 | JADE1 |
| 50821544 | 50824353 | chr12 | + | exonic | hsa_circ_0003664 | 2.4658 | 0.029911 | LARP4 |
| 25315871 | 25326656 | chr2 | + | exonic | hsa_circ_0053015 | −1.5688 | 0.029975 | EFR3B |
| 37734480 | 37744829 | chr21 | + | exonic | N/A | 1.5913 | 0.030044 | MORC3 |
| 50342357 | 50346517 | chr20 | − | exonic | hsa_circ_0008253 | −1.5162 | 0.030051 | ATP9A |
| 2521314 | 2521523 | chr1 | − | antisense | hsa_circ_0000010 | −1.8810 | 0.030073 | FAM213B |
| 662145 | 671451 | chr18 | + | exonic | hsa_circ_0004163 | −1.7358 | 0.030097 | TYMS |
| 109466421 | 109468140 | chr6 | + | exonic | hsa_circ_0004131 | 2.1070 | 0.030194 | CEP57L1 |
| 81503338 | 81545875 | chr12 | + | exonic | N/A | −1.7575 | 0.030211 | ACSS3 |
| 21490762 | 21498937 | chr16 | − | exonic | hsa_circ_0038436 | 1.7331 | 0.030224 | LOC100271836 |
| 46783379 | 46798673 | chr18 | − | exonic | hsa_circ_0047641 | −1.6630 | 0.030277 | DYM |
| 43527914 | 43541338 | chr6 | − | exonic | N/A | −1.9635 | 0.030291 | XPO5 |
| 58275620 | 58292135 | chr17 | − | exonic | hsa_circ_0044927 | −1.6815 | 0.030330 | USP32 |

TABLE 9-continued (MAOI R 8 week vs MAOI R baseline)

| TxStart | TxEnd | Chrom | Strand | circRNA type | Alias | Fold change | P-value | GeneSymbol |
|---|---|---|---|---|---|---|---|---|
| 70178323 | 70180131 | chr16 | + | exonic | hsa_circ_0040148 | −1.6565 | 0.030365 | PDPR |
| 28811231 | 28819771 | chr17 | + | exonic | hsa_circ_0007460 | 1.9381 | 0.030397 | GOSR1 |
| 170077486 | 170079217 | chr3 | + | exonic | hsa_circ_0067938 | 1.7090 | 0.030407 | SKIL |
| 67799536 | 67802707 | chr13 | − | exonic | hsa_circ_0000492 | −1.8190 | 0.030431 | PCDH9 |
| 109247226 | 109254142 | chr8 | − | exonic | N/A | 1.6191 | 0.030436 | EIF3E |
| 8832793 | 8860897 | chr11 | − | exonic | hsa_circ_0021110 | −1.5416 | 0.030442 | ST5 |
| 117221450 | 117278834 | chr10 | + | exonic | hsa_circ_0020097 | −1.7943 | 0.030447 | ATRNL1 |
| 108175911 | 108179689 | chr13 | − | intronic | hsa_circ_0003145 | −2.0848 | 0.030549 | FAM155A |
| 43748089 | 43749416 | chr15 | − | exonic | hsa_circ_0006327 | −1.6344 | 0.030554 | TP53BP1 |
| 2184780 | 2343345 | chrX | − | exonic | hsa_circ_0003473 | −1.5151 | 0.030569 | DHRSX |
| 99802639 | 99812219 | chr2 | + | exonic | hsa_circ_0001051 | 2.2538 | 0.030607 | MRPL30 |
| 143586380 | 143586631 | chr5 | + | sense overlapping | N/A | −1.6971 | 0.030678 | KCTD16 |
| 82984689 | 82989872 | chr11 | − | exonic | N/A | 2.2072 | 0.030708 | CCDC90B |
| 1099947 | 1101761 | chr6 | − | sense overlapping | N/A | −1.7418 | 0.030730 | LOC285768 |
| 125396193 | 125396954 | chr12 | − | exonic | hsa_circ_0029352 | −1.5581 | 0.030806 | UBC |
| 114153316 | 114158328 | chr4 | + | exonic | hsa_circ_0070703 | −1.6657 | 0.030851 | ANK2 |
| 20211604 | 20213263 | chrX | − | exonic | N/A | 1.6387 | 0.030884 | RPS6KA3 |
| 53017589 | 53018231 | chr18 | − | exonic | hsa_circ_0047733 | −2.0633 | 0.030995 | TCF4 |
| 185153374 | 185200840 | chr1 | + | exonic | hsa_circ_0015677 | 3.3514 | 0.030997 | SWT1 |
| 100169614 | 100170072 | chrX | − | sense overlapping | N/A | −1.7581 | 0.031022 | XKRX |
| 9020437 | 9021799 | chr12 | + | exonic | hsa_circ_0025388 | −1.9303 | 0.031066 | A2ML1 |
| 119222378 | 119232566 | chr3 | + | exonic | hsa_circ_0066875 | 1.7782 | 0.031087 | TIMMDC1 |
| 151116656 | 151119791 | chr6 | − | antisense | N/A | −1.7980 | 0.031095 | PLEKHG1 |
| 118453893 | 118455359 | chr11 | + | exonic | hsa_circ_0007383 | 1.7955 | 0.031125 | ARCN1 |
| 47285639 | 47285806 | chr19 | − | exonic | hsa_circ_0051637 | −1.5317 | 0.031177 | SLC1A5 |
| 88898935 | 88939642 | chr12 | − | exonic | hsa_circ_0002375 | −1.5279 | 0.031238 | KITLG |
| 138897036 | 138908982 | chrX | − | exonic | hsa_circ_0002372 | 1.7484 | 0.031245 | ATP11C |
| 42796230 | 42797910 | chr6 | + | exonic | hsa_circ_0076412 | −1.6546 | 0.031272 | GLTSCR1L |
| 179041465 | 179041560 | chr5 | − | sense overlapping | hsa_circ_0001562 | −1.5269 | 0.031374 | HNRNPH1 |
| 51208062 | 51208222 | chr12 | + | exonic | hsa_circ_0026286 | 1.5997 | 0.031393 | ATF1 |
| 150258841 | 150259405 | chr1 | + | sense overlapping | hsa_circ_0008958 | −1.6064 | 0.031468 | CIART |
| 97986529 | 98009889 | chr13 | + | exonic | hsa_circ_0030643 | −1.5048 | 0.031479 | MBNL2 |
| 61712902 | 61717911 | chr2 | − | exonic | hsa_circ_0005050 | 1.5583 | 0.031503 | XPO1 |
| 110863745 | 110866331 | chr3 | + | exonic | hsa_circ_0007315 | −1.7917 | 0.031596 | PVRL3 |
| 95110953 | 95111328 | chr10 | − | exonic | N/A | −1.7334 | 0.031631 | MYOF |
| 30267304 | 30274704 | chr17 | + | exonic | hsa_circ_0042962 | 2.2393 | 0.031672 | SUZ12 |
| 151999510 | 152037907 | chrX | + | exonic | hsa_circ_0091726 | −1.5341 | 0.031712 | NSDHL |
| 51454240 | 51456330 | chr3 | − | exonic | hsa_circ_0065898 | −1.5028 | 0.031750 | VPRBP |
| 3252272 | 3256234 | chr18 | + | exonic | hsa_circ_0046753 | −1.7912 | 0.031765 | MYL12A |
| 119952789 | 119954260 | chr5 | + | exonic | N/A | −1.5893 | 0.031782 | PRR16 |
| 69747508 | 69747884 | chr15 | + | exonic | hsa_circ_0036090 | −1.6044 | 0.031788 | RPLP1 |
| 159026298 | 159029782 | chr6 | + | exonic | hsa_circ_0078510 | 2.1073 | 0.031806 | TMEM181 |
| 17661883 | 17665616 | chr6 | − | exonic | hsa_circ_0075728 | 1.5687 | 0.031824 | NUP153 |
| 103432671 | 103436193 | chr10 | − | exonic | hsa_circ_0000255 | 2.1489 | 0.031859 | FBXW4 |
| 108483817 | 108510471 | chr9 | + | exonic | N/A | −1.6511 | 0.031863 | TMEM38B |
| 18650180 | 18654383 | chr19 | − | exonic | hsa_circ_0050125 | 1.5831 | 0.031875 | FKBP8 |
| 128768965 | 129202693 | chr10 | + | exonic | hsa_circ_0020407 | −1.6665 | 0.031877 | DOCK1 |
| 11778020 | 11830089 | chr16 | − | exonic | hsa_circ_0037866 | −1.8650 | 0.031957 | TXNDC11 |
| 151682934 | 151729550 | chr4 | − | exonic | hsa_circ_0071185 | 2.0226 | 0.031962 | LRBA |
| 24075537 | 24075871 | chrX | + | exonic | N/A | 1.5638 | 0.031978 | EIF2S3 |
| 68155889 | 68157024 | chr16 | + | exonic | hsa_circ_0005615 | 2.7460 | 0.031992 | NFATC3 |
| 17747023 | 17747548 | chr10 | + | intronic | N/A | −1.6813 | 0.032003 | STAM |
| 70033516 | 70035321 | chr2 | + | sense overlapping | N/A | −1.5730 | 0.032010 | ANXA4 |
| 97177439 | 97200810 | chr9 | + | exonic | hsa_circ_0003092 | −1.6974 | 0.032039 | HIATL1 |
| 107429298 | 107451870 | chr3 | + | exonic | hsa_circ_0001325 | 1.6848 | 0.032055 | BBX |
| 115249247 | 115337531 | chr9 | + | exonic | hsa_circ_0088102 | −2.0346 | 0.032059 | KIAA1958 |
| 49372452 | 49373029 | chr3 | − | intronic | hsa_circ_0001301 | 2.0855 | 0.032082 | USP4 |
| 13684435 | 13686502 | chrX | + | exonic | hsa_circ_0002871 | 1.6249 | 0.032082 | TCEANC |
| 1918887 | 1919441 | chr19 | + | intronic | N/A | −1.5076 | 0.032082 | SCAMP4 |
| 62171487 | 62175109 | chr1 | − | sense overlapping | hsa_circ_0000077 | −1.9294 | 0.032086 | TM2D1 |
| 65471271 | 65472542 | chr15 | − | exonic | hsa_circ_0004374 | 1.9613 | 0.032216 | CLPX |
| 74649111 | 74659608 | chr18 | + | exonic | hsa_circ_0047997 | −1.6376 | 0.032301 | ZNF236 |
| 45447802 | 45473343 | chr17 | + | exonic | N/A | 1.8839 | 0.032311 | EFCAB13 |
| 48216600 | 48246391 | chr19 | + | exonic | hsa_circ_0051695 | −1.8732 | 0.032360 | EHD2 |
| 85617884 | 85724620 | chr4 | − | exonic | hsa_circ_0070294 | −1.6573 | 0.032373 | WDFY3 |
| 138189034 | 138223548 | chr7 | + | exonic | hsa_circ_0082574 | 1.7164 | 0.032424 | TRIM24 |
| 77327195 | 77340944 | chr11 | − | exonic | hsa_circ_0023690 | 2.1782 | 0.032438 | CLNS1A |
| 60613530 | 60642498 | chr17 | + | exonic | hsa_circ_0045128 | 2.0868 | 0.032482 | TLK2 |
| 47777523 | 47787483 | chr3 | − | exonic | hsa_circ_0065307 | 1.6308 | 0.032506 | SMARCC1 |

TABLE 9-continued (MAOI R 8 week vs MAOI R baseline)

| TxStart | TxEnd | Chrom | Strand | circRNA type | Alias | Fold change | P-value | GeneSymbol |
|---|---|---|---|---|---|---|---|---|
| 74570202 | 74632392 | chr11 | − | exonic | hsa_circ_0023598 | −1.6735 | 0.032554 | XRRA1 |
| 137320945 | 137346838 | chr5 | − | exonic | hsa_circ_0074079 | 1.7639 | 0.032555 | FAM13B |
| 132203484 | 132207864 | chr6 | + | exonic | N/A | −1.6424 | 0.032598 | ENPP1 |
| 29313942 | 29314417 | chr1 | + | exonic | hsa_circ_0011167 | 2.7541 | 0.032628 | EPB41 |
| 98831367 | 98864830 | chr8 | + | exonic | hsa_circ_0085018 | −1.8042 | 0.032645 | LAPTM4B |
| 49459454 | 49464519 | chr19 | + | exonic | hsa_circ_0051800 | −1.6108 | 0.032692 | BAX |
| 33986757 | 34017187 | chr9 | − | exonic | hsa_circ_0086735 | 2.1388 | 0.032728 | UBAP2 |
| 170906490 | 170912424 | chr3 | − | exonic | hsa_circ_0002387 | 1.8584 | 0.032742 | TNIK |
| 59152280 | 59161925 | chr17 | + | exonic | hsa_circ_0045006 | −1.6232 | 0.032848 | BCAS3 |
| 76518189 | 76588078 | chr15 | − | exonic | hsa_circ_0036391 | 1.5950 | 0.032852 | ETFA |
| 103918254 | 103923549 | chr14 | + | exonic | hsa_circ_0033475 | 1.6580 | 0.032856 | MARK3 |
| 10459084 | 10480201 | chr1 | + | exonic | hsa_circ_0009723 | −2.1081 | 0.032888 | PGD |
| 57643406 | 57658165 | chr3 | − | exonic | N/A | 1.5879 | 0.032893 | DENND6A |
| 19462590 | 19463125 | chr22 | − | exonic | hsa_circ_0062261 | −1.7496 | 0.032902 | UFD1L |
| 30745214 | 30753229 | chr16 | + | exonic | hsa_circ_0039109 | 1.6815 | 0.032915 | SRCAP |
| 48630533 | 48631277 | chr19 | − | exonic | hsa_circ_0051718 | −1.7468 | 0.032945 | LIG1 |
| 37424841 | 37429051 | chr9 | + | exonic | hsa_circ_0087060 | −1.5121 | 0.032948 | GRHPR |
| 27900161 | 27900791 | chr2 | + | exonic | hsa_circ_0006023 | 1.6348 | 0.032966 | SLC4A1AP |
| 70650274 | 70674110 | chr8 | − | exonic | hsa_circ_0084727 | −1.6001 | 0.032974 | SLCO5A1 |
| 58118534 | 58149057 | chr3 | + | exonic | hsa_circ_0066361 | 1.8437 | 0.033031 | FLNB |
| 18648410 | 18649243 | chr19 | − | exonic | hsa_circ_0050119 | 1.6262 | 0.033103 | FKBP8 |
| 104284516 | 104284815 | chr10 | + | intronic | N/A | −1.6607 | 0.033111 | SUFU |
| 26974589 | 26975761 | chr13 | + | exonic | hsa_circ_0003489 | 1.9149 | 0.033120 | CDK8 |
| 44169153 | 44169936 | chr2 | − | intronic | N/A | −1.7710 | 0.033122 | LRPPRC |
| 122369651 | 122372262 | chr12 | + | exonic | N/A | −1.7549 | 0.033122 | WDR66 |
| 68300495 | 68300624 | chr16 | + | exonic | hsa_circ_0039943 | 1.7538 | 0.033137 | SLC7A6 |
| 14693760 | 14698083 | chr16 | − | exonic | hsa_circ_0037972 | 1.8075 | 0.033162 | PARN |
| 131796425 | 131801156 | chr2 | + | exonic | hsa_circ_0056473 | −1.6074 | 0.033182 | ARHGEF4 |
| 21288178 | 21288275 | chr22 | − | antisense | hsa_circ_0001207 | −1.5178 | 0.033247 | CRKL |
| 182346324 | 182350719 | chr2 | + | exonic | N/A | 1.6937 | 0.033277 | ITGA4 |
| 70758070 | 70781249 | chr1 | − | exonic | hsa_circ_0000085 | 1.9948 | 0.033336 | ANKRD130 |
| 46067916 | 46098727 | chr22 | + | exonic | hsa_circ_0063763 | 2.2988 | 0.033360 | ATXN10 |
| 6456257 | 6456552 | chr7 | − | exonic | hsa_circ_0002067 | −1.6662 | 0.033393 | DAGLB |
| 12531282 | 12538053 | chr3 | + | exonic | hsa_circ_0064340 | −1.5556 | 0.033397 | TSEN2 |
| 32715986 | 32717410 | chrX | − | exonic | hsa_circ_0090181 | −1.6197 | 0.033401 | DMD |
| 8386383 | 8387280 | chr19 | + | exonic | hsa_circ_0049055 | −1.5040 | 0.033412 | RPS28 |
| 134353337 | 134353833 | chr9 | + | intronic | N/A | −1.5100 | 0.033503 | PRRC2B |
| 459786 | 461490 | chr12 | − | exonic | hsa_circ_0006599 | 1.6914 | 0.033510 | KDM5A |
| 16089867 | 16097953 | chr17 | − | exonic | hsa_circ_0005471 | −1.5046 | 0.033571 | NCOR1 |
| 36865777 | 36868169 | chr17 | + | sense overlapping | hsa_circ_0000760 | 2.2332 | 0.033580 | MLLT6 |
| 30330343 | 30389603 | chr20 | + | exonic | hsa_circ_0059711 | −1.6496 | 0.033599 | TPX2 |
| 31315699 | 31315949 | chr20 | − | exonic | hsa_circ_0059797 | −1.7236 | 0.033602 | COMMD7 |
| 45241245 | 45244412 | chr1 | + | exonic | hsa_circ_0012172 | −1.8809 | 0.033614 | RPS8 |
| 53848509 | 53865591 | chr12 | + | exonic | hsa_circ_0026640 | −1.7135 | 0.033641 | PCBP2 |
| 6679862 | 6680397 | chr1 | + | exonic | hsa_circ_0009535 | −1.5960 | 0.033677 | PHF13 |
| 74484998 | 74489999 | chr9 | − | exonic | hsa_circ_0001862 | −1.5907 | 0.033682 | ABHD17B |
| 22041881 | 22048257 | chr1 | − | exonic | hsa_circ_0000028 | 2.0983 | 0.033684 | USP48 |
| 79229219 | 79258971 | chr4 | + | exonic | hsa_circ_0070133 | −1.5929 | 0.033712 | FRAS1 |
| 46622935 | 46624417 | chr12 | − | sense overlapping | hsa_circ_0000395 | −2.0935 | 0.033767 | SLC38A1 |
| 52478187 | 52553491 | chr16 | − | exonic | N/A | −1.6976 | 0.033780 | TOX3 |
| 114680116 | 114682502 | chr1 | − | exonic | hsa_circ_0013626 | −1.5343 | 0.033823 | SYT6 |
| 67662272 | 67663436 | chr16 | + | exonic | hsa_circ_0008272 | 1.5393 | 0.033860 | CTCF |
| 155547476 | 155560408 | chr3 | − | exonic | hsa_circ_0067772 | 1.9196 | 0.033877 | SLC33A1 |
| 5964676 | 5993389 | chr1 | − | exonic | hsa_circ_0009449 | −1.8135 | 0.033935 | NPHP4 |
| 19867164 | 19983103 | chr20 | + | exonic | hsa_circ_0059550 | −1.5567 | 0.033936 | RIN2 |
| 27426100 | 27427799 | chr2 | − | exonic | hsa_circ_0053162 | −1.5118 | 0.034006 | SLC5A6 |
| 18877942 | 18882804 | chr16 | − | exonic | hsa_circ_0038288 | 2.8615 | 0.034055 | SMG1 |
| 26848538 | 26869175 | chr12 | − | exonic | N/A | 1.5283 | 0.034075 | ITPR2 |
| 94006145 | 94032104 | chr4 | + | exonic | hsa_circ_0070446 | −1.5968 | 0.034087 | GRID2 |
| 76152218 | 76175765 | chr15 | + | exonic | hsa_circ_0036374 | 1.6743 | 0.034151 | UBE2Q2 |
| 197541778 | 197547301 | chr3 | + | exonic | hsa_circ_0002266 | 1.8197 | 0.034163 | LRCH3 |
| 19070216 | 19076702 | chr9 | − | exonic | hsa_circ_0086444 | −1.7911 | 0.034191 | HAUS6 |
| 147227077 | 147230127 | chr4 | − | sense overlapping | N/A | −1.7625 | 0.034204 | SLC10A7 |
| 37428784 | 37431886 | chr2 | + | exonic | hsa_circ_0054104 | 1.5593 | 0.034206 | CEBPZOS |
| 42509874 | 42510962 | chr19 | − | exonic | hsa_circ_0051260 | −1.5931 | 0.034230 | GRIK5 |
| 20107645 | 20109225 | chr17 | + | exonic | hsa_circ_0000745 | 3.6566 | 0.034261 | SPECC1 |
| 2489353 | 2493801 | chr16 | + | exonic | hsa_circ_0004603 | −1.5815 | 0.034262 | CCNF |
| 131071878 | 131073731 | chr7 | + | exonic | hsa_circ_0002117 | 2.1014 | 0.034286 | MKLN1 |
| 135878388 | 135881816 | chr2 | + | exonic | hsa_circ_0056548 | −1.6714 | 0.034384 | RAB3GAP1 |
| 104678572 | 104681470 | chr7 | + | exonic | hsa_circ_0007395 | 1.5933 | 0.034426 | KMT2E |
| 100623093 | 100625394 | chr2 | − | exonic | hsa_circ_0001055 | 1.6243 | 0.034427 | AFF3 |
| 20113099 | 20113439 | chr22 | + | intronic | hsa_circ_0092314 | −1.7176 | 0.034429 | RANBP1 |
| 77618762 | 77633517 | chr11 | − | exonic | N/A | −1.5166 | 0.034441 | INTS4 |

TABLE 9-continued (MAOI R 8 week vs MAOI R baseline)

| TxStart | TxEnd | Chrom | Strand | circRNA type | Alias | Fold change | P-value | GeneSymbol |
|---|---|---|---|---|---|---|---|---|
| 128995614 | 128996148 | chr4 | + | exonic | hsa_circ_0070933 | 2.1137 | 0.034508 | LARP1B |
| 121220457 | 121222396 | chr12 | − | exonic | hsa_circ_0003472 | −1.5198 | 0.034513 | SPPL3 |
| 17669523 | 17669777 | chr6 | − | exonic | hsa_circ_0075736 | −1.7435 | 0.034553 | NUP153 |
| 46515157 | 46529920 | chr11 | − | exonic | hsa_circ_0007001 | −1.6162 | 0.034630 | AMBRA1 |
| 68467096 | 68470236 | chr5 | + | exonic | hsa_circ_0072758 | −1.6703 | 0.034653 | CCNB1 |
| 61391748 | 61396451 | chr17 | + | exonic | hsa_circ_0045190 | −1.6797 | 0.034682 | TANC2 |
| 72361889 | 72362548 | chr2 | − | exonic | hsa_circ_0055161 | −1.8622 | 0.034689 | CYP26B1 |
| 77270158 | 77275895 | chrX | + | exonic | hsa_circ_0001934 | 2.5546 | 0.034759 | ATP7A |
| 12462922 | 12465283 | chr11 | + | intronic | N/A | −1.5839 | 0.034799 | PARVA |
| 101450683 | 101451498 | chr3 | + | exonic | hsa_circ_0066701 | −1.7020 | 0.034846 | CEP97 |
| 21644103 | 21663045 | chr18 | + | exonic | hsa_circ_0047270 | 2.0662 | 0.034929 | TTC39C |
| 103558598 | 103567658 | chr10 | − | exonic | hsa_circ_0019612 | 2.7479 | 0.034937 | MGEA5 |
| 134305476 | 134308181 | chr9 | + | exonic | hsa_circ_0001895 | 1.7326 | 0.034949 | PRRC2B |
| 35832287 | 35838568 | chr20 | + | exonic | hsa_circ_0060262 | −1.5988 | 0.034955 | RPN2 |
| 41036244 | 41037457 | chr15 | − | exonic | hsa_circ_0004942 | 2.4559 | 0.034971 | RMDN3 |
| 75823317 | 75875495 | chr6 | − | exonic | hsa_circ_0077032 | −1.6229 | 0.034986 | COL12A1 |
| 196793574 | 196846401 | chr3 | − | exonic | hsa_circ_0068684 | −1.5464 | 0.035042 | DLG1 |
| 34974539 | 34975843 | chr21 | − | exonic | hsa_circ_0061554 | −1.6706 | 0.035048 | CRYZL1 |
| 24762046 | 24788679 | chr16 | + | exonic | hsa_circ_0006008 | 2.2155 | 0.035100 | TNRC6A |
| 21987790 | 21999817 | chr13 | − | exonic | hsa_circ_0006732 | 2.6583 | 0.035191 | ZDHHC20 |
| 50724534 | 50731374 | chr15 | + | exonic | N/A | −1.5628 | 0.035195 | USP8 |
| 32745359 | 32750312 | chr3 | + | exonic | hsa_circ_0064690 | 1.5948 | 0.035227 | CNOT10 |
| 9263787 | 9275665 | chr18 | + | exonic | hsa_circ_0046854 | −1.6609 | 0.035288 | ANKRD12 |
| 72855734 | 72864506 | chr15 | + | exonic | hsa_circ_0036232 | 1.6414 | 0.035344 | ARIH1 |
| 31947298 | 31949280 | chr15 | − | exonic | hsa_circ_0034325 | −1.5054 | 0.035346 | OTUD7A |
| 99860426 | 99864304 | chr6 | − | exonic | hsa_circ_0001630 | 1.7942 | 0.035357 | PNISR |
| 33002948 | 33012216 | chr2 | + | exonic | hsa_circ_0053882 | −1.6670 | 0.035379 | TTC27 |
| 24181170 | 24207701 | chr2 | + | exonic | hsa_circ_0052967 | 2.1456 | 0.035383 | UBXN2A |
| 243736227 | 244006584 | chr1 | − | exonic | hsa_circ_0017248 | 2.8393 | 0.035421 | AKT3 |
| 96485180 | 96489456 | chr13 | − | exonic | hsa_circ_0008274 | −1.5274 | 0.035485 | UGGT2 |
| 14825489 | 14840755 | chr11 | + | exonic | N/A | 1.6198 | 0.035514 | PDE3B |
| 124904502 | 124915333 | chr12 | − | exonic | hsa_circ_0029308 | 1.8387 | 0.035553 | NCOR2 |
| 143486218 | 143605362 | chr6 | + | exonic | hsa_circ_0078051 | −1.5171 | 0.035566 | AIG1 |
| 51123962 | 51364771 | chr10 | − | exonic | hsa_circ_0018343 | 1.8967 | 0.035582 | PARG |
| 133326545 | 133326845 | chr5 | − | exonic | hsa_circ_0073930 | −1.6936 | 0.035591 | VDAC1 |
| 75302560 | 75302889 | chr10 | − | exonic | hsa_circ_0018824 | −2.0558 | 0.035622 | USP54 |
| 50596162 | 50596330 | chr15 | − | exonic | hsa_circ_0035208 | −1.6581 | 0.035625 | GABPB1 |
| 65432717 | 65435353 | chr7 | − | exonic | hsa_circ_0080319 | 1.6867 | 0.035652 | GUSB |
| 29402788 | 29405659 | chr11 | + | antisense | N/A | −1.5343 | 0.035678 | RP11-460B17.3 |
| 135710404 | 135715781 | chr7 | + | sense overlapping | N/A | 2.3591 | 0.035683 | AC024084.1 |
| 43133561 | 43135467 | chr20 | − | intronic | N/A | −1.9316 | 0.035714 | SERINC3 |
| 133494145 | 133509713 | chr5 | − | exonic | hsa_circ_0003711 | 1.7889 | 0.035715 | SKP1 |
| 44620882 | 44673174 | chr15 | + | exonic | hsa_circ_0035052 | 1.6829 | 0.035731 | CASC4 |
| 10554828 | 10555880 | chr17 | − | exonic | N/A | −1.7026 | 0.035732 | MYH3 |
| 61271351 | 61278318 | chr17 | + | exonic | hsa_circ_0004006 | −1.7562 | 0.035779 | TANC2 |
| 39902045 | 39904080 | chr4 | − | exonic | hsa_circ_0069524 | 1.5486 | 0.035836 | PDS5A |
| 19499357 | 19501527 | chr1 | − | exonic | hsa_circ_0010358 | −1.7702 | 0.035866 | UBR4 |
| 137597736 | 137600758 | chr7 | − | exonic | hsa_circ_0001753 | −1.7054 | 0.035879 | CREB3L2 |
| 32617574 | 32619410 | chr20 | + | sense overlapping | N/A | 1.7915 | 0.035910 | RALY |
| 37126308 | 37147442 | chr9 | + | intronic | N/A | 3.1086 | 0.035939 | ZCCHC7 |
| 82821160 | 82824865 | chr15 | − | exonic | hsa_circ_0036566 | −1.6042 | 0.035948 | RPS17L |
| 21921956 | 21978323 | chr22 | + | sense overlapping | hsa_circ_0062415 | −1.6601 | 0.035950 | UBE2L3 |
| 146209155 | 146216108 | chr6 | − | sense overlapping | N/A | 3.5994 | 0.035963 | SHPRH |
| 102542007 | 102559661 | chr12 | + | exonic | hsa_circ_0000432 | −1.5085 | 0.035980 | PARPBP |
| 17847367 | 17851128 | chr8 | + | exonic | hsa_circ_0002887 | 1.7053 | 0.035996 | PCM1 |
| 78022381 | 78032779 | chr17 | + | exonic | N/A | −1.6306 | 0.036035 | CCDC40 |
| 96965240 | 96966735 | chr2 | − | intronic | N/A | −1.8240 | 0.036068 | SNRNP200 |
| 48769716 | 48805947 | chr8 | − | exonic | hsa_circ_0084353 | −1.5545 | 0.036101 | PRKDC |
| 179334378 | 179337869 | chr2 | − | exonic | N/A | −1.5520 | 0.036175 | FKBP7 |
| 4286037 | 4298496 | chr9 | − | exonic | hsa_circ_0086248 | −1.5703 | 0.036181 | GLIS3 |
| 101189031 | 101190071 | chr7 | + | intronic | hsa_circ_0092287 | −1.6015 | 0.036190 | COL26A1 |
| 77378740 | 77387395 | chr7 | + | sense overlapping | hsa_circ_0001720 | −1.5617 | 0.036202 | RSBN1L |
| 151043647 | 151049345 | chr5 | − | exonic | hsa_circ_0004104 | −1.6959 | 0.036243 | SPARC |
| 165859440 | 165872516 | chr1 | + | exonic | hsa_circ_0015081 | −1.6976 | 0.036270 | UCK2 |
| 205138290 | 205156934 | chr1 | − | exonic | hsa_circ_0016199 | −1.7470 | 0.036274 | DSTYK |
| 102033995 | 102038934 | chr2 | − | exonic | hsa_circ_0004814 | −1.5597 | 0.036282 | RFX8 |
| 38273472 | 38275126 | chr1 | + | exonic | hsa_circ_0011717 | −1.7108 | 0.036282 | C1orf122 |
| 22047528 | 22048257 | chr1 | − | exonic | hsa_circ_0004808 | 2.4119 | 0.036287 | USP48 |
| 16327848 | 16345099 | chr3 | + | exonic | hsa_circ_0001273 | 2.0908 | 0.036311 | OXNAD1 |
| 114357089 | 114364762 | chrX | − | exonic | hsa_circ_0003300 | −1.8373 | 0.036324 | LRCH2 |
| 138707735 | 138774924 | chr9 | − | exonic | hsa_circ_0089475 | 1.6094 | 0.036432 | CAMSAP1 |

TABLE 9-continued (MAOI R 8 week vs MAOI R baseline)

| TxStart | TxEnd | Chrom | Strand | circRNA type | Alias | Fold change | P-value | GeneSymbol |
|---|---|---|---|---|---|---|---|---|
| 58472758 | 58476205 | chr19 | − | sense overlapping | hsa_circ_0000965 | −1.6222 | 0.036444 | C19orf18 |
| 6620185 | 6628610 | chr7 | + | exonic | hsa_circ_0079381 | −1.6759 | 0.036499 | ZDHHC4 |
| 67431907 | 67525503 | chr14 | + | exonic | hsa_circ_0032254 | −1.5500 | 0.036506 | GPHN |
| 204110568 | 204150455 | chr2 | + | exonic | N/A | −1.5425 | 0.036527 | CYP20A1 |
| 42992722 | 42993879 | chr6 | + | exonic | N/A | 1.7147 | 0.036542 | RRP36 |
| 75696982 | 75697501 | chr16 | + | intronic | N/A | −1.6958 | 0.036583 | TERF2IP |
| 15969938 | 16026822 | chrX | + | intergenic | N/A | −1.9542 | 0.036634 | |
| 67973788 | 67974381 | chr16 | − | sense overlapping | hsa_circ_0000710 | −1.6963 | 0.036647 | LCAT |
| 68015271 | 68018210 | chr8 | + | exonic | hsa_circ_0084666 | 1.7449 | 0.036721 | CSPP1 |
| 49269563 | 49270871 | chr17 | − | exonic | N/A | 1.6986 | 0.036741 | MBTD1 |
| 31764759 | 31766195 | chr1 | − | exonic | hsa_circ_0011267 | −1.5444 | 0.036798 | SNRNP40 |
| 53017589 | 53018234 | chr18 | − | exonic | hsa_circ_0004223 | −1.9618 | 0.036848 | TCF4 |
| 17446976 | 17447274 | chr8 | + | exonic | hsa_circ_0003134 | −1.8476 | 0.036858 | PDGFRL |
| 107677627 | 107684231 | chr5 | − | sense overlapping | hsa_circ_0001517 | 1.8821 | 0.036962 | FBXL17 |
| 107236366 | 107254190 | chr12 | + | exonic | hsa_circ_0028021 | 1.8230 | 0.036973 | RIC8B |
| 42745686 | 42792796 | chr12 | + | exonic | hsa_circ_0004815 | 1.5541 | 0.036992 | PPHLN1 |
| 97373450 | 97400263 | chr2 | − | exonic | N/A | −1.6599 | 0.036998 | LMAN2L |
| 39123240 | 39127595 | chr19 | + | exonic | hsa_circ_0050894 | −1.5294 | 0.037042 | EIF3K |
| 29585016 | 29587415 | chr1 | + | exonic | hsa_circ_0003904 | −1.6076 | 0.037045 | PTPRU |
| 214625147 | 214638300 | chr1 | − | exonic | hsa_circ_0007015 | −1.5033 | 0.037077 | PTPN14 |
| 133245396 | 133248908 | chr12 | − | exonic | hsa_circ_0029531 | −1.5193 | 0.037141 | POLE |
| 95099211 | 95119667 | chr5 | + | exonic | hsa_circ_0006725 | 2.0948 | 0.037142 | RHOBTB3 |
| 123661905 | 123683844 | chr10 | − | exonic | hsa_circ_0002850 | 1.6929 | 0.037162 | ATE1 |
| 155644800 | 155649303 | chr1 | − | exonic | hsa_circ_0003608 | 2.0741 | 0.037176 | YY1AP1 |
| 112723882 | 112724819 | chr10 | + | exonic | hsa_circ_0000261 | 2.3440 | 0.037186 | SHOC2 |
| 77779390 | 77818086 | chr13 | − | exonic | hsa_circ_0030509 | 1.9935 | 0.037198 | MYCBP2 |
| 48189458 | 48190874 | chr18 | + | exonic | hsa_circ_0047688 | −1.5531 | 0.037218 | MAPK4 |
| 17665469 | 17669777 | chr6 | − | exonic | hsa_circ_0007268 | 2.0673 | 0.037272 | NUP153 |
| 51381438 | 51387763 | chr10 | + | exonic | hsa_circ_0006820 | 1.9938 | 0.037287 | TIMM23B |
| 43702432 | 43704859 | chr18 | + | exonic | hsa_circ_0002481 | 1.7326 | 0.037303 | HAUS1 |
| 20212215 | 20212724 | chr3 | − | exonic | N/A | −1.8615 | 0.037312 | SGOL1 |
| 10283765 | 10288043 | chr19 | − | exonic | hsa_circ_0000889 | 2.6178 | 0.037319 | DNMT1 |
| 15427196 | 15449371 | chr2 | − | exonic | hsa_circ_0008491 | −1.7692 | 0.037339 | NBAS |
| 39623696 | 39629569 | chr18 | + | exonic | hsa_circ_0006527 | 2.1203 | 0.037351 | PIK3C3 |
| 89236034 | 89237562 | chr1 | + | exonic | hsa_circ_0002008 | 2.2282 | 0.037399 | PKN2 |
| 227729319 | 227729842 | chr2 | + | exonic | hsa_circ_0001104 | 3.1249 | 0.037430 | RHBDD1 |
| 61632920 | 61633008 | chr2 | + | antisense | hsa_circ_0001015 | −1.8576 | 0.037443 | USP34 |
| 34951655 | 34957074 | chr21 | − | exonic | hsa_circ_0061548 | −1.7627 | 0.037488 | DONSON |
| 45766370 | 45769539 | chr19 | + | exonic | hsa_circ_0051449 | 1.9914 | 0.037490 | MARK4 |
| 17124850 | 17127457 | chr17 | − | exonic | N/A | −1.5675 | 0.037504 | FLCN |
| 70246900 | 70266475 | chr10 | − | exonic | hsa_circ_0007778 | −1.5642 | 0.037570 | SLC25A16 |
| 93480747 | 93482948 | chr15 | + | exonic | hsa_circ_0000654 | 1.8508 | 0.037593 | CHD2 |
| 49394608 | 49395791 | chr3 | − | exonic | hsa_circ_0065638 | −1.6972 | 0.037600 | GPX1 |
| 50438785 | 50442435 | chrX | − | sense overlapping | N/A | −1.7749 | 0.037608 | SHROOM4 |
| 43514307 | 43516197 | chr6 | − | exonic | hsa_circ_0076560 | −1.6717 | 0.037612 | XPO5 |
| 31904555 | 31920473 | chr7 | − | exonic | hsa_circ_0079751 | −1.6667 | 0.037614 | PDE1C |
| 50875285 | 50878685 | chr15 | − | exonic | hsa_circ_0035226 | 1.9093 | 0.037634 | TRPM7 |
| 97818240 | 97820478 | chr2 | + | exonic | hsa_circ_0055734 | −1.7163 | 0.037640 | ANKRD36 |
| 4497954 | 4498912 | chr19 | + | exonic | N/A | −1.6294 | 0.037642 | HDGFRP2 |
| 82324537 | 82336803 | chr9 | + | exonic | hsa_circ_0087305 | −1.5191 | 0.037668 | TLE4 |
| 33397466 | 33427756 | chr7 | + | exonic | hsa_circ_0008336 | 1.8549 | 0.037688 | BBS9 |
| 180663927 | 180670906 | chr5 | − | exonic | hsa_circ_0075379 | −1.7571 | 0.037700 | GNB2L1 |
| 126384726 | 126395456 | chr10 | − | exonic | hsa_circ_0008456 | 1.5661 | 0.037728 | FAM53B |
| 186756529 | 186761098 | chr3 | + | exonic | hsa_circ_0068481 | −1.6457 | 0.037758 | ST6GAL1 |
| 170428187 | 170459062 | chr4 | − | exonic | N/A | 1.5211 | 0.037795 | NEK1 |
| 50847159 | 50850753 | chr2 | − | exonic | hsa_circ_0054525 | −1.6192 | 0.037796 | NRXN1 |
| 7414685 | 7414883 | chr5 | + | exonic | N/A | −1.8505 | 0.037797 | ADCY2 |
| 17746429 | 17747740 | chr10 | + | exonic | hsa_circ_0008311 | 1.8816 | 0.037811 | STAM |
| 99896085 | 99896878 | chr13 | + | exonic | hsa_circ_0030722 | 2.3705 | 0.037858 | UBAC2 |
| 34835001 | 34835393 | chr6 | + | exonic | hsa_circ_0076070 | −1.6471 | 0.037890 | UHRF1BP1 |
| 75933300 | 75933614 | chr7 | + | exonic | hsa_circ_0080788 | −1.6203 | 0.037908 | HSPB1 |
| 37579940 | 37582023 | chr19 | + | exonic | N/A | −1.6177 | 0.038014 | ZNF420 |
| 76711302 | 76711950 | chr4 | + | exonic | hsa_circ_0007096 | 1.6577 | 0.038040 | USO1 |
| 118832460 | 118887479 | chr6 | − | exonic | hsa_circ_0077736 | 2.2289 | 0.038062 | CEP85L |
| 86293355 | 86297981 | chr9 | − | exonic | hsa_circ_0001866 | 3.1179 | 0.038073 | UBQLN1 |
| 33996220 | 33998862 | chr9 | − | exonic | hsa_circ_0086736 | 2.5637 | 0.038085 | UBAP2 |
| 21662876 | 21710381 | chr18 | + | exonic | hsa_circ_0047281 | 1.6389 | 0.038108 | TTC39C |
| 125911111 | 125929096 | chr5 | − | exonic | hsa_circ_0073736 | −1.7978 | 0.038121 | ALDH7A1 |
| 71623270 | 71645769 | chr2 | + | exonic | hsa_circ_0055151 | 1.8748 | 0.038128 | ZNF638 |
| 46190711 | 46195443 | chr19 | − | exonic | hsa_circ_0051546 | −1.9103 | 0.038139 | SNRPD2 |
| 114911523 | 114919893 | chr9 | − | exonic | hsa_circ_0088062 | 1.5779 | 0.038169 | SUSD1 |
| 47767859 | 47768203 | chr19 | + | exonic | hsa_circ_0000944 | 2.1194 | 0.038212 | CCDC9 |

TABLE 9-continued (MAOI R 8 week vs MAOI R baseline)

| TxStart | TxEnd | Chrom | Strand | circRNA type | Alias | Fold change | P-value | GeneSymbol |
|---|---|---|---|---|---|---|---|---|
| 2807472 | 2810500 | chr16 | + | exonic | hsa_circ_0037563 | 2.6022 | 0.038329 | SRRM2 |
| 32684462 | 32686439 | chr20 | − | exonic | hsa_circ_0007938 | 1.6348 | 0.038334 | EIF2S2 |
| 152004981 | 152006276 | chr1 | − | exonic | hsa_circ_0014205 | −1.8786 | 0.038343 | S100A11 |
| 10342614 | 10359778 | chr3 | − | exonic | hsa_circ_0064277 | −1.5969 | 0.038357 | SEC13 |
| 104483222 | 104574295 | chr3 | − | sense overlapping | hsa_circ_0004993 | −1.7001 | 0.038369 | XLOC_003195 |
| 43455389 | 43460330 | chr22 | − | exonic | hsa_circ_0063681 | −1.8019 | 0.038375 | TTLL1 |
| 74949767 | 74950157 | chr16 | − | exonic | hsa_circ_0004910 | 1.9312 | 0.038407 | WDR59 |
| 44514580 | 44515853 | chr21 | − | exonic | hsa_circ_0001198 | 1.8643 | 0.038415 | U2AF1 |
| 132426884 | 132428481 | chr5 | + | exonic | hsa_circ_0001531 | 1.7262 | 0.038431 | HSPA4 |
| 138824814 | 138853226 | chr9 | − | exonic | hsa_circ_0089507 | −1.7533 | 0.038445 | UBAC1 |
| 39881347 | 39924368 | chr4 | − | exonic | hsa_circ_0069519 | 1.5370 | 0.038448 | PDS5A |
| 75692832 | 75695930 | chr7 | + | exonic | hsa_circ_0080782 | −1.5891 | 0.038499 | MDH2 |
| 40027197 | 40041630 | chr7 | + | exonic | hsa_circ_0001699 | 2.5848 | 0.038546 | CDK13 |
| 152132729 | 152150709 | chr3 | + | exonic | hsa_circ_0001349 | 1.9078 | 0.038552 | MBNL1 |
| 3076997 | 3081350 | chr6 | + | exonic | hsa_circ_0003886 | 1.6973 | 0.038569 | RIPK1 |
| 36685939 | 36694658 | chr20 | + | sense overlapping | hsa_circ_0007673 | 1.9395 | 0.038575 | RPRD1B |
| 65792943 | 65804902 | chr15 | − | exonic | hsa_circ_0006807 | 1.6161 | 0.038623 | DPP8 |
| 201721404 | 201722812 | chr2 | − | exonic | hsa_circ_0057725 | 1.8665 | 0.038640 | CLK1 |
| 64271341 | 64295792 | chrX | + | sense overlapping | hsa_circ_0001924 | 3.9544 | 0.038670 | XLOC_007999 |
| 34574331 | 34574681 | chr6 | − | exonic | hsa_circ_0006757 | 1.7489 | 0.038728 | C6orf106 |
| 41704366 | 41704793 | chr19 | + | exonic | N/A | −1.5337 | 0.038754 | CYP2S1 |
| 122514815 | 122519100 | chr2 | + | exonic | hsa_circ_0002847 | 2.0751 | 0.038799 | TSN |
| 110321942 | 110350696 | chr2 | − | exonic | hsa_circ_0002076 | −1.6813 | 0.038807 | SEPT10 |
| 71590282 | 71597135 | chr2 | + | exonic | hsa_circ_0001028 | 2.4690 | 0.038825 | ZNF638 |
| 65139030 | 65141244 | chr1 | + | exonic | hsa_circ_0012850 | −1.7637 | 0.038845 | CACHD1 |
| 28970037 | 28970421 | chr16 | + | exonic | hsa_circ_0038883 | −1.5397 | 0.038852 | NFATC2IP |
| 95938199 | 95944335 | chr8 | − | exonic | hsa_circ_0084956 | −1.7442 | 0.038892 | TP53INP1 |
| 160148151 | 160177351 | chr6 | + | sense overlapping | hsa_circ_0078543 | −1.5789 | 0.038900 | WTAP |
| 102233626 | 102239279 | chr11 | + | exonic | hsa_circ_0004103 | 1.7618 | 0.038938 | BIRC2 |
| 49372459 | 49373029 | chr3 | − | intronic | N/A | 2.2655 | 0.038956 | USP4 |
| 47531309 | 47549512 | chr16 | + | exonic | hsa_circ_0000698 | 2.2830 | 0.038982 | PHKB |
| 186504915 | 186505671 | chr3 | + | exonic | hsa_circ_0068465 | 2.1506 | 0.038985 | EIF4A2 |
| 13604092 | 13610799 | chr20 | − | exonic | hsa_circ_0059476 | −1.7781 | 0.039001 | TASP1 |
| 30370051 | 30385318 | chr20 | + | exonic | hsa_circ_0003209 | −1.5541 | 0.039001 | TPX2 |
| 45587230 | 45599993 | chr14 | − | sense overlapping | N/A | 2.5333 | 0.039002 | FKBP3 |
| 50943657 | 50943763 | chr22 | − | exonic | hsa_circ_0064001 | −1.7574 | 0.039006 | LMF2 |
| 19093168 | 19096767 | chr9 | − | exonic | N/A | 1.7795 | 0.039069 | HAUS6 |
| 110922882 | 110925748 | chr12 | + | exonic | hsa_circ_0004516 | 2.2596 | 0.039077 | FAM216A |
| 61608136 | 61609229 | chr3 | + | intronic | hsa_circ_0002134 | −1.6867 | 0.039227 | PTPRG |
| 52785363 | 52786666 | chr19 | + | exonic | hsa_circ_0052095 | 1.9468 | 0.039227 | ZNF766 |
| 116730126 | 116734144 | chr10 | + | exonic | hsa_circ_0020092 | 1.7123 | 0.039231 | TRUB1 |
| 113832487 | 113833403 | chr13 | − | exonic | N/A | −1.5814 | 0.039259 | PCID2 |
| 33953282 | 33963789 | chr9 | − | exonic | hsa_circ_0001847 | 2.3559 | 0.039279 | UBAP2 |
| 99196947 | 99197507 | chr10 | − | exonic | hsa_circ_0004896 | 1.5822 | 0.039318 | EXOSC1 |
| 139819703 | 139828890 | chr5 | + | exonic | hsa_circ_0001541 | 2.0669 | 0.039334 | ANKHD1 |
| 84376847 | 84412965 | chr1 | − | exonic | N/A | −1.6099 | 0.039339 | TTLL7 |
| 224077 | 233215 | chr11 | − | exonic | hsa_circ_0006467 | −1.6037 | 0.039408 | SIRT3 |
| 26518046 | 26519239 | chr17 | + | exonic | N/A | −1.6682 | 0.039449 | NLK |
| 73072005 | 73072154 | chrX | + | sense overlapping | hsa_circ_0001929 | −1.6815 | 0.039459 | XLOC_008015 |
| 32206506 | 32215211 | chr22 | + | exonic | N/A | −1.5024 | 0.039466 | DEPDC5 |
| 33073307 | 33078670 | chr21 | − | exonic | hsa_circ_0007207 | −1.7576 | 0.039526 | SCAF4 |
| 19473732 | 19474599 | chr11 | + | intronic | N/A | −1.6759 | 0.039603 | NAV2 |
| 66444138 | 66444562 | chr11 | − | exonic | hsa_circ_0004144 | 1.8964 | 0.039606 | RBM4B |
| 54248444 | 54250043 | chr4 | + | exonic | hsa_circ_0069738 | 1.5272 | 0.039627 | FIP1L1 |
| 75506613 | 75509180 | chr14 | − | exonic | hsa_circ_0032644 | −1.6434 | 0.039639 | MLH3 |
| 100587885 | 100589861 | chr8 | + | exonic | hsa_circ_0085096 | 1.9689 | 0.039666 | VPS13B |
| 25650607 | 25654354 | chr15 | − | exonic | hsa_circ_0034168 | 2.6199 | 0.039681 | UBE3A |
| 32602655 | 32620661 | chr2 | + | exonic | hsa_circ_0053441 | 1.8227 | 0.039707 | BIRC6 |
| 130928324 | 130928494 | chrX | − | exonic | hsa_circ_0091558 | −1.5121 | 0.039718 | LOC286467 |
| 47444334 | 47446190 | chrX | + | exonic | hsa_circ_0090449 | −1.5772 | 0.039778 | TIMP1 |
| 89961445 | 89977071 | chr16 | + | exonic | hsa_circ_0041100 | −1.7861 | 0.039783 | TCF25 |
| 65941524 | 65972074 | chr17 | | exonic | hsa_circ_0000799 | 2.4852 | 0.039835 | BPTF |
| 46559797 | 46563115 | chr13 | + | antisense | hsa_circ_0000480 | −1.6691 | 0.039846 | ZC3H13 |
| 151656409 | 151729550 | chr4 | − | exonic | hsa_circ_0071174 | 2.0893 | 0.039849 | LRBA |
| 57523349 | 57526305 | chr15 | + | exonic | hsa_circ_0006380 | −1.5629 | 0.039866 | TCF12 |
| 37126308 | 37127260 | chr9 | + | intronic | N/A | 1.7772 | 0.039876 | ZCCHC7 |
| 203818727 | 203820481 | chr2 | + | exonic | hsa_circ_0003493 | 1.8620 | 0.039922 | CARF |
| 67864287 | 67868100 | chr1 | − | intergenic | N/A | −1.6259 | 0.039958 | |
| 45340349 | 45341367 | chr1 | − | exonic | hsa_circ_0012185 | −1.5089 | 0.039971 | EIF2B3 |
| 43679047 | 43680248 | chr7 | − | exonic | hsa_circ_0001700 | −1.5321 | 0.039987 | COA1 |

TABLE 9-continued

| (MAOI R 8 week vs MAOI R baseline) | | | | | | | | |
|---|---|---|---|---|---|---|---|---|
| TxStart | TxEnd | Chrom | Strand | circRNA type | Alias | Fold change | P-value | GeneSymbol |
| 98923108 | 98923600 | chr13 | + | intronic | hsa_circ_0003907 | −1.5043 | 0.040000 | FARP1 |
| 74130250 | 74137504 | chr5 | − | exonic | hsa_circ_0004405 | 1.5984 | 0.040016 | FAM169A |
| 132273520 | 132273720 | chr2 | + | intronic | hsa_circ_0092325 | −1.6604 | 0.040089 | RNU6-81P |
| 75625762 | 75634722 | chr7 | − | sense overlapping | hsa_circ_0001718 | −1.5981 | 0.040103 | STYXL1 |
| 22399613 | 22404422 | chr4 | − | intronic | N/A | −1.6187 | 0.040108 | GPR125 |
| 194947437 | 194947585 | chr3 | − | exonic | hsa_circ_0068563 | −1.6320 | 0.040113 | XXYLT1 |
| 100976372 | 101023156 | chr3 | − | exonic | N/A | −1.7513 | 0.040141 | IMPG2 |
| 20101609 | 20104725 | chr11 | + | exonic | hsa_circ_0004819 | −1.5829 | 0.040220 | NAV2 |
| 3789810 | 3789974 | chr11 | − | exonic | hsa_circ_0020913 | −1.5412 | 0.040230 | NUP98 |
| 175779785 | 175816930 | chr2 | − | exonic | hsa_circ_0007941 | −1.6281 | 0.040320 | CHN1 |
| 113734352 | 113735838 | chr9 | − | exonic | hsa_circ_0087960 | −1.8020 | 0.040329 | LPAR1 |
| 556530 | 565135 | chr17 | − | exonic | hsa_circ_0002879 | 1.6266 | 0.040388 | VPS53 |
| 132227855 | 132228810 | chr5 | − | exonic | hsa_circ_0001529 | 1.7778 | 0.040389 | AFF4 |
| 26486247 | 26500028 | chr2 | + | exonic | hsa_circ_0008257 | 1.7056 | 0.040411 | HADHB |
| 42748962 | 42781337 | chr12 | + | exonic | N/A | 1.6997 | 0.040417 | PPHLN1 |
| 35055435 | 35078948 | chr14 | − | exonic | hsa_circ_0031608 | 1.5261 | 0.040499 | SNX6 |
| 59999085 | 60002460 | chr17 | − | exonic | hsa_circ_0007759 | 1.7762 | 0.040556 | INTS2 |
| 381340 | 385707 | chr8 | + | exonic | N/A | 2.6519 | 0.040565 | FBXO25 |
| 68163533 | 68172161 | chr8 | − | exonic | hsa_circ_0001807 | 1.7792 | 0.040572 | ARFGEF1 |
| 180286875 | 180286984 | chr5 | − | intronic | N/A | −1.6131 | 0.040576 | ZFP62 |
| 72082738 | 72091059 | chr9 | − | exonic | hsa_circ_0004129 | −1.5318 | 0.040600 | APBA1 |
| 40152499 | 40155575 | chr17 | − | exonic | N/A | −2.0860 | 0.040635 | DNAJC7 |
| 19538077 | 19538212 | chr2 | + | antisense | hsa_circ_0000980 | −1.6870 | 0.040652 | AC092594.1 |
| 121220457 | 121221555 | chr12 | − | exonic | hsa_circ_0028935 | −1.7212 | 0.040676 | SPPL3 |
| 36064839 | 36104804 | chr14 | − | exonic | hsa_circ_0031668 | −1.5980 | 0.040680 | RALGAPA1 |
| 46455023 | 46534363 | chr11 | − | exonic | hsa_circ_0021845 | −1.5241 | 0.040686 | AMBRA1 |
| 126194344 | 126207514 | chr8 | + | sense overlapping | N/A | −1.5686 | 0.040690 | NSMCE2 |
| 20910208 | 20914622 | chr17 | − | exonic | hsa_circ_0042458 | −1.6296 | 0.040709 | USP22 |
| 47100675 | 47100849 | chrX | + | exonic | hsa_circ_0090429 | −1.6245 | 0.040730 | USP11 |
| 21660548 | 21663045 | chr18 | + | exonic | hsa_circ_0002403 | 2.3424 | 0.040852 | TTC39C |
| 86294689 | 86297981 | chr9 | − | exonic | hsa_circ_0001867 | 2.9493 | 0.040852 | UBQLN1 |
| 49348626 | 49348873 | chr19 | − | exonic | hsa_circ_0051781 | −1.7537 | 0.040858 | PLEKHA4 |
| 32560384 | 32566163 | chr1 | + | exonic | hsa_circ_0003601 | −1.6039 | 0.040911 | TMEM39B |
| 120828957 | 120830597 | chr10 | − | exonic | hsa_circ_0020151 | −1.5461 | 0.040932 | EIF3A |
| 86328535 | 86329135 | chr6 | − | exonic | hsa_circ_0006131 | 2.3265 | 0.040969 | SYNCRIP |
| 214564330 | 214571344 | chr1 | − | exonic | hsa_circ_0008659 | −1.6658 | 0.040976 | PTPN14 |
| 27331510 | 27339333 | chr1 | − | exonic | hsa_circ_0011047 | −1.5398 | 0.041021 | FAM46B |
| 228193393 | 228195562 | chr2 | + | exonic | hsa_circ_0003081 | 1.5012 | 0.041039 | MFF |
| 190315628 | 190316621 | chr2 | + | exonic | hsa_circ_0057462 | −1.6273 | 0.041135 | WDR75 |
| 35644044 | 36220485 | chr13 | + | exonic | hsa_circ_0029987 | −1.5982 | 0.041156 | NBEA |
| 183896644 | 183896910 | chr3 | + | exonic | hsa_circ_0068282 | 2.1050 | 0.041171 | AP2M1 |
| 89628044 | 89629313 | chr14 | − | intronic | hsa_circ_0000558 | 1.5817 | 0.041175 | FOXN3 |
| 99394503 | 99396732 | chr3 | + | intronic | N/A | −1.6094 | 0.041202 | COL8A1 |
| 96717725 | 96728643 | chr12 | − | exonic | hsa_circ_0002762 | 1.7723 | 0.041213 | CDK17 |
| 47497792 | 47581459 | chr16 | + | exonic | hsa_circ_0039254 | 2.0393 | 0.041225 | PHKB |
| 72050664 | 72054207 | chr12 | − | sense overlapping | hsa_circ_0000420 | −1.5030 | 0.041227 | ZFC3H1 |
| 44986659 | 45000952 | chr3 | − | exonic | hsa_circ_0065052 | −1.6617 | 0.041295 | ZDHHC3 |
| 15964801 | 15978390 | chr1 | + | exonic | hsa_circ_0000020 | 2.0831 | 0.041320 | DDI2 |
| 53322669 | 53329829 | chr1 | + | exonic | hsa_circ_0002361 | −1.7889 | 0.041342 | ZYG11A |
| 6291961 | 6293703 | chr1 | − | exonic | hsa_circ_0007427 | −1.8497 | 0.041360 | ICMT |
| 41886323 | 41888573 | chr17 | − | exonic | N/A | −1.7591 | 0.041374 | MPP3 |
| 3740641 | 3774638 | chr11 | − | exonic | N/A | 1.7773 | 0.041378 | NUP98 |
| 15564438 | 15567918 | chr2 | − | exonic | hsa_circ_0052760 | −1.5399 | 0.041405 | NBAS |
| 21478701 | 21479419 | chr18 | + | exonic | hsa_circ_0047253 | −1.5892 | 0.041474 | LAMA3 |
| 122237752 | 122239714 | chr12 | − | exonic | hsa_circ_0029021 | −1.6152 | 0.041513 | LINC01089 |
| 6776706 | 6777567 | chr7 | + | exonic | hsa_circ_0007607 | 1.6662 | 0.041526 | PMS2CL |
| 168073714 | 168074132 | chr1 | − | exonic | hsa_circ_0015136 | −1.5101 | 0.041557 | GPR161 |
| 50708583 | 50714058 | chr10 | − | exonic | hsa_circ_0018331 | 1.5889 | 0.041567 | ERCC6 |
| 57535669 | 57535748 | chr15 | + | exonic | hsa_circ_0035426 | −1.6321 | 0.041597 | TCF12 |
| 16955966 | 16977910 | chr8 | + | sense overlapping | N/A | −1.6219 | 0.041610 | MICU3 |
| 9435370 | 9435456 | chr19 | + | exonic | hsa_circ_0049138 | −1.7622 | 0.041649 | ZNF559 |
| 38612700 | 38613982 | chr17 | + | exonic | hsa_circ_0043553 | −1.6324 | 0.041660 | IGFBP4 |
| 12999419 | 13059311 | chr18 | + | exonic | hsa_circ_0047003 | 2.0128 | 0.041662 | CEP192 |
| 16871028 | 16871799 | chrX | − | intronic | N/A | −1.6462 | 0.041673 | RBBP7 |
| 22324940 | 22326529 | chr16 | + | exonic | hsa_circ_0038516 | −1.5107 | 0.041727 | POLR3E |
| 20632714 | 20641530 | chr13 | + | exonic | hsa_circ_0029636 | 1.8913 | 0.041752 | ZMYM2 |
| 23634493 | 23635749 | chr14 | − | exonic | hsa_circ_0031282 | −1.5611 | 0.041759 | SLC7A8 |
| 176954915 | 176958522 | chr5 | − | intronic | N/A | −1.5608 | 0.041767 | FAM193B |
| 56600621 | 56601081 | chr3 | + | exonic | hsa_circ_0001312 | 2.3221 | 0.041831 | CCDC66 |
| 172821858 | 172823470 | chr2 | + | exonic | hsa_circ_0006532 | 1.5124 | 0.041836 | HAT1 |
| 52729602 | 52729673 | chr4 | + | exonic | hsa_circ_0069714 | 1.6176 | 0.041861 | DCUN1D4 |
| 120830753 | 120836157 | chr2 | + | exonic | hsa_circ_0001064 | 1.9950 | 0.041873 | EPB41L5 |

TABLE 9-continued (MAOI R 8 week vs MAOI R baseline)

| TxStart | TxEnd | Chrom | Strand | circRNA type | Alias | Fold change | P-value | GeneSymbol |
|---|---|---|---|---|---|---|---|---|
| 2052758 | 2052991 | chr16 | − | intronic | N/A | −1.5195 | 0.041918 | TCRBV20S1 |
| 73450163 | 73450660 | chr2 | + | exonic | N/A | −1.5270 | 0.041929 | SMYD5 |
| 42132937 | 42134918 | chr3 | + | intronic | hsa_circ_0001286 | −2.0422 | 0.041931 | TRAK1 |
| 99930628 | 99958106 | chr6 | − | exonic | N/A | −1.8166 | 0.041970 | USP45 |
| 236192849 | 236201553 | chr1 | − | exonic | hsa_circ_0017109 | −1.7199 | 0.041997 | NID1 |
| 76566752 | 76580286 | chr15 | − | exonic | hsa_circ_0036399 | 1.7775 | 0.042000 | ETFA |
| 22055264 | 22065197 | chr22 | − | sense overlapping | hsa_circ_0001208 | −1.5745 | 0.042032 | YPEL1 |
| 170626457 | 170639638 | chr6 | + | exonic | hsa_circ_0001666 | −1.6441 | 0.042096 | FAM120B |
| 151934651 | 151936377 | chrX | − | exonic | hsa_circ_0091722 | −1.6118 | 0.042109 | MAGEA3 |
| 29061914 | 29086557 | chr17 | + | exonic | N/A | 1.9625 | 0.042147 | SUZ12P1 |
| 18236682 | 18258636 | chr6 | − | exonic | hsa_circ_0075796 | 2.2046 | 0.042182 | DEK |
| 105903546 | 105907553 | chr12 | + | sense overlapping | N/A | −1.6690 | 0.042194 | XLOC_I2_003133 |
| 132990021 | 133002144 | chr7 | + | sense overlapping | hsa_circ_0001749 | −2.0072 | 0.042228 | EXOC4 |
| 19112421 | 19115455 | chr19 | − | exonic | N/A | −1.7105 | 0.042272 | SUGP2 |
| 36121010 | 36128402 | chr14 | − | exonic | hsa_circ_0004823 | 1.7490 | 0.042287 | RALGAPA1 |
| 104536316 | 104574319 | chr3 | − | sense overlapping | N/A | −1.5129 | 0.042346 | XLOC_003195 |
| 76642965 | 76662315 | chr14 | + | exonic | hsa_circ_0032746 | 1.7885 | 0.042353 | GPATCH2L |
| 91924202 | 91981956 | chr7 | + | exonic | hsa_circ_0002744 | 2.3543 | 0.042391 | ANKIB1 |
| 13579682 | 13584457 | chr6 | + | exonic | hsa_circ_0007218 | 2.1338 | 0.042405 | SIRT5 |
| 53478829 | 53488778 | chr17 | − | exonic | N/A | −1.5701 | 0.042408 | MMD |
| 50045984 | 50093067 | chr5 | + | exonic | hsa_circ_0072431 | 1.7018 | 0.042411 | PARP8 |
| 10407213 | 10426634 | chr5 | + | exonic | hsa_circ_0071862 | −1.6342 | 0.042430 | MARCH6 |
| 86292641 | 86297981 | chr9 | − | exonic | hsa_circ_0006466 | 3.3124 | 0.042436 | UBQLN1 |
| 31424825 | 31425448 | chr14 | − | exonic | hsa_circ_0007656 | 1.8917 | 0.042486 | STRN3 |
| 37455242 | 37457328 | chr17 | − | exonic | hsa_circ_0000761 | 1.8988 | 0.042568 | FBXL20 |
| 68334481 | 68343511 | chr11 | + | exonic | hsa_circ_0002038 | 2.4377 | 0.042578 | PPP6R3 |
| 93637042 | 93639999 | chr9 | − | antisense | hsa_circ_0001873 | −1.6224 | 0.042586 | SYK |
| 168920009 | 168986268 | chr2 | − | exonic | hsa_circ_0005882 | 1.9423 | 0.042604 | STK39 |
| 32874967 | 32875262 | chr22 | + | exonic | hsa_circ_0008832 | 2.0516 | 0.042607 | FBXO7 |
| 132551514 | 132551875 | chr12 | + | intronic | N/A | −1.6808 | 0.042639 | EP400 |
| 48744511 | 48747484 | chr20 | − | exonic | hsa_circ_0002168 | −1.6524 | 0.042680 | TMEM189 |
| 93300335 | 93303190 | chr1 | + | exonic | hsa_circ_0013181 | 1.6017 | 0.042682 | RPL5 |
| 118451960 | 118455359 | chr11 | + | exonic | hsa_circ_0006374 | 2.4482 | 0.042747 | ARCN1 |
| 100384118 | 100387214 | chr14 | + | exonic | hsa_circ_0033163 | −1.5761 | 0.042752 | EML1 |
| 65941524 | 65944422 | chr17 | + | exonic | hsa_circ_0000798 | 2.7567 | 0.042766 | BPTF |
| 72370568 | 72373320 | chr5 | + | exonic | hsa_circ_0002490 | 1.6695 | 0.042884 | FCHO2 |
| 136085784 | 136141886 | chr3 | − | exonic | N/A | 1.6855 | 0.042890 | STAG1 |
| 14821320 | 14821476 | chrY | + | exonic | hsa_circ_0092232 | −1.6017 | 0.042988 | USP9Y |
| 20245345 | 20246103 | chr13 | + | sense overlapping | N/A | −1.5875 | 0.043033 | MPHOSPH8 |
| 186946056 | 186951097 | chr2 | − | sense overlapping | hsa_circ_0005843 | 1.5442 | 0.043055 | LINC01473 |
| 50140753 | 50141436 | chr13 | − | sense overlapping | hsa_circ_0000484 | −1.5356 | 0.043059 | RCBTB1 |
| 101906400 | 101910728 | chr15 | − | exonic | hsa_circ_0037096 | −1.6503 | 0.043061 | PCSK6 |
| 45011271 | 45016256 | chr7 | − | exonic | hsa_circ_0080099 | 2.3124 | 0.043062 | MYO1G |
| 8076452 | 8114825 | chr18 | + | exonic | hsa_circ_0003063 | −1.6220 | 0.043075 | PTPRM |
| 140807631 | 140811883 | chr9 | + | exonic | hsa_circ_0089757 | −1.6390 | 0.043127 | CACNA1B |
| 89396991 | 89400658 | chr4 | + | exonic | hsa_circ_0070421 | −1.5990 | 0.043167 | HERC5 |
| 39607406 | 39629569 | chr18 | + | exonic | hsa_circ_0007765 | 2.3028 | 0.043191 | PIK3C3 |
| 242396161 | 242415402 | chr2 | + | exonic | N/A | −1.8424 | 0.043204 | FARP2 |
| 135639656 | 135644462 | chr6 | − | exonic | N/A | −1.6108 | 0.043208 | AHI1 |
| 26000343 | 26015440 | chr22 | + | intronic | hsa_circ_0001213 | −1.5438 | 0.043224 | ADRBK2 |
| 102606930 | 102609897 | chr9 | + | exonic | hsa_circ_0002643 | −1.5295 | 0.043225 | NR4A3 |
| 11526612 | 11527733 | chr19 | − | exonic | hsa_circ_0006941 | −1.5713 | 0.043253 | RGL3 |
| 904262 | 908576 | chr5 | + | exonic | N/A | −1.7440 | 0.043331 | TRIP13 |
| 7849045 | 7849304 | chr17 | + | exonic | hsa_circ_0008310 | −1.5220 | 0.043349 | CNTROB |
| 127025579 | 127026209 | chr7 | − | sense overlapping | N/A | −1.6458 | 0.043362 | ZNF800 |
| 7826418 | 7841374 | chr7 | + | sense overlapping | hsa_circ_0001676 | 1.9449 | 0.043395 | UMAD1 |
| 39623414 | 39628754 | chr14 | − | exonic | N/A | 1.6928 | 0.043424 | TRAPPC6B |
| 99584817 | 99585905 | chr3 | + | intronic | N/A | −1.7416 | 0.043456 | CMSS1 |
| 76576097 | 76585041 | chr15 | − | exonic | hsa_circ_0005036 | 1.6698 | 0.043458 | ETFA |
| 76907603 | 76912143 | chrX | − | exonic | hsa_circ_0001932 | 1.5840 | 0.043486 | ATRX |
| 60734614 | 60737990 | chr15 | − | sense overlapping | hsa_circ_0000606 | 1.6870 | 0.043491 | ICE2 |
| 1828213 | 1830915 | chr8 | + | exonic | N/A | −1.6189 | 0.043519 | ARHGEF10 |
| 84301451 | 84303379 | chrX | + | intronic | N/A | −1.7572 | 0.043581 | APOOL |
| 138221900 | 138223331 | chr5 | + | exonic | hsa_circ_0074166 | 1.5027 | 0.043601 | CTNNA1 |
| 87017739 | 87018273 | chr3 | − | exonic | hsa_circ_0003806 | −1.6154 | 0.043621 | VGLL3 |
| 34111725 | 34113603 | chr11 | + | exonic | hsa_circ_0004851 | 2.6533 | 0.043685 | CAPRIN1 |

TABLE 9-continued

| (MAOI R 8 week vs MAOI R baseline) | | | | | | | | |
|---|---|---|---|---|---|---|---|---|
| TxStart | TxEnd | Chrom | Strand | circRNA type | Alias | Fold change | P-value | GeneSymbol |
| 33160465 | 33161645 | chr1 | − | exonic | hsa_circ_0004895 | −1.6813 | 0.043790 | SYNC |
| 75197502 | 75203206 | chr7 | − | exonic | hsa_circ_0080724 | −1.5448 | 0.043793 | HIP1 |
| 44785299 | 44804994 | chr1 | − | exonic | hsa_circ_0005246 | −1.5508 | 0.043899 | ERI3 |
| 69983264 | 69985939 | chr12 | + | exonic | hsa_circ_0000418 | 2.9124 | 0.043906 | CCT2 |
| 107260799 | 107289013 | chr11 | − | exonic | hsa_circ_0006868 | 2.1442 | 0.043915 | CWF19L2 |
| 50025688 | 50042096 | chr13 | + | exonic | hsa_circ_0030254 | 1.6311 | 0.043929 | SETDB2 |
| 118750908 | 118754014 | chrX | − | exonic | hsa_circ_0091412 | −1.7120 | 0.043940 | SEPT6 |
| 27224905 | 27226329 | chr16 | + | exonic | hsa_circ_0038704 | 1.9008 | 0.043963 | KDM8 |
| 128525762 | 128528578 | chr2 | − | exonic | hsa_circ_0056362 | 1.7103 | 0.043980 | WDR33 |
| 148543588 | 148544397 | chr7 | − | exonic | hsa_circ_0005284 | 1.5348 | 0.043984 | EZH2 |
| 120347369 | 120348235 | chr11 | + | exonic | hsa_circ_0002089 | 2.3400 | 0.043995 | ARHGEF12 |
| 34107610 | 34113603 | chr11 | + | exonic | hsa_circ_0000287 | 2.6054 | 0.044021 | CAPRIN1 |
| 39738530 | 39743147 | chr17 | − | exonic | hsa_circ_0043614 | −1.6678 | 0.044033 | KRT14 |
| 31695861 | 31719046 | chr19 | − | antisense | N/A | −1.6085 | 0.044038 | CTC-439O9.3 |
| 18256591 | 18258636 | chr6 | − | exonic | hsa_circ_0008846 | 2.5491 | 0.044120 | DEK |
| 186286613 | 186287960 | chr1 | − | exonic | N/A | −1.6619 | 0.044126 | TPR |
| 54398613 | 54426184 | chr18 | + | exonic | hsa_circ_0047744 | 2.2944 | 0.044183 | WDR7 |
| 5968018 | 5988545 | chr9 | − | exonic | N/A | 1.6107 | 0.044225 | KIAA2026 |
| 53289511 | 53302038 | chr16 | + | exonic | hsa_circ_0039365 | 2.4443 | 0.044226 | CHD9 |
| 167915606 | 167921655 | chr5 | + | exonic | hsa_circ_0001550 | 2.4321 | 0.044296 | RARS |
| 180651121 | 180653019 | chr3 | + | exonic | hsa_circ_0068129 | 2.0132 | 0.044309 | FXR1 |
| 89206670 | 89206971 | chr1 | + | exonic | hsa_circ_0000089 | 1.6658 | 0.044326 | PKN2 |
| 34929549 | 34936026 | chr19 | + | exonic | hsa_circ_0050532 | 1.5883 | 0.044337 | UBA2 |
| 37775055 | 37783902 | chr21 | + | exonic | hsa_circ_0006898 | −1.5107 | 0.044354 | CHAF1B |
| 96986391 | 96991728 | chr14 | + | exonic | hsa_circ_0002120 | 1.8941 | 0.044376 | PAPOLA |
| 138824814 | 138847261 | chr9 | − | exonic | hsa_circ_0089506 | −1.7458 | 0.044434 | UBAC1 |
| 25605039 | 25606501 | chr6 | + | exonic | hsa_circ_0075881 | −1.6408 | 0.044466 | LRRC16A |
| 179976936 | 179977117 | chr5 | + | intronic | N/A | 2.0252 | 0.044513 | CNOT6 |
| 27373960 | 27374248 | chr16 | + | intronic | hsa_circ_0000684 | −1.6873 | 0.044514 | IL4R |
| 75703832 | 75706652 | chr15 | − | exonic | hsa_circ_0000636 | 1.5533 | 0.044539 | SIN3A |
| 22477517 | 22496137 | chr16 | + | exonic | hsa_circ_0038539 | 1.8669 | 0.044548 | SMG1P1 |
| 29432408 | 29432626 | chr18 | − | exonic | hsa_circ_0000841 | 1.9773 | 0.044643 | TRAPPC8 |
| 33606862 | 33613800 | chr18 | − | exonic | hsa_circ_0000842 | 1.9318 | 0.044682 | RPRD1A |
| 94767247 | 94828743 | chr8 | + | sense overlapping | N/A | −1.6827 | 0.044698 | TMEM67 |
| 983990 | 1004666 | chr16 | − | exonic | N/A | −1.5377 | 0.044724 | LMF1 |
| 35800605 | 35800763 | chr17 | + | exonic | hsa_circ_0006220 | 1.9190 | 0.044752 | TADA2A |
| 171867882 | 171884915 | chr2 | − | exonic | hsa_circ_0057028 | 1.6931 | 0.044760 | TLK1 |
| 62515438 | 62522318 | chr17 | + | exonic | hsa_circ_0045308 | −1.5348 | 0.044823 | CEP95 |
| 171486729 | 171557644 | chr1 | + | exonic | hsa_circ_0015204 | −1.6949 | 0.044841 | PRRC2C |
| 100676720 | 100691953 | chr12 | + | exonic | hsa_circ_0006258 | 1.9998 | 0.044885 | SCYL2 |
| 220752695 | 220754460 | chr1 | + | exonic | hsa_circ_0016519 | −1.5141 | 0.044887 | MARK1 |
| 60629662 | 60631116 | chr17 | + | exonic | hsa_circ_0008438 | 2.8461 | 0.044889 | TLK2 |
| 103273041 | 103273253 | chr9 | + | intronic | N/A | −1.7171 | 0.044895 | TMEFF1 |
| 25477659 | 25477979 | chr20 | − | intronic | hsa_circ_0092338 | −1.9276 | 0.044915 | NINL |
| 76285013 | 76315227 | chr10 | + | intronic | N/A | −1.6474 | 0.044928 | ADK |
| 111406810 | 111419418 | chr2 | − | exonic | hsa_circ_0056037 | −1.5240 | 0.044939 | BUB1 |
| 53701835 | 53714476 | chr12 | − | exonic | hsa_circ_0026616 | −1.8741 | 0.044969 | AAAS |
| 94008811 | 94009042 | chr14 | + | exonic | hsa_circ_0033049 | −1.7422 | 0.044982 | UNC79 |
| 1902352 | 1941505 | chr4 | + | exonic | hsa_circ_0005881 | −1.6221 | 0.044988 | WHSC1 |
| 121154725 | 121157906 | chr12 | − | antisense | hsa_circ_0000449 | −1.6480 | 0.045015 | UNC119B |
| 108286344 | 108286691 | chr9 | + | intronic | N/A | 1.6054 | 0.045038 | FSD1L |
| 45690588 | 45690998 | chr19 | + | exonic | N/A | −1.6371 | 0.045065 | AC005779.2 |
| 97686267 | 97718297 | chr9 | + | exonic | N/A | −1.6257 | 0.045065 | C9orf3 |
| 131249167 | 131249240 | chr8 | − | exonic | hsa_circ_0085613 | 2.9167 | 0.045068 | ASAP1 |
| 89468952 | 89487246 | chr10 | + | exonic | N/A | −1.5128 | 0.045091 | PAPSS2 |
| 53448969 | 53449629 | chr12 | + | exonic | hsa_circ_0026542 | −1.5485 | 0.045111 | TNS2 |
| 87920168 | 87928449 | chr6 | + | intronic | hsa_circ_0004383 | 1.6919 | 0.045126 | ZNF292 |
| 95839490 | 95854716 | chr8 | + | exonic | hsa_circ_0001814 | 1.7262 | 0.045136 | INTS8 |
| 6617220 | 6628610 | chr7 | + | exonic | hsa_circ_0079373 | −1.6585 | 0.045180 | ZDHHC4 |
| 8043537 | 8110761 | chr7 | + | exonic | N/A | 1.5864 | 0.045286 | GLCCI1 |
| 1004361 | 1004666 | chr16 | − | intronic | N/A | −1.6208 | 0.045310 | LMF1 |
| 136467002 | 136467801 | chr2 | + | exonic | hsa_circ_0056586 | 1.5216 | 0.045323 | R3HDM1 |
| 183580540 | 183585848 | chr3 | − | exonic | hsa_circ_0068255 | 1.5692 | 0.045325 | PARL |
| 89799889 | 89804313 | chr16 | + | exonic | hsa_circ_0040987 | −1.6182 | 0.045340 | ZNF276 |
| 76342171 | 76344097 | chr5 | + | exonic | hsa_circ_0008620 | 2.8560 | 0.045370 | AGGF1 |
| 34147027 | 34149837 | chr17 | + | exonic | hsa_circ_0043138 | 3.3215 | 0.045377 | TAF15 |
| 231090078 | 231097049 | chr1 | − | exonic | hsa_circ_0000195 | 2.1211 | 0.045381 | TTC13 |
| 47767862 | 47768203 | chr19 | + | sense overlapping | N/A | 2.1338 | 0.045383 | CCDC9 |
| 114133569 | 114183238 | chr11 | + | exonic | hsa_circ_0024326 | −1.6263 | 0.045495 | NNMT |
| 184563675 | 184563944 | chr4 | − | intronic | N/A | −1.6140 | 0.045531 | RWDD4 |
| 34144719 | 34149837 | chr17 | + | exonic | N/A | 3.6754 | 0.045532 | TAF15 |
| 45767941 | 45769539 | chr19 | + | exonic | hsa_circ_0051454 | 1.6306 | 0.045558 | MARK4 |
| 214174782 | 214239843 | chr2 | + | exonic | hsa_circ_0058040 | −1.5003 | 0.045569 | SPAG16 |
| 113734352 | 113798481 | chr9 | − | intronic | hsa_circ_0004135 | −1.7101 | 0.045577 | LPAR1 |

TABLE 9-continued (MAOI R 8 week vs MAOI R baseline)

| TxStart | TxEnd | Chrom | Strand | circRNA type | Alias | Fold change | P-value | GeneSymbol |
|---|---|---|---|---|---|---|---|---|
| 146747016 | 146757164 | chr1 | + | exonic | hsa_circ_0013953 | 1.8930 | 0.045591 | CHD1L |
| 40949651 | 40950704 | chr17 | − | sense overlapping | hsa_circ_0043912 | −1.6227 | 0.045613 | COA3 |
| 62421173 | 62422143 | chr20 | − | exonic | hsa_circ_0061179 | −1.5789 | 0.045622 | ZBTB46 |
| 54852135 | 54866870 | chr8 | + | exonic | N/A | −1.5484 | 0.045707 | RGS20 |
| 43628823 | 43652158 | chr15 | + | sense overlapping | N/A | −1.7736 | 0.045711 | ADAL |
| 81059688 | 81060008 | chr10 | + | intronic | hsa_circ_0092353 | −1.5610 | 0.045721 | ZMIZ1 |
| 2967410 | 2969120 | chr20 | + | exonic | hsa_circ_0001127 | 1.7857 | 0.045734 | PTPRA |
| 178735010 | 178743013 | chr3 | − | exonic | hsa_circ_0068067 | −1.5999 | 0.045761 | ZMAT3 |
| 71799391 | 71803602 | chr16 | − | exonic | hsa_circ_0007770 | −1.5515 | 0.045789 | AP1G1 |
| 69726439 | 69752439 | chr10 | − | exonic | hsa_circ_0003308 | 2.3044 | 0.045793 | HERC4 |
| 26918715 | 26920084 | chr17 | − | exonic | hsa_circ_0006686 | −1.5918 | 0.045821 | SPAG5 |
| 28290542 | 28310335 | chr22 | − | exonic | hsa_circ_0062688 | 2.0304 | 0.045966 | PITPNB |
| 19989289 | 19990955 | chr19 | + | exonic | N/A | 1.8692 | 0.045986 | ZNF253 |
| 102076623 | 102094483 | chr11 | + | exonic | hsa_circ_0005990 | −1.7967 | 0.046054 | YAP1 |
| 101643844 | 101650220 | chr2 | − | exonic | hsa_circ_0004471 | −1.5648 | 0.046066 | TBC1D8 |
| 52771601 | 52773650 | chr3 | − | exonic | hsa_circ_0001308 | 2.2130 | 0.046074 | NEK4 |
| 17629628 | 17633596 | chr4 | + | sense overlapping | N/A | −1.5564 | 0.046084 | MED28 |
| 34922765 | 34955036 | chr19 | + | exonic | hsa_circ_0050518 | 1.7077 | 0.046104 | UBA2 |
| 22646156 | 22659753 | chr12 | − | exonic | hsa_circ_0025614 | 1.6743 | 0.046136 | C2CD5 |
| 70732539 | 70796508 | chr16 | − | exonic | hsa_circ_0040319 | −1.5515 | 0.046170 | VAC14 |
| 31205314 | 31214563 | chr1 | − | exonic | hsa_circ_0011205 | −1.5192 | 0.046185 | LAPTM5 |
| 126355758 | 126370948 | chr10 | − | exonic | hsa_circ_0020321 | 1.5706 | 0.046234 | FAM53B |
| 130705441 | 130705609 | chr9 | + | antisense | hsa_circ_0001892 | −1.5823 | 0.046301 | FAM102A |
| 54265896 | 54294350 | chr4 | + | exonic | hsa_circ_0005912 | 1.8115 | 0.046321 | FIP1L1 |
| 72183904 | 72185784 | chr5 | + | exonic | hsa_circ_0072940 | 1.5703 | 0.046323 | TNPO1 |
| 3088665 | 3117990 | chr4 | + | exonic | hsa_circ_0003850 | −1.6604 | 0.046339 | HTT |
| 4445266 | 4445746 | chr17 | − | intronic | hsa_circ_0092308 | −1.5234 | 0.046353 | MYBBP1A |
| 65860865 | 65864782 | chr7 | − | exonic | N/A | −1.6232 | 0.046362 | LINC00174 |
| 186901894 | 186934725 | chr1 | + | exonic | N/A | −1.5029 | 0.046417 | PLA2G4A |
| 12825860 | 12825983 | chr19 | − | exonic | hsa_circ_0049586 | −1.6306 | 0.046441 | TNPO2 |
| 103427642 | 103436193 | chr10 | − | exonic | hsa_circ_0008362 | 1.8358 | 0.046448 | FBXW4 |
| 19615443 | 19653155 | chr12 | + | exonic | hsa_circ_0006128 | 1.8772 | 0.046457 | AEBP2 |
| 41173043 | 41195087 | chr22 | − | exonic | hsa_circ_0063459 | −1.6296 | 0.046457 | SLC25A17 |
| 23614293 | 23618574 | chr20 | − | exonic | hsa_circ_0059617 | −1.5012 | 0.046466 | CST3 |
| 44773981 | 44785416 | chr1 | − | exonic | hsa_circ_0012144 | −1.5585 | 0.046468 | ERI3 |
| 28830428 | 28855516 | chr13 | + | exonic | hsa_circ_0029853 | 1.7712 | 0.046540 | PAN3 |
| 88231964 | 88233730 | chr10 | − | exonic | hsa_circ_0005828 | −1.5733 | 0.046548 | WAPAL |
| 77330650 | 77340944 | chr11 | − | exonic | hsa_circ_0008342 | 1.8527 | 0.046578 | CLNS1A |
| 95609446 | 95616975 | chr1 | + | exonic | hsa_circ_0000095 | 1.6920 | 0.046584 | TMEM56 |
| 27668989 | 27689252 | chr7 | − | exonic | hsa_circ_0006773 | 1.7336 | 0.046619 | HIBADH |
| 107459490 | 107460490 | chr2 | − | exonic | hsa_circ_0055957 | −1.8083 | 0.046627 | ST6GAL2 |
| 141220790 | 141235273 | chr3 | + | sense overlapping | N/A | 1.8315 | 0.046641 | RASA2 |
| 28458581 | 28544344 | chr12 | + | exonic | hsa_circ_0008250 | 2.2086 | 0.046647 | CCDC91 |
| 33478807 | 33480195 | chr1 | − | exonic | hsa_circ_0011462 | −1.7273 | 0.046654 | AK2 |
| 56642903 | 56643409 | chr16 | + | exonic | hsa_circ_0039460 | −1.6565 | 0.046718 | MT2A |
| 126021212 | 126021585 | chr8 | + | exonic | N/A | −1.5036 | 0.046737 | SQLE |
| 41129508 | 41129987 | chr19 | + | exonic | hsa_circ_0051123 | −1.6907 | 0.046759 | LTBP4 |
| 136770511 | 136771563 | chr5 | − | intronic | N/A | −1.7224 | 0.046784 | SPOCK1 |
| 42914234 | 42927450 | chr8 | + | exonic | hsa_circ_0084170 | 1.6570 | 0.046786 | FNTA |
| 388708 | 391408 | chr20 | + | exonic | hsa_circ_0059148 | −1.7437 | 0.046790 | RBCK1 |
| 56989531 | 57025950 | chr6 | + | exonic | N/A | 1.8560 | 0.046920 | ZNF451 |
| 76344422 | 76388643 | chr6 | + | exonic | hsa_circ_0001613 | 3.0132 | 0.047070 | SENP6 |
| 128977551 | 129015614 | chr5 | + | exonic | N/A | −1.5033 | 0.047100 | ADAMTS19 |
| 99113384 | 99114391 | chr9 | − | exonic | hsa_circ_0087620 | −1.5384 | 0.047104 | SLC35D2 |
| 242195015 | 242195594 | chr2 | + | antisense | hsa_circ_0004528 | −1.6049 | 0.047197 | HDLBP |
| 111434013 | 111440514 | chr1 | + | exonic | hsa_circ_0013480 | 1.5117 | 0.047252 | CD53 |
| 42315491 | 42328684 | chr20 | + | exonic | hsa_circ_0060456 | 1.6718 | 0.047281 | MYBL2 |
| 33996220 | 34017187 | chr9 | − | exonic | hsa_circ_0003410 | 2.7203 | 0.047285 | UBAP2 |
| 42041214 | 42050989 | chr1 | − | exonic | hsa_circ_0011950 | −1.6522 | 0.047319 | HIVEP3 |
| 10417222 | 10417519 | chr1 | + | intronic | N/A | −1.7095 | 0.047349 | KIF1B |
| 65922338 | 65931191 | chr14 | + | intronic | N/A | 2.1334 | 0.047389 | FUT8 |
| 21971315 | 21972024 | chr14 | − | exonic | hsa_circ_0000523 | 1.9294 | 0.047419 | METTL3 |
| 107083899 | 107097934 | chrX | + | exonic | hsa_circ_0002153 | 1.5848 | 0.047423 | MID2 |
| 74093876 | 74097944 | chr17 | − | exonic | hsa_circ_0045775 | 1.5088 | 0.047454 | EXOC7 |
| 124911167 | 124934413 | chr12 | − | exonic | hsa_circ_0000461 | 2.0777 | 0.047488 | NCOR2 |
| 2951660 | 2952972 | chr4 | − | exonic | hsa_circ_0006737 | 2.0266 | 0.047516 | NOP14 |
| 142779220 | 142780417 | chr5 | − | exonic | hsa_circ_0001543 | 1.5520 | 0.047547 | NR3C1 |
| 24523655 | 24524213 | chr20 | + | exonic | N/A | −1.5742 | 0.047551 | SYNDIG1 |
| 29356520 | 29390406 | chr2 | + | exonic | hsa_circ_0003475 | 1.6656 | 0.047568 | CLIP4 |
| 74561481 | 74563895 | chr18 | + | exonic | hsa_circ_0004979 | 2.2360 | 0.047600 | ZNF236 |
| 94532555 | 94533477 | chr11 | + | exonic | hsa_circ_0004214 | −1.7988 | 0.047609 | AMOTL1 |
| 50516660 | 50530353 | chr20 | − | antisense | N/A | −1.5634 | 0.047708 | RNU6-347P |

TABLE 9-continued (MAOI R 8 week vs MAOI R baseline)

| TxStart | TxEnd | Chrom | Strand | circRNA type | Alias | Fold change | P-value | GeneSymbol |
|---|---|---|---|---|---|---|---|---|
| 20315704 | 20333558 | chr13 | − | exonic | N/A | 1.7843 | 0.047715 | PSPC1 |
| 69120278 | 69121169 | chr12 | + | exonic | hsa_circ_0027485 | 1.7032 | 0.047718 | NUP107 |
| 96434640 | 96438798 | chr5 | + | sense overlapping | N/A | 1.5407 | 0.047721 | CTD-2215E18.1 |
| 21137230 | 21139732 | chr1 | − | exonic | hsa_circ_0010450 | −1.5739 | 0.047726 | EIF4G3 |
| 118625413 | 118627996 | chr11 | − | exonic | hsa_circ_0024490 | 4.4050 | 0.047741 | DDX6 |
| 30428647 | 30437426 | chr21 | − | exonic | hsa_circ_0061372 | −1.6809 | 0.047744 | CCT8 |
| 43872481 | 43918886 | chr13 | − | exonic | N/A | −1.5162 | 0.047752 | ENOX1 |
| 74119495 | 74131270 | chr7 | + | exonic | hsa_circ_0006944 | 1.5979 | 0.047801 | GTF2I |
| 129767529 | 129773423 | chr4 | + | exonic | hsa_circ_0070953 | 1.6417 | 0.047874 | JADE1 |
| 99890680 | 99896878 | chr13 | + | exonic | hsa_circ_0030720 | 2.2580 | 0.047931 | UBAC2 |
| 76410959 | 76415806 | chr17 | + | exonic | hsa_circ_0045905 | −1.5854 | 0.047934 | PGS1 |
| 113734352 | 113800365 | chr9 | − | exonic | hsa_circ_0087962 | −1.6150 | 0.047995 | LPAR1 |
| 52446826 | 52448603 | chr3 | + | exonic | hsa_circ_0004912 | 2.3680 | 0.048024 | PHF7 |
| 99718694 | 99719539 | chr8 | − | exonic | hsa_circ_0004592 | 1.6102 | 0.048107 | STK3 |
| 243708811 | 243859018 | chr1 | − | exonic | N/A | 1.7832 | 0.048122 | AKT3 |
| 18243356 | 18250970 | chr17 | − | exonic | hsa_circ_0042339 | −1.5888 | 0.048122 | SHMT1 |
| 150923840 | 150935195 | chr1 | + | exonic | hsa_circ_0006352 | −1.6342 | 0.048180 | SETDB1 |
| 5268416 | 5271763 | chr17 | + | exonic | hsa_circ_0004621 | 1.6135 | 0.048208 | RABEP1 |
| 113057425 | 113057606 | chr2 | + | exonic | hsa_circ_0001062 | 1.7531 | 0.048214 | ZC3H6 |
| 58290118 | 58291514 | chr19 | + | intronic | N/A | 1.6683 | 0.048230 | ZNF587 |
| 222997197 | 223000943 | chr1 | + | exonic | N/A | −1.5079 | 0.048257 | RP11-452F19.3 |
| 78197050 | 78201759 | chr17 | + | exonic | N/A | −1.7706 | 0.048265 | SLC26A11 |
| 63711737 | 63798760 | chr2 | − | exonic | hsa_circ_0006759 | 1.6666 | 0.048276 | WDPCP |
| 68155889 | 68225678 | chr16 | + | exonic | hsa_circ_0039929 | 3.8119 | 0.048314 | NFATC3 |
| 93608139 | 93611093 | chr10 | + | exonic | hsa_circ_0008332 | 1.9873 | 0.048341 | TNKS2 |
| 10031484 | 10035530 | chrX | + | exonic | hsa_circ_0007685 | 2.2108 | 0.048375 | WWC3 |
| 86292641 | 86301070 | chr9 | − | exonic | hsa_circ_0003715 | 2.2321 | 0.048423 | UBQLN1 |
| 68717321 | 68795482 | chr2 | + | sense overlapping | hsa_circ_0001024 | 2.8269 | 0.048436 | APLF |
| 225140371 | 225195246 | chr1 | + | exonic | hsa_circ_0016601 | −1.5969 | 0.048452 | DNAH14 |
| 50741596 | 50763992 | chr15 | + | exonic | hsa_circ_0000599 | 2.1917 | 0.048475 | USP8 |
| 17059499 | 17059748 | chr3 | − | antisense | hsa_circ_0001275 | −1.6394 | 0.048492 | PLCL2 |
| 42730785 | 42744343 | chr1 | − | exonic | hsa_circ_0006848 | 1.9668 | 0.048515 | FOXJ3 |
| 45059428 | 45059793 | chr15 | + | sense overlapping | N/A | −1.5666 | 0.048516 | TRIM69 |
| 113960799 | 113977741 | chr13 | + | exonic | hsa_circ_0030997 | −1.9238 | 0.048549 | LAMP1 |
| 155640110 | 155644887 | chr1 | − | exonic | N/A | 1.7437 | 0.048571 | YY1AP1 |
| 51829537 | 51831701 | chr1 | − | exonic | hsa_circ_0012417 | −1.5006 | 0.048574 | EPS15 |
| 96314841 | 96322374 | chr5 | + | exonic | hsa_circ_0001513 | −1.6224 | 0.048600 | LNPEP |
| 26512204 | 26512291 | chr17 | + | exonic | hsa_circ_0042521 | −1.7144 | 0.048603 | NLK |
| 34699833 | 34706566 | chr19 | + | exonic | hsa_circ_0050461 | 1.7387 | 0.048603 | LSM14A |
| 103002341 | 103027210 | chr9 | + | exonic | N/A | −1.5099 | 0.048610 | INVS |
| 88983057 | 88987031 | chr4 | + | exonic | hsa_circ_0004577 | 2.0058 | 0.048614 | PKD2 |
| 141811902 | 141820683 | chr3 | − | exonic | hsa_circ_0008304 | 1.9262 | 0.048630 | TFDP2 |
| 15601324 | 15651474 | chr2 | − | exonic | hsa_circ_0052767 | −1.6095 | 0.048637 | NBAS |
| 146209155 | 146216113 | chr6 | − | exonic | hsa_circ_0001649 | 3.6196 | 0.048689 | SHPRH |
| 41365625 | 41366763 | chr15 | − | exonic | hsa_circ_0034677 | 1.5681 | 0.048692 | INO80 |
| 72958135 | 72960247 | chr2 | − | exonic | hsa_circ_0001030 | 2.6652 | 0.048784 | EXOC6B |
| 68337215 | 68343511 | chr11 | + | exonic | hsa_circ_0023233 | 2.5336 | 0.048799 | PPP6R3 |
| 3330258 | 3395596 | chr9 | − | exonic | hsa_circ_0086242 | −1.5953 | 0.048815 | RFX3 |
| 66828270 | 66839043 | chr15 | + | exonic | hsa_circ_0008168 | 1.6055 | 0.048828 | ZWILCH |
| 216269111 | 216300791 | chr2 | − | exonic | hsa_circ_0058123 | −1.5843 | 0.048837 | FN1 |
| 53024621 | 53027487 | chr17 | + | exonic | hsa_circ_0044695 | −1.6500 | 0.048840 | TOM1L1 |
| 62407030 | 62422143 | chr20 | − | exonic | hsa_circ_0002805 | −1.5111 | 0.048849 | ZBTB46 |
| 118890859 | 118892596 | chr11 | + | exonic | N/A | −1.5821 | 0.048857 | TRAPPC4 |
| 24523658 | 24524213 | chr20 | + | sense overlapping | N/A | −1.5850 | 0.048909 | SYNDIG1 |
| 103384501 | 103436193 | chr10 | − | exonic | hsa_circ_0005741 | 1.8303 | 0.048914 | FBXW4 |
| 73215386 | 73228707 | chr2 | − | exonic | hsa_circ_0004699 | −1.6055 | 0.048942 | SFXN5 |
| 47098310 | 47103836 | chr3 | − | exonic | hsa_circ_0065149 | 1.9961 | 0.048942 | SETD2 |
| 37580879 | 37584043 | chr17 | − | exonic | hsa_circ_0007539 | 1.6363 | 0.048972 | MED1 |
| 145838898 | 145842016 | chr3 | − | exonic | N/A | 1.6749 | 0.049063 | PLOD2 |
| 20240809 | 20240905 | chr2 | − | intronic | hsa_circ_0000981 | −1.5621 | 0.049092 | LAPTM4A |
| 122273422 | 122280607 | chr10 | + | exonic | hsa_circ_0008896 | −1.7486 | 0.049145 | PPAPDC1A |
| 162669971 | 162688935 | chr1 | + | sense overlapping | N/A | −1.5593 | 0.049149 | DDR2 |
| 75464743 | 75464836 | chr10 | − | exonic | hsa_circ_0018844 | 1.6211 | 0.049166 | BMS1P4 |
| 116627861 | 116631668 | chr11 | − | exonic | N/A | −1.6555 | 0.049174 | BUD13 |
| 64564228 | 64608670 | chr13 | − | exonic | hsa_circ_0030388 | −1.5922 | 0.049227 | AK057471 |
| 77700452 | 77703365 | chr13 | − | exonic | hsa_circ_0000495 | 2.0293 | 0.049270 | MYCBP2 |
| 100889777 | 100908552 | chr1 | + | exonic | hsa_circ_0000097 | 2.5880 | 0.049302 | CDC14A |
| 29916172 | 29917448 | chr16 | + | exonic | N/A | −1.5676 | 0.049326 | ASPHD1 |
| 129102786 | 129157976 | chr9 | + | exonic | hsa_circ_0008240 | −1.6017 | 0.049331 | MVB12B |
| 70644941 | 70645407 | chr17 | − | exonic | hsa_circ_0045526 | −1.6152 | 0.049477 | SLC39A11 |
| 30890069 | 30898940 | chr7 | + | exonic | hsa_circ_0079743 | −1.5094 | 0.049478 | FAM188B |

TABLE 9-continued (MAOI R 8 week vs MAOI R baseline)

| TxStart | TxEnd | Chrom | Strand | circRNA type | Alias | Fold change | P-value | GeneSymbol |
|---|---|---|---|---|---|---|---|---|
| 33060883 | 33063720 | chr7 | − | exonic | hsa_circ_0079800 | 2.0259 | 0.049480 | NT5C3A |
| 50131343 | 50141145 | chr14 | − | exonic | hsa_circ_0031787 | 2.0293 | 0.049484 | POLE2 |
| 89600213 | 89650899 | chr6 | − | exonic | hsa_circ_0003393 | 1.6569 | 0.049533 | RNGTT |
| 20975317 | 20976684 | chr19 | + | exonic | N/A | 1.9439 | 0.049537 | ZNF66 |
| 46521466 | 46546422 | chr1 | − | exonic | hsa_circ_0012300 | −1.7168 | 0.049603 | PIK3R3 |
| 7491497 | 7491864 | chr17 | − | exonic | hsa_circ_0041939 | −1.8056 | 0.049657 | SOX15 |
| 133135707 | 133138703 | chr6 | + | exonic | hsa_circ_0077877 | −1.7925 | 0.049706 | RPS12 |
| 103432671 | 103433430 | chr10 | − | exonic | hsa_circ_0019591 | 2.9278 | 0.049713 | FBXW4 |
| 126323958 | 126326678 | chr10 | − | intronic | N/A | −1.7013 | 0.049727 | FAM53B |
| 134076752 | 134079742 | chr5 | + | exonic | hsa_circ_0003154 | 2.5024 | 0.049804 | CAMLG |
| 136389287 | 136396692 | chr2 | + | exonic | hsa_circ_0001069 | 1.8110 | 0.049820 | R3HDM1 |
| 31532050 | 31532424 | chr1 | − | exonic | hsa_circ_0000045 | 1.8460 | 0.049895 | PUM1 |
| 91947919 | 91952074 | chr14 | − | exonic | hsa_circ_0003045 | 1.8909 | 0.049933 | SMEK1 |
| 18852886 | 18856973 | chr16 | − | exonic | hsa_circ_0006434 | 2.8869 | 0.049933 | SMG1 |
| 3524281 | 3524706 | chr17 | − | sense overlapping | N/A | −1.5436 | 0.049933 | SHPK |
| 25443870 | 25444056 | chr14 | − | exonic | hsa_circ_0031408 | −1.6068 | 0.049959 | STXBP6 |
| 43623730 | 43629994 | chr20 | + | exonic | hsa_circ_0060530 | 2.9913 | 0.049967 | STK4 |
| 10077970 | 10081529 | chr3 | + | exonic | hsa_circ_0001266 | −1.6458 | 0.049967 | FANCD2 |
| 42294506 | 42323435 | chr8 | − | exonic | hsa_circ_0001795 | −1.5879 | 0.049972 | SLC20A2 |

TABLE 10

(MDD baseline vs Control baseline)

| TxStart | TxEnd | Chrom | Strand | circRNA type | Alias | Fold change | P-value | GeneSymbol |
|---|---|---|---|---|---|---|---|---|
| 37159809 | 37161502 | chr20 | + | exonic | hsa_circ_0060342 | 2.1899 | 1.4000E−10 | RALGAPB |
| 6998051 | 7006651 | chr4 | + | exonic | hsa_circ_0003201 | 1.7526 | 6.0000E−10 | TBC1D14 |
| 27447477 | 27447615 | chr10 | + | exonic | hsa_circ_0018031 | 2.0229 | 1.3800E−09 | MASTL |
| 132990630 | 133002144 | chr7 | + | exonic | hsa_circ_0082440 | 1.7027 | 5.5600E−09 | EXOC4 |
| 54675169 | 54680872 | chr12 | + | exonic | hsa_circ_0026700 | 1.6491 | 7.0800E−09 | HNRNPA1 |
| 37105033 | 37105170 | chr2 | − | exonic | hsa_circ_0054033 | 2.2505 | 8.7600E−09 | STRN |
| 224746658 | 224760347 | chr2 | − | exonic | hsa_circ_0001101 | 2.5327 | 2.5170E−08 | WDFY1 |
| 42069936 | 42084913 | chr22 | − | exonic | hsa_circ_0063598 | 1.8846 | 3.9120E−08 | NHP2L1 |
| 53585106 | 53590604 | chr12 | − | exonic | hsa_circ_0026568 | 1.7467 | 1.3749E−07 | ITGB7 |
| 169663839 | 169664181 | chr1 | − | intronic | hsa_circ_0000157 | 2.1239 | 3.9378E−07 | SELL |
| 114905750 | 114905903 | chr9 | − | exonic | hsa_circ_0088059 | 1.7553 | 0.000001 | SUSD1 |
| 21335426 | 21338430 | chr20 | + | exonic | N/A | 1.8442 | 0.000001 | XRN2 |
| 134353337 | 134353833 | chr9 | + | intronic | N/A | 1.6014 | 0.000001 | PRRC2B |
| 8138461 | 8139361 | chr19 | − | intronic | hsa_circ_0092332 | 1.9221 | 0.000002 | FBN3 |
| 145522974 | 145547828 | chr5 | − | exonic | hsa_circ_0074407 | 1.7462 | 0.000002 | LARS |
| 896779 | 901546 | chr5 | + | exonic | hsa_circ_0071681 | 1.5686 | 0.000003 | TRIP13 |
| 6452441 | 6456552 | chr7 | − | exonic | hsa_circ_0006093 | 1.5476 | 0.000003 | DAGLB |
| 140458885 | 140459606 | chr9 | − | exonic | hsa_circ_0006502 | 1.5114 | 0.000003 | DPH7 |
| 10186276 | 10188722 | chr2 | − | exonic | N/A | 1.6714 | 0.000003 | KLF11 |
| 145144493 | 145205763 | chr5 | − | exonic | hsa_circ_0008132 | 1.6215 | 0.000004 | PRELID2 |
| 6456257 | 6456552 | chr7 | − | exonic | hsa_circ_0002067 | 1.5473 | 0.000004 | DAGLB |
| 126434011 | 126496057 | chr6 | + | antisense | N/A | 1.7018 | 0.000005 | MIR5695 |
| 34941169 | 34957919 | chr19 | + | exonic | hsa_circ_0050547 | 1.7190 | 0.000005 | UBA2 |
| 17910716 | 17974508 | chr4 | − | exonic | N/A | 1.7549 | 0.000005 | LCORL |
| 79818266 | 79842185 | chr7 | + | exonic | N/A | 1.5269 | 0.000006 | GNAI1 |
| 135979320 | 136002789 | chr3 | + | exonic | N/A | 1.9035 | 0.000006 | PCCB |
| 10865809 | 10868382 | chr12 | − | exonic | hsa_circ_0025460 | 1.9557 | 0.000007 | YBX3 |
| 25265498 | 25266456 | chr8 | + | exonic | hsa_circ_0007618 | 1.5590 | 0.000007 | DOCK5 |
| 171537385 | 171540560 | chr1 | + | exonic | hsa_circ_0015232 | 1.8032 | 0.000009 | PRRC2C |
| 64587155 | 64595958 | chr5 | − | exonic | hsa_circ_0002529 | 1.5201 | 0.000010 | ADAMTS6 |
| 43628823 | 43652158 | chr15 | + | sense overlapping | N/A | 1.6297 | 0.000011 | ADAL |
| 43668295 | 43669265 | chr15 | + | exonic | hsa_circ_0034953 | 1.6629 | 0.000011 | TUBGCP4 |
| 142593 | 150507 | chr16 | − | exonic | hsa_circ_0037128 | 1.5644 | 0.000016 | NPRL3 |
| 170626457 | 170632347 | chr6 | + | exonic | hsa_circ_0078768 | 1.7188 | 0.000018 | FAM120B |
| 170667931 | 170669824 | chr5 | + | exonic | hsa_circ_0004738 | 1.7801 | 0.000021 | RANBP17 |
| 23381682 | 23391205 | chr7 | − | exonic | N/A | 1.6812 | 0.000022 | IGF2BP3 |
| 89853414 | 89866052 | chr12 | − | exonic | N/A | 2.0398 | 0.000024 | POC1B |
| 52777367 | 52786352 | chr3 | − | exonic | hsa_circ_0066113 | 1.5949 | 0.000025 | NEK4 |
| 23495059 | 23502883 | chr14 | − | exonic | hsa_circ_0031268 | 1.5649 | 0.000027 | PSMB5 |
| 73775150 | 73775265 | chr17 | − | intronic | hsa_circ_0000803 | 1.5082 | 0.000029 | H3F3B |
| 10015311 | 10016172 | chr3 | − | exonic | hsa_circ_0064195 | 1.5026 | 0.000035 | EMC3 |
| 33825619 | 33840156 | chr21 | + | exonic | hsa_circ_0061481 | 1.8141 | 0.000037 | EVA1C |
| 23735156 | 23745632 | chr1 | − | exonic | N/A | 1.7692 | 0.000039 | TCEA3 |
| 4516153 | 4519466 | chr16 | − | exonic | hsa_circ_0007788 | 2.6511 | 0.000043 | NMRAL1 |

TABLE 10-continued (MDD baseline vs Control baseline)

| TxStart | TxEnd | Chrom | Strand | circRNA type | Alias | Fold change | P-value | GeneSymbol |
|---|---|---|---|---|---|---|---|---|
| 50904191 | 50904503 | chr22 | − | exonic | hsa_circ_0063982 | 1.5809 | 0.000044 | SBF1 |
| 100895143 | 100901720 | chr6 | − | exonic | hsa_circ_0007217 | 1.5329 | 0.000049 | SIM1 |
| 89289564 | 89291210 | chr16 | + | exonic | N/A | 1.5708 | 0.000055 | ZNF778 |
| 44513849 | 44515020 | chr22 | + | sense overlapping | N/A | 1.5767 | 0.000057 | PARVB |
| 29237938 | 29246335 | chr18 | − | exonic | hsa_circ_0047351 | 1.7543 | 0.000058 | B4GALT6 |
| 207988497 | 207989128 | chr2 | − | exonic | N/A | 1.5061 | 0.000061 | KLF7 |
| 73584563 | 73584911 | chr17 | − | antisense | hsa_circ_0000802 | 1.5116 | 0.000066 | MYO15B |
| 22669237 | 22683186 | chrY | − | sense overlapping | N/A | 1.6356 | 0.000068 | TTTY10 |
| 84112887 | 84132553 | chr14 | + | intergenic | N/A | 1.6952 | 0.000073 | |
| 23495059 | 23495584 | chr14 | − | exonic | hsa_circ_0031267 | 1.7319 | 0.000074 | PSMB5 |
| 75104453 | 76279715 | chr7 | − | sense overlapping | hsa_circ_0006766 | 1.7258 | 0.000077 | CCL24 |
| 4076755 | 4080626 | chr11 | + | exonic | hsa_circ_0020934 | 1.6010 | 0.000082 | STIM1 |
| 127337917 | 127341124 | chr3 | − | antisense | hsa_circ_0001334 | 2.1228 | 0.000083 | MCM2 |
| 30611319 | 30630569 | chr10 | − | exonic | N/A | 1.5507 | 0.000084 | MTPAP |
| 181846744 | 181848820 | chr2 | + | exonic | hsa_circ_0007011 | 1.5784 | 0.000091 | UBE2E3 |
| 37425918 | 37426651 | chr9 | + | exonic | hsa_circ_0087063 | −1.6982 | 0.000099 | GRHPR |
| 4797948 | 4798348 | chr17 | + | intronic | hsa_circ_0092278 | −1.7597 | 0.000115 | MINK1 |
| 74433139 | 74434317 | chr7 | + | exonic | hsa_circ_0080638 | 1.6877 | 0.000118 | GATSL1 |
| 125472197 | 125474142 | chr11 | + | exonic | hsa_circ_0024766 | 1.8617 | 0.000122 | STT3A |
| 7849045 | 7849304 | chr17 | + | exonic | hsa_circ_0008310 | 1.5689 | 0.000133 | CNTROB |
| 173726114 | 173744981 | chr1 | + | exonic | hsa_circ_0015278 | 2.9012 | 0.000139 | KLHL20 |
| 44290402 | 44303983 | chr1 | + | exonic | hsa_circ_0012107 | 1.5908 | 0.000142 | ST3GAL3 |
| 18770594 | 18781183 | chr17 | + | exonic | hsa_circ_0042359 | 1.6172 | 0.000143 | PRPSAP2 |
| 82302569 | 82372915 | chr1 | + | exonic | hsa_circ_0013048 | 1.6057 | 0.000148 | LPHN2 |
| 16133348 | 16208501 | chr11 | − | exonic | N/A | 1.8915 | 0.000152 | SOX6 |
| 105953535 | 105955124 | chr14 | + | exonic | hsa_circ_0033628 | 1.9354 | 0.000153 | CRIP1 |
| 40669428 | 40681774 | chr22 | + | exonic | hsa_circ_0063411 | 1.9219 | 0.000155 | TNRC6B |
| 68501974 | 68503656 | chr15 | − | exonic | hsa_circ_0036052 | 1.6291 | 0.000159 | CLN6 |
| 52693054 | 52729678 | chr19 | + | exonic | hsa_circ_0052067 | 1.5208 | 0.000172 | PPP2R1A |
| 224918163 | 224918276 | chr1 | + | exonic | hsa_circ_0016598 | 1.6261 | 0.000182 | CNIH3 |
| 48866179 | 48869991 | chr8 | − | exonic | hsa_circ_0084464 | 1.6031 | 0.000187 | PRKDC |
| 27834800 | 27834884 | chr6 | − | sense overlapping | hsa_circ_0001596 | 1.9419 | 0.000190 | HIST1H1B |
| 131860291 | 131860929 | chr9 | − | exonic | hsa_circ_0003362 | 1.6191 | 0.000194 | CRAT |
| 59376327 | 59377984 | chr15 | + | exonic | hsa_circ_0035482 | 1.5132 | 0.000201 | RNF111 |
| 105563560 | 105573453 | chr6 | − | exonic | hsa_circ_0077527 | 1.5044 | 0.000225 | BVES |
| 13532533 | 13581264 | chr20 | − | intronic | N/A | 3.4574 | 0.000232 | TASP1 |
| 175426288 | 175426438 | chr2 | − | sense overlapping | hsa_circ_0001082 | 1.5918 | 0.000241 | WIPF1 |
| 56600621 | 56601081 | chr3 | + | exonic | hsa_circ_0001312 | −1.5787 | 0.000250 | CCDC66 |
| 3988781 | 4080626 | chr11 | + | exonic | hsa_circ_0020929 | 1.5585 | 0.000255 | STIM1 |
| 32354656 | 32358098 | chr20 | + | exonic | hsa_circ_0059880 | 1.5646 | 0.000264 | ZNF341 |
| 147131761 | 147131890 | chr1 | − | exonic | hsa_circ_0013959 | 1.6670 | 0.000272 | ACP6 |
| 155411422 | 155448734 | chr6 | + | exonic | hsa_circ_0078383 | 1.5447 | 0.000288 | TIAM2 |
| 168110970 | 168112932 | chr5 | − | exonic | hsa_circ_0074903 | 1.6422 | 0.000296 | SLIT3 |
| 77214859 | 77230123 | chr7 | + | exonic | hsa_circ_0003764 | −1.5464 | 0.000311 | PTPN12 |
| 6646085 | 6647162 | chr12 | + | exonic | hsa_circ_0025196 | 1.6680 | 0.000312 | GAPDH |
| 146432295 | 146451816 | chrX | − | intergenic | N/A | 1.5010 | 0.000327 | |
| 25402743 | 25402983 | chr12 | + | antisense | hsa_circ_0000383 | 1.5773 | 0.000330 | KRAS |
| 58562378 | 58594266 | chr16 | − | exonic | hsa_circ_0039626 | 1.9614 | 0.000338 | CNOT1 |
| 39073734 | 39073896 | chr5 | + | antisense | hsa_circ_0001477 | 1.5883 | 0.000346 | RICTOR |
| 131193709 | 131196192 | chr7 | − | exonic | hsa_circ_0001973 | 1.5834 | 0.000359 | PODXL |
| 36036501 | 36038429 | chr19 | + | exonic | hsa_circ_0050607 | 1.5209 | 0.000370 | TMEM147 |
| 57535669 | 57535748 | chr15 | + | exonic | hsa_circ_0035426 | 1.5482 | 0.000392 | TCF12 |
| 33315062 | 33324562 | chr20 | − | exonic | hsa_circ_0004468 | 1.5141 | 0.000396 | NCOA6 |
| 100035289 | 100052403 | chr2 | − | exonic | hsa_circ_0001052 | 1.8217 | 0.000446 | REV1 |
| 36245469 | 36247930 | chr19 | − | exonic | hsa_circ_0050649 | 1.7294 | 0.000456 | HSPB6 |
| 3205916 | 3209234 | chr10 | − | exonic | hsa_circ_0003022 | 1.5189 | 0.000463 | PITAM1 |
| 48597719 | 48597913 | chr4 | − | intronic | N/A | 1.5893 | 0.000467 | FRYL |
| 17059499 | 17059748 | chr3 | − | antisense | hsa_circ_0001275 | 1.5249 | 0.000486 | PLCL2 |
| 23371395 | 23380612 | chr14 | − | exonic | hsa_circ_0031235 | −1.8396 | 0.000488 | RBM23 |
| 201786215 | 201796102 | chr1 | + | exonic | hsa_circ_0015911 | 1.5037 | 0.000493 | NAV1 |
| 52478187 | 52553491 | chr16 | − | exonic | N/A | 1.5181 | 0.000495 | TOX3 |
| 46515157 | 46515754 | chr11 | − | exonic | hsa_circ_0009155 | 1.5496 | 0.000523 | AMBRA1 |
| 1352719 | 1356247 | chr20 | − | exonic | hsa_circ_0059181 | 1.6053 | 0.000563 | FKBP1A |
| 51797729 | 51800460 | chr18 | + | exonic | hsa_circ_0007180 | −1.5088 | 0.000612 | POLI |
| 44257772 | 44303983 | chr1 | + | exonic | hsa_circ_0012103 | 1.5086 | 0.000746 | ST3GAL3 |
| 151116991 | 151122005 | chr6 | − | exonic | hsa_circ_0078264 | 2.1360 | 0.000776 | PLEKHG1 |
| 23378691 | 23380612 | chr14 | − | exonic | hsa_circ_0000524 | −1.7970 | 0.000799 | RBM23 |
| 42231920 | 42232779 | chr17 | + | exonic | hsa_circ_0004239 | 1.5690 | 0.000857 | C17orf53 |
| 33608730 | 33610023 | chr19 | + | exonic | hsa_circ_0050444 | 1.7095 | 0.000866 | GPATCH1 |
| 29483000 | 29497015 | chr17 | + | exonic | hsa_circ_0007542 | 1.5898 | 0.000874 | NF1 |

TABLE 10-continued (MDD baseline vs Control baseline)

| TxStart | TxEnd | Chrom | Strand | circRNA type | Alias | Fold change | P-value | GeneSymbol |
|---|---|---|---|---|---|---|---|---|
| 153004802 | 153005376 | chr1 | + | exonic | hsa_circ_0014213 | 1.7147 | 0.000876 | SPRR1B |
| 34832618 | 34832848 | chr20 | + | exonic | hsa_circ_0060176 | 1.5585 | 0.000900 | AAR2 |
| 98831367 | 98864830 | chr8 | + | exonic | hsa_circ_0085018 | 1.5362 | 0.000909 | LAPTM4B |
| 144464661 | 144465125 | chr4 | + | exonic | hsa_circ_0001445 | −1.7820 | 0.000913 | SMARCA5 |
| 196544755 | 196548630 | chr2 | + | exonic | hsa_circ_0057551 | −1.7222 | 0.000946 | SLC39A10 |
| 196118683 | 196120490 | chr3 | − | exonic | hsa_circ_0005051 | −1.9549 | 0.000960 | UBXN7 |
| 10204997 | 10211619 | chr1 | − | exonic | N/A | 1.7848 | 0.000994 | UBE4B |
| 107260799 | 107263621 | chr11 | − | exonic | N/A | −1.5347 | 0.001068 | CWF19L2 |
| 156468903 | 156489628 | chr6 | − | intergenic | hsa_circ_0001655 | 1.6709 | 0.001153 | |
| 59204761 | 59209198 | chr15 | − | exonic | hsa_circ_0000605 | −1.6035 | 0.001181 | SLTM |
| 88726648 | 88727530 | chr15 | − | exonic | hsa_circ_0036667 | 1.5092 | 0.001197 | TRK3 |
| 89165951 | 89185063 | chr11 | − | exonic | hsa_circ_0023990 | 2.1834 | 0.001281 | NOX4 |
| 19627435 | 19663412 | chr16 | + | exonic | hsa_circ_0005699 | 1.9055 | 0.001317 | C16orf62 |
| 19042277 | 19042456 | chr2 | + | intronic | hsa_circ_0000979 | 1.5164 | 0.001398 | XLOC_001374 |
| 3474817 | 3477249 | chr17 | − | exonic | N/A | 1.5279 | 0.001431 | TRPV1 |
| 57237616 | 57250507 | chr4 | − | exonic | N/A | 1.6077 | 0.001433 | AASDH |
| 69644908 | 69656342 | chr12 | − | exonic | hsa_circ_0000417 | −1.6831 | 0.001465 | CPSF6 |
| 981641 | 1004666 | chr16 | − | exonic | hsa_circ_0037274 | 1.6416 | 0.001517 | LMF1 |
| 98643320 | 98645505 | chr7 | − | exonic | N/A | 2.5275 | 0.001559 | SMURF1 |
| 91723962 | 91727541 | chr9 | − | sense overlapping | hsa_circ_0007738 | 1.5919 | 0.001636 | SHC3 |
| 196118683 | 196129888 | chr3 | − | intronic | N/A | −1.7073 | 0.001718 | UBXN7 |
| 171965322 | 171969331 | chr3 | + | exonic | hsa_circ_0006156 | −1.5436 | 0.001784 | FNDC3B |
| 16386664 | 16415895 | chr21 | − | exonic | hsa_circ_0004771 | −1.7792 | 0.001847 | NRIP1 |
| 59204757 | 59209198 | chr15 | − | sense overlapping | N/A | −1.6006 | 0.001847 | SLTM |
| 121004627 | 121009094 | chr12 | − | exonic | hsa_circ_0028912 | 1.6792 | 0.001853 | RNF10 |
| 23375403 | 23380612 | chr14 | − | exonic | hsa_circ_0031241 | −1.6616 | 0.001914 | RBM23 |
| 103432671 | 103433430 | chr10 | − | exonic | hsa_circ_0019591 | −1.5849 | 0.002007 | FBXW4 |
| 104714065 | 104717880 | chr7 | + | exonic | hsa_circ_0001736 | −1.7675 | 0.002110 | KMT2E |
| 112723882 | 112724819 | chr10 | + | exonic | hsa_circ_0000261 | −1.6331 | 0.002130 | SHOC2 |
| 21295966 | 21307720 | chr1 | − | exonic | hsa_circ_0000025 | 1.5051 | 0.002152 | EIF4G3 |
| 183361267 | 183390272 | chr3 | + | exonic | hsa_circ_0001368 | −1.5765 | 0.002241 | KLHL24 |
| 74666420 | 74670475 | chr16 | − | exonic | hsa_circ_0007548 | 1.5107 | 0.002243 | RFWD3 |
| 76344422 | 76388643 | chr6 | + | exonic | hsa_circ_0001613 | −1.6425 | 0.002336 | SENP6 |
| 13579682 | 13584457 | chr6 | + | exonic | hsa_circ_0007218 | −1.5507 | 0.002374 | SIRT5 |
| 162546566 | 162567648 | chr1 | + | exonic | hsa_circ_0004646 | 1.5406 | 0.002560 | UAP1 |
| 61632920 | 61633008 | chr2 | + | antisense | hsa_circ_0001015 | 1.6227 | 0.002756 | USP34 |
| 197592293 | 197602646 | chr3 | + | exonic | hsa_circ_0008351 | −1.5878 | 0.002848 | LRCH3 |
| 37971709 | 37974243 | chr8 | + | exonic | hsa_circ_0083957 | −1.5497 | 0.002888 | ASH2L |
| 205585605 | 205593019 | chr1 | − | exonic | hsa_circ_0000175 | −1.6656 | 0.003035 | ELK4 |
| 51804072 | 51813781 | chr18 | + | exonic | hsa_circ_0003428 | −1.5491 | 0.003070 | POLI |
| 196118683 | 196129890 | chr3 | − | exonic | hsa_circ_0001380 | −1.6377 | 0.003120 | UBXN7 |
| 30495147 | 30495584 | chr16 | + | exonic | hsa_circ_0000690 | −1.6252 | 0.003144 | ITGAL |
| 57014000 | 57016139 | chr20 | + | exonic | hsa_circ_0001173 | −1.6775 | 0.003163 | VAPB |
| 151960100 | 152012423 | chr7 | − | exonic | hsa_circ_0006784 | −1.6438 | 0.003167 | KMT2C |
| 103427642 | 103433430 | chr10 | − | exonic | hsa_circ_0019589 | −1.6189 | 0.003306 | FBXW4 |
| 31139461 | 31144271 | chr14 | + | exonic | hsa_circ_0009140 | −1.6134 | 0.003403 | SCFD1 |
| 197597030 | 197602646 | chr3 | + | exonic | hsa_circ_0005873 | −1.5149 | 0.003424 | LRCH3 |
| 122495211 | 122495481 | chr12 | − | antisense | hsa_circ_0000453 | 1.6547 | 0.003478 | BCL7A |
| 13632601 | 13644961 | chr6 | − | exonic | hsa_circ_0001577 | −1.5681 | 0.003762 | RANBP9 |
| 28458581 | 28544344 | chr12 | + | exonic | hsa_circ_0008250 | −1.6479 | 0.003821 | CCDC91 |
| 169854206 | 169863309 | chr3 | − | exonic | hsa_circ_0001965 | −1.5974 | 0.003901 | PHC3 |
| 76082583 | 76083174 | chr17 | + | exonic | hsa_circ_0045862 | 1.5371 | 0.003928 | TNRC6C |
| 33741700 | 33747412 | chr1 | + | exonic | N/A | 1.7535 | 0.004037 | ZNF362 |
| 5815804 | 5828013 | chr10 | − | exonic | hsa_circ_0000210 | −1.5221 | 0.004089 | GDI2 |
| 33091993 | 33101669 | chr13 | − | exonic | hsa_circ_0000471 | −1.7130 | 0.004106 | N4BP2L2 |
| 41515056 | 41518061 | chr13 | − | exonic | hsa_circ_0030051 | −1.5119 | 0.004131 | ELF1 |
| 117944807 | 118009049 | chr1 | + | exonic | hsa_circ_0000120 | −1.5664 | 0.004236 | MAN1A2 |
| 150496687 | 150512748 | chr5 | − | exonic | hsa_circ_0074598 | −1.5490 | 0.004404 | ANXA6 |
| 109046047 | 109048186 | chr12 | − | exonic | hsa_circ_0000437 | −1.7666 | 0.004534 | CORO1C |
| 144464665 | 144465125 | chr4 | + | sense overlapping | N/A | −1.6861 | 0.004635 | SMARCA5 |
| 151656409 | 151729550 | chr4 | − | exonic | hsa_circ_0071174 | −1.5250 | 0.004681 | LRBA |
| 50073902 | 50093067 | chr5 | + | exonic | hsa_circ_0072437 | −1.6152 | 0.004851 | PARP8 |
| 17135209 | 17138460 | chr21 | − | exonic | hsa_circ_0001178 | −1.5592 | 0.005276 | USP25 |
| 89628179 | 89628539 | chr16 | + | intronic | hsa_circ_0092337 | 1.5648 | 0.005368 | RPL13 |
| 191765289 | 191789319 | chr2 | + | exonic | hsa_circ_0001085 | −1.6748 | 0.005486 | GLS |
| 30954186 | 30956926 | chr20 | + | exonic | hsa_circ_0001136 | −1.5449 | 0.005489 | ASXL1 |
| 58996272 | 58996401 | chr1 | − | exonic | hsa_circ_0012722 | −1.8912 | 0.005495 | OMA1 |
| 58992932 | 59002413 | chr1 | − | exonic | hsa_circ_0000073 | −1.9835 | 0.005698 | OMA1 |
| 196129822 | 196134264 | chr3 | − | exonic | hsa_cire_0068655 | −1.6312 | 0.005789 | UBXN7 |
| 16415815 | 16415895 | chr21 | − | exonic | hsa_circ_0061276 | −1.6981 | 0.005840 | NRIP1 |
| 151727422 | 151729550 | chr4 | − | exonic | hsa_circ_0071196 | −1.6542 | 0.005891 | LRBA |
| 57808781 | 57816308 | chr17 | + | exonic | hsa_circ_0006508 | −1.5673 | 0.006135 | VMP1 |

TABLE 10-continued (MDD baseline vs Control baseline)

| TxStart | TxEnd | Chrom | Strand | circRNA type | Alias | Fold change | P-value | GeneSymbol |
|---|---|---|---|---|---|---|---|---|
| 86292641 | 86301070 | chr9 | − | exonic | hsa_circ_0003715 | −1.5228 | 0.006135 | UBQLN1 |
| 62299506 | 62306191 | chr15 | − | exonic | hsa_circ_0000607 | −1.7661 | 0.006584 | VPS13C |
| 77631183 | 77632364 | chr9 | − | exonic | hsa_circ_0004189 | −1.5416 | 0.006625 | C9orf41 |
| 111883774 | 111890244 | chr10 | + | exonic | hsa_circ_0003357 | −1.6058 | 0.006760 | ADD3 |
| 223084858 | 223097002 | chr2 | − | exonic | hsa_circ_0007333 | 1.5029 | 0.006891 | PAX3 |
| 16386664 | 16386787 | chr21 | − | exonic | hsa_circ_0061274 | −1.5185 | 0.007149 | NRIP1 |
| 183368083 | 183369064 | chr3 | + | exonic | hsa_circ_0001369 | −1.6858 | 0.007305 | KLHL24 |
| 58971731 | 59004982 | chr1 | − | exonic | hsa_circ_0002316 | −1.9032 | 0.007362 | OMA1 |
| 36245469 | 36246795 | chr19 | − | exonic | hsa_circ_0050648 | 1.5251 | 0.007523 | HSPB6 |
| 140086068 | 140086817 | chr9 | − | exonic | hsa_circ_0089652 | 1.5283 | 0.007763 | TPRN |
| 117910084 | 117957453 | chr1 | + | exonic | hsa_circ_0013729 | −1.6278 | 0.007949 | MAN1A2 |
| 25477659 | 25477979 | chr20 | − | intronic | hsa_circ_0092338 | 1.5077 | 0.007970 | NINL |
| 76910271 | 76928416 | chr10 | + | exonic | hsa_circ_0018905 | 3.2318 | 0.008020 | SAMD8 |
| 75264433 | 75264514 | chr3 | + | sense overlapping | hsa_circ_0006169 | 1.7377 | 0.008179 | HNRNPA3P6 |
| 7826418 | 7841374 | chr7 | + | sense overlapping | hsa_circ_0001676 | −1.6815 | 0.008222 | UMAD1 |
| 123924133 | 123928458 | chr9 | + | exonic | hsa_circ_0088333 | −1.5415 | 0.008290 | CNTRL |
| 45860527 | 45860957 | chr19 | − | exonic | hsa_circ_0051470 | 1.5151 | 0.008387 | ERCC2 |
| 64791491 | 64792365 | chr15 | + | sense overlapping | hsa_circ_0000615 | −1.7506 | 0.008448 | ZNF609 |
| 33095509 | 33111164 | chr13 | − | exonic | hsa_circ_0029937 | −1.7115 | 0.008655 | N4BP2L2 |
| 155457868 | 155473602 | chr7 | + | exonic | hsa_circ_0001771 | −1.5273 | 0.008865 | RBM33 |
| 80412669 | 80415142 | chr15 | − | exonic | hsa_circ_0000643 | −1.5059 | 0.008874 | ZFAND6 |
| 52729602 | 52729875 | chr4 | + | exonic | hsa_circ_0069715 | −1.5194 | 0.008878 | DCUN1D4 |
| 195415403 | 195416309 | chr3 | + | exonic | hsa_circ_0008267 | −1.7764 | 0.008968 | LINC00969 |
| 11958205 | 11984847 | chr17 | + | exonic | hsa_circ_0007508 | −1.5263 | 0.009008 | MAP2K4 |
| 24357988 | 24369956 | chr2 | + | exonic | hsa_circ_0000982 | −1.6753 | 0.009052 | FAM228B |
| 243858892 | 244006584 | chr1 | − | exonic | hsa_circ_0004649 | −1.5988 | 0.009084 | AKT3 |
| 34147027 | 34149837 | chr17 | + | exonic | hsa_circ_0043138 | −1.6329 | 0.009485 | TAF15 |
| 124071293 | 124074996 | chr12 | + | exonic | hsa_circ_0000458 | −1.5815 | 0.009493 | TMED2 |
| 134381500 | 134381840 | chr9 | + | exonic | hsa_circ_0001897 | −1.6056 | 0.009640 | POMT1 |
| 68155889 | 68160513 | chr16 | + | exonic | hsa_circ_0000711 | −1.6774 | 0.009848 | NFATC3 |
| 76910271 | 76910864 | chr10 | + | exonic | hsa_circ_0006148 | 2.1478 | 0.009911 | SAMD8 |
| 24190831 | 24197887 | chrX | + | exonic | hsa_circ_0007108 | −1.5053 | 0.010060 | ZFX |
| 52773404 | 52773806 | chr8 | − | exonic | hsa_circ_0001801 | −1.6011 | 0.010107 | PCMTD1 |
| 77055327 | 77065626 | chr4 | − | exonic | hsa_circ_0070039 | −1.6076 | 0.010478 | NUP54 |
| 86292641 | 86293514 | chr9 | − | exonic | hsa_circ_0001865 | −1.5970 | 0.010501 | UBQLN1 |
| 109048081 | 109095099 | chr12 | − | exonic | hsa_circ_0028072 | −1.5209 | 0.010592 | CORO1C |
| 86293355 | 86301070 | chr9 | − | exonic | hsa_circ_0087357 | −1.6302 | 0.010932 | UBQLN1 |
| 153591507 | 153591640 | chr2 | + | exonic | hsa_circ_0056754 | 1.5085 | 0.010936 | ARL6IP6 |
| 21668877 | 21743273 | chr6 | + | exonic | N/A | 1.5480 | 0.011030 | LINC00340 |
| 24357988 | 24362320 | chr2 | + | exonic | hsa_circ_0007270 | −1.5960 | 0.011200 | FAM228B |
| 37633006 | 37640126 | chr4 | − | exonic | hsa_circ_0001400 | −1.5496 | 0.011484 | RELL1 |
| 191765289 | 191775047 | chr2 | + | exonic | hsa_circ_0057521 | −1.6111 | 0.011720 | GLS |
| 28408513 | 28460682 | chr12 | + | exonic | N/A | −1.6773 | 0.011777 | CCDC91 |
| 37126308 | 37126939 | chr9 | + | exonic | hsa_circ_0001860 | .1.6263 | 0.011819 | ZCCHC7 |
| 149613259 | 149639014 | chr3 | + | exonic | hsa_circ_0006801 | −1.6487 | 0.011862 | RNF13 |
| 227729319 | 227729842 | chr2 | + | exonic | hsa_circ_0001104 | −1.6119 | 0.012110 | RHBDD1 |
| 49609654 | 49613024 | chr10 | + | exonic | hsa_circ_0018315 | −1.5416 | 0.012113 | MAPK8 |
| 41191341 | 41196173 | chr15 | + | exonic | hsa_circ_0034642 | 1.5609 | 0.012128 | VPS18 |
| 1125950 | 1132297 | chr10 | + | exonic | hsa_circ_0017446 | −1.5005 | 0.012219 | WDR37 |
| 132609079 | 132609271 | chr12 | − | antisense | hsa_circ_0000463 | 1.6392 | 0.012317 | EP400NL |
| 88116475 | 88116842 | chr4 | − | exonic | hsa_circ_0002538 | −1.5972 | 0.012434 | KLHL8 |
| 88200377 | 88248289 | chr9 | − | exonic | hsa_circ_0087386 | −1.5369 | 0.012702 | AGTPBP1 |
| 36681395 | 36681695 | chr22 | − | intronic | hsa_circ_0092283 | 1.7541 | 0.012745 | MYH9 |
| 13639794 | 13644961 | chr6 | − | exonic | hsa_circ_0001578 | −1.7350 | 0.012978 | RANBP9 |
| 62303908 | 62305446 | chr20 | + | exonic | hsa_circ_0061170 | 1.5096 | 0.013009 | RTEL1 |
| 65473657 | 65492309 | chr2 | + | exonic | hsa_circ_0008529 | −1.9516 | 0.013128 | ACTR2 |
| 117944807 | 117948267 | chr1 | + | exonic | hsa_circ_0000116 | −1.5077 | 0.013242 | MAN1A2 |
| 36230203 | 36231267 | chr4 | − | exonic | hsa_circ_0069399 | −1.6597 | 0.013280 | ARAP2 |
| 9195548 | 9221997 | chr18 | + | exonic | hsa_circ_0046843 | −1.5540 | 0.013288 | ANKRD12 |
| 141710989 | 141716304 | chr8 | − | exonic | hsa_circ_0005273 | −1.5593 | 0.013316 | PTK2 |
| 117957334 | 117963271 | chr1 | + | exonic | hsa_circ_0013737 | −1.6259 | 0.013554 | MAN1A2 |
| 231226328 | 231307814 | chr2 | + | sense overlapping | hsa_circ_0001108 | −1.5033 | 0.013775 | SP100 |
| 58999624 | 59000003 | chr1 | − | exonic | N/A | −1.7938 | 0.014087 | OMA1 |
| 34151081 | 34165557 | chr17 | + | exonic | hsa_circ_0000758 | −1.6301 | 0.014441 | TAF15 |
| 58971731 | 59002413 | chr1 | − | exonic | hsa_circ_0000072 | −1.8395 | 0.014681 | OMA1 |
| 155465560 | 155473602 | chr7 | + | exonic | hsa_circ_0001772 | −1.6315 | 0.014733 | RBM33 |
| 38792600 | 38868560 | chr21 | + | exonic | hsa_circ_0061694 | −1.9027 | 0.014842 | DYRK1A |
| 122881110 | 122893258 | chr5 | + | exonic | hsa_circ_0001522 | −1.6015 | 0.014993 | CSNK1G3 |
| 58755107 | 58755971 | chr20 | − | intronic | hsa_circ_0001174 | −1.6509 | 0.015149 | RP5-1043L13.1 |
| 57814813 | 57816308 | chr17 | + | exonic | hsa_circ_0044875 | −1.6159 | 0.015479 | VMP1 |
| 86292641 | 86297981 | chr9 | − | exonic | hsa_circ_0006466 | −1.5677 | 0.015619 | UBQLN1 |

TABLE 10-continued (MDD baseline vs Control baseline)

| TxStart | TxEnd | Chrom | Strand | circRNA type | Alias | Fold change | P-value | GeneSymbol |
|---|---|---|---|---|---|---|---|---|
| 41961025 | 41962156 | chr15 | + | exonic | hsa_circ_0000591 | −1.7867 | 0.015894 | MGA |
| 1712336 | 1714425 | chrX | + | exonic | hsa_circ_0007352 | 2.3769 | 0.016035 | AKAP17A |
| 137015277 | 137041727 | chr6 | − | exonic | hsa_circ_0007798 | −1.5039 | 0.016362 | MAP3K5 |
| 86297865 | 86301070 | chr9 | − | exonic | hsa_circ_0005142 | −1.5442 | 0.017590 | UBQLN1 |
| 65473318 | 65492309 | chr2 | + | sense overlapping | hsa_circ_0001022 | −1.8832 | 0.017655 | ACTR2 |
| 53068519 | 53069224 | chr12 | − | exonic | hsa_circ_0026462 | 1.5932 | 0.017705 | KRT1 |
| 86293355 | 86297981 | chr9 | − | exonic | hsa_circ_0001866 | −1.5660 | 0.018454 | UBQLN1 |
| 117676687 | 117680079 | chrX | + | exonic | N/A | −1.5136 | 0.019918 | DOCK11 |
| 86294689 | 86297981 | chr9 | − | exonic | hsa_circ_0001867 | −1.5461 | 0.020072 | UBQLN1 |
| 44046021 | 44048964 | chr15 | + | exonic | hsa_circ_0002151 | −1.5256 | 0.020098 | PDIA3 |
| 34144719 | 34149837 | chr17 | − | exonic | N/A | −1.5324 | 0.020422 | TAF15 |
| 49742748 | 49752790 | chr13 | + | exonic | hsa_circ_0006978 | −1.5156 | 0.020568 | FNDC3A |
| 22999874 | 23030758 | chr7 | − | exonic | hsa_circ_0008951 | −1.6035 | 0.020586 | FAM126A |
| 15863654 | 15889942 | chr10 | − | exonic | hsa_circ_0000220 | −1.6783 | 0.020726 | FAM188A |
| 85718584 | 85742653 | chr11 | − | exonic | hsa_circ_0023936 | −1.6351 | 0.020757 | PICALM |
| 58971731 | 58971881 | chr1 | − | exonic | hsa_circ_0012717 | −1.8194 | 0.020927 | OMA1 |
| 85722072 | 85742653 | chr11 | − | exonic | hsa_circ_0000347 | −1.6175 | 0.021189 | PICALM |
| 219467402 | 219468493 | chr1 | + | sense overlapping | N/A | 1.9661 | 0.021292 | XLOC_000566 |
| 68155889 | 68225678 | chr16 | − | exonic | hsa_circ_0039929 | −1.5678 | 0.021514 | NFATC3 |
| 85733409 | 85742653 | chr11 | − | exonic | hsa_circ_0023942 | −1.6052 | 0.022072 | PICALM |
| 88920106 | 88924932 | chr9 | − | exonic | hsa_circ_0001869 | −1.5116 | 0.022137 | ZCCHC6 |
| 23650789 | 23651172 | chr7 | + | exonic | hsa_circ_0001684 | −1.6386 | 0.022337 | CCDC126 |
| 88190229 | 88211364 | chr9 | − | exonic | hsa_circ_0005202 | −1.5283 | 0.022634 | AGTPBP1 |
| 151719232 | 151738409 | chr4 | − | exonic | hsa_circ_0008618 | −1.5606 | 0.022650 | LRBA |
| 56277780 | 56284152 | chr4 | + | exonic | hsa_circ_0001414 | −1.5491 | 0.022953 | TMEM165 |
| 72850146 | 72857113 | chr5 | − | exonic | N/A | 1.5617 | 0.023205 | ANKRA2 |
| 20811404 | 20811554 | chr14 | − | sense overlapping | hsa_circ_0000518 | −1.5112 | 0.023626 | RPPH1 |
| 45715378 | 45780869 | chr2 | − | exonic | N/A | −1.7093 | 0.024533 | SRBD1 |
| 189850390 | 189859058 | chr2 | + | exonic | hsa_circ_0057360 | 1.5029 | 0.024692 | COL3A1 |
| 5691329 | 5691678 | chr19 | + | exonic | hsa_circ_0048766 | 1.5155 | 0.025229 | RPL36 |
| 231307651 | 231314970 | chr2 | + | exonic | hsa_circ_0003922 | −1.6348 | 0.025257 | SP100 |
| 49694940 | 49707217 | chr5 | − | sense overlapping | hsa_circ_0001481 | −1.7633 | 0.025613 | EMB |
| 23023562 | 23030758 | chr7 | − | exonic | hsa_circ_0001682 | −1.5073 | 0.025614 | FAM126A |
| 65466985 | 65482828 | chr2 | + | exonic | N/A | −1.8183 | 0.025923 | ACTR2 |
| 65284462 | 65290692 | chr5 | + | exonic | hsa_circ_0001492 | −1.5178 | 0.026119 | ERBB2IP |
| 16611602 | 16612362 | chr19 | + | exonic | N/A | 1.7358 | 0.026765 | C19orf44 |
| 131060182 | 131084192 | chr7 | + | exonic | hsa_circ_0001746 | −1.5414 | 0.026968 | MKLN1 |
| 15875628 | 15889942 | chr10 | − | exonic | hsa_circ_0006665 | −1.6238 | 0.027054 | FAM188A |
| 1499235 | 1499964 | chr12 | + | intronic | N/A | 1.6699 | 0.027830 | ERC1 |
| 57197912 | 57207781 | chr16 | − | exonic | hsa_circ_0006886 | −1.6077 | 0.028126 | FAM192A |
| 85737333 | 85742653 | chr11 | − | exonic | hsa_circ_0002433 | −1.5509 | 0.030839 | PICALM |
| 118635916 | 118657227 | chr11 | − | exonic | hsa_circ_0024501 | −1.5079 | 0.031452 | DDX6 |
| 7839009 | 7844817 | chr10 | + | exonic | hsa_circ_0007292 | −1.8482 | 0.031475 | ATP5C1 |
| 85742510 | 85742653 | chr11 | − | exonic | hsa_circ_0023944 | −1.5591 | 0.031536 | PICALM |
| 63988322 | 64008672 | chr15 | − | exonic | hsa_circ_0035796 | −1.5056 | 0.031870 | HERC1 |
| 40655612 | 40657444 | chr2 | − | exonic | hsa_circ_0000994 | −1.6486 | 0.032094 | SLCBA1 |
| 118625413 | 118627996 | chr11 | − | exonic | hsa_circ_0024490 | −1.5471 | 0.032208 | DDX6 |
| 149563797 | 149570383 | chr3 | + | exonic | hsa_circ_0006697 | −1.6320 | 0.032286 | RNF13 |
| 231314886 | 231328865 | chr2 | + | exonic | hsa_circ_0058619 | −1.7735 | 0.033120 | SP100 |
| 5690345 | 5691678 | chr19 | + | exonic | hsa_circ_0048764 | 1.8351 | 0.033371 | RPL36 |
| 38949785 | 38951231 | chr19 | + | exonic | hsa_circ_0050834 | 1.6713 | 0.034502 | RYR1 |
| 40655612 | 40657441 | chr2 | − | exonic | hsa_circ_0005232 | −1.6174 | 0.036285 | SLC8A1 |
| 119155637 | 119155825 | chr3 | − | exonic | hsa_circ_0066859 | 1.7156 | 0.036564 | TMEM394 |
| 134011326 | 134022971 | chr9 | + | exonic | hsa_circ_0089153 | 1.7119 | 0.036651 | NUP214 |
| 153413350 | 153414506 | chr5 | − | exonic | hsa_circ_0007691 | −1.5622 | 0.039327 | FAM114A2 |
| 66597490 | 66605377 | chr12 | + | exonic | hsa_circ_0000414 | −1.5800 | 0.039423 | IRAK3 |
| 158552176 | 158557544 | chr7 | − | exonic | hsa_circ_0001776 | −1.5163 | 0.041866 | ESYT2 |
| 94562928 | 94580249 | chr12 | + | exonic | N/A | −1.6377 | 0.043770 | PLXNC1 |
| 99924615 | 99925522 | chr14 | − | exonic | hsa_circ_0033149 | −1.5309 | 0.044765 | SETD3 |
| 7844232 | 7844817 | chr10 | + | exonic | hsa_circ_0017675 | −1.6420 | 0.045053 | ATP5C1 |
| 45773870 | 45780869 | chr2 | − | exonic | hsa_circ_0005542 | −1.6117 | 0.045599 | SRBD1 |
| 149563797 | 149629870 | chr3 | + | exonic | hsa_circ_0003502 | −1.5257 | 0.046423 | RNF13 |
| 46633461 | 46633676 | chr12 | − | exonic | N/A | −1.5083 | 0.048956 | SLC38A1 |

TABLE 11

| (MDD 8 week vs Control 8 week) | | | | | | | | |
|---|---|---|---|---|---|---|---|---|
| TxStart | TxEnd | Chrom | Strand | circRNA type | Alias | Fold change | P-value | GeneSymbol |
| 33290913 | 33318767 | chr1 | + | exonic | hsa_circ_0011451 | 1.5812 | 0.000772 | S100PBP |
| 187498055 | 187506315 | chr2 | + | exonic | hsa_circ_0057319 | −1.5317 | 0.001856 | ITGAV |
| 76910271 | 76928416 | chr10 | + | exonic | hsa_circ_0018905 | 8.9513 | 0.002519 | SAMD8 |
| 16415815 | 16415895 | chr21 | − | exonic | hsa_circ_0061276 | −1.5780 | 0.002951 | NRIP1 |
| 1712336 | 1714425 | chrX | + | exonic | hsa_circ_0007352 | 6.0828 | 0.003293 | AKAP17A |
| 6998051 | 7006651 | chr4 | + | exonic | hsa_circ_0003201 | 1.8277 | 0.003688 | TBC1D14 |
| 54675169 | 54680872 | chr12 | + | exonic | hsa_circ_0026700 | 1.6060 | 0.007410 | HNRNPA1 |
| 76166897 | 76167135 | chr17 | + | exonic | hsa_circ_0045871 | −1.5935 | 0.007442 | SYNGR2 |
| 37159809 | 37161502 | chr20 | + | exonic | hsa_circ_0060342 | 1.6468 | 0.009009 | RALGAPB |
| 16611602 | 16612362 | chr19 | + | exonic | N/A | 3.3940 | 0.009844 | C19orf44 |
| 76910271 | 76910864 | chr10 | + | exonic | hsa_circ_0006148 | 3.7615 | 0.010885 | SAMD8 |
| 16655365 | 16664706 | chr7 | − | sense overlapping | N/A | 1.6882 | 0.012939 | ANKMY2 |
| 101654702 | 101656154 | chr10 | − | exonic | hsa_circ_0092382 | −1.6100 | 0.014111 | DNMBP |
| 64084777 | 64100213 | chr5 | + | exonic | hsa_circ_0072654 | 2.7483 | 0.015568 | CWC27 |
| 43628823 | 43652158 | chr15 | + | sense overlapping | N/A | 1.6259 | 0.016941 | ADAL |
| 109046047 | 109096774 | chr12 | − | exonic | hsa_circ_0028067 | −1.5847 | 0.022584 | CORO1C |
| 75040222 | 75041120 | chr4 | + | exonic | hsa_circ_0069977 | 2.1851 | 0.022589 | MTHFD2L |
| 151116991 | 151122005 | chr6 | + | exonic | hsa_circ_0078264 | 2.4817 | 0.024390 | PLEKHG1 |
| 232099936 | 232100094 | chr2 | + | exonic | hsa_circ_0058651 | 2.0184 | 0.027295 | ARMC9 |
| 13519798 | 13520085 | chr19 | − | intronic | N/A | 1.9908 | 0.028778 | CAONA1A |
| 33012788 | 33018263 | chr13 | − | exonic | hsa_circ_0029934 | 2.0833 | 0.033220 | N4BP2L2 |
| 39648294 | 39648666 | chr14 | + | exonic | hsa_circ_0101802 | −1.5473 | 0.038273 | PNN |
| 38019339 | 38019640 | chr22 | + | sense overlapping | N/A | 2.0641 | 0.038958 | GGA1 |

TABLE 12

| (BD baseline vs Control baseline) | | | | | | | | |
|---|---|---|---|---|---|---|---|---|
| TxStart | TxEnd | Chrom | Strand | circRNA type | Alias | Fold change | P−value | GeneSymbol |
| 70856839 | 70864567 | chr10 | + | exonic | hsa_circ_0018594 | −1.5166 | 5.2141E−06 | SRGN |
| 102185289 | 102187102 | chr15 | − | exonic | hsa_circ_0003813 | 1.5074 | 1.2818E−05 | TM2D3 |
| 228356262 | 228389631 | chr2 | + | exonic | hsa_circ_0058514 | −1.8810 | 2.1302E−05 | AGFG1 |
| 112321531 | 112339774 | chr5 | + | exonic | hsa_circ_0001520 | −2.3418 | 2.4776E−05 | DCP2 |
| 228384663 | 228389631 | chr2 | + | exonic | hsa_circ_0058520 | −1.7328 | 3.2761E−05 | AGFG1 |
| 142170730 | 142173528 | chr8 | + | exonic | N/A | −1.7089 | 3.6165E−05 | DENND3 |
| 176050287 | 176055026 | chr1 | − | exonic | hsa_circ_0015364 | −1.5571 | 3.9521E−05 | RFWD2 |
| 116668337 | 116675510 | chr12 | − | sense overlapping | hsa_circ_0000443 | −2.1744 | 5.0083E−05 | MED13L |
| 112321531 | 112337371 | chr5 | + | exonic | hsa_circ_0073608 | −2.3577 | 5.6277E−05 | DCP2 |
| 101910475 | 101911643 | chr2 | − | exonic | hsa_circ_0001058 | −2.0181 | 5.8946E−05 | RNF149 |
| 41651792 | 41660071 | chr1 | − | sense overlapping | hsa_circ_0005303 | 1.6055 | 0.000073 | SCMH1 |
| 95606995 | 95608085 | chr14 | − | exonic | hsa_circ_0000564 | −1.6752 | 0.000078 | DICER1 |
| 28362054 | 28374937 | chr1 | − | exonic | hsa_circ_0008057 | −1.5248 | 0.000081 | EYA3 |
| 176563659 | 176564731 | chr1 | + | exonic | hsa_circ_0015382 | 1.5697 | 0.000091 | PAPPA2 |
| 45741524 | 45742524 | chr17 | + | exonic | hsa_circ_0044301 | −1.5049 | 0.000094 | KPNB1 |
| 57842331 | 57851305 | chr17 | + | intronic | N/A | −1.9460 | 0.000104 | VMP1 |
| 84267098 | 84300811 | chr9 | − | exonic | hsa_circ_0087331 | 1.5409 | 0.000117 | TLE1 |
| 30387492 | 30394846 | chr22 | + | exonic | hsa_circ_0001219 | −1.8440 | 0.000120 | MTMR3 |
| 116668237 | 116675510 | chr12 | − | sense overlapping | hsa_circ_0000442 | −1.9621 | 0.000138 | MED13L |
| 166141085 | 166184511 | chr4 | + | exonic | hsa_circ_0071375 | −2.0802 | 0.000140 | KLHL2 |
| 48597719 | 48597913 | chr4 | − | intronic | N/A | 1.5382 | 0.000142 | FRYL |
| 211192124 | 211192598 | chr1 | − | exonic | hsa_circ_0016348 | 1.5045 | 0.000155 | KCNH1 |
| 85711685 | 85742653 | chr11 | − | exonic | hsa_circ_0023928 | −1.9863 | 0.000159 | PICALM |
| 28811231 | 28819771 | chr17 | + | exonic | hsa_circ_0007460 | −1.5163 | 0.000160 | GOSR1 |
| 228384663 | 228401709 | chr2 | + | exonic | hsa_circ_0058521 | −1.5297 | 0.000166 | AGFG1 |
| 17135209 | 17172162 | chr21 | + | exonic | N/A | −1.5364 | 0.000193 | USP25 |
| 65078566 | 65088674 | chr12 | + | sense overlapping | hsa_circ_0008087 | −1.5009 | 0.000193 | RASSF3 |
| 57842331 | 57889147 | chr17 | + | exonic | hsa_circ_0044879 | −1.6611 | 0.000196 | VMP1 |
| 155095122 | 155116273 | chr6 | + | exonic | hsa_circ_0001654 | −1.5372 | 0.000201 | SCAF8 |
| 103635594 | 103647840 | chr4 | − | exonic | hsa_circ_0001432 | −1.8761 | 0.000202 | MANBA |
| 114372213 | 114377061 | chr1 | − | exonic | hsa_circ_0000110 | −1.6185 | 0.000203 | PTPN22 |
| 37614541 | 37625720 | chr13 | − | exonic | hsa_circ_0000475 | −1.8117 | 0.000204 | SUPT20H |
| 147743428 | 147744289 | chrX | + | exonic | hsa_circ_0001947 | −2.9440 | 0.000212 | AFF2 |
| 50045984 | 50059076 | chr5 | + | exonic | hsa_circ_0005809 | −1.6002 | 0.000214 | PARP8 |

TABLE 12-continued (BD baseline vs Control baseline)

| TxStart | TxEnd | Chrom | Strand | circRNA type | Alias | Fold change | P-value | GeneSymbol |
|---|---|---|---|---|---|---|---|---|
| 88116475 | 88116842 | chr4 | − | exonic | hsa_circ_0002538 | −2.2442 | 0.000223 | KLHL8 |
| 8043537 | 8099878 | chr7 | + | exonic | hsa_circ_0001678 | −1.6141 | 0.000225 | GLCCI1 |
| 85707868 | 85742653 | chr11 | − | exonic | hsa_circ_0023923 | −2.5808 | 0.000227 | PICALM |
| 88307603 | 88327481 | chr9 | − | exonic | hsa_circ_0007351 | −2.0860 | 0.000228 | AGTPBP1 |
| 34793786 | 34805178 | chr21 | + | exonic | hsa_circ_0002113 | −1.6891 | 0.000228 | IFNGR2 |
| 45740454 | 45745776 | chr17 | + | exonic | hsa_circ_0002854 | −1.5570 | 0.000236 | KPNB1 |
| 68590619 | 68609870 | chr5 | − | exonic | hsa_circ_0001496 | −1.5782 | 0.000238 | CCDC125 |
| 68590619 | 68607031 | chr5 | − | exonic | hsa_circ_0072780 | −1.5090 | 0.000241 | CCDC125 |
| 63884074 | 63938159 | chr3 | + | exonic | hsa_circ_0002634 | −1.5013 | 0.000242 | ATXN7 |
| 113196219 | 113202401 | chr1 | + | exonic | hsa_circ_0000109 | −1.5830 | 0.000251 | CAPZA1 |
| 34804483 | 34805178 | chr21 | + | exonic | hsa_circ_0001185 | −1.9291 | 0.000255 | IFNGR2 |
| 85707868 | 85712201 | chr11 | − | exonic | hsa_circ_0002513 | −2.5733 | 0.000256 | PICALM |
| 22399613 | 22404422 | chr4 | − | intronic | hsa_circ_0126020 | 1.5013 | 0.000257 | GPR125 |
| 46321391 | 46321685 | chr12 | + | antisense | hsa_circ_0000393 | 1.5162 | 0.000259 | SCAF11 |
| 9583114 | 9595100 | chr18 | − | exonic | hsa_circ_0009022 | −1.5623 | 0.000260 | PPP4R1 |
| 147733519 | 147744289 | chrX | + | exonic | hsa_circ_0091669 | −2.3673 | 0.000261 | AFF2 |
| 137015277 | 137018525 | chr6 | − | exonic | hsa_circ_0006554 | −1.7175 | 0.000272 | MAP3K5 |
| 45741524 | 45752148 | chr17 | + | exonic | hsa_circ_0000780 | −1.6101 | 0.000278 | KPNB1 |
| 94224583 | 94248681 | chr5 | − | exonic | hsa_circ_0001512 | −1.8977 | 0.000278 | MCTP1 |
| 57808781 | 57816308 | chr17 | + | exonic | hsa_circ_0006508 | −1.8114 | 0.000284 | VMP1 |
| 95099211 | 95119667 | chr5 | + | exonic | hsa_circ_0006725 | −1.7574 | 0.000286 | RHOBTB3 |
| 57842331 | 57851246 | chr17 | + | exonic | hsa_circ_0004027 | −1.8297 | 0.000288 | VMP1 |
| 13579682 | 13584457 | chr6 | + | exonic | hsa_circ_0007218 | −1.8698 | 0.000292 | SIRT5 |
| 68434283 | 68457142 | chr15 | + | exonic | hsa_circ_0036044 | −1.5709 | 0.000293 | PIAS1 |
| 32678875 | 32824967 | chr2 | + | exonic | hsa_circ_0053651 | −1.5073 | 0.000298 | BIRC6 |
| 23650789 | 23651172 | chr7 | + | exonic | hsa_circ_0001684 | −2.1641 | 0.000301 | CCDC126 |
| 5808203 | 5815904 | chr10 | − | exonic | N/A | −1.5240 | 0.000304 | GDI2 |
| 14825489 | 14840755 | chr11 | + | exonic | N/A | −1.5030 | 0.000306 | PDE3B |
| 208589523 | 208607066 | chr2 | + | exonic | hsa_circ_0002556 | −1.6290 | 0.000314 | CCNYL1 |
| 172013152 | 172028671 | chr3 | + | exonic | hsa_circ_0067997 | −1.7342 | 0.000318 | FNDC3B |
| 30374430 | 30384551 | chr22 | + | exonic | N/A | −1.6843 | 0.000335 | MTMR3 |
| 201721404 | 201722812 | chr2 | − | exonic | hsa_circ_0057725 | −1.5054 | 0.000355 | CLK1 |
| 85685750 | 85742653 | chr11 | − | exonic | hsa_circ_0023891 | −2.1165 | 0.000362 | PICALM |
| 85685750 | 85714494 | chr11 | − | exonic | hsa_circ_0002998 | −2.0172 | 0.000367 | PICALM |
| 30509775 | 30510291 | chr17 | + | exonic | N/A | −1.5167 | 0.000374 | RHOT1 |
| 88190229 | 88211364 | chr9 | − | exonic | hsa_circ_0005202 | −2.0221 | 0.000378 | AGTPBP1 |
| 85692787 | 85707972 | chr11 | − | exonic | hsa_circ_0002264 | −2.0083 | 0.000378 | PICALM |
| 50616725 | 50616948 | chr14 | − | exonic | hsa_circ_0007695 | −1.6773 | 0.000384 | SOS2 |
| 112498073 | 112499192 | chr12 | − | exonic | N/A | 1.5919 | 0.000386 | NAA25 |
| 50571209 | 50618904 | chr13 | − | exonic | hsa_circ_0006475 | −1.5038 | 0.000393 | DLEU2 |
| 30267304 | 30300250 | chr17 | + | exonic | hsa_circ_0005804 | −1.6205 | 0.000400 | SUZ12 |
| 6646085 | 6647162 | chr12 | + | exonic | hsa_circ_0025196 | 1.5348 | 0.000402 | GAPDH |
| 94899365 | 94945248 | chr15 | + | exonic | hsa_circ_0000660 | −1.8842 | 0.000403 | MCTP2 |
| 30267304 | 30267505 | chr17 | + | exonic | hsa_circ_0042961 | −1.6745 | 0.000413 | SUZ12 |
| 114676884 | 114678116 | chr9 | + | exonic | hsa_circ_0006435 | −1.8348 | 0.000415 | UGCG |
| 9583114 | 9595151 | chr18 | − | exonic | hsa_circ_0007509 | −1.8549 | 0.000418 | PPP4R1 |
| 30498061 | 30503232 | chr17 | + | exonic | hsa_circ_0008604 | −2.2003 | 0.000438 | RHOT1 |
| 30693541 | 30702014 | chr21 | + | exonic | hsa_circ_0001181 | −1.5207 | 0.000444 | BACH1 |
| 171969049 | 172025291 | chr3 | + | exonic | hsa_circ_0067991 | −1.5644 | 0.000449 | FNDC3B |
| 32751430 | 32754357 | chr12 | + | exonic | N/A | −1.9995 | 0.000450 | FGD4 |
| 85742510 | 85742653 | chr11 | − | exonic | hsa_circ_0023944 | −2.3232 | 0.000453 | PICALM |
| 30267304 | 30274704 | chr17 | + | exonic | hsa_circ_0042962 | −1.6014 | 0.000457 | SUZ12 |
| 85701292 | 85742653 | chr11 | − | exonic | hsa_circ_0023918 | −1.7923 | 0.000460 | PICALM |
| 85733409 | 85742653 | chr11 | − | exonic | hsa_circ_0023942 | −2.3159 | 0.000468 | PICALM |
| 231090078 | 231097049 | chr1 | − | exonic | hsa_circ_0000195 | −1.5371 | 0.000471 | TTC13 |
| 197621364 | 197627499 | chr1 | − | exonic | hsa_circ_0015796 | −1.5223 | 0.000472 | DENND1B |
| 116675272 | 116675510 | chr12 | − | exonic | hsa_circ_0028587 | −1.8971 | 0.000473 | MED13L |
| 85707868 | 85714494 | chr11 | − | exonic | hsa_circ_0023919 | −2.2783 | 0.000473 | PICALM |
| 31644075 | 31676727 | chr10 | + | intronic | hsa_circ_0002765 | −1.7961 | 0.000475 | ZEB1 |
| 30384468 | 30387659 | chr22 | + | exonic | hsa_circ_0062813 | −1.5856 | 0.000481 | MTMR3 |
| 118453893 | 118455359 | chr11 | + | exonic | hsa_circ_0007383 | −1.6198 | 0.000489 | ARCN1 |
| 63824845 | 63852169 | chr15 | + | exonic | hsa_circ_0035649 | −1.7275 | 0.000490 | USP3 |
| 47388673 | 47390207 | chr17 | − | exonic | hsa_circ_0000782 | −1.5885 | 0.000490 | ZNF652 |
| 85692171 | 85707972 | chr11 | − | exonic | hsa_circ_0002884 | −2.1302 | 0.000498 | PICALM |
| 170667931 | 170669824 | chr5 | + | exonic | hsa_circ_0004738 | 1.5675 | 0.000504 | RANBP17 |
| 45734225 | 45736026 | chr17 | + | exonic | hsa_circ_0044287 | −1.5150 | 0.000508 | KPNB1 |
| 105767934 | 105778666 | chr10 | + | exonic | hsa_circ_0000259 | −1.7892 | 0.000512 | SLK |
| 118451960 | 118455359 | chr11 | + | exonic | hsa_circ_0006374 | −1.6659 | 0.000524 | ARCN1 |
| 30500849 | 30503232 | chr17 | + | exonic | hsa_circ_0005397 | −1.7542 | 0.000537 | RHOT1 |
| 85718584 | 85742653 | chr11 | + | exonic | hsa_circ_0023936 | −2.3381 | 0.000543 | PICALM |
| 76342171 | 76344097 | chr5 | + | exonic | hsa_circ_0008620 | −1.7109 | 0.000553 | AGGF1 |
| 46780439 | 46835308 | chr22 | − | exonic | hsa_circ_0063811 | 1.5002 | 0.000564 | CELSR1 |
| 66597490 | 66622150 | chr12 | + | exonic | hsa_circ_0005505 | −2.0836 | 0.000570 | IRAK3 |
| 112399680 | 112421007 | chr5 | − | exonic | hsa_circ_0009054 | 1.5183 | 0.000584 | MCC |
| 13435076 | 13466728 | chr11 | − | exonic | hsa_circ_0003234 | −1.7208 | 0.000586 | BTBD10 |

TABLE 12-continued (BD baseline vs Control baseline)

| TxStart | TxEnd | Chrom | Strand | circRNA type | Alias | Fold change | P-value | GeneSymbol |
|---|---|---|---|---|---|---|---|---|
| 113196219 | 113209767 | chr1 | + | exonic | hsa_circ_0005664 | −1.5597 | 0.000592 | CAPZA1 |
| 85722072 | 85742653 | chr11 | − | exonic | hsa_circ_0000347 | −2.2798 | 0.000594 | PICALM |
| 71071739 | 71075089 | chr8 | − | exonic | hsa_circ_0001810 | −1.5186 | 0.000595 | NCOA2 |
| 52941283 | 52945896 | chr6 | + | exonic | hsa_circ_0076780 | −1.5661 | 0.000596 | FBXO9 |
| 176085759 | 176105683 | chr1 | − | exonic | hsa_circ_0015373 | −1.5168 | 0.000598 | RFWD2 |
| 166141085 | 166160051 | chr4 | + | exonic | hsa_circ_0071374 | 2.0015 | 0.000622 | KLHL2 |
| 28011580 | 28030080 | chr17 | − | exonic | hsa_circ_0000754 | −1.7412 | 0.000623 | SSH2 |
| 32760890 | 32764217 | chr12 | + | exonic | hsa_circ_0000390 | −2.2464 | 0.000626 | FGD4 |
| 62193423 | 62194373 | chr14 | + | exonic | hsa_circ_0032136 | −1.7608 | 0.000632 | HIF1A |
| 94204037 | 94248681 | chr5 | − | exonic | hsa_circ_0005540 | −1.9679 | 0.000652 | MCTP1 |
| 142393644 | 142437312 | chr5 | + | exonic | N/A | −1.6854 | 0.000671 | ARHGAP26 |
| 85692787 | 85737409 | chr11 | − | exonic | hsa_circ_0023908 | −2.3170 | 0.000673 | PICALM |
| 119144577 | 119156276 | chr11 | + | exonic | hsa_circ_0000363 | −1.5457 | 0.000673 | CBL |
| 40872407 | 40882768 | chr1 | + | exonic | hsa_circ_0011898 | −1.5648 | 0.000680 | SMAP2 |
| 66597490 | 66605377 | chr12 | + | exonic | hsa_circ_0000414 | −2.2440 | 0.000687 | IRAK3 |
| 88091230 | 88116842 | chr4 | − | exonic | hsa_circ_0070389 | −1.6189 | 0.000690 | KLHL8 |
| 68434283 | 68439038 | chr15 | + | exonic | hsa_circ_0008378 | −1.6279 | 0.000695 | PIAS1 |
| 73951646 | 73952028 | chr17 | − | exonic | hsa_circ_0008557 | −1.6932 | 0.000705 | ACOX1 |
| 72157634 | 72168547 | chr5 | + | exonic | hsa_circ_0072917 | −1.5603 | 0.000705 | TNPO1 |
| 30495147 | 30495584 | chr16 | + | exonic | hsa_circ_0000690 | −1.8659 | 0.000719 | ITGAL |
| 27867712 | 27877119 | chr12 | + | exonic | hsa_circ_0000384 | −1.6608 | 0.000723 | MRPS35 |
| 94841429 | 94858866 | chr15 | + | exonic | N/A | −1.6964 | 0.000739 | MCTP2 |
| 52935854 | 52941341 | chr6 | + | exonic | hsa_circ_0003700 | −1.9539 | 0.000752 | FBXO9 |
| 9083315 | 9098771 | chr2 | − | exonic | hsa_circ_0007334 | −1.7564 | 0.000763 | MBOAT2 |
| 37619814 | 37620866 | chr21 | + | exonic | hsa_circ_0001187 | −1.8254 | 0.000777 | DOPEY2 |
| 59963381 | 59964938 | chr15 | − | exonic | hsa_circ_0035537 | −1.5489 | 0.000777 | BNIP2 |
| 1125950 | 1126416 | chr10 | + | exonic | hsa_circ_0004277 | −1.5450 | 0.000778 | WDR37 |
| 112116954 | 112121111 | chr12 | − | exonic | hsa_circ_0006396 | −1.5534 | 0.000781 | BRAP |
| 62188226 | 62188541 | chr14 | + | exonic | hsa_circ_0007976 | −1.5609 | 0.000785 | HIF1A |
| 71590282 | 71597135 | chr2 | + | exonic | hsa_circ_0001028 | −1.9959 | 0.000785 | ZNF638 |
| 6925099 | 6925838 | chr4 | + | exonic | hsa_circ_0001394 | −1.5006 | 0.000790 | TBC1D14 |
| 202010100 | 202014558 | chr2 | + | exonic | hsa_circ_0001092 | −1.8669 | 0.000794 | CFLAR |
| 32381495 | 32385259 | chr1 | − | exonic | hsa_circ_0007364 | −1.8232 | 0.000796 | PTP4A2 |
| 77214859 | 77230123 | chr7 | + | exonic | hsa_circ_0003764 | −1.6156 | 0.000802 | PTPN12 |
| 54245398 | 54251644 | chr19 | + | sense overlapping | N/A | 1.5744 | 0.000806 | MIR520H |
| 49742748 | 49752790 | chr13 | + | exonic | hsa_circ_0006978 | −2.0826 | 0.000811 | FNDC3A |
| 28003837 | 28030080 | chr17 | − | exonic | hsa_circ_0000753 | −1.6547 | 0.000816 | SSH2 |
| 74585341 | 74601048 | chr8 | − | exonic | hsa_circ_0001811 | −2.1020 | 0.000817 | STAU2 |
| 30701807 | 30702014 | chr21 | + | exonic | hsa_circ_0061396 | −1.8575 | 0.000818 | BACH1 |
| 40590077 | 40590586 | chr21 | − | exonic | hsa_circ_0061721 | −1.5125 | 0.000827 | BRWD1 |
| 208841374 | 208842310 | chr2 | − | exonic | hsa_circ_0001095 | −1.6101 | 0.000828 | PLEKHM3 |
| 17267718 | 17273932 | chr19 | + | exonic | hsa_circ_0006590 | −1.5985 | 0.000834 | MYO9B |
| 94983404 | 95001475 | chr15 | + | exonic | hsa_circ_0003333 | −1.8420 | 0.000852 | MCTP2 |
| 34241449 | 34246936 | chr20 | − | intronic | hsa_circ_0001146 | −1.5820 | 0.000859 | CPNE1 |
| 88920106 | 88924932 | chr9 | − | exonic | hsa_circ_0001869 | −1.8576 | 0.000861 | ZCCHC6 |
| 41247862 | 41276132 | chr17 | − | exonic | hsa_circ_0008673 | −1.5061 | 0.000871 | BRCA1 |
| 85707868 | 85718626 | chr11 | − | exonic | hsa_circ_0023920 | −2.4059 | 0.000877 | PICALM |
| 31661953 | 31676727 | chr10 | + | intronic | N/A | −1.7853 | 0.000883 | ZEB1 |
| 89624210 | 89693008 | chr10 | + | sense overlapping | hsa_circ_0002232 | −1.6826 | 0.000892 | PTEN |
| 197592293 | 197598333 | chr3 | + | exonic | hsa_circ_0008106 | −1.5346 | 0.000898 | LRCH3 |
| 211952259 | 211966532 | chr1 | − | exonic | hsa_circ_0002274 | −1.9320 | 0.000900 | LPGAT1 |
| 57808781 | 57851246 | chr17 | + | exonic | hsa_circ_0005077 | −1.7794 | 0.000904 | VMP1 |
| 86292641 | 86297981 | chr9 | − | exonic | hsa_circ_0006466 | −2.0101 | 0.000906 | UBQLN1 |
| 94562928 | 94580249 | chr12 | + | exonic | N/A | −2.5601 | 0.000915 | PLXNC1 |
| 70236227 | 70236759 | chr14 | + | intronic | hsa_circ_0000549 | −2.4365 | 0.000925 | SRSF5 |
| 9079949 | 9098771 | chr2 | − | intronic | hsa_circ_0000973 | −1.7658 | 0.000935 | MBOAT2 |
| 175976295 | 175986268 | chr2 | − | exonic | hsa_circ_0007967 | −1.5056 | 0.000944 | ATF2 |
| 101898320 | 101911643 | chr2 | − | exonic | hsa_circ_0055904 | −1.7339 | 0.000946 | RNF149 |
| 197592293 | 197602646 | chr3 | + | exonic | hsa_circ_0008351 | −2.1268 | 0.000949 | LRCH3 |
| 140037802 | 140046483 | chr4 | − | exonic | N/A | −1.5794 | 0.000956 | ELF2 |
| 15456270 | 15456465 | chr21 | + | exonic | hsa_circ_0061265 | 2.3224 | 0.000961 | BC048201 |
| 213046019 | 213062599 | chr1 | + | exonic | hsa_circ_0016414 | −1.7672 | 0.000971 | FLVCR1 |
| 6995910 | 7002978 | chr4 | + | exonic | hsa_circ_0006681 | −1.8083 | 0.000972 | TBC1D14 |
| 154520801 | 154535410 | chr6 | − | exonic | hsa_circ_0078336 | −1.5712 | 0.000976 | IPCEF1 |
| 86294689 | 86297981 | chr9 | − | exonic | hsa_circ_0001867 | −1.9841 | 0.000976 | UBQLN1 |
| 45391429 | 45423180 | chr18 | − | exonic | hsa_circ_0000847 | −1.8056 | 0.000977 | SMAD2 |
| 113483526 | 113506881 | chr4 | − | exonic | hsa_circ_0070680 | −1.5328 | 0.001023 | ZGRF1 |
| 32381491 | 32385259 | chr1 | − | intronic | hsa_circ_0005067 | −1.7408 | 0.001030 | RP11-84A19.4 |
| 43341245 | 43345284 | chr3 | + | exonic | hsa_circ_0004089 | −2.3359 | 0.001034 | SNRK |
| 58971731 | 59004982 | chr1 | − | exonic | hsa_circ_0002316 | −2.4158 | 0.001034 | OMA1 |
| 85723323 | 85742653 | chr11 | − | exonic | hsa_circ_0023940 | −2.3540 | 0.001043 | PICALM |
| 118890859 | 118892596 | chr11 | + | exonic | N/A | 1.5243 | 0.001050 | TRAPPC4 |
| 196118683 | 196129890 | chr3 | − | exonic | hsa_circ_0001380 | −1.8287 | 0.001050 | UBXN7 |

TABLE 12-continued

| (BD baseline vs Control baseline) | | | | | | | | |
|---|---|---|---|---|---|---|---|---|
| TxStart | TxEnd | Chrom | Strand | circRNA type | Alias | Fold change | P-value | GeneSymbol |
| 137015277 | 137041727 | chr6 | − | exonic | hsa_circ_0007798 | −1.8706 | 0.001055 | MAP3K5 |
| 85737333 | 85742653 | chr11 | − | exonic | hsa_circ_0002433 | −2.1667 | 0.001059 | PICALM |
| 129304794 | 129305562 | chr3 | − | exonic | N/A | 1.5212 | 0.001067 | PLXND1 |
| 33825619 | 33840156 | chr21 | + | exonic | hsa_circ_0061481 | 1.5914 | 0.001067 | EVA1C |
| 191523883 | 191537878 | chr2 | + | exonic | hsa_circ_0002024 | −1.7193 | 0.001072 | NAB1 |
| 142264087 | 142264728 | chr8 | − | exonic | hsa_circ_0001829 | −1.8479 | 0.001086 | SLC45A4 |
| 31266516 | 31269158 | chr15 | − | exonic | N/A | −1.5599 | 0.001101 | MTMR10 |
| 113196219 | 113212227 | chr1 | + | exonic | hsa_circ_0013533 | −1.5422 | 0.001114 | CAPZA1 |
| 77227158 | 77230123 | chr7 | + | exonic | hsa_circ_0080845 | −1.8012 | 0.001118 | PTPN12 |
| 65273201 | 65275931 | chr15 | − | exonic | hsa_circ_0035875 | −1.6494 | 0.001121 | SPG21 |
| 17135209 | 17138460 | chr21 | + | exonic | hsa_circ_0001178 | −2.0880 | 0.001128 | USP25 |
| 80042674 | 80042829 | chr17 | − | exonic | N/A | 1.6060 | 0.001142 | FASN |
| 74500670 | 74528759 | chr11 | + | exonic | hsa_circ_0006705 | −1.5566 | 0.001145 | RNF169 |
| 70178323 | 70180131 | chr16 | + | exonic | hsa_circ_0040148 | 1.5327 | 0.001170 | PDPR |
| 12999419 | 13001581 | chr18 | + | exonic | hsa_circ_0046995 | −1.6287 | 0.001190 | CEP192 |
| 47098310 | 47103836 | chr3 | − | exonic | hsa_circ_0065149 | −1.7417 | 0.001198 | SETD2 |
| 197597030 | 197602646 | chr3 | + | exonic | hsa_circ_0005873 | −1.9681 | 0.001211 | LRCH3 |
| 81837331 | 81837529 | chr14 | − | exonic | hsa_circ_0032832 | 1.5782 | 0.001211 | STON2 |
| 172336669 | 172341841 | chr5 | + | exonic | hsa_circ_0075048 | −1.5630 | 0.001221 | ERGIC1 |
| 56542126 | 56546968 | chr5 | + | exonic | hsa_circ_0072547 | −1.7708 | 0.001221 | GPBP1 |
| 57814813 | 57851246 | chr17 | + | exonic | hsa_circ_0003127 | −1.8541 | 0.001234 | VMP1 |
| 117718697 | 117724265 | chrX | + | exonic | hsa_circ_0091382 | −1.6924 | 0.001251 | DOCK11 |
| 32372021 | 32385259 | chr1 | − | exonic | hsa_circ_0011333 | −1.7255 | 0.001251 | PTP4A2 |
| 58971731 | 59002413 | chr1 | − | exonic | hsa_circ_0000072 | −2.2575 | 0.001264 | OMA1 |
| 45740454 | 45752148 | chr17 | + | exonic | hsa_circ_0003650 | −1.5146 | 0.001310 | KPNB1 |
| 58275961 | 58316858 | chr2 | + | exonic | N/A | −1.5466 | 0.001319 | VRK2 |
| 13639794 | 13644961 | chr6 | − | exonic | hsa_circ_0001578 | −2.3746 | 0.001328 | RANBP9 |
| 32749557 | 32764217 | chr12 | + | sense overlapping | hsa_circ_0000389 | −2.0127 | 0.001330 | FGD4 |
| 50073902 | 50093067 | chr5 | + | exonic | hsa_circ_0072437 | −1.8988 | 0.001331 | PARP8 |
| 196118683 | 196129888 | chr3 | − | intronic | N/A | −1.8155 | 0.001347 | UBXN7 |
| 35693826 | 35696589 | chr20 | − | exonic | N/A | −1.5663 | 0.001357 | RBL1 |
| 185580493 | 185599548 | chr4 | + | exonic | hsa_circ_0003788 | −1.6012 | 0.001366 | PRIMPOL |
| 153579366 | 153585514 | chr1 | − | exonic | hsa_circ_0014239 | 1.6366 | 0.001403 | S100A16 |
| 114397092 | 114397671 | chr1 | − | exonic | hsa_circ_0013609 | −1.8361 | 0.001405 | PTPN22 |
| 36297027 | 36301594 | chr1 | + | exonic | N/A | −1.5115 | 0.001417 | AGO4 |
| 133734285 | 133769540 | chr8 | − | exonic | hsa_circ_0008205 | −1.8092 | 0.001425 | TMEM71 |
| 34304661 | 34313077 | chr20 | − | exonic | hsa_circ_0001147 | −1.8759 | 0.001429 | RBM39 |
| 30366964 | 30375041 | chr22 | + | exonic | hsa_circ_0006303 | −1.5478 | 0.001429 | MTMR3 |
| 12039670 | 12056183 | chr10 | − | exonic | hsa_circ_0000213 | −1.5606 | 0.001431 | UPF2 |
| 86293355 | 86297981 | chr9 | − | exonic | hsa_circ_0001866 | −1.9930 | 0.001433 | UBQLN1 |
| 6420911 | 6434173 | chr9 | + | exonic | hsa_circ_0002359 | −1.5385 | 0.001455 | UHRF2 |
| 70847874 | 70856944 | chr10 | + | sense overlapping | hsa_circ_0000241 | −1.6596 | 0.001459 | SRGN |
| 156549086 | 156619438 | chr7 | − | exonic | hsa_circ_0003511 | −1.7268 | 0.001464 | LMBR1 |
| 21742126 | 21742538 | chr13 | − | exonic | hsa_circ_0000467 | −1.8305 | 0.001467 | SKA3 |
| 40578033 | 40584633 | chr21 | − | exonic | N/A | −1.5915 | 0.001474 | BRWD1 |
| 19144163 | 19148055 | chr18 | − | exonic | hsa_circ_0009110 | −1.6436 | 0.001487 | ESCO1 |
| 86297865 | 86301070 | chr9 | − | exonic | hsa_circ_0005142 | −1.8003 | 0.001494 | UBQLN1 |
| 58340777 | 58347472 | chr12 | + | exonic | hsa_circ_0000412 | −1.7336 | 0.001495 | XRCC6BP1 |
| 31661946 | 31709678 | chr10 | + | intronic | hsa_circ_0000229 | −1.7101 | 0.001499 | ZEB1 |
| 197592293 | 197593090 | chr3 | + | exonic | hsa_circ_0008439 | −1.8546 | 0.001514 | LRCH3 |
| 56863017 | 56882352 | chr8 | + | exonic | hsa_circ_0007920 | −1.7204 | 0.001525 | LYN |
| 131193709 | 131196192 | chr7 | − | exonic | hsa_circ_0001973 | 1.6050 | 0.001543 | PODXL |
| 213037066 | 213058738 | chr1 | + | exonic | hsa_circ_0000182 | −1.9603 | 0.001546 | FLVCR1 |
| 129399477 | 129411699 | chr12 | + | exonic | hsa_circ_0029405 | −1.5282 | 0.001557 | GLT1D1 |
| 29218606 | 29246335 | chr18 | − | exonic | N/A | −1.7563 | 0.001570 | B4GALT6 |
| 50045984 | 50074484 | chr5 | + | exonic | hsa_circ_0072430 | −1.6896 | 0.001576 | PARP8 |
| 65307876 | 65310553 | chr5 | + | exonic | hsa_circ_0001494 | −1.6188 | 0.001605 | ERBB2IP |
| 3819408 | 3830758 | chr3 | − | exonic | hsa_circ_0003910 | −1.5937 | 0.001616 | SUMF1 |
| 9588086 | 9588851 | chr18 | − | exonic | hsa_circ_0046881 | −1.7126 | 0.001626 | PPP4R1 |
| 33307958 | 33309057 | chr11 | + | exonic | hsa_circ_0000284 | −1.5053 | 0.001631 | HIPK3 |
| 74561481 | 74583781 | chr18 | + | exonic | hsa_circ_0001993 | −1.7004 | 0.001649 | ZNF236 |
| 85692787 | 85693046 | chr11 | − | exonic | hsa_circ_0023904 | −2.0210 | 0.001650 | PICALM |
| 21629185 | 21629395 | chr16 | + | exonic | hsa_circ_0038439 | −1.5922 | 0.001656 | METTL9 |
| 131006155 | 131014868 | chr5 | − | exonic | hsa_circ_0073859 | −1.7571 | 0.001681 | FNIP1 |
| 35604790 | 35614627 | chr6 | − | intronic | N/A | −1.6290 | 0.001714 | FKBP5 |
| 153640928 | 153642354 | chr1 | − | exonic | hsa_circ_0014280 | 2.0265 | 0.001718 | ILF2 |
| 149613259 | 149639014 | chr3 | + | exonic | hsa_circ_0006801 | −2.2877 | 0.001728 | RNF13 |
| 37838091 | 37838774 | chr19 | + | exonic | N/A | 3.5752 | 0.001730 | HKR1 |
| 191520702 | 191537878 | chr2 | + | exonic | hsa_circ_0008961 | −1.5001 | 0.001734 | NAB1 |
| 153413350 | 153414506 | chr5 | − | exonic | hsa_circ_0007691 | −2.0389 | 0.001739 | FAM114A2 |
| 38792600 | 38868560 | chr21 | + | exonic | hsa_circ_0061694 | −2.1472 | 0.001740 | DYRK1A |
| 37633006 | 37640126 | chr4 | − | exonic | hsa_circ_0001400 | −2.2989 | 0.001755 | RELL1 |
| 131060182 | 131084192 | chr7 | + | exonic | hsa_circ_0001746 | −1.7670 | 0.001778 | MKLN1 |

TABLE 12-continued (BD baseline vs Control baseline)

| TxStart | TxEnd | Chrom | Strand | circRNA type | Alias | Fold change | P-value | GeneSymbol |
|---|---|---|---|---|---|---|---|---|
| 86627164 | 86649052 | chr5 | + | exonic | hsa_circ_0004317 | −1.5556 | 0.001799 | RASA1 |
| 58999624 | 59000003 | chr1 | − | exonic | N/A | −2.1190 | 0.001849 | OMA1 |
| 28163979 | 28167848 | chr16 | − | exonic | hsa_circ_0007807 | −1.6108 | 0.001866 | XPO6 |
| 5815804 | 5828013 | chr10 | − | exonic | hsa_circ_0000210 | −1.7661 | 0.001871 | GD12 |
| 15860731 | 15863309 | chr1 | + | exonic | hsa_circ_0000018 | −1.6466 | 0.001876 | DNAJC16 |
| 50330964 | 50339661 | chr15 | − | exonic | hsa_circ_0035197 | −1.6667 | 0.001892 | ATP8B4 |
| 42513408 | 42515462 | chr2 | + | exonic | hsa_circ_0054241 | −1.6242 | 0.001902 | EML4 |
| 45715378 | 45780869 | chr2 | − | exonic | N/A | 2.0772 | 0.001912 | SRBD1 |
| 85230855 | 85234875 | chr15 | − | exonic | hsa_circ_0036599 | −1.6724 | 0.001916 | SEC11A |
| 179135239 | 179136060 | chr5 | + | exonic | hsa_circ_0005778 | −1.6796 | 0.001920 | CANX |
| 56863017 | 56866543 | chr8 | + | exonic | hsa_circ_0006022 | −1.8591 | 0.001928 | LYN |
| 39408363 | 39409453 | chr19 | − | exonic | hsa_circ_0050954 | 1.5258 | 0.001957 | SARS2 |
| 45741524 | 45755779 | chr17 | + | exonic | hsa_circ_0004796 | −1.5171 | 0.001991 | KPNB1 |
| 21987790 | 21999817 | chr13 | − | exonic | hsa_circ_0006732 | −1.5829 | 0.002009 | ZDHHC20 |
| 149563797 | 149613357 | chr3 | + | exonic | hsa_circ_0003956 | 2.1466 | 0.002010 | RNF13 |
| 211952259 | 211961069 | chr1 | − | exonic | N/A | −1.7527 | 0.002021 | LPGAT1 |
| 45773870 | 45780869 | chr2 | − | exonic | hsa_circ_0005542 | −1.9682 | 0.002022 | SRBD1 |
| 61749745 | 61761038 | chr2 | − | exonic | hsa_circ_0001017 | −1.8162 | 0.002025 | XPO1 |
| 169673708 | 169673894 | chr1 | − | exonic | hsa_circ_0000158 | −1.5151 | 0.002025 | SELL |
| 73614502 | 73614802 | chr14 | + | exonic | hsa_circ_0008521 | −1.6536 | 0.002026 | PSEN1 |
| 57814813 | 57816308 | chr17 | + | exonic | hsa_circ_0044875 | −1.9743 | 0.002028 | VMP1 |
| 72157634 | 72161556 | chr5 | + | exonic | hsa_circ_0002692 | −1.5239 | 0.002040 | TNPO1 |
| 131860291 | 131860929 | chr9 | − | exonic | hsa_circ_0003362 | 1.5193 | 0.002043 | CRAT |
| 122881110 | 122893258 | chr5 | + | exonic | hsa_circ_0001522 | −2.1154 | 0.002043 | CSNK1G3 |
| 183361267 | 183369064 | chr3 | + | exonic | hsa_circ_0001367 | −1.5150 | 0.002052 | KLHL24 |
| 48444479 | 48458730 | chr18 | + | exonic | hsa_circ_0047700 | −1.6692 | 0.002053 | ME2 |
| 12999419 | 13042333 | chr18 | + | exonic | hsa_circ_0046999 | −1.5093 | 0.002056 | CEP192 |
| 58996272 | 58996401 | chr1 | − | exonic | hsa_circ_0012722 | −2.0461 | 0.002081 | OMA1 |
| 58971731 | 58971881 | chr1 | − | exonic | hsa_circ_0012717 | −2.1657 | 0.002092 | OMA1 |
| 5836847 | 5842668 | chr10 | − | exonic | hsa_circ_0002665 | −1.5489 | 0.002107 | GDI2 |
| 17270204 | 17273932 | chr19 | + | exonic | hsa_circ_0007396 | −1.6174 | 0.002128 | MYO9B |
| 38791690 | 38792852 | chr4 | − | sense overlapping | N/A | −1.8704 | 0.002129 | TLR1 |
| 21097422 | 21100103 | chr1 | − | exonic | hsa_circ_0005782 | −1.8660 | 0.002167 | HP1BP3 |
| 61556601 | 61560085 | chr11 | − | exonic | hsa_circ_0022358 | 1.6110 | 0.002170 | TMEM258 |
| 23495059 | 23495584 | chr14 | − | exonic | hsa_circ_0031267 | 1.5979 | 0.002180 | PSMB5 |
| 17205666 | 17214859 | chr21 | + | exonic | hsa_circ_0005238 | −1.6193 | 0.002182 | USP25 |
| 183368083 | 183369064 | chr3 | + | exonic | hsa_circ_0001369 | −2.0321 | 0.002192 | KLHL24 |
| 54956488 | 54959380 | chr20 | − | exonic | hsa_circ_0004887 | −1.5974 | 0.002209 | AURKA |
| 96717725 | 96728643 | chr12 | − | exonic | hsa_circ_0002762 | −1.5130 | 0.002223 | CDK17 |
| 89165951 | 89185063 | chr11 | − | exonic | hsa_circ_0023990 | 2.1133 | 0.002280 | NOX4 |
| 174819600 | 174820960 | chr2 | − | exonic | hsa_circ_0002642 | −1.5692 | 0.002340 | SP3 |
| 149563797 | 149629870 | chr3 | + | exonic | hsa_circ_0003502 | −2.0160 | 0.002352 | RNF13 |
| 47139444 | 47147610 | chr3 | − | exonic | hsa_circ_0001290 | −1.8435 | 0.002373 | SETD2 |
| 139819703 | 139828890 | chr5 | + | exonic | hsa_circ_0001541 | −1.5373 | 0.002389 | ANKHD1 |
| 129913321 | 129960251 | chr4 | − | exonic | hsa_circ_0001440 | −1.9605 | 0.002400 | SCLT1 |
| 61707544 | 61714152 | chr8 | + | exonic | N/A | −1.8159 | 0.002405 | CHD7 |
| 108243000 | 108250718 | chr6 | − | exonic | hsa_circ_0001635 | −1.8852 | 0.002410 | SEC63 |
| 86627164 | 86633908 | chr5 | + | exonic | hsa_circ_0007507 | −1.6122 | 0.002420 | RASA1 |
| 13435076 | 13443385 | chr11 | − | exonic | hsa_circ_0008967 | −1.5624 | 0.002422 | BTBD10 |
| 14057494 | 14068652 | chr1 | + | exonic | hsa_circ_0005986 | −1.9573 | 0.002458 | PRDM2 |
| 58992932 | 59002413 | chr1 | − | exonic | hsa_circ_0000073 | −2.2642 | 0.002465 | OMA1 |
| 144966169 | 144969146 | chr2 | − | exonic | hsa_circ_0001072 | −1.8435 | 0.002468 | GTDC1 |
| 50592985 | 50593565 | chr15 | − | exonic | hsa_circ_0002551 | −1.6280 | 0.002480 | GABPB1 |
| 128103455 | 128109220 | chr9 | + | exonic | hsa_circ_0005249 | −1.5272 | 0.002483 | GAPVD1 |
| 120916382 | 120930794 | chr11 | + | exonic | hsa_circ_0003302 | −1.8424 | 0.002487 | TBCEL |
| 131060182 | 131130662 | chr7 | + | exonic | hsa_circ_0003047 | −1.7542 | 0.002491 | MKLN1 |
| 122363276 | 122363756 | chr2 | − | exonic | hsa_circ_0007052 | −1.5864 | 0.002496 | CLASP1 |
| 150076352 | 150078193 | chr5 | − | exonic | N/A | 2.0881 | 0.002516 | RBM22 |
| 167921037 | 167944253 | chr1 | + | exonic | hsa_circ_0000154 | −1.5891 | 0.002534 | DCAF6 |
| 88200377 | 88248289 | chr9 | − | exonic | hsa_circ_0087386 | −1.7839 | 0.002540 | AGTPBP1 |
| 62299506 | 62306191 | chr15 | − | exonic | hsa_circ_0000607 | −2.1888 | 0.002541 | VPS13C |
| 119109304 | 119139926 | chr9 | + | exonic | hsa_circ_0088252 | 1.5568 | 0.002541 | PAPPA |
| 86292641 | 86301070 | chr9 | − | exonic | hsa_circ_0003715 | −1.7613 | 0.002542 | UBQLN1 |
| 15863654 | 15885271 | chr10 | − | exonic | hsa_circ_0008178 | −1.5729 | 0.002575 | FAM188A |
| 129396968 | 129411699 | chr12 | + | exonic | hsa_circ_0029403 | −1.6695 | 0.002583 | GLT1D1 |
| 65638006 | 65638129 | chr11 | − | exonic | hsa_circ_0022917 | 1.5197 | 0.002613 | EFEMP2 |
| 68434283 | 68446033 | chr15 | + | exonic | hsa_circ_0003916 | −1.7700 | 0.002614 | PIAS1 |
| 90376995 | 90419967 | chr7 | + | exonic | hsa_circ_0001722 | −1.6517 | 0.002622 | CDK14 |
| 93579026 | 93602148 | chr10 | + | exonic | N/A | −1.5463 | 0.002627 | TNKS2 |
| 245530135 | 245530669 | chr1 | + | exonic | hsa_circ_0009150 | 1.5334 | 0.002634 | KIF26B |
| 86292641 | 86293514 | chr9 | − | exonic | hsa_circ_0001865 | −1.7902 | 0.002662 | UBQLN1 |
| 24124293 | 24135302 | chr16 | + | exonic | hsa_circ_0038655 | −1.6206 | 0.002668 | PRKCB |
| 29130918 | 29131126 | chr17 | − | exonic | N/A | −1.5294 | 0.002684 | CRLF3 |
| 189850390 | 189859058 | chr2 | + | exonic | hsa_circ_0057360 | 1.7875 | 0.002708 | COL3A1 |

TABLE 12-continued (BD baseline vs Control baseline)

| TxStart | TxEnd | Chrom | Strand | circRNA type | Alias | Fold change | P-value | GeneSymbol |
|---|---|---|---|---|---|---|---|---|
| 9048750 | 9098771 | chr2 | − | exonic | hsa_circ_0000972 | −1.7538 | 0.002710 | MBOAT2 |
| 17273159 | 17273932 | chr19 | + | exonic | hsa_circ_0000909 | −1.6244 | 0.002722 | MYO9B |
| 23023562 | 23030758 | chr7 | − | exonic | hsa_circ_0001682 | −1.8631 | 0.002748 | FAM126A |
| 140482820 | 140487384 | chr7 | − | exonic | N/A | −1.5617 | 0.002751 | BRAF |
| 56694758 | 56707753 | chr3 | − | exonic | hsa_circ_0001315 | −1.5761 | 0.002766 | FAM208A |
| 149563797 | 149570383 | chr3 | + | exonic | hsa_circ_0006697 | −2.4451 | 0.002767 | RNF13 |
| 31661946 | 31791437 | chr10 | + | exonic | hsa_circ_0004126 | −1.5871 | 0.002769 | ZEB1 |
| 169854206 | 169863309 | chr3 | − | exonic | hsa_circ_0001965 | −1.9038 | 0.002770 | PHC3 |
| 33632307 | 33637797 | chr20 | − | exonic | N/A | −1.5513 | 0.002795 | TRPC4AP |
| 755878 | 760253 | chr11 | + | exonic | hsa_circ_0003307 | −1.5155 | 0.002801 | TALDO1 |
| 100587885 | 100589861 | chr8 | + | exonic | hsa_circ_0085096 | −1.5582 | 0.002809 | VPS13B |
| 36737414 | 36745300 | chr22 | − | exonic | hsa_circ_0004470 | −1.8983 | 0.002861 | MYH9 |
| 58342772 | 58348842 | chr17 | − | exonic | hsa_circ_0000793 | −1.5391 | 0.002866 | USP32 |
| 160103505 | 160109274 | chr6 | − | exonic | hsa_circ_0004662 | −2.2634 | 0.002867 | SOD2 |
| 72420914 | 72422544 | chr11 | − | exonic | hsa_circ_0003557 | −1.6802 | 0.002890 | ARAP1 |
| 202010100 | 202013775 | chr2 | + | exonic | hsa_circ_0057748 | −1.7420 | 0.002938 | CFLAR |
| 129585852 | 129599405 | chr3 | − | intronic | N/A | −1.5919 | 0.002943 | TMCC1 |
| 32142994 | 32157204 | chr2 | − | exonic | hsa_circ_0007385 | −1.7036 | 0.002946 | MEMO1 |
| 77210743 | 77212967 | chr7 | + | exonic | hsa_circ_0008139 | −1.6687 | 0.002976 | PTPN12 |
| 137015277 | 137019820 | chr6 | − | exonic | hsa_circ_0006856 | −1.5998 | 0.002982 | MAP3K5 |
| 49459454 | 49464519 | chr19 | + | exonic | hsa_circ_0051800 | 1.5740 | 0.003002 | BAX |
| 62559687 | 62562375 | chr20 | + | exonic | hsa_circ_0007609 | −1.6462 | 0.003002 | DNAJC5 |
| 108222573 | 108246136 | chr6 | − | exonic | hsa_circ_0008925 | −1.5238 | 0.003003 | SEC63 |
| 69726439 | 69752439 | chr10 | − | exonic | hsa_circ_0003308 | −1.6172 | 0.003034 | HERC4 |
| 18851019 | 18853776 | chr16 | − | exonic | hsa_circ_0008216 | −1.7651 | 0.003047 | SMG1 |
| 155628480 | 155643155 | chr3 | + | exonic | hsa_circ_0008184 | −1.5035 | 0.003079 | GMPS |
| 10031484 | 10066619 | chrX | + | exonic | hsa_circ_0001910 | −1.9211 | 0.003080 | WWC3 |
| 196118683 | 196120490 | chr3 | − | exonic | hsa_circ_0005051 | −2.0969 | 0.003080 | UBXN7 |
| 171969049 | 172028671 | chr3 | + | exonic | hsa_circ_0003692 | −1.8143 | 0.003112 | FNDC3B |
| 1404670 | 1409402 | chrX | + | exonic | N/A | −1.7508 | 0.003144 | CSF2RA |
| 129429870 | 129442188 | chr12 | + | exonic | hsa_circ_0029410 | −1.6317 | 0.003146 | GLT1D1 |
| 34011624 | 34017187 | chr9 | − | exonic | hsa_circ_0086740 | 1.8232 | 0.003146 | UBAP2 |
| 63821212 | 63866602 | chr15 | + | exonic | N/A | −1.5954 | 0.003156 | USP3 |
| 96233422 | 96278551 | chr9 | + | exonic | hsa_circ_0087531 | −1.8286 | 0.003157 | FAM120A |
| 153413350 | 153414527 | chr5 | − | exonic | hsa_circ_0001546 | −1.8733 | 0.003159 | FAM114A2 |
| 33091993 | 33101669 | chr13 | − | exonic | hsa_circ_0000471 | −1.9183 | 0.003172 | N4BP2L2 |
| 73614502 | 73614814 | chr14 | + | exonic | hsa_circ_0003848 | −1.5940 | 0.003174 | PSEN1 |
| 196129822 | 196134264 | chr3 | − | exonic | hsa_circ_0068655 | −1.9948 | 0.003196 | UBXN7 |
| 52238276 | 52248315 | chr1 | + | exonic | N/A | 1.5121 | 0.003204 | OSBPL9 |
| 26056122 | 26056299 | chr6 | − | sense overlapping | hsa_circ_0001583 | −2.1320 | 0.003232 | HIST1H1C |
| 37633006 | 37636745 | chr4 | − | exonic | hsa_circ_0002194 | −1.8689 | 0.003241 | RELL1 |
| 46934593 | 46950619 | chr16 | + | exonic | hsa_circ_0039219 | 1.5030 | 0.003243 | GPT2 |
| 77270158 | 77275895 | chrX | + | exonic | hsa_circ_0001934 | −1.5711 | 0.003261 | ATP7A |
| 38801306 | 38803739 | chr8 | + | exonic | hsa_circ_0084021 | −2.0820 | 0.003270 | PLEKHA2 |
| 122514815 | 122519100 | chr2 | + | exonic | hsa_circ_0002847 | −1.6336 | 0.003282 | TSN |
| 150774187 | 150774323 | chr7 | − | exonic | hsa_circ_0082917 | 1.5580 | 0.003298 | FASTK |
| 52935854 | 52947416 | chr6 | + | exonic | hsa_circ_0076777 | −1.7818 | 0.003324 | FBXO9 |
| 230705537 | 230725247 | chr2 | − | exonic | hsa_circ_0004079 | −1.6896 | 0.003327 | TRIP12 |
| 28748408 | 28771483 | chr13 | + | exonic | hsa_circ_0008760 | −1.5804 | 0.003339 | PAN3 |
| 129913321 | 129925031 | chr4 | − | exonic | hsa_circ_0001439 | −2.0367 | 0.003370 | SCLT1 |
| 45574118 | 45574781 | chr22 | + | exonic | hsa_circ_0002077 | −1.5502 | 0.003399 | NUP50 |
| 96233422 | 96261168 | chr9 | + | exonic | hsa_circ_0001875 | −1.7207 | 0.003410 | FAM120A |
| 49694940 | 49707217 | chr5 | − | sense overlapping | hsa_circ_0001481 | −2.5600 | 0.003481 | EMB |
| 235993525 | 235996967 | chr1 | − | exonic | hsa_circ_0005899 | −2.0098 | 0.003486 | LYST |
| 180665652 | 180667131 | chr3 | + | exonic | hsa_circ_0002004 | −1.5175 | 0.003506 | FXR1 |
| 4076755 | 4080626 | chr11 | + | exonic | hsa_circ_0020934 | 1.5648 | 0.003523 | STIM1 |
| 76301164 | 76415337 | chr13 | + | exonic | hsa_circ_0030448 | 3.3117 | 0.003555 | LMO7 |
| 4186092 | 4200109 | chr17 | − | exonic | hsa_circ_0003239 | −1.5795 | 0.003605 | UBE2G1 |
| 96238537 | 96259881 | chr9 | + | exonic | hsa_circ_0087540 | −1.5870 | 0.003635 | FAM120A |
| 12999419 | 13059311 | chr18 | + | exonic | hsa_circ_0047003 | −1.5648 | 0.003646 | CEP192 |
| 239090705 | 239093928 | chr2 | − | exonic | hsa_circ_0001116 | −1.5536 | 0.003693 | ILKAP |
| 63845913 | 63855207 | chr15 | + | exonic | hsa_circ_0008153 | −1.8731 | 0.003736 | USP3 |
| 27977671 | 28030080 | chr17 | − | exonic | hsa_circ_0042806 | −1.7328 | 0.003770 | SSH2 |
| 11984672 | 12016677 | chr17 | + | exonic | hsa_circ_0007456 | −1.7084 | 0.003821 | MAP2K4 |
| 1499235 | 1499964 | chr12 | + | intronic | N/A | 1.8500 | 0.003854 | ERC1 |
| 26918715 | 26926848 | chr17 | − | intronic | N/A | 1.5712 | 0.003871 | RP11-192H23.4 |
| 10077970 | 10081529 | chr3 | + | exonic | hsa_circ_0001266 | 1.5799 | 0.003873 | FANCD2 |
| 177632652 | 177650900 | chr4 | − | exonic | hsa_circ_0004496 | 1.6121 | 0.003873 | VEGFC |
| 65284462 | 65290692 | chr5 | + | exonic | hsa_circ_0001492 | −1.9009 | 0.003874 | ERBB2IP |
| 31617887 | 31621588 | chr3 | + | exonic | hsa_circ_0001278 | −1.6531 | 0.003893 | STT3B |
| 56160560 | 56161804 | chr5 | + | exonic | hsa_circ_0001485 | −1.9218 | 0.003907 | MAP3K1 |
| 74650518 | 74652103 | chr8 | − | exonic | N/A | −1.8273 | 0.003908 | STAU2 |
| 35800605 | 35802753 | chr17 | + | exonic | hsa_circ_0005101 | −1.5214 | 0.003916 | TADA2A |

TABLE 12-continued (BD baseline vs Control baseline)

| TxStart | TxEnd | Chrom | Strand | circRNA type | Alias | Fold change | P-value | GeneSymbol |
|---|---|---|---|---|---|---|---|---|
| 34906884 | 34907626 | chr21 | − | exonic | hsa_circ_0008795 | 1.7132 | 0.003926 | GART |
| 13632601 | 13659064 | chr6 | − | exonic | hsa_circ_0075650 | −1.9407 | 0.003939 | RANBP9 |
| 234296902 | 234299129 | chr2 | + | exonic | hsa_circ_0001112 | −1.6492 | 0.003959 | DGKD |
| 118451960 | 118454073 | chr11 | + | exonic | N/A | −1.6150 | 0.003971 | ARCN1 |
| 8910799 | 8917022 | chr2 | − | exonic | hsa_circ_0005315 | −1.5236 | 0.003975 | KIDINS220 |
| 76910271 | 76910864 | chr10 | + | exonic | hsa_circ_0006148 | 2.9872 | 0.004025 | SAMD8 |
| 80537076 | 80546772 | chr9 | − | sense overlapping | N/A | −1.8201 | 0.004073 | GNAQ |
| 169018296 | 169038600 | chr2 | − | exonic | hsa_circ_0001079 | −1.5973 | 0.004080 | STK39 |
| 109048081 | 109095099 | chr12 | − | exonic | hsa_circ_0028072 | −1.7431 | 0.004098 | CORO1C |
| 94244955 | 94259726 | chr5 | − | exonic | hsa_circ_0008417 | −1.7562 | 0.004141 | MCTP1 |
| 26620695 | 26624553 | chr1 | − | exonic | N/A | 1.5472 | 0.004153 | UBXN11 |
| 96233422 | 96259881 | chr9 | + | exonic | hsa_circ_0005218 | −1.8134 | 0.004157 | FAM120A |
| 149905066 | 149905920 | chrX | + | exonic | hsa_circ_0006764 | −1.5113 | 0.004172 | MTMR1 |
| 15863654 | 15889942 | chr10 | − | exonic | hsa_circ_0000220 | 2.0034 | 0.004186 | FAM188A |
| 45010607 | 45011361 | chr7 | + | antisense | hsa_circ_0001702 | 1.5202 | 0.004233 | MYO1G |
| 89236034 | 89237562 | chr1 | + | exonic | hsa_circ_0002008 | −1.5404 | 0.004245 | PKN2 |
| 58342772 | 58366043 | chr17 | − | exonic | N/A | −1.5119 | 0.004272 | USP32 |
| 61749745 | 61753656 | chr2 | − | exonic | hsa_circ_0001016 | −1.6502 | 0.004278 | XPO1 |
| 71623270 | 71645769 | chr2 | + | exonic | hsa_circ_0055151 | −1.6116 | 0.004302 | ZNF638 |
| 47098310 | 47108608 | chr3 | − | exonic | hsa_circ_0002569 | −1.7472 | 0.004307 | SETD2 |
| 147227077 | 147230127 | chr4 | − | sense overlapping | N/A | 1.5019 | 0.004310 | SLC10A7 |
| 114377531 | 114397671 | chr1 | − | exonic | N/A | −1.5936 | 0.004331 | PTPN22 |
| 22236974 | 22237296 | chr16 | + | exonic | hsa_circ_0038487 | 1.5160 | 0.004346 | EEF2K |
| 149563797 | 149619949 | chr3 | + | exonic | hsa_circ_0004565 | −1.6456 | 0.004383 | RNF13 |
| 11958205 | 12016681 | chr17 | + | sense overlapping | N/A | −1.7016 | 0.004399 | MAP2K4 |
| 17908029 | 17915413 | chr7 | − | exonic | hsa_circ_0005519 | −1.5384 | 0.004407 | SNX13 |
| 104714065 | 104717880 | chr7 | + | exonic | hsa_circ_0001736 | −2.2501 | 0.004438 | KMT2E |
| 30361928 | 30362658 | chr17 | + | exonic | hsa_circ_0042994 | −1.5002 | 0.004455 | LRRC37B |
| 30698379 | 30702014 | chr21 | + | exonic | hsa_circ_0061395 | −1.6296 | 0.004462 | BACH1 |
| 80409378 | 80412564 | chr9 | − | exonic | hsa_circ_0006459 | 1.7017 | 0.004490 | GNAQ |
| 128655032 | 128658211 | chr7 | − | exonic | hsa_circ_0001741 | −1.7408 | 0.004570 | TNPO3 |
| 45391429 | 45396935 | chr18 | − | exonic | hsa_circ_0003694 | −1.7658 | 0.004612 | SMAD2 |
| 155054511 | 155116273 | chr6 | + | exonic | hsa_circ_0078353 | −1.5376 | 0.004612 | SCAF8 |
| 6727768 | 6741097 | chr1 | − | exonic | hsa_circ_0008389 | 4.9621 | 0.004648 | DNAJC11 |
| 53289511 | 53302038 | chr16 | + | exonic | hsa_circ_0039365 | −1.6940 | 0.004650 | CHD9 |
| 34093272 | 34093534 | chr11 | + | exonic | hsa_circ_0008227 | −1.5773 | 0.004666 | CAPRIN1 |
| 5289579 | 5290906 | chr11 | − | exonic | hsa_circ_0020967 | 1.5384 | 0.004669 | HBE1 |
| 178274461 | 178281831 | chr4 | + | exonic | hsa_circ_0001460 | −1.6476 | 0.004705 | NEIL3 |
| 133740043 | 133769540 | chr8 | − | exonic | hsa_circ_0006050 | −1.6094 | 0.004708 | TMEM71 |
| 73944358 | 73958017 | chr4 | − | exonic | hsa_circ_0006693 | −1.6408 | 0.004709 | ANKRD17 |
| 22999874 | 23030758 | chr7 | − | exonic | hsa_circ_0008951 | −1.9364 | 0.004759 | FAM126A |
| 51804072 | 51813781 | chr18 | + | exonic | hsa_circ_0003428 | −1.6288 | 0.004798 | POLI |
| 28003837 | 28004759 | chr17 | − | exonic | hsa_circ_0042817 | −1.6171 | 0.004802 | SSH2 |
| 105563560 | 105573453 | chr6 | − | exonic | hsa_circ_0077527 | 1.5442 | 0.004822 | BVES |
| 133894452 | 133901915 | chr3 | − | exonic | hsa_circ_0067434 | −1.5244 | 0.004824 | RYK |
| 100676720 | 100691953 | chr12 | + | exonic | hsa_circ_0006258 | −1.5637 | 0.004851 | SCYL2 |
| 103557736 | 103567658 | chr10 | − | exonic | hsa_circ_0019608 | −1.5431 | 0.004897 | MGEA5 |
| 84644859 | 84680000 | chr1 | + | exonic | hsa_circ_0004083 | −1.5247 | 0.004911 | PRKACB |
| 151181822 | 151188100 | chr7 | − | exonic | hsa_circ_0082951 | −1.5144 | 0.005018 | RHEB |
| 183361267 | 183390272 | chr3 | + | exonic | hsa_circ_0001368 | −1.6525 | 0.005063 | KLHL24 |
| 85223943 | 85234875 | chr15 | − | exonic | hsa_circ_0000647 | −1.5309 | 0.005085 | SEC11A |
| 51501542 | 51509135 | chr13 | + | exonic | hsa_circ_0030286 | −1.7849 | 0.005104 | RNASEH2B |
| 195101737 | 195112876 | chr3 | − | exonic | hsa_circ_0007331 | −1.5350 | 0.005111 | ACAP2 |
| 41961025 | 41962156 | chr15 | + | exonic | hsa_circ_0000591 | −1.9186 | 0.005116 | MGA |
| 191765289 | 191789319 | chr2 | + | exonic | hsa_circ_0001085 | −1.5814 | 0.005143 | GLS |
| 171879381 | 171902872 | chr2 | − | exonic | N/A | −1.7755 | 0.005146 | TLK1 |
| 119219541 | 119232566 | chr3 | + | exonic | hsa_circ_0006884 | −1.6569 | 0.005184 | TIMMDC1 |
| 14042035 | 14075982 | chr1 | − | exonic | N/A | −1.6423 | 0.005206 | PRDM2 |
| 1737913 | 1749314 | chr1 | − | exonic | hsa_circ_0009357 | −1.7315 | 0.005223 | GNB1 |
| 58755107 | 58755971 | chr20 | + | intronic | hsa_circ_0001174 | −1.9470 | 0.005260 | RP5-1043L13.1 |
| 167915606 | 167919852 | chr5 | + | exonic | hsa_circ_0009145 | −1.7612 | 0.005268 | RARS |
| 26789747 | 26802589 | chr10 | + | exonic | N/A | −1.7970 | 0.005290 | APBB1IP |
| 46290104 | 46295253 | chr1 | + | exonic | hsa_circ_0012277 | 1.5048 | 0.005307 | MAST2 |
| 42231920 | 42232779 | chr17 | + | exonic | hsa_circ_0004239 | 1.5662 | 0.005328 | C17orf53 |
| 47164293 | 47166311 | chr10 | − | exonic | hsa_circ_0018293 | 1.5530 | 0.005329 | ANXA8 |
| 101550654 | 101551042 | chr15 | + | exonic | hsa_circ_0037078 | 1.7203 | 0.005341 | LRRK1 |
| 13632601 | 13644961 | chr6 | − | exonic | hsa_circ_0001577 | −2.0136 | 0.005358 | RANBP9 |
| 119219541 | 119236162 | chr3 | + | exonic | hsa_circ_0066874 | −1.6752 | 0.005376 | TIMMDC1 |
| 10031484 | 10078060 | chrX | + | exonic | hsa_circ_0089866 | −1.6789 | 0.005379 | WWC3 |
| 128065409 | 128066156 | chr2 | − | intronic | N/A | 1.6596 | 0.005411 | MAP3K2 |
| 71880664 | 71948928 | chr14 | + | intronic | hsa_circ_0000552 | −1.6801 | 0.005451 | SIPA1L1 |
| 76412360 | 76421132 | chr6 | + | exonic | hsa_circ_0077096 | −1.5156 | 0.005456 | SENP6 |

TABLE 12-continued (BD baseline vs Control baseline)

| TxStart | TxEnd | Chrom | Strand | circRNA type | Alias | Fold change | P-value | GeneSymbol |
|---|---|---|---|---|---|---|---|---|
| 15875628 | 15889942 | chr10 | − | exonic | hsa_circ_0006665 | −1.9476 | 0.005498 | FAM188A |
| 56626997 | 56628056 | chr3 | + | exonic | hsa_circ_0001313 | −2.0735 | 0.005503 | CCDC66 |
| 77210743 | 77221573 | chr7 | + | exonic | hsa_circ_0002458 | −1.6228 | 0.005514 | PTPN12 |
| 171965322 | 171969331 | chr3 | + | exonic | hsa_circ_0006156 | −1.8761 | 0.005525 | FNDC3B |
| 37971709 | 37974243 | chr8 | + | exonic | hsa_circ_0083957 | −1.8365 | 0.005556 | ASH2L |
| 12123470 | 12133683 | chr10 | + | exonic | hsa_circ_0003074 | −1.5521 | 0.005558 | DHTKD1 |
| 119219541 | 119222868 | chr3 | + | exonic | hsa_circ_0001329 | −1.6406 | 0.005566 | TIMMDC1 |
| 128419929 | 128434922 | chr9 | − | exonic | hsa_circ_0001890 | −1.5159 | 0.005636 | MAPKAP1 |
| 28830428 | 28835595 | chr13 | + | exonic | hsa_circ_0008902 | −1.5877 | 0.005646 | PAN3 |
| 1756835 | 1770677 | chr1 | − | exonic | hsa_circ_0009362 | −1.7776 | 0.005668 | GNB1 |
| 63845913 | 63852169 | chr15 | + | exonic | hsa_circ_0000613 | −1.7337 | 0.005697 | USP3 |
| 180953812 | 180962561 | chr1 | − | exonic | hsa_circ_0007905 | −1.5959 | 0.005725 | STX6 |
| 179007947 | 179020646 | chr5 | + | exonic | N/A | −1.7293 | 0.005758 | RUFY1 |
| 77200394 | 77221573 | chr7 | + | exonic | hsa_circ_0008901 | −1.6260 | 0.005774 | PTPN12 |
| 76069566 | 76069928 | chr7 | + | exonic | hsa_circ_0080802 | 1.5031 | 0.005775 | ZP3 |
| 111883774 | 111890244 | chr10 | + | exonic | hsa_circ_0003357 | −1.8048 | 0.005790 | ADD3 |
| 31661946 | 31750166 | chr10 | + | exonic | hsa_circ_0000230 | −1.6464 | 0.005802 | ZEB1 |
| 39595439 | 39609405 | chr18 | + | exonic | hsa_circ_0002560 | −1.7145 | 0.005818 | PIK3C3 |
| 11958205 | 12016677 | chr17 | + | exonic | hsa_circ_0005603 | −1.7415 | 0.005828 | MAP2K4 |
| 65466985 | 65482828 | chr2 | + | exonic | N/A | −2.5011 | 0.005837 | ACTR2 |
| 80352271 | 80415142 | chr15 | + | exonic | hsa_circ_0036506 | −1.5198 | 0.005889 | ZFAND6 |
| 155823066 | 155823597 | chr1 | − | exonic | hsa_circ_0000139 | −1.6269 | 0.005904 | GON4L |
| 47920060 | 47920607 | chr19 | − | exonic | hsa_circ_0051685 | 1.5121 | 0.005914 | MEIS3 |
| 19615443 | 19626289 | chr12 | + | exonic | hsa_circ_0006420 | −1.8393 | 0.006019 | AE8P2 |
| 47691321 | 47707559 | chr20 | + | exonic | hsa_circ_0001168 | −1.6206 | 0.006060 | CSE1L |
| 224918163 | 224918276 | chr1 | + | exonic | hsa_circ_0016598 | 1.6249 | 0.006064 | CNIH3 |
| 38792600 | 38845182 | chr21 | + | exonic | hsa_circ_0005955 | −1.6112 | 0.006087 | DYRK1A |
| 71942238 | 71942518 | chr11 | + | intronic | N/A | 1.6419 | 0.006103 | INPPL1 |
| 37318089 | 37324209 | chr5 | − | exonic | hsa_circ_0072251 | 1.5644 | 0.006145 | NUP155 |
| 83799882 | 83803093 | chr4 | − | exonic | hsa_circ_0006618 | −1.6512 | 0.006188 | SEC31A |
| 151727422 | 151729550 | chr4 | − | exonic | hsa_circ_0071196 | −1.9821 | 0.006190 | LRBA |
| 167935866 | 167944253 | chr1 | + | exonic | hsa_circ_0009109 | −1.5118 | 0.006246 | DCAF6 |
| 89653781 | 89653866 | chr10 | + | exonic | hsa_circ_0019058 | −1.6239 | 0.006260 | PTEN |
| 49609654 | 49618211 | chr10 | + | exonic | hsa_circ_0002968 | −1.5279 | 0.006288 | MAPK8 |
| 202277555 | 202278059 | chr2 | − | intronic | hsa_circ_0005655 | −1.5011 | 0.006311 | TRAK2 |
| 87925620 | 87928449 | chr6 | + | exonic | hsa_circ_0004058 | −1.5165 | 0.006330 | ZNF292 |
| 109479800 | 109479932 | chr1 | − | intronic | hsa_circ_0000102 | 4.9293 | 0.006352 | AKNAD1 |
| 3988781 | 4080626 | chr11 | + | exonic | hsa_circ_0020929 | 1.5335 | 0.006376 | STIM1 |
| 149563797 | 149613347 | chr3 | + | exonic | hsa_circ_0067717 | −1.6662 | 0.006391 | RNF13 |
| 125032151 | 125050082 | chr3 | − | exonic | hsa_circ_0001333 | −1.7911 | 0.006411 | ZNF148 |
| 43623730 | 43629994 | chr20 | + | exonic | hsa_circ_0060530 | −1.7064 | 0.006420 | STK4 |
| 99621041 | 99621555 | chr7 | + | exonic | hsa_circ_0081379 | −1.5624 | 0.006438 | ZKSCAN1 |
| 86292641 | 86292876 | chr9 | − | exonic | hsa_circ_0087354 | −1.5540 | 0.006485 | UBQLN1 |
| 118656760 | 118657227 | chr11 | − | exonic | hsa_circ_0004293 | −1.7132 | 0.006496 | DDX6 |
| 62593526 | 62596747 | chr8 | − | exonic | hsa_circ_0084615 | −1.6381 | 0.006501 | ASPH |
| 44380003 | 44383675 | chr17 | + | exonic | hsa_circ_0044195 | −1.6588 | 0.006508 | LRRC37A |
| 33397466 | 33427756 | chr7 | + | exonic | hsa_circ_0008336 | −1.5524 | 0.006509 | BBS9 |
| 18419661 | 18462483 | chr3 | − | exonic | hsa_circ_0064555 | −1.5717 | 0.006522 | SATB1 |
| 39191239 | 39200116 | chr19 | + | exonic | hsa_circ_0050900 | −1.6702 | 0.006552 | ACTN4 |
| 73637504 | 73640415 | chr14 | + | exonic | hsa_circ_0032506 | −1.5043 | 0.006555 | PSEN1 |
| 72617462 | 72618644 | chr7 | + | exonic | hsa_circ_0002284 | −1.6271 | 0.006590 | GTF2IP1 |
| 73956383 | 73958017 | chr4 | − | exonic | hsa_circ_0007883 | −1.5161 | 0.006590 | ANKRD17 |
| 108559662 | 108577564 | chr11 | + | exonic | hsa_circ_0024246 | 1.6113 | 0.006624 | DDX10 |
| 49458943 | 49464519 | chr19 | + | exonic | hsa_circ_0051799 | 1.5695 | 0.006655 | BAX |
| 88918000 | 88919862 | chr9 | − | exonic | hsa_circ_0007037 | −1.5632 | 0.006683 | ZCCHC6 |
| 71743025 | 71748859 | chr3 | − | exonic | N/A | −2.2342 | 0.006689 | EIF4E3 |
| 114697535 | 114709422 | chr2 | + | exonic | hsa_circ_0056199 | −1.6128 | 0.006701 | ACTR3 |
| 36723505 | 36737571 | chr22 | − | exonic | hsa_circ_0063147 | −1.8322 | 0.006723 | MYH9 |
| 95091099 | 95099324 | chr5 | + | exonic | hsa_circ_0007444 | −1.5949 | 0.006767 | RHOBTB3 |
| 30954186 | 30956926 | chr20 | + | exonic | hsa_circ_0001136 | −1.5280 | 0.006864 | ASXL1 |
| 38205014 | 38205733 | chr8 | − | exonic | hsa_circ_0083996 | −1.6642 | 0.006921 | WHSC1L1 |
| 18852886 | 18856973 | chr16 | − | exonic | hsa_circ_0006434 | −1.6798 | 0.006989 | SMG1 |
| 33467081 | 33481417 | chr3 | − | exonic | hsa_circ_0064743 | −1.5194 | 0.006991 | UBP1 |
| 34685382 | 34706566 | chr19 | + | exonic | hsa_circ_0008030 | −1.7145 | 0.007026 | LSM14A |
| 45773870 | 45789895 | chr2 | − | exonic | hsa_circ_0000997 | −1.7312 | 0.007035 | SRBD1 |
| 1735857 | 1737977 | chr1 | − | exonic | hsa_circ_0000007 | −1.5956 | 0.007083 | GNB1 |
| 155465560 | 155473602 | chr7 | + | exonic | hsa_circ_0001772 | −2.0965 | 0.007090 | RBM33 |
| 59204757 | 59209198 | chr15 | − | sense overlapping | N/A | −1.6880 | 0.007093 | SLTM |
| 171851260 | 171969331 | chr3 | + | exonic | hsa_circ_0007148 | −1.8899 | 0.007099 | FNDC3B |
| 76412360 | 76412788 | chr6 | + | exonic | hsa_circ_0001614 | −1.5604 | 0.007119 | SENP6 |
| 48371865 | 48396670 | chr4 | + | sense overlapping | N/A | −1.5146 | 0.007187 | SLAIN2 |
| 62864579 | 62865284 | chr17 | − | exonic | hsa_circ_0045337 | −1.5407 | 0.007238 | LRRC37A3 |
| 19353584 | 19359646 | chr18 | + | exonic | hsa_circ_0008741 | −1.7249 | 0.007276 | MIB1 |

TABLE 12-continued (BD baseline vs Control baseline)

| TxStart | TxEnd | Chrom | Strand | circRNA type | Alias | Fold change | P-value | GeneSymbol |
|---|---|---|---|---|---|---|---|---|
| 62531536 | 62566219 | chr8 | − | exonic | hsa_circ_0084606 | −1.7013 | 0.007292 | ASPH |
| 36492117 | 36507984 | chr6 | − | exonic | hsa_circ_0003131 | −1.8817 | 0.007328 | STK38 |
| 213134507 | 213147412 | chr1 | + | exonic | hsa_circ_0016418 | 1.6001 | 0.007395 | VASH2 |
| 33095509 | 33111164 | chr13 | − | exonic | hsa_circ_0029937 | −1.6736 | 0.007463 | N4BP2L2 |
| 49372452 | 49373029 | chr3 | − | intronic | hsa_circ_0001301 | −1.5477 | 0.007481 | USP4 |
| 28128638 | 28133083 | chr16 | − | exonic | hsa_circ_0038799 | −1.5248 | 0.007531 | XPO6 |
| 59805629 | 59812070 | chr1 | + | exonic | hsa_circ_0000076 | −1.5837 | 0.007543 | FGGY |
| 134076752 | 134079742 | chr5 | + | exonic | hsa_circ_0003154 | −1.6208 | 0.007544 | CAMLG |
| 59811918 | 59844509 | chr1 | + | exonic | N/A | −1.6063 | 0.007557 | FGGY |
| 119222378 | 119222868 | chr3 | + | exonic | hsa_circ_0008394 | −1.5912 | 0.007619 | TIMMDC1 |
| 99924615 | 99932150 | chr14 | − | exonic | hsa_circ_0000567 | −1.9398 | 0.007622 | SETD3 |
| 83799882 | 83803090 | chr4 | − | exonic | hsa_circ_0001421 | −1.6173 | 0.007639 | SEC31A |
| 99924615 | 99925522 | chr14 | − | exonic | hsa_circ_0033149 | −1.8907 | 0.007647 | SETD3 |
| 27867712 | 27878600 | chr12 | + | exonic | N/A | 1.5075 | 0.007726 | MRPS35 |
| 107260799 | 107263621 | chr11 | − | exonic | N/A | −1.6701 | 0.007741 | CWF19L2 |
| 151174418 | 151188100 | chr7 | − | exonic | hsa_circ_0082950 | −1.5727 | 0.007795 | RHEB |
| 11958205 | 11984847 | chr17 | + | exonic | hsa_circ_0007508 | −1.7556 | 0.007831 | MAP2K4 |
| 26789747 | 26792203 | chr10 | + | exonic | hsa_circ_0006063 | −1.7916 | 0.007844 | APBB1IP |
| 62546241 | 62596747 | chr8 | − | exonic | hsa_circ_0008337 | −1.5495 | 0.007911 | ASPH |
| 120445494 | 120489922 | chr10 | − | exonic | N/A | −1.5266 | 0.007939 | CACUL1 |
| 59805629 | 59844509 | chr1 | + | exonic | hsa_circ_0006633 | −1.6173 | 0.007951 | FGGY |
| 35586872 | 35614627 | chr6 | − | intronic | hsa_circ_0001600 | −1.5339 | 0.007964 | FKBP5 |
| 25650607 | 25654354 | chr15 | − | exonic | hsa_circ_0034168 | −1.6724 | 0.008062 | UBE3A |
| 55516082 | 55527154 | chr15 | − | sense overlapping | N/A | −1.7831 | 0.008100 | RAB27A |
| 29691716 | 29691882 | chr18 | + | exonic | hsa_circ_0047376 | −1.5719 | 0.008104 | RNF138 |
| 80409378 | 80430686 | chr9 | − | exonic | hsa_circ_0087264 | −1.6754 | 0.008156 | GNAQ |
| 61013821 | 61041513 | chr13 | + | exonic | hsa_circ_0003441 | −1.6553 | 0.008190 | TDRD3 |
| 7402357 | 7402810 | chr17 | + | exonic | hsa_circ_0000741 | −1.7121 | 0.008223 | POLR2A |
| 63824845 | 63855207 | chr15 | + | exonic | hsa_circ_0002138 | −1.5453 | 0.008286 | USP3 |
| 149563797 | 149639014 | chr3 | + | exonic | hsa_circ_0001346 | −1.5958 | 0.008326 | RNF13 |
| 77779390 | 77818086 | chr13 | − | exonic | hsa_circ_0030509 | −1.5501 | 0.008336 | MYCBP2 |
| 77631183 | 77632364 | chr9 | − | exonic | hsa_circ_0004189 | −1.6579 | 0.008446 | C9orf41 |
| 52729602 | 52729875 | chr4 | + | exonic | hsa_circ_0069715 | −1.6856 | 0.008451 | DCUN1D4 |
| 30354787 | 30358477 | chr17 | + | exonic | hsa_circ_0042992 | −1.6098 | 0.008494 | LRRC378 |
| 88061088 | 88071617 | chr16 | + | exonic | hsa_circ_0040823 | −1.8006 | 0.008576 | BANP |
| 1125950 | 1132297 | chr10 | + | exonic | hsa_circ_0017446 | −1.7683 | 0.008612 | WDR37 |
| 34111725 | 34113603 | chr11 | + | exonic | hsa_circ_0004851 | −1.5571 | 0.008719 | CAPRIN1 |
| 63821212 | 63829355 | chr15 | + | exonic | hsa_circ_0008104 | −1.5543 | 0.008793 | USP3 |
| 127965678 | 127983624 | chr3 | + | exonic | hsa_circ_0067209 | 2.2925 | 0.008855 | EEFSEC |
| 38890634 | 38897285 | chr22 | − | exonic | hsa_circ_0002211 | −1.7830 | 0.008898 | DDX17 |
| 80390757 | 80415142 | chr15 | + | exonic | hsa_circ_0000642 | −1.5520 | 0.009010 | ZFAND6 |
| 116668337 | 116678267 | chr12 | − | sense overlapping | hsa_circ_0000444 | −2.0630 | 0.009033 | MED13L |
| 32142994 | 32168452 | chr2 | − | exonic | hsa_circ_0053394 | −1.5973 | 0.009055 | MEMO1 |
| 131164981 | 131181313 | chr8 | − | exonic | hsa_circ_0001824 | −1.7945 | 0.009070 | ASAP1 |
| 80063751 | 80088663 | chr5 | + | exonic | hsa_circ_0073177 | −1.6014 | 0.009140 | MSH3 |
| 60629662 | 60631116 | chr17 | + | exonic | hsa_circ_0008438 | −1.6484 | 0.009187 | TLK2 |
| 86293355 | 86301070 | chr9 | − | exonic | hsa_circ_0087357 | −1.8947 | 0.009200 | UBQLN1 |
| 63988322 | 64008672 | chr15 | − | exonic | hsa_circ_0035796 | −1.9977 | 0.009393 | HERC1 |
| 59204761 | 59205895 | chr15 | − | exonic | hsa_circ_0003713 | −1.7129 | 0.009413 | SLTM |
| 223084858 | 223097002 | chr2 | − | exonic | hsa_circ_0007333 | 1.6610 | 0.009463 | PAX3 |
| 25650607 | 25657118 | chr15 | − | exonic | hsa_circ_0000586 | −1.5249 | 0.009518 | UBE3A |
| 98698895 | 98703416 | chr8 | + | exonic | hsa_circ_0002961 | −1.5258 | 0.009525 | MTDH |
| 45079431 | 45115960 | chr21 | + | exonic | hsa_circ_0061880 | 1.6333 | 0.009525 | RRP1B |
| 23375403 | 23378804 | chr14 | − | exonic | hsa_circ_0004137 | −1.6756 | 0.009528 | RBM23 |
| 22347957 | 22357656 | chr7 | − | exonic | N/A | 1.5070 | 0.009561 | RAPGEF5 |
| 71502781 | 71518729 | chr14 | + | exonic | hsa_circ_0032446 | −1.5141 | 0.009617 | PCNX |
| 131164981 | 131193126 | chr8 | − | exonic | hsa_circ_0008934 | −1.7986 | 0.009658 | ASAP1 |
| 5942291 | 5949747 | chr7 | + | exonic | hsa_circ_0004169 | −1.5192 | 0.009688 | CCZ1 |
| 155742856 | 155753880 | chr1 | − | exonic | hsa_circ_0014628 | −1.5672 | 0.009708 | GON4L |
| 57197912 | 57207781 | chr16 | − | exonic | hsa_circ_0006886 | −2.0392 | 0.009732 | FAM192A |
| 23375403 | 23380612 | chr14 | − | exonic | hsa_circ_0031241 | −1.8507 | 0.009756 | RBM23 |
| 123718838 | 123721032 | chr10 | − | exonic | hsa_circ_0020256 | −1.6376 | 0.009765 | NSMCE4A |
| 35586872 | 35610620 | chr6 | − | exonic | hsa_circ_0001599 | −1.6491 | 0.009781 | FKBP5 |
| 48308935 | 48320523 | chr8 | + | exonic | hsa_circ_0001798 | −1.7112 | 0.009807 | SPIDR |
| 39821342 | 39829143 | chr7 | + | exonic | hsa_circ_0079926 | −1.7923 | 0.009813 | LINC00265 |
| 44382874 | 44383675 | chr17 | + | exonic | hsa_circ_0044197 | −1.6131 | 0.009823 | LRRC37A |
| 38949785 | 38951231 | chr19 | + | exonic | hsa_circ_0050834 | 1.9337 | 0.009840 | RYR1 |
| 186517507 | 186517774 | chr3 | − | intronic | N/A | 1.7052 | 0.009847 | RFC4 |
| 61838273 | 61842207 | chr17 | − | exonic | hsa_circ_0045219 | −1.6465 | 0.009850 | CCDC47 |
| 19965129 | 19965469 | chr22 | − | intronic | hsa_circ_0092330 | 1.5451 | 0.009871 | ARVCF |
| 21117754 | 21120167 | chr19 | + | intronic | N/A | −1.5453 | 0.009933 | ZNF85 |
| 1735857 | 1756938 | chr1 | − | exonic | hsa_circ_0006869 | −1.7401 | 0.009948 | GNB1 |
| 59787207 | 59812070 | chr1 | + | exonic | hsa_circ_0000075 | −1.8079 | 0.009979 | FGGY |

TABLE 12-continued (BD baseline vs Control baseline)

| TxStart | TxEnd | Chrom | Strand | circRNA type | Alias | Fold change | P-value | GeneSymbol |
|---|---|---|---|---|---|---|---|---|
| 7839009 | 7844817 | chr10 | + | exonic | hsa_circ_0007292 | −2.5586 | 0.010299 | ATP5C1 |
| 667396 | 678730 | chr1 | − | exonic | hsa_circ_0009181 | −1.7851 | 0.010328 | LOC100133331 |
| 34312491 | 34313077 | chr20 | − | exonic | hsa_circ_0007632 | −1.6460 | 0.010337 | RBM39 |
| 35586872 | 35604935 | chr6 | − | exonic | hsa_circ_0076155 | −1.5550 | 0.010413 | FKBP5 |
| 216916171 | 216923699 | chr2 | − | exonic | N/A | 1.5390 | 0.010527 | PECR |
| 149563797 | 149589941 | chr3 | + | exonic | hsa_circ_0067716 | −1.5811 | 0.010668 | RNF13 |
| 41515056 | 41518061 | chr13 | − | exonic | hsa_circ_0030051 | −1.7142 | 0.010672 | ELF1 |
| 61133516 | 61135470 | chr11 | + | exonic | hsa_circ_0002058 | −1.6171 | 0.010675 | TMEM138 |
| 124071293 | 124074996 | chr12 | + | exonic | hsa_circ_0000458 | −1.9594 | 0.010724 | TMED2 |
| 75103969 | 75104454 | chr7 | − | exonic | hsa_circ_0006098 | −1.6733 | 0.010743 | POM121C |
| 24357988 | 24362320 | chr2 | + | exonic | hsa_circ_0007270 | −1.9270 | 0.010811 | FAM228B |
| 34107610 | 34113603 | chr11 | + | exonic | hsa_circ_0000287 | −1.5687 | 0.010862 | CAPRIN1 |
| 40655612 | 40657444 | chr2 | − | exonic | hsa_circ_0000994 | −1.9818 | 0.010970 | SLC8A1 |
| 112723882 | 112724819 | chr10 | + | exonic | hsa_circ_0000261 | −1,6869 | 0.010973 | SHOC2 |
| 38341277 | 38351497 | chr1 | − | exonic | N/A | 1.5779 | 0.010974 | INPP5B |
| 173726114 | 173744981 | chr1 | + | exonic | hsa_circ_0015278 | 1.7723 | 0.010975 | KLHL20 |
| 21662876 | 21710381 | chr18 | + | exonic | hsa_circ_0047281 | −1.5016 | 0.010989 | TTC39C |
| 42730785 | 42744343 | chr1 | − | exonic | hsa_circ_0006848 | −1.5434 | 0.011106 | FOXJ3 |
| 76910271 | 76928416 | chr10 | + | exonic | hsa_circ_0018905 | 4.1759 | 0.011151 | SAMD8 |
| 38128842 | 38137473 | chr21 | − | exonic | N/A | 1.5584 | 0.011196 | HLCS |
| 151116991 | 151122005 | chr6 | + | exonic | hsa_circ_0078264 | 1.7703 | 0.011292 | PLEKHG1 |
| 168920009 | 168986268 | chr2 | − | exonic | hsa_circ_0005882 | −1.5109 | 0.011294 | STK39 |
| 21216261 | 21216990 | chr19 | + | exonic | hsa_circ_0008838 | −1.5472 | 0.011322 | ZNF430 |
| 65887959 | 65890281 | chr17 | + | exonic | hsa_circ_0005347 | −1.6275 | 0.011356 | BPTF |
| 37732032 | 37735069 | chr8 | − | exonic | hsa_circ_0083946 | −1.6362 | 0.011538 | RAB11FIP1 |
| 102195835 | 102196253 | chr11 | − | antisense | hsa_circ_0000352 | 1.5615 | 0.011547 | BIRC3 |
| 167915606 | 167921655 | chr5 | + | exonic | hsa_circ_0001550 | −1.5525 | 0.011564 | RARS |
| 59204761 | 59209198 | chr15 | − | exonic | hsa_circ_0000605 | −1.6587 | 0.011574 | SLTM |
| 140476711 | 140508795 | chr7 | − | exonic | hsa_circ_0007178 | −1.8102 | 0.011648 | BRAF |
| 60733932 | 60735153 | chr14 | + | exonic | N/A | 1.5920 | 0.011694 | PPM1A |
| 77336007 | 77336863 | chr11 | − | exonic | hsa_circ_0000343 | −1.6009 | 0.011713 | CLNS1A |
| 155457868 | 155473602 | chr7 | + | exonic | hsa_circ_0001771 | −1.6459 | 0.011726 | RBM33 |
| 44395274 | 44401035 | chr18 | − | exonic | hsa_circ_0047585 | 1.5102 | 0.011783 | PIAS2 |
| 191765289 | 191775047 | chr2 | + | exonic | hsa_circ_0057521 | −1.5264 | 0.011810 | GLS |
| 73429657 | 73429763 | chr11 | − | exonic | hsa_circ_0023509 | −1.6522 | 0.011878 | RAB6A |
| 233651859 | 233660931 | chr2 | + | exonic | hsa_circ_0058733 | −1.5648 | 0.011883 | GIGYF2 |
| 32761408 | 32807433 | chr10 | + | exonic | N/A | −1.7664 | 0.011982 | CCDC7 |
| 119529812 | 119549381 | chr4 | + | exonic | hsa_circ_0005433 | −1.6073 | 0.012148 | LOC729218 |
| 57014000 | 57016139 | chr20 | + | exonic | hsa_circ_0001173 | 2.0519 | 0.012442 | VAPB |
| 21660548 | 21663045 | chr18 | + | exonic | hsa_circ_0002403 | −1.7668 | 0.012470 | TTC390 |
| 36415395 | 36424928 | chr11 | + | intronic | hsa_circ_0005044 | −1.6964 | 0.012482 | PRR5L |
| 24613084 | 24708279 | chr7 | + | exonic | hsa_circ_0079614 | −1.5883 | 0.012594 | MPP6 |
| 20811404 | 20811554 | chr14 | − | sense overlapping | hsa_circ_0000518 | −1.6670 | 0.012597 | RPPH1 |
| 169831147 | 169840532 | chr3 | − | exonic | hsa_circ_0006893 | −1.6698 | 0.012619 | PHC3 |
| 103372298 | 103373854 | chr8 | − | exonic | hsa_circ_0001819 | −1.5842 | 0.012666 | UBR5 |
| 28408513 | 28460682 | chr12 | + | exonic | N/A | −1.8799 | 0.012772 | CCDC91 |
| 40655612 | 40657441 | chr2 | − | exonic | hsa_circ_0005232 | −1.9271 | 0.012905 | SLC8A1 |
| 6840578 | 6841154 | chr7 | − | exonic | hsa_circ_0007135 | −1.5336 | 0.012906 | CCZ1B |
| 41736871 | 41737203 | chr19 | + | exonic | hsa_circ_0002945 | 1.5114 | 0.012955 | AXL |
| 36685933 | 36694658 | chr20 | + | exonic | hsa_circ_0007365 | −1.5484 | 0.012997 | RPRD1B |
| 19358063 | 19359646 | chr18 | + | exonic | hsa_circ_0008190 | −1.6792 | 0.013010 | MIB1 |
| 18010143 | 18029623 | chr11 | − | exonic | hsa_circ_0021412 | −1.5431 | 0.013076 | SERGEF |
| 56661064 | 56662642 | chr3 | − | exonic | hsa_circ_0001314 | −1.7291 | 0.013088 | FAM208A |
| 27106071 | 27106460 | chr6 | − | exonic | hsa_circ_0075900 | 1.5327 | 0.013099 | HIST1H2BK |
| 36492117 | 36507981 | chr6 | − | exonic | N/A | −1.8114 | 0.013190 | STK38 |
| 119624601 | 119635021 | chr3 | − | exonic | hsa_circ_0004225 | −1.5085 | 0.013275 | GSK3B |
| 124997967 | 125032500 | chr3 | − | exonic | hsa_circ_0067100 | −1.6250 | 0.013327 | ZNF148 |
| 61632920 | 61633008 | chr2 | + | antisense | hsa_circ_0001015 | 1.7187 | 0.013418 | USP34 |
| 77611362 | 77632364 | chr9 | − | exonic | hsa_circ_0087220 | −1.7002 | 0.013446 | C9orf41 |
| 118625413 | 118627996 | chr11 | − | exonic | hsa_circ_0024490 | −1.9146 | 0.013472 | DDX6 |
| 34302106 | 34313077 | chr20 | − | exonic | hsa_circ_0004870 | −1.5536 | 0.013679 | RBM39 |
| 27975161 | 27977818 | chr17 | − | exonic | hsa_circ_0042799 | −1.5822 | 0.013680 | SSH2 |
| 7837219 | 7841492 | chr1 | + | exonic | hsa_circ_0009548 | −1.5193 | 0.013685 | VAMP3 |
| 65941524 | 65972074 | chr17 | + | exonic | hsa_circ_0000799 | −1.5870 | 0.013710 | BPTF |
| 104702610 | 104722244 | chr7 | + | exonic | N/A | −1.5147 | 0.013718 | KMT2E |
| 227729319 | 227729842 | chr2 | + | exonic | hsa_circ_0001104 | −1.7282 | 0.013778 | RHBDD1 |
| 9195548 | 9221997 | chr18 | + | exonic | hsa_circ_0046843 | 2.0639 | 0.013950 | ANKRD12 |
| 243736227 | 244006584 | chr1 | − | exonic | hsa_circ_0017248 | −1.6245 | 0.014106 | AKT3 |
| 57535669 | 57535748 | chr15 | + | exonic | hsa_circ_0035426 | 1.5011 | 0.014117 | TCF12 |
| 109046047 | 109048186 | chr12 | − | exonic | hsa_circ_0000437 | −1.7804 | 0.014117 | CORO1C |
| 20811404 | 20811492 | chr14 | − | sense overlapping | hsa_circ_0000517 | −1.6570 | 0.014296 | RPPH1 |
| 68717321 | 68795482 | chr2 | + | sense overlapping | hsa_circ_0001024 | −1.8899 | 0.014417 | APLF |

TABLE 12-continued (BD baseline vs Control baseline)

| TxStart | TxEnd | Chrom | Strand | circRNA type | Alias | Fold change | P-value | GeneSymbol |
|---|---|---|---|---|---|---|---|---|
| 134381500 | 134381840 | chr9 | + | exonic | hsa_circ_0001897 | −1.7225 | 0.014454 | POMT1 |
| 78293666 | 78320990 | chr13 | + | exonic | N/A | −1.6276 | 0.014538 | SLAIN1 |
| 103558598 | 103567658 | chr10 | − | exonic | hsa_circ_0019612 | −1.5080 | 0.014641 | MGEA5 |
| 7402357 | 7402812 | chr17 | + | sense overlapping | N/A | −1.7102 | 0.014697 | POLR2A |
| 73950965 | 73958017 | chr4 | − | exonic | hsa_circ_0001417 | −1.5636 | 0.014725 | ANKRD17 |
| 65473657 | 65492309 | chr2 | + | exonic | hsa_circ_0008529 | 2.2413 | 0.014788 | ACTR2 |
| 25650607 | 25660989 | chr15 | − | sense overlapping | hsa_circ_0005147 | −1.5137 | 0.015103 | UBE3A |
| 9524591 | 9525849 | chr18 | + | exonic | hsa_circ_0005158 | −1.5807 | 0.015219 | RALBP1 |
| 77055327 | 77065626 | chr4 | − | exonic | hsa_circ_0070039 | −1.7244 | 0.015268 | NUP54 |
| 44054401 | 44054671 | chr1 | + | exonic | hsa_circ_0012077 | −1.5930 | 0.015416 | PTPRF |
| 14685190 | 14685289 | chr12 | + | intronic | hsa_circ_0000379 | 1.5973 | 0.015447 | RP11-502N13.2 |
| 43436412 | 43447330 | chr7 | + | exonic | hsa_circ_0008258 | 1.5631 | 0.015454 | HECW1 |
| 1747194 | 1756938 | chr1 | − | exonic | hsa_circ_0000008 | −1.6113 | 0.015600 | GNB1 |
| 76344422 | 76388643 | chr6 | + | exonic | hsa_circ_0001613 | −1.6714 | 0.015696 | SENP6 |
| 21644103 | 21663045 | chr18 | + | exonic | hsa_circ_0047270 | −1.5006 | 0.015710 | TTC39C |
| 11342991 | 11343191 | chr19 | − | intronic | hsa_circ_0092357 | 1.5597 | 0.015787 | DOCK6 |
| 80412669 | 80415142 | chr15 | + | exonic | hsa_circ_0000643 | −1.6787 | 0.015842 | ZFAND6 |
| 59787207 | 59844509 | chr1 | + | exonic | hsa_circ_0005354 | −1.7697 | 0.015848 | FGGY |
| 46751425 | 46754867 | chr10 | − | exonic | hsa_circ_0007010 | −1.6264 | 0.016039 | BMS1P5 |
| 17059499 | 17059748 | chr3 | − | antisense | hsa_circ_0001275 | 1.5014 | 0.016101 | PLCL2 |
| 35805450 | 35805551 | chr10 | + | exonic | hsa_circ_0018203 | −1.6444 | 0.016134 | CCNY |
| 7844232 | 7844817 | chr10 | + | exonic | hsa_circ_0017675 | −2.0196 | 0.016249 | ATP5C1 |
| 83940591 | 83945972 | chr16 | + | exonic | N/A | −1.5385 | 0.016316 | MLYCD |
| 127337917 | 127341124 | chr3 | − | antisense | hsa_circ_0001334 | 1.5392 | 0.016363 | MCM2 |
| 24357988 | 24369956 | chr2 | + | exonic | hsa_circ_0000982 | −1.8698 | 0.016457 | FAM228B |
| 34574331 | 34614575 | chr6 | − | exonic | hsa_circ_0009095 | −1.5170 | 0.016461 | C6orf106 |
| 47905209 | 47907363 | chr4 | − | exonic | hsa_circ_0008828 | 1.7237 | 0.016473 | NFXL1 |
| 144464661 | 144465125 | chr4 | + | exonic | hsa_circ_0001445 | −1.8686 | 0.016497 | SMARCA5 |
| 34699833 | 34706566 | chr19 | + | exonic | hsa_circ_0050461 | −1.5501 | 0.016526 | LSM14A |
| 53701835 | 53714476 | chr12 | − | exonic | hsa_circ_0026616 | 1.5466 | 0.016574 | AAAS |
| 56277780 | 56284152 | chr4 | + | exonic | hsa_circ_0001414 | −1.8167 | 0.016620 | TMEM165 |
| 49372459 | 49373029 | chr3 | − | intronic | N/A | −1.5060 | 0.016742 | USP4 |
| 135625089 | 135626611 | chr2 | − | exonic | hsa_circ_0117334 | 4.7247 | 0.016785 | CCNT2-AS1 |
| 44046021 | 44048964 | chr15 | + | exonic | hsa_circ_0002151 | −1.6484 | 0.016999 | PDIA3 |
| 80071512 | 80088663 | chr5 | + | exonic | hsa_circ_0001508 | −1.7125 | 0.017014 | MSH3 |
| 35824525 | 35827390 | chr1 | + | exonic | hsa_circ_0011536 | −1.6249 | 0.017053 | ZMYM4 |
| 24663284 | 24708279 | chr7 | + | exonic | hsa_circ_0001686 | −1.5610 | 0.017099 | MPP6 |
| 26204839 | 26205043 | chr6 | + | sense overlapping | hsa_circ_0001588 | −1.7516 | 0.017251 | HIST1H4E |
| 34144719 | 34149837 | chr17 | + | exonic | N/A | −1.9436 | 0.017375 | TAF15 |
| 19345732 | 19359646 | chr18 | + | exonic | hsa_circ_0000835 | −1.6757 | 0.017393 | MIB1 |
| 56600621 | 56601081 | chr3 | + | exonic | hsa_circ_0001312 | −1.6582 | 0.017531 | CCDC66 |
| 158552176 | 158557544 | chr7 | − | exonic | hsa_circ_0001776 | −1.7820 | 0.017675 | ESYT2 |
| 45860527 | 45860957 | chr19 | − | exonic | hsa_circ_0051470 | 1.5378 | 0.017786 | ERCC2 |
| 91030185 | 91035943 | chr15 | + | exonic | hsa_circ_0007201 | −1.9038 | 0.017796 | IQGAP1 |
| 123924133 | 123928458 | chr9 | + | exonic | hsa_circ_0088333 | −1.6313 | 0.017798 | CNTRL |
| 61607643 | 61609229 | chr3 | + | intronic | hsa_circ_0006226 | 1.9549 | 0.017811 | PTPRG |
| 48541721 | 48542148 | chr7 | + | intronic | hsa_circ_0001707 | −1.9428 | 0.018083 | ABCA13 |
| 9204473 | 9211782 | chr18 | + | exonic | hsa_circ_0000827 | −1.9014 | 0.018537 | ANKRD12 |
| 196544755 | 196548630 | chr2 | + | exonic | hsa_circ_0057551 | −1.7413 | 0.018592 | SLC39A10 |
| 29210921 | 29238052 | chr18 | − | exonic | hsa_circ_0047347 | −1.5250 | 0.018612 | B4GALT6 |
| 49609654 | 49613024 | chr10 | + | exonic | hsa_circ_0018315 | −1.5317 | 0.018754 | MAPK8 |
| 59179173 | 59179739 | chr15 | − | exonic | hsa_circ_0000604 | −1.5721 | 0.018831 | SLTM |
| 89853414 | 89866052 | chr12 | − | exonic | N/A | 1.5316 | 0.018963 | POC1B |
| 128282270 | 128289036 | chr7 | + | exonic | hsa_circ_0082179 | −1.6808 | 0.018972 | LINC01000 |
| 118635916 | 118657227 | chr11 | − | exonic | hsa_circ_0024501 | −1.7823 | 0.019044 | DDX6 |
| 78293666 | 78327493 | chr13 | + | exonic | hsa_circ_0000497 | −1.5476 | 0.019063 | SLAIN1 |
| 28306951 | 28310335 | chr22 | − | exonic | hsa_circ_0003056 | −1.5700 | 0.019141 | PITPNB |
| 9388037 | 9388418 | chr18 | + | exonic | N/A | 1.5537 | 0.019358 | TWSG1 |
| 103427642 | 103433430 | chr10 | − | exonic | hsa_circ_0019589 | −1.6117 | 0.019452 | FBXW4 |
| 169947225 | 170001116 | chr1 | − | sense overlapping | N/A | −1.5298 | 0.019460 | KIFAP3 |
| 57250018 | 57255327 | chr16 | + | exonic | hsa_circ_0039557 | 1.5475 | 0.019672 | RSPRY1 |
| 97178494 | 97222866 | chr12 | + | exonic | N/A | 1.5679 | 0.019732 | C12orf55 |
| 16386664 | 16415895 | chr21 | − | exonic | hsa_circ_0004771 | −1.5842 | 0.019817 | NRIP1 |
| 128281294 | 128289036 | chr7 | + | exonic | hsa_circ_0082178 | −1.6717 | 0.020135 | LINC01000 |
| 21076215 | 21100103 | chr1 | − | exonic | hsa_circ_0000023 | −1.5059 | 0.020269 | HP1BP3 |
| 810107 | 814799 | chr7 | + | exonic | hsa_circ_0001667 | 1.7430 | 0.020659 | DNAAF5 |
| 155691307 | 155695810 | chr1 | + | exonic | hsa_circ_0014613 | −1.5779 | 0.020970 | DAP3 |
| 72361165 | 72361649 | chr7 | + | exonic | hsa_circ_0003261 | −1.6145 | 0.021016 | POM121 |
| 125032151 | 125042288 | chr3 | − | exonic | hsa_circ_0007557 | −1.6146 | 0.021048 | ZNF148 |
| 37971709 | 37976881 | chr8 | + | exonic | hsa_circ_0001790 | −1.6219 | 0.021252 | ASH2L |
| 68337215 | 68343511 | chr11 | + | exonic | hsa_circ_0023233 | −1.5100 | 0.021260 | PPP6R3 |

TABLE 12-continued (BD baseline vs Control baseline)

| TxStart | TxEnd | Chrom | Strand | circRNA type | Alias | Fold change | P-value | GeneSymbol |
|---|---|---|---|---|---|---|---|---|
| 54249939 | 54256040 | chr4 | + | exonic | hsa_circ_0001411 | −1.5055 | 0.021359 | FIP1L1 |
| 92264128 | 92268765 | chr14 | − | exonic | hsa_circ_0032969 | −1.7495 | 0.021606 | TC2N |
| 107429298 | 107435696 | chr3 | + | exonic | hsa_circ_0001324 | −1.5725 | 0.021639 | BBX |
| 125587224 | 125591814 | chr12 | + | exonic | hsa_circ_0006078 | 1.5185 | 0.021679 | AACS |
| 105953535 | 105955124 | chr14 | + | exonic | hsa_circ_0033628 | 1.5500 | 0.021831 | CRIP1 |
| 41515056 | 41515506 | chr13 | − | exonic | hsa_circ_0030050 | −1.6983 | 0.021896 | ELF1 |
| 198703490 | 198704278 | chr1 | + | sense overlapping | hsa_circ_0000170 | −1.6096 | 0.021906 | PTPRC |
| 21698477 | 21702388 | chr14 | − | exonic | hsa_circ_0003643 | −1.5005 | 0.022360 | HNRNPC |
| 48573339 | 48573890 | chr2 | + | exonic | hsa_circ_0001002 | −1.5149 | 0.022436 | FOXN2 |
| 201966446 | 201969143 | chr1 | + | exonic | hsa_circ_0015962 | 1.6482 | 0.023513 | RNPEP |
| 144464665 | 144465125 | chr4 | + | sense overlapping | N/A | −1.8539 | 0.023728 | SMARCA5 |
| 121354581 | 121356103 | chr3 | − | exonic | N/A | −1.5275 | 0.023941 | HCLS1 |
| 37126308 | 37126939 | chr9 | + | exonic | hsa_circ_0001860 | −1.6839 | 0.024025 | ZCCHC7 |
| 38724057 | 38734535 | chr10 | + | exonic | hsa_circ_0018224 | −1.6149 | 0.024077 | LINC00999 |
| 38894089 | 38897285 | chr22 | − | exonic | hsa_circ_0063331 | −1.5499 | 0.024121 | DDX17 |
| 65473318 | 65492309 | chr2 | + | sense overlapping | hsa_circ_0001022 | −2.0458 | 0.024212 | ACTR2 |
| 110064315 | 110068928 | chr9 | + | exonic | hsa_circ_0006174 | −1.5004 | 0.024960 | RAD23B |
| 110893390 | 110895439 | chr12 | − | exonic | hsa_circ_0028202 | 1.7138 | 0.025093 | GPN3 |
| 35526224 | 35526947 | chr20 | − | exonic | N/A | −1.5711 | 0.025123 | SAMHD1 |
| 106739425 | 106774574 | chr2 | − | exonic | hsa_circ_0055943 | −1.6515 | 0.025143 | UXS1 |
| 48175347 | 48177671 | chr11 | + | exonic | N/A | −1.6333 | 0.025199 | PTPRJ |
| 243858892 | 244006584 | chr1 | − | exonic | hsa_circ_0004649 | −1.7019 | 0.025249 | AKT3 |
| 77193578 | 77211816 | chr18 | + | exonic | N/A | −1.6041 | 0.025653 | NFATC1 |
| 23791389 | 23792692 | chr14 | + | exonic | hsa_circ_0031286 | −1.5394 | 0.025745 | PABPN1 |
| 107419754 | 107420500 | chr6 | − | exonic | N/A | 1.5963 | 0.025796 | BEND3 |
| 9182379 | 9221997 | chr18 | + | exonic | hsa_circ_0000826 | −1.9773 | 0.025889 | ANKRD12 |
| 23378691 | 23380612 | chr14 | − | exonic | hsa_circ_0000524 | −1.8286 | 0.025912 | RBM23 |
| 247319707 | 247323115 | chr1 | − | sense overlapping | N/A | −1.5779 | 0.026010 | ZNF124 |
| 243222779 | 243242354 | chr1 | − | exonic | hsa_circ_0017202 | −1.6347 | 0.026356 | LINC01347 |
| 18770594 | 18781183 | chr17 | + | exonic | hsa_circ_0042359 | −1.5844 | 0.026643 | PRPSAP2 |
| 1747194 | 1749314 | chr1 | − | exonic | hsa_circ_0009360 | −1.5012 | 0.026696 | GNB1 |
| 126140467 | 126168493 | chr5 | + | exonic | hsa_circ_0073748 | −1.7460 | 0.026751 | LMNB1 |
| 99786012 | 99787892 | chr2 | − | exonic | hsa_circ_0001050 | −1.5178 | 0.027387 | MITD1 |
| 110062421 | 110084399 | chr9 | + | exonic | hsa_circ_0087856 | −1.6714 | 0.027926 | RAD23B |
| 50289531 | 50290616 | chr3 | + | exonic | hsa_circ_0007083 | −1.5244 | 0.028370 | GNAI2 |
| 136610762 | 136610850 | chr6 | − | intronic | hsa_circ_0001644 | 1.6472 | 0.028565 | BCLAF1 |
| 2066700 | 2087531 | chr1 | + | exonic | hsa_circ_0009366 | 1.5128 | 0.028672 | PRKCZ |
| 128281256 | 128289036 | chr7 | + | sense overlapping | hsa_circ_0005921 | −1.6193 | 0.028981 | LINC01000 |
| 155471301 | 155473602 | chr7 | + | exonic | hsa_circ_0083092 | −1.7559 | 0.029369 | RBM33 |
| 66625443 | 66625662 | chr11 | − | intronic | hsa_circ_0000331 | 1.5323 | 0.029514 | PC |
| 37170553 | 37190529 | chr3 | − | exonic | hsa_circ_0003264 | −1.5547 | 0.029739 | LRRFIP2 |
| 9204473 | 9221997 | chr18 | + | exonic | hsa_circ_0003865 | −1.6300 | 0.030236 | ANKRD12 |
| 114886536 | 114919893 | chr9 | − | exonic | hsa_circ_0004286 | −1.5682 | 0.030370 | SUSD1 |
| 222652709 | 224149975 | chr1 | − | sense overlapping | hsa_circ_0003163 | −1.5298 | 0.030486 | TLR5 |
| 16611602 | 16612362 | chr19 | + | exonic | N/A | 1.8669 | 0.030617 | C19orf44 |
| 95494501 | 95507595 | chr4 | + | exonic | hsa_circ_0070467 | −1.5135 | 0.030692 | PDLIM5 |
| 149778518 | 149778894 | chr5 | + | sense overlapping | hsa_circ_0001545 | 1.5064 | 0.031065 | TCOF1 |
| 122273422 | 122280607 | chr10 | + | exonic | hsa_circ_0008896 | 1.5580 | 0.031627 | PPAPDC1A |
| 65349233 | 65350779 | chr5 | + | exonic | hsa_circ_0072732 | −1.5053 | 0.031952 | ERBB2IP |
| 23371395 | 23380612 | chr14 | − | exonic | hsa_circ_0031235 | −1.7542 | 0.032042 | RBM23 |
| 151719232 | 151729550 | chr4 | − | exonic | hsa_circ_0004636 | −1.5688 | 0.032154 | LRBA |
| 158552176 | 158580784 | chr7 | − | exonic | hsa_circ_0083211 | −1.5585 | 0.032794 | ESYT2 |
| 141874410 | 141900868 | chr8 | − | exonic | hsa_circ_0002483 | −1.5843 | 0.033104 | PTK2 |
| 133587 | 139152 | chr11 | − | exonic | hsa_circ_0020596 | −1.5659 | 0.033123 | LOC100133161 |
| 54978779 | 54981849 | chr17 | − | exonic | hsa_circ_0000787 | −1.6027 | 0.033238 | TRIM25 |
| 48371865 | 48385801 | chr4 | + | exonic | N/A | −1.6538 | 0.033590 | SLAIN2 |
| 88061088 | 88069000 | chr16 | + | exonic | hsa_circ_0040822 | −1.5032 | 0.033807 | BANP |
| 224142178 | 224149975 | chr1 | − | intronic | hsa_circ_0001978 | −1.5307 | 0.034241 | XLOC_I2_001331 |
| 107126327 | 107126712 | chr7 | − | intronic | N/A | 1.5368 | 0.034351 | COG5 |
| 68155889 | 68160513 | chr16 | + | exonic | hsa_circ_0000711 | −1.8554 | 0.034698 | NFATC3 |
| 77632385 | 77633517 | chr11 | − | exonic | hsa_circ_0023736 | 1.5243 | 0.034880 | INTS4 |
| 44048846 | 44055404 | chr15 | + | exonic | hsa_circ_0002891 | −1.5906 | 0.035470 | PDIA3 |
| 7830092 | 7844817 | chr10 | + | exonic | hsa_circ_0017667 | −1.8984 | 0.035695 | ATP5C1 |
| 674213 | 678730 | chr1 | − | sense overlapping | hsa_circ_0007211 | −1.5909 | 0.035740 | AK310751 |
| 7181356 | 7189555 | chr6 | + | exonic | hsa_circ_0007429 | −1.5431 | 0.035905 | RREB1 |
| 3076997 | 3078169 | chr6 | + | exonic | hsa_circ_0001571 | −1.5706 | 0.035990 | RIPK1 |
| 24663284 | 24690331 | chr7 | + | exonic | hsa_circ_0001685 | −1.5052 | 0.036339 | MPP6 |

TABLE 12-continued (BD baseline vs Control baseline)

| TxStart | TxEnd | Chrom | Strand | circRNA type | Alias | Fold change | P-value | GeneSymbol |
|---|---|---|---|---|---|---|---|---|
| 141828375 | 141900868 | chr8 | − | exonic | hsa_circ_0005982 | −1.5397 | 0.036388 | PTK2 |
| 247318867 | 247323115 | chr1 | − | sense overlapping | hsa_circ_0002922 | −1.5034 | 0.036711 | ZNF124 |
| 32197099 | 32199491 | chr10 | − | exonic | hsa_circ_0000231 | −1.5007 | 0.037246 | ARHGAP12 |
| 118832460 | 118887479 | chr6 | − | exonic | hsa_circ_0077736 | −1.5111 | 0.037441 | CEP85L |
| 103432671 | 103433430 | chr10 | − | exonic | hsa_circ_0019591 | −1.5164 | 0.037549 | FBXW4 |
| 108186549 | 108206688 | chr11 | + | exonic | hsa_circ_0024231 | −1.5552 | 0.037765 | ATM |
| 77065301 | 77065626 | chr4 | − | exonic | hsa_circ_0070040 | −1.6115 | 0.037807 | NUP54 |
| 89289564 | 89291210 | chr16 | + | exonic | N/A | −1.5398 | 0.038861 | ZNF778 |
| 38726471 | 38734535 | chr10 | + | exonic | hsa_circ_0018225 | −1.5510 | 0.039591 | LINC00999 |
| 146209155 | 146216113 | chr6 | − | exonic | hsa_circ_0001649 | −1.6766 | 0.040662 | SHPRH |
| 20939730 | 20939965 | chr2 | − | exonic | hsa_circ_0052877 | 1.5268 | 0.041558 | C2orf43 |
| 117676687 | 117680079 | chrX | + | exonic | N/A | −1.5042 | 0.041889 | DOCK11 |
| 38089338 | 38089486 | chr22 | + | sense overlapping | hsa_circ_0001229 | 1.5396 | 0.042553 | NOL12 |
| 128350085 | 128360471 | chr11 | − | exonic | hsa_circ_0002083 | −1.8127 | 0.042745 | ETS1 |
| 52773404 | 52773806 | chr8 | − | exonic | hsa_circ_0001801 | −1.7835 | 0.043337 | PCMTD1 |
| 34147027 | 34149837 | chr17 | + | exonic | hsa_circ_0043138 | −1.7762 | 0.044311 | TAF15 |
| 117957334 | 117963271 | chr1 | + | exonic | hsa_circ_0013737 | −2.0007 | 0.045042 | MAN1A2 |
| 42103080 | 42105299 | chr15 | + | exonic | hsa_circ_0034762 | 1.5789 | 0.045753 | MAPKBP1 |
| 46633461 | 46633676 | chr12 | − | exonic | N/A | −1.6204 | 0.046201 | SLC38A1 |
| 140086068 | 140086817 | chr9 | − | exonic | hsa_circ_0089652 | 1.5222 | 0.046218 | TPRN |
| 68915840 | 68916286 | chr5 | + | exonic | hsa_circ_0072797 | −1.5327 | 0.046468 | SMA |
| 7826418 | 7841374 | chr7 | + | sense overlapping | hsa_circ_0001676 | −1.5647 | 0.046972 | UMAD1 |
| 117944807 | 117948267 | chr1 | + | exonic | hsa_circ_0000116 | −1.8227 | 0.047262 | MAN1A2 |
| 99090662 | 99092254 | chr7 | − | intronic | hsa_circ_0001726 | −1.5273 | 0.047494 | ZNF394 |
| 69206201 | 69206389 | chr5 | + | exonic | hsa_circ_0072805 | −1.5570 | 0.047619 | SMA4 |
| 117910084 | 117957453 | chr1 | + | exonic | hsa_circ_0013729 | −1.8889 | 0.047710 | MAN1A2 |
| 23356961 | 23377013 | chr1 | + | exonic | hsa_circ_0009061 | −1.5138 | 0.048295 | KDM1A |
| 96375495 | 96377506 | chr13 | + | exonic | hsa_circ_0002473 | −1.5112 | 0.048416 | DNAJC3 |
| 110084263 | 110087285 | chr9 | + | exonic | hsa_circ_0001880 | −1.5319 | 0.048666 | RAD23B |
| 212977661 | 212981190 | chr1 | + | exonic | hsa_circ_0000181 | 1.5229 | 0.049313 | TATDN3 |

TABLE 13

(BD 8 week vs Control 8 week)

| TxStart | TxEnd | Chrom | Strand | circRNA type | Alias | Fold change | P-value | GeneSymbol |
|---|---|---|---|---|---|---|---|---|
| 200233327 | 200298237 | chr2 | − | exonic | hsa_circ_0003915 | 48.2714 | 0.0000E+00 | SATB2 |
| 124273706 | 124274424 | chr10 | + | exonic | hsa_circ_0020275 | 25.2733 | 0.0000E+00 | HTRA1 |
| 28250417 | 28252532 | chr11 | + | intronic | N/A | 5.7391 | 0.0000E+00 | METTL15 |
| 200173482 | 200298237 | chr2 | − | exonic | hsa_circ_0007422 | 36.6374 | 1.0000E−11 | SATB2 |
| 113162074 | 113202401 | chr1 | + | exonic | hsa_circ_0013526 | 46.0121 | 1.0000E−11 | CAPZA1 |
| 88084709 | 88116842 | chr4 | − | sense overlapping | hsa_circ_0127236 | 30.5882 | 1.0000E−11 | KLHL8 |
| 21979173 | 22020771 | chr6 | + | exonic | hsa_circ_0075826 | 10.8276 | 6.0000E−11 | CASC15 |
| 117054494 | 117054855 | chr11 | + | exonic | hsa_circ_0024379 | 12.2603 | 7.0000E−11 | SIDT2 |
| 100189289 | 100189525 | chr7 | + | exonic | hsa_circ_0081481 | 20.0530 | 7.0000E−11 | FBXO24 |
| 158703294 | 158735300 | chr6 | + | sense overlapping | hsa_circ_0131196 | 14.6652 | 7.0000E−11 | TULP4 |
| 62197441 | 62197777 | chr20 | − | sense overlapping | hsa_circ_0001176 | 8.4707 | 8.0000E−11 | HELZ2 |
| 44128265 | 44131942 | chr19 | − | exonic | N/A | 3.0654 | 9.0000E−11 | CADM4 |
| 123298105 | 123325218 | chr10 | − | exonic | N/A | 6.9946 | 1.1000E−10 | FGFR2 |
| 142593 | 143323 | chr16 | − | exonic | hsa_circ_0037127 | 5.3055 | 1.2000E−10 | NPRL3 |
| 18609120 | 18609801 | chr22 | + | exonic | hsa_circ_0062191 | 6.6578 | 1.2000E−10 | TUBA8 |
| 36572334 | 36577714 | chr19 | + | exonic | N/A | 5.3062 | 1.2000E−10 | WDR62 |
| 130634122 | 130662267 | chr6 | − | sense overlapping | N/A | 7.8248 | 1.7000E−10 | SAMD3 |
| 53290970 | 53292303 | chr12 | − | exonic | hsa_circ_0026467 | 5.6016 | 1.8000E−10 | KRT8 |
| 28250417 | 28255132 | chr11 | + | intronic | hsa_circ_0000282 | 3.8756 | 2.1000E−10 | METTL15 |
| 71761715 | 71762097 | chr15 | + | intronic | N/A | 21.3345 | 2.1000E−10 | THSD4 |
| 85667519 | 85682357 | chr16 | + | exonic | hsa_circ_0040726 | 8.9850 | 2.6000E−10 | GSE1 |
| 5404774 | 5431405 | chr6 | + | exonic | hsa_circ_0075533 | 8.9233 | 2.7000E−10 | FARS2 |
| 37700501 | 37723145 | chr17 | + | sense overlapping | N/A | 1.7828 | 3.5000E−10 | CDK12 |
| 33148403 | 33245340 | chr20 | − | sense overlapping | hsa_circ_0001142 | 2.6590 | 3.9000E−10 | PIGU |
| 29105993 | 29130715 | chr22 | − | exonic | hsa_circ_0004128 | 10.1839 | 4.5000E−10 | CHEK2 |

TABLE 13-continued (BD 8 week vs Control 8 week)

| TxStart | TxEnd | Chrom | Strand | circRNA type | Alias | Fold change | P-value | GeneSymbol |
|---|---|---|---|---|---|---|---|---|
| 120776652 | 120799686 | chr2 | + | exonic | hsa_circ_0056264 | 7.4505 | 5.5000E−10 | EPB41L5 |
| 30078554 | 30081741 | chr16 | + | exonic | hsa_circ_0038981 | 7.9328 | 5.6000E−10 | ALDOA |
| 75848953 | 75854219 | chr10 | + | exonic | hsa_circ_0018886 | 8.3411 | 8.2000E−10 | VCL |
| 113703700 | 113773970 | chr9 | − | exonic | hsa_circ_0004928 | 8.1170 | 9.3000E−10 | LPAR1 |
| 55996226 | 56002769 | chr18 | + | exonic | N/A | 6.6257 | 1.0500E−09 | NEDD4L |
| 79179293 | 79193564 | chr9 | + | sense overlapping | N/A | 2.3967 | 1.3800E−09 | AL161626.1 |
| 86335196 | 86335470 | chr15 | − | intronic | hsa_circ_0000648 | 1.7180 | 2.0400E−09 | KLHL25 |
| 134655200 | 134679497 | chrX | + | sense overlapping | hsa_circ_0001945 | 5.1169 | 3.4900E−09 | DDX26B |
| 64537930 | 64569274 | chr5 | − | exonic | N/A | 4.9297 | 4.3500E−09 | ADAMTS6 |
| 56981238 | 56999504 | chr15 | − | exonic | hsa_circ_0035410 | 3.9707 | 4.4400E−09 | ZNF280D |
| 36782074 | 36788753 | chr18 | − | sense overlapping | N/A | 3.8272 | 6.4900E−09 | LINC00669 |
| 25630392 | 25638642 | chr17 | + | exonic | hsa_circ_0005336 | 5.6159 | 7.1100E−09 | WSB1 |
| 18195958 | 18198099 | chr17 | − | exonic | hsa_circ_0042330 | 1.9858 | 8.1400E−09 | TOP3A |
| 74927307 | 74929309 | chr15 | − | sense overlapping | hsa_circ_0000632 | 2.0455 | 9.3400E−09 | EDC3 |
| 62594626 | 62595103 | chr11 | − | exonic | hsa_circ_0022537 | 1.9566 | 1.0760E−08 | STX5 |
| 170737226 | 170737501 | chr4 | + | intergenic | hsa_circ_0001457 | 2.6585 | 1.3290E−08 | |
| 21703797 | 21705514 | chr18 | + | exonic | hsa_circ_0047285 | 4.7231 | 1.5270E−08 | TTC39C |
| 55420603 | 55420882 | chr19 | + | exonic | hsa_circ_0052165 | 3.9312 | 1.5510E−08 | NCR1 |
| 26385242 | 26388522 | chr6 | + | exonic | hsa_circ_0001590 | 1.7317 | 1.7080E−08 | BTN2A2 |
| 5711031 | 5717503 | chr11 | − | intronic | hsa_circ_0000276 | 3.7632 | 1.7100E−08 | TRIM5 |
| 37600088 | 37600198 | chr20 | − | antisense | hsa_circ_0001157 | 1.7558 | 1.8390E−08 | DHX35 |
| 8604615 | 8604944 | chr19 | + | antisense | hsa_circ_0008990 | 6.0568 | 1.8810E−08 | MYO1F |
| 176686989 | 176687169 | chr5 | + | exonic | hsa_circ_0075166 | 2.0986 | 2.6310E−08 | NSD1 |
| 133341934 | 133343019 | chr3 | − | exonic | hsa_circ_0008069 | 1.9182 | 2.6960E−08 | TOPBP1 |
| 65326097 | 65359043 | chr10 | + | exonic | N/A | 1.5213 | 3.3230E−08 | REEP3 |
| 50080770 | 50087302 | chr13 | + | exonic | N/A | 3.6263 | 3.4180E−08 | PHF11 |
| 41313097 | 41319934 | chr15 | − | exonic | hsa_circ_0034657 | 3.2218 | 3.79205−08 | INO80 |
| 85459039 | 85460676 | chr12 | + | exonic | N/A | 2.7132 | 4.4850E−08 | LRRIQ1 |
| 178287348 | 178287568 | chr5 | + | intronic | hsa_circ_0092298 | 7.0036 | 4.52205−08 | ZNF354B |
| 50321822 | 50322261 | chr16 | + | exonic | hsa_circ_0000699 | 2.6002 | 4.5790E−08 | ADCY7 |
| 183894738 | 183901879 | chr3 | + | exonic | hsa_circ_0068281 | 2.2651 | 4.9080E−08 | AP2M1 |
| 50596162 | 50596330 | chr15 | − | exonic | hsa_circ_0035208 | 2.9131 | 5.0610E−08 | GABPB1 |
| 109865553 | 109867711 | chr1 | − | exonic | hsa_circ_0013433 | 2.2099 | 5.4260E−08 | SORT1 |
| 22312863 | 22330179 | chr22 | − | exonic | N/A | 2.4095 | 6.5550E−08 | TOP3B |
| 46455023 | 46534363 | chr11 | − | exonic | hsa_circ_0021845 | 2.4707 | 6.7570E−08 | AMBRA1 |
| 69170598 | 69177292 | chr16 | + | exonic | hsa_circ_0008700 | 1.8418 | 9.4280E−08 | CIRH1A |
| 90446447 | 90454051 | chr15 | − | exonic | hsa_circ_0036750 | 1.8284 | 9.6440E−08 | ARPIN |
| 61574338 | 61575044 | chr20 | + | exonic | hsa_circ_0003574 | 1.8844 | 1.1874E−07 | GID8 |
| 42269709 | 42269921 | chr18 | + | intronic | hsa_circ_0000844 | 2.0706 | 1.3470E−07 | SETBP1 |
| 56552657 | 56552839 | chr12 | − | antisense | hsa_circ_0000406 | 2.5784 | 1.4109E−07 | MYL6 |
| 79203973 | 79205702 | chr4 | + | exonic | N/A | 2.0795 | 1.5915E−07 | FRAS1 |
| 145223197 | 145255444 | chr8 | + | exonic | hsa_circ_0001832 | 2.6808 | 1.6234E−07 | MROH1 |
| 45802132 | 45802362 | chr7 | − | intronic | hsa_circ_0001703 | 2.2635 | 1.8649E−07 | SEPT7P2 |
| 52675969 | 52677359 | chr3 | − | exonic | hsa_circ_0066083 | 2.0925 | 2.0853E−07 | PBRM1 |
| 118897646 | 118898434 | chr11 | − | exonic | hsa_circ_0024516 | 3.7102 | 2.1486E−07 | SLC37A4 |
| 60015345 | 60017170 | chr18 | + | sense overlapping | N/A | 2.4062 | 2.2003E−07 | TNFRSF11A |
| 80914570 | 80923622 | chr17 | − | exonic | hsa_circ_0046598 | 2.9229 | 2.27778−07 | B3GNTL1 |
| 33283175 | 33324476 | chr1 | + | sense overlapping | hsa_circ_0011449 | 2.6369 | 2.6680E−07 | S100PBP |
| 74526955 | 74551664 | chr12 | − | exonic | hsa_circ_0027588 | 3.1513 | 2.9667E−07 | LOC100507377 |
| 53331118 | 53331571 | chr14 | − | exonic | hsa_circ_0031968 | 1.9412 | 3.05888−07 | FERMT2 |
| 10980998 | 10981370 | chr8 | − | intronic | hsa_circ_0001779 | 2.8035 | 3.1159E−07 | XKR6 |
| 242033691 | 242036842 | chr2 | − | exonic | N/A | 2.0737 | 3.2418E−07 | MTERF4 |
| 232879544 | 232894790 | chr2 | + | exonic | hsa_circ_0007321 | 2.3824 | 3.5618E−07 | DIS3L2 |
| 187540330 | 187540654 | chr2 | + | exonic | N/A | 1.7564 | 3.8238E−07 | ITGAV |
| 7916911 | 7923977 | chr7 | + | intronic | N/A | 1.5278 | 4.2386E−07 | RPA3-AS1 |
| 34100754 | 34101636 | chr6 | − | exonic | hsa_circ_0076041 | 2.5460 | 4.3329E−07 | GRM4 |
| 983990 | 1004666 | chr16 | − | exonic | N/A | 2.1744 | 0.000001 | LMF1 |
| 39104849 | 39106177 | chr22 | + | intronic | N/A | 1.5146 | 0.000001 | GTPBP1 |
| 100506410 | 100506635 | chr2 | − | intronic | hsa_circ_0001054 | 3.3630 | 0.000001 | AFF3 |
| 27135705 | 27143560 | chr12 | − | exonic | N/A | 1.6746 | 0.000001 | TM7SF3 |
| 24730377 | 24734445 | chr22 | + | exonic | hsa_circ_0003720 | 2.7491 | 0.000001 | SPECC1L |
| 640897 | 666007 | chr8 | − | intronic | N/A | 1.7905 | 0.000001 | ERICH1 |
| 138203933 | 138235925 | chr7 | − | exonic | hsa_circ_0082580 | 1.6101 | 0.000001 | TRIM24 |
| 48552608 | 48553595 | chr4 | − | exonic | hsa_circ_0069681 | 2.0688 | 0.000001 | FRYL |
| 23424768 | 23430148 | chr16 | − | exonic | N/A | 1.5241 | 0.000001 | COG7 |
| 62396665 | 62398655 | chr11 | − | exonic | hsa_circ_0022482 | 1.6914 | 0.000001 | GANAB |
| 73315177 | 73316443 | chr2 | − | exonic | hsa_circ_0007273 | 2.6323 | 0.000001 | RAB11FIP5 |
| 60713226 | 60716000 | chr20 | − | exonic | hsa_circ_0061036 | 1.8599 | 0.000001 | PSMA7 |
| 100109595 | 100112837 | chr9 | + | exonic | hsa_circ_0087659 | −1.5849 | 0.000001 | CCDC180 |

TABLE 13-continued

| (BD 8 week vs Control 8 week) | | | | | | | | |
|---|---|---|---|---|---|---|---|---|
| TxStart | TxEnd | Chrom | Strand | circRNA type | Alias | Fold change | P-value | GeneSymbol |
| 29151053 | 29151137 | chr17 | − | intronic | hsa_circ_0000755 | 2.4098 | 0.000001 | CRLF3 |
| 113869721 | 113869956 | chr13 | + | intronic | hsa_circ_0000507 | 2.1233 | 0.000001 | CUL4A |
| 192880233 | 192880611 | chr1 | − | intergenic | N/A | 2.0627 | 0.000001 | |
| 15162025 | 15168718 | chr16 | − | exonic | hsa_circ_0038020 | 1.5296 | 0.000001 | RAN3 |
| 52132662 | 52134024 | chr6 | − | exonic | hsa_circ_0076742 | 1.8525 | 0.000001 | MCM3 |
| 143956599 | 144023646 | chr3 | + | intergenic | N/A | 1.7754 | 0.000002 | |
| 13054580 | 13054850 | chr19 | + | sense overlapping | hsa_circ_0000897 | 1.8029 | 0.000002 | CALR |
| 17124850 | 17127457 | chr17 | − | exonic | N/A | 3.5115 | 0.000002 | FLON |
| 184104555 | 184114861 | chr4 | + | sense overlapping | hsa_circ_0003631 | 1.5575 | 0.000002 | WWC2 |
| 77051808 | 77057565 | chr4 | − | exonic | hsa_circ_0008128 | 2.0925 | 0.000002 | NUP54 |
| 46529740 | 46534363 | chr11 | − | exonic | hsa_circ_0003110 | 2.3690 | 0.000002 | AMBRA1 |
| 109762831 | 109763131 | chr6 | + | intronic | N/A | 1.6867 | 0.000002 | SMPD2 |
| 100169609 | 100170072 | chrX | − | sense overlapping | N/A | 2.1139 | 0.000002 | XKRX |
| 8674619 | 8716500 | chr1 | − | exonic | hsa_circ_0005039 | 4.0039 | 0.000002 | RERE |
| 51076920 | 51080465 | chr12 | + | exonic | N/A | 1.6407 | 0.000002 | DIP2B |
| 175749275 | 175772569 | chr5 | + | exonic | hsa_circ_0001557 | 1.5255 | 0.000002 | SIMC1 |
| 123489400 | 123489932 | chr11 | + | exonic | hsa_circ_0024731 | 2.5140 | 0.000002 | GRAMD1B |
| 50059614 | 50062337 | chr12 | − | exonic | hsa_circ_0006802 | 1.5656 | 0.000002 | FMNL3 |
| 125843206 | 125856803 | chr3 | − | exonic | hsa_circ_0067127 | 1.9884 | 0.000002 | ALDH1L1 |
| 58764121 | 58804477 | chr5 | − | intronic | N/A | 1.6938 | 0.000003 | PDE4D |
| 2929251 | 2930958 | chr12 | + | exonic | hsa_circ_0000374 | 3.8615 | 0.000003 | ITFG2 |
| 198351307 | 198351922 | chr2 | − | exonie | hsa_circ_0057659 | 2.0485 | 0.000003 | HSPD1 |
| 40313099 | 40318290 | chr15 | + | exonic | hsa_circ_0034559 | 1.6176 | 0.000004 | EIF2AK4 |
| 124640186 | 124650369 | chr10 | + | sense overlapping | N/A | 2.0843 | 0.000004 | LOC399815 |
| 62479014 | 62483619 | chr1 | + | intronic | N/A | 1.8289 | 0.000004 | INADL |
| 127064214 | 127076264 | chr9 | + | exonic | hsa_circ_0088485 | 2.5035 | 0.000004 | NEK6 |
| 26861063 | 26884883 | chr9 | − | exonic | hsa_circ_0002781 | 1.9274 | 0.000004 | CAAP1 |
| 44970017 | 44970136 | chr11 | − | intronic | hsa_circ_0000293 | 2.1772 | 0.000004 | TP53I11 |
| 70644547 | 70666787 | chr11 | − | exonic | N/A | 1.8607 | 0.000004 | SHANK2 |
| 151223776 | 151247050 | chr4 | − | exonic | hsa_circ_0001450 | 1.7503 | 0.000005 | LRBA |
| 44643022 | 44645125 | chr20 | + | sense overlapping | hsa_circ_0001162 | 1.5045 | 0.000005 | MMP9 |
| 75790426 | 75790887 | chr3 | − | exonic | hsa_circ_0002609 | 1.5700 | 0.000005 | ZNF717 |
| 61044064 | 61045948 | chr11 | − | exonic | hsa_circ_0022249 | 2.0047 | 0.000005 | VWCE |
| 18105081 | 18111057 | chr11 | − | exonic | hsa_circ_0002778 | 1.8442 | 0.000005 | SAAL1 |
| 34024320 | 34101636 | chr6 | − | exonic | hsa_circ_0076039 | 2.4669 | 0.000005 | GRM4 |
| 85625142 | 85626408 | chr2 | − | exonic | hsa_circ_0055412 | 2.1439 | 0.000006 | CAPG |
| 3725324 | 3740986 | chr16 | − | exonic | N/A | 1.6268 | 0.000006 | TRAP1 |
| 42819829 | 42821476 | chr6 | + | exonic | hsa_circ_0076413 | 3.9054 | 0.000007 | GLTSCR1L |
| 46515157 | 46515754 | chr11 | − | exonic | hsa_circ_0009155 | −2.2226 | 0.000007 | AMBRA1 |
| 46515157 | 46534363 | chr11 | − | exonic | hsa_circ_0007061 | 2.5951 | 0.000007 | AMBRA1 |
| 56552657 | 56552820 | chr12 | − | antisense | hsa_circ_0000405 | 1.8657 | 0.000008 | MYL6 |
| 175996707 | 175996824 | chr1 | − | exonic | hsa_circ_0015358 | 1.6514 | 0.000008 | RFWD2 |
| 7556130 | 7586290 | chr12 | − | exonic | hsa_circ_0025349 | 1.9724 | 0.000009 | CD163L1 |
| 40728446 | 40730445 | chr5 | − | exonic | hsa_circ_0006141 | 2.9474 | 0.000009 | TTC33 |
| 85619092 | 85652361 | chr15 | + | exonic | N/A | 2.0838 | 0.000009 | PDE8A |
| 129870387 | 129871702 | chr10 | + | sense overlapping | hsa_circ_0000269 | 1.5314 | 0.000010 | PTPRE |
| 184114751 | 184130178 | chr4 | + | exonic | hsa_circ_0003437 | 1.8009 | 0.000012 | WWC2 |
| 28800065 | 28800663 | chr1 | + | exonic | hsa_circ_0002909 | 1.5468 | 0.000012 | PHACTR4 |
| 27173370 | 27183073 | chr3 | − | exonic | hsa_circ_0003052 | 1.5454 | 0.000012 | NEK10 |
| 5269501 | 5270820 | chr11 | − | exonic | hsa_circ_0020960 | 1.8348 | 0.000012 | HBG1 |
| 17366614 | 17395067 | chr9 | + | exonic | N/A | 1.7728 | 0.000014 | CNTLN |
| 150634289 | 150636239 | chr1 | − | exonic | N/A | −1.7096 | 0.000014 | GOLPH3L |
| 29847024 | 29848279 | chr16 | + | exonic | hsa_circ_0007258 | 1.8440 | 0.000015 | MVP |
| 424004 | 427848 | chr16 | − | exonic | hsa_circ_0000663 | 2.0462 | 0.000015 | TMEM8A |
| 111311746 | 111313913 | chr3 | − | exonic | hsa_circ_0066781 | 1.7835 | 0.000016 | ZBED2 |
| 33163212 | 33163532 | chr11 | − | exonic | N/A | 2.0609 | 0.000016 | CSTF3 |
| 13233298 | 13234568 | chr10 | + | exonio | hsa_circ_0004477 | 1.5190 | 0.000018 | MCM10 |
| 196386979 | 196388380 | chr3 | − | antisense | hsa_circ_0001381 | 1.6315 | 0.000019 | NRROS |
| 213302869 | 213349835 | chr1 | + | exonic | hsa_circ_0007772 | 2.1722 | 0.000021 | RPS6KC1 |
| 43552465 | 43555513 | chr17 | − | exonic | hsa_circ_0003434 | 2.2356 | 0.000022 | PLEKHM1 |
| 101790176 | 101799759 | chr12 | − | exonic | hsa_circ_0027902 | 1.6002 | 0.000024 | ARL1 |
| 145806229 | 145806661 | chr8 | − | exonic | hsa_circ_0086154 | 1.7315 | 0.000025 | ARHGAP39 |
| 23408712 | 23410184 | chr1 | + | exonic | hsa_circ_0010844 | 1.7194 | 0.000026 | KDM1A |
| 150432224 | 150438785 | chr2 | − | exonic | N/A | 1.5756 | 0.000026 | MMADHC |
| 52693054 | 52729678 | chr19 | + | exonic | hsa_circ_0052067 | 2.8896 | 0.000030 | PPP2R1A |
| 33376629 | 33402809 | chr22 | − | exonic | hsa_circ_0062997 | 1.7445 | 0.000031 | SYN3 |
| 133534776 | 133536765 | chr5 | − | exonic | hsa_circ_0073942 | 1.7985 | 0.000031 | PPP2CA |
| 201475259 | 201475620 | chr1 | − | intronic | hsa_circ_0000172 | 1.5623 | 0.000032 | CSRP1 |
| 62817884 | 62820990 | chr17 | − | exonic | hsa_circ_0004702 | 1.9100 | 0.000034 | PLEKHM1P |

TABLE 13-continued (BD 8 week vs Control 8 week)

| TxStart | TxEnd | Chrom | Strand | circRNA type | Alias | Fold change | P-value | GeneSymbol |
|---|---|---|---|---|---|---|---|---|
| 47274548 | 47290742 | chr22 | + | exonic | hsa_circ_0003343 | 1.5111 | 0.000035 | TBC1D22A |
| 75101156 | 75118768 | chr10 | − | sense overlapping | N/A | 1.7213 | 0.000035 | CFAP70 |
| 88116475 | 88116842 | chr4 | − | exonic | hsa_circ_0002538 | −3.4145 | 0.000036 | KLHL8 |
| 30715384 | 30715636 | chr16 | + | exonic | hsa_circ_0039076 | 1.6712 | 0.000037 | SRCAP |
| 45089764 | 45093836 | chr21 | + | exonic | N/A | 1.8045 | 0.000038 | RRP1B |
| 179316734 | 179319566 | chr1 | + | exonic | hsa_circ_0015454 | 2.2491 | 0.000038 | SOAT1 |
| 122797769 | 122798857 | chr2 | + | intergenic | N/A | 1.8961 | 0.000039 | |
| 114153316 | 114158328 | chr4 | + | exonic | hsa_circ_0070703 | 1.8218 | 0.000039 | ANK2 |
| 112256581 | 112269109 | chr3 | − | exonic | hsa_circ_0066801 | −1.5181 | 0.000040 | ATG3 |
| 7225183 | 7225329 | chr17 | − | exonic | hsa_circ_0041821 | 1.9815 | 0.000041 | NEURL4 |
| 77798585 | 77807398 | chr13 | − | exonic | hsa_circ_0030514 | 1.6269 | 0.000044 | MYCBP2 |
| 41988272 | 41989221 | chr15 | + | exonic | hsa_circ_0034734 | 1.5628 | 0.000044 | MGA |
| 25877593 | 25885213 | chr17 | + | exonic | N/A | 1.5407 | 0.000046 | KSR1 |
| 34059659 | 34101636 | chr6 | − | exonic | hsa_circ_0076040 | 2.1517 | 0.000047 | GRM4 |
| 97686267 | 97718297 | chr9 | + | exonic | N/A | 1.8991 | 0.000049 | C9orf3 |
| 31535338 | 31535540 | chr14 | + | sense overlapping | N/A | 1.8134 | 0.000053 | AP4S1 |
| 52277731 | 52325551 | chr13 | + | exonic | N/A | 1.5760 | 0.000054 | WDFY2 |
| 12645634 | 12647798 | chr3 | − | exonic | hsa_circ_0064365 | 2.1633 | 0.000055 | RAF1 |
| 217005908 | 217026771 | chr2 | + | exonic | hsa_circ_0058175 | 1.5154 | 0.000060 | XRCC5 |
| 150088308 | 150095224 | chr5 | − | exonic | hsa_circ_0074559 | 2.6653 | 0.000062 | DCTN4 |
| 47285639 | 47287816 | chr19 | − | exonic | hsa_circ_0002311 | 1.9014 | 0.000065 | SLC1A5 |
| 3205916 | 3209234 | chr10 | − | exonic | hsa_circ_0003022 | −1.9356 | 0.000066 | PITRM1 |
| 55340765 | 55341720 | chr1 | − | exonic | hsa_circ_0012673 | 1.6255 | 0.000069 | DHCR24 |
| 106797630 | 106802256 | chr7 | + | exonic | hsa_circ_0081881 | 1.6944 | 0.000069 | PRKAR2B |
| 127294245 | 127294652 | chr3 | − | exonic | hsa_circ_0067159 | 1.6930 | 0.000070 | TPRA1 |
| 58142964 | 58143287 | chr12 | − | exonic | hsa_circ_0006606 | 1.6456 | 0.000073 | CDK4 |
| 98276327 | 98276412 | chr2 | − | intronic | hsa_circ_0001049 | 1.5934 | 0.000073 | ACTR1B |
| 151122382 | 151122520 | chr5 | − | exonic | hsa_circ_0074657 | 1.6493 | 0.000079 | ATOX1 |
| 14821320 | 14837158 | chrY | + | exonic | hsa_circ_0001954 | 1.6392 | 0.000082 | USP9Y |
| 43523572 | 43535091 | chr6 | − | exonic | hsa_circ_0002037 | 1.5724 | 0.000083 | XPO5 |
| 44346195 | 44346638 | chr13 | − | intronic | N/A | 2.0021 | 0.000086 | ENOX1 |
| 47285639 | 47285806 | chr19 | − | exonic | hsa_circ_0051637 | 1.7894 | 0.000087 | SLC1A5 |
| 99538969 | 99560389 | chr8 | − | exonic | hsa_circ_0003593 | 2.0562 | 0.000098 | STK3 |
| 156638555 | 156645132 | chr1 | − | exonic | hsa_circ_0014771 | 2.2921 | 0.000108 | NES |
| 75264607 | 75265184 | chr10 | − | exonic | hsa_circ_0018818 | 1.6352 | 0.000117 | USP54 |
| 73215386 | 73228707 | chr2 | − | exonic | hsa_circ_0004699 | 1.9725 | 0.000121 | SFXN5 |
| 76393373 | 76393472 | chr17 | + | intronic | N/A | 1.6195 | 0.000122 | PGS1 |
| 72361889 | 72362548 | chr2 | − | exonic | hsa_circ_0055161 | 1.8143 | 0.000140 | CYP26B1 |
| 96058342 | 96066564 | chr5 | + | exonic | hsa_circ_0007003 | 1.5707 | 0.000150 | CAST |
| 5274420 | 5275744 | chr11 | − | exonic | hsa_circ_0020964 | 1.7381 | 0.000157 | HBG2 |
| 237023132 | 237026854 | chr1 | + | exonic | hsa_circ_0003929 | −1.6428 | 0.000159 | MTR |
| 50592985 | 50596330 | chr15 | − | exonic | hsa_circ_0007983 | 1.5887 | 0.000164 | GABPB1 |
| 49054148 | 49063055 | chr12 | − | exonic | hsa_circ_0026036 | 1.6849 | 0.000172 | KANSL2 |
| 89123719 | 89131833 | chr14 | − | exonic | N/A | 1.8537 | 0.000179 | EML5 |
| 36252919 | 36253257 | chr19 | + | exonic | hsa_circ_0000928 | 1.6617 | 0.000180 | PROSER3 |
| 20113099 | 20113439 | chr22 | + | intronic | hsa_circ_0092314 | 2.2413 | 0.000182 | RANBP1 |
| 10015311 | 10016172 | chr3 | − | exonic | hsa_circ_0064195 | −1.6809 | 0.000189 | EMC3 |
| 203818727 | 203820481 | chr2 | + | exonic | hsa_circ_0003493 | −2.0811 | 0.000195 | CARF |
| 16846216 | 16847893 | chrX | + | exonic | hsa_circ_0006931 | 1.7211 | 0.000197 | TXLNG |
| 159664587 | 159664757 | chr5 | − | antisense | hsa_circ_0001549 | 1.9195 | 0.000214 | FABP6 |
| 129799616 | 129813722 | chrX | − | exonic | N/A | 1.6017 | 0.000225 | ENOX2 |
| 24663284 | 24690331 | chr7 | + | exonic | hsa_circ_0001685 | −2.2762 | 0.000236 | MPP6 |
| 122363276 | 122363756 | chr2 | − | exonic | hsa_circ_0007052 | −2.3376 | 0.000268 | CLASP1 |
| 88091230 | 88116842 | chr4 | − | exonic | hsa_circ_0070389 | −1.9075 | 0.000280 | KLHL8 |
| 1191424 | 1203372 | chr1 | − | exonic | hsa_circ_0009246 | 1.7378 | 0.000285 | UBE2J2 |
| 91409421 | 91444868 | chr14 | − | exonic | N/A | −1.7459 | 0.000288 | RPS6KA5 |
| 9770162 | 9770654 | chr1 | + | exonic | hsa_circ_0009654 | 1.5010 | 0.000290 | PIK3CD |
| 50054354 | 50057699 | chr13 | + | exonic | hsa_circ_0000483 | −1.5364 | 0.000298 | SETDB2 |
| 90397884 | 90398971 | chr14 | − | exonic | hsa_circ_0032891 | 1.7943 | 0.000299 | EFCAB11 |
| 45203311 | 45204674 | chr11 | + | exonic | N/A | 2.1541 | 0.000299 | PROM11 |
| 105767934 | 105778666 | chr10 | + | exonic | hsa_circ_0000259 | −2.9598 | 0.000312 | SLK |
| 131271154 | 131271376 | chr9 | + | exonic | hsa_circ_0088807 | 1.5184 | 0.000324 | GLE1 |
| 32973011 | 32973508 | chr7 | − | exonic | N/A | 2.4660 | 0.000327 | RP9P |
| 2828699 | 2856298 | chrX | − | sense overlapping | N/A | 1.8048 | 0.000334 | ARSE |
| 65131739 | 65141666 | chr1 | + | exonic | hsa_circ_0007009 | 1.5865 | 0.000340 | CACHD1 |
| 126131327 | 126132928 | chr6 | + | intronic | N/A | 1.5628 | 0.000375 | NCOA7 |
| 90261231 | 90398157 | chr5 | + | exonic | N/A | 2.0738 | 0.000379 | GPR98 |
| 64846522 | 64847170 | chr11 | + | antisense | hsa_circ_0000323 | 1.6864 | 0.000391 | CDCA5 |
| 35163017 | 35163328 | chr11 | + | intronic | hsa_circ_0000291 | 1.5289 | 0.000420 | CD44 |
| 69565029 | 69565697 | chr2 | − | exonic | hsa_circ_0001025 | 1.8218 | 0.000461 | GFPT1 |
| 172325397 | 172325966 | chr2 | + | sense overlapping | hsa_circ_0007529 | 1.5724 | 0.000469 | DCAF17 |

TABLE 13-continued (BD 8 week vs Control 8 week)

| TxStart | TxEnd | Chrom | Strand | circRNA type | Alias | Fold change | P-value | GeneSymbol |
|---|---|---|---|---|---|---|---|---|
| 23836176 | 23836434 | chr1 | − | sense overlapping | hsa_circ_0000030 | 1.5377 | 0.000480 | E2F2 |
| 50289531 | 50290616 | chr3 | + | exonic | hsa_circ_0007083 | −2.4983 | 0.000483 | GNAI2 |
| 39882005 | 39882224 | chr15 | + | exonic | hsa_circ_0034510 | 1.7291 | 0.000498 | THBS1 |
| 28199932 | 28200152 | chr | + | intronic | hsa_circ_0000036 | 2.1099 | 0.000503 | THEMIS2 |
| 9588086 | 9595100 | chr18 | − | exonic | hsa_circ_0046882 | 1.5595 | 0.000592 | PPP4R1 |
| 120600873 | 120622046 | chr12 | − | exonic | hsa_circ_0028826 | 1.6403 | 0.000594 | GCN1L1 |
| 58971731 | 58971881 | chr1 | − | exonic | hsa_circ_0012717 | −2.5849 | 0.000596 | OMA1 |
| 65924470 | 65925603 | chr17 | + | exonic | hsa_circ_0004392 | −1.5911 | 0.000598 | BPTF |
| 24002051 | 24026054 | chr22 | − | exonic | hsa_circ_0062545 | −2.0571 | 0.000603 | GUSBP11 |
| 70245970 | 70246161 | chr14 | + | antisense | hsa_circ_0000550 | 1.6046 | 0.000618 | SLC10A1 |
| 17907047 | 17945940 | chr1 | + | exonic | hsa_circ_0010206 | 1.5408 | 0.000628 | ARHGEF10L |
| 45740454 | 45742524 | chr17 | + | exonic | hsa_circ_0008586 | −1.5245 | 0.000676 | KPNB1 |
| 61634149 | 61634467 | chr11 | + | sense overlapping | hsa_circ_0000313 | 1.5880 | 0.000734 | FADS2 |
| 47388673 | 47390207 | chr17 | − | exonic | hsa_circ_0000782 | −1.7060 | 0.000745 | ZNF652 |
| 51797729 | 51813781 | chr18 | + | exonic | hsa_circ_0047721 | −1.5288 | 0.000771 | POLI |
| 104119940 | 104120152 | chr10 | + | exonic | hsa_circ_0003839 | 1.5678 | 0.000772 | GBF1 |
| 66286967 | 66313803 | chr3 | + | exonic | hsa_circ_0003101 | 1.7176 | 0.000793 | SLC25A26 |
| 71623270 | 71645769 | chr2 | + | exonic | hsa_circ_0055151 | −2.0020 | 0.000802 | ZNF638 |
| 12788710 | 12788908 | chr12 | + | exonic | hsa_circ_0002873 | 1.5867 | 0.000811 | CREBL2 |
| 69792863 | 69792948 | chr5 | − | exonic | hsa_circ_0072837 | −1.8568 | 0.000821 | SMA5 |
| 12326937 | 12395884 | chr1 | + | exonic | hsa_circ_0009962 | 1.7134 | 0.000921 | VPS13D |
| 20240809 | 20240905 | chr2 | − | intronic | hsa_circ_0000981 | 1.7032 | 0.000929 | LAPTM4A |
| 47882366 | 47884745 | chr3 | + | exonic | hsa_circ_0001298 | 1.5440 | 0.000942 | DHX30 |
| 52128811 | 52146973 | chr6 | − | exonic | hsa_circ_0076734 | 1.6937 | 0.000944 | MCM3 |
| 21461899 | 21470081 | chr18 | + | exonic | hsa_circ_0047232 | 1.5439 | 0.000952 | LAMA3 |
| 82222843 | 82249070 | chr10 | + | exonic | N/A | 1.6538 | 0.000960 | TSPAN14 |
| 26056122 | 26056299 | chr6 | − | sense overlapping | hsa_circ_0001583 | −3.4106 | 0.000995 | HIST1H1C |
| 170728745 | 170735084 | chr2 | + | exonic | hsa_circ_0002603 | −1.7006 | 0.001060 | UBR3 |
| 74385612 | 74395072 | chr17 | − | exonic | hsa_circ_0045799 | 1.9954 | 0.001078 | UBE2O |
| 144086397 | 144086935 | chr6 | + | exonic | hsa_circ_0007769 | 1.9578 | 0.001091 | PHACTR2 |
| 17907047 | 17914974 | chr1 | + | exonic | hsa_circ_0005562 | 1.5189 | 0.001099 | ARHGEF10L |
| 109048081 | 109095099 | chr12 | − | exonic | hsa_circ_0028072 | −2.6429 | 0.001153 | CORO1C |
| 76886266 | 77067234 | chr18 | + | exonic | hsa_circ_0048009 | −1.6919 | 0.001157 | ATP9B |
| 69206201 | 69216694 | chr5 | + | exonic | hsa_circ_0004837 | −2.1322 | 0.001169 | SMA4 |
| 46700538 | 46700969 | chr11 | + | antisense | hsa_circ_0000297 | 1.6021 | 0.001171 | ARHGAP1 |
| 102056748 | 102076805 | chr11 | + | exonic | hsa_circ_0002320 | 1.5858 | 0.001201 | YAP1 |
| 40596333 | 40601362 | chr21 | − | exonic | hsa_circ_0001194 | −1.6191 | 0.001206 | BRWD1 |
| 17135209 | 17138460 | chr21 | + | exonic | hsa_circ_0001178 | −3.4252 | 0.001209 | USP25 |
| 37331786 | 37333735 | chr5 | − | exonic | hsa_circ_0072263 | 1.6394 | 0.001222 | NUP155 |
| 19948721 | 19951822 | chr22 | + | exonic | hsa_circ_0062277 | −1.5651 | 0.001291 | COMT |
| 15858833 | 15889942 | chr10 | − | exonic | hsa_circ_0000219 | −1.7391 | 0.001325 | FAM188A |
| 58996272 | 58996401 | chr1 | − | exonic | hsa_circ_0012722 | −2.4146 | 0.001353 | OMA1 |
| 69908548 | 69908983 | chr14 | + | exonic | N/A | 1.5282 | 0.001361 | SLC39A9 |
| 54811039 | 54817857 | chr4 | − | antisense | N/A | 1.5212 | 0.001365 | PDGFRA |
| 114357089 | 114364762 | chrX | − | exonic | hsa_circ_0003300 | 1.7139 | 0.001369 | LRCH2 |
| 19063007 | 19068019 | chr16 | + | exonic | hsa_circ_0038314 | 2.0177 | 0.001375 | TMC7 |
| 70493472 | 70500177 | chr5 | − | exonic | hsa_circ_0072876 | −2.1126 | 0.001409 | GUSBP9 |
| 169673708 | 169673894 | chr1 | − | exonic | hsa_circ_0000158 | 1.6999 | 0.001418 | SELL |
| 21087948 | 21099138 | chr18 | + | exonic | hsa_circ_0002757 | 1.5503 | 0.001501 | C18orf8 |
| 91409421 | 91526993 | chr14 | − | exonic | hsa_circ_0032942 | −1.5677 | 0.001565 | RPS6KA5 |
| 58999624 | 59000003 | chr1 | − | exonic | N/A | −2.6623 | 0.001580 | OMA1 |
| 171969049 | 172025291 | chr3 | + | exonic | hsa_circ_0067991 | −1.5112 | 0.001586 | FNDC3B |
| 44383247 | 44386611 | chrX | − | sense overlapping | hsa_circ_0007290 | −1.9157 | 0.001612 | FUNDC1 |
| 1004356 | 1004666 | chr16 | − | exonic | hsa_circ_0007701 | 1.5056 | 0.001627 | LMF1 |
| 29691716 | 29691882 | chr18 | + | exonic | hsa_circ_0047376 | −2.0810 | 0.001686 | RNF138 |
| 58971731 | 59004982 | chr1 | − | exonic | hsa_circ_0002316 | −2.4968 | 0.001762 | OMA1 |
| 186375214 | 186388209 | chr1 | + | sense overlapping | hsa_circ_0000166 | 1.5945 | 0.001790 | C1orf27 |
| 45073658 | 45290704 | chr6 | − | exonic | N/A | 1.7472 | 0.001827 | SUPT3H |
| 232099936 | 232100094 | chr2 | + | exonic | hsa_circ_0058651 | 1.6285 | 0.001865 | ARMC9 |
| 179135239 | 179136060 | chr5 | + | exonic | hsa_circ_0005778 | −2.0200 | 0.001898 | CANX |
| 77592249 | 77592394 | chr18 | − | antisense | hsa_circ_0000861 | 1.6405 | 0.001957 | XLOC_012735 |
| 114840817 | 114842445 | chr9 | − | exonic | hsa_circ_0088036 | 1.6294 | 0.002039 | SUSD1 |
| 47316514 | 47316617 | chr20 | − | intronic | hsa_circ_0001167 | 2.1038 | 0.002067 | PREX1 |
| 58992932 | 59002413 | chr1 | − | exonic | hsa_circ_0000073 | −2.7379 | 0.002106 | OMA1 |
| 109462051 | 109468159 | chr8 | + | exonic | N/A | −1.9300 | 0.002116 | EMC2 |
| 116668337 | 116678267 | chr12 | − | sense overlapping | hsa_circ_0000444 | −2.9230 | 0.002116 | MED13L |
| 136432901 | 136437894 | chr2 | + | exonic | hsa_circ_0001070 | −1.6020 | 0.002125 | R3HDM1 |
| 103557736 | 103567658 | chr10 | − | exonic | hsa_circ_0019608 | −− 1.8901 | 0.002127 | MGEA5 |
| 122159084 | 122363756 | chr2 | − | exonic | hsa_circ_0056297 | −1.8057 | 0.002245 | CLASP1 |

TABLE 13-continued (BD 8 week vs Control 8 week)

| TxStart | TxEnd | Chrom | Strand | circRNA type | Alias | Fold change | P-value | GeneSymbol |
|---|---|---|---|---|---|---|---|---|
| 74963795 | 74967483 | chr15 | − | exonic | hsa_circ_0000633 | −3.1930 | 0.002248 | EDC3 |
| 40578033 | 40584633 | chr21 | − | exonic | N/A | −1.7392 | 0.002262 | BRWD1 |
| 14042035 | 14075982 | chr1 | + | exonic | N/A | −2.1346 | 0.002299 | PRDM2 |
| 89236034 | 89237562 | chr1 | + | exonic | hsa_circ_0002008 | −1.7877 | 0.002304 | PKN2 |
| 101132116 | 101132358 | chr13 | + | intronic | N/A | 1.5324 | 0.002337 | PCCA |
| 7402357 | 7402810 | chr17 | + | exonic | hsa_circ_0000741 | −3.2715 | 0.002340 | POLR2A |
| 84644859 | 84680000 | chr1 | + | exonic | hsa_circ_0004083 | −1.8648 | 0.002366 | PRKACB |
| 156395748 | 156395874 | chr3 | − | antisense | hsa_circ_0001354 | 1.5291 | 0.002415 | TIPARP |
| 31661946 | 31709678 | chr10 | + | intronic | hsa_circ_0000229 | −2.1375 | 0.002469 | ZEB1 |
| 104702610 | 104722244 | chr7 | + | exonic | N/A | −1.9917 | 0.002482 | KMT2E |
| 38287206 | 38287466 | chr8 | − | intronic | N/A | 1.5093 | 0.002504 | FGFR1 |
| 96986391 | 96991728 | chr14 | + | exonic | hsa_circ_0002120 | −1.5545 | 0.002506 | PAPOLA |
| 29691716 | 29706763 | chr18 | + | exonic | hsa_circ_0005122 | −1.5719 | 0.002525 | RNF138 |
| 132990630 | 133002144 | chr7 | + | exonic | hsa_circ_0082440 | 1.9212 | 0.002665 | EXOC4 |
| 27207184 | 27207404 | chr17 | + | antisense | hsa_circ_0000746 | 1.8419 | 0.002700 | FLOT2 |
| 110064315 | 110068928 | chr9 | + | exonic | hsa_circ_0006174 | −2.2789 | 0.002731 | RAD23B |
| 109046047 | 109096774 | chr12 | − | exonic | hsa_circ_0028067 | −2.4298 | 0.002731 | CORO1C |
| 112321531 | 112339774 | chr5 | + | exonic | hsa_circ_0001520 | −2.0057 | 0.002738 | DCP2 |
| 21644103 | 21663045 | chr18 | + | exonic | hsa_circ_0047270 | −1.9396 | 0.002765 | TTC39C |
| 183368083 | 183369064 | chr3 | + | exonic | hsa_circ_0001369 | −2.1759 | 0.002834 | KLHL24 |
| 40590077 | 40590586 | chr21 | − | exonic | hsa_circ_0061721 | −1.5634 | 0.002856 | BRWD1 |
| 191765289 | 191789319 | chr2 | + | exonic | hsa_circ_0001085 | −1.9781 | 0.002864 | GLS |
| 186988982 | 187003844 | chr3 | − | intronic | hsa_circ_0009169 | 1.5054 | 0.002894 | MASP1 |
| 194877177 | 194947585 | chr3 | − | exonic | hsa_circ_0008219 | 1.5034 | 0.002898 | XXYLT1 |
| 21097422 | 21100103 | chr1 | − | exonic | hsa_circ_0005782 | −2.4380 | 0.002953 | HP1BP3 |
| 5113044 | 5126779 | chr17 | + | exonic | hsa_circ_0000738 | 1.6898 | 0.002983 | LOC100130950 |
| 89289564 | 89291210 | chr16 | + | exonic | N/A | −1.8756 | 0.002994 | ZNF778 |
| 107260799 | 107263621 | chr11 | − | exonic | N/A | −2.2878 | 0.002998 | CWF19L2 |
| 136162128 | 136221621 | chr3 | − | exonic | N/A | −1.5300 | 0.003011 | STAG1 |
| 10524467 | 10525312 | chr16 | + | exonic | hsa_circ_0037807 | −1.9327 | 0.003047 | ATF7IP2 |
| 58971731 | 59002413 | chr1 | − | exonic | hsa_circ_0000072 | −2.0887 | 0.003047 | OMA1 |
| 29119457 | 29120690 | chr17 | − | exonic | hsa_circ_0042860 | −1.5977 | 0.003063 | CRLF3 |
| 151111900 | 151112566 | chr1 | − | exonic | N/A | 1.5123 | 0.003064 | SEMA6C |
| 35604790 | 35614627 | chr6 | − | intronic | N/A | −1.8418 | 0.003119 | FKBP5 |
| 132426884 | 132428481 | chr5 | + | exonic | hsa_circ_0001531 | −1.6102 | 0.003132 | HSPA4 |
| 23375403 | 23378804 | chr14 | − | exonic | hsa_circ_0004137 | −2.4570 | 0.003138 | RBM23 |
| 47285639 | 47291842 | chr19 | − | exonic | hsa_circ_0051638 | 1.5968 | 0.003151 | SLC1A5 |
| 16435552 | 16437522 | chr9 | − | exonic | hsa_circ_0086414 | 1.5215 | 0.003171 | BNC2 |
| 34450934 | 34459751 | chr20 | + | exonic | hsa_circ_0060158 | −1.7472 | 0.003200 | PHF20 |
| 154736558 | 154754293 | chrX | − | exonic | hsa_circ_0007183 | −1.6075 | 0.003212 | TMLHE |
| 149905066 | 149905920 | chrX | + | exonic | hsa_circ_0006764 | −1.7183 | 0.003239 | MTMR1 |
| 17135209 | 17172162 | chr21 | + | exonic | N/A | −1.6347 | 0.003304 | USP25 |
| 24357988 | 24362320 | chr2 | + | exonic | hsa_circ_0007270 | −2.8884 | 0.003321 | FAM228B |
| 34614377 | 34622556 | chr6 | − | exonic | N/A | −1.5005 | 0.003340 | C6orf106 |
| 69785302 | 69804320 | chr10 | − | exonic | hsa_circ_0007113 | −1.6877 | 0.003397 | HERC4 |
| 9524591 | 9525849 | chr18 | + | exonic | hsa_circ_0005158 | −2.0718 | 0.003423 | RALBP1 |
| 55844499 | 55844644 | chr20 | − | antisense | hsa_circ_0001171 | 1.5533 | 0.003551 | BC037891 |
| 6172119 | 6219748 | chr12 | − | exonic | hsa_circ_0025114 | 1.8011 | 0.003554 | VWF |
| 31617887 | 31641951 | chr3 | + | exonic | hsa_circ_0003338 | −1.5924 | 0.003644 | STT3B |
| 151174418 | 151188100 | chr7 | − | exonic | hsa_circ_0082950 | −2.0352 | 0.003671 | RHEB |
| 41361767 | 41362745 | chr15 | − | exonic | hsa_circ_0007489 | −1.6312 | 0.003697 | INO80 |
| 26234499 | 26234709 | chr6 | − | sense overlapping | hsa_circ_0001589 | −2.2556 | 0.003795 | HIST1H1D |
| 115005725 | 115006178 | chr1 | − | exonic | hsa_circ_0013637 | −1.5236 | 0.003800 | TRIM33 |
| 35586872 | 35614627 | chr6 | − | intronic | hsa_circ_0001600 | −1.9440 | 0.003840 | FKBP5 |
| 51797729 | 51800460 | chr18 | + | exonic | hsa_circ_0007180 | −1.7137 | 0.003881 | POLI |
| 54921379 | 54925426 | chr17 | + | exonic | hsa_circ_0044709 | −1.5371 | 0.003885 | DGKE |
| 70847874 | 70856944 | chr10 | + | sense overlapping | hsa_circ_0000241 | −1.9723 | 0.003935 | SRGN |
| 122514815 | 122520660 | chr2 | + | exonic | hsa_circ_0003789 | −1.6196 | 0.003946 | TSN |
| 24840803 | 24841057 | chr1 | + | exonic | hsa_circ_0003553 | −1.6339 | 0.003980 | RCAN3 |
| 46622935 | 46623422 | chr12 | − | exonic | N/A | −- 1.6426 | 0.003994 | SLC38A1 |
| 2492063 | 2502465 | chr4 | + | exonic | hsa_circ_0004803 | −1.5544 | 0.004061 | RNF4 |
| 33095509 | 33111164 | chr13 | − | exonic | hsa_circ_0029937 | −2.6665 | 0.004099 | N4BP2L2 |
| 23631224 | 23636741 | chr3 | + | intronic | hsa_circ_0004555 | 1.7566 | 0.004216 | MIR548AC |
| 14880588 | 14882912 | chr11 | + | exonic | hsa_circ_0000278 | −1.5123 | 0.004230 | PDE3B |
| 124071293 | 124074996 | chr12 | + | exonic | hsa_circ_0000458 | −- 2.9320 | 0.004309 | TMED2 |
| 13579682 | 13584457 | chr6 | + | exonic | hsa_circ_0007218 | −1.9030 | 0.004360 | SIRT5 |
| 28003837 | 28004759 | chr17 | − | exonic | hsa_circ_0042817 | −1.8472 | 0.004373 | SSH2 |
| 38894089 | 38897285 | chr22 | − | exonic | hsa_circ_0063331 | −2.2401 | 0.004440 | DDX17 |
| 166141085 | 166160051 | chr4 | + | exonic | hsa_circ_0071374 | −2.6012 | 0.004458 | KLHL2 |
| 122514815 | 122519100 | chr2 | + | exonic | hsa_circ_0002847 | −1.8322 | 0.004467 | TSN |
| 18770594 | 18781183 | chr17 | + | exonic | hsa_circ_0042359 | −2.0386 | 0.004487 | PRPSAP2 |
| 6840578 | 6841154 | chr7 | − | exonic | hsa_circ_0007135 | −2.4122 | 0.004517 | CCZ1B |
| 381340 | 385707 | chr8 | + | exonic | N/A | −1.9091 | 0.004544 | FBXO25 |

TABLE 13-continued

| (BD 8 week vs Control 8 week) | | | | | | | | |
|---|---|---|---|---|---|---|---|---|
| TxStart | TxEnd | Chrom | Strand | circRNA type | Alias | Fold change | P-value | GeneSymbol |
| 6859878 | 6860842 | chr12 | − | exonic | hsa_circ_0025249 | 1.5720 | 0.004550 | MLF2 |
| 179972308 | 179975702 | chr1 | + | exonic | hsa_circ_0003942 | −1.6477 | 0.004563 | CEP350 |
| 28003837 | 28030080 | chr17 | − | exonic | hsa_circ_0000753 | −1.7793 | 0.004590 | SSH2 |
| 59204761 | 59205895 | chr15 | − | exonic | hsa_circ_0003713 | −2.3451 | 0.004661 | SLTM |
| 246754813 | 246755243 | chr1 | + | exonic | hsa_circ_0017310 | −1.6817 | 0.004666 | CNST |
| 19345732 | 19359646 | chr18 | + | exonic | hsa_circ_0000835 | −2.3964 | 0.004671 | MIB1 |
| 28290542 | 28310335 | chr22 | − | exonic | hsa_circ_0062688 | −1.5739 | 0.004701 | PITPNB |
| 96692646 | 96694138 | chr12 | − | exonic | hsa_circ_0007881 | −1.6004 | 0.004705 | CDK17 |
| 34312491 | 34313077 | chr20 | − | exonic | hsa_circ_0007632 | −2.1150 | 0.004725 | RBM39 |
| 139865173 | 139866645 | chr5 | + | exonic | hsa_circ_0074264 | 1.6685 | 0.004753 | ANKHD1 |
| 45773870 | 45780869 | chr2 | − | exonic | hsa_circ_0005542 | −2.5462 | 0.004757 | SRBD1 |
| 70251370 | 70253697 | chr11 | + | exonic | hsa_circ_0003376 | 1.5264 | 0.004763 | CTTN |
| 233651859 | 233660931 | chr2 | + | exonic | hsa_circ_0058733 | −1.6144 | 0.004858 | GIGYF2 |
| 72861593 | 72884813 | chr7 | − | exonic | hsa_circ_0001714 | 1.5034 | 0.004859 | BAZ1B |
| 23375403 | 23380612 | chr14 | − | exonic | hsa_circ_0031241 | −2.5710 | 0.004866 | RBM23 |
| 134381500 | 134382901 | chr9 | + | exonic | hsa_circ_0089237 | −1.7012 | 0.004906 | POMT1 |
| 73429657 | 73429763 | chr11 | − | exonic | hsa_circ_0023509 | −2.4600 | 0.004936 | RAB6A |
| 24357988 | 24369956 | chr2 | + | exonic | hsa_circ_0000982 | −3.0550 | 0.004973 | FAM228B |
| 76342171 | 76344097 | chr5 | + | exonic | hsa_circ_0008620 | −2.1019 | 0.004976 | AGGF1 |
| 108137897 | 108138069 | chr11 | + | exonic | hsa_circ_0007694 | −1.7689 | 0.005019 | ATM |
| 69585460 | 69590802 | chr2 | − | exonic | hsa_circ_0002863 | −1.5307 | 0.005020 | GFPT1 |
| 134381500 | 134381840 | chr9 | + | exonic | hsa_circ_0001897 | −2.2650 | 0.005040 | POMT1 |
| 73614502 | 73614802 | chr14 | + | exonic | hsa_circ_0008521 | −2.0607 | 0.005094 | PSEN1 |
| 10186276 | 10188722 | chr2 | + | exonic | N/A | −1.5581 | 0.005116 | KLF11 |
| 191765289 | 191775047 | chr2 | + | exonic | hsa_circ_0057521 | −2.0160 | 0.005139 | GLS |
| 202010100 | 202014558 | chr2 | + | exonic | hsa_circ_0001092 | −2.3209 | 0.005160 | CFLAR |
| 57197912 | 57207781 | chr16 | − | exonic | hsa_circ_0006886 | −3.1064 | 0.005169 | FAM192A |
| 28011580 | 28030080 | chr17 | − | exonic | hsa_circ_0000754 | −1.8810 | 0.005236 | SSH2 |
| 20511996 | 20527147 | chr2 | − | exonic | hsa_circ_0052870 | −1.5357 | 0.005245 | PUM2 |
| 179054762 | 179057224 | chr1 | + | exonic | N/A | 1.5059 | 0.005260 | TOR3A |
| 196129822 | 196134264 | chr3 | − | exonic | hsa_circ_0068655 | −2.6811 | 0.005294 | UBXN7 |
| 66293626 | 66313803 | chr3 | + | exonic | hsa_circ_0004113 | −1.8325 | 0.005354 | SLC25A26 |
| 196533449 | 196539722 | chr3 | + | exonic | hsa_circ_0004950 | −1.5050 | 0.005355 | PAK2 |
| 56600621 | 56601081 | chr3 | + | exonic | hsa_circ_0001312 | −2.3247 | 0.005377 | CCDC66 |
| 65922338 | 65931191 | chr14 | + | intronic | N/A | −1.6352 | 0.005486 | FUT8 |
| 42730785 | 42776781 | chr1 | − | exonic | hsa_circ_0004416 | −1.5196 | 0.005500 | FOXJ3 |
| 21645975 | 21663045 | chr18 | + | exonic | hsa_circ_0047274 | −1.7407 | 0.005503 | TTC39C |
| 14793482 | 14810788 | chr11 | + | exonic | hsa_circ_0000277 | −1.9900 | 0.005547 | PDE3B |
| 76342171 | 76344812 | chr5 | + | exonic | N/A | −1.5758 | 0.005626 | AGGF1 |
| 104714065 | 104717880 | chr7 | + | exonic | hsa_circ_0001736 | −3.3329 | 0.005668 | KMT2E |
| 65924470 | 65928135 | chr17 | + | exonic | hsa_circ_0045462 | −1.7786 | 0.005684 | BPTF |
| 45773870 | 45789895 | chr2 | − | exonic | hsa_circ_0000997 | −2.1759 | 0.005718 | SRBD1 |
| 33091993 | 33101669 | chr13 | − | exonic | hsa_circ_0000471 | 2.4879 | 0.005727 | N4BP2L2 |
| 155471301 | 155473602 | chr7 | + | exonic | hsa_circ_0083092 | −3.0509 | 0.005759 | RBM33 |
| 61205096 | 61205585 | chr11 | + | exonic | hsa_circ_0000311 | –– 1.6448 | 0.005766 | SDHAF2 |
| 62325639 | 62336454 | chr15 | − | exonic | hsa_circ_0005761 | −1.6990 | 0.005767 | VPS13C |
| 88918000 | 88919862 | chr9 | − | exonic | hsa_circ_0007037 | −2.0666 | 0.005787 | ZCCHC6 |
| 76166897 | 76167135 | chr17 | + | exonic | hsa_circ_0045871 | −1.5009 | 0.005807 | SYNGR2 |
| 34317233 | 34320057 | chr20 | − | exonic | hsa_circ_0008817 | −1.9735 | 0.005816 | RBM39 |
| 158552176 | 158557544 | chr7 | − | exonic | hsa_circ_0001776 | −2.2278 | 0.005836 | ESYT2 |
| 71590282 | 71597135 | chr2 | + | exonic | hsa_circ_0001028 | −2.0589 | 0.005862 | ZNF638 |
| 1080738 | 1080845 | chr1 | − | intergenic | hsa_circ_0000001 | 1.5832 | 0.005937 | |
| 50045984 | 50059076 | chr5 | + | exonic | hsa_circ_0005809 | −1.6806 | 0.005957 | PARP8 |
| 71492833 | 71502874 | chr14 | + | exonic | hsa_circ_0007996 | −1.6086 | 0.005962 | PCNX |
| 85737333 | 85742653 | chr11 | − | exonic | hsa_circ_0002433 | −3.0350 | 0.005982 | PICALM |
| 45740454 | 45745776 | chr17 | + | exonic | hsa_circ_0002854 | −1.5859 | 0.005988 | KPNB1 |
| 76152218 | 76175765 | chr15 | + | exonic | hsa_circ_0036374 | −1.6764 | 0.006037 | UBE2Q2 |
| 107260799 | 107289013 | chr11 | − | exonic | hsa_circ_0006868 | −1.7977 | 0.006088 | CWF19L2 |
| 208589523 | 208607066 | chr2 | + | exonic | hsa_circ_0002556 | −1.5997 | 0.006097 | CCNYL1 |
| 48573339 | 48573890 | chr2 | + | exonic | hsa_circ_0001002 | −1.6612 | 0.006131 | FOXN2 |
| 80071512 | 80088663 | chr5 | + | exonic | hsa_circ_0001508 | −2.2277 | 0.006147 | MSH3 |
| 11958205 | 11984847 | chr17 | + | exonic | hsa_circ_0007508 | −2.4574 | 0.006230 | MAP2K4 |
| 88190229 | 88211364 | chr9 | − | exonic | hsa_circ_0005202 | −2.3305 | 0.006256 | AGTPBP1 |
| 151167656 | 151195266 | chr7 | − | exonic | N/A | −1.5092 | 0.006260 | RHEB |
| 122881110 | 122893258 | chr5 | + | exonic | hsa_circ_0001522 | −2.8156 | 0.006340 | CSNK1G3 |
| 5268416 | 5271763 | chr17 | + | exonic | hsa_circ_0004621 | −1.5650 | 0.006355 | RABEP1 |
| 63821212 | 63829355 | chr15 | + | exonic | hsa_circ_0008104 | −1.6956 | 0.006407 | USP3 |
| 77336007 | 77336863 | chr11 | − | exonic | hsa_circ_0000343 | −2.1429 | 0.006417 | CLNS1A |
| 99220665 | 99220823 | chr9 | + | sense overlapping | N/A | −1.6888 | 0.006423 | HABP4 |
| 49694940 | 49707217 | chr5 | − | sense overlapping | hsa_circ_0001481 | −3.7182 | 0.006462 | EMB |
| 88307603 | 88327481 | chr9 | − | exonic | hsa_circ_0007351 | −2.2323 | 0.006488 | AGTPBP1 |
| 17270204 | 17273932 | chr19 | + | exonic | hsa_circ_0007396 | −1.7978 | 0.006490 | MYO9B |
| 23371395 | 23380612 | chr14 | − | exonic | hsa_circ_0031235 | 2.8227 | 0.006584 | RBM23 |

TABLE 13-continued (BD 8 week vs Control 8 week)

| TxStart | TxEnd | Chrom | Strand | circRNA type | Alias | Fold change | P-value | GeneSymbol |
|---|---|---|---|---|---|---|---|---|
| 28811231 | 28819771 | chr17 | + | exonic | hsa_circ_0007460 | −1.6414 | 0.006599 | GOSR1 |
| 128655032 | 128658211 | chr7 | − | exonic | hsa_circ_0001741 | −2.1708 | 0.006599 | TNPO3 |
| 20811404 | 20811554 | chr14 | − | sense overlapping | hsa_circ_0000518 | −2.6755 | 0.006607 | RPPH1 |
| 153640928 | 153642354 | chr1 | − | exonic | hsa_circ_0014280 | 2.0174 | 0.006624 | ILF2 |
| 128995614 | 128996148 | chr4 | + | exonic | hsa_circ_0070933 | −1.8661 | 0.006629 | LARP1B |
| 50045984 | 50074484 | chr5 | + | exonic | hsa_circ_0072430 | −1.9192 | 0.006649 | PARP8 |
| 31617887 | 31621588 | chr3 | + | exonic | hsa_circ_0001278 | −1.7538 | 0.006665 | STT3B |
| 26204839 | 26205043 | chr6 | + | sense overlapping | hsa_circ_0001588 | −2.9154 | 0.006674 | HIST1H4E |
| 20975317 | 20976684 | chr19 | + | exonic | N/A | −1.7388 | 0.006685 | ZNF66 |
| 133734285 | 133769540 | chr8 | − | exonic | hsa_circ_0008205 | −2.0374 | 0.006712 | TMEM71 |
| 45715378 | 45780869 | chr2 | − | exonic | N/A | −2.3798 | 0.006738 | SRBD1 |
| 109466421 | 109468140 | chr6 | + | exonic | hsa_circ_0004131 | −1.5393 | 0.006764 | CEP57L1 |
| 243056789 | 243064606 | chr2 | + | exonic | N/A | −1.6695 | 0.006835 | LOC728323 |
| 28408513 | 28460682 | chr12 | + | exonic | N/A | −2.3402 | 0.006835 | CCDC91 |
| 119219541 | 119222868 | chr3 | + | exonic | hsa_circ_0001329 | −2.1144 | 0.006844 | TIMMDC1 |
| 4763319 | 4763528 | chr20 | + | antisense | hsa_circ_0001128 | 1.5482 | 0.006912 | RASSF2 |
| 17273159 | 17273932 | chr19 | + | exonic | hsa_circ_0000909 | −1.7914 | 0.007045 | MYO9B |
| 18877942 | 18882804 | chr16 | − | exonic | hsa_circ_0038288 | −1.8285 | 0.007052 | SMG1 |
| 1125950 | 1126416 | chr10 | + | exonic | hsa_circ_0004277 | −1.7349 | 0.007059 | WDR37 |
| 77631183 | 77632364 | chr9 | − | exonic | hsa_circ_0004189 | −1.8794 | 0.007075 | C9orf41 |
| 14057494 | 14068652 | chr1 | + | exonic | hsa_circ_0005986 | −2.4678 | 0.007107 | PRDM2 |
| 247318867 | 247323115 | chr1 | − | sense overlapping | hsa_circ_0002922 | −2.0274 | 0.007141 | ZNF124 |
| 77327195 | 77340944 | chr11 | − | exonic | hsa_circ_0023690 | −1.7884 | 0.007228 | CLNS1A |
| 65078566 | 65082233 | chr12 | + | exonic | N/A | −1.5132 | 0.007228 | RASSF3 |
| 95606995 | 95608085 | chr14 | − | exonic | hsa_circ_0000564 | −1.5011 | 0.007334 | DICER1 |
| 86494712 | 86508177 | chr14 | + | intronic | N/A | −1.6068 | 0.007359 | LOC101928767 |
| 31661946 | 31791437 | chr10 | + | exonic | hsa_circ_0004126 | −1.6409 | 0.007385 | ZEB1 |
| 133740043 | 133769540 | chr8 | − | exonic | hsa_circ_0006050 | −1.6723 | 0.007454 | TMEM71 |
| 68590619 | 68609870 | chr5 | − | exonic | hsa_circ_0001496 | −1.6370 | 0.007458 | CCDC125 |
| 179007947 | 179020646 | chr5 | + | exonic | N/A | −1.9547 | 0.007470 | RUFY1 |
| 25650607 | 25654354 | chr15 | − | exonic | hsa_circ_0034168 | −2.0261 | 0.007504 | UBE3A |
| 21117754 | 21120167 | chr19 | + | intronic | N/A | −1.9363 | 0.007555 | ZNF85 |
| 10031484 | 10035530 | chrX | + | exonic | hsa_circ_0007685 | −1.6564 | 0.007557 | WWC3 |
| 141231004 | 141259451 | chr3 | + | exonic | hsa_circ_0067582 | −1.7061 | 0.007581 | RASA2 |
| 119222378 | 119222868 | chr3 | + | exonic | hsa_circ_0008394 | −2.0002 | 0.007620 | TIMMDC1 |
| 34978930 | 35006275 | chr11 | + | exonic | hsa_circ_0003768 | −1.7015 | 0.007643 | PDHX |
| 49609654 | 49613024 | chr10 | + | exonic | hsa_circ_0018315 | −2.0064 | 0.007686 | MAPK8 |
| 19615443 | 19626289 | chr12 | + | exonic | hsa_circ_0006420 | −2.0422 | 0.007691 | AEBP2 |
| 99001020 | 99002576 | chr7 | − | exonic | N/A | −2.4407 | 0.007696 | PDAP1 |
| 53196123 | 53201713 | chr13 | + | exonic | hsa_circ_0008868 | 2.1859 | 0.007697 | HNRNPA1L2 |
| 153413350 | 153414506 | chr5 | − | exonic | hsa_circ_0007691 | −2.0897 | 0.007722 | FAM114A2 |
| 140961878 | 140963182 | chr5 | − | exonic | hsa_circ_0008982 | −1.6615 | 0.007782 | DIAPH1 |
| 103558598 | 103567658 | chr10 | − | exonic | hsa_circ_0019612 | −1.9293 | 0.007831 | MGEA5 |
| 111883774 | 111890244 | chr10 | + | exonic | hsa_circ_0003357 | −2.2553 | 0.007832 | ADD3 |
| 34093272 | 34093534 | chr11 | + | exonic | hsa_circ_0008227 | −1.8078 | 0.007868 | CAPRIN1 |
| 201966446 | 201969143 | chr1 | + | exonic | hsa_circ_0015962 | 1.6027 | 0.007875 | RNPEP |
| 118451960 | 118455359 | chr11 | + | exonic | hsa_circ_0006374 | −1.8200 | 0.007888 | ARCN1 |
| 59204761 | 59209198 | chr15 | − | exonic | hsa_circ_0000605 | −2.2554 | 0.007888 | SLTM |
| 98673299 | 98703416 | chr8 | + | exonic | hsa_circ_0002114 | −1.5453 | 0.007946 | MTDH |
| 23378691 | 23380612 | chr14 | − | exonic | hsa_circ_0000524 | −3.1070 | 0.007957 | RBM23 |
| 72604105 | 72607065 | chr7 | + | exonic | hsa_circ_0007927 | −1.5892 | 0.007982 | GTF2IP1 |
| 46083263 | 46083463 | chr1 | + | intronic | hsa_circ_0092293 | −1.6031 | 0.007986 | NASP |
| 29959413 | 29962002 | chr8 | + | exonic | hsa_circ_0007353 | −1.5282 | 0.008007 | LEPROTL1 |
| 91723962 | 91727541 | chr9 | − | sense overlapping | hsa_circ_0007738 | 1.9773 | 0.008020 | SHC3 |
| 117788564 | 117788924 | chrX | + | exonic | hsa_circ_0007733 | −1.5435 | 0.008079 | DOCK11 |
| 127965678 | 127983624 | chr3 | + | exonic | hsa_circ_0067209 | 2.2965 | 0.008118 | EEFSEC |
| 35586872 | 35610620 | chr6 | − | exonic | hsa_circ_0001599 | −2.0096 | 0.008128 | FKBP5 |
| 151181822 | 151188100 | chr7 | − | exonic | hsa_circ_0082951 | −1.7411 | 0.008144 | RHEB |
| 80063751 | 80088663 | chr5 | + | exonic | hsa_circ_0073177 | −1.8326 | 0.008166 | MSH3 |
| 208841374 | 208842310 | chr2 | − | exonic | hsa_circ_0001095 | −1.6344 | 0.008187 | PLEKHM3 |
| 11984672 | 12016677 | chr17 | + | exonic | hsa_circ_0007456 | −2.0190 | 0.008196 | MAP2K4 |
| 59204757 | 59209198 | chr15 | − | sense overlapping | N/A | −2.1632 | 0.008197 | SLTM |
| 8520288 | 8528570 | chr19 | + | exonic | hsa_circ_0006382 | −2.2906 | 0.008207 | HNRNPM |
| 9991948 | 9995685 | chr1 | − | exonic | hsa_circ_0007803 | −1.7768 | 0.008210 | LZIC |
| 18419661 | 18462483 | chr3 | − | exonic | hsa_circ_0064555 | −1.7718 | 0.008226 | SATB1 |
| 129913321 | 129925031 | chr4 | − | exonic | hsa_circ_0001439 | −2.3810 | 0.008236 | SCLT1 |
| 46633461 | 46633676 | chr12 | − | exonic | N/A | −2.3214 | 0.008240 | SLC38A1 |
| 31661953 | 31676727 | chr10 | + | intronic | N/A | −1.8109 | 0.008262 | ZEB1 |
| 19701940 | 19713859 | chrX | − | exonic | hsa_circ_0001913 | −1.6515 | 0.008273 | SH3KBP1 |
| 75167801 | 75173934 | chr11 | − | exonic | hsa_circ_0023624 | 1.5200 | 0.008284 | GDPD5 |

TABLE 13-continued

| (BD 8 week vs Control 8 week) | | | | | | | | |
|---|---|---|---|---|---|---|---|---|
| TxStart | TxEnd | Chrom | Strand | circRNA type | Alias | Fold change | P-value | GeneSymbol |
| 76344422 | 76388643 | chr6 | + | exonic | hsa_circ_0001613 | −2.1021 | 0.008380 | SENP6 |
| 202010100 | 202013775 | chr2 | + | exonic | hsa_circ_0057748 | −2.0932 | 0.008414 | CFLAR |
| 196118683 | 196129890 | chr3 | − | exonic | hsa_circ_0001380 | −2.0627 | 0.008445 | UBXN7 |
| 176085759 | 176105683 | chr1 | − | exonic | hsa_circ_0015373 | −1.5752 | 0.008504 | RFWD2 |
| 62864579 | 62865284 | chr17 | − | exonic | hsa_circ_0045337 | −1.8780 | 0.008505 | LRRC37A3 |
| 70193988 | 70195501 | chr12 | + | exonic | hsa_circ_0000419 | −1.8658 | 0.008571 | RAB3IP |
| 44054401 | 44054671 | chr1 | + | exonic | hsa_circ_0012077 | −2.4578 | 0.008591 | PTPRF |
| 29313942 | 29323831 | chr1 | + | exonic | hsa_circ_0011168 | −1.5546 | 0.008657 | EPB41 |
| 68434283 | 68439038 | chr15 | + | exonic | hsa_circ_0008378 | −1.5223 | 0.008661 | PIAS1 |
| 197592293 | 197602646 | chr3 | + | exonic | hsa_circ_0008351 | −2.4894 | 0.008715 | LRCH3 |
| 19358063 | 19359646 | chr18 | + | exonic | hsa_circ_0008190 | −2.0985 | 0.008785 | MIB1 |
| 34952950 | 35006275 | chr11 | + | exonic | hsa_circ_0021708 | −1.6482 | 0.008814 | PDHX |
| 111738706 | 111739797 | chr1 | − | intronic | N/A | 1.5679 | 0.008815 | DENND2D |
| 20811436 | 20811534 | chr14 | − | sense overlapping | hsa_circ_0000519 | −1.6194 | 0.008828 | RPPH1 |
| 103432671 | 103436193 | chr10 | − | exonic | hsa_circ_0000255 | −1.6538 | 0.008867 | FBXW4 |
| 20507738 | 20527139 | chr2 | − | exonic | hsa_circ_0052867 | −1.8152 | 0.008891 | PUM2 |
| 85722072 | 85742653 | chr11 | − | exonic | hsa_circ_0000347 | −2.8443 | 0.008942 | PICALM |
| 129913321 | 129960251 | chr4 | − | exonic | hsa_circ_0001440 | −2.0934 | 0.008944 | SCLT1 |
| 108098321 | 108106561 | chr11 | + | exonic | hsa_circ_0003641 | −1.8783 | 0.009033 | ATM |
| 14685190 | 14685289 | chr12 | + | intronic | hsa_circ_0000379 | 1.7658 | 0.009045 | RP11-502N13.2 |
| 72157634 | 72161556 | chr5 | + | exonic | hsa_circ_0002692 | −1.6214 | 0.009063 | TNPO1 |
| 116668237 | 116675510 | chr12 | − | sense overlapping | hsa_circ_0000442 | −2.1162 | 0.009161 | MED13L |
| 155465560 | 155473602 | chr7 | + | exonic | hsa_circ_0001772 | −3.1163 | 0.009173 | RBM33 |
| 38890634 | 38897285 | chr22 | − | exonic | hsa_circ_0002211 | −2.4374 | 0.009181 | DDX17 |
| 34241449 | 34246936 | chr20 | − | intronic | hsa_circ_0001146 | −1.7677 | 0.009222 | CPNE1 |
| 71942238 | 71942518 | chr11 | + | intronic | N/A | 1.7808 | 0.009302 | INPPL1 |
| 24075537 | 24075871 | chrX | + | exonic | N/A | −1.5382 | 0.009311 | EIF283 |
| 27747415 | 27747744 | chr1 | + | antisense | hsa_circ_0000035 | 1.5112 | 0.009314 | WASF2 |
| 90376995 | 90419967 | chr7 | + | exonic | hsa_circ_0001722 | −1.8587 | 0.009315 | CDK14 |
| 54127017 | 54128696 | chr2 | − | exonic | N/A | −1.5350 | 0.009333 | PSME4 |
| 103610730 | 103651893 | chr4 | − | sense overlapping | hsa_circ_0001431 | −1.5237 | 0.009340 | MANBA |
| 9991948 | 9994918 | chr1 | − | exonic | hsa_circ_0000014 | −1.5007 | 0.009384 | LZIC |
| 37126308 | 37126939 | chr9 | + | exonic | hsa_circ_0001860 | −2.4074 | 0.009415 | ZCCHC7 |
| 20026088 | 20027464 | chr19 | + | exonic | hsa_circ_0050273 | −1.5048 | 0.009435 | ZNF93 |
| 53430497 | 53430825 | chrX | − | exonic | hsa_circ_0001921 | −2.2393 | 0.009462 | SMC1A |
| 14643337 | 14643566 | chr10 | − | intronic | hsa_circ_0000217 | −1.7090 | 0.009498 | FAM107B |
| 68590619 | 68607031 | chr5 | − | exonic | hsa_circ_0072780 | −1.5715 | 0.009501 | CCDC125 |
| 155691307 | 155695810 | chr1 | + | exonic | hsa_circ_0014613 | −2.1516 | 0.009527 | DAP3 |
| 31661946 | 31750166 | chr10 | + | exonic | hsa_circ_0000230 | −1.8255 | 0.009558 | ZEB1 |
| 108057208 | 108061227 | chr11 | − | exonic | N/A | −1.6349 | 0.009577 | NPAT |
| 142264087 | 142264728 | chr8 | − | exonic | hsa_circ_0001829 | −2.1320 | 0.009579 | SLC45A4 |
| 50741596 | 50763992 | chr15 | + | exonic | hsa_circ_0000599 | −1.6489 | 0.009601 | USP8 |
| 149563797 | 149570383 | chr3 | + | exonic | hsa_circ_0006697 | −2.7405 | 0.009610 | RNF13 |
| 30495147 | 30495584 | chr16 | + | exonic | hsa_circ_0000690 | −2.2768 | 0.009611 | ITGAL |
| 23015828 | 23030758 | chr7 | − | exonic | hsa_circ_0005251 | −1.5492 | 0.009621 | FAM126A |
| 239082174 | 239093928 | chr2 | − | exonic | hsa_circ_0006014 | −1.6672 | 0.009680 | ILKAP |
| 124997967 | 125032500 | chr3 | − | exonic | hsa_circ_0067100 | −1.9916 | 0.009687 | ZNF148 |
| 134508189 | 134509862 | chr5 | + | sense overlapping | hsa_circ_0006652 | 1.6270 | 0.009698 | C5orf66 |
| 158580694 | 158591763 | chr7 | − | exonic | hsa_circ_0001777 | −1.7064 | 0.009699 | ESYT2 |
| 27822449 | 27824309 | chr2 | + | exonic | hsa_circ_0000985 | −1.7978 | 0.009736 | ZNF512 |
| 52192351 | 52194233 | chr15 | + | exonic | hsa_circ_0004773 | −1.6027 | 0.009753 | TMOD3 |
| 37126308 | 37127260 | chr9 | + | intronic | N/A | −1.5804 | 0.009758 | ZCCHC7 |
| 51860052 | 51913807 | chr1 | − | exonic | hsa_circ_0012425 | −1.6182 | 0.009834 | EPS15 |
| 85718584 | 85742653 | chr11 | − | exonic | hsa_circ_0023936 | −2.8745 | 0.009849 | PICALM |
| 24663284 | 24708279 | chr7 | + | exonic | hsa_circ_0001686 | −1.9218 | 0.009871 | MPP6 |
| 38253957 | 38259261 | chr7 | + | exonic | N/A | 1.5131 | 0.009876 | STARD3NL |
| 1125950 | 1132297 | chr10 | + | exonic | hsa_circ_0017446 | −2.2364 | 0.009881 | WDR37 |
| 810107 | 814799 | chr7 | + | exonic | hsa_circ_0001667 | 1.9202 | 0.009909 | DNAAF5 |
| 5604593 | 5604947 | chr19 | − | exonic | hsa_circ_0000880 | −1.5396 | 0.009927 | SAFB2 |
| 85685750 | 85742653 | chr11 | − | exonic | hsa_circ_0023891 | −2.3538 | 0.009929 | PICALM |
| 71071739 | 71075089 | chr8 | − | exonic | hsa_circ_0001810 | −1.6562 | 0.009958 | NCOA2 |
| 85707868 | 85718626 | chr11 | − | exonic | hsa_circ_0023920 | −2.9939 | 0.009967 | PICALM |
| 101910475 | 101911643 | chr2 | − | exonic | hsa_circ_0001058 | −2.0897 | 0.010023 | RNF149 |
| 98921663 | 98931350 | chr12 | + | exonic | hsa_circ_0003517 | −1.6783 | 0.010043 | TMPO |
| 32749557 | 32764217 | chr12 | + | sense overlapping | hsa_circ_0000389 | −2.2066 | 0.010076 | FGD4 |
| 118451960 | 118454073 | chr11 | + | exonic | N/A | −1.7046 | 0.010108 | ARCN1 |
| 100078957 | 100081447 | chr2 | − | exonic | hsa_circ_0001053 | −1.7091 | 0.010186 | REV1 |
| 91855033 | 91855996 | chr7 | − | exonic | N/A | −1.5695 | 0.010192 | KRIT1 |
| 80537076 | 80546772 | chr9 | − | sense overlapping | N/A | −2.0744 | 0.010212 | GNAQ |

TABLE 13-continued (BD 8 week vs Control 8 week)

| TxStart | TxEnd | Chrom | Strand | circRNA type | Alias | Fold change | P-value | GeneSymbol |
|---|---|---|---|---|---|---|---|---|
| 47887514 | 47888016 | chr4 | − | exonic | hsa_circ_0069655 | 1.6221 | 0.010225 | NFXL1 |
| 56277780 | 56284152 | chr4 | + | exonic | hsa_circ_0001414 | 2.3889 | 0.010237 | TMEM165 |
| 123924133 | 123928458 | chr9 | + | exonic | hsa_circ_0088333 | −1.9621 | 0.010263 | CNTRL |
| 36492117 | 36507981 | chr6 | − | exonic | N/A | −2.4083 | 0.010293 | STK38 |
| 47768925 | 47769734 | chr21 | + | exonic | hsa_circ_0002903 | −1.8680 | 0.010319 | PCNT |
| 37727937 | 37735069 | chr8 | − | exonic | hsa_circ_0005630 | −1.5455 | 0.010430 | RAB11FIP1 |
| 37126308 | 37147442 | chr9 | + | intronic | N/A | −2.1584 | 0.010467 | ZCCHC7 |
| 107528605 | 107535189 | chr9 | + | exonic | hsa_circ_0087800 | 1.6807 | 0.010517 | NIPSNAP3B |
| 110062421 | 110068928 | chr9 | + | exonic | hsa_circ_0087855 | −1.8259 | 0.010549 | RAD23B |
| 129960195 | 130003528 | chr4 | − | exonic | N/A | −1.5397 | 0.010600 | SOLT1 |
| 47779518 | 47787483 | chr3 | − | exonic | hsa_circ_0065308 | −1.7087 | 0.010653 | SMARCC1 |
| 31139461 | 31144271 | chr14 | + | exonic | hsa_circ_0009140 | −1.7899 | 0.010653 | SCFD1 |
| 9204473 | 9211782 | chr18 | + | exonic | hsa_circ_0000827 | −2.8353 | 0.010697 | ANKRD12 |
| 85723323 | 85742653 | chr11 | − | exonic | hsa_circ_0023940 | −3.1896 | 0.010699 | PICALM |
| 68300495 | 68300624 | chr16 | + | exonic | hsa_circ_0039943 | −1.5452 | 0.010744 | SLC7A6 |
| 112321531 | 112337371 | chr5 | + | exonic | hsa_circ_0073608 | −1.8237 | 0.010760 | DCP2 |
| 57814813 | 57816308 | chr17 | + | exonic | hsa_circ_0044875 | −2.4573 | 0.010780 | VMP1 |
| 140037802 | 140046483 | chr4 | − | exonic | N/A | −1.6217 | 0.010812 | ELF2 |
| 96717725 | 96728643 | chr12 | − | exonic | hsa_circ_0002762 | −1.5139 | 0.010844 | CDK17 |
| 22255610 | 22256366 | chr19 | + | exonic | hsa_circ_0050301 | −1.6612 | 0.010847 | ZNF257 |
| 38991050 | 38996984 | chr5 | − | exonic | hsa_circ_0072338 | −1.5511 | 0.010895 | RICTOR |
| 154315413 | 154318485 | chr4 | + | exonic | hsa_circ_0006225 | −1.5246 | 0.010911 | MND1 |
| 42812236 | 42814457 | chr8 | + | exonic | hsa_circ_0084162 | −1.5754 | 0.010976 | HOOK3 |
| 119219541 | 119236162 | chr3 | + | exonic | hsa_circ_0066874 | −1.9037 | 0.010976 | TIMMDC1 |
| 211952259 | 211961069 | chr1 | − | exonic | N/A | −1.8691 | 0.010987 | LPGAT1 |
| 51804072 | 51813781 | chr18 | + | exonic | hsa_circ_0003428 | −1.6029 | 0.011027 | POLI |
| 33606862 | 33613800 | chr18 | − | exonic | hsa_circ_0000842 | −1.6512 | 0.011036 | RPRD1A |
| 20811404 | 20811492 | chr14 | − | sense overlapping | hsa_circ_0000517 | −2.6208 | 0.011063 | RPPH1 |
| 113196219 | 113202401 | chr1 | + | exonic | hsa_circ_0000109 | −1.7243 | 0.011144 | CAPZA1 |
| 64004084 | 64004810 | chr7 | − | exonic | hsa_circ_0002566 | −1.8010 | 0.011156 | ZNF680 |
| 79613111 | 79614128 | chr10 | − | exonic | hsa_circ_0006649 | −1.5524 | 0.011161 | DLG5 |
| 9195548 | 9221997 | chr18 | + | exonic | hsa_circ_0046843 | −2.9322 | 0.011166 | ANKRD12 |
| 47127684 | 47139571 | chr3 | − | exonic | N/A | −1.7241 | 0.011177 | SETD2 |
| 125032151 | 125032500 | chr3 | − | exonic | hsa_circ_0067103 | −1.5989 | 0.011195 | ZNF148 |
| 74148264 | 74149874 | chr7 | + | exonic | N/A | −1.6710 | 0.011351 | GTF21 |
| 56626997 | 56628056 | chr3 | + | exonic | hsa_circ_0001313 | −2.4319 | 0.011389 | CCDC66 |
| 21644103 | 21649235 | chr18 | + | exonic | hsa_circ_0000839 | −1.8403 | 0.011396 | TTC39C |
| 29313942 | 29314417 | chr1 | + | exonic | hsa_circ_0011167 | −1.5782 | 0.011430 | EPB41 |
| 58275961 | 58316858 | chr2 | + | exonic | N/A | −1.6817 | 0.011521 | VRK2 |
| 77611362 | 77632364 | chr9 | − | exonic | hsa_circ_0087220 | −2.0058 | 0.011544 | C9orf41 |
| 37633006 | 37640126 | chr4 | − | exonic | hsa_circ_0001400 | −3.1521 | 0.011552 | RELL1 |
| 7837219 | 7841492 | chr1 | + | exonic | hsa_circ_0009548 | −2.1464 | 0.011584 | VAMP3 |
| 169840378 | 169843795 | chr3 | − | sense overlapping | hsa_circ_0007854 | −2.1181 | 0.011605 | PHC3 |
| 159004985 | 159006457 | chr6 | + | exonic | hsa_circ_0003345 | −1.7005 | 0.011648 | TMEM181 |
| 72205086 | 72222904 | chr4 | + | exonic | hsa_circ_0008676 | 1.5493 | 0.011662 | SLC4A4 |
| 46067916 | 46098727 | chr22 | + | exonic | hsa_circ_0063763 | −1.5658 | 0.011681 | ATXN10 |
| 69726439 | 69752439 | chr10 | − | exonic | hsa_circ_0003308 | −1.7505 | 0.011734 | HERC4 |
| 196118683 | 196129888 | chr3 | − | intronic | N/A | −1.9017 | 0.011749 | UBXN7 |
| 65471271 | 65472542 | chr15 | − | exonic | hsa_circ_0004374 | −1.5800 | 0.011774 | CLPX |
| 120916382 | 120930794 | chr11 | + | exonic | hsa_circ_0003302 | −2.0326 | 0.011783 | TBCEL |
| 61707544 | 61714152 | chr8 | + | exonic | N/A | −2.0768 | 0.011797 | CHD7 |
| 247322307 | 247323115 | chr1 | − | exonic | hsa_circ_0017348 | −1.8988 | 0.011808 | ZNF124 |
| 86328535 | 86329135 | chr6 | − | exonic | hsa_circ_0006131 | −1.7285 | 0.011821 | SYNCRIP |
| 85692787 | 85737409 | chr11 | − | exonic | hsa_circ_0023908 | −2.7090 | 0.011840 | PICALM |
| 155457868 | 155473602 | chr7 | + | exonic | hsa_circ_0001771 | −2.1724 | 0.011848 | RBM33 |
| 133907680 | 133914026 | chr3 | − | exonic | hsa_circ_0005768 | −1.7210 | 0.011854 | RYK |
| 113196219 | 113212227 | chr1 | + | exonic | hsa_circ_0013533 | −1.6005 | 0.011878 | CAPZA1 |
| 59805629 | 59844509 | chr1 | + | exonic | hsa_circ_0006633 | −2.0004 | 0.011898 | FGGY |
| 18846213 | 18856973 | chr16 | − | exonic | hsa_circ_0038258 | −1.7649 | 0.011913 | SMG1 |
| 59963381 | 59964938 | chr15 | − | exonic | hsa_circ_0035537 | −1.5504 | 0.011932 | BNIP2 |
| 64096074 | 64100213 | chr5 | + | exonic | N/A | −1.7618 | 0.011948 | CWC27 |
| 67356836 | 67371058 | chr1 | − | exonic | hsa_circ_0006677 | −1.5401 | 0.011957 | WDR78 |
| 21319681 | 21324846 | chr20 | + | exonic | hsa_circ_0001134 | −1.5347 | 0.011975 | XRN2 |
| 25650607 | 25657118 | chr15 | − | exonic | hsa_circ_0000586 | −1.9131 | 0.011991 | UBE3A |
| 59805629 | 59812070 | chr1 | + | exonic | hsa_circ_0000076 | −2.0937 | 0.012056 | FGGY |
| 76412360 | 76412788 | chr6 | + | exonic | hsa_circ_0001614 | −1.7026 | 0.012059 | SENP6 |
| 167915606 | 167919852 | chr5 | + | exonic | hsa_circ_0009145 | −2.0850 | 0.012081 | RARS |
| 104925455 | 104937980 | chr7 | − | intronic | hsa_circ_0003656 | −1.5260 | 0.012092 | SRPK2 |
| 211952259 | 211966532 | chr1 | − | exonic | hsa_circ_0002274 | −1.8539 | 0.012111 | LPGAT1 |
| 52773420 | 52773806 | chr8 | − | exonic | hsa_circ_0001802 | −2.9826 | 0.012130 | PCMTD1 |
| 17205666 | 17214859 | chr21 | + | exonic | hsa_circ_0005238 | −1.8629 | 0.012155 | USP25 |
| 6776706 | 6777567 | chr7 | + | exonic | hsa_circ_0007607 | −1.5176 | 0.012187 | PMS2CL |
| 101550654 | 101551042 | chr15 | + | exonic | hsa_circ_0037078 | 1.6928 | 0.012301 | LRRK1 |

TABLE 13-continued (BD 8 week vs Control 8 week)

| TxStart | TxEnd | Chrom | Strand | circRNA type | Alias | Fold change | P-value | GeneSymbol |
|---|---|---|---|---|---|---|---|---|
| 21698477 | 21702388 | chr14 | – | exonic | hsa_circ_0003643 | –1.9042 | 0.012372 | HNRNPC |
| 86292641 | 86293514 | chr9 | – | exonic | hsa_circ_0001865 | –2.0831 | 0.012387 | UBQLN1 |
| 28163979 | 28167848 | chr16 | – | exonic | hsa_circ_0007807 | –– 1.6604 | 0.012428 | XPO6 |
| 33099245 | 33099673 | chr1 | – | exonic | hsa_circ_0011426 | –1.6838 | 0.012440 | ZBTB8OS |
| 31644075 | 31676727 | chr10 | + | intronic | hsa_circ_0002765 | –1.7387 | 0.012451 | ZEB1 |
| 35846859 | 35854683 | chr1 | + | exonic | hsa_circ_0000051 | –1.5066 | 0.012506 | ZMYM4 |
| 114397092 | 114397671 | chr1 | – | exonic | hsa_circ_0013609 | –2.0538 | 0.012517 | PTPN22 |
| 57842331 | 57851305 | chr17 | + | intronic | N/A | –2.0538 | 0.012520 | VMP1 |
| 62188226 | 62188541 | chr14 | + | exonic | hsa_circ_0007976 | –1.5828 | 0.012542 | HIF1A |
| 118656760 | 118657227 | chr11 | – | exonic | hsa_circ_0004293 | –2.1044 | 0.012545 | DDX6 |
| 27975161 | 27977818 | chr17 | – | exonic | hsa_circ_0042799 | –1.9939 | 0.012561 | SSH2 |
| 79940776 | 79940857 | chr13 | + | antisense | hsa_circ_0000499 | 1.7038 | 0.012593 | RBM26 |
| 10031484 | 10066619 | chrX | + | exonic | hsa_circ_0001910 | –2.0023 | 0.012616 | WWC3 |
| 197592293 | 197598333 | chr3 | + | exonic | hsa_circ_0008106 | –1.6172 | 0.012657 | LRCH3 |
| 21698477 | 21699231 | chr14 | – | exonic | hsa_circ_0031147 | –1.6831 | 0.012673 | HNRNPC |
| 45695715 | 45696530 | chr17 | + | exonic | hsa_circ_0004622 | –1.5350 | 0.012781 | NPEPPS |
| 85742510 | 85742653 | chr11 | – | exonic | hsa_circ_0023944 | –2.7786 | 0.012806 | PICALM |
| 77330650 | 77340944 | chr11 | – | exonic | hsa_circ_0008342 | –1.6340 | 0.012817 | CLNS1A |
| 23023562 | 23030758 | chr7 | – | exonic | hsa_circ_0001682 | –2.1744 | 0.012842 | FAM126A |
| 29432408 | 29432626 | chr18 | – | exonic | hsa_circ_0000841 | –1.5347 | 0.012847 | TRAPPC8 |
| 85701292 | 85742653 | chr11 | – | exonic | hsa_circ_0023918 | –2.0028 | 0.012876 | PICALM |
| 139818912 | 139820329 | chr7 | – | exonic | N/A | –1.5068 | 0.012918 | KDM7A |
| 58755107 | 58755971 | chr20 | + | intronic | hsa_circ_0001174 | –1.8430 | 0.012946 | RP5-1043L13.1 |
| 108243000 | 108250718 | chr6 | – | exonic | hsa_circ_0001635 | –2.3553 | 0.012947 | SEC63 |
| 47762155 | 47787483 | chr3 | – | exonic | hsa_circ_0065301 | –1.5063 | 0.012957 | SMARCC1 |
| 38792600 | 38868560 | chr21 | + | exonic | hsa_circ_0061694 | –2.7439 | 0.012965 | DYRK1A |
| 74561481 | 74563895 | chr18 | + | exonic | hsa_circ_0004979 | –1.7239 | 0.013021 | ZNF236 |
| 114202540 | 114239805 | chr2 | + | exonic | N/A | –1.5470 | 0.013078 | CBWD2 |
| 23650789 | 23651172 | chr7 | + | exonic | hsa_circ_0001684 | –2.4407 | 0.013183 | CCDC126 |
| 459786 | 463400 | chr12 | – | exonic | hsa_circ_0002881 | –1.5455 | 0.013209 | KDM5A |
| 68215377 | 68217269 | chr16 | + | exonic | hsa_circ_0039934 | –1.6267 | 0.013263 | NFATC3 |
| 43436412 | 43447330 | chr7 | + | exonic | hsa_circ_0008258 | 1.6042 | 0.013283 | HECW1 |
| 72157634 | 72168547 | chr5 | + | exonic | hsa_circ_0072917 | –1.6300 | 0.013322 | TNPO1 |
| 44894175 | 44913200 | chrX | + | exonic | hsa_circ_0090328 | 1.5327 | 0.013356 | KDM6A |
| 47139444 | 47147610 | chr3 | – | exonic | hsa_circ_0001290 | –2.0699 | 0.013363 | SETD2 |
| 85223943 | 85234875 | chr15 | – | exonic | hsa_circ_0000647 | –1.8339 | 0.013389 | SEC11A |
| 7826418 | 7841374 | chr7 | + | sense overlapping | hsa_circ_0001676 | –1.9206 | 0.013394 | UMAD1 |
| 73614502 | 73614814 | chr14 | + | exonic | hsa_circ_0003848 | –1.7928 | 0.013440 | PSEN1 |
| 125032151 | 125050082 | chr3 | – | exonic | hsa_circ_0001333 | –1.9135 | 0.013479 | ZNF148 |
| 64791491 | 64792365 | chr15 | + | sense overlapping | hsa_circ_0000615 | –2.8710 | 0.013544 | ZNF609 |
| 29481207 | 29481422 | chr1 | – | exonic | hsa_circ_0006602 | –1.8813 | 0.013562 | SRSF4 |
| 77779390 | 77818086 | chr13 | – | exonic | hsa_circ_0030509 | –1.7764 | 0.013596 | MYCBP2 |
| 67546221 | 67548719 | chr3 | – | exonic | hsa_circ_0003060 | –1.7902 | 0.013626 | SUCLG2 |
| 9079949 | 9098771 | chr2 | – | intronic | hsa_circ_0000973 | –1.9172 | 0.013631 | MBOAT2 |
| 34144719 | 34149837 | chr17 | + | exonic | N/A | –2.6181 | 0.013666 | TAF15 |
| 11958205 | 12016677 | chr17 | + | exonic | hsa_circ_0005603 | –2.0678 | 0.013702 | MAP2K4 |
| 74524751 | 74528329 | chr7 | + | exonic | hsa_circ_0080649 | –1.6149 | 0.013738 | GTF2IRD2 |
| 94983404 | 95001475 | chr15 | + | exonic | hsa_circ_0003333 | –2.0541 | 0.013804 | MCTP2 |
| 74500670 | 74528759 | chr11 | + | exonic | hsa_circ_0006705 | –1.5518 | 0.013806 | RNF169 |
| 68915840 | 68916286 | chr5 | + | exonic | hsa_circ_0072797 | –1.8316 | 0.013819 | SMA |
| 21629185 | 21629395 | chr16 | + | exonic | hsa_circ_0038439 | –– 1.6288 | 0.013909 | METTL9 |
| 61484604 | 61497374 | chr8 | + | exonic | N/A | –1.5135 | 0.013965 | RAB2A |
| 52935854 | 52941341 | chr6 | + | exonic | hsa_circ_0003700 | –2.0209 | 0.013987 | FBXO9 |
| 122369651 | 122372262 | chr12 | + | exonic | N/A | 1.5494 | 0.013989 | WDR66 |
| 21076215 | 21100103 | chr1 | – | exonic | hsa_circ_0000023 | –1.6395 | 0.013999 | HP1BP3 |
| 39595439 | 39609405 | chr18 | + | exonic | hsa_circ_0002560 | –1.9162 | 0.014045 | PIK3C3 |
| 61749745 | 61753656 | chr2 | – | exonic | hsa_circ_0001016 | –2.0508 | 0.014144 | XPO1 |
| 74972047 | 74976724 | chr16 | – | exonic | hsa_circ_0006691 | 1.5338 | 0.014160 | WDR59 |
| 144464661 | 144465125 | chr4 | + | exonic | hsa_circ_0001445 | –2.7373 | 0.014174 | SMARCA5 |
| 41892941 | 41910892 | chr13 | + | exonic | hsa_circ_0030069 | –1.5284 | 0.014193 | NAA16 |
| 28013458 | 28019595 | chr8 | + | exonic | hsa_circ_0001785 | –1.5913 | 0.014224 | ELP3 |
| 110062421 | 110074018 | chr9 | + | exonic | hsa_circ_0008812 | –1.7394 | 0.014229 | RAD23B |
| 169831147 | 169840532 | chr3 | – | exonic | hsa_circ_0006893 | –2.1356 | 0.014261 | PHC3 |
| 85733409 | 85742653 | chr11 | – | exonic | hsa_circ_0023942 | –2.7155 | 0.014277 | PICALM |
| 73418464 | 73429935 | chr11 | – | exonic | hsa_circ_0004596 | –1.9231 | 0.014312 | RAB6A |
| 70096955 | 70101437 | chr10 | + | exonic | hsa_circ_0018499 | 1.5512 | 0.014347 | HNRNPH3 |
| 52935854 | 52947416 | chr6 | + | exonic | hsa_circ_0076777 | –1.9652 | 0.014371 | FBXO9 |
| 124090477 | 124090706 | chr12 | + | exonic | hsa_circ_0029235 | 1.6527 | 0.014391 | DDX55 |
| 103427642 | 103436193 | chr10 | – | exonic | hsa_circ_0008362 | –1.6684 | 0.014392 | FBXW4 |
| 185580493 | 185599548 | chr4 | + | exonic | hsa_circ_0003788 | –1.5767 | 0.014407 | PRIMPOL |
| 35565024 | 35614627 | chr6 | – | sense overlapping | N/A | –1.5117 | 0.014420 | FKBP5 |
| 37633006 | 37636745 | chr4 | – | exonic | hsa_circ_0002194 | –2.1753 | 0.014442 | RELL1 |

TABLE 13-continued (BD 8 week vs Control 8 week)

| TxStart | TxEnd | Chrom | Strand | circRNA type | Alias | Fold change | P-value | GeneSymbol |
|---|---|---|---|---|---|---|---|---|
| 72958135 | 72960247 | chr2 | − | exonic | hsa_circ_0001030 | −1.8655 | 0.014510 | EXOC6B |
| 153413350 | 153414527 | chr5 | − | exonic | hsa_circ_0001546 | −1.8308 | 0.014522 | FAM114A2 |
| 36492117 | 36507984 | chr6 | − | exonic | hsa_circ_0003131 | −2.3004 | 0.014525 | STK38 |
| 13632601 | 13644961 | chr6 | − | exonic | hsa_circ_0001577 | −2.5155 | 0.014550 | RANBP9 |
| 74239461 | 74248066 | chr7 | − | exonic | hsa_circ_0005811 | −1.6666 | 0.014588 | GTF2IRD2 |
| 57059987 | 57064148 | chr12 | − | exonic | hsa_circ_0027089 | −1.7072 | 0.014618 | PTGES3 |
| 197592293 | 197593090 | chr3 | + | exonic | hsa_circ_0008439 | −2.0222 | 0.014627 | LRCH3 |
| 197597030 | 197602646 | chr3 | + | exonic | hsa_circ_0005873 | −2.1941 | 0.014664 | LRCH3 |
| 43600718 | 43625947 | chr20 | + | exonic | N/A | −1.7321 | 0.014754 | STK4 |
| 73614502 | 73640415 | chr14 | + | exonic | hsa_circ_0002564 | −1.5594 | 0.014754 | PSEN1 |
| 38991050 | 39021238 | chr5 | − | exonic | hsa_circ_0006308 | −1.7308 | 0.014760 | RICTOR |
| 144464665 | 144465125 | chr4 | + | sense overlapping | N/A | −2.5838 | 0.014797 | SMARCA5 |
| 7402357 | 7402812 | chr17 | + | sense overlapping | N/A | −2.1245 | 0.014907 | POLR2A |
| 76412360 | 76421132 | chr6 | + | exonic | hsa_circ_0077096 | −1.5473 | 0.014908 | SENP6 |
| 109046047 | 109048186 | chr12 | − | exonic | hsa_circ_0000437 | −2.6494 | 0.014978 | CORO1C |
| 70758070 | 70781249 | chr1 | − | exonic | hsa_circ_0000085 | −1.5663 | 0.015031 | ANKRD13C |
| 61749745 | 61761038 | chr2 | − | exonic | hsa_circ_0001017 | −2.1437 | 0.015085 | XPO1 |
| 114697535 | 114709422 | chr2 | + | exonic | hsa_circ_0056199 | −1.8994 | 0.015136 | ACTR3 |
| 65307876 | 65310553 | chr5 | + | exonic | hsa_circ_0001494 | −1.6374 | 0.015161 | ERBB2IP |
| 85707868 | 85742653 | chr11 | − | exonic | hsa_circ_0023923 | −2.6049 | 0.015221 | PICALM |
| 50616725 | 50616948 | chr14 | − | exonic | hsa_circ_0007695 | −1.7529 | 0.015310 | SOS2 |
| 103384501 | 103436193 | chr10 | − | exonic | hsa_circ_0005741 | −1.6447 | 0.015357 | FBXW4 |
| 17267718 | 17273932 | chr19 | + | exonic | hsa_circ_0006590 | −1.6435 | 0.015410 | MYO9B |
| 157839891 | 157841780 | chr3 | + | exonic | hsa_circ_0001355 | −1.8787 | 0.015565 | RSRC1 |
| 99802639 | 99812219 | chr2 | + | exonic | hsa_circ_0001051 | −1.5987 | 0.015622 | MRPL30 |
| 59787207 | 59844509 | chr1 | + | exonic | hsa_circ_0005354 | −2.1578 | 0.015627 | FGGY |
| 30310017 | 30315516 | chr17 | + | exonic | hsa_circ_0002629 | −1.6350 | 0.015628 | SUZ12 |
| 116668337 | 116675510 | chr12 | − | sense overlapping | hsa_circ_0000443 | −2.0498 | 0.015630 | MED13L |
| 65288537 | 65310553 | chr5 | + | exonic | hsa_circ_0005649 | −1.6394 | 0.015650 | ERBB2IP |
| 11958205 | 12016681 | chr17 | + | sense overlapping | N/A | −1.9167 | 0.015675 | MAP2K4 |
| 140476711 | 140508795 | chr7 | − | exonic | hsa_circ_0007178 | −2.2149 | 0.015684 | BRAF |
| 86297865 | 86301070 | chr9 | − | exonic | hsa_circ_0005142 | −1.8391 | 0.015705 | UBQLN1 |
| 63824845 | 63855207 | chr15 | + | exonic | hsa_circ_0002138 | −1.6423 | 0.015728 | USP3 |
| 74585341 | 74601048 | chr8 | − | exonic | hsa_circ_0001811 | −2.3682 | 0.015756 | STAU2 |
| 131060182 | 131130662 | chr7 | + | exonic | hsa_circ_0003047 | −1.7640 | 0.015929 | MKLN1 |
| 15863654 | 15889942 | chr10 | − | exonic | hsa_circ_0000220 | −2.2877 | 0.015948 | FAM188A |
| 15875628 | 15889942 | chr10 | − | exonic | hsa_circ_0006665 | −2.3264 | 0.015948 | FAM188A |
| 28003837 | 28022541 | chr17 | − | exonic | hsa_circ_0042819 | −1.5134 | 0.015997 | SSH2 |
| 108046972 | 108047817 | chr11 | − | exonic | hsa_circ_0006208 | −1.6845 | 0.015998 | NPAT |
| 119144577 | 119156276 | chr11 | + | exonic | hsa_circ_0000363 | −1.5026 | 0.016006 | CBL |
| 5836847 | 5842668 | chr10 | − | exonic | hsa_circ_0002665 | −1.6209 | 0.016047 | GDI2 |
| 42739466 | 42742954 | chr13 | + | exonic | hsa_circ_0030131 | 1.5407 | 0.016061 | DGKH |
| 47691321 | 47707559 | chr20 | + | exonic | hsa_circ_0001168 | −1.5864 | 0.016123 | CSE1L |
| 32381495 | 32385259 | chr1 | − | exonic | hsa_circ_0007364 | −1.6448 | 0.016168 | PTP4A2 |
| 170906490 | 170912424 | chr3 | − | exonic | hsa_circ_0002387 | −1.5140 | 0.016185 | TNIK |
| 149563797 | 149613357 | chr3 | + | exonic | hsa_circ_0003956 | −2.3450 | 0.016217 | RNF13 |
| 67546221 | 67559327 | chr3 | − | exonic | hsa_circ_0004276 | −1.8069 | 0.016245 | SUCLG2 |
| 50073902 | 50093067 | chr5 | + | exonic | hsa_circ_0072437 | −2.0298 | 0.016255 | PARP8 |
| 35349801 | 35360267 | chr10 | − | exonic | hsa_circ_0000234 | −1.5863 | 0.016265 | CUL2 |
| 32760890 | 32764217 | chr12 | + | exonic | hsa_circ_0000390 | −2.2451 | 0.016399 | FGD4 |
| 16126965 | 16130460 | chr16 | + | exonic | hsa_circ_0002078 | 1.5733 | 0.016432 | ABCC1 |
| 120830753 | 120836157 | chr2 | + | exonic | hsa_circ_0001064 | −1.5134 | 0.016433 | EPB41L5 |
| 65284462 | 65290692 | chr5 | + | exonic | hsa_circ_0001492 | −1.9897 | 0.016527 | ERBB2IP |
| 103610730 | 103612114 | chr4 | − | exonic | hsa_circ_0001429 | −1.6371 | 0.016540 | MANBA |
| 49372459 | 49373029 | chr3 | − | intronic | N/A | −1.8279 | 0.016549 | USP4 |
| 213037066 | 213058738 | chr1 | + | exonic | hsa_circ_0000182 | −2.2282 | 0.016560 | FLVCR1 |
| 86293355 | 86301070 | chr9 | − | exonic | hsa_circ_0087357 | −2.2513 | 0.016698 | UBQLN1 |
| 52773404 | 52773806 | chr8 | − | exonic | hsa_circ_0001801 | −2.9043 | 0.016715 | PCMTD1 |
| 21216261 | 21216990 | chr19 | + | exonic | hsa_circ_0008838 | −1.8738 | 0.016776 | ZNF430 |
| 87925620 | 87928449 | chr6 | + | exonic | hsa_circ_0004058 | −1.6158 | 0.016808 | ZNF292 |
| 22999874 | 23030758 | chr7 | − | exonic | hsa_circ_0008951 | −2.1011 | 0.016861 | FAM126A |
| 167915606 | 167921655 | chr5 | + | exonic | hsa_circ_0001550 | −1.6855 | 0.016905 | RARS |
| 125032151 | 125042288 | chr3 | − | exonic | hsa_circ_0007557 | −1.8587 | 0.016965 | ZNF148 |
| 32874967 | 32875262 | chr22 | + | exonic | hsa_circ_0008832 | −1.5895 | 0.017026 | FBXO7 |
| 26851121 | 26853222 | chr6 | − | exonic | hsa_circ_0075896 | −1.6020 | 0.017040 | GUSBP2 |
| 7830092 | 7844817 | chr10 | + | exonic | hsa_circ_0017667 | −2.6114 | 0.017094 | ATP5C1 |
| 77065301 | 77065626 | chr4 | − | exonic | hsa_circ_0070040 | −2.1031 | 0.017097 | NUP54 |
| 53289511 | 53302038 | chr16 | + | exonic | hsa_circ_0039365 | −1.6887 | 0.017209 | CHD9 |
| 243222779 | 243242354 | chr1 | − | exonic | hsa_circ_0017202 | −1.9878 | 0.017249 | LINC01347 |
| 39739039 | 39757359 | chr4 | + | exonic | hsa_circ_0009154 | −1.5960 | 0.017336 | UBE2K |
| 171851260 | 171969331 | chr3 | + | exonic | hsa_circ_0007148 | −2.4547 | 0.017341 | FNDC3B |

TABLE 13-continued (BD 8 week vs Control 8 week)

| TxStart | TxEnd | Chrom | Strand | circRNA type | Alias | Fold change | P-value | GeneSymbol |
|---|---|---|---|---|---|---|---|---|
| 73956383 | 73958017 | chr4 | − | exonic | hsa_circ_0007883 | −1.5382 | 0.017391 | ANKRD17 |
| 64852814 | 64853814 | chr7 | + | exonic | hsa_circ_0004150 | −1.7071 | 0.017480 | ZNF92 |
| 101898320 | 101911643 | chr2 | − | exonic | hsa_circ_0055904 | −1.8193 | 0.017510 | RNF149 |
| 37732032 | 37735069 | chr8 | − | exonic | hsa_circ_0083946 | −1.9007 | 0.017512 | RAB11FIP1 |
| 3182193 | 3186394 | chr3 | + | exonic | N/A | −1.8934 | 0.017547 | TRNT1 |
| 195101737 | 195112876 | chr3 | − | exonic | hsa_circ_0007331 | −1.7031 | 0.017586 | ACAP2 |
| 86292641 | 86297981 | chr9 | − | exonic | hsa_circ_0006466 | −1.9482 | 0.017606 | UBQLN1 |
| 158552176 | 158580784 | chr7 | − | exonic | hsa_circ_0083211 | −1.6963 | 0.017703 | ESYT2 |
| 94562928 | 94580249 | chr12 | + | exonic | N/A | −3.2821 | 0.017725 | PLXNC1 |
| 104702610 | 104707254 | chr7 | + | exonic | hsa_circ_0081813 | −1.5296 | 0.017733 | KMT2E |
| 33971648 | 33973235 | chr9 | − | exonic | hsa_circ_0001851 | −1.8818 | 0.017815 | UBAP2 |
| 96233422 | 96261168 | chr9 | + | exonic | hsa_circ_0001875 | −1.7939 | 0.017909 | FAM120A |
| 91924202 | 91981956 | chr7 | + | exonic | hsa_circ_0002744 | −1.7105 | 0.017975 | ANKIB1 |
| 40986531 | 40991029 | chr17 | + | exonic | N/A | −1.5630 | 0.017979 | PSME3 |
| 36723505 | 36737571 | chr22 | − | exonic | hsa_circ_0063147 | −2.0989 | 0.018048 | MYH9 |
| 116675272 | 116675510 | chr12 | − | exonic | hsa_circ_0028587 | −1.9287 | 0.018091 | MED13L |
| 128281256 | 128289036 | chr7 | + | sense overlapping | hsa_circ_0005921 | −1.9292 | 0.018115 | LINC01000 |
| 117910084 | 117957453 | chr1 | + | exonic | hsa_circ_0013729 | −3.3192 | 0.018157 | MAN1A2 |
| 8910799 | 8917022 | chr2 | − | exonic | hsa_circ_0005315 | −1.6197 | 0.018173 | KIDINS220 |
| 83799882 | 83803090 | chr4 | − | exonic | hsa_circ_0001421 | −1.9695 | 0.018182 | SEC31A |
| 61607643 | 61609229 | chr3 | + | intronic | hsa_circ_0006226 | 2.0400 | 0.018201 | PTPRG |
| 7844232 | 7844817 | chr10 | + | exonic | hsa_circ_0017675 | −2.5043 | 0.018213 | ATP5C1 |
| 60733932 | 60735153 | chr14 | + | exonic | N/A | 1.6053 | 0.018306 | PPM1A |
| 108186549 | 108206688 | chr11 | + | exonic | hsa_circ_0024231 | −2.0696 | 0.018328 | ATM |
| 1735857 | 1756938 | chr1 | − | exonic | hsa_circ_0006869 | −2.2427 | 0.018335 | GNB1 |
| 30267304 | 30274704 | chr17 | + | exonic | hsa_circ_0042962 | −1.6442 | 0.018348 | SUZ12 |
| 39002636 | 39021238 | chr5 | − | exonic | hsa_circ_0001475 | −1.6985 | 0.018425 | RICTOR |
| 5815804 | 5828013 | chr10 | − | exonic | hsa_circ_0000210 | −1.8534 | 0.018551 | GDI2 |
| 52959282 | 52975384 | chr1 | − | exonic | hsa_circ_0003632 | −1.7368 | 0.018590 | ZCCHC11 |
| 24124293 | 24135302 | chr16 | + | exonic | hsa_circ_0038655 | −1.7403 | 0.018618 | PRKCB |
| 26789747 | 26792203 | chr10 | + | exonic | hsa_circ_0006063 | −2.0430 | 0.018639 | APBB1IP |
| 75587212 | 75590926 | chr14 | − | exonic | hsa_circ_0032682 | −1.5935 | 0.018640 | NEK9 |
| 34300940 | 34313077 | chr20 | − | exonic | hsa_circ_0008143 | −1.5438 | 0.018694 | RBM39 |
| 42541471 | 42562042 | chr6 | + | exonic | hsa_circ_0076347 | −1.5915 | 0.018717 | UBR2 |
| 30954186 | 30956926 | chr20 | + | exonic | hsa_circ_0001136 | −1.7632 | 0.018738 | ASXL1 |
| 30354787 | 30358477 | chr17 | + | exonic | hsa_circ_0042992 | −1.7853 | 0.018752 | LRRC37B |
| 19144163 | 19148055 | chr18 | − | exonic | hsa_circ_0009110 | −1.5966 | 0.018827 | ESCO1 |
| 27977671 | 28030080 | chr17 | − | exonic | hsa_circ_0042806 | −2.0120 | 0.018844 | SSH2 |
| 145594038 | 145595220 | chr1 | − | exonic | hsa_circ_0003693 | −1.5275 | 0.018898 | POLR3C |
| 42513408 | 42515462 | chr2 | + | exonic | hsa_circ_0054241 | −1.5092 | 0.018935 | EML4 |
| 224746658 | 224760347 | chr2 | − | exonic | hsa_circ_0001101 | −1.9456 | 0.019020 | WDFY1 |
| 247319707 | 247323115 | chr1 | − | sense overlapping | N/A | −1.9622 | 0.019042 | ZNF124 |
| 61838273 | 61842207 | chr17 | − | exonic | hsa_circ_0045219 | −1.8177 | 0.019085 | CCDC47 |
| 57014000 | 57016139 | chr20 | + | exonic | hsa_circ_0001173 | −2.5960 | 0.019109 | VAPB |
| 33632307 | 33637797 | chr20 | − | exonic | N/A | −1.5553 | 0.019144 | TRPC4AP |
| 54013510 | 54014377 | chrX | − | exonic | hsa_circ_0009069 | −1.6796 | 0.019188 | PHF8 |
| 57808781 | 57816308 | chr17 | + | exonic | hsa_circ_0006508 | −1.8795 | 0.019208 | VMP1 |
| 42553155 | 42560230 | chr15 | − | exonic | hsa_circ_0034803 | −1.6638 | 0.019308 | TMEM87A |
| 24613084 | 24708279 | chr7 | + | exonic | hsa_circ_0079614 | −1.7907 | 0.019342 | MPP6 |
| 57276883 | 57282379 | chr3 | + | exonic | hsa_circ_0001317 | −1.7370 | 0.019367 | APPL1 |
| 128281294 | 128289036 | chr7 | + | exonic | hsa_circ_0082178 | −1.9825 | 0.019381 | LINC01000 |
| 37126308 | 37327831 | chr9 | + | exonic | hsa_circ_0087047 | −1.9773 | 0.019431 | ZCCHC7 |
| 119219541 | 119232566 | chr3 | + | exonic | hsa_circ_0006884 | −1.9087 | 0.019476 | TIMMDC1 |
| 9588086 | 9588851 | chr18 | − | exonic | hsa_circ_0046881 | −1.8428 | 0.019512 | PPP4R1 |
| 1747194 | 1756938 | chr1 | − | exonic | hsa_circ_0000008 | −2.0789 | 0.019515 | GNB1 |
| 38724057 | 38734535 | chr10 | + | exonic | hsa_circ_0018224 | −2.0086 | 0.019554 | LINC00999 |
| 38205014 | 38205733 | chr8 | − | exonic | hsa_circ_0083996 | −1.7944 | 0.019588 | WHSC1L1 |
| 45391429 | 45396935 | chr18 | − | exonic | hsa_circ_0003694 | −2.0701 | 0.019630 | SMAD2 |
| 10031484 | 10078060 | chrX | + | exonic | hsa_circ_0089866 | −1.7534 | 0.019648 | WWC3 |
| 32761408 | 32807433 | chr10 | + | exonic | N/A | −2.1029 | 0.019656 | CCDC7 |
| 93480747 | 93482948 | chr15 | + | exonic | hsa_circ_0000654 | −1.6368 | 0.019702 | CHD2 |
| 78293666 | 78320990 | chr13 | + | exonic | N/A | −1.8392 | 0.019706 | SLAIN1 |
| 43341245 | 43345284 | chr3 | + | exonic | hsa_circ_0004089 | 2.2076 | 0.019725 | SNRK |
| 128103455 | 128109220 | chr9 | + | exonic | hsa_circ_0005249 | −1.5158 | 0.019771 | GAPVD1 |
| 166141085 | 166184511 | chr4 | + | exonic | hsa_circ_0071375 | −2.0573 | 0.019879 | KLHL2 |
| 171965322 | 171969331 | chr3 | − | exonic | hsa_circ_0006156 | −2.4151 | 0.019927 | FNDC3B |
| 16415815 | 16415895 | chr21 | − | exonic | hsa_circ_0061276 | −1.6763 | 0.019945 | NRIP1 |
| 40872407 | 40882768 | chr1 | + | exonic | hsa_circ_0011898 | −1.5745 | 0.020093 | SMAP2 |
| 132671168 | 132720832 | chr9 | − | exonic | hsa_circ_0089074 | −1.6061 | 0.020195 | FNBP1 |
| 32142994 | 32168452 | chr2 | − | exonic | hsa_circ_0053394 | −1.9365 | 0.020203 | MEMO1 |
| 44713610 | 44717214 | chr1 | − | intronic | hsa_circ_0000065 | 1.5084 | 0.020299 | ERI3 |
| 77055327 | 77065626 | chr4 | − | exonic | hsa_circ_0070039 | −1.9401 | 0.020339 | NUP54 |
| 68434283 | 68446033 | chr15 | + | exonic | hsa_circ_0003916 | −1.9192 | 0.020342 | PIAS1 |

TABLE 13-continued (BD 8 week vs Control 8 week)

| TxStart | TxEnd | Chrom | Strand | circRNA type | Alias | Fold change | P-value | GeneSymbol |
|---|---|---|---|---|---|---|---|---|
| 77210743 | 77212967 | chr7 | + | exonic | hsa_circ_0008139 | 2.0818 | 0.020365 | PTPN12 |
| 138244331 | 138256189 | chr3 | − | exonic | N/A | −1.5129 | 0.020376 | CEP70 |
| 167927595 | 167929110 | chr5 | + | exonic | hsa_circ_0007958 | −1.5376 | 0.020385 | RARS |
| 224142178 | 224149975 | chr1 | − | intronic | hsa_circ_0001978 | −1.8259 | 0.020387 | XLOC_I2_001331 |
| 49372452 | 49373029 | chr3 | − | intronic | hsa_circ_0001301 | −1.7843 | 0.020424 | USP4 |
| 50875285 | 50878685 | chr15 | − | exonic | hsa_circ_0035226 | −1.6037 | 0.020478 | TRPM7 |
| 34147027 | 34149837 | chr17 | + | exonic | hsa_circ_0043138 | −2.5262 | 0.020524 | TAF15 |
| 12903120 | 12903230 | chr19 | − | intronic | hsa_circ_0000895 | 1.5998 | 0.020544 | HOOK2 |
| 72863871 | 72865324 | chr7 | − | exonic | N/A | −1.5624 | 0.020596 | BAZ1B |
| 167915606 | 167924353 | chr5 | + | exonic | hsa_circ_0001551 | −1.5390 | 0.020608 | RARS |
| 51123962 | 51364771 | chr10 | − | exonio | hsa_circ_0018343 | −1.8017 | 0.020641 | PARG |
| 130915557 | 130916831 | chr8 | − | exonic | hsa_circ_0085567 | −1.5742 | 0.020711 | FAM49B |
| 73418464 | 73431944 | chr11 | − | exonic | hsa_circ_0003908 | −1.9142 | 0.020799 | RAB6A |
| 222652709 | 224149975 | chr1 | − | sense overlapping | hsa_circ_0003163 | −1.7719 | 0.020831 | TLR5 |
| 196118683 | 196120490 | chr3 | − | exonic | hsa_circ_0005051 | −2.3000 | 0.020852 | UBXN7 |
| 156220621 | 156220731 | chr1 | − | intronic | hsa_circ_0000141 | 1.5533 | 0.020943 | SMG5 |
| 243776972 | 244006584 | chr1 | − | exonic | hsa_circ_0017252 | −2.0541 | 0.020988 | AKT3 |
| 26789747 | 26802589 | chr10 | + | exonic | N/A | −1.9973 | 0.020997 | APBB1IP |
| 163876310 | 163899928 | chr6 | + | exonic | hsa_circ_0005328 | −1.6009 | 0.021016 | QKI |
| 41961025 | 41962156 | chr15 | + | exonic | hsa_circ_0000591 | −1.9296 | 0.021046 | MGA |
| 35800605 | 35802753 | chr17 | + | exonic | hsa_circ_0005101 | −- 1.6459 | 0.021049 | TADA2A |
| 21660548 | 21663045 | chr18 | + | exonic | hsa_circ_0002403 | −1.8649 | 0.021129 | TTC39C |
| 61013821 | 61041513 | chr13 | + | exonic | hsa_circ_0003441 | −1.7544 | 0.021171 | TDRD3 |
| 243858892 | 244006584 | chr1 | − | exonic | hsa_circ_0004649 | −2.1116 | 0.021209 | AKT3 |
| 85554223 | 85554349 | chr2 | − | sense overlapping | hsa_circ_0001036 | −1.6936 | 0.021249 | TGOLN2 |
| 47497895 | 47501947 | chr12 | + | sense overlapping | hsa_circ_0004650 | −1.5690 | 0.021254 | PCED1B |
| 155695172 | 155695810 | chr1 | + | exonic | hsa_circ_0014614 | −1.8901 | 0.021263 | DAP3 |
| 32703702 | 32704685 | chr2 | + | exonic | hsa_circ_0002408 | −1.5626 | 0.021269 | BIRC6 |
| 69983264 | 69985939 | chr12 | + | exonic | hsa_circ_0000418 | −1.6328 | 0.021271 | CCT2 |
| 72361165 | 72361649 | chr7 | + | exonic | hsa_circ_0003261 | 2.0489 | 0.021281 | POM121 |
| 6995910 | 7002978 | chr4 | + | exonic | hsa_circ_0006681 | −1.8865 | 0.021298 | TBC1D14 |
| 151719232 | 151738409 | chr4 | − | exonic | hsa_circ_0008618 | −1.8840 | 0.021341 | LRBA |
| 117013217 | 117047785 | chr6 | + | exonic | hsa_circ_0006146 | −1.9081 | 0.021429 | KPNA5 |
| 135611502 | 135636378 | chr7 | − | exonic | hsa_circ_0082547 | −2.1097 | 0.021448 | MTPN |
| 19353584 | 19359646 | chr18 | + | exonic | hsa_circ_0008741 | −1.9642 | 0.021454 | MIB1 |
| 118453893 | 118455359 | chr11 | + | exonic | hsa_circ_0007383 | −1.5564 | 0.021468 | ARCN1 |
| 117957334 | 117963271 | chr1 | + | exonic | hsa_circ_0013737 | −3.1943 | 0.021562 | MAN1A2 |
| 118635916 | 118657227 | chr11 | − | exonic | hsa_circ_0024501 | −2.3926 | 0.021591 | DDX6 |
| 155547476 | 155560408 | chr3 | − | exonic | hsa_circ_0067772 | −1.5898 | 0.021610 | SLC33A1 |
| 111819470 | 111826847 | chr9 | − | exonic | hsa_circ_0004109 | −1.5409 | 0.021675 | TMEM245 |
| 13639794 | 13644961 | chr6 | − | exonic | hsa_circ_0001578 | −2.6321 | 0.021703 | RANBP9 |
| 51501542 | 51509135 | chr13 | + | exonic | hsa_circ_0030286 | −1.7867 | 0.021706 | RNASEH2B |
| 155742856 | 155753880 | chr1 | − | exonic | hsa_circ_0014628 | −1.6938 | 0.021716 | GON4L |
| 13632601 | 13659064 | chr6 | − | exonic | hsa_circ_0075650 | −2.2974 | 0.021727 | RANBP9 |
| 57842331 | 57851246 | chr17 | + | exonic | hsa_circ_0004027 | −1.8161 | 0.021857 | VMP1 |
| 74650518 | 74652103 | chr8 | − | exonic | N/A | −2.1106 | 0.021876 | STAU2 |
| 9048750 | 9098771 | chr2 | − | exonic | hsa_circ_0000972 | −2.0001 | 0.021880 | MBOAT2 |
| 86294689 | 86297981 | chr9 | − | exonic | hsa_circ_0001867 | −1.8316 | 0.022019 | UBQLN1 |
| 63821212 | 63866602 | chr15 | + | exonic | N/A | −1.5392 | 0.022041 | USP3 |
| 42798455 | 42823357 | chr8 | + | exonic | N/A | −1.5041 | 0.022146 | HOOK3 |
| 9182379 | 9221997 | chr18 | + | exonic | hsa_circ_0000826 | −2.8774 | 0.022220 | ANKRD12 |
| 63845913 | 63852169 | chr15 | + | exonic | hsa_circ_0000613 | −1.9582 | 0.022342 | USP3 |
| 235993525 | 235996967 | chr1 | − | exonic | hsa_circ_0005899 | 2.3197 | 0.022344 | LYST |
| 128434594 | 128434922 | chr9 | − | exonic | hsa_circ_0088603 | −1.5596 | 0.022389 | MAPKAP1 |
| 36737414 | 36745300 | chr22 | − | exonic | hsa_circ_0004470 | −2.0219 | 0.022451 | MYH9 |
| 65473318 | 65492309 | chr2 | + | sense overlapping | hsa_circ_0001022 | −2.9380 | 0.022501 | ACTR2 |
| 94204037 | 94248681 | chr5 | − | exonic | hsa_circ_0005540 | −1.8972 | 0.022536 | MCTP1 |
| 24663284 | 24681487 | chr7 | + | exonic | hsa_circ_0079619 | −1.5785 | 0.022559 | MPP6 |
| 167921037 | 167944253 | chr1 | + | exonic | hsa_circ_0000154 | −1.5964 | 0.022568 | DCAF6 |
| 9083315 | 9098771 | chr2 | − | exonic | hsa_circ_0007334 | −1.8636 | 0.022600 | MBOAT2 |
| 103432671 | 103433430 | chr10 | − | exonic | hsa_circ_0019591 | −1.8190 | 0.022613 | FBXW4 |
| 25650607 | 25660989 | chr15 | − | sense overlapping | hsa_circ_0005147 | −1.6947 | 0.022696 | UBE3A |
| 19989289 | 19990955 | chr19 | + | exonic | N/A | −1.6281 | 0.022865 | ZNF253 |
| 40506435 | 40525830 | chr1 | + | sense overlapping | hsa_circ_0000058 | −1.6161 | 0.022868 | CAP1 |
| 107429298 | 107435696 | chr3 | + | exonic | hsa_circ_0001324 | −1.9186 | 0.022875 | BBX |
| 49609654 | 49618211 | chr10 | + | exonic | hsa_circ_0002968 | −1.5280 | 0.022897 | MAPK8 |
| 171482591 | 171484477 | chr5 | − | exonic | hsa_circ_0001555 | −1.6407 | 0.022958 | STK10 |
| 46125304 | 46136418 | chr22 | + | exonic | hsa_circ_0001247 | −1.5010 | 0.022972 | ATXN10 |
| 30374430 | 30375041 | chr22 | + | exonic | hsa_circ_0062808 | 1.5869 | 0.023003 | MTMR3 |

TABLE 13-continued (BD 8 week vs Control 8 week)

| TxStart | TxEnd | Chrom | Strand | circRNA type | Alias | Fold change | P-value | GeneSymbol |
|---|---|---|---|---|---|---|---|---|
| 56160560 | 56161804 | chr5 | + | exonic | hsa_circ_0001485 | −1.9243 | 0.023048 | MAP3K1 |
| 15374347 | 15410596 | chr6 | + | exonic | hsa_circ_0075671 | −1.6021 | 0.023106 | JARID2 |
| 144966169 | 144969146 | chr2 | − | exonic | hsa_circ_0001072 | −1.9022 | 0.023235 | GTDC1 |
| 33953282 | 33963789 | chr9 | − | exonic | hsa_circ_0001847 | −1.6836 | 0.023236 | UBAP2 |
| 54398613 | 54426184 | chr18 | + | exonic | hsa_circ_0047744 | −1.6312 | 0.023310 | WDR7 |
| 85230855 | 85234875 | chr15 | − | exonic | hsa_circ_0036599 | −1.8045 | 0.023314 | SEC11A |
| 22024201 | 22029404 | chr22 | + | exonic | hsa_circ_0062426 | −1.6260 | 0.023338 | PPIL2 |
| 43623730 | 43629994 | chr20 | + | exonic | hsa_circ_0060530 | −1.8995 | 0.023345 | STK4 |
| 103923478 | 103928798 | chr14 | + | exonic | hsa_circ_0033480 | −1.5018 | 0.023530 | MARK3 |
| 32108454 | 32157204 | chr2 | − | exonic | hsa_circ_0004215 | −1.6002 | 0.023615 | MEMO1 |
| 37971709 | 37974243 | chr8 | + | exonic | hsa_circ_0083957 | −2.3085 | 0.023629 | ASH2L |
| 1159211 | 1159348 | chr1 | − | exonic | hsa_circ_0009245 | −1.7535 | 0.023690 | SDF4 |
| 106739425 | 106774574 | chr2 | − | exonic | hsa_circ_0055943 | −1.9256 | 0.023781 | UXS1 |
| 123983090 | 123984083 | chr12 | − | exonic | hsa_circ_0007552 | −1.6491 | 0.023810 | RILPL1 |
| 42730785 | 42744343 | chr1 | − | exonic | hsa_circ_0006848 | −1.5636 | 0.023944 | FOXJ3 |
| 74561481 | 74583781 | chr18 | + | exonic | hsa_circ_0001993 | −1.5939 | 0.023973 | ZNF236 |
| 89653781 | 89653866 | chr10 | + | exonic | hsa_circ_0019058 | −1.8845 | 0.023991 | PTEN |
| 68337215 | 68343511 | chr11 | + | exonic | hsa_circ_0023233 | −1.7589 | 0.024006 | PPP6R3 |
| 56661064 | 56662642 | chr3 | − | exonic | hsa_circ_0001314 | −2.0378 | 0.024020 | FAM208A |
| 103372298 | 103373854 | chr8 | − | exonic | hsa_circ_0001819 | −1.9052 | 0.024043 | UBR5 |
| 86293355 | 86297981 | chr9 | − | exonic | hsa_circ_0001866 | −1.8876 | 0.024080 | UBQLN1 |
| 14693760 | 14698083 | chr16 | − | exonic | hsa_circ_0037972 | −1.5689 | 0.024244 | PARN |
| 240944626 | 240961757 | chr2 | − | exonic | hsa_circ_0058923 | −1.5183 | 0.024310 | NDUFA10 |
| 128922303 | 128928858 | chr2 | + | exonic | hsa_circ_0008298 | −1.5627 | 0.024348 | UGGT1 |
| 151719232 | 151729550 | chr4 | − | exonic | hsa_circ_0004636 | −1.8075 | 0.024374 | LABA |
| 103427642 | 103433430 | chr10 | − | exonic | hsa_circ_0019589 | −1.8296 | 0.024540 | FBXW4 |
| 65349233 | 65350779 | chr5 | + | exonic | hsa_circ_0072732 | −1.7449 | 0.024628 | ERBB2IP |
| 48541721 | 48542148 | chr7 | + | intronic | hsa_circ_0001707 | −2.4704 | 0.024661 | ABCA13 |
| 39607406 | 39629569 | chr18 | + | exonic | hsa_circ_0007765 | −1.5939 | 0.024688 | PIK3C3 |
| 29210921 | 29238052 | chr18 | − | exonic | hsa_circ_0047347 | −1.5554 | 0.024709 | B4GALT6 |
| 72301330 | 72302378 | chr7 | + | sense overlapping | hsa_circ_0006688 | −1.6485 | 0.024714 | SBDSP1 |
| 7839009 | 7844817 | chr10 | + | exonic | hsa_circ_0007292 | −2.8290 | 0.024982 | ATP5C1 |
| 106739425 | 106782539 | chr2 | − | exonic | hsa_circ_0055945 | −1.5861 | 0.025053 | UXS1 |
| 667396 | 678730 | chr1 | − | exonic | hsa_circ_0009181 | −2.0123 | 0.025073 | LOC100133331 |
| 133493397 | 133509713 | chr5 | − | sense overlapping | hsa_circ_0004145 | −1.5611 | 0.025133 | SKP1 |
| 18010143 | 18029623 | chr11 | − | exonic | hsa_circ_0021412 | −1.6270 | 0.025140 | SERGEF |
| 118625413 | 118627996 | chr11 | − | exonic | hsa_circ_0024490 | −2.5008 | 0.025216 | DDX6 |
| 18852886 | 18856973 | chr16 | − | exonic | hsa_circ_0006434 | −1.8367 | 0.025239 | SMG1 |
| 50330964 | 50339661 | chr15 | − | exonic | hsa_circ_0035197 | −1.7672 | 0.025328 | ATP8B4 |
| 59787207 | 59812070 | chr1 | + | exonic | hsa_circ_0000075 | −1.9441 | 0.025354 | FGGY |
| 1749275 | 1770677 | chr1 | − | exonic | hsa_circ_0009361 | −1.5223 | 0.025389 | GNB1 |
| 99786012 | 99787892 | chr2 | − | exonic | hsa_circ_0001050 | −1.8760 | 0.025408 | MITD1 |
| 94899365 | 94945248 | chr15 | + | exonic | hsa_circ_0000660 | −1.7649 | 0.025429 | MCTP2 |
| 64295353 | 64295792 | chrX | + | sense overlapping | hsa_circ_0002532 | −1.6096 | 0.025429 | XLOC_008000 |
| 88200377 | 88248289 | chr9 | − | exonic | hsa_circ_0087386 | −1.8812 | 0.025436 | AGTPBP1 |
| 117023156 | 117034608 | chr11 | + | exonic | hsa_circ_0007827 | −1.5492 | 0.025488 | PAFAH1B2 |
| 34093272 | 34098189 | chr11 | + | exonic | hsa_circ_0005974 | −1.5987 | 0.025490 | CAPRIN1 |
| 39623696 | 39629569 | chr18 | + | exonic | hsa_circ_0006527 | −1.5411 | 0.025583 | PIK3C3 |
| 85554139 | 85554349 | chr2 | − | sense overlapping | hsa_circ_0001035 | −1.6563 | 0.025640 | TGOLN2 |
| 75103969 | 75104454 | chr7 | − | exonic | hsa_circ_0006098 | −1.9551 | 0.025674 | POM121C |
| 151611363 | 151611595 | chr1 | + | exonic | hsa_circ_0000130 | −1.6530 | 0.025702 | SNX27 |
| 45079431 | 45115960 | chr21 | + | exonic | hsa_circ_0061880 | 1.6496 | 0.025811 | RRP1B |
| 30267304 | 30300250 | chr17 | + | exonic | hsa_circ_0005804 | −1.5340 | 0.025832 | SUZ12 |
| 112723882 | 112724819 | chr10 | + | exonic | hsa_circ_0000261 | −1.7701 | 0.025885 | SHOC2 |
| 11273608 | 11276922 | chr12 | − | intronic | N/A | −1.6495 | 0.026034 | PRB4 |
| 44514580 | 44515853 | chr21 | − | exonic | hsa_circ_0001198 | −1.5291 | 0.026126 | U2AF1 |
| 36282482 | 36292436 | chr1 | + | exonic | hsa_circ_0003986 | −1.5008 | 0.026130 | AGO4 |
| 120916382 | 120924441 | chr11 | + | exonic | hsa_circ_0000365 | −1.5225 | 0.026144 | TBCEL |
| 30387492 | 30394846 | chr22 | + | exonic | hsa_circ_0001219 | −1.6259 | 0.026251 | MTMR3 |
| 54249939 | 54256040 | chr4 | + | exonic | hsa_circ_0001411 | −1.9565 | 0.026322 | FIP1L1 |
| 3900297 | 3901010 | chr16 | − | exonic | hsa_circ_0007637 | −1.5353 | 0.026329 | CREBBP |
| 73950965 | 73958017 | chr4 | − | exonic | hsa_circ_0001417 | −1.6786 | 0.026502 | ANKRD17 |
| 83799882 | 83803093 | chr4 | − | exonic | hsa_circ_0006618 | −1.8920 | 0.026589 | SEC31A |
| 113196219 | 113209767 | chr1 | + | exonic | hsa_circ_0005664 | −1.6079 | 0.026624 | CAPZA1 |
| 117825700 | 117828459 | chr7 | + | exonic | hsa_circ_0001740 | −1.5058 | 0.026695 | NAA38 |
| 117944807 | 117948267 | chr1 | + | exonic | hsa_circ_0000116 | −2.7153 | 0.026748 | MAN1A2 |
| 99924615 | 99932150 | chr14 | − | exonic | hsa_circ_0000567 | −1.9741 | 0.026772 | SETD3 |
| 7187666 | 7189555 | chr6 | − | exonic | hsa_circ_0075561 | −1.5451 | 0.026776 | RREB1 |
| 52729602 | 52729875 | chr4 | + | exonic | hsa_circ_0069715 | −1.7311 | 0.026866 | DOUN1D4 |
| 48308935 | 48320523 | chr8 | + | exonic | hsa_circ_0001798 | −1.9974 | 0.026874 | SPIDR |
| 52785363 | 52786666 | chr19 | + | exonic | hsa_circ_0052095 | −1.5083 | 0.026901 | ZNF766 |

TABLE 13-continued

| (BD 8 week vs Control 8 week) | | | | | | | | |
|---|---|---|---|---|---|---|---|---|
| TxStart | TxEnd | Chrom | Strand | circRNA type | Alias | Fold change | P-value | GeneSymbol |
| 37347101 | 37349807 | chr2 | − | exonic | N/A | −1.5003 | 0.026951 | EIF2AK2 |
| 129585852 | 129599405 | chr3 | − | intronic | N/A | −1.6795 | 0.026952 | TMCC1 |
| 110922882 | 110925748 | chr12 | + | exonic | hsa_circ_0004516 | −1.5375 | 0.026959 | FAM216A |
| 7181356 | 7189555 | chr6 | + | exonic | hsa_circ_0007429 | −1.8533 | 0.027005 | RREB1 |
| 149833290 | 149838586 | chr6 | − | exonic | hsa_circ_0009074 | −1.5918 | 0.027100 | PPIL4 |
| 151727422 | 151729550 | chr4 | − | exonic | hsa_circ_0071196 | −2.0567 | 0.027136 | LRBA |
| 70719561 | 70720005 | chr10 | + | exonic | hsa_circ_0008865 | −1.6065 | 0.027201 | DDX21 |
| 49742748 | 49752790 | chr13 | + | exonic | hsa_circ_0006978 | −2.0659 | 0.027207 | FNDC3A |
| 63845913 | 63855207 | chr15 | + | exonic | hsa_circ_0008153 | −2.0244 | 0.027224 | USP3 |
| 128419929 | 128434922 | chr9 | − | exonic | hsa_circ_0001890 | −1.5464 | 0.027274 | MAPKAP1 |
| 62299506 | 62306191 | chr15 | − | exonic | hsa_circ_0000607 | −2.4307 | 0.027299 | VPS13C |
| 149563797 | 149629870 | chr3 | + | exonic | hsa_circ_0003502 | −1.9691 | 0.027326 | RNF13 |
| 63824845 | 63852169 | chr15 | + | exonic | hsa_circ_0035649 | −1.5765 | 0.027330 | USP3 |
| 41515056 | 41515506 | chr13 | − | exonic | hsa_circ_0030050 | −2.0037 | 0.027412 | ELF1 |
| 133587 | 139152 | chr11 | − | exonic | hsa_circ_0020596 | −1.8148 | 0.027443 | LOC100133161 |
| 74229605 | 74230755 | chr6 | − | exonic | hsa_circ_0077007 | −1.8753 | 0.027564 | EEF1A1 |
| 131060182 | 131084192 | chr7 | + | exonic | hsa_circ_0001746 | −1.7767 | 0.027619 | MKLN1 |
| 23999828 | 24105618 | chr16 | + | exonic | hsa_circ_0038644 | −1.5615 | 0.027647 | PRKCB |
| 71880664 | 71933964 | chr14 | + | intronic | hsa_circ_0006783 | −1.5085 | 0.027680 | SIPA1L1 |
| 58342772 | 58366043 | chr17 | − | exonic | N/A | −1.5929 | 0.027744 | USP32 |
| 62291306 | 62292503 | chr11 | − | intronic | hsa_circ_0000319 | −1.8335 | 0.027847 | AHNAK |
| 243736227 | 244006584 | chr1 | − | exonic | hsa_circ_0017248 | −1.9665 | 0.027937 | AKT3 |
| 40161688 | 40179999 | chr20 | − | exonic | hsa_circ_0001159 | −1.7367 | 0.028000 | CHD6 |
| 118619175 | 118619412 | chr12 | − | exonic | hsa_circ_0000446 | −1.6730 | 0.028041 | TAOK3 |
| 73418464 | 73429763 | chr11 | − | exonic | hsa_circ_0000339 | −2.0171 | 0.028081 | RAB6A |
| 149613259 | 149639014 | chr3 | + | exonic | hsa_circ_0006801 | −2.1731 | 0.028333 | RNF13 |
| 36297027 | 36301594 | chr1 | + | exonic | N/A | −1.5151 | 0.028342 | AGO4 |
| 1735857 | 1737977 | chr1 | − | exonic | hsa_circ_0000007 | −1.7403 | 0.028456 | GNB1 |
| 40027197 | 40041630 | chr7 | + | exonic | hsa_circ_0001699 | −1.6549 | 0.028652 | CDK13 |
| 12183625 | 12183966 | chr11 | + | exonic | N/A | 1.5352 | 0.028727 | MICAL2 |
| 73114707 | 73115261 | chr7 | − | sense overlapping | hsa_circ_0009012 | −1.8432 | 0.028728 | STX1A |
| 57808781 | 57851246 | chr17 | + | exonic | hsa_circ_0005077 | −1.8944 | 0.028862 | VMP1 |
| 28306951 | 28310335 | chr22 | − | exonic | hsa_circ_0003056 | −1.9141 | 0.028924 | PITPNB |
| 35586872 | 35604935 | chr6 | − | exonic | hsa_circ_0076155 | −1.7084 | 0.028988 | FKBP5 |
| 57064058 | 57066849 | chr12 | − | exonic | hsa_circ_0027093 | −1.7477 | 0.029032 | PTGES3 |
| 34906884 | 34907626 | chr21 | − | exonic | hsa_circ_0008795 | 1.6311 | 0.029055 | GART |
| 16386664 | 16415895 | chr21 | − | exonic | hsa_circ_0004771 | −1.7940 | 0.029184 | NRIP1 |
| 1158623 | 1159348 | chr1 | − | exonic | hsa_circ_0000002 | −1.8878 | 0.029189 | SDF4 |
| 233334684 | 233344435 | chr1 | − | exonic | hsa_circ_0005223 | −1.5133 | 0.029222 | PCNXL2 |
| 71743025 | 71748859 | chr3 | − | exonic | N/A | −2.8131 | 0.029301 | EIF4E3 |
| 86627164 | 86649052 | chr5 | + | exonic | hsa_circ_0004317 | −1.6012 | 0.029421 | RASA1 |
| 88920106 | 88924932 | chr9 | − | exonic | hsa_circ_0001869 | −1.8524 | 0.029441 | ZCCHC6 |
| 45587230 | 45599993 | chr14 | − | sense overlapping | N/A | −2.2644 | 0.029486 | FKBP3 |
| 70236227 | 70236759 | chr14 | + | intronic | hsa_circ_0000549 | −2.6235 | 0.029501 | SRSF5 |
| 132719638 | 132720832 | chr9 | − | exonic | hsa_circ_0007426 | −1.5789 | 0.029684 | FNBP1 |
| 37105033 | 37105170 | chr2 | − | exonic | hsa_circ_0054033 | −1.8966 | 0.029724 | STRN |
| 151960100 | 152012423 | chr7 | − | exonic | hsa_circ_0006784 | −1.5467 | 0.029745 | KMT2C |
| 58340777 | 58347472 | chr12 | + | exonic | hsa_circ_0000412 | −1.7138 | 0.029781 | XRCC6BP1 |
| 103635594 | 103647840 | chr4 | − | exonic | hsa_circ_0001432 | −1.7530 | 0.029893 | MANBA |
| 65466985 | 65482828 | chr2 | + | exonic | N/A | −3.0442 | 0.029919 | ACTR2 |
| 30498061 | 30503232 | chr17 | + | exonic | hsa_circ_0008604 | −2.2057 | 0.029977 | RHOT1 |
| 73951646 | 73952028 | chr17 | − | exonic | hsa_circ_0008557 | −1.7811 | 0.030032 | ACOX1 |
| 32142994 | 32157204 | chr2 | − | exonic | hsa_circ_0007385 | −1.9253 | 0.030185 | MEMO1 |
| 180953812 | 180957481 | chr1 | − | exonic | hsa_circ_0015524 | −− 1.6563 | 0.030288 | STX6 |
| 30267304 | 30303633 | chr17 | + | exonic | hsa_circ_0042965 | −1.7344 | 0.030579 | SUZ12 |
| 180953812 | 180962561 | chr1 | − | exonic | hsa_circ_0007905 | −1.7765 | 0.030615 | STX6 |
| 77700452 | 77703365 | chr13 | − | exonic | hsa_circ_0000495 | −1.5481 | 0.030703 | MYCBP2 |
| 36415395 | 36424928 | chr11 | + | intronic | hsa_circ_0005044 | −1.7144 | 0.030936 | PRR5L |
| 131164981 | 131181313 | chr8 | − | exonic | hsa_circ_0001824 | −2.1034 | 0.030974 | ASAP1 |
| 65271199 | 65272066 | chr11 | + | sense overlapping | hsa_circ_0002082 | −− 3.3403 | 0.030989 | MALAT1 |
| 53421565 | 53421972 | chr12 | + | exonic | hsa_circ_0007889 | −1.6183 | 0.031165 | EIF4B |
| 142170730 | 142173528 | chr8 | + | exonic | N/A | −1.5305 | 0.031382 | DENND3 |
| 111690263 | 111703918 | chr1 | + | exonic | hsa_circ_0000106 | −1.8289 | 0.031411 | CEPT1 |
| 38726471 | 38734535 | chr10 | + | exonic | hsa_circ_0018225 | −1.7157 | 0.031464 | LINC00999 |
| 128282270 | 128289036 | chr7 | + | exonic | hsa_circ_0082179 | −1.8448 | 0.031578 | LINC01000 |
| 190670377 | 190682906 | chr2 | + | exonic | N/A | −1.5577 | 0.031594 | PMS1 |
| 24108020 | 24109780 | chr22 | − | exonic | hsa_circ_0062557 | 1.9822 | 0.031680 | CHCHD10 |
| 171969049 | 172028671 | chr3 | + | exonic | hsa_circ_0003692 | −1.8247 | 0.031708 | FNDC3B |
| 243542022 | 243589860 | chr1 | + | exonic | N/A | −1.5715 | 0.031829 | SDCCAG8 |
| 71880664 | 71948928 | chr14 | + | intronic | hsa_circ_0000552 | −1.7565 | 0.031854 | SIPA1L1 |
| 76301164 | 76415337 | chr13 | + | exonic | hsa_circ_0030448 | 3.1166 | 0.031859 | LMO7 |
| 9204473 | 9221997 | chr18 | + | exonic | hsa_circ_0003865 | −1.9443 | 0.031893 | ANKRD12 |

TABLE 13-continued (BD 8 week vs Control 8 week)

| TxStart | TxEnd | Chrom | Strand | circRNA type | Alias | Fold change | P-value | GeneSymbol |
|---|---|---|---|---|---|---|---|---|
| 111690263 | 111703922 | chr1 | + | sense overlapping | N/A | −1.6561 | 0.031936 | CEPT1 |
| 30267304 | 30267505 | chr17 | + | exonic | hsa_circ_0042961 | −1.7324 | 0.031988 | SUZ12 |
| 73944358 | 73958017 | chr4 | − | exonic | hsa_circ_0006693 | −1.7215 | 0.032020 | ANKRD17 |
| 73238416 | 73239651 | chr17 | − | exonic | hsa_circ_0003684 | −1.5682 | 0.032241 | GGA3 |
| 149563797 | 149639014 | chr3 | + | exonic | hsa_circ_0001346 | −1.5435 | 0.032264 | RNF13 |
| 201790558 | 201796171 | chr2 | − | exonic | N/A | 1.5422 | 0.032278 | ORC2 |
| 167935866 | 167944253 | chr1 | + | exonic | hsa_circ_0009109 | −1.6250 | 0.032313 | DCAF6 |
| 65473657 | 65492309 | chr2 | + | exonic | hsa_circ_0008529 | −3.0332 | 0.032368 | ACTR2 |
| 59811918 | 59844509 | chr1 | + | exonic | N/A | −1.6652 | 0.032387 | FGGY |
| 15863654 | 15885271 | chr10 | − | exonic | hsa_circ_0008178 | −1.6051 | 0.032513 | FAM188A |
| 99924615 | 99925522 | chr14 | − | exonic | hsa_circ_0033149 | −1.9460 | 0.032523 | SETD3 |
| 168920009 | 168986268 | chr2 | − | exonic | hsa_circ_0005882 | −1.5550 | 0.032545 | STK39 |
| 68717321 | 68795482 | chr2 | + | sense overlapping | hsa_circ_0001024 | −1.8873 | 0.032664 | APLF |
| 191523883 | 191537878 | chr2 | + | exonic | hsa_circ_0002024 | −1.6985 | 0.032680 | NAB1 |
| 61509864 | 61512143 | chr14 | + | exonic | N/A | 1.5458 | 0.032893 | SLC38A6 |
| 147733519 | 147744289 | chrX | + | exonic | hsa_circ_0091669 | −1.8675 | 0.032901 | AFF2 |
| 128093445 | 128100770 | chr2 | − | exonic | N/A | −1.5553 | 0.032907 | MAP3K2 |
| 52758220 | 52782950 | chr8 | − | exonic | hsa_circ_0001800 | −1.5712 | 0.033064 | PCMTD1 |
| 228356262 | 228389631 | chr2 | + | exonic | hsa_circ_0058514 | −1.6860 | 0.033064 | AGFG1 |
| 76069566 | 76069928 | chr7 | + | exonic | hsa_circ_0080802 | 1.5058 | 0.033094 | ZP3 |
| 23015828 | 23023664 | chr7 | − | exonic | hsa_circ_0001971 | −1.5285 | 0.033140 | FAM126A |
| 33996220 | 33998862 | chr9 | − | exonic | hsa_circ_0086736 | −1.7842 | 0.033261 | UBAP2 |
| 674213 | 678730 | chr1 | − | sense overlapping | hsa_circ_0007211 | −1.8814 | 0.033323 | AK310751 |
| 117944807 | 118009049 | chr1 | + | exonic | hsa_circ_0000120 | −− 2.8355 | 0.033327 | MAN1A2 |
| 89291126 | 89292039 | chr16 | + | exonic | hsa_circ_0004203 | −1.5383 | 0.033400 | ZNF778 |
| 48444479 | 48458730 | chr18 | + | exonic | hsa_circ_0047700 | −1.5830 | 0.033445 | ME2 |
| 28458581 | 28544344 | chr12 | + | exonic | hsa_circ_0008250 | −1.5825 | 0.033513 | CCDC91 |
| 3076997 | 3081350 | chr6 | + | exonic | hsa_circ_0003886 | −1.5823 | 0.033544 | RIPK1 |
| 34304661 | 34313077 | chr20 | − | exonic | hsa_circ_0001147 | −1.7658 | 0.033566 | RBM39 |
| 1268152 | 1273035 | chr17 | − | exonic | hsa_circ_0041195 | −1.5943 | 0.033651 | YWHAE |
| 39648294 | 39648666 | chr14 | + | exonic | N/A | −1.7853 | 0.033666 | PNN |
| 48175347 | 48177671 | chr11 | + | exonic | N/A | −1.7556 | 0.033707 | PTPRJ |
| 196544755 | 196548630 | chr2 | + | exonic | hsa_circ_0057551 | −2.0751 | 0.033723 | SLC39A10 |
| 44382874 | 44383675 | chr17 | + | exonic | hsa_circ_0044197 | −1.7444 | 0.033768 | LRRC37A |
| 28748408 | 28771483 | chr13 | + | exonic | hsa_circ_0008760 | −1.6152 | 0.033795 | PAN3 |
| 62288378 | 62288522 | chr11 | − | intronic | hsa_circ_0000317 | −2.2177 | 0.033829 | AHNAK |
| 32381491 | 32385259 | chr1 | − | intronic | hsa_circ_0005067 | −1.5013 | 0.033836 | RP11-84A19.4 |
| 231222519 | 231226412 | chr2 | + | exonic | hsa_circ_0008382 | −1.6309 | 0.033846 | SP140L |
| 160103505 | 160109274 | chr6 | − | exonic | hsa_circ_0004662 | −2.4044 | 0.033882 | SOD2 |
| 34895553 | 34895895 | chr19 | + | exonic | hsa_circ_0000927 | 1.5857 | 0.033895 | PDCD2L |
| 34151081 | 34165557 | chr17 | + | exonic | hsa_circ_0000758 | −2.2305 | 0.034018 | TAF15 |
| 37614541 | 37625720 | chr13 | − | exonic | hsa_circ_0000475 | −1.6673 | 0.034072 | SUPT20H |
| 18851019 | 18853776 | chr16 | − | exonic | hsa_circ_0008216 | −1.7076 | 0.034127 | SMG1 |
| 38894089 | 38894578 | chr22 | − | exonic | hsa_circ_0063329 | −1.5909 | 0.034169 | DDX17 |
| 92264128 | 92268765 | chr14 | − | exonic | hsa_circ_0032969 | −1.7952 | 0.034294 | TC2N |
| 142393644 | 142437312 | chr5 | + | exonic | N/A | −1.7792 | 0.034323 | ARHGAP26 |
| 30590251 | 30601744 | chr7 | − | exonic | hsa_circ_0001693 | 1.6805 | 0.034359 | LOC401320 |
| 1747194 | 1770677 | chr1 | − | exonic | hsa_circ_0008702 | −1.5441 | 0.034491 | GNB1 |
| 72302181 | 72302378 | chr7 | + | exonic | hsa_circ_0008708 | −− 1.7045 | 0.034586 | SBDSP1 |
| 131006155 | 131014868 | chr5 | − | exonic | hsa_circ_0073859 | −1.5985 | 0.034720 | FNIP1 |
| 117676687 | 117680079 | chrX | + | exonic | N/A | −1.7772 | 0.035120 | DOCK11 |
| 82832825 | 82850857 | chr5 | + | exonic | hsa_circ_0073239 | −1.5281 | 0.035191 | VCAN |
| 47905209 | 47907363 | chr4 | − | exonic | hsa_circ_0008828 | 1.6059 | 0.035334 | NFXL1 |
| 50388196 | 50399175 | chr12 | − | exonic | hsa_circ_0026195 | 1.5897 | 0.035349 | RACGAP1 |
| 183361267 | 183390272 | chr3 | + | exonic | hsa_circ_0001368 | −1.5787 | 0.035396 | KLHL24 |
| 33467081 | 33467233 | chr3 | − | exonic | hsa_circ_0064742 | −1.5362 | 0.035456 | UBP1 |
| 2951660 | 2952972 | chr4 | − | exonic | hsa_circ_0006737 | −1.6921 | 0.035522 | NOP14 |
| 50358643 | 50367353 | chr7 | + | exonic | hsa_circ_0001708 | −1.5104 | 0.035539 | IKZF1 |
| 44380003 | 44383675 | chr17 | + | exonic | hsa_circ_0044195 | −1.7026 | 0.035564 | LRRC37A |
| 65941524 | 65944422 | chr17 | + | exonic | hsa_circ_0000798 | −1.8128 | 0.035596 | BPTF |
| 62559687 | 62562375 | chr20 | + | exonic | hsa_circ_0007609 | −1.6363 | 0.035785 | DNAJC5 |
| 56879273 | 56882352 | chr8 | + | exonic | hsa_circ_0084552 | −1.5385 | 0.035831 | LYN |
| 20315704 | 20356931 | chr13 | − | exonic | hsa_circ_0000464 | −1.6272 | 0.035849 | PSPC1 |
| 39821342 | 39829143 | chr7 | + | exonic | hsa_circ_0079926 | −1.8396 | 0.035902 | LINC00265 |
| 53413693 | 53416411 | chr12 | + | exonic | hsa_circ_0026512 | −1.6276 | 0.035939 | EIF4B |
| 134076752 | 134079742 | chr5 | + | exonic | hsa_circ_0003154 | −1.6024 | 0.036003 | CAMLG |
| 195415403 | 195416309 | chr3 | + | exonic | hsa_circ_0008267 | −1.6790 | 0.036004 | LINC00969 |
| 155547476 | 155551830 | chr3 | − | exonic | hsa_circ_0001350 | −1.5356 | 0.036056 | SLC33A1 |
| 30374430 | 30384551 | chr22 | + | exonic | N/A | −1.5881 | 0.036244 | MTMR3 |
| 169854206 | 169863309 | chr3 | − | exonic | hsa_circ_0001965 | −2.2262 | 0.036269 | PHC3 |
| 77200394 | 77221573 | chr7 | + | exonic | hsa_circ_0008901 | −1.8216 | 0.036378 | PTPN12 |
| 106761645 | 106782539 | chr2 | − | exonic | hsa_circ_0004029 | −1.6077 | 0.036425 | UXS1 |

TABLE 13-continued (BD 8 week vs Control 8 week)

| TxStart | TxEnd | Chrom | Strand | circRNA type | Alias | Fold change | P-value | GeneSymbol |
|---|---|---|---|---|---|---|---|---|
| 109263579 | 109263891 | chrX | + | intronic | N/A | −1.7410 | 0.036568 | TMEM164 |
| 25630392 | 25636298 | chr17 | + | exonic | hsa_circ_0007716 | −1.5071 | 0.036587 | WSB1 |
| 52446826 | 52448603 | chr3 | + | exonic | hsa_circ_0004912 | −1.5234 | 0.036636 | PHF7 |
| 156549086 | 156619438 | chr7 | − | exonic | hsa_circ_0003511 | −1.5771 | 0.036651 | LMBR1 |
| 101654702 | 101656154 | chr10 | − | exonic | N/A | −1.7988 | 0.036702 | DNMBP |
| 96233422 | 96259881 | chr9 | + | exonic | hsa_circ_0005218 | −1.8227 | 0.036787 | FAM120A |
| 20811305 | 20811534 | chr14 | − | sense overlapping | hsa_circ_0000515 | −1.8859 | 0.036801 | RPPH1 |
| 123718838 | 123721032 | chr10 | − | exonic | hsa_circ_0020256 | −1.5305 | 0.036898 | NSMCE4A |
| 69206201 | 69206389 | chr5 | + | exonic | hsa_circ_0072805 | −1.6830 | 0.036978 | SMA4 |
| 155644800 | 155649303 | chr1 | − | exonic | hsa_circ_0003608 | −1.6612 | 0.037294 | YY1AP1 |
| 35280078 | 35280549 | chr6 | + | exonic | hsa_circ_0076125 | −1.6777 | 0.037327 | DEF6 |
| 130916744 | 130924663 | chr8 | − | exonic | hsa_circ_0001822 | −1.5987 | 0.037329 | FAM49B |
| 30500849 | 30503232 | chr17 | + | exonic | hsa_circ_0005397 | −1.5700 | 0.037377 | RHOT1 |
| 180962498 | 180974599 | chr1 | − | exonic | hsa_circ_0000165 | −1.5484 | 0.037396 | STX6 |
| 12049221 | 12052747 | chr1 | + | exonic | hsa_circ_0009910 | 1.6664 | 0.037653 | MFN2 |
| 62297840 | 62298224 | chr11 | − | intronic | hsa_circ_0000320 | −2.0236 | 0.037858 | AHNAK |
| 57814813 | 57851246 | chr17 | + | exonic | hsa_circ_0003127 | −1.9865 | 0.037878 | VMP1 |
| 58256381 | 58256569 | chr6 | − | exonic | hsa_circ_0076917 | −1.6285 | 0.037969 | GUSBP4 |
| 97299803 | 97327072 | chr14 | + | exonic | hsa_circ_0000566 | −1.5641 | 0.038040 | VRK1 |
| 100889777 | 100908552 | chr1 | + | exonic | hsa_circ_0000097 | −1.6598 | 0.038072 | CDC14A |
| 228384663 | 228389631 | chr2 | + | exonic | hsa_circ_0058520 | −1.6221 | 0.038176 | AGFG1 |
| 142264862 | 142311690 | chr5 | + | exonic | hsa_circ_0074362 | −1.7572 | 0.038210 | ARHGAP26 |
| 30384468 | 30387659 | chr22 | + | exonic | hsa_circ_0062813 | −1.5636 | 0.038238 | MTMR3 |
| 3076997 | 3078169 | chr6 | + | exonic | hsa_circ_0001571 | −1.7981 | 0.038246 | RIPK1 |
| 147743428 | 147744289 | chrX | + | exonic | hsa_circ_0001947 | −2.7804 | 0.038272 | AFF2 |
| 31424825 | 31425448 | chr14 | − | exonic | hsa_circ_0007656 | −1.5871 | 0.038345 | STRN3 |
| 97312431 | 97327072 | chr14 | + | exonic | N/A | −1.5969 | 0.038655 | VRK1 |
| 9991948 | 9992956 | chr1 | − | exonic | hsa_circ_0009677 | −1.5620 | 0.038682 | LZIC |
| 30701807 | 30702014 | chr21 | + | exonic | hsa_circ_0061396 | −1.6640 | 0.038780 | BACH1 |
| 38949785 | 38951231 | chr19 | + | exonic | hsa_circ_0050834 | 1.6320 | 0.038780 | RYR1 |
| 234296902 | 234299129 | chr2 | + | exonic | hsa_circ_0001112 | −1.6803 | 0.038827 | DGKD |
| 3178943 | 3186394 | chr3 | + | exonic | N/A | −1.7301 | 0.038864 | TANT1 |
| 28840851 | 28845003 | chr13 | + | exonic | hsa_circ_0000469 | −1.5068 | 0.038968 | PAN3 |
| 15644268 | 15679480 | chr2 | − | exonic | hsa_circ_0004665 | −1.5537 | 0.039004 | NBAS |
| 11426664 | 11427862 | chr2 | − | exonic | hsa_circ_0006526 | −1.8267 | 0.039342 | ROCK2 |
| 9583114 | 9595151 | chr18 | − | exonic | hsa_circ_0007509 | −1.6162 | 0.039375 | PPP4R1 |
| 47767859 | 47768203 | chr19 | + | exonic | hsa_circ_0000944 | −1.6250 | 0.039550 | CCDC9 |
| 62546241 | 62596747 | chr8 | − | exonic | hsa_circ_0008337 | −1.5591 | 0.039721 | ASPH |
| 755878 | 760253 | chr11 | + | exonic | hsa_circ_0003307 | −1.6536 | 0.039722 | TALDO1 |
| 1737913 | 1749314 | chr1 | − | exonic | hsa_circ_0009357 | −1.9076 | 0.039877 | GNB1 |
| 40655612 | 40657441 | chr2 | − | exonic | hsa_circ_0005232 | −2.2703 | 0.039959 | SLC8A1 |
| 75484866 | 75486869 | chr17 | + | sense overlapping | hsa_circ_0000808 | −1.5096 | 0.039973 | SEPT9 |
| 37971709 | 37976881 | chr8 | + | exonic | hsa_circ_0001790 | −1.9408 | 0.040008 | ASH2L |
| 239090705 | 239093928 | chr2 | − | exonic | hsa_circ_0001116 | −1.6130 | 0.040029 | ILKAP |
| 185153374 | 185200840 | chr1 | + | exonic | hsa_circ_0015677 | −1.8073 | 0.040062 | SWT1 |
| 142434003 | 142437312 | chr5 | + | exonic | hsa_circ_0074371 | −1.6804 | 0.040303 | ARHGAP26 |
| 53189837 | 53191453 | chr16 | + | exonic | hsa_circ_0039353 | −1.5355 | 0.040382 | CHD9 |
| 1756835 | 1770677 | chr1 | − | exonic | hsa_circ_0009362 | −2.0395 | 0.040846 | GNB1 |
| 40655612 | 40657444 | chr2 | − | exonic | hsa_circ_0000994 | −2.3515 | 0.040862 | SLC8A1 |
| 108559662 | 108577564 | chr11 | + | exonic | hsa_circ_0024246 | 1.5292 | 0.040863 | DDX10 |
| 33467081 | 33481417 | chr3 | − | exonic | hsa_circ_0064743 | −1.5435 | 0.040926 | UBP1 |
| 153581139 | 153581292 | chrX | − | exonic | hsa_circ_0091894 | −1.5394 | 0.040965 | FLNA |
| 198703490 | 198704278 | chr1 | + | sense overlapping | hsa_circ_0000170 | −1.8146 | 0.041041 | PTPRC |
| 114676884 | 114678116 | chr9 | + | exonic | hsa_circ_0006435 | −1.6003 | 0.041074 | UGCG |
| 146209155 | 146216108 | chr6 | − | sense overlapping | N/A | −1.9972 | 0.041253 | SHPRH |
| 101659675 | 101659823 | chr10 | − | exonic | hsa_circ_0005796 | −1.5723 | 0.041475 | DNMBP |
| 96238537 | 96259881 | chr9 | + | exonic | hsa_circ_0087540 | −1.5881 | 0.041609 | FAM120A |
| 243242289 | 243265046 | chr1 | − | exonic | hsa_circ_0017215 | −1.8449 | 0.041748 | LINC01347 |
| 38801306 | 38803739 | chr8 | + | exonic | hsa_circ_0084021 | −2.0922 | 0.041770 | PLEKHA2 |
| 61133516 | 61135470 | chr11 | + | exonic | hsa_circ_0002058 | −1.6271 | 0.042043 | TMEM138 |
| 93608139 | 93611093 | chr10 | + | exonic | hsa_circ_0008332 | −1.5507 | 0.042283 | TNKS2 |
| 135010665 | 135012215 | chr2 | + | exonic | hsa_circ_0001068 | −1.5594 | 0.042496 | MGAT5 |
| 39191239 | 39200116 | chr19 | + | exonic | hsa_circ_0050900 | −1.9281 | 0.042503 | ACTN4 |
| 91030185 | 91035943 | chr15 | + | exonic | hsa_circ_0007201 | −2.0414 | 0.042535 | IQGAP1 |
| 85707868 | 85714494 | chr11 | − | exonic | hsa_circ_0023919 | −1.9294 | 0.042910 | PICALM |
| 33996220 | 34017187 | chr9 | − | exonic | hsa_circ_0003410 | −1.8104 | 0.043065 | UBAP2 |
| 65941524 | 65972074 | chr17 | + | exonic | hsa_circ_0000799 | −1.6342 | 0.043213 | BPTF |
| 99090662 | 99092254 | chr7 | − | intronic | hsa_circ_0001726 | −1.7265 | 0.043256 | ZNF394 |
| 63988322 | 64008672 | chr15 | − | exonic | hsa_circ_0035796 | −2.2727 | 0.043390 | HERC1 |
| 117944807 | 117984947 | chr1 | + | exonic | hsa_circ_0000119 | −1.8780 | 0.043417 | MAN1A2 |
| 68155889 | 68225678 | chr16 | + | exonic | hsa_circ_0039929 | −2.1897 | 0.043436 | NFATC3 |

TABLE 13-continued (BD 8 week vs Control 8 week)

| TxStart | TxEnd | Chrom | Strand | circRNA type | Alias | Fold change | P-value | GeneSymbol |
|---|---|---|---|---|---|---|---|---|
| 52771601 | 52775515 | chr3 | − | exonic | hsa_circ_0001309 | −1.5830 | 0.043478 | NEK4 |
| 146209155 | 146216113 | chr6 | − | exonic | hsa_circ_0001649 | −2.0492 | 0.043598 | SHPRH |
| 35824525 | 35827390 | chr1 | + | exonic | hsa_circ_0011536 | −1.7773 | 0.043621 | ZMYM4 |
| 24680620 | 24681035 | chr14 | − | exonic | hsa_circ_0031359 | −1.7296 | 0.043675 | CHMP4A |
| 89206670 | 89206971 | chr1 | + | exonic | hsa_circ_0000089 | −1.5754 | 0.043930 | PKN2 |
| 47767862 | 47768203 | chr19 | + | sense overlapping | N/A | −1.6927 | 0.043962 | CCDC9 |
| 54956488 | 54959380 | chr20 | − | exonic | hsa_circ_0004887 | −1.5901 | 0.044021 | AURKA |
| 15860731 | 15863309 | chr1 | + | exonic | hsa_circ_0000018 | −1.5348 | 0.044063 | DNAJC16 |
| 95494501 | 95507595 | chr4 | + | exonic | hsa_circ_0070467 | −1.6430 | 0.044133 | PDLIM5 |
| 61605249 | 61615756 | chr11 | + | exonic | hsa_circ_0022383 | −1.7928 | 0.044176 | FADS2 |
| 10283765 | 10288043 | chr19 | − | exonic | hsa_circ_0000889 | −1.8879 | 0.044477 | DNMT1 |
| 10077970 | 10081529 | chr3 | + | exonic | hsa_circ_0001266 | 1.5299 | 0.044483 | FANCD2 |
| 107031202 | 107050797 | chr6 | − | exonic | hsa_circ_0008514 | −1.5042 | 0.044867 | RTN4IP1 |
| 29412046 | 29419420 | chr18 | − | exonic | hsa_circ_0003805 | −1.5754 | 0.044921 | TRAPPC8 |
| 59179173 | 59179739 | chr15 | − | exonic | hsa_circ_0000604 | −1.7058 | 0.044993 | SLTM |
| 117654716 | 117658311 | chr1 | − | sense overlapping | N/A | 1.5352 | 0.045037 | TRIM45 |
| 102661274 | 102676199 | chr14 | + | exonic | hsa_circ_0002553 | −1.5027 | 0.045317 | WDR20 |
| 41515056 | 41518061 | chr13 | − | exonic | hsa_circ_0030051 | −1.7018 | 0.045592 | ELF1 |
| 211192124 | 211192598 | chr1 | − | exonic | hsa_circ_0016348 | 1.6693 | 0.045720 | KCNH1 |
| 53155459 | 53155541 | chr16 | + | intronic | hsa_circ_0000700 | −1.5764 | 0.045754 | CHD9 |
| 74239461 | 74251505 | chr7 | − | exonic | hsa_circ_0080628 | −1.5161 | 0.045943 | GTF2IRD2 |
| 96233422 | 96278551 | chr9 | + | exonic | hsa_circ_0087531 | −1.7318 | 0.046052 | FAM120A |
| 85707868 | 85712201 | chr11 | − | exonic | hsa_circ_0002513 | −2.1705 | 0.046308 | PICALM |
| 131164981 | 131193126 | chr8 | − | exonic | hsa_circ_0008934 | −2.0759 | 0.046654 | ASAP1 |
| 38792600 | 38794168 | chr21 | + | exonic | hsa_circ_0001190 | −1.5729 | 0.047078 | DYRK1A |
| 74493579 | 74497377 | chr16 | − | exonic | hsa_circ_0003315 | −1.7870 | 0.047316 | GLG1 |
| 77210743 | 77221573 | chr7 | + | exonic | hsa_circ_0002458 | −1.7821 | 0.047369 | PTPN12 |
| 65887959 | 65890281 | chr17 | + | exonic | hsa_circ_0005347 | −1.5518 | 0.047402 | BPTF |
| 126140467 | 126168493 | chr5 | + | exonic | hsa_circ_0073748 | −1.7771 | 0.047449 | LMNB1 |
| 77270158 | 77275895 | chrX | + | exonic | hsa_circ_0001934 | −1.5165 | 0.047452 | ATP7A |
| 22404921 | 22413359 | chr1 | + | exonic | hsa_circ_0005576 | −1.7571 | 0.047797 | CDC42 |
| 67513932 | 67514758 | chr8 | − | exonic | hsa_circ_0004863 | −1.5906 | 0.047917 | MYBL1 |
| 80412669 | 80415142 | chr15 | + | exonic | hsa_circ_0000643 | −1.9134 | 0.047933 | ZFAND6 |
| 64271341 | 64295792 | chrX | + | sense overlapping | hsa_circ_0001924 | −2.4063 | 0.048117 | XLOC_007999 |
| 3214459 | 3216950 | chr3 | − | exonic | hsa_circ_0064022 | −1.5661 | 0.048541 | CRBN |
| 128350085 | 128360471 | chr11 | − | exonic | hsa_circ_0002083 | −1.9151 | 0.048594 | ETS1 |
| 121354581 | 121356103 | chr3 | − | exonic | N/A | −1.6723 | 0.048655 | HCLS1 |
| 77227158 | 77230123 | chr7 | + | exonic | hsa_circ_0080845 | −1.7118 | 0.048713 | PTPN12 |
| 56078736 | 56086030 | chr14 | + | exonic | hsa_circ_0032029 | −1.5606 | 0.048753 | KTN1 |
| 69644908 | 69656342 | chr12 | + | exonic | hsa_circ_0000417 | −2.0327 | 0.048909 | CPSF6 |
| 215645283 | 215657169 | chr2 | − | exonic | hsa_circ_0001099 | −1.5065 | 0.048953 | BARD1 |
| 85692787 | 85693046 | chr11 | − | exonic | hsa_circ_0023904 | −1.9646 | 0.048989 | PICALM |
| 110068659 | 110074018 | chr9 | + | exonic | hsa_circ_0087861 | −1.5912 | 0.049243 | RAD23B |
| 58785259 | 58796887 | chr14 | + | exonic | hsa_circ_0000542 | −1.5942 | 0.049443 | ARID4A |
| 61118817 | 61128218 | chr2 | + | exonic | hsa_circ_0001011 | −1.5812 | 0.049581 | REL |
| 37838091 | 37838774 | chr19 | + | exonic | N/A | 2.7883 | 0.049684 | HKR1 |
| 45391429 | 45423180 | chr18 | − | exonic | hsa_circ_0000847 | −1.6572 | 0.049782 | SMAD2 |
| 12645634 | 12653561 | chr3 | − | exonic | N/A | −1.5392 | 0.049891 | RAF1 |

TABLE 14

(BD 8 weeks vs BD baseline)

| TxStart | TxEnd | Chrom | Strand | circRNA type | Alias | Fold change | P-value | GeneSymbol |
|---|---|---|---|---|---|---|---|---|
| 100189289 | 100189525 | chr7 | + | exonic | hsa_circ_0081481 | 21.4103 | 4.14305-08 | FBXO24 |
| 200173482 | 200298237 | chr2 | − | exonic | hsa_circ_0007422 | 39.0293 | 6.8060E−08 | SATB2 |
| 124273706 | 124274424 | chr10 | + | exonic | hsa_circ_0020275 | 24.2326 | 6.9380E−08 | HTRA1 |
| 88084709 | 88116842 | chr4 | − | sense overlapping | N/A | 31.1631 | 7.8650E−08 | KLHL8 |
| 113162074 | 113202401 | chr1 | + | exonic | hsa_circ_0013526 | 47.4214 | 1.4069E−07 | CAPZA1 |
| 200233327 | 200298237 | chr2 | − | exonic | hsa_circ_0003915 | 46.2190 | 1.4552E−07 | SATB2 |
| 28250417 | 28255132 | chr11 | + | intronic | hsa_circ_0000282 | 4.4270 | 1.7687E−07 | METTL15 |
| 28250417 | 28252532 | chr11 | + | intronic | N/A | 5.6538 | 2.0178E−07 | METTL15 |
| 158703294 | 158735300 | chr6 | + | sense overlapping | hsa_circ_0131196 | 16.2448 | 3.5714E−07 | TULP4 |
| 5404774 | 5431405 | chr6 | + | exonic | hsa_circ_0075533 | 10.4675 | 4.3364E−07 | FARS2 |
| 21979173 | 22020771 | chr6 | + | exonic | hsa_circ_0075826 | 10.7285 | 4.4485E−07 | CASC15 |

TABLE 14-continued (BD 8 weeks vs BD baseline)

| TxStart | TxEnd | Chrom | Strand | circRNA type | Alias | Fold change | P-value | GeneSymbol |
|---|---|---|---|---|---|---|---|---|
| 176686989 | 176687169 | chr5 | + | exonic | hsa_circ_0075166 | 2.2803 | 0.000001 | NSD1 |
| 117054494 | 117054855 | chr11 | + | exonic | hsa_circ_0024379 | 10.5601 | 0.000001 | SIDT2 |
| 71761715 | 71762097 | chr15 | + | intronic | N/A | 18.8286 | 0.000001 | THSD4 |
| 120776652 | 120799686 | chr2 | + | exonic | hsa_circ_0056264 | 7.8467 | 0.000001 | EPB41L5 |
| 142593 | 143323 | chr16 | − | exonic | hsa_circ_0037127 | 5.4308 | 0.000001 | NPRL3 |
| 123298105 | 123325218 | chr10 | − | exonic | N/A | 6.9027 | 0.000001 | FGFR2 |
| 62197441 | 62197777 | chr20 | − | sense overlapping | hsa_circ_0001176 | 7.6145 | 0.000001 | HELZ2 |
| 36572334 | 36577714 | chr19 | + | exonic | N/A | 5.3195 | 0.000001 | WDR62 |
| 85667519 | 85682357 | chr16 | + | exonic | hsa_circ_0040726 | 8.7796 | 0.000001 | GSE1 |
| 18609120 | 18609801 | chr22 | + | exonic | hsa_circ_0062191 | 5.7355 | 0.000002 | TUBA8 |
| 29105993 | 29130715 | chr22 | − | exonic | hsa_circ_0004128 | 10.8850 | 0.000002 | CHEK2 |
| 130634122 | 130662267 | chr6 | − | sense overlapping | N/A | 7.1705 | 0.000002 | SAMD3 |
| 44128265 | 44131942 | chr19 | − | exonic | N/A | 2.9469 | 0.000002 | CADM4 |
| 8604615 | 8604944 | chr19 | + | antisense | hsa_circ_0008990 | 6.0696 | 0.000002 | MYO1F |
| 33148403 | 33245340 | chr20 | − | sense overlapping | hsa_circ_0001142 | 2.6445 | 0.000002 | PIGU |
| 113703700 | 113773970 | chr9 | − | exonic | hsa_circ_0004928 | 7.5622 | 0.000002 | LPAR1 |
| 75848953 | 75854219 | chr10 | + | exonic | hsa_circ_0018886 | 8.1970 | 0.000002 | VCL |
| 62594626 | 62595103 | chr11 | − | exonic | hsa_circ_0022537 | 2.0498 | 0.000003 | STX5 |
| 53290970 | 53292303 | chr12 | − | exonic | hsa_circ_0026467 | 5.0893 | 0.000003 | KRT8 |
| 56981238 | 56999504 | chr15 | − | exonic | hsa_circ_0035410 | 4.2220 | 0.000004 | ZNF280D |
| 55996226 | 56002769 | chr18 | + | exonic | N/A | 6.1390 | 0.000005 | NEDD4L |
| 30078554 | 30081741 | chr16 | + | exonic | hsa_circ_0038981 | 6.9491 | 0.000007 | ALDOA |
| 85459039 | 85460676 | chr12 | + | exonic | N/A | 2.4112 | 0.000007 | LRRIQ1 |
| 5396865 | 5431405 | chr6 | + | sense overlapping | hsa_circ_0005893 | 1.5103 | 0.000007 | FARS2 |
| 91723962 | 91727541 | chr9 | − | sense overlapping | hsa_circ_0007738 | 2.2945 | 0.000007 | SHC3 |
| 134655200 | 134679497 | chrX | + | sense overlapping | hsa_circ_0001945 | 5.2931 | 0.000008 | DDX26B |
| 50080770 | 50087302 | chr13 | + | exonic | N/A | 3.8389 | 0.000009 | PHF11 |
| 25630392 | 25638642 | chr17 | + | exonic | hsa_circ_0005336 | 5.4123 | 0.000009 | WSB1 |
| 64537930 | 64569274 | chr5 | − | exonic | N/A | 4.4400 | 0.000010 | ADAMTS6 |
| 242033691 | 242036842 | chr2 | − | exonic | N/A | 2.0487 | 0.000010 | MTERF4 |
| 42269709 | 42269921 | chr18 | + | intronic | hsa_circ_0000844 | 2.3327 | 0.000011 | SETBP1 |
| 21703797 | 21705514 | chr18 | + | exonic | hsa_circ_0047285 | 5.0116 | 0.000012 | TTC39C |
| 42819829 | 42821476 | chr6 | + | exonic | hsa_circ_0076413 | 4.4450 | 0.000013 | GLTSOR1L |
| 55420603 | 55420882 | chr19 | + | exonic | hsa_circ_0052165 | 3.6633 | 0.000013 | NCR1 |
| 22312863 | 22330179 | chr22 | − | exonic | N/A | 2.4460 | 0.000016 | TOP3B |
| 170737226 | 170737501 | chr4 | + | intergenic | hsa_circ_0001457 | 2.5295 | 0.000017 | |
| 36782074 | 36788753 | chr18 | − | sense overlapping | N/A | 3.5861 | 0.000018 | LINC00669 |
| 37600088 | 37600198 | chr20 | − | antisense | hsa_circ_0001157 | 1.6749 | 0.000020 | DHX35 |
| 133341934 | 133343019 | chr3 | − | exonic | hsa_circ_0008069 | 2.0825 | 0.000021 | TOPBP1 |
| 45802132 | 45802362 | chr7 | − | intronic | hsa_circ_0001703 | 2.3040 | 0.000033 | SEPT7P2 |
| 77051808 | 77057565 | chr4 | − | exonic | hsa_circ_0008128 | 2.1631 | 0.000033 | NUP54 |
| 39104849 | 39106177 | chr22 | + | intronic | N/A | 1.5686 | 0.000034 | GTPBP1 |
| 44643022 | 44645125 | chr20 | + | sense overlapping | hsa_circ_0001162 | 1.6491 | 0.000036 | MMP9 |
| 29151053 | 29151137 | chr17 | − | intronic | hsa_circ_0000755 | 2.9898 | 0.000037 | CRLF3 |
| 18195958 | 18198099 | chr17 | − | exonic | hsa_circ_0042330 | 1.8787 | 0.000045 | TOP3A |
| 65326097 | 65359043 | chr10 | + | exonic | N/A | 1.6050 | 0.000047 | REEP3 |
| 183894738 | 183901879 | chr3 | + | exonic | hsa_circ_0068281 | 2.2853 | 0.000048 | AP2M1 |
| 90261231 | 90398157 | chr5 | + | exonic | N/A | 2.3374 | 0.000053 | GPR98 |
| 32973011 | 32973508 | chr7 | − | exonic | N/A | 2.6631 | 0.000053 | RP9P |
| 41988272 | 41989221 | chr15 | + | exonic | hsa_circ_0034734 | 1.7620 | 0.000053 | MGA |
| 50321822 | 50322261 | chr16 | + | exonic | hsa_circ_0000699 | 2.2559 | 0.000055 | ADCY7 |
| 50596162 | 50596330 | chr15 | − | exonic | hsa_circ_0035208 | 2.9499 | 0.000056 | GABPB1 |
| 26861063 | 26884883 | chr9 | − | exonic | hsa_circ_0002781 | 2.1855 | 0.000058 | CAAP1 |
| 138203933 | 138235925 | chr7 | + | exonic | hsa_circ_0082580 | 1.6932 | 0.000060 | TRIM24 |
| 74526955 | 74551664 | chr12 | − | exonic | hsa_circ_0027588 | 2.9947 | 0.000061 | LOC100507377 |
| 52675969 | 52677359 | chr3 | − | exonic | hsa_circ_0066083 | 2.1928 | 0.000064 | PBRM1 |
| 56552657 | 56552839 | chr12 | − | antisense | hsa_circ_0000406 | 2.6026 | 0.000066 | MYL6 |
| 47285639 | 47287816 | chr19 | − | exonic | hsa_circ_0002311 | 1.8604 | 0.000068 | SLC1A5 |
| 81124205 | 81124712 | chr16 | − | exonic | N/A | 1.5094 | 0.000073 | GCSH |
| 80750269 | 80767564 | chr15 | + | exonic | hsa_circ_0007978 | 1.5771 | 0.000076 | ARNT2 |
| 34100754 | 34101636 | chr6 | − | exonic | hsa_circ_0076041 | 2.4066 | 0.000076 | GRM4 |
| 48552608 | 48553595 | chr4 | − | exonic | hsa_circ_0069681 | 2.1340 | 0.000084 | FRYL |
| 15162025 | 15168718 | chr16 | − | exonic | hsa_circ_0038020 | 1.5354 | 0.000087 | RRN3 |
| 74927307 | 74929309 | chr15 | − | sense overlapping | hsa_circ_0000632 | 1.9251 | 0.000092 | EDC3 |
| 60015345 | 60017170 | chr18 | + | sense overlapping | N/A | 2.4108 | 0.000096 | TNFRSF11A |

TABLE 14-continued (BD 8 weeks vs BD baseline)

| TxStart | TxEnd | Chrom | Strand | circRNA type | Alias | Fold change | P-value | GeneSymbol |
|---|---|---|---|---|---|---|---|---|
| 178287348 | 178287568 | chr5 | + | intronic | hsa_circ_0092298 | 6.4346 | 0.000096 | ZNF354B |
| 27135705 | 27143560 | chr12 | – | exonic | N/A | 1.8614 | 0.000101 | TM7SF3 |
| 79203973 | 79205702 | chr4 | + | exonic | N/A | 1.9128 | 0.000106 | FRAS1 |
| 46455023 | 46534363 | chr11 | – | exonic | hsa_circ_0021845 | 2.2452 | 0.000109 | AMBRA1 |
| 144086397 | 144086935 | chr6 | + | exonic | hsa_circ_0007769 | 2.0171 | 0.000115 | PHACTR2 |
| 192444969 | 192463145 | chr3 | – | sense overlapping | N/A | 2.0683 | 0.000121 | FGF12 |
| 46515157 | 46534363 | chr11 | – | exonic | hsa_circ_0007061 | 2.4213 | 0.000126 | AMBRA1 |
| 12645634 | 12647798 | chr3 | – | exonic | hsa_circ_0064365 | 2.6215 | 0.000131 | RAF1 |
| 232879544 | 232894790 | chr2 | + | exonic | hsa_circ_0007321 | 2.3993 | 0.000143 | DIS3L2 |
| 102295068 | 102308010 | chr12 | + | exonic | hsa_circ_0004655 | 1.5132 | 0.000145 | DRAM1 |
| 10980998 | 10981370 | chr8 | – | intronic | hsa_circ_0001779 | 2.6320 | 0.000146 | XKR6 |
| 24730377 | 24734445 | chr22 | + | exonic | hsa_circ_0003720 | 2.6000 | 0.000148 | SPECCIL |
| 187540330 | 187540654 | chr2 | + | exonic | N/A | 1.6754 | 0.000148 | ITGAV |
| 8674619 | 8716500 | chr1 | – | exonic | hsa_circ_0005039 | 5.0312 | 0.000155 | RERE |
| 143956599 | 144023646 | chr3 | + | intergenic | N/A | 1.7954 | 0.000158 | |
| 113869721 | 113869956 | chr13 | + | intronic | hsa_circ_0000507 | 2.0692 | 0.000162 | CUL4A |
| 124640186 | 124650369 | chr10 | + | sense overlapping | N/A | 2.1493 | 0.000163 | LOC399815 |
| 198351307 | 198351922 | chr2 | – | exonic | hsa_circ_0057659 | 2.0885 | 0.000166 | HSPD1 |
| 23408712 | 23410184 | chr1 | + | exonic | hsa_circ_0010844 | 1.8234 | 0.000169 | KDMIA |
| 80914570 | 80923622 | chr17 | – | exonic | hsa_circ_0046598 | 2.7992 | 0.000180 | B3GNTL1 |
| 37700501 | 37723145 | chr17 | + | sense overlapping | N/A | 1.6335 | 0.000184 | CDK12 |
| 125843206 | 125856803 | chr3 | – | exonic | hsa_circ_0067127 | 2.0801 | 0.000194 | ALDHIL1 |
| 145223197 | 145255444 | chr8 | + | exonic | hsa_circ_0001832 | 2.3388 | 0.000214 | MROH1 |
| 213302869 | 213349835 | chr1 | + | exonic | hsa_circ_0007772 | 2.5061 | 0.000215 | RPS6KC1 |
| 127064214 | 127076264 | chr9 | + | exonic | hsa_circ_0088485 | 2.4077 | 0.000226 | NEK6 |
| 90446447 | 90454051 | chr15 | – | exonic | hsa_circ_0036750 | 1.6419 | 0.000233 | ARPIN |
| 14821320 | 14837158 | chrY | + | exonic | hsa_circ_0001954 | 1.7963 | 0.000238 | USP9Y |
| 151223776 | 151247050 | chr4 | – | exonic | hsa_circ_0001450 | 1.7575 | 0.000249 | LRBA |
| 33283175 | 33324476 | chr1 | + | sense overlapping | hsa_circ_0011449 | 2.5487 | 0.000258 | S100PBP |
| 61574338 | 61575044 | chr20 | + | exonic | hsa_circ_0003574 | 1.8533 | 0.000259 | GID8 |
| 61044064 | 61045948 | chr11 | – | exonic | hsa_circ_0022249 | 1.8756 | 0.000260 | VWCE |
| 118897646 | 118898434 | chr11 | – | exonic | hsa_circ_0024516 | 3.4028 | 0.000283 | SLC37A4 |
| 17366614 | 17395067 | chr9 | + | exonic | N/A | 1.8681 | 0.000310 | CNTLN |
| 40728446 | 40730445 | chr5 | – | exonic | hsa_circ_0006141 | 3.3462 | 0.000335 | TTC33 |
| 5711031 | 5717503 | chr11 | – | intronic | hsa_circ_0000276 | 3.0147 | 0.000357 | TRIM5 |
| 46515157 | 46515754 | chr11 | – | exonic | hsa_circ_0009155 | −2.1969 | 0.000391 | AMBRA1 |
| 85625142 | 85626408 | chr2 | – | exonic | hsa_circ_0055412 | 2.1575 | 0.000397 | CAPG |
| 79179293 | 79193564 | chr9 | + | sense overlapping | N/A | 2.0447 | 0.000437 | AL161626.1 |
| 100169609 | 100170072 | chrX | – | sense overlapping | N/A | 2.1041 | 0.000444 | XKRX |
| 2929251 | 2930958 | chr12 | + | exonic | hsa_circ_0000374 | 3.6206 | 0.000468 | ITFG2 |
| 111311746 | 111313913 | chr3 | – | exonic | hsa_circ_0066781 | 1.7881 | 0.000470 | ZBED2 |
| 62479014 | 62483619 | chr1 | + | intronic | N/A | 1.7057 | 0.000480 | INADL |
| 47316514 | 47316617 | chr20 | – | intronic | hsa_circ_0001167 | 2.6974 | 0.000480 | PREX1 |
| 47285639 | 47285806 | chr19 | – | exonic | hsa_circ_0051637 | 1.8628 | 0.000488 | SLC1A5 |
| 175996707 | 175996824 | chr1 | – | exonic | hsa_circ_0015358 | 1.6457 | 0.000502 | RFWD2 |
| 41313097 | 41319934 | chr15 | – | exonic | hsa_circ_0034657 | 2.8382 | 0.000548 | INO80 |
| 120600873 | 120622046 | chr12 | – | exonic | hsa_circ_0028826 | 1.8535 | 0.000550 | GON1L1 |
| 62396665 | 62398655 | chr11 | – | exonic | hsa_circ_0022482 | 1.6115 | 0.000553 | GANAB |
| 7556130 | 7586290 | chr12 | – | exonic | hsa_circ_0025349 | 2.1239 | 0.000564 | CD163L1 |
| 34024320 | 34101636 | chr6 | – | exonic | hsa_circ_0076039 | 2.3967 | 0.000576 | GRM4 |
| 86335196 | 86335470 | chr15 | – | intronic | hsa_circ_0000648 | 1.5995 | 0.000590 | KLHL25 |
| 44970017 | 44970136 | chr11 | – | intronic | hsa_circ_0000293 | 2.1389 | 0.000590 | TP53111 |
| 77798585 | 77807398 | chr13 | – | exonic | hsa_circ_0030514 | 1.5005 | 0.000596 | MYCBP2 |
| 112256581 | 112269109 | chr3 | – | exonic | hsa_circ_0066801 | −1.5896 | 0.000606 | ATG3 |
| 101790176 | 101799759 | chr12 | – | exonic | hsa_circ_0027902 | 1.6155 | 0.000618 | ARL1 |
| 33376629 | 33402809 | chr22 | – | exonic | hsa_circ_0062997 | 1.8102 | 0.000631 | SYN3 |
| 49054148 | 49063055 | chr12 | – | exonic | hsa_circ_0026036 | 1.8864 | 0.000635 | KANSL2 |
| 983990 | 1004666 | chr16 | – | exonic | N/A | 1.9166 | 0.000654 | LMF1 |
| 129799616 | 129813722 | chrX | – | exonic | N/A | 1.6888 | 0.000674 | ENOX2 |
| 123489400 | 123489932 | chr11 | + | exonic | hsa_circ_0024731 | 2.3795 | 0.000679 | GRAMD1B |
| 16586010 | 16658132 | chr6 | – | exonic | hsa_circ_0002353 | 1.5538 | 0.000718 | ATXN1 |
| 85619092 | 85652361 | chr15 | + | exonic | N/A | 2.0107 | 0.000784 | PDE8A |
| 56552657 | 56552820 | chr12 | – | antisense | hsa_circ_0000405 | 1.8673 | 0.000805 | MYL6 |
| 73315177 | 73316443 | chr2 | – | exonic | hsa_circ_0007273 | 2.4945 | 0.000816 | RAB11FIP5 |
| 17124850 | 17127457 | chr17 | – | exonic | N/A | 3.2861 | 0.000823 | FLON |
| 640897 | 666007 | chr8 | – | intronic | N/A | 1.7127 | 0.000837 | ERICH1 |
| 60713226 | 60716000 | chr20 | – | exonic | hsa_circ_0061036 | 1.7660 | 0.000957 | PSMA7 |
| 33163212 | 33163532 | chr11 | – | exonic | N/A | 2.1576 | 0.000970 | CSTF3 |
| 27173370 | 27183073 | chr3 | – | exonic | hsa_circ_0003052 | 1.5269 | 0.001007 | NEK10 |

TABLE 14-continued (BD 8 weeks vs BD baseline)

| TxStart | TxEnd | Chrom | Strand | circRNA type | Alias | Fold change | P-value | GeneSymbol |
|---|---|---|---|---|---|---|---|---|
| 75790426 | 75790887 | chr3 | − | exonic | hsa_circ_0002609 | 1.5418 | 0.001008 | ZNF717 |
| 70644547 | 70666787 | chr11 | − | exonic | N/A | 1.7508 | 0.001124 | SHANK2 |
| 133534776 | 133536765 | chr5 | − | exonic | hsa_circ_0073942 | 1.9503 | 0.001163 | PPP2CA |
| 52132662 | 52134024 | chr6 | − | exonic | hsa_circ_0076742 | 1.9826 | 0.001200 | MCM3 |
| 127294245 | 127294652 | chr3 | − | exonic | hsa_circ_0067159 | 1.5781 | 0.001201 | TPRA1 |
| 13054580 | 13054850 | chr19 | + | sense overlapping | hsa_circ_0000897 | 1.5011 | 0.001202 | CALR |
| 78865519 | 78867665 | chr17 | + | exonic | hsa_circ_0000813 | 1.5651 | 0.001228 | RPTOR |
| 12788710 | 12788908 | chr12 | + | exonic | hsa_circ_0002873 | 1.6064 | 0.001249 | CREBL2 |
| 46529740 | 46534363 | chr11 | − | exonic | hsa_circ_0003110 | 2.1176 | 0.001252 | AMBRA1 |
| 109865553 | 109867711 | chr1 | − | exonic | hsa_circ_0013433 | 1.9222 | 0.001 273 | SORT1 |
| 150092297 | 150111194 | chr6 | + | exonic | hsa_circ_0078244 | 1.6609 | 0.001277 | PCMT1 |
| 100109595 | 100112837 | chr9 | + | exonic | hsa_circ_0087659 | −1.5005 | 0.001301 | CCDC180 |
| 109762831 | 109763131 | chr6 | + | intronic | N/A | 1.6278 | 0.001332 | SMPD2 |
| 34059659 | 34101636 | chr6 | − | exonic | hsa_circ_0076040 | 2.1607 | 0.001417 | GRM4 |
| 139982526 | 139996695 | chr9 | + | exonic | hsa_circ_0089630 | 1.5608 | 0.001581 | MAN1B1 |
| 31535338 | 31535540 | chr14 | + | sense overlapping | N/A | 1.7681 | 0.001638 | AP4S1 |
| 58764121 | 58804477 | chr5 | − | intronic | N/A | 1.7533 | 0.001660 | PDE4D |
| 45089764 | 45093836 | chr21 | + | exonic | N/A | 1.8521 | 0.001685 | RRP1B |
| 10015311 | 10016172 | chr3 | − | exonic | hsa_circ_0064195 | −1.5647 | 0.001698 | EMC3 |
| 55340765 | 55341720 | chr1 | − | exonic | hsa_circ_0012673 | 1.6621 | 0.001716 | DHCR24 |
| 192880233 | 192880611 | chr1 | − | intergenic | N/A | 1.9746 | 0.001750 | |
| 15564438 | 15567918 | chr2 | − | exonic | hsa_circ_0052760 | 1.5070 | 0.001771 | NBAS |
| 169673708 | 169673894 | chr1 | − | exonic | hsa_circ_0000158 | 2.1121 | 0.001796 | SELL |
| 132990630 | 133002144 | chr7 | + | exonic | hsa_circ_0082440 | 2.0936 | 0.001810 | EXOC4 |
| 151122382 | 151122520 | chr5 | − | exonic | hsa_circ_0074657 | 1.5653 | 0.001848 | ATOX1 |
| 43523572 | 43535091 | chr6 | − | exonic | hsa_circ_0002037 | 1.7626 | 0.001894 | XPO5 |
| 58142964 | 58143287 | chr12 | − | exonic | hsa_circ_0006606 | 1.5625 | 0.001904 | CDK4 |
| 100506410 | 100506635 | chr2 | − | intronic | hsa_circ_0001054 | 2.8699 | 0.001943 | AFF3 |
| 99224632 | 99234828 | chr8 | − | exonic | N/A | 1.5189 | 0.001998 | NIPAL2 |
| 52693054 | 52729678 | chr19 | + | exonic | hsa_circ_0052067 | 2.7458 | 0.002049 | PPP2R1A |
| 145806229 | 145806661 | chr8 | − | exonic | hsa_circ_0086154 | 1.7813 | 0.002118 | ARHGAP39 |
| 12326937 | 12395884 | chri | + | exonic | hsa_circ_0009962 | 1.9528 | 0.002307 | VPS13D |
| 47274548 | 47290742 | chr22 | + | exonic | hsa_circ_0003343 | 1.5647 | 0.002376 | TBC1D22A |
| 53331118 | 53331571 | chr14 | − | exonic | hsa_circ_0031968 | 1.7185 | 0.002385 | FERMT2 |
| 26385242 | 26388522 | chr6 | + | exonic | hsa_circ_0001590 | 1.6112 | 0.002394 | BTN2A2 |
| 15855582 | 15874923 | chri | + | exonic | hsa_circ_0010041 | 1.5101 | 0.002429 | DNAJC16 |
| 30715384 | 30715636 | chr16 | + | exonic | hsa_circ_0039076 | 1.7625 | 0.002439 | SRCAP |
| 131271154 | 131271376 | chr9 | + | exonic | hsa_circ_0088807 | 1.5545 | 0.002704 | GLE1 |
| 98276327 | 98276412 | chr2 | − | intronic | hsa_circ_0001049 | 1.7226 | 0.002902 | ACTR1B |
| 184114751 | 184130178 | chr4 | + | exonic | hsa_circ_0003437 | 1.6231 | 0.002917 | WWC2 |
| 20240809 | 20240905 | chr2 | − | intronic | hsa_circ_0000981 | 2.0439 | 0.002981 | LAPTM4A |
| 76393373 | 76393472 | chr17 | + | intronic | N/A | 1.6951 | 0.002985 | PGS1 |
| 25877593 | 25885213 | chr17 | + | exonic | N/A | 1.5367 | 0.003134 | KSR1 |
| 20113099 | 20113439 | chr22 | + | intronic | hsa_circ_0092314 | 2.3039 | 0.003151 | RANBP1 |
| 45203311 | 45204674 | chr11 | + | exonic | N/A | 1.8114 | 0.003155 | PRDM11 |
| 18105081 | 18111057 | chr11 | − | exonic | hsa_circ_0002778 | 1.6227 | 0.003158 | SAAL1 |
| 9588086 | 9595100 | chr18 | − | exonic | hsa_circ_0046882 | 1.8023 | 0.003249 | PPP4R1 |
| 69170598 | 69177292 | chr16 | + | exonic | hsa_circ_0008700 | 1.6919 | 0.003277 | CIRH1A |
| 114357089 | 114364762 | chrX | − | exonic | hsa_circ_0003300 | 2.0612 | 0.003348 | LRCH2 |
| 196386979 | 196388380 | chr3 | − | antisense | hsa_circ_0001381 | 1.5963 | 0.003541 | NRROS |
| 74385612 | 74395072 | chr17 | − | exonic | hsa_circ_0045799 | 2.3368 | 0.003659 | UBE20 |
| 3205916 | 3209234 | chr10 | − | exonic | hsa_circ_0003022 | −1.9568 | 0.003970 | PITRM1 |
| 9770162 | 9770654 | chr1 | + | exonic | hsa_circ_0009654 | 1.6018 | 0.004290 | PIK3CD |
| 217005908 | 217026771 | chr2 | + | exonic | hsa_circ_0058175 | 1.5553 | 0.004291 | XRCC5 |
| 150634289 | 150636239 | chri | − | exonic | N/A | −1.7443 | 0.004667 | GOLPH3L |
| 69565029 | 69565697 | chr2 | − | exonic | hsa_circ_0001025 | 1.9435 | 0.004674 | GFPT1 |
| 99538969 | 99560389 | chr8 | − | exonic | hsa_circ_0003593 | 2.1103 | 0.004941 | STK3 |
| 32395264 | 32400308 | chr5 | − | exonic | N/A | 1.6288 | 0.004972 | ZFR |
| 62817884 | 62820990 | chr17 | − | exonic | hsa_circ_0004702 | 1.8247 | 0.005097 | PLEKHM1P |
| 150432224 | 150438785 | chr2 | − | exonic | N/A | 1.5060 | 0.005410 | MMADHC |
| 52277731 | 52325551 | chr13 | + | exonic | N/A | 1.5268 | 0.005412 | WDFY2 |
| 50592985 | 50596330 | chr15 | − | exonic | hsa_circ_0007983 | 1.6366 | 0.005443 | GABPB1 |
| 171830241 | 171944737 | chr3 | + | exonic | hsa_circ_0006948 | 1.6027 | 0.005632 | FNDC3B |
| 7976672 | 7990962 | chr20 | − | exonic | hsa_circ_0001130 | 1.6476 | 0.005853 | TMX4 |
| 32987845 | 32995095 | chr11 | + | exonic | N/A | 1.5518 | 0.005881 | QSER1 |
| 47285639 | 47291842 | chr19 | − | exonic | hsa_circ_0051638 | 1.6050 | 0.005964 | SLO1A5 |
| 73215386 | 73228707 | chr2 | − | exonic | hsa_circ_0004699 | 1.8851 | 0.006204 | SFXN5 |
| 29847024 | 29848279 | chr16 | + | exonic | hsa_circ_0007258 | 1.7680 | 0.006313 | MVP |
| 73414865 | 73428368 | chr15 | + | exonic | N/A | 1.6964 | 0.006341 | NEO1 |
| 89123719 | 89131833 | chr14 | − | exonic | N/A | 1.7828 | 0.006537 | EML5 |
| 1191424 | 1203372 | chrt | − | exonic | hsa_circ_0009246 | 1.7910 | 0.006545 | UBE2J2 |
| 114840817 | 114842445 | chr9 | − | exonic | hsa_circ_0088036 | 1.6596 | 0.006694 | SUSD1 |
| 72361889 | 72362548 | chr2 | − | exonic | hsa_circ_0055161 | 1.6899 | 0.006744 | CYP26B1 |

TABLE 14-continued (BD 8 weeks vs BD baseline)

| TxStart | TxEnd | Chrom | Strand | circRNA type | Alias | Fold change | P-value | GeneSymbol |
|---|---|---|---|---|---|---|---|---|
| 106797630 | 106802256 | chr7 | + | exonic | hsa_circ_0081881 | 1.6347 | 0.006804 | PRKAR2B |
| 65924470 | 65925603 | chr17 | + | exonic | hsa_circ_0004392 | −1.5099 | 0.006936 | BPTF |
| 126434011 | 126452004 | chr6 | + | antisense | N/A | 1.5800 | 0.007050 | MIR5695 |
| 4763319 | 4763528 | chr20 | + | antisense | hsa_circ_0001128 | 1.6270 | 0.007151 | RASSF2 |
| 27207184 | 27207404 | chr17 | + | antisense | hsa_circ_0000746 | 2.3495 | 0.007154 | FLOT2 |
| 74533340 | 74562028 | chr9 | + | exonic | N/A | 1.5359 | 0.007183 | C9orf85 |
| 30590251 | 30601744 | chr7 | − | exonic | hsa_circ_0001693 | 1.5444 | 0.007558 | LOC401320 |
| 43552465 | 43555513 | chr17 | − | exonic | hsa_circ_0003434 | 2.1571 | 0.007685 | PLEKHM1 |
| 16846216 | 16847893 | chrX | + | exonic | hsa_circ_0006931 | 1.9757 | 0.007932 | TXLNG |
| 17948284 | 18031686 | chr11 | − | sense overlapping | N/A | 1.5992 | 0.008081 | SERGEF |
| 172325397 | 172325966 | chr2 | + | sense overlapping | hsa_circ_0007529 | 1.5709 | 0.009171 | DCAF17 |
| 179316734 | 179319566 | chri | + | exonic | hsa_circ_0015454 | 2.1541 | 0.009211 | SOAT1 |
| 65131739 | 65141666 | chri | + | exonic | hsa_circ_0007009 | 1.5575 | 0.009682 | CACHD1 |
| 201475259 | 201475620 | chrt | − | intronic | hsa_circ_0000172 | 1.5087 | 0.010211 | CSRP1 |
| 114153316 | 114158328 | chr4 | + | exonic | hsa_circ_0070703 | 1.6440 | 0.010707 | ANK2 |
| 424004 | 427848 | chr16 | − | exonic | hsa_circ_0000663 | 1.7663 | 0.011638 | TMEMBA |
| 79940776 | 79940857 | chr13 | + | antisense | hsa_circ_0000499 | 1.7620 | 0.011646 | RBM26 |
| 12903120 | 12903230 | chr19 | − | intronic | hsa_circ_0000895 | 1.7439 | 0.011826 | HOOK2 |
| 3088665 | 3117990 | chr4 | + | exonic | hsa_circ_0003850 | 1.5566 | 0.012046 | HTT |
| 7225183 | 7225329 | chr17 | − | exonic | hsa_circ_0041821 | 1.6598 | 0.012536 | NEURL4 |
| 21087948 | 21099138 | chr18 | + | exonic | hsa_circ_0002757 | 1.5744 | 0.013471 | C18orf8 |
| 26343183 | 26349097 | chr13 | + | exonic | N/A | 1.5093 | 0.013757 | ATP8A2 |
| 97686267 | 97718297 | chr9 | + | exonic | N/A | 1.9280 | 0.014540 | C9orf3 |
| 122797769 | 122798857 | chr2 | + | intergenic | N/A | 1.6333 | 0.014872 | |
| 104119940 | 104120152 | chr10 | + | exonic | hsa_circ_0003839 | 1.5038 | 0.014937 | GBF1 |
| 23631224 | 23636741 | chr3 | + | intronic | hsa_circ_0004555 | 1.7160 | 0.014967 | MIR548AC |
| 10186276 | 10188722 | chr2 | + | exonic | N/A | −1.5298 | 0.015546 | KLF11 |
| 39882005 | 39882224 | chr15 | + | exonic | hsa_circ_0034510 | 1.7896 | 0.015681 | THBS1 |
| 48839753 | 48842572 | chr8 | − | exonic | hsa_circ_0084443 | 1.5042 | 0.016074 | PRKDC |
| 66286967 | 66313803 | chr3 | + | exonic | hsa_circ_0003101 | 1.8940 | 0.016150 | SLC25A26 |
| 88116475 | 88116842 | chr4 | − | exonic | hsa_circ_0002538 | −2.2772 | 0.016411 | KLHL8 |
| 69908548 | 69908983 | chr14 | + | exonic | N/A | 1.6023 | 0.017343 | SLC39A9 |
| 71433787 | 72057538 | chr15 | + | exonic | hsa_circ_0036127 | 1.5230 | 0.017981 | THSD4 |
| 128166326 | 128256170 | chrX | − | sense overlapping | N/A | 1.5627 | 0.018476 | RP11-41L14.1 |
| 159664587 | 159664757 | chr5 | − | antisense | hsa_circ_0001549 | 1.9399 | 0.019087 | FABP6 |
| 151775682 | 151779258 | chr6 | + | intronic | N/A | 1.5085 | 0.019122 | C6orf211 |
| 90397884 | 90398971 | chr14 | − | exonic | hsa_circ_0032891 | 1.6823 | 0.019576 | EFCAB11 |
| 5113044 | 5126779 | chr17 | + | exonic | hsa_circ_0000738 | 1.7028 | 0.020181 | LOC100130950 |
| 2828699 | 2856298 | chrX | − | sense overlapping | N/A | 1.6760 | 0.020671 | ARSE |
| 44346195 | 44346638 | chr13 | − | intronic | N/A | 1.8189 | 0.020730 | ENOX1 |
| 100035289 | 100052403 | chr2 | − | exonic | hsa_circ_0001052 | 1.5085 | 0.021860 | REV1 |
| 171830241 | 171830380 | chr3 | + | exonic | hsa_circ_0067971 | 1.5164 | 0.022367 | FNDC3B |
| 70245970 | 70246161 | chr14 | + | antisense | hsa_circ_0000550 | 1.5395 | 0.023032 | SLC10A1 |
| 150088308 | 150095224 | chr5 | − | exonic | hsa_circ_0074559 | 2.1958 | 0.023337 | DCTN4 |
| 132426884 | 132428481 | chr5 | + | exonic | hsa_circ_0001531 | −1.5663 | 0.025140 | HSPA4 |
| 24549443 | 24553954 | chr14 | − | sense overlapping | N/A | 1.5209 | 0.025703 | NRL |
| 90098243 | 90098338 | chr16 | + | intronic | hsa_circ_0000729 | 1.5290 | 0.026706 | GAS8 |
| 50289531 | 50290616 | chr3 | + | exonic | hsa_circ_0007083 | −2.2657 | 0.027141 | GNAI2 |
| 183831943 | 183848110 | chr2 | − | exonic | N/A | 1.5875 | 0.028484 | NCKAP1 |
| 105767934 | 105778666 | chr10 | + | exonic | hsa_circ_0000259 | −2.1436 | 0.031732 | SLK |
| 42604156 | 42604482 | chr12 | − | exonic | hsa_circ_0000392 | 1.6641 | 0.032567 | YAF2 |
| 38493707 | 38527396 | chr5 | − | exonic | hsa_circ_0072303 | 1.5036 | 0.033540 | LIFR |
| 122363276 | 122363756 | chr2 | − | exonic | hsa_circ_0007052 | −1.7833 | 0.034362 | CLASP1 |
| 110832905 | 110834257 | chr12 | − | exonic | hsa_circ_0028198 | 1.5590 | 0.036574 | ANAPC7 |
| 35615069 | 35633000 | chr13 | + | exonic | hsa_circ_0029975 | 1.6530 | 0.037626 | NBEA |
| 156220621 | 156220731 | chr1 | − | intronic | hsa_circ_0000141 | 1.5240 | 0.038162 | SMG5 |
| 55844499 | 55844644 | chr20 | − | antisense | hsa_circ_0001171 | 1.5554 | 0.039612 | BC037891 |
| 19948721 | 19951822 | chr22 | + | exonic | hsa_circ_0062277 | −1.5224 | 0.039942 | COMT |
| 15858833 | 15889942 | chr10 | − | exonic | hsa_circ_0000219 | −1.6248 | 0.043286 | FAM188A |
| 179972308 | 179975702 | chrt | + | exonic | hsa_circ_0003942 | −1.5300 | 0.046242 | CEP350 |
| 99481790 | 99483412 | chr9 | + | sense overlapping | N/A | 1.5131 | 0.047374 | RP11-535M15.1 |
| 108137897 | 108138069 | chr11 | + | exonic | hsa_circ_0007694 | −1.7692 | 0.047379 | ATM |
| 70096955 | 70101437 | chr10 | + | exonic | hsa_circ_0018499 | 1.6232 | 0.048472 | HNRNPH3 |
| 20811436 | 20811534 | chr14 | − | sense overlapping | hsa_circ_0000519 | −1.5645 | 0.049787 | RPPH1 |

TABLE 15

(Sert R vs NR baseline)

| TxStart | TxEnd | Chrom | Strand | circRNA type | Allas | Fold change | P-value | GeneSymbol |
|---|---|---|---|---|---|---|---|---|
| 30856464 | 30857207 | chr6 | + | exonic | hsa_circ_0005133 | 2.1223 | 0.0000E+00 | DDR1 |
| 69699344 | 69700862 | chr10 | − | exonic | hsa_circ_0007997 | 1.8107 | 0.0000E+00 | HERC4 |
| 21461899 | 21470081 | chr18 | + | exonic | hsa_circ_0047232 | −1.5784 | 0.0000E+00 | LAMA3 |
| 52773707 | 52790516 | chr20 | − | exonic | hsa_circ_0060930 | −1.6509 | 0.0000E+00 | CYP24A1 |
| 109319715 | 109323546 | chr6 | − | exonic | hsa_circ_0077578 | −1.5986 | 0.0000E+00 | SESN1 |
| 45059428 | 45059793 | chr15 | + | sense overlapping | hsa_circ_0103668 | −1.5267 | 0.0000E+00 | TRIM69 |
| 168233450 | 168250336 | chr5 | − | exonic | hsa_circ_0074930 | 2.0476 | 1.0000E−11 | SLIT3 |
| 66221780 | 66232349 | chr12 | + | exonic | hsa_circ_0027446 | −1.6520 | 2.0000E−11 | HMGA2 |
| 2012061 | 2014827 | chr16 | − | exonic | hsa_circ_0037376 | −1.5300 | 2.0000E−11 | RPS2 |
| 26208168 | 26220646 | chr12 | + | exonic | hsa_circ_0025638 | −1.7398 | 3.0000E−11 | RASSF8 |
| 162890861 | 162891808 | chr5 | + | exonic | hsa_circ_0128496 | −1.6999 | 5.0000E−11 | HMMR |
| 304627 | 311962 | chr6 | + | exonic | hsa_circ_0075410 | 1.5074 | 8.0000E−11 | DUSP22 |
| 10395790 | 10397291 | chr19 | + | exonic | hsa_circ_0049241 | 2.7999 | 1.0000E−10 | ICAM1 |
| 89628179 | 89628539 | chr16 | + | intronic | hsa_circ_0092337 | 3.9146 | 1.2000E−10 | RPL13 |
| 72361889 | 72362548 | chr2 | − | exonic | hsa_circ_0055161 | −1.6039 | 2.9000E−10 | CYP26B1 |
| 52311410 | 52358462 | chr15 | + | exonic | hsa_circ_0035301 | −1.5552 | 3.0000E−10 | MAPK6 |
| 40949651 | 40950704 | chr17 | − | sense overlapping | hsa_circ_0043912 | −1.6800 | 3.2000E−10 | CCDC56 |
| 55748067 | 55748333 | chr19 | + | antisense | hsa_circ_0000959 | −1.7523 | 5.0000E−10 | PPP6R1 |
| 43514307 | 43516197 | chr6 | − | exonic | hsa_circ_0076560 | −1.7378 | 5.6000E−10 | XPO5 |
| 41705097 | 41795980 | chr3 | − | exonic | hsa_circ_0123780 | −1.5524 | 5.6000E−10 | ULK4 |
| 48018065 | 48023202 | chr2 | + | exonic | hsa_circ_0054474 | −1.5198 | 5.7000E−10 | MSH6 |
| 5624475 | 5624965 | chr11 | + | exonic | hsa_circ_0002969 | 1.5094 | 6.7000E−10 | TRIM6-TRIM34 |
| 32142994 | 32145979 | chr2 | − | exonic | hsa_circ_0006790 | −1.5665 | 6.9000E−10 | MEMO1 |
| 57056124 | 57069951 | chr18 | − | sense overlapping | hsa_circ_0007105 | −1.5503 | 7.2000E−10 | TCONS_00026722 |
| 94721980 | 94735290 | chr12 | − | sense overlapping | hsa_circ_0000429 | 1.6302 | 7.4000E−10 | CCDC41 |
| 64526630 | 64527428 | chr7 | + | exonic | hsa_circ_0080302 | −1.5708 | 7.9000E−10 | CCT6P3 |
| 57561274 | 57570191 | chr3 | − | exonic | hsa_circ_0008107 | −1.6476 | 8.1000E−10 | ARF4 |
| 144994590 | 145021167 | chr1 | − | exonic | hsa_circ_0008390 | 1.8253 | 9.0000E−10 | PDE4DIP |
| 27546443 | 27574979 | chr14 | + | exonic | N/A | −1.6378 | 9.0000E−10 | RP11-38434.2 |
| 67799536 | 67802707 | chr13 | − | exonic | hsa_circ_0000492 | −1.5920 | 9.1000E−10 | PCDH9 |
| 71680927 | 71681075 | chr2 | − | antisense | hsa_circ_0001029 | 1.9280 | 1.09005−09 | DYSF |
| 128810558 | 128821588 | chr10 | + | exonic | N/A | 1.6369 | 1.1300E−09 | DOCK1 |
| 42041214 | 42050989 | chr1 | − | exonic | hsa_circ_0011950 | −1.5832 | 1.2500E−09 | HIVEP3 |
| 5664833 | 5699374 | chr4 | − | exonic | hsa_circ_0069059 | 1.8860 | 1.7900E−09 | EVC2 |
| 167424300 | 167447459 | chr6 | + | exonic | hsa_circ_0078668 | −1.5577 | 1.79005−09 | FGFR1OP |
| 153759605 | 153764260 | chrX | − | exonic | hsa_circ_0092108 | −1.5669 | 1.8000E−09 | G6PD |
| 58275620 | 58292135 | chr17 | − | exonic | hsa_circ_0044927 | −1.7553 | 1.8400E−09 | USP32 |
| 222803446 | 222803648 | chr1 | + | intronic | hsa_circ_0000186 | 1.7094 | 2.8000E−09 | MIA3 |
| 128973475 | 128975403 | chr10 | − | exonic | hsa_circ_0093074 | −1.7367 | 2.8900E−09 | FAM196A |
| 896779 | 901546 | chr5 | + | exonic | hsa_circ_0071681 | −1.7731 | 3.0700E−09 | TRIP13 |
| 27041298 | 27044443 | chr17 | − | exonic | hsa_circ_0042691 | −1.5173 | 3.0900E−09 | RAB34 |
| 5827104 | 5842668 | chr10 | − | exonic | hsa_circ_0005379 | 2.5431 | 3.4400E−09 | GD12 |
| 72945231 | 72960247 | chr2 | − | exonic | hsa_circ_0009043 | 1.5122 | 3.85005−09 | EXOC6B |
| 203378441 | 203379702 | chr2 | + | exonic | hsa_circ_0057805 | −1.6049 | 4.1500E−09 | BMPR2 |
| 28141776 | 28155940 | chr13 | − | exonic | hsa_circ_0000468 | 2.1506 | 4.1700E−09 | LNX2 |
| 90653627 | 90665417 | chr10 | + | sense overlapping | hsa_circ_0008629 | −1.5496 | 4.3400E−09 | STAMBPL1 |
| 39738530 | 39743147 | chr17 | − | exonic | hsa_circ_0043614 | −1.5392 | 4.5800E−09 | KRT14 |
| 4953886 | 4960950 | chr16 | − | exonic | N/A | −1.5418 | 5.8500E−09 | PPL |
| 76978820 | 76979114 | chr10 | + | exonic | hsa_circ_0007335 | −1.7556 | 6.1400E−09 | VDAC2 |
| 50821993 | 50831048 | chr15 | − | exonic | hsa_circ_0035222 | −1.5835 | 6.3300E−09 | USP50 |
| 79660683 | 79661883 | chr17 | + | exonic | hsa_circ_0004721 | 1.7732 | 6.4600E−09 | HGS |
| 37352838 | 37358253 | chr5 | − | exonic | hsa_circ_0072279 | 1.6953 | 7.1500E−09 | NUP155 |
| 136035782 | 136048826 | chr3 | + | exonic | N/A | 1.6483 | 7.7400E−09 | PCCB |
| 145197456 | 145205763 | chr5 | − | exonic | hsa_circ_0006528 | −1.5630 | 7.7800E−09 | PRELID2 |
| 128691933 | 128697886 | chr9 | + | exonic | hsa_circ_0004804 | −1.5514 | 8.0800E−09 | PBX3 |
| 10460449 | 10480201 | chr1 | + | exonic | hsa_circ_0009725 | −1.5405 | 9.0500E−09 | PGD |
| 115202366 | 115205825 | chr5 | + | exonic | hsa_circ_0002919 | 2.6267 | 9.7900E−09 | AP381 |
| 225600155 | 225607500 | chr1 | − | exonic | N/A | 1.5037 | 9.9800E−09 | LBR |
| 196544755 | 196583056 | chr2 | + | exonic | hsa_circ_0057552 | −1.5088 | 1.1300E−08 | SLC39A10 |
| 4935748 | 4937971 | chr6 | + | exonic | hsa_circ_0075522 | −1.5189 | 1.2470E−08 | CDYL |
| 61013821 | 61034674 | chr13 | + | exonic | hsa_circ_0004245 | −1.5424 | 1.4600E−08 | TDRD3 |
| 186988982 | 187003844 | chr3 | − | intronic | hsa_circ_0009169 | −1.5170 | 1.4860E−08 | MASP1 |
| 30693541 | 30744883 | chr21 | + | sense overlapping | N/A | 1.5291 | 1.5380E−08 | BACH1 |
| 65922338 | 66028484 | chr14 | + | exonic | hsa_circ_0001998 | −1.5521 | 1.5850E−08 | FUT8 |
| 20436712 | 20466338 | chr1C | + | exonic | hsa_circ_0000224 | −1.5332 | 1.6440E−08 | PLXDC2 |
| 41361767 | 41362745 | chr15 | − | exonic | hsa_circ_0007489 | 1.5016 | 1.6930E−08 | INO80 |
| 13049413 | 13055304 | chr19 | + | exonic | hsa_circ_0049637 | 3.3950 | 2.0530E−08 | CALR |
| 53854798 | 53858636 | chr12 | + | exonic | hsa_circ_0026646 | 1.6492 | 2.0650E−08 | PCBP2 |
| 12462922 | 12465283 | chr11 | + | intronic | N/A | −1.5578 | 2.0670E−08 | PARVA |

TABLE 15-continued (Sert R vs NR baseline)

| TxStart | TxEnd | Chrom | Strand | circRNA type | Allas | Fold change | P-value | GeneSymbol |
|---|---|---|---|---|---|---|---|---|
| 28654060 | 28671129 | chr8 | − | exonic | N/A | −1.7105 | 2.2950E−08 | INTS9 |
| 27668989 | 27672064 | chr7 | − | exonic | hsa_circ_0003958 | −1.5584 | 2.3880E−08 | HIBADH |
| 9020437 | 9021799 | chr12 | + | exonic | hsa_circ_0025388 | −1.5387 | 2.3900E−08 | A2ML1 |
| 124911167 | 124934413 | chr12 | − | exonic | hsa_circ_0000461 | 1.5741 | 2.6700E−08 | NCOR2 |
| 102056748 | 102076805 | chr11 | + | exonic | hsa_circ_0002320 | −1.5432 | 2.7120E−08 | YAP1 |
| 38273472 | 38275126 | chr1 | + | exonic | hsa_circ_0011717 | −1.5021 | 2.7160E−08 | C1orf122 |
| 65220766 | 65221561 | chr7 | + | exonic | N/A | −1.6462 | 2.7830E−08 | CCT6P1 |
| 51454240 | 51456330 | chr3 | − | exonic | hsa_circ_0065898 | 1.5344 | 2.9610E−08 | VPRBP |
| 122669065 | 122670847 | chr12 | + | exonic | N/A | −1.6045 | 2.9740E−08 | LRRC43 |
| 61013821 | 61068709 | chr13 | + | exonic | N/A | −1.5176 | 3.3140E−08 | TDRD3 |
| 5568791 | 5570232 | chr7 | − | exonic | hsa_circ_0079276 | 1.9169 | 3.7990E−08 | ACTB |
| 32557275 | 32566163 | chr1 | + | exonic | hsa_circ_0006349 | −2.0370 | 4.0520E−08 | TMEM39B |
| 114572086 | 114588952 | chr5 | − | exonic | hsa_circ_0073634 | −1.6337 | 4.1830E−08 | PGGT1B |
| 69874028 | 69876023 | chr16 | + | exonic | hsa_circ_0040097 | 1.7718 | 4.3750E−08 | WWP2 |
| 8555122 | 8617582 | chr1 | − | exonic | hsa_circ_0006837 | −1.5054 | 4.4550E−08 | RERE |
| 35436177 | 35438558 | chr6 | + | exonic | hsa_circ_0076138 | −1.5554 | 4.5600E−08 | RPL10A |
| 47725960 | 47728788 | chr1 | − | exonic | N/A | −1.5185 | 4.9570E−08 | STIL |
| 91247081 | 91252672 | chr14 | − | exonic | hsa_circ_0000560 | −1.5008 | 5.0480E−08 | TTO7B |
| 29677910 | 29678100 | chr16 | + | intronic | hsa_circ_0000686 | 1.5764 | 5.45605−08 | SPN |
| 25644553 | 25645709 | chr1 | − | intronic | N/A | −1.7327 | 5.8410E−08 | C1orf63 |
| 24495906 | 24507344 | chr1 | − | exonic | hsa_circ_0010906 | 1.8698 | 6.0250E−08 | IL28RA |
| 122031337 | 122031452 | chr12 | + | sense overlapping | N/A | 1.5955 | 6.1450E−08 | RP13-941N14.1 |
| 74561481 | 74580819 | chr18 | + | exonic | hsa_circ_0002799 | 1.5148 | 6.3420E−08 | ZNF236 |
| 16046228 | 16047883 | chr1 | + | exonic | hsa_circ_0002733 | 1.5528 | 6.6020E−08 | PLEKHM2 |
| 113258782 | 113260758 | chr2 | + | exonic | N/A | −1.6002 | 7.0390E−08 | TTL |
| 118969734 | 119033695 | chr9 | + | exonic | hsa_circ_0008792 | −1.6301 | 7.8620E−08 | PAPPA |
| 172305190 | 172314987 | chr2 | + | exonic | hsa_circ_0001081 | 2.0165 | 7.96405−08 | DCAF17 |
| 140954867 | 140955044 | chr3 | − | antisense | hsa_circ_0001343 | −1.6247 | 8.6220E−08 | ACPL2 |
| 45883610 | 45893784 | chr11 | + | exonic | hsa_circ_0000295 | 1.5059 | 9.2890E−08 | CRY2 |
| 46751033 | 46752171 | chr1 | − | exonic | hsa_circ_0004070 | −1.5546 | 9.8620E−08 | LRRC41 |
| 100826890 | 100828258 | chr14 | − | exonic | hsa_circ_0033191 | −1.5481 | 1.0038E−07 | WARS |
| 55756487 | 55757046 | chr19 | − | exonic | hsa_circ_0005746 | 1.5602 | 1.0424E−07 | PPP6R1 |
| 16526335 | 16528616 | chr10 | + | exonic | hsa_circ_0017854 | −2.0031 | 1.0493E−07 | PTER |
| 211092981 | 211093411 | chr1 | − | exonic | hsa_circ_0006123 | −1.6106 | 1.0496E−07 | KCNH1 |
| 38029408 | 38055959 | chr4 | + | exonic | N/A | −1.6108 | 1.1200E−07 | TBC1D1 |
| 56409123 | 56409324 | chr17 | − | sense overlapping | hsa_circ_0000792 | 1.6113 | 1.3977E−07 | LOC100506779 |
| 45073658 | 45290704 | chr6 | − | exonic | N/A | −1.7263 | 1.8051E−07 | SUPT3H |
| 176964873 | 176966148 | chr5 | − | exonic | hsa_circ_0075236 | 1.5403 | 1.8507E−07 | FAM193B |
| 242396161 | 242415402 | chr2 | + | exonic | N/A | −1.5055 | 1.9976E−07 | FARP2 |
| 173371969 | 173380275 | chr5 | + | exonic | hsa_circ_0008042 | −1.5279 | 2.0856E−07 | CPEB4 |
| 19760861 | 19761115 | chr19 | − | intronic | hsa_circ_0000919 | 1.5815 | 2.1806E−07 | ATP13A1 |
| 27445667 | 27449008 | chr16 | + | exonic | hsa_circ_0038728 | −1.5741 | 2.3419E−07 | IL21R |
| 48271490 | 48272189 | chr17 | − | exonic | hsa_circ_0044556 | 1.6644 | 2.6291E−07 | COL1A1 |
| 14369008 | 14369452 | chr5 | + | intronic | N/A | 2.5157 | 3.3045E−07 | TRIO |
| 159664587 | 159664757 | chr5 | − | antisense | hsa_circ_0001549 | 1.6256 | 3,4921E−07 | FABP6 |
| 41916541 | 41929074 | chr19 | + | exonic | hsa_circ_0000937 | 2.1013 | 3.5069E−07 | BCKDHA |
| 136770511 | 136771563 | chr5 | − | intronic | N/A | −1.5044 | 3.5838E−07 | SPOCK1 |
| 172305190 | 172314585 | chr2 | + | exonic | hsa_circ_0005904 | 1.5743 | 3.7614E−07 | DCAF17 |
| 42819829 | 42821476 | chr6 | + | exonic | hsa_circ_0076413 | −1.5301 | 4.2787E−07 | KIAA0240 |
| 36681395 | 36681695 | chr22 | − | intronic | hsa_circ_0092283 | −1.8003 | 4.4168E−07 | MYH9 |
| 85331067 | 85331821 | chr1 | − | exonic | hsa_circ_0004390 | −1.6453 | 4.7503E−07 | LPAR3 |
| 6657590 | 6657991 | chr12 | − | exonic | hsa_circ_0000375 | 1.9318 | 0.000001 | IFFO1 |
| 99148008 | 99148381 | chr10 | − | exonic | hsa_circ_0019337 | −1.5410 | 0.000001 | RRP12 |
| 196793574 | 196846401 | chr3 | − | exonic | hsa_circ_0068684 | −1.5455 | 0.000001 | DLG1 |
| 38894089 | 38894578 | chr22 | − | exonic | hsa_circ_0063329 | 2.3324 | 0.000001 | DDX17 |
| 5691329 | 5691678 | chr19 | + | exonic | hsa_circ_0048766 | 1.6880 | 0.000001 | RPL36 |
| 131761180 | 131761386 | chr5 | + | intronic | hsa_circ_0001525 | 2.1665 | 0.000001 | CSorf56 |
| 121675707 | 121732604 | chr4 | − | exonic | hsa_circ_0005654 | 1.9972 | 0.000001 | PRDM5 |
| 80721840 | 80726442 | chr17 | + | exonic | hsa_circ_0046462 | −1.6260 | 0.000001 | TBCD |
| 66312474 | 66313803 | chr3 | + | exonic | hsa_circ_0066465 | 1.6395 | 0.000001 | SLC25A26 |
| 76602357 | 76603236 | chr10 | + | exonic | hsa_circ_0005235 | −1.6042 | 0.000001 | KAT6B |
| 94023872 | 94027070 | chr7 | + | exonic | hsa_circ_0081055 | 1.5685 | 0.000001 | COL1A2 |
| 3252272 | 3256234 | chr18 | + | exonic | hsa_circ_0046753 | −1.5253 | 0.000001 | MYL12A |
| 13424714 | 13466728 | chr11 | − | exonic | N/A | 1.5306 | 0.000001 | BTBD10 |
| 13710566 | 13710870 | chr19 | − | exonic | N/A | 1.5348 | 0.000001 | CACNA1A |
| 8946801 | 8949183 | chr16 | − | sense overlapping | hsa_circ_0037798 | −1.5128 | 0.000001 | CARHSP1 |
| 201966446 | 201969143 | chr1 | + | exonic | hsa_circ_0015962 | −1.9816 | 0.000001 | RNPEP |
| 90670648 | 90670832 | chr6 | + | antisense | hsa_circ_0001623 | 1.6650 | 0.000001 | BACH2 |
| 33113327 | 33116872 | chr19 | − | exonic | hsa_circ_0050386 | 1.5300 | 0.000001 | ANKRD27 |
| 80772106 | 80783018 | chr2 | + | exonic | hsa_circ_0055377 | −1.7518 | 0.000001 | CTNNA2 |
| 7301567 | 7303659 | chr12 | + | exonic | N/A | −1.8136 | 0.000002 | CLSTN3 |
| 112399680 | 112421007 | chr5 | − | exonic | hsa_circ_0009054 | 2.0313 | 0.000002 | MCC |

TABLE 15-continued (Sert R vs NR baseline)

| TxStart | TxEnd | Chrom | Strand | circRNA type | Allas | Fold change | P-value | GeneSymbol |
|---|---|---|---|---|---|---|---|---|
| 6582390 | 6605349 | chr8 | + | exonic | hsa_cire_0002682 | 1.6771 | 0.000002 | AGPAT5 |
| 55833019 | 55919286 | chr18 | + | exonic | N/A | 2.2127 | 0.000002 | NEDD4L |
| 53732144 | 53737018 | chr1 | − | exonic | hsa_circ_0012592 | −1.5298 | 0.000002 | LRP8 |
| 40176084 | 40176486 | chr17 | − | antisense | hsa_circ_0000764 | −1.5185 | 0.000002 | NKIRAS2 |
| 127965678 | 127983624 | chr3 | + | exonic | hsa_circ_0067209 | 1.5506 | 0.000002 | EEFSEC |
| 28872327 | 28884970 | chr10 | + | exonic | hsa_circ_0007503 | −1.5297 | 0.000002 | WAC |
| 119526738 | 119542682 | chr4 | + | exonic | hsa_circ_0070739 | 1.5471 | 0.000002 | TCONS_00008208 |
| 149563797 | 149629870 | chr3 | + | exonic | hsa_circ_0003502 | −1.5417 | 0.000002 | RNF13 |
| 22925975 | 22926065 | chr15 | + | exonic | hsa_circ_0034067 | −2.4854 | 0.000002 | CYFIP1 |
| 79613111 | 79614128 | chr10 | − | exonic | hsa_circ_0006649 | 1.8846 | 0.000002 | DLG5 |
| 68018139 | 68028357 | chr8 | + | exonic | hsa_circ_0001806 | −1.5401 | 0.000003 | CSPP1 |
| 96965240 | 96966735 | chr2 | − | intronic | N/A | −1.5588 | 0.000003 | SNRNP200 |
| 4760668 | 4766974 | chr20 | − | exonic | hsa_circ_0059354 | 1.8301 | 0.000003 | RASSF2 |
| 53410256 | 53416411 | chr12 | + | exonic | hsa_circ_0026497 | −1.5026 | 0.000003 | EIF4B |
| 120916382 | 120924441 | chr11 | + | exonic | hsa_circ_0000365 | 2.1086 | 0.000003 | TBCEL |
| 95500310 | 95500614 | chr9 | − | intronic | hsa_circ_0001874 | 1.5341 | 0.000003 | BICD2 |
| 141004774 | 141009692 | chr5 | − | exonic | hsa_circ_0074332 | 1.7448 | 0.000003 | HDAC3 |
| 3976434 | 3976629 | chr19 | − | intronic | hsa_circ_0000872 | 1.6625 | 0.000004 | EEF2 |
| 49343147 | 49349087 | chr3 | − | exonic | hsa_circ_0004581 | −1.5683 | 0.000004 | USP4 |
| 79186178 | 79188586 | chr4 | + | exonic | hsa_circ_0070113 | 1.5108 | 0.000004 | FRAS1 |
| 54292038 | 54294350 | chr4 | + | exonic | hsa_circ_0069748 | 1.7488 | 0.000004 | FIP1L1 |
| 98276327 | 98276412 | chr2 | − | intronic | hsa_circ_0001049 | 1.5128 | 0.000004 | ACTRIB |
| 89747293 | 89750866 | chr14 | − | exonic | hsa_circ_0000559 | −1.5849 | 0.000004 | FOXN3 |
| 50596162 | 50596330 | chr15 | − | exonic | hsa_circ_0035208 | −1.5373 | 0.000004 | GABPB1 |
| 175426288 | 175426438 | chr2 | − | sense overlapping | hsa_circ_0001082 | −1.5241 | 0.000004 | WIPF1 |
| 3726429 | 3733958 | chr11 | − | exonic | N/A | −1.5359 | 0.000005 | NUP98 |
| 113705647 | 113707650 | chr12 | + | exonic | hsa_circ_0002857 | 1.6852 | 0.000005 | TPON1 |
| 103299660 | 103300494 | chr8 | − | exonic | hsa_circ_0001818 | 2.4036 | 0.000005 | UBR5 |
| 140444507 | 140450374 | chr4 | − | exonic | hsa_circ_0001442 | −1.5275 | 0.000005 | SETD7 |
| 77065301 | 77065626 | chr4 | − | exonic | hsa_circ_0070040 | 1.9776 | 0.000006 | NUP54 |
| 9792628 | 9793633 | chr3 | + | exonic | hsa_circ_0008027 | 1.5105 | 0.000006 | OGG1 |
| 57237616 | 57250507 | chr4 | − | exonic | N/A | −1.5608 | 0.000007 | AASDH |
| 51680350 | 51680428 | chr16 | + | sense overlapping | hsa_circ_0005008 | 2.1673 | 0.000008 | TCONS_I2_00009739 |
| 188202379 | 188242575 | chr3 | + | exonic | hsa_circ_0006517 | 1.5366 | 0.000009 | LPP |
| 43008874 | 43011764 | chr15 | + | sense overlapping | N/A | 1.9950 | 0.000009 | STARD9 |
| 128356641 | 128363826 | chr3 | − | exonic | hsa_circ_0067231 | 1.5535 | 0.000009 | RPN1 |
| 22669237 | 22683186 | chrY | − | sense overlapping | N/A | −1.5582 | 0.000010 | TTTY10 |
| 3474817 | 3477249 | chr17 | − | exonic | N/A | −1.5849 | 0.000011 | TRPV1 |
| 61912498 | 61913166 | chr11 | + | sense overlapping | hsa_circ_0000315 | 3.6734 | 0.000011 | INCENP |
| 40120400 | 40120586 | chr1 7 | − | antisense | hsa_circ_0000763 | 3.2927 | 0.000012 | CNP |
| 154743639 | 154744117 | chr6 | − | exonic | hsa_circ_0078346 | −1.5876 | 0.000012 | CNKSR3 |
| 102603979 | 102669865 | chr7 | − | exonic | N/A | −1.5564 | 0.000013 | FBXL13 |
| 189022209 | 189026744 | chr4 | − | exonic | N/A | 1.6871 | 0.000013 | TRIML2 |
| 45203311 | 45204674 | chr11 | + | exonic | N/A | −1.5148 | 0.000013 | PRDM11 |
| 114157810 | 114175048 | chr13 | + | exonic | hsa_circ_0007760 | −1.5865 | 0.000014 | TMCO3 |
| 50592985 | 50596330 | chr15 | − | exonic | hsa_circ_0007983 | −1.5143 | 0.000014 | GABPB1 |
| 47380394 | 47397280 | chr11 | − | exonic | hsa_circ_0000303 | 1.7318 | 0.000017 | SPI1 |
| 44060686 | 44061844 | chr15 | + | exonic | N/A | 1.6563 | 0.000017 | PDIA3 |
| 118890859 | 118892596 | chr11 | + | exonic | N/A | 1.8155 | 0.000017 | TRAPPC4 |
| 104702610 | 104722244 | chr7 | + | exonic | N/A | 1.6253 | 0.000018 | KMT2E |
| 77830227 | 77835260 | chr11 | − | exonic | hsa_circ_0023787 | −1.6163 | 0.000022 | ALG8 |
| 76388556 | 76411108 | chr17 | + | exonic | hsa_circ_0045890 | 1.5043 | 0.000023 | PGS1 |
| 26233194 | 26236101 | chr7 | − | exonic | hsa_circ_0001691 | 1.5162 | 0.000027 | HNRNPA2B1 |
| 81121205 | 81124712 | chr16 | − | exonic | N/A | −2.8034 | 0.000029 | GOSH |
| 57409052 | 57430887 | chr17 | + | exonic | hsa_circ_0044837 | 3.2159 | 0.000030 | YPEL2 |
| 14513408 | 14515374 | chr19 | + | exonic | hsa_circ_0004853 | 1.5870 | 0.000034 | CD97 |
| 15374347 | 15410596 | chr6 | + | exonic | hsa_circ_0075671 | 1.8480 | 0.000035 | JARID2 |
| 34107610 | 34112225 | chr11 | + | exonic | hsa_circ_0021647 | 2.1746 | 0.000042 | CAPRIN1 |
| 1735857 | 1770677 | chr1 | − | exonic | hsa_circ_0005907 | 1.5318 | 0.000043 | GNB1 |
| 10283765 | 10288043 | chr19 | − | exonic | hsa_circ_0000889 | 1.5118 | 0.000046 | DNMT1 |
| 123718838 | 123721032 | chr10 | − | exonic | hsa_circ_0020256 | −2.1983 | 0.000050 | NSMCE4A |
| 34110941 | 34112225 | chr11 | + | exonic | hsa_circ_0021652 | 2.2841 | 0.000052 | CAPRIN1 |
| 32659871 | 32666359 | chr20 | + | exonic | hsa_circ_0001140 | 1.5530 | 0.000058 | RALY |
| 34111725 | 34112225 | chr11 | + | exonic | hsa_circ_0000288 | 2.4433 | 0.000064 | CAPRIN1 |
| 17117929 | 17128675 | chr22 | + | exonic | hsa_circ_0062142 | 1.6161 | 0.000066 | psiTPTE22 |
| 72850146 | 72857113 | chr5 | − | exonic | N/A | −1.9558 | 0.000066 | ANKRA2 |
| 140920348 | 140920479 | chr4 | − | intronic | hsa_circ_0001443 | 1.5718 | 0.000070 | MAML3 |
| 28199932 | 28200152 | chr1 | + | intronic | hsa_circ_0000036 | 1.5645 | 0.000072 | C1orf38 |
| 103916775 | 103917971 | chr10 | + | exonic | hsa_circ_0000257 | −1.7953 | 0.000073 | NOLC1 |
| 68155889 | 68157024 | chr16 | + | exonic | hsa_circ_0005615 | 1.7410 | 0.000095 | NFATC3 |

TABLE 15-continued (Sert R vs NR baseline)

| TxStart | TxEnd | Chrom | Strand | circRNA type | Allas | Fold change | P-value | GeneSymbol |
|---|---|---|---|---|---|---|---|---|
| 33429698 | 33429839 | chrt | + | antisense | hsa_circ_0000049 | −1.5792 | 0.000100 | RNF19B |
| 1003727 | 1006847 | chr12 | + | exonic | hsa_circ_0003251 | 1.6634 | 0.000109 | WNK1 |
| 38894089 | 38897285 | chr22 | − | exonic | hsa_circ_0063331 | 1.7359 | 0.000114 | DDX17 |
| 110064315 | 110068928 | chr9 | + | exonic | hsa_circ_0006174 | 1.7792 | 0.000117 | RAD23B |
| 20507738 | 20527139 | chr2 | − | exonic | hsa_circ_0052867 | 1.7939 | 0.000125 | PUM2 |
| 85554139 | 85554349 | chr2 | − | sense overlapping | hsa_circ_0001035 | 1.9799 | 0.000128 | TGOLN2 |
| 5690345 | 5691678 | chr19 | + | exonic | hsa_circ_0048764 | −1.8978 | 0.000129 | RPL36 |
| 42284534 | 42284717 | chr2 | + | intronic | N/A | 1.5309 | 0.000141 | PKDCC |
| 185318552 | 185327138 | chr3 | + | exonic | N/A | 1.6713 | 0.000143 | SENP2 |
| 22940727 | 22947086 | chr15 | + | exonic | hsa_circ_0034072 | 1.5428 | 0.000188 | CYFIP1 |
| 124517260 | 124518071 | chr11 | − | exonic | hsa_circ_0000367 | 2.9762 | 0.000204 | SIAE |
| 31093273 | 31093358 | chr16 | − | antisense | hsa_circ_0000691 | 2.8594 | 0.000217 | ZNF646 |
| 219467402 | 219468493 | chr1 | + | sense overlapping | N/A | −1.8208 | 0.000228 | XLOC_000566 |
| 27834800 | 27834884 | chr6 | − | sense overlapping | hsa_circ_0001596 | 2.3704 | 0.000255 | HIST1H1B |
| 110068659 | 110081160 | chr9 | + | exonic | hsa_circ_0087862 | 2.0376 | 0.000263 | RAD23B |
| 19627435 | 19663412 | chr16 | + | exonic | hsa_circ_0005699 | −1.8947 | 0.000271 | C16orf62 |
| 8059547 | 8059653 | chr17 | − | intronic | hsa_circ_0000742 | 1.8092 | 0.000277 | None |
| 243056789 | 243064606 | chr2 | + | exonic | N/A | 1.5008 | 0.000279 | LOC728323 |
| 349113 | 349256 | chr6 | + | intronic | hsa_circ_0001568 | 3.2945 | 0.000279 | DUSP22 |
| 85554223 | 85554349 | chr2 | − | sense overlapping | hsa_circ_0001036 | 1.9445 | 0.000287 | TGOLN2 |
| 54292038 | 54310270 | chr4 | + | exonic | hsa_circ_0001413 | 1.5144 | 0.000309 | FIP1L1 |
| 45391429 | 45396935 | chr18 | − | exonic | hsa_circ_0003694 | 1.5112 | 0.000323 | SMAD2 |
| 109479800 | 109479932 | chrt | − | intronic | hsa_circ_0000102 | 2.4968 | 0.000333 | CLCC1 |
| 208589523 | 208598771 | chr2 | + | exonic | N/A | 2.2119 | 0.000353 | CCNYL1 |
| 47098310 | 47108608 | chr3 | − | exonic | hsa_circ_0002569 | 1.7014 | 0.000356 | SETD2 |
| 240098108 | 240158360 | chr2 | − | exonic | hsa_circ_0003445 | 1.5169 | 0.000369 | HDAC4 |
| 85667519 | 85695371 | chr16 | + | exonic | hsa_circ_0040730 | 2.0527 | 0.000378 | KIAA0182 |
| 1032390 | 1036245 | chr19 | + | exonic | hsa_circ_0048140 | 1.5077 | 0.000394 | CNN2 |
| 25288601 | 25300954 | chr20 | − | exonic | hsa_circ_0059665 | −4.5148 | 0.000414 | ABHD12 |
| 3988781 | 3988912 | chr11 | + | exonic | hsa_circ_0020926 | 1.5706 | 0.000419 | STIM1 |
| 89458787 | 89459087 | chr16 | − | intronic | N/A | −3.7837 | 0.000436 | ANKRD11 |
| 110084263 | 110087285 | chr9 | + | exonic | hsa_circ_0001880 | 1.6568 | 0.000442 | RAD23B |
| 42103080 | 42105299 | chr15 | + | exonic | hsa_circ_0034762 | 2.9061 | 0.000446 | MAPKBP1 |
| 47098310 | 47103836 | chr3 | − | exonic | hsa_circ_0065149 | 1.6431 | 0.000469 | SETD2 |
| 56558216 | 56558309 | chr12 | + | antisense | hsa_circ_0000407 | 2.0151 | 0.000501 | SMARCC2 |
| 37838091 | 37838774 | chr19 | + | exonic | N/A | 1.9796 | 0.000505 | HKR1 |
| 39191239 | 39200116 | chr19 | + | exonic | hsa_circ_0050900 | 1.9380 | 0.000508 | ACTN4 |
| 47441689 | 47446190 | chrX | + | exonic | hsa_circ_0090446 | −1.7940 | 0.000512 | TIMP1 |
| 41191341 | 41196173 | chr15 | + | exonic | hsa_circ_0034642 | 2.4043 | 0.000517 | VPS18 |
| 118774654 | 118787003 | chrX | − | exonic | hsa_circ_0008350 | 1.5184 | 0.000557 | SEPT6 |
| 110068659 | 110074018 | chr9 | + | exonic | hsa_circ_0087861 | 1.6059 | 0.000558 | RAD23B |
| 1737913 | 1749314 | chr1 | − | exonic | hsa_circ_0009357 | 1.8344 | 0.000559 | GNB1 |
| 27975161 | 27977818 | chr17 | − | exonic | hsa_circ_0042799 | 1.6566 | 0.000596 | SSH2 |
| 171965322 | 171969331 | chr3 | + | exonic | hsa_ciro_0006156 | 1.6358 | 0.000653 | FNDC3B |
| 133587 | 139152 | chr11 | − | exonic | hsa_circ_0020596 | 1.7952 | 0.000692 | None |
| 243242289 | 243265046 | chr1 | − | exonic | hsa_circ_0017215 | 2.3701 | 0.000700 | TCONS_I2_00002816 |
| 224142178 | 224149975 | chr1 | − | intronic | hsa_circ_0001978 | 1.8065 | 0.000738 | TCONS_I2_00001804 |
| 36282482 | 36292436 | chr1 | + | exonic | hsa_circ_0003986 | 1.5016 | 0.000755 | EIF2C4 |
| 13701322 | 13717044 | chr10 | − | exonic | hsa_circ_0004183 | 2.0844 | 0.000770 | FRMD4A |
| 99220660 | 99233376 | chr9 | + | exonic | hsa_circ_0087631 | 1.9825 | 0.000781 | HABP4 |
| 36245469 | 36247930 | chr19 | + | exonic | hsa_circ_0050649 | −1.5321 | 0.000785 | HSPB6 |
| 222652709 | 224149975 | chr1 | + | sense overlapping | hsa_circ_0003163 | 1.7536 | 0.000789 | TCONS_I2_00001808 |
| 128354717 | 128360471 | chr11 | − | exonic | hsa_circ_0004296 | 1.5194 | 0.000791 | ETS1 |
| 128350085 | 128360471 | chr11 | − | exonic | hsa_circ_0002083 | 1.7828 | 0.000810 | ETS1 |
| 129662158 | 129679387 | chr7 | − | exonic | hsa_circ_0082319 | 1.9825 | 0.000849 | ZC3HC1 |
| 43334706 | 43342194 | chr21 | − | exonic | hsa_circ_0061817 | 1.5101 | 0.000953 | C2CD2 |
| 36245469 | 36246795 | chr19 | − | exonic | hsa_circ_0050648 | −1.5132 | 0.000958 | HSPB6 |
| 129665997 | 129679387 | chr7 | − | exonic | hsa_circ_0082326 | 2.0344 | 0.001025 | ZC3HC1 |
| 171851260 | 171969331 | chr3 | + | exonic | hsa_circ_0007148 | 1.6007 | 0.001029 | FNDC3B |
| 1712336 | 1714425 | chrX | + | exonic | hsa_circ_0007352 | 1.8194 | 0.001032 | None |
| 10610070 | 10610756 | chr19 | − | exonic | hsa_circ_0049271 | 1.6312 | 0.001121 | KEAP1 |
| 66764014 | 66766408 | chr16 | − | intronic | hsa_circ_0000706 | −1.5542 | 0.001153 | DYNC1L12 |
| 35800605 | 35800763 | chr17 | + | exonic | hsa_circ_0006220 | 2.0383 | 0.001183 | TADA2A |
| 110062421 | 110084399 | chr9 | + | exonic | hsa_circ_0087856 | 2.0977 | 0.001186 | RAD23B |
| 36415395 | 36440853 | chr11 | + | sense overlapping | N/A | 1.9009 | 0.001193 | PRR5L |
| 128281256 | 128289036 | chr7 | + | sense overlapping | hsa_circ_0005921 | 2.2043 | 0.001212 | FLJ45340 |
| 127083737 | 127089724 | chr9 | + | exonic | hsa_circ_0088494 | −1.6498 | 0.001268 | NEK6 |
| 2929251 | 2930958 | chr12 | + | exonic | hsa_circ_0000374 | 1.6079 | 0.001290 | ITFG2 |

TABLE 15-continued

| (Sert R vs NR baseline) | | | | | | | | |
|---|---|---|---|---|---|---|---|---|
| TxStart | TxEnd | Chrom | Strand | circRNA type | Alias | Fold change | P-value | GeneSymbol |
| 28163979 | 28167848 | chr16 | − | exonic | hsa_circ_0007807 | 1.5584 | 0.001379 | XPO6 |
| 20107645 | 20109225 | chr17 | + | exonic | hsa_circ_0000745 | 2.2785 | 0.001395 | SPECC1 |
| 35797838 | 35800763 | chr17 | + | exonic | hsa_circ_0043278 | 2.1025 | 0.001399 | TADA2A |
| 65473318 | 65492309 | chr2 | + | sense overlapping | hsa_circ_0001022 | 2.4615 | 0.001434 | ACTR2 |
| 6727768 | 6741097 | chr1 | − | exonic | hsa_circ_0008389 | 2.3891 | 0.001518 | DNAJC11 |
| 78337590 | 78338212 | chr17 | + | intronic | N/A | 1.5123 | 0.001577 | RNF213 |
| 16198836 | 16199930 | chr19 | + | exonic | hsa_circ_0005855 | 1.5063 | 0.001591 | TPM4 |
| 33935836 | 33941860 | chr9 | − | exonic | hsa_circ_0008344 | 1.6934 | 0.001628 | UBAP2 |
| 4891946 | 4892613 | chr6 | + | exonic | hsa_circ_0008285 | 2.5292 | 0.001650 | CDYL |
| 59058742 | 59058878 | chr19 | + | exonic | hsa_circ_0052372 | 1.5645 | 0.001765 | TRIM28 |
| 76301164 | 76415337 | chr13 | + | exonic | hsa_circ_0030448 | 1.5529 | 0.001835 | LMO7 |
| 8366 | 14149 | chrM | − | exonic | hsa_circ_0089763 | 1.5468 | 0.001840 | None |
| 22896855 | 22898646 | chr10 | − | exonic | hsa_circ_0003826 | 1.6000 | 0.001893 | PIP4K2A |
| 34151081 | 34165557 | chr17 | + | exonic | hsa_circ_0000758 | 1.5351 | 0.001904 | TAF15 |
| 34147027 | 34149837 | chr17 | + | exonic | hsa_circ_0043138 | 1.7719 | 0.001915 | TAF15 |
| 38726471 | 38734535 | chr10 | + | exonic | hsa_circ_0018225 | 1.6343 | 0.001928 | LOC399744 |
| 36737414 | 36745300 | chr22 | − | exonic | hsa_circ_0004470 | 2.1458 | 0.001995 | MYH9 |
| 134011326 | 134022971 | chr9 | + | exonic | hsa_circ_0089153 | −1.6596 | 0.002050 | NUP214 |
| 186504915 | 186505373 | chr3 | + | exonic | hsa_circ_0068464 | −1.8312 | 0.002084 | EIF4A2 |
| 65473657 | 65492309 | chr2 | + | exonic | hsa_circ_0008529 | 2.5924 | 0.002120 | ACTR2 |
| 38890634 | 38897285 | chr22 | − | exonic | hsa_circ_0002211 | 1.6285 | 0.002243 | DDX17 |
| 128282270 | 128289036 | chr7 | + | exonic | hsa_circ_0082179 | 1.9995 | 0.002328 | FLJ45340 |
| 107513236 | 107535189 | chr9 | + | exonic | hsa_circ_0087798 | 1.7850 | 0.002433 | NIPSNAP3A |
| 34144719 | 34149837 | chr17 | + | exonic | N/A | 1.6605 | 0.002459 | TAF15 |
| 36680448 | 36702653 | chr22 | − | exonic | hsa_circ_0063089 | 1.6978 | 0.002494 | MYH9 |
| 113933932 | 113935290 | chr11 | + | exonic | N/A | 1.9491 | 0.002525 | ZBTB16 |
| 128281294 | 128289036 | chr7 | + | exonic | hsa_circ_0082178 | 2.0034 | 0.002624 | FLJ45340 |
| 35800609 | 35800763 | chr17 | + | exonic | N/A | 1.9586 | 0.002733 | TADA2A |
| 131164981 | 131181313 | chr8 | − | exonic | hsa_circ_0001824 | 1.5086 | 0.002763 | ASAP1 |
| 40278772 | 40282608 | chr17 | − | exonic | N/A | 1.5348 | 0.002764 | RAB5C |
| 38072992 | 38075809 | chr22 | + | exonic | hsa_circ_0063227 | −1.6189 | 0.002864 | LGALS1 |
| 51743841 | 51747425 | chr15 | − | exonic | hsa_circ_0035277 | 1.6721 | 0.002868 | DMXL2 |
| 73775150 | 73775265 | chr17 | − | intronic | hsa_circ_0000803 | −2.1936 | 0.002941 | H3F3B |
| 674213 | 678730 | chr1 | − | sense overlapping | hsa_circ_0007211 | 2.0379 | 0.003055 | None |
| 104638135 | 104638748 | chr10 | + | exonic | N/A | 1.5456 | 0.003104 | AS3MT |
| 38724057 | 38734535 | chr10 | + | exonic | hsa_circ_0018224 | 2.0307 | 0.003141 | LOC399744 |
| 25328542 | 25339121 | chr15 | + | exonic | N/A | 1.7208 | 0.003211 | SNURF-SNRPN |
| 36865777 | 36868169 | chr17 | + | sense overlapping | hsa_circ_0000760 | 1.6241 | 0.003252 | MLLT6 |
| 153583192 | 153585991 | chrX | − | exonic | hsa_circ_0091934 | 1.9558 | 0.003331 | FLNA |
| 68155889 | 68160513 | chr16 | + | exonic | hsa_circ_0000711 | 2.0923 | 0.003346 | NEATC3 |
| 119529812 | 119549381 | chr4 | + | exonic | hsa_circ_0005433 | 1.8111 | 0.003553 | TCONS_I2_00020705 |
| 135625089 | 135626611 | chr2 | − | exonic | N/A | 2.4162 | 0.003563 | CONT2-AS1 |
| 18877942 | 18882804 | chr16 | − | exonic | hsa_circ_0038288 | 1.5506 | 0.003602 | SMG1 |
| 47719687 | 47727660 | chr3 | − | exonic | hsa_circ_0001296 | 1.8923 | 0.003865 | SMARCC1 |
| 236332005 | 236343328 | chr1 | + | exonic | N/A | 2.1745 | 0.004185 | GPR137B |
| 3735585 | 3747433 | chrX | − | sense overlapping | N/A | 1.6391 | 0.004186 | LOC389906 |
| 1747194 | 1756938 | chr1 | − | exonic | hsa_circ_0000008 | 1.5992 | 0.004716 | GNB1 |
| 75264433 | 75264514 | chr3 | + | sense overlapping | hsa_circ_0006169 | 2.0641 | 0.004755 | TCONS_I2_00018657 |
| 134353337 | 134353833 | chr9 | + | intronic | N/A | 1.5060 | 0.004877 | PRRC2B |
| 160103505 | 160109274 | chr6 | − | exonic | hsa_circ_0004662 | 1.9621 | 0.005102 | SOD2 |
| 667396 | 678730 | chrt | − | exonic | hsa_circ_0009181 | 1.9594 | 0.005603 | None |
| 125472197 | 125474142 | chr11 | + | exonic | hsa_circ_0024766 | −2.0628 | 0.005743 | STT3A |
| 12903120 | 12903230 | chr19 | − | intronic | hsa_circ_0000895 | 1.5433 | 0.005894 | JUNB |
| 27977671 | 28030080 | chr17 | − | exonic | hsa_circ_0042806 | 1.5412 | 0.006010 | SSH2 |
| 65271199 | 65272066 | chr11 | + | sense overlapping | hsa_circ_0002082 | 2.6013 | 0.006366 | MALAT1 |
| 20070853 | 20070981 | chr22 | + | intronic | hsa_circ_0001204 | 1.6972 | 0.006578 | DGCR8 |
| 180609838 | 180610653 | chr1 | + | intronic | N/A | 1.5846 | 0.006830 | XPR1 |
| 243222779 | 243242354 | chr1 | − | exonic | hsa_circ_0017202 | 1.8957 | 0.007036 | TCONS_I2_00002816 |
| 39821342 | 39829143 | chr7 | + | exonic | hsa_circ_0079926 | 1.8411 | 0.007262 | LINC00265 |
| 13933667 | 13937011 | chr1 | + | exonic | hsa_circ_0010027 | 1.6079 | 0.007276 | PDPN |
| 85723323 | 85742653 | chr11 | − | exonic | hsa_circ_0023940 | 1.7406 | 0.008123 | PICALM |
| 66413497 | 66413944 | chr11 | + | exonic | hsa_circ_0023016 | 2.1502 | 0.008273 | RBM4 |
| 64791491 | 64792365 | chr15 | + | sense overlapping | hsa_circ_0000615 | 1.6217 | 0.008482 | ZNF609 |
| 202010100 | 202013775 | chr2 | + | exonic | hsa_circ_0057748 | 1.5730 | 0.008816 | CFLAR |
| 62288378 | 62288522 | chr11 | − | intronic | hsa_circ_0000317 | 1.6892 | 0.009292 | AHNAK |
| 41850651 | 41854360 | chr19 | − | exonic | hsa_circ_0051218 | 1.5534 | 0.009747 | TGFB1 |
| 57059987 | 57064148 | chr12 | − | exonic | hsa_circ_0027089 | 1.5236 | 0.009767 | PTGES3 |
| 38801306 | 38803739 | chr8 | + | exonic | hsa_circ_0084021 | 1.7316 | 0.009834 | PLEKHA2 |

TABLE 15-continued (Sert R vs NR baseline)

| TxStart | TxEnd | Chrom | Strand | circRNA type | Alias | Fold change | P-value | GeneSymbol |
|---|---|---|---|---|---|---|---|---|
| 4516153 | 4519466 | chr16 | − | exonic | hsa_circ_0007788 | −1.6779 | 0.010135 | NMRAL1 |
| 150496687 | 150502572 | chr5 | − | exonic | hsa_circ_0074595 | 1.6178 | 0.010653 | ANXA6 |
| 1735857 | 1756938 | chr1 | − | exonic | hsa_circ_0006869 | 1.6584 | 0.010995 | GNB1 |
| 56854413 | 56866543 | chr8 | + | exonic | hsa_circ_0001803 | 1.5284 | 0.011144 | LYN |
| 18459757 | 18466821 | chr19 | + | exonic | hsa_circ_0050102 | 1.6034 | 0.011353 | PGPEP1 |
| 57088080 | 57089646 | chr19 | + | intronic | N/A | 2.2080 | 0.011952 | ZNF470 |
| 45302384 | 45323900 | chr21 | + | sense overlapping | N/A | 1.5032 | 0.012285 | AGPAT3 |
| 27047048 | 27047688 | chr17 | + | intronic | hsa_circ_0092360 | 1.6244 | 0.012777 | RPL23A |
| 29313942 | 29314417 | chr1 | + | exonic | hsa_circ_0011167 | 1.5621 | 0.013036 | EPB41 |
| 13532533 | 13581264 | chr20 | − | intronic | N/A | −1.7094 | 0.013269 | TASP1 |
| 65466985 | 65482828 | chr2 | + | exonic | N/A | 2.1184 | 0.013385 | ACTR2 |
| 22880557 | 22880710 | chr10 | − | exonic | hsa_circ_0017972 | 1.5809 | 0.013400 | PIP4K2A |
| 12645634 | 12653561 | chr3 | − | exonic | N/A | 1.5344 | 0.013717 | RAF1 |
| 62297840 | 62298224 | chr11 | − | intronic | hsa_circ_0000320 | 1.7299 | 0.014255 | AHNAK |
| 26204839 | 26205043 | chr6 | + | sense overlapping | hsa_circ_0001588 | 2.1392 | 0.014941 | HIST1H4E |
| 18650180 | 18653782 | chr19 | − | exonic | hsa_circ_0050124 | 1.5759 | 0.015275 | FKBP8 |
| 77977114 | 77987558 | chr4 | − | exonic | N/A | 1.5398 | 0.015611 | CON1 |
| 131357380 | 131357465 | chr12 | + | exonic | hsa_circ_0029426 | 1.8044 | 0.016257 | RAN |
| 126434011 | 126496057 | chr6 | + | antisense | hsa_circ_0130587 | 1.5550 | 0.017326 | MIR5695 |
| 25072253 | 25077915 | chr13 | − | exonic | hsa_circ_0005198 | 1.7871 | 0.017894 | PARP4 |
| 18650180 | 18654383 | chr19 | − | exonic | hsa_circ_0050125 | 1.5647 | 0.017977 | FKBP8 |
| 141595217 | 141616013 | chr8 | − | intronic | hsa_circ_0007313 | 1.5033 | 0.018636 | EIF202 |
| 73585593 | 73594262 | chr10 | − | exonic | hsa_circ_0018722 | 1.5447 | 0.019135 | PSAP |
| 1756835 | 1770677 | chr1 | − | exonic | hsa_circ_0009362 | 1.6141 | 0.019322 | GNB1 |
| 47379617 | 47379952 | chr11 | − | intronic | hsa_circ_0000301 | 1.5300 | 0.019336 | SPI1 |
| 45954567 | 45959775 | chr10 | − | exonic | hsa_circ_0018273 | 1.6968 | 0.019939 | MARCH8 |
| 48726970 | 48728915 | chr3 | − | exonic | hsa_circ_0003748 | 1.7712 | 0.020903 | IP6K2 |
| 10865809 | 10868382 | chr12 | − | exonic | hsa_circ_0025460 | −1.7081 | 0.021864 | CSDA |
| 68155889 | 68225678 | chr16 | + | exonic | hsa_circ_0039929 | 1.6247 | 0.021868 | NEATC3 |
| 50618381 | 50618469 | chr22 | + | sense overlapping | hsa_circ_0001255 | 1.7460 | 0.023961 | PANX2 |
| 169854206 | 169863309 | chr3 | − | exonic | hsa_circ_0001965 | 1.5572 | 0.025222 | PHC3 |
| 18650180 | 18650530 | chr19 | − | exonic | hsa_circ_0000915 | 1.5546 | 0.026969 | FKBP8 |
| 42903447 | 42905047 | chr6 | + | intronic | hsa_circ_0001605 | 1.8272 | 0.028064 | CNPY3 |
| 36723505 | 36737571 | chr22 | − | exonic | hsa_circ_0063147 | 1.5672 | 0.035510 | MYH9 |
| 135748304 | 135778851 | chr6 | − | exonic | hsa_circ_0077930 | 1.7329 | 0.035759 | AHM1 |
| 5680784 | 5692141 | chr7 | − | exonic | hsa_circ_0079284 | −1.6052 | 0.039779 | RNF216 |
| 151306734 | 151327356 | chr5 | + | intergenic | N/A | 1.6262 | 0.044454 | |
| 45247282 | 45249430 | chr17 | − | exonic | hsa_circ_0044234 | 1.5007 | 0.046115 | CDC27 |
| 29313942 | 29323831 | chr1 | + | exonic | hsa_circ_0011168 | 1.5011 | 0.046748 | EPB41 |

TABLE 16

(Sert B vs NR 1 week)

| TxStart | TxEnd | Chrom | Strand | circRNA type | Alias | Fold change | P-value | GeneSymbol |
|---|---|---|---|---|---|---|---|---|
| 2017333 | 2017502 | chr9 | + | intronic | hsa_circ_0001834 | 1.5191 | 9.4800E−09 | SMARCA2 |
| 19965129 | 19965469 | chr22 | − | intronic | hsa_circ_0092330 | 1.5944 | 8.4710E−08 | ARVCF |
| 21735928 | 21746820 | chr13 | − | exonic | hsa_circ_0029696 | 1.5662 | 0.000002 | SKA3 |
| 74561481 | 74580819 | chr18 | + | exonic | hsa_circ_0002799 | 1.5784 | 0.000003 | ZNF236 |
| 62303908 | 62305446 | chr20 | + | exonic | hsa_circ_0061170 | 2.1299 | 0.000006 | RTEL1-TNFRSF6B |
| 33608730 | 33610023 | chr19 | + | exonic | hsa_circ_0050444 | 1.5421 | 0.000007 | GPATCH1 |
| 58562378 | 58594266 | chr16 | − | exonic | hsa_circ_0039626 | 1.5087 | 0.000013 | CNOT1 |
| 1125950 | 1151181 | chr10 | + | exonic | hsa_circ_0017449 | 1.5118 | 0.000020 | WDR37 |
| 32479446 | 32483505 | chr3 | + | sense overlapping | hsa_circ_0005414 | 1.5601 | 0.000025 | CMTM7 |
| 71680927 | 71681075 | chr2 | − | antisense | hsa_circ_0001029 | 1.5336 | 0.000030 | DYSF |
| 126434011 | 126496057 | chr6 | + | antisense | hsa_circ_0130587 | 1.7600 | 0.000077 | MIR5695 |
| 68059317 | 68072052 | chr16 | + | exonic | hsa_circ_0039908 | 1.7525 | 0.000080 | DUS2L |
| 37159809 | 37161502 | chr20 | + | exonic | hsa_circ_0060342 | 1.5079 | 0.000096 | RALGAPB |
| 87765294 | 87797542 | chr7 | + | exonic | hsa_circ_0080968 | 1.8150 | 0.000113 | ADAM22 |
| 17212469 | 17213367 | chr19 | + | exonic | hsa_circ_0000907 | 1.5679 | 0.000484 | MYO9B |
| 47098310 | 47103836 | chr3 | − | exonic | hsa_circ_0065149 | 1.6204 | 0.000571 | SETD2 |
| 78682870 | 78722267 | chr9 | + | exonic | hsa_circ_0087234 | 1.5477 | 0.000683 | POSK5 |
| 32379220 | 32388780 | chr5 | − | exonic | hsa_circ_0072088 | 1.5435 | 0.000948 | ZFR |
| 103372298 | 103373854 | chr8 | − | exonic | hsa_circ_0001819 | 1.5058 | 0.001416 | UBR5 |
| 47098310 | 47108608 | chr3 | − | exonic | hsa_circ_0002569 | 1.6043 | 0.001591 | SETD2 |
| 129662158 | 129679387 | chr7 | − | exonic | hsa_circ_0082319 | 1.8259 | 0.001781 | ZC3HC1 |

TABLE 16-continued (Sert B vs NR 1 week)

| TxStart | TxEnd | Chrom | Strand | circRNA type | Alias | Fold change | P-value | GeneSymbol |
|---|---|---|---|---|---|---|---|---|
| 197597030 | 197602646 | chr3 | + | exonic | hsa_circ_0005873 | 1.5432 | 0.002468 | LRCH3 |
| 197592293 | 197602646 | chr3 | + | exonic | hsa_circ_0008351 | 1.6466 | 0.002547 | LRCH3 |
| 22696395 | 22777499 | chr11 | + | exonic | hsa_circ_0095626 | 1.5510 | 0.002784 | GAS2 |
| 18650180 | 18650530 | chr19 | − | exonic | hsa_circ_0000915 | 1.6077 | 0.003266 | FKBP8 |
| 10865809 | 10868382 | chr12 | − | exonic | hsa_circ_0025460 | 2.0476 | 0.003306 | CSDA |
| 77977114 | 77987558 | chr4 | − | exonic | hsa_circ_0127000 | 1.5210 | 0.003476 | CONI |
| 7839009 | 7844817 | chr10 | + | exonic | hsa_circ_0007292 | 1.6888 | 0.003505 | ATP501 |
| 40669428 | 40681774 | chr22 | + | exonic | hsa_circ_0063411 | 1.5696 | 0.003529 | TNRC6B |
| 68155889 | 68157024 | chr16 | + | exonic | hsa_circ_0005615 | 1.5617 | 0.004577 | NFATC3 |
| 61133516 | 61135470 | chr11 | + | exonic | hsa_circ_0002058 | 1.5230 | 0.004816 | TMEM138 |
| 68155889 | 68160513 | chr16 | + | exonic | hsa_circ_0000711 | 1.8483 | 0.004964 | NFATC3 |
| 18650180 | 18653782 | chr19 | − | exonic | hsa_circ_0050124 | 1.5338 | 0.005899 | FKBP8 |
| 68155889 | 68225678 | chr16 | + | exonic | hsa_circ_0039929 | 1.6637 | 0.006010 | NFATC3 |
| 22880557 | 22880710 | chr10 | − | exonic | hsa_circ_0017972 | 1.5245 | 0.006480 | PIP4K2A |
| 79613111 | 79614128 | chr10 | − | exonic | hsa_circ_0006649 | 1.5045 | 0.006750 | DLG5 |
| 128281294 | 128289036 | chr7 | + | exonic | hsa_circ_0082178 | 1.7327 | 0.007843 | FLJ45340 |
| 38724057 | 38734535 | chr10 | + | exonic | hsa_circ_0018224 | 1.7322 | 0.008313 | LOC399744 |
| 1737913 | 1749314 | chr1 | − | exonic | hsa_circ_0009357 | 1.5780 | 0.008414 | GNB1 |
| 18650180 | 18654383 | chr19 | − | exonic | hsa_circ_0050125 | 1.5192 | 0.008836 | FKBP8 |
| 128281256 | 128289036 | chr7 | + | sense overlapping | hsa_circ_0005921 | 1.7142 | 0.009315 | FLJ45340 |
| 674213 | 678730 | chri | − | sense overlapping | hsa_circ_0007211 | 1.7337 | 0.010236 | |
| 38894089 | 38897285 | chr22 | − | exonic | hsa_circ_0063331 | 1.5074 | 0.010364 | DDX17 |
| 667396 | 678730 | chri | − | exonic | hsa_circ_0009181 | 1.7400 | 0.010693 | |
| 85692787 | 85693046 | chr11 | − | exonic | hsa_circ_0023904 | 1.5305 | 0.010876 | PICALM |
| 243222779 | 243242354 | chri | − | exonic | hsa_circ_0017202 | 1.6837 | 0.011214 | TCONS_I2_00002816 |
| 20507738 | 20527139 | chr2 | − | exonic | hsa_circ_0052867 | 1.5063 | 0.011538 | PUM2 |
| 169854206 | 169863309 | chr3 | − | exonic | hsa_circ_0001965 | 1.5259 | 0.012958 | PHC3 |
| 119529812 | 119549381 | chr4 | + | exonic | hsa_circ_0005433 | 1.5200 | 0.013854 | TCONS_I2_00020705 |
| 128282270 | 128289036 | chr7 | + | exonic | hsa_circ_0082179 | 1.6585 | 0.014047 | FLJ45340 |
| 39821342 | 39829143 | chr7 | + | exonic | hsa_circ_0079926 | 1.6340 | 0.015078 | LING00265 |
| 89628179 | 89628539 | chr16 | + | intronic | hsa_circ_0092337 | 1.5921 | 0.015429 | RPL13 |
| 26204839 | 26205043 | chr6 | + | sense overlapping | hsa_circ_0001588 | 1.8646 | 0.015738 | HIST1H4E |
| 64791491 | 64792365 | chr15 | + | sense overlapping | hsa_circ_0000615 | 1.5156 | 0.019165 | ZNF609 |
| 13639794 | 13644961 | chr6 | − | exonic | hsa_circ_0001578 | 1.5204 | 0.019191 | RANBP9 |
| 227729319 | 227729842 | chr2 | + | exonic | hsa_circ_0001104 | 1.6632 | 0.019383 | RHBDD1 |
| 85692171 | 85707972 | chr11 | − | exonic | hsa_circ_0002884 | 1.5499 | 0.022197 | PICALM |
| 85707868 | 85712201 | chr11 | − | exonic | hsa_circ_0002513 | 1.6604 | 0.024690 | PICALM |
| 63988322 | 64008672 | chr15 | − | exonic | hsa_circ_0035796 | 1.7005 | 0.028407 | HERC1 |
| 4891946 | 4892613 | chr6 | + | exonic | hsa_circ_0008285 | 1.8595 | 0.028770 | CDYL |
| 85707868 | 85742653 | chr11 | − | exonic | hsa_circ_0023923 | 1.6296 | 0.033058 | PICALM |
| 153583192 | 153585991 | chrX | − | exonic | hsa_circ_0091934 | 1.5309 | 0.034179 | FLNA |
| 110062421 | 110084399 | chr9 | + | exonic | hsa_circ_0087856 | 1.5079 | 0.035654 | RAD23B |
| 36737414 | 36745300 | chr22 | − | exonic | hsa_circ_0004470 | 1.5815 | 0.036653 | MYH9 |
| 17270204 | 17273932 | chr19 | + | exonic | hsa_circ_0007396 | 1.7108 | 0.040381 | MYO98 |
| 74229605 | 74230755 | chr6 | − | exonic | hsa_circ_0077007 | 1.5248 | 0.047161 | EEF1A1 |

TABLE 17

(Sert R 1 week vs SERT R baseline)

| TxStart | TxEnd | Chrom | Strand | circRNA type | Allas | Fold change | P-value | GeneSymbol |
|---|---|---|---|---|---|---|---|---|
| 71680927 | 71681075 | chr2 | − | antisense | hsa_circ_0001029 | 1.5518 | 9.5874E−06 | DYSF |
| 30856464 | 30857207 | chr6 | + | exonic | hsa_circ_0005133 | 1.5607 | 5.4492E−05 | DDR1 |
| 37105033 | 37105170 | chr2 | − | exonic | hsa_circ_0054033 | −1.5937 | 0.000068 | STRN |
| 155448623 | 155451551 | chr6 | + | exonic | hsa_circ_0008289 | −1.6278 | 0.000111 | TIAM2 |
| 170667931 | 170669824 | chr5 | + | exonic | hsa_circ_0004738 | −1.6344 | 0.000115 | RANBP17 |
| 69699344 | 69700862 | chr10 | − | exonic | hsa_circ_0007997 | 1.7230 | 0.000264 | HERC4 |
| 59058742 | 59058878 | chr19 | + | exonic | hsa_circ_0052372 | 1.5588 | 0.000501 | TRIM28 |
| 89628179 | 89628539 | chr16 | + | intronic | hsa_circ_0092337 | 2.0496 | 0.000584 | RPL13 |
| 61912498 | 61913166 | chr11 | + | sense overlapping | hsa_circ_0000315 | −2.5489 | 0.001013 | INCENP |
| 5827104 | 5842668 | chr10 | − | exonic | hsa_circ_0005379 | 1.5646 | 0.001059 | GDI2 |
| 104702610 | 104722244 | chr7 | + | exonic | N/A | 1.5109 | 0.001139 | KMT2E |
| 40872407 | 40882768 | chr1 | + | exonic | hsa_circ_0011898 | 1.5128 | 0.001201 | SMAP2 |
| 10395790 | 10397291 | chr19 | + | exonic | hsa_circ_0049241 | 1.7069 | 0.001364 | ICAM1 |
| 99220660 | 99233376 | chr9 | + | exonic | hsa_circ_0087631 | 1.7952 | 0.001682 | HABP4 |

TABLE 17-continued (Sert R 1 week vs SERT R baseline)

| TxStart | TxEnd | Chrom | Strand | circRNA type | Allas | Fold change | P-value | GeneSymbol |
|---|---|---|---|---|---|---|---|---|
| 13049413 | 13055304 | chr19 | + | exonic | hsa_circ_0049637 | 1.8774 | 0.001705 | CALR |
| 31093273 | 31093358 | chr16 | − | antisense | hsa_circ_0000691 | 2.0382 | 0.002473 | ZNF646 |
| 47316514 | 47316617 | chr20 | − | intronic | hsa_circ_0001167 | −1.5018 | 0.002486 | PREX1 |
| 14369008 | 14369452 | chr5 | + | intronic | N/A | 1.5495 | 0.002603 | TRIO |
| 115202366 | 115205825 | chr5 | + | exonic | hsa_circ_0002919 | 1.6065 | 0.002604 | AP3S1 |
| 129662158 | 129679387 | chr7 | − | exonic | hsa_circ_0082319 | 1.7514 | 0.002788 | ZC3HC1 |
| 41916541 | 41929074 | chr19 | + | exonic | hsa_circ_0000937 | 1.5266 | 0.003536 | BCKDHA |
| 13933667 | 13937011 | chr1 | + | exonic | hsa_circ_0010027 | 1.5430 | 0.003779 | PDPN |
| 85554139 | 85554349 | chr2 | − | sense overlapping | hsa_circ_0001035 | 1.6238 | 0.004196 | TGOLN2 |
| 13701322 | 13717044 | chr10 | − | exonic | hsa_circ_0004183 | 1.7338 | 0.004215 | FRMD4A |
| 236332005 | 236343328 | chr1 | + | exonic | N/A | 1.9290 | 0.004873 | GPR137B |
| 20070853 | 20070981 | chr22 | + | intronic | hsa_circ_0001204 | −1.6487 | 0.005299 | DGCR8 |
| 124517260 | 124518071 | chr11 | − | exonic | hsa_circ_0000367 | 2.3036 | 0.005925 | SIAE |
| 44060686 | 44061844 | chr15 | + | exonic | N/A | 1.5928 | 0.006101 | PDIA3 |
| 99481790 | 99483412 | chr9 | + | sense overlapping | hsa_circ_0139435 | −1.5265 | 0.006109 | RP11-535M15.1 |
| 208589523 | 208598771 | chr2 | + | exonic | N/A | 1.7973 | 0.007051 | CONYL1 |
| 1737913 | 1749314 | chr1 | − | exonic | hsa_circ_0009357 | 1.5612 | 0.007207 | GNB1 |
| 35797838 | 35800763 | chr17 | + | exonic | hsa_circ_0043278 | 1.7374 | 0.007535 | TADA2A |
| 85554223 | 85554349 | chr2 | − | sense overlapping | hsa_circ_0001036 | 1.5794 | 0.007657 | TGOLN2 |
| 40120400 | 40120586 | chr17 | − | antisense | hsa_circ_0000763 | −1.9105 | 0.008423 | CNP |
| 107513236 | 107535189 | chr9 | + | exonic | hsa_circ_0087798 | −1.6302 | 0.008912 | NIPSNAP3A |
| 34107610 | 34112225 | chr11 | + | exonic | hsa_circ_0021647 | 1.6600 | 0.009048 | CAPRIN1 |
| 135625089 | 135626611 | chr2 | − | exonic | N/A | −2.2992 | 0.009423 | CONT2-AS1 |
| 34111725 | 34112225 | chr11 | + | exonic | hsa_circ_0000288 | 1.7832 | 0.009666 | CAPRIN1 |
| 25325262 | 25326442 | chr15 | + | intronic | hsa_circ_0092367 | −1.5545 | 0.010503 | SNORD116-14 |
| 34110941 | 34112225 | chr11 | + | exonic | hsa_circ_0021652 | 1.7157 | 0.010585 | CAPRIN1 |
| 160103505 | 160109274 | chr6 | − | exonic | hsa_circ_0004662 | 1.7477 | 0.011042 | SOD2 |
| 6727768 | 6741097 | chr1 | − | exonic | hsa_circ_0008389 | −2.0709 | 0.011334 | DNAJC11 |
| 109479800 | 109479932 | chri | − | intronic | hsa_circ_0000102 | −1.9089 | 0.011358 | CLCC1 |
| 37838091 | 37838774 | chr19 | + | exonic | hsa_circ_0109543 | −1.6436 | 0.013260 | HKR1 |
| 57409052 | 57430887 | chr17 | + | exonic | hsa_circ_0044837 | −1.9894 | 0.014362 | YPEL2 |
| 35800609 | 35800763 | chr17 | + | exonic | N/A | 1.6269 | 0.015350 | TADA2A |
| 57409052 | 57430887 | chr17 | + | exonic | hsa_circ_0044837 | 1.5281 | 0.016471 | YPEL2 |
| 85737333 | 85742653 | chr11 | − | exonic | hsa_circ_0002433 | 1.5807 | 0.017092 | PICALM |
| 61653517 | 61657356 | chr5 | + | exonic | hsa_circ_0001490 | −1.7235 | 0.018494 | KIF2A |
| 35800605 | 35800763 | chr17 | + | exonic | hsa_circ_0006220 | 1.5815 | 0.018778 | TADA2A |
| 127338260 | 127339678 | chr5 | − | intronic | N/A | −1.5810 | 0.018978 | CTC-228N24.3 |
| 27834800 | 27834884 | chr6 | − | sense overlapping | hsa_circ_0001596 | −1.7043 | 0.018989 | HIST1H1B |
| 85742510 | 85742653 | chr11 | − | exonic | hsa_circ_0023944 | 1.5576 | 0.019117 | PICALM |
| 20107645 | 20109225 | chr17 | + | exonic | hsa_circ_0000745 | 1.8404 | 0.019201 | SPECC1 |
| 85733409 | 85742653 | chr11 | − | exonic | hsa_circ_0023942 | 1.5380 | 0.020666 | PICALM |
| 85722072 | 85742653 | chr11 | − | exonic | hsa_circ_0000347 | 1.5543 | 0.020692 | PICALM |
| 68155889 | 68160513 | chr16 | + | exonic | hsa_circ_0000711 | 1.6089 | 0.022377 | NFATC3 |
| 349113 | 349256 | chr6 | + | intronic | hsa_circ_0001568 | −1.9028 | 0.024417 | DUSP22 |
| 57088080 | 57089646 | chr19 | + | intronic | hsa_circ_0109937 | −1.8962 | 0.024697 | ZNF470 |
| 42103080 | 42105299 | chr15 | + | exonic | hsa_circ_0034762 | −1.7911 | 0.025582 | MAPKBP1 |
| 85718584 | 85742653 | chr11 | − | exonic | hsa_circ_0023936 | 1.5342 | 0.026461 | PICALM |
| 103299660 | 103300494 | chr8 | − | exonic | hsa_circ_0001818 | 1.5398 | 0.028160 | UBR5 |
| 76910271 | 76928416 | chr10 | + | exonic | hsa_circ_0018905 | −1.7044 | 0.028734 | SAMD8 |
| 51680350 | 51680428 | chr16 | + | sense overlapping | hsa_circ_0005008 | 1.5721 | 0.029597 | TCONS_I2_00009739 |
| 65272490 | 65272586 | chr11 | + | intronic | hsa_circ_0000326 | 1.8138 | 0.032164 | TCONS_I2_00004572 |
| 47719687 | 47727660 | chr3 | − | exonic | hsa_circ_0001296 | −1.5743 | 0.032858 | SMARCC1 |
| 128281256 | 128289036 | chr7 | + | sense overlapping | hsa_circ_0005921 | 1.5063 | 0.033970 | FLJ45340 |
| 151306734 | 151327356 | chr5 | + | intergenic | N/A | −1.5474 | 0.035109 | |
| 26204839 | 26205043 | chr6 | + | sense overlapping | hsa_circ_0001588 | 1.7324 | 0.035201 | HIST1H4E |
| 135748304 | 135778851 | chr6 | − | exonic | hsa_circ_0077930 | −1.6504 | 0.035785 | AHI1 |
| 45247282 | 45259003 | chr17 | − | exonic | hsa_circ_0044235 | 1.6283 | 0.036041 | CDC27 |
| 66413497 | 66413944 | chr11 | + | exonic | hsa_circ_0023016 | −1.7310 | 0.036135 | RBM4 |
| 25072253 | 25077915 | chr13 | − | exonic | hsa_circ_0005198 | −1.6020 | 0.037039 | PARP4 |
| 50618381 | 50618469 | chr22 | + | sense overlapping | hsa_circ_0001255 | −1.6199 | 0.037149 | PANX2 |
| 26056122 | 26056299 | chr6 | − | sense overlapping | hsa_circ_0001583 | 1.5430 | 0.039109 | HIST1H1C |
| 243242289 | 243265046 | chr1 | − | exonic | hsa_circ_0017215 | 1.5036 | 0.041981 | TCONS_I2_00002816 |
| 85723323 | 85742653 | chr11 | − | exonic | hsa_circ_0023940 | 1.6653 | 0.043048 | PICALM |

TABLE 18

| (Sert NR 1 week vs SERT NR baseline) | | | | | | | | |
|---|---|---|---|---|---|---|---|---|
| TxStart | TxEnd | Chrom | Strand | circRNA type | Alias | Fold change | P-value | GeneSymbol |
| 71680927 | 71681075 | chr2 | − | antisense | hsa_circ_0001029 | 1.5518 | 0.000010 | DYSF |
| 30856464 | 30857207 | chr6 | + | exonic | hsa_circ_0005133 | 1.5607 | 0.000054 | DDR1 |
| 46515157 | 46515754 | chr11 | − | exonic | hsa_circ_0009155 | −1.5209 | 0.000055 | AMBRA1 |
| 22669237 | 22683186 | chrY | − | sense overlapping | hsa_circ_0142668 | −1.5912 | 0.000079 | TTTY10 |
| 69699344 | 69700862 | chr10 | − | exonic | hsa_circ_0007997 | 1.7230 | 0.000264 | HERC4 |
| 72850146 | 72857113 | chr5 | − | exonic | hsa_circ_0129585 | −1.5755 | 0.000450 | ANKRA2 |
| 17910716 | 17974508 | chr4 | − | exonic | hsa_circ_0125866 | −1.5534 | 0.000478 | LCORL |
| 59058742 | 59058878 | chr19 | + | exonic | hsa_circ_0052372 | 1.5588 | 0.000501 | TRIM28 |
| 89628179 | 89628539 | chr16 | + | intronic | hsa_circ_0092337 | 2.0496 | 0.000584 | RPL13 |
| 186504915 | 186505373 | chr3 | + | exonic | hsa_circ_0068464 | −1.6788 | 0.000933 | EIF4A2 |
| 5827104 | 5842668 | chr10 | − | exonic | hsa_circ_0005379 | 1.5646 | 0.001059 | GD12 |
| 104702610 | 104722244 | chr7 | + | exonic | N/A | 1.5109 | 0.001139 | KMT2E |
| 40872407 | 40882768 | chr1 | + | exonic | hsa_circ_0011898 | 1.5128 | 0.001201 | SMAP2 |
| 10395790 | 10397291 | chr19 | + | exonic | hsa_circ_0049241 | 1.7069 | 0.001364 | ICAM1 |
| 32557275 | 32566163 | chr1 | + | exonic | hsa_circ_0006349 | −1.5483 | 0.001526 | TMEM39B |
| 99220660 | 99233376 | chr9 | + | exonic | hsa_circ_0087631 | 1.7952 | 0.001682 | HABP4 |
| 13049413 | 13055304 | chr19 | + | exonic | hsa_circ_0049637 | 1.8774 | 0.001705 | CALR |
| 31093273 | 31093358 | chr16 | − | antisense | hsa_circ_0000691 | 2.0382 | 0.002473 | ZNF646 |
| 14369008 | 14369452 | chr5 | + | intronic | N/A | 1.5495 | 0.002603 | TRIO |
| 115202366 | 115205825 | chr5 | + | exonic | hsa_circ_0002919 | 1.6065 | 0.002604 | AP3S1 |
| 129662158 | 129679387 | chr7 | − | exonic | hsa_circ_0082319 | 1.7514 | 0.002788 | ZO3HC1 |
| 41916541 | 41929074 | chr19 | + | exonic | hsa_circ_0000937 | 1.5266 | 0.003536 | BCKDHA |
| 13933667 | 13937011 | chr1 | + | exonic | hsa_circ_0010027 | 1.5430 | 0.003779 | PDPN |
| 201966446 | 201969143 | chr1 | + | exonic | hsa_circ_0015962 | −1.5149 | 0.004025 | RNPEP |
| 85554139 | 85554349 | chr2 | − | sense overlapping | hsa_circ_0001035 | 1.6238 | 0.004196 | TGOLN2 |
| 13701322 | 13717044 | chr10 | − | exonic | hsa_circ_0004183 | 1.7338 | 0.004215 | FRMD4A |
| 236332005 | 236343328 | chr1 | + | exonic | hsa_circ_0112550 | 1.9290 | 0.004873 | GPR137B |
| 7301567 | 7303659 | chr12 | + | exonic | hsa_circ_0099201 | −1.5004 | 0.005010 | CLSTN3 |
| 124517260 | 124518071 | chr11 | − | exonic | hsa_circ_0000367 | 2.3036 | 0.005925 | SIAE |
| 44060686 | 44061844 | chr15 | + | exonic | N/A | 1.5928 | 0.006101 | PDIA3 |
| 208589523 | 208598771 | chr2 | + | exonic | hsa_circ_0118936 | 1.7973 | 0.007051 | CCNYL1 |
| 1737913 | 1749314 | chr1 | − | exonic | hsa_circ_0009357 | 1.5612 | 0.007207 | GNB1 |
| 35797838 | 35800763 | chr17 | + | exonic | hsa_circ_0043278 | 1.7374 | 0.007535 | TADA2A |
| 85554223 | 85554349 | chr2 | − | sense overlapping | hsa_circ_0001036 | 1.5794 | 0.007657 | TGOLN2 |
| 5680784 | 5692141 | chr7 | − | exonic | hsa_circ_0079284 | −1.8035 | 0.008327 | RNF216 |
| 34107610 | 34112225 | chr11 | + | exonic | hsa_circ_0021647 | 1.6600 | 0.009048 | CAPRIN1 |
| 34111725 | 34112225 | chr11 | + | exonic | hsa_circ_0000288 | 1.7832 | 0.009666 | CAPRIN1 |
| 22925975 | 22926065 | chr15 | + | exonic | hsa_circ_0034067 | −1.6612 | 0.010502 | CYFIP1 |
| 34110941 | 34112225 | chr11 | + | exonic | hsa_circ_0021652 | 1.7157 | 0.010585 | CAPRIN1 |
| 160103505 | 160109274 | chr6 | − | exonic | hsa_circ_0004662 | 1.7477 | 0.011042 | SOD2 |
| 73114707 | 73115261 | chr7 | − | sense overlapping | hsa_circ_0009012 | −1.5020 | 0.011180 | STX1A |
| 35800609 | 35800763 | chr17 | + | exonic | hsa_circ_0106717 | 1.6269 | 0.015350 | TADA2A |
| 57409052 | 57430887 | chr17 | + | exonic | hsa_circ_0044837 | 1.5281 | 0.016471 | YPEL2 |
| 85737333 | 85742653 | chr11 | − | exonic | hsa_circ_0002433 | 1.5807 | 0.017092 | PICALM |
| 35800605 | 35800763 | chr17 | + | exonic | hsa_circ_0006220 | 1.5815 | 0.018778 | TADA2A |
| 85742510 | 85742653 | chr11 | − | exonic | hsa_circ_0023944 | 1.5576 | 0.019117 | PICALM |
| 20107645 | 20109225 | chr17 | + | exonic | hsa_circ_0000745 | 1.8404 | 0.019201 | SPECC1 |
| 85733409 | 85742653 | chr11 | - | exonic | hsa_circ_0023942 | 1.5380 | 0.020666 | PICALM |
| 85722072 | 85742653 | chr11 | - | exonic | hsa_circ_0000347 | 1.5543 | 0.020692 | PICALM |
| 81121205 | 81124712 | chr16 | − | exonic | N/A | −2.0542 | 0.022021 | GCSH |
| 68155889 | 68160513 | chr16 | + | exonic | hsa_circ_0000711 | 1.6089 | 0.022377 | NFATC3 |
| 85718584 | 85742653 | chr11 | − | exonic | hsa_circ_0023936 | 1.5342 | 0.026461 | PICALM |
| 103299660 | 103300494 | chr8 | − | exonic | hsa_circ_0001818 | 1.5398 | 0.028160 | UBR5 |
| 51680350 | 51680428 | chr16 | + | sense overlapping | hsa_circ_0005008 | 1.5721 | 0.029597 | TCONS_I2_00009739 |
| 65272490 | 65272586 | chr11 | + | intronic | hsa_circ_0000326 | 1.8138 | 0.032164 | TCONS_I2_00004572 |
| 128281256 | 128289036 | chr7 | + | sense overlapping | hsa_circ_0005921 | 1.5063 | 0.033970 | FLJ45340 |
| 26204839 | 26205043 | chr6 | + | sense overlapping | hsa_circ_0001588 | 1.7324 | 0.035201 | HIST1H4E |
| 45247282 | 45259003 | chr17 | − | exonic | hsa_circ_0044235 | 1.6283 | 0.036041 | CDC27 |
| 26056122 | 26056299 | chr6 | − | sense overlapping | hsa_circ_0001583 | 1.5430 | 0.039109 | HIST1H1C |
| 243242289 | 243265046 | chr | − | exonic | hsa_circ_0017215 | 1.5036 | 0.041981 | TCONS_I2_00002816 |
| 85723323 | 85742653 | chr11 | − | exonic | hsa_circ_0023940 | 1.6653 | 0.043048 | PICALM |

Exemplary Embodiments

The disclosure provides a composition comprising a panel of from 1 up to 20 or more circRNAs, where the circRNAs are MDD- or BD-associated circRNA biomarkers or circRNA biomarkers for predicting response or remission after antidepressant treatment. In one embodiment, at least one of the circRNAs in the expression profile may be circTULP4. In one embodiment, at least one of the circRNAs in the expression profile may be circCDR1as. In one embodiment, at least one of the circRNAs in the expression profile may be circCHIC1. In one embodiment, at least one of the circRNAs in the expression profile may be circPICALM. In one embodiment, at least one of the circRNAs in the expression profile may be circSATB2. In one embodiment, at least one of the circRNAs in the expression profile may be circCOMT. In one embodiment, at least one of the circRNAs in the expression profile may be circRERE. In one specific embodiment, at least one of the circRNAs in the expression profile may be circMIR5695. In one embodiment, at least one of the circRNAs in the expression profile may be DDX50. In one embodiment, at least one of the circRNAs in the expression profile may be circRALGAPB. In one embodiment, at least one of the circRNAs in the expression profile may be circlCAM1. In one specific embodiment, at least one of the circRNAs in the expression profile may be circDDR1. In one specific embodiment, at least one of the circRNAs in the expression profile may be circADAM22. In one embodiment, at least one of the circRNAs in the expression profile may be circMALAT1. In one embodiment, at least one of the circRNAs in the expression profile may be circHMGA2. In one embodiment, at least one of the circRNAs in the expression profile may be circCYP24A1. In one embodiment, at least one of the circRNAs in the expression profile may be circDLG5. According to another specific embodiment, at least one of the circRNAs in the expression profile may be circMYO9B. In one embodiment, at least one of the circRNAs in the expression profile may be circNFATC3. In one embodiment, at least one of the circRNAs in the expression profile may be circDUSP22. In one embodiment, at least one of the circRNAs in the expression profile may be circFKBP8. In one embodiment, at least one of the circRNAs in the expression profile may be circVDAC2. In one embodiment, at least one of the circRNAs in the expression profile may be circTRIM69. In one embodiment, at least one of the circRNAs is derived from the differentially altered circRNAs shown in tables 1-18. In one embodiment, at least one of the circRNAs is derived from the differentially altered circRNAs according to SEQ ID NOs. 1-241. In one embodiment, the circRNA or probe comprises a sequence that spans the backspliced junction of the circRNA in an asymmetric manner.

Also provided is an assay for detecting MDD or BD comprising: one or more probes or one or more primers configured to identify the presence of or amplify at least one brain disorder-associated circRNA biomarker. In one embodiment, at least one of the circRNAs is circTULP4. In one embodiment, at least one of the circRNAs is circSATB2. In one embodiment, the circRNA, probe or PCR primer comprises a sequence selected from the group of sequences shown in FIG. 27 (SEQ ID NO.'s 242-287) and FIG. 28 (SEQ ID NO.'s 288-433) or a sequence having at least 80%, 85%, 90%, 95%, 96%, 97%, 98% or 99% nucleic acid sequence identity thereto, or to the complement thereof. In one embodiment, the circRNA or probe comprises a sequence that spans the backspliced junction of the circRNA in an asymmetric manner. In one embodiment, the one or more primers are configured to amplify at least one MDD/BD- or antidepressant response/treatment-associated circRNA biomarker. It should be noted that the exemplary primers and sequences provided herein include a representative number of species directed to a representative number of circRNAs and is not intended to be exhaustive of the entire genus of possible primers useful to amplify circRNAs.

Also provided is an assay for detecting MDD or BD comprising: one or more probes or one or more primers configured to identify the presence of or amplify at least one brain disorder-associated circRNA biomarker selected from the circRNA biomarker according to Tables 1-18. In one embodiment, the circRNA, probe or PCR primer comprises a sequence selected from the group of sequences shown in FIG. 27 and FIG. 28 or a sequence having at least 80%, 85%, 90%, 95%, 96%, 97%, 98% or 99% nucleic acid sequence identity thereto, or to the complement thereof. In one embodiment, the circRNA or probe comprises a sequence that spans the backspliced junction of the circRNA in an asymmetric manner. In one embodiment, the one or more primers are configured to amplify at least one MDD/BD- or antidepressant response/treatment-associated circRNA biomarker.

Further provided is a method for assessing MDD or BD in a subject comprising: obtaining a sample from the patient; assaying the sample using probes and/or primers configured to identify the presence of and/or amplify one or more brain disorder-associated circRNA biomarkers; producing an expression profile of the one or more brain disorder-associated circRNA biomarkers based on the assay; and comparing the expression profile to a control.

The disclosure also provides for a composition comprising one or more isolated circRNAs selected from circCDR1as, circTULP4, circCHIC1, circMIR5695, circRALGAPB, circCOMT, circPICALM, circDDX50, circRERE, circSATB2, circICAM1, circDDR1, circADAM22, circMALAT1, circHMGA2, circCYP24A1, circDLG5, circMYO9B, circNFATC3, circDUSP22, circFKBP8, circVDAC2, or circTRIM69, or any combination thereof, one or more probes specific for circCDR1as, circTULP4, circCHIC1, circMIR5695, circRALGAPB, circCOMT, circPICALM, circDDX50, circRERE, or circSATB2, circICAM1, circDDR1, circADAM22, circMALAT1, circHMGA2, circCYP24A1, circDLG5, circMYO9B, circNFATC3, circDUSP22, circFKBP8, circVDAC2, circTRIM69, or any combination thereof, or one or more primers specific for circCDR1as, circTULP4, circCHIC1, circMIR5695, circRALGAPB, circCOMT, circPICALM, circDDX50, circRERE, or circSATB2, circICAM1, circDDR1, circADAM22, circMALAT1, circHMGA2, circCYP24A1, circDLG5, circMYO9B, circNFATC3, circDUSP22, circFKBP8, circVDAC2, circTRIM69, or any combination thereof.

A kit is provided comprising a panel of probes comprising probes specific for one or more of circCDR1as, circTULP4, circCHIC1, circMIR5695, circRALGAPB, circCOMT, circPICALM, circDDX50, circRERE, or circSATB2, circICAM1, circDDR1, circADAM22, circMALAT1, circHMGA2, circCYP24A1, circDLG5, circMYO9B, circNFATC3, circDUSP22, circFKBP8, circVDAC2, circTRIM69, or any combination thereof, or comprising a plurality of primers specific for one or more of circCDR1as, circTULP4, circCHIC1, circMIR5695, circRALGAPB, circCOMT, circPICALM, circDDX50, circRERE, or circSATB2, circICAM1, circDDR1, circADAM22, circMALAT1, circHMGA2, circCYP24A1, circDLG5, circMYO9B, circNFATC3, circDUSP22, circFKBP8, circVDAC2, circ TRIM69, or any combination thereof.

An assay is provided for detecting a mammal having or at risk of having MDD or BD, or for detecting response or remission to an anti-depressant in a mammal, comprising: one or more probes configured to identify the presence of at least one circRNA selected from circCDR1as, circTULP4, circCHIC1, circMIR5695, circRALGAPB, circCOMT, circPICALM, circDDX50, circRERE, or circSATB2, circICAM1, circDDR1, circADAM22, circMALAT1, circHMGA2, circCYP24A1, circDLG5, circMYO9B, circNFATC3, circDUSP22, circFKBP8, circVDAC2, circTRIM69, or any combination thereof, or one or more primers specific for circCDR1as, circTULP4, circCHIC1, circMIR5695, circRALGAPB, circCOMT, circPICALM, circDDX50, circRERE, or circSATB2, circlCAM1, circDDR1, circADAM22, circMALAT1, circHMGA2, circCYP24A1, circDLG5, circMYO9B, circNFATC3, circDUSP22, circFKBP8, circVDAC2, circTRIM69.

In one embodiment, the probe comprises a sequence specific for circCHIC1, circMIR5695, circRALGAPB, circCOMT, circDDX50, or a combination thereof.

In one embodiment, the probe comprises a sequence specific for circCHIC1, circCOMT, circPICALM, circDDX50, circRERE, or a combination thereof.

In one embodiment, one or more primers configured to amplify a sequence specific for two or more of circCDR1as, circTULP4, circCHIC1, circMIR5695, circRALGAPB, circCOMT, circPICALM, circDDX50, circRERE, or circSATB2, circICAM1, circDDR1, circADAM22, circMALAT1, circHMGA2, circCYP24A1, circDLG5, circMYO9B, circNFATC3, circDUSP22, circFKBP8, circVDAC2, circTRIM69, or any combination thereof.

In one embodiment, the primer comprises a sequence specific for circCHIC1, circMIR5695, circRALGAPB, circCOMT, circDDX50, or a combination thereof.

In one embodiment, the primer comprises a sequence specific for circCHIC1, circCOMT, circPICALM, circDDX50, circRERE, or a combination thereof.

In one embodiment, the primer includes a sequence that spans the splice junction of the circRNA in an asymmetric manner.

Further provided is a method for diagnosing MDD or BD in a mammal, comprising: providing a test physiological sample from the mammal; and detecting the presence or amount of circCDR1as, circTULP4, circCHIC1, circMIR5695, circRALGAPB, circCOMT, circPICALM, circDDX50, circRERE, or circSATB2, circICAM1, circDDR1, circADAM22, circMALAT1, circHMGA2, circCYP24A1, circDLG5, circMYO9B, circNFATC3, circDUSP22, circFKBP8, circVDAC2, circTRIM69 in the test sample using probes and/or primers configured to identify the presence of and/or amplify circCDR1as, circTULP4, circCHIC1, circMIR5695, circRALGAPB, circCOMT, circPICALM, circDDX50, circRERE, or circSATB2, circICAM1, circDDR1, circADAM22, circMALAT1, circHMGA2, circCYP24A1, circDLG5, circMYO9B, circNFATC3, circDUSP22, circFKBP8, circVDAC2, circ TRIM69.

A method is provided to predict response or remission to an anti-depressant in a mammal, comprising: providing a test physiological sample from the mammal; and detecting the presence or amount of circCDR1as, circTULP4, circCHIC1, circMIR5695, circRALGAPB, circCOMT, circPICALM, circDDX50, circRERE, or circSATB2, circICAM1, circDDR1, circADAM22, circMALAT1, circHMGA2, circCYP24A1, circDLG5, circMYO9B, circNFATC3, circDUSP22, circFKBP8, circVDAC2, circTRIM69, in the test sample using probes and/or primers configured to identify the presence of and/or amplify circCDR1as, circTULP4, circCHIC1, circMIR5695, circRALGAPB, circCOMT, circPICALM, circDDX50, circRERE, or circSATB2, circICAM1, circDDR1, circADAM22, circMALAT1, circHMGA2, circCYP24A1, circDLG5, circMYO9B, circNFATC3, circDUSP22, circFKBP8, circVDAC2, circTRIM69. In one embodiment, the anti-depressant is for MDD.

A method to monitor progression of, or relapse of, MDD or BD in a mammal is provided. The method includes providing a test physiological sample from the mammal; and comparing the presence or amount of circCDR1as, circTULP4, circCHIC1, circMIR5695, circRALGAPB, circCOMT, circPICALM, circDDX50, circRERE, or circSATB2, circICAM1, circDDR1, circADAM22, circMALAT1, circHMGA2, circCYP24A1, circDLG5, circMYO9B, circNFATC3, circDUSP22, circFKBP8, circVDAC2, circTRIM69 in the test sample to a sample from the mammal obtained at an earlier point in time.

In one embodiment, the step of detecting comprises one or more probes or primers that include a sequence that spans the splice junction of circCDR1as, circTULP4, circCHIC1, circMIR5695, circRALGAPB, circCOMT, circPICALM, circDDX50, circRERE, or circSATB2, circICAM1, circDDR1, circADAM22, circMALAT1, circHMGA2, circCYP24A1, circDLG5, circMYO9B, circNFATC3, circDUSP22, circFKBP8, circVDAC2, circTRIM69 in an asymmetric manner. In one embodiment, the sample is a physiological fluid sample. In one embodiment, the sample is a blood sample. In one embodiment, the sample is a cellular sample. In one embodiment, the mammal is a human.

In addition, a method for assessing MDD or BD in a subject is provided. The method includes providing a sample from the subject; assaying the sample using probes and/or primers configured to identify the presence of and/or amplify one or more brain disorder-associated circRNA biomarkers; and determining whether the sample has altered levels of the one or more brain disorder-associated circRNAs or a different expression profile of the one or more brain disorder-associated circRNAs relative to a control representing levels of the one or more brain disorder-associated circRNAs or an expression profile of the one or more brain disorder-associated circRNAs in non-MDD or non-BD humans.

Exemplary circRNAs

SEQ ID NO. 1 *Homo Sapiens* - hsa_circ_0068464|NM_001967|EIF4A2
SEQ ID NO. 2 *Homo Sapiens* - hsa_circ_0054033|NM_003162|STRN
SEQ ID NO. 3 *Homo Sapiens* - hsa_circ_0111746|ENST00000367187.3|PIK3C2B
SEQ ID NO. 4 *Homo Sapiens* - hsa_circ_0066556|NM_002942|ROBO2
SEQ ID NO. 5 *Homo Sapiens* - hsa_circ_0013953|NM_004284|CHD1L
SEQ ID NO. 6 *Homo Sapiens* - hsa_circ_0009574|NM_012102|RERE
SEQ ID NO. 7 *Homo Sapiens* - hsa_circ_0049241|NM_000201|ICAM1

-continued

| Exemplary circRNAs |
| --- |
| SEQ ID NO. 8 *Homo Sapiens* - hsa_circ_0007352\|None\|None |
| SEQ ID NO. 9 *Homo Sapiens* - hsa_circ_0018594\|NM_002727\|SRGN |
| SEQ ID NO. 10 *Homo Sapiens* - hsa_circ_0017449\|NM_014023/WDR37 |
| SEQ ID NO. 11 *Homo Sapiens* - hsa_circ_0062191\|NM_018943\|TUBA8 |
| SEQ ID NO. 12 *Homo Sapiens* - hsa_circ_0010210\|NM_018125\|ARHGEF10L |
| SEQ ID NO. 13 *Homo Sapiens* - hsa_circ_0006148\|NM_144660\|SAMD8 |
| SEQ ID NO. 14 *Homo Sapiens* - hsa_circ_0029696\|NM_145061\|SKA3 |
| SEQ ID NO. 15 *Homo Sapiens* - hsa_circ_0123503\|NM_015141\|GPD1L |
| SEQ ID NO. 16 *Homo Sapiens* - hsa_circ_0052712\|NM_015909\|NBAS |
| SEQ ID NO. 17 *Homo Sapiens* - hsa_circ_0063526\|NM_002883\|RANGAP1 |
| SEQ ID NO. 18 *Homo Sapiens* - hsa_circ_0103668\|ENST00000558173.1\|TRIM69 |
| SEQ ID NO. 19 *Homo Sapiens* - hsa_circ_0000442\|NM_015335\|MED13L |
| SEQ ID NO. 20 *Homo Sapiens* - hsa_circ_0008305\|NM_001199649\|PTK2 |
| SEQ ID NO. 21 *Homo Sapiens* - hsa_circ_0025638\|NM_001164746\|RASSF8 |
| SEQ ID NO. 22 *Homo Sapiens* - hsa_circ_0087903\|NM_032012\|C9orf5 |
| SEQ ID NO. 23 *Homo Sapiens* - hsa_circ_0015382\|NM_020318\|PAPPA2 |
| SEQ ID NO. 24 *Homo Sapiens* - hsa_circ_0006349\|NM_018056\|TMEM39B |
| SEQ ID NO. 25 *Homo Sapiens* - hsa_circ_0029975\|NM_015678\|NBEA |
| SEQ ID NO. 26 *Homo Sapiens* - hsa_circ_0000157\|NM_000655\|SELL |
| SEQ ID NO. 27 *Homo Sapiens* - hsa_circ_0001176\|NM_001037335\|PRIC285 |
| SEQ ID NO. 28 *Homo Sapiens* - hsa_circ_0001101\|NM_020830\|WDFY1 |
| SEQ ID NO. 29 *Homo Sapiens* - hsa_circ_0001520\|NM_152624\|DCP2 |
| SEQ ID NO. 30 *Homo Sapiens* - hsa_circ_0008857\|NM_007348\|ATF6 |
| SEQ ID NO. 31 *Homo Sapiens* - hsa_circ_0058058\|NM_004044\|ATIC |
| SEQ ID NO. 32 *Homo Sapiens* - hsa_circ_0092330\|NM_001670\|ARVCF |
| SEQ ID NO. 33 *Homo Sapiens* - hsa_circ_0098630\|NM_030674\|SLC38A1 |
| SEQ ID NO. 34 *Homo Sapiens* - hsa_circ_0009012\|NM_004603\|STXIA |
| SEQ ID NO. 35 *Homo Sapiens* - hsa_circ_0001240\|NM_145912\|NFAM1 |
| SEQ ID NO. 36 *Homo Sapiens* - hsa_circ_0000959\|NM_014931\|PPP6R1 |
| SEQ ID NO. 37 *Homo Sapiens* - hsa_circ_0057551\|NM_001127257\|SLC39A10 |
| SEQ ID NO. 38 *Homo Sapiens* - hsa circ_0001655\|None\|None |
| SEQ ID NO. 39 *Homo Sapiens* - hsa_circ_0029934\|NM_033111\|N4BP2L2 |
| SEQ ID NO. 40 *Homo Sapiens* - hsa_circ_0042488\|NM_015626\|WSB1 |
| SEQ ID NO. 41 *Homo Sapiens* - hsa_circ_0115791\|ENST00000286827.3\|TIAM1 |
| SEQ ID NO. 42 *Homo Sapiens* - hsa_circ_0003915\|NM_001172509\|SATB2 |
| SEQ ID NO. 43 *Homo Sapiens* - hsa_circ_0001009\|NM_018062\|FANCL |
| SEQ ID NO. 44 *Homo Sapiens* - hsa_circ_0001820\|NM_145647\|WDR67 |
| SEQ ID NO. 45 *Homo Sapiens* - hsa_circ_0058651\|NM_025139\|ARMC9 |
| SEQ ID NO. 46 *Homo Sapiens* - hsa_circ_0080968\|NM_021723\|ADAM22 |
| SEQ ID NO. 47 *Homo Sapiens* - hsa_circ_0005387\|NM_004667\|HERC2 |
| SEQ ID NO. 48 *Homo Sapiens* - hsa_circ_0008132\|NM_138492\|PRELID2 |
| SEQ ID NO. 49 *Homo Sapiens* - hsa_circ_0108522\|ENST00000300605.6\|HDHD2 |
| SEQ ID NO. 50 *Homo Sapiens* - hsa_circ_0005303\|NM_001172218\|SCMH1 |
| SEQ ID NO. 51 *Homo Sapiens* - hsa_circ_0011451\|NM_022753\|S100PBP |
| SEQ ID NO. 52 *Homo Sapiens* - hsa_circ_0025597NM_001174097\|LDHB |
| SEQ ID NO. 53 *Homo Sapiens* - hsa_circ_0071375\|NM_007246\|KLHL2 |
| SEQ ID NO. 54 *Homo Sapiens* - hsa_circ_0120478\|NR_036441\|VRK2 |
| SEQ ID NO. 55 *Homo Sapiens* - hsa_circ_0060930\|NM_000782\|CYP24A1 |
| SEQ ID NO. 56 *Homo Sapiens* - hsa_circ_0015364\|NM_022457\|RFWD2 |
| SEQ ID NO. 57 *Homo Sapiens* - hsa_circ_0072654\|NM_005869\|CWC27 |
| SEQ ID NO. 58 *Homo Sapiens* - hsa_circ_0043912\|NM_001040431\|CCDC56 |
| SEQ ID NO. 59 *Homo Sapiens* - hsa_circ_0008912\|NM_144982\|ZFC3H1 |
| SEQ ID NO. 60 *Homo Sapiens* - hsa_circ_0001819\|NM_015902\|UBR5 |
| SEQ ID NO. 61 *Homo Sapiens* - hsa_circ_0000564\|NM_030621\|DICER1 |
| SEQ ID NO. 62 *Homo Sapiens* - hsa_circ_0027446\|NM_003483\|HMGA2 |
| SEQ ID NO. 63 *Homo Sapiens* - hsa_circ_0018031\|NM_001172303\|MASTL |
| SEQ ID NO. 64 *Homo Sapiens* - hsa_circ_0002067\|NM_139179\|DAGLB |
| SEQ ID NO. 65 *Homo Sapiens* - hsa_circ_0084904\|NM_015496\|KIAA1429 |
| SEQ ID NO. 66 *Homo Sapiens* - hsa_circ_0131987\|ENST00000370733.4\|KIAA1586 |
| SEQ ID NO. 67 *Homo Sapiens* - hsa_circ_0058520\|NM_001135187\|AGFG1 |
| SEQ ID NO. 68 *Homo Sapiens* - hsa_circ 0002474\|NM_001083\|PDE5A |
| SEQ ID NO. 69 *Homo Sapiens* - hsa_circ_0037139\|NM_000517\|HBA2 |
| SEQ ID NO. 70 *Homo Sapiens* - hsa_circ_0041694\|NM_002532\|NUP88 |
| SEQ ID NO. 71 *Homo Sapiens* - hsa_circ_0006093\|NM_139179\|DAGLB |
| SEQ ID NO. 72 *Homo Sapiens* - hsa_circ_0000691\|NM_014699\|ZNF646 |
| SEQ ID NO. 73 *Homo Sapiens* - hsa_circ_0003653\|NM_001142966\|GREB1L |
| SEQ ID NO. 74 *Homo Sapiens* - hsa_circ_0062277\|NM_000754\|COMT |
| SEQ ID NO. 75 *Homo Sapiens* - hsa_circ_0130587\|None\|None |
| SEQ ID NO. 76 *Homo Sapiens* - hsa_circ_0001167\|NM_020820\|PREX1 |
| SEQ ID NO. 77 *Homo Sapiens* - hsa_circ_0073009\|NM_003633\|ENC1 |
| SEQ ID NO. 78 *Homo Sapiens* - hsa_circ_0077578\|NM_014454\|SESN1 |
| SEQ ID NO. 79 *Homo Sapiens* - hsa_circ_0035944\|NM_001144823\|DENND4A |
| SEQ ID NO. 80 *Homo Sapiens* - hsa_circ_0044301\|NM_002265\|KPNB1 |
| SEQ ID NO. 81 *Homo Sapiens* - hsa_circ_0070805\|NM_001083\|PDESA |
| SEQ ID NO. 82 *Homo Sapiens* - hsa_circ_0076560\|NM_020750\|XPO5 |
| SEQ ID NO. 83 *Homo Sapiens* - hsa_circ_0082319\|NM_016478\|ZC3HC1 |
| SEQ ID NO. 84 *Homo Sapiens* - hsa_circ_0018309\|NM_001040084\|ANXA8 |

-continued

Exemplary circRNAs

SEQ ID NO. 85 *Homo Sapiens* - hsa_circ_0005379|NM_001494|GDI2
SEQ ID NO. 86 *Homo Sapiens* - hsa_circ_0002569|NM_014159|SETD2
SEQ ID NO. 87 *Homo Sapiens* - hsa_circ_0055161|NM_019885|CYP26B1
SEQ ID NO. 88 *Homo Sapiens* - hsa_circ_0001142|NM_080476|PIGU
SEQ ID NO. 89 *Homo Sapiens* - hsa_circ_0049965|NM_031941|USHBP1
SEQ ID NO. 90 *Homo Sapiens* - hsa_circ_0087631|NM_014282|HABP4
SEQ ID NO. 91 *Homo Sapiens* - hsa_circ_0008057|NM_001990|EYA3
SEQ ID NO. 92 *Homo Sapiens* - hsa_circ_0035301|NM_002748|MAPK6
SEQ ID NO. 93 *Homo Sapiens* - hsa_circ_0060342|NM_020336|RALGAPB
SEQ ID NO. 94 *Homo Sapiens* - hsa_circ_0000041|NM_001166006|EPB41
SEQ ID NO. 95 *Homo Sapiens* - hsa_circ_0063598|NM_001003796|NHP2L1
SEQ ID NO. 96 *Homo Sapiens* - hsa_circ_0000740|NM_020162|DHX33
SEQ ID NO. 97 *Homo Sapiens* - hsa_circ_0028198|NM_016238|ANAPC7
SEQ ID NO. 98 *Homo Sapiens* - hsa_circ_0000636|NM_001145358|SIN3A
SEQ ID NO. 99 *Homo Sapiens* - hsa_circ_0072954|NM_138782|FCHO2
SEQ ID NO. 100 *Homo Sapiens* - hsa_circ_0089131|NM_007313|ABL1
SEQ ID NO. 101 *Homo Sapiens* - hsa_circ_0125866|NM_001166139|LCORL
SEQ ID NO. 102 *Homo Sapiens* - hsa_circ_0127236|ENST00000273963.5|KLHL8
SEQ ID NO. 103 *Homo Sapiens* - hsa_circ_0061170|NR_037882|RTEL1-TNFRSF6B
SEQ ID NO. 104 *Homo Sapiens* - hsa_circ_0082440|NM_021807|EXOC4
SEQ ID NO. 105 *Homo Sapiens* - hsa_circ_0081481|NM_033506|FBXO24
SEQ ID NO. 106 *Homo Sapiens* - hsa_circ_0037376|NM_002952|RPS2
SEQ ID NO. 107 *Homo Sapiens* - hsa_circ_0004928|NM_057159|LPAR1
SEQ ID NO. 108 *Homo Sapiens* - hsa_circ_0024379|NM_001040455|SIDT2
SEQ ID NO. 109 *Homo Sapiens* - hsa_circ_0001160|NM_001098797|TOX2
SEQ ID NO. 110 *Homo Sapiens* - hsa_circ_0031570|NM_015473|HEATR5A
SEQ ID NO. 111 *Homo Sapiens* - hsa_circ_0007021|NM_006734IHIVEP2
SEQ ID NO. 112 *Homo Sapiens* - hsa_circ_0010027|NM_006474|PDPN
SEQ ID NO. 113 *Homo Sapiens* - hsa_circ_0052372|NM_005762|TRIM28
SEQ ID NO. 114 *Homo Sapiens* - hsa_circ_0091072|NM_001039840|CHIC1
SEQ ID NO. 115 *Homo Sapiens* - hsa_circ_0011898|NM_022733|SMAP2
SEQ ID NO. 116 *Homo Sapiens* - hsa_circ_0075826|NR_015410|LINC00340
SEQ ID NO. 117 *Homo Sapiens* - hsa_circ_0000315|NM_020238|INCENP
SEQ ID NO. 118 *Homo Sapiens* - hsa_circ_0020275|NM_002775|HTRA1
SEQ ID NO. 119 *Homo Sapiens* - hsa_circ_0082218|NM_001458|FLNC
SEQ ID NO. 120 *Homo Sapiens* - hsa_circ_0005133|None|None
SEQ ID NO. 121 *Homo Sapiens* - hsa_circ_0000937|NM_000709|BCKDHA
SEQ ID NO. 122 *Homo Sapiens* - hsa_circ_0006615|NM_022782|MPHOSPH9
SEQ ID NO. 123 *Homo Sapiens* - hsa_circ_0000543|NM_014992|DAAM1
SEQ ID NO. 124 *Homo Sapiens* - hsa_circ_0000282|NM_001113528|METTL15
SEQ ID NO. 125 *Homo Sapiens* - hsa_circ_0025984|NM_018976|SLC38A2
SEQ ID NO. 126 *Homo Sapiens* - hsa_circ_0006404|NM_001455|FOXO3
SEQ ID NO. 127 *Homo Sapiens* - hsa_circ_0008289|NM_012454|TIAM2
SEQ ID NO. 128 *Homo Sapiens* - hsa_circ_0018905|NM_144660|SAMD8
SEQ ID NO. 129 *Homo Sapiens* - hsa_circ_0028628|NM_181578|RFC5
SEQ ID NO. 130 *Homo Sapiens* - hsa_circ_0087888|NM_032012|C9orf5
SEQ ID NO. 131 *Homo Sapiens* - hsa_circ_0008990|NM_012335|MYO1F
SEQ ID NO. 132 *Homo Sapiens* - hsa_circ_0005414|NM_138410|CMTM7
SEQ ID NO. 133 *Homo Sapiens* - hsa_circ_0092382|ENST00000324109.4|DNMBP
SEQ ID NO. 134 *Homo Sapiens* - hsa_circ_0035957|NM_001144823|DENND4A
SEQ ID NO. 135 *Homo Sapiens* - hsa_circ_0006688|TCONS_12_00026000|TCONS_12_00026000
SEQ ID NO. 136 *Homo Sapiens* - hsa_circ_0008348|NM_001193485|LIMS1
SEQ ID NO. 137 *Homo Sapiens* - hsa_circ_0016348|NM_172362|KCNH1
SEQ ID NO. 138 *Homo Sapiens* - hsa_circ_0050444|NM_018025|GPATCH1
SEQ ID NO. 139 *Homo Sapiens* - hsa_circ_0084789|NM_024721|ZFHX4
SEQ ID NO. 140 *Homo Sapiens* - hsa_circ_0088511|NM_033334|NR6A1
SEQ ID NO. 141 *Homo Sapiens* - hsa_circ_0026467|NM_002273|KRT8
SEQ ID NO. 142 *Homo Sapiens* - hsa_circ_0022623|NM_024771|NAA40
SEQ ID NO. 143 *Homo Sapiens* - hsa_circ_0008584|NM_001105244|PTPRM
SEQ ID NO. 144 *Homo Sapiens* - hsa_circ_0087497|NM_013417|IARS
SEQ ID NO. 145 *Homo Sapiens* - hsa_circ_0045871|NM_004710|SYNGR2
SEQ ID NO. 146 *Homo Sapiens* - hsa_circ_0001730|NM_004444|EPHB4
SEQ ID NO. 147 *Homo Sapiens* - hsa_circ_0001029|NM_003494|DYSF
SEQ ID NO. 148 *Homo Sapiens* - hsa_circ_0056390|NM_001145928|SAP130
SEQ ID NO. 149 *Homo Sapiens* - hsa_circ_0004858|NM_017798|YTHDF1
SEQ ID NO. 150 *Homo Sapiens* - hsa_circ_0088059|NM_022486|SUSD1
SEQ ID NO. 151 *Homo Sapiens* - hsa_circ_0056264|NM_020909|EPB41L5
SEQ ID NO. 152 *Homo Sapiens* - hsa_circ_0006502|NM_138778|WDR85
SEQ ID NO. 153 *Homo Sapiens* - hsa_circ_0080217|NM_015198|COBL
SEQ ID NO. 154 *Homo Sapiens* - hsa_circ_0003813|NM_078474|TM2D3
SEQ ID NO. 155 *Homo Sapiens* - hsa_circ_0045581|NM_001545|ICT1
SEQ ID NO. 156 *Homo Sapiens* - hsa_circ_0049637|NM_004343ICALR
SEQ ID NO. 157 *Homo Sapiens* - hsa_circ_0038011|NM_015027|PDXDC1
SEQ ID NO. 158 *Homo Sapiens* - hsa_circ_0128496|NM_001142556|HMMR
SEQ ID NO. 159 *Homo Sapiens* - hsa_circ_0001834|NM_003070|SMARCA2
SEQ ID NO. 160 *Homo Sapiens* - hsa_circ_0075410|NM_020185|DUSP22
SEQ ID NO. 161 *Homo Sapiens* - hsa_circ_0001151|NM_018840|C20orf24

-continued

| Exemplary circRNAs |
|---|
| SEQ ID NO. 162 *Homo Sapiens* - hsa_circ_0028067\|NM_014325\|CORO1C |
| SEQ ID NO. 163 *Homo Sapiens* - hsa_circ_0032777\|NM_012111\|AHSA1 |
| SEQ ID NO. 164 *Homo Sapiens* - hsa_circ_0007097\|NM_024045\|DDX50 |
| SEQ ID NO. 165 *Homo Sapiens* - hsa_circ_0006530\|NM_024766\|CAMKMT |
| SEQ ID NO. 166 *Homo Sapiens* - hsa_circ_0004771\|NM_003489\|NRIP1 |
| SEQ ID NO. 167 *Homo Sapiens* - hsa_circ_0073608\|NM_152624\|DCP2 |
| SEQ ID NO. 168 *Homo Sapiens* - hsa_circ_0005210\|NM_031922\|REPS1 |
| SEQ ID NO. 169 *Homo Sapiens* - hsa_circ_0007765\|NM_002647\|PIK3C3 |
| SEQ ID NO. 170 *Homo Sapiens* - hsa_circ_0101802\|NM_002687\|PNN |
| SEQ ID NO. 171 *Homo Sapiens* - hsa_circ_0072088\|NM_016107\|ZFR |
| SEQ ID NO. 172 *Homo Sapiens* - hsa_circ_0047232\|NM_198129\|LAMA3 |
| SEQ ID NO. 173 *Homo Sapiens* - hsa_circ_0074407\|NM_020117\|LARS |
| SEQ ID NO. 174 *Homo Sapiens* - hsa_circ_0003695\|NM_007166\|PICALM |
| SEQ ID NO. 175 *Homo Sapiens* - hsa_circ_0087234\|NM_001190482\|PCSK5 |
| SEQ ID NO. 176 *Homo Sapiens* - hsa_circ_0009581\|NM_012102\|RERE |
| SEQ ID NO. 177 *Homo Sapiens* - hsa_circ_0129585\|NM_023039\|ANKRA2 |
| SEQ ID NO. 178 *Homo Sapiens* - hsa_circ_0001062\|NM_198581\|ZC3H6 |
| SEQ ID NO. 179 *Homo Sapiens* - hsa_circ_0071210\|NM_001199282\|LRBA |
| SEQ ID NO. 180 *Homo Sapiens* - hsa_circ_0053907\|NM_206943\|LTBP1 |
| SEQ ID NO. 181 *Homo Sapiens* - hsa_circ_0007422\|NM_001172509\|SATB2 |
| SEQ ID NO. 182 *Homo Sapiens* - hsa_circ_0027966\|NM_032148\|SLC41A2 |
| SEQ ID NO. 183 *Homo Sapiens* - hsa_circ_0008030\|NM_001114093\|LSM14A |
| SEQ ID NO. 184 *Homo Sapiens* - hsa_circ_0001348\|NM_207296\|MBNL1 |
| SEQ ID NO. 185 *Homo Sapiens* - hsa_circ_0050547\|NM_005499\|UBA2 |
| SEQ ID NO. 186 *Homo Sapiens* - hsa_circ_0001058\|NM_173647\|RNF149 |
| SEQ ID NO. 187 *Homo Sapiens* - hsa_circ_0041623\|NM_015528\|RNF167 |
| SEQ ID NO. 188 *Homo Sapiens* - hsa_circ_0074930\|NM_003062\|SLIT3 |
| SEQ ID NO. 189 *Homo Sapiens* - hsa_circ_0092332\|NM_032447\|FBN3 |
| SEQ ID NO. 190 *Homo Sapiens* - hsa_circ_0023928\|NM_007166\|P\|CALM |
| SEQ ID NO. 191 *Homo Sapiens* - hsa_circ_0007997\|NM_022079\|HERC4 |
| SEQ ID NO. 192 *Homo Sapiens* - hsa_circ_0000185\|NM_006085\|BPNT1 |
| SEQ ID NO. 193 *Homo Sapiens* - hsa_circ_0001216\|NM_001079539\|XBP1 |
| SEQ ID NO. 194 *Homo Sapiens* - hsa_circ_0039908\|NM_017803\|DUS2L |
| SEQ ID NO. 195 *Homo Sapiens* - hsa_circ_0075533\|NM_006567\|FARS2 |
| SEQ ID NO. 196 *Homo Sapiens* - hsa_circ_0001219\|NM_153051\|MTMR3 |
| SEQ ID NO. 197 *Homo Sapiens* - hsa_circ_0006491\|NM_015559\|SETBP1 |
| SEQ ID NO. 198 *Homo Sapiens* - hsa_circ_0003195\|NM_017735\|TTC27 |
| SEQ ID NO. 199 *Homo Sapiens* - hsa_circ_0057319\|NM_002210\|ITGAV |
| SEQ ID NO. 200 *Homo Sapiens* - hsa_circ_0026700\|NM_031157\|HNRNPA1 |
| SEQ ID NO. 201 *Homo Sapiens* - hsa_circ_0009155\|NM_017749\|AMBRA1 |
| SEQ ID NO. 202 *Homo Sapiens* - hsa_circ_0005273\|NM_001199649\|PTK2 |
| SEQ ID NO. 203 *Homo Sapiens* - hsa_circ_0078264\|NM_001029884\|PLEKHG1 |
| SEQ ID NO. 204 *Homo Sapiens* - hsa_circ_0071439\|NM_017867\|C4orf27 |
| SEQ ID NO. 205 *Homo Sapiens* - hsa_circ_0037127\|NM_001243249\|NPRL3 |
| SEQ ID NO. 206 *Homo Sapiens* - hsa_circ_0142668\|ENST00000455084.1\|TTTY10 |
| SEQ ID NO. 207 *Homo Sapiens* - hsa_circ_0092337\|NM_033251\|RPL13 |
| SEQ ID NO. 208 *Homo Sapiens* - hsa_circ_0038981\|NM_000034\|ALDOA |
| SEQ ID NO. 209 *Homo Sapiens* - hsa_circ_0002799\|NM_007345\|ZNF236 |
| SEQ ID NO. 210 *Homo Sapiens* - hsa_circ_0069977\|NM_001144978\|MTHFD2L |
| SEQ ID NO. 211 *Homo Sapiens* - hsa_circ_0017972\|NM_005028\|PIP4K2A |
| SEQ ID NO. 212 *Homo Sapiens* - hsa_circ_0003201\|NM_020773\|TBC1D14 |
| SEQ ID NO. 213 *Homo Sapiens* - hsa_circ_0065149\|NM_014159\|SETD2 |
| SEQ ID NO. 214 *Homo Sapiens* - hsa_circ_0071681\|NM_004237\|TRIP13 |
| SEQ ID NO. 215 *Homo Sapiens* - hsa_circ_0084642\|NM_001080416\|MYBL1 |
| SEQ ID NO. 216 *Homo Sapiens* - hsa_circ_0053317\|NM_199193\|BRE |
| SEQ ID NO. 217 *Homo Sapiens* - hsa_circ_0000443\|NM_015335\|MED13L |
| SEQ ID NO. 218 *Homo Sapiens* - hsa_circ_0040726\|NM_014615\|KIAA0182 |
| SEQ ID NO. 219 *Homo Sapiens* - hsa_circ_0087331\|NM_005077\|TLE1 |
| SEQ ID NO. 220 *Homo Sapiens* - hsa_circ_0073942\|NM_002715\|PPP2CA |
| SEQ ID NO. 221 *Homo Sapiens* - hsa_circ_0013526\|NM_006135\|CAPZA1 |
| SEQ ID NO. 222 *Homo Sapiens* - hsa_circ_0131196\|TCONS_00011401\|TCONS_00011401 |
| SEQ ID NO. 223 *Homo Sapiens* - hsa_circ_0004738\|NM_022897\|RANBP17 |
| SEQ ID NO. 224 *Homo Sapiens* - hsa_circ_0026568\|NM_000889\|ITGB7 |
| SEQ ID NO. 225 *Homo Sapiens* - hsa_circ_0061276\|NM_003489\|NRIP1 |
| SEQ ID NO. 226 *Homo Sapiens* - hsa_circ_0002919\|NM_001284\|AP3S1 |
| SEQ ID NO. 227 *Homo Sapiens* - hsa_circ_0000907\|NM_004145\|MYO9B |
| SEQ ID NO. 228 *Homo Sapiens* - hsa_circ_0023115\|NM_000852\|GSTP1 |
| SEQ ID NO. 229 *Homo Sapiens* - hsa_circ_0001816\|NM_014754\|PTDSS1 |
| SEQ ID NO. 230 *Homo Sapiens* - hsa_circ_0004128\|NM_001005735\|CHEK2 |
| SEQ ID NO. 231 *Homo Sapiens* - hsa_circ_0077109\|NM_001010844\|IRAK1BP1 |
| SEQ ID NO. 232 *Homo Sapiens* - hsa_circ_0014724\|NR_036564\|CCT3 |
| SEQ ID NO. 233 *Homo Sapiens* - hsa_circ_0039626\|NM_016284\|CNOT1 |
| SEQ ID NO. 234 *Homo Sapiens* - hsa_circ_0075166\|NM_022455\|NSD1 |
| SEQ ID NO. 235 *Homo Sapiens* - hsa_circ_0123780\|ENST00000301831.4\|ULK4 |
| SEQ ID NO. 236 *Homo Sapiens* - hsa_circ_0077032\|NM_004370\|COL12A1 |
| SEQ ID NO. 237 *Homo Sapiens* - hsa_circ_0099053\|ENST00000359742.4\|GRIP1 |
| SEQ ID NO. 238 *Homo Sapiens* - hsa_circ_0002082\|NR_002819\|MALAT1 |

-continued

| Exemplary circRNAs |
|---|
| SEQ ID NO. 239 *Homo Sapiens* - hsa_circ_0007335\|NM_001184783\|VDAC2 |
| SEQ ID NO. 240 *Homo Sapiens* - hsa circ_0050124\|NM_012181\|FKBP8 |
| SEQ ID NO. 241 *Homo Sapiens* - hsa_circ_0005615\|NM_004555\|NFATC3 |

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

What is claimed is:

1. A method for assessing major depressive disorder (MDD) or bipolar disorder (BD) in a subject comprising:

obtaining a first sample from the subject;

assaying the first sample using probes and/or primers configured to identify the presence of and/or amplify one or more brain disorder-associated circRNA biomarkers;

producing an expression profile of the one or more brain disorder-associated circRNA biomarkers based on the assay;

comparing the expression profile to a control expression profile or to an expression profile from a second sample obtained from the subject after administration of an antidepressant treatment;

and administering, changing, or discontinuing an antidepressant therapy for said subject based on the differential expression of said brain disorder-associated circRNA biomarkers in said first sample compared to said control or to said second sample;

and wherein the antidepressant therapy is selected from: administering a Selective Serotonin Reuptake Inhibitors (SSRIs), administering a serotonin and norepinephrine reuptake inhibitors (SNRIs), administering a Monoamine oxidase inhibitors (MAOIs), or any combination thereof;

and wherein the brain disorder-associated circRNA biomarkers comprise one or more circRNAs selected from SEQ ID NOs: 1-45 or 47-241.

2. The method of claim 1, wherein said first and/or second sample comprises a physiological fluid sample.

3. The method of claim 2, wherein said physiological fluid sample comprises blood, cell, or tissue sample.

4. The method of claim 1, wherein said subject is a human.

5. The method of claim 1, wherein the primers include a sequence that spans a splice junction of any of the one or more brain disorder-associated circRNA biomarkers in an asymmetric manner.

6. The method of claim 1, wherein one or more of the primers comprises a PCR primer sequence selected from the group of sequences according to SEQ ID NOs: 242-283 or 286-433, or a sequence having at least 80%, 85%, 90%, 95%, 96%, 97%, 98% or 99% nucleic acid sequence identity thereto, or to the complement thereof.

7. The method of claim 1, wherein the circRNA biomarkers are selected from: circCDR1as, circTULP4, circCHIC1, circMIR5695, circRALGAPB, circCOMT, circPICALM, circDDX50, circRERE, or circSATB2, circICAM1, circDDR1, circMALAT1, circHMGA2, circCYP24A1, circDLG5, circMYO9B, circNFATC3, circDUSP22, circFKBP8, circVDAC2, or circTRIM69, or any combination thereof.

8. The method of claim 1, further comprising administering a tricyclic antidepressant.

9. A method for assessing MDD or BD in a subject comprising:
- providing a sample from the subject;
- assaying the sample using primers configured to identify the presence of and/or amplify one or more brain disorder-associated circRNA biomarkers;
- and determining whether the sample has altered levels of the one or more brain disorder-associated circRNAs, or a different expression profile of the one or more brain disorder-associated circRNAs, relative to a control representing levels of the one or more brain disorder-associated circRNAs, or an expression profile of the one or more brain disorder-associated circRNAs, in non-MDD or non-BD humans,
- wherein the primers include a sequence that spans a splice junction of any of the one or more brain disorder-associated circRNA biomarkers in an asymmetric manner,
- wherein the brain disorder-associated circRNA biomarkers comprise one or more circRNAs selected from SEQ ID NOs: 1-45 or 47-241.

10. The method of claim 9, wherein said sample comprises a physiological fluid sample.

11. The method of claim 10, wherein said physiological fluid sample comprises blood, cell, or tissue sample.

12. The method of claim 9, wherein said subject is a human.

13. The method of claim 9, wherein one or more of the primers comprises a PCR primer sequence selected from the group of sequences according to SEQ ID NOs: 242-283 or 286-433, or a sequence having at least 80%, 85%, 90%, 95%, 96%, 97%, 98% or 99% nucleic acid sequence identity thereto, or to the complement thereof.

14. The method of claim 9, wherein the circRNA biomarkers are selected from: circCDR1as, circTULP4, circCHIC1, circMIR5695, circRALGAPB, circCOMT, circPICALM, circDDX50, circRERE, or circSATB2, circICAM1, circDDR1, circMALAT1, circHMGA2, circCYP24A1, circDLG5, circMYO9B, circNFATC3, circDUSP22, circFKBP8, circVDAC2, or circTRIM69, or any combination thereof.

15. A method of treating a MDD or BD condition in a patient who is predicted to benefit or not to benefit from therapeutic administration of an antidepressant treatment comprising:
- detecting in a first sample of the patient the expression levels of one or more MDD/BD or antidepressant response/treatment-associated circRNA biomarkers to establish an expression profile of said patient;
- administering to said patient an antidepressant treatment to treat MDD or BD wherein the antidepressant treatment medication is selected from the group consisting of: Selective Serotonin Reuptake Inhibitors (SSRIs), serotonin and norepinephrine reuptake inhibitors (SNRIs), Monoamine oxidase inhibitors (MAOIs), and tricyclic antidepressants;
- detecting in a second sample of said patient the expression levels of said MDD- or BD-associated circRNA biomarkers after administration of said antidepressant treatment; and
- correlating the levels of expression in said first and second samples to determine if the antidepressant treatment is effective at treating the condition, and continuing to administer the antidepressant treatment to treat MDD or BD based on said correlation, or stopping administering the antidepressant treatment to treat MDD or BD, or administering a different antidepressant treatment to treat MDD or BD,
- wherein the circRNA biomarkers comprise one or more circRNAs selected from SEQ ID NOs: 1-45 or 47-241.

16. The method of claim 15, wherein said first and/or second sample comprises a physiological fluid sample.

17. The method of claim 16, wherein said physiological fluid sample comprises blood, cell, or tissue sample.

18. The method of claim 15, wherein said patient is a human.

19. The method of claim 15, wherein the circRNA biomarkers are selected from the group consisting of: circCDR1as, circTULP4, circCHIC1, circMIR5695, circRALGAPB, circCOMT, circPICALM, circDDX50, circRERE, or circSATB2, circICAM1, circDDR1, circMALAT1, circHMGA2, circCYP24A1, circDLG5, circMYO9B, circNFATC3, circDUSP22, circFKBP8, circ VDAC2, and circTRIM69.

* * * * *